US 6,995,174 B2

United States Patent
Wang et al.

(10) Patent No.: US 6,995,174 B2
(45) Date of Patent: Feb. 7, 2006

(54) HEPATITIS C VIRUS INHIBITORS

(75) Inventors: Xiangdong Alan Wang, Guilford, CT (US); Li-Qiang Sun, Glastonbury, CT (US); Sing-Yuen Sit, Meriden, CT (US); Ny Sin, East Hampton, CT (US); Paul Michael Scola, Glastonbury, CT (US); Piyasena Hewawasam, Middletown, CT (US); Andrew Charles Good, Wallingford, CT (US); Yan Chen, Guilford, CT (US); Jeffrey Allen Campbell, Cheshire, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 10/441,657

(22) Filed: May 20, 2003

(65) Prior Publication Data

US 2004/0106559 A1 Jun. 3, 2004

Related U.S. Application Data

(60) Provisional application No. 60/382,055, filed on May 20, 2002.

(51) Int. Cl.
*C07D 215/38* (2006.01)
*C07D 401/04* (2006.01)
*C07D 207/46* (2006.01)
*A61K 31/47* (2006.01)
*A61K 31/40* (2006.01)

(52) U.S. Cl. .................... 514/312; 514/313; 514/314; 514/343; 514/423; 514/422; 546/159; 546/160; 546/279.1; 546/153; 548/537

(58) Field of Classification Search ............. 546/153, 546/159, 160, 279.1; 514/312, 314, 313, 514/343, 423, 422; 548/537
See application file for complete search history.

(56) References Cited

U.S. PATENT DOCUMENTS

| | | | |
|---|---|---|---|
| 5,633,388 A | 5/1997 | Diana et al. | |
| 5,866,684 A | 2/1999 | Attwood et al. | |
| 5,869,253 A | 2/1999 | Draper et al. | |
| 6,018,020 A | 1/2000 | Attwood et al. | |
| 6,225,284 B1 | 5/2001 | Albert et al. | |
| 6,265,380 B1 | 7/2001 | Tung et al. | |
| 6,268,207 B1 | 7/2001 | Bailey | |
| 6,323,180 B1 | 11/2001 | Linas-Brunet et al. | |
| 6,410,531 B1 | 6/2002 | Linas-Brunet et al. | |
| 6,420,380 B2 | 7/2002 | Linas-Brunet et al. | |
| 6,534,523 B1 | 3/2003 | Linas-Brunet et al. | |
| 6,642,204 B2 * | 11/2003 | Llinas-Brunet et al. ....... 514/18 |
| 2002/0111313 A1 | 8/2002 | Campbell et al. | |

FOREIGN PATENT DOCUMENTS

| | | |
|---|---|---|
| EP | 1162196 A1 | 12/2000 |
| WO | WO 95/33764 | 12/1995 |
| WO | WO 97/06804 | 2/1997 |
| WO | WO 97/43310 | 11/1997 |
| WO | WO 98/17679 | 4/1998 |
| WO | WO 98/22496 | 5/1998 |
| WO | WO 98/46597 | 10/1998 |
| WO | WO 98/46630 | 10/1998 |
| WO | WO 99/07733 | 2/1999 |
| WO | WO 99/07734 | 2/1999 |
| WO | WO 99/38888 | 8/1999 |
| WO | WO 99/50230 | 10/1999 |

(Continued)

OTHER PUBLICATIONS

Kolykhalov, A.A., J of Virology, vol. 74, No. 4, pp. 2046–2051, Feb. 2000.
Taliani, M., Analytical Biochemistry, vol. 240, pp 80–87, 1998.
Lauer et al. (2001) New England Journal of Medicine, vol. 345 No. 1, pp. 41–52.
Zeuzem et al. (2000) The New England Journal of Medicine, vol. 343 No. 23, pp. 1666–1672.
Poynard et al. (1998) The Lancet, vol. 352, pp. 1426–1432.
Poupart et al. (2001) The Journal of Organic Chemistry, vol. 66 No. 14, pp. 4743–4751.
Steinkuhier et al. (1998) Biochemistry, vol. 37, pp. 8899–8905.
Ingallinella et al. (1998) Biochemistry, vol. 37, pp. 8906–8914.
Chu et al. (1996) Tetrahedron Letters, vol. 37 No. 40, pp. 7229–7232.
Matsumoto et al. (1996) Antiviral Research, vol. 30 No. 1, p. A23, Abstract 19.

*Primary Examiner*—D. Margaret Seaman
(74) *Attorney, Agent, or Firm*—Warren K. Volles

(57) ABSTRACT

Hepatitis C virus inhibitors are disclosed having the general formula:

(I)

wherein $R_1$, $R_2$, $R_3$, R', B, Y and X are described in the description.
Compositions comprising the compounds and methods for using the compounds to inhibit HCV are also disclosed.

48 Claims, No Drawings

FOREIGN PATENT DOCUMENTS

| WO | WO 99/64442 | | 12/1999 |
| WO | WO 00/06529 | | 2/2000 |
| WO | WO 00/09543 | * | 2/2000 |
| WO | WO 00/09558 | | 2/2000 |
| WO | WO 00/10573 | | 3/2000 |
| WO | WO 00/13708 | | 3/2000 |
| WO | WO 00/18231 | | 4/2000 |
| WO | WO 00/59929 | | 10/2000 |
| WO | WO 01/32153 A2 | | 5/2001 |
| WO | WO 01/85172 A1 | | 11/2001 |
| WO | WO 02/04425 A2 | | 1/2002 |
| WO | WO 02/06246 A1 | | 1/2002 |
| WO | WO 02/060926 A2 | | 8/2002 |
| WO | WO 03/064416 A1 | | 8/2003 |
| WO | WO 03/064455 A2 | | 8/2003 |
| WO | WO 03/064456 A1 | | 8/2003 |
| WO | WO 03/066103 A1 | | 8/2003 |

* cited by examiner

HEPATITIS C VIRUS INHIBITORS

CROSS REFERENCE TO RELATED APPLICATION

The non-provisional application claims priority from the provisional application U.S. Ser. No. 60/382,055 filed May 20, 2002.

FIELD OF THE INVENTION

The present invention is generally directed to antiviral compounds, and more specifically directed to compounds which inhibit the functioning of the NS3 protease encoded by Hepatitis C virus (HCV), compositions comprising such compounds and, methods for inhibiting the functioning of the NS3 protease.

BACKGROUND OF THE INVENTION

HCV is a major human pathogen, infecting an estimated 170 million persons worldwide—roughly five times the number infected by human immunodeficiency virus type 1. A substantial fraction of these HCV infected individuals develop serious progressive liver disease, including cirrhosis and hepatocellular carcinoma. (Lauer, G. M.; Walker, B. D. *N. Engl. J. Med.* (2001), 345, 41–52).

Presently, the most effective HCV therapy employs a combination of alpha-interferon and ribavirin, leading to sustained efficacy in 40% of patients. (Poynard, T. et al. *Lancet* (1998), 352, 1426–1432). Recent clinical results demonstrate that pegylated alpha-interferon is superior to unmodified alpha-interferon as monotherapy (Zeuzem, S. et al. *N. Engl. J. Med.* (2000), 343, 1666–1672). However, even with experimental therapeutic regimens involving combinations of pegylated alpha-interferon and ribavirin, a substantial fraction of patients do not have a sustained reduction in viral load. Thus, there is a clear and long-felt need to develop effective therapeutics for treatment of HCV infection.

HCV is a positive-stranded RNA virus. Based on a comparison of the deduced amino acid sequence and the extensive similarity in the 5' untranslated region, HCV has been classified as a separate genus in the Flaviviridae family. All members of the Flaviviridae family have enveloped virions that contain a positive stranded RNA genome encoding all known virus-specific proteins via translation of a single, uninterrupted, open reading frame.

Considerable heterogeneity is found within the nucleotide and encoded amino acid sequence throughout the HCV genome. At least six major genotypes have been characterized, and more than 50 subtypes have been described. The major genotypes of HCV differ in their distribution worldwide, and the clinical significance of the genetic heterogeneity of HCV remains elusive despite numerous studies of the possible effect of genotypes on pathogenesis and therapy.

The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature non-structural proteins (NS2, NS3, NS4A, NS4B, NS5A, and NS5B) is effected by two viral proteases. The first one, as yet poorly characterized, cleaves at the NS2-NS3 junction; the second one is a serine protease contained within the N-terminal region of NS3 (henceforth referred to as NS3 protease) and mediates all the subsequent cleavages downstream of NS3, both in cis, at the NS3-NS4A cleavage site, and in trans, for the remaining NS4A-NS4B, NS4B-NS5A, NS5A-NS5B sites. The NS4A protein appears to serve multiple functions, acting as a cofactor for the NS3 protease and possibly assisting in the membrane localization of NS3 and other viral replicase components. The complex formation of the NS3 protein with NS4A seems necessary to the processing events, enhancing the proteolytic efficiency at all of the sites. The NS3 protein also exhibits nucleoside triphosphatase and RNA helicase activities. NS5B is a RNA-dependent RNA polymerase that is involved in the replication of HCV.

Among the compounds that have demonstrated efficacy in inhibiting HCV replication, as selective HCV serine protease inhibitors, are the peptide compounds disclosed in U.S. Pat. No. 6,323,180.

SUMMARY OF THE INVENTION

The present invention provides a compound of formula I, including pharmaceutically acceptable salts, solvates or prodrugs thereof,

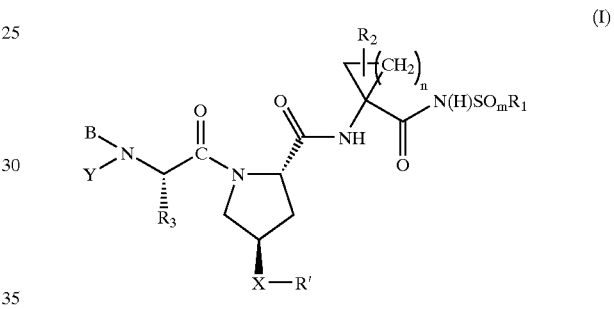

wherein:
(a) $R_1$ is $C_{1-8}$ alkyl, $C_{3-7}$ cycloalkyl, or $C_{4-10}$ alkylcycloalkyl;
(b) m is 1 or 2;
(c) n is 1 or 2;
(d) $R_2$ is H $C_{1-6}$ alkyl, $C_{2-6}$ alkenyl or $C_{3-7}$ cycloalkyl, each optionally substituted with halogen;
(e) $R_3$ is $C_{1-8}$ alkyl optionally substituted with halo, cyano, amino, $C_{1-6}$ dialkylamino, $C_{6-10}$ aryl, $C_{7-14}$ alkylaryl, $C_{1-6}$ alkoxy, carboxy, hydroxy, aryloxy, $C_{7-14}$ alkylaryloxy, $C_{2-6}$ alkylester, $C_{8-15}$ alkylarylester; $C_{3-12}$ alkenyl, $C_{3-7}$ cycloalkyl, or $C_{4-10}$ alkylcycloalkyl, wherein the cycloalkyl or alkylcycloalkyl are optionally substituted with hydroxy, $C_{1-6}$ alkyl, $C_{2-6}$ alkenyl or $C_{1-6}$ alkoxy; or $R_3$ together with the carbon atom to which it is attached forms a $C_{3-7}$ cycloalkyl group optionally substituted with $C_{2-6}$ alkenyl;
(f) Y is H, phenyl substituted with nitro, pyridyl substituted with nitro, or $C_{1-6}$ alkyl optionally substituted with cyano, OH or $C_{3-7}$ cycloalkyl; provided that if $R_4$ or $R_5$ is H then Y is H;
(g) B is H, $C_{1-6}$ alkyl, $R_4$—(C=O)—, $R_4O(C=O)$—, $R_4$—N($R_5$)—C(=O)—, $R_4$—N($R_5$)—C(=S)—, $R_4SO_2$—, or $R_4$—N($R_5$)—$SO_2$—;
(h) $R_4$ is (i) $C_{1-10}$ alkyl optionally substituted with phenyl, carboxyl, $C_{1-6}$ alkanoyl, 1–3 halogen, hydroxy, —OC(O)$C_{1-6}$ alkyl, $C_{1-6}$ alkoxy, amino optionally substituted with $C_{1-6}$ alkyl, amido, or (lower alkyl) amido;
(ii) $C_{3-7}$ cycloalkyl, $C_{3-7}$ cycloalkoxy, or $C_{4-10}$ alkylcycloalklyl, each optionally substituted with hydroxy, carboxyl, ($C_{1-6}$ alkoxy)carbonyl, amino optionally substituted with $C_{1-6}$ alkyl, amido, or (lower alkyl)amido; (iii) $C_{6-10}$ aryl or $C_{7-16}$ arylalkyl, each optionally substituted with $C_{1-6}$ alkyl, halogen, nitro, hydroxy, amido, (lower alkyl) amido, or amino optionally substituted with $C_{1-6}$ alkyl; (iv) Het; (v) bicyclo (1.1.1)pentane; or (vi) —C(O)O$C_{1-6}$alkyl, $C_{2-6}$alkenyl or $C_{2-6}$ alkynyl;

(i) $R_5$ is H; $C_{1-6}$ alkyl optionally substituted with 1–3 halogens; or $C_{1-6}$ alkoxy provided $R_4$ is $C_{1-10}$ alkyl;

(j) X is O, S, SO, $SO_2$, $OCH_2$, $CH_2O$ or NH;

(k) R' is Het; or $C_{6-10}$ aryl or $C_{7-14}$ alkylaryl, optionally substituted with $R^a$; and (l) $R^a$ is $C_{1-6}$ alkyl, $C_{3-7}$ cycloalkyl, $C_{1-6}$ alkoxy, $C_{3-7}$ cycloalkoxy, halo-$C_{1-6}$ alkyl, $CF_3$, mono-or di-halo-$C_{1-6}$ alkoxy, cyano, halo, thioalkyl, hydroxy, alkanoyl, $NO_2$, SH,) amino, $C_{1-6}$ alkylamino, di($C_{1-6}$) alkylamino, di ($C_{1-6}$) alkylamide, carboxyl, ($C_{1-6}$) carboxyester, $C_{1-6}$ alkylsulfone, $C_{1-6}$ alkylsulfonamide, di($C_{1-6}$)alkyl(alkoxy)amine, $C_{6-10}$ aryl, $C_{7-14}$ alkylaryl, or a 5–7 membered monocyclic heterocycle;

with the proviso that X—R' is not

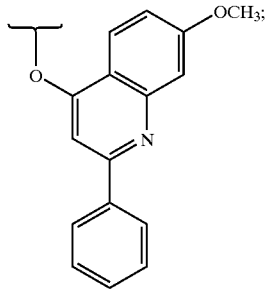

or a pharmaceutically acceptable salt, solvate or prodrug thereof.

The present invention also provides compositions comprising the compounds or pharmaceutically acceptable salts, solvates or prodrugs thereof and a pharmaceutically acceptable carrier. In particular, the present invention provides pharmaceutical compositions useful for inhibiting HCV NS3 comprising a therapeutically effective amount of a compound of the present invention, or a pharmaceutically acceptable salt, solvate or prodrug thereof, and a pharmaceutically acceptable carrier.

The present invention further provides methods for treating patients infected with HCV, comprising administering to the patient a therapeutically effective amount of a compound of the present invention, or a pharmaceutically acceptable salt, solvate or prodrug thereof. Additionally, the present invention provides methods of inhibiting HCV NS3 protease by administering to a patient an effective amount of a compound of the present invention.

By virute of the present invention, it is now possible to provide improved drugs comprising the compounds of the invention which can be effective in the treatment of patients infected with HCV. Specifically, the present invention provides peptide compounds that can inhibit the functioning of the NS3 protease, e.g., in combination with the NS4A protease.

DETAILED DESCRIPTION OF THE INVENTION

Stereochemical definitions and conventions used herein generally follow McGraw-Hill Dictionary of Chemical Terms, S. P. Parker, Ed., McGraw-Hill Book Company, New York (1984) and Stereochemistry of Organic Compounds, Eliel, E. and Wilen, S., John Wiley & Sons, Inc., New York (1994). Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or 1 meaning that the compound is levorotatory and (+) or d, meaning the compound, is dextrorotatory. For a given chemical structure, these compounds, called stereoisomers, are identical except that they are mirror images of one another. A specific stereoisomer of a mirror image pair may also be referred to as an enantiomer, and a mixture of such isomers is often called an enantiomeric mixture.

The nomenclature used to describe organic radicals, e.g., hydrocarbons and substituted hydrocarbons, generally follows standard nomenclature known in the art, unless otherwise specifically defined. Combinations of groups, e.g., alkylalkoxyamine, include all possible stable configurations, unless otherwise specifically stated. Certain radicals and combinations are defined below for purposes of illustration.

The terms "racemic mixture" and "racemate" refer to an equimolar mixture of two enantiomeric species, devoid of optical activity.

The term "chiral" refers to molecules which have the property of non-superimposability of the mirror image partner, while the term "achiral" refers to molecules which are superimposable on their mirror image partner.

The term "stereoisomers" refers to compounds which have identical chemical composition, but differ with regard to the arrangement of the atoms or groups in space.

The term "diastereomer" refers to a stereoisomer which is not an enantiomer, e.g., a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

The term "enantiomers" refers to two stereoisomers of a compound which are non-superimposable mirror images of one another.

The term "pharmaceutically acceptable salt" is intended to include nontoxic salts synthesized from a compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 18th ed., Mack Publishing Company, Easton, Pa., 1990, p. 1445. The compounds of the present invention are useful in the form of the free base or acid or in the form of a pharmaceutically acceptable salt thereof. All forms are within the scope of the invention.

The term "therapeutically effective amount" means the total amount of each active component that is sufficient to show a meaningful patient benefit, e.g., a sustained reduction in viral load. When applied to an individual active ingredient, administered alone, the term refers to that ingredient alone. When applied to a combination, the term refers to combined amounts of the active ingredients that result in the therapeutic effect, whether administered in combination, serially or simultaneously.

The term "compounds of the invention", and equivalent expressions, are meant to embrace compounds of Formula I, and pharmaceutically acceptable salts, and solvates, e.g. hydrates. Similarly, reference to intermediates, is meant to embrace their salts, and solvates, where the context so permits. References to the compound of the invention also include the preferred compounds of Formula II and III.

The term "derivative" means a chemically modified compound wherein the modification is considered routine by the ordinary skilled chemist, such as an ester or an amide of an acid, protecting groups, such as a benzyl group for an alcohol or thiol, and tert-butoxycarbonyl group for an amine.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, and the like.

The term "prodrug" as used herein means derivatives of the compounds of the invention which have chemically or metabolically cleavable groups and become, by solvolysis or under physiological conditions, the compounds of the invention which are pharmaceutically active in vivo. A prodrug of a compound may be formed in a conventional manner with a functional group of the compounds such as with an amino, hydroxy or carboxy group when present. The prodrug derivative form often offers advantages of solubility, tissue compatibility, or delayed release in a mammalian organism (see, Bundgard, H., Design of Prodrugs, pp. 7–9, 21–24, Elsevier, Amsterdam 1985). Prodrugs include acid derivatives well known to practitioners of the art, such as, for example, esters prepared by reaction of the parent acidic compound with a suitable alcohol, or amides prepared by reaction of the parent acid compound with a suitable amine.

The term "patient" includes both human and other mammals.

The term "pharmaceutical composition" means a composition comprising a compound of the invention in combination with at least one additional pharmaceutical carrier, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Ingredients listed in Remington's Pharmaceutical Sciences, 18$^{th}$ ed., Mack Publishing Company, Easton, Pa. (1999) for example, may be used.

The phrase "pharmaceutically acceptable" is employed herein to refer to those compounds, materials, compositions, and/or dosage forms which are, within the scope of sound medical judgment, suitable for use in contact with the tissues of patients without excessive toxicity, irritation, allergic response, or other problem or complication commensurate with a reasonable risk/benefit ratio.

The term "treating" refers to: (i) preventing a disease, disorder or condition from occurring in a patient which may be predisposed to the disease, disorder and/or condition but has not yet been diagnosed as having it; (ii) inhibiting the disease, disorder or condition, i.e., arresting its development; and (iii) relieving the disease, disorder or condition, i.e., causing regression of the disease, disorder and/or condition. The term "substituted" as used herein includes substitution at from one to the maximum number of possible binding sites on the core, e.p., organic radical, to which the subsitutent is bonded, e.g., mono-, di-, tri- or tetra-substituted, unless otherwise specifically stated.

The term "halo" as used herein means a halogen substituent selected from bromo, chloro, fluoro or iodo. The term "haloalkyl" means an alkyl group that in substituted with one or more halo substituents.

The term "alkyl" as used herein means acyclic, straight or branched chain alkyl substituents and includes, for example, methyl, ethyl, propyl, butyl, tert-butyl, hexyl, 1-methylethyl, 1-methylpropyl, 2-methypropyl, 1,1-dimethylethyl. Thus, $C_{1-6}$ alkyl refers to an alkyl group having from one to six carbon atoms. The term "lower alkyl" means an alkyl group having from one to six, preferably from one to four carbon atoms. The term "alkylester" means an alkyl group additionally containing on ester group. Generally, a stated carbon number range, e.g., $C_{2-6}$ alkylester, includes all of the carbon atoms in the radical.

The term "alkenyl" as used herein means an alkyl radical containing at least one double bond, e.g., ethenyl (vinyl) and alkyl.

The term "alkoxy" as used herein means an alkyl group with the indicated number of carbon atoms attached to an oxygen atom. Alkoxy includes, for example, methoxy, ethoxy, propoxy, 1-methylethoxy, butoxy and 1,1-dimethylethoxy. The latter radical is referred to in the art as tert-butoxy. The term "alkoxycarbonyl" means an alkoxy group additionally containing a carbonyl group.

The term "cycloalkyl" as used herein means a cycloalkyl substituent containing the indicated number of carbon atoms and includes, for example, cyclopropyl, cyclobutyl, cyclopentyl, cyclohexyl, cycloheptyl and spiro cyclic groups such as spirocyclopropyl as spirocyclobutyl. The term "cycloalkoxy" as used herein means a cycloalkyl group linked to an oxygen atom, such as, for example, cyclobutyloxy or cyclopropyloxy. The term "alkylcycloalkyl" means a cycloalkyl group linked to an alkyl group. The stated carbon number range includes the total number of carbons in the radical, unless otherwise specfically stated. This a $C_{4-10}$ alkylcycloalkyl may contain from 1–7 carbon atoms in the alkyl group and from 3–9 carbon atoms in the ring, e.g., cyclopropylmethyl or cyclohexylethyl.

The term "aryl" as used herein means an aromatic moiety containing the indicated number of carbon atoms, such as, but not limited to phenyl, indanyl or naphthyl. For example, $C_{6-10}$ aryl refers to an aromatic moiety having from six to ten carbon atoms which may be in the form of a monocyclic or bicyclic structure. The term "haloaryl" as used herein refers to an aryl mono, di or tri substituted with one or more halogen atoms. The terms "alkylaryl", "arylalkyl" and "aralalkyl" mean an aryl group substituted with one or more alkyl groups. Thus, a $C_{7-14}$ alkylaryl group many have from 1–8 carbon atoms in the alkyl group for a monocyclic aromatic and from 1–4 carbon atoms in the alkyl group for a fused aromatic. The aryl radicals include those substituted with typical substituents known to those skilled in the art, e.g., halogen, hydroxy, carboxy, carbonyl, nitro, sulfo, amino, cyano, dialkylamino haloalkyl, $CF_3$, haloalkoxy, thioalkyl, alkanoyl, SH, alkylamino, alkylamide, dialkylamide, carboxyester, alkylsulfone, alkylsulfonamide and alkyl(alkoxy)amine. Examples of alkylaryl groups include benzyl, butylphenyl and 1-naphthylmethyl.

The terms "alkylaryloxy" and "alkylarylester" mean alkylaryl groups containing an oxygen atom and ester group, respectively.

The term "carboxyalkyl" as used herein means a carboxyl group (COOH) linked through an alkyl group as defined above and includes, for example, butyric acid.

The term "alkanoyl" as used herein means straight or branched 1-oxoalkyl radicals containing the indicated number of carbon atoms and includes, for example, formyl, acetyl, 1-oxopropyl (propionyl), 2-methyl-1-oxopropyl, 1-oxohexyl and the like.

The term "amino aralkyl" as used herein means an amino group substituted with an aralkyl group, such as the following amino aralkyl

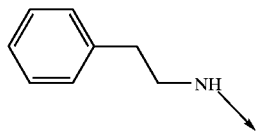

The term "alkylamide" as used herein means an amide mono-substituted with an alkyl, such as

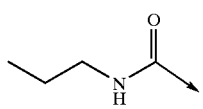

The term "carboxyalkyl" as used herein means a carboxyl group (COOH) linked through a alkyl group as defined above and includes, for example, butyric acid.

The term "heterocycle", also referred to as "Het", as used herein means 7–12 membered bicyclic heterocycles and 5–7 membered monocyclic heterocycles.

Preferred bicyclic heterocycles are 7–12 membered fused bicyclic ring systems (both rings share an adjacent pair of atoms) containing from one to four heteroatoms selected from nitrogen, oxygen and sulfur, wherein both rings of the heterocycle are fully unsaturated. The nitrogen and sulfur heteroatoms atoms may be optionally oxidized. The bicyclic heterocycle may contain the heteroatoms in one or both rings. The bicyclic heterocycle may also contain substituents on any of the ring carbon atoms, e.g., one to three substituents. Examples of suitable substituents include $C_{1-6}$ alkyl, $C_{3-7}$ cycloalkyl, $C_{1-6}$ alkoxy, $C_{3-7}$ cycloalkoxy, halo-$C_{1-6}$ alkyl, $CF_3$, mono-or di-halo-$C_{1-6}$ alkoxy, cyano, halo, thioalkyl, hydroxy, alkanoyl, $NO_2$, SH, ) amino, $C_{1-6}$ alkylamino, di($C_{1-6}$)alkylamino, di($C_{1-6}$)alkylamide, carboxyl, ($C_{1-6}$) carboxyester, $C_{1-6}$alkylsulfone, $C_{1-6}$alkylsulfonamide, $C_{1-6}$alkylsulfoxide, di($C_{1-6}$) alkyl (alkoxy)amine, $C_{6-10}$ aryl, $C_{7-14}$ alkylaryl, and a 5–7 membered monocyclic heterocycle. When two substituents are attached to vicinal carbon atoms of the bicyclic heterocycle, they can join to form a ring, e.g., a five, six or seven membered ring system containing up to two heteroatoms selecting from oxygen and nitrogen. The bicyclic heterocycle may be attached to its pendant group, e.g. X in Formula I, at any atom in the ring and preferably carbon.

Examples of bicyclic heterocycles include, but are not limited to, the following ring systems:

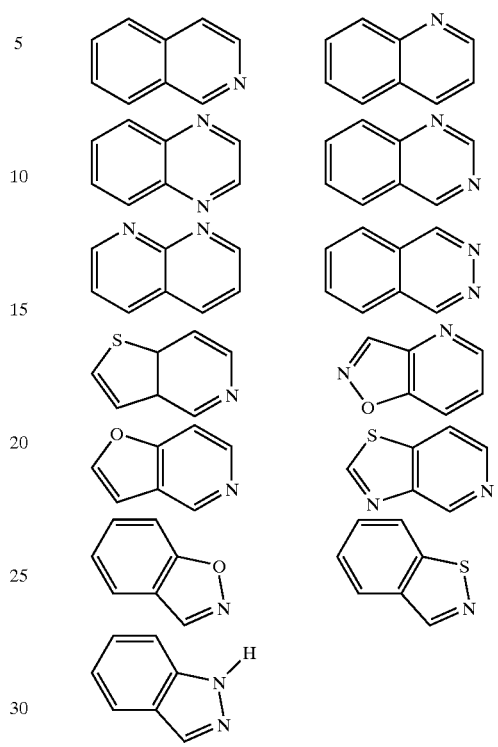

Preferred monocyclic heterocycles are 5–7 membered saturated, partially saturated or fully unsaturated ring system (this latter subset herein referred to as unsaturated heteroaromatic) containing in the ring from one to four heteroatoms selected from nitrogen, oxygen and sulfur, wherein the sulfur and nitrogen heteroatoms may be optionally oxidized. The monocyclic heterocycle may also contain substituents on any of the ring atoms, e.g., one to three substituents. Examples of suitable substituents include $C_{1-6}$ alkyl, $C_{3-7}$ cycloalkyl, $C_{1-6}$ alkoxy, $C_{3-7}$ cycloalkoxy, halo-$C_{1-6}$ alkyl, $CF_3$, mono-or di-halo-$C_{1-6}$ alkoxy, cyano, halo, thioalkyl, hydroxy, alkanoyl, $NO_2$, SH, ) amino, $C_{1-6}$ alkylamino, di($C_{1-6}$) alkylamino, di($C_{1-6}$)alkylamide carboxyl, ($C_{1-6}$) carboxyester, $C_{1-6}$ alkylsulfone, $C_{1-6}$alkylsulfoxide, $C_{1-6}$alkylsulfonaride, di($C_{1-6}$) alkyl (alkoxy)amine, $C_{6-10}$aryl, $C_{7-14}$ alkylaryl and 5–7 membered monocyclic heterocycle. The monocyclic heterocycle may be attached to its pendant group, e.g. X in Formula I, at any atom in the ring Examples of monocyclic heterocycles include, but are not limited to, the following:

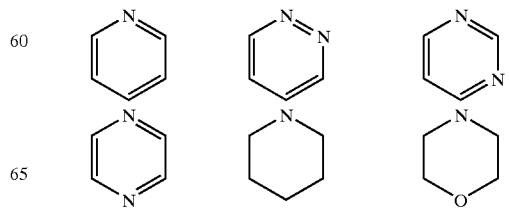

-continued

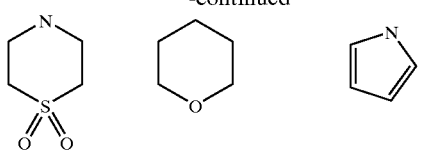

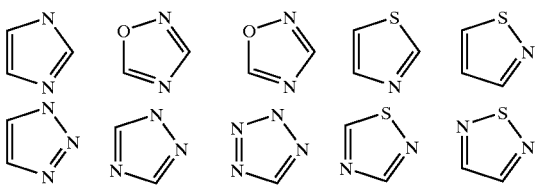

Those skilled in the art will recognize that the heterocycles used in the compounds of the present invention should be stable. Generally, stable compounds are those which can be synthesized, isolated and formulated using techniques known the those skilled in the art without degradation of the compound.

Where used in naming compounds of the present invention, the designations "P1', P1, P2, P3 and P4", as used herein, map the relative positions of the amino acid residues of a protease inhibitor binding relative to the binding of the natural peptide cleavage substrate. Cleavage occurs in the natural substrate between P1 and P1' where the nonprime positions designate amino acids starting from the C-terminus end of the peptide natural cleavage site extending towards the N-terminus; whereas, the prime positions emanate from the N-terminus end of the cleavage site designation and extend towards the C-terminus. For example, P1' refers to the first position away from the right hand end of the C-terminus of the cleavage site (ie. N-terminus first position); whereas P1 starts the numbering from the left hand side of the C-terminus cleavage site, P2: second position from the C-terminus, etc.) (see Berger A. & Schechter I., Transactions of the Royal Society London series (1970), B257, 249–264.

Thus in the compounds of formula I, the "P1' to P4" portions of the molecule are indicated below:

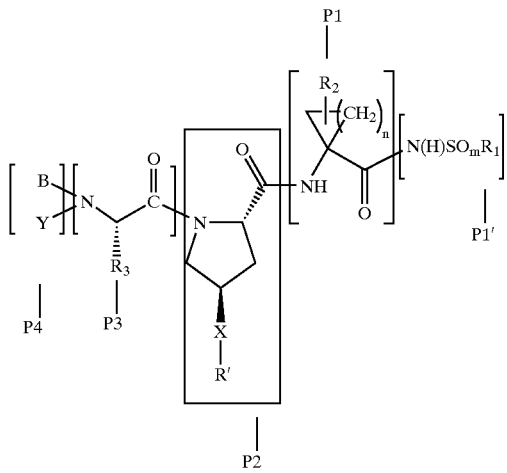

As used herein the term "1-aminocyclopropyl-carboxylic acid" (Acca) refers to a compound of formula:

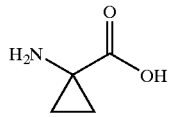

As used herein the term "tert-butylglycine" refers to a compound of the formula:

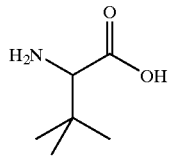

The term "residue" with reference to an amino acid or amino acid derivative means a radical derived from the corresponding α-amino acid by eliminating the hydroxyl of the carboxy group and one hydrogen of the α-amino acid group. For instance, the terms Gln, Ala, Gly, Ile, Arg, Asp, Phe, Ser, Leu, Cys, Asn, Sar and Tyr represent the "residues" of L-glutamine, L-alanine, glycine, L-isoleucine, L-arginine, L-aspartic acid, L-phenylalanine, L-serine, L-leucine, L-cysteine, L-asparagine, sarcosine and L-tyrosine, respectively.

The term "side chain" with reference to an amino acid or amino acid residue means a group attached to the α-carbon atom of the α-amino acid. For example, the R-group side chain for glycine is hydrogen, for alanine it is methyl, for valine it is isopropyl. For the specific R-groups or side chains of the α-amino acids reference is made to A. L. Lehninger's text on Biochemistry (see chapter 4).

The compounds of the present invention have the structure of Formula I:

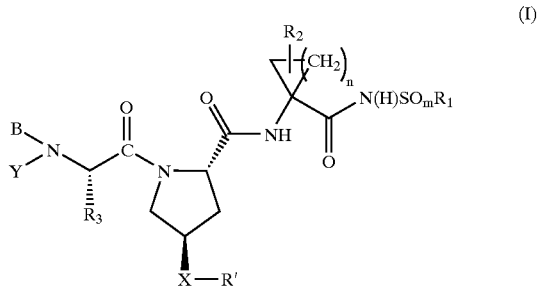

wherein:
(a) $R_1$ is $C_{1-8}$ alkyl, $C_{3-7}$ cycloalkyl, or $C_{4-10}$ alkylcycloalkyl;
(b) m is 1 or 2;
(c) n is 1 or 2;
(d) $R_2$ is H $C_{1-6}$ alkyl, $C_{2-6}$ alkenyl or $C_{3-7}$ cycloalkyl, each optionally substituted with halogen;
(e) $R_3$ is $C_{1-8}$ alkyl optionally substituted with halo, cyano, amino, $C_{1-6}$ dialkylamino, $C_{6-10}$ aryl, $C_{7-14}$ alkylaryl, $C_{1-6}$ alkoxy, carboxy, hydroxy, aryloxy, $C_{7-14}$ alkylaryloxy, $C_{2-6}$ alkylester, $C_{8-15}$ alkylarylester; $C_{3-12}$ alkenyl, $C_{3-7}$ cycloalkyl, or $C_{4-10}$ alkylcycloalkyl, wherein the cycloalkyl or alkylcycloalkyl are optionally substituted with hydroxy, $C_{1-6}$ alkyl, $C_{2-6}$ alkenyl or $C_{1-6}$ alkoxy; or $R_3$ together with the carbon atom to which it is attached forms a $C_{3-7}$ cycloalkyl group optionally substituted with $C_{2-6}$ alkenyl;

(f) Y is H, phenyl substituted with nitro, pyridyl substituted with nitro, or $C_{1-6}$ alkyl optionally substituted with cyano, OH or $C_{3-7}$ cycloalkyl; provided that if $R_4$ or $R_5$ is H then Y is H;

(g) B is H, $C_{1-6}$ alkyl, $R_4$—(C=O)—, $R_4O(C=O)$—, $R_4$—N($R_5$)—C(=O)—, $R_4$—N($R_5$)—C(=S)—, $R_4SO_2$—, or $R_4$—N($R_5$)—$SO_2$—;

(h) $R_4$ is (i) $C_{1-10}$ alkyl optionally substituted with phenyl, carboxyl, $C_{1-6}$ alkanoyl, 1–3 halogen, hydroxy, —OC(O)$C_{1-6}$ alkyl, $C_{1-6}$ alkoxy, amino optionally substituted with C-6 alkyl, amido, or (lower alkyl) amido; (ii) $C_{3-7}$ cycloalkyl, $C_{3-7}$ cycloalkoxy, or $C_{4-10}$ alkylcycloalklyl, each optionally substituted with hydroxy, carboxyl, ($C_{1-6}$ alkoxy)carbonyl, amino optionally substituted with $C_{1-6}$ alkyl, amido, or (lower alkyl)amido; (iii) $C_{6-10}$ aryl or $C_{7-16}$ arylalkyl, each optionally substituted with $C_{1-6}$ alkyl, halogen, nitro, hydroxy, amido, (lower alkyl)amido, or amino optionally substituted with $C_{1-6}$ alkyl; (iv) Het; (v) bicyclo (1.1.1)pentane; or (vi) —C(O)O$C_{1-6}$ alkyl, $C_{2-6}$alkenyl or $C_{2-6}$ alkynyl;

(i) $R_5$ is H; $C_{1-6}$ alkyl optionally substituted with 1–3 halogens; or $C_{1-6}$ alkoxy provided $R_4$ is $C_{1-10}$ alkyl;

(j) X is O, S, SO, $SO_2$, $OCH_2$, $CH_2O$ or NH;

(k) R' is Het; or $C_{6-10}$ aryl or $C_{7-14}$ alkylaryl, optionally substituted with $R^a$; and (l) $R^a$ is $C_{1-6}$ alkyl, $C_{3-7}$ cycloalkyl, $C_{1-6}$ alkoxy, $C_{3-7}$ cycloalkoxy, halo-$C_{1-6}$ alkyl, $CF_3$, mono-or di-halo-$C_{1-6}$ alkoxy, cyano, halo, thioalkyl, hydroxy, alkanoyl, $NO_2$, SH, ) amino, $C_{1-6}$ alkylamino, di($C_{1-6}$) alkylamino, di($C_{1-6}$)alkylamide carboxyl, ($C_{1-6}$) carboxyester, C-6 alkylsulfone, $C_{1-6}$ alkylsulfonamide, di($C_{1-6}$) alkyl(alkoxy)amine, $C_{6-10}$ aryl, $C_{7-14}$ alkylaryl, or a 5–7 membered monocyclic heterocycle; with the proviso that X—R' is not

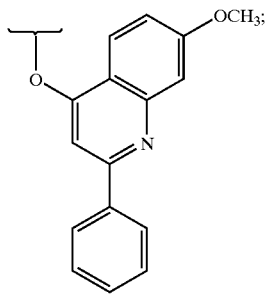

or a pharmaceutically acceptable salt, solvate or prodrug thereof.

Preferably, $R_2$ is $C_{2-6}$ alkenyl; $R_3$ is $C_{1-8}$ alkyl optionally substituted with $C_{1-6}$ alkoxy, or $C_{3-7}$ cycloalkyl; Y is H; B is $R_4$—(C=O)—, $R_4O(C=O)$—, or $R_4$—N($R_5$)—C (=O)—; $R_4$ is $C_{1-10}$ alkyl optionally substituted with 1–3 halogen or $C_{1-6}$ alkoxy; or $C_{3-7}$ cycloalkyl or $C_{4-10}$ alkylcycloalklyl; $R_5$ is H; X is O or NH; and R' is Het.

The substituents from each grouping may be selected individually and combined in any combination which provides a stable compound in accordance with the present invention. Also, more than one substituent from each group may be substituted on the core group provided there are sufficient available binding sites. For example, each of the following $R^a$ substituents, $C_{1-6}$ alkoxy, $C_6$ aryl and a 5–7 membered monocyclic heterocycle, may be substituted on a bicyclic heterocycle R'.

In a preferred aspect, the compounds of the present invention have the structure of Formula II:

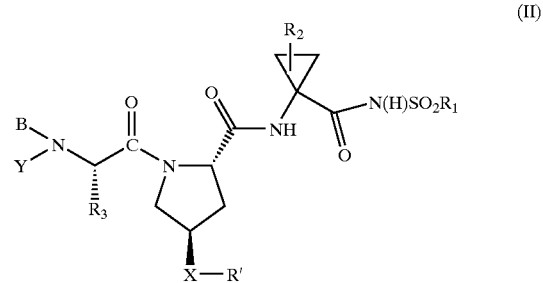

(II)

wherein:

(a) $R_1$ is $C_{3-7}$ cycloalkyl;

(b) $R_2$ is $C_{1-6}$ alkyl, $C_{2-6}$ alkenyl or $C_{3-7}$ cycloalkyl;

(c) $R_3$ is $C_{1-8}$ alkyl optionally substituted with $C_6$ aryl, $C_{1-6}$ alkoxy, carboxy, hydroxy, aryloxy, $C_{7-14}$ alkylaryloxy, $C_{2-6}$ alkylester, $C_{8-15}$ alkylarylester; $C_{3-12}$ alkenyl, $C_{3-7}$ cycloalkyl, or $C_{4-10}$ alkylcycloalkyl;

(d) Y is H;

(e) B is H, $C_{1-6}$ alkyl, $R_4$—(C=O)—, $R_4O(C=O)$—, $R_4$—N($R_5$)—C(=O)—, $R_4$—N($R_5$)—C(=S)—, $R_4SO_2$—, or $R_4$—N($R_5$)—$SO_2$—;

(f) $R_4$ is (i) $C_{1-10}$ alkyl optionally substituted with phenyl, carboxyl, $C_{1-6}$ alkanoyl, 1–3 halogen, hydroxy, $C_{1-6}$ alkoxy; (ii) $C_{3-7}$ cycloalkyl, $C_{3-7}$ cycloalkoxy, or $C_{4-10}$ alkylcycloalklyl; or (iii) $C_{6-10}$ aryl or $C_{7-16}$ arylalkyl, each optionally substituted with $C_{1-6}$ alkyl or halogen;

(g) $R_5$ is H or $C_{1-6}$ alkyl optionally substituted with 1–3 halogens;

(h) X is O or NH;

(i) R' is Het; or $C_{6-10}$ aryl optionally substituted with $R^a$; and (j) $R^a$ is $C_{1-6}$ alkyl, $C_{3-7}$ cycloalkyl, $C_{1-6}$ alkoxy, halo-$C_{1-6}$ alkyl, halo, amino, $C_6$ aryl, or a 5–7 membered monocyclic heterocycle;

with the proviso that $X_a$—R' is not

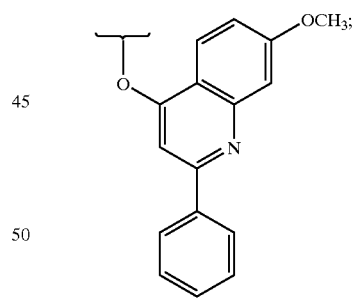

or a pharmaceutically acceptable salt, solvate or prodrug thereof.

In one preferred aspect of the invention, R' is a bicyclic heterocycle. Preferably, the bicyclic heterocycle contains 1 or 2 nitrogen atoms and optionally a sulfur atom or an oxygen atom in the ring. Preferably, the heterocycle is substituted with at least one of $C_{1-6}$ alkyl, $C_{1-6}$ alkoxy, halo, $C_6$ aryl, and a 5–7 membered monocyclic heterocycle. More preferably, R' is a bicyclic heterocycle containing 1 nitrogen atom and substituted with methoxy and at least one of a $C_6$ aryl and a 5–7 membered monocyclic heterocycle.

In another preferred aspect of the invention, R' is a monocyclic heterocycle. Preferably, the heterocycle contains 1 or 2 nitrogen atoms and optionally a sulfur atom or an oxygen atom in the ring. Preferably, the heterocycle is substituted with at least one of $C_{1-6}$ alkyl, $C_{1-6}$ alkoxy, halo, $C_{6-10}$aryl, $C_{7-14}$ alkylaryl, or a 5–7 membered monocyclic heterocycle. More preferably, R' is a monoyclic heterocycle containing 1 or 2 nitrogen atoms and substituted with methoxy and at least one of a $C_6$ aryl and a 5–7 membered monocyclic heterocycle.

In a more preferred aspect of the invention, the compounds have the structure of Formula III

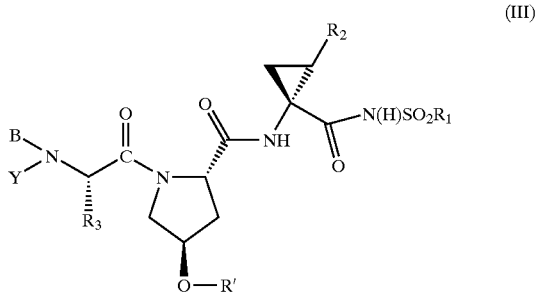

wherein:
(a) $R_1$ is $C_{3-7}$ cycloalkyl;
(b) $R_2$ is $C_{2-6}$ alkenyl;
(c) $R_3$ is $C_{1-8}$ alkyl;
(d) Y is H;
(e) B is $R_4O(C=O)-$, or $R_4-N(R_5)-C(=O)-$;
(f) $R_4$ is $C_{1-10}$ alkyl;
(g) $R_5$ is H;
(h) R' is a bicyclic heterocycle optionally substituted with $R^a$; and
(i) $R^a$ is $C_{1-6}$ alkyl, $C_{1-6}$ alkoxy, halo, $C_6$ aryl, or a 5–7 membered monocyclic heterocycle; with the proviso that O—R' is not

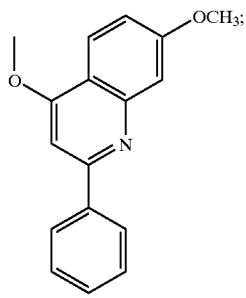

or a pharmaceutically acceptable salt, solvate or prodrug thereof.

Preferably, $R_1$ is cyclopropyl or cyclobutyl, $R_2$ is vinyl, $R_3$ is t-butyl, $R_4$ is t-butyl and R' is quinoline or isoquinoline optionally substituted with $R^a$. Preferably, $R^a$ includes at least one of $C_{1-6}$ alkoxy, $C_6$ aryl and a 5–7 membered monocyclic heterocycle. In a preferred aspect of the invention, $R_1$ is cyclopropyl, $R_2$ is vinyl, $R_3$ is t-butyl, $R_4$ is t-butyl, and R' is isoquinoline substituted with $C_{1-6}$ alkoxy and at least one of $C_6$ aryl or a 5–7 membered monocyclic heterocycle.

The compounds of the present invention, by virtue of their basic moiety, can form salts by the addition of a pharmaceutically acceptable acid. The acid addition salts are formed from a compound of Formula I and a pharmaceutically acceptable inorganic acid, including but not limited to hydrochloric, hydrobromic, hydroiodic, sulfuric, phosphoric, or organic acid such as p-toluenesulfonic, methanesulfonic, acetic, benzoic, citric, malonic, fumaric, maleic, oxalic, succinic, sulfamic, or tartaric. Thus, examples of such pharmaceutically acceptable salts include chloride, bromide, iodide, sulfate, phosphate, methanesulfonate, citrate, acetate, malonate, fumarate, sulfamate, and tartrate.

Salts of an amine group may also comprise quaternary ammonium salts in which the amino nitrogen carries a suitable organic group such as an alkyl, alkenyl, alkynyl or aralkyl moiety.

Compounds of the present invention, which are substituted with an acidic group, may exist as salts formed through base addition. Such base addition salts include those derived from inorganic bases which include, for example, alkali metal salts (e.g. sodium and potassium), alkaline earth metal salts (e.g. calcium and magnesium), aluminum salts and ammonium salts. In addition, suitable base addition salts include salts of physiologically acceptable organic bases such as trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl)amine, procaine, dibenzylpiperidine, N-benzyl-β-phenethylamine, dehydroabietylamine, N,N'-bishydroabietylamine, glucamine, N-methylglucamine, collidine, quinine, quinoline, ethylenediamine, ornithine, choline, N,N'-benzylphenethylamine, chloroprocaine, diethanolamine, diethylamine, piperazine, tris(hydroxymethyl)aminomethane and tetramethylammonium hydroxide and basic amino acids such as lysine, arginine and N-methylglutamine. These salts may be prepared by methods known to those skilled in the art.

Certain compounds of the present invention, and their salts, may also exist in the form of solvates with water, for example hydrates, or with organic solvents such as methanol, ethanol or acetonitrile to form, respectively, a methanolate, ethanolate or acetonitrilate. The present invention includes each solvate and mixtures thereof.

In addition, compounds of the present invention, or a salt or solvate thereof, may exhibit polymorphism. The present invention also encompasses any such polymorphic form.

The compounds of the present invention also contain two or more chiral centers. For example, the compounds may include P1 cyclopropyl element of formula

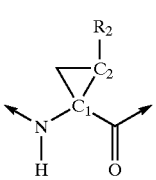

wherein $C_1$ and $C_2$ each represent an asymmetric carbon atom at positions 1 and 2 of the cyclopropyl ring. Not withstanding other possible asymmetric centers at other segments of the compounds, the presence of these two asymmetric centers means that the compounds can exist as racemic mixtures of diastereomers, such as the diastereomers wherein $R_2$ is configured either syn to the amide or syn to the carbonyl as shown below.

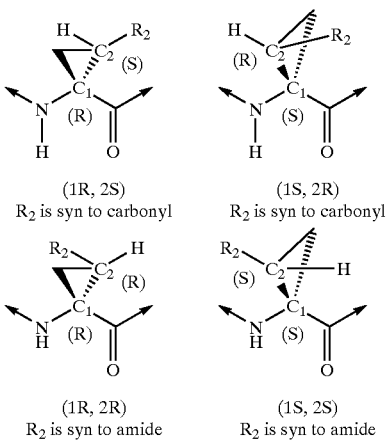

(1R, 2S)
R₂ is syn to carbonyl (1S, 2R)
R₂ is syn to carbonyl (1R, 2R)
R₂ is syn to amide (1S, 2S)
R₂ is syn to amide The present invention includes both enantiomers and mixtures of enantiomers such as racemic mixtures.

The enantiomers may be resolved by methods known to those skilled in the art, for example, by formation of diastereoisomeric salts which may be separated by crystallization, gas-liquid or liquid chromatography, selective reaction of one enantiomer with an enantiomer-specific reagent. It will be appreciated that where the desired enantiomer is converted into another chemical entity by a separation technique, then an additional step is required to form the desired enantiomeric form. Alternatively, specific enantiomers may be synthesized by asymmetric synthesis using optically active reagents, substrates, catalysts or solvents, or by converting one enantiomer into the other by asymmetric transformation.

The compounds of the present invention may be in the form of a prodrug. Simple aliphatic or aromatic esters derived from, when present, acidic groups pendent on the compounds of this invention are preferred prodrugs. In some cases it is desirable to prepare double ester type prodrugs such as (acyloxy) alkyl esters or (alkoxycarbonyl)oxy)alkyl esters.

Certain compounds of the present invention may also exist in different stable conformational forms which may be separable. Torsional asymmetry due to restricted rotation about an asymmetric single bond, for example because of steric hindrance or ring strain, may permit separation of different conformers. The present invention includes each conformational isomer of these compounds and mixtures thereof.

Certain compounds of the present invention may exist in zwitterionic form and the present invention includes each zwitterionic form of these compounds and mixtures thereof.

The starting materials useful to synthesize the compounds of the present invention are known to those skilled in the art and can be readily manufactured or are commercially available.

The compounds of the present invention can be manufactured by methods known to those skilled in the art, see e.p., U.S. Pat. No. 6,323,180 and U.S. patent appl. 20020111313 A1. The following methods set forth below are provided for illustrative purposes and are not intended to limit the scope of the claimed invention. It will be recognized that it may be preferred or necessary to prepare such a compound in which a functional group is protected using a conventional protecting group then to remove the protecting group to provide a compound of the present invention. The details concerning the use of protecting groups in accordance with the present invention are known to those skilled in the art.

The compounds of the present invention may, for example, be synthesized according to a general process as illustrated in Scheme I (wherein CPG is a carboxyl protecting group and APG is an amino protecting group):

Scheme I

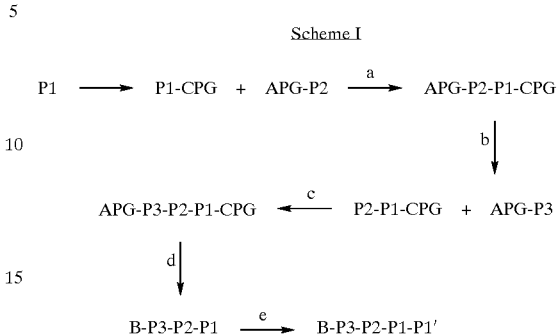

Briefly, the P1, P2, and P3 can be linked by well known peptide coupling techniques. The P1, P2, and P3 groups may be linked together in any order as long as the final compound corresponds to peptides of the invention. For example, P3 can be linked to P2-P1; or P1 linked to P3-P2.

Generally, peptides are elongated by deprotecting the α-amino group of the N-terminal residue and coupling the unprotected carboxyl group of the next suitably N-protected amino acid through a peptide linkage using the methods described. This deprotection and coupling procedure is repeated until the desired sequence is obtained. This coupling can be performed with the constituent amino acids in stepwise fashion, as depicted in Scheme I.

Coupling between two amino acids, an amino acid and a peptide, or two peptide fragments can be carried out using standard coupling procedures such as the azide method, mixed carbonic-carboxylic acid anhydride(isobutyl chloroformate) method, carbodiimide (dicyclohexylcarbodiimide, diisopropylcarbodiimide, or water-soluble carbodiimide)method, active ester (ρ-nitrophenyl ester, N-hydroxysuccinic imido ester) method, Woodward reagent κ-method, carbonyldiimidazole method, phosphorus reagents or oxidation-reduction methods. Some of these methods (especially the carbodiimide method) can be enhanced by adding 1-hydroxybenzotriazole or 4-DMAP. These coupling reactions can be performed in either solution (liquid phase) or solid phase.

More explicitly, the coupling step involves the dehydrative coupling of a free carboxyl of one reactant with the free amino group of the other reactant in the present of a coupling agent to form a linking amide bond. Descriptions of such coupling agents are found in general textbooks on peptide chemistry, for example, M. Bodanszky, "Peptide Chemistry", $2^{nd}$ rev ed., Springer-Verlag, Berlin, Germany, (1993). Examples of suitable coupling agents are N,N'-dicyclohexylcarbodiimide, 1-hydroxybenzotriazole in the presence of N,N'-dicyclohexylcarbodiimide or N-ethyl-N'-[(3-dimethylamino)propyl]carbodiimide. A practical and useful coupling agent is the commercially available (benzotriazol-1-yloxy)tris-(dimethylamino)phosphonium hexafluorophosphate, either by itself or in the present of 1-hydroxybenzotriazole or 4-DMAP. Another practical and useful coupling agent is commercially available 2-(1H-benzotriazol-1-yl)-N,N, N',N'-tetramethyluronium tetrafluoroborate. Still another practical and useful coupling agent is commercially available O-(7-azabenzotrizol-1-yl)-N,N,N',N'-tetramethyluronium hexafluorophosphate. The coupling reaction is conducted in an inert solvent, e.g. dichloromethane, acetonitrile or dimethylformamide. An excess of a tertiary amine, e.g. diisopropylethylamine, N-methylmorpholine, N-methylpyrrolidine or 4-DMAP is added to maintain the reaction mixture at a pH of about 8. The reaction temperature usually ranges between 0° C. and 50° C. and the reaction time usually ranges between 15 min and 24 h.

The functional groups of the constituent amino acids generally must be protected during the coupling reactions to avoid formation of undesired bonds. Protecting groups that can be used are listed, for example, in Greene, "Protective Groups in Organic Chemistry", John Wiley & Sons, New York (1981) and "The Peptides: Analysis, Synthesis, Biology", Vol. 3, Academic Press, New York (1981), the disclosures of which are hereby incorporated by reference.

The β-amino group of each amino acid to be coupled to the growing peptide chain must be protected (APG). Any protecting group known in the art can be used. Examples of such groups include: 1) acyl groups such as formyl, trifluoroacetyl, phthalyl, and p-toluenesulfonyl; 2) aromatic carbamate groups such as benzyloxycarbonyl(Cbz or Z) and substituted bensyloxycarbonyls, and 9-fluorenylmethyloxycarbonyl(Fmoc); 3) aliphatic carbamate groups such as tert-butyloxycarbonyl(Boc), ethoxycarbonyl, diisopropylmethoxycarbonyl, and allyloxycarbonyl; 4) cyclic alkyl carbamate groups such as cyclopentyloxycarbonyl and adamantyloxycarbonyl; 5) alkyl groups such as triphenylmethyl and benzyl; 6)trialkylsilyl such as trimethylsilyl; and 7) thiol containing groups such as phenylthiocarbonyl and dithiasuccinoyl.

The preferred α-amino protecting group is either Boc or Fmoc. Many amino acid derivatives suitably protected for peptide synthesis are commercially available. The α-amino protecting group of the newly added amino acid residue is cleaved prior to the coupling of the next amino acid. When the Boc group is used, the methods of choice are trifluoroacetic acid, neat or in dichloromethane, or HCl in dioxane or in ethyl acetate. The resulting ammonium salt is then neutralized either prior to the coupling or in situ with basic solutions such as aqueous buffers, or tertiary amines in dichloromethane or acetonitrile or dimethylformamide. When the Fmoc group is used, the reagents of choice are piperidine or substituted piperidine in dimethylformamide, but any secondary amine can be used. The deprotection is carried out at a temperature between 0° C. and room temperature (rt or RT) usually 20–22° C.

Any of the amino acids having side chain functionalities must be protected during the preparation of the peptide using any of the above-described groups. Those skilled in the art will appreciate that the selection and use of appropriate protecting groups for these side chain functionalities depend upon the amino acid and presence of other protecting groups in the peptide. The selection of such protecting groups is important in that the group must not be removed during the deprotection and coupling of the α-amino group.

For example, when Boc is used as the β-amino protecting group, the following side chain protecting group are suitable: p-toluenesulfonyl (tosyl) moieties can be used to protect the amino side chain of amino acids such as Lys and Arg; acetamidomethyl, benzyl (Bn), or tert-butylsulfonyl moieties can be used to protect the sulfide containing side chain of cysteine; bencyl (Bn) ethers can be used to protect the hydroxy containing side chains of serine, threonine or hydroxyproline; and benzyl esters can be used to protect the carboxy containing side chains of aspartic acid and glutamic acid.

When Fmoc is chosen for the α-amine protection, usually tert-butyl based protecting groups are acceptable. For instance, Boc can be used for lysine and arginine, tert-butyl ether for serine, threonine and hydroxyproline, and tert-butyl ester for aspartic acid and glutamic acid. Triphenylmethyl (Trityl) moiety can be used to protect the sulfide containing side chain of cysteine.

Once the elongation of the peptide is completed all of the protecting groups are removed. When a liquid phase synthesis is used, the protecting groups are removed in whatever manner is dictated by the choice of protecting groups. These procedures are well known to those skilled in the art.

Further, the following guidance may be followed in the preparation of compounds of the present invention. For example, to form a compound where $R_4$—C(O)—, $R_4$—S(O)$_2$, a protected P3 or the whole peptide or a peptide segment is coupled to an appropriate acyl chloride or sulfonyl chloride respectively, that is either commercially available or for which the synthesis is well known in the art. In preparing a compound where $R_4$O—C(O)—, a protected P3 or the whole peptide or a peptide segment is coupled to an appropriate chloroformate that is either commercially available or for which the synthesis is well known in the art. For Boc-derivatives (Boc)$_2$O is used.

For example:

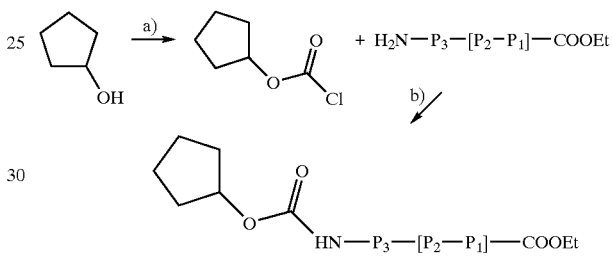

Cyclopentanol is treated with phosgene to furnish the corresponding chloroformate.

The chloroformate is treated with the desired NH$_2$-tripeptide in the presence of a base such as triethylamine to afford the cyclopentylcarbamate.

In preparing a compound where $R_4$—N(R$_5$)—C(O)—, or $R_4$—NH-C(S)—, a protected P3 or the whole peptide or a peptide segment is treated with phosgene followed by amine as described in SynLett. February 1995; (2); 142–144 or is reacted with the commercially available isocyanate and a suitable base such as triethylamine.

In preparing a compound where $R_4$—N(R$_5$)—S(O$_2$), a protected P3 or the whole peptide or a peptide segment is treated with either a freshly prepared or commercially available sulfamyl chloride followed by amine as described in patent Ger. Offen.(1998), 84 pp. DE 19802350 or WO 98/32748.

The α-carboxyl group of the C-terminal residue is usually protected as an ester (CPG) that can be cleaved to give the carboxylic acid. Protecting groups that can be used include: 1) alkyl esters such as methyl, trimethylsilylethyl and t-butyl, 2) aralkyl esters such as benzyl and substituted benzyl, or 3) esters that can be cleaved by mild base treatment or mild reductive means such as trichloroethyl and phenacyl esters.

The resulting α-carboxylic acid (resulting from cleavage by mild acid, mild base treatment or mild reductive means) is coupled with a $R_1SO_2NH_2$ [prepared by treatment of $R_1SO_2Cl$ in ammonia saturated tetrahydrofuran solution] in the presence of peptide coupling agent such as CDI or EDAC in the presence of a base such as 4-dimethylaminopyridine(4-DMAP) and/or 1,8-diazabicyclo[5.4.0]undec-7-ene(DBU) to incorporate the P1' moiety, effectively assembling the tripeptide P1'-P1-P2-P3-APG. Typically, in this process, 1–5 equivalents of P1' coupling agents are used.

Furthermore, if the P3 protecting group APG is removed and replaced with a B moiety by the methods described above, and the resulting α-carboxylic acid resulting from cleavage (resulting from cleavage by mild acid, mild base treatment or mild reductive means) is coupled with a $R_1SO_2NH_2$ [prepared by treatment of $R_1SO_2Cl$ in ammonia saturated tetrahydrofuran solution or alternative methods described herein] in the presence of peptide coupling agent such as CDI or EDAC in the presence of a base such as 4-dimethylaminopyridine(4-DMAP) and/or 1,8-diazabicyclo[5.4.0]undec-7-ene(DBU) to incorporate the P1' moiety, the tripeptide P1'-P1-P2-P3-B is prepared. Typically, in this process, 1–5 equivalents of P1' coupling agents are used.

Compounds of the present invention can be prepared by many methods including those described in the examples, below, and as described in U.S. Pat. No. 6,323,180 and U.S. patent application Ser. No. 10/001,850 filed on Nov. 20, 2001. The teachings of U.S. Pat. No. 6,323,180 and U.S. patent application Ser. No. 10/001,850 are incorporated herein, in their entirety, by reference.

Scheme II further shows the general process wherein compounds of Formula I are constructed by the coupling of tripeptide carboxylic acid intermediate (1) with a P1' sulfonamide. (It should be noted that the groups $R_6$, $R_7$, $R_8$, $R_9$, $R_{10}$, $R_{11}$ as shown below represent substituents of the heterocyclic system.) Said coupling reaction requires treatment of carboxylic acid (1) with a coupling reagent such as carbonyl diimidazole in a solvent such as THF, which can be heated to reflux, followed by the addition of the formed derivative of (1), to the P1' sulfonamide, in a solvent such as THF or methylene chloride in the presence of a base such as DBU.

Scheme II

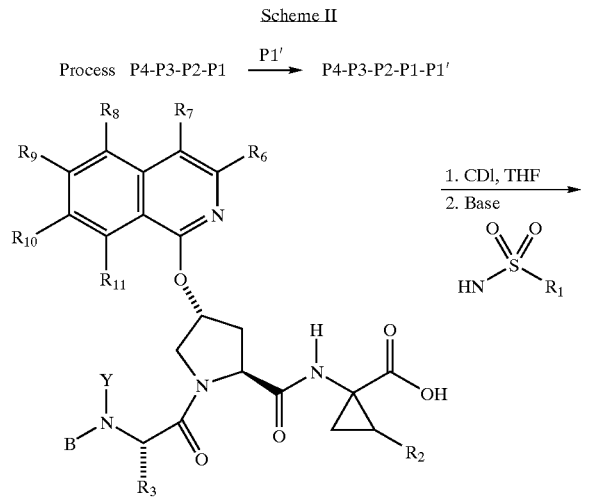

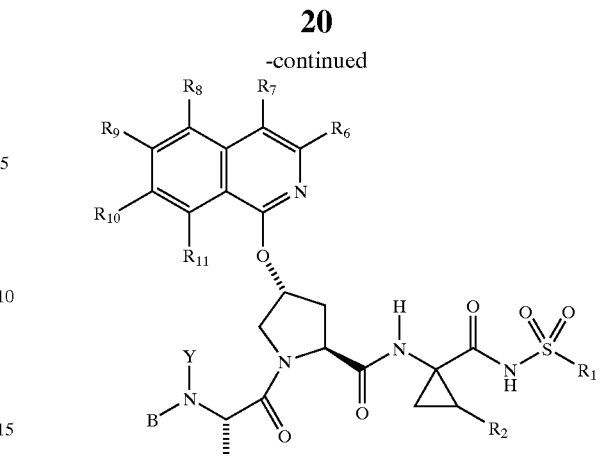

An alternative process for the construction of compounds of Formula I is shown in Scheme III. Therein the P1' sulfonamide element is coupled to the P1 element using the process employed in Scheme 1. The resulting P1-1' moiety can then be deprotected at it's amino terminus. In this general example a Boc protecting group is employed but one skilled in the art would recognize that a number of suitable amino protecting groups could be employed in this process. Said Boc protecting group can be removed using acid such as trifluoroacetic acid in a solvent such as dichloroethane to provide the deprotected amine as the TFA salt. Said TFA amine salt can be directly employed in the subsequent coupling reaction or as an alternative the TFA amine salt can be first converted to the HCl amine salt, and this HCl amine salt is used in said coupling reaction as shown in Scheme III. The coupling of said HCl amine salt (3) with the carboxyl terminus a P4-P3-P2 intermediate can be achieved using coupling reagents, such as HATU, in solvents such as dichloromethane to provide compounds of Formula I (4).

Scheme III

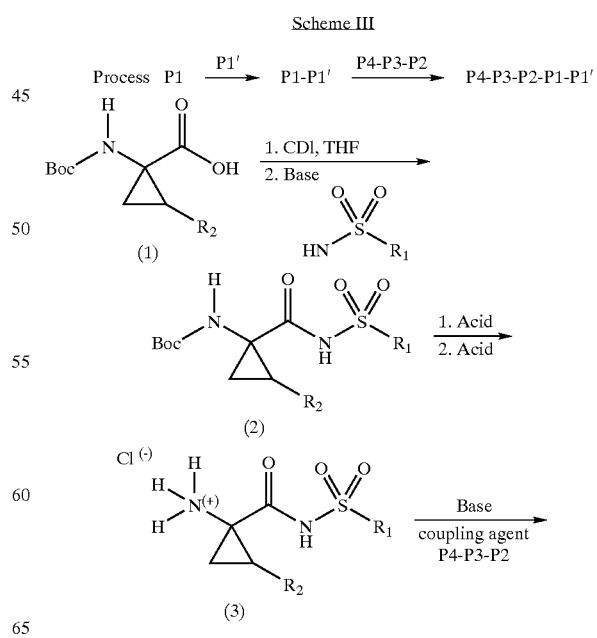

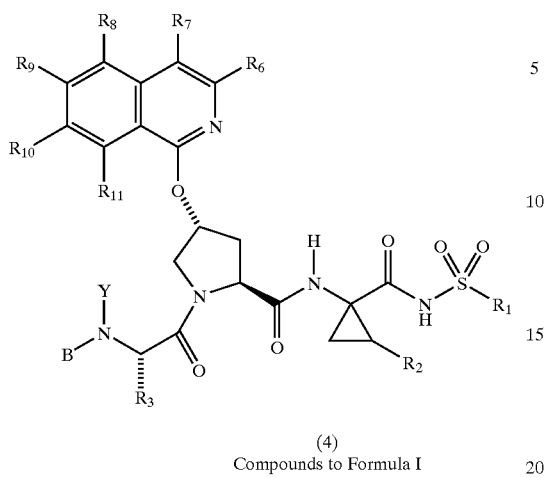

(4)
Compounds to Formula I

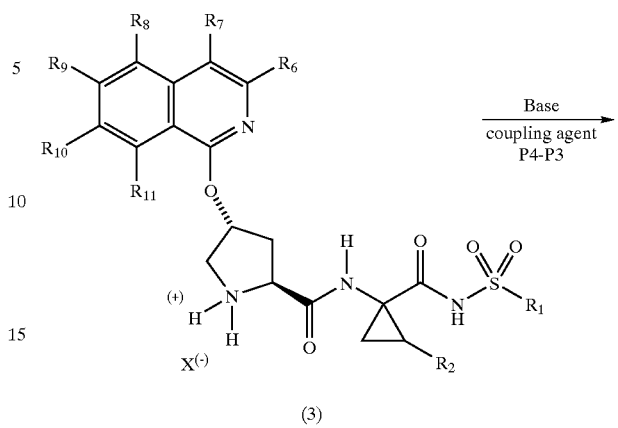

(3)

An alternative process for the construction of compounds of Formula I is shown in Scheme IV. Herein the hydrochloride salt of the P1-P1' terminal amine (1) is coupled to the free carboxyl group of the P2 element using coupling agents such as PyBOP, in the presence of a base such as diisopropyl amine, and in a solvent such as methylene chloride. The resulting P2-P1-P1' intermediate can be converted to compounds of Formula I in a two step process wherein the first step is deprotection of the P2 amine terminus using an acid such as TFA in a solvent such as methylene chloride. The resulting trifluoroacetic acid salt can be coupled with the carboxyl terminus of the P4-P3 element using standard coupling agents such as PyBop in the presence of base such as diisopropyl amine, and using solvents such methylene chloride to provide compounds of Formula I (4).

Scheme IV

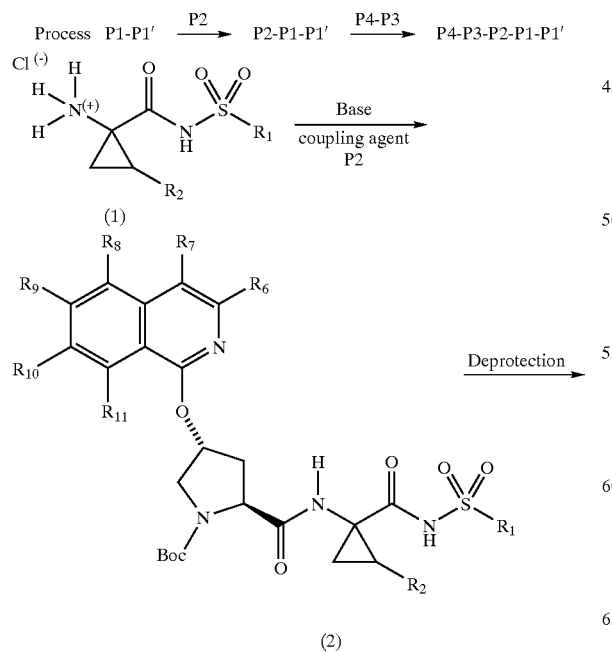

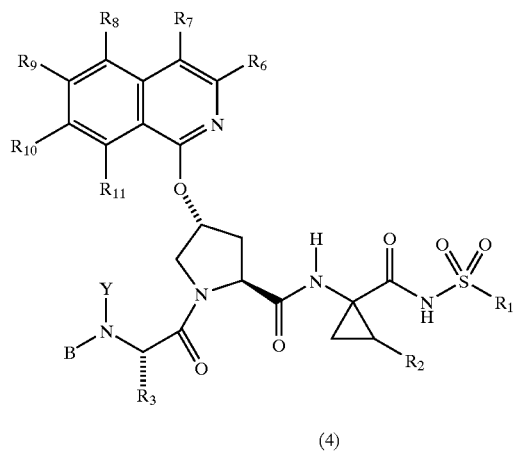

(4)
Compounds to Formula I

The P4-P3-P2 intermediate utilized in the above schemes can be constructed as previously described with a further description of this process shown in general Scheme V. Therein the free carboxyl terminus of the P4-P3 intermediate (1), can be coupled to the amino terminus of the P2 element to provide the P4-P3-P2 dipeptide (2). The carboxyl terminus of the P4-P3-P2 intermediate can be deprotected by saponification of the ester group to provide P4-P3-P2 as the free carboxylic acid (3). Intermediates like (3) can be converted to compounds of Formula I using the methods described herein.

Scheme V

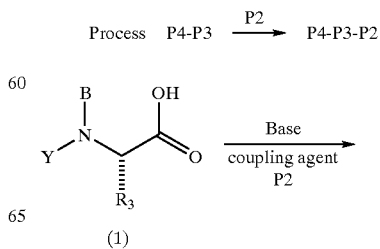

Scheme VI

Process  P4-P3-P2-P1-P1' → P3-P2-P1-P1' → P4-P3-P2-P1-P1'

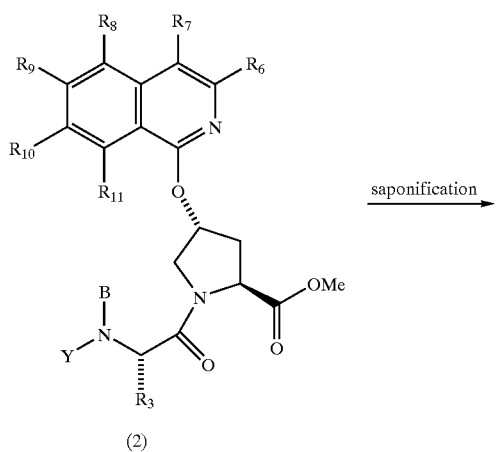

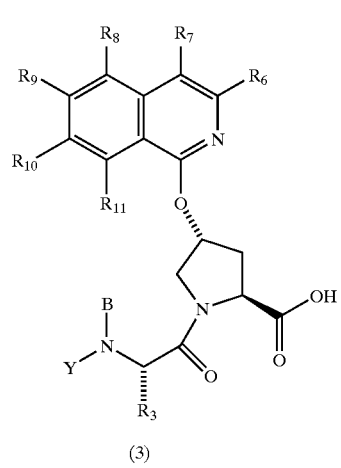

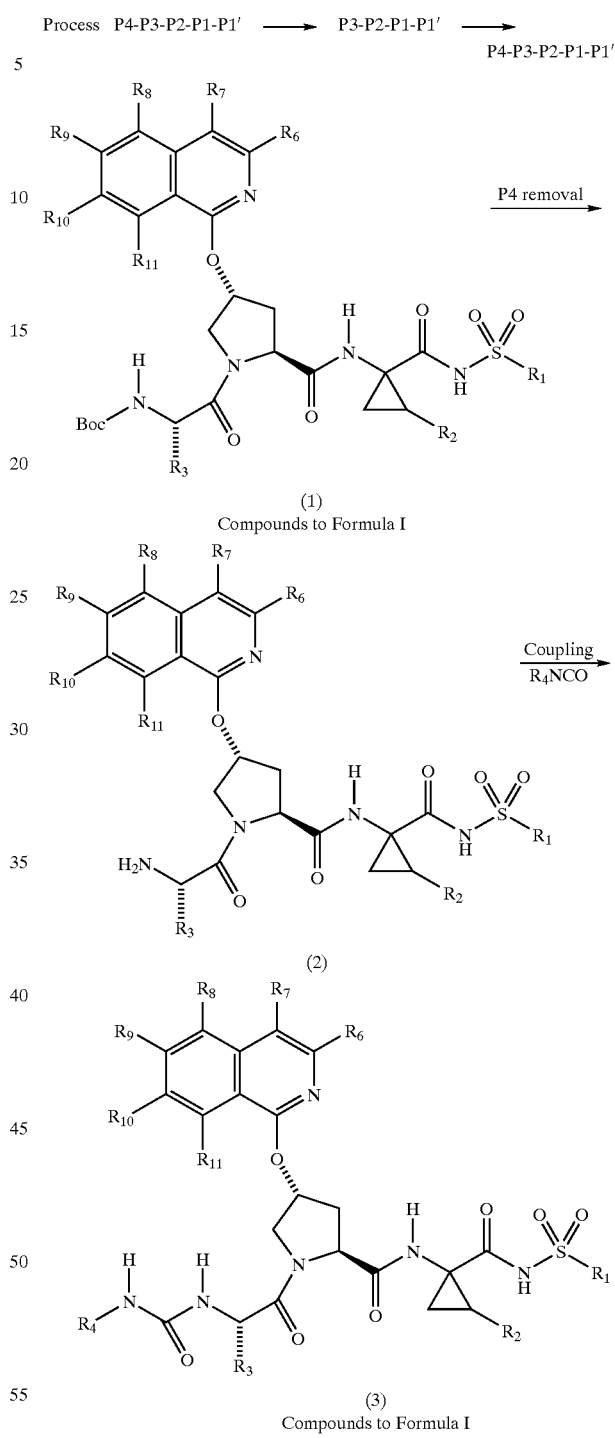

Compounds of Formula I can also be converted into other compounds of Formula I as described herein. An example of such a process is shown in Scheme VI wherein a compound of Formula I (1) which bears a Boc group at the P4 position is converted in a compound of Formula I (3) wherein said compound bears a urea group at the P4 position. The conversion of (1) to (3) can be carried out in a two step process the first of which is the conversion of (1) to amine (2) by treatment of (1) with an acid such as TFA in a solvent such as methylene chloride. The resulting amine TFA salt can be treated with an isocyanate in the presence of one equivalent of base to provide a compound of Formula I (3) wherein the P3 moiety is capped with a urea. As previously noted one skilled in the art will recognize that intermediate (2) can be used as starting materials for the preparation of compounds of Formula I wherein the P3 group is capped with an amide or a sulfonamide, or thiourea, or a sulfamide. The construction of said compounds of Formula I can be achieved using standard conditions for the formation of said P4 functionalities from amines.

In the construction of compounds of Formula I, the P1' terminus is incorporated into the molecules using one of the general processes outlined above and described in more detail below. In some examples the P1' elements, that is the cycloalkyl- or alkyl sulfonamides are commercially available or can be prepared from the corresponding alkyl- or cycloalkyl-sulfonyl chloride by treating said sulfonyl chloride with ammonia. Alternatively, these sulfonamides can be synthesized using the general process outline in Scheme VII.

Therein commercially available 3-chloro-propylsulfonyl chloride (1) is converted to a suitable protected sulfonamide as for example by treatment with tert-butyl amine. The sulfonamide obtained (2) is then converted to the corresponding cycloalkylsulfonamide by treatment with two equivalents of a base such as butyl lithium in a solvent such as THF at low temperature. The resulting cycloalkylsulfonamide can be deprotected by treatment with an acid to provide the desired unprotected cycloalkylsulfoamide.

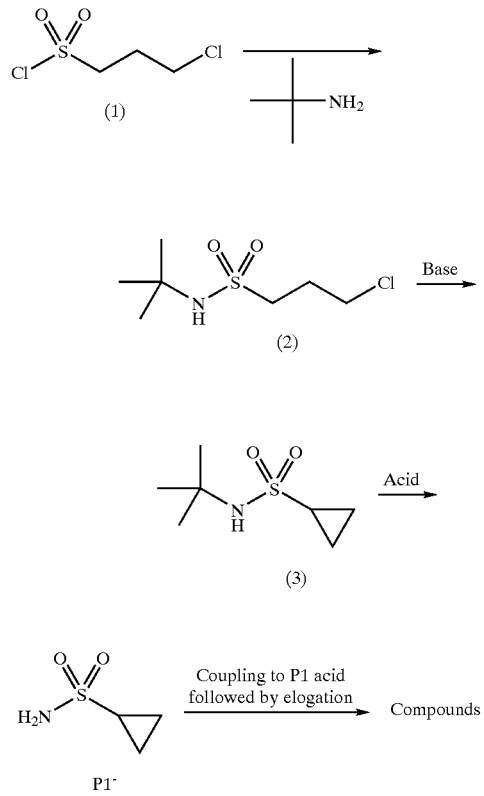

Scheme VII

The P1 elements utilized in generating compounds of Formula I are in some cases commercially available, but are otherwise synthesized using the methods described herein and subsequently incorporated into compounds of Formula I using the methods described herein. The substituted P1 cyclopropylamino acids can be synthesized following the general process outline in Scheme VIII.

Treatment of commercially available or easily synthesized imine (1) with 1,4-dihalobutene (2) in presence of a base produces, provides the resulting imine (3). Acid hydrolysis of 3 then provides 4, which has an allyl substituent syn to the carboxyl group as a major product. The amine moiety of 4 can protected using a Boc group to provide the fully protected amino acid 5. This intermediate is a racemate which can be resolved by an enzymatic process wherein the ester moiety of 5 is cleaved by a protease to provide the corresponding carboxylic acid. Without being bound to any particular theory, it is believed that this reaction is selective in that one of the enantiomers undergoes the reaction at a much greater rate than its mirror image providing for a kinetic resolution of the intermediate racemate. In the examples cited herein, the more preferred stereoisomer for integration into compounds of Formula I is 5a which houses the (1R, 2S) stereochemistry. In the presence of the enzyme, this enantiomer does not undergo ester cleavage and thereby this enantiomer 5a is recovered from the reaction mixture. However, the less preferred enantiomer, 5b with houses the (1S, 2R) stereochemistry undergoes ester cleavage, i.e., hydrolysis, to provide the free acid 6. Upon completion of this reaction, the ester 5a can be separated from the acid product 6 by routine methods such as, for example, aqueous extraction methods or chromatography.

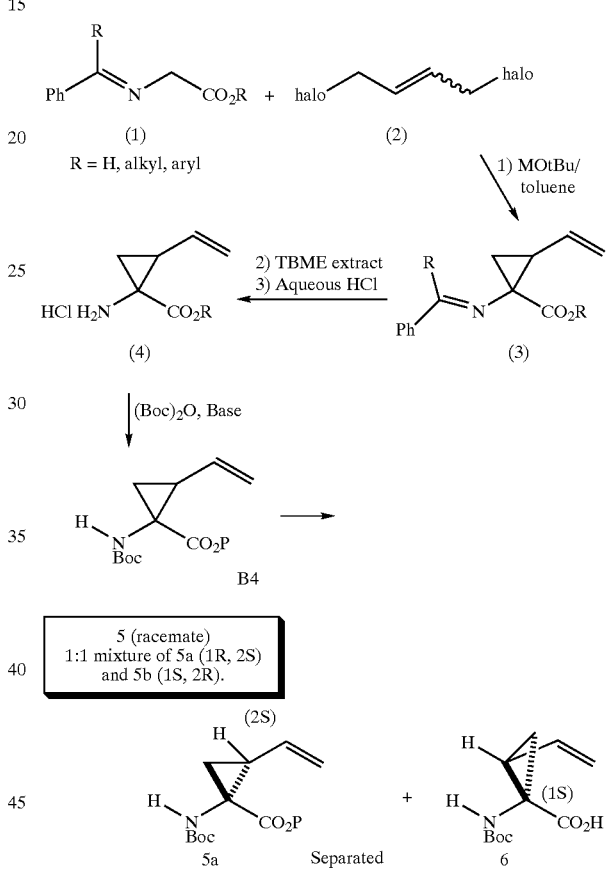

Scheme VIII

Procedures for making P2 intermediates and compounds of Formula I are shown in the Schemes below. It should be noted that in many cases reactions are depicted for only one position of an intermediate. However, it is to be understood that such reactions could be used to impart modifications to other positions within this intermediate. Moreover, said intermediates, reaction conditions and methods given in the specific examples are broadly applicable to compounds with other substitution patterns. The general Schemes outlined below are followed with examples herein. Both general and specific examples are non-limiting, as for example the isoquinoline nucleus is shown as part of the general scheme, Scheme IX, however, this pathway represents a viable process for the construction of alternate heterocycle substituents as replacements for the isoquinoline element, such as quinolines, or pyridines.

Scheme IX

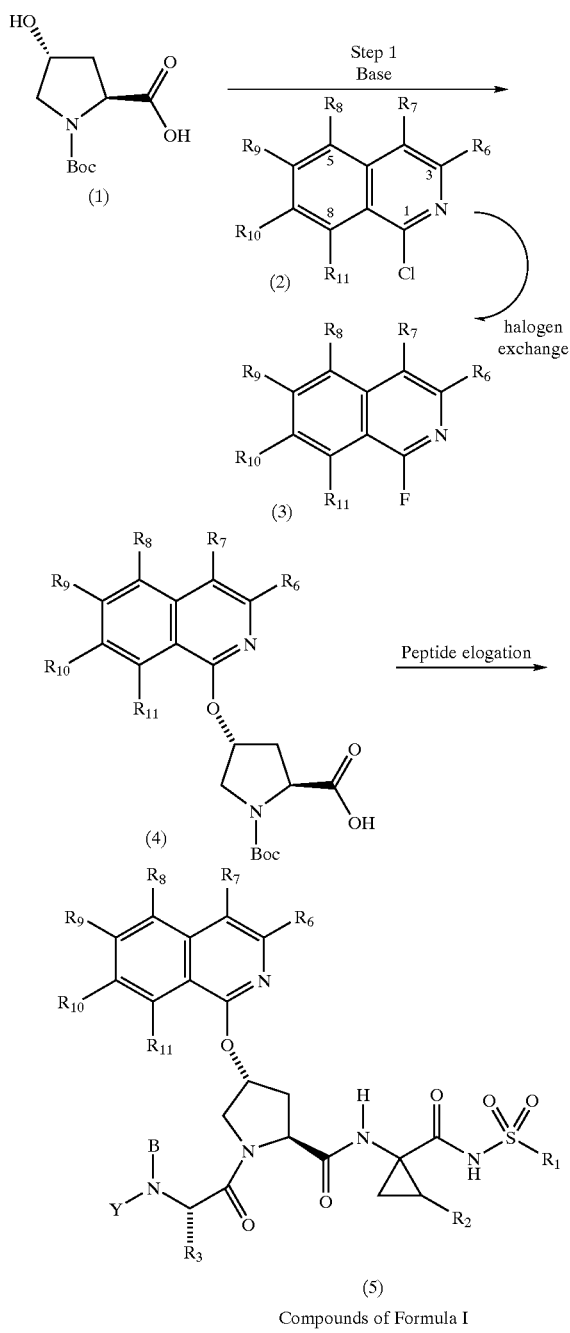

Compounds of Formula I

Scheme IX shows the coupling of an N-protected C4-hydroxyproline moiety with a heterocycle to form intermediate (4) and the subsequent modification of said intermediate (4) to a compound of Formula I by the process of peptide elongation as described herein. It should be noted that in the first step, that is the coupling of the C4-hydroxy proline group with the heteroaryl element, a base is employed. One skilled in the art would recognized that this coupling can be done using bases such as potassium tert-butoxide, or sodium hydride, in solvent such as DMF or DMSO or THF. This coupling to the isoquinoline ring system occurs at the C1 position (numbering for isoquinoline ring system shown in intermediate 2 of Scheme IX) and is directed by the chloro group which is displaced in this process. It should be noted that the alternative leaving groups can be utilized at this position such as a fluoro as shown in the Scheme. Said fluoro intermediates (3) are available from the corresponding chloro compound using literature procedures described herein. It should also be noted that the position of the leaving group (chloro or fluoro) in a given ring system can vary as shown in Scheme X, wherein the leaving group (fluoro in this example) is in the C6 position of the isoquinoline ring system of intermediate (2).

Scheme X

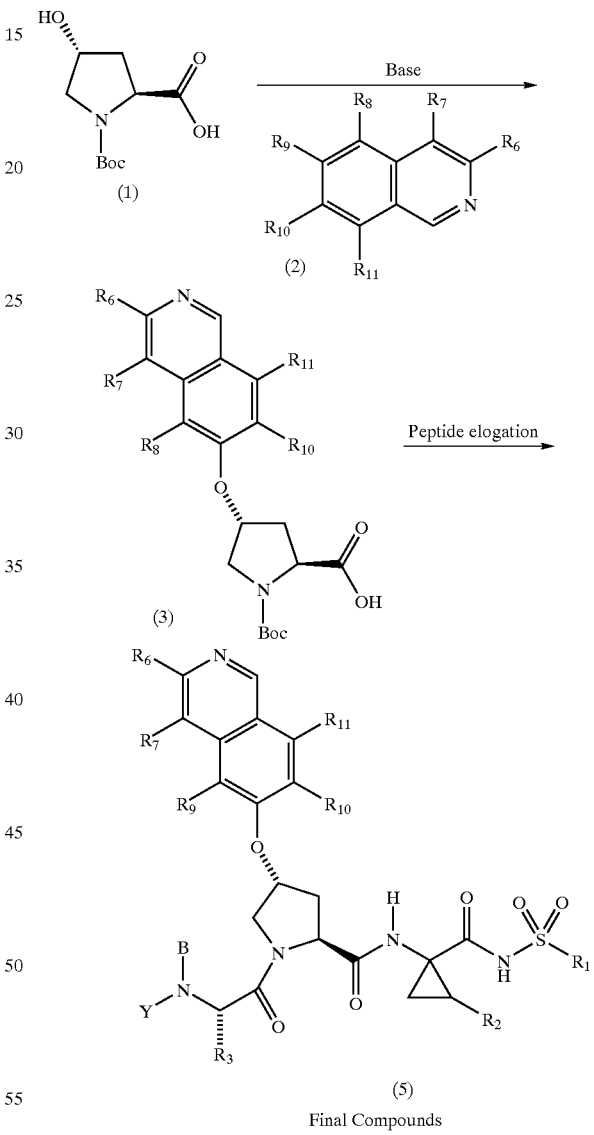

Final Compounds

It should be further noted that the position of the ring heteroatom(s) in intermediates like (2) of Scheme 1x and Scheme X is also variable, as defined by the term heterocycle described herein. In Scheme X intermediate (2) can be coupled to a C4 hydroxy proline derivative to provide the P2 element (3). This C6-substituted isoquinoline derivative can be converted to compounds of Formula I using the methods described herein.

An alternative to the method described above for the coupling of the C4-hydroxyproline to aromatics and heteroaromatics, is provided in the Mitsunobu reaction as depicted in

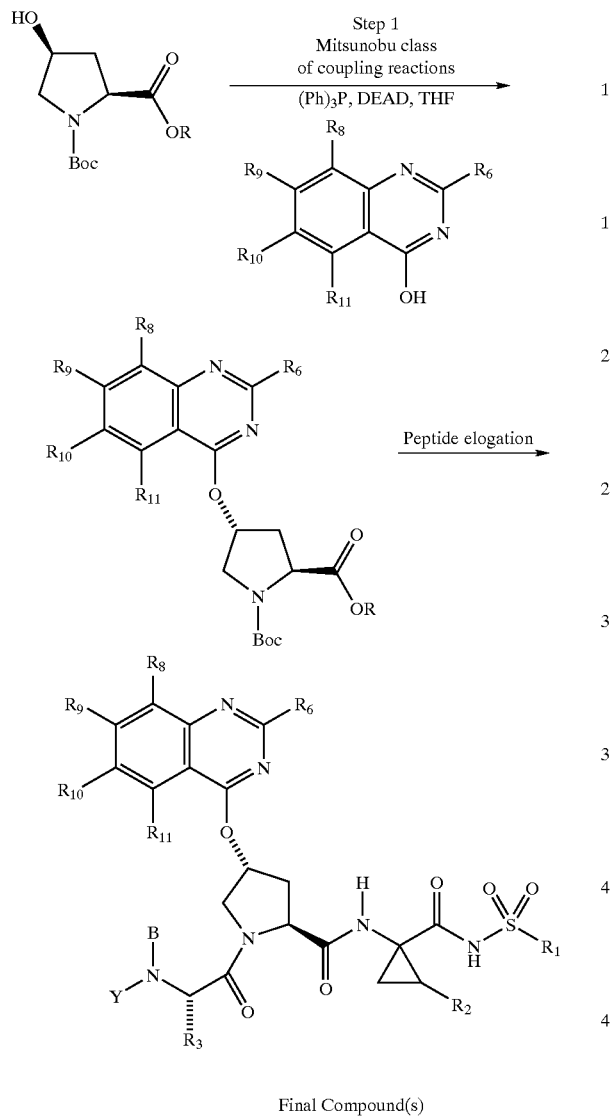

Scheme XI

Final Compound(s)

step 1 of Scheme XI. In this general reaction Scheme a C4-hydroxy proline derivative is coupled to a quinazoline ring system. This reaction makes use of reagents such as triphenylphosphine and DEAD (diethylazodicarboxylate) in aprotic solvents such as THF or dioxane and can be used for the formation of aryl and heteroaryl ethers. Note that in the course of this coupling reaction the stereochemistry of the C4 chiral center in the C4-hydroxyproline derivative is inverted and thereby it is necessary to use the C4-hydroxyproline derivative housing the (S) stereochemistry at the C4 position as starting material. (as shown in Scheme XI). It should be noted that numerous modifications and improvements of the Mitsunobu reaction have been described in the literature, the teachings of which are incorporated herein.

In a subset of examples herein, isoquinolines are incorporated into the final compounds and specifically into the P2 region of said compounds. One skilled in the art would recognize that a number of general methods are available for the synthesis of isoquinolines. Moreoever, said isoquinolines generated by these methods can be readily incorporated into final compounds of Formula I using the processes described herein. One general methodology for the synthesis of isoquinolines is shown in Scheme XII, wherein cinnamic acid derivatives, shown in general form as structure (2) are

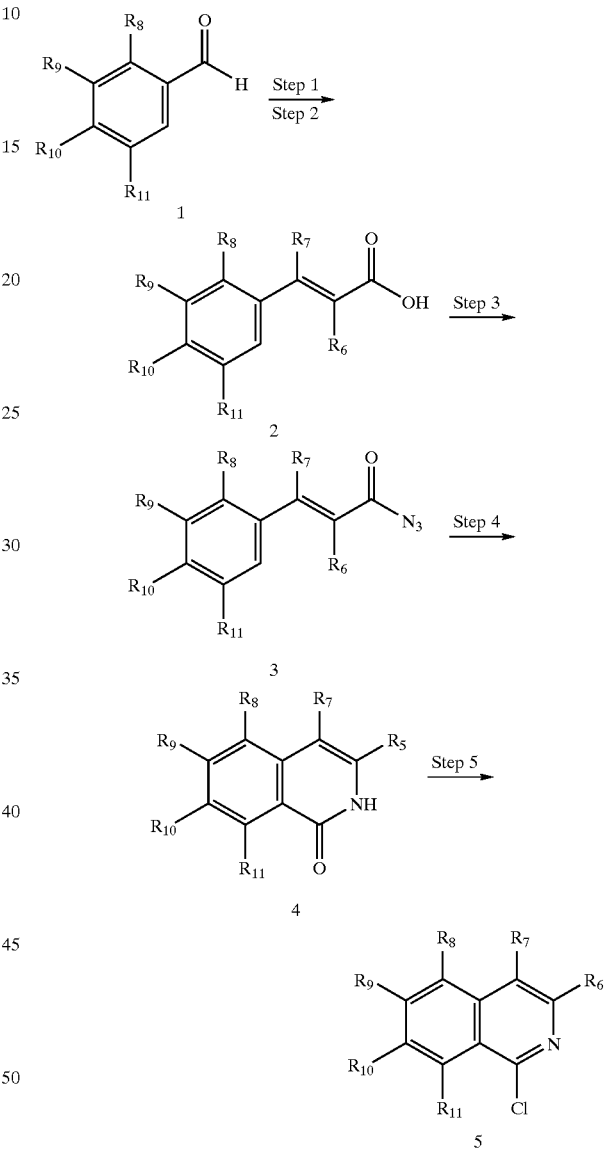

Scheme XII

Reference: N. Briet at al, Tetrahedron, 2002, 5761 converted to 1-chloroisoquinolines in a four step process. Said chloroisoquinolines can be subsequently used in coupling reactions to C4-hydroxyproline derivatives as described herein. The conversion of cinnamic acids to chloroquinolines begins with the treatment of cinnamic acid with an alkylcholorformate in the presence of a base. The resulting anhydride is then treated with sodium azide which results in the formation of an acylazide (3) as shown in the Scheme. Alternate methods are available for the formation of acylazides from carboxylic acids as for example said carboxylic acid can be treated with diphenylphosphorylazide (DPPA) in an aprotic solvent such as methylene chloride in the presence of a base. In the next step of the reaction sequence the acylazide (3) is coverted to the corresponding isoquinolone (4) as shown in the Scheme. In the event the acylazide is heated to a temperature of approximately 190 degress celcius in a high boiling solvent such a diphenylmethane. This reaction is general and provides moderate to good yields of substituted isoquinolone from the corresponding cinnamic acid derivatives. It should noted that said cinnamic acid derivatives are available commercially or can be obtained from the corresponding benzaldehyde (1) derivative by direct condensation with malonic acid or derivatives thereof and also by employing a Wittig reaction. The intermediate isoquinolones (4) of Scheme XII can be converted to the corresponding 1-chloroisoquinoline by treatment with phosphorous oxychloride. This reaction is general and can be applied to any of the isoquinolones, quinolones or additional heterocycles as shown herein to covert a hydroxy substituent to the corresponding chloro compound when said hydroxy is in conjugation with a nitrogen atom in said heterocylic ring systems.

An alternative method for the synthesis of the isoquinoline ring system is the Pomeranz-Fritsch procedure. This general method is outlined in Scheme XIII. The process begins with the conversion of a benzaldehyde derivative (1) to a functionalized imine (2). Said imine is then converted to the isoquinoline ring system by treatment with acid at elevated Scheme XIII

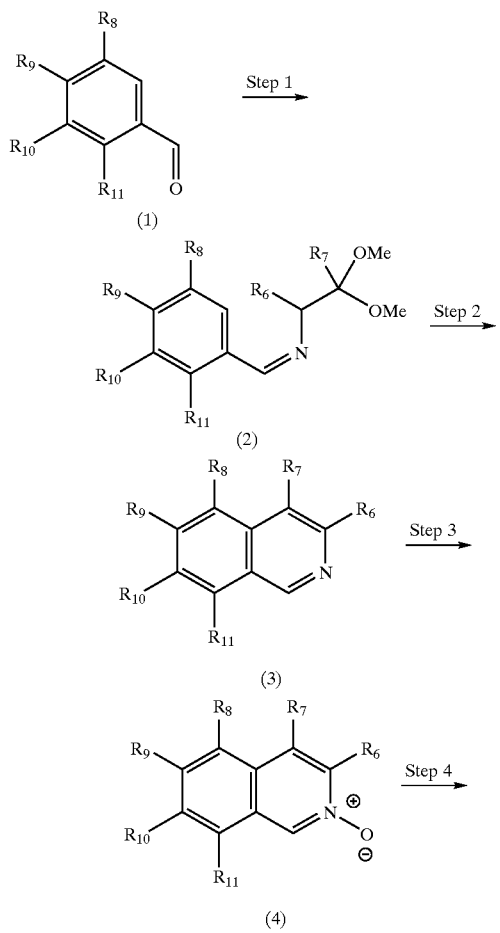

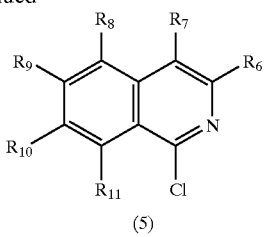

Pomeranz-Fritsch synthesis
K. Hirao, R. Tsuchiya, Y. Yano, H. Tsue, Heterocycles 42(1) 1996, 415-422 temperature. This isoquinoline synthesis of Scheme XIII is general, and it should be noted that this process is particularly useful in procuring isoquinoline intermediates that are substituted at the C8 position (note: in intermediate (3) of Scheme XIII the C8 position of the isoquinoline ring is substituted with substutuent $R_{11}$). The intermediate isoquinolines (3) can be converted to the corresponding 1-chloroquinolines (5) in a two step process as shown. The first step in this sequence is the formation of the isoquinoline N-oxide(4) by treatment of isoquinoline (3) with meta-chloroperbenzoic acid in an aprotic solvent such as dichloromethane. Intermediate (4) can be converted to the corresponding 1-chloroquinoline by treatment with phosphorous oxychloroide in refluxing chloroform. Note this two step process is general and can be employed to procure chloroisoquinolines and chloroquinolines from the corresponding isoquinolines and quinolines respectively.

Another method for the synthesis of the isoquinoline ring system is shown in Scheme XIV. In this process an ortho-alkylbenzamide derivative (1) is treated with a strong Scheme XIV

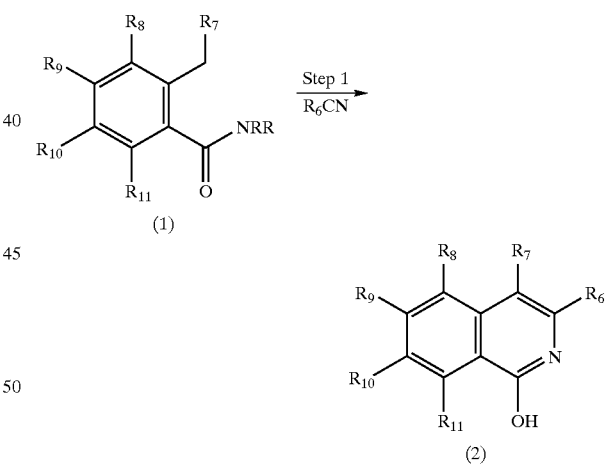

base such as tert-butyl lithium in a solvent such as THF at low temperature. To this reaction mixture is then added a nitrile derivative, which undergoes an addition reaction with the anion derived from deprotonation of (1), resulting in the formation of (2). This reaction is general and can be used for the formation of substituted isoquinolines. Intermediate (2) of Scheme XIV can be converted to the corresponding 1-chloroquinoline by the methods described herein.

An additional method for the synthesis of isoquinolines is shown in Scheme XV. The deprotonation of intermediate (1) using tert-butyl lithium is described above. In the present method however, said intermediate anion is trapped by an ester, resulting in the formation of intermediate (2) as shown below. In a subsequent reaction ketone (2) is condensed with ammonium acetate at elevated temperature providing for the formation of quinolone (3). This reaction is general and can be applied for the construction of substituted isoquinolones which can then be converted to the corresponding 1-chloroisoquinolines as described herein.

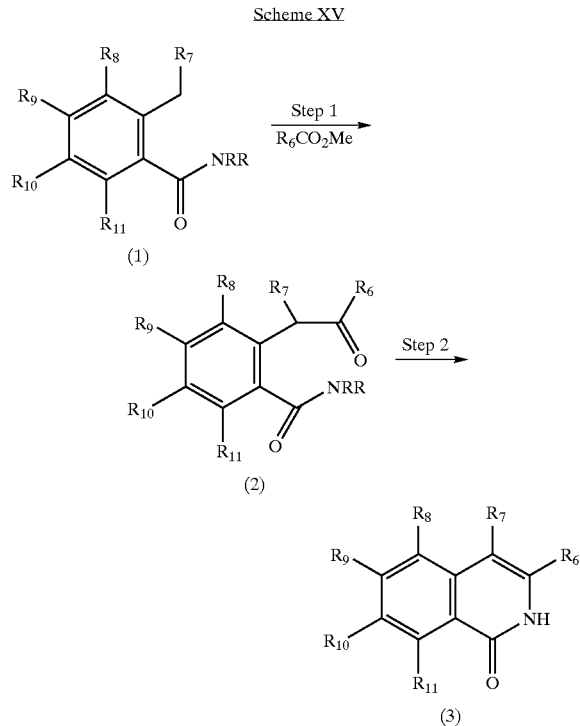

Yet an additional method for the construction of isoquinolines is found in Scheme XVI. In the first step of this process an ortho-alkylarylimine derivatives such as (1) is subjected to deprotonation conditions (sec-butyl lithium, THF) and the resulting anion is quenched by

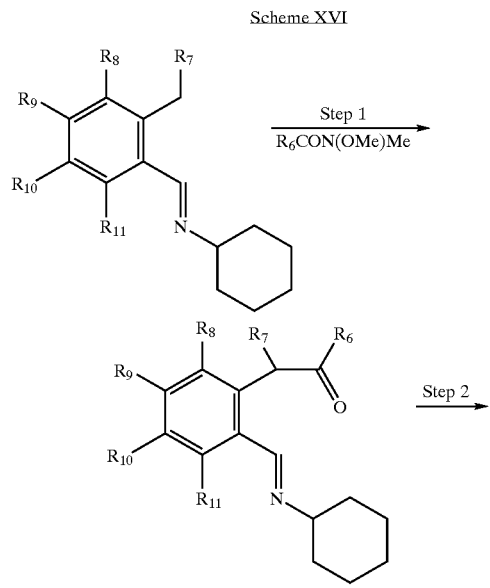

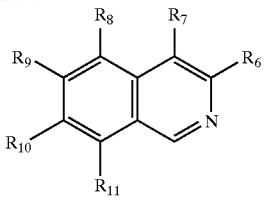

L. Flippin, J. Muchowski, JOC, 1993, 2631–2632 the addition of an activated carboxylic acid derivative such as a Weinreb amide. The resulting keto imine (2) can be converted to the corresponding isoquinoline by condensation with ammonium acetate at elevated temperatures. This method is general and can be used for the synthesis of substituted isoquinolines. Said isoquinolines can be converted to the corresponding 1-chloroquinoline by the methods described herein.

The heterocycles described herein, and which are incorporated into the compounds of Formula I can be further functionalized. It is obvious to one skilled in the art that additional functionalization of said heterocycles can be done either before or after incorporation of these functionalities into compounds of Formula I. The following Schemes illustrate this point. For example Scheme XVII shows the conversion of a 1-chloro-

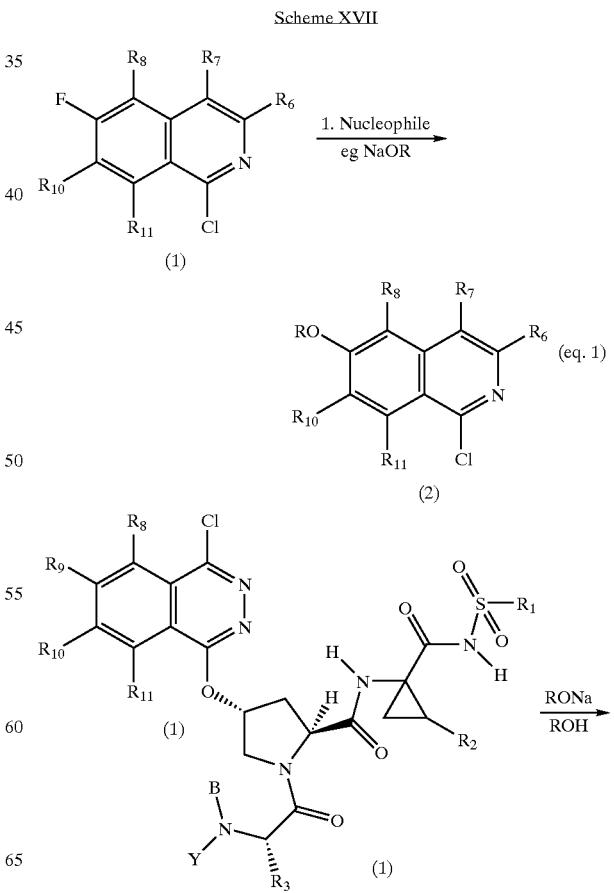

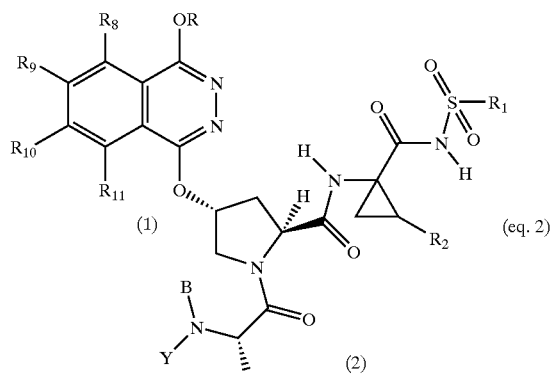

6-fluoro-isoquinoline to the corresponding 1-chloro-6-alkoxy-isoquinoline species, by treatment of (1) of (eq.1) with a sodium or potassium alkoxide species in the alcohol solvent from which the alkoxide is derived at room temperature. In some cases it may be necessary to heat the reaction to drive it to completion. Said chloroquinoline can be incorporated into a compound of Formula I using the art described herein. Modifications of a P2 heterocyclic element can also be done after it's incorporation into compounds of Formula I as shown in (eq.2) of Scheme VXII. Specifically compounds such as (1) in (eq. 2) which contain a leaving group in the pthalazine nucleus can be displaced by a nucleophile such as an alkoxide in solvents such as the corresponding alcohol from which the alkoxide is derived. These reaction scan be conducted at room temperature but in some cases it may be necessary to heat the reaction to drive it to completion.

Scheme XVIII provides a general example for the modification of heterocycles as defined herein by employing palladium mediated coupling reactions. Said couplings can be employed to functionalize a heterocycle at each position of the ring system providing said ring is suitably activated or functionalized, as for example with a chloride as shown in the Scheme. This sequence begins with 1-chloroisoquinoline (1) which upon treatment with metachloroperbenzoic acid can be converted to the corresponding N-oxide (2). Said intermediate (2) can be converted to the corresponding 1,3-dichloroisoquinoline (3) by treatment with phosphorous oxychloride in refluxing chloroform. Intermediate (3) can be coupled with N-Boc-4-hydroxyproline by the methods described herein to provide intermediate (5) as shown in the Scheme. Intermediate (5) can undergo a Suzuki coupling with an aryl boronic acid, in the presence of a palladium reagent and base, and in a solvent such as THF or toluene or DMF to provide the C3-arylisoquinoline intermediate (6).

Heteroarylboronic acids can also be employed in this Pd mediated coupling process to provide C3-heteroarylisoquinolines. Intermediate (6) can be converted into final compounds of Formula I by the methods described herein.

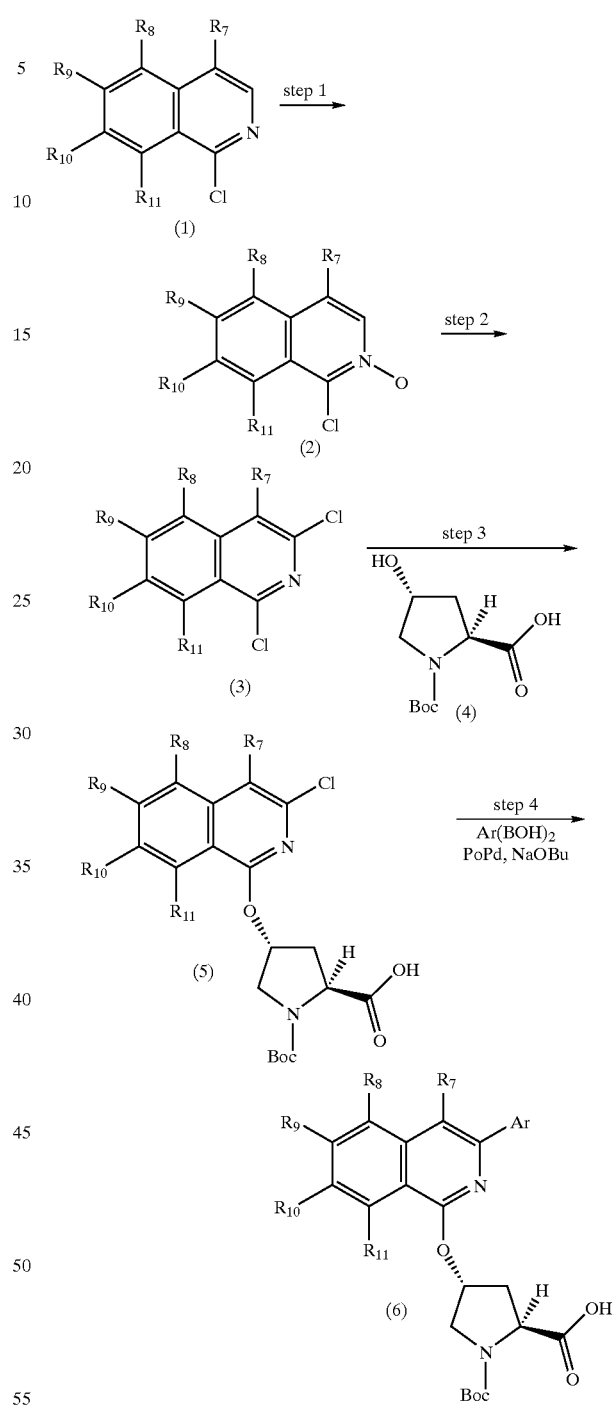

Palladium mediated couplings of heteroaryl systems with aryl or heteroaryl elements can also be employed at a later synthetic stage in the construction of compounds of Formula I as shown in Scheme IXX. Therein tripeptide acylsulfonamide intermediate (1) is coupled to a 1-chloro-3-bromoisoquinoline (2) using the previously described process of alkoxide displacement of an heteroarylhalo moiety to provide intermediate (3). The coupling of (1) and (2) is most efficient in the presence of a catalyst such as lanthanum chloride as described herein. The isoquinoline ring system of intermediate (3) can be further functionalized by employing either Suzuki couplings (Process 1: subjecting (3) to heteroaryl or aryl boronic acids in the presence of a palladium catalyst such as palladium tetra(triphenylphosphine) and a base such as cesium carbonate in solvents such as DMF) or Stille couplings (Process 2: subjecting (3) to heteraryl or aryl tin dervatives in the presence of palladium catalyst such as palladium tetra(triphenylphosphine in solvents such as toluene).

Scheme IXX

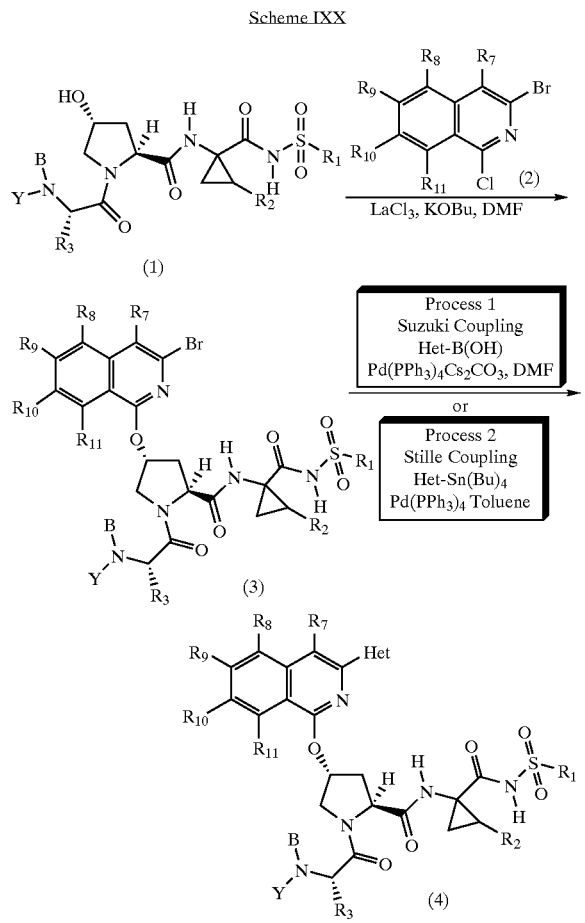

Palladium reactions can also be employed to couple C4-amino proline elements with functionalized heterocycles. Scheme XX shows intermediate (1) coupling with a functionalized isoquinoline in the presence of a palladium catalyst and a base in a solvent such as toluene. Intermediates like (3) can be converted to compounds of Formula I using the methods described herein.

Scheme XX

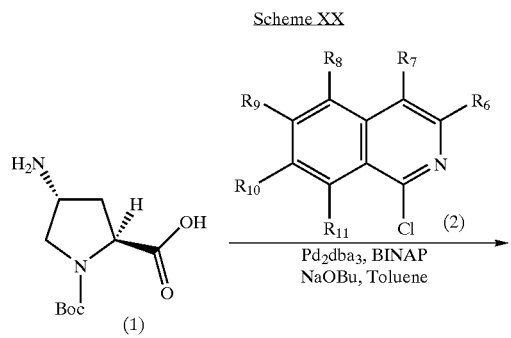

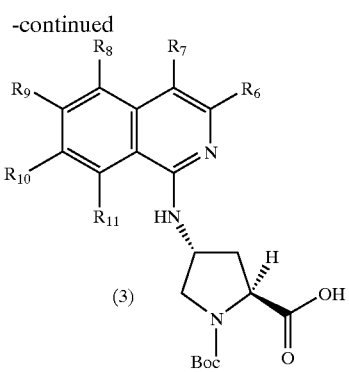

The construction of functionalized isoquinoline ring systems is also possible employing [4+2] cycloaddition reactions. For example (Scheme XXI) the use of vinyl isocyantes (1) in cycloaddition reactions with benzyne precusors (2) provides functionalized isoquinolones (3). Said isoquinolines can be incorporated into compounds of Formula I using the methods described herein.

Scheme XXI

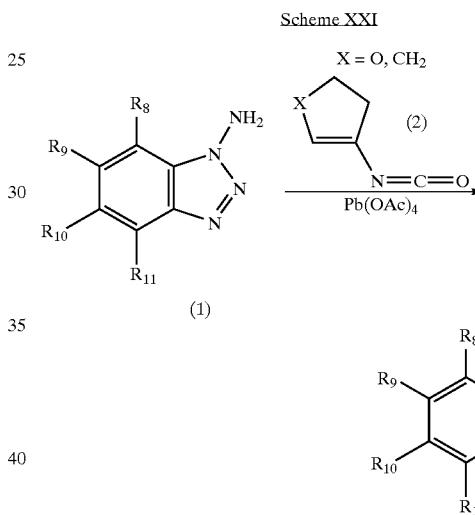

The present invention also provides compositions comprising a compound of the present invention, or a pharmaceutically acceptable salt, solvate or prodrug thereof, and a pharmaceutically acceptable carrier. Pharmaceutical compositions of the present invention comprise a therapeutically effective amount of a compound of the invention, or a pharmaceutically acceptable salt, solvate or prodrug thereof, and a pharmaceutically acceptable carrier, with a pharmaceutically acceptable carrier, e.g., excipient, or vehicle diluent.

The active ingredient, i.e., compound, in such compositions typically comprises from 0.1 weight percent to 99.9 percent by weight of the composition, and often comprises from about 5 to 95 weight percent.

The pharmaceutical compositions of this invention may be administered orally, parenterally or via an implanted reservoir. Oral administration or administration by injection are preferred. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intra-articular, intrasynovial, intrasternal, intrathecal, and intralesional injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents and suspending agents. The details concerning the preparation of such compounds are known to those skilled in the art.

When orally administered, the pharmaceutical compositions of this invention may be administered in any orally acceptable dosage form including, but not limited to, capsules, tablets, and aqueous suspensions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavoring and/or coloring agents may be added.

Other suitable carriers for the above noted compositions can be found in standard pharmaceutical texts, e.g. in "Remington's Pharmaceutical Sciences", 19 th ed., Mack Publishing Company, Easton, Penn., 1995. Further details concerning the design and preparation of suitable delivery forms of the pharmaceutical compositions of the invention are known to those skilled in the art.

Dosage levels of between about 0.01 and about 1000 milligram per kilogram ("mg/kg") body weight per day, preferably between about 0.5 and about 250 mg/kg body weight per day of the compounds of the invention are typical in a monotherapy for the prevention and treatment of HCV mediated disease. Typically, the pharmaceutical compositions of this invention will be administered from about 1 to about 5 times per day or alternatively, as a continuous infusion. Such administration can be used as a chronic or acute therapy. The amount of active ingredient that may be combined with the carrier materials to produce a single dosage form will vary depending upon the host treated and the particular mode of administration.

As the skilled artisan will appreciate, lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the infection, the patient's disposition to the infection and the judgment of the treating physician. Generally, treatment is initiated with small dosages substantially less than the optimum dose of the peptide. Thereafter, the dosage is increased by small increments until the optimum effect under the circumstances is reached. In general, the compound is most desirably administered at a concentration level that will generally afford antivirally effective results without causing any harmful or deleterious side effects.

When the compositions of this invention comprise a combination of a compound of the invention and one or more additional therapeutic or prophylactic agent, both the compound and the additional agent are usually present at dosage levels of between about 10 to 100%, and more preferably between about 10 and 80% of the dosage normally administered in a monotherapy regimen.

When these compounds or their pharmaceutically acceptable salts, solvates or prodrugs are formulated together with a pharmaceutically acceptable carrier, the resulting composition may be administered in vivo to mammals, such as man, to inhibit HCV NS3 protease or to treat or prevent HCV virus infection. Such treatment may also-be achieved using the compounds of this invention in combination with agents which include, but are not limited to: immunomodulatory agents, such as interferons; other antiviral agents such as ribavirin, amantadine; other inhibitors of HCV NS3 protease; inhibitors of other targets in the HCV life cycle such as helicase, polymerase, metalloprotease, or internal ribosome entry site; or combinations thereof. The additional agents may be combined with the compounds of this invention to create a single dosage form. Alternatively these additional agents may be separately administered to a mammal as part of a multiple dosage form.

Accordingly, another aspect of this invention provides methods of inhibiting HVC NS3 protease activity in patients by administering a compound of the present invention or a pharmaceutically acceptable salt or solvate thereof, wherein the substituents are as defined above.

In a preferred embodiment, these methods are useful in decreasing HCV NS3 protease activity in the patient. If the pharmaceutical composition comprises only a compound of this invention as the active component, such methods may additionally comprise the step of administering to said patient an agent selected from an immunomodulatory agent, an antiviral agent, a HCV protease inhibitor, or an inhibitor of other targets in the HCV life cycle such as, for example, helicase, polymerase, or metalloprotease. Such additional agent may be administered to the patient prior to, concurrently with, or following the administration of the compounds of this invention.

In an alternate preferred aspect, these methods are useful for inhibiting viral replication in a patient. Such methods can be useful in treating or preventing HCV disease.

The compounds of the invention may also be used as laboratory reagents. Compounds may be instrumental in providing research tools for designing of viral replication assays, validation of animal assay systems and structural biology studies to further enhance knowledge of the HCV disease mechanisms.

The compounds of this invention may also be used to treat or prevent viral contamination of materials and therefore reduce the risk of viral infection of laboratory or medical personnel or patients who come in contact with such materials, e.g., blood, tissue, surgical instruments and garments, laboratory instruments and garments, and blood collection or transfusion apparatuses and materials.

EXAMPLES

The specific examples that follow illustrate the syntheses of the compounds of the instant invention, and are not to be construed as limiting the invention in sphere or scope. The methods may be adapted to variations in order to produce compounds embraced by this invention but not specifically disclosed. Further, variations of the methods to produce the same compounds in somewhat different manner will also be evident to one skilled in the art.

Solution percentages express a weight to volume relationship, and solution ratios express a volume to volume relationship, unless stated otherwise. Nuclear magnetic resonance (NMR) spectra were recorded either on a Bruker 300, 400 or 500 MHz spectrometer; the chemical shifts ($\delta$) are reported in parts per million. Flash chromatography was carried out on silica gel ($SiO_2$) according to Still's flash chromatography technique (W. C. Still et al., J. Org. Chem., (1978), 43, 2923).

All Liquid Chromatography (LC) data were recorded on a Shimadzu LC-10AS liquid chromatograph using a SPD- 10AV UV-Vis detector and Mass Spectrometry (MS) data were determined with a Micromass Platform for LC in electrospray mode (ES+).

Unless otherwise noted, in the following examples each compound was analyzed by LC/MS, using one of seven methodologies, having the following conditions.

Columns: (Method A)—YMC ODS S7 C18 3.0×50 mm
    (Method B)—YMC ODS-A S7 C18 3.0×50 mm
    (Method C)—YMC S7 C18 3.0×50 mm
    (Method D)—YMC Xterra ODS S7 3.0×50 mm
    (Method E)—YMC Xterra ODS S7 3.0×50 mm
    (Method F)—YMC ODS-A S7 C 18 3.0×50 mm
    (Method G)—YMC C18 S5 4.6×50 mm
Gradient: 100% Solvent A/0% Solvent B to
0% Solvent A/100% Solvent B
Gradient time: 2 min. (A, B, D, F, G); 8 min. (C, E)
Hold time: 1 min. (A, B, D, F, G); 2 min. (C, E)
Flow rate: 5 mL/min
Detector Wavelength: 220 nm
Solvent A: 10% MeOH/90% $H_2O$/0.1% TFA
Solvent B: 10% $H_2O$/90% MeOH/0.1% TFA.

The abbreviations used in the present application, including particularly in the illustrative examples which follow, are well-known to those skilled in the art. Some of the abbreviations used are as follows:

| | |
|---|---|
| rt | room temperature |
| Boc | tert-butyloxycarbonyl |
| DMSO | dimethylsulfoxide |
| EtOAc | ethyl acetate |
| t-BuOK | potassium t-butoxide |
| $Et_2O$ | diethyl ether |
| TBME | tert-butylmethyl ether |
| THF | tetrahydrofuran |
| CDI | carbonyldiimidazole |
| DBU | 1,8-diazabicyclo[5.4.0]undec-7-ene |
| TFA | trifluoroacetic acid |
| NMM | N-methylmorpholine |
| HATU | O-7-azabenzotriazol-1-yl |
| HBTU | O-{1H-benzotriazol-1-yl)-N,N,N',N'-tetramethyluronium hexafluorophosphate |
| HOBT | N-hydroxybenzotriazole |
| PyBrop | bromo-bis-pyrrolidine-phosphonium hexafluorophosphate |
| DMF | dimethylformamide |
| MeOH | methanol |
| EDTA | ethylenediaminetetraacetic acid |
| HRMS | high resolution mass spectrometry |
| DMAP | 4-dimethylaminopyridine |
| DIPEA | diisopropylethylamine |
| DCM | dichloromethane |
| DCE | dichloroethane |

The compounds and chemical intermediates of the present invention, described in the following examples, were prepared according to the following methods. It should be noted that the following exemplification section is presented in sections. The sections are titled Section A through K. Example numbers and compound numbers are not contiguous throughout the entire Examples portion of the application and hence, each section indicates a "break" in the numbering. The numbering within each section is generally contiguous. Section L describes the biological activity of the compounds. Section M describes a subset of additional compounds that could be made using the methods described herein.

Section A:
Preparation of Intermediates:
Preparation of P1 Intermediates:
    The P1 intermediates described in this section can be used to prepare compounds of Formula I by the methods described herein.
I P1 Elements:
1. Preparation of Racemic (1R,2S)/(1S,2R)-1-amino-2-vinylcyclopropane carboxylic acid ethyl ester

Method A

Step 1

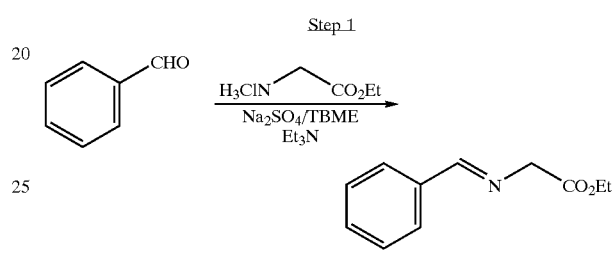

Glycine ethyl ester hydrochloride (303.8 g, 2.16 mole) was suspended in tert-butylmethyl ether (1.6 L). Benzaldehyde (231 g, 2.16 mole) and anhydrous sodium sulfate (154.6 g, 1.09 mole) were added and the mixture cooled to 0° C. using an ice-water bath. Triethylamine (455 mL, 3.26 mole) was added dropwise over 30 min and the mixture stirred for 48 h at rt. The reaction was then quenched by addition of ice-cold water (1 L) and the organic layer was separated. The aqueous phase was extracted with tert-butylmethyl ether (0.5 L) and the combined organic phases washed with a mixture of saturated aqueous $NaHCO_3$ (1 L) and brine (1 L). The solution was dried over $MgSO_4$, concentrated in vacuo to afford 392.4 g of the N-benzyl imine product as a thick yellow oil that was used directly in the next step. $^1$H NMR ($CDCl_3$, 300 MHz) δ 1.32 (t, J=7.1 Hz, 3H), 4.24 (q, J=7.1 Hz, 2H), 4.41 (d, J=1.1.1 Hz, 2H), 7.39–7.47 (m, 3H), 7.78–7.81 (m, 2H), 8.31 (s, 1H).

Step 2

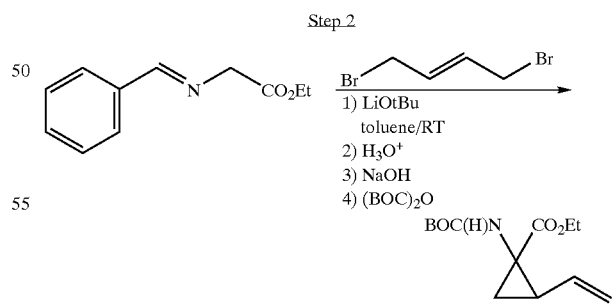

To a suspension of lithium tert-butoxide (84.06 g, 1.05 mol) in dry toluene (1.2 L), was added dropwise a mixture of the N-benzyl imine of glycine ethyl ester (100.4 g, 0.526 mol) and trans-1,4-dibromo-2-butene (107.0 g, 0.500 mol) in dry toluene (0.6 L) over 60 min. After completion of the addition, the deep red mixture was quenched by addition of water (1 L) and tert-butylmethyl ether (TBME, 1 L). The aqueous phase was separated and extracted a second time with TBME (1 L). The organic phases were combined, 1 N HCl (1 L) was added and the mixture stirred at room temperature for 2 h. The organic phase was separated and extracted with water (0.8 L). The aqueous phases were then combined, saturated with salt (700 g), TBME (1 L) was added and the mixture cooled to 0° C. The stirred mixture was then basified to pH 14 by the dropwise addition of 10 N NaOH, the organic layer separated, and the aqueous phase extracted with TBME (2×500 mL). The combined organic extracts were dried (MgSO$_4$) and concentrated to a volume of 1L. To this solution of free amine, was added BOC$_2$O or di-tert-butyldicarbonate (131.0 g, 0.6 mol) and the mixture stirred 4 days at rt. Additional di-tert-butyldicarbonate (50 g, 0.23 mol) was added to the reaction, the mixture refluxed for 3 h, and was then allowed cool to room temperature overnight. The reaction mixture was dried over MgSO$_4$ and concentrated in vacuo to afford 80 g of crude material. This residue was purified by flash chromatography (2.5 Kg of SiO$_2$, eluted with 1% to 2% MeOH/CH$_2$Cl$_2$) to afford 57 g (53%) of racemic N-Boc-(1R,2S)/(1S,2R)-1-amino-2-vinylcyclopropane carboxylic acid ethyl ester as a yellow oil which solidified while sitting in the refrigerator: $^1$H NMR (CDCl$_3$, 300 MHz) δ 1.26 (t, J=7.1 Hz, 3H), 1.46 (s, 9H), 1.43–1.49 (m, 1H), 1.76–1.82 (br m, 1H), 2.14 (q, J=8.6 Hz, 1H), 4.18 (q, J=7.2 Hz, 2H), 5.12 (dd J=10.3, 1.7 Hz, 1H), 5.25 (br s, 1H), 5.29 (dd, J=17.6, 1.7 Hz, 1H), 5.77 (ddd, J=17.6, 10.3, 8.9 Hz, 1H); MS m/z 254.16 (M–1)

Step 3 Preparation of Racemic (1R,2S)/(1S,2R) 1-amino-2-vinylcyclopropane carboxylic acid ethyl ester hydrochloride

N-Boc-(1R,2S)/(1S,2R)-1-amino-2-vinylcyclopropane carboxylic acid ethyl ester (9.39 g, 36.8 mmol) was dissolved in 4 N HCl/dioxane (90 ml, 360 mmol) and was stirred for 2 h at rt. The reaction mixture was concentrated to supply (1R,2S)/(1S,2R)-1-amino-2-vinylcyclopropane carboxylic acid ethyl ester hydrochloride in quanitative yield (7 g, 100%). $^1$H NMR (methanol-d$_4$) δ 1.32 (t, J=7.1, 3H), 1.72 (dd, J=10.2, 6.6 Hz, 1H), 1.81 (dd, J=8.3, 6.6 Hz, 1H), 2.38 (q, J=8.3 Hz, 1H), 4.26–4.34 (m, 2H), 5.24 (dd, 10.3, 1.3 Hz, 1H) 5.40 (d, J=17.2 Hz, 1H), 5.69–5.81 (m, 1H).

Alternate Route for the Preparation of Racemic N-Boc-1-amino-2-vinylcyclopropane carboxylic acid ethyl ester hydrochloride

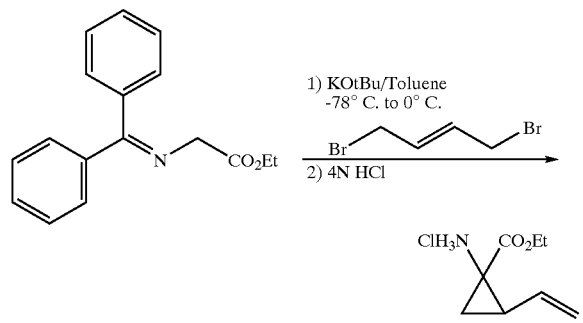

To a solution of potassium tert-butoxide (11.55 g, 102.9 mmol) in THF (450 mL) at −78° C. was added the commercially available N,N-dibenzyl imine of glycine ethyl ester (25.0 g, 93.53 mmol) in THF (112 mL). The reaction mixture was warmed to 0° C., stirred for 40 min, and was then cooled back to −78° C. To this solution was added trans-1,4-dibromo-2-butene (20.0 g, 93.50 mmol), the mixture stirred for 1 h at 0° C. and was cooled back to −78° C. Potassium tert-butoxide (11.55 g, 102.9 mmol) was added, the mixture immediately warmed to 0° C., and was stirred one more hour before concentrating in vacuo. The crude product was taken up in Et$_2$O (530 mL), 1N aq. HCl solution (106 mL, 106 mmol) added and the resulting biphasic mixture stirred for 3.5 h at rt. The layers were separated and the aqueous layer was washed with Et$_2$O (2×) and basified with a saturated aq. NaHCO$_3$ solution. The desired amine was extracted with Et$_2$O (3×) and the combined organic extract was washed with brine, dried (MgSO$_4$), and concentrated in vacuo to obtain the free amine. This material was treated with a 4N HCl solution in dioxane (100 mL, 400 mmol) and concentrated to afford (1R,2S)/(1S,2R)-1-amino-2-vinylcyclopropane carboxylic acid ethyl ester hydrochloride as a brown semisolid (5.3 g, 34% yield) identical to the material obtained from procedure A, except for the presence of a small unidentified aromatic impurity (8%).

Resolution of N-Boc-(1R,2S)/(1S,2R)-1-amino-2-vinylcyclopropane carboxylic acid ethyl ester

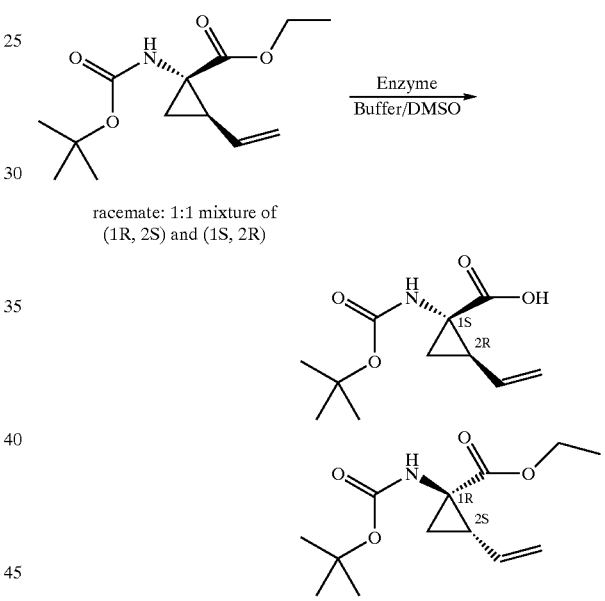

racemate: 1:1 mixture of (1R, 2S) and (1S, 2R)

Resolution A

To an aqueous solution of sodium phosphate buffer (0.1 M, 4.25 liter ("L"), pH 8) housed in a 12 Liter jacked reactor, maintained at 39° C., and stirred at 300 rpm was added 511 grams of Acalase 2.4L (about 425 mL) (Novozymes North America Inc.). When the temperature of the mixture reached 39° C., the pH was adjusted to 8.0 by the addition of a 50% NaOH in water. A solution of the racemic N-Boc-(1R,2S)/(1S,2R)-1-amino-2-vinylcyclopropane carboxylic acid ethyl ester (85 g) in 850 mL of DMSO was then added over a period of 40 min. The reaction temperature was then maintained at 40° C. for 24.5 h during which time the pH of the mixture was adjusted to 8.0 at the 1.5 h and 19.5 h time points using 50% NaOH in water. After 24.5 h, the enantio-excess of the ester was determined to be 97.2%, and the reaction was cooled to room temperature (26° C.) and stirred overnight (16 h) after which the enantio-excess of the ester was determined to be 100%. The pH of the reaction mixture was then adjusted to 8.5 with 50% NaOH and the resulting mixture was extracted with MTBE (2×2 L). The combined MTBE extract was then washed with 5% NaHCO₃ (3×100 mL), water (3×100 mL), and evaporated in vacuo to give the enantiomerically pure N-Boc-(1R,2S)/-1-amino-2-vinylcyclopropane carboxylic acid ethyl ester as light yellow solid (42.55 g; purity: 97% @ 210 nm, containing no acid; 100% enantiomeric excess ("ee").

The aqueous layer from the extraction process was then acidified to pH 2 with 50% H₂SO₄ and extracted with MTBE (2×2 L). The MTBE extract was washed with water (3×100 mL) and evaporated to give the acid as light yellow solid (42.74 g; purity: 99% @ 210 nm, containing no ester).

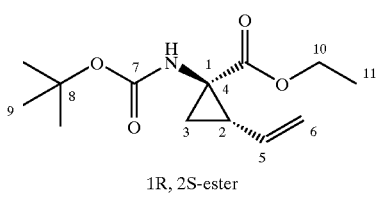

1R, 2S-ester

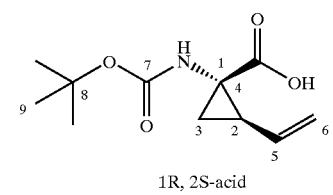

1R, 2S-acid

| | ester | acid |
|---|---|---|
| High Resolution Mass Spec | (+) ESI, C13H22NO4, [M + H]⁺, cal. 256.1549, found 256.1542 | (-) ESI, C11H16NO4, [M - H]⁻, cal. 226.1079, found 226.1089 |

NMR observed chemical shift
  Solvent: CDCl3 (proton δ 7.24 ppm, C-13 δ 77.0 ppm)
  Bruker DRX-500C: proton 500.032 MHz, carbon 125.746 MHz

| Position | Proton (pattern) ppm | C-13 ppm | Proton (pattern) ppm | C-13 ppm |
|---|---|---|---|---|
| 1 | — | 40.9 | — | 40.7 |
| 2 | 2.10(q, J=9.0Hz) | 34.1 | 2.17(q, J=9.0 Hz) | 35.0 |
| 3a | 1.76 (br) | 23.2 | 1.79 (br) | 23.4 |
| 3b | 1.46 (br) | | 1.51, (br) | |
| 4 | — | 170.8 | — | 75.8 |
| 5 | 5.74 (ddd, J=9.0, 10.0, 17.0Hz) | 133.7 | 5.75 (m) | 133.4 |
| 6a | 5.25 (d, J=17.0Hz) | 117.6 | 5.28(d, J=17.0 Hz) | 118.1 |
| 6b | 5.08 (dd, J=10 0, 1.5 Hz) | | 5.12(d, J=10.5 Hz) | |
| 7 | — | 155.8 | — | 156.2 |
| 8 | — | 80.0 | — | 80.6 |
| 9 | 1.43 (s) | 28.3 | 1.43 (s) | 28.3 |
| 10 | 4.16 (m) | 61.3 | — | — |
| 11 | 1.23(t, J=7.5Hz) | 14.2 | — | — |

Resolution B

To 0.5 mL 100 mM Heps•Na buffer (pH 8.5) in a well of a 24 well plate (capacity: 10 ml/well), 0.1 mL of Savinase 16.0L (protease from *Bacillus clausii*) (Novozymes North America Inc.) and a solution of the racemic N-Boc-(1R,2S)/(1S,2R)-1-amino-2-vinylcyclopropane carboxylic acid ethyl ester (10 mg) in 0.1 mL of DMSO were added. The plate was sealed and incubated at 250 rpm at 40° C. After 18 h, enantio-excess of the ester was determined to be 44.3% as following: 0.1 mL of the reaction mixture was removed and mixed well with 1 mL ethanol; after centrifugation, 10 microliter ("μl") of the supernatant was analyzed with the chiral HPLC. To the remaining reaction mixture, 0.1 mL of DMSO was added, and the plate was incubated for additional 3 days at 250 rpm at 40° C., after which four mL of ethanol was added to the well. After centrifugation, 10 μl of the supernatant was analyzed with the chiral HPLC and enantio-excess of the ester was determined to be 100%.

Resolution C

To 0.5 ml 100 mM Heps•Na buffer (pH 8.5) in a well of a 24 well plate (capacity: 10 mL/well), 0.1 ml of Esperase 8.0L, (protease from *Bacillus halodurans*) (Novozymes North America Inc.) and a solution of the racemic N-Boc-(1R,2S)/(1S,2R)-1-amino-2-vinylcyclopropane carboxylic acid ethyl ester (10 mg) in 0.1 mL of DMSO were added. The plate was sealed and incubated at 250 rpm at 40° C. After 18 hour, enantio-excess of the ester was determined to be 39.6% as following: 0.1 mL of the reaction mixture was removed and mixed well with 1 mL ethanol; after cenrifugation, 10 μl of the supernatant was analyzed with the chiral HPLC. To the remaining reaction mixture, 0.1 mL of DMSO was added, and the plate was incubated for additional 3 days at 250 rpm at 40° C., after which four mL of ethanol was added to the well. After centrifugation, 10 μl of the supernatant was analyzed with the chiral HPLC and enantio-excess of the ester was determined to be 100%.

Samples analysis was carried out in the following manner:

1) Sample preparation: About 0.5 ml of the reaction mixture was mixed well with 10 volume of EtOH. After centrifugation, 10 μl of the supernatant was injected onto HPLC column.

2) Conversion determination:

Column: YMC ODS A, 4.6×50 mm, S-5 μm
Solvent: A, 1 mM HCl in water; B, MeCN
Gradient: 30% B for 1 min; 30% to 45% B over 0.5 min; 45% B for 1.5 min; 45% to 30% B over 0.5 min.
Flow rate: 2 ml/min
UV Detection: 210 nm
Retention time: acid, 1.2 min; ester, 2.8 min.

3) Enantio-excess determination for the ester:

Column: CHIRACEL OD-RH, 4.6×150 mm, S-5 μm
Mobile phase: MeCN/50 mM HClO₄ in water (67/33)
Flow rate: 0.75 ml/min.
UV Detection: 210 nm.
Retention time:
(1S, 2R) isomer as acid: 5.2 min;
Rcaemate: 18.5 min and 20.0 min;
(1R, 2S) isomer as ester: 18.5 min.

2. Preparation of N-Boc-(1R,2S)-1-amino-2-cyclopropylcyclopropane carboxylic acid ethyl ester

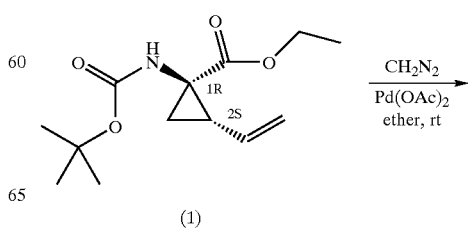

(1)

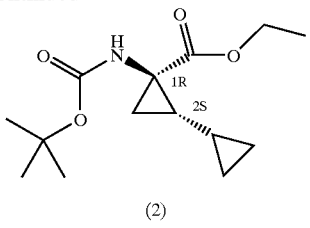

(2)

A solution of N-Boc-(1R,2S)-1-amino-2-vinylcyclopropane carboxylic acid (255 mg, 1.0 mmol) in ether (10 mL) was treated with palladium acetate (5 mg, 0.022 mmol). The orange/red solution was placed under an atmosphere of $N_2$. An excess of diazomethane in ether was added dropwise over the course of 1 h. The resulting solution was stirred at rt for 18 h. The excess diazomethane was removed using a stream of nitrogen. The resulting solution was concentrated by rotary evaporation to give the crude product. Flash chromatography (10% EtOAc/hexane) provided 210 mg (78%) of N-Boc-(1R,2S)-1-amino-2-cyclopropylcyclopropane carboxylic acid ethyl ester as a colorless oil. LC-MS (retention time: 2.13, similar to method A except: gradient time 3 min, Xterra MS C18 S7 3.0×50 mm column), MS m/e 270 ($M^+$+1).

3.1-tert-butoxycarbonylamino-cyclopropane-carboxylic acid is Commercially Available

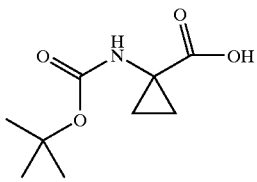

4. Preparation of 1-aminocyclobutanecarboxylic acid Methyl ester-hydrochloride

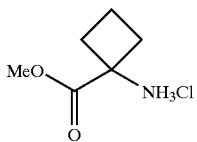

1-aminocyclobutanecarboxylic acid (100 mg, 0.869 mmol) (Tocris) was dissolved in 10 mL of MeOH, HCl gas was bubbled in for 2 h. The reaction mixture was stirred for 18 h, and then concentrated in vacuo to give 144 mg of a yellow oil. Trituration with 10 mL of ether provided 100 mg of the titled product as a white solid. $^1$H NMR (CDCl$_3$) δ 2.10–2.25 (m, 1H), 2.28–2.42 (m, 1H), 2.64–2.82 (m, 4H), 3.87 (s, 3H), 9.21 (br s, 3H).

5. Preparation of Racemic (1R,2R)/(1S,2S) 1-Amino-2-ethylcyclopropanecarboxylic acid tert-butyl ester, Shown Below.

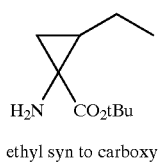

ethyl syn to carboxy

Step 1: Preparation of 2-Ethylcyclopropane-1,1-dicarboxylic acid di-tert-butyl ester, Shown Below.

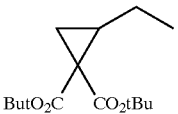

To a suspension of benzyltriethylammonium chloride (21.0 g, 92.2 mmol) in a 50% aqueous NaOH solution (92.4 g in 185 mL H$_2$O) was added 1,2-dibromobutane (30.0 g, 138.9 mmol) and di-tert-butylmalonate (20.0 g, 92.5 mmol). The reaction mixture was vigorously stirred 18 h at rt, a mixture of ice and water was then added. The crude product was extracted with CH$_2$Cl$_2$ (3×) and sequentially washed with water (3×), brine and the organic extracts combined. The organic layer was dried (MgSO$_4$), filtered and concentrated in vacuo. The resulting residue was flash chromatographed (100 g SiO$_2$, 3% Et$_2$O in hexane) to afford the titled product (18.3 g, 67.8 mmol, 73% yield) which was used directly in the next reaction.

Step 2: Preparation of Racemic 2-Ethylcyclopropane-1,1-dicarboxylic acid tert-butyl ester, Shown Below.

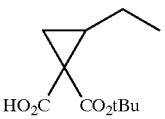

The product of Step 1 (18.3 g, 67.8 mmol) was added to a suspension of potassium tert-butoxide (33.55 g, 299.0 mmol) in dry ether (500 mL) at 0° C., followed by H$_2$O (1.35 mL, 75.0 mmol) and was vigorously stirred overnight at rt. The reaction mixture was poured in a mixture of ice and water and washed with ether (3×). The aqueous layer was acidified with a 10% aq. citric acid solution at 0° C. and extracted with EtOAc (3×). The combined organic layers were washed with water (2×), brine, dried (MgSO$_4$) and concentrated in vacuo to afford the titled product as a pale yellow oil (10 g, 46.8 mmol, 69% yield).

Step 3: Preparation of (1R,2R)/(1S,2S) 2-Ethyl-1-(2-trimethylsilanylethoxycarbonylamino)cyclopropane-carboxylic acid tert-butyl ester, Shown Below.

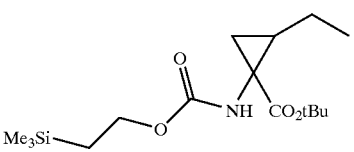

To a suspension, of the product of Step 2 (10 g, 46.8 mmol) and 3 g of freshly activated 4A molecular sieves in dry benzene (160 mL), was added Et$_3$N (7.50 mL, 53.8 mmol) and DPPA (11 mL, 10.21 mmol). The reaction mixture was refluxed for 3.5 h, 2-trimethylsilyl-ethanol (13.5 mL, 94.2 mmol) was then added, and the reaction mixture was refluxed overnite. The reaction mixture was filtered, diluted with Et$_2$O, washed with a 10% aqueous citric acid solution, water, saturated aqueous NaHCO$_3$, water (2×), brine (2×), dried (MgSO$_4$) and concentrated in vacuo. The residue was suspended with 10 g of Aldrich polyisocyanate scavenger resin in 120 mL of CH$_2$Cl$_2$, stirred at rt overnite and filtered to afford the titled product (8 g, 24.3 mmol; 52%) as a pale yellow oil: $^1$H NMR (CDCl$_3$) δ 0.03 (s, 9H), 0.97 (m, 5H), 1.20 (bm, 1H), 1.45 (s, 9H), 1.40–1.70 (m, 4H), 4.16 (m, 2H), 5.30 (bs, 1H).

Step 4: Preparation of Racemic (1R,2R)/(1S,2S) 1-Amino-2-ethylcyclopropanecarboxylic acid tert-butyl ester, Shown Below.

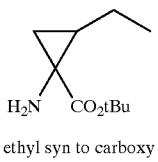

ethyl syn to carboxy

To the product of Step 3 (3 g, 9 mmol) was added a 1.0 M TBAF solution in THF (9.3 mL, 9.3 mmol) and the mixture heated to reflux for 1.5 h, cooled to rt and then diluted with 500 ml of EtOAc. The solution was successively washed with water (2×100 mL), brine (2×100 mL), dried (MgSO$_4$), concentrated in vacuo to provide the title intermediate II P1' Elements:

The P1' elements prepared below can be used to preapre compounds of Formula I by using the methods described herein.

1. Preparation of cyclopropylsulfonamide:

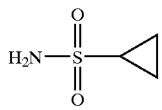

Step 1: Preparation of N-tert-Butyl-(3-chloro) propylsulfonamide

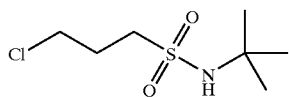

tert-Butylamine (3.0 mol, 315.3 mL) was dissolved in THF (2.5 L). The solution was cooled to −20° C. 3-Chloropropanesulfonyl chloride (1.5 mol, 182.4 mL) was added slowly. The reaction mixture was allowed to warm to rt and stirred for 24 h. The mixture was filtered, and the filtrate was concentrated in vacuo. The residue was dissolved in CH$_2$Cl$_2$ (2.0 L). The resulting solution was washed with 1 N HCl (1.0 L), water (1.0 L), brine (1.0 L) and dried over Na$_2$SO$_4$. It was filtered and concentrated in vacuo to give a slightly yellow solid, which was crystallized from hexane to afford the product as a white solid (316.0 g, 99%).

$^1$H NMR (CDCl$_3$) δ 1.38 (s, 9H), 2.30–2.27 (m, 2H), 3.22 (t, J=7.35 Hz, 2H), 3.68 (t, J=6.2 Hz, 2H), 4.35 (b, 1H).

Step 2: preparation of Cyclopropanesulfonic acid tert-butylamide

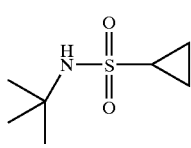

To a solution of N-tert-butyl-(3-chloro) propylsulfonamide (2.14 g, 10.0 mmol) in THF (100 mL) was added n-BuLi (2.5 M in hexane, 8.0 mL, 20.0 mmol) at −78° C. The reation mixture was allowed to warm up to room temperature over period of 1 h. The volatiles were removed in vacuo. The residue was partitioned between EtOAC and water (200 mL, 200 mL). The separated organic phase was washed with brine, dried over Na$_2$SO$_4$, filtered and concentrated in vacuo. The residue was recrystallized from hexane to yield the desired product as a white solid (1.0 g, 56%).

$^1$H NMR (CDCl$_3$) δ 0.98–1.00 (m, 2H), 1.18–1.19 (m, 2H), 1.39 (s, 9H), 2.48–2.51 (m, 1H), 4.19 (b, 1H).

Step 3: Preparation of cyclopropylsulfonamide

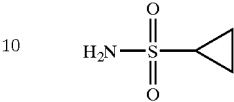

A solution of cyclopropanesulfonic acid tert-butylamide (110.0 g, 0.62 mol) in TFA (500 mL) was stirred at room temperature for 16 h. The volatile was removed in vacuo. The residue was recrystallized from EtOAC/hexane (60 mL/240 mL) to yield the desired product as a white solid (68.5 g, 91%).

$^1$H NMR (DMSO-d$_6$) δ 0.84–0.88 (m, 2H), 0.95–0.98 (m, 2H), 2.41–2.58 (m, 1H), 6.56 (b, 2H).

2. Alternate Procedure for the Preparation of cyclopropyl sulfonamide

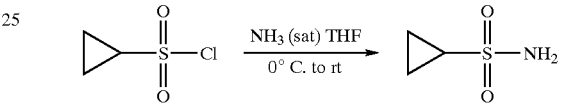

To a solution of 100 mL of THF cooled to 0° C. was bubbled in gaseous ammonia until saturation was reached. To this solution was added a solution of 5 g (28.45 mmol) of cyclopropylsulfonyl chloride (purchased from Array Biopharma) in 50 mL of THF, the solution warmed to rt overnite and stirred one additional day. The, mixture was concentrated until 1–2 mL of solvent remained, applied onto 30 g plug of SiO$_2$ (eluted with 30% to 60% EtOAc/Hexanes) to afford 3.45 g (100%) of cyclopropyl sulfonamide as a white solid. $^1$H NMR (Methanol-d4) δ 0.94–1.07 (m, 4H), 2.52–2.60 (m, 1H); $^{13}$C NMR (methanol-d$_4$) δ 5.92, 33.01.

3. Preparation of cyclobutyl sulfonamide

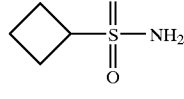

To a solution of 5.0 g (37.0 mmol) of cyclobutyl bromide in 30 mL of anhydrous diethyl ether (Et$_2$O) cooled to −78° C. was added 44 mL (74.8 mmol) of 1.7M tert-butyl lithium in pentanes and the solution slowly warmed to −35° C. over 1.5 h. This mixture was cannulated slowly into a solution of 5.0 g (37.0 mmol) freshly distilled sulfuryl chloride in 100 mL of hexanes cooled to −40° C., warmed to 0° C. over 1 h and carefully concentrated in vacuo. This mixture was redissolved in Et$_2$O, washed once with some ice-cold water, dried (MgSO$_4$) and concentrated carefully. This mixture was redissolved in 20 mL of THF, added dropwise to 500 mL of saturated NH$_3$ in THF and was allowed to stir overnite. The mixture was concentrated in vacuo to a crude yellow solid and was recrystallized from the minimum amount of CH$_2$Cl$_2$ in hexanes with 1–2 drops of MeOH to afford 1.90 g (38%) of cyclobutylsulfonamide as a white solid. $^1$H NMR (CDCl$_3$) δ 1.95–2.06 (m, 2H), 2.30–2.54 (m, 4H), 3.86 (p, J=8 Hz, 1H), 4.75 (brs, 2H); $^{13}$C NMR (CDCl$_3$) δ 16.43, 23.93, 56.29. HRMS m/z (M−H)$^-$ calcd for C$_4$H$_8$NSO$_2$: 134.0276, found 134.0282.

4. Preparation of cyclopentyl sulfonamide

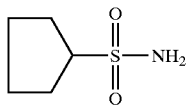

A solution of 18.5 mL (37.0 mmol) of 2M cyclopentylmagnesium chloride in ether was added dropwise to a solution of 3.0 mL (37.0 mmol) freshly distilled sulfuryl chloride (obtained from Aldrich) in 100 mL of hexanes cooled to −78° C. The mixture was warmed to 0° C. over 1 h and was then carefully concentrated in vacuo.

This mixture was redissolved in $Et_2O$ (200 mL), washed once with some ice-cold water (200 mL), dried ($MgSO_4$) and concentrated carefully. This mixture was redissolved in 35 mL of THF, added dropwise to 500 mL of saturated $NH_3$ in THF and was allowed to stir overnite. The mixture was concentrated in vacuo to a crude yellow solid, the residue filtered through 50 g of silica gel using 70% EtOAc-hexanes as the eluent and the solution was then concentrated. The residue was recrystallized from the minimum amount of $CH_2Cl_2$ in hexanes with 1–2 drops of MeOH to afford 2.49 g (41%) of cyclopentylsulfonamide as a white solid. $^1H$ NMR ($CDCl_3$) δ 1.58–1.72 (m, 2H), 1.74–1.88 (m, 2H), 1.94–2.14 (m, 4H), 3.48–3.59 (m, 1H), 4.80 (bs, 2H); $^{13}C$ NMR ($CDCl_3$) δ 25.90, 28.33, 63.54; MS m/e 148 (M−H)—.

5. Preparation of cyclohexyl sulfonamide

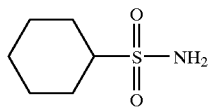

A solution of 18.5 mL (37.0 mmol) of 2M cyclohexylmagnesium chloride (TCI Americas) in ether was added dropwise to a solution of 3.0 mL (37.0 mmol) freshly distilled sulfuryl chloride in 100 mL of hexanes cooled to −78° C. The mixture was warmed to 0° C. over 1 h and was then carefully concentrated in vacuo. This mixture was redissolved in $Et_2O$ (200 mL), washed once with some ice-cold water (200 mL), dried ($MgSO_4$) and concentrated carefully This mixture was redissolved in 35 mL of THF, added dropwise to 500 mL of saturated $NH_3$ in THF and was allowed to stir overnite. The mixture was concentrated in vacuo to a crude yellow solid, the residue filtered through 50 g of silica gel using 70% EtOAc-hexanes as the eluent and was concentrated. The residue was recrystallized from the minimum amount of $CH_2Cl_2$ in hexanes with 1–2 drops of MeOH to afford 1.66 g (30%) of cyclohexyl sulfonamide as a white solid: $^1H$ NMR ($CDCl_3$) δ 1.11–1.37 (m, 3H), 1.43–1.56 (m, 2H), 1.67–1.76 (m, 1H), 1.86–1.96 (m, 2H), 2.18–2.28 (m, 2H), 2.91 (tt, J=12, 3.5 Hz, 1H), 4.70 (bs, 2H); $^{13C}H$ NMR ($CDCl_3$) δ 25.04, 25.04, 26.56, 62.74; MS m/e 162 (M−1)⁻.

6. Preparation of neopentylsulfonamide

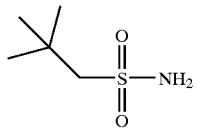

Following the procedure for the prep of cyclohexyl sulfonamide, 49 mL (37 mmol) of 0.75M neopentylmagnesium chloride (Alfa) in ether was converted to 1.52 g (27%) of neopentylsulfonamide as a white solid. $^1H$ NMR ($CDCl_3$) δ 1.17 (s, 9H), 3.12 (s, 2H), 4.74 (brs, 2H); $^{13}C$ NMR ($CDCl_3$) δ 29.46, 31.51, 67.38; MS m/e 150 (M−1)⁻.

7. Preparation of cyclobutylcarbinyl-sulfonamide

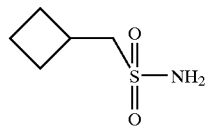

A solution of 12.3 g (83 mmol) of cyclobutylcarbinyl bromide (Aldrich) and 13.7 g (91 mmol) of sodium iodide in 150 mL of acetone was refluxed overnite and then cooled to rt. The inorganic solids were filtered off and the acetone and cyclopropylcarbinyl iodide (8.41 g, 46%) distilled off at ambient and 150 torr at 80° C., respectively.

A solution of 4.0 g (21.98 mmol) of cyclobutyl carbinyl iodide in 30 mL of anhydrous diethyl ether ($Et_2O$) cooled to −78° C. was cannulated into a solution of 17 mL (21.98 mmol) of 1.3M sec-butyl lithium in cyclohexanes and the solution was stirred for 5 min. To this mixture was cannulated a solution of 3.0 g (21.98 mmol) of freshly distilled sulfuryl chloride in 110 mL of hexanes cooled to −78° C., the mixture warmed to rt over 1 h and was then carefully concentrated in vacuo. This mixture was redissolved in $Et_2O$, washed once with some ice-cold water, dried ($MgSO_4$) and concentrated carefully. This mixture was redissolved in 30 mL of THF, added dropwise to 500 mL of saturated $NH_3$ in THF and was allowed to stir overnight. The mixture was concentrated in vacuo to a crude yellow solid and was recrystallized from the minimum amount of $CH_2Cl_2$ in hexanes with 1–2 drops of MeOH to afford 1.39 g (42%) of cyclobutyl carbinylsulfonamide as a white solid. $^1H$ NMR ($CDCl_3$) δ 1.81–2.03 (m, 4H), 2.14–2.28 (m, 2H), 2.81–2.92 (m, 1H), 3.22 (d, J=7 Hz, 2H), 4.74 (brs, 2H); $^{13}C$ NMR ($CDCl_3$) δ 19.10, 28.21, 30.64, 60.93; MS m/e 148 (M−1)⁻. time: 1.73, method B), 818 (M⁺+H)

8. Preparation of cyclopropylcarbinyl-sulfonamide

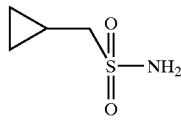

Using the procedure employed for the preparation of cyclobutylcarbinyl-sulfonamide, cyclopropylcarbinyl sulfonamide was prepared from cyclopropylcarbinyl bromide (Aldrich) (see also JACS 1981, p.442–445). $^1H$ NMR ($CDCl_3$) δ 0.39–0.44 (m, 2H), 0.67–0.76 (m, 2H), 1.13–1.27 (m, 1H), 3.03 (d, J=7.3 Hz, 2H), 4.74 (brs, 2H); $^{13}C$ NMR ($CDCl_3$) δ 4.33, 5.61, 59.93; MS m/e 134 (M−1).

III Heterocycles to be Used as Starting Material in the Construction of P2 Elements for Subsequent Incorporation into Compounds of Formula I.

1. Isoquinolines

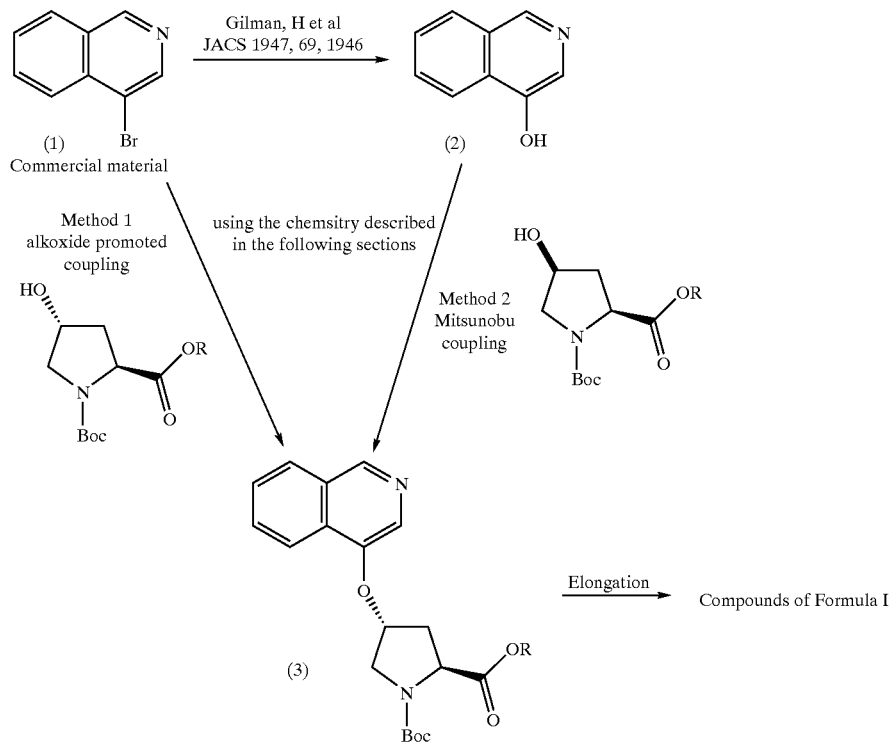

Isoquinoline (1) and substituted analogues thereof, can be incorporated into P2 elements using the two methods outline above and described in detail herein. Said P2 elements (3) can then be converted into compounds of Formula I using procedures analogous to those described herein for similar isoquinoline analogues.

2. Isoxazolepyridine and Oxazolepyridine(1)

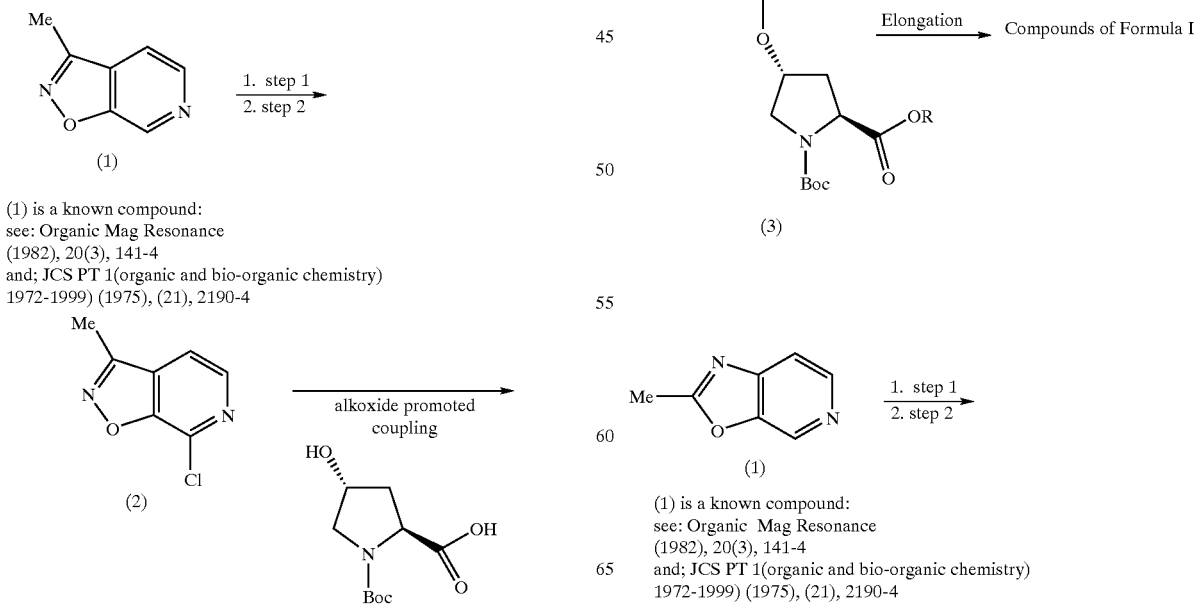

(1) is a known compound:
see: Organic Mag Resonance
(1982), 20(3), 141-4
and; JCS PT 1(organic and bio-organic chemistry)
1972-1999) (1975), (21), 2190-4

-continued

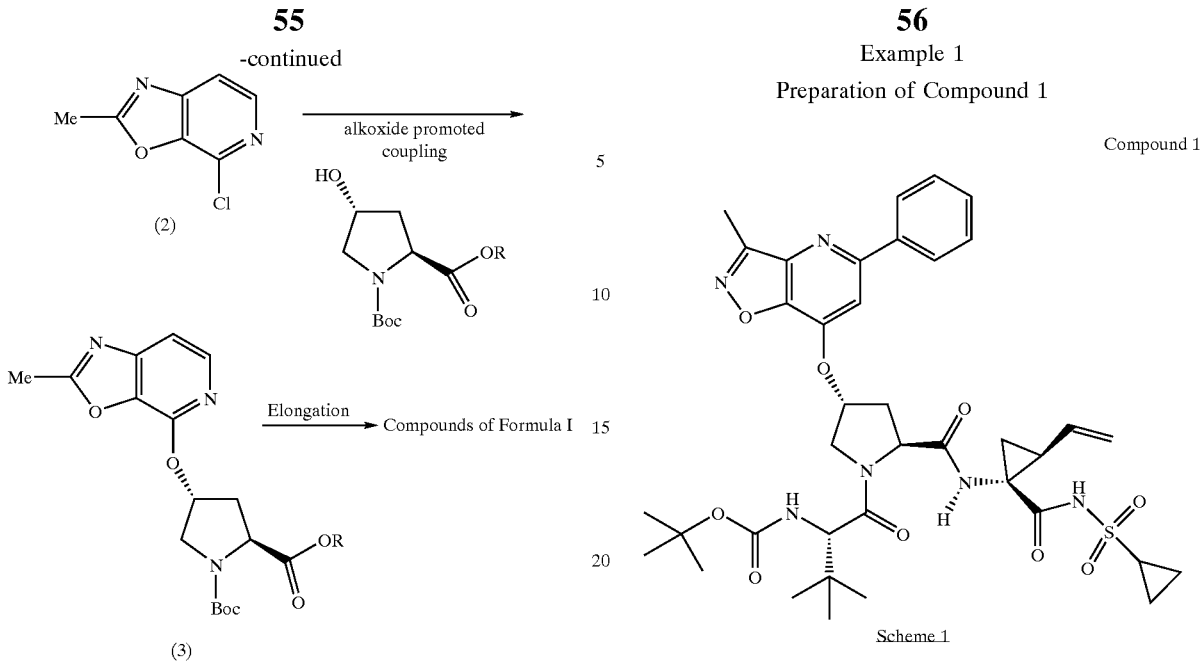

Isoxazole and oxazole heterocycle (1) and analogues thereof can be prepared using know chemistry and incorporated into compounds of Formula I using the chemistry described herein for similar isoxazolepyridine intermediates as shown in section B.

Section B:

In Section B the following conditions were used for LC/MS analysis.

Columns: Method A: YMC ODS-A C18 S7 (4.6×33 mm)
Method B: YMC Xterra ODS S7 (3.0×50 mm)
Method C: Xterra ms C18 (4.6×33 mm)
Method D: YMC ODS-A C18 S3 (4.6×33 mm)
Gradient: 100% solvent A/0% solvent B to 0% solvent A/100% solvent B
Gradient time: 3 min.
Hold Time: 1 min.
Flow Rate: 5 mL/min.
Detector Wavelength: 220 nm.
Solvents: Solvent A: 10% MeOH/90% water/0.1% TFA.
Solvent B: 90% MeOH/10% water/0.1% TFA.

The following conditions were used for prep-HPLC separation.
Columns: Phenomenex-Luna 30×100 mm, S5
Gradient: 60% solvent A/40% solvent B to 0% solvent A/100% solvent B
Gradient time: 15 min.
Stop Time: 20 min.
Flow Rate: 30 mL/min.
Detector Wavelength: 220 nm.
Solvents: Solvent A: 10% MeOH/90% water/0.1% TFA.
Solvent B: 90% MeOH/10% water/0.1% TFA.

Example 1

Preparation of Compound 1

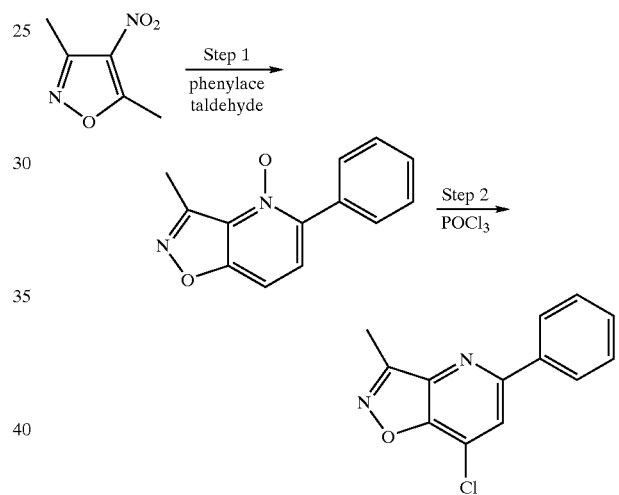

Step 1:
A mixture of 3,5-dimethyl-4-nitro-isoxazole (1.42 g, 10.0 mmol), phenylacetaldehyde (1.32 g, 11.0 mmol) in piperidine (1 mL) and ethanol (10 mL) was heated to reflux for, 16 h. After cooling down to the ambient temperature, the product precipitated out was collected by filtration. The cake was washed with cold ethanol thoroughly to afford 1.20 g (53%) of the desired product as a white solid.
$^1$H NMR (CDCl$_3$) δ 2.87 (s, 3H), 7.46–7.50 (m, 3H), 7.56 (d, J=8.5 Hz, 1H), 7.7–7.80 (m, 2H);
LC-MS (retention time: 1.19 min, method B), MS m/z 227 (M$^+$+H).
Step 2:
A solution of 3-methyl-5-phenyl-isoxazolo[4,5-b]pyridine 4-oxide (1.00 g, 4.40 mmol) and POCl$_3$ (2.71 g, 17.7 mmol) in chloroform (10 mL) was heated to reflux for 1 h. After cooling down to the ambient temperature, the final solution was diluted with chloroform (50 mL) and washed with NaHCO$_3$ (aq.) (two 50 mL portions) and brine, dried over MgSO$_4$, filtered, evaporated. The residue was purified by flash chromatography (4:1 hexane-EtOAc) to afford 790 mg (73%) of the desired product as a white solid.
$^1$H NMR (CDCl$_3$) δ 2.72 (s, 3H), 7.46–7.54 (m, 3H), 7.91 (s, 1H), 8.00–8.03 (m, 2H);

LC-MS (retention time: 1.76 min, method B), MS m/z 245, 247 (M⁺+H).

Scheme 2

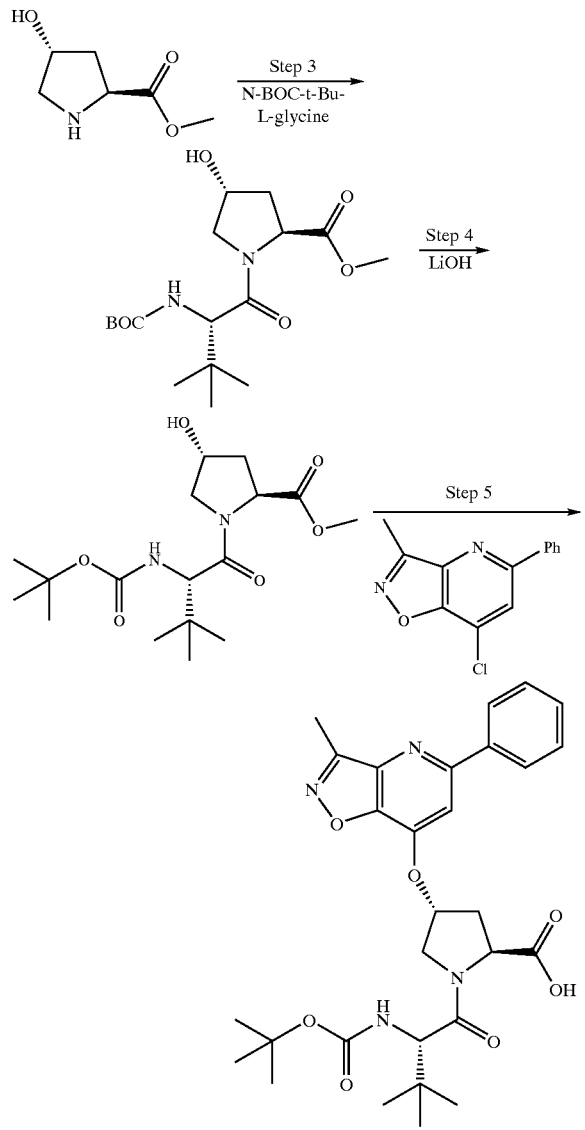

Step 3:
To a mixture of 4-hydroxy-pyrrolidine-2-carboxylic acid methyl ester (H-Hyp-OMe HCl) (1.81 g, 10.0 mmol), HATU (5.70 g, 15.0 mmol), and N-BOC-t-butyl-L-glycine (2.42 g, 10.5 mmol) in CH₂Cl₂ (100 mL) was added DIPEA (3.47 g, 31.0 mmol) at 0° C. After stirring at the ambient temperature for 12 h, the formed solution was diluted with CH₂Cl₂ (100 mL), washed with iced 5% citric acid (aq). The organic layer was washed with 5% citric acid, 1M NaOH, brine respectively, dried over MgSO₄, and filtered. The filtrate was evaporated in vacuo to provide 3.55 g (99%) of the desired product as an off-white foam. This product was used for the next reaction as crude without further purification.

¹H NMR (CD₃OD) δ 1.04 (s, 9H), 1.43 (s, 9H), 1.99–2.03 (m, 1H), 2.20–2.30 (m, 1H), 3.69 (s, 3H), 3.70–3.79 (m, 2H), 4.28 (b, 1H), 4.46 (b, 1H), 4.74–4.80 (m, 1H);

LC-MS (retention time: 1.28 min, method B), MS m/z 359 (M⁺+H).

Step 4:

A mixture of the product of Step 3 (3.55 g, 9.9 mmol) in THF (50 mL), MeOH (50 mL) and LiOH monohydrate (0.83 g, 19.9 mmol in 50 mL H₂O) was stirred at the ambient temperature over night. After removal of the volatiles in vacuo, the residue was dissolved in 0.1 M NaOH (100 mL). This aqueous solution was washed with ether (50 mL), acidified by 1M HCl to pH 4. Extracted with EtOAc (100 mL). The organic layer was washed with 5% citric acid and brine, dried over MgSO₄, evaporated to dryness to give 3.20 g (95%) of the desired product as a white foam. This product was used as crude without further purification.

¹H NMR (CD₃OD) δ 1.02 (s, 9H), 1.43 (s, 9H), 2.01–2.09 (m, 1H), 2.25–2.32 (m, 1H), 3.70–3.85 (m, 2H), 4.26–4.30 (m, 1H), 4.46–4.51 (m, 2H), 6.37–6.41 (m, 1H);

LC-MS (retention time: 1.14 min, method B), MS m/z 345 (M⁺+H).

Step 5:
To a solution of the product of Step 4 (1.01 g, 2.93 mmol) in DMSO (30 mL) was added potassium tert-butoxide (1.02 g, 9.08 mmol). The formed solution was stirred at the ambient temperature for 1 h before addition of 7-chloro-3-methyl-5-phenyl-isoxazolo[4,5-b]pyridine (0.75 g, 3.08 mmol). The final solution was stirred for 12 h. Then was quenched with iced water, acidified with 1M HCl to pH 4, extracted with EtOAc (two 200 mL portions). The organic layers were washed with brine, dried over MgSO₄, filtered, evaporated. The residue was purified by prep-HPLC (60% B–100% B, 15 min gradient) to afford 305 mg (19%) of the desired product as a pale yellow solid.

¹H NMR (CD₃OD) δ 1.02 (s, 9H), 1.17 (s, 9H), 2.37–2.47 (m, 1H), 2.64 (s, 3H), 2.85–2.93 (m, 1H), 4.00–4.08 (m, 1H), 4.14 (b, 1H), 4.49–4.55 (m, 1H), 4.62–4.71 (m, 1H), 5.70 (m, 1H), 7.45–7.53 (m, 3H), 7.56 (s, 1H), 8.03–8.06 (m, 2H);

LC-MS (retention time: 1.89 min, method B), MS m/z 553 (M⁺+H).

Scheme 3

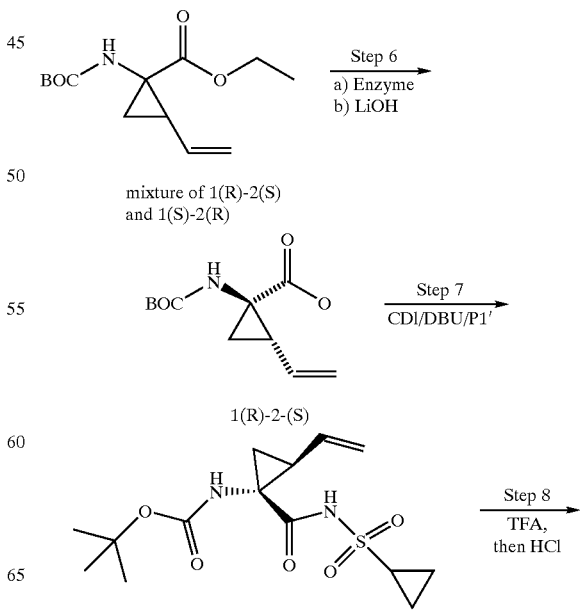

-continued

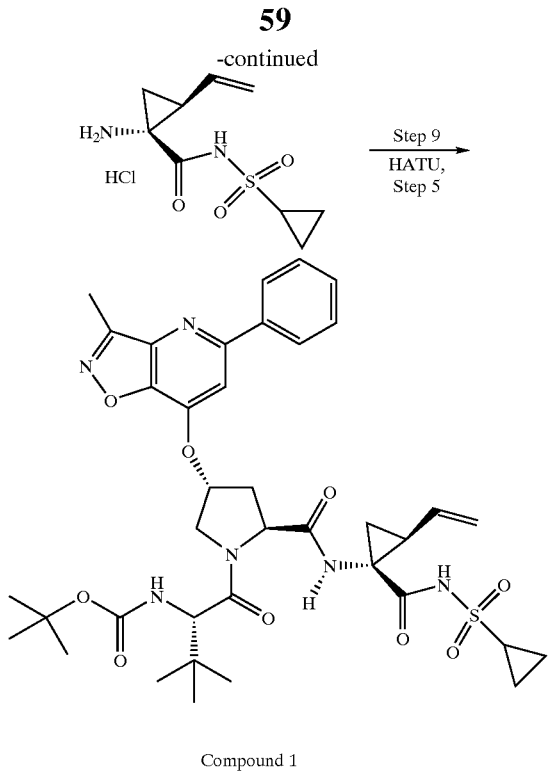

Compound 1

Step 6a
As described in section A.
Step 6b:
To a solution of 1(R)-tert-butoxycarbonylamino-2(S)-vinyl-cyclopropanecarboxylic acid ethyl ester, the product of Step 6a (3.28 g, 13.2 mmol) in THF (7 mL) and methanol (7 mL) was added a suspension of LiOH (1.27 g, 53.0 mmol) in water (14 mL). The mixture was stirred overnight at room temperature and quenched with 1N NaOH (15 mL) and water (20 mL). The resulting mixture was washed with EtOAc (20 mL), and the organic phase was extracted with 20 mL 0.5N NaOH. The combined aqueous phases were acidified with 1N HCl until pH 4 and extracted with EtOAc (3×40 mL). The combined organic extracts were washed with brine and dried (MgSO$_4$) to yield the title compound as a white solid (2.62 g, 87%).
$^1$H NMR: (DMSO-d$_6$) δ 1.22–1.26 (m, 1H), 1.37 (s, 9H), 1.50–1.52 (m, 1H), 2.05 (q, J=9 Hz, 1H), 5.04 (d, J=10 Hz, 1H), 5.22 (d, J=17 Hz, 1H), 5.64–5.71 (m, 1H), 7.18, 7.53 (s, NH (rotamers), 12.4 (br s, 1H));
LC-MS (retention time: 1.67 min, method B), MS m/z 228 (M$^+$+H).
Step 7:
A solution of the product of Step 6 (2.62 g, 11.5 mmol) and CDI (2.43 g, 15.0 mmol) in THF (40 mL) was heated at reflux for 50 min under nitrogen. The solution was cooled to room temperature and transferred by cannula to a solution of cyclopropylsulfonamide (1.82 g, 15.0 mmol) in THF (10 mL). To the resulting solution was added DBU (2.40 mL, 16.1 mmol) and stirring was continued for 20 h. The mixture was quenched with 1N HCl to pH 1 and THF was evaporated in vacuo. The suspension was extracted with EtOAc (2×50 mL) and the combined organic extracts dried (Na2SO4). Purification by recystallization from hexanes-EtOAc (1:1) afforded the title compound (2.4 g) as a white solid. The mother liquor was purified by a Biotage 40S column (eluted 9% acetone in DCM) to give a second batch of the title compound (1.1 g). Both batches were combined (total yield 92%).

$^1$H NMR: (DMSO-d$_6$) δ 0.96–1.10 (m, 4H), 1.22 (dd, J=5.5, 9.5 Hz, 1H), 1.39 (s, 9H), 1.70 (t, J=5.5 Hz, 1H), 2.19–2.24 (m, 1H), 2.90 (m, 1H), 5.08 (d, J=10 Hz, 1H), 5.23 (d, J=17 Hz, 1H), 5.45 (m, 1H), 6.85, 7.22 (s, NH (rotamers);
LC-MS (retention time: 1.70 min, method B), MS m/z 331 (M$^+$+H).
Step 8:
A solution of the product of Step 7 (3.5 g, 10.6 mmol) in DCM (35 mL) and TFA (32 mL) was stirred at room temperature for 1.5 h. The volatiles were removed in vacuo and the residue suspended in 1N HCl in diethyl ether (20 mL) and concentrated in vacuo. This procedure was repeated once. The resulting mixture was triturated from pentane and filtered to give the title compound as a hygroscopic, off-white solid (2.60 g, 92%).
$^1$H NMR: (DMSO-d$_6$) δ 1.01–1.15 (m, 4H), 1.69–1.73 (m, 1H), 1.99–2.02 (m, 1H), 2.38 (q, J=9 Hz, 1H), 2.92–2.97 (m, 1H), 5.20 (d, J=11 Hz, 1H), 5.33 (d, J=17 Hz, 1H), 5.52–5.59 (m, 1H), 9.17 (br s, 3H);
LC-MS (retention time: 0.24 min, method B), MS m/z 231 (M$^+$+H).
Step 9:
To an iced mixture of the product of Step 5 (70 mg, 0.13 mmol), (1R,2S)-cyclopropanesulfonic acid(1-amino-2-vinyl-cyclopropanecarbonyl)amide hydrochloride, the product of Step 8 (37 mg, 0.14 mmol) and HATU (72 mg, 0.19 mmol) in DCM (2 mL) was added diisopropylethylamine (50 mg, 0.39 mmol). The formed solution was allowed to warm up to the ambient temperature for 12 h and evaporated in vacuo. The residue was purified by prep-HPLC (60% B–100% B, 15 min gradient) to afford 52 mg (54%) of Compound 1 as a grayish solid.
$^1$H NMR (CD$_3$OD) δ 0.96–1.09 (m, 12H), 1.16–1.25 (m, 10H), 1.44–1.48 (m, 1H), 1.87–1.91 (m, 1H), 2.20–2.40 (m, 2H), 2.63–2.65 (m, 4H), 2.89–2.98 (m, 1H), 4.08–4.20 (m, 2H), 4.44–4.65 (m, 2H), 5.13 (d, J=11.7 Hz, 1H), 5.32 (d, J=15 Hz, 1H), 5.72–5.85 (b, 2H), 6.62 (d, J=15.0 Hz, 1H), 7.46–7.53 (m, 3H), 7.58 (s, 1H), 8.04–8.07 (m, 2H);
LC-MS (retention time: 1.92 min, method B), MS m/z 765 (M$^+$+H).

Example 2

Preparation of Compound 2

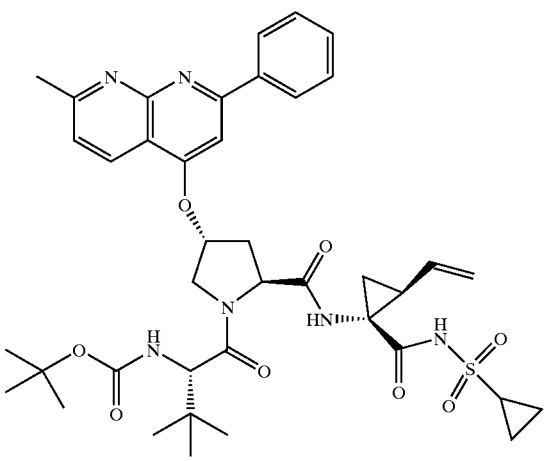

Compound 2

-continued
Scheme 1

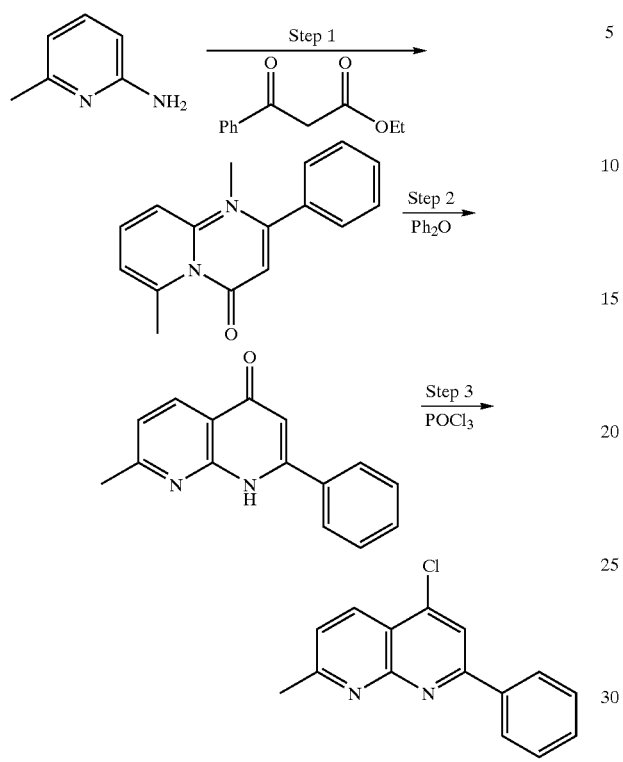

Step 1:
A mixture of 2-amino-6-methylpyridine (1.08 g, 10.0 mmol), ethyl benzoylacetate (2.30 g, 12.0 mmol) and polyphosphoric acid (6.00 g, 61.2 mmol) was heated to 110° C. for 5 h. After cooling to the ambient temperature, the mixture was poured into iced water (20 mL) and neutralized to pH 7 with 10 M NaOH. Extracted with CHCl$_3$. The organic layer was washed with brine, dried over MgSO$_4$, filtered, evaporated. The residue was purified by flash chromatography (1:1 hexane-EtOAc) to afford 510 mg (22%) of the desired product as a pale yellow solid.

$^1$H NMR (CDCl$_3$) δ 3.08 (s, 3H), 6.64 (d, J=7.0 Hz, 1H), 6.71 (s, 1H), 7.42–7.52 (m, 5H), 8.04–8.06 (m, 2H);

LC-MS (retention time: 1.21 min, method B), MS m/z 237 (M$^+$+H).

Step 2:
A solution of 6-methyl-2-phenyl-pyrido[1,2a]pyrimidin-4-one (489 mg, 2.07 mmol) in melted diphenyl ether (5 mL) was heated to gentle reflux for 5 h. After cooling to the ambient temperature, the formed suspension was diluted with diethyl ether (10 mL), filtered. The cake was washed with diethyl ether thoroughly to afford 450 mg (92%) of the desired product as a brownish solid.

LC-MS (retention time: 1.25 min, method B), MS m/z 237 (M$^+$+H).

Step 3:
A suspension of 7-methyl-2-phenyl-1H-[1,8]naphthyridin-4-one (450 mg, 1.91 mmol) in POCl$_3$ (10 mL) was heated to gentle reflux for 3 h. Evaporated in vacuo. The residue was poured into iced water (20 mL) and neutralized to pH 10 with 10 M NaOH. Extracted with CHCl$_3$. The organic layer was washed with brine, dried over MgSO$_4$, filtered, evaporated. The residue was purified by flash chromatography (2:1 hexane-EtOAc) to afford 450 mg (92%) of the desired product as a pink solid.

$^1$H NMR (CD$_3$OD) δ 2.80 (s, 3H), 7.54–7.56 (m, 3H), 7.61 (d, J=8.4 Hz, 1H), 8.25–8.30 (m, 3H), 8.58 (d, J=8.4 Hz, 1H);

LC-MS (retention time: 1.39 min, method B), MS m/z 255, 257 (M$^+$+H).

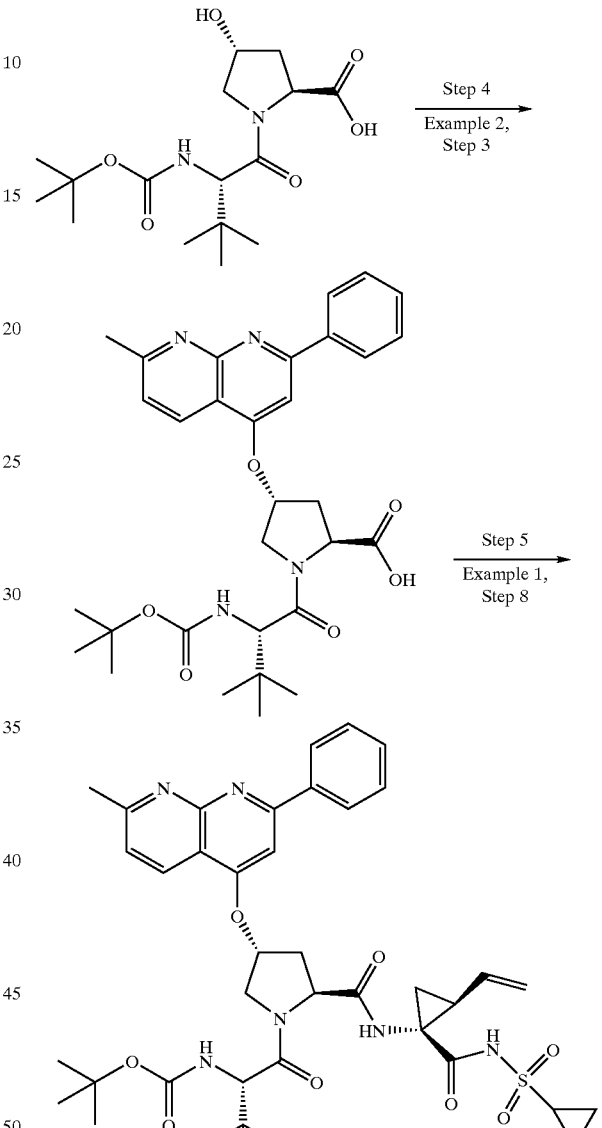

Step 4:
This product was prepared by the same procedure as described in Example 1, Step 5, except using 4-chloro-7-methyl-2-phenyl-[1,8]naphthyridine from Example 2, Step 3 instead.

LC-MS (retention time: 1.55 min. method B), MS m/z 563 (M$^+$+H).

Step 5:
Compound 2 was prepared by the same procedure as described in Example 1, Step 9, except using the product of Example 2, Step 4 instead.

$^1$H NMR (CD$_3$OD) δ 1.01–1.10 (m, 12H), 1.21–1.26 (m, 10H), 1.40–1.45 (m, 1H), 1.86–1.91 (m, 1H), 2.20–2.29 (m,

1H), 2.39–2.49 (m, 1H), 2.72–2.81 (m, 1H), 2.92–2.95 (m, 4H), 4.10–4.16 (m, 2H), 4.55–4.65 (m, 2H), 5.14 (d, J=12.0 Hz, 1H), 5.30 (d, J=15.0 Hz, 1H), 5.67–5.82 (m, 2H), 7.60–7.80 (m, 3H), 7.78 (d, J=8.6 Hz, 1H), 7.87 (s, 1H), 8.26–8.29 (m, 2H), 8.95 (d, J=8.4 Hz, 1H);

LC-MS (retention time: 1.62 min, method B), MS m/z 775 (M⁺+H).

Example 3

Preparation of Compound 3

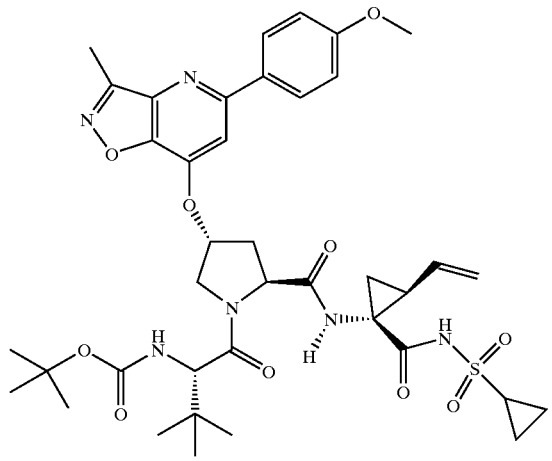

Compound 3

Scheme 1

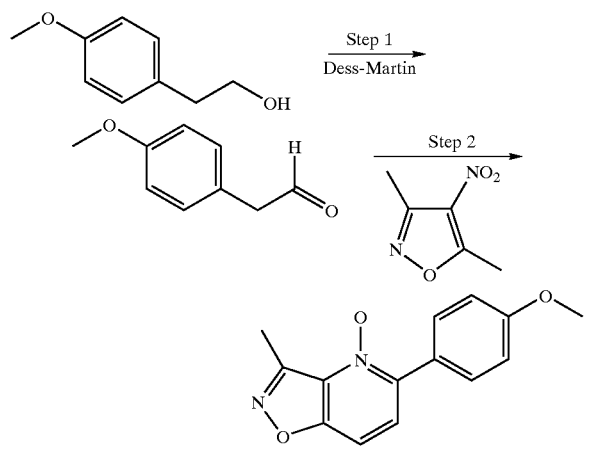

Step 1:

To a solution of 4-methoxyphenethyl alcohol (1.52 g, 10.0 mmol) in CH₂Cl₂ (50 mL) at 0° C. was added Dess-Martin reagent (4.45 g, 10.5 mmol) in one portion. The formed mixture was allowed to warm to the ambient temperature for 1 h. Washed with sat. Na₂S₂O₃ (aq) and 1M NaOH, brine respectively. Dried over MgSO₄, evaporated in vacuo to give 1.50 g (100%) of the desired aldehyde as a viscous oil. This product was used as crude without any further purification.

Step 2:

A solution of 3,5-dimethyl-4-nitro-isoxazole (142 mg, 1.0 mmol), 4-methoxyphenylacetaldehyde from Example 3, Step 1 (180 mg, 1.1 mmol) in piperidine (0.1 mL) and ethanol (2 mL) was heated to reflux for 12 h. After cooling down to the ambient temperature, the product precipitated out was collected by filtration. The cake was washed with cold ethanol thoroughly to afford 130 mg (51%) of the desired product as a grayish solid.

¹H NMR (CDCl₃) δ 2.88 (s, 3H), 3.87 (s, 3H), 7.02 (d, J=8.5 Hz, 2H), 7.50 (d, J=9.0 Hz, 1H), 7.57 (d, J=9.0 Hz, 1H), 7.81 (d, J=8.5 Hz, 2H);

LC-MS (retention time: 1.24 min, method B), MS m/z 257 (M⁺+H).

Step 3:

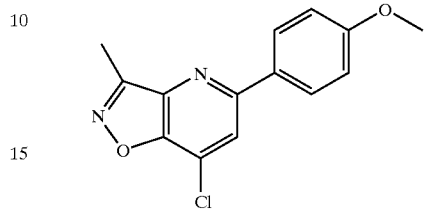

This product was prepared by the same procedure as described in Example 1, Step 2, except using the product of Example 3, Step 2 instead.

¹H NMR (CDCl₃) δ 2.70 (s, 3H), 3.87 (s, 3H), 7.00–7.03 (m, 2H), 7.84 (s, 1H), 7.96–7.98 (m, 2H);

LC-MS (retention time: 1.96 min, method B), MS m/z 275, 277 (M⁺+H).

Step 4:

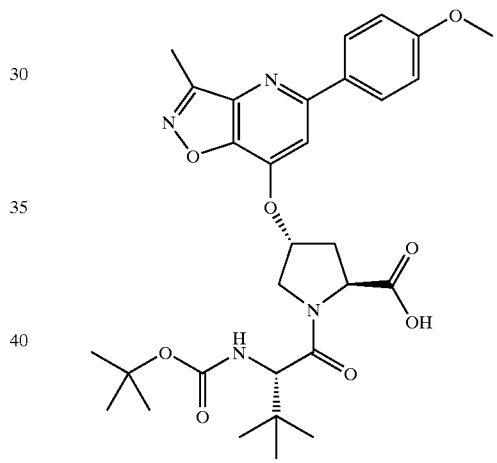

This product was prepared by the same procedure as described in Example 1, Step 5, except using the product of Example 3, Step 3 instead.

¹H NMR (CD₃OD) δ 1.02 (s, 9H), 1.18 (s, 9H), 2.39–2.43 (m, 1H), 2.63 (s, 3H), 2.75–2.80 (m, 1H), 3.87 (s, 3H), 4.00–4.08 (m, 1H), 4.17 (b, 1H), 4.49–4.55 (m, 1H), 4.62–4.71 (m, 1H), 5.68 (b, 1H), 7.05 (d, J=8.5 Hz, 2H), 7.49 (s, 1H), 8.00 (d, J=8.5 Hz, 2H);

LC-MS (retention time: 1.89 min, method B), MS m/z 583 (M⁺+H).

Step 5:

Compound 3 was prepared by the same procedure as described in Example 1, Step 9, except using the product of Example 3, Step 4 instead.

¹H NMR (CD₃OD) δ 1.01–1.09 (m, 12H), 1.17–1.26 (m, 10H), 1.44–1.47 (m, 1H), 1.87–1.91 (m, 1H), 2.20–2.40 (m, 2H), 2.63–2.65 (m, 4H), 2.89–2.98 (m, 1H), 3.87 (s, 3H), 4.08–4.20 (m, 2H), 4.44–4.65 (m, 2H), 5.13 (d, J=11.7 Hz, 1H), 5.32 (d, J=15.0 Hz, 1H), 5.72–5.85 (m, 2H), 7.05 (d, J=8.5 Hz, 2H), 7.06 (s, 1H), 8.01 (d, J=8.5 Hz, 2H);

LC-MS (retention time: 1.96 min, method B), MS m/z 795 (M⁺+H).

Example 4

Preparation of Compound 4

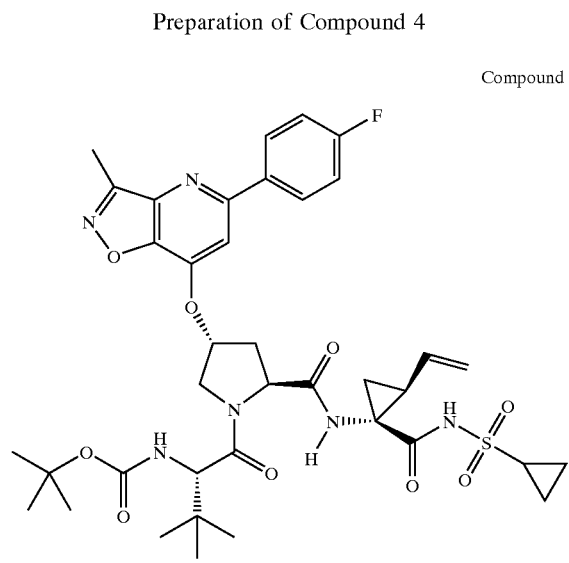

Compound 4

Step 1:

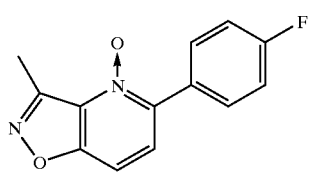

This product was prepared by the same procedure as described in Example 3, Step 1&2, except using 4-fluorophenethyl alcohol instead.

LC-MS (retention time: 1.18 min, method B), MS m/z 245 (M⁺+H).

Step 2:

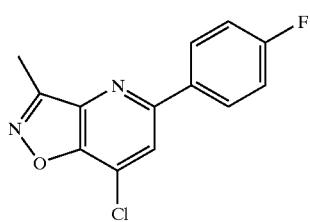

This product was prepared by the same procedure as described in Example 1, Step 2, except using the product of Example 4, Step 1 instead.

$^1$H NMR (CDCl$_3$) δ 2.71 (s, 3H), 7.17–7.20 (m, 2H), 7.86 (s, 1H), 8.00–8.02 (m, 2H);

LC-MS (retention time: 1.71 min, method B), MS m/z 263, 265 (M⁺+H).

Step 3:

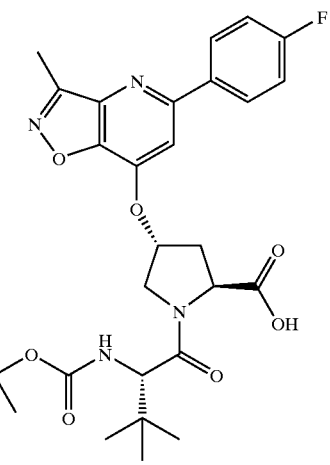

This product was prepared by the same procedure as described in Example 1, Step 5, except using the product of Example 4, Step 2 instead.

LC-MS (retention time: 1.91 min, method B), MS m/z 571 (M⁺+H).

Step 4:

Compound 4 was prepared by the same procedure as described in Example 1, Step 9, except using the product of Example 4, Step 3 instead.

$^1$H NMR (CD$_3$OD) δ 1.01–1.09 (m, 12H), 1.17–1.26 (m, 10H), 1.44–1.47 (m, 1H), 1.87–1.91 (m, 1H), 2.20–2.40 (m, 2H), 2.63–2.65 (m, 4H), 2.89–2.98 (m, 1H), 4.08–4.20 (m, 2H), 4.44–4.65 (m, 2H), 5.13 (d, J=11.7 Hz, 1H), 5.32 (d, J=15.0 Hz, 1H), 5.72–5.85 (m, 2H), 7.20–7.26 (m, 2H), 7.60 (s, 1H), 8.09–8.14 (m, 2H), 9.26 (b, 1H);

LC-MS (retention time: 1.91 min, method B), MS m/z 783 (M⁺+H).

Example 5

Preparation of Compound 5

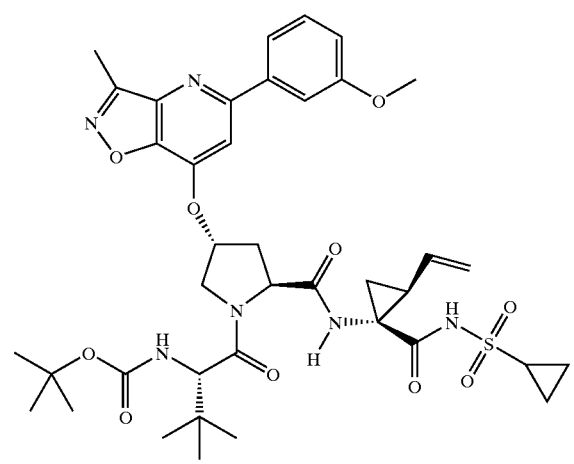

Compound 5

Step 1:

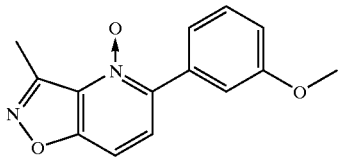

This product was prepared by the same procedure as described in Example 3, Step 1&2, except using 3-methoxyphenethyl alcohol instead.

LC-MS (retention time: 1.03 min, method B), MS m/z 257 (M$^+$+H).

Step 2:

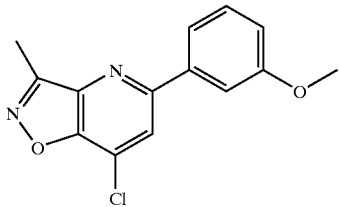

This product was prepared by the same procedure as described in Example 1, Step 2, except using the product of Example 5, Step 1 instead.

$^1$H NMR (CDCl$_3$) δ 2.72 (s, 3H), 3.90 (s, 3H), 7.00–7.02 (m, 1H), 7.41 (t, J=8.0 Hz, 1H), 7.55 (d, J=7.5 Hz, 1H), 7.59 (d, J=2.0 Hz, 1H), 7.89 (s, 1H);

LC-MS (retention time: 1.89 min, method B), MS m/z 275, 277 (M$^+$+H).

Step 3:

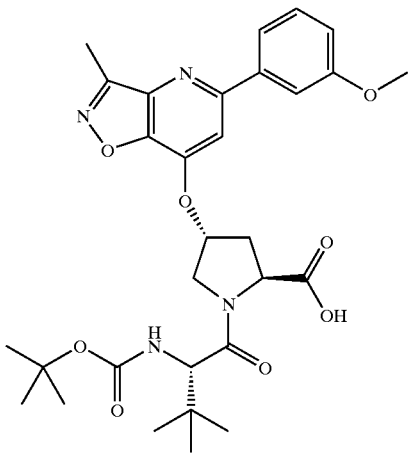

This product was prepared by the same procedure as described in Example 1, Step 5, except using the product of Example 5, Step 2 instead.

$^1$H NMR (CD$_3$OD) δ 1.02 (s, 9H), 1.18 (s, 9H), 2.37–2.47 (m, 1H), 2.64 (s, 3H), 2.85–2.93 (m, 1H), 3.88 (s, 3H), 4.00–4.08 (m, 1H), 4.14 (b, 1H), 4.49–4.55 (m, 1H), 4.62–4.71 (m, 1H), 5.71 (b, 1H), 7.02–7.04 (m, 1H), 7.40 (t, J=8.0 Hz, 1H), 7.58–7.62 (m, 3H);

LC-MS (retention time: 1.90 min, method B), MS m/z 583 (M$^+$+H).

Step 4:

Compound 5 was prepared by the same procedure as described in Example 1, Step 9, except using the product of Example 5, Step 3 instead.

$^1$H NMR (CD$_3$OD) δ 1.01–1.09 (m, 12H), 1.17–1.29 (m, 10H), 1.44–1.47 (m, 1H), 1.87–1.91 (m, 1H), 2.20–2.40 (m, 2H), 2.63–2.65 (m, 4H), 2.89–2.98 (m, 1H), 3.89 (s, 3H), 4.08–4.20 (m, 2H), 4.44–4.65 (m, 2H), 5.13 (d, J=111.7 Hz, 1H), 5.32 (d, J=15.0 Hz, 1H), 5.72–5.85 (m, 2H), 7.02–7.05 (m, 1H), 7.41 (t, J=8.0 Hz, 1H), 7.55–7.61 (m, 3H);

LC-MS (retention time: 1.96 min, method B), MS m/z 795 (M$^+$+H).

Example 6

Preparation of Compound 6

Compound 6

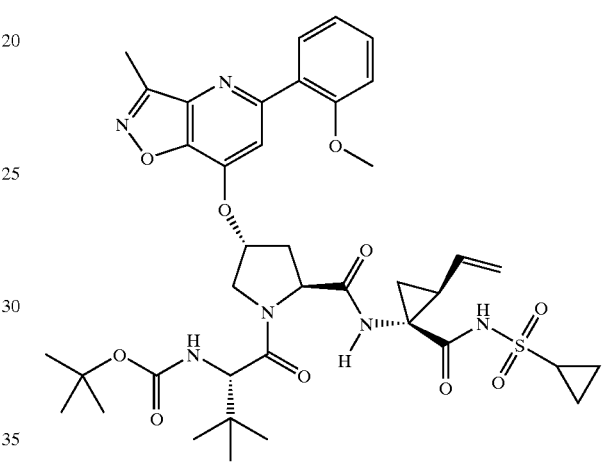

Step 1:

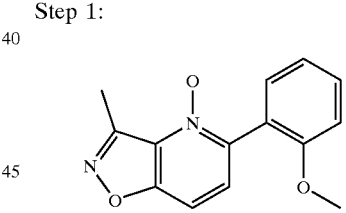

This product was prepared by the same procedure as described in Example 3, Step 1&2, except using 2-methoxyphenethyl alcohol instead.

LC-MS (retention time: 1.10 min, method B), MS m/z 257 (M$^+$+H).

Step 2:

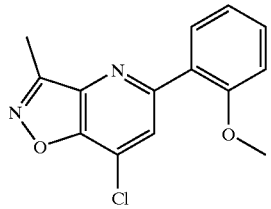

This product was prepared by the same procedure as described in Example 1, Step 2, except using the product of Example 6, Step 1 instead.

¹H NMR (CDCl₃) δ 2.721 (s, 3H), 3.88 (s, 3H), 7.03 (d, J=8.0 Hz, 1H), 7.11 (t, J=7.5 Hz, 1H), 7.41–7.44 (m, 1H), 7.79–7.81 (m, 1H), 8.04 (s, 1H);

LC-MS (retention time: 1.92 min, method B), MS m/z 275, 277 (M⁺+H).

Step 3:

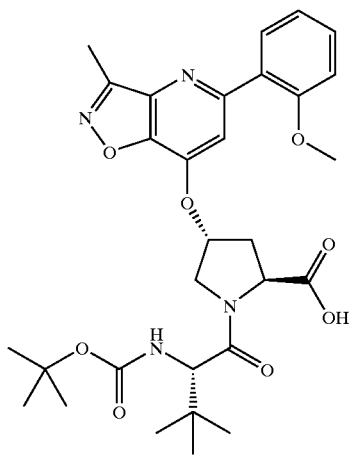

This product was prepared by the same procedure as described in Example 1, Step 5, except using the product of Example 6, Step 2 instead.

¹H NMR (CD₃OD) δ 1.02 (s, 9H), 1.20 (s, 9H), 2.37–2.47 (m, 1H), 2.63 (s, 3H), 2.85–2.93 (m, 1H), 3.89 (s, 3H), 4.00–4.08 (m, 1H), 4.14 (b, 1H), 4.49–4.55 (m, 1H), 4.62–4.71 (m, 1H), 5.56 (b, 1H), 7.09 (t, J=7.5 Hz, 1H), 7.15 (d, J=8.5 Hz, 1H), 7.41–7.44 (m, 1H), 7.52 (s, 1H), 7.67 (d, J=8.0 Hz, 1H);

LC-MS (retention time: 1.76 min, method B), MS m/z 583 (M⁺+H).

Step 4:

Compound 6 was prepared by the same procedure as described in Example 1, Step 9, except using the product of Example 6, Step 3 instead.

¹H NMR (CD₃OD) δ 1.01–1.08 (m, 12H), 1.17–1.26 (m, 10H), 1.44–1.47 (m, 1H), 1.87–1.91 (m, 1H), 2.20–2.40 (m, 2H), 2.63–2.65 (m, 4H), 2.89–2.98 (m, 1H), 3.88 (s, 3H), 4.08–4.12 (m, 1H), 4.19 (b, 1H), 4.44–4.65 (m, 2H), 5.13 (d, J=11.7 Hz, 1H), 5.32 (d, J=15.0 Hz, 1H), 5.59 (b, 1H), 5.72–5.80 (m, 1H), 7.09 (t, J=7.5 Hz, 1H), 7.15 (d, J=8.5 Hz, 1H), 7.41–7.45 (m, 1H), 7.66 (s, 1H), 7.66–7.67 (m, 1H);

LC-MS (retention time: 1.93 min, method B), MS m/z 795 (M⁺+H).

Example 7

Preparation of Compound 7

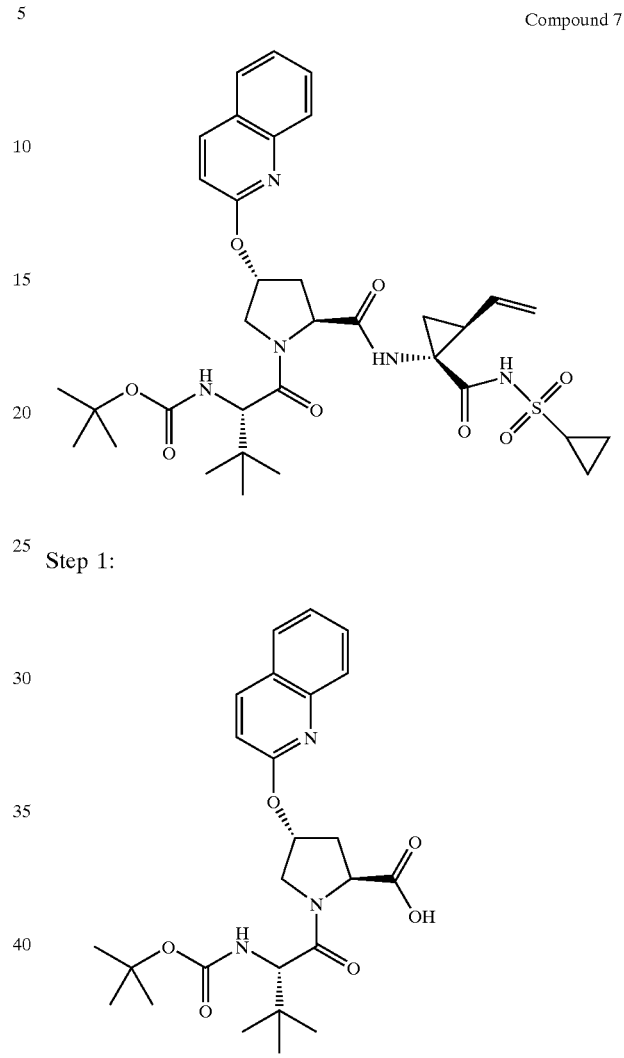

Compound 7

Step 1:

This product was prepared by the same procedure as described in Example 1, Step 5, except using 2-chloroquinoline instead.

LC-MS (retention time: 1.73 min, method B), MS m/z 472 (M⁺+H).

Step 2:

Compound 7 was prepared by the same procedure as described in Example 1, Step 9, except using the product of Example 7, Step 1 instead.

¹H NMR (CD₃OD) δ 1.01–1.08 (m, 12H), 1.17–1.26 (m, 10H), 1.44–1.47 (m, 1H), 1.87–1.91 (m, 1H), 2.23–2.30 (m, 2H), 2.52–2.57 (m, 1H), 2.89–2.98 (m, 1H), 4.10–4.14 (m, 1H), 4.09–4.15 (m, 2H), 4.47–4.51 (m, 1H), 5.13 (d, J=10.0 Hz, 1H), 5.32 (d, J=17.0 Hz, 1H), 5.73–5.78 (m, 1H), 5.92 (b, 1H), 6.90–6.92 (m, 1H), 7.42 (t, J=7.5 Hz, 1H), 7.64 (t, J=7.5 Hz, 1H), 7.78–7.82 (m, 2H), 8.13 (d, J=7.5 Hz, 1H), 9.18 (d, 1H);

LC-MS (retention time: 1.75 min, method B), MS m/z 684 (M⁺+H).

Example 8

Preparation of Compound 8

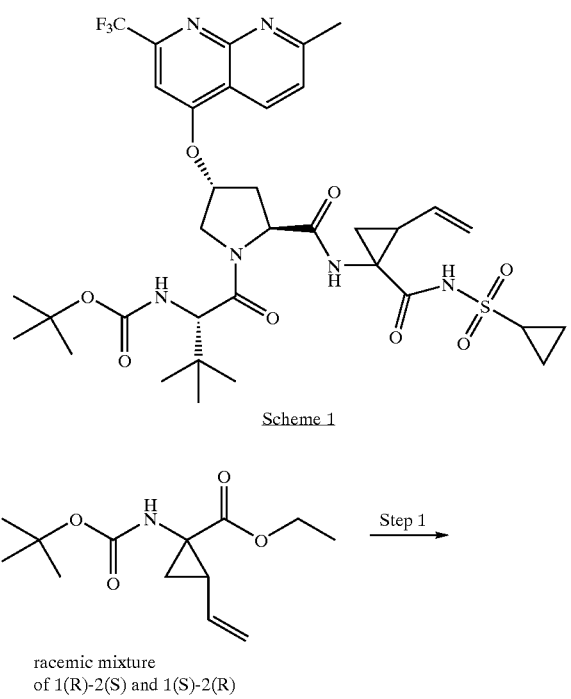

Scheme 1

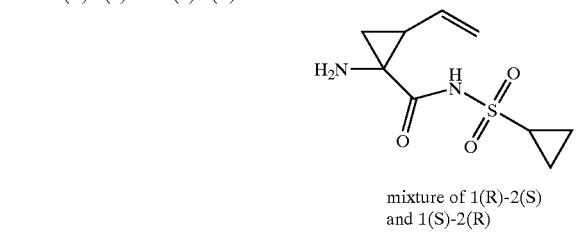

racemic mixture
of 1(R)-2(S) and 1(S)-2(R)

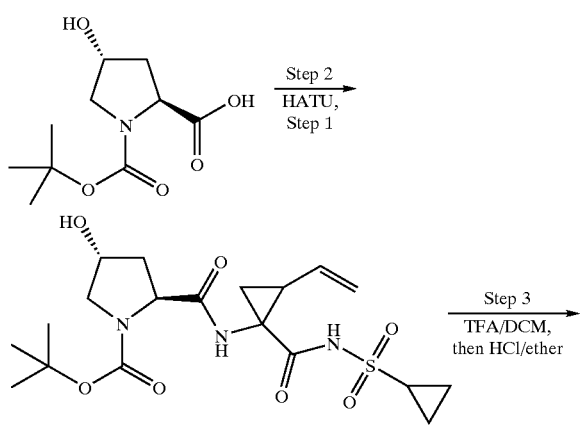

mixture of 1(R)-2(S)
and 1(S)-2(R)

Step 1:

This product was prepared by the same procedure as described in Example 1, Step 6b through 8, without using Step 6a, an enzymatic resolution step.

LC-MS (retention time: 0.24 min, method B), MS m/z 231 (M$^+$+H).

Scheme 2

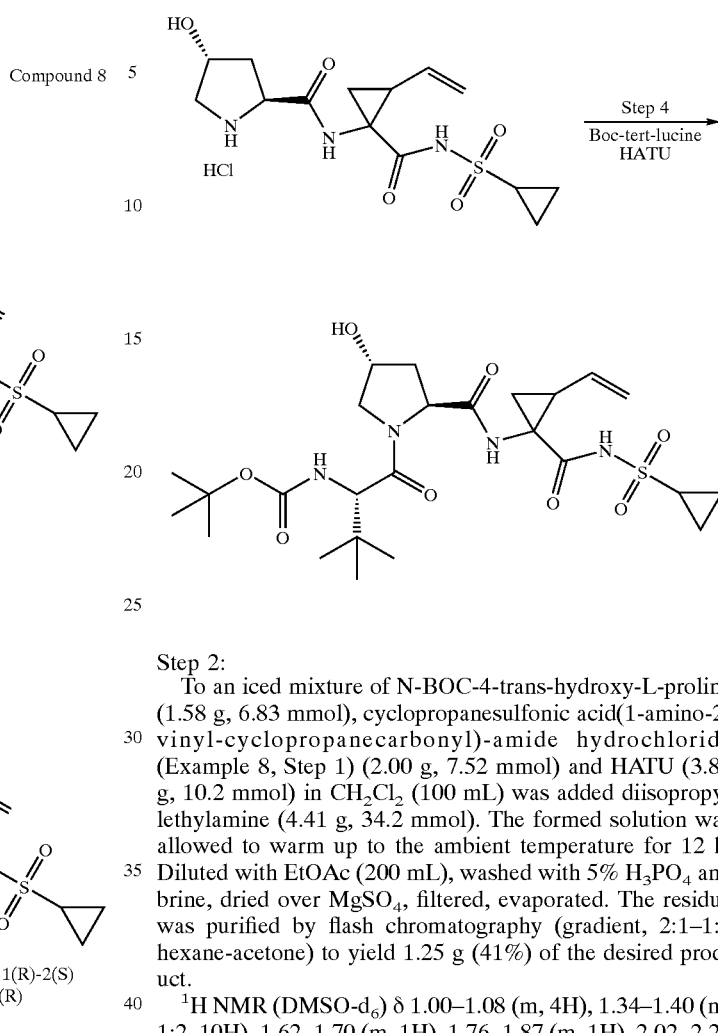

Step 2:

To an iced mixture of N-BOC-4-trans-hydroxy-L-proline (1.58 g, 6.83 mmol), cyclopropanesulfonic acid(1-amino-2-vinyl-cyclopropanecarbonyl)-amide hydrochloride (Example 8, Step 1) (2.00 g, 7.52 mmol) and HATU (3.89 g, 10.2 mmol) in CH$_2$Cl$_2$ (100 mL) was added diisopropylethylamine (4.41 g, 34.2 mmol). The formed solution was allowed to warm up to the ambient temperature for 12 h. Diluted with EtOAc (200 mL), washed with 5% H$_3$PO$_4$ and brine, dried over MgSO$_4$, filtered, evaporated. The residue was purified by flash chromatography (gradient, 2:1–1:1 hexane-acetone) to yield 1.25 g (41%) of the desired product.

$^1$H NMR (DMSO-d$_6$) δ 1.00–1.08 (m, 4H), 1.34–1.40 (m, 1:2, 10H), 1.62–1.70 (m, 1H), 1.76–1.87 (m, 1H), 2.02–2.21 (m, 2H), 2.81–2.95 (m, 1H), 3.20–3.45 (m, 2H), 4.04–4.09 (m, 1H), 4.26 (b, 1H), 5.08–5.12 (m, 1H), 5.26 (d, J=17.1 Hz, 1H), 5.59–5.69 (m, 1H), 8.59, 8:87 (rotamers, 1:2, 1H), 10.48–11.15 (rotamers, 2:1, 1H);

LC-MS (retention time: 1.25 min, method B), MS m/e 444 (M$^+$+H).

Step 3:

This product was prepared by the same procedure as described in Example 1, Step 8, except using the product of Example 8, Step 2 instead.

LC-MS (retention time: 1.02 min, method B), MS m/e 344 (M$^+$+H).

Step 4:

To an iced mixture of N-BOC-4-trans-hydroxy-L-proline (1.58 g, 6.83 mmol), cyclopropanesulfonic acid (1-amino-2-vinyl-cyclopropanecarbonyl)-amide hydrochloride (Example 8, Step 3) (2.00 g, 7.52 mmol) and HATU (3.89 g, 10.2 mmol) in CH$_2$Cl$_2$ (100 mL) was added diisopropylethylamine (4.41 g, 34.2 mmol). The formed solution was allowed to warm up to the ambient temperature for 12 h. Diluted with EtOAc (200 mL), washed with 5% H$_3$PO$_4$ and brine, dried over MgSO$_4$, filtered, evaporated. The residue was purified by flash chromatography (gradient, 2:1–1:1 hexane-acetone) to yield 1.25 g (41%) of the desired product.

$^1$H NMR (CD$_3$OD) δ 0.99–1.07 (m, 11H), 1.35–1.44 (m, 13H), 1.75–1.87 (m, 1H), 2.09–2.22 (m, 2H), 2.88–2.94 (m, 1H), 3.74–3.82 (m, 2H), 4.28–4.30 (m, 1H), 4.33–4.38 (m, 1H), 4.48 (b, 1H), 5.11–5.13 (m, 1H), 5.30 (d, J=15.0 Hz, 1H), 5.70–5.78 (m, 1H), 6.51–6.61 (m, 1H);

LC-MS (retention time: 1.26 min, method B), MS m/e 557 (M$^+$+H).

Scheme 3

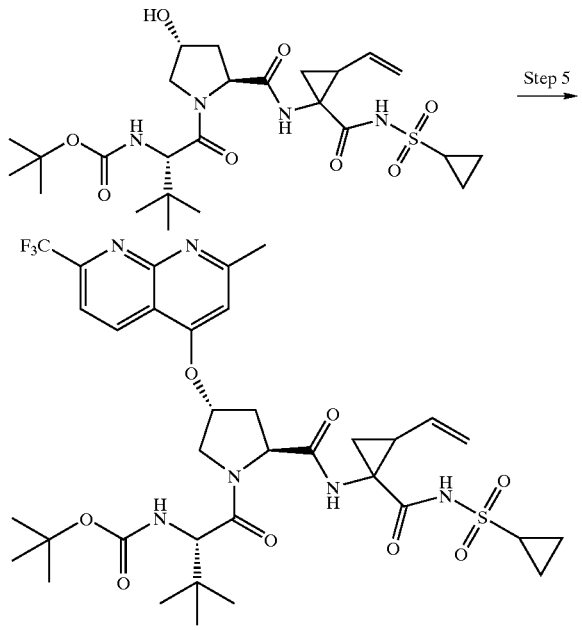

Compound 8

Step 5:

To a solution of the product of Example 8, Step 4 (56 mg, 0.1 mmol) in DMSO (2 mL) was added potassium tert-butoxide (49 mg, 0.44 mmol). The formed solution was stirred at the ambient temperature for 1 h before addition of 4-chloro-7-methyl-2-trifluoromethyl-[1,8]naphthyridine (P. Ferrarini et al, J Heterocyclic Chem, 1983, p1053) (30 mg, 0.12 mmol). The final solution was stirred for 12 h. Quenched with iced water, acidified with 1M HCl to pH 4, extracted with EtOAc (20 mL, ×2). The organic layers were washed with brine, dried over MgSO$_4$, filtered, evaporated. The residue was purified by prep-HPLC to yield 16 mg (21%) of Compound 8 as a pink solid.

$^1$H NMR (CD$_3$OD) δ 0.92–0.99 (m, 11H), 1.01–1.04 (m, 11H), 1.22–1.45 (m, 2H), 1.76–1.85 (m, 1H), 2.18–2.40 (m, 2H), 2.76 (s, 3H), 2.86–2.97 (m, 1H), 4.00–4.11 (m, 2H), 4.48–4.58 (m, 2H), 5.09–5.12 (m, 1H), 5.28–5.31 (m, 1H), 5.59 (b, 1H), 5.69–5.78 (m, 1H), 6.39–6.48 (m, 1H), 7.58–7.64 (m, 2H), 8.08 (s, 1H), 8.64–8.68 (m, 1H), 8.85–8.91 (m, 1H);

LC-MS (retention time: 1.89 min, method B), MS m/e 767 (M$^+$+H).

Example 9

Preparation of Compound 9

Compound 9

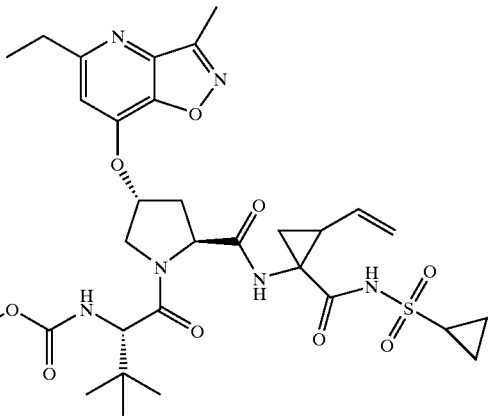

Compound 9 was prepared by the same procedure as described in Example 8, Step 5, except using 7-chloro-5-ethyl-3-methyl-isoxazolo[4,5-b]pyridine (R. Nesi et al, Synth Comm. 1992, 22(16), 2349) instead.

$^1$H NMR (CD$_3$OD) δ 1.01–1.09 (m, 11H), 1.21–1.25 (m, 11H), 1.36 (t, J=7.8 Hz, 3H), 1.38–1.47 (m, 2H), 1.80–1.90 (m, 1H), 2.20–2.31 (m, 2H), 2.59 (s, 3H), 2.90–3.00 (m, 3H), 4.01–4.18 (m, 2H), 4.41–4.51 (m, 2H), 5.11–5.15 (m, 1H), 5.27–5.32 (m, 1H), 5.58 (b, 1H), 5.70–5.80 (m, 1H), 7.11 (s, 1H), 7.72, 7.98 (1:1, 1H), 9.00, 9.22 (1:1, 1H);

LC-MS (retention time: 1.75 min, method B), MS m/e 717 (M$^+$+H).

Example 10

Preparation of Compound 10

Compound 10

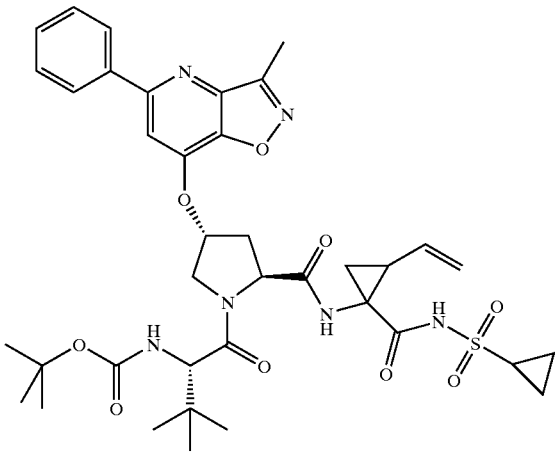

Compound 10 was prepared by the same procedure as described in Example 8, Step 5, except using 7-chloro-5-phenyl-3-methyl-isoxazolo[4,5-b]pyridine (Example 1, Step 2) instead.

$^1$H NMR (CD$_3$OD) δ 1.00–1.09 (m, 12H), 1.16–1.25 (m, 10H), 1.44–1.48 (m, 1H), 1.79–1.89 (m, 1H), 2.20–2.40 (m,

2H), 2.64–2.66 (m, 4H), 2.89–2.98 (m, 1H), 4.08–4.20 (m, 2H), 4.44–4.55 (m, 2H), 5.11–5.16 (m, 1H), 5.27–5.31 (m, 1H), 5.72–5.74 (m, 2H), 7.20–7.35 (m, 1H), 7.46–7.51 (m, 2H), 7.55–7.68 (m, 1H), 8.05–8.06 (m, 2H);

LC-MS (retention time: 1.97 min, method B), MS m/z 765 (M$^+$+H).

Example 11

Preparation of Compound 11

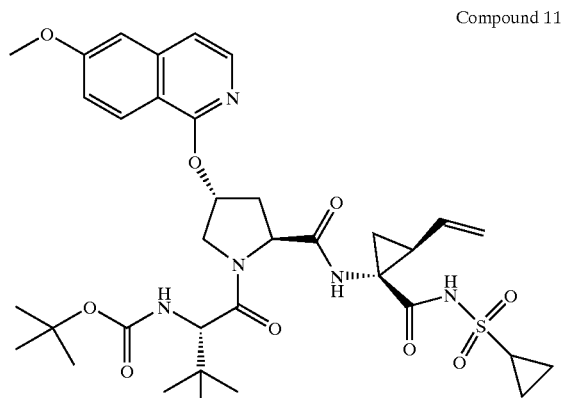

Compound 11

Scheme 1

Step 1:

To a solution of 3-methoxy cinnamic acid (11.04 g, 62 mmol) and triethylamine (12.52 g, 124 mmol) in acetone (80 mL) was added ethyl chloroformate (approximately 1.5 equivalents) dropwise at 0° C. After stirring at this temperature for 1 h, aqueous NaN$_3$ (6.40 g, 100 mmol in 35 mL H$_2$O) was added dropwise and the reaction mixture was stirred for 16 h at the ambient temperature. Water (100 mL) was added to the mixture and the volatile was removed in vacuo. The resulting slurry was extracted with toluene (3×50 mL) and the combined organic layers were dried over MgSO$_4$. This dried solution was added dropwise to a heated solution of diphenylmethane (50 mL) and tributylamine (30 mL) at 190° C. The toluene was distilled off as added. After complete addition, the reaction temperature was raised to 210° C. for 2 h. After cooling, the precipitated product was collected by filtration, washed with hexane (2×50 mL), and dried to yield the desired product as a white solid (5.53 g, 51%) (Nicolas Briet at el, Tetrahedron, 2002, 5761–5766).

LC-MS (retention time: 0.82 min, method B), MS m/z 176 (M$^+$+H).

Step 2:

6-Methoxy-2H-isoquinolin-1-one (5.0 g, 28.4 mmol) in POCl$_3$ (10 mL) was heated to gentle reflux for 3 h the evaporated in vacuo (Nicolas Briet at el, Tetrahedron, 2002, 5761–5766). The residue was poured into iced water (20 mL) and neutralized to pH 10 with 10 M NaOH. Extracted with CHCl$_3$. The organic layer was washed with brine, dried over MgSO$_4$, filtered, evaporated. The residue was purified by flash chromatography (1:1 hexane-EtOAc) to afford 4.41 g (80%) of the desired product as a white solid.

$^1$H NMR (CD$_3$OD) δ 3.98 (s, 3H), 7.34–7.38 (m, 2H), 7.69 (d, J=5.5 Hz, 1H), 8.10 (d, J=6.0 Hz, 1H), 8.23 (d, J=9.5 Hz, 1H);

LC-MS (retention time: 1.42 min, method B), MS m/z 194 (M$^+$+H).

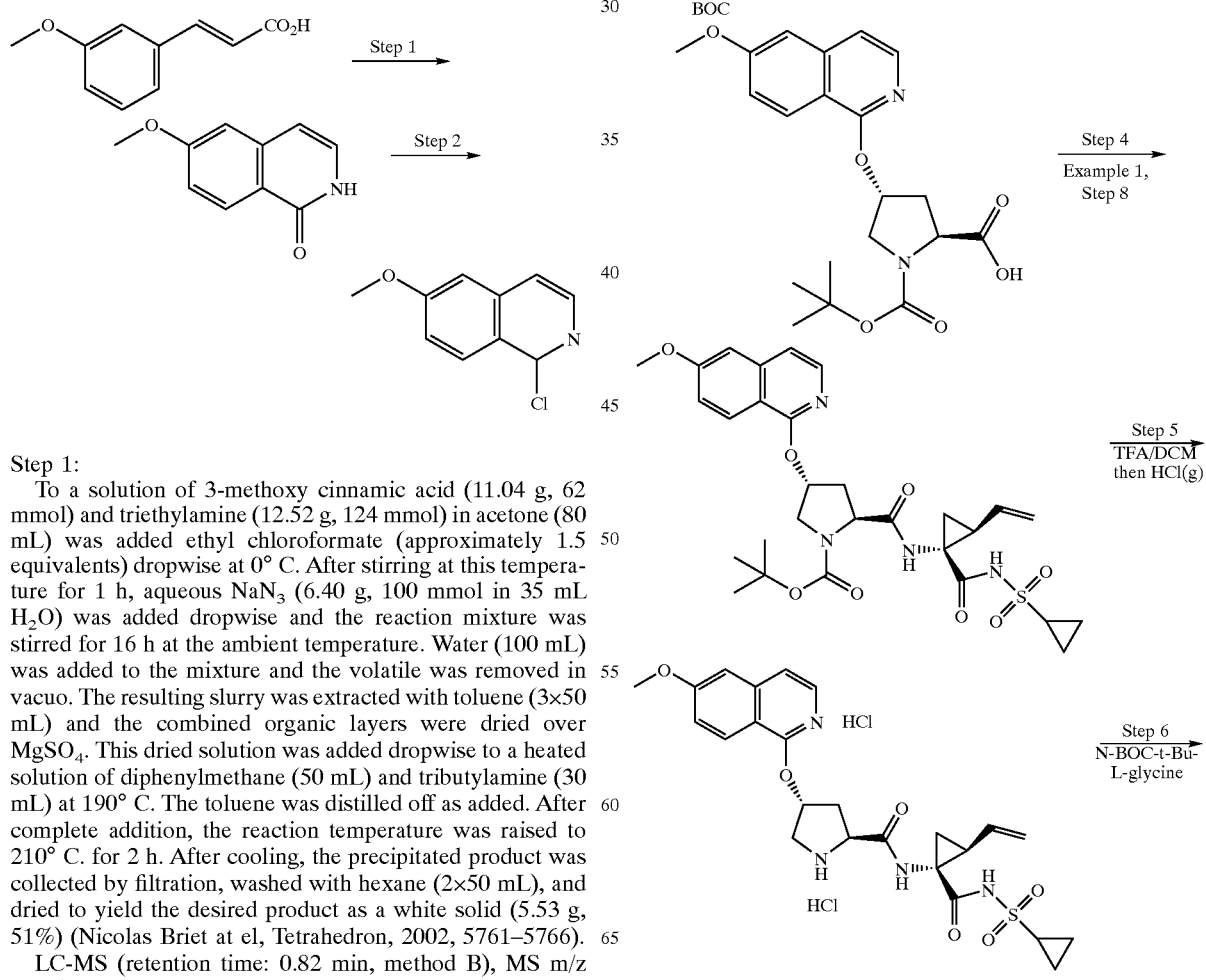

Scheme 2

-continued

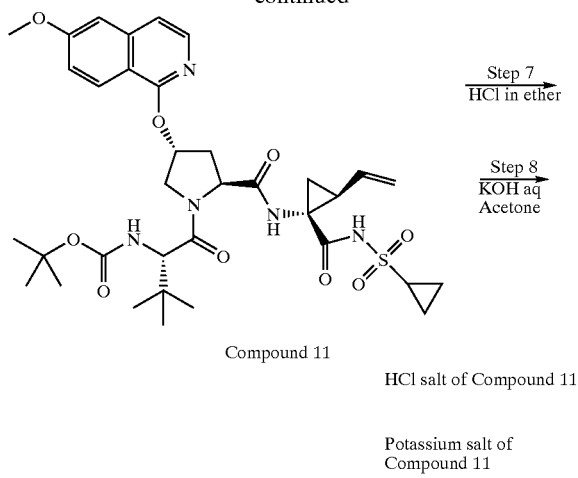

Compound 11

HCl salt of Compound 11

Potassium salt of Compound 11

Step 3:

To a solution of N-BOC-3-(R)-hydroxy-L-proline (892 mg, 3.89 mmol) in DMSO (40 mL) at the ambient temperature was added potassium tert-butoxide (1.34 g, 12.0 mmol) in one portion. The formed suspension was stirred at this temperature for 30 min before being cooled to 10° C. 1-chloro-6-methoxy-isoquinoline (example 11, Step 2) (785 mg, 4.05 mmol) was added as solid in one portion and the final mixture was stirred at the ambient temperature for 12 h. Quenched with iced 5% citric acid (aq), extracted with EtOAC (100 mL). The aqueous phase was extracted with EtOAC again. The combined organic layers were washed with 5% citric acid (aq) and brine respectively, dried over $MgSO_4$, filtered. The filtrate was evaporated in vacuo to dryness to yield 1.49 g (99%) of the desired product as an off-white foam. This material was used in the next step reaction as crude without further purification.

$^1$H NMR ($CD_3OD$) δ 1.42, 1.44 (rotamers, 9H), 2.38–2.43 (m, 1H), 2.66–2.72 (m, 1H), 3.80–3.87 (m, 2H), 3.92 (s, 3H), 4.44–4.52 (m, 1H), 5.73 (b, 1H), 7.16–7.18 (m, 2H), 7.24–7.25 (m, 1H), 7.87–7.88 (m, 1H), 8.07 (d, J=8.5 Hz, 1H);

LC-MS (retention time: 1.62 min, method B), MS m/z 389 ($M^+$+H).

Step 4:

To a mixture of the product of Example 11, Step 3 (1.49 g, 3.84 mmol), HATU (2.19 g, 5.76 mmol), and cyclopropanesulfonic acid (1-(R)-amino-2-(S)-vinyl-cyclopropanecarbonyl)-amide HCl salt (Example 1, Step 8) (1.12 g, 4.22 mmol) in $CH_2Cl_2$ (50 mL) was added DIPEA (1.29 g, 11.5 mmol) at 0° C. After stirring at the ambient temperature for 12 h, the formed solution was diluted with $CH_2Cl_2$ (50 mL), washed with iced 5% citric acid (aq). The organic layer was washed with 5% citric acid (aq) and brine respectively, dried over $MgSO_4$, and filtered. The filtrate was evaporated in vacuo to dryness. The residue was recrystallized from methanol to yield 1.60 g (70%) of the desired product as a white solid.

$^1$H NMR ($CD_3OD$) δ 1.05–1.08 (m, 2H), 1.16–1.20 (m, 1H), 1.24–1.27 (m, 1H), 1.42–1.45 (m, 10H), 1.88 (dd, J=8.09, 5.34 Hz, 1H), 2.24–2.30 (m, 2H), 2.53–2.57 (m, 1H), 2.94–2.98 (m, 1H), 3.80 (d, J=12.5 Hz, 1H), 3.86–3.89 (m, 1H), 3.93 (s, 3H), 4.40–4.42 (m, 1H), 5.13 (d, J=10.5 Hz, 1H), 5.32 (d, J=18.0 Hz, 1H), 5.72–5.81 (m, 2H), 7.17–7.20 (m, 2H), 7.26 (d, J=6.0 Hz, 1H), 7.88 (d, J=6.0 Hz, 1H), 8.07 (d, J=9.0 Hz, 1H);

LC-MS (retention time: 1.74 min, method B), MS m/z 601 ($M^+$+H).

Step 5:

To an iced solution of the product of Example 11, Step 4 (1.50 g, 2.50 mmol) in $CH_2Cl_2$ (10 mL) was added TFA (10 mL). The formed solution was allowed to warm to the ambient temperature for 2 h. The solvent was removed in vacuo. The residue was triturated with 1M HCl in ether. Filtered, washed with ether to yield 1.43 g (99.8%) of the desired product as a hygroscopic white solid.

$^1$H NMR ($CD_3OD$) δ 1.03–1.208 (m, 4H), 1.26–1.31 (m, 1H), 1.37–1.40 (m, 1H), 1.95–1.97 (m, 1H), 2.32–2.37 (m, 1H), 2.42–2.48 (m, 1H), 2.95–2.99 (m, 1H), 3.88 (d, J=12.5 Hz, 2H), 3.98 (s, 3H), 4.40–4.42 (m, 1H), 5.16 (d, J=10.5 Hz, 1H), 5.33 (d, J=18.0 Hz, 1H), 5.62–5.69 (m, 1H), 5.97 (b, 1H), 7.30–7.34 (m, 2H), 7.47 (d, J=6.0 Hz, 1H), 7.90 (d, J=6.5 Hz, 1H), 8.34 (d, J=9.0 Hz, 1H), 9.14 (b, 1H);

LC-MS (retention time: 1.12 min, method B), MS m/z 501 ($M^+$+H).

Step 6:

To a mixture of the product of Example 11, Step 5 (1.49 g, 3.84 mmol), HATU (2.19 g, 5.76 mmol), and N-BOC-t-butyl-L-glycine (1.12 g, 4.22 mmol) in $CH_2Cl_2$ (50 mL) was added DIPEA (1.29 g, 11.5 mmol) at 0° C. After stirring at the ambient temperature for 12 h, the formed solution was diluted with $CH_2Cl_2$ (50 mL), washed with iced 5% citric acid (aq). The organic layer was washed with 5% citric acid (aq) and brine respectively, dried over $MgSO_4$, and filtered. The filtrate was evaporated in vacuo to dryness. The residue was purified by prep-HPLC (40% B to 100% B, 15 min gradient time) to yield 1.60 g (70%) of Compound 11 as a white solid.

$^1$H NMR ($CD_3OD$) δ 1.00–1.08 (m, 12H), 1.23–1.25 (m, 1H), 1.27 (s, 9H), 1.40–1.45 (m, 1H), 1.85–1.88 (m, 1H), 2.20–2.30 (m, 2H), 2.55–2.61 (m, 1H), 2.91–2.97 (m, 1H), 3.92 (s, 3H), 4.02–4.06 (m, 1H), 4.21–4.24 (m, 1H), 4.40–4.42 (m, 1H), 4.49–4.51 (m, 1H), 5.12 (d, J=10.5 Hz, 1H), 5.28 (d, J=18.0 Hz, 1H), 5.69–5.74 (m, 1H), 5.81 (b, 1H), 6.60 (d, J=10.0 Hz, 1H), 7.08–7.10 (m, 1H), 7.18 (s, 1H), 7.25 (d, J=6.0 Hz, 1H), 7.88 (d, J=6.0 Hz, 1H), 8.09 (d, J=9.0 Hz, 1H);

LC-MS (retention time: 1.75 min, method B), MS m/z 714 ($M^+$+H);

Anal. Calcd for $C_{35}H_{47}N_5O_9S$-$0.5H_2O$: C, 58.16; H, 6.69; N, 9.69, Found: C, 58.01; H, 6.46; N, 9.55.

Step 7:

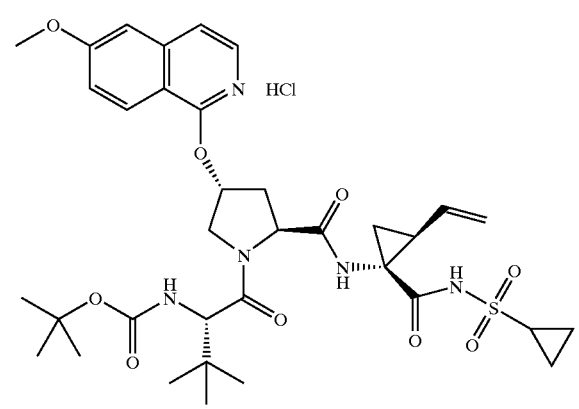

To a solution of Compound 11 (71 mg, 0.1 mmol) in $CH_2Cl_2$ (5 mL) at −78° C. was added 1M HCl in ether (0.2 mL, 0.2 mmol). After stirring at this temperature for 10 min, the volatile was removed in vacuo without heating bath. The residue was triturated with ether, filtered, washed with ether and dried to yield 61 mg (85%) of the desired HCl salt of Compound 11 as a very fine solid.

¹H NMR (CD₃OD) δ 1.00–1.08 (m, 12H), 1.19 (s, 9H), 1.23–1.25 (m, 1H), 1.40–1.45 (m, 1H), 1.85–1.91 (m, 1H), 2.20–2.26 (m, 1H), 2.31–2.42 (m, 1H), 2.65–2.78 (m, 1H), 2.92–2.97 (m, 1H), 4.00 (s, 3H), 4.10–4.16 (m, 2H), 4.51–4.64 (m, 2H), 5.13 (d, J=10.5 Hz, 1H), 5.30 (d, J=18 Hz, 1H), 5.69–5.79 (m, 1H), 5.84 (b, 1H), 7.28 (d, J=9.3 Hz, 1H), 7.40 (s, 1H), 7.55 (d, J=6.3 Hz, 1H), 7.89–7.92 (m, 1H), 8.29 (d, J=9.0 Hz, 1H), 9.21 (b, 1H);

LC-MS (retention time: 1.75 min, method B), MS m/z 714 (M⁺+H).

Anal. Calcd for C₃₅H₄₇N₅O₉S.1.0 HCl: C, 56.02; H, 6.44; N, 9.33; Cl, 4.72: S, 4.27. Found: C, 55.80; H, 6.42; N, 9.15; Cl, 4.56: S, 4.09.

Step 8:

To a 25 ml 2 neck flask was added a stir bar, septa and N₂ gas adapter. Compound 11 (99.7 mg, 0.140 mmol) was weighed out and added to the reaction flask. The reaction flask was purged and placed under a N₂ atmosphere. 850 ul of acetone was added to the flask to provide a clear solution. To this solution at room temperature was added 780 ul of a 0.179 M solution of KOH (aq.) prepared by the dissolution of solid KOH (502.8 mg, 8.97 mmol) in 50 ml of H₂O. The solution warmed slightly upon addition of the KOH but remained clear. The clear solution was allowed to stir at RT for 2 hours. The product crystallized out of solution and was isolated by filtration. The cake was washed with cold acetone to afford 42 mg (40% yield) of the desired product as fine white needles: ¹H NMR (DMSO) δ 0.68 (m, 1H), 0.72 (m, 1H), 0.88 (s, 1H), 0.92 (s, 1H), 1.24 (s, 1H), 1.38 (s, 1H), 1.50 (b, 1H), 1.81 (b, 1H), 2.68 (b, 2H), 3.90 (s, 3H), 3.95–4.10 (m, 3H), 4.40 (t, J=10 Hz, 1H), 4.85 (m, 1H), 5.04 (m, 1H), 5.71 (b, 1H), 6.01 (b, 1H), 6.64 (d, J=10 Hz, 1H), 7.10 (m, 1H), 7.30 (m, J=5 Hz, 2H), 7.95 (d, J=10 Hz, 1H), 8.08 (d, J=15 Hz, 1H).

Elemental analysis for C₃₅H₄₆KN₅O₉S.H₂O; calc. C, 54.60; H, 6.28; K, 5.08; N, 9.10 actual C, 54.88; H, 6.23; K, 5.05; N, 9.01; MS m/e 714 (MH⁺);

Example 12

Preparation of Compound 12

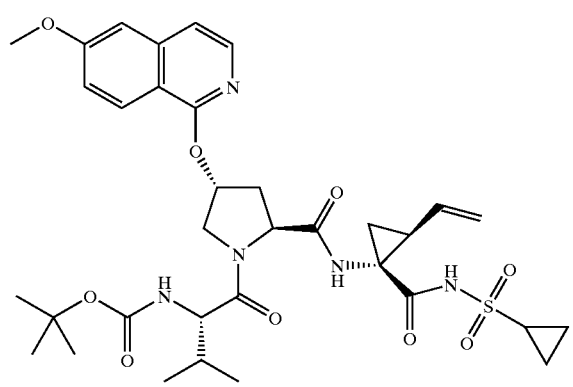

Compound 12

Compound 12 was prepared by the same procedure as described in Example 11, Step 6, except using N-BOC-L-valine instead.

¹H NMR (CD₃OD) δ 0.94–0.98 (m, 6H), 1.07–1.09 (m, 3H), 1.21–1.25 (m, 10H), 1.40–1.43 (m, 1H), 1.88–1.89 (m, 1H), 2.05–2.09 (m, 1H), 2.22–2.35 (m, 2H), 2.57–2.61 (m, 1H), 2.94–2.97 (m, 1H), 3.92 (s, 3H), 4.03–4.06 (m, 2H), 4.47–4.55 (m, 2H), 5.12 (d, J=10.5 Hz, 1H), 5.32 (d, J=18.1 Hz, 1H), 5.74–5.81 (m, 1H), 5.86 (b, 1H), 7.10 (d, J=9.0 Hz, 1H), 7.18 (s, 1H), 7.25 (d, J=6.0 Hz, 1H), 7.88 (d, J=6.0 Hz, 1H), 8.10 (d, J=9.0 Hz, 1H);

LC-MS (retention time: 1.71 min, method B), MS m/z 700 (M⁺+H).

Example 13

Preparation of Compound 13

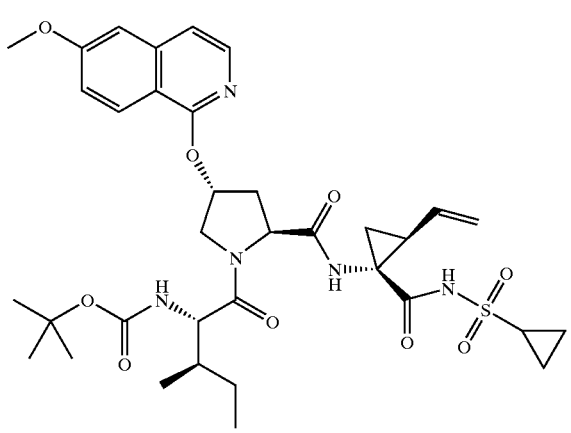

Compound 13

Compound 13 was prepared by the same procedure as described in Example 11, Step 6, except using N-BOC-L-alloisoleucine instead.

¹H NMR (CD₃OD) δ 0.89–0.96 (m, 6H), 1.07–1.18 (m, 5H), 1.28 (s, 9H), 1.42–1.45 (m, 1H), 1.50–1.54 (m, 1H), 1.87–1.89 (m, 2H), 2.23–2.34 (m, 2H), 2.57–2.61 (m, 1H), 2.92–2.95 (m, 1H), 3.92 (s, 3H), 4.05–4.07 (m, 1H), 4.22–4.24 (m, 1H), 4.37–4.40 (m, 1H), 4.54–4.56 (m, 1H), 5.13 (d, J=10.5 Hz, 1H), 5.32 (d, J=18.0 Hz, 1H), 5.75–5.82 (m, 1H), 5.86 (b, 1H), 7.12 (d, J=9.0 Hz, 1H), 7.19 (s, 1H), 7.24 (d, J=6.0Hz, 1H), 7.88 (d, J=6.0 Hz, 1H), 8.10 (d, J=9.0 Hz, 1H);

LC-MS (retention time: 1.77 min, method B), MS m/z 714 (M⁺+H).

Example 14

Preparation of Compound 14

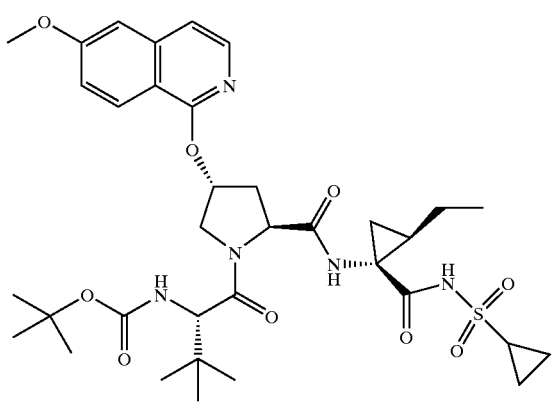

Compound 14

81
-continued
Scheme 1

Cmpd 11 →(Step 1, Pd(OH)₂)

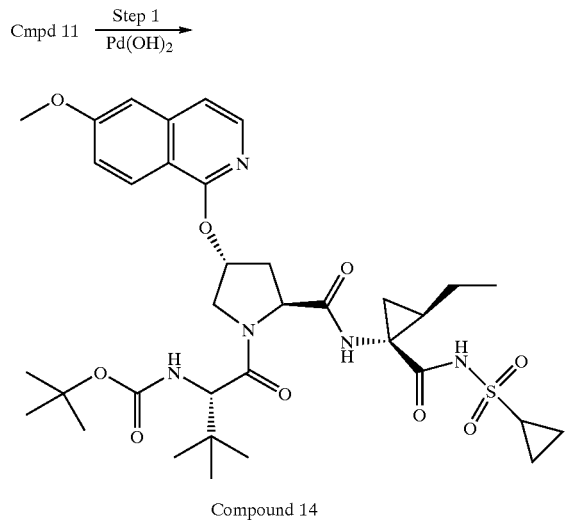

Compound 14

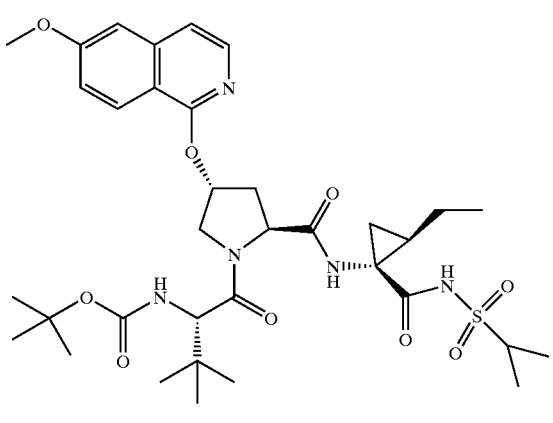

Compound 15

Step 1:

A mixture of Compound 11 (150 mg, 0.21 mmol) and Pearlmann's catalyst (Pd(OH)₂, 15 mg) in EtOAc (10 mL) was placed on Parr shaker for 20 min under 10 psi H₂. Filtered through celite. The filtrate was evaporated in vacuo. The residue was purified by prep-HPLC to provide 67 mg (45%) of Compound 14 as a white solid.

$^1$H NMR (CD₃OD) δ 0.96–0.99 (m, 4H), 1.04 (s, 9H), 1.07–1.09 (m, 2H), 1.21–1.24 (m, 2H), 1.27 (s, 9H), 1.51–1.65 (m, 4H), 2.25–2.27 (m, 1H), 2.55–2.61 (m, 1H), 2.94–2.98 (m, 1H), 3.92 (s, 3H), 4.02–4.06 (m, 1H), 4.21–4.24 (m, 1H), 4.40–4.42 (m, 1H), 4.49–4.51 (m, 1H), 5.81 (b, 1H), 6.59 (d, J=10.0 Hz, 1H), 7.08–7.10 (m, 1H), 7.18 (d, J=1.5 Hz, 1H), 7.24 (d, J=6.0 Hz, 1H), 7.88 (d, J=6.0 Hz, 1H), 8.08 (d, J=9.0 Hz, 1H);

LC-MS (retention time: 1.76 min, method B), MS m/z 716 (M⁺+H).

82

Example 15

Preparation of Compound 15

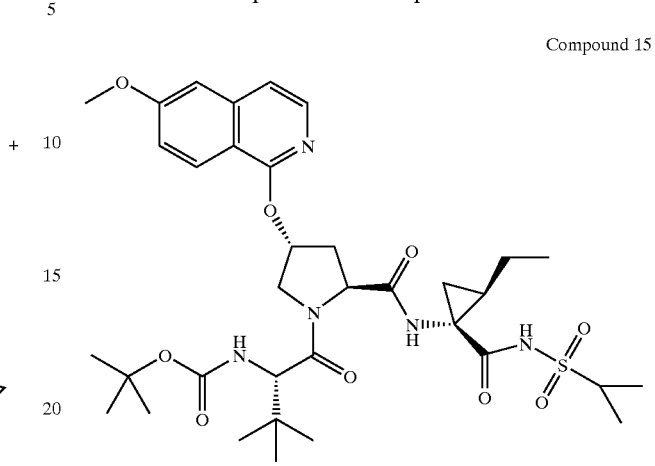

Compound 15

Compound 15 was isolated form the same reaction of making Compound 14 with a slightly longer retention time as a by-product in 15% yield.

$^1$H NMR (CD₃OD) δ 0.92–1.10 (m, 17H), 1.26–1.36 (m, 13H), 1.64–1.72 (m, 1H), 1.90–1.96 (m, 1H), 2.30–2.40 (m, 1H), 2.63–2.67 (m, 1H), 2.96–3.00 (m, 1H), 3.92 (s, 3H), 4.03–4.07 (m, 1H), 4.24 (b, 1H), 4.40–4.42 (m, 1H), 4.49–4.51 (m, 1H), 5.83 (b, 1H), 7.08–7.11 (m, 1H), 7.19 (d, J=2.0 Hz, 1H), 7.25 (d, J=6.0 Hz, 1H), 7.89 (d, J=6.0 Hz, 1H), 8.10 (d, J=9.0 Hz, 1H), 8.51 (b, 1H);

LC-MS (retention time: 1.83 min, method B), MS m/z 718 (M⁺+H).

Example 16

Preparation of Compound 16

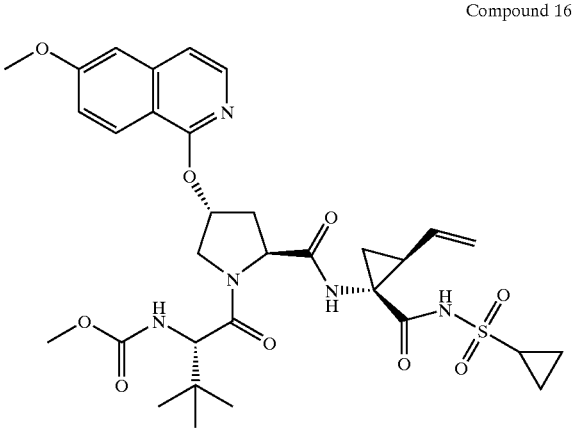

Compound 16

Scheme 1

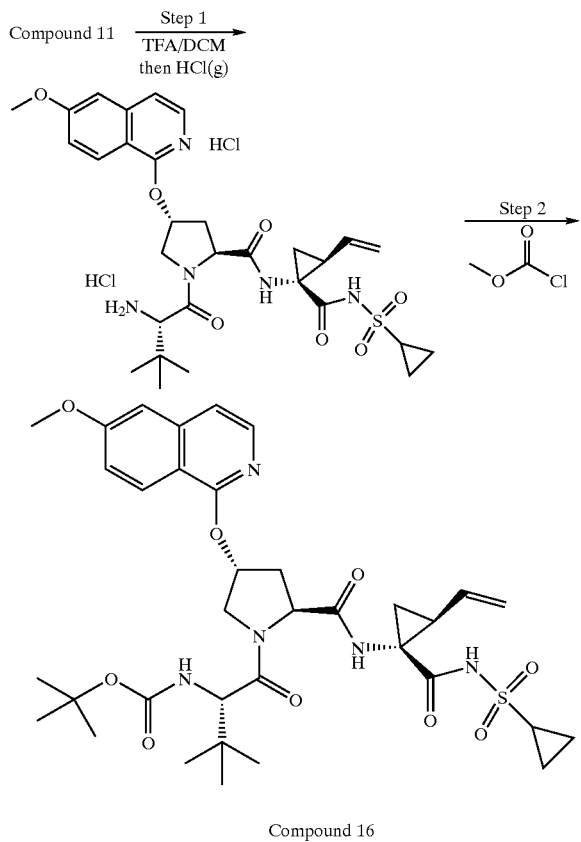

Step 1:

To a solution of Compound 11 (420 mg, 0.59 mmol) in DCM (5 mL) at 0° C. was added TFA (5 mL). After stirring at this temperature for 2 h, the volatile was removed in vacuo. The residue was triturated with 1M HCl in ether (5 mL), filtered, washed with ether and dried to yield 360 mg (89%) of the desired HCl salt as a very fine solid.

LC-MS (retention time: 1.28 min, method B), MS m/z 614 (M$^+$+H).

Step 2:

To a suspension of the product of Example 16, Step 1 (39 mg, 0.06 mmol), and DIPEA (20 mg, 0.18 mmol) in DCM (1 mL) at 0° C. was added methyl chloroformate (6.8 mg, 0.072 mmol). After stirring at this temperature for 2 h, the volatile was removed in vacuo. The residue was purified by prep-HPLC to give 21 mg (58%) of Compound 16 as a white crystal.

$^1$H NMR (CD$_3$OD) δ 1.05–1.09 (m, 11H), 1.22–1.25 (m, 2H), 1.41–1.44 (m, 1H), 1.86–1.89 (m, 1H), 2.22–2.32 (m, 2H), 2.59–2.63 (m, 1H), 2.89–2.93 (m, 1H), 3.48 (s, 3H), 3.92 (s, 3H), 4.06–4.10 (m, 1H), 4.31–4.33 (m, 1H), 4.38–4.40 (m, 1H), 4.50–4.52 (m, 1H), 5.12 (d, J=10.5 Hz, 1H), 5.30 (d, J=18.0 Hz, 1H), 5.71–5.80 (m, 1H), 5.85 (b, 1H), 6.95 (d, J=10.0 Hz, 1H), 7.13–7.16 (m, 1H), 7.19 (s, 1H), 7.25 (d, J=6.0 Hz, 1H), 7.88 (d, J=6.0 Hz, 1H), 8.09 (d, J=9.0 Hz, 1H);

LC-MS (retention time: 1.54 min, method B), MS m/z 672 (M$^+$+H).

Example 17

Preparation of Compound 17

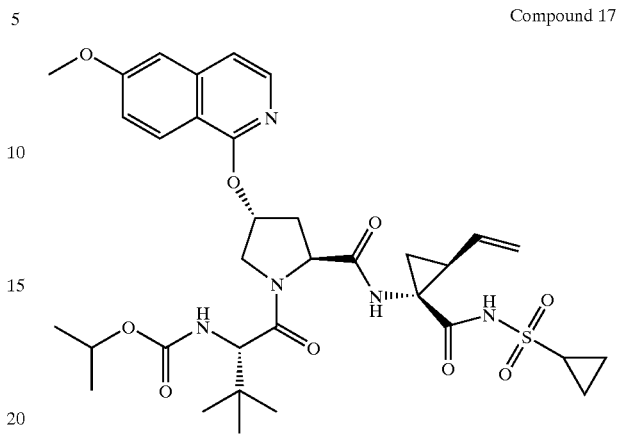

Compound 17

Compound 17 was prepared by the same procedure as described in Example 16, Step 2, except using isopropyl chloroformate instead.

$^1$H NMR (CD$_3$OD) δ 1.00–1.09 (m, 15H), 1.13–1.16 (m, 2H), 1.24–1.26 (m, 2H), 1.40–1.45 (m, 1H), 1.86–1.89 (m, 1H), 2.21–2.31 (m, 2H), 2.55–2.61 (m, 1H), 2.91–2.97 (m, 1H), 3.92 (s, 3H), 4.04–4.08 (m, 1H), 4.30 (b, 1H), 4.40 (d, J=10 Hz, 1H), 4.49–4.54 (m, 2H), 5.12 (d, J=10.5 Hz, 1H), 5.29 (d, J=18.0 Hz, 1H), 5.71–5.77 (m, 1H), 5.84 (b, 1H), 6.80 (d, J=10.0 Hz, 1H), 7.11 (d, J=9.0 Hz, 1H), 7.19 (s, 1H), 7.25 (d, J=6.0 Hz, 1H), 7.88 (d, J=6.0 Hz, 1H), 8.08 (d, J=9.0 Hz, 1H);

LC-MS (retention time: 1.74 min, method B), MS m/z 700 (M$^+$+H).

Example 18

Preparation of Compound 18

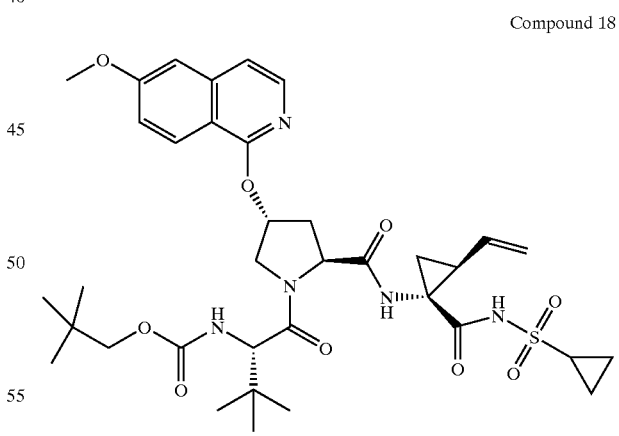

Compound 18

Compound 18 was prepared by the same procedure as described in Example 16, Step 2, except using neopentyl chloroformate instead.

$^1$H NMR (CD$_3$OD) δ 0.61 (b, 1H), 0.84 (s, 8H), 1.05–1.09 (m, 11H), 1.23–1.25 (m, 2H), 1.39–1.44 (m, 1H), 1.85–1.88 (m, 1H), 2.20–2.30 (m, 2H), 2.56–2.62 (m, 1H), 2.91–2.97 (m, 1H), 3.38 (d, J=9.0 Hz, 1H), 3.55 (d, J=9.0 Hz, 1H), 3.92 (s, 3H), 4.02–4.06 (m, 1H), 4.32 (d, J=9.5 Hz, 1H), 4.41 (d, J=9.0 Hz, 1H), 4.49–4.51 (m, 1H), 5.12 (d, J=10.5 Hz, 1H), 5.28 (d, J=18.0 Hz, 1H), 5.69–5.74 (m, 1H), 5.81 (b, 1H), 6.90 (d, J=10.0 Hz, 1H), 7.08–7.10 (m, 1H), 7.19 (s, 1H), 7.26 (d, J=6.0 Hz, 1H), 7.88 (d, J=6.0 Hz, 1H), 8.07 (d, J=9.0 Hz, 1H);

LC-MS (retention time: 1.84 min, method B), MS m/z 728 (M⁺+H).

Example 19

Preparation of Compound 19

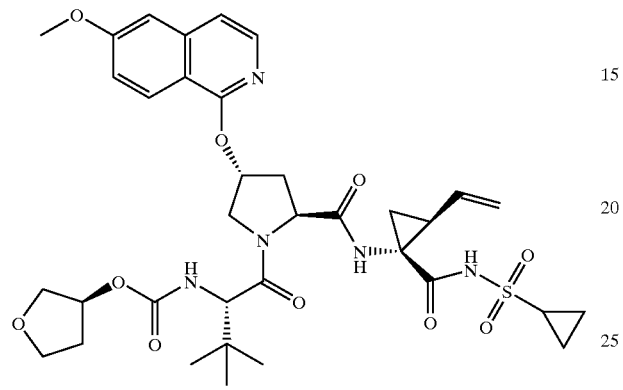

Compound 19

Compound 19 was prepared by the same procedure as described in Example 16, Step 2, except using (S)-3-furanochloroformate (J. Campbell, A. Good, WO 20020808) instead.

¹H NMR (CD₃OD) δ 1.03–1.08 (m, 11H), 1.23–1.26 (m, 2H), 1.38–1.46 (m, 1H), 1.64–1.71 (m, 1H), 1.85–1.90 (m, 2H), 2.20–2.30 (m, 2H), 2.55–2.61 (m, 1H), 2.91–2.97 (m, 1H), 3.66–3.72 (m, 4H), 3.93 (s, 3H), 4.05–4.09 (m, 1H), 4.27–4.29 (m, 1H), 4.40–4.42 (m, 1H), 4.55–4.59 (m, 1H), 4.75–4.77 (m, 1H), 5.12 (d, J=10.5 Hz, 1H), 5.28 (d, J=18 Hz, 1H), 5.73–5.80 (m, 1H), 5.85 (b, 1H), 7.06 (d, J=10.0 Hz, 1H), 7.13 (d, J=9.0 Hz, 1H), 7.20 (s, 1H), 7.25 (d, J=6.0 Hz, 1H), 7.89 (d, J=6.0 Hz, 1H), 8.07 (d, J=9.0 Hz, 1H);

LC-MS (retention time: 1.52 min, method B), MS m/z 728 (M⁺+H).

Example 20

Preparation of Compound 20

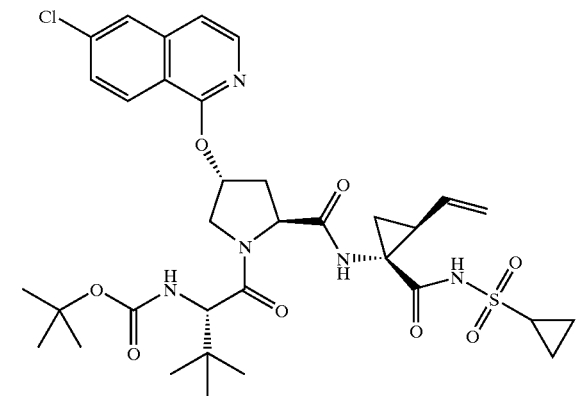

Compound 20

Step 1:

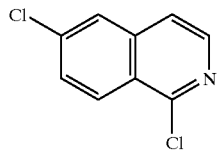

This product was prepared by the same procedure as described in Example 11, Step 2, except using 6-chloro-2H-isoquinolin-1-one ((Nicolas Briet at el, Tetrahedron, 2002, 5761–5766) instead.

LC-MS (retention time: 1.07 min, method B), MS m/z 180 (M⁺+H).

Step 2:

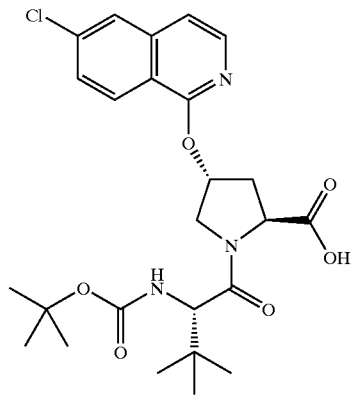

This product was prepared by the same procedure as described in Example 1, Step 5, except using the product of Example 20, Step 1 instead.

¹H NMR (CD₃OD) δ 1.04 (s, 9H), 1.20 (s, 9H), 2.36–2.41 (m, 1H), 2.74–2.78 (m, 1H), 4.01–4.04 (m, 1H), 4.19–4.21 (m, 1H), 4.47–4.49 (m, 1H), 4.67–4.70 (m, 1H), 5.84 (b, 1H), 7.28 (d, J=6.0 Hz, 1H), 7.47 (d, J=6.0 Hz, 1H), 7.84 (s, 1H), 8.00 (d, J=6.0 Hz, 1H), 8.20 (d, J=9.0 Hz, 1H);

LC-MS (retention time: 1.88 min, method B), MS m/z 506 (M⁺+H).

Step 3:

Compound 20 was prepared by the same procedure as described in Example 1, Step 9, except using the product of Example 20, Step 2 instead.

¹H NMR (CD₃OD) δ 0.99–1.11 (m, 12H), 1.20–1.26 (m, 10H), 1.43–1.46 (m, 1H), 1.87–1.90 (m, 1H), 2.22–2.31 (m, 2H), 2.60–2.64 (m, 1H), 2.92–2.97 (m, 1H), 4.06–4.08 (m, 1H), 4.21–4.23 (m, 1H), 4.45–4.47 (m, 1H), 4.53–4.56 (m, 1H), 5.13 (d, J=10.5 Hz, 1H), 5.29 (d, J=18.0 Hz, 1H), 5.72–5.80 (m, 1H), 5.88 (b, 1H), 6.58 (d, J=10.0 Hz, 1H), 7.29 (d, J=6.0 Hz, 1H), 7.47 (d, J=9.0 Hz, 1H), 7.86 (s, 1H), 8.01 (d, J=6.0 Hz, 1H), 8.18 (d, J=9.0 Hz, 1H);

LC-MS (retention time: 1.94 min, method B), MS m/z 718 (M⁺+H).

Example 21

Preparation of Compound 21

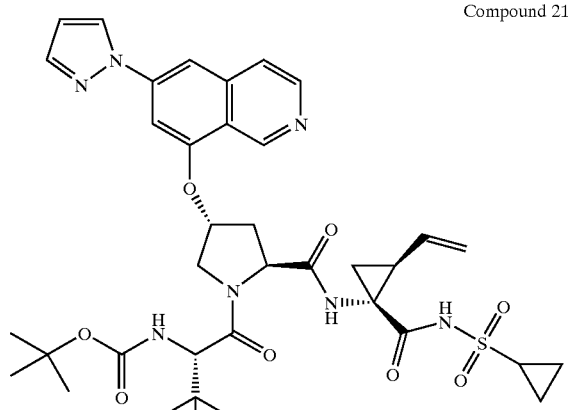

Scheme 1

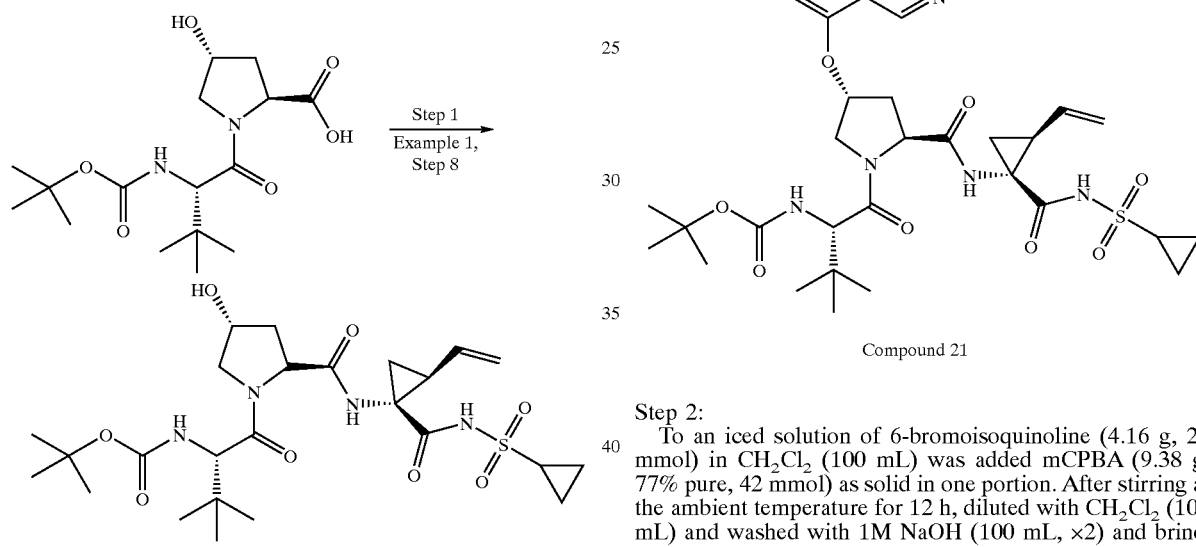

Scheme 2

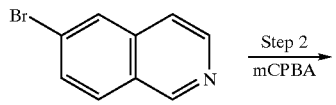

Step 1:

To a mixture of the product of Example 1, Step 4 (3.00 g, 8.72 mmol), HATU (4.97 g, 13.1 mmol), and product of Example 1, Step 8 (2.55 g, 9.59 mmol) in CH$_2$Cl$_2$ (100 mL) was added DIPEA (3.02 g, 27.0 mmol) at 0° C. After stirring at the ambient temperature for 12 h, the formed solution was diluted with CH$_2$Cl$_2$ (100 mL), washed with iced 5% citric acid (aq). The organic layer was washed with 5% citric acid (aq) and brine respectively, dried over MgSO$_4$, and filtered. The filtrate was evaporated in vacuo to dryness. The residue was purified by flash column (1:1 hexane:acetone) to yield 3.64 g (75%) of the desired product as a foam.

LC-MS (retention time: 1.41 min, method B), MS m/z 557 (M$^+$+H).

Step 2:

To an iced solution of 6-bromoisoquinoline (4.16 g, 20 mmol) in CH$_2$Cl$_2$ (100 mL) was added mCPBA (9.38 g, 77% pure, 42 mmol) as solid in one portion. After stirring at the ambient temperature for 12 h, diluted with CH$_2$Cl$_2$ (100 mL) and washed with 1M NaOH (100 mL, ×2) and brine. The organic layer was dried over MgSO$_4$, filtered, evaporated to dryness to yield 3.83 g (86%) of the desired product as a white solid. This material was used as crude without further purification.

LC-MS (retention time: 0.77 min, method B), MS m/z 224, 226(M$^+$+H).

Step 3:

A mixture of 6-bromo-isoquinoline 2-oxide (88 mg, 0.2 mmol), pyrazole (68 mg, 1.0 mmol), CuBr (57 mg, 0.4 mmol) and cesium carbonate (130 mg, 0.4 mmol) in DMF (2 mL) was heated to 140° C. for 4 h in a sealed tube. After filtration, the filtrated was purified by prep-HPLC to yield 41 mg (98%) of the desired product as an off-white solid.

$^1$H NMR (CDCl$_3$) δ 6.58–6.59 (m, 1H), 7.82 (d, J=1.0 Hz, 1H), 7.89 (d, J=7.0 Hz, 1H), 8.02 (d, J=9.0 Hz, 1H), 8.11 (d, J=2.5 Hz, 1H), 8.18–8.22 (m, 2H), 8.29 (d, J=7.0 Hz, 1H), 9.07 (b, 1H);

LC-MS (retention time: 0.77 min, method B), MS m/z 212 (M$^+$+H).

Step 4:

This product was prepared by the same procedure as described in Example 11, Step 2 as an off-white solid, except using 6-pyrazol-isoquinoline 2-oxide instead.

$^1$H NMR (CD$_3$OD) δ 7.82–7.83 (m, 2H), 8.23–8.32 (m, 4H), 8.44–8.49 (m, 2H);

LC-MS (retention time: 1.35 min, method B), MS m/z 230, (M+ +H).
Step 5:
To a solution of product of Example 21, Step 1 (45 mg, 0.08 mmol) in DMSO (2 mL) was added potassium tert-butoxide (41 mg, 0.37 mmol). The formed solution was stirred at the ambient temperature for 30 min before addition of 1-chloro-6-pyrazol-1-yl-isoquinoline (17 mg, 0.07 mmol). The final solution was stirred for 12 h. Quenched with iced water, acidified with 1M HCl to pH 4, extracted with EtOAc (20 mL, ×2). The organic layers were washed with brine, dried over MgSO$_4$, filtered, evaporated. The residue was purified by prep-HPLC to yield 10 mg (16%) of Compound 21 as a pink solid.

$^1$H NMR (CD$_3$OD) δ 1.04–1.10 (m, 12H), 1.23–1.27 (m, 10H), 1.43–1.47 (m, 1H), 1.87–1.91 (m, 1H), 2.22–2.29 (m, 2H), 2.61–2.68 (m, 1H), 2.92–2.98 (m, 1H), 4.07–4.11 (m, 1H), 4.24 (b, 1H), 4.46–4.60 (m, 2H), 5.13 (d, J=10.5 Hz, 1H), 5.29 (d, J=18 Hz, 1H), 5.70–5.83 (m, 1H), 5.89 (b, 1H), 6.59–6.61 (m, 1H), 7.40 (d, J=10.0 Hz, 1H), 7.80 (d, J=2.5 Hz, 1H), 8.01 (d, J=10.0 Hz, 2H), 8.15 (s, 1H), 8.31 (d, J=15.0 Hz, 1H), 8.42 (d, J=4.5 Hz, 1H);

LC-MS (retention time: 1.77 min, method B), MS m/z 750 (M+ +H).

Example 22

Preparation of Compound 22

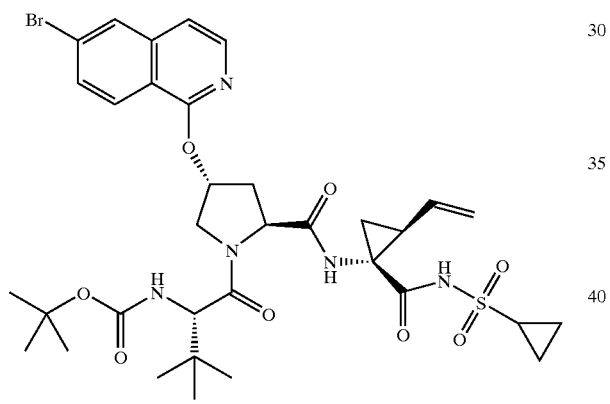

Compound 22

Step 1:

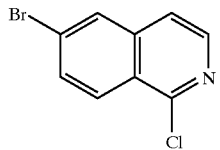

This product was prepared by the same procedure as described in Example 11, Step 2 as an off-white solid, except using 6-bromo-isoquinoline 2-oxide instead.

$^1$H NMR (CD$_3$OD) δ 7.73 (d, J=5.5 Hz, 1H), 7.85–7.91 (m, 1H), 8.22–8.31 (m, 3H);

LC-MS (retention time: 1.53 min, method B), MS m/z 241, 243, 245 (M+ +H).
Step 2:
Compound 22 was prepared by the same procedure as described in Example 21, Step 5 as a white solid, except using 1-chloro-6-bromo-isoquinoline instead.

$^1$H NMR (CD$_3$OD) δ 0.99–1.09 (m, 12H), 1.22–1.27 (m, 10H), 1.40–1.47 (m, 1H), 1.86–1.91 (m, 1H), 2.20–2.34 (m, 2H), 2.57–2.66 (m, 1H), 2.90–2.97 (m, 1H), 4.05–4.09 (m, 1H), 4.21 (b 1H), 4.44–4.57 (m, 2H), 5.13 (d, J=10.5 Hz, 1H), 5.29 (d, J=18.0 Hz, 1H), 5.70–5.82 (m, 1H), 5.88 (b, 1H), 7.29 (d, J=9.5 Hz, 1H), 7.60–7.63 (m, 1H), 8.00–8.12 (m, 3H);

LC-MS (retention time: 1.90 min, method B), MS m/z 762, 764 (M+ +H).

Example 23

Preparation of Compound 23

Step 1:

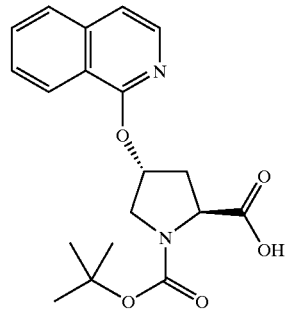

This product was prepared by the same procedure as described in Example 11, Step 3 as a white solid, except using 1-chloro-isoquinoline instead.

$^1$H NMR (CD$_3$OD) δ 1.42, 1.44 (rotamers, 9H), 2.39–2.44 (m, 1H), 2.68–2.72 (m, 1H), 3.80–3.87 (m, 2H), 4.44–4.52 (m, 1H), 5.78 (b, 1H), 7.32–7.33 (m, 1H), 7.58 (t, J=7.8 Hz, 1H), 7.71 (t, J=7.5 Hz, 1H), 7.81 (d, J=8.0 Hz, 1H), 7.95 (d, J=6.0 Hz, 1H), 8.19 (d, J=8.0 Hz, 1H);

LC-MS (retention time: 1.61 min, method B), MS m/z 359 (M+ +H).
Step 2:

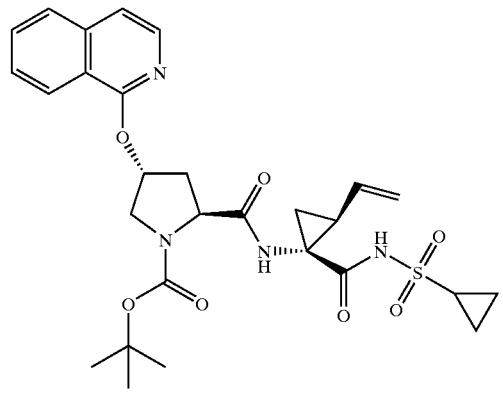

This product was prepared by the same procedure as described in Example 11, Step 4, except using the product of Example 23, Step 1 instead.

$^1$H NMR (DMSO-d6) δ 1.00–1.09 (m, 4H), 1.35–1.38 (m, 10H), 1.69–1.84 (m, 1H), 2.11–2.66 (m, 3H), 2.89–2.93 (m, 1H), 3.62–3.89 (m, 2H), 4.31 (t, J=8.1 Hz, 1H), 5.12 (d, J=10.8 Hz, 1H), 5.27 (d, J=16.8 Hz, 1H), 5.58–5.70 (m, 1H), 5.76 (b, 1H), 7.43 (d, J=5.7 Hz, 1H), 7.66 (t, J=7.4 Hz, 1H), 7.79 (t, J=7.5 Hz, 1H), 7.92 (d, J=8.1 Hz, 1H), 8.02 (d, J=10.0 Hz, 1H), 8.13 (d, J=8.1 Hz, 1H), 9.02 (b, 1H);

LC-MS (retention time: 1.72 min, method B), MS m/z 571 (M+ +H).

Step 3:

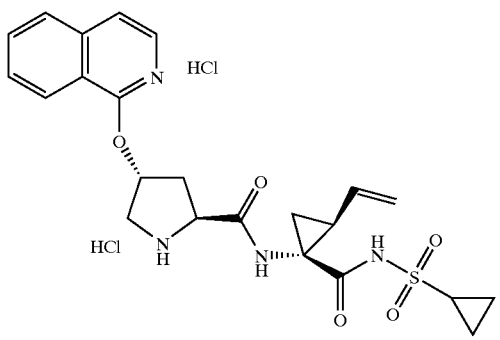

This product was prepared by the same procedure as described in Example 11, Step 5, except using the product of Example 23, Step 2 instead.

LC-MS (retention time: 1.16 min, method B), MS m/z 471 (M$^+$+H).

Step 4:

Compound 23 was prepared by the same procedure as described in Example 11, Step 6 as a white solid, except using the product of Example 23, Step 3 instead.

$^1$H NMR (CD$_3$OD) δ 1.00–1.09 (m, 12H), 1.25–1.27 (m, 10H), 1.42–1.46 (m, 1H), 1.86–1.90 (m, 1H), 2.22–2.34 (m, 2H), 2.60–2.67 (m, 1H), 2.92–2.99 (m, 1H), 4.06–4.11 (m, 1H), 4.26 (b, 1H), 4.45–4.57 (m, 2H), 5.12 (d, J=10.2 Hz, 1H), 5.27 (d, J=16.8 Hz, 1H), 5.70–5.82 (m, 1H), 5.88 (b, 1H), 7.32 (d, J=6.0 Hz, 1H), 7.52 (t, J=7.4 Hz, 1H), 7.70 (t, J=7.5 Hz, 1H), 7.80 (d, J=8.1 Hz, 1H), 7.97 (d, J=6 Hz, 1H), 8.20 (d, J=8.4 Hz, 1H), 9.18 (b, 1H);

LC-MS (retention time: 1.80 min, method B), MS m/z 684 (M$^+$+H).

Example 24

Preparation of Compound 24

Compound 24

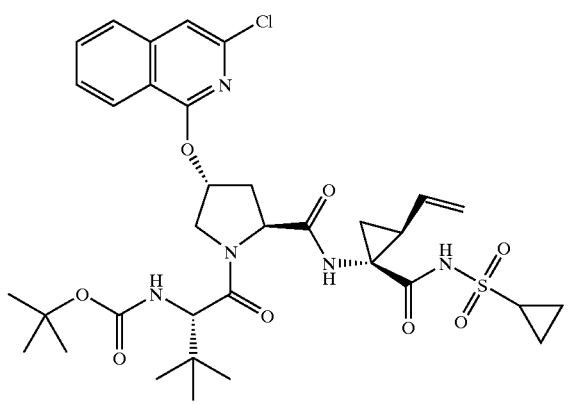

Scheme 1

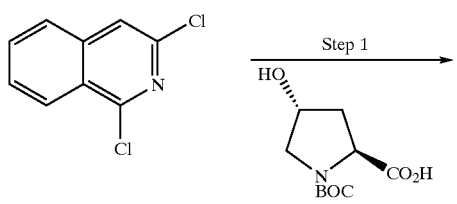

Step 1:

To a solution of N-BOC-3-(R)-hydroxy-L-proline (6.22 g, 26.9 mmol) in DMF (250 mL) at 0° C. was added NaH (60%, 3.23 g, 80.8 mmol) by several portions. The formed suspension was stirred at this temperature for 30 min. 1,3-dichloro-isoquinoline (5.33 g, 26.9 mmol) was added as solid in one portion and the final mixture was stirred at the ambient temperature for 12 h. Quenched with iced 5% citric acid (aq), extracted with EtOAC (300 mL). The aqueous phase was extracted with EtOAC again. The combined organic layers were washed with 5% citric acid (aq) and brine respectively, dried over MgSO$_4$, filtered. The filtrate was evaporated in vacuo to dryness to yield 10.53 g (99.8%) of 4-(6-methoxy-isoquinolin-1-yloxy)-pyrrolidine-1,2-dicarboxylic acid 1-tert-butyl ester as an off-white foam. This material was used in the next step reaction as crude without further purification.

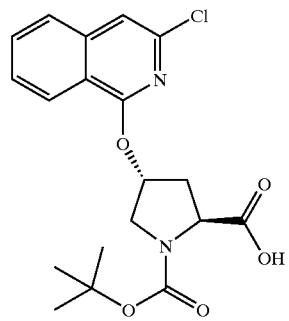

$^1$H NMR (CD$_3$OD) δ 1.43, 1.44 (rotamers, 9H), 2.39–2.44 (m, 1H), 2.68–2.72 (m, 1H), 3.80–3.90 (m, 2H), 4.44–4.52 (m, 1H), 5.77 (b, 1H), 7.39 (s, 1H), 7.58 (t, J=7.3 Hz, 1H), 7.71–7.78 (m, 2H), 8.16 (d, J=7.5 Hz, 1H);

LC-MS (retention time: 1.80 min, method B), MS m/z 392 (M$^+$+H).

Step 2:

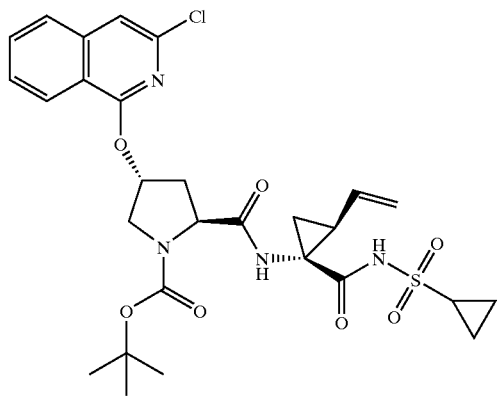

This product was prepared by the same procedure as described in Example 11, Step 4, except using the product of Example 24, Step 1 instead.

$^1$H NMR (CD$_3$OD) δ 1.02–1.08 (m, 2H), 1.18–1.26 (m, 2H), 1.44–1.48 (m, 10H), 1.84–1.91 (m, 1H), 2.22–2.36 (m,

2H), 2.57–2.60 (m, 1H), 2.95–2.99 (m, 1H), 3.81–3.93 (m, 2H), 4.38–4.41 (m, 1H), 5.13 (d, J=10.8 Hz, 1H), 5.31 (d, J=16.8 Hz, 1H), 5.75–5.82 (m, 2H), 7.41 (s, 1H), 7.59 (t, J=7.4 Hz, 1H), 7.74–7.79 (m, 2H), 8.16 (d, J=8.0 Hz, 1H);

LC-MS (retention time: 1.82 min, method B), MS m/z 605 (M⁺+H).

Step 3:

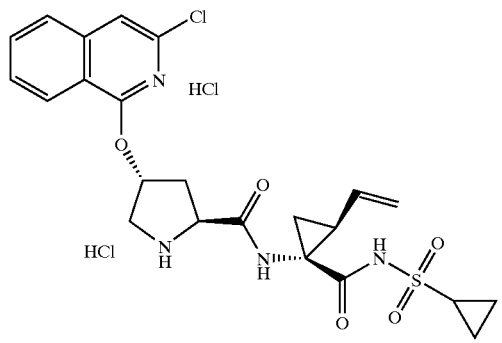

This product was prepared by the same procedure as described in Example 11, Step 5, except using the product of Example 24, Step 2 instead.

LC-MS (retention time: 1.30 min, method B), MS m/z 505 (M⁺+H).

Step 4:

Compound 24 was prepared by the same procedure as described in Example 11, Step 6 as a white solid, except using the product of Example 24, Step 3 instead.

¹H NMR (CD₃OD) δ 0.99–1.09 (m, 12H), 1.22–1.29 (m, 10H), 1.42–1.46 (m, 1H), 1.86–1.90 (m, 1H), 2.21–2.34 (m, 2H), 2.62–2.66 (m, 1H), 2.92–2.99 (m, 1H), 4.06–4.11 (m, 1H), 4.26 (b, 1H), 4.46–4.56 (m, 2H), 5.13 (d, J=10.5 Hz, 1H), 5.29 (d, J=17.2 Hz, 1H), 5.72–5.79 (m, 1H), 5.89 (b, 1H), 7.40 (d, J=6.0 Hz, 1H), 7.52 (t, J=7.4 Hz, 1H), 7.72–7.76 (m, 2H), 8.18 (d, J=8.5 Hz, 1H);

LC-MS (retention time: 1.95 min, method B), MS m/z 718(M⁺+H).

Example 25

Compound 25

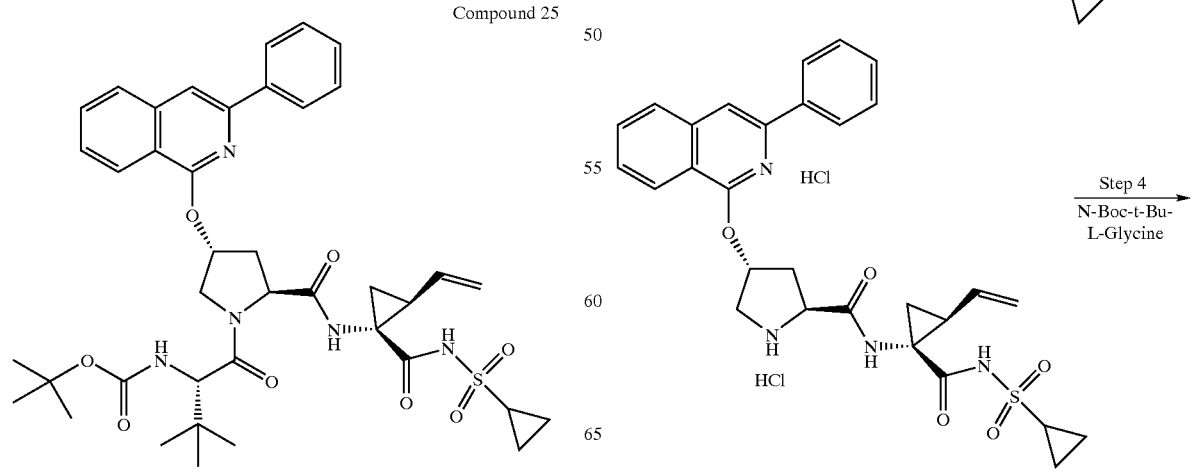

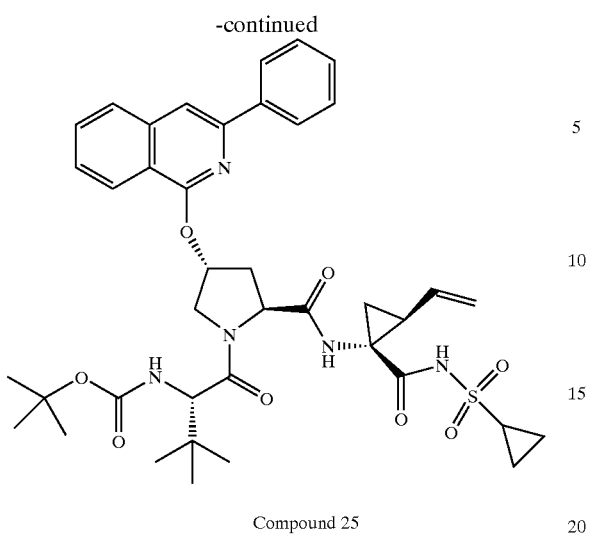

Compound 25

Step 1:

A mixture of Example 24, Step 1 (39 mg, 0.10 mmol), phenylboronic acid (14.6 mg, 0.12 mmol), sodium tert-butoxide (38 mg, 0.40 mmol) and ((t-Bu)$_2$POH)$_2$PdCl$_2$ (POPd) (5 mg, 0.01 mmol) in THF (2 mL) was heated to reflux for 4 h. After cooling down, the formed mixture was quenched with 5% citric acid (aq) and extracted with EtOAc (20 mL). The organic layer was washed with brine, dried over MgSO$_4$, filtered, evaporated. The residue was purified by prep-HPLC to yield 36 mg (83%) of the desired product as an off-white foam.

$^1$H NMR (CD$_3$OD) δ 1.43, 1.45 (rotamers, 9H), 2.51–2.56 (m, 1H), 2.74–2.82 (m, 1H), 3.88–3.92 (m, 1H), 3.98–4.01 (m, 11H), 4.50–4.57 (m, 1H), 5.95 (b, 1H), 7.36–7.39 (m, 1H), 7.45–7.48 (m, 2H), 7.55 (t, J=7.3 Hz, 1H), 7.70 (t, J=7.5 Hz, 1H), 7.84–7.89 (m, 2H), 8.14–8.17 (m, 3H), 9.05 (b, 1H);

LC-MS (retention time: 1.97 min, method B), MS m/z 435 (M$^+$+H).

Step 2:

This product was prepared by the same procedure as described in Example 11, Step 4, except using the product of Example 25, Step 1 instead.

$^1$H NMR (DMSO-d6) δ 0.98–1.10 (m, 4H), 1.38–1.41 (m, 10H), 1.74–1.81 (m, 1H), 2.18–2.34 (m, 2H), 2.47–2.49 (m, 1H), 2.95–2.99 (m, 1H), 3.74–3.96 (m, 2H), 4.34–4.37 (m, 1H), 5.12 (d, J=10.5 Hz, 1H), 5.26 (d, J=17.8 Hz, 1H), 5.75–5.82 (m, 1H), 5.95 (b, 1H), 7.41–7.45 (m, 1H), 7.51–7.54 (m, 2H), 7.61–7.64 (m, 1H), 7.78–7.82 (m, 1H), 7.98 (d, J=9.0 Hz, 1H), 8.06 (s, 1H), 8.13–8.14 (m, 1H), 8.18–8.20 (m, 2H), 9.05 (b, 1H), 10.34 (b, 1H);

LC-MS (retention time: 1.99 min, method B), MS m/z 647 (M$^+$+H).

Step 3:

This product, was prepared by the same procedure as described in Example 11, Step 5 as a white solid, except using the product of Example 25, Step 2 instead.

LC-MS (retention time: 1.55 min, method B), MS m/z 547 (M$^+$+H).

Step 4:

Compound 25 was prepared by the same procedure as described in Example 11, Step 6 as a white solid, except using the product of Example 25, Step 3 instead.

$^1$H NMR (CD$_3$OD) δ 0.92–1.09 (m, 12H), 1.26–1.30 (m, 10H), 1.43–1.46 (m, 1H), 1.87–1.90 (m, 1H), 2.21–2.26 (m, 1H), 2.36–2.41 (m, 1H), 2.70–2.75 (m, 1H), 2.93–2.97 (m, 1H), 4.18–4.30 (m, 2H), 4.46–4.48 (m, 1H), 4.55–4.58 (m, 1H), 5.12 (d, J=10.5 Hz, 1H), 5.29 (d, J=18.0 Hz, 1H), 5.72–5.79 (m, 1H), 6.10 (b, 1H), 7.37–7.40 (m, 1H), 7.46–7.49 (m, 3H), 7.70 (t, J=7.5 Hz, 1H), 7.85–7.89 (m, 2H), 8.16–8.20 (m, 3H);

LC-MS (retention time: 2.08 min, method B), MS m/z 760 (M$^+$+H).

Example 26

Preparation of Compound 26

Compound 26

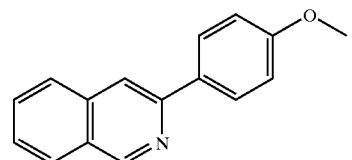

Step 1:

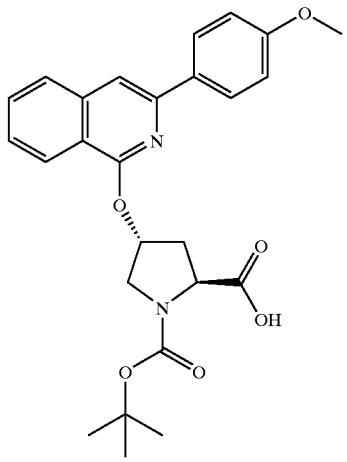

This product was prepared by the same procedure as described in Example 25, Step 1, except using 4-methoxyphenylboronic acid instead.

$^1$H NMR (CD$_3$OD) δ 1.40, 1.45 (rotamers, 9H), 2.50–2.55 (m, 1H), 2.73–2.81 (m, 1H), 3.81–3.89 (m, 4H), 3.98–4.01 (m, 1H), 4.50–4.57 (m, 1H), 5.93 (b, 1H), 7.02 (d, J=9.0 Hz, 2H), 7.50 (t, J=7.3 Hz, 1H), 7.67 (t, J=7.5 Hz, 1H), 7.73 (s, 1H), 7.83 (d, J=8.5 Hz, 1H), 8.09 (d, J=8.5 Hz, 2H), 8.15 (d, J=8.0 Hz, 1H);

LC-MS (retention time: 2.00 min. method B), MS m/z 465 (M$^+$+H).

Step 2:

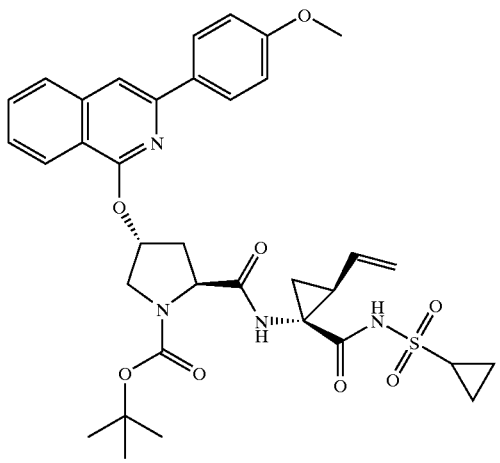

This product was prepared by the same procedure as described in Example 11, Step 4, except using the product of Example 26, Step 1 instead.

$^1$H NMR (CD$_3$OD) δ 1.06–1.09 (m, 2H), 1.17–1.27 (m, 2H), 1.42–1.47 (m, 10H), 1.88–1.90 (m, 1H), 2.21–2.26 (m, 1H), 2.33–2.39 (m, 1H), 2.61–2.65 (m, 1H), 2.95–2.99 (m, 1H), 3.85 (s, 3H), 3.86–3.90 (m, 1H), 3.99–4.00 (m, 1H), 4.43–4.45 (m, 1H), 5.13 (d, J=10.8 Hz, 1H), 5.31 (d, J=18.0 Hz, 1H), 5.77–5.80 (m, 1H), 5.99 (b, 1H), 7.02 (d, J=9.0 Hz, 2H), 7.51 (t, J=7.3 Hz, 1H), 7.68 (t, J=7.5 Hz, 1H), 7.76 (s, 1H), 7.84 (d, J=8.5 Hz, 1H), 8.09 (d, J=8.5 Hz, 2H), 8.15 (d, J=8.0 Hz, 1H);

LC-MS (retention time: 2.02 min, method B), MS m/z 677 (M$^+$+H).

Step 3:

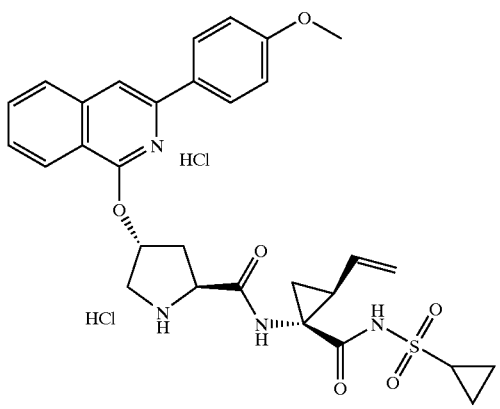

This product was prepared by the same method as described in Example 11, Step 5 as a white solid, except using the product of Example 26, Step 2 instead.

LC-MS (retention time: 1.53 min, method B), MS m/z 577 (M$^+$+H).

Step 4:

Compound 26 was prepared by the same method as described in Example 11, Step 6, except using the product of Example 26, Step 3 instead.

$^1$H NMR (CD$_3$OD) δ 0.93–1.09 (m, 12H), 1.26–1.30 (m, 10H), 1.44–1.46 (m, 1H), 1.87–1.90 (m, 1H), 2.21–2.26 (m, 1H), 2.36–2.41 (m, 1H), 2.70–2.75 (m, 1H), 2.93–2.97 (m, 1H), 3.86 (s, 3H), 4.18–4.25 (m, 1H), 4.30 (b, 1H), 4.46–4.48 (m, 1H), 4.55–4.58 (m, 1H), 5.12 (d, J=10.5 Hz, 1H), 5.29 (d, J=18.0 Hz, 1H), 5.72–5.79 (m, 1H), 6.08 (b, 1H), 7.02 (d, J=9.0 Hz, 2H), 7.44 (t, J=7.3 Hz, 1H), 7.66 (t, J=7.5 Hz, 1H), 7.75 (s, 1H), 7.83 (d, J=8.5 Hz, 1H), 8.09 (d, J=8.5 Hz, 2H), 8.15 (d, J=8.0 Hz, 1H);

LC-MS (retention time: 2.03 min, method B), MS m/z 790 (M$^+$+H).

Example 27

Preparation of Compound 27

Compound 27

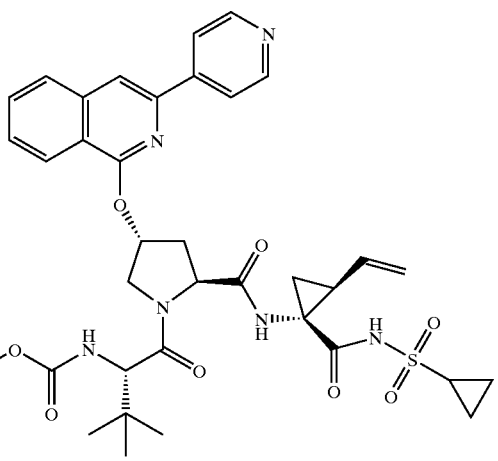

Step 1:

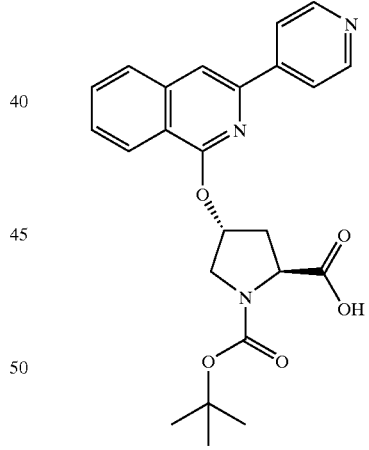

This product was prepared by the same method as described in Example 25, Step 1, except using 4-pyridylboronic acid instead.

$^1$H NMR (CD$_3$OD) δ 1.43, 1.46 (rotamers, 9H), 2.53–2.56 (m, 1H), 2.80–2.89 (m, 1H), 3.90–3.93 (m, 1H), 4.00–4.05 (m, 1H), 4.50–4.57 (m, 1H), 6.00, 6.05 (rotamers, 1H), 7.80 (t, J=7.3 Hz, 1H), 7.87 (t, J=7.5 Hz, 1H), 8.08 (d, J=8.5 Hz, 1H), 8.32 (d, J=8.0 Hz, 1H), 8.49 (s, 1H), 8.84 (d, J=6.0 Hz, 2H), 8.84 (d, J=6.5 Hz, 2H);

LC-MS (retention time: 1.39 min, method B), MS m/z 436 (M$^+$+H).

Step 2:

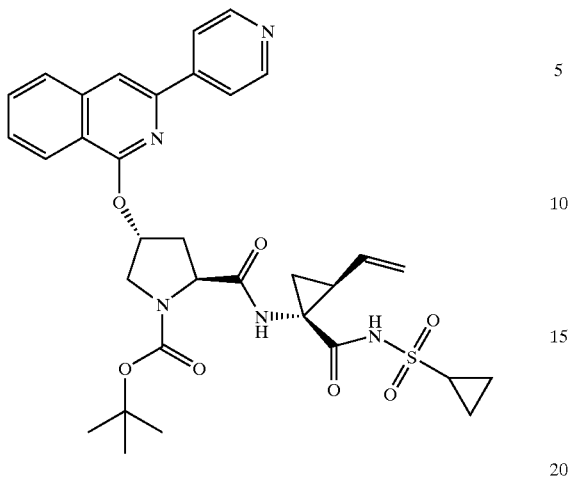

The product was prepared by the same method as described in Example 11, Step 4, except using the product of Example 27, Step 1 instead.

$^1$H NMR (CD$_3$OD) δ 1.06–1.09 (m, 2H), 1.17–1.27 (m, 2H), 1.42–1.46 (m, 10H), 1.88–1.90 (m, 1H), 2.21–2.26 (m, 1H), 2.33–2.39 (m, 1H), 2.61–2.65 (m, 1H), 2.95–2.99 (m, 1H), 3.88–3.90 (m, 1H), 4.01–4.08 (m, 1H), 4.43–4.45 (m, 1H), 5.15 (d, J=10.8 Hz, 1H), 5.32 (d, J=18.0 Hz, 1H), 5.77–5.80 (m, 1H), 6.10 (b, 1H), 7.79 (t, J=7.3 Hz, 1H), 7.88 (t, J=7.5 Hz, 1H), 8.08 (d, J=8.5 Hz, 1H), 8.31 (d, J=8.0 Hz, 1H), 8.47 (s, 1H), 8.79 (d, J=7.0 Hz, 2H), 8.86 (d, J=6.5 Hz, 2H);

LC-MS (retention time: 1.49 min, method B), MS m/z 648 (M$^+$+H).

Step 3:

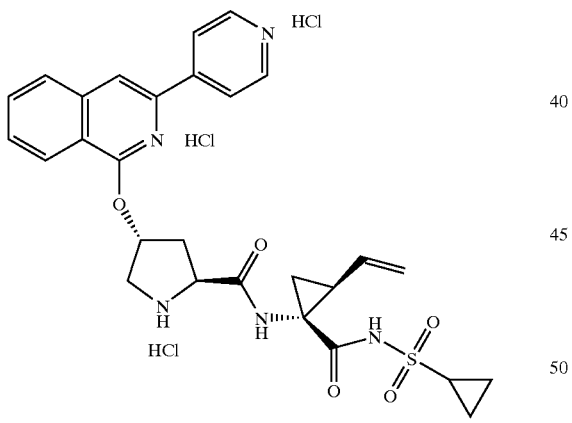

This product was prepared by the same method as described in Example 11, Step 5 as a white solid, except using the product of Example 27, Step 2 instead.

LC-MS (retention time: 0.96 min, method B), MS m/z 548 (M$^+$+H).

Step 4:

Compound 27 was prepared by the same method as described in Example 11, Step 6, except using the product of Example 27, Step 3 instead.

$^1$H NMR (CD$_3$OD) δ 0.94–1.09 (m, 12H), 1.22–1.26 (m, 10H), 1.44–1.49 (m, 1H), 1.88–1.92 (m, 1H), 2.22–2.25 (m, 1H), 2.41–2.44 (m, 1H), 2.70–2.75 (m, 1H), 2.93–2.98 (m, 1H), 4.18–4.21 (m, 1H), 4.25 (b, 1H), 4.53–4.62 (m, 2H), 5.12 (d, J=10.0 Hz, 1H), 5.29 (d, J=20.0 Hz, 1H), 5.72–5.77 (m, 1H), 6.12 (b, 1H), 7.67 (t, J=7.3 Hz, 1H), 7.82 (t, J=7.5 Hz, 1H), 8.02 (d, J=8.5 Hz, 1H), 8.29 (d, J=8.0 Hz, 1H), 8.31 (s, 1H), 8.55 (d, J=7.0 Hz, 2H), 8.76 (d, J=6.5 Hz, 2H);

LC-MS (retention time: 1.49 min, method B), MS m/z 761 (M$^+$+H).

Example 28

Preparation of Compound 28

Compound 28

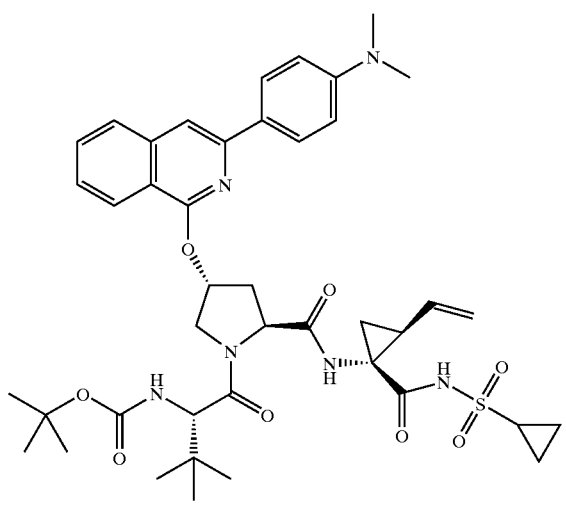

Step 1:

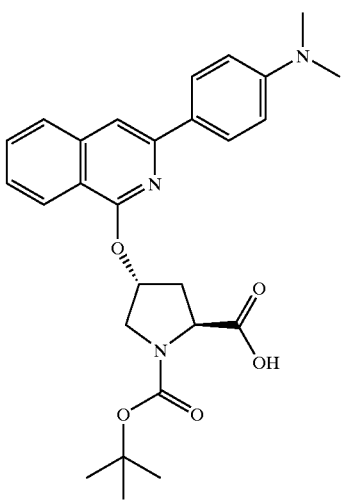

This product was prepared by the same method as described in Example 25, Step 1, except using 4-N,N-dimethylamino-phenylboronic acid instead.

LC-MS (retention time: 1.64 min, method B), MS m/z 478 (M$^+$+H).

Step 2:

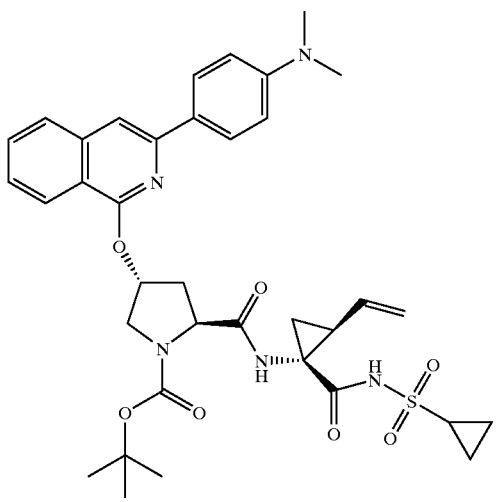

This product was prepared by the same method as described in Example 11, Step 4, except using the product of Example 28, Step 1 instead.
LC-MS (retention time: 1.70 min, method B), MS m/z 690 (M⁺+H).

Step 3:

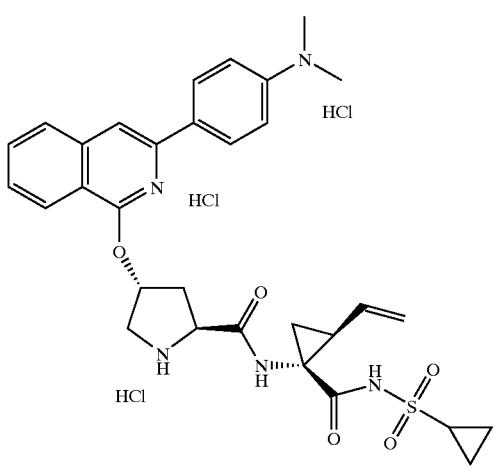

This product was prepared by the same method as described in Example 11, Step 5 as a white solid, except using the product of Example 28, Step 2 instead.
LC-MS (retention time: 1.20 min, method B), MS m/z 590 (M⁺+H).

Step 4:
Compound 28 was prepared by the same method as described in Example 11, Step 6, except using the product of Example 28, Step 3 instead.
$^1$H NMR (d$_6$-DMSO) δ 0.92–1.10 (m, 13H), 1.30 (s, 9H), 1.35–1.38 (m, 1H), 1.68–1.71 (m, 1H), 2.12–3.00 (m, 2H), 2.59–2.62 (m, 1H), 2.91–2.95 (m, 1H), 2.99 (s, 6H), 3.93–4.10 (m, 2H), 4.32–4.40 (m, 2H), 5.09 (d, J=11.5 Hz, 1H), 5.23 (d, J=19.0 Hz, 1H), 5.54–5.64 (m, 1H), 5.92 (b, 1H), 6.83 (d, J=9.0 Hz, 2H), 7.42 (t, J=7.3 Hz, 1H), 7.70 (t, J=7.5 Hz, 1H), 7.81 (s, 1H), 7.87 (d, J=8.5 Hz, 1H), 8.04 (d, J=9.0 Hz, 2H), 8.15 (d, J=8.0 Hz, 1H);

LC-MS (retention time: 1.72 min, method B), MS m/z 803 (M⁺+H).

Example 29

Preparation of Compound 29

Compound 29

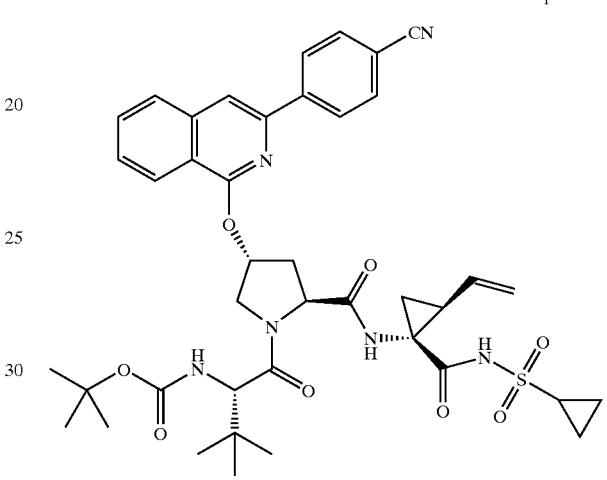

Step 1:

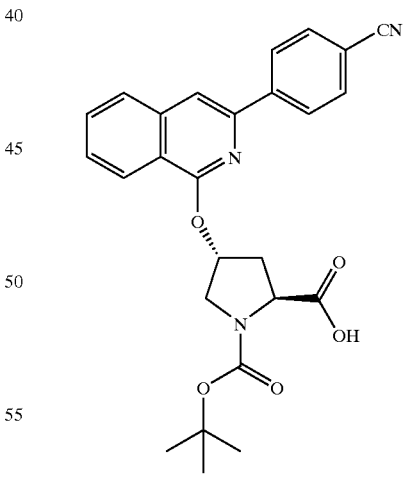

This product was prepared by the same method as described in Example 25, Step 1, except using 4-cyanophenylboronic acid instead.

LC-MS (retention time: 1.87 min, method B), MS m/z 460 (M⁺+H).

Step 2:

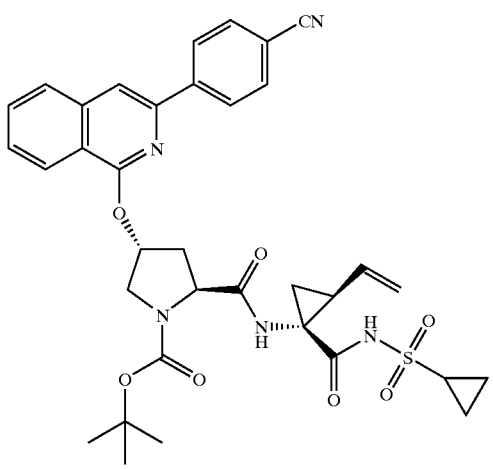

This product was prepared by the same method as described in Example 11, Step 4, except using the product of Example 29, Step 1 instead.

LC-MS (retention time: 1.88 min, method B), MS m/z 672 (M+ +H).

Step 3:

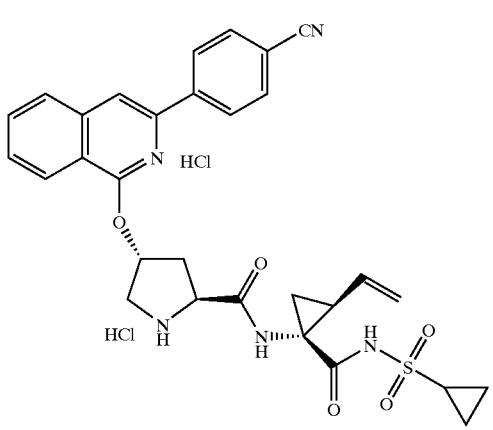

This product was prepared by the same method as described in Example 11, Step 5 as a white solid, except using the product of Example 29, Step 2 instead.

LC-MS (retention time: 1.41 min, method B), MS m/z 572 (M+ +H).

Step 4:

Compound 29 was prepared by the same method as described in Example 11, Step 6 as a white solid, except using the product of Example 29, Step 3 instead.

$^1$H NMR (CD$_3$OD) δ 0.92–1.09 (m, 12H), 1.25–1.26 (m, 10H), 1.42–1.46 (m, 1H), 1.86–1.89 (m, 1H), 2.20–2.22 (m, 1H), 2.33–2.34 (m, 1H), 2.68–2.71 (m, 1H), 2.93–2.95 (m, 1H), 4.13–4.28 (m, 2H), 4.49–4.60 (m, 2H), 5.12 (d, J=10.5 Hz, 1H), 5.28 (d, J=18.0 Hz, 1H), 5.71–5.80 (m, 1H), 6.09 (b, 1H), 7.56 (t, J=7.3 Hz, 1H), 7.74 (t, J=7.5 Hz, 1H), 7.83 (d, J=10.5 Hz, 2H), 7.93 (d, J=7.5 Hz, 1H), 8.01 (s, 1H), 8.22 (d, J=7.5 Hz, 1H), 8.37 (d, J=10.5 Hz, 2H);

LC-MS (retention time: 1.87 min, method B), MS m/z 785 (M+ +H).

Example 30

Preparation of Compound 30

Compound 30

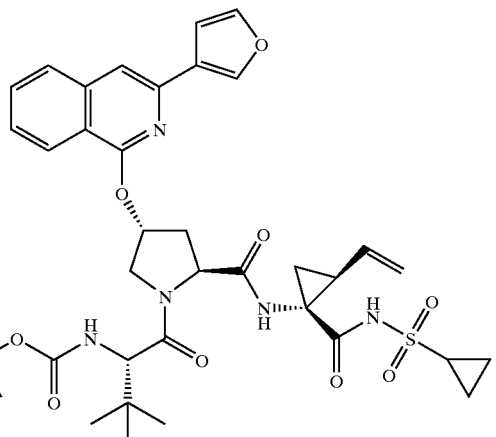

Step 1:

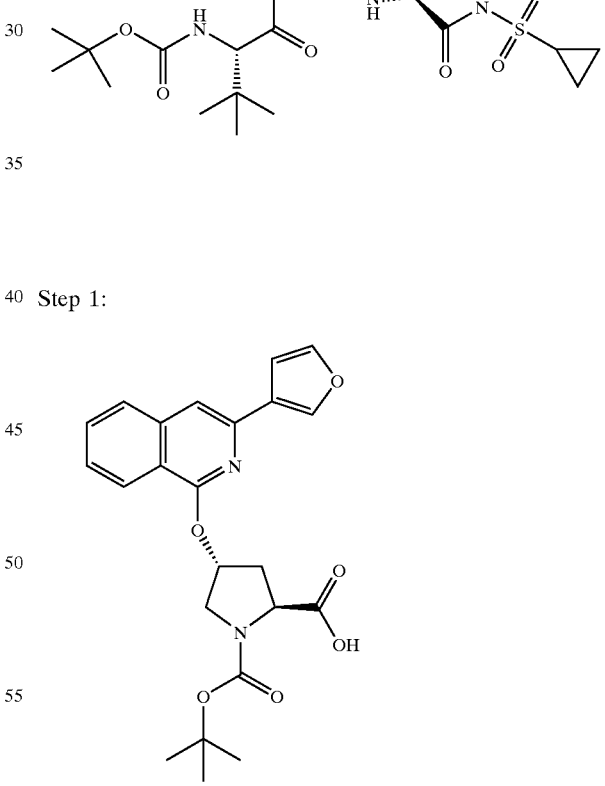

This product was prepared by the same method as described in Example 25, Step 1, except using 3-furanoboronic acid instead.

LC-MS (retention time: 1.85 min, method B), MS m/z 425 (M+ +H).

Step 2:

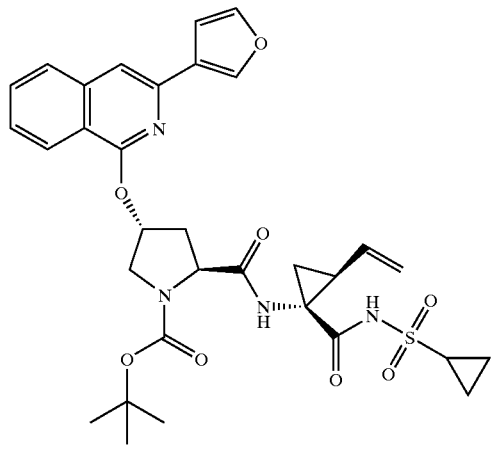

This product was prepared by the same method as described in Example 11, Step 4, except using the product of Example 30, Step 1 instead.

LC-MS (retention time: 1.88 min, method B), MS m/z 637 (M⁺+H).

Step 3:

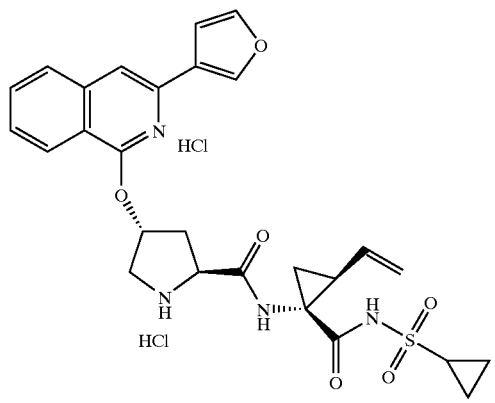

This product was prepared by the same method as described in Example 11, Step 5, except using the product of Example 30, Step 2 instead.

LC-MS (retention time: 1.38 min, method B), MS m/z 537 (M⁺+H).

Step 4:

Compound 30 was prepared by the same method as described in Example 11, Step 6 as a white solid, except using the product of Example 30, Step 3 instead.

$^1$H NMR (CD$_3$OD) δ 0.95–1.09 (m, 12H), 1.23–1.30 (m, 10H), 1.43–1.46 (m, 1H), 1.87–1.90 (m, 1H), 2.21–2.23 (m, 1H), 2.30–2.34 (m, 1H), 2.64–2.70 (m, 1H), 2.93–2.96 (m, 1H), 4.11–4.29 (m, 2H), 4.41–4.44 (m, 1H), 4.54–4.56 (m, 1H), 5.12 (d, J=10.5 Hz, 1H), 5.29 (d, J=17.5 Hz, 1H), 5.71–5.80 (m, 1H), 6.02 (b, 1H), 7.00 (s, 1H), 7.44 (t, J=7.2 Hz, 1H), 7.52 (s, 1H), 7.57 (s, 1H), 7.66 (t, J=7.0 Hz, 1H), 7.79 (d, J=8.0 Hz, 1H), 8.14–8.17 (m, 2H);

LC-MS (retention time: 1.93 min, method B), MS m/z 750 (M⁺+H).

Example 31

Preparation of Compound 31

Compound 31

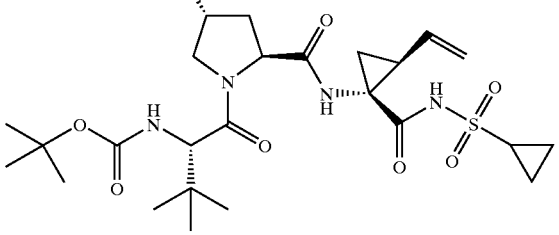

Scheme 1

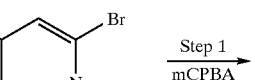
Step 1
mCPBA

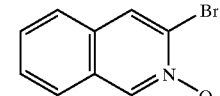
Step 2
POCl₃

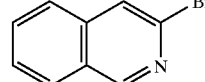
Step 3

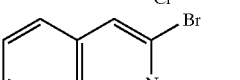
Step 4
pyrazinetin

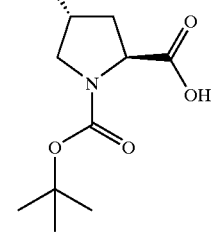

-continued

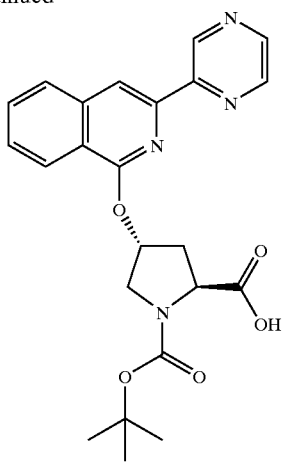

Step 1:

This product was prepared by the same method as described in making of Example 21, Step 2 as a white solid, except using 3-bromo-isoquinoline (Atkins et al, JOC, 1973, 400) instead.

$^1$H NMR (CDCl$_3$) δ 7.60–7.62 (m, 2H), 7.71–7.73 (m, 2H), 8.12 (s, 1H), 8.99 (s, 1H);

LC-MS (retention time: 0.78 min, method B), MS m/z 224, 226 (M$^+$+H).

Step 2:

This product was prepared by the same method as described in Example 11, Step 2 as white solid, except using 3-bromo-isoquinoline 2-oxide instead.

$^1$H NMR (CDCl$_3$) δ 7.66–7.71 (m, 1H), 7.74–7.76 (m, 2H), 7.83 (s, 1H), 8.29 (d, J=8.5 Hz, 1H);

LC-MS (retention time: 1.55 min, method B), MS m/z 242, 244 (M$^+$+H).

Step 3:

This product was prepared by the same method as described in Example 11, Step 3 as a foam, except using 3-bromo-1-chloro-isoquinoline instead.

$^1$H NMR (CD$_3$OD) δ 1.43, 1.44 (rotamers, 9H), 2.41–2.47 (m, 1H), 2.69–2.72 (m, 1H), 3.80–3.84 (m, 1H), 3.88–3.90 (m, 1H), 4.46–4.52 (m, 1H), 5.76 (b, 1H), 7.57–7.61 (m, 2H), 7.73–7.75 (m, 2H), 8.15 (d, J=8.0 Hz, 1H);

LC-MS (retention time: 1.79 min, method B), MS m/z 437, 439 (M$^+$+H).

Step 4:

A mixture of 2-tributylstannanyl-pyrazine (44 mg, 0.12 mmol), tetrakis(triphenylphosphine)palladium (0) (12 mg, 0.01 mmol) and the product of Example 31, Step 3 (44 mg, 0.1 mmol) in toluene (1 mL) was heated to reflux for 3 h. After removing the volatiles in vacuo, the residue was purified by prep-HPLC to yield 35 mg (80%) of the desired product as a yellow solid.

LC-MS (retention time: 1.77 min, method B), MS m/z 437 (M$^+$+H).

Step 5:

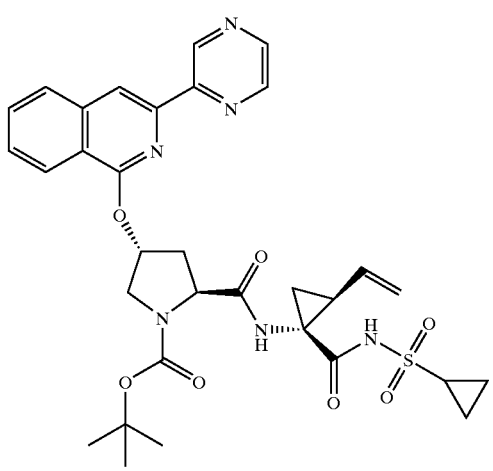

This product was prepared by the same method as described in Example 11, Step 4, except using the product of Example 31, Step 4 instead.

LC-MS (retention time: 1.78 min, method B), MS m/z 649 (M$^+$+H).

Step 6:

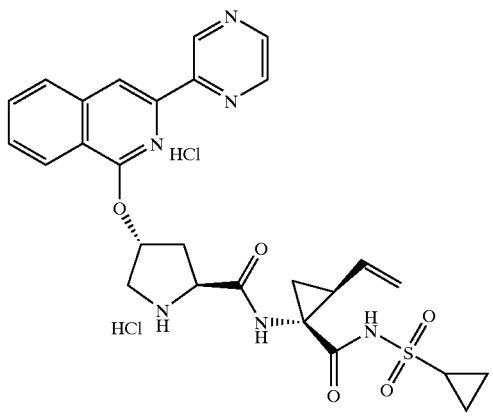

This product was prepared by the same method as described in Example 11, Step 5 as a white solid, except using the product of Example 31, Step 5 instead.

LC-MS (retention time: 1.26 min, method B), MS m/z 549 (M$^+$+H).

Step 7:

Compound 31 was prepared by the same method as described in Example 11, Step 6, except using the product of Example 31, Step 6 instead.

$^1$H NMR (CD$_3$OD) δ 0.95–1.10 (m, 12H), 1.24–1.27 (m, 10H), 1.44–1.47 (m, 1H), 1.87–1.90 (m, 1H), 2.19–2.22 (m, 1H), 2.38–2.44 (m, 1H), 2.71–2.76 (m, 1H), 2.93–2.96 (m, 1H), 4.18–4.28 (m, 2H), 4.50–4.61 (m, 2H), 5.12 (d, J=10.5 Hz, 1H), 5.29 (d, J=17.5 Hz, 1H), 5.71–5.80 (m, 1H), 6.12 (b, 1H), 7.60 (t, J=7.2 Hz, 1H), 7.77 (t, J=7.0 Hz, 1H), 7.97 (d, J=8.5 Hz, 1H), 8.26 (d, J=8.5 Hz, 1H), 8.44 (s, 1H), 8.59 (s, 1H), 8.70 (s, 1H), 9.61 (s, 1H);

LC-MS (retention time: 1.84 min, method B), MS m/z 762 (M$^+$+H).

Example 32

Preparation of Compound 32

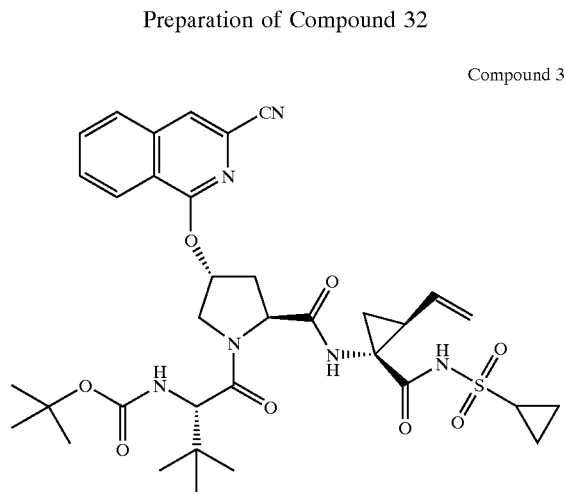

Compound 32

Step 1:

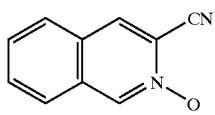

This product, 2-oxy-isoquinoline-3-carbonitrile, was prepared by the same method as described in Example 21, Step 2 as a white solid, except using 3-cyano-isoquinoline instead.

$^1$H NMR (DMSO-d$_6$) δ 7.74 (t, J=8.0 Hz, 1H), 7.84 (t, J=8.2 Hz, 1H), 7.97 (d, J=8.5 Hz, 1H), 8.03 (d, J=8.5 Hz, 1H), 8.85 (s, 1H), 9.17 (s, 1H);

LC-MS (retention time: 0.48 min, method B), MS m/z 171 (M$^+$+H).

Step 2:

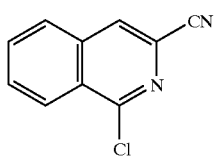

This product, 1-chloro-isoquinoline-3-carbonitrile was prepared by the same method as described in Example 11, Step 2 as white solid, except using 3-cyano-isoquinoline2-oxide instead.

$^1$H NMR (CDCl$_3$) δ 7.87–7.91 (m, 2H), 7.92–7.94 (m, 1H), 8.09 (s, 1H), 8.42–8.44 (m, 1H);

LC-MS (retention time: 1.22 min, method B), MS m/z 189 (M$^+$+H).

Step 3:

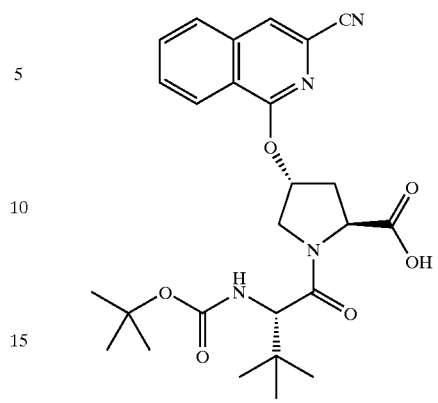

This product was prepared by the same method as described in Example 1, Step 5, except using 1-chloro-isoquinoline-3-carbonitrile instead.

$^1$HNMR (CD$_3$OD) δ 1.05 (s, 9H), 1.17 (s, 9H), 2.34–2.40 (m, 1H), 2.71–2.78 (m, 1H), 4.09–4.11 (m, 1H), 4.21 (b, 1H), 4.48–4.52 (m, 1H), 4.68–4.72 (m, 1H), 5.89 (b, 1H), 7.74 (t, J=7.5 Hz, 1H), 7.86 (t, J=7.5 Hz, 1H), 7.94–7.97 (m, 2H), 8.31 (d, J=8.0 Hz, 1H);

LC-MS (retention time: 1.66 min, method B), MS m/z 497 (M$^+$+H).

Step 4:

Compound 32 was prepared by the same method as described in Example 1, Step 9 as a white solid, except using the product of Example 32, Step 3 instead.

$^1$H NMR (CD$_3$OD) δ 1.04–1.09 (m, 12H), 1.20–1.27 (m, 10H), 1.39–1.45 (m, 1H), 1.85–1.88 (m, 1H), 2.20–2.30 (m, 2H), 2.63–2.71 (m, 1H), 2.91–2.97 (m, 1H), 4.09–4.13 (m, 1H), 4.23 (d, J=9.3 Hz, 1H), 4.49–4.58 (m, 2H), 5.13 (d, J=10.5 Hz, 1H), 5.28 (d, J=18.0 Hz, 1H), 5.69–5.81 (m, 1H), 5.92 (b, 1H), 6.60 (d, J=10.0 Hz, 1H), 7.72 (t, J=7.5 Hz, 1H), 7.86 (t, J=7.5 Hz, 1H), 7.96–7.99 (m, 2H), 8.29 (d, J=8.0 Hz, 1H);

LC-MS (retention time: 1.75 min, method B), MS m/z 714 (M$^+$+H).

Example 33

Preparation of Compound 33

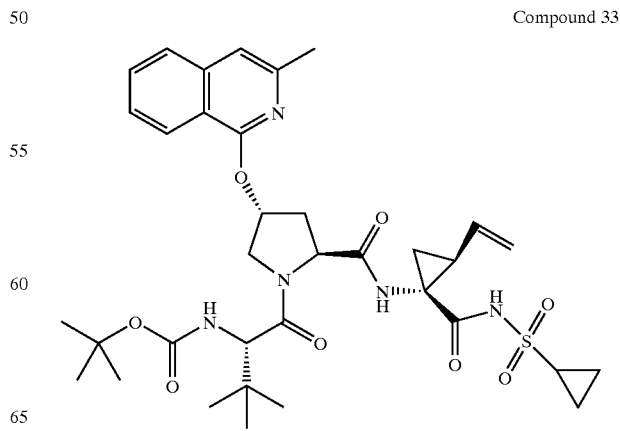

Compound 33

Step 1:

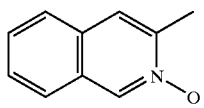

This product, 3-methyl-isoquinoline 2-oxide, was prepared by the same method as described in Example 21, Step 2 as a white solid, except using 3-methyl-isoquinoline instead.

$^1$H NMR (CD$_3$OD) δ 2.64 (s, 3H), 7.64–7.72 (m, 2H), 7.88–7.95 (m, 2H), 9.05 (s, 1H);
LC-MS (retention time: 0.61 min, method B), MS m/z 160 (M$^+$+H).

Step 2:

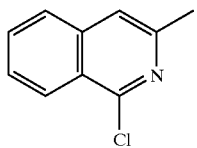

This product, 1-chloro-3-methyl-isoquinoline was prepared by the same method as described in Example 11, Step 2 as white solid, except using 3-methyl-isoquinoline2-oxide instead.

$^1$H NMR (CDCl$_3$) δ 2.65 (s, 3H), 7.25 (s, 1H), 7.61 (t, J=7.5 Hz, 1H), 7.69 (t, J=7.5 Hz, 1H), 7.74 (d, J=8.0 Hz, 1H), 8.27 (d, J=8.5 Hz, 1H);
LC-MS (retention time: 1.47 min, method B), MS m/z 178 (M$^+$+H).

Step 3:

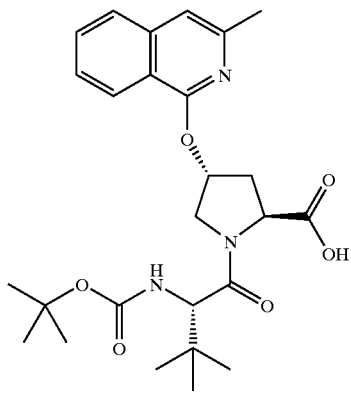

This product was prepared by the same method as described in Example 1, Step 5 as a white solid, except using 1-chloro-3-methyl-isoquinoline instead.

$^1$HNMR (CD$_3$OD) δ 1.05 (s, 9H), 1.23 (s, 9H), 2.51 (s, 3H), 2.34–2.40 (m, 1H), 2.72–2.78 (m, 1H), 4.05–4.12 (m, 1H), 4.26 (b, 1H), 4.41 (d, J=10 Hz, 1H), 4.62–4.67 (m, 1H), 5.90 (b, 1H), 7.14 (s, 1H), 7.38 (t, J=7.5 Hz, 1H), 7.62 (t, J=7.5 Hz, 1H), 7.68 (d, J=8.0 Hz, 1H), 8.14 (d, J=8.0 Hz, 1H);
LC-MS (retention time: 1.84 min, method B), MS m/z 486 (M$^+$+H).

Step 4:
Compound 33 was prepared by the same method as described in Example 1, Step 9 as a white solid, except using the product of Example 33, Step 3 instead.

$^1$H NMR (CD$_3$OD) δ 0.99–1.09 (m, 12H), 1.23–1.25 (m, 10H), 1.41–1.45 (m, 1H), 1.86–1.90 (m, 1H), 2.21–2.31 (m, 2H), 2.52 (s, 3H), 2.58–2.61 (m, 1H), 2.91–2.97 (m, 1H), 4.08–4.12 (m, 1H), 4.28 (b, 1H), 4.40 (d, J=10.0 Hz, 1H), 4.50–4.55 (m, 1H), 5.12 (d, J=10.0 Hz, 1H), 5.30 (d, J=18.0 Hz, 1H), 5.71–5.81 (m, 1H), 5.93 (b, 1H), 7.13 (s, 1H), 7.38 (t, J=7.5 Hz, 1H), 7.62 (t, J=7.5 Hz, 1H), 7.68 (d, J=8.0 Hz, 1H), 8.12 (d, J=8.0 Hz, 1H), 9.12 (b, 1H);
LC-MS (retention time: 1.85 min, method B), MS m/z 698 (M$^+$+H).

Example 34

Preparation of Compound 34

Compound 34

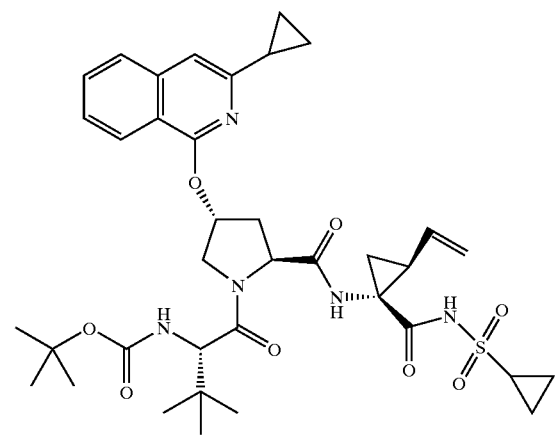

Step 1:

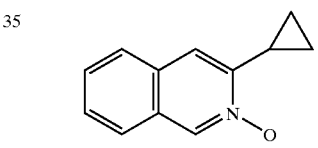

This product, 3-cyclopropyl-isoquinoline 2-oxide was prepared by the same method as described in Example 21, Step 2 as a white solid, except using 3-cyclopropyl-isoquinoline (L. Flippin, J. Muchowski, J. O. C, 1993, 2631–2632) instead.

LC-MS (retention time: 0.95 min, method B), MS m/z 186 (M$^+$+H).

Step 2:

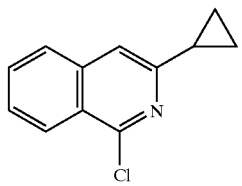

This product, 1-chloro-3-cyclopropyl-isoquinoline was prepared by the same method as described in Example 11, Step 2 as white solid, except using 3-cyclopropyl-isoquinoline2-oxide instead.

$^1$H NMR (CD$_3$OD) δ 1.00–1.04 (m, 4H), 2.11–2.18 (m, 1H), 7.55 (s, 1H), 7.61 (t, J=8.0 Hz, 1H), 7.72 (t, J=8.0 Hz, 1H), 7.83 (d, J=13.5 Hz, 1H), 8.27 (d, J=14.5 Hz, 1H);
LC-MS (retention time: 1.70 min, method B), MS m/z 204 (M$^+$+H).

Step 3:

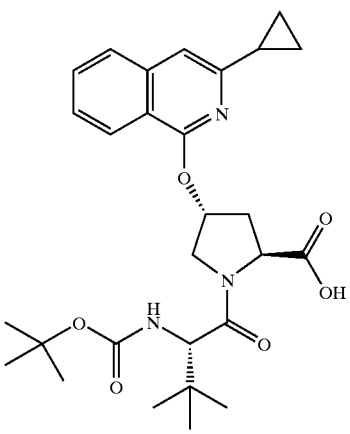

This product was prepared by the same method as described in Example 1, Step 5 as a white solid, except using 1-chloro-3-cyclopropyl-isoquinoline instead.

$^1$HNMR (CD$_3$OD) δ 0.93–1.05 (m, 13H), 1.29 (s, 9H), 2.06–2.10 (m, 1H), 2.39–2.44 (m, 1H), 2.70–2.76 (m, 1H), 4.05–4.12 (m, 1H), 4.27 (b, 1H), 4.35 (d, J=10.0 Hz, 1H), 4.62–4.67 (m, 1H), 5.78 (b, 1H), 7.18 (s, 1H), 7.38 (t, J=7.5 Hz, 1H), 7.61 (t, J=7.5 Hz, 1H), 7.66 (d, J=8.0 Hz, 1H), 8.09 (d, J=8.0 Hz, 1H);

LC-MS (retention time: 1.96 min, method B), MS m/z 512 (M$^+$+H).

Step 4:

Compound 34 was prepared by the same method as described in Example 1, Step 9 as a white solid, except using the product of Example 34, Step 3 instead.

$^1$HNMR (CD$_3$OD) δ 0.93–1.09 (m, 16H), 1.24–1.30 (m, 10H), 1.42–1.46 (m, 1H), 1.87–1.90 (m, 1H), 2.06–2.11 (m, 1H), 2.21–2.32 (m, 2H), 2.56–2.61 (m, 1H), 2.92–2.97 (m, 1H), 4.08–4.12 (m, 1H), 4.28 (b, 1H), 4.32 (d, J=10.0 Hz, 1H), 4.48–4.53 (m, 1H), 5.12 (d, J=10.5 Hz, 1H), 5.30 (d, J=17.5 Hz, 1H), 5.72–5.77 (m, 1H), 5.82 (b, 1H), 7.18 (s, 1H), 7.36 (t, J=7.5 Hz, 1H), 7.60 (t, J=7.5 Hz, 1H), 7.67 (d, J=8.0 Hz, 1H), 8.07 (d, J=8.0 Hz, 1H);

LC-MS (retention time: 2.00 min, method B), MS m/z 724 (M$^+$+H).

Example 35

Preparation of Compound 35

Compound 35

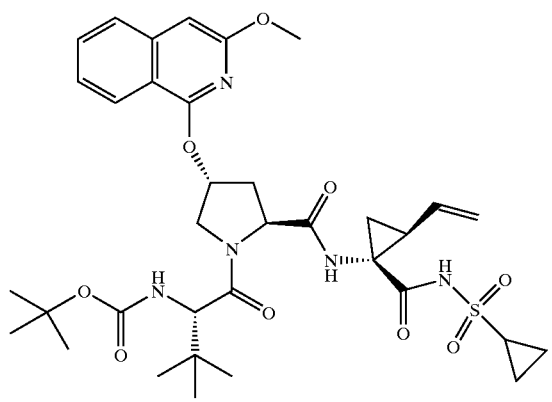

-continued

Scheme 1

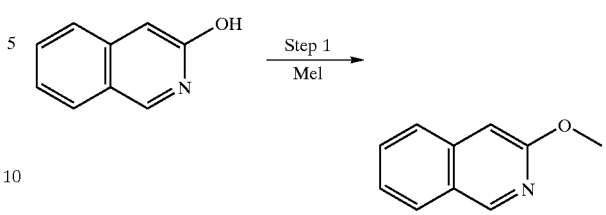

Step 1:

A mixture of 3-hydroxy-isoquinoline (725 mg, 5.0 mmol), cesium carbonate (4.89 g, 15.0 mmol), MeI (781 mg, 5.5 mmol) in DMF (50 mL) was stirred at the ambient temperature for 12 h. The mixture was diluted with EtOAc (200 mL), filtered, washed with water (200 mL, ×2) and 1M NaOH (aq), brine respectively. The organic layer was dried over MgSO$_4$, filtered, evaporated. The residue was purified by prep-HPLC to yield 120 mg (15%) of the desired product as a white solid.

$^1$H NMR (CDCl$_3$) δ 4.03 (s, 3H), 6.99 (s, 1H), 7.36 (t, J=8.0 Hz, 1H), 7.56 (t, J=8.2 Hz, 1H), 7.68 (d, J=8.5 Hz, 1H), 7.87 (J8.5 Hz, 1H);

LC-MS (retention time: 0.54 min. method B), MS m/z 160 (M$^+$+H).

Step 2:

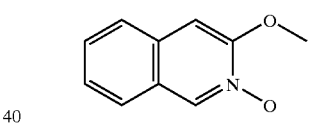

This product, 3-methoxy-isoquinoline 2-oxide, was prepared by the same method as described in Example 21, Step 2 as a white solid, except using 3-methoxy-isoquinoline instead.

LC-MS (retention time: 0.83 min. method B), MS m/z 176 (M$^+$+H).

Step 3:

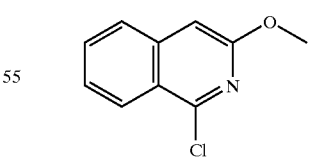

This product, 1-chloro-3-methoxy-isoquinoline was prepared by the same method as described in Example 11, Step 2 as white solid, except using 3-methoxy-isoquinoline 2-oxide instead.

LC-MS (retention time: 1.62 min, method B), MS m/z 194 (M$^+$+H).

Step 4:

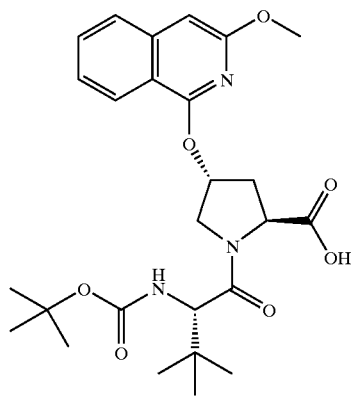

This product was prepared by the same method as described in Example 1, Step 5 as a white solid, except using 1-chloro-3-methoxy-isoquinoline instead.

$^1$HNMR (CD$_3$OD) δ 1.05 (s; 9H), 1.23 (s, 9H), 2.35–2.43 (m, 1H), 2.72–2.79 (m, 1H), 3.96 (s, 3H), 4.01–4.11 (m, 1H), 4.26 (b, 1H), 4.48 (d, J=10.0 Hz, 1H), 4.62–4.67 (m, 1H), 5.83 (b, 1H), 6.61 (s, 1H), 7.25 (t, J=7.5 Hz, 1H), 7.54 (t, J=7.5 Hz, 1H), 7.63 (d, J=8.1 Hz, 1H), 8.08 (d, J=8.4 Hz, 1H);

LC-MS (retention time: 1.82 min, method B), MS m/z 502 (M$^+$+H).

Step 5:

Compound 35 was prepared by the same method as described in Example 1, Step 9 as a white solid, except using the product of Example 35, Step 4 instead.

$^1$H NMR (CD$_3$OD) δ 1.04–1.08 (m, 12H), 1.24–1.27 (m, 10H), 1.43–1.45 (m, 1H), 1.86–1.89 (m, 1H), 2.21–2.26 (m, 1H), 2.30–2.34 (m, 1H), 2.62–2.66 (m, 1H), 2.91–2.97 (m, 1H), 3.99 (s, 3H), 4.09–4.12 (m, 1H), 4.27–4.28 (m, 1H), 4.46 (d, J=10.0 Hz, 1H), 4.51–4.58 (m, 1H), 5.12 (d, J=10.5 Hz, 1H), 5.30 (d, J=18.0 Hz, 1H), 5.72–5.76 (m, 1H), 5.88 (b, 1H), 6.62 (s, 1H), 7.26 (t, J=7.5 Hz, 1H), 7.55 (t, J=7.5 Hz, 1H), 7.65 (d, J=8.0 Hz, 1H), 8.06 (d, J=8.5 Hz, 1H);

LC-MS (retention time: 1.85 min, method B), MS m/z 714 (M$^+$+H).

Example 36

Preparation of Compound 36

Compound 36

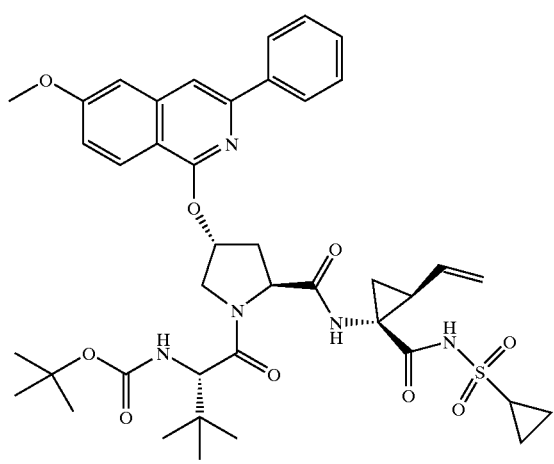

-continued
Scheme 1

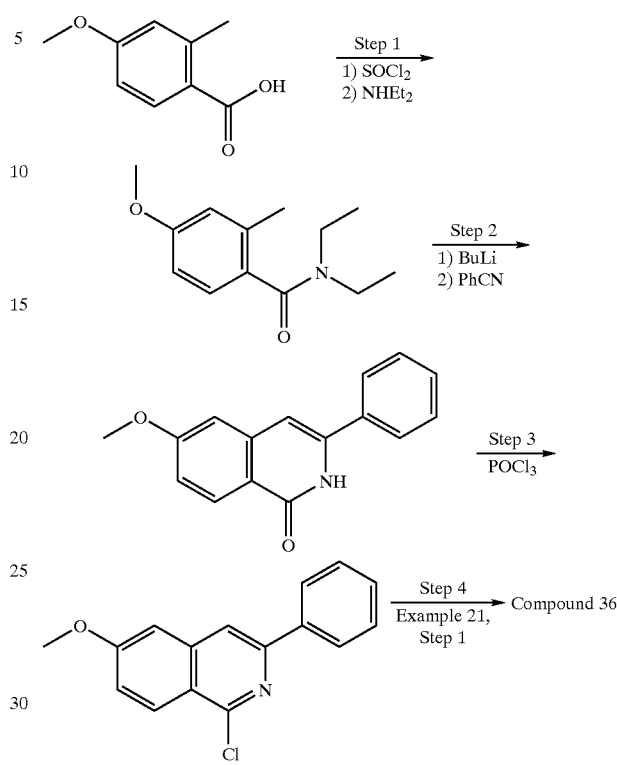

Step 1:

A mixture of 4-methoxy-2-methyl-benzoic acid (5.00 g, 30.1 mmol) and thionyl chloride (20.0 g, 0.17 mol) was heated to reflux for 30 min. Removed the volatile in vacuo. After pumping overnight, the viscous oily acid chloride was used as crude for the next reaction without any purification.

To a solution of 4-methoxy-2-methyl-benzoyl chloride in CH$_2$Cl$_2$ (60 mL) at 0° C. was added diethylamine dropwise. The formed mixture was allowed to warm up to the ambient temperature for 2 h with stirring. Removed the volatiles in vacuo. The residue was triturated with EtOAc (100 mL) and filtered. The filtrate was washed with 1M HCl, 1M NaOH and brine, dried over MgSO$_4$. Evaporation of the solvent yielded 6.51 g (98%) of the desired product as a viscous oil.

LC-MS (retention time: 1.20 min, method B), MS m/z 222 (M$^+$+H).

Step 2:

To a solution of N,N-diethyl-4-methoxy-2-methyl-benzamide (221 mg, 1.0 mmol) in THF (2 mL) at −78° C. was added n-BuLi (0.84 mL of 2.5 M in hexane, 2.10 mmol) dropwise. The formed orange solution was kept at this temperature for additional 30 min before dropwise addition of benzonitrile (103 mg, 1.0 mmol). The final solution was allowed to warm up to the ambient temperature over night with stirring. Quenched with iced 5% citric acid. Filtered, washed with water, dried. Trituration with 2:1 hexane-EtOAc (5 mL) yielded 205 mg (82%) of the desired product as a white solid.

$^1$H NMR (d$_6$-DMSO) δ 3.89 (s, 3H), 6.84 (s, 1H), 7.05–7.07 (m, 1H), 7.18 (d, J=2.5 Hz, 1H), 7.44–7.51 (m, 3H), 7.78 (d, J=7.0 Hz, 1H), 8.11 (d, J=9.0 Hz, 1H);

LC-MS (retention time: 1.20 min, method B), MS m/z 252 (M$^+$+H).

Step 3:

This product, 1-chloro-6-methoxy-3-phenyl-isoquinoline, was prepared by the same method as described in Example 11, Step 2 as a white solid, except using 6-methoxy-3-phenyl-2H-isoquinolin-1-one instead.

$^1$H NMR (CDCl$_3$) δ 3.97 (s, 3H), 7.12 (d, J=2.5 Hz, 1H), 7.23–7.26 (m, 1H), 7.40–7.42 (m, 1H), 7.46–7.50 (m, 2H), 7.89 (s, 1H), 8.08 (d, J=7.0 Hz, 2H), 8.21 (d, J=9.0 Hz, 1H);

LC-MS (retention time: 1.90 min, method B), MS m/z 270, 271 (M$^+$+H).

Step 4:

To a solution of the product of Example 21, Step 1 (320 mg, 0.57 mmol) in DMSO (5 mL) was added potassium tert-butoxide (321 mg, 2.87 mmol). The formed solution was stirred at the ambient temperature for 30 min before addition of 1-chloro-6-methoxy-3-phenyl-isoquinoline (Example 36, Step 3) (155 mg, 0.57 mmol). The final solution was stirred for 12 h. Quenched with iced water, acidified with 1M HCl to pH 4, extracted with EtOAc (20 mL, ×2). The organic layers were washed with brine, dried over MgSO$_4$, filtered, evaporated. The residue was purified by prep-HPLC (40% B to 100% B, 15 min grdient) to yield 289 mg (64%) of Compound 36 as a white solid.

$^1$H NMR (CD$_3$OD) δ 0.95–1.05 (m, 12H), 1.24–1.32 (m, 10H), 1.44–1.46 (m, 1H), 1.87–1.90 (m, 1H), 2.20–2.26 (m, 1H), 2.30–2.36 (m. 1H), 2.65–2.71 (m, 1H), 2.93–2.97 (m, 1H), 3.94 (s, 3H), 4.12–4.28 (m, 2H), 4.38–4.52 (m, 2H), 5.12 (d, J=10.0 Hz, 1H), 5.28 (d, J=17.0 Hz, 1H), 5.69–5.74 (m, 1H), 6.05 (b, 1H), 7.06–7.07 (m, 1H), 7.26 (s, 1H), 7.37–7.39 (m, 1H), 7.44–7.48 (m, 2H), 7.77 (s, 1H), 8.07 (d, J=9.0 Hz, 1H), 8.15 (d, J=8.5 Hz, 2H);

LC-MS (retention time: 2.02 min, method B), MS m/z 790 (M$^+$+H).

Example 37

Preparation of Compound 37

Compound 37

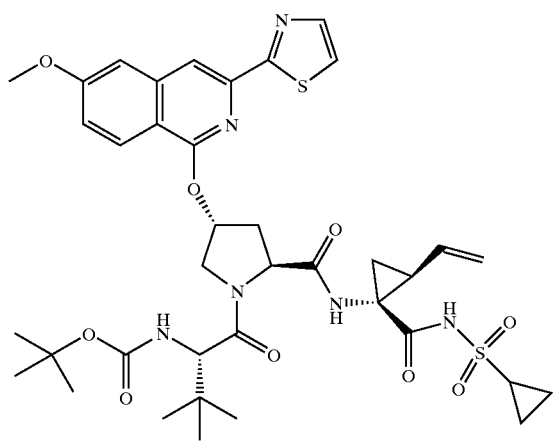

Scheme 1

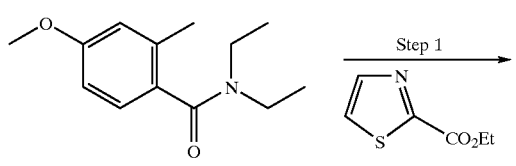

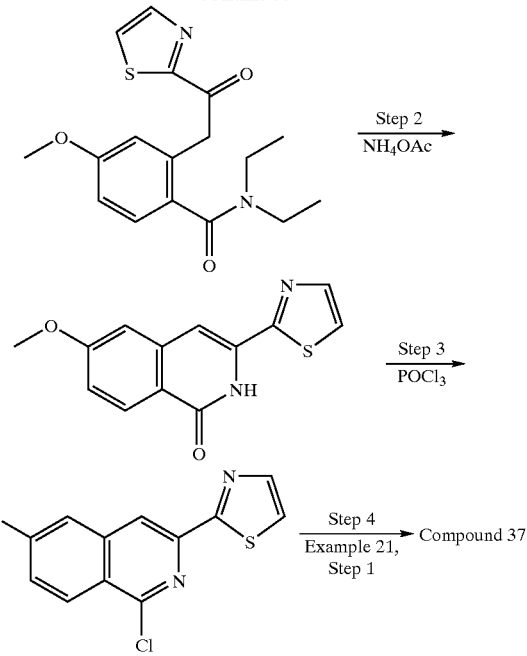

Step 1:

To a solution of N,N-diethyl-4-methoxy-2-methyl-benzamide (633 mg, 2.9 mmol) in THF (15 mL) at −78° C. was added n-BuLi (2.3 mL of 2.5 M in hexane, 5.74 mmol) dropwise. The formed red solution was kept at this temperature for additional 30 min before being cannulated to a solution of thiazole-2-carboxylic acid ethyl ester (A. Medici et al, Tetrahedron Lett. 1983, p2901) (450 mg, 2.9 mmol) in THF (5 mL) at −78° C. The final dark green solution was kept to this temperature for 2 h with stirring. Quenched with sat. NH$_4$Cl (aq) and extracted with EtOAc (50 mL). The organic layer was washed with sat. NH$_4$Cl (aq) and brine, dried, purified by flash column chromatography, eluting with 2:1 EtOAc:hexane to provide 405 mg (45%) of the desired product as an off-white viscous oil.

$^1$H NMR (CDCl$_3$) δ 1.08 (t, J=7.0 Hz, 6H), 3.22 (b, 2H), 3.44 (b, 2H), 3.79 (s, 3H), 4.59 (s, 2H), 6.79–6.81 (m, 1H), 6.86 (d, J=2.5 Hz, 1H), 7.16 (d, J=8.5 Hz, 1H), 7.66 (d, J=3.0 Hz, 1H), 8.00 (d, J=3.0 Hz, 1H);

LC-MS (retention time: 1.30 min, method B), MS m/z 333 (M$^+$+H).

Step 2:

A mixture of N,N-diethyl-4-methoxy-2-(2-oxo-2-thiazol-2-yl-ethyl)-benzamide (405 mg, 1.22 mmol) and NH$_4$OAc (3.0 g, 38.9 mmol) was heated to 140° C. in a sealed tube for 1 h. The melted solution was poured into iced water, filtered, washed the cake thoroughly with water. The dried brownish solid (240 mg, 76%) was used as crude for the next reaction without further purification.

LC-MS (retention time: 1.24 min, method B), MS m/z 259 (M$^+$+H).

Step 3:

This product, 1-chloro-6-methoxy-3-thiazol-2-yl-isoquinoline, was prepared by the same method as described in Example 11, Step 2 as a white solid, except using 6-methoxy-3-thiazol-2-yl-2H-isoquinolin-1-one instead.

$^1$H NMR (CDCl$_3$) δ 3.97 (s, 3H), 7.16 (d, J=4.0 Hz, 1H), 7.27–7.31 (m, 1H), 7.46 (d, J=5.0 Hz, 1H), 7.93 (d, J=5.5 Hz, 1H), 8.22 (d, J=15.5 Hz, 1H), 8.39 (s, 1H);

LC-MS (retention time: 1.66 min, method B), MS m/z 277 (M$^+$+H).

Step 4:

Compound 37 was prepared by the same method as described in Example 36, Step 4, except using 1-chloro-6-methoxy-3-thiazol-2-yl-isoquinoline instead.

$^1$H NMR (CD$_3$OD) δ 0.97–1.09 (m, 12H), 1.24–1.29 (m, 10H), 1.44–1.46 (m, 1H), 1.87–1.90 (m, 1H), 2.20–2.26 (m, 1H), 2.30–2.36 (m. 1H), 2.65–2.71 (m, 1H), 2.93–2.96 (m, 1H), 3.96 (s, 3H), 4.12–4.27 (m, 2H), 4.38–4.52 (m, 2H), 5.12 (d, J=10.5 Hz, 1H), 5.29 (d, J=17.5 Hz, 1H), 5.69–5.74 (m, 1H), 5.99 (b, 1H), 7.14 (d, J=9.0 Hz, 1H), 7.33 (s, 1H), 7.66 (d, J=3.5 Hz, 1H), 7.93 (d, J=3.0 Hz, 1H), 8.05 (s, 1H), 8.11 (d, J=9.0 Hz, 1H), 9.14 (b, 1H);

LC-MS (retention time: 1.89 min, method B), MS m/z 797 (M$^+$+H).

Example 38

Preparation of Compound 38

Compound 38

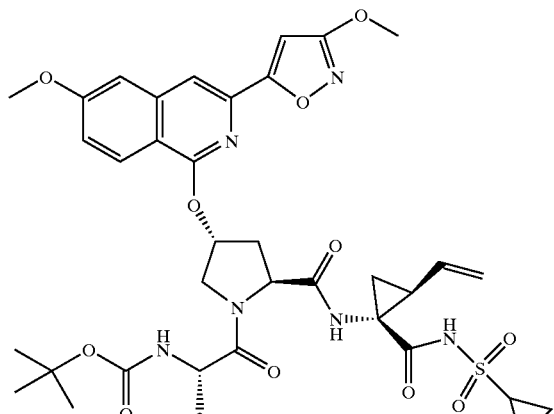

Scheme 1

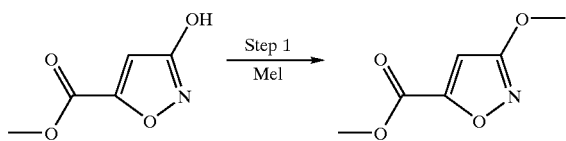

Step 1:

A mixture of 3-hydroxy-isoxazole-5-carboxylic acid methyl ester (5.72 g, 0.04 mol), methyl iodide (6.82 g, 0.044 mol) and cesium carbonate (39.1 g, 0.12 mol) in DMF (200 mL) was stirred at the ambient temperature over night. Diluted with EtOAc (lL), filtered. The filtrate was washed with water (lL, ×2), 1M NaOH and brine respectively, dried over MgSO4, evaporated in vacuo to afford 4.80 g (76%) of the desired product as a white solid. The product obtained here was used as crude without further purification.

$^1$H NMR (CDCl$_3$) δ 3.92 (s, 3H), 4.00 (s, 3H), 6.51 (s, 1H);

LC-MS (retention time: 0.69 min, method B), MS m/z 158 (M$^+$+H).

Step 2:

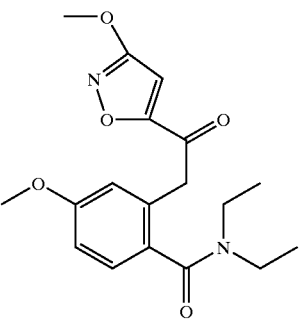

This product, N,N-diethyl-4-methoxy-2-[2-(3-methoxy-isoxazol-5-yl)-2-oxo-ethyl]-benzamide, was prepared by the same method as described in Example 37, Step 1, except using 3-methoxy-isoxazole-5-carboxylic acid methyl ester instead.

LC-MS (retention time: 1.28 min, method B), MS m/z 347 (M$^+$+H).

Step 3:

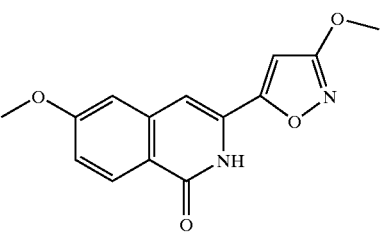

This product, 6-methoxy-3-(3-methoxy-isoxazol-5-yl)-2H-isoquinolin-1-one, was prepared by the same method as described in Example 37, Step 2, except using N,N-diethyl-4-methoxy-2-[2-(3-methoxy-isoxazol-5-yl)-2-oxo-ethyl]-benzamide instead.

$^1$H NMR (DMSO-d$_6$) δ 3.89 (s, 3H), 3.97 (s, 3H), 7.01 (s, 1H), 7.14–7.16 (m, 2H), 7.43 (s, 1H), 8.13 (d, J=8.5 Hz, 1H);

LC-MS (retention time: 1.31 min, method B), MS m/z 273 (M$^+$+H).

Step 4:

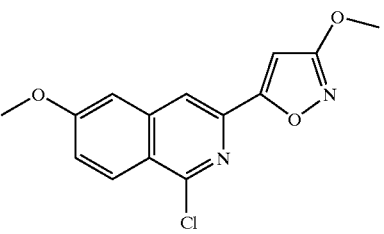

This product, 1-chloro-6-methoxy-3-(3-methoxy-isoxazol-5-yl)-isoquinoline, was prepared by the same method as described in Example 11, Step 2 as a white solid, except using 6-methoxy-3-(3-methoxy-isoxazole-5-yl)-2H-isoquinolin-1-one instead.

$^1$H NMR (CDCl$_3$) δ 3.97 (s, 3H), 4.04 (s, 3H), 6.60 (s, 1H), 7.17 (d, J=2.5 Hz, 1H), 7.31–7.33 (m, 1H), 8.02 (s, 1H), 8.23 (d, J=9.0 Hz, 1H);

LC-MS (retention time: 1.73 min, method B), MS m/z 291, 293 (M$^+$+H).

Step 5:

Compound 38 was prepared by the same method as described in Example 36, Step 4, except using 1-chloro-6-methoxy-3-(3-methoxy-isoxazole-5-yl)-isoquinoline instead.

¹H NMR (CD₃OD) δ 0.99–1.09 (m, 12H), 1.23–1.28 (m, 10H), 1.44–1.46 (m, 1H), 1.87–1.90 (m, 1H), 2.20–2.26 (m, 1H), 2.30–2.36 (m, 1H), 2.65–2.71 (m, 1H), 2.93–2.96 (m, 1H), 3.95 (s, 3H), 4.02 (s, 3H), 4.13–4.14 (m, 1H), 4.24–4.26 (m, 1H), 4.41–4.42 (m, 1H), 4.52–4.55 (m, 1H), 5.12 (d, J=10.5 Hz, 1H), 5.29 (d, J=17.0 Hz, 1H), 5.72–5.79 (m, 1H), 5.96 (b, 1H), 6.60 (s, 1H), 7.15–7.17 (m, 1H), 7.32 (s, 1H), 7.80 (s, 1H), 8.10 (d, J=9.0 Hz, 1H);

LC-MS (retention time: 1.95 min, method B), MS m/z 811 (M⁺+H).

Example 39

Preparation of Compound 39

Compound 39

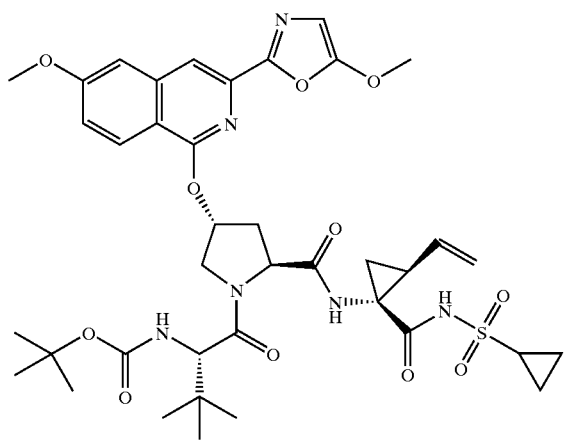

Step 1:

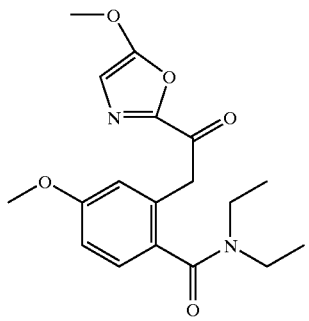

This product, N,N-diethyl-4-methoxy-2-[2-(5-methoxy-oxazol-2-yl)-2-oxo-ethyl]-benzamide, was prepared by the same method as described in Example 37, Step 1, except using 5-methoxy-oxazole-2-carboxylic acid ethyl ester instead.

LC-MS (retention time: 1.24 min, method B), MS m/z 347 (M⁺+H).

Step 2:

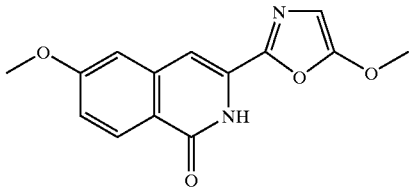

This product, 6-methoxy-3-(5-methoxy-oxazol-2-yl)-2H-isoquinolin-1-one, was prepared by the same method as described in Example 37, Step 2, except using N,N-diethyl-4-methoxy-2-[2-(5-methoxy-oxazol-2-yl)-2-oxo-ethyl]-benzamide instead.

¹H NMR (DMSO-d₆) δ 3.94 (s, 3H), 4.01 (s, 3H), 6.34 (s, 1H), 6.99 (d, J=2.0 Hz, 1H), 7.12–7.14 (m, 1H), 7.25 (s, 1H), 8.32 (d, J=9.0 Hz, 1H);

LC-MS (retention time: 1.22 min, method B), MS m/z 274 (M⁺+H).

Step 3:

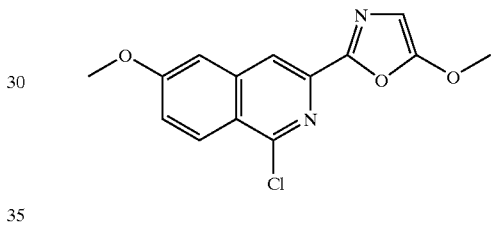

This product, 1-chloro-6-methoxy-3-(5-methoxy-oxazol-2-yl)-isoquinoline, was prepared by the same method as described in Example 11, Step 2 as a white solid, except using 6-methoxy-3-(5-methoxy-oxazole-2-yl)-2H-isoquinolin-1-one instead.

¹H NMR (CDCl₃) δ 3.96 (s, 3H), 4.00 (s, 3H), 6.34 (s, 1H), 7.12 (d, J=2.5 Hz, 1H), 7.28–7.31 (m, 1H), 8.13 (s, 1H), 8.23 (d, J=9.0 Hz, 1H);

LC-MS (retention time: 1.58 min, method B), MS m/z 291, 293 (M⁺+H).

Step 4:

Compound 39 was prepared by the same method as described in Example 36, Step 4, except using 1-chloro-6-methoxy-3-(3-methoxy-isoxazole-5-yl)-isoquinoline instead.

¹H NMR (CD₃OD) δ 0.99–1.09 (m, 12H), 1.23–1.28 (m, 10H), 1.44–1.46 (m, 1H), 1.87–1.90 (m, 1H), 2.20–2.26 (m, 1H), 2.30–2.36 (m, 1H), 2.65–2.71 (m, 1H), 2.93–2.96 (m, 1H), 3.95 (s, 3H), 4.02 (s, 3H), 4.13–4.14 (m, 1H), 4.25 (b, 1H), 4.41–4.42 (m, 1H), 4.52–4.55 (m, 1H), 5.12 (d, J=10.0 Hz, 1H), 5.29 (d, J=17.0 Hz, 1H), 5.72–5.79 (m, 1H), 6.07 (b, 1H), 6.45 (s, 1H), 7.15–7.16 (m, 1H), 7.29 (s, 1H), 7.85 (s, 1H), 8.10 (d, J=9.0 Hz, 1H), 9.11 (b, 1H);

LC-MS (retention time: 1.75 min, method B), MS m/z 811 (M⁺+H).

Example 40

Preparation of Compound 40

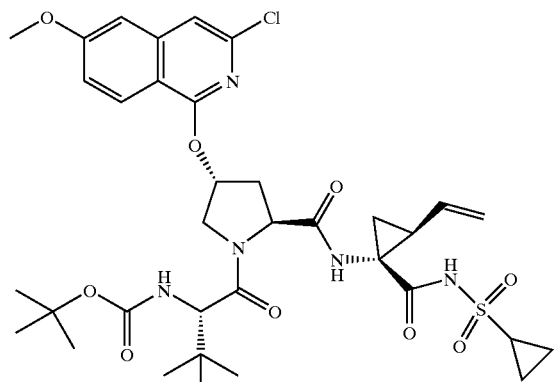

Scheme 1

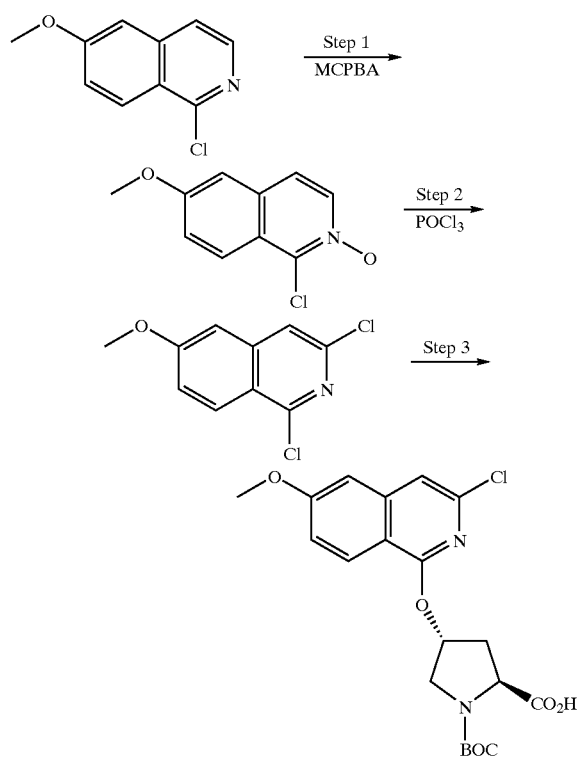

Step 1:

This product, 1-chloro-6-methoxy-isoquinoline 2-oxide was prepared by the same method as described in Example 21, Step 2, except using 1-chloro-6-methoxy-isoquinoline (the product of Example 11, Step 2) instead.

$^1$H NMR (CDCl$_3$) δ 4.00 (s, 3H), 7.14 (d, J=2.5 Hz, 1H), 7.41–7.43 (m, 1H), 7.62 (d, J=7.0 Hz, 1H), 8.15 (d, J=9.5 Hz, 1H), 8.36 (d, J=7.0 Hz. 1H);

LC-MS (retention time: 0.85 min. method B), MS m/z 210 (M$^+$+H).

Step 2:

This product, 1,3-dichloro-6-methoxy-isoquinoline was prepared by the same method as described in Example 11, Step 2, except using 1-chloro-6-methoxy-isoquinoline 2-oxide instead.

$^1$H NMR (CDCl$_3$) δ 3.94 (s, 3H), 6.98 (s, 1H), 7.25–7.26 (m, 1H), 7.52 9s, 1H), 8.16 (d, J=9.5 Hz, 1H);

LC-MS (retention time: 1.54 min. method B), MS m/z 228, 230 (M$^+$+H).

Step 3:

This product was prepared by the same method as described in Example 24, Step 1 as a foam, except using 1,3-dichloro-6-methoxy-isoquinoline instead.

$^1$H NMR (CD$_3$OD) δ 1.43, 1.44 (rotamers, 9H), 2.39–2.44 (m, 1H), 2.68–2.72 (m, 1H), 3.80–3.90 (m, 2H), 3.91 (s, 3H), 4.79–4.82 (m, 1H), 5.71 (b, 1H), 7.10–7.14 (m, 2H), 7.26 (s, 1H), 7.99–8.01 (m, 1H);

LC-MS (retention time: 1.79 min method B), MS m/z 422 (M$^+$+H).

Step 4:

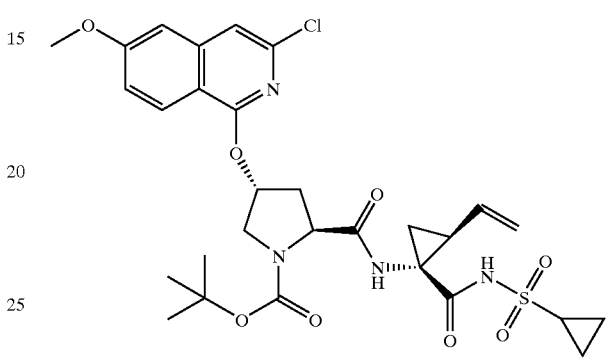

This product was prepared by the same method as described in Example 11, Step 4, except using the product of Example 40, Step 3 instead.

LC-MS (retention time: 1.83 min, method B), MS m/z 635 (M$^+$+H).

Step 5:

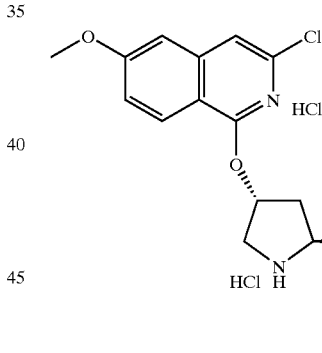

This product was prepared by the same method as described in Example 11, Step 5 as a white solid, except using the product of Example 40, Step 4 instead.

LC-MS (retention time: 1.36 min, method B), MS m/z 535 (M$^+$+H).

Step 6:

Compound 40 was prepared by the same method as described in Example 11, Step 6 as a white solid, except using the product of Example 40, Step 5 instead.

$^1$H NMR (CD$_3$OD) δ 1.07–1.11 (m, 12H), 1.26–1.30 (m, 10H), 1.46–1.48 (m, 1H), 1.87–1.91 (m, 1H), 2.21–2.34 (m, 2H), 2.62–2.66 (m, 1H), 2.94–2.99 (m, 1H), 3.95 (s, 3H), 4.06–4.11 (m, 1H), 4.26–4.28 (m, 1H), 4.46–4.56 (m, 2H), 5.15 (d, J=10.0 Hz, 1H), 5.29 (d, J=17.0 Hz, 1H), 5.72–5.79 (m, 1H), 5.89 (b, 1H), 6.63 (d, J=9.0 Hz, 1H), 7.08–7.09 (m, 1H), 7.18 (s, 1H), 7.34 (s, 1H), 8.08 (d, J=9.5 Hz, 1H);

LC-MS (retention time: 1.99 min, method B), MS m/z 748 (M$^+$+H).

Example 41

Preparation of Compound 41

Compound 41

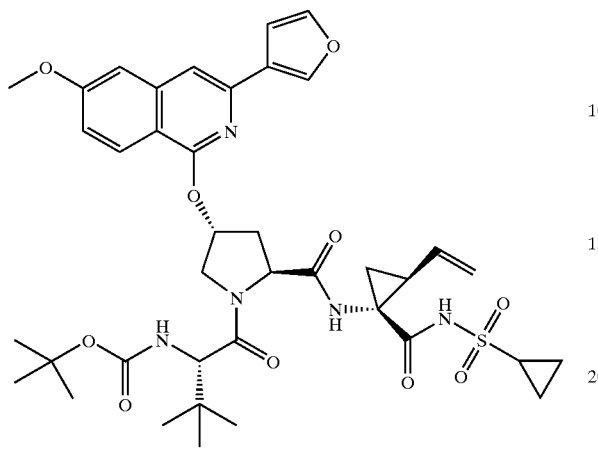

Step 1:

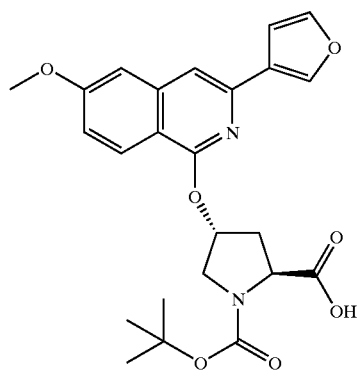

This product was prepared by the same method as described in Example 30, Step 1, except using the product of Example 40, Step 3 instead.

LC-MS (retention time: 1.85 min, method B), MS m/z 455 (M$^+$+H).

Step 2:

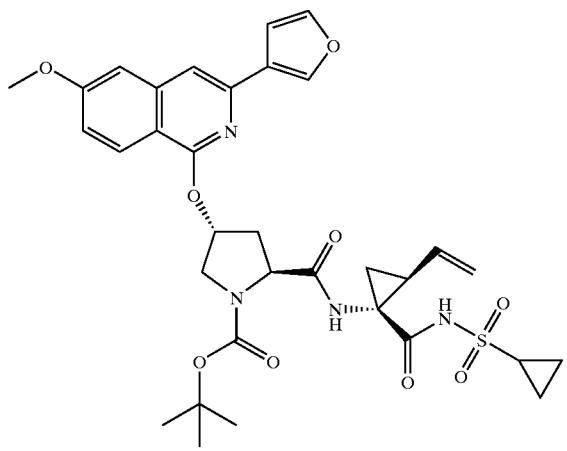

This product was prepared by the same method as described in Example 11, Step 4 as a foam, except using the product of Example 41, Step 1 instead.

LC-MS (retention time: 1.88 min, method B), MS m/z 667 (M$^+$+H).

Step 3:

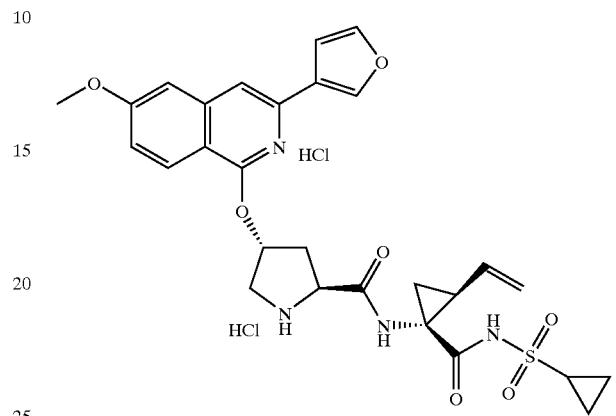

This product was prepared by the same method as described in Example 11, Step 5 as a white solid, except using the product of Example 41, Step 2 instead.

LC-MS (retention time: 1.38 min, method B), MS m/z 567 (M$^+$+H).

Step 4:

Compound 41 was prepared by the same method as described in Example 11, Step 6 as a white solid, except using the product of Example 41, Step 3 instead.

$^1$H NMR (CD$_3$OD) δ 0.99–1.04 (m, 12H), 1.22–1.31 (m, 10H), 1.43–1.45 (m, 1H), 1.87–1.89 (m, 1H), 2.22–2.24 (m, 1H), 2.30–2.34 (m, 1H), 2.65–2.68 (m, 1H), 2.93–2.96 (m, 1H), 3.92 (s, 3H), 4.11–4.14 (m, 1H), 4.28–4.30 (m, 1H), 4.38–4.42 (m, 1H), 4.53–4.55 (m, 1H), 5.12 (d, J=10.0 Hz, 1H), 5.29 (d, J=18.0 Hz, 1H), 5.72–5.77 (m, 1H), 5.99 (b, 1H), 6.61 (d, J=5.0 Hz, 1H), 6.98 (s, 1H), 6.99–7.02 (m, 1H), 7.17 (s, 1H), 7.44 (s, 1H), 7.57 (d, J=5.0 Hz, 1H), 8.03 (d, J=10.0 Hz, 1H), 8.14 (s, 1H);

LC-MS (retention time: 1.92 min, method B), MS m/z 780 (M$^+$+H).

Example 42

Preparation of Compound 42

Prepared following the procedures used in the preparation of Example 11. Compound 11, except that 6-ethoxy cinnamic acid was used in place of 6-methoxy cinnamic acid as starting material for the P2 element.

Compound 42

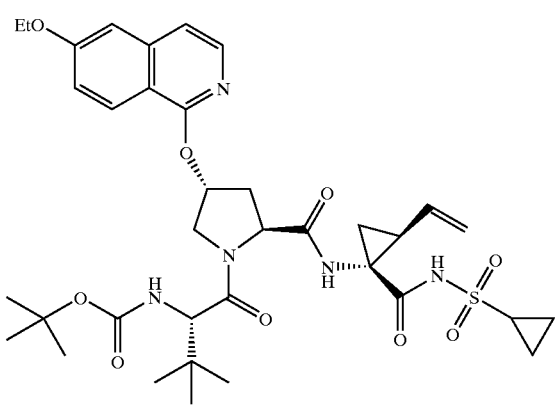

¹H NMR (500 MHz, CD₃OD) δ ppm 0.98–1.09 (m, 15H), 1.24–1.31 (m, 10H), 1.42–1.46 (m, 1H), 1.85–1.90 (m, 1H), 2.19–2.32 (m, 2H), 2.57–2.63 (m, 1H), 2.91–2.97 (m, 1H), 4.03–4.09 (m, 1H), 4.17 (q, J=7.0 Hz, 2H), 4.42 (d, J=11.3 Hz, 1H), 4.49–4.54 (m, 1H), 5.12 (d, J=17.4 Hz, 1H), 5.72–5.78 (m, 1H), 5.83 (s, 1H), 7.07–7.10 (M, 1H), 7.15 (s, 1H), 7.22 (d, J=5.8 Hz, 1H), 7.87 (d, J=5.8 Hz, 1H), 8.08 (d, J=8.8 Hz, 1H);

MS: (M+H)⁺ 728.

Section C:

Example 45

Preparation of Compound 45

Compound 45

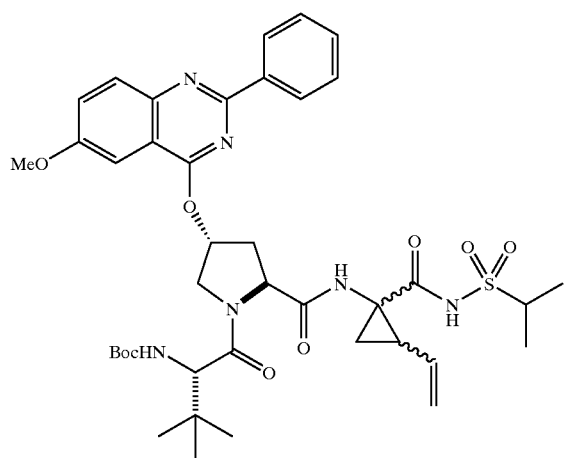

(1R,2S) and (1S,2R), 1:1 Mixture at P1

Scheme 1

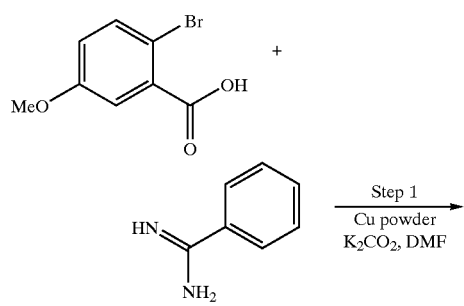

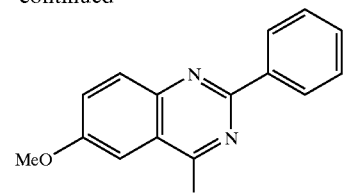

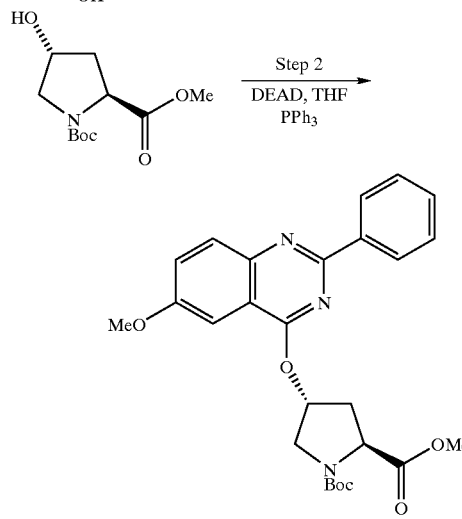

Step 1:

To a solution of 2-bromo-5-methoxybenzoic acid (1.68 g, 7.27 mmol) in DMF (50 mL) in a medium pressure flask (Chemglass) was added benzamidine (1.25 g, 8.00 mmol), K₂CO₃ (6.0 g, 43.6 mmol), and copper powder,(336 mg, 1.45 mmol). The reaction mixture was heated to 180C° for 1 h. Copper and excess K₂CO₃ were removed by vacuum filtration and washed with MeOH. The filtrate was concentrated and the resulting crude was purified by flash column chromatography (SiO₂, 5% MeOH in DCM) to give a light green solid (1.55 g, 84% yield): ¹H NMR (DMSO-d₆) δ 3.84 (s, 3H), 7.26 (d, J=7.8 Hz, 1H), 7.46 (br s, 5H), 7.57 (s, 1H), 8.38 (br s, 1H);

MS m/z (MH⁺) 253.

Step 2:

To a 0° C. slurry of Boc-cis-Hydroxyproline-OMe (2.0 g, 8.15 mmol) and the product from Example 45, Step 1 (2.26 g, 8.97 mmol) in THF (82 mL) was added Ph₃P and diisopropyl azocarboxylate (1.98 g, 8.97 mmol). After stirring at rt for 17 h, the reaction mixture was diluted with EtOAc (100 mL) and washed with H₂O (50 mL). The aqueous layer was separated and back-extracted with EtOAc (2×50 mL). The combined organic layer was washed with brine, dried over MgSO₄ and concentrated to give a viscous oil which was redissolved in minimal amount of EtOAc and hexanes was added to effect the precipitation of most of the Ph₃PO by-product. Ph₃PO was removed by vacuum filtration and the liquid filtrate was concentrated. The resulting viscous oil was purified by a flash column chromatography (SiO₂, 4:1 hex:EtOAc) to give a white solid product (1.76 g, 45% yield): ¹H NMR (60/40 rotomers, CDCl₃) δ 1.47 (s, 9H), 2.49–2.55 (m, 1H), 2.73–2.83 (m, 1H), 3.80 (s, 1.8H), 3.81 (s, 1.2H), 3.96 (s, 3H), 4.03–4.09 (m, 1H), 4.54 (t, J=8.0 Hz, 0.6H), 4.66 (t, J=7.8 Hz), 4.96–5.06 (m, 1H), 5.97 (br s, 0.6H), 6.04 (br s, 0.4H), 7.33 (dd, J=6.1, 2.7 Hz, 1H), 7.46–7.51 (m, 4H), 7.91 (d, J=9.2 Hz, 1H), 8.49 (t, J=8.5 Hz, 2H);

$^{13}$C NMR (rotomers, CDCl$_3$) δ 21.7, 22.0, 28.3, 28.4, 35.8, 36.8, 52.3, 52.4, 52.6, 55.8, 55.9, 57.9, 58.3, 74.5, 74.9, 80.6, 101.2, 101.3, 115.7, 125.8, 126.0, 128.1, 128.5, 129.7, 130.2, 137.9, 147.8, 153.8, 157.7, 158.0, 158.0, 164.8, 173.1, 173.3; MS m/z (MH$^+$) 480.

Scheme 2

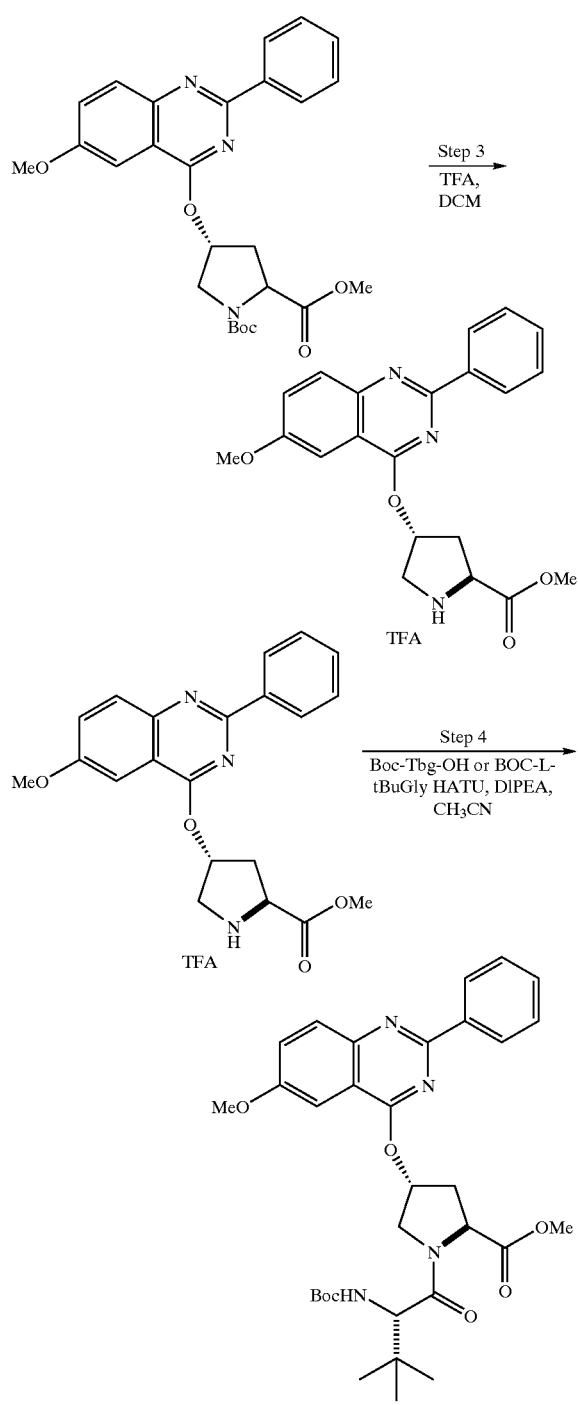

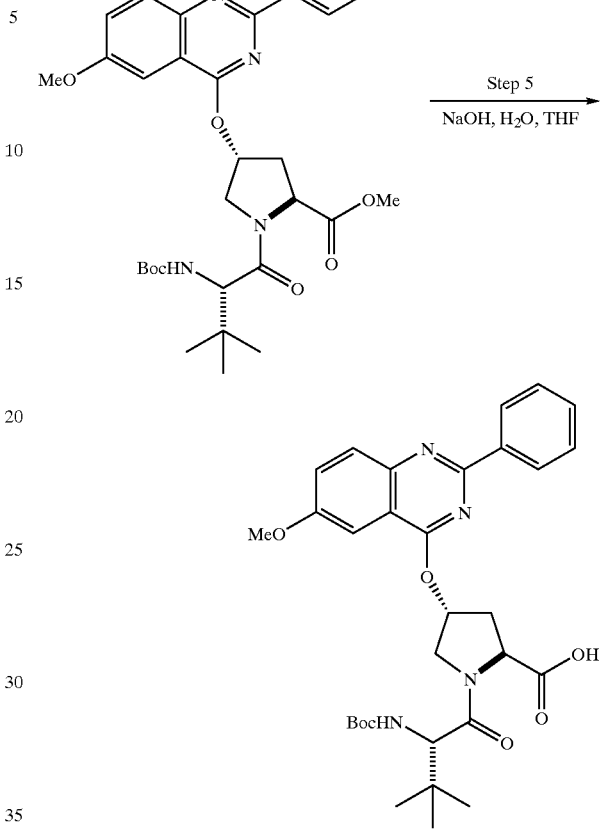

Step 3:
The product from Example 45, Step 2 (760.0 mg, 1.59 mmol) was dissolved in 50% TFA in DCM and stirred at rt for 2 h. The solvent was concentrated and the resulting brown viscous oil was dried in vacuo overnight. The product was used directly for the next reaction.

Step 4:
To a solution of the brown viscous oil product from Example 45, Step 3 (963 mg, 1.59 mmol) and DIPEA (1.23 g, 9.54 mmol) in DCM (11 mL) were added N-BOC L-tBuGly (440 mg, 1.90 mmole), HBTU (902 mg, 2.38 mmole) and HOBt (364 mg, 2.38 mmole). After stirring at rt for 14 h, the solvent and excess DIPEA was concentrated and the resulting brown viscous oil was purified by flash column (SiO$_2$, 4:1 hex:EtOAc) to give a white solid (0.922 mg, 98% yield for the two steps): $^1$H NMR (CDCl$_3$/MeOD) δ 0.94 (s, 9H), 1.15 (s, 9H), 2.38–2.42 (m, 1H), 2.60–2.73 (m, 1H), 3.61 (s, 3H), 3.83 (s, 3H), 4.08–4.17 (m, 2H), 4.25 (d, J=11.5 Hz, 1H), 4.69 (t, J=8.0 Hz, 1H), 5.99 (br s, 1H), 7.13 (s, 1H), 7.38 (s, 5H), 7.80 (d, J=9.0 Hz, 1H), 8.32 (d, J=5.5 Hz, 1H); $^{13}$C NMR (CDCl$_3$/MeOD) δ 29.6, 31.4, 31.6, 33.04, 38.2, 39.0, 55.8, 56.9, 59.2, 61.5, 62.1, 78.3, 83.1, 105.0, 119.0, 129.4, 131.5, 131.9, 132.6 133.8, 141.2, 151.0, 161.4, 161.6, 168.2, 175.2, 175.7; MS m/z (MH$^+$) 593.

Step 5:
To a solution of the product from Example 45, Step 4 (409 mg, 0.69 mmol) in THF (10 mL) was added 1N NaOH (2 mL). After stirring at rt for 19 h, the reaction was acidified with concentrated HCl to about pH 5 and extracted with DCM (3×50 mL). The combined organic layer was dried over MgSO$_4$ and concentrated to give a yellow solid product (370 mg, 92% yield) which was used directly in the next reaction after drying in vacuo: $^1$H NMR (CDCl$_3$) δ 1.05 (s, 9H), 1.25 (s, 9H), 2.76–2.83 (m, 2H), 3.94 (s, 3H), 4.23–4.27 (m, 2H), 4.41 (d, J=11.6 Hz, 1H), 4.92 (t, J=7.6 Hz, 1H), 5.20 (d, J=8.9 Hz, 1H), 6.08 (br s, 1H), 7.31 (s, 1H), 7.46–7.50 (m, 5H), 7.93 (d, J=9.15 Hz, 1H), 8.51 (d, J=7.3 Hz, 2H); MS m/z (MH$^+$) 579.

Scheme 3

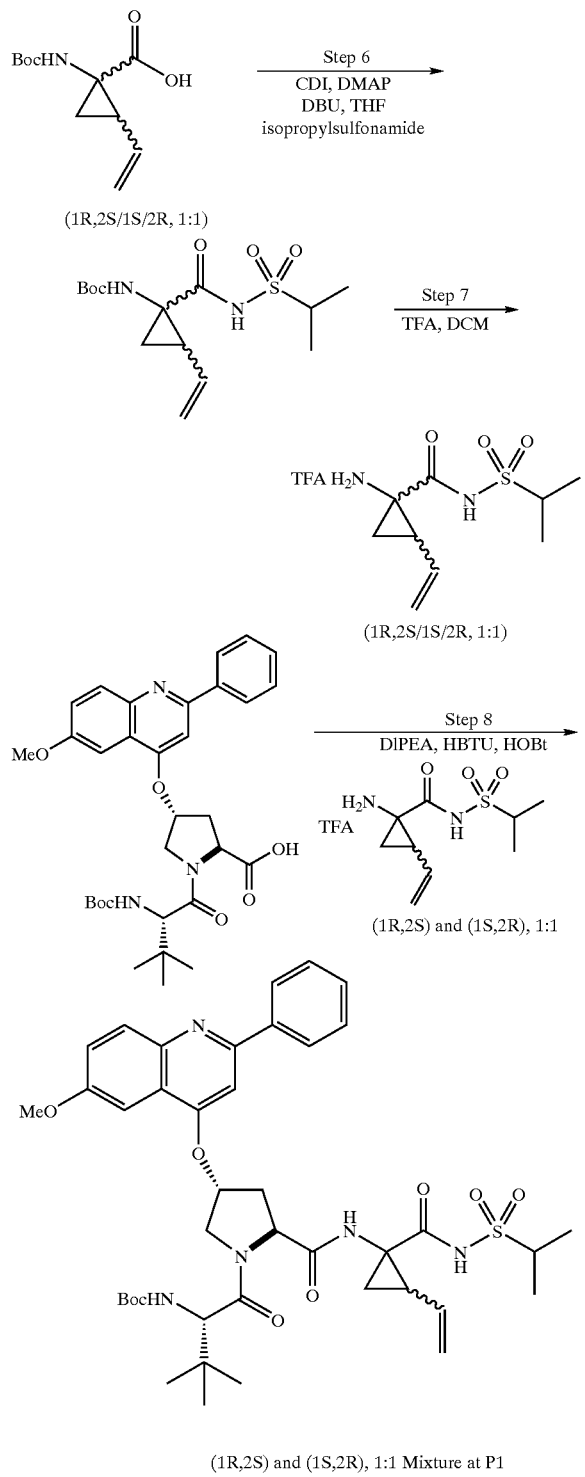

Compound 45

Step 6:

To a solution N-Boc-vinylcyclopropanecarboxylic acid (1R, 2S/1S, 2R 1:1 mixture) (1.01 g, 4.46 mmol) in THF (20 mL) and DMSO (2 mL) was added CDI (1.08 g, 6.69 mmol) and DMAP (817 mg, 6.69 mmol). After stirring at 70° C. for 1 h, the reaction mixture was allowed to cool to rt and was treated with isopropylsulfonamide (1.1 g, 8.92 mmol) and DBU (1.36 g, 8.92 mmol). The reaction mixture was stirred at rt for 16 h and it was concentrated and purified by flash column chromatography (SiO$_2$, 5% MeOH in DCM) to give a brown viscous oil (1.4 g, 98% yield): $^1$H NMR (Methanol-d4) δ 1.25 (m, 1H), 1.33 (d, J=6.7 Hz, 3H), 1.36 (d, J=6.7 Hz, 3H), 1.45 (s, 9H), 1.84 (dd, J=7.6, 5.2 Hz, 1H), 2.16 (d, J=7.6 Hz, 1H), 3.58 (br s, 1H), 5.08 (d, J=11.6 Hz, 1H), 5.27 (d, J=15.6 Hz, 1H), 5.58–5.66 (m, 1H); MS m/z (MH$^+$) 332.

Step 7:

The product from Example 45, Step 6 (113 mg, 0.34 mmol) was treated with a 50% solution of trifluoroacetic acid in DCM (10 mL) and stirred at rt for 1.4 h. Solvent and excess trifluoroacetic acid were removed in vacuo. The resulting brown viscous oil was dried in vacuo (1.3 g, 99% yield) and used without further purification: $^1$H NMR (DMSO-d$_6$) δ 1.24 (d, J=6.7 Hz, 3H), 1.26 (d, J=6.7 Hz, 3H), 1.54 (dd, J=9.6, 6.6 Hz, 1H), 1.99 (t, J=6.9 Hz, 1H), 2.24 (d, J=8.5 Hz, 1H), 3.58–3.63 (m, 1H), 5.18 (d, J=10.4 Hz, 1H), 5.33 (d, J=17.1 Hz, 1H), 5.61–5.69 (m, 1H), 8.83 (br s, 3H); $^{13}$C NMR (DMSO-d$_6$) δ 15.2, 15.9, 16.5, 29.9, 41.6, 52.1, 116.0, 118.9, 132.0, 158.2, 167.3; MS m/z (MH$^+$) 233.

Step 8:

To a mixture of the product from Example 45, Step 5 (117 mg, 0.338 mmol) and DIPEA (174 mg, 1.35 mmol) in DCM (5 mL) was added HBTU (128 mg, 0.338 mmole), HOBt (52 mg, 0.338 mmole) and the product from Example 45, Step 7 (130 mg, 0.225 mmol) After stirring at rt for 16 h, the mixture was concentrated and the resulting brown viscous oil was purified by flash column chromatography (SiO$_2$, 1:3 hex:EtOAc then 95:5 DCM:MeOH) to give an off white solid product (150 mg, 84% yield) The final product, Compound 45, is a mixture of isomers; the variation occuring at the P1 vinylcyclopropyl portion of the molecule (1R, 2S/1S, 2R 1:1 mixture): $^1$H NMR (Methanol-d$_4$) δ 0.92 (br s, $^2$H), 1.03 (s, 9H), 1.17 (s, 9H), 1.27–1.38 (m, 9H), 1.42–1.46 (m, 1H), 1.83 (dd, J=8.1, 5.3 Hz, 0.4H), 1.90 (dd, J=7.9, 5.5 Hz, 0.6H), 2.24–2.31 (m, 1H), 2.37–2.45 (m, 1H), 2.67–2.75 (m, 1H), 3.73–3.79 (m, 1H), 3.90 (s, 3H), 4.21 (dd, J=9.3, 6.0 Hz, 2H), 4.48 (d, J=11.3 Hz, 1H), 4.61 (q, J=8.9 Hz, 1H), 5.14 (t, J=9.0 Hz, 1H), 5.33 (t, J=17.9 Hz, 1H), 5.70–5.76 (m, 1H), 6.06 (d, J=11.9 Hz, 1H), 6.61 (d, J=8.9 Hz, 1H), 7.34 (d, J=2.8 Hz, 1H), 7.49 (br s, 5H), 7.87 (d, J=8.9 Hz, 1H), 8.46 (d, J=4.3 Hz, 2H); $^{13}$C NMR (Methanol-d$_4$) δ 15.7, 16.1, 16.5, 16.8, 23.9, 27.1, 28.6, 35.8, 36.0, 36.2, 36.3, 36.4, 42.6, 42.8, 54.7, 54.8, 55.5, 56.4, 61.1, 61.2, 80.5, 102.9, 117.0, 118.8, 118.9, 126.8, 129.4, 129.6, 130.2, 131.5, 134.4, 139.2, 148.8, 158.0, 159.3, 159.8, 166.3, 171.1, 175.1, 184.3; m/z (MH$^+$) 793.

Example 46

Preparation of Compound 46

Compound 46

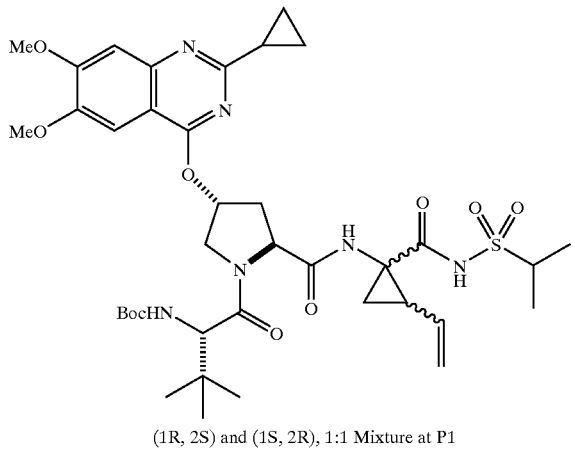

(1R, 2S) and (1S, 2R), 1:1 Mixture at P1

Compound 46 was prepared by following Steps 1 through 5 and Step 8 of Example 45 except that the following modifications were made:

Step 1:

Modifications: 2-bromo-4,5-dimethoxybenzoic acid and cyclopropylcarbamidine hydrochloride were utilized as starting materials.

Product:

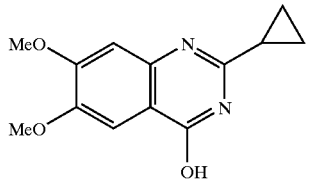

Data: $^1$H NMR (DMSO-d$_6$) δ 0.97–1.01 (m, 2H), 1.03–1.06 (m, 2H), 1.90–1.94 (m, 1H), 3.84 (s, 3H), 3.87 (s, 3H), 6.93 (s, 1H), 7.37 (s, 3H), 12.28 (s, 1H); $^{13}$C NMR (DMSO-d$_6$) δ 9.03, 13.17, 55.47, 55.73, 104.81, 107.27, 113.26, 145.16, 147.48, 154.44, 157.21, 160.89; MS m/z (MH$^+$) 247.

Step 2:

Modifications: The product from Example 46, Step 1 was used as starting material in place of the product from Example 45, Step 1.

Product:

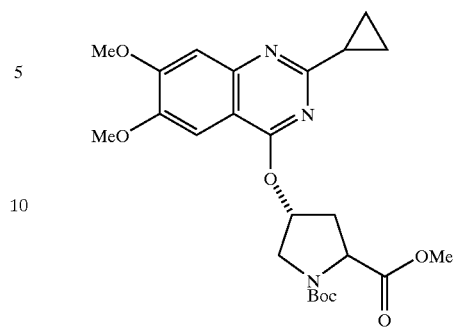

Data: $^1$HNMR (CDCl$_3$) δ 1.00–1.04 (m, 2H), 1.07–1.11 (m, 2H), 1.43 (s, 5.4H), 1.46 (s, 3.6H), 2.17–2.21 (m, 1H), 2.37–2.43 (m, 1H), 2.62–2.69 (m, 1H), 3.75 (s, 1.8H), 3.78 (s, 1.2H), 3.92 (d, J=2.8 Hz, 1H), 4.00 (s, 3.6H), 4.01 (s, 2.4H), 4.48 (t, J=8.0 Hz, 0.6H), 4.59 (t, J=7.6 Hz, 0.4H), 5.7 (br s, 0.6H), 5.74 (br s, 0.4H), 7.18 (s, 1H), 7.20 (s, 1H); $^{13}$C NMR (CDCl$_3$) δ 9.6, 9.7, 18.1, 28.3, 28.4, 35.8, 36.7, 52.2, 52.4, 56.3, 57.8, 58.2, 74.0, 74.5, 80.5, 80.6, 101.0, 101.1, 106.3, 108.6, 148.8, 149.1, 153.8, 155.4, 164.4, 165.9, 172.9, 173.2; LC-MS m/z (MH$^+$) 474.

Steps 3 and 4:

The product from Example 46, Step 2 was used as starting material in place of the product from Example 45, Step 2.

Product:

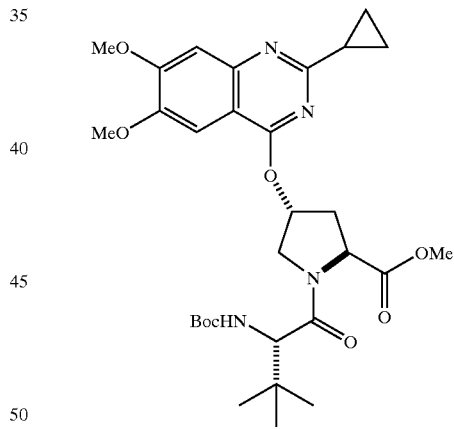

Data: $^1$H NMR (Methanol-d$_4$) δ 1.04 (s, 9H), 1.08–1.21 (m, 4H), 1.14 (s, 9H), 2.17–2.21 (m, 1H), 2.39–2.41 (m, 1H), 2.74–2.77 (m, 1H), 3.77 (s, 3H), 3.92 (s, 3H), 3.98 (m, 3H), 4.09 (dd, J=11.4, 3.8 Hz, 1H), 4.17 (d, J=8.9 Hz, 1H), 4.42 (d, J=11.3 Hz, 1H), 4.76 (t, J=8.2 Hz, 1H), 5.81 (br s, 1H), 6.43 (d, J=8.6 Hz, 1H), 7.14 (d, J=6.1 Hz, 1H), 7.27 (d, J=5.8 Hz, 1H); $^{13}$C NMR (Methanol-d$_4$) δ 10.0, 10.3, 18.6, 26.9, 28.5, 28.8, 35.8, 36.1, 38.9, 52.8, 54.9, 56.7, 59.6, 60.5, 76.6, 80.4, 102.7, 106.2, 109.9, 149.8, 150.7, 157.6, 166.0, 167.3, 173.5, 173.6; MS m/z (MH$^+$) 587.

Step 5:

The product from Example 46, Step 4 was used as starting material in place of the product from Example 45, Step 4.

Product:

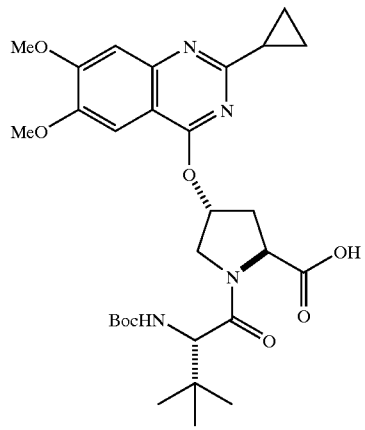

Data: $^1$H NMR (Methanol-d$_4$) δ 1.03 (s, 9H), 1.13 (s, 9H), 1.20–1.23 (m, 4H), 2.15–2.19 (m, 1H), 2.40–2.45 (m, 1H), 2.70–2.76 (m, 1H), 3.90 (s, 3H), 3.96 (s, 3H), 4.08 (dd, J=11.4, 3.8 Hz, 1H), 4.17 (d, J=5.8 Hz, 1H), 4.37 (d, J=11.3 Hz, 1H), 4.71 (t, J=8.1 Hz, 1H), 5.77 (br s, 1H), 7.09 (s, 1H), 7.20 (s, 1H); $^{13}$C NMR (Methanol-d$_4$) δ 10.2, 10.5, 18.6, 26.9, 28.5, 28.8, 36.0, 36.3, 54.9, 56.8, 59.7, 60.4, 76.8, 80.4, 102.6, 105.9, 109.9, 126.9, 127.9, 149.3, 150.8, 157.65, 157.8, 166.1, 167.3, 173.3, 175.1; MS m/z (MH$^+$) 573.

Step 8:

The product from Example 46, Step 5 was used as starting material in place of the product from Example 45, Step 5. The final product, Compound 46, is a mixture of isomers; the variation occuring at the P1 vinylcyclopropyl portion of the molecule (1R, 2S/1S, 2R 1:1 mixture).

Product:

Compound 46

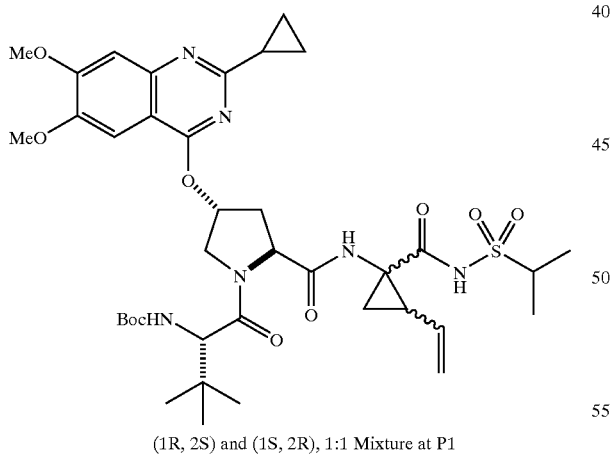

(1R, 2S) and (1S, 2R), 1:1 Mixture at P1

Data: $^1$H NMR (Methanol-d$_4$) δ 1.03 (s, 9H), 1.05–1.09 (m, 4H), 1.16 (s, 4.5H), 1.17 (s, 4.5H), 1.19–1.22 (m, 1H), 1.31 (d, J=6.7 Hz, 2H), 1.33–1.38 (m, 7H), 1.18–1.89 (m, 1H), 2.15–2.20 (m, 2H), 2.35–2.44 (m, 1H), 3.23 (q, J=7.4 Hz, 1H), 3.70–3.75 (m, 1H), 3.91 (s, 3H), 3.98 (s, 3H), 4.08–4.13 (m, 2H), 4.16 (dd, J=8.9, 3.1 Hz, 1H), 4.38 (t, J=13.1 Hz, 1H), 4.58–4.62 (m, 1H), 4.06 (m, 1H), 5.29 (t, J=15.2 Hz, 1H), 5.83 (br s, 1H), 7.15 (s, 1H), 7.27 (d, J=4.3 Hz, 1H); MS m/z (MH$^+$) 787.

Example 47

Preparation of Compound 47

Compound 47

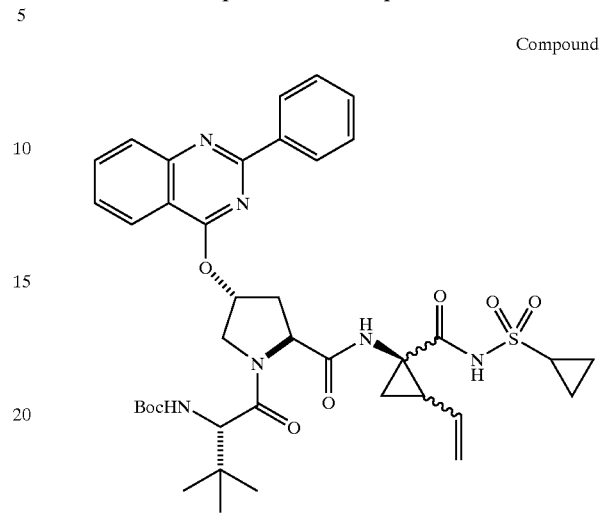

Compound 47 was prepared by following analogous steps used to procure Compound 45 of Example 45. ortho-bromobenzoic acid used as starting material as was cyclopropanesulfonic acid (1R-amino-2S-vinyl-cyclopropanecarbonyl)-amide hydrochloride salt. Compound 47: MH$^+$=761

Example 48

Preparation of Compound 48

Compound 48

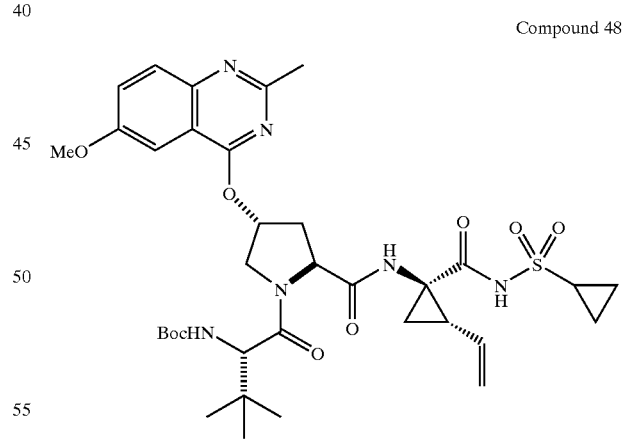

Compound 48 was prepared by following Steps 1 through 5 and Step 8 of Example 45 except that the following modifications were made:

Step 1:

Modifications: Acetamidine hydrochloride and 2-bromo-5-methoxybenzoic acid were utilized as starting materials.

Product:

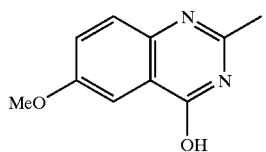

Data: $^1$H NMR (DMSO) δ 2.31 (s, 3H), 3.85 (s, 3H), 7.36 (d, J=6.2 Hz, 1H), 7.37 (s, 1H), 7.51 (d, J=7.8 Hz, 1H), 12.15 (s, 1H); $^{13}$C NMR (DMSO) δ 21.11, 55.41, 105.57, 121.22, 123.59, 128.12, 143.34, 151.68, 157.00, 161.45; LC-MS m/e (MH$^+$) 191.

Step 2:
Modifications: The product from Example 48, Step 1 was used as starting material in place of the product from Example 45, Step 1.
Product:

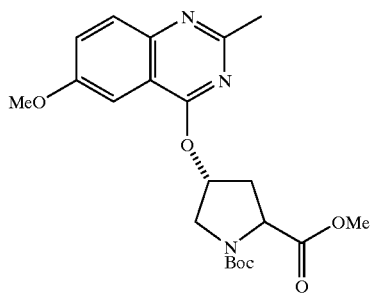

Data: $^1$H NMR (CDCl$_3$) δ 1.43 (s, 5.4H), 1.45 (s, 3.6H), 2.38–2.45 (m, 1H), 2.62–2.71 (m, 1H), 2.66 (s, 1.8H), 2.68 (s, 1.2H), 3.77 (1.8H), 3.79 (s, 1.2H), 3.92 (s, 3H), 3.93–3.98 (m, 2H), 4.49 (t, J=8.0 Hz, 0.6H), 4.61 (t, J=7.8 Hz, 0.4H), 5.82 (t, J=2.1 Hz, 0.6H), 5.89 (t, J=2.3 Hz, 0.4H), 7.26 (dd, J=4.7, 3.2 Hz, 1H), 7.42 (dd, J=6.3, 2.8 Hz, 1H), 7.75 (d, J=9.15 Hz, 1H); $^{13}$C NMR (CDCl$_3$) δ 26.1, 28.3, 28.4, 35.8, 36.7, 52.2, 52.2, 52.4, 52.5, 55.755.8, 57.9, 58.2, 74.1, 74.7, 80.6, 101.0, 101.2, 114.9, 125.6, 125.9, 128.6, 147.3, 153.8, 154.5, 157.6, 157.6, 161.2, 164.6, 173.0, 173.3; LC-MS m/e (MH$^+$) 418.

Steps 3 and 4:
Modifications: The product from Example 48, Step 2 was used as starting material in place of the product from Example 45, Step 2.
Product:

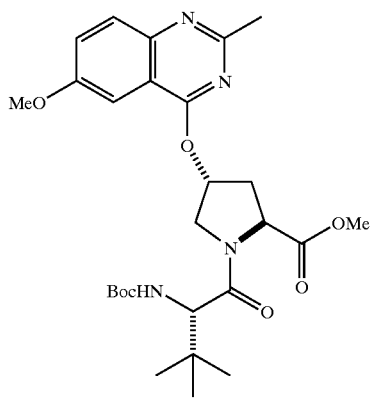

Data: $^1$HNMR (MeOD) δ 1.03 (s, 9H), 1.07 (s, 9H), 2.38–2.42 (m, 1H), 2.68 (s, 3H), 2.80 (q, J=7.8 Hz, 1H), 3.76 (s, 3H), 3.89 (s, 3H), 4.07 (dd, J=11.9, 3.4 Hz, 1H), 4.13 (br s, 1H), 4.55 (d, J=12.2 Hz, 1H), 4.78 (t, J=8.7 Hz, 1H), 5.93 (s, 1H), 7.37 (d, J=2.75 Hz, 1H), 7.48–7.51 (m, 2H), 7.70 (d, J=5.7 Hz, 1H); $^{13}$C NMR (MeOD) δ 25.6, 26.9, 28.4, 28.8, 35.9, 52.8, 55.0, 56.4, 59.7, 60.6, 77.2, 80.4, 102.9, 111.6, 116.5, 127.0, 128.4, 147.5, 162.7, 166.4, 173.6; LC-MS m/e (MH$^+$) 531.

Step 5:
Modifications: The product from Example 48, Step 4 was used as starting material in place of the product from Example 45, Step 4.
Product:

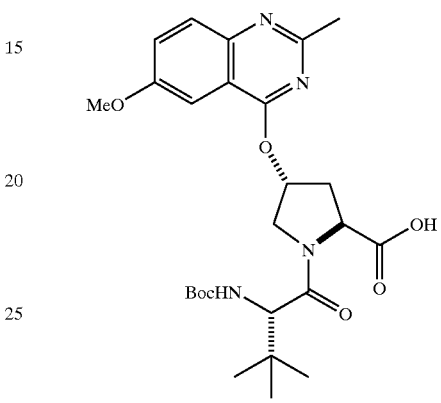

Data: $^1$H NMR (MeOD) δ 1.03 (s, 9H), 1.08 (s, 9H), 2.41–2.46 (m, 1H), 2.68 (s, 3H), 2.81 (q, J=8.1 Hz, 1H), 3.89 (s, 3H), 4.07 (dd, J=11.8, 3.2 Hz, 1H), 4.18 (d, J=5.5 Hz, 1H), 4.52 (d, J=11.9 Hz, 1H), 4.74 (t, J=8.7 Hz, 1H), 5.93 (br s, 1H), 7.37 (d, J=2.81 Hz, 1H), 7.49 (dd, J=9.2, 2.4 Hz, 1H), 7.71 (d, J=9.2 Hz, 1H); $^{13}$C NMR (MeOD) δ 25.7, 26.9, 28.5, 36.1, 55.0, 56.4, 59.7, 60.5, 77.1, 80.4, 103.0, 116.5, 127.0, 128.5, 147.7, 157.8, 159.6, 162.7, 166.4, 173.5, 174.9; LC-MS m/e (MH$^+$) 517.

Example 48

Preparation of Compound 48

Compound 48

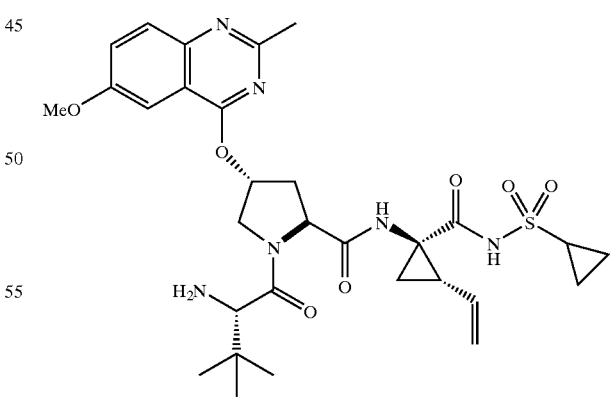

Step 8:
To a solution of the product from Example 48, Step 5 (45.8 mg, 0.089 mmol), cyclopropanesulfonic acid (1R-amino-2S-vinyl-cyclopropanecarbonyl)-amide hydrochloride salt (21.0 mg, 0.089 mmol) and DIEA (34.5 mg, 0.267 mmol) in DCM (1 mL) was added HATU (44.0 mg, 0.116 mmol). After stirring at rt overnight, the reaction mixture was washed with 5% aqueous NaHCO₃ (1 mL). The aqueous layer was extracted was 2×2 mL DCM. The organic layer was washed with 5% aqueous citric acid (1 mL), brine, dried over MgSO4, concentrated and purified by reversed prep-HPLC. This purification step resulted in the loss of the N-BOC protecting group at the P3 tert-leucine portion of the molecule: $^1$H NMR (MeOD) δ 1.07–1.12 (m, 2H) 1.14 (s, 2H) 1.14–1.16 (m, 2H) 1.17 (s, 9H) 1.20–1.30 (m, 3H) 1.45 (dd, J=9.46, 5.49 Hz, 1H) 1.56 (s, 1H) 1.92 (dd, J=8.20, 5.60 Hz, 1H) 2.25–2.31 (m, 1H) 2.39–2.45 (m, 1H) 2.73 (m, 1H) 2.76 (s, 3H) 2.93–2.97 (m, 1H) 3.94 (s, 1H) 3.96 (s, 3H) 4.07 (s, 1H) 4.21 (d, J=3.97 Hz, 0.4H) 4.23 (d, J=3.97 Hz, 0.6H) 4.31 (m, 1H) 4.73 (dd, J=10.38, 7.02 Hz, 1H) 5.15 (dd, J=10.38, 1.52 Hz, 1H) 5.32 (dd, J=17.1, 1.52 Hz, 1H), 5.71–5.78 (m, 1H) 6.1t (t, J=3.51 Hz, 1H) 7.46 (d, J=2.75 Hz, 1H) 7.67 (d, J=3.06 Hz, 0.4H) 7.69 (d, J=3.05 Hz, 0.6H) 7.82 (s, 0.6H) 7.84 (s, 0.4H).

Example 49

Preparation of Compound 49

Compound 49

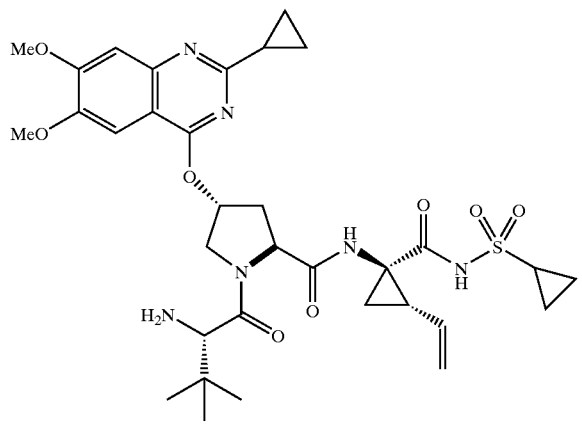

Compound 49 was prepared by the same method as described for the preparation of Compound 48, except the product from Example 46, Step 5 and cyclopropanesulfonic acid (1R-amino-2S-vinyl-cyclopropanecarbonyl)-amide hydrochloride salt were used as starting material. The preparative HPLC purification step resulted in the loss of the N-BOC protecting group at the P3 tert-leucine portion of the molecule: $^1$HNMR (MeOD) δ 1.09 (m, 2H) 1.14 (d, J=3.97 Hz, 2H) 1.17 (s, 9H) 1.25 (m, 3H) 1.37 (m, 3H) 1.44 (dd, J=9.31, 5.65 Hz, 2H) 1.57 (s, 1H) 1.92 (dd, J=8.09, 5.65 Hz, 1H) 2.28 (dd, J=17.70, 8.55 Hz, 1H) 2.32 (m, 1H) 2.68 (dd, J=14.19, 7.78 Hz, 1H) 2.95 (m, 1H) 3.98 (s, 3H) 4.06 (s, 3H) 4.08 (s, 1H) 4.22 (d, J=2.75 Hz, 1H) 4.70 (dd, J=9.77, 7.32 Hz, 1H) 5.15 (dd, J=10.38, 1.53 Hz, 1H) 5.32 (dd, J=17.40, 1.22 Hz, 1H) 5.74 (m, 1H) 6.04 (m, 1H) 7.24 (s, 1H) 7.37 (s, 1H)

Example 50

Preparation of Compound 50

Compound 50

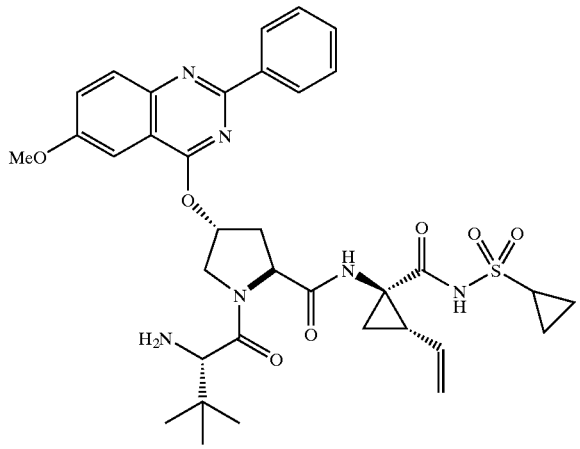

Compound 50 was prepared by the same method as described for the preparation of Compound 48, except the product from Example 45, Step 5 and cyclopropanesulfonic acid (1R-amino-2S-vinyl-cyclopropanecarbonyl)-amide hydrochloride salt were used as starting material. The preparative HPLC purification step resulted in the loss of the N-BOC protecting group at the P3 tert-leucine portion of the molecule: $^1$H NMR (MeOD) δ 1.10 (m, 2H) 1.14 (s, 1H) 1.15 (d, J=3.36 Hz, 1H) 1.17 (d, J=3.05 Hz, 9H) 1.22 (m, 1H) 1.27 (m, 2H) 1.46 (dd, J=9.46, 5.49 Hz, 1H) 1.56 (s, 1H) 1.93 (dd, J=8.24, 5.49 Hz, 1H) 2.29 (q, J=8.55 Hz, 1H) 2.48 (m, 1H) 2.78 (dd, J=13.89, 8.09 Hz, 1H) 2.97 (m, 1H) 3.96 (s, 2H) 4.07 (s, 1H) 4.32 (d, J=2.14 Hz, 2H) 4.76 (d, J=7.02 Hz, 1H) 4.78 (m, 1H) 4.86 (d, J=3.05 Hz, 1H) 5.32 (dd, J=17.09, 1.22 Hz, 1H) 5.75 (m, 1H) 6.24 (d, J=2.44 Hz, 1H) 7.45 (d, J=2.75 Hz, 1H) 7.52 (m, 3H) 7.61 (dd, J=9.16, 2.75 Hz, 1H) 7.96 (d, J=9.16 Hz, 1H).

Example 51

Preparation of Compound 51

Compound 51

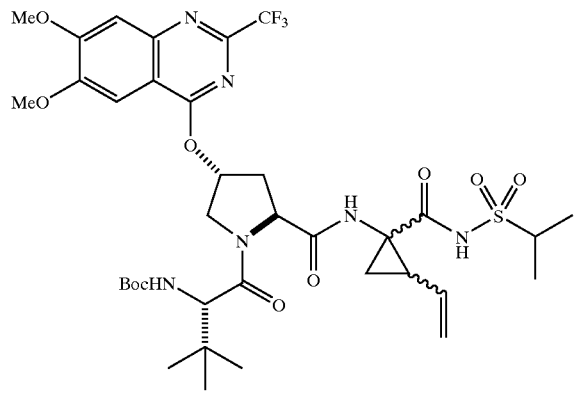

(1R, 2S) and (1S, 2R), 1:1 Mixture at P1

Compound 51 was prepared by following Steps 1 through 5 and Step 8 of Example 45 except that the following modifications were made:

Step 1:
Modifications: 2-bromo-4,5-dimethoxybenzoic acid and trifluoroamidine were utilized as starting materials.
Product:

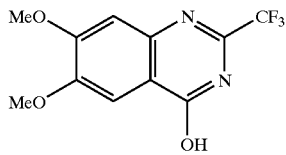

Data: ¹H NMR (DMSO) δ 3.92 (s, 3H), 3.94 (s, 3H), 7.33 (s, 1H), 7.50 (s, 1H), 13.40 (br s, 1H); ¹³C NMR (DMSO) δ 55.8, 56.1, 104.9, 108.7, 150.2, 155.0; LC-MS m/e (MH⁺) 275.

Step 2:
Modifications: The product from Example 51, Step 1 was used as starting material in place of the product from Example 45, Step 1.
Product:

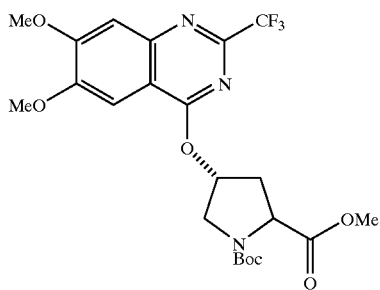

Data: ¹H NMR (CDCl₃) δ 1.42 (s, 3.6H), 1.44 (s, 5.4H), 2.42–2.49 (m, 1H), 2.67–2.73 (m, 1H), 3.37 (s, 1.2H), 3.78 (s, 1.8H), 3.97 (t, J=6.5 Hz, 1H), 4.02 (s, 2.4H), 4.04 (s, 3.6H), 4.48 (t, J=7.9 Hz, 0.6H), 4.60 (t, J=7.7 Hz, 0.4H), 5.86 (br s, 0.6H), 5.90 (br s, 0.4H), 7.27–7.29 (m, 1H), 7.38–7.44 (m, 1H); ¹³C NMR (CDCl₃) δ 8.2, 28.3, 35.7, 36.7, 52.1, 52.2, 52.4, 56.5, 57.8, 58.2, 75.5, 76.0, 80.7, 100.8, 107.6, 111.0, 119.7, 148.2, 150.2, 151.4, 153.8, 154.5, 156.4, 165.1, 172.7, 173.0; LC-MS m/e (MH⁺) 502.

Steps 3 and 4:
Modifications: The product from Example 51, Step 2 was used as starting material in place of the product from Example 45, Step 2.
Product:

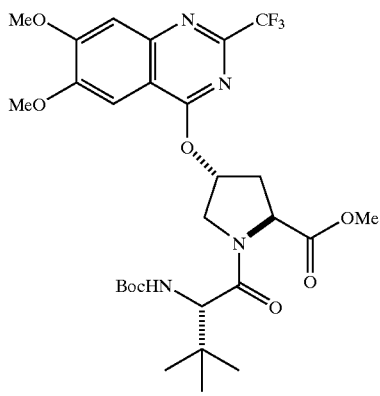

Data: ¹H NMR (MeOD) δ 1.03 (s, 9H), 1.08 (s, 9H), 2.41–2.45 (m, 1H), 2.80–2.84 (m, 1H), 3.76 (s, 3H), 3.96 (s, 3H), 4.00 (s, 3H), 4.10–4.14 (m, 2H), 4.52 (d, J=11.6 Hz, 1H), 4.80 (t, J=8.7 Hz, 1H), 5.92 (br s, 1H), 7.35 (br s, 2H); ¹³C NMR (MeOD) [26.9, 28.4, 28.8, 35.7, 36.0, 52.8, 54.8, 56.9, 59.6, 60.7, 77.9, 80.3, 102.2, 107.9, 112.4, 120.3, 149.3, 153.2, 157.8, 158.3, 173.5; LC-MS m/e (MH⁺) 615.

Step 5:
Modifications: The product from Example 51, Step 4 was used as starting material in place of the product from Example 45, Step 4.
Product:

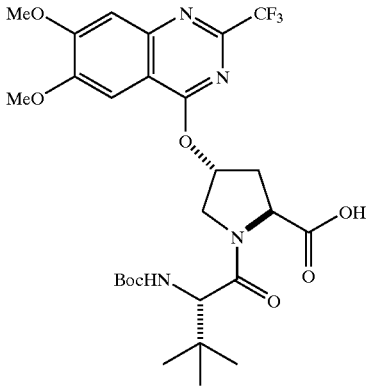

Data: ¹H NMR (MeOD) δ 1.03 (s, 9H), 1.09 (s, 9H), 2.44–2.49 (m, 1H), 2.80–2.84 (m, 1H), 3.97 (s, 3H), 4.01 (s, 3H), 4.10–4.24 (m, 3H), 4.50 (d, J=11.9 Hz, 1H), 4.76 (t, J=7.9 Hz, 1H), 5.93 (br s, 1H), 7.36 (br s, 2H); ¹³C NMR (MeOD) δ 26.9, 28.4, 28.8, 36.0, 36.1, 54.8, 56.9, 57.0, 60.6, 77.9, 80.3, 102.3, 108.0, 112.5, 120.3, 149.3, 151.3, 153.2, 158.2, 158.3, 166.7, 173.5; LC-MS m/e (MH⁺) 601.

Step 8:
Modifications: The product from Example 51, Step 5 was used as starting material in place of the product from Example 45, Step 5. The final product, Compound 51, is a mixture of isomers; the variation occuring at the P1 vinyl-cyclopropyl portion of the molecule (1R, 2S/1S, 2R 1:1 mixture).
Product:

Compound 51

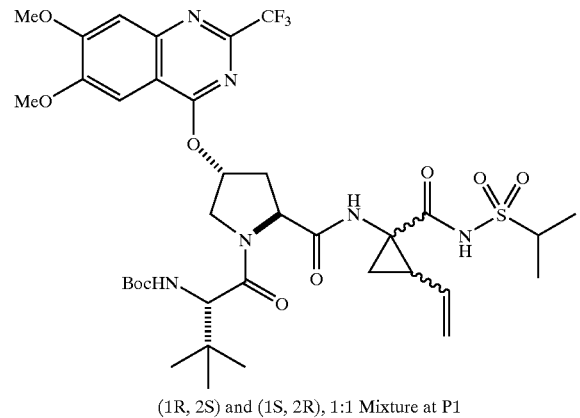

(1R, 2S) and (1S, 2R), 1:1 Mixture at P1

Data: ¹H NMR (DMSO) δ 0.23 (s, 4.5H), 0.23 (s, 4.5H), 0.35 (s, 4.5H), 0.36 (s, 4.5H), 0.45–0.59 (m, 8H), 0.63–0.66 (m, 1H), 1.04 (dd, J=8.2, 5.2 Hz, 1H), 1.10 (dd, J=8.2, 5.5 Hz, 1H), 1.47–1.53 (m, 1H), 1.58–1.61 (m, 1H), 1.87–1.90 (m, 1H), 2.95–3.01 (m, 1H), 3.17 (s, 1.5H), 3.18 (s, 1.5H), 3.22 (s, 3H), 3.37 (br s, 2H), 3.68 (q, J=5.9 Hz, 1H), 3.82 (q, J=8.6 Hz, 1H), 4.33–4.37 (m, 1H), 4.54 (t, J=16.5 Hz, 1H), 4.93 (q, J=8.9 Hz, 1H), 5.17 (d, J=15.9 Hz, 1H), 6.53 (s, 1H), 6.58 (s, 1H); $^{13}$C NMR (DMSO) δ 12.8, 13.2, 13.7, 13.9, 19.5, 20.6, 21.1, 24.3, 25.6, 32.9, 33.1, 33.4, 33.6, 36.1, 39.7, 39.9, 51.8, 51.9, 52.4, 54.0, 54.2, 57.7, 57.7, 58.1, 58.3, 75.1, 75.3, 77.5, 84.1, 99.2, 105.2, 107.9, 109.5, 116.0, 116.1, 118.7, 123.9, 127.4, 131.5, 146.5, 148.6, 150.3, 155.1, 155.5, 163.7, 164.7, 168.2, 168.3, 170.7, 172.2; LC-MS m/e (MH$^+$) 815.

Example 52

Preparation of Compound 52

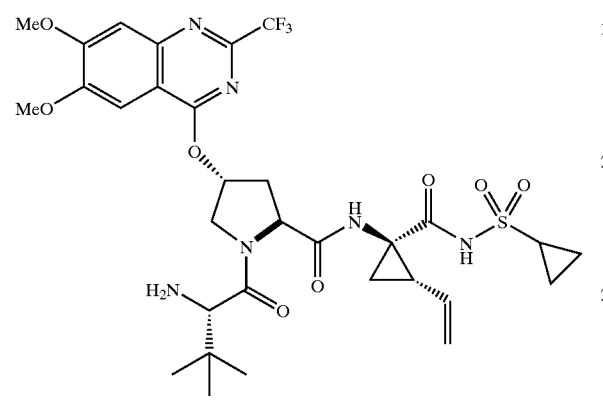

Compound 52

Compound 52 was prepared by the same method as described for the preparation of Compound 48, except the product from Example 51, Step 5 and cyclopropanesulfonic acid (1R-amino-2S-vinyl-cyclopropanecarbonyl)-amide hydrochloride salt were used as starting material. The preparative HPLC purification step resulted in the loss of the N-BOC protecting group at the P3 tert-leucine portion of the molecule: $^1$H NMR (MeOD) δ 1.11 (m, 3H) 1.17 (s, 9H) 1.25 (m, 3H) 1.46 (dd, J=9.46, 5.49 Hz, 1H) 1.92 (dd, J=8.24, 5.49 Hz, 1H) 2.28 (q, J=8.95 Hz, 1H) 2.42 (m, 1H) 2.72 (dd, J=14.19, 7.17 Hz, 1H) 2.96 (m, 1H) 4.01 (s, 3H) 4.04 (m, 5H) 4.24 (m, 2H) 4.73 (dd, J=10.22, 7.17 Hz, 1H) 5.15 (dd, J=10.53, 1.37 Hz, 1H) 5.32 (d, J=17.09 Hz, 1H) 5.75 (m, 1H) 6.07 (s, 1H) 7.41 (s, 1H) 7.47 (s, 1H).

Example 53

Preparation of Compound 53

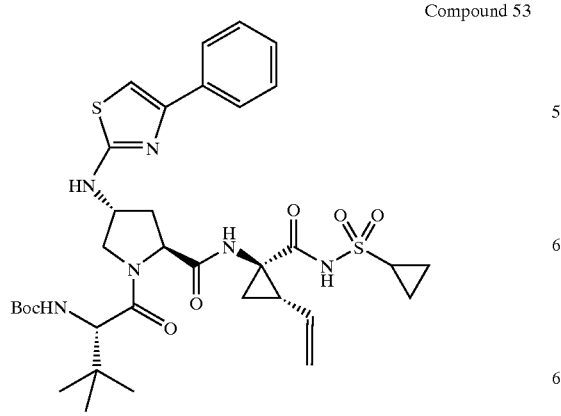

Compound 53

-continued
Scheme 1

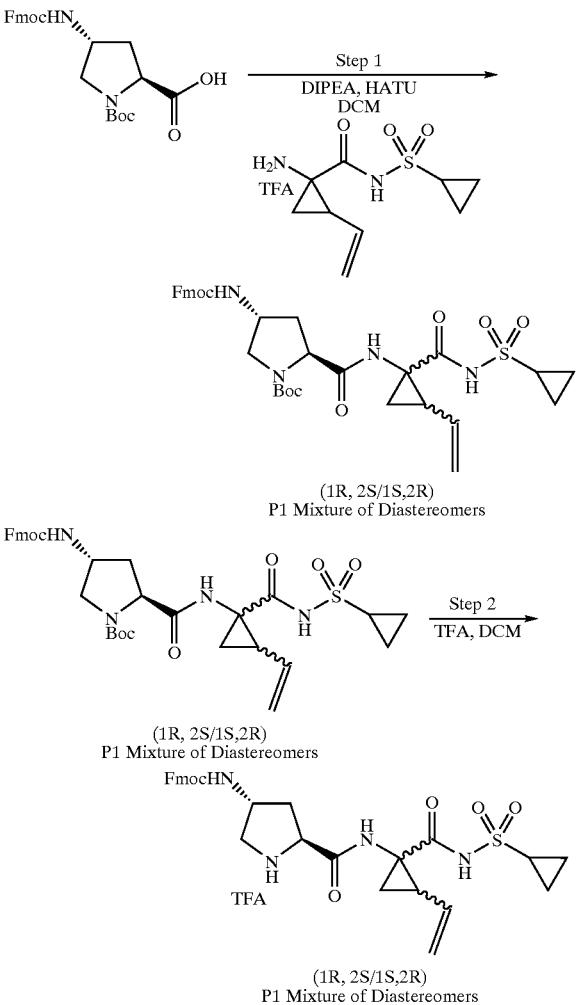

Step 1:
To a solution of (1R, 2S/1S, 2R 1:1 mixture) cyclopropanesulfonic acid (1-amino-2-vinyl-cyclopropanecarbonyl)-amide trifluoro acetic acid salt (626 mg, 1.82 mmol) in DCM (17 mL) was added and DICEA (555 mg, 4.29 mmol) in DCM (17 mL), HATU (754 mg, 1.98 mmole), and (2S, 4R)Fmoc-4-amino-1-boc-pyrrolidine-2-carboxylic acid (747 mg, 1.65 mmol). After stirring at rt for 24 h, the mixture was washed with 1N HCl (10 mL), 5% aqueous NaHCO$_3$ (4 mL). Each aqueous layer was extracted with DCM (25 mL). The combined DCM was dried over MgSO4 and concentrated. The resulting brown viscous oil was purified by flash column chromatography (SiO$_2$, 95:5 DCM:MeOH) to give a yellow solid 822 mg, 75% yield):
$^1$H NMR (DMSO-d$_6$) δ 1.04–1.09 (m, 3H), 1.15–1.27 (m, 4H), 1.38–1.44 (m, 7H), 1.47 (s, 9H), 1.84 (dd, J=8.2, 5.2 Hz, 1H), 2.01–2.30 (m, 4H), 2.90–2.98 (m, 1H), 3.64–3.71 (m, 11H), 4.16–4.22 (m, 4H), 4.39 (bs, 2H), 5.13 (dd, J=10.7, 0.9 Hz, 11H), 3.31 (d, J=17.1 Hz, 11H), 5.72–5.79 (m, 1H), 7.31 (t, J=7.3 Hz, 3H), 7.38 (t, J=7.5 Hz, 3H), 7.64 (d, J=7.02 Hz, 3H), 7.79 (d, J=7.63 Hz, 3H); LC-MS m/e (Na+MH$^+$) 687.
Step 2:
The product from Example 53, Step 1 (500 mg, 0.752 mmol) was treated with 50% TFA in DCM (10 mL). After stirring at rt for 0.5 h, the resulting brown reaction mixture was concentrated to give a brown solid (489 mg, 84% yield): ¹H NMR (DMSO-d₆) δ 1.03–1.19 (m, 4H), 1.24–1.26 (m, 1H), 1.35 (dd, J=9.5, 5.5 Hz, 1H), 1.91–1.96 (m, 1H), 2.22–2.30 (m, 1H), 2.40 (bs, 1H), 2.93–2.98 (m, 1H), 3.60 (bs, 1H), 4.21 (t, J=5.6 Hz, 2H), 4.47 (bs, 3H), 5.17 (d, J=9.2 Hz, 1H), 5.32 (d, J=17.1 Hz, 1H), 5.64–5.67 (m, 1H), 7.31 (t, J=7.3 Hz, 3H), 7.39 (t, J=7.5 Hz, 3H), 7.63 (d, J=7.3 Hz, 2H), 7.80 (d, J=7.3 Hz, 2H); (LC-MS m/e (MH⁺) 565.

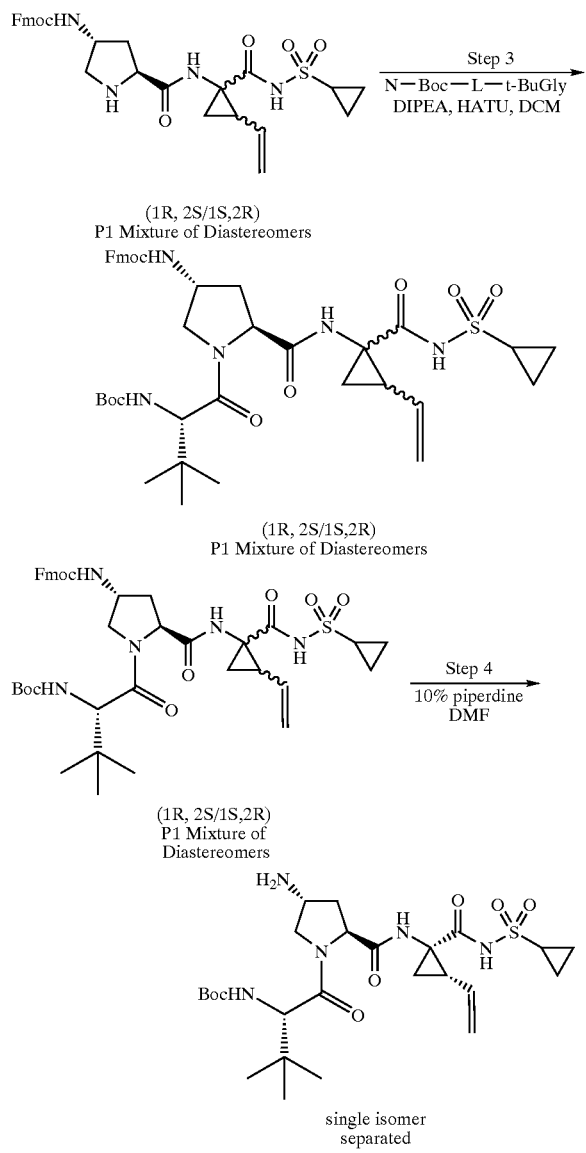

Step 3:
To a solution of the product from Example 53, Step 2 (260 mg, 0.383 mmol) in DCM (4 mL) was added DIPEA (218 mg, 1.69 mmol), HATU (165 mg, 0.422 mmol), and N-BOC L-tBuGly (100 mg, 0.422 mmol). After stirring at rt for 16 h, the reaction mixture was diluted with H₂O (3 mL), acidified with 1N HCl to pH=1. The aqueous layer was extracted with DCM (2×15 mL). The combined organic layer was washed with 5% NaHCO₃ (3 mL), brine (5 mL), dried over MgSO4 and concentrated. The resulting brown viscous oil was purified by flashed column chromatography (SiO₂, 95:5 DCM:MeOH) to give a brown foamy solid (281 mg, 94% yield): ¹H NMR (DMSO-d₆) δ 0.96–1.08 (m, 4H), 1.05 (s, 9H), 1.15–1.26 (m, 2H), 1.35–1.38 (m, 5H), 1.42 (s, 9H), 1.85 (dd, J=9.5, 5.5 Hz, 1H), 2.07 (bs, 1H), 2.22 (q, J=8.7 Hz, 1H), 2.92–2.95 (m, 1H), 3.90 (bs, 1H), 4.20 (d, J=6.4 Hz, 3H), 4.29–4.39 (m, 5H), 5.13 (d, J=10.7, 1H), 5.31 (dd, J=18.0, 5.8 Hz, 11H), 5.70–5.77 (m, 1H), 7.30 (t, J=7.3 Hz, 3H), 7.39 (t, J=7.3 Hz, 4H), 7.63 (dd, J=6.7, 2.8 Hz, 3H), 8.80 (d, J=7.63 Hz, 3H); LC-MS m/z (MH⁺) 678.

Step 4:
The product from Example 53, Step 3 was treated with 10% piperidine in DMF (3.3 mL). After stirring at rt for 14 hr, solvent was removed and the resulting brown viscous oil was purified by flash column chromatography (SiO₂, 95:5 DCM:MeOH) to isolate the pure highest Rf 1R,2S P1 diastereomer as a pale yellow solid (31 mg). The other isomer was isolated in a mixture and was not used: LC-MS m/z (MH⁺)556.

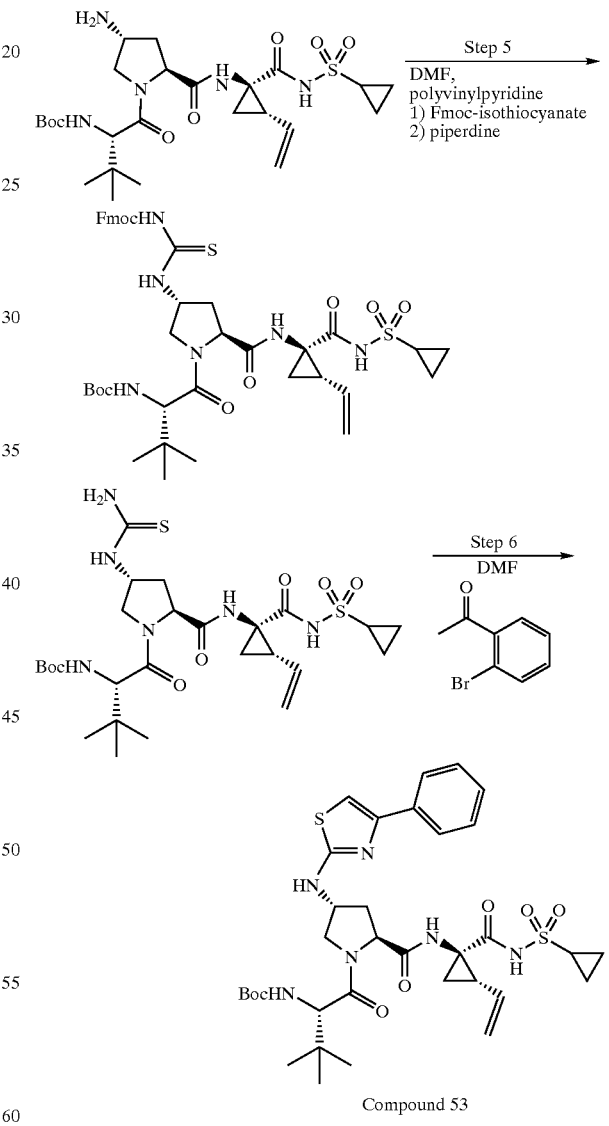

Steps 5 and 6:
To a solution of the product from Example 53, Step 4 in DMF (2 mL) was added polyvinylpyridine (13 mg) and Fmoc-isothiocyanate. After stirring at rt for 14 h, the reaction mixture was treated with piperidine (172 mg, 2.02 mmol). The reaction was stirred at rt for an additional 6 h after which it was concentrated and dried under vacuo overnight. The crude residue was re-dissolved in DMF (2 mL) and treated with 2-bromoacetophenone and stirred at rt for another 14 h. The reaction mixture was concentrated and the resulting residue was purified by flash column chromatography (SiO$_2$, 95:5 DCM:MeOH) to give Compound 53 as a light yellow solid (21.9 mg, 50% yield): $^1$H NMR (DMSO-d$_6$) δ 0.87–0.92 (m, 1H), 1.05 (bs, 13H), 1.16–1.25 (m, 4H), 1.34–1.38 (m, 2H), 1.42 (s, 9H), 1.87 (t, J=6.6 Hz, 1H), 2.22–2.25 (m, 2H), 2.48 (t, J=10.7 Hz, 1H), 2.93 (bs, 1H), 3.04 (q, J=7.3 Hz, 11H) 3.30–3.31 (m, 2H), 3.43–3.49 (m, 1H), 4.01 (d, J=10.4 Hz, 1H), 4.07–4.12 (m, 1H), 4.27 (t, J=9.5 Hz, 1H), 4.44 (t, J=7.0 Hz, 1H), 4.58 (bs, 1H), 5.11 (d, J=10.1 Hz, 1H), 5.30 (dd, J=16.8, 9.6 Hz, 1H), 5.73–5.78 (m, 1H), 6.69 (d, J=8.2 Hz, 1H), 6.86 (s, 1H), 7.25 (t, J=7.3 Hz, 1H), 7.35 (t, J=7.63 Hz, 2H), 7.82 (d, J=8.2 Hz, 2H); LC-MS m/z (MH$^+$) 715.

Reversed Phase Prep-HPLC Conditions for Compound 55 through 155 as Indicated:

Waters Xterra Prep MS C18 column, 5 mm (this means 5 micron particle size), 30 mm×100 mm
Solvent A: 10% MeOH, 90% H$_2$O, 10 mM NH$_4$OAc
Solvent B: 90% MeOH, 10% H$_2$O, 10 mM NH$_4$OAc
50 mL/min flow rate
Gradient: 0% B to 100% B for 10 min, hold at 100% B for 4 min Example 55

Preparation of Compound 55

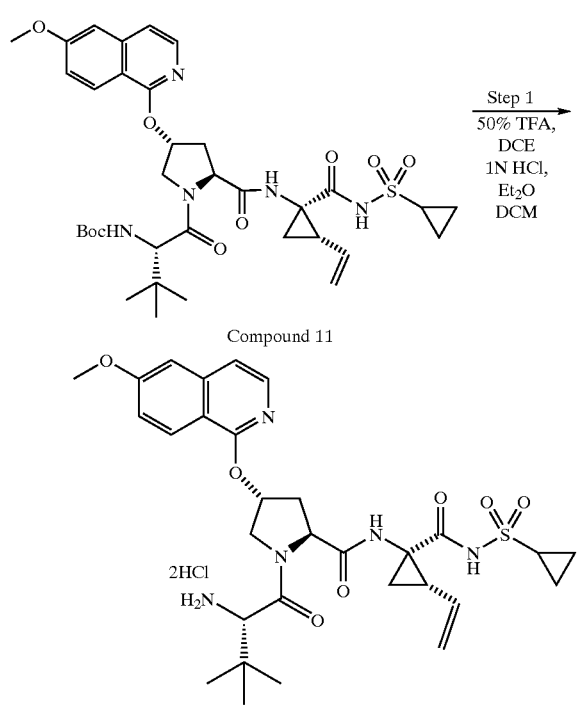

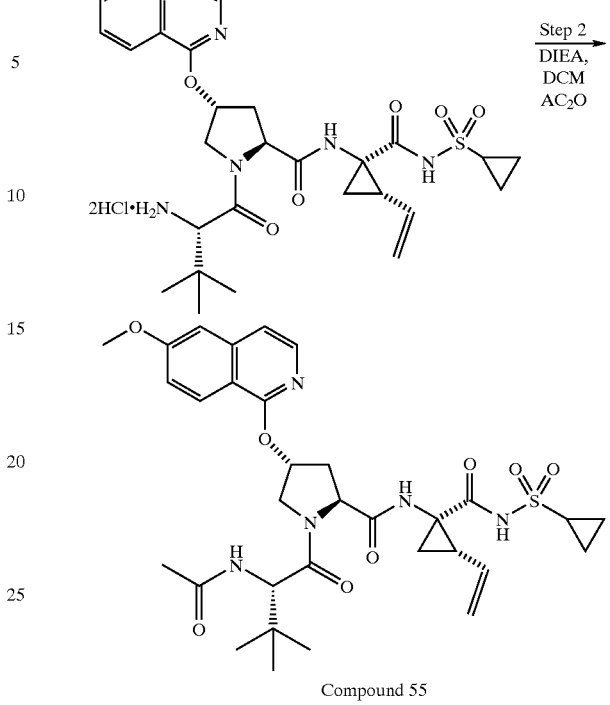

Step 1:
To a solution of Compound 11 (1.5 g, 2.10 mmol) in DCE (25 mL) was added TFA (25 mL). After stirring at rt for 15 min, the reaction mixture was concentrated. The resulting red viscous oil was re-dissolved in DCE (50 mL) and reconcentrated. It was then redissolved in DCM (15 mL) and treated with a solution of 1N HCl in Et$_2$O (25 mL). The resulting suspension was chilled at 0° C., vacuum filtrated, washed with Et$_2$O and dried in vacuum oven to give product of step 1 as a white solid (1.4 g, 97% yield): 1 (CD$_3$OD, 500 MHz) δ 1.07–11.2 (m, 3 H) 1.14 (t, J=4.12 Hz, 1 H) 1.17 (s, 9 H) 1.22 (dd, J=10.53, 4.43 Hz, 1 H) 1.21–1.27 (m, 2 H) 1.42 (dd, J=9.61, 5.34 Hz, 1 H) 1.91 (dd, J=7.93, 5.49 Hz, 1 H) 2.27 (q, J=8.85 Hz, 1 H) 2.32–2.38 (m, 1 H) 2.70 (dd, J=13.43, 6.71 Hz, 1 H), 2.93–2.98 (m, 1 H) 3.96 (s, 3 H) 4.09 (s, 1 H) 4.14 (dd, J=12.21, 3.66 Hz, 1 H) 4.32–4.35 (m, 1 H) 4.69 (dd, J=10.53, 6.87 Hz, 1 H) 5.14 (dd, J=10.38, 1.53 Hz, 1 H) 5.31 (dd, J=17.40, 1.22 Hz, 1 H) 5.70–5.77 (m, 1 H) 5.90 (t, J=3.51 Hz, 1 H) 7.24–7.27 (m, 1 H) 7.29 (d, J=4.27 Hz, 1 H) 7.39 (t, J=4.88 Hz, 1 H) 7.90 (d, J=6.10 Hz, 1 H) 8.19 (m, 1 H) 9.22 (s, 1 H).

Step 2:
To a solution mixture of product from step 1 of Example 55 (70.0 mg, 0.108 mmol) and DIEA (41.8 mg, 0.323 mmol) in DCM (2 mL) was added acetic anhydride (33.0 mg, 0.323 mmol). After stirring at rt for 14 h, solvent was removed and product was purified by reversed phase prep-HPLC to give Compound 55 (39.1 mg, 14% yield): $^1$ HNMR(CD$_3$OD, 500 MHz) δ 1.00–1.03 (m, 1 H), 1.06 (s, 9 H), 1.07–1.10 (m, 1 H), 1.21–1.28 (m, 2 H), 1.43 (dd, J=9.46, 5.19 Hz, 1 H), 1.88 (dd, J=8.55, 5.49 Hz, 1 H), 2.23 (q, J=8.85 Hz, 1 H), 2.27–2.32 (m, 1 H), 2.59 (dd, J=13.73, 7.02 Hz, 1 H), 2.92–2.97 (m, 1 H), 3.93 (s, 3 H), 4.12 (dd, J=11.90, 3.97 Hz, 1 H), 4.35 (d, J=11.60 Hz, 1 H), 4.51 (dd, J=10.38, 7.02 Hz, 1 H), 4.61 (dd, J=5.80, 3.05 Hz, 1 H), 4.80 (d, J=4.27 Hz, 1 H), 4.88 (d, J=3.96 Hz, 1 H), 5.12 (dd, J=10.38, 1.83 Hz, 1 H), 5.29 (dd, J=17.24, 1.37 Hz, 1 H), 5.73–5.78 (m, 1 H), 5.84 (t, J=3.66 Hz, 1 H), 7.15 (dd, J=8.85, 2.44 Hz, 1 H), 7.19 (d, J=2.44 Hz, 1 H), 7.25 (d, J=6.10 Hz, 1 H), 7.88 (d, J=6.10 Hz, 1 H), 8.06 (d, J=9.16 Hz, 1 H); LC-MS (retention time: 1.49 min.), MS m/z 656 (MH⁺).

Example 56

Preparation of Compound 56

Compound 56

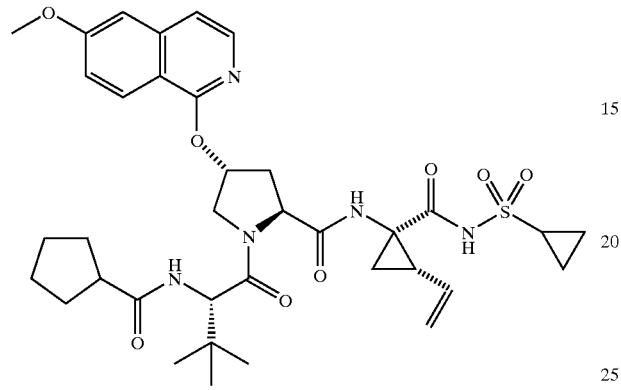

Compound 56 was prepared by the same method as Compound 55 with the following modifications:

Modifications: Cyclopentanecarbonyl chloride was used as a starting material to give Compound 56 (18.0 mg, 24% yield): $^1$H NMR(CD$_3$OD, 500 MHz) δ 1.00–1.03 (m, 1 H), 1.05 (s, 9 H), 1.06–1.10 (m, 2 H), 1.24–1.27 (m, 2 H), 1.25–1.61 (m, 9 H), 1.80–1.83 (m, 1 H), 1.88 (dd, J=8.24, 5.49 Hz, 1 H), 2.22–2.31 (m, 2 H), 2.58–2.65 (m, 2H), 2.93–2.98 (m, 1 H), 3.92 (s, 3 H), 4.10 (dd, J=11.90, 3.66 Hz, 1 H), 4.35 (d, J=11.91 Hz, 1 H), 4.52 (dd, J=10.38, 7.02 Hz, 1 H), 4.65 (d, J=9.46 Hz, 1 H), 4.80 (d, J=5.49 Hz, 1 H), 4.88 (d, J=5.19 Hz, 1 H), 5.13 (dd, J=10.37, 1.83 Hz, 1 H), 5.30 (dd, J=16.80, 1.22 Hz, 1 H), 5.73–5.78 (m, 1 H), 5.84 (t, J=4.27 Hz, 1 H), 7.11 (dd, J=9.16, 2.44 Hz, 1 H), 7.19 (d, J=2.44 Hz, 1 H), 7.25 (d, J=5.80 Hz, 1 H), 7.88 (d, J=6.10 Hz, 1 H), 8.05 (d, J=9.16 Hz, 1 H)); LC-MS (retention time: 1.71 min.), MS m/z 710 (MH⁺).

Example 57

Preparation of Compound 57

Compound 57

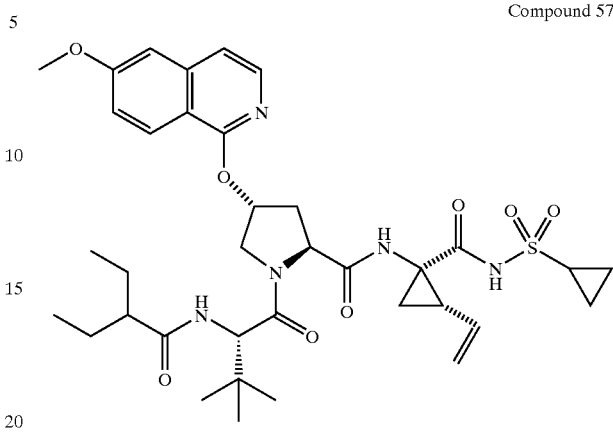

Compound 57 was prepared by the same method as Compound 55 with the following modifications:

Modifications: 2-Ethylbutyryl chloride was used as a starting material to give Compound 57 (20.7 mg, 27% yield): $^1$H NMR(CD$_3$OD, 500 MHz) δ 0.66 (t, J=7.32 Hz, 3 H), 0.85 (t, J=7.32 Hz, 3 H), 1.02–1.05 (m, 1 H), 1.07 (s, 9 H), 1.10–1.12 (m, 1H), 1.24–1.33 (m, 4 H), 1.36–1.39 (m, 1 H), 1.43 (dd, J=9.46, 5.19 Hz, 1 H), 1.48–1.51 (m, 1 H), 1.88 (dd, J=8.24, 5.19 Hz, 1 H), 2.12–2.14 (m, 1 H), 2.22 (q, J=8.85 Hz, 1 H), 2.26–2.30 (m, 1 H), 2.59 (dd, J=13.73, 6.71 Hz, 1 H), 2.94–2.97 (m, 1 H), 3.92 (s, 3 H), 4.11 (dd, J=11.90, 3.66 Hz, 1 H), 4.40 (d, J=11.90 Hz, 1 H), 4.50 (dd, J=10.68, 7.02 Hz, 1 H), 4.75 (d, J=9.46 Hz, 1 H), 4.81 (d, J=9.16 Hz, 1 H), 4.89 (d, J=9.16 Hz, 1 H), 5.12 (dd, J=10.38, 1.53 Hz, 1 H), 5.29 (dd, J=17.09, 1.22 Hz, 1 H), 5.72–5.79 (m, 1 H), 5.85 (t, J=3.66 Hz, 1 H), 7.08 (dd, J=9.16, 2.44 Hz, 1 H), 7.19 (d, J=2.44 Hz, 1 H), 7.25 (d, J=5.80 Hz, 1 H), 7.88 (d, J=6.10 Hz, 1 H), 7.98 (d, J=9.16 Hz, 1 H), 8.02 (d, J=9.16 Hz, 1 H); LC-MS (retention time: 1.73 min.), MS m/z 712 (MH⁺).

Example 58

Preparation of Compound 58

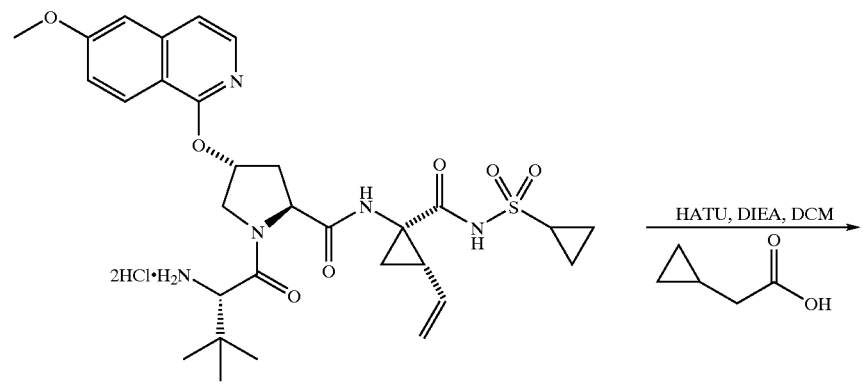

Product from step 1 of Example 55

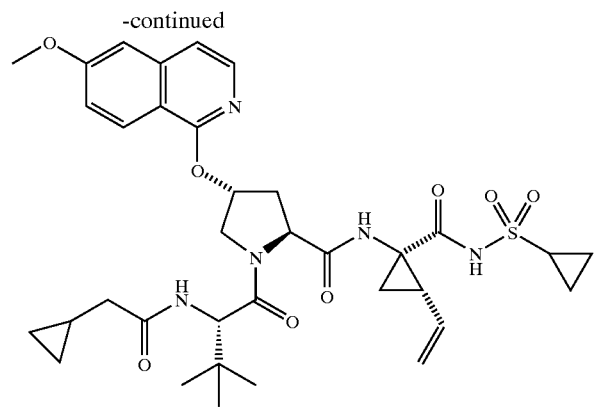

Compound 58

To a solution mixture of product from step 1 of example 55 (70.0 mg, 0.108 mmol), DIEA (41.8 mg, 0.323 mmol) and cyclopropaneacetic acid (16.2 mg, 0.162 mmol) in DCM (2 mL) was added HATU (61.6 mg, 0.162 mmol). After stirring the reaction mixture at rt overnight, it was washed with 5% aqueous NaHCO$_3$ (1 mL). The aqueous layer was extracted with 2×2 mL DCM. The combined organic layer was washed with 5% aqueous citric acid (2 mL), brine, dried over MgSO$_4$ and concentrated. Product was purified by reversed phase prep-HPLC to give Compound 58 (21.9 mg, 29% yield): $^1$H NMR(CD$_3$OD, 500 MHz) δ 0.11–0.14 (m, 2 H), 0.43–0.47 (m, 2 H), 0.87–0.09 (m, 1 H), 1.01–1.04 (m, 1 H), 1.07 (s, 9 H), 1.09–1.12 (m, 1 H), 1.23–1.27 (m, 2 H), 1.45 (dd, J=9.46, 5.49 Hz, 1 H), 1.88 (dd, J=8.24, 5.49 Hz, 1 H), 2.03 (d, J=7.32 Hz, 2 H), 2.23 (q, J=8.75 Hz, 1 H), 2.27–2.31 (m, 1 H), 2.59 (dd, J=13.73, 7.02 Hz, 1 H), 2.92–2.96 (m, 1 H), 3.93 (m, 3 H), 4.13 (dd, J=11.90, 3.97 Hz, 1 H), 4.34 (d, J=11.90 Hz, 1 H), 4.53 (dd, J=10.38, 7.02 Hz, 1H), 4.66 (d, J=9.46 Hz, 1 H), 4.81 (d, J=6.10 Hz, 1 H), 4.89 (d, J=6.10 Hz, 1 H), 5.12 (dd, J=10.37, 1.52 Hz, 1 H), 5.30 (dd, J=17.09, 1.22 Hz, 1 H), 5.75–5.81 (m, 1 H), 5.86 (s, 1 H), 7.12 (dd, J=9.16, 2.44 Hz, 1 H), 7.19 (d, J=2.44 Hz, 1H), 7.81 (d, J=9.46 Hz, 1 H), 7.89 (d, J=5.80 Hz, 1 H), 8.06 (d, J=9.16 Hz, 1 H); LC-MS (retention time: 1.63 min.), MS m/z 696 (MH$^+$).

Example 59

Preparation of Compound 59

Compound 59

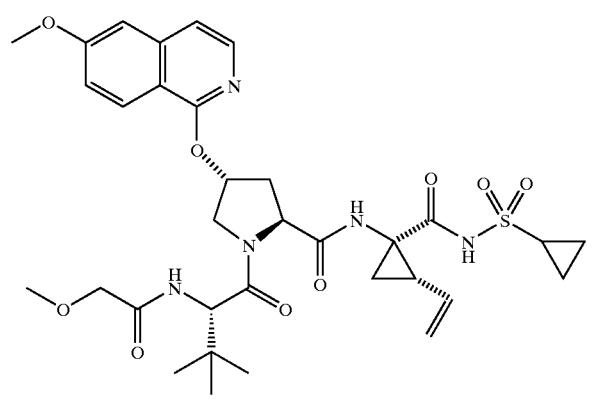

Compound 59 was prepared by the same method as Compound 58 with the following modifications:

Modifications: Methoxyacetic acid was used as a starting material to give Compound 59 (23.5 mg, 32% yield): $^1$HNMR(CD$_3$OD, 500 MHz) δ 10.99–1.04 (m, 2 H), 1.06 (s, 9 H), 1.09–1.12 (m, 1 H), 1.22–1.27 (m, 2 H), 1.45 (dd, J=9.46, 5.49 Hz, 1 H), 1.88 (dd, J=8.24, 5.49 Hz, 1 H), 2.22 (q, J=8.85 Hz, 1 H), 2.29–2.32 (m, 1 H), 2.60 (dd, J=13.89, 6.87 Hz, 1 H), 2.92–2.97 (m, 1 H), 3.35 (s, 3 H), 3.70 (d, J=15.26 Hz, 1 H), 3.84 (d, J=15.26 Hz, 1 H), 3.93 (s, 3 H), 4.13 (dd, J=111.90, 3.97 Hz, 1 H), 4.32 (d, J=11.60 Hz, 1 H), 4.54 (dd, J=10.38, 7.02 HZ, 1 H), 4.65 (s, 1 H), 4.81 (d, J=7.32 Hz, 1 H), 4.89 (d, J=7.32 Hz, 1 H), 5.12 (d, J=10.38 Hz, 1 H), 5.30 (d, J=16.79 Hz, 1 H), 5.74–5.81 (m, 1 H), 5.86 (t, J=3.36 Hz, 1 H), 7.14 (dd, J=9.00, 2.59 Hz, 1 H), 7.19 (d, J=2.44 Hz, 1 H), 7.26 (d, J=6.10 Hz, 1 H), 7.89 (d, J=6.10 Hz, 1 H), 8.04 (d, J=9.16 Hz, 1 H); LC-MS (retention time: 1.54 min.), MS m/z 686 (MH$^+$).

Example 60

Preparation of Compond 60

Compound 60

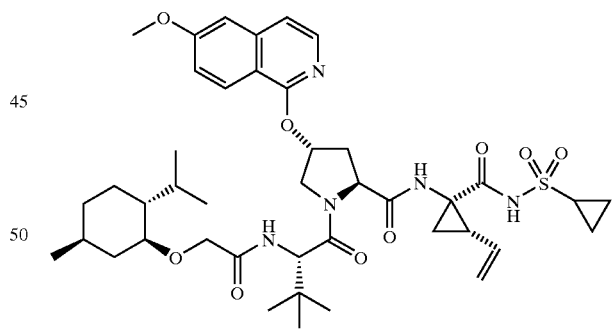

Compound 60 was prepared by the same method as Compound 58 with the following modifications:

Modifications: (+)-Methoxyacetic acid was used as a starting material to give Compound 60 (23.8 mg, 27% yield): $^1$ HNMR (CD$_3$OD, 500 MHz) δ 0.78 (d, J=7.02 Hz, 3 H), 0.83–0.88 (m, 2 H), 0.92 (t, J=7.17 Hz, 6 H), 0.94–0.98 (m, 1 H), 1.00–1.03 (m, 2 H), 1.06 (s, 9 H), 1.07–1.11 (m, 1 H), 1.22–1.26 (m, 2 H), 1.31–1.36 (m, 2 H), 1.45 (dd, J=9.46, 5.49 Hz, 0.1 H), 1.63–1.68 (m, 2 H), 1.89 (dd, J=8.09, 5.34 Hz, 1 H), 2.01–2.04 (m, 1 H), 2.17–2.21 (m, 1

H), 2.24 (q, J=9.00 Hz, 2 H), 2.28–2.33 (m, 1 H), 2.60 (dd, J=13.73, 7.02 Hz, 1 H), 2.93–2.98 (m, 1 H), 3.15–3.20 (m, 1 H), 3.77 (d, J=15.26 Hz, 1 H), 3.87 (d, J=15.26 Hz, 1 H), 3.93 (s, 3 H), 4.12 (dd, J=11.90, 3.66 Hz, 1 H), 4.32 (d, J=11.90 Hz, 1 H), 4.56 (dd, J=10.38, 7.02 Hz, 1 H), 4.65 (d, J=9.77 Hz, 1 H), 4.81 (d, J=5.80 Hz, 1 H), 4.89 (d, J=5.80 Hz, 1 H), 5.13 (dd, J=10.22, 1.68 Hz, 1 H), 5.30 (dd, J=17.09, 1.53 Hz, 1 H), 5.75–5.79 (m, 1 H), 5.85 (t, J=3.66 Hz, 1 H), 7.14 (dd, J=9.16, 2.44 Hz, 1 H), 7.19 (d, J=2.44 Hz, 1 H), 7.26 (d, J=5.80 Hz, 1 H), 7.52 (d, J=9.77 Hz, 1 H), 7.89 (d, J=5.80 Hz, 1 H), 8.03 (d, J=9.16 Hz, 1 H); LC-MS (retention time: 2.043 min.), MS m/z 810 (MH$^+$).

Example 61

Preparation of Compound 61

Compound 61

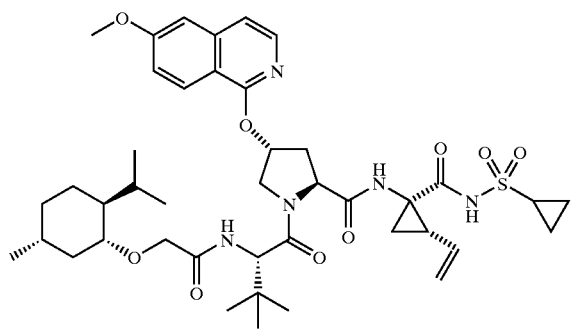

Compound 61 was prepared by the same method as Compound 58 with the following modifications:

Modifications: (–)-Methoxyacetic acid was used as a starting material to give Compound 61 (26.4 mg, 30% yield): $^1$HNMR(CD$_3$OD, 500 MHz) δ 0.78 (d, J=7.02 Hz, 3 H), 0.82–084 (m, 1 H), 0.88 (dd, J=8.39, 3.81 Hz, 1 H), 0.91 (d, J=7.01 Hz, 3H), 0.92 (d, J=6.41 Hz, 3 H), 0.94–0.99 (m, 2 H), 1.00–1.03 (m, 2 H), 1.06 (s, 9 H), 1.08–1.10 (m, 1 H), 1.23–1.26 (m, 2 H), 1.30–1.37 (m, 2 H), 1.44 (dd, J=9.61, 5.34 Hz, 1 H), 1.62–1.68 (m, 2 H), 1.89 (dd, J=8.24, 5.49 Hz, 1 H), 1.98–2.02 (m, 1 H), 2.13–2.16 (m, 1 H), 2.24 (q, J=8.85 Hz, 1 H), 2.28–2.32 (m, 1 H), 2.60 (dd, J=13.73, 7.02 Hz, 1 H), 2.94–2.98 (m, 1 H), 3.08–3.13 (m, 1 H), 3.63 (d, J=15.56 Hz, 1 H), 3.93 (S, 3 H), 4.11 (dd, J=12.05, 3.81 Hz, 1 H), 4.32 (d, J=11.90 Hz, 1 H), 4.56 (dd, J=10.38, 7.02 Hz, 1 H), 4.62 (d, J=9.46 Hz, 1 H), 4.81 (d, J=6.41 Hz, 1 H), 4.89 (d, J=6.72 Hz, 1 H), 5.13 (dd, J=10.38, 1.83 Hz, 1 H), 5.30 (dd, J=17.09, 1.23 Hz, 1 H), 5.76–5.80 (m, 1 H), 5.85 (t, J=3.51 Hz, 1 H), 7.14 (dd, J=9.00, 2.59 Hz, 1 H), 7.20 (d, J=2.44 Hz, 1 H), 7.26 (d, J=5.80 Hz, 1 H), 7.52 (d, J=9.77 Hz, 1 H), 7.89 (d, J=6.10 Hz, 1 H), 8.04 (d, J=9.16 Hz, 1 H); LC-MS (retention time: 2.05 min.), MS m/z 810 (MH$^+$).

Example 62

Preparation of Compound 62

Compound 62

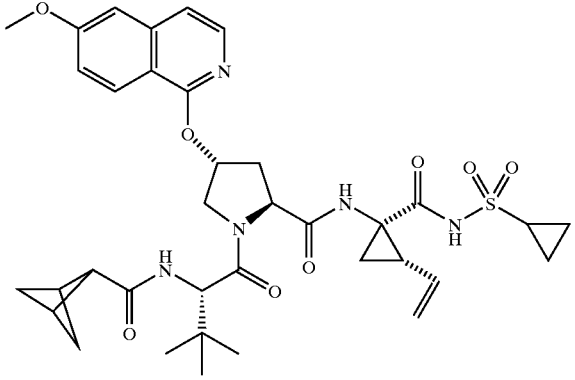

Compound 62 was prepared by the same method as Compound 58 with the following modifications:

Modifications: Bicyclo[1.1.1]pentane-2-carboxylic acid was used as a starting material to give Compound 62 (35.1, 45% yield): $^1$HNMR(CD$_3$OD, 500 MHz) δ 1.03 (d, J=5.49 Hz, 1 H), 1.06 (s, 9 H), 1.08–1.11 (m, 3 H), 1.23–1.29 (m, 3 H), 1.37 (dd, J=7.02, 3.36 Hz, 13 H), 1.46 (dd, J=9.46, 5.19 Hz, 1 H), 1.65 (dd, J=9.77, 2.14 Hz, 1 H), 1.69 (d, J=2.14 Hz, 1 H), 1.72 (dd, J=7.32, 3.05 Hz, 1 H), 1.88 (dd, J=8.09, 5.34 Hz, 1 H), 2.12 (dd, J=9.77, 3.05 Hz, 1 H), 2.23 (d, J=8.85 Hz, 1 H), 2.27–2.31 (m, 1 H), 2.60 (t, J=6.87 Hz, 1 H), 2.63 (d, J=1.83 Hz, 2 H), 2.68 (d, J=7.63 Hz, 1H), 2.93–2.96 (m, 1 H), 3.23 (q, J=7.43 Hz, 2 H), 3.70–3.75 (m, 2 H), 3.93 (s, 3 H), 4.11 (dd, J=11.90, 3.66 Hz, 1 H), 4.35 (d, J=11.90 Hz, 1 H), 4.53 (dd, J=10.53, 6.87 Hz, 1 H), 4.71 (d, J=9.46 Hz, 1 H), 4.79 (d, J=5.80 Hz, 2 H), 4.87 (d, J=5.49 Hz, 2H), 5.13 (dd, J=10.38, 1.83 Hz, 1 H), 5.30 (dd, J=17.24, 1.37 Hz, 1 H), 5.74–5.79 (m, 1 H), 5.86 (t, J=3.20 Hz, 1 H), 7.12 (dd, J=9.16, 2.44 Hz, 1 H), 7.19 (d, J=2.44 Hz, 1H), 7.25 (d, J=5.80 Hz, 1 H), 7.72 (d, J=9.46 Hz, 1 H), 7.88 (d, J=5.80 Hz, 1 H), 8.05 (d, J=9.16 Hz, 1 H); LC-MS (retention time: 1.16 min.), MS m/z 708 (MH$^+$).

Example 63

Preparation of Compound 63

Compound 63

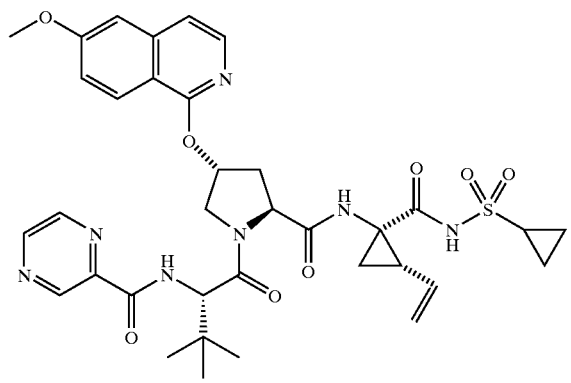

Compound 63 was prepared by the same method as Compound 58 with the following modifications:

Modifications: pyrazine-2-carboxylic acid was used as a starting material to give Compound 63 (42.3, 54% yield): 1HNMR (CD$_3$OD, 500 MHz) δ 1.00–1.04 (m, 3 H), 1.05–1.09 (m, 1 H), 1.10 (s, 9 H), 1.15 (s, 1 H), 1.18–1.22 (m, 2 H), 1.43 (dd, J=9.46, 5.49 Hz, 1 H), 1.88 (dd, J=7.93, 5.49 Hz, 1 H), 2.17 (q, J=8.65 Hz, 1 H), 2.37–2.42 (m, 1 H) 2.64 (dd, J=13.73, 7.32 Hz, 1 H), 2.91–2.95 (m, 1 H), 3.88 (s, 3 H), 3.93 (d, J=3.35 Hz, 1 H), 4.13 (dd, J=11.90, 3.36 Hz, 1 H), 4.46 (d, J=11.90 Hz, 1 H), 4.61 (dd, J=10.07, 7.32 Hz, 1 H), 4.76 (s, 1 H), 4.80 (d, J=7.63 Hz, 1 H), 4.88 (d, J=7.93 Hz, 1 H), 5.09 (d, J=10.38 Hz, 1 H), 5.27 (d, J=17.09 Hz, 1 H), 5.77–5.83 (m, 1 H), 5.85 (s, 1 H), 6.85 (dd, J=9.16, 2.44 Hz, 1 H), 7.08 (d, J=2.14 Hz, 1 H), 7.23 (d, J=5.80 Hz, 1 H), 7.87 (d, J=8.85 Hz, 1 H), 7.90 (d, J=6.10 Hz, 1 H), 8.57 (d, J=1.53 Hz, 1 H), 8.73 (d, J=2.44 Hz, 1 H), 8.81 (s, 1 H).

Example 64

Preparation of Compound 64

To a solution mixture of product from step 1 of example 55 (70.0 mg, 0.108 mmol) and DIEA (41.8 mg, 0.323 mmol) in DCM (2 mL) was added benzyl chloroformate (55.1 mg, 0.323 mmol). After stirring at rt for 14 h, solvent was removed and product was purified by reversed phase prep-HPLC to give Compound 64 (26.9 mg, 31% yield): 1 (CD$_3$OD, 500 MHz) δ 1.00 (d, J=2.14 Hz, 1 H), 1.02 (d, J=5.80 Hz, 1 H), 1.04 (s, 9 H), 1.08–1.14 (m, 1 H), 1.16 (d, J=6.71 Hz, 1 H), 1.18–1.22 (m, 2H), 1.43 (dd, J=9.46, 5.19 Hz, 1 H), 1.87 (dd, J=8.09, 5.34 Hz, 1 H), 2.17–2.22 (m, 1H), 2.30–2.35 (m, 1 H), 2.62 (dd, J=13.73, 7.02 Hz, 1 H), 2.90–2.95 (m, 1 H), 3.88 (s, 3 H), 4.08 (dd, J=11.90, 3.66 Hz, 1 H), 4.31 (s, 1 H), 4.43 (d, J=11.60 Hz, 1 H), 4.55 (dd, J=10.07, 7.32 Hz, 1 H), 4.74 (d, J=12.21 Hz, 1 H), 4.81 (d, J=6.10 Hz, 1 H), 4.89 (d, J=5.79 Hz, 1 H), 5.10 (d, J=9.16 Hz, 1 H), 5.16 (s, 1 H), 5.28 (d, J=17.09 Hz, 1 H), 5.75–5.81 (m, 1 H), 5.83 (s, 1 H), 7.07 (dd, J=9.16, 2.44 Hz, 1 H), 7.17 (d, J=2.44 Hz, 1 H), 7.20 (d, J=7.32 Hz, 2 H), 7.25 (t, J=5.65 Hz, 3 H), 7.30–7.33 (m, 1H), 7.34–7.37 (m, 2 H), 7.89 (d, J=5.80 Hz, 1 H), 8.07 (d, J=9.16 Hz, 1 H); LC-MS (retention time: 1.79 min.), MS m/z 748 (MH$^+$).

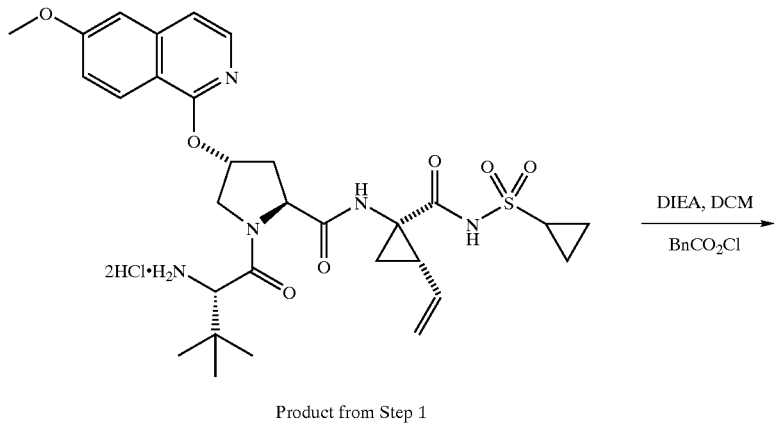

Product from Step 1 of example 55

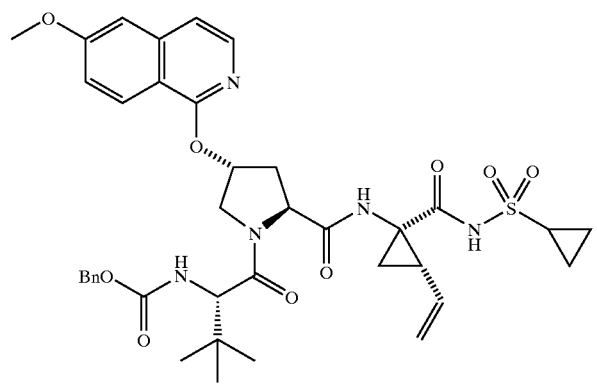

Compound 64

Example 65

Preparation of Compound 65

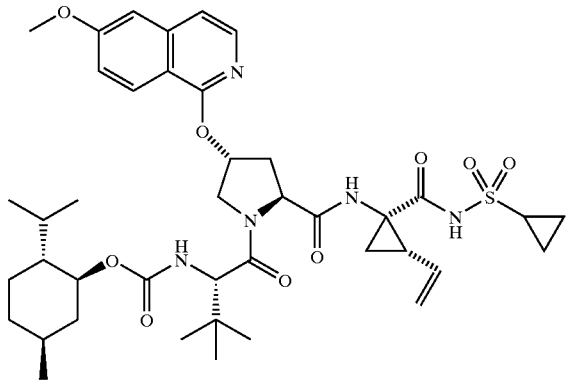

Compound 65

Compound 65 was prepared by the same method as Compound 64 with the following modifications:

Modifications: (+)-Methyl chloroformate was used as a starting material to give Compound 65 (28.8 mg, 36% yield): $^1$H NMR(CD$_3$OD, 500 MHz) δ 0.72 (d, J=6.71 Hz, 3 H), 0.80 (t, J=5.80 Hz, 6 H), 0.87 (d, J=7.02 Hz, 4 H), 0.90–0.95 (m, 6 H), 0.98–1.02 (m, 5 H), 1.05 (s, 9 H), 1.07–1.12 (m, 2 H), 1.18–1.23 (m, 2 H), 1.32–1.38 (m, 3 H), 1.41 (dd, J=9.46, 5.19 Hz, 1 H), 1.46–1.48 (m, 1 H), 1.63–1.71 (m, 5H), 1.85 (dd, J=7.93, 5.49 Hz, 1 H), 1.89–1.93 (m, 1 H), 2.00–2.03 (m, 1 H), 2.15 (q, J=8.70 Hz, 1 H), 2.34–2.38 (m, 1 H), 2.61 (dd, J=13.73, 7.33 Hz, 1 H), 2.89–2.93 (m, 1 H), 3.73 (s, 2 H), 3.92 (s, 3 H), 4.10 (dd, J=11.60, 3.36 Hz, 1 H), 4.33 (s, 1 H), 4.41 (d, J=11.29 Hz, 1 H), 4.46–4.52 (m, 1 H), 4.54 (dd, J=9.76, 7.90 Hz, 1 H), 4.81 (d, J=5.80 Hz, 1 H), 4.89 (m, 1 H), 5.08 (d, J=11.60 Hz, 1 H), 5.26 (d, J=17.09 Hz, 1 H), 5.77–5.81 (m, 1 H), 5.83 (d, J=3.97 Hz, 1 H), 7.11 (dd, J=11.29, 1.83 Hz, 1 H), 7.18 (d, J=10.83 Hz, 1 H), 7.24 (d, J=5.80. Hz, 1 H), 7.88 (d, J=6.10 Hz, 1 H), 8.08 (d, J=8.85 Hz, 1 H); LC-MS (retention time: 2.06 min.), MS m/z 796 (MH$^+$).

Example 66

Preparation of Compound 66

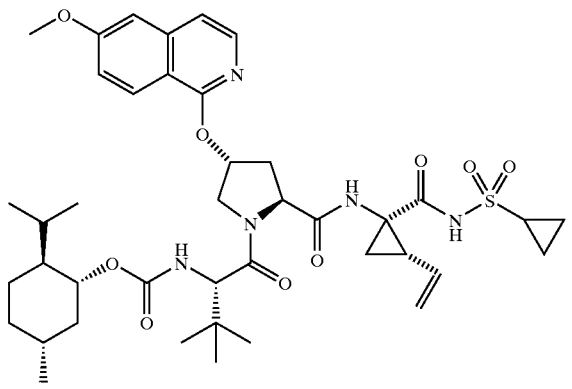

Compound 66

Compound 66 was prepared by the same method as Compound 64 with the following modifications:

Modifications: (−)-Methyl chloroformate was used as a starting material to give Compound 66 (26.9 mg, 31% yield): $^1$H NMR(CD$_3$OD, 500 MHz) δ 0.35 (d, J=6.41 Hz, 1 H), 0.51 (d, J=6.71 Hz, 2 H), 0.68 (d, J=6.71 Hz, 1 H), 0.73 (d, J=7.02 Hz, 2 H), 0.77–0.82 (m, 4 H), 0.88–0.98 (m, 10 H), 1.0–1.03 (m, 2 H), 1.05 (s, 9 H), 1.09–1.18 (m, 3 H), 1.25–1.29 (m, 1 H), 1.3–1.41 (m, 3 H), 1.60–1.71 (m, 3 H), 1.82–1.89 (m, 3 H), 2.00–2.04 (m, J=2.14 Hz, 1 H), 2.10 (q, J=8.24 Hz, 1 H), 2.39–2.43 (m, 1 H), 2.61 (dd, J=14.04, 7.32 Hz, 1 H), 2.87–2.91 (m, 1 H), 3.73 (s, 1 H), 3.92 (s, 3 H), 4.13 (dd, J=11.75, 3.51 Hz, 1 H), 4.22–4.27 (m, 2 H), 4.30 (s, 1 H), 4.39 (d, J=11.90 Hz, 1 H), 4.48–4.55 (m, 1 H), 4.79 (d, J=5.19 Hz, 1 H), 4.87 (d, J=4.27 Hz, 1H), 5.05 (d, J=10.07 Hz, 1 H), 5.22 (d, J=16.79 Hz, 1 H), 5.78–5.85 (m, 2 H), 7.09 (dd, J=9.16, 1.83 Hz, 1 H), 7.17 (d, J=1.83 Hz, 1 H), 7.23 (d, J=5.80 Hz, 1 H), 7.88 (d, J=5.80 Hz, 1 H) 8.09 (d, J=9.16 Hz, 1 H); LC-MS (retention time: 2.05 min.), MS m/z 796 (MH$^+$).

Example 67

Preparation of Compound 67

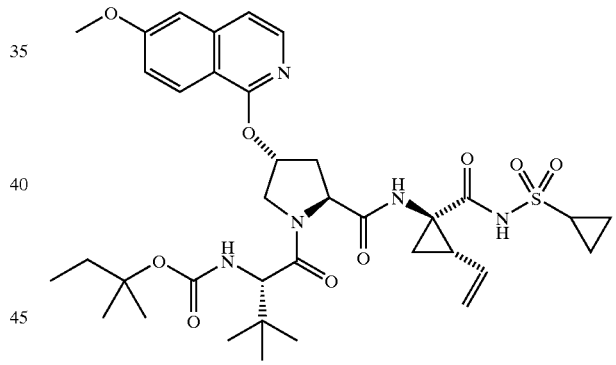

Compound 67

Compound 67 was prepared by the same method as Compound 64 with the following modifications:

Modifications: Di-tert-amyl dicarbonate was used as a starting material to give Compound 67 (35.3 mg, 41% yield): $^1$H NMR(CD$_3$OD, 500 MHz) δ 0.78 (t, J=7.17 Hz, 3 H), 0.89–0.95 (m, 6 H), 1.04 (s, 9 H), 1.005–1.09 (m, 3 H), 1.15 (s, 1 H), 1.22 (d, J=12.51 Hz, 6 H), 1.40 (s, 2 H), 1.42–1.46 (m, 1 H), 1.48 (s, 3 H), 1.56–1.66 (m, 2H), 1.78 (q, J=7.63 Hz, 1 H), 1.84 (q, J=7.53 Hz, 1 H), 1.88 (d, J=5.80 Hz, 1 H), 2.22 (d, J=8.55 Hz, 1 H), 2.27–2.31 (m, 1 H), 2.61 (dd, J=13.73, 7.02 Hz, 1 H), 2.91–2.96 (m, 1 H), 3.92 (s, 3 H), 4.08 (d, J=12.21 Hz, 1 H), 4.26 (d, J=9.16 Hz, 1 H), 4.42 (d, J=11.29 Hz, 1 H), 4.52 (t, J=7.93 Hz, 1 H), 5.12 (d, J=10.07 Hz, 1 H), 5.29 (d, J=17.09 Hz, 1 H), 5.73–5.80 (m, 1 H), 5.84 (s, 1 H), 6.57 (d, J=8.85 Hz, 1 H), 7.09 (d, J=8.54 Hz, 1 H), 7.18 (s, 1 H), 7.25 (d, J=5.80 Hz, 1 H), 7.89 (d, J=5.80 Hz, 1 H), 8.08 (d, J=9.16 Hz, 1 H); LC-MS (retention time: 1.82 min.), MS m/z 728 (MH+).

Example 68

Preparation of Compound 68

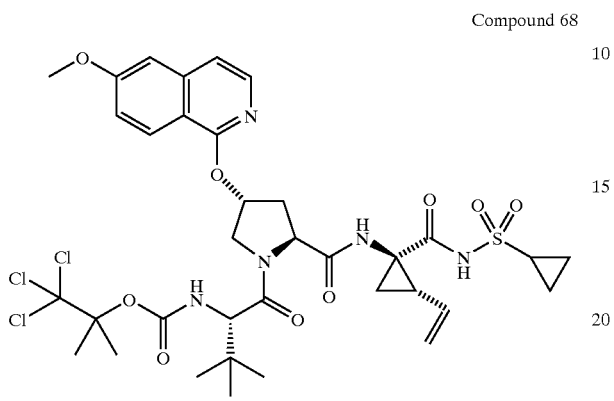

Compound 68

Compound 68 was prepared by the same method as Compound 64 with the following modifications:

Modifications: 2,2,2-Trichloro-1,1-dimethyl chloroformate was used as a starting material to give Compound 68 (30.5 mg, 37% yield): $^1$H NMR (CD$_3$OD, 500 MHz) δ 0.99 (s, 9 H), 1.04 (s, 6 H), 1.08–1.09 (m, 3 H), 1.23–1.26 (m, 3 H), 1.44 (s, 2 H), 1.46 (d, J=5.80 Hz, 1 H), 1.71 (s, 2 H), 2.23–2.33 (m, 2 H), 2.60–2.64 (m, 1 H), 2.93–2.96 (m, 1 H), 3.70 (m, 1 H), 3.71 (s, 3 H), 3.93 (s, 3 H), 4.04–4.06 (m, 2 H), 4.27 (d, J=9.16 Hz, 1 H), 4.41 (d, J=11.60 Hz, 1 H), 4.57 (d, J=10.98, 6.11 Hz, 1 H), 5.14 (d, J=12.21 Hz, 1 H), 5.32 (d, J=17.70 Hz, 1 H), 5.75–5.80 (m, 1 H), 5.84 (s, 1 H), 7.10 (dd, J=9.16, 2.44 Hz, 1 H), 7.19 (d, J=2.44 Hz, 1 H), 7.26 (d, J=6.10 Hz, 1 H), 7.90 (d, J=5.80 Hz, 1 H), 8.07 (d, J=9.16 Hz, 1 H)); LC-MS (retention time: 1.95 min.), MS m/z 816 (MH+).

Example 69

Preparation of Compound 69

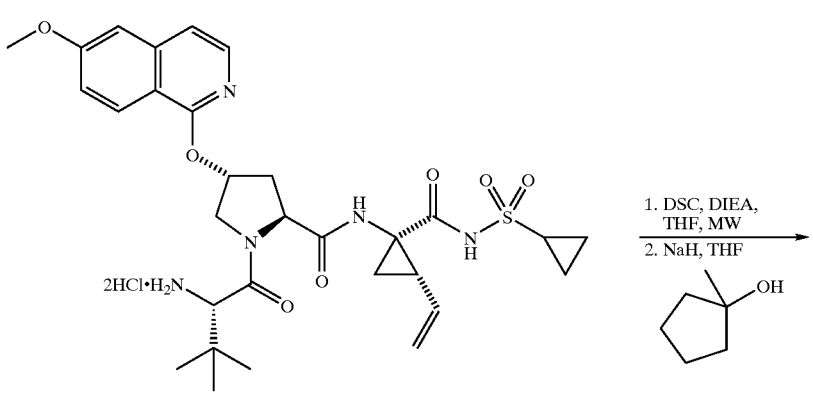

Product from Step 1 of example 55

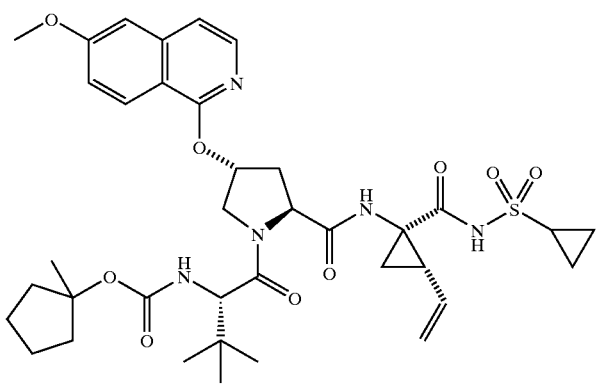

Compound 69

161

To a solution mixture of product from step 1 of example 55 (102 mg, 0.149 mmol) and DIEA (48.2, 0.373 mmol) in THF (2 mL) was added N,N'-dissucinimidyl carbonate (57.1 mg, 0.223 mmol). The resulting suspension was irradiated in a microwave to 80° C. for 15 min. Then was added a slurry solution of sodium 1-methyl cyclopentoxide which was prepared by treating a 0° C. solution of 1-methyl cyclopentanol (149.2 mg, 1.49 mmol) in THF (1 mL) with NaH (60% in oil, 59.6 mg, 1.49 mmol) for 15 min at rt. After stirring at rt 15 min, thee reaction was quenched with saturated aqueous ammonium chloride (3 mL) and extracted with EtOAc (10 mL). The organic layer was then passed through a celite hydromatrix column, concentrated and purified by reversed phase prep-HPLC to give Compound 69 (49.0 mg, 44%): $^1$H NMR(CD$_3$OD, 500 MHz) δ 0.95–0.98 (m, 3 H), 0.99–1.01 (m, J=12.51 Hz, 1 H), 1.03 (s, 9 H), 1.14–1.18 (m, 2 H), 1.30 (s, 3 H), 1.40–1.47 (m, 3 H), 1.50–1.56 (m, 3 H), 1.60–1.64 (m, 1 H), 1.76–1.81 (m, 1 H), 1.83–1.85 (m, 1 H), 2.10–2.19 (m, 1 H), 2.36–2.43 (m, 1 H), 2.63 (dd, J=14.50, 7.17 Hz, 1 H), 2.86–2.90 (m, 1H), 3.92 (s, 3 H), 4.09 (d, J=12.51 Hz, 1 H), 4.25 (d, J=1.53 Hz, 1 H), 4.43 (d, J=10.99 Hz, 1 H), 4.51–4.55 (m, 1 H), 5.06 (d, J=11.60 Hz, 1 H), 5.23 (d, J=16.78 Hz, 1 H), 5.80–5.85 (m, J=12.67, 12.67 Hz, 2 H), 7.09 (d, J=8.55 Hz, 1 H), 7.17 (s, 1H), 7.24 (d, J=5.49 Hz, 1 H), 8.07 (d, J=9.16 Hz, 1 H)); LC-MS (retention time: 1.87 min.), MS m/z 740 (MH$^+$).

Example 70

Preparation of Compound 70

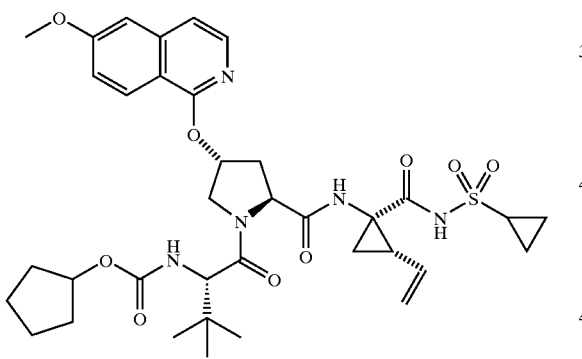

Compound 70

Compound 70 was prepared by the same method as Compound 69 with the following modifications:

Modifications: Cyclopentanol was used as a starting material to give Compound 70 (85.1 mg, 40% yield): $^1$H NMR (CD$_3$OD, 500 MHz) δ 0.98 (s, 1 H), 1.00 (d, J=4.88 Hz, 1 H), 1.03 (s, 9 H), 1.06–110 (m, 2 H), 1.24–1.29 (m, 3 H), 1.36–1.40 (m, 2 H), 1.44 (dd, J=9.31, 5.04 Hz, 2 H), 1.57–1.62 (m, 5 H), 1.69–1.73 (m, 2 H), 1.88 (dd, J=8.09, 5.65 Hz, 1 H), 2.22–29 (m, 2 H), 2.59–2.62 (m, 1 H), 2.92–2.96 (m, 1 H), 3.93 (s, 3 H), 4.07 (dd, J=10.99, 2.44 Hz, 1 H), 4.29 (s, 1 H), 4.42 (dd, J=12.51, 1.53 Hz, 1H), 4.55 (dd, J=9.77, 7.93 Hz, 1 H), 4.68–4.71 (m, 1 H), 4.81 (d, J=8.55 Hz, 1 H), 4.89 (d, J=9.46 Hz, 1 H), 5.13 (d, J=10.68 Hz, 1 H), 5.30 (d, J=16.48 Hz, 1 H), 5.73–5.78 (m, 1 H), 5.84 (s, 1 H), 7.12 (dd, J=9.15, 1.83 Hz, 1 H), 7.20 (d, J=2.14 Hz, 1 H), 7.27 (d, J=5.80 Hz, 1H), 7.89 (d, J=5.80 Hz, 1 H), 8.09 (d, J=8.85 Hz, 1 H); LC-MS (retention time: 1.81 min.), MS m/z 726 (MH$^+$).

162

Example 71

Preparation of Compound 71

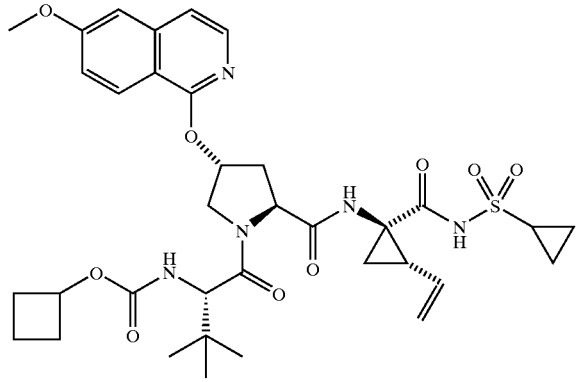

Compound 71

Compound 71 was prepared by the same method as Compound 69 with the following modifications:

Modifications: Cyclobutanol was used as a starting material to give Compound 71 (16.2 mg, 39% yield): $^1$H NMR (CD$_3$OD, 500 MHz) δ 0.97 (s, 3 H), 1.03 (s, 0.9 H), 1.06–1.08 (m, 2 H), 1.17–1.22 (m, 3 H), 1.37–1.44 (m, 1 H), 1.82–1.85 (m, 1 H), 2.02–2.08 (m, 1 H), 2.15–2.21 (m, 1 H), 2.30–2.36 (m, 1 H), 2.49–2.54 (m, 0.4 H), 2.59–2.67 (m, 0.6 H), 2.90–2.94 (m, 1 H), 3.93 (s, 3 H), 4.09 (dd, J=8.09, 4.73 Hz, 1 H), 4.20 (d, J=10.68 Hz, 0.4 H), 4.38 (d, J=10.68 Hz, 0.6 H), 4.46 (dd, J10.22, 7.17 Hz, 0.4 H), 4.48–4.56 (m, 1 H), 5.07–5.11 (m, 1 H), 5.26 (d, J=17.24 Hz, 0.4 H), 5.28 (d, J=17.24 Hz, 0.6 H), 5.71–5.79 (m, 1 H), 5.84 (s, 1 H), 7.07 (dd, J=8.39, 2.90 Hz, 1 H), 7.14 (d, J=2.14 Hz, 1 H), 7.20 (d, J=2.44 Hz, 1 H), 7.25 (d, J=5.80 Hz, 1 H), 7.59 (d, J=5.80 Hz, 1 H), 7.88 (m, 1 H), 8.00 (d, J=9.16 Hz, 0.4 H), 8.07 (d, J=8.85 Hz, 0.6H)); LC-MS (retention time: 1.25 min.), MS m/z 712 (MH$^+$).

Example 72

Preparation of Compound 72

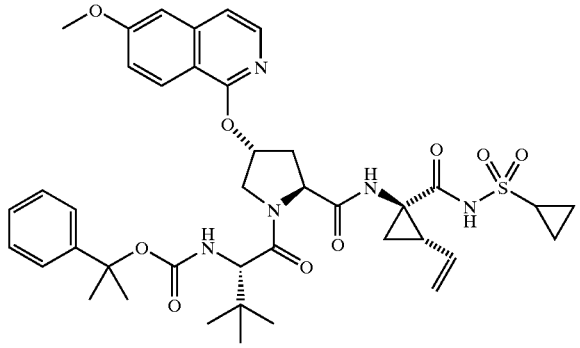

Compound 72

Compound 72 was prepared by the same method as Compound 69 with the following modifications:

Modifications: 2-Phenyl-2-propanol was used as a starting material to give Compound 72 (19.0 mg, 42% yield): $^1$H NMR(CD$_3$OD, 500 MHz) δ 0.97 (m, 1 H), 1.03 (s, 9 H), 1.06–1.09 (m, 3 H), 1.16–1.22 (m, 4 H), 1.41–1.44 (m, 1 H), 1.57 (s, 3H), 1.86 (t, J=7.80 Hz, 1 H), 2.14–2.18 (m, 1 H), 2.30–2.35 (m, 1 H), 2.57–2.61 (m, 1 H), 2.90–2.94 (m, 1 H), 3.92 (d, J=4.27 Hz, 1 H), 3.94 (s, 3 H), 4.04 (dd, J=10.99, 3.66 Hz, 1 H), 4.18 (s, 1 H), 4.24 (d, J=10.99 Hz, 1 H), 4.52 (s, 1 H), 5.09 (d, J=10.07 Hz, 1 H), 5.26 (d, J=14.95 Hz, 1 H), 5.78–5.82 (m, 2 H), 7.07–7.12 (m, 2 H), 7.16–7.20 (m, 3 H), 7.23 (d, J=5.19 Hz, 1 H), 7.29 (d, J=7.02 Hz, 2 H), 7.84 (d, J=5.80 Hz, 1 H), 8.03 (d, J=9.46 Hz, 1 H)); LC-MS (retention time: 1.84 min.), MS m/z 776 (MH$^+$).

Example 73

Preparation of Compound 73

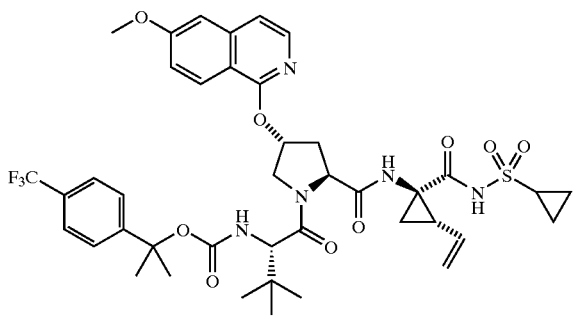

Compound 73

Compound 73 was prepared by the same method as Compound 69 with the following modifications:

Modifications: 4-(Trifluoromethyl)phenyl dimethyl carbinol was used as a starting material to give Compound 73 (22.1 mg, 45% yield): $^1$H NMR(CD$_3$OD, 500 MHz) δ 0.91 (s, 1 H), 0.97–1.00 (m, J=15.56 Hz, 4 H), 1.04 (s, 9 H), 1.07–1.10 (m, 2 H), 1.16–1.20 (m, 3 H), 1.30–1.31 (m, 1 H), 1.41 (dd, J=9.61, 5.34 Hz, 1 H), 1.55 (d, J=7.32 Hz, 6 H), 1.83–1.87 (m, 1 H), 2.11–2.14 (m, 1 H), 2.34–2.39 (m, 1 H), 2.57–2.62 (m, 1 H), 2.89–2.92 (m, J=11.60, 4.27 Hz, 1 H), 3.92 (s, 2 H), 3.94 (s, 3 H), 4.02–4.05 (m, 1 H); 4.17 (s, 1 H), 4.26 (d, J=11.90 Hz, 1 H), 4.53 (t, J=8.85 Hz, 1 H), 5.07 (d, J=10.07 Hz, 1 H), 5.24 (d, J=18.01 Hz, 1 H), 5.78–5.83 (m, 2 H), 7.08 (d, J=7.02 Hz, 1 H), 7.19 (s, 1 H), 7.22 (d, J=5.80 Hz, 1 H), 7.45 (dd, J=13.74, 7.63 Hz, 3 H), 7.60 (d, J=6.41 Hz, 1 H), 7.67 (d, J=7.63 Hz, 1 H), 7.84 (d, J=5.80 Hz, 1 H), 8.02 (d, J=8.54 Hz, 1 H)); LC-MS (retention time: 1.92 min.), MS m/z 844 (MH$^+$).

Example 74

Preparation of Compound 74

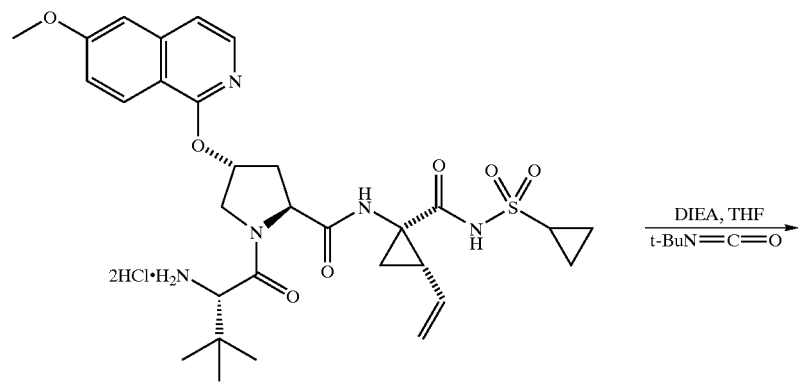

Product from step 1 of example 55

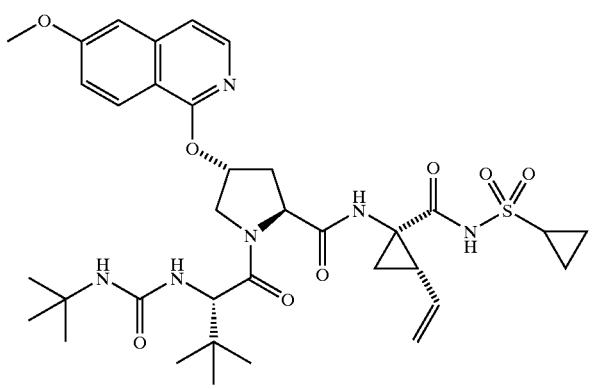

Compound 74

To a solution mixture of the product from step 1 of example 55 (70.0 mg, 0.108 mmol) and DIEA (41.8 mg, 0.323 mmol) in DCM (2 mL) was added t-butylisocyanate (32.0, 0.323 mmol). After stirring at rt overnight, the reaction was concentrated and purified by reversed-phase prep-HPLC to give Compound 74 (42.3 mg, 55% yield): $^1$H NMR(CD$_3$OD, 500 MHz) δ 0.96–1.00 (m, 1 H) 1.04 (s, 9 H) 1.08–1.10 (m, 3 H) 1.19 (s, 9 H) 1.22–1.31 (m, 2 H) 1.30 (m, 1 H) 1.41 (dd, J=9.46, 5.49 Hz, 1 H) 1.87 (dd, J=8.24, 5.49 Hz, 1 H) 2.20–2.29 (m, 2 H) 2.61 (dd, J=14.04, 6.72 Hz, 1 H) 2.92–2.97 (m, 1 H) 3.92 (s, 3 H) 4.08 (dd, J=11.60, 3.97 Hz, 1 H) 4.36 (s, 1 H) 4.47–4.52 (m, 2 H) 4.81 (d, J=3.36 Hz, 1 H) 4.88 (d, J=8.85 Hz, 1 H) 5.11 (dd, J=10.22, 1.68 Hz, 1 H) 5.28 (dd, J=17.09, 1.53 Hz, 1 H) 5.72–5.76 (m, 1 H) 5.85 (s, 1 H) 7.08 (dd, J=9.16, 2.44 Hz, 1 H) 7.18 (d, J=2.14 Hz, 1 H) 7.24 (d, J=5.80 Hz, 1 H) 7.88 (d, J=6.10 Hz, 1 H) 8.12 (d, J=9.16 Hz, 1 H); LC-MS (retention time: 1.70 min.), MS m/z 713 (MH$^+$).

Example 75

Preparation of Compound 75

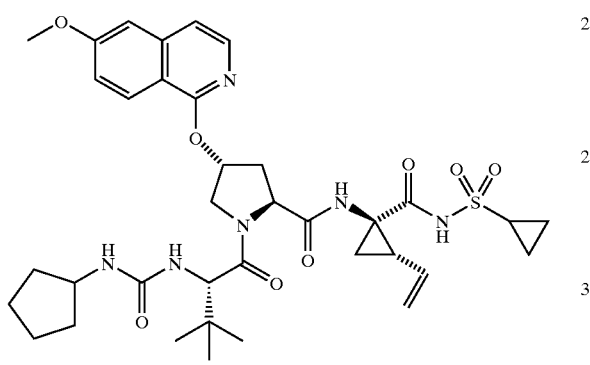

Compound 75

Compound 75 was prepared by the same method as Compound 74 with the following modifications:

Modifications: Cyclopentyl isocyanate was used as a starting material to give Compound 75 (38.5 mg, 49%): $^1$H NMR(CD$_3$OD, 500 MHz) δ 0.92 (d, J=7.63 Hz, 1 H) 0.96 (s, 9 H) 0.98–1.02 (m, 1 H) 1.05 (s, 9 H) 1.07–1.10 (m, 2 H) 1.21–1.25 (m, 3 H) 1.28–1.34 (m, 1 H) 1.36–1.55 (m, 8 H) 1.58–1.65 (m, 13 H) 1.81 (m, 1 H) 1.88 (m, 6 H) 2.23 (dd, J=18.01, 8.85 Hz, 1 H) 2.29 (m, 1 H) 2.59 (dd, J=13.73, 7.02 Hz, 1 H) 2.94 (m, 1 H) 3.27 (d, J=1.83 Hz, 1 H) 3.35 (d, J=1.53 Hz, 1 H) 3.75 (m, 1 H) 3.92 (s, 3 H) 3.95 (d, J=6.41 Hz, 1 H) 3.97 (s, 1 H) 4.09 (m, 2 H) 4.40 (s, 1 H) 4.45 (d, J=11.90 Hz, 1 H) 4.52 (dd, J=10.07, 7.02 Hz, 1 H) 4.81 (d, J=7.02 Hz, 1 H) 4.89 (d, J=7.02 Hz, 1 H) 5.11 (m, 1 H) 5.29 (d, J=17.40 Hz, 1 H) 5.75 (m, 1 H) 5.85 (s, 1 H) 7.11 (dd, J=9.16, 2.44 Hz, 1 H) 7.18 (d, J=2.44 Hz, 1 H) 7.25 (d, J=5.80 Hz, 1 H) 7.88 (d, J=6.10 Hz, 1 H) 7.95 (m, 1 H) 8.12 (d, J=9.16 Hz, 1 H)); LC-MS (retention time: 1.67 min.), MS m/z 725 (MH$^+$).

Example 76

Preparation of Compound 76

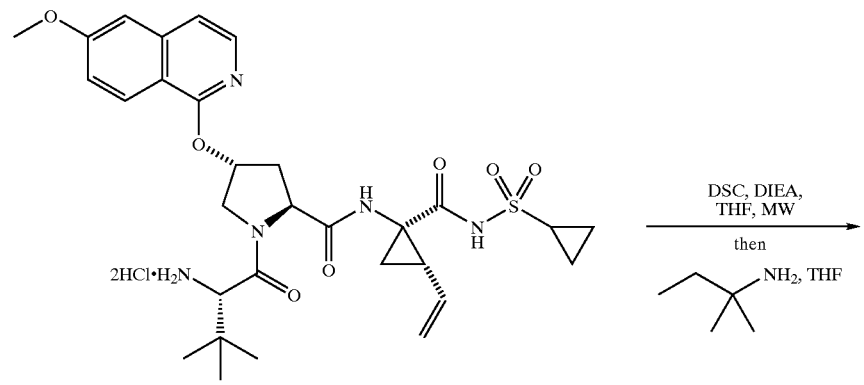

Product from step 1 of example 55

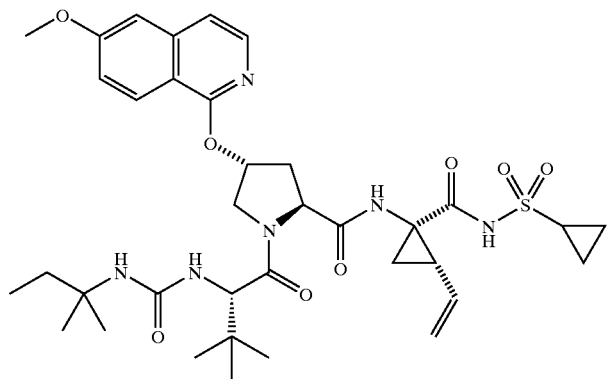

Compound 76

To a solution mixture of the product from step 1 of example 55 (70 mg, 0.102 mmol) and DIEA (33.0 mg, 0.255 mmol) in THF (2 mL) was added N,N'-dissucinimidyl carbonate (39.2 mg, 0.153 mmol). The resulting suspension was irradiated in a microwave to 80° C. for 15 min. Then it was treated with tert-amylamine (88.9 mg, 1.02 mmol). After stirring at rt 15 min, the reaction was concentrated and purified by reversed phase prep-HPLC to give Compound 76 (51 mg, 69%): $^1$H NMR (CD$_3$OD, 500 MHz) δ 0.76 (t, J=7.48 Hz, 4 H), 0.97 (s, 1 H), 1.04 (s, 9 H), 1.13 (s, 6 H), 1.22–1.25 (m, 2 H), 1.41 (dd, J=9.61, 5.34 Hz, 1 H), 1.53 (dd, J=13.89, 7.48 Hz, 1 H), 1.58–1.62 (m, 1 H), 1.87 (dd, J=7.93, 5.49 Hz, 1 H), 2.20 (q, J=8.65 Hz, 1 H), 2.27–2.31 (m, 1 H), 2.60 (dd, J=13.73, 7.32 Hz, 1 H), 2.92–2.96 (m, 1 H), 3.92 (s, 3 H), 4.08 (dd, J=11.75, 3.81 Hz, 1 H), 4.36 (s, 1 H), 4.46 (d, J=11.90 Hz, 1 H), 4.50 (dd, J=10.22, 7.17 Hz, 1 H), 5.10 (dd, J=10.22, 1.37 Hz, 1 H), 5.27 (dd, J=16.94, 1.07 Hz, 1 H), 5.73–5.77 (m, 1 H), 5.84 (t, J=3.51 Hz, 1 H), 7.09 (dd, J=9.16, 2.44 Hz, 1H), 7.18 (d, J=2.44 Hz, 1 H), 7.24 (d, J=5.80 Hz, 1 H), 7.88 (d, J=6.10 Hz, 1 H), 8.11 (d, J=9.16 Hz, 1 H); LC-MS (retention time: 1.753 min.), MS m/z 727 (MH$^+$).

Example 77

Preparation of Compound 77

Compound 77

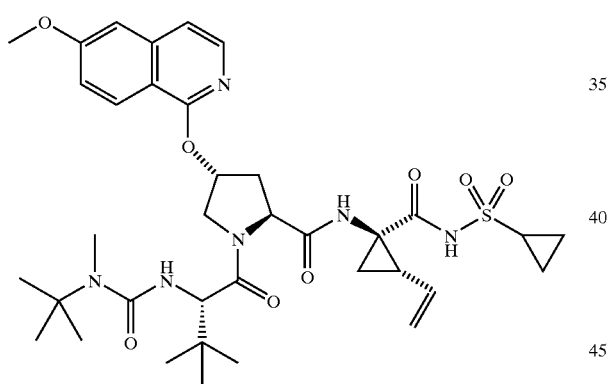

Compound 77 was prepared by the same method as Compound 76 with the following modifications:

Modifications: tert-Butyl methylamine was used as a starting material to give Compound 77 (160.7 mg, 74% yield): $^1$HNMR(CD$_3$OD, 500 MHz) δ 0.96–1.10 (m, 1 H), 1.06 (s, 9 H), 1.08–1.12 (m, J=5.80 Hz, 3 H), 1.26 (s, 9 H), 1.46 (dd, J=9.46, 5.19 Hz, 1 H), 1.87 (dd, J=7.93, 5.49 Hz, 1 H), 2.21 (q, J=8.75 Hz, 1 H), 2.26–2.31 (m, 1 H), 2.57–2.62 (m, 1 H), 2.86 (s, 3 H), 2.91–2.95 (m, 1 H), 3.92 (s, 3 H), 4.09 (dd, J=11.90, 3.66 Hz, 1 H), 4.43 (s, 1 H), 4.46 (d, J=11.90 Hz, 1 H), 4.52 (dd, J=10.68, 7.02 Hz, 1 H), 5.11 (dd, J=10.22, 1.37 Hz, 1 H), 5.29 (d, J=17.09 Hz, 1 H), 5.75–5.82 (m, 1 H), 5.86 (s, 1 H), 7.09 (dd, J=9.16, 2.14 Hz, 1 H), 7.18 (d, J=2.44 Hz, 1 H), 7.24 (d, J=5.80 Hz, 1 H), 7.88 (d, J=5.80 Hz, 1 H), 8.09 (d, J=8.85 Hz, 1 H));

LC-MS (retention time: 1.76 min.), MS m/z 727 (MH$^+$).

Example 78

Preparation of Compound 78

Compound 78

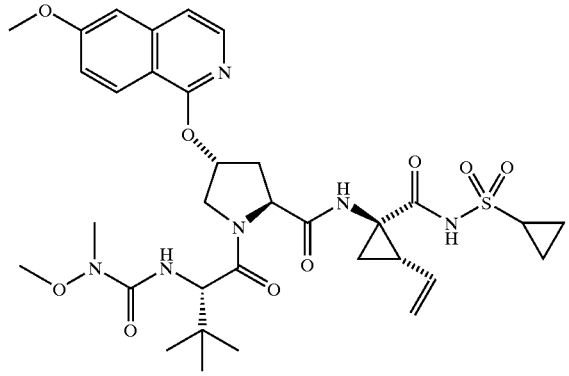

Compound 78 was prepared by the same method as Compound 76 with the following modifications:

Modifications: N,O-Dimethylhydroxylamine hydrochloride was used as a starting material to give Compound 78 (62.1 mg, 60% yield): $^1$ HNMR(CD$_3$OD, 500 MHz) δ 0.99 (t, J=6.10 Hz, 1 H), 1.07 (s, 11 H), 1.22–1.26 (m, J=3.97 Hz, 2 H), 1.47 (dd, J=9.46, 5.49 Hz, 1 H), 1.88 (dd, J=8.24, 5.49 Hz, 1 H), 2.22 (d, J=8.54 Hz, 1 H), 2.3–30–2.33 (m, 1 H), 2.60 (dd, J=13.43, 7.02 Hz, 1 H), 2.92 (s, 3 H), 2.93–2.96 (m, 1 H), 3.66 (s, 3 H), 3.92 (s, 3 H), 4.12 (dd, J=11.90, 3.66 Hz, 1 H), 4.34 (d, J=12.21 Hz, 1 H), 4.44 (d, J=9.46 Hz, 1 H), 4.54 (dd, J=10.53, 6.87 Hz, 1 H), 5.12 (d, J=10.38 Hz, 1 H), 5.30 (d, J=17.09 Hz, 1 H), 5.75–5.83 (m, 1 H), 5.86 (t, J=3.97 Hz, 1 H), 6.70 (d, J=9.77 Hz, 1 H), 7.13 (dd, J=9.16, 2.44 Hz, 1 H), 7.19 (d, J=2.44 Hz, 1 H), 7.25 (d, J=6.10 Hz, 1 H), 7.88 (d, J=5.80 Hz, 1 H), 8.07 (d, J=9.16 Hz, 1 H)); LC-MS (retention time: 1.59 min.), MS m/z 701 (MH$^+$).

Example 79

Preparation of Compound 79

Compound 79

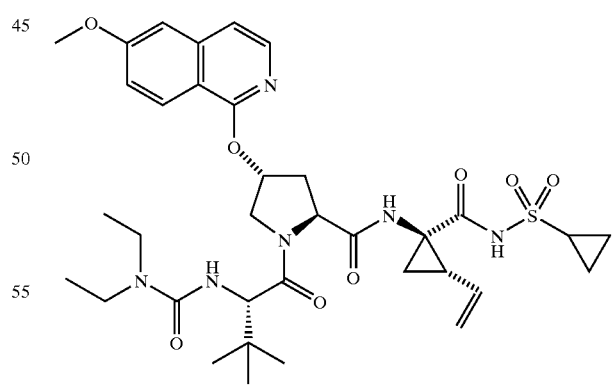

Compound 79 was prepared by the same method as Compound 76 with the following modifications:

Modifications: Diethylamine was used as a starting material to give Compound 79 (56.5 mg, 54% yield): $^1$ HNMR (CD$_3$OD, 500 MHz) δ 1.03 (q, J=15.6 Hz, 4 H), 1.06 (d, J=1.53 Hz, 9 H), 1.05–1.10 (m, 3 H), 1.13–1.23 (m, 4 H), 1.46 (dd, J=9.46, 5.19 Hz, 1 H), 1.86 (dd, J=7.93, 5.30 Hz, 1 H), 2.17 (q, J=8.85 Hz, 1 H), 2.32–2.36 (m, 1 H), 2.60 (dd, J=14.04, 7.32 Hz, 1 H), 2.89–2.93 (m, 1 H), 3.16–3.24 (m, 4 H), 3.92 (s, 3 H), 4.14 (dd, J=11.90, 3.66 Hz, 1 H), 4.37 (d, J=11.60 Hz, 1 H), 4.51–4.55 (m, 2 H), 5.09 (d, J=10.07 Hz, 1 H), 5.27 (d, J=17.09 Hz, 1 H), 5.55 (d, J=9.46 Hz, 1 H), 5.79–5.84 (m, 1 H), 5.86 (s, 1 H), 7.11 (dd, J=8.85, 2.44 Hz, 1 H), 7.18 (d, J=2.44 Hz, 1 H), 7.24 (d, J=5.80 Hz, 1 H), 7.88 (d, J=5.80 Hz, 1 H), 8.08 (d, J=9.16 Hz, 1 H));

LC-MS (retention time: 1.68 min.), MS m/z 713 (MH$^+$).

Example 80

Preparation of Compound 80

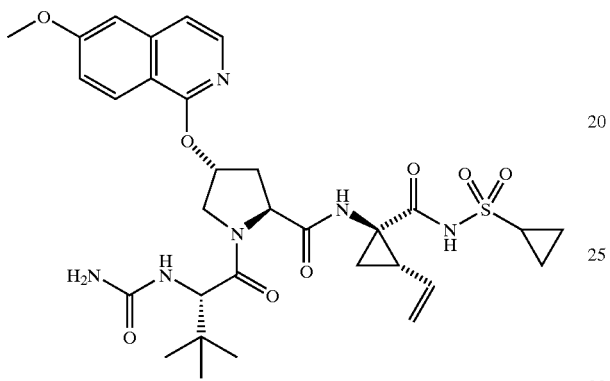

Compound 80

Compound 80 was prepared by the same method as Compound 76 with the following modifications:

Modifications: Saturated aqueous ammonium chloride was used as a starting material to give Compound 76 (12.2 mg, 32% yield): $^1$HNMR(CD$_3$OD, 500 MHz) δ 1.00–1.03 (m, 3 H), 1.06 (s, 9 H), 1.20–1.25 (m, 2 H), 1.42 (dd, J=9.31, 5.34 Hz, 1 H), 2.22 (d, J=9.77 Hz, 1 H), 2.29–2.35 (m, 1 H), 2.59 (dd, J=13.28, 6.87 Hz, 1 H), 2.92–2.96 (m, 1 H), 3.92 (s, 3 H), 4.14 (dd, J=11.75, 4.12 Hz, 1 H), 4.38–4.43 (m, 1 H), 4.51 (dd, J=9.92, 6.87 Hz, 1 H), 5.11 (d, J=11.90 Hz, 1 H), 5.28 (d, J=17.70 Hz, 1 H), 5.72–5.79 (m, 1 H), 5.84 (s, 1 H), 7.15 (d, J=2.44 Hz, 1 H), 7.17 (d, J=2.75 Hz, 1 H), 7.23 (d, J=5.80 Hz, 1 H), 7.87 (d, J=7.87 Hz, 1 H), 8.10 (d, J=8.85 Hz, 1 H)); LC-MS (retention time: 1.43 min.), MS m/z 657 (MH$^+$).

Example 81

Preparation of Compound 81

Compound 81

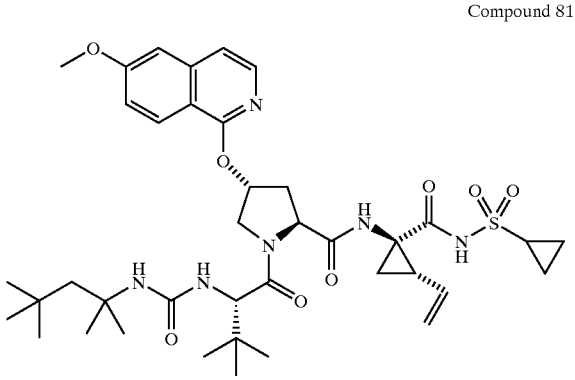

Compound 81 was prepared by the same method as Compound 76 with the following modifications:

Modifications: tert-Octylamine was used as a starting material to give Compound 81 (16.1 mg, 48% yield): $^1$HNMR(CD$_3$OD, 500 MHz). δ 0.88 (s, 9 H), 1.00 (d, J=9.77 Hz, 5 H), 1.04 (s, 9 H), 1.17 (s, 3 H), 1.18–1.20 (m, 1 H), 1.21 (s, 3 H), 1.35 (d, J=2.44 Hz, 1 H), 1.40–1.43 (m, 1 H), 1.57 (d, J=14.95 Hz, 1 H), 1.67 (d, J=14.65 Hz, 1 H), 1.85 (dd, J=8.09, 5.34 Hz, 1 H), 2.15 (d, J=8.24 Hz, 1 H), 2.34–2.43 (m, 1 H), 2.60 (dd, J=13.73, 7.02 Hz, 1 H), 2.89–2.93 (m, 1 H), 3.92 (s, 3 H), 4.13 (dd, J=11.60, 3.97 Hz, 1 H), 4.38 (s, 1 H), 4.43 (d, J=11.90 Hz, 1 H), 4.50 (dd, J=9.77, 7.32 Hz, 1 H), 5.07 (d, J=10.38 Hz, 1 H), 5.24 (d, J=17.09 Hz, 1 H), 5.75–5.81 (m, 1 H), 5.84 (s, 1 H), 7.09 (dd, J=9.16, 2.44 Hz, 1 H), 7.17 (d, J=2.44 Hz, 1 H), 7.23 (d, J=5.80 Hz, 1 H), 7.88 (d, J=5.80 Hz, 1 H), 8.10 (d, J=9.16 Hz, 1 H)); LC-MS (retention time: 1.92 min.), MS m/z 769 (MH$^+$).

Example 82

Preparation of Compound 82

Compound 82

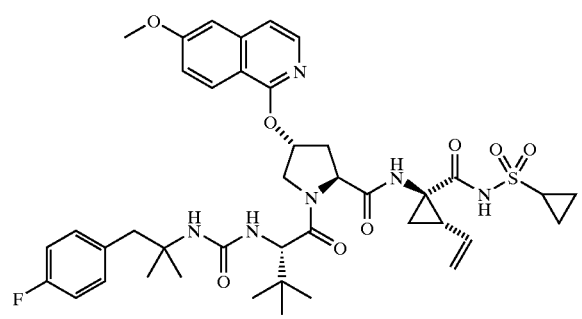

Compound 82 was prepared by the same method as Compound 76 with the following modifications:

Modifications: 1-(4-fluorophenyl)-2-methyl-2-propylamine was used as a starting material to give Compound 82 (14.8 mg, 42% yield): $^1$HNMR 1 (CD$_3$OD, 500 MHz) δ 0.88 (s, 9 H), 1.00 (d, J=9.46 Hz, 6 H), 1.04 (s, 9 H), 1.17 (s, 3 H), 1.21 (s, 3 H), 1.32–1.37 (m, 2 H), 1.39–1.43 (m, 1 H), 1.57 (d, J=14.65 Hz, 1 H), 1.67 (d, J=14.96 Hz, 1 H), 1.82–1.86 (m, 1 H), 2.15 (t, J=9.46 Hz, 1 H), 2.33–2.43 (m, 2 H), 2.58–2.62 (dd, J=14.50, 7.78 Hz, 1 H), 2.89–2.93 (m, 1 H), 3.92 (s, 3 H), 4.12 (dd, J=11.90, 3.97 Hz, 1 H), 4.38 (s, 1 H), 4.43 (d, J=12.82 Hz, 1 H), 4.49–4.52 (m, 1 H), 5.24 (d, J=16.48 Hz, 1 H), 5.76–5.82 (m, 1 H), 5.83–5.85 (m, 1 H), 7.09 (dd, J=9.00, 2.59 Hz, 1 H), 7.17 (d, J=2.14 Hz, 1 H), 7.23 (d, J=5.80 Hz, 1 H), 7.88 (d, J=5.80 Hz, 1 H), 8.10 (d, J=9.16 Hz, 1 H)); LC-MS (retention time: 1.40 min.), MS m/z 807 (MH$^+$).

Example 83

Preparation of Compound 83

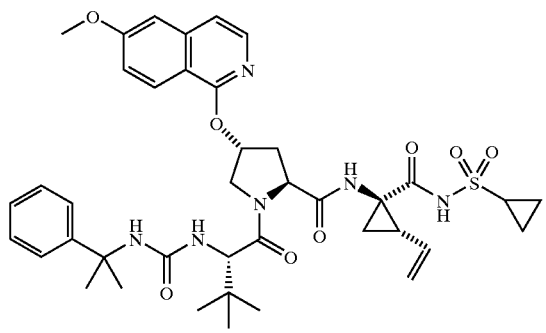

Compound 83

Compound 83 was prepared by the same method as Compound 76 with the following modifications:

Modifications: Cumylamine was used as a starting material to give Compound 83 (64.6 mg, 57% yield): $^1$HNMR (CD$_3$OD, 500 MHz) δ 0.87–0.91 (m, 1 H), 0.98 (d, J=9.46 Hz, 2 H), 1.01 (s, 9 H), 1.02–1.05 (m, 1 H), 1.17–1.21 (m, 3 H), 1.29 (s, 2 H), 1.40 (dd, J=9.46, 5.19 Hz, 1 H), 1.51 (d, J=3.05 Hz, 5 H), 1.85 (dd, J=8.09, 5.34 Hz, 1 H), 2.17 (q, J=8.85 Hz, 1 H), 2.30–2.33 (m, 1 H), 2.58 (dd, J=13.58, 7.48 Hz, 1 H), 2.91–2.94 (m, 1 H), 3.92 (d, J=2.14 Hz, 1 H), 3.93 (s, 3 H), 4.05 (dd, J=11.60, 3.66 Hz, 1 H), 4.32 (d, J=9.77 Hz, 1 H), 4.51 (dd, J=9.92, 7.17 Hz, 1 H), 5.09 (dd, J=11.59, 1.52 Hz, 1 H), 5.27 (dd, J=16.71, 1.22 Hz, 1 H), 5.74–5.78 (m, 1 H), 5.82 (s, 1 H), 7.05–7.09 (m, 1 H), 7.18 (d, J=2.44 Hz, 1 H), 7.19 (d, J=7.33 Hz, 1 H), 7.22 (d, J=5.80 Hz, 1 H), 7.33 (d, J=7.63 Hz, 1 H), 7.84 (d, J=5.80 Hz, 1 H); LC-MS (retention time: 1.76 min.), MS m/z 775 (MH$^+$).

Example 84

Preparation of Compound 84

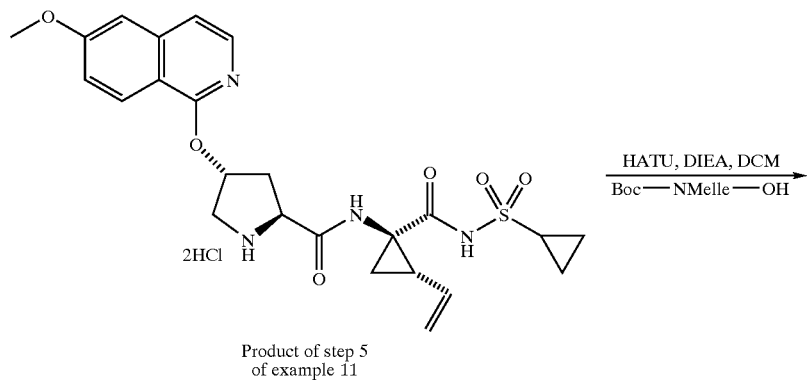

Product of step 5 of example 11

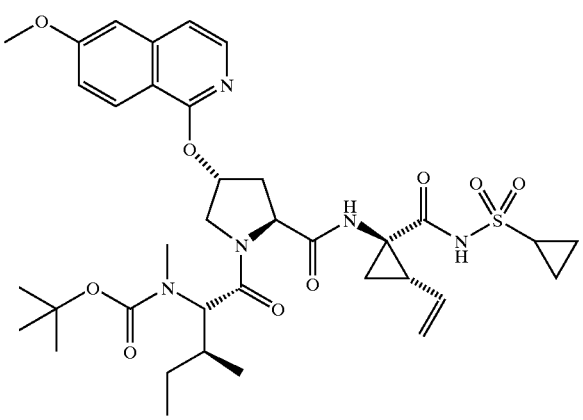

Compound 84

To a solution of the product of step 5 of example 11 (77.0 mg, 0.136 mmol), DIEA (70.4 mg, 0.544 mmol) and HATU (77.5 mg, 0.204 mmol) was added Boc-Melle-OH (43.4 mg, 0.177 mmol). After stirring at rt for 14 hr, the reaction mixture was washed with 5% aqueous NaHCO₃ (1 mL). The aqueous layer was extracted with 2×2 mL DCM. The combined organic layer was washed with 5% aqueous citric acid (2 mL), brine, dried over MgO₄, concentrated and purified by flash column chromatography (SiO₂, 97:3 DCM:MeOH) to give Compound 84 (68.4 mg, 69% yield): ¹H NMR(CD₃OD, 500 MHz) δ 0.89 (t, J=7.32 Hz, 3 H) 0.94 (dd, J=5.95, 4.43 Hz, 3 H) 1.07 (d, J=7.63 Hz, 3 H) 1.13 (s, 5 H) 1.16–1.20 (m, J=4.88 Hz, 2 H) 1.23 (s, 3 H) 1.28 (m, 1 H) 1.34–1.38 (m, 1 H) 1.41–1.47 (m, 1 H) 1.55–1.60 (m, J=7.63 Hz, 1 H) 1.87–1.91 (m, 1 H) 2.22–2.26 (m, 2 H) 2.36–2.38 (m, 1 H) 2.56–2.62 (m, 1 H) 2.81 (d, J=11.30 Hz, 2 H) 2.94–2.99 (m, 1 H) 3.92 (s, 3 H) 4.05–4.12 (m, 2 H) 4.48–4.57 (m, 2 H) 5.12 (d, J=10.07 Hz, 1 H) 5.32 (m, 1 H) 5.75–5.82 (m, 1 H) 5.84–5.88 (m, 1 H) 7.09–7.13 (m, 1 H) 7.16–7.20 (m, 1 H) 7.23–7.27 (m, 1 H) 7.88 (dd, J=5.95, 2.29 Hz, 1 H) 8.04 (d, J=9.16 Hz, 0.6 H) 8.09 (d, J=9.46 Hz, 0.4 H); LC-MS (retention time: 1.83 min.), MS m/z 728 (MH⁺).

Example 85

Preparation of Example 85

Compound 85

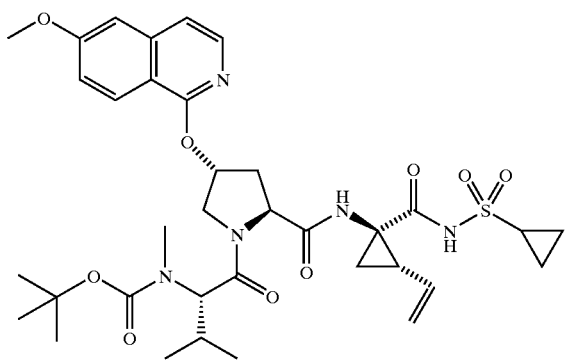

Compound 85 was prepared by the same method as Compound 84 with the following modifications:

Modifications: Boc-MeVal-OH was used as a starting material to give Compound 84 (72.1 mg, 74% yield): ¹H NMR(CD₃OD, 500 MHz) δ 0.84 (t, J=5.80 Hz, 3 H), 0.96 (d, J=6.41 Hz, 3 H), 1.08 (d, J=7.32 Hz, 2 H), 1.13 (s, 6 H), 1.16 (s, 4 H), 1.18–1.21 (m, 1 H), 1.23–1.29 (m, 1 H), 1.44 (dd, J=9.61, 5.34 Hz, 1 H), 1.88–1.92 (m, 1 H), 2.24 (d, J=10.07 Hz, 1 H), 2.32–2.39 (m, 2 H), 2.58 (dd, J=13.89, 6.26 Hz, 1 H), 2.80 (s, 3 H), 2.93–2.98 (m, 1 H), 3.93 (s, 3 H), 4.01 (dd, J=11.90, 3.36 Hz, 0.6 H), 4.12 (d, J=11.90, 3.66 Hz, 0.4 H), 4.16 (d, J=11.29 Hz, 0.6 H), 4.38 (d, J=10.99 Hz, 0.4 H), 4.45 (d, J=10.68 Hz, 1 H), 4.47 (d, J=10.69 Hz, 0.6 H), 4.53 (dd, J=10.38, 7.02 Hz, 0.4 H), 4.58 (dd, J=10.07, 7.02 Hz, 1 H), 5.12 (d, J=4.28 Hz, 0.6 H), 5.14 (d, J=4.27 Hz, 0.4 H), 5.30 (d, J=7.32 Hz, 0.6 H), 5.34 (d, J=7.32 Hz, 0.4 H), 5.78–5.85 (m, 1 H), 5.88 (t, J=3.05 Hz, 0.6 H), 5.96 (t, J=3.97 Hz, 0.4 H), 7.13 (dd, J=9.00, 2.29 Hz, 0.6 H), 7.16 (dd, J=9.46, 2.44 Hz, 0.4 H), 7.19 (m, 1 H), 7.24 (d, J=6.10 Hz, 0.6 H), 7.26 (d, J=6.10 Hz, 0.4 H), 7.88 (d, J=5.80 Hz, 1 H), 8.02 (d, J=9.16 Hz, 0.6 H) 8.05 (d, J=9.16 Hz, 0.4 H).

Example 86

Preparation of Compound 86

Compound 86

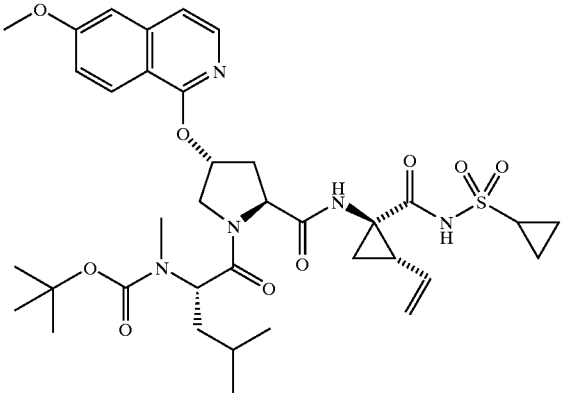

Compound 86 was prepared by the same method as Compound 84 with the following modifications:

Modifications: Boc-MeLeu-OH was used as a starting material to give Compound 85 (56.5 mg, 57% yield): ¹H NMR (CD₃OD, 500 MHz) δ 0.94–0.96 (m, 6 H), 1.04–1.13 (m, 2 H), 1.17 (s,4.5 H), 1.18 (s, 4.5 H), 1.26–1.31 (m, 1 H), 1.42 (dd, J=9.46, 5.49 Hz, 1 H), 1.46–1.51 (m, 2 H), 1.56–1.60 (m, 0.5 H), 1.69–1.72 (m, 0.5 H), 1.75–1.81 (m, 0.5 H), 1.90 (q, J=7.50 Hz, 1 H), 2.27 (dd, J=13.89, 7.78 Hz, 1 H), 2.32–2.38 (m, 1 H), 2.58 (dd, J=14.80, 7.48 Hz, 1 H), 2.75 (s, 3 H), 2.95–2.99 (m, 1 H), 3.93 (s, 3 H), 4.03 (d, J=12.21 Hz, 1 H), 4.11–15 (m, 0.5 H), 4.28 (d, J=12.21 Hz, 1 H), 4.53 (t, J=8.50 Hz, 0.5 H), 4.59 (t, J=8.55 Hz, 0.5 H), 4.83–4.87 (m, J=6.41 Hz, 0.5 H), 4.96 (m, 0.5 H), 5.14 (dd, J=11.14, 4.73 Hz, 1 H), 5.32 (dd, J=17.70, 6.41 Hz, 1 H), 5.75–5.82 (m, 1 H), 5.90 (s, 0.5 H), 5.92 (s, 0.5 H), 7.13–7.18 m, 1 H), 7.20 (s, 1 H), 7.25–7.27 (m, 1 H), 7.87 (t, J=4.40 Hz, 1 H) 8.05 (d, J=8.85 Hz, 1 H).

Example 87

Preparation of Compound 87

Compound 87

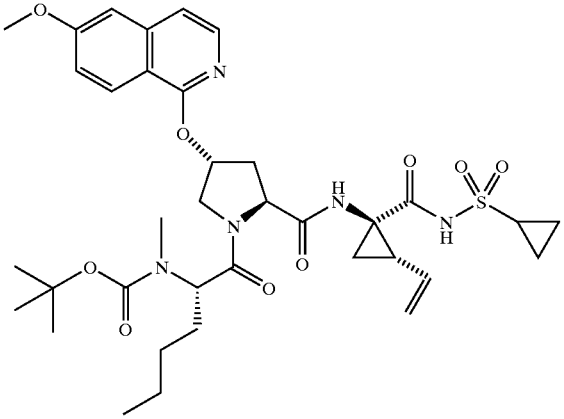

Compound 87 was prepared by the same method as Compound 84 with the following modifications:

Modifications: Boc-MeNle-OH was used as a starting material to give Compound 87 (82.3 mg, 83% yield): ¹H NMR(CD₃OD, 500 MHz) δ 0.90–0.96 (q, J=7.63 Hz, 3 H) 1.05–1.10 (m, 2 H) 1.18 (s, 4.5 H) 1.20 (s, 4.5 H) 1.24–1.30 (m, 3 H) 1.31–1.38 (m, 1 H) 1.42 (dd, J=9.46, 5.19 Hz, 2 H) 1.72–1.81 (m, 2 H) 1.88–1.92 (m, 1 H) 2.22–2.29 (m, 1 H)

2.32–2.38 (m, 1 H) 2.58 (dd, J=13.89, 7.17 Hz, 1 H) 2.72 (s, 3 H) 2.94–2.99 (m, 1 H) 3.93 (s, 3 H) 4.02 (dd, J=9.77, 4.27 Hz, 1 H) 4.12 (dd, J=11.90, 3.35 Hz, 0.5 H) 4.24 (dd, J=11.90, 0.6 Hz, 0.5 H) 4.51–4.60 (m, 1 H) 5.14 (d, J=10.38 Hz, 1 H) 5.33 (dd, J=17.24, 4.73 Hz, 1 H) 5.75–5.82 (m, 1 H) 5.91 (s, 1 H) 7.15 (dd, J=14.34, 7.63 Hz, 1 H) 7.20 (d, J=2.44 Hz, 1 H) 7.25 (d, J=5.80 Hz, 1 H) 7.87 (t, J=4.37 Hz, 1 H) 8.05 (d, J=8.85 Hz, 1 H).

Example 88

Preparative of Compound 88

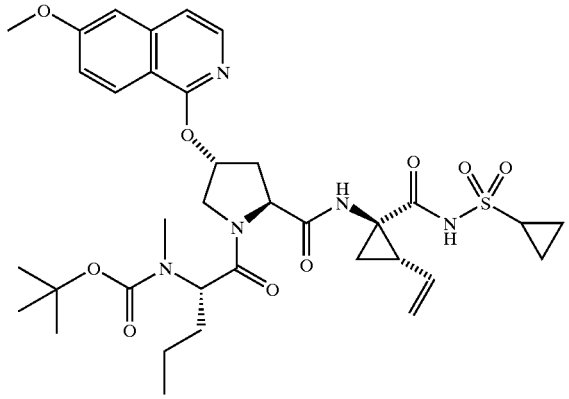

Compound 88

Compound 88 was prepared by the same method as Compound 84 with the following modifications:

Modifications: Boc-N-Me-NVa-OH was used as a starting material to give Compound 88 (70.5 mg, 73% yield): $^1$H NMR(CD$_3$OD, 500 MHz) δ 0.96 (d, J=6.41 Hz, 3 H) 1.06–1.10 (m, 2 H) 1.18 (s, 9 H) 1.27–1.30 (m, 4 H) 1.42 (dd, J=9.46, 5.49 Hz, 1 H) 1.66–1.80 (m, 2 H) 1.88–1.92 (m, 1 H) 2.23–2.29 (m, 1 H) 2.30–2.37 (m, 1 H) 2.58 (dd, J=13.58, 7.17 Hz, 1 H) 2.73 (s, 3 H) 2.94–2.98 (m, 1 H) 3.93 (s, 3 H) 4.00–4.04 (m, 1 H) 4.12 (d, J=12.82 Hz, 0.5 H) 4.25 (d, J=12.21 Hz, 0.5 H) 4.51–4.60 (m, 1 H) 5.13 (d, J=10.68 Hz, 1 H) 5.32 (d, J=17.09 Hz, 1 H) 5.75–5.81 (m, 1 H) 5.90 (s, 1 H) 7.13–7.18 (m, 1 H) 7.20 (d, J=2.14 Hz, 1 H) 7.25 (d, J=5.80 Hz, 1 H) 7.87 (s, 1 H) 8.05 (d, J=9.16 Hz, 1 H).

Example 89

Preparation of Compound 89

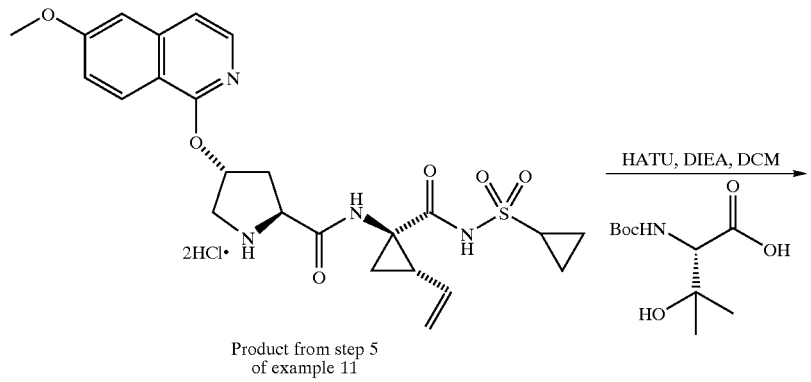

Product from step 5 of example 11

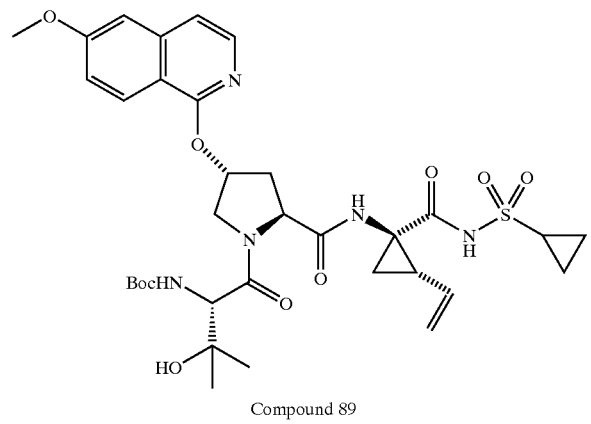

Compound 89

To a solution of the product from step 5 of example 11 (66.0 mg, 0.123 mmol), DIEA (63.7 mg, 0.492 mmol) and HATU (70.0, 0.184 mmol) was added 2S-tert-butoxycarbonylamino-3-hydroxy-3-methyl-butyric acid (34.0 mg, 0.147 mmol). After stirring at rt for 14 hr, the reaction mixture was washed with 5% aqueous NaHCO₃ (1 mL). The aqueous layer was extracted with 2×2 mL DCM. The combined organic layer was washed with 5% aqueous citric acid (2 mL), brine, dried over MgO₄, concentrated and purified by reversed phase prep-HPLC to give Compound 89 (36.1 mg, 41% yield): $^1$H NMR(CD$_3$OD, 500 MHz) δ 1.07 (d, J=7.93 Hz, 2 H), 1.18 (s, 1 H), 1.20 (s, 9 H), 1.24–1.27 (m, J=11.60 Hz, 3 H), 1.30 (s, 3 H), 1.43–1.48 (m, 10 H), 1.59 (s, 1 H), 1.65 (s, 1 H), 1.87 (dd, J=8.24, 5.19 Hz, 1 H), 2.24 (q, J=9.16 Hz, 1 H), 2.33–2.36 (m, 1 H), 2.63 (dd, J=12.97, 6.56 Hz, 1 H), 2.94–2.99 (m, 1 H), 3.92 (s, 3 H), 3.93 (s, 1 H), 4.12 (dd, J=11.60, 3.05 Hz, 1 H), 4.27–4.31 (m, 1 H), 4.54 (t, J=9.77 Hz, 1 H), 5.12 (dd, J=10.53, 1.37 Hz, 1 H), 5.30 (d, J=17.09 Hz, 1 H), 5.79–5.83 (m, 1 H), 5.85 (s, 1 H), 7.11 (dd, J=8.55, 1.83 Hz, 1 H), 7.18 (d, J=2.24 Hz, 1 H), 7.24 (d, J=5.49 Hz, 1 H), 7.88 (m, 1 H), 8.10 (d, J=8.85 Hz, 1 H)); LC-MS (retention time: 1.637 min.), MS m/z 716 (MH⁺).

Example 91

Preparation of Compound 91

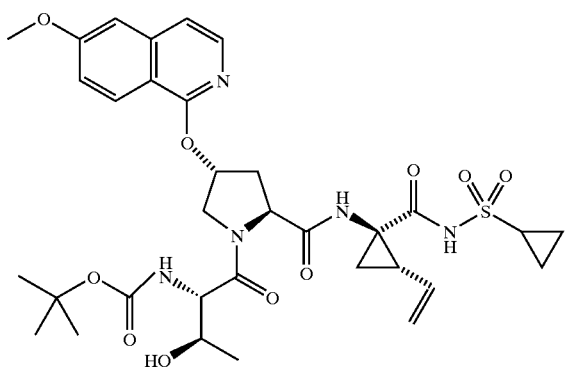

Compound 91

Compound 91 was prepared by the same method as Compound 89 with the following modifications:

Modifications: Boc-L-Thr-OH was used as a starting material to give Compound 91 (80.5 mg, 66% yield): $^1$H NMR(CD$_3$OD, 500 MHz) δ 0.93 (dd, J=8.24, 2.14 Hz, 2 H), 1.08–1.18 (m, 4 H), 1.20 (d, J=6.10 Hz, 3 H), 1.29 (s, 9 H), 1.32 (dd, J=9.61, 5.04 Hz, 1 H), 1.45 (d, J=4.27 Hz, 1 H), 1.84 (dd, J=7.63, 5.19 Hz, 1 H), 2.15 (q, J=8.85 Hz, 1 H), 2.42–2.48 (m, 1 H), 2.64 (dd, J=14.04, 7.63 Hz, 1 H), 2.85–2.89 (m, 1 H), 3.92 (s, 3 H), 4.1–4.14 (m, 2 H), 4.30 (d, J=4.88 Hz, 1 H), 4.38 (d, J=11.60 Hz, 1 H), 4.60 (t, J=8.55 Hz, 1 H), 5.04 (dd, J=10.22, 1.68 Hz, 1 H), 5.80–5.84 (m, 2 H), 7.11 (d, J=9.16 Hz, 1 H), 7.17 (d, J=1.83 Hz, 1 H), 7.23 (d, J=5.80 Hz, 1 H), 7.87 (d, J=5.80 Hz, 1 H), 8.10 (d, J=8.85 Hz, 1 H); LC-MS (retention time: 1.560 min.), MS m/z 702 (MH⁺).

Example 92

Preparation of Compound 92

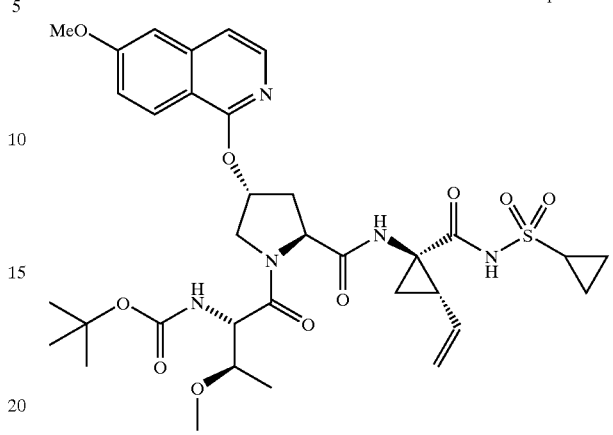

Compound 92

Compound 92 was prepared by the same method as Compound 89 with the following modifications:

Modifications: Boc-L-Thr(Me)-OH was used as a starting material to give Compound 92 (47.1 mg, 69% yield): $^1$H NMR(CD$_3$OD, 500 MHz) δ 0.95 (d, J=4.27 Hz, 2 H), 1.11–1.16 (m, 3 H), 1.18 (d, J=6.10 Hz, 6 H), 1.32 (s, 9 H), 1.38 (dd, J=9.31, 5.04 Hz, 1 H), 1.45 (s, 1 H), 1.85 (dd, J=7.78, 5.04 Hz, 1 H), 2.13 (d, J=9.15 Hz, 1 H), 2.46–2.51 (m, 1 H), 2.63 (dd, J=14.19, 7.78 Hz, 1 H), 2.81–2.91 (m, 1 H), 3.68–3.73 (m, 1 H), 3.92 (s, 4 H), 4.14 (d, J=12.21 Hz, 1 H), 4.35 (d, J=5.80 Hz, 1 H), 4.42 (d, J=11.29 Hz, 1 H), 4.60 (t, J=8.70 Hz, 1 H), 5.05 (d, J=10.68 Hz, 1 H), 5.24 (dd, J=16.79, 0.92 Hz, 1 H), 5.81–5.85 (m, 2 H), 7.11 (dd, J=9.16, 0.92 Hz, 1 H), 7.17 (s, 1 H), 7.24 (d, J=5.80 Hz, 1 H), 7.88 (d, J=5.80 Hz, 1 H), 8.11 (d, J=8.55 Hz, 1 H); LC-MS (retention time: 1.660 min.), MS m/z 716 (MH⁺).

Example 93

Preparation of Compound 93

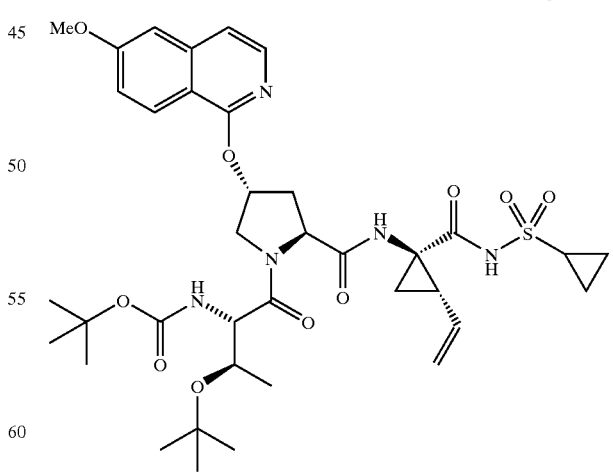

Compound 93

Compound 93 was prepared by the same method as Compound 89 with the following modifications:

Modifications: Boc-L-Thr(tBu)-OH was used as a starting material to give Compound 93 (52.7 mg, 53% yield): $^1$H NMR(CD₃OD, 500 MHz) δ 1.09 (dd, J=8.24, 2.44 Hz, 2 H), 1.201.24 (m, 3 H), 1.28 (s, 9 H), 1.45 (s, 9 H), 1.89 (dd, J=7.93, 5.19 Hz, 1 H), 2.25 (q, J=8.34 Hz, 1 H), 2.32–2.36 (m, 1 H), 2.59 (dd, J=12.82, 6.41 Hz, 1 H), 2.95–3.00 (m, 1 H), 3.71 (s, 2 H), 3.92 (s, 3 H), 3.93–3.99 (m, 1 H), 4.10 (d, J=7.02 Hz, 1 H), 4.15 (d, J=11.90 Hz, 1 H), 4.22 (dd, J=6.10, 2.44 Hz, 2 H), 4.40 (d, J=11.60 Hz, 1 H), 4.54 (dd, J=10.01, 6.71 Hz, 1 H), 5.13 (d, J=10.38 Hz, 1 H), 5.31 (d, J=17.09 Hz, 1 H), 5.76–5.83 (m, 1 H), 5.87 (s, 1 H), 6.06 (d, J=9.46 Hz, 1 H), 6.36 (d, J=7.02 Hz, 1 H), 7.11 (d, J=8.85 Hz, 1 H), 7.18 (s, 1 H), 7.24 (d, J=5.49 Hz, 1 H), 7.88 (m, 1 H), 8.08 (d, J=9.16 Hz, 1 H).

Example 94

Preparation of Compound 94

Compound 94

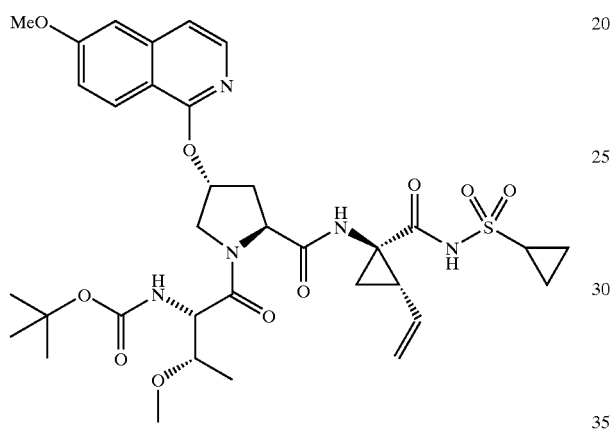

Compound 94 was prepared by the same method as Compound 89 with the following modifications:

Modifications: Boc-(2S,3S)-2-amino-3-methoxybutanoic acid was used as a starting material to give Compound 94 (150.2 mg, 80% yield): ¹H NMR(CD₃OD, 500 MHz) δ 1.04–1.13 (m, 3 H), 1.17 (d, J=6.10 Hz, 3 H), 1.20–1.24 (m, 2 H), 1.27 (s, 9 H), 1.44–1.48 (m, 2 H), 1.86 (dd, J=7.93, 5.49 Hz, 1 H), 2.24 (q, J=8.65 Hz, 1 H), 2.34–2.37 (m, 1 H), 2.61 (dd, J=14.19, 7.17 Hz, 1 H), 2.94–2.99 (m, 1 H), 3.66 (m, 1 H), 3.92 (s, 3 H), 4.13 (dd, J=12.36, 3.81 Hz, 1 H), 4.37 (dd, J=22.58, 10.99 Hz, 2 H), 4.54 (dd, J=10.38, 7.63 Hz, 1 H), 5.12 (d, J=10.68 Hz, 1 H), 5.31 (d, J=17.40 Hz, 1 H), 5.77–5.82 (m, 1 H), 5.85 (s, 1 H), 7.12 (d, J=9.16 Hz, 1 H), 7.18 (s, 1 H), 7.25 (d, J=6.10 Hz, 1 H), 7.89 (d, J=5.80 Hz, 1 H), 8.10 (d, J=8.85 Hz, 1 H); LC-MS (retention time: 1.673 min.), MS m/z 716 (MH⁺).

Example 95

Preparation of Compound 95

Scheme 1

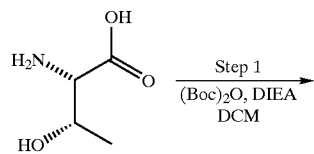

Product of step 5 of example 11

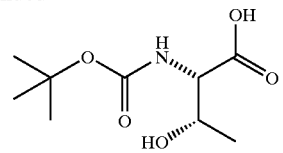

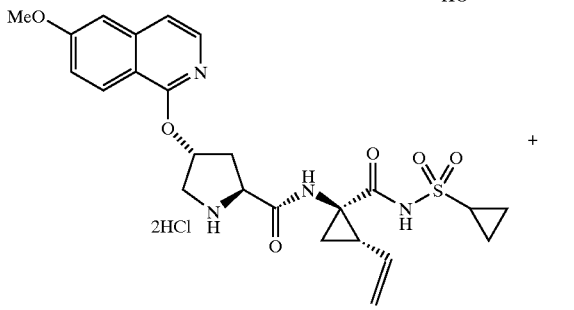

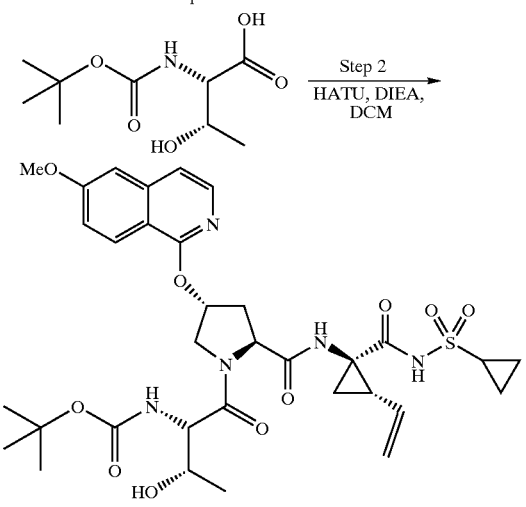

Compound 95

Step 1

To a mixture of H-allo-THr-OH (5.0 g, 41.98 mmol) and DIEA (10.9 g, 83.96 mmol) in DCM (150 mL) was added di-tert-butyl dicarbonate (13.7 g, 62.97 mmol). After stirring at rt for 14 h, the reaction mixture was washed with 3×100 mL DCM. The combined organic layer was dried over MgSO₄ and conentrated. LC/MS indicated most product stayed in the H₂O layer. Thus the water layer was concentrated. The product was purified by a flash column chromatography (SiO2, 90:10 DCM:MeOH) to give Boc-allo-THr-OH; LC-MS (retention time: 0.727 min.), MS m/z 242 (MNa⁺).

Step 2

To a solution of the product from step 5 of example 11 (100.0 mg, 0.174 mmol), DIEA (67.6 mg, 0.522 mmol) and HATU (106.0 mg, 0.278 mmol) was added the product from step 1 above (57.3 mg, 0.262 mmol). After stirring at rt for 3 hr, the reaction mixture was washed with 5% aqueous NaHCO₃ (1 mL). The aqueous layer was extracted with 2×2 mL DCM. The combined organic layer was washed with 5% aqueous citric acid (2 mL), brine, dried over MgO₄, concentrated and purified by reversed phase prep-HPLC to give Compound 95 (39.1 mg, 32% yield): ¹H NMR(CD₃OD, 500 MHz) δ 1.02 (d, J=8.55 Hz1 H), 1.18–1.23 (m, 3 H), 1.25 (s, 9 H), 1.38 (dd, J=9.15, 6.30 Hz, 1 H), 1.84 (dd, J=7.93, 5.19 Hz, 1 H), 2.19–2.24 (m, 1 H), 2.38–2.43 (m, 1 H), 2.65 (dd, J=14.19, 6.87 Hz, 1 H), 2.92–2.96 (m, 1 H), 3.92 (s, 3 H), 3.93 (s, 2 H), 4.16–4.19 (m, 1 H), 4.23 (d, J=8.24 Hz, 1 H), 4.44 (d, J=12.21 Hz, 1 H), 4.57–5.81 (m, 1 H), 5.09 (d, J=10.68 Hz, 1 H), 5.29 (d, J=17.09 Hz, 1 H), 5.75–5.81 (m, 1 H), 5.83–5.85 (m, 1 H), 7.11 (d, J=10.38 Hz, 1 H), 7.18 (d, J=1.83 Hz, 1 H), 7.24 (d, J=6.41 Hz, 1 H), 7.88 (d, J=5.80 Hz, 1 H), 8.11 (d, J=9.16 Hz, 1 H); LC-MS (retention time: 1.583 min.), MS m/z 702 (MH$^+$).

Example 96

Preparation of Compound 96

Scheme 1

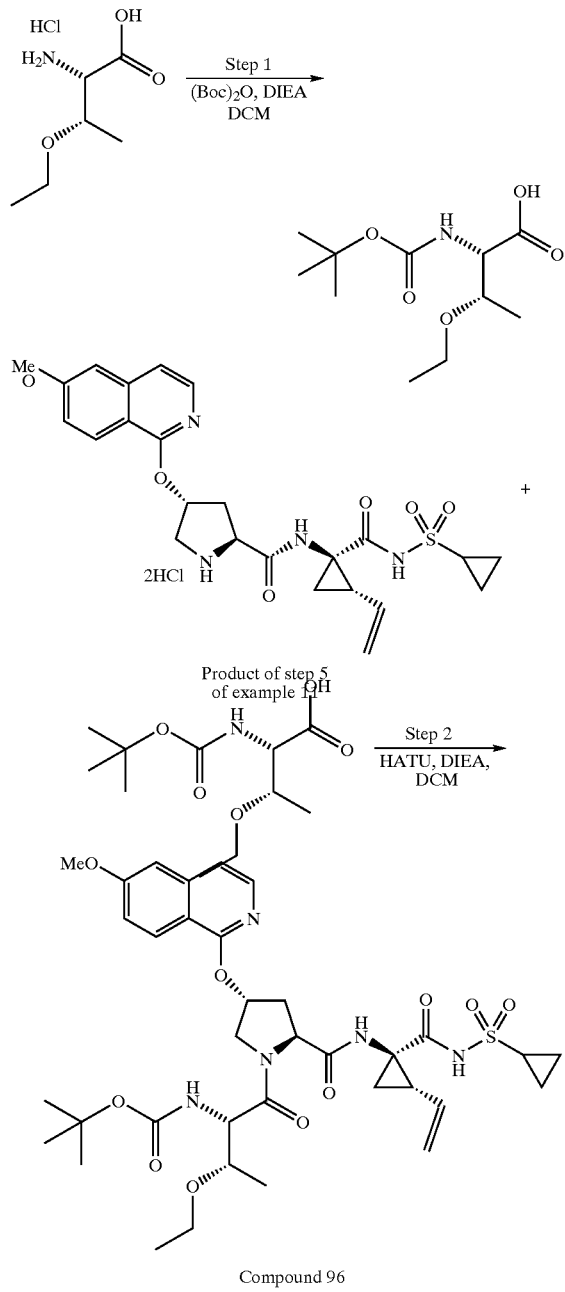

Compound 96

Compound 96 was prepared by the same method as Compound 95 with the following modifications:

Modifications:

Step 1

(2S,3S)-2-Amino-3-ethoxybutanoic acid hydrochloride was used as a starting material in step 1 to give Boc-(2S, 3S)-2-Amino-3-ethoxybutanoic acid; LC-MS (retention time: 1.067 min.), MS m/z 270 (M+Na$^+$).

Step 2

The product from step 1 was then coupled the same way with the product from step 5 of example 11 to give Compound 96 (55.3 mg, 44% yield): $^1$H NMR(CD$_3$OD, 500 MHz) δ 0.94 (t, J=6.87 Hz, 1 H), 0.97–1.03 (m, 2 H), 1.08–1.11 (m, 2 H), 1.13–1.15 (m, 2 H), 1.17 (d, J=6.10 Hz, 6 H), 1.29 (s, 9 H), 1.41–1.45 (m, 3 H), 1.85 (dd, J=7.48, 5.34 Hz, 1 H), 2.12–2.19 (m, 1 H), 2.43–2.49 (m, 1 H), 2.60 (dd, J=13.73, 6.80 Hz, 1 H), 2.89–2.93 (m, 1 H), 3.50–3.57 (m, 2 H), 3.73–3.78 (m, 1 H), 3.92 (s, 3 H), 4.18 (d, J=8.85 Hz, 1 H), 4.35 (d, J=12.21 Hz, 1 H), 4.39 (d, J=8.55 Hz, 1 H), 4.53 (t, J=7.78 Hz, 1 H), 5.07 (d, J=9.16 Hz, 1 H), 5.25 (d, J=18.01 Hz, 1 H), 5.82 (t, J=9.85 Hz, 1 H), 5.88 (t, J=9.80 Hz, 1 H), 7.11 (d, J=5.19 Hz, 1 H), 7.18 (d, J=2.14 Hz, 1 H), 7.24 (d, J=5.49 Hz, 1 H), 7.88 (d, J=6.10 Hz, 1 H), 8.10 (d, J=8.85 Hz, 1 H); LC-MS (retention time: 1.743 min.), MS m/z 730 (MH$^+$).

Example 97

Preparation of Compound 97

Scheme 1

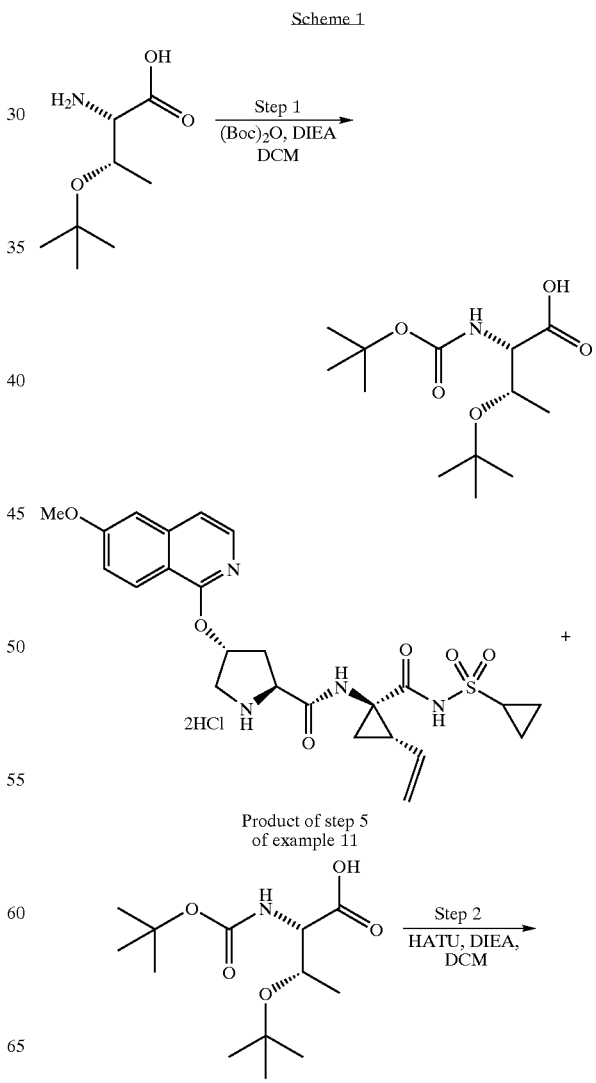

183

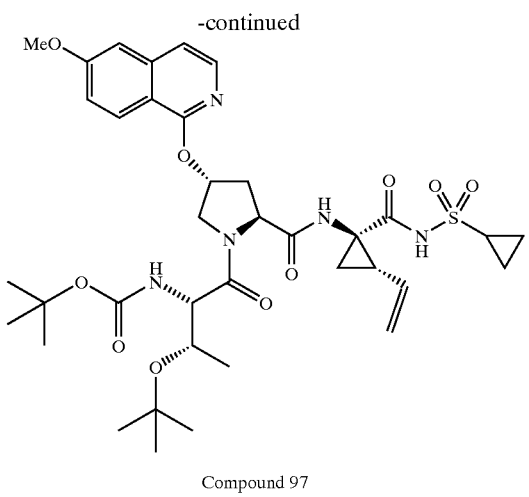

Compound 97

Compound 97 was prepared by the same method as Compound 95 with the following modifications:
Modifications:
Step 1
H-allo-Thr(t-Bu)-OH was used as a starting material in step 1 to give Boc-(2S,3S)-2-Amino-3-ethoxybutanoic acid; LC-MS (retention time: 1.363 min.), MS m/z 298 (M+Na$^+$).
Step 2
The product from step 1 was then coupled the same way with the product from step 5 of example 11 to give Compound 97 (48.2 mg, 37% yield): LC-MS (retention time: 1.820 min.), MS m/z 758 (MH$^+$).

Example 99

Preparation of Compound 99

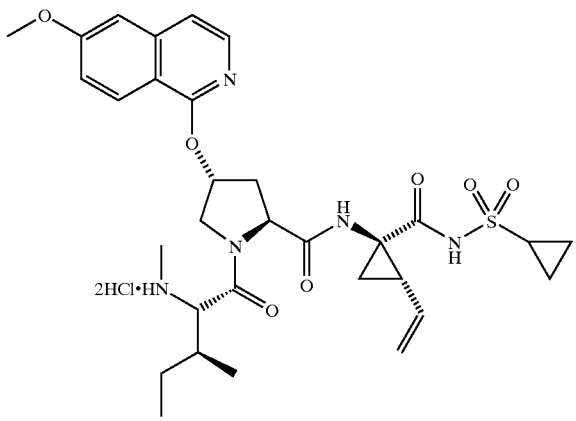

Compound 99

Compound 99 was prepared by the same method as step 1 of Example 55 with the following modifications:

Modifications: Compound 84 was used as a starting material to give Compound 99 (60.3 mg, 98% yield): $^1$H NMR(CD$_3$OD, 500 MHz) δ 1.00 (q, J=7.12 Hz, 3 H) 1.10–113 (m, 5 H) 1.20–1.31 (m, 3 H) 1.41 (dd, J=9.46, 5.49 Hz, 1 H) 1.61–1.68 (m, 1 H) 1.92 (dd, J=8.24, 5.49 Hz, 1 H) 2.04–2.09 (m, 1 H) 2.28 (q, J=8.55 Hz, 1 H) 2.34–2.39 (m, 1 H) 2.57 (s, 3 H) 2.64–2.70 (m, 1 H) 2.94–2.97 (m, 1 H) 3.93 (s, 3 H) 4.07–4.14 (dd, J=12.05, 3.81 Hz, 1 H) 4.13 (d, J=6.10 Hz, 1 H) 4.18 (d, J=5.80 Hz, 1 H) 4.25 (d, J=12.21

184

Hz, 1 H) 4.66–4.73 (m, 1 H) 5.15 (d, J=10.68 Hz, 1 H) 5.32 (d, J=17.09 Hz, 1 H) 5.70–5.79 (m, 1 H) 5.92 (t, J=3.66 Hz, 0.4 H) 5.95 (t, J=3.66 Hz, 0.6 H) 7.17 (dd, J=9.16, 2.44 Hz, 1 H) 7.22 (d, J=2.14 Hz, 1 H) 7.28 (dd, J=5.80, 3.36 Hz, 1 H) 7.91 (dd, J=5.80, 4.27 Hz, 1 H) 8.03 (d, J=8.85 Hz, 0.6 H) 8.07 (d, J=9.16 Hz, 0.4 H); LC-MS (retention time: 1.33 min.), MS m/z 6.28 (MH$^+$).

Example 100

Preparation of Compound 100

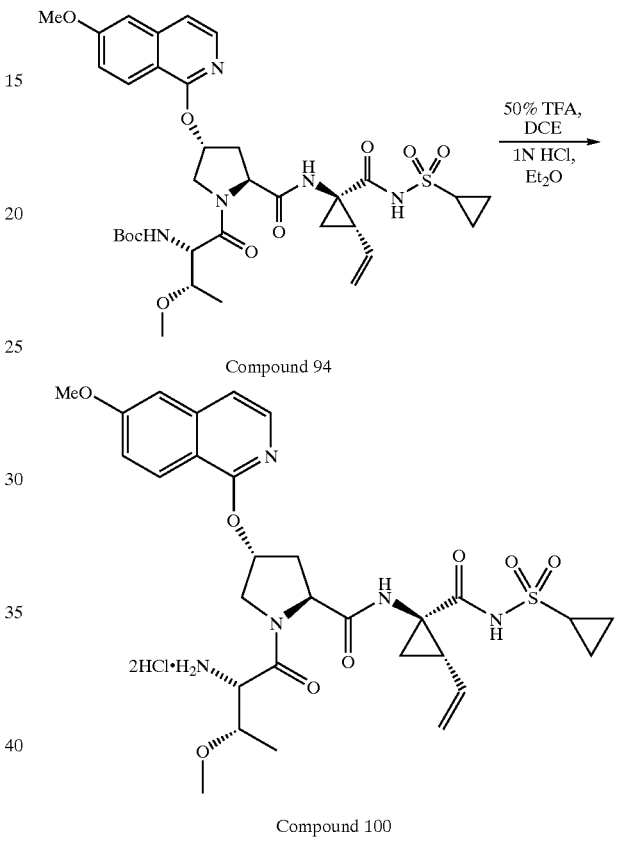

To a solution of Compound 94 (0.600 g, 0.838 mmol) in DCE (3 mL) was added TFA (3 mL). After stirring at rt for 15 min, the reaction mixture was concentrated. The resulting viscous oil was re-dissolved in DCE (5 mL) and reconcentrated. It was then redissolved in DCM (2 mL) and treated with a solution of 1N HCl in Et$_2$O (10 mL). The resulting suspension was chilled at 0° C., vacuum filtrated, washed with Et$_2$O and dried in vacuum oven to give the product as a bis-hydrochloride salt as a white solid (527.1 g, 91% yield): $^1$H NMR(CD$_3$OD, 500 MHz) δ 1.08–1.15 (m, 2 H), 1.21 (d, J=6.71 Hz, 4 H), 1.28–1.33 (m, 1 H), 1.41 (dd, J=9.46, 5.49 Hz, 1 H), 1.91 (dd, J=8.24, 5.49 Hz, 1 H), 2.28 (q, J=8.65 Hz, 1 H), 2.34–2.37 (m, 1 H), 2.68 (dd, J=13.12, 7.02 Hz, 1 H), 2.81 (s, 3 H), 2.93–2.98 (m, 1 H), 3.45 (s, 3 H), 3.94 (s, 3 H), 3.96–4.00 (m, 1 H), 4.16 (dd, J=11.90, 3.66 Hz, 1 H), 4.27 (d, J=11.60 Hz, 1 H), 4.59 (d, J=4.58 Hz, 1 H), 4.69 (dd, J=10.07, 7.02 Hz, 1 H), 5.14 (dd, J=10.53, 1.37 Hz, 1 H), 5.32 (d, J=17.09 Hz, 1 H), 5.70–5.77 (m, 1 H), 5.94 (t, J=3.66 Hz, 1 H), 7.19 (d, J=9.16 Hz, 1 H), 7.24 (s, 1 H), 7.32 (s, 1 H), 7.91 (d, J=5.80 Hz, 1 H), 8.09 (d, J=9.16 Hz, 1 H); LC-MS (retention time: 1.213 min.), MS m/z 616 (MH$^+$).

Example 101

Preparation of Compound 101

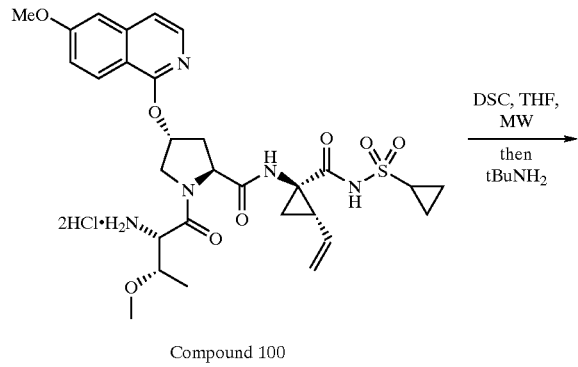

Compound 100

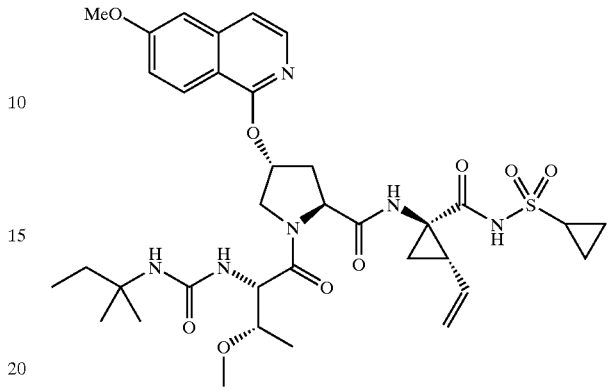

Compound 101

To a solution mixture of Compound 100 (80 mg, 0.116 mmol) and DIEA (31.5 mg, 0.244 mmol) in THF (2 mL) was added N,N'-dissucinimidyl carbonate (44.6 mg, 0.174 mmol). The resulting suspension was irradiated in a microwave to 80° C. for 15 min. Then it was treated with tert-amylamine (84.8 mg, 1.16 mmol). After stirring at rt 15 min, the reaction was concentrated and purified by reversed phase prep-HPLC to give Compound 101 (65.1 mg, 79%): $^1$H NMR(CD$_3$OD, 500 MHz) δ 1.03–1.08 (m, 3 H), 1.16 (d, J=6.41 Hz, 3 H), 1.19 (s, 9 H), 1.21–1.25 (m, 2 H), 1.27 (d, J=6.10 Hz, 1 H), 1.45 (dd, J=9.46, 5.19 Hz, 1 H), 1.85 (dd, J=8.24, 5.19 Hz, 1 H), 2.23 (q, J=9.46 Hz, 1 H), 2.34–2.41. (m, 1 H), 2.61 (dd, J=14.34, 7.32 Hz, 1 H), 2.94–2.97 (m, 1 H), 3.58–3.63 (m, 1 H), 3.92 (s, 3 H), 4.15 (dd, J=12.05, 3.81 Hz, 1 H), 4.39 (d, J=11.60 Hz, 1 H), 4.55 (dd, J=9.92, 7.48 Hz, 1 H), 5.11 (d, J=10.68 Hz, 1 H), 5.29 (d, J=17.40 Hz, 1 H), 5.77–5.83 (m, 1 H), 5.86 (s, 1 H), 7.12 (dd, J=9.00, 2.29 Hz, 1 H), 7.18 (d, J=2.14 Hz, 1 H), 7.24 (d, J=5.80 Hz, 1 H), 7.88 (d, J=5.80 Hz, 1 H), 8.10 (d, J=9.16 Hz, 1 H); LC-MS (retention time: 1.617 min.), MS m/z 715 (MH$^+$).

Example 102

Preparation of Compound 102

Compound 102

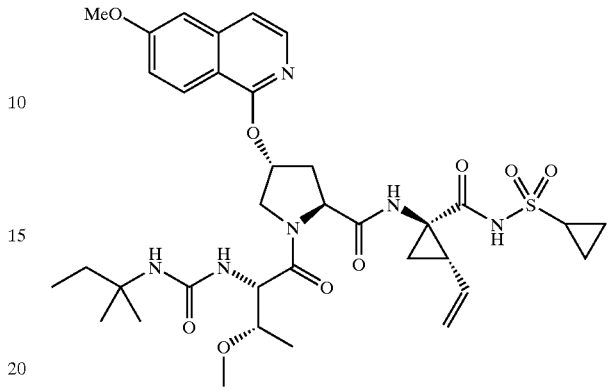

Compound 102 was prepared by the same method as Compound 101 with the following modifications:

Modifications: tert-amylamine was used as a starting material to give Compound 102 (62.5 mg, 74% yield): $^1$H NMR(CD$_3$OD, 500 MHz) δ 0.77 (t, J=7.48 Hz, 2 H), 0.84 (t, J=7.48 Hz, 1 H), 1.04–1.08 (m, 2 H), 1.13 (d, J=1.22 Hz, 9 H), 1.16 (d, J=6.41 Hz, 3 H), 1.21 (s, 1 H), 1.22–1.28 (m, 2 H), 1.44 (dd, J=9.46, 5.19 Hz, 1 H), 1.52–1.57 (m, 1 H), 1.58–1.62 (m, 1 H), 1.85 (dd, J=7.93, 5.19 Hz, 1 H), 2.21–2.25 (m, 1 H), 2.34–2.39 (m, 1 H), 2.61 (dd, J=13.58, 7.17 Hz, 1 H), 2.93–2.98 (m, 1 H), 3.59–3.64 (m, 1 H), 4.15 (dd, J=11.75, 3.81 Hz, 1 H), 4.38 (d, J=12.51 Hz, 1 H), 4.50 (d, J=7.63 Hz, 1 H), 4.55 (dd, J=9.92, 7.78 Hz, 1 H), 5.11 (d, J=9.77 Hz, 1 H), 5.29 (d, J=16.79 Hz, 1 H), 5.77–5.83 (m, 1 H), 5.86 (t, J=4.73 Hz, 1 H), 7.12 (dd, J=8.85, 2.44 Hz, 1 H), 7.18 (d, J=2.44 Hz, 1 H), 7.24 (d, J=6.10 Hz, 1 H), 7.88 (d, J=5.80 Hz, 1 H), 8.10 (d, J=9.16 Hz, 1 H); LC-MS (retention time: 1.690 min.), MS m/z 729 (MH$^+$).

Example 103

Preparation of Compound 103

Compound 103

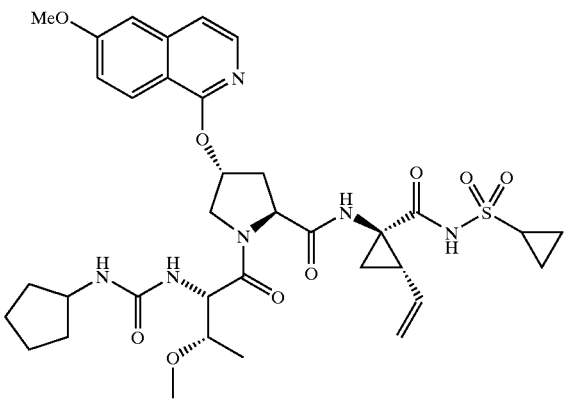

Compound 103 was prepared by the same method as Compound 101 with the following modifications:

Modifications: cyclopentylamine was used as a starting material to give Compound 103 (56.4 mg, 67% yield): $^1$H NMR(CD$_3$OD, 500 MHz) δ 1.01–1.08 (m, 2 H), 1.07 (d, J=6.10 Hz, 1 H), 1.16 (d, J=6.10 Hz, 3 H), 1.21–1.25 (m, 3 H), 1.30–1.33 (m, 1 H), 1.44 (dd, J=9.77, 5.19 Hz, 1 H), 1.51–1.56 (m, 2 H), 1.60–1.65 (m, 2 H), 1.71–1.75 (m, 1 H), 1.80–1.84 (m, 1 H), 1.86 (dd, J=8.09; 5.34 Hz, 1 H), 2.20–2.25 (m, 1 H), 2.37–2.41 (m, 1 H), 2.61 (dd, J=14.04, 7.32 Hz, 1 H), 2.93–2.98 (m, 1H), 3.60–3.65 (m, 1 H), 3.75–3.80 (m, 1 H), 3.92 (s, 3 H), 4.17 (dd, J=12.05, 3.81 Hz, 1H), 4.37 (d, J=11.90 Hz, 1 H), 4.55–4.59 (m, 2 H), 5.10 (d, J=11.60 Hz, 1 H), 5.29 (d, J=16.48 Hz, 1 H), 5.78–5.83 (m, 1 H), 5.85 (d, J=2.44 Hz, 1 H), 7.13 (dd, J=9.16, 2.44 Hz, 1 H), 7.18 (d, J=2.44 Hz, 1 H), 7.24 (d, J=5.80 Hz, 1 H), 7.88 (d, J=5.80 Hz, 1 H), 8.09 (d, J=9.16 Hz, 1 H); LC-MS (retention time: 1.607 min.), MS m/z 727 (MH$^+$)

Example 104

Preparation of Compound 104 wave to 80° C. for 15 min. Then was added a slurry solution of sodium cyclopentoxide which was prepared by treating a 0° C. solution of cyclopentanol (110 mg, 1.28 mmol) in THF (1 mL) with NaH (60% in oil, 46.4 mg, 1.16 mmol) for 15 min at rt. After stirring at rt 15 min, thee reaction was quenched with saturated aqueous ammonium chloride (1 mL) and extracted with EtOAc (5 mL). The organic layer was then passed through a celite hydromatrix column, concentrated and purified by reversed phase prep-HPLC to give Compound 104 (38.2 mg, 45%): $^1$H NMR(CD$_3$OD, 500 MHz) δ 1.03–1.09 (m, 3 H), 1.16 (d, J=6.10 Hz, 3 H), 1.201.25 (m, 1 H), 1.25–1.30 (m, J=10.22, 5.34 Hz, 1 H), 1.40–1.45 (m, J=10.83, 3.81 Hz, 1 H), 1.46 (dd, J=9.61, 5.34 Hz, 1 H), 1.58–1.63 (m, 3 H), 1.70–1.75 (m, 2 H), 1.86 (dd, J=7.63, 5.49 Hz, 1 H), 2.22–2.26 (m, 1 H), 2.34–2.39 (m, 1 H), 2.59–2.64 (m, 1 H), 2.94–2.98 (m, 1 H), 3.67 (dd, J=7.78, 6.56 Hz, 1 H), 3.92 (s, 3 H), 4.13 (dd, J=10.83, 4.12 Hz, 1H), 4.37–4.42 (m, 1 H), 4.56 (dd, J=10.07, 7.32 Hz, 1 H), 4.71–4.76 (m, 1 H), 5.12 (d, J=10.68 Hz, 1 H), 5.31 (d,

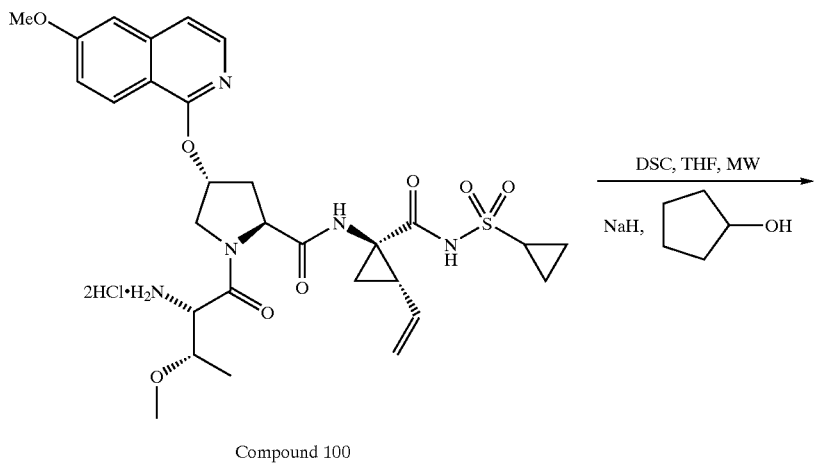

Compound 100

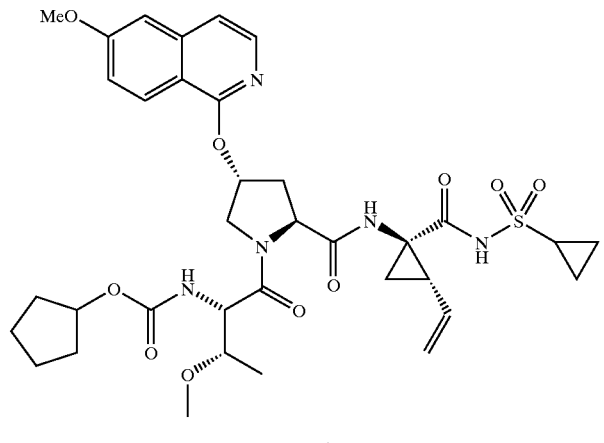

Compound 104

To a solution mixture of Compound 100 (80 mg, 0.116 mmol) and DIEA (31.5 mg, 0.244 mmol) in THF (2 mL) was added N,N'-dissucinimidyl carbonate (44.6 mg, 0.174 mmol). The resulting suspension was irradiated in a micro- J=16.79 Hz, 1 H), 5.80 (m, 1 H), 5.85 (s, 1 H), 7.13 (d, J=10.68 Hz, 1 H), 7.19 (d, J=1.83 Hz, 1 H), 7.25 (d, J=6.10 Hz, 1 H), 7.89 (d, J=5.80 Hz, 1 H), 8.09 (d, J=9.16 Hz, 1 H); LC-MS (retention time: 1.697 min.), MS m/z 728 (MH$^+$).

Example 105

Preparation of Compound 105

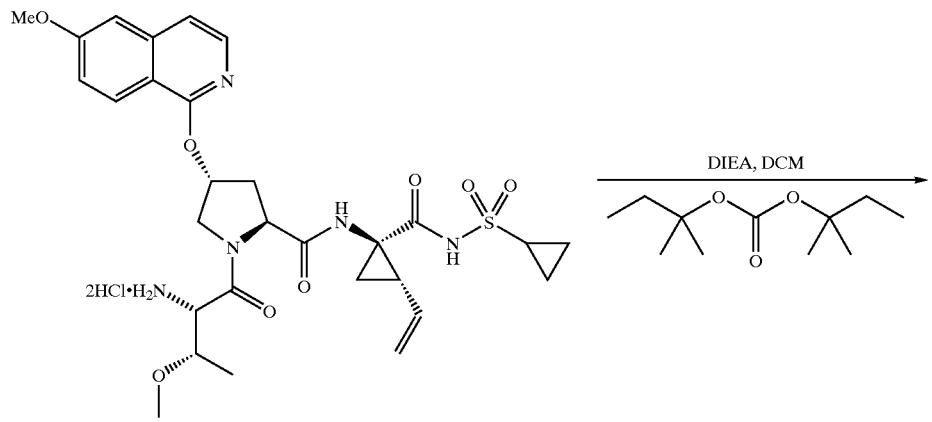

Compound 100

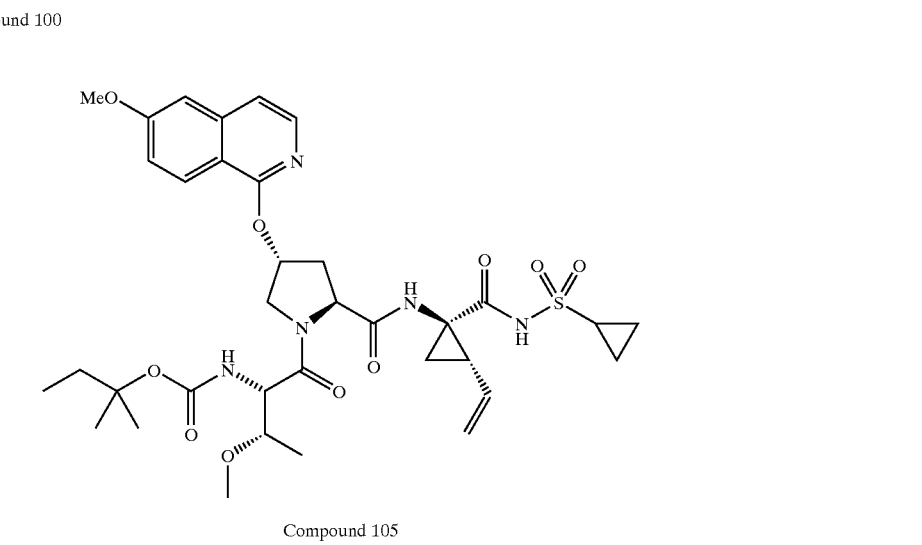

Compound 105

To a solution mixture of Compound 100 (80.0 mg, 0.116 mmol) and DIEA (31.5 mg, 0.244 mmol) in DCM (2 mL) was added di-tert-amyl dicarbonate (57.1 mg, 0.232 mmol). After stirring at rt for 14 h, solvent was removed and product was purified by reversed phase prep-HPLC to give Compound 105 (62.5 mg, 74% yield): $^1$H NMR(CD$_3$OD, 500 MHz) δ 0.79 (t, J=7.48 Hz, 3 H), 1.04–1.08 (m, 3 H), 1.17 (d, J=6.10 Hz, 3 H), 1.19–1.23 (s, 3 H), 1.24 (s, 3 H), 1.39–1.43 (m, 1 H), 1.46 (dd, J=9.61, 5.34 Hz, 1 H), 1.60–1.65 (m, 2 H), 1.86 (dd, J=7.93, 5.49 Hz, 1 H), 2.22 (q, J=8.85 Hz, 1 H), 2.35–2.40 (m, 1 H), 2.61 (dd, J=14.04, 7.15 Hz, 1 H), 2.94–3.00 (m, 1 H), 3.64–4.00 (m, 1 H), 3.92 (s, 4 H), 4.14 (dd, J=11.90, 3.05 Hz, 1 H), 4.35 (d, J=7.93 Hz, 1 H), 4.40 (d, J=11.90 Hz, 1 H), 4.55 (dd, J=9.31, 7.78 Hz, 1 H), 5.11 (d, J=10.68 Hz, 1 H), 5.30 (d, J=16.79 Hz, 1 H), 5.79–5.83 (m, 1 H), 5.85 (s, 1 H), 7.12 (d, J=9.16 Hz, 1 H), 7.18 (s, 1 H), 7.25 (d, J=5.80 Hz, 1 H), 7.86–7.90 (m, 1 H), 8.09 (d, J=9.16 Hz, 1 H); LC-MS (retention time: 1.740 min.), MS m/z 730 (MH$^+$).

Example 106

Preparation of Compound 106

Compound 106

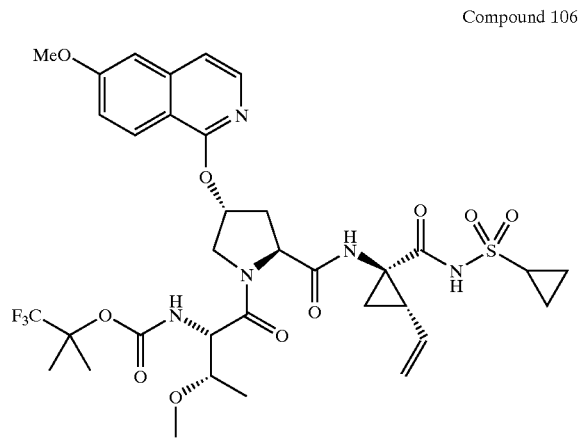

Compound 106 was prepared by the same method as Compound 105 with the following modifications:

Modifications: Carbonic acid pyridin-2-yl ester 2,2,2-trifluoro-1,1-dimethyl-ethyl ester was used as a starting material to give Compound 106 (58.1 mg, 65% yield): $^1$H NMR(CD$_3$OD, 500 MHz) δ 1.04–1.08 (m, 3 H), 1.17 (d, J=6.10 Hz, 3 H), 1.19.1.23 (m, 1 H), 1.23–1.27 (m, 1 H), 1.28 (s, 3 H), 1.46 (dd, J=9.46, 5.19 Hz, 2 H), 1.49 (s, 2 H), 1.86 (dd, J=8.09, 5.34 Hz, 1 H), 2.21 (q, J=8.85 Hz, 1 H), 2.36–2.40 (m, 1 H), 2.62 (dd, J=13.74, 7.32 Hz, 1 H), 2.93–2.98 (m, 1 H), 3.65–3.70 (m, 1 H), 3.92 (s, 3 H), 4.12 (dd, J=11.90, 3.66 Hz, 1 H), 4.31 (d, J=8.24 Hz, 1 H), 4.42 (d, J=11.90 Hz, 1 H), 4.57 (dd, J=10.07, 7.32 Hz, 1 H), 5.11 (d, J=10.38 Hz, 1 H), 5.30 (d, J=16.79 Hz, 1 H), 5.78–5.83 (m, 1 H), 5.84 (s, 1 H), 7.12 (dd, J=9.00, 2.29 Hz, 1 H), 7.19 (d, J=2.14 Hz, 1 H), 7.25 (d, J=5.80 Hz, 1 H), 7.89 (d, J=6.10 Hz, 1 H), 8.09 (d, J=8.85 Hz, 1 H); LC-MS (retention time: 1.770 min.), MS m/z 770 (MH$^+$).

Example 107

Preparation of Compound 107

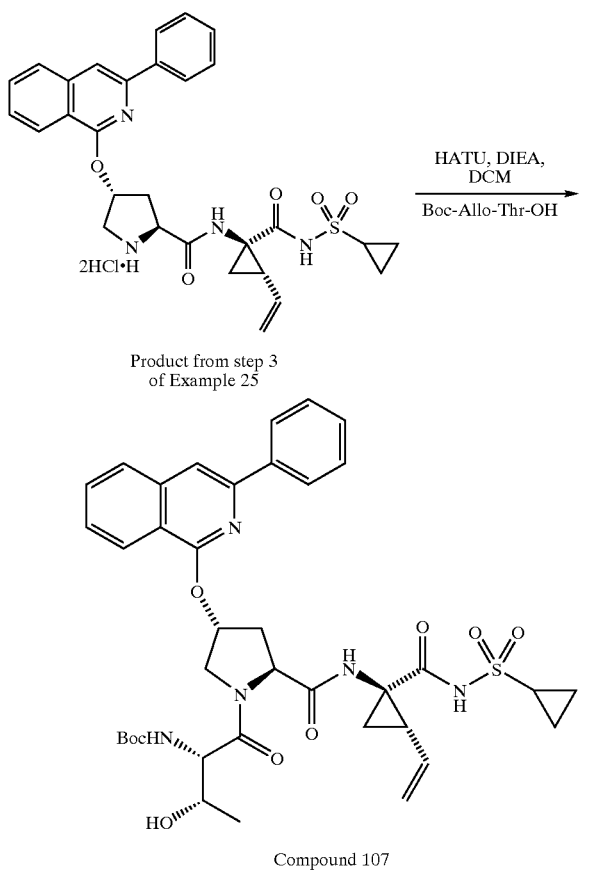

Product from step 3 of Example 25

Compound 107

To a solution of the product from step 3 of Example 25 (100.0 mg, 0.116 mmol), DIEA (62.5 mg, 0.483 mmol) and HATU (92.0 mg, 0.242 mmol) was added Boc-allo-Thr-OH (43.5 mg, 0.177 mmol). After stirring at rt for 3 hr, the reaction mixture was washed with 5% aqueous NaHCO$_3$ (1 mL). The aqueous layer was extracted with 2×2 mL DCM. The combined organic layer was washed with 5% aqueous citric acid (1 mL), brine, dried over MgO$_4$, concentrated and purified by reversed phase prep-HPLC to give Compound 107 (62.5 mg, 52% yield): $^1$HNMR(CD$_3$OD, 500 MHz) δ 0.8–1.02 (m, 1 H), 1.04–1.08 (m, 2 H), 1.23–1.27 (m, 12 H), 1.42 (dd, J=9.46, 5.19 Hz, 1 H), 1.86 (t, J=6.26 Hz, 1 H), 2.23–2.27 (m, 1 H), 2.46–2.50 (m, 1 H), 2.76 (dd, J=14.04, 6.71 Hz, 1 H), 2.95–2.99 (m, 1 H), 3.94–3.98 (m, 1 H), 4.28 (d, J=7.32 Hz, 2 H), 4.52 (d, J=12.51 Hz, 1 H), 4.63 (t, J=9.00 Hz, 1 H), 5.12 (d, J=10.07 Hz, 1 H), 5.31 (d, J=16.79 Hz, 1 H), 5.77–5.83 (m, 1 H), 6.09 (s, 1 H), 7.36–7–41 (m, 1 H), 7.47 (t, J=7.17 Hz, 3 H), 7.52 (d, J=7.63 Hz, 1 H), 7.70 (t, J=7.17 Hz, 1 H), 7.85 (s, 1 H), 7.88 (d, J=8.24 Hz, 1 H), 8.17 (d, J=7.93 Hz, 2 H), 8.22 (d, J=7.63 Hz, 1 H); LC-MS (retention time: 1.937 min.), MS m/z 748 (MH$^+$).

Example 108

Preparation of Compound 108

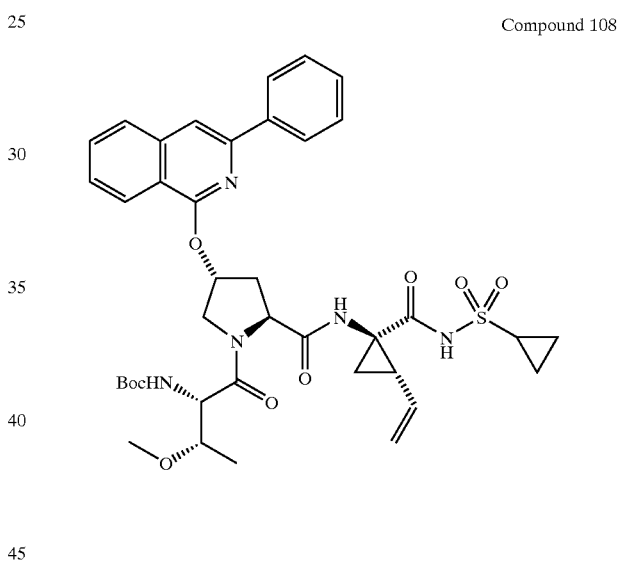

Compound 108

Compound 108 was prepared by the same method as Compound 107 with the following modifications:

Modifications: Boc-(2S, 3S)-Amino-3-methoxybutanoic acid was used as a starting material to give Compound 108 (75.1 mg, 51% yield): $^1$H NMR(CD$_3$OD, 500 MHz) δ 0.80–1.02 (m, 4 H), 1.18 (d, J=6.10 Hz, 3 H), 1.28 (s, 9 H), 1.44 (dd, J=9.77, 1.30 Hz, 1 H), 1.45–1.50 (m, 1 H), 1.85–1.90 (m, 1 H), 2.14–2.18 (m, 1 H), 2.55–2.59 (m, 1 H), 2.72–2.76 (m, 1 H), 2.91–2.95 (m, 1 H), 3.34 (s, 3 H), 3.65–3.69 (m, 1 H), 4.32 (d, J=10.68 Hz, 1 H), 4.40 (d, J=7.93 Hz, 1 H), 4.46 (d, J=13.12 Hz, 1 H); 4.60 (t, J=8.24 Hz, 1 H), 5.07 (d, J=9.46 Hz, 1 H), 5.26 (d, J=17.40 Hz, 1 H), 5.82–5.86 (m, 1 H), 6.08 (s, 1 H), 7.38 (dd, J=7.32, 6.10 Hz, 1 H), 7.47 (t, J=7.02 Hz, 3 H), 7.51 (d, J=5.80 Hz, 1 H), 7.69 (t, J=6.56 Hz, 1 H), 7.69 (t, J=6.56 Hz, 1 H), 7.85 (s, 1 H), 7.88 (d, J=7.63 Hz, 1 H), 8.18 (d, J=8.24 Hz, 3 H), 8.21 (d, J=9.16 Hz, 1 H); LC-MS (retention time: 1.973 min.), MS m/z 762 (MH$^+$).

Example 109

Preparation of Compound 109

Compound 109

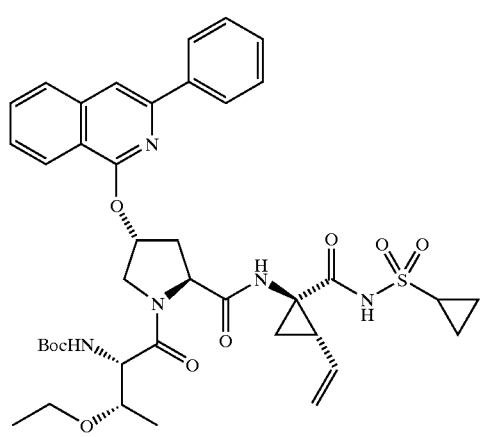

Compound 109 was prepared by the same method as Compound 107 with the following modifications:

Modifications: Boc-(2S, 3S)-Amino-3-ethoxybutanoic acid was used as a starting material to give Compound 109 (57.2 mg, 47% yield): $^1$H NMR(CD$_3$OD, 500 MHz) δ 1.02–1.08 (m, 4 H), 1.17 (d, J=6.10 Hz, 6 H), 1.19 (s, 1 H), 1.19–1.24 (m, 1 H), 1.23–1.27 (m, J=3.97 Hz, 1 H), 1.30 (S, 9 H), 1.44 (dd, J=9.77, 5.50 Hz, 1 H), 1.46 (s, 1 H), 1.88 (dd, J=7.78, 5.95 Hz, 1 H), 2.20–1.25 (m, 1 H), 2.49–2.54 (me, 1 H), 2.69–2.73 (m, 1 H), 2.93–2.97 (m, 1 H), 3.53–3.57 (m, 2 H), 3.75–3.80 (m, 1 H), 4.34 (dd, J=11.75, 3.20 Hz, 1 H), 4.42 (t, J=8.30 Hz, 2 H), 4.57 (t, J=8.09 Hz, 1 H), 5.11 (d, J=10.38 Hz, 1 H), 5.29 (d, J=17.40 Hz, 1 H), 5.78–5.83 (m, 1 H), 6.09 (s, 1 H), 7.38 (t, J=7.32 Hz, 1 H), 7.47 (t, J=7.63 Hz, 2 H), 7.52 (d, J=7.02 Hz, 1 H), 7.70 (t, J=7.93 Hz, 1 H), 7.86 (s, 1 H), 7.88 (d, J=7.93 Hz, 1 H), 8.18 (d, J=7.32 Hz, 2 H), 8.22 (d, J=8.24 Hz, 1 H); LC-MS (retention time: 2.030 min.), MS m/z 776 (MH$^+$).

Example 110

Preparation of Compound 110

Compound 110

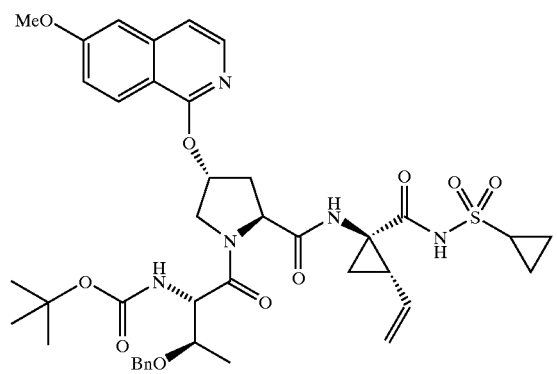

Compound 110 was prepared by the same method as Compound 89 with the following modifications:

Modifications: Boc-L-Thr(Bn)-OH was used as a starting material to give Compound 110 (49.8 mg, 48% yield)); LC-MS (retention time: 1.857 min.), MS m/z 792 (MH$^+$).

Section D:

Example 120

Preparation of Compound 120

Compound 120

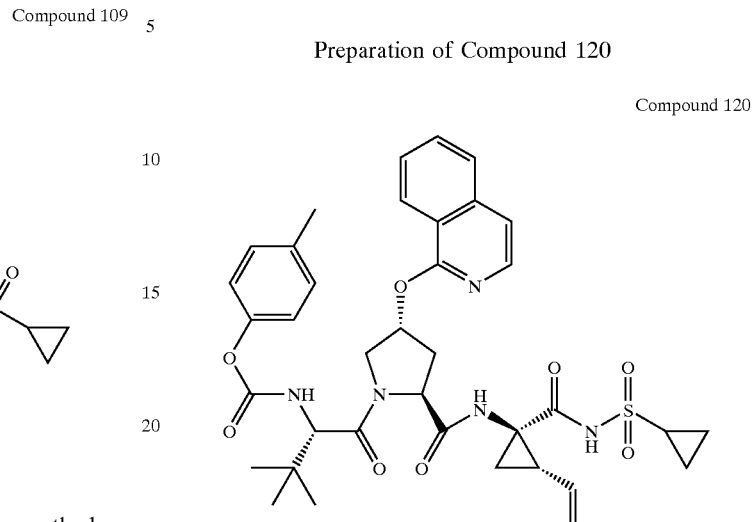

Scheme 1

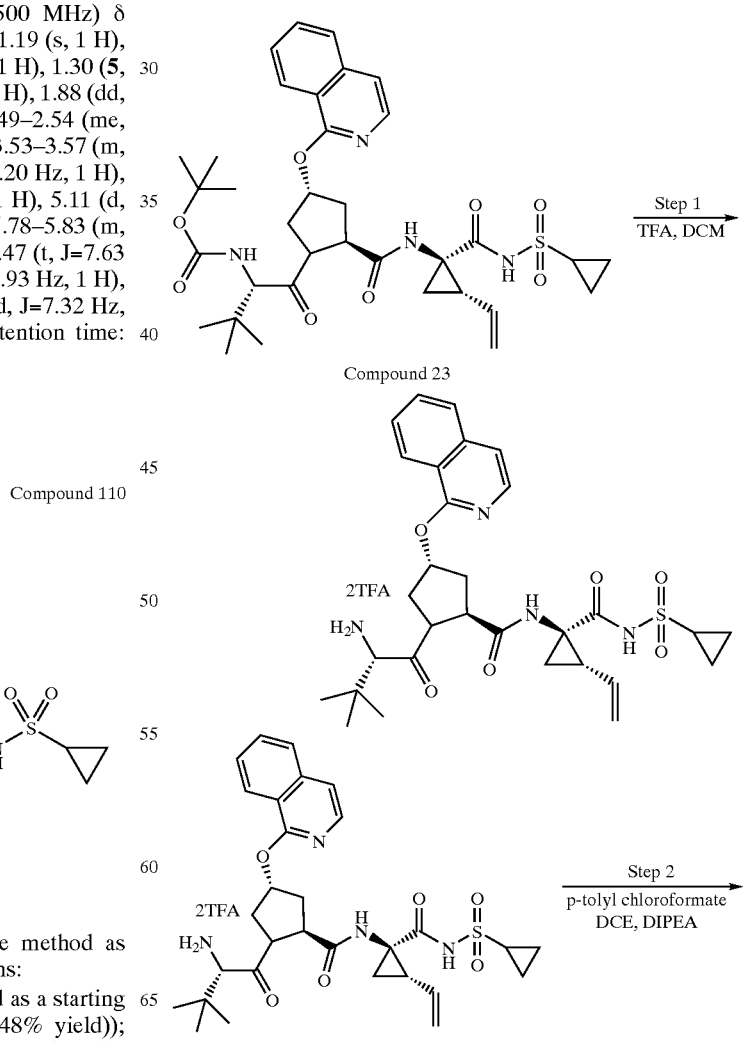

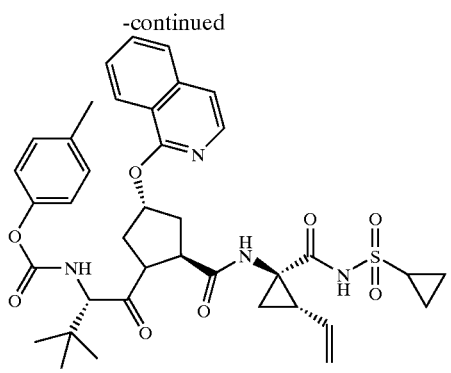

Compound 120

Step 1:
A solution of Compound 23 (see Example 23) (1.50 g, 2.19 mmol) in DCM (50 mL) and trifluoroacetic acid (50 mL) was stirred for 3 h at rt. The mixture was concentrated in vacuo to a viscous residue, and was then dissolved in 1,2-dichloroethane and again concentrated in vacuo to give the desired bis-trifluoroacetic acid salt product as an off-white glassy solid (quantitative). The material was used directly in the next step without purification.

Step 2:
To a solution of the product from Example 120, Step 1 (118 mg, 0.146 mmol) in 1,2-dichloroethane (3 mL) was added p-tolyl chloroformate (32.4 mg, 0.190 mmol) and N,N-diisopropylethylamine (94.5 mg, 0.731 mmol). The mixture was agitated at rt for 72 h. The reaction mixture was washed with pH=4 buffer solution (3×3 mL), and the washes were back-extracted with 1,2-dichloroethane (3 mL). The organic phases were combined and concentrated in vacuo. The crude product was then dissolved in MeOH and purified by reverse phase preparative HPLC to give the title compound (Compound 120) as a yellow glassy solid (64.2 mg, 61.1% yield): $^1$H NMR (CD$_3$OD) δ 1.06–1.10 (m, 3 H), 1.12 (s, 9 H), 1.24–1.28 (m, 2 H), 1.44 (dd, J=9.31, 5.34 Hz, 1 H), 1.89 (dd, J=7.93, 5.49 Hz, 1 H), 2.21–2.28 (m, 2 H), 2.31 (s, 3 H), 2.62–2.66 (m, 1 H), 2.93–2.99 (m, 1 H), 4.12 (dd, J=11.90, 3.66 Hz, 1 H), 4.42 (d, J=11.60 Hz, 1 H), 4.57 (dd, J=10.22, 7.17 Hz, 1 H), 5.13 (d, J=10.38 Hz, 1 H), 5.30 (d, J=17.09 Hz, 1 H), 5.76 (ddd, J=17.09, 9.77, 9.46 Hz, 1 H), 5.87 (s, 1 H), 6.79 (d, J=8.24 Hz, 2 H), 7.07 (d, J=8.24 Hz, 2 H), 7.30 (d, J=6.10 Hz, 1 H), 7.40 (t, J=7.63 Hz, 1 H), 7.68 (t, J=7.63 Hz, 1 H), 7.79 (d, J=8.24 Hz, 1 H), 7.93 (d, J=5.80 Hz, 1 H), 8.17 (d, J=8.24 Hz, 1 H); MS m/z 718 (MH$^+$).

Example 121

Preparation of Compound 121

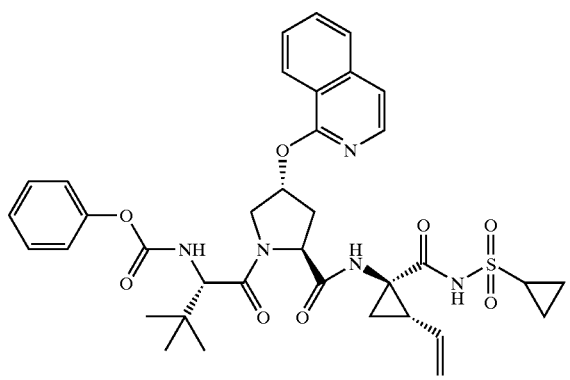

Compound 121

Compound 121 was prepared by following Scheme 1 of Example 120 except that phenyl chloroformate was used in place of p-tolyl chloroformate in step 2.

Step 2:
Modifications: 30 mg (0.19 mmol) phenyl chloroformate used, 89.0 mg product obtained as a yellow glassy solid (50% yield): MS m/z 704 (MH$^+$).

Example 122

Preparation of Compound 122

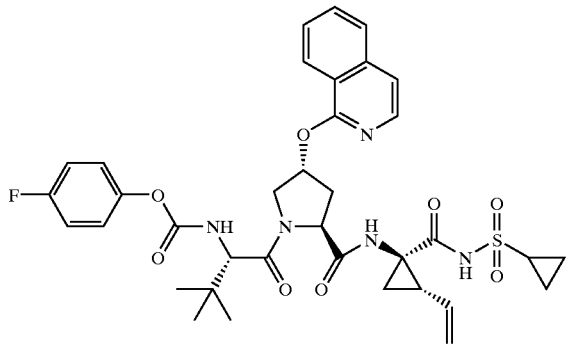

Compound 122

Compound 122 was prepared by following Scheme 1 of Example 120 except that 4-fluorophenyl chloroformate was used in place of p-tolyl chloroformate in step 2.

Step 2:
Modifications: 33 mg (0.19 mmol) 4-fluorophenyl chloroformate used, 83.1 mg product obtained as a sticky yellow oil (78.8% yield): MS m/z 722 (MH$^+$).

Example 123

Preparation of Compound 123

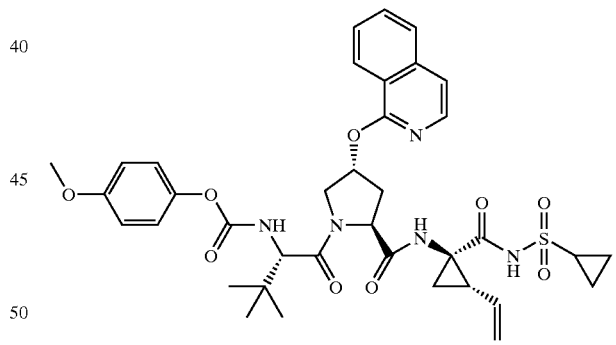

Compound 123

Compound 123 was prepared by following Scheme 1 of Example 120 except that 4-methoxyphenyl chloroformate was used in place of p-tolyl chloroformate in step 2.

Step 2:
Modifications: 35 mg (0.19 mmol) 4-methoxyphenyl chloroformate used, 70.2 mg product obtained as a yellow glassy solid (65.4% yield): $^1$H NMR (CD$_3$OD) δ 1.06–1.10 (m, 3 H), 1.11 (s, 9 H), 1.24–1.28 (m, 2 H), 1.44 (dd, J=9.46, 5.49 Hz, 1 H), 1.89 (dd, J=7.93, 5.49 Hz, 1 H), 2.24 (q, J=8.85 Hz, 1 H), 2.31 (ddd, J=13.81, 10.30, 3.97 Hz, 1 H), 2.62–2.66 (m, 1 H), 2.94–2.98 (m, 1 H), 3.77 (s, 3 H), 4.12 (dd, J=11.60, 3.66 Hz, 1 H), 4.42 (d, J=11.60 Hz, 1 H), 4.57 (dd, J=10.07, 7.32 Hz, 1 H), 5.13 (d, J=10.68 Hz, 1 H), 5.30 (d, J=16.79 Hz, 1 H), 5.72–5.80 (m, 1 H), 5.87 (s, 1 H), 6.80 (d, J=2.44 Hz, 4 H), 7.30 (d, J=5.80 Hz, 1 H), 7.42 (t, J=7.48

Hz, 1 H), 7.69 (t, J=7.63 Hz, 1 H), 7.80 (d, J=7.93 Hz, 1 H), 7.93 (d, J=5.80 Hz, 1 H), 8.18 (d, J=8.24 Hz, 1 H); MS m/z 734 (MH$^+$).

Example 124

Preparation of Compound 124

Compound 124

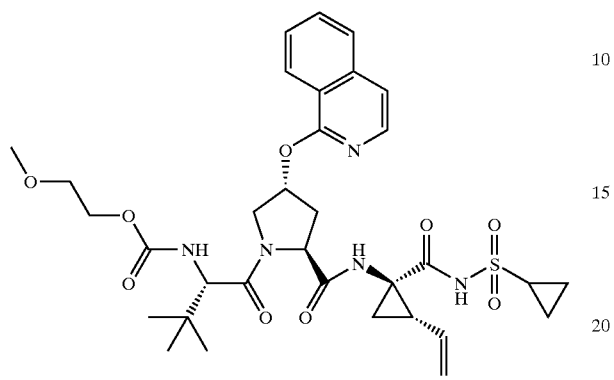

Compound 124 was prepared by following Scheme 1 of Example 120 except that chloroformic acid 2-methoxyethyl ester was used in place of p-tolyl chloroformate in Step 2.

Step 2:

Modifications: 26 mg (0.19 mmol) chloroformic acid 2-methoxyethyl ester used, 87.4 mg product obtained as a sticky yellow oil (87.2% yield): $^1$H NMR (CD$_3$OD) δ 0.96–1.02 (m, 3 H), 1.05 (s, 9 H), 1.16–1.18 (m, 2 H), 1.40 (dd, J=9.46, 5.19 Hz, 1 H), 1.85 (dd, J=7.93, 5.19 Hz, 1 H), 2.15 (q, J=8.75 Hz, 1 H), 2.40 (ddd, J=13.89, 10.07, 4.12 Hz, 1 H), 2.65 (dd, J=13.58, 7.17 Hz, 1 H), 2.90 (ddd, J=12.89, 8.16, 4.88 Hz, 1 H), 3.27 (s, 3 H), 3.36–3.44 (m, 2 H), 3.81–3.84 (m, 1 H), 3.92–3.96 (m, 1 H), 4.12 (dd, J=11.60, 3.36 Hz, 1 H), 4.44 (d, J=11.60 Hz, 1 H), 4.57 (dd, J=9.46, 7.93 Hz, 1 H), 5.07 (d, J=10.38 Hz, 1 H), 5.25 (d, J=17.09 Hz, 1 H), 5.80 (ddd, J=17.32, 9.77, 9.54 Hz, 1 H), 5.87 (s, 1 H), 7.32 (d, J=5.80 Hz, 1 H), 7.55 (t, J=7.32 Hz, 1 H), 7.70 (t, J=7.48 Hz, 1 H), 7.80 (d, J=7.93 Hz, 1 H), 7.96 (d, J=5.80 Hz, 1 H), 8.19 (d, J=8.24 Hz, 1 H); MS m/z 686 (MH$^+$).

Example 125

Preparation of Compound 125

Compound 125

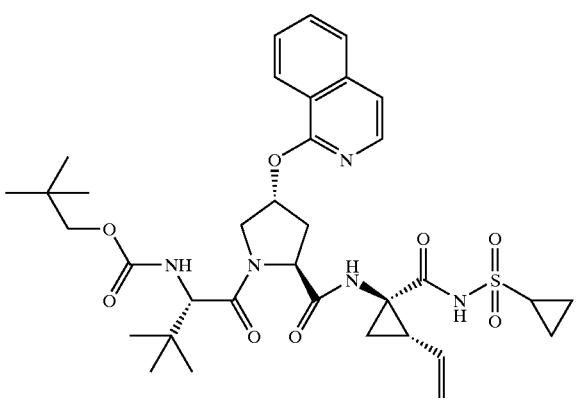

Compound 125 was prepared by following Scheme 1 of Example 120 except that neopentyl chloroformate was used in place of p-tolyl chloroformate in step 2.

Step 2:

Modifications: 29 mg (0.19 mmol) neopentyl chloroformate used, 57.4 mg product obtained as a yellow glassy solid (56.2% yield): $^1$H NMR (CD$_3$OD) δ 0.83 (s, 9 H), 1.05 (d, J=2.44 Hz, 9 H), 1.07–1.09 (m, 2 H), 1.23–1.27 (m, 2 H), 1.43–1.46 (m, 1 H), 1.87–1.90 (m, 1 H), 2.21–2.25 (m, 1 H), 2.29–2.33 (m, 1 H), 2.61–2.65 (m, 1 H), 2.92–2.96 (m, 1 H), 3.42 (d, J=10.07 Hz, 1 H), 3.56 (d, J=10.07 Hz, 1 H), 4.09–4.11 (m, 1 H), 4.33 (d, J=9.16 Hz, 1 H), 4.43 (d, J=11.29 Hz, 1 H), 4.54–4.57 (m, 1 H), 5.12 (d, J=10.07 Hz, 1 H), 5.30 (d, J=17.40 Hz, 1 H), 5.73–5.80 (m, 1 H), 5.88 (s, 1 H), 7.33 (d, J=5.49 Hz, 1 H), 7.53 (m, 1 H), 7.71 (t, J=6.87 Hz, 1 H), 7.81 (d, J=7.93 Hz, 1 H), 7.97 (d, J=5.80 Hz, 1 H), 8.19 (d, J=7.63 Hz, 1 H); MS m/z 698 (MH$^+$).

Example 126

Preparation of Compound 126

Compound 126

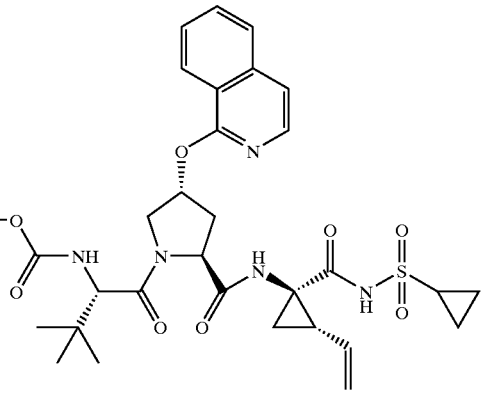

Compound 126 was prepared by following Scheme 1 of Example 120 except that 2-fluoroethyl chloroformate was used in place of p-tolyl chloroformate in step 2.

Step 2:

Modifications: 24 mg (0.19 mmol) 2-fluoroethyl chloroformate used, 58.9 mg product obtained as a yellow glassy solid (59.8% yield): $^1$H NMR (CD$_3$OD) δ 1.05 (d, J=2.14 Hz, 9 H), 1.07–1.09 (m, 2 H), 1.22–1.27 (m, 2 H), 1.42–1.45 (m, 1 H), 1.87–1.90 (m, 1 H), 2.24 (q, J=8.75 Hz, 1 H), 2.28–2.33 (m, 1 H), 2.63 (dd, J=13.43, 6.41 Hz, 1 H), 2.92–2.96 (m, 1 H), 3.92–4.10 (m, 3 H), 4.31–4.37 (m, 2 H), 4.42–4.46 (m, 2 H), 4.54–4.57 (m, 1 H), 5.12 (d, J=10.38 Hz, 1 H), 5.29 (d, J=17.09 Hz, 1 H), 5.71–5.79 (m, 1 H), 5.88 (s, 1 H), 7.33 (d, J=5.80 Hz, 1 H), 7.55 (t, J=7.17 Hz, 1 H), 7.71 (m, 1 H), 7.81 (d, J=7.93 Hz, 1 H), 7.96 (d, J=5.80 Hz, 1 H), 8.19 (d, J=7.63 Hz, 1 H); MS m/z 674 (MH$^+$).

Example 127

Preparation of Compound 127

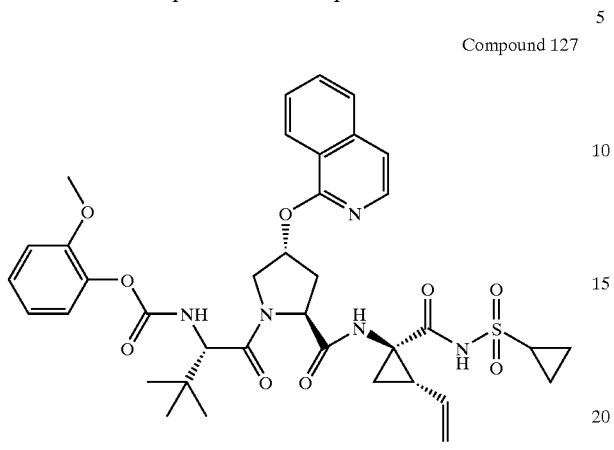

Compound 127

Compound 127 was prepared by following Scheme 1 of Example 120 except that 2-methoxyphenyl chloroformate was used in place of p-tolyl chloroformate in step 2.

Step 2:

Modifications: 35 mg (0.19 mmol) 2-methoxyphenyl chloroformate used, 97.6 mg product obtained as a sticky yellow oil (91.0% yield): MS m/z 734 (MH$^+$).

Example 128

Preparation of Compound 128

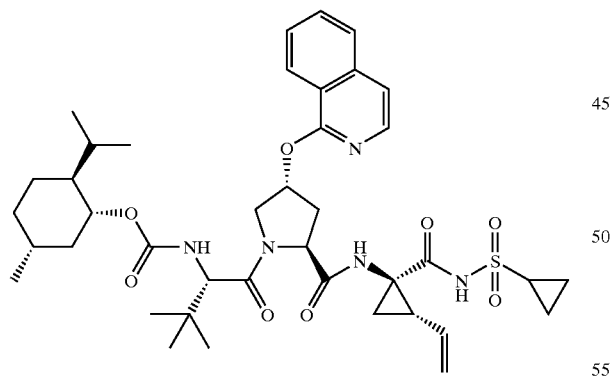

Compound 128

Compound 128 was prepared by following Scheme 1 of Example 120 except that 2-(−)-(1R)-menthyl chloroformate was used in place of p-tolyl chloroformate in step 2.

Step 2:

Modifications: 42 mg (0.19 mmol) (−)-(1R)-menthyl chloroformate used, 69.1 mg product obtained as a white glassy solid (61.7% yield): MS m/z 766 (MH$^+$).

Example 129

Preparation of Compound 129

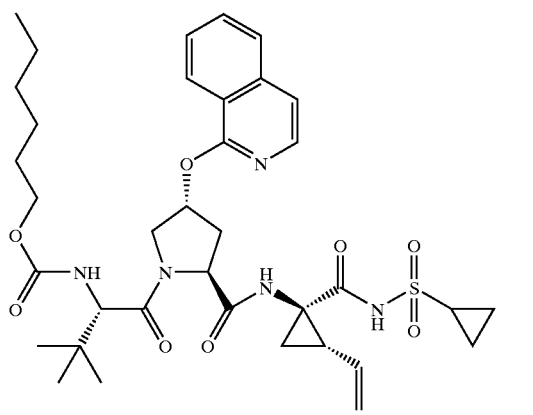

Compound 129

Compound 129 was prepared by following Scheme 1 of Example 120 except that hexyl chloroformate was used in place of p-tolyl chloroformate in step 2.

Step 2:

Modifications: 31 mg (0.19 mmol) hexyl chloroformate used, 66.7 mg product obtained as a yellow glassy solid (64.1% yield): $^1$H NMR (CD$_3$OD) δ 0.87–0.99 (m, 5 H), 1.05 (s, 9 H), 1.07–1.09 (m, 2 H), 1.22–1.28 (m, 6 H), 1.43–1.48 (m, 3 H), 1.88 (dd, J=8.24, 5.49 Hz, 1 H), 2.24 (q, J=8.85 Hz, 1 H), 2.28–2.33 (m, 1 H), 2.63 (dd, J=14.34, 7.63 Hz, 1 H), 2.92–2.97 (m, 1 H), 3.72 (dt, J=10.61, 6.60 Hz, 1 H), 3.81–3.86 (m, 1 H), 4.10 (dd, J=11.60, 3.36 Hz, 1 H), 4.32 (d, J=8.85 Hz, 1 H), 4.43 (d, J=11.90 Hz, 1 H), 4.55 (dd, J=9.77, 7.32 Hz, 1 H), 5.13 (d, J=10.38 Hz, 1 H), 5.30 (d, J=17.09 Hz, 1 H), 5.76 (ddd, J=17.09, 10.07, 9.16 Hz, 1 H), 5.89 (s, 1 H), 7.33 (d, J=5.80 Hz, 1 H), 7.54 (t, J=7.48 Hz, 1 H), 7.69–7.72 (m, 1 H), 7.81 (d, J=8.24 Hz, 1 H), 7.97 (d, J=6.10 Hz, 1 H), 8.20 (d, J=8.24 Hz, 1 H); MS m/z 712 (MH$^+$).

Example 130

Preparation of Compound 130

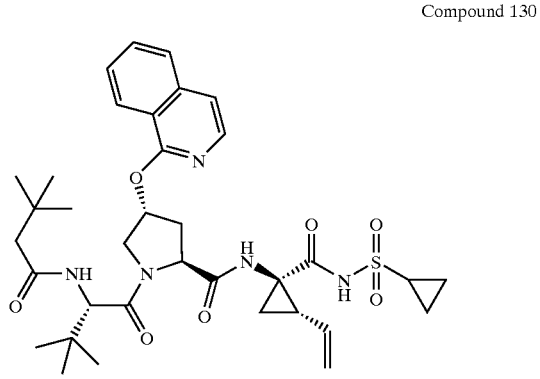

Compound 130

-continued
Scheme 1

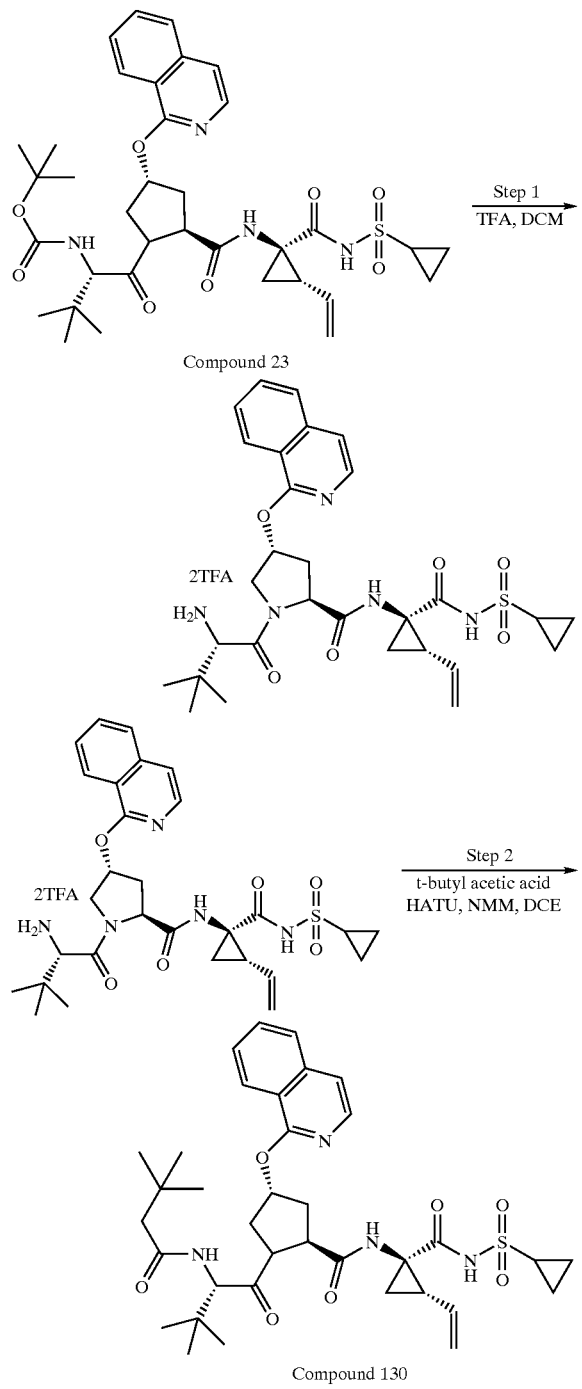

Compound 23

Compound 130

Step 1:
A solution of Compound 23 (see Example 23) (1.50 g, 2.19 mmol) in DCM (50 mL) and trifluoroacetic acid (50 mL) was stirred for 3 h at rt. The mixture was concentrated in vacuo to a viscous residue, and was then dissolved in 1,2-dichloroethane and again concentrated in vacuo to give the desired bis-trifluoroacetic acid salt product as an off-white glassy solid (quantitative). The material was used directly in the next step without purification.

Step 2:
A mixture of the product from step 1 (118 mg, 0.146 mmol), tert-butyl acetic acid (22 mg, 0.19 mmol), HATU (72 mg, 0.19 mmol) and N-methylmorpholine (59 mg, 0.58 mmol) in 1,2-dichloroethane was stirred for 24 h at rt. The reaction mixture was washed with pH=4 buffer solution (3×3 mL), and the washes were back-extracted with 1,2-dichloroethane (3 mL). The organic phases were combined and concentrated in vacuo. The crude product was then dissolved in MeOH and purified by reverse phase preparative HPLC to give the title compound (Compound 130) as a slightly yellow glassy solid (43.4 mg, 43.5% yield): $^1$H NMR (CD$_3$OD) δ 0.82 (d, J=1.83 Hz, 9 H), 1.06 (d, J=2.14 Hz, 9 H), 1.07–1.10 (m, 2 H), 1.22–1.28 (m, 2 H), 1.43–1.46 (m, 1 H), 1.87–1.90 (m, 1 H), 1.99 (d, J=1.83 Hz, 2 H), 2.20–2.26 (m, 1 H), 2.27–2.33 (m, 1 H), 2.59–2.64 (m, 1 H), 2.93–2.97 (m, 1 H), 4.12–4.14 (m, 1 H), 4.42 (d, J=11.60 Hz, 1 H), 4.51–4.55 (m, 1 H), 4.67 (dd, J=9.31, 1.98 Hz, 1 H), 5.11–5.14 (m, 1 H), 5.29 (d, J=17.40 Hz, 1 H), 5.72–5.80 (m, 1 H), 5.89 (d, J=1.83 Hz, 1 H), 7.32 (dd, J=5.80, 2.14 Hz, 1 H), 7.52–7.55 (m, 1 H), 7.69–7.72 (m, 1 H), 7.81 (d, J=8.24 Hz, 1 H), 7.96 (dd, J=5.80, 1.83 Hz, 1 H), 8.17 (d, J=8.24 Hz, 1 H); MS m/z 682 (MH$^+$).

Example 131

Preparation of Compound 131

Compound 131

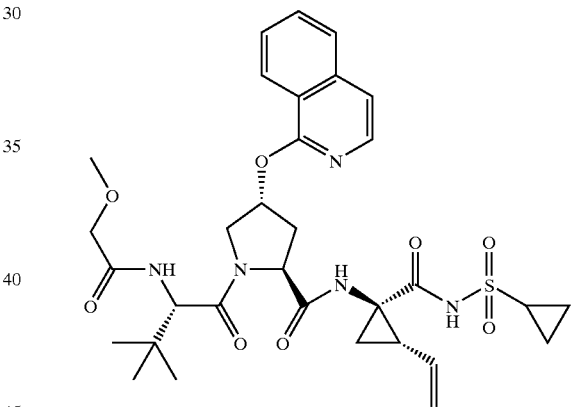

Compound 131 was prepared by following Scheme 1 of Example 130 except that methoxyacetic acid was used in place of tert-butyl acetic acid in step 2.

Step 2:
Modifications: 17 mg (0.19 mmol) methoxyacetic acid used, 49.9 mg product obtained as a slightly yellow glassy solid (52.0% yield): $^1$H NMR (CD$_3$OD) δ 1.05–1.08 (m, 11 H), 1.24–1.26 (m, 2 H), 1.45 (ddd, J=9.31, 5.34, 3.66 Hz, 1 H), 1.88 (ddd, J=8.39, 5.19, 3.81 Hz, 1 H), 2.21–2.27 (m, 1 H), 2.29–2.35 (m, 1 H), 2.60–2.64 (m, 1 H), 2.91–2.97 (m, 1 H), 3.34 (d, J=3.66 Hz, 3 H), 3.69 (dd, J=15.26, 3.66 Hz, 1 H), 3.81–3.85 (m, 1 H), 4.15 (dt, J=11.67, 3.62 Hz, 1 H), 4.35 (d, J=11.90 Hz, 1 H), 4.55 (ddd, J=10.30, 6.94, 3.20 Hz, 1 H), 4.66 (dd, J=9.61, 3.51 Hz, 1 H), 5.11–5.14 (m, 1 H), 5.28–5.32 (m, 1 H), 5.73–5.81 (m, 1 H), 5.90 (d, J=3.36 Hz, 1 H), 7.33 (dd, J=5.65, 3.20 Hz, 1 H), 7.54–7.58 (m, 1 H), 7.69–7.73 (m, 1 H), 7.80–7.82 (m, 1 H), 7.95–7.97 (m, 1 H), 8.15 (dd, J=8.39, 2.59 Hz, 1 H); MS m/z 656 (MH$^+$).

Example 132

Preparation of Compound 132

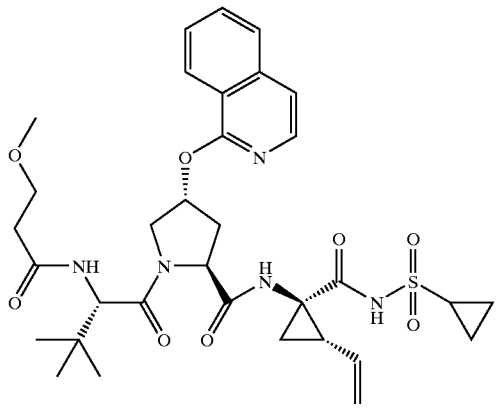

Compound 132

Compound 132 was prepared by following Scheme 1 of Example 130 except that methoxypropionic acid was used in place of tert-butyl acetic acid in step 2.

Step 2:

Modifications: 20 mg (0.19 mmol) methoxypropionic acid used, 50.0 mg product obtained as a yellow glassy solid (51.1% yield), $^1$H NMR (CD$_3$OD) δ 1.06 (d, J=1.83 Hz, 9 H), 1.07–1.09 (m, 2 H), 1.23–1.27 (m, 2 H), 1.44 (ddd, J=9.38, 5.26, 1.83 Hz, 1 H), 1.87–1.90 (m, 1 H), 2.21–2.27 (m, 1 H), 2.29–2.33 (m, 2 H), 2.40–2.46 (m, 1 H), 2.59–2.64 (m, 1 H), 2.92–2.97 (m, 1 H): 3.25 (d, J=1.83 Hz, 3 H), 3.45–3.54 (m, 2 H), 4.12–4.16 (m, 1 H), 4.37 (d, J=11.60 Hz, 1 H), 4.52–4.55 (m, 1 H), 4.65 (dd, J=9.16, 1.83 Hz, 1 H), 5.12 (d, J=10.38 Hz, 1 H), 5.30 (d, J=17.40 Hz, 1 H), 5.72–5.80 (m, 1 H), 5.89 (s, 1 H), 7.33 (dd, J=5.65, 1.98 Hz, 1 H), 7.54–7.58 (m, 1 H), 7.69–7.73 (m, 1 H), 7.81 (d, J=8.24 Hz, 1 H), 7.96 (dd, J=6.10, 1.83 Hz, 1 H), 8.18 (d, J=8.24 Hz, 1 H); MS m/z 670 (MH$^+$).

Example 133

Preparation of Compound 133

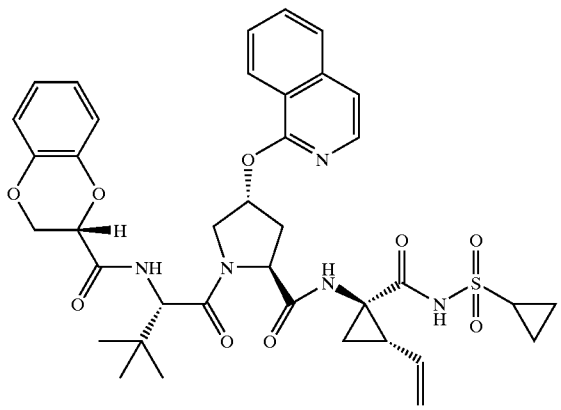

Compound 133

Compound 133 was prepared by following Scheme 1 of Example 130 except that (S)-1,4-benzodioxane-2-carboxylic acid was used in place of tert-butyl acetic acid in Step 2.

Step 2:

Modifications: 35 mg (0.19 mmol) (S)-1,4-benzodioxane-2-carboxylic acid used, 54.0 mg product obtained as a slightly yellow glassy solid (49.5% yield): $^1$H NMR (CD$_3$OD) δ 0.83 (d, J=3.36 Hz, 9 H), 1.05–1.08 (m, 2 H), 1.20–1.25 (m, 1 H), 1.26–1.31 (m, 1 H), 1.45–1.49 (m, 1 H), 1.86–1.90 (m, 1 H), 2.21–2.25 (m, 1 H), 2.28–2.34 (m, 1 H), 2.59–2.65 (m, 1 H), 2.90–2.94 (m, 1 H), 4.12–4.17 (m, 2 H), 4.32 (d, J=11.90 Hz, 1 H), 4.35–4.39 (m, 1 H), 4.55–4.61 (m, 3 H), 5.11–5.14 (m, 1 H), 5.28–5.32 (m, 1 H), 5.75–5.83 (m, 1 H), 5.90 (d, J=3.66 Hz, 1 H), 6.80–6.89 (m, 3 H), 7.03–7.07 (m, 1 H), 7.32–7.34 (m, 1 H), 7.55–7.58 (m, 1 H), 7.68–7.72 (m, 1 H), 7.80–7.82 (m, 1 H), 7.96–7.98 (m, 1 H), 8.15–8.18 (m, 1 H); MS m/z 746 (MH$^+$).

Example 134

Preparation of Compound 134

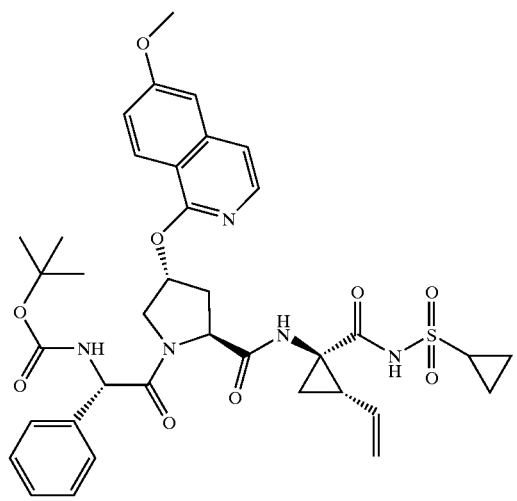

Compound 134

Scheme 1

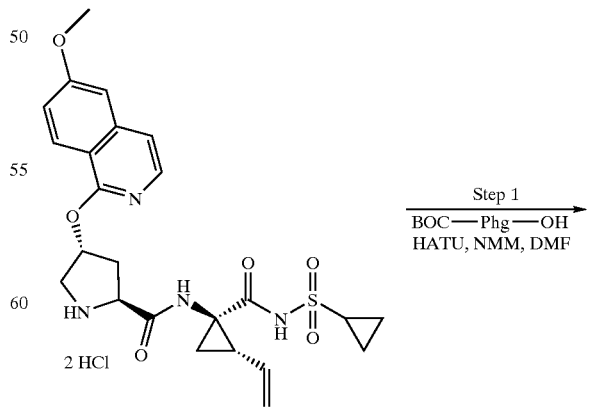

Product of Example 11, Step 5

Step 1
BOC—Phg—OH
HATU, NMM, DMF

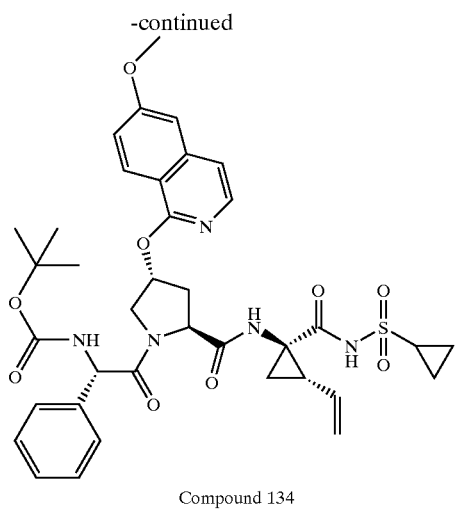

Compound 134

Step 1:

A mixture of the product from Example 11, Step 5 (100 mg, 0.172 mmol), N-α-tert-butoxycarbonyl-L-phenylglycine (45.3 mg, 0.180 mmol), HATU (84.9 mg, 0.223 mmol), and N-methylmorpholine (87.0 mg, 0.859 mmol) in DMF (1.0 mL) was stirred at rt for 18 h. The mixture was purified directly by reverse phase preparative HPLC to give 29.7 mg (23.6% yield) of Compound 134 as a white powder: $^1$H NMR (CD$_3$OD) δ 0.97–1.07 (m, 2 H), 1.12–1.17 (m, 1 H), 1.22–1.32 (m, 2 H), 1.38 (s, 9 H), 1.90 (dd, J=8.09, 5.34 Hz, 1 H), 2.20–2.28 (m, 2 H), 2.54 (dd, J=13.58, 6.56 Hz, 1 H), 2.85–2.89 (m, J=8.24 Hz, 1 H), 3.50 (d, J=10.99 Hz, 1 H), 3.93 (s, 3 H), 4.11 (d, J=11.60 Hz, 1 H), 4.63 (dd, J=9.46, 7.32 Hz, 1 H), 5.13 (dd, J=10.38, 1.53 Hz, 1 H), 5.32 (d, J=17.09 Hz, 1 H), 5.47 (s, 1 H), 5.74–5.84 (m, 2 H), 7.16–7.19 (m, 1 H), 7.25 (d, J=5.80 Hz, 1 H), 7.32–7.43 (m, 6 H), 7.86 (d, J=5.80 Hz, 1 H), 8.13 (d, J=9.16 Hz, 1 H); MS m/z 734 (MH$^+$).

Example 135

Preparation of Compound 135

Compound 135

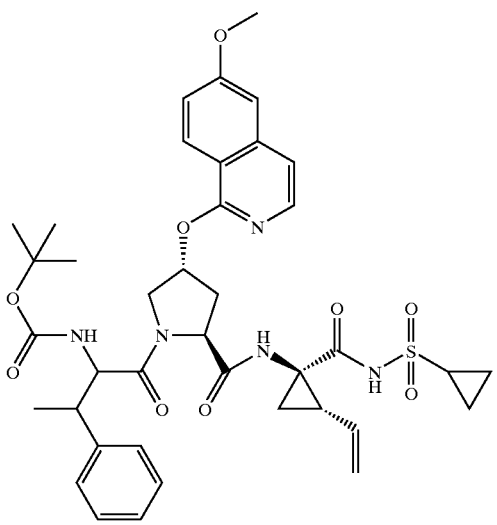

Compound 135 was prepared by following Scheme 1 of Example 134 except that N-α-tert-butoxycarbonyl-erythro-DL-β-methylphenylalanine was used in place of N-α-tert-butoxycarbonyl-L-phenylglycine in step 1. Compound 135 was prepared from a mixture of N-α-tert-butoxycarbonyl-erythro DL β-methylphenylalanine and the resulting two diastereomers were separated by reverse phase preparative HPLC. This compound is the single isomer which eluted first from the preparative HPLC column. The exact stereochemistry at the β-methyl phenylalanine portion of the molecule is unknown.

Step 1:

Modifications: 50.4 mg (0.180 mmol) N-α-tert-butoxycarbonyl-erythro-DL-β-methylphenylalanine used, 29.7 mg product obtained as a white powder (22.7% yield): $^1$H NMR (CD$_3$OD) δ 1.11 (d, J=7.93 Hz, 2 H), 1.15 (d, J=6.10 Hz, 3 H), 1.24–1.32 (m, 11 H), 1.44 (dd, J=9.16, 5.19 Hz, 1 H), 1.90–1.94 (m, 1 H), 2.25–2.29 (m, 1 H), 2.36 (t, J=13.28 Hz, 1 H), 2.62 (dd, J=13.58, 7.17 Hz, 1 H), 2.98–3.02 (m, 1 H), 3.20–3.24 (m, 1 H), 3.91 (s, 3 H), 4.11 (dd, J=11.60, 3.05 Hz, 1 H), 4.51 (d, J=10.68 Hz, 1 H), 4.57 (dd, J=10.07, 7.32 Hz, 1 H), 4.63 (d, J=12.21 Hz, 1 H), 5.14 (d, J=10.07 Hz, 1 H), 5.32 (d, J=16.79 Hz, 1 H), 5.76–5.84 (m, 1 H), 5.88 (s, 1 H), 7.08 (dd, J=8.70, 1.68 Hz, 1 H), 7.16–7.18 (m, 2 H), 7.23–7.27 (m, 5 H), 7.89 (d, J=5.80 Hz, 1 H), 8.09 (d, J=9.46 Hz, 1 H); MS m/z 762 (MH$^+$).

Example 136

Preparation of Compound 136

Compound 136

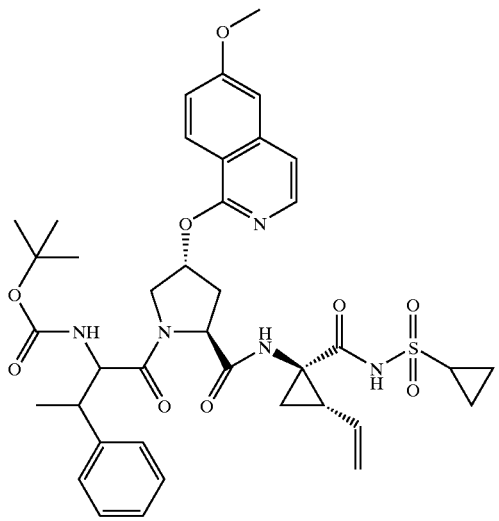

Compound 136 was prepared by following Scheme 1 of Example 134 except that N-α-tert-butoxycarbonyl-erythro-DL-β-methylphenylalanine was used in place of N-α-tert-butoxycarbonyl-L-phenylglycine in step 1. Compound 136 was prepared from a mixture of N-tert-butoxycarbonyl-erythro DL β-methylphenylalanine and the resulting two diastereomers were separated by reverse phase preparative HPLC. This compound is the single isomer which eluted second from the preparative HPLC column. The exact stereochemistry at the β-methyl phenylalanine portion of the molecule is unknown.

Step 1:

Modifications: 50.4 mg (0.180 mmol) N-α-tert-butoxycarbonyl-erythro-DL- β-methylphenylalanine used, 26.3 mg product obtained as a white powder (20.1% yield): $^1$H NMR (CD$_3$OD) δ 1.04 (s, 1 H), 1.13 (d, J=6.71 Hz, 3 H), 1.12–1.17 (m, 2 H), 1.30 (s, 9 H), 1.33–1.36 (m, 1 H), 1.41 (dd, J=9.46, 5.19 Hz, 1 H), 1.87 (dd, J=7.78, 5.34 Hz, 1 H), 2.29 (q, J=8.85 Hz, 1 H), 2.36 (ddd, J=13.81, 9.99, 4.27 Hz, 1 H), 2.54 (dd, J=13.58, 7.17 Hz, 1 H), 3.00–3.04 (m, 1 H), 3.05–3.08 (m, 1 H), 3.80 (d, J=11.90 Hz, 1 H), 3.94 (s, 3 H), 4.10 (dd, J=12.05, 3.81 Hz, 1 H), 4.53–4.57 (m, 1 H), 4.59 (d, J=8.24 Hz, 1 H), 5.14 (d, J=10.38 Hz, 1 H), 5.34 (d, J=17.09 Hz, 1 H), 5.78–5.85 (m, 2 H), 6.75 (t, J=7.32 Hz, 1 H), 7.03 (t, J=7.48 Hz, 2 H), 7.12 (s, 1 H), 7.14 (s, 1 H), 7.19 (dd, J=9.31, 1.68 Hz, 1 H), 7.22 (s, 1 H), 7.28 (d, J=6.10 Hz, 1 H), 7.89 (d, J=5.80 Hz, 1 H), 8.03 (d, J=8.85 Hz, 1 H); MS m/z 762 (MH$^+$).

Example 137

Preparation of Compound 137

Compound 137

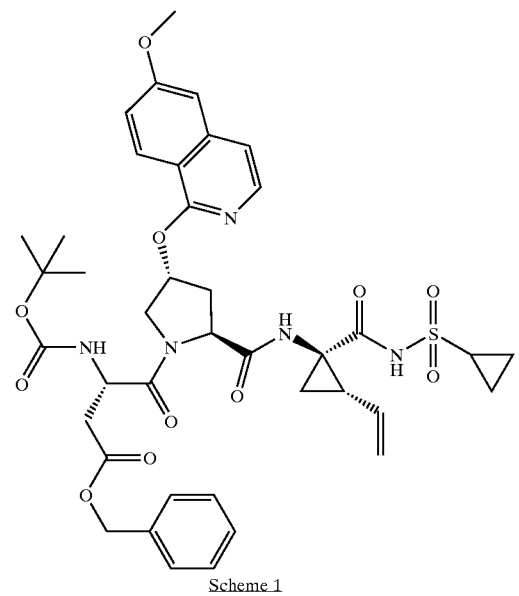

Scheme 1

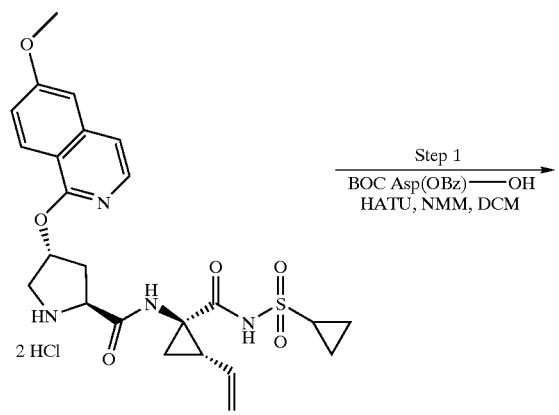

Product of Example 11, Step 5

→ Step 1
BOC Asp(OBz)—OH
HATU, NMM, DCM

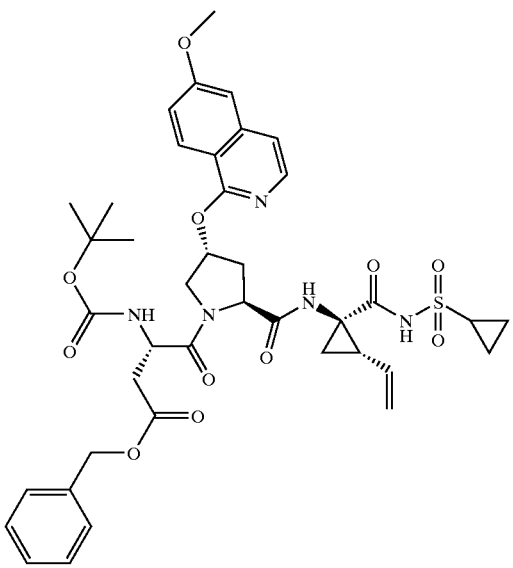

Compound 137

Step 1:

A mixture of the product from Example 11, Step 5 (100 mg, 0.172 mmol), N-α-tert-butoxycarbonyl-L-aspartic acid 4-benzyl ester (59.5 mg, 0.180 mmol), HATU (84.9 mg, 0.223 mmol), and N-methylmorpholine (87.0 mg, 0.859 mmol) in DCM (3.0 mL) was stirred at rt for 18 h. The reaction mixture was washed with pH=4 buffer solution (3×3 mL), and the washes were back-extracted with DCM (3 mL). The organic phases were combined and concentrated in vacuo. The crude product was then dissolved in MeOH and purified by reverse phase preparative HPLC to give Compound 137 as a slightly off-white glassy solid (26.0 mg, 18.8% yield): $^1$H NMR (CD$_3$OD) δ 0.95–1.01 (m, 2 H), 1.16 (s, 9 H), 1.22–1.29 (m, 2 H), 1.44 (dd, J=9.46, 5.19 Hz, 1 H), 1.86 (dd, J=7.93, 5.19 Hz, 1 H), 2.26 (q, J=8.85 Hz, 1 H), 2.32–2.37 (m, 1 H), 2.61 (dd, J=13.73, 7.32 Hz, 1 H), 2.66 (dd, J=16.48, 6.10 Hz, 1 H), 2.89 (ddd, J=12.67, 8.09, 4.88 Hz, 1 H), 3.05 (dd, J=16.63, 8.39 Hz, 1 H), 3.92 (s, 3 H), 4.04–4.07 (m, 1 H), 4.47 (d, J=11.90 Hz, 1 H), 4.52–4.56 (m, 1 H), 4.75 (dd, J=8.24, 6.41 Hz, 1 H), 5.12–5.14 (m, 1 H), 5.14 (s, 2 H), 5.31 (d, J=17.09 Hz, 1 H), 5.75–5.82 (m, 2 H), 7.12 (d, J=9.16 Hz, 1 H), 7.18 (d, J=2.14 Hz, 1 H), 7.24 (d, J=5.80 Hz, 1 H), 7.31–7.33 (m, 1 H), 7.36 (t, J=7.32 Hz, 2 H), 7.39 (s, 1 H), 7.41 (s, 1 H), 7.88 (d, J=6.10 Hz, 1 H), 8.10 (d, J=9.16 Hz, 1 H); MS m/z 806 (MH$^+$).

Example 138
Preparation of Compound 138

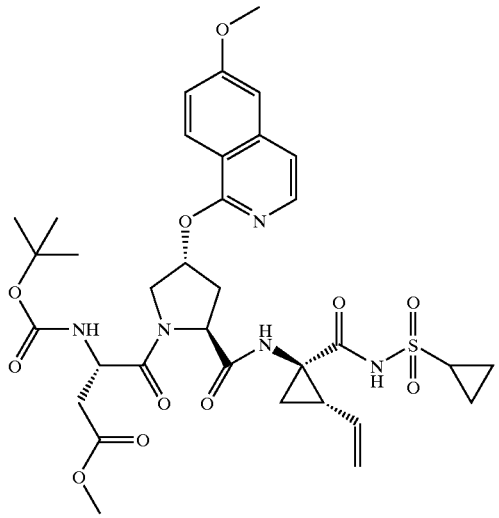

Compound 138

Compound 138 was prepared by following Scheme 1 of Example 137 except that N-tert-butoxycarbonyl-L-aspartic acid 4-methyl ester was used in place of N-α-tert-butoxycarbonyl-L-aspartic acid 4-benzyl ester in step 1.

Step 1:

Modifications: 45.5 mg (0.180 mmol) N-tert-butoxycarbonyl-L-aspartic acid 4-methyl ester used, 93.5 mg product obtained as an off-white glassy solid (74.6% yield): $^1$H NMR (CD$_3$OD) δ 1.07–1.09 (m, 2 H), 1.17 (s, 9 H), 1.20–1.29 (m, 2 H), 1.41–1.44 (m, 1 H), 1.84–1.86 (m, 1 H), 2.26 (q, J=8.85 Hz, 1 H), 2.33–2.38 (m, 1 H), 2.58–2.64 (m, 2 H), 2.92–3.02 (m, 2 H), 3.69 (s, 3 H), 3.92 (s, 3 H), 4.15 (dd, J=11.44, 2.29 Hz, 1 H), 4.49–4.56 (m, 2 H), 4.72–4.76 (m, 1 H), 5.13 (d, J=10.38 Hz, 1 H), 5.32 (d, J=17.09 Hz, 1 H), 5.74–5.82 (m, 1 H), 5.87 (s, 1 H), 7.12 (d, J=9.16 Hz, 1 H), 7.18 (s, 1 H), 7.24 (d, J=5.80 Hz, 1 H), 7.88 (dd, J=5.80, 0.92 Hz, 1 H), 8.10 (d, J=8.85 Hz, 1 H); MS m/z 730 (MH$^+$).

Example 139
Preparation of Compound 139

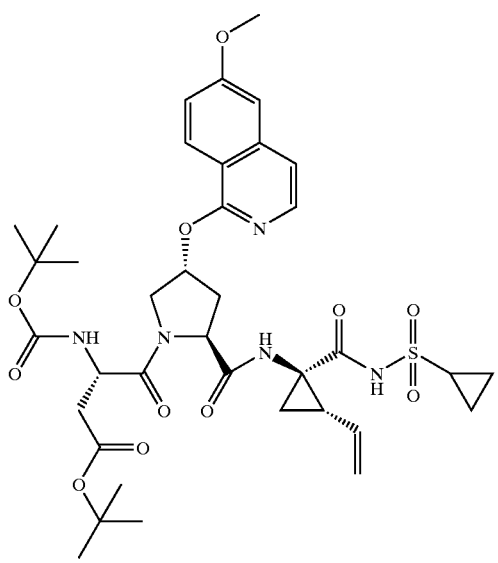

Compound 139

Compound 139 was prepared by following Scheme 1 of Example 137 except that N-tert-butoxycarbonyl-L-aspartic acid 4-tert-butyl ester was used in place of N-α-tert-butoxycarbonyl-L-aspartic acid 4-benzyl ester in step 1.

Step 1:

Modifications: 52.2 mg (0.180 mmol) N-tert-butoxycarbonyl-L-aspartic acid 4-tert-butyl ester used, 125 mg product obtained as an off-white glassy solid (99.8% yield): $^1$H NMR (CD$_3$OD) δ 1.08–1.10 (m, 2 H), 1.17 (s, 9 H), 1.21–1.29 (m, 2 H), 1.46 (s, 10 H), 1.82 (dd, J=7.78, 5.34 Hz, 1 H), 2.26 (q, J=8.75 Hz, 1 H), 2.32–2.38 (m, 1 H), 2.51 (dd, J=16.33, 7.17 Hz, 1 H), 2.63 (dd, J=14.04, 7.02 Hz, 1 H), 2.89 (dd, J=16.48, 7.63 Hz, 1 H), 2.92–2.98 (m, 1 H), 3.92 (s, 3 H), 4.15 (dd, J=11.60, 3.05 Hz, 1 H), 4.50–4.57 (m, 2 H), 4.70–4.75 (m, 1 H), 5.13 (dd, J=10.38, 1.53 Hz, 1 H), 5.32 (d, J=17.40 Hz, 1 H), 5.76–5.83 (m, 1 H), 5.87 (s, 1 H), 7.13 (dd, J=8.85, 1.53 Hz, 1 H), 7.18 (d, J=2.14 Hz, 1 H), 7.25 (d, J=5.80 Hz, 1 H), 7.88 (d, J=5.80 Hz, 1 H), 8.10 (d, J=9.16 Hz, 1 H); MS m/z 772 (MH$^+$).

Example 140
Preparation of Compound 140

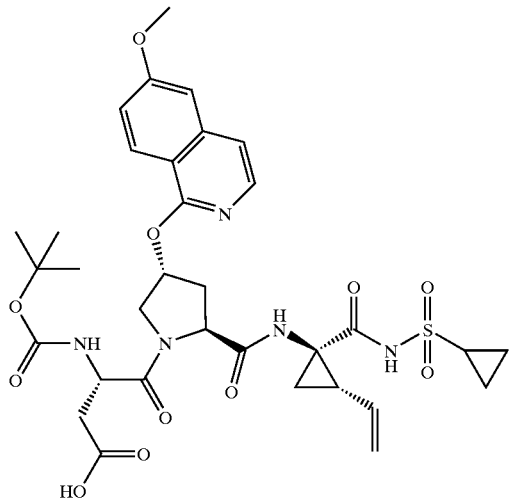

Compound 140

Scheme 1

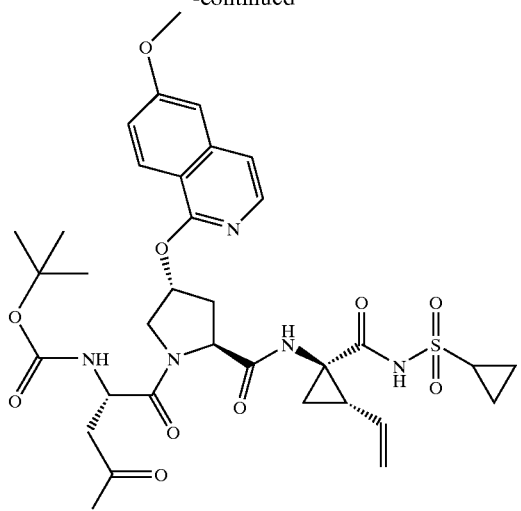

Compound 140

Compound 138 (50.0 mg, 0.0685 mmol) was dissolved in a mixture of THF (1 mL), MeOH (1 mL), and 1.0 M aqueous NaOH (0.137 mL, 0.137 mmol). After 3 h, the reaction mixture was neutralized by the addition of 1.0 M aqueous HCl (0.137 mL, 0.137 mmol). The crude mixture was concentrated in vacuo, then pH=4 buffer solution (3 mL) and DCM (3 mL) were added and the mixture was shaken. The layers were separated and the aqueous layer was further extracted with DCM (2×1 mL). The organic phases were combined, dried over anhydrous MgSO$_4$, filtered and concentrated in vacuo to give 48.0 mg (97.9% yield) of Compound 140 as an off white glassy solid: $^1$H NMR (CD$_3$OD) δ 1.04–1.07 (m, 2 H), 1.17 (s, 9 H), 1.22–1.25 (m, 2 H), 1.38 (dd, J=9.31, 5.34 Hz, 1 H), 1.78 (dd, J=7.78, 5.34 Hz, 1 H), 2.30 (q, J=8.75 Hz, 1 H), 2.37–2.42 (m, 1 H), 2.48 (dd, J=15.87, 4.58 Hz, 1 H), 2.72 (dd, J=13.12, 7.63 Hz, 1 H), 2.88 (dd, J=15.72, 10.53 Hz, 1 H), 2.90–2.95 (m, 1 H), 3.92 (s, 3 H), 4.21 (dd, J=11.44, 2.90 Hz, 1 H), 4.57 (t, J=8.70 Hz, 1 H), 4.62–4.65 (m, 2 H), 5.10 (d, J=10.68 Hz, 1 H), 5.34 (d, J=17.09 Hz, 1 H), 5.69–5.76 (m, 1 H), 5.83 (s, 1 H), 7.10 (d, J=9.16 Hz, 1 H), 7.17 (s, 11 H), 7.23 (d, J=6.10 Hz, 1 H), 7.88 (d, J=6.10 Hz, 1 H), 8.12 (d, J=8.85 Hz, 1 H); MS m/z 716 (MH$^+$).

Example 141

Preparation of Compound 141

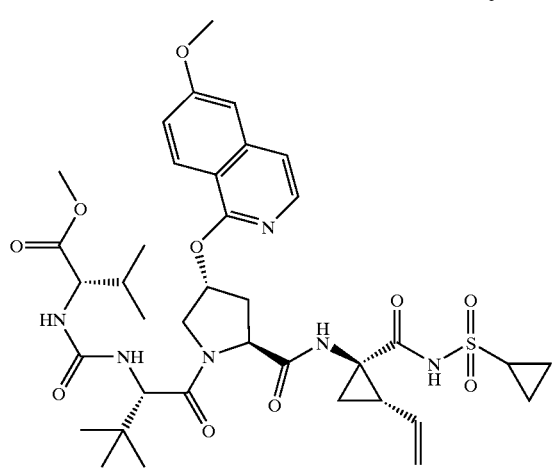

Compound 141

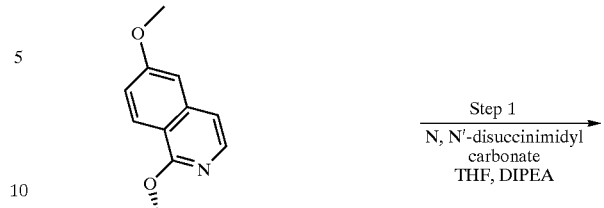

Product of Example 55, Step 1

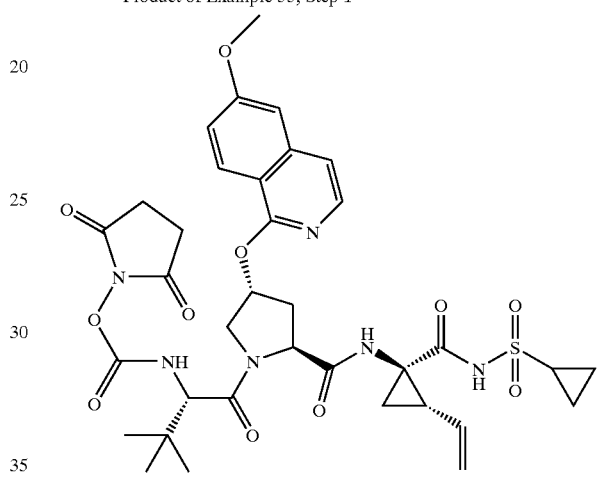

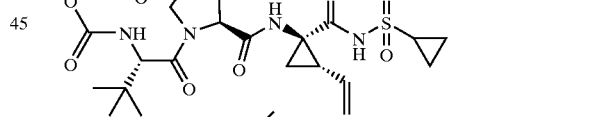

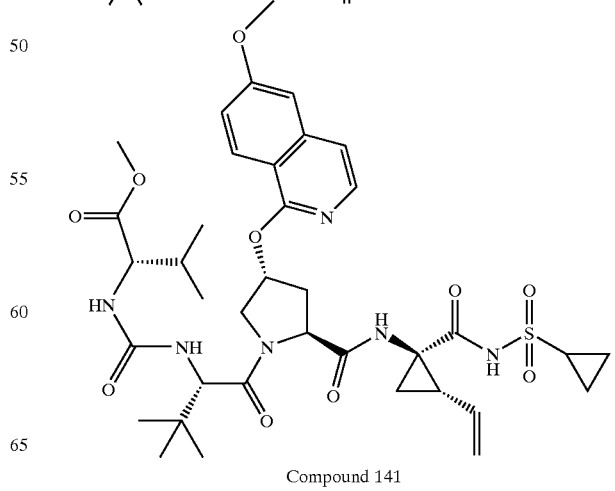

Compound 141

Step 1:

The product of Example 55, Step 1 (65 mg, 0.0947 mmol), N,N'-disuccinimidyl carbonate (41.0 mg, 0.142 mmol) and N,N-diisopropylethylamine (30.6 mg, 0.237 mmol) were combined with anhydrous THF (1 mL) and the resulting suspension was heated to 80° C. in a microwave reactor for 15 min. Upon cooling to rt, this crude mixture was used directly in the next step.

Step 2:

The crude reaction mixture from step 1 was treated with a mixture of L-valine methyl ester hydrochloride (159 mg, 0.947 mmol) and N,N-diisopropylethylamine (122 mg, 0.947 mmol) in anhydrous THF (2 mL). The resulting mixture was stirred for 18 h at rt. Solvent was removed in vacuo, and the residue was taken up in DCM (2 mL) and washed with pH=4 buffer solution (3×2 mL). The buffer washes were combined and back-extracted with DCM (2 mL). The combined DCM phases were concentrated in vacuo, and the resulting residue was dissolved in MeOH and purified by reverse phase preparative HPLC to give 38.1 mg (52.2% yield) of Compound 141 as a white powder: $^1$H NMR (CD$_3$OD) δ 0.83 (dd, J=6.87, 3.81 Hz, 6 H), 1.06 (s, 1 H), 1.21–1.26 (m, 2 H), 1.41 (dd, J=9.46, 5.49 Hz, 1 H), 1.87 (dd, J=8.09, 5.34 Hz, 1 H), 1.95–2.02 (m, 1 H), 2.21 (q, J=8.85 Hz, 1 H), 2.29 (ddd, J=13.89, 9.92, 4.27 Hz, 1 H), 2.60 (dd, J=13.73, 7.02 Hz, 1 H), 2.91–2.97 (m, 1 H), 3.67 (s, 3 H), 3.93 (s, 3 H), 4.00 (d, J=5.49 Hz, 1 H), 4.09 (dd, J=11.90, 3.97 Hz, 1 H), 4.40–4.43 (m, 2 H), 4.52 (dd, J=10.07, 7.02 Hz, 1 H), 5.11 (dd, J=10.38, 1.53 Hz, 1 H), 5.28 (dd, J=17.09, 1.22 Hz, 1 H), 5.75 (ddd, J=17.17, 10.15, 9.00 Hz, 1 H), 5.83 (s, 1 H), 7.11 (dd, J=9.16, 2.44 Hz, 1 H), 7.18 (d, J=2.44 Hz, 1 H), 7.24 (d, J=5.80 Hz, 1 H), 7.87 (d, J=6.10 Hz, 1 H), 8.10 (d, J=8.85 Hz, 1 H); MS nm/z 771 (MH$^+$).

Example 142

Preparation of Compound 142

Compound 142

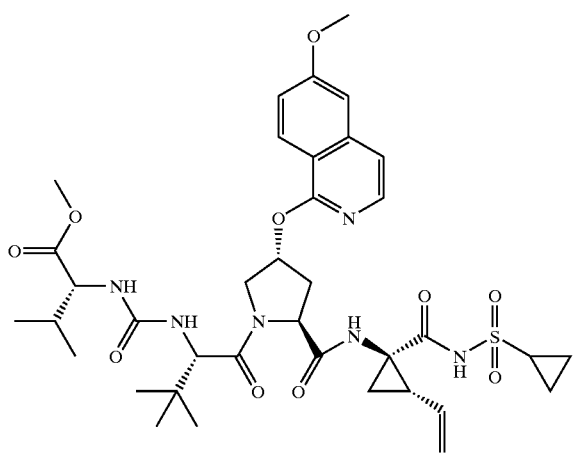

Compound 142 was prepared by following Scheme 1 of Example 141 except that D-valine methyl ester hydrochloride was used in place of L-valine methyl ester hydrochloride in step 2.

Step 2:

Modifications: 159 mg (0.947 mmol) D-valine methyl ester hydrochloride used, 23.0 mg product obtained as a white powder (31.5% yield): $^1$H NMR (CD$_3$OD) δ 0.88 (dd, J=13.89, 6.87 Hz, 6 H), 1.06 (s, 9 H), 1.07–1.09 (m, 2 H), 1.23–1.27 (m, 2 H), 1.41 (dd, J=9.46, 5.49 Hz, 1 H), 1.88 (dd, J=7.93, 5.49 Hz, 1 H), 2.01–2.07 (m, 1 H), 2.23 (q, J=9.05 Hz, 1 H), 2.31 (ddd, J=14.11, 9.99, 4.27 Hz, 1 H), 2.63 (dd, J=13.89, 7.17 Hz, 1 H), 2.93–2.98 (m, 1 H), 3.62 (s, 3 H), 3.96 (s, 3 H), 4.03 (d, J=5.19 Hz, 1 H), 4.09 (dd, J=11.75, 3.81 Hz, 1 H), 4.38 (s, 1 H), 4.48–4.54 (m, 2 H), 5.12 (dd, J=10.38, 1.22 Hz, 1 H), 5.29 (dd, J=17.24, 1.07 Hz, 1 H), 5.70–5.77 (m, 1 H), 5.83 (s, 1 H), 7.22 (dd, J=9.00, 2.59 Hz, 1 H), 7.25 (d, J=2.44 Hz, 1 H), 7.35 (d, J=6.10 Hz, 1 H), 7.87 (d, J=6.10 Hz, 1 H), 8.16 (d, J=9.16 Hz, 1 H); MS m/z 771 (MH$^+$).

Example 143

Preparation of Compound 143

Compound 143

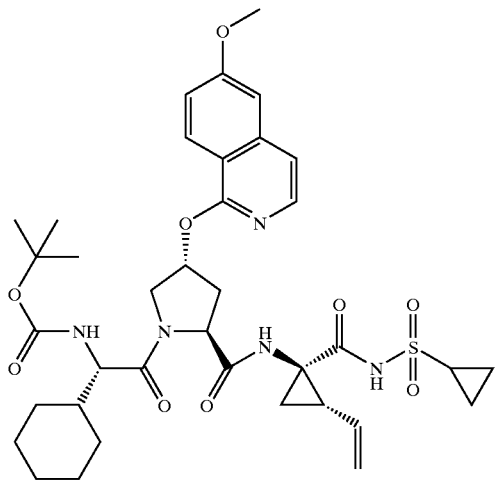

Compound 143 was prepared by following Scheme 1 of Example 137 except that N-tert-butoxycarbonyl-L-cyclohexylglycine was used in place of N-α-tert-butoxycarbonyl-L-aspartic acid 4-benzyl ester in step 1.

Step 1:

Modifications: 46.2 mg (0.180 mmol) N-tert-butoxycarbonyl-L-cyclohexylglycine used, 93.9 mg product obtained as a white powder (73.8% yield): $^1$H NMR (CD$_3$OD) δ 1.04–1.08 (dd, J=7.78, 2.29 Hz, 4 H), 1.19–1.26 (m, 4 H), 1.25 (s, 9 H), 1.41 (dd, J=9.46, 5.19 Hz, 1 H), 1.63–1.82 (m, 7 H), 1.88 (dd, J=7.93, 5.49 Hz, 1 H), 2.22 (q, J=9.05 Hz, 1 H), 2.32–2.37 (m, 1 H), 2.59 (dd, J=13.58, 6.87 Hz, 1 H), 2.91–2.96 (m, 1 H), 3.92 (s, 3 H), 4.05 (dd, J=11.75, 3.20 Hz, 1 H), 4.09 (d, J=8.85 Hz, 1 H), 4.47 (d, J=11.90 Hz, 1 H), 4.53 (dd, J=10.22, 7.17 Hz, 1 H), 5.11 (d, J=10.38 Hz, 1 H), 5.29 (d, J=16.79 Hz, 1 H), 5.79 (ddd, J=16.86, 9.92, 9.54 Hz, 1 H), 5.84 (s, 1 H), 7.10 (d, J=8.85 Hz, 1 H), 7.17 (d, J=1.53 Hz, 1 H), 7.24 (d, J=5.80 Hz, 1 H), 7.88 (d, J=6.10 Hz, 1 H), 8.09 (d, J=8.85 Hz, 1 H); MS m/z 740 (MH+).

Example 144

Preparation of Compound 144

Compound 144

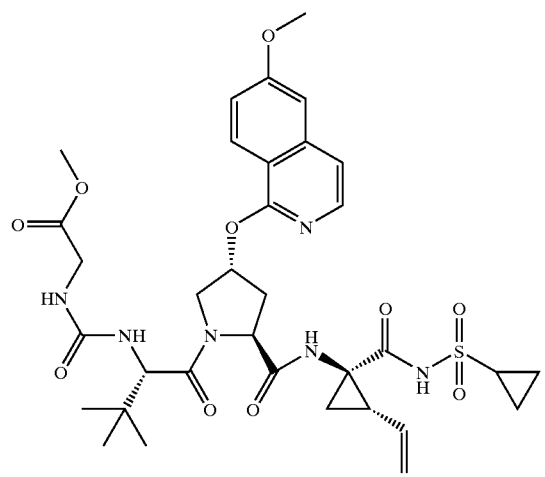

Compound 144 was prepared by following Scheme 1 of Example 141 except that the scale was increased and that glycine methyl ester hydrochloride was used in place of L-valine methyl ester hydrochloride in step 2.

Step 1:

Modifications: 100 mg (0.146 mmol) of the product of Example 55, Step 1; 62.2 mg (0.219 mmol) N,N'-disuccinimidyl carbonate, 47.0 mg (0.364 mmol) N,N-diisopropylethylamine used.

Step 2:

Modifications: 183 mg (1.46 mmol) glycine methyl ester hydrochloride, 188 mg (1.46 mmol) N,N-diisopropylethylamine used, 56.3 mg product obtained as a white powder (52.9% yield): $^1$H NMR (CD$_3$OD) δ 1.01–1.04 (m, 2 H), 1.05 (s, 9 H), 1.17–1.21 (m, 2 H), 1.40 (dd, J=9.46, 5.49 Hz, 1 H), 1.85 (dd, J=7.78, 5.34 Hz, 1 H), 2.18 (q, J=8.55 Hz, 1 H), 2.33 (ddd, J=13.89, 9.92, 4.27 Hz, 1 H), 2.61 (dd, J=13.73, 7.32 Hz, 1 H), 2.89–2.94 (m, 1 H), 3.65 (s, 3 H), 3.69–3.77 (m, 2 H), 3.92 (s, 3 H), 4.10 (dd, J=11.75, 3.81 Hz, 1 H), 4.40–4.42 (m, 2 H), 4.53 (dd, J=9.92, 7.17 Hz, 1 H), 5.08 (d, J=10.38 Hz, 1 H), 5.26 (d, J=17.09 Hz, 1 H), 5.77 (ddd, J=17.09, 10.22, 9.00 Hz, 1 H), 5.83 (s, 1 H), 7.13 (dd, J=8.85, 2.44 Hz, 1 H), 7.17 (s, 1 H), 7.23 (d, J=5.80 Hz, 1 H), 7.87 (d, J=5.80 Hz, 1 H), 8.09 (d, J=8.85 Hz, 1 H); MS m/z 729 (MH+).

Example 145

Preparation of Compound 145

Compound 145

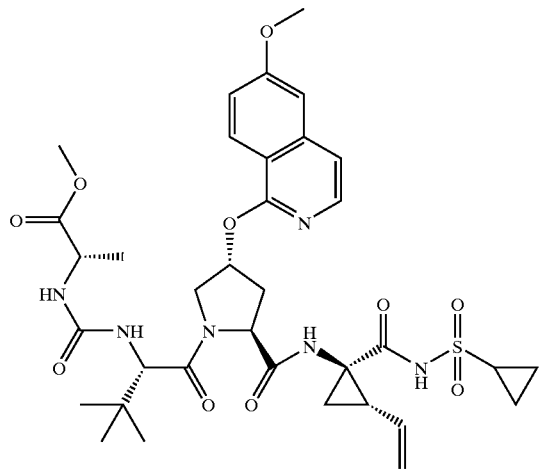

Compound 145 was prepared by following Scheme 1 of Example 141 except that the scale was increased and that L-alanine methyl ester hydrochloride was used in place of L-valine methyl ester hydrochloride in step 2.

Step 1:

Modifications: 100 mg (0.146 mmol) of the product of Example 55, Step 1; 62.2 mg (0.219 mmol) N,N'-disuccinimidyl carbonate, 47.0 mg (0.364 mmol) N,N-diisopropylethylamine used.

Step 2:

Modifications: 203 mg (1.46 mmol) L-alanine methyl ester hydrochloride, 188 mg (1.46 mmol) N,N-diisopropylethylamine used, 64.3 mg product obtained as a white powder (59.3% yield): $^1$H NMR (CD$_3$OD) δ 0.97–1.02 (m, 2 H), 1.05 (s, 9 H), 1.19 (d, J=7.02 Hz, 3 H), 1.18–1.22 (m, 2 H), 1.41 (dd, J=9.46, 5.19 Hz, 1 H), 1.86 (dd, J=8.09, 5.34 Hz, 1 H), 2.19 (q, J=8.85 Hz, 1 H), 2.32 (ddd, J=13.81, 9.84, 4.43 Hz, 1 H), 2.61 (dd, J=13.73, 7.02 Hz, 1 H), 2.93 (ddd, J=12.82, 8.09, 4.73 Hz, 1 H), 3.65 (s, 3 H), 3.93 (s, 3 H), 3.99 (q, J=7.22 Hz, 1 H), 4.08 (dd, J=11.75, 3.81 Hz, 1 H), 4.38 (s, 1 H), 4.42 (d, J=11.60 Hz, 1 H), 4.53 (dd, J=10.07, 7.32 Hz, 1 H), 5.09 (dd, J=10.38, 1.53 Hz, 1 H), 5.27 (dd, J=17.09, 1.22 Hz, 1 H), 5.77 (ddd, J=17.09, 10.07, 9.16 Hz, 1 H), 5.82 (s, 1 H), 7.13 (dd, J=9.16, 2.44 Hz, 1 H), 7.18 (d, J=2.44 Hz, 1 H), 7.24 (d, J=5.80 Hz, 1 H), 7.87 (d, J=5.80 Hz, 1 H), 8.10 (d, J=9.16 Hz, 1 H); MS m/z 743 (MH+).

Example 146

Preparation of Compound 146

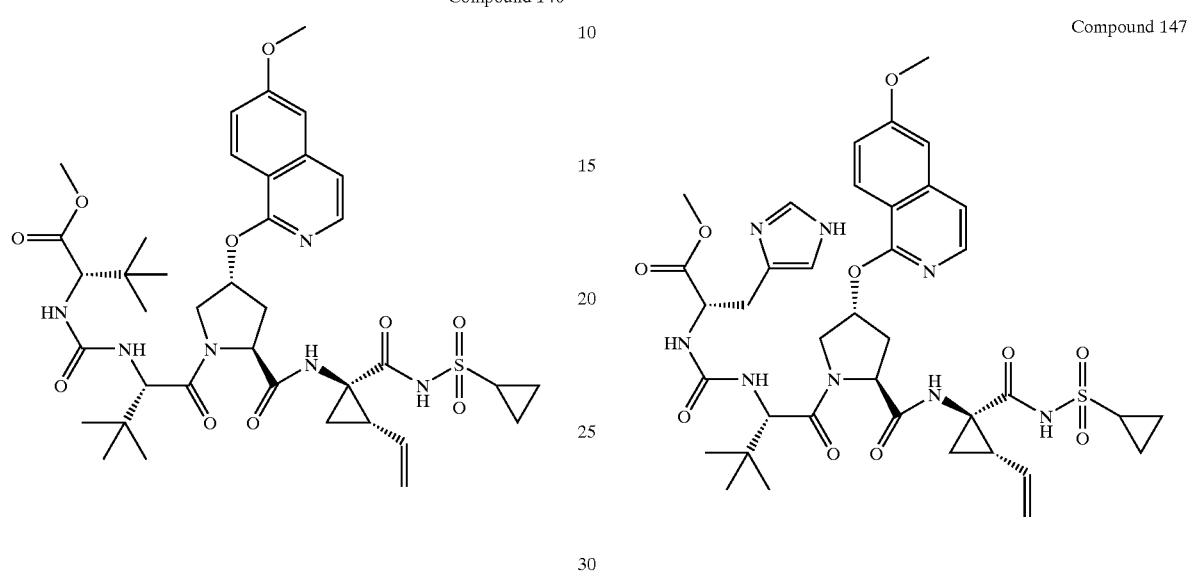

Step 1:

Modifications: 100 mg (0.146 mmol) of the product of Example 55, Step 1; 62.2 mg (0.219 mmol) N,N'-disuccinimidyl carbonate, 47.0 mg (0.364 mmol) N,N-diisopropylethylamine used.

Step 2:

Modifications: 265 mg (1.46 mmol) L-tert-leucine methyl ester hydrochloride, 188 mg (1.46 mmol) N,N-diisopropylethylamine used, 68.3 mg product obtained as a white powder (59.6% yield): $^1$H NMR (CD$_3$OD) δ 0.88 (s, 9 H), 0.97–1.03 (m, 2 H), 1.06 (s, 9 H), 1.18–1.24 (m, 2 H), 1.41 (dd, J=9.46, 5.49 Hz, 1 H), 1.86 (dd, J=7.93, 5.49 Hz, 1 H), 2.19 (q, J=8.75 Hz, 1 H), 2.30 (ddd, J=13.89, 10.07, 4.43 Hz, 1 H), 2.60 (dd, J=13.73, 7.32 Hz, 1 H), 2.91–2.96 (m, 1 H), 3.65 (s, 3 H), 3.91 (s, 1 H), 3.93 (s, 3 H), 4.09 (dd, J=11.60, 3.97 Hz, 1 H), 4.38 (s, 1 H), 4.43 (d, J=11.60 Hz, 1 H), 4.51 (dd, J=10.07, 7.32 Hz, 1 H), 5.10 (dd, J=10.38, 1.53 Hz, 1 H), 5.27 (dd, J=17.24, 1.37 Hz, 1 H), 5.76 (ddd, J=17.09, 10.07, 9.16 Hz, 1 H), 5.82 (s, 1 H), 7.12 (dd, J=9.16, 2.44 Hz, 1 H), 7.18 (d, J=2.14 Hz, 1 H), 7.24 (d, J=6.10 Hz, 1 H), 7.87 (d, J=5.80 Hz, 1 H), 8.11 (d, J=9.16 Hz, 1 H); MS m/z 785 (MH$^+$).

Example 147

Preparation of Compound 147

Compound 147 was prepared by following Scheme 1 of Example 141 except that the scale was increased and that L-tert-leucine methyl ester hydrochloride was used in place of L-valine methyl ester hydrochloride in step 2.

Compound 147 was prepared by following Scheme 1 of Example 141 except that the scale was increased and that L-histidine methyl ester hydrochloride was used in place of L-valine methyl ester hydrochloride in step 2, and the amount of N,N-diisopropylethylamine used in step 2 was doubled.

Step 1:

Modifications: 100 mg (0.146 mmol) of the product of Example 55, Step 1; 62.2 mg (0.219 mmol) N,N'-disuccinimidyl carbonate, 47.0 mg (0.364 mmol) N,N-diisopropylethylamine used.

Step 2:

Modifications: 352 mg (1.46 mmol) L-histidine methyl ester hydrochloride, 377 mg (2.91 mmol) N,N-diisopropylethylamine used, 51.0 mg product obtained as a white powder (43.2% yield): $^1$H NMR (CD$_3$OD) δ 1.04 (s, 11 H), 1.20–1.22 (m, 2 H), 1.41 (ddd, J=9.46, 5.34, 1.07 Hz, 1 H), 1.86–1.88 (m, 1 H), 2.23 (q, J=8.75 Hz, 1 H), 2.28–2.33 (m, 1 H), 2.60 (dd, J=13.73, 7.02 Hz, 1 H), 2.92 (d, J=6.41 Hz, 2 H), 2.92–2.96 (m, 1 H), 3.64 (s, 3 H), 3.91 (d, J=1.53 Hz, 3 H), 4.04 (dd, J=11.90, 3.66 Hz, 1 H), 4.35 (s, 1 H), 4.36–4.41 (m, 2 H), 4.53 (dd, J=9.77, 7.63 Hz, 1 H), 5.10 (d, J=10.38 Hz, 1 H), 5.28 (d, J=17.40 Hz, 1 H), 5.73–5.78 (m, 1 H), 5.81 (s, 1 H), 6.82 (s, 1 H), 7.06–7.09

(m, 1 H), 7.15 (s, 1 H), 7.23 (d, J=5.80 Hz, 1 H), 7.63 (s, 1 H), 7.87 (dd, J=5.80, 1.22 Hz, 1 H), 8.08 (d, J=9.16 Hz, 1 H); MS m/z 809 (MH⁺).

Example 148

Preparation of Compound 148

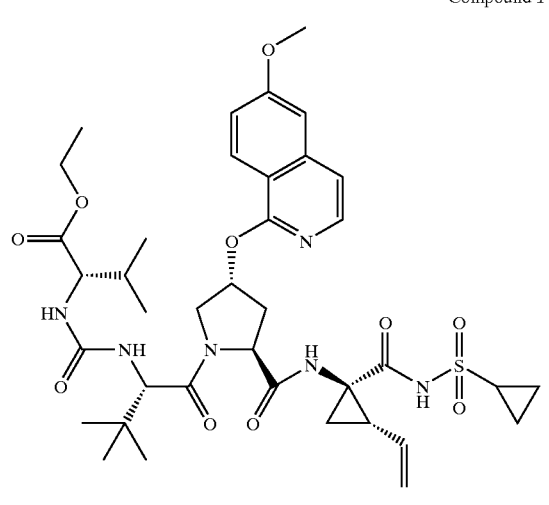

Compound 148

Compound 148 was prepared by following Scheme 1 of Example 141 except that the scale was increased and that L-valine ethyl ester hydrochloride was used in place of L-valine methyl ester hydrochloride in step 2.

Step 1:

Modifications: 100 mg (0.146 mmol) of the product of Example 55, Step 1; 62.2 mg (0.219 mmol) N,N'-disuccinimidyl carbonate, 47.0 mg (0.364 mmol) NAN-diisopropylethylamine used.

Step 2:

Modifications: 265 mg (1.46 mmol) L-valine ethyl ester hydrochloride, 188 mg (1.46 mmol) N,N-diisopropylethylamine used, 69.2 mg product obtained as a white powder (60.4% yield): ¹H NMR (CD₃OD) δ 0.83 (dd, J=6.71, 5.19 Hz, 6 H), 1.01–1.03 (m, 2 H), 1.06 (s, 9 H), 1.17–1.22 (m, 2 H), 1.23 (t, J=7.17 Hz, 3 H), 1.40 (dd, J=9.46, 5.19 Hz, 1 H), 1.86 (dd, J=8.09, 5.34 Hz, 1 H), 1.95–2.02 (m, 1 H), 2.18 (q, J=9.05 Hz, 1 H), 2.33 (ddd, J=13.89, 9.92, 4.27 Hz, 1 H), 2.60 (dd, J=13.89, 7.17 Hz, 1 H), 2.92 (ddd, J=12.82, 8.09, 4.73 Hz, 1 H), 3.93 (s, 3 H), 3.98 (d, J=5.19 Hz, 1 H), 4.08–4.17 (m, 3 H), 4.41 (s, 1 H), 4.41–4.43 (m, 1 H), 4.52 (dd, J=10.07, 7.32 Hz, 1 H), 5.09 (dd, J=10.38, 1.53 Hz, 1 H), 5.26 (dd, J=17.09, 1.22 Hz, 1 H), 5.77 (ddd, J=17.09, 10.07, 9.16 Hz, 1 H), 5.82 (s, 1 H), 7.12 (dd, J=9.16, 2.44 Hz, 1 H), 7.18 (d, J=2.44 Hz, 1 H), 7.23 (d, J=6.10 Hz, 1 H), 7.87 (d, J=6.10 Hz, 1 H), 8.10 (d, J=9.16 Hz, 1 H); MS m/z 785(MH⁺).

Example 149

Preparation of Compound 149

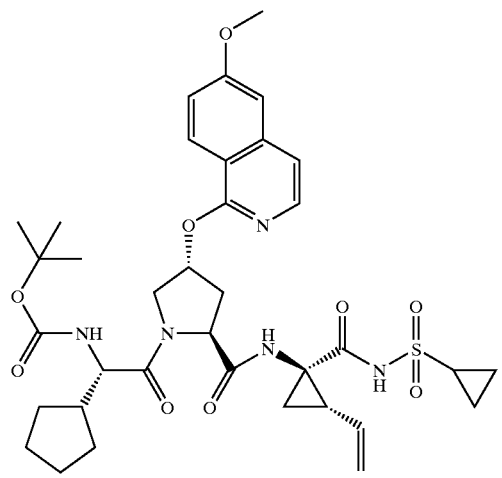

Compound 149

Compound 149 was prepared by following Scheme 1 of Example 137 except that N-tert-butoxycarbonyl-L-cyclopentylglycine dicyclohexylamine salt was used in place of N-α-tert-butoxycarbonyl-L-aspartic acid 4-benzyl ester in step 1.

Step 1:

Modifications: 76.2 mg (0.180 mmol) N-tert-butoxycarbonyl-L-cyclopentylglycine dicyclohexylamine salt used, 111 mg product obtained as a white powder (89.3% yield): ¹H NMR (CD₃OD) δ 0.98 (d, J=8.24 Hz, 2 H), 1.15–1.18 (m, 2 H), 1.24 (s, 9 H), 1.29–1.32 (m, J=18.01 Hz, 2 H), 1.38–1.40 (m, 1 H), 1.44 (dd, J=4.88, 1.53 Hz, 1 H), 1.49–1.55 (m, 2 H), 1.62–1.67 (m, 2 H), 1.74–1.80 (m, 1 H), 1.85–1.88 (m, 1 H), 2.16 (q, J=8.75 Hz, 1 H), 2.21–2.26 (m, 1 H), 2.42 (t, J=11.90 Hz, 1 H), 2.60–2.64 (m, 1 H), 2.89–2.93 (m, 1 H), 3.92 (d, J=1.53 Hz, 3 H), 4.06–4.11 (m, 2 H), 4.51–4.57 (m, 2 H), 5.07 (d, J=10.38 Hz, 1 H), 5.25 (d, J=17.09 Hz, 1 H), 5.78–5.85 (m, 2 H), 7.10 (d, J=8.85 Hz, 1 H), 7.17 (s, 1 H), 7.23 (d, J=4.27 Hz, 1 H), 7.88 (dd, J=5.95, 1.68 Hz, 1 H), 8.10 (d, J=9.16 Hz, 1 H); MS m/z 726 (MH⁺).

Example 150

Preparation of Compound 150

Compound 150

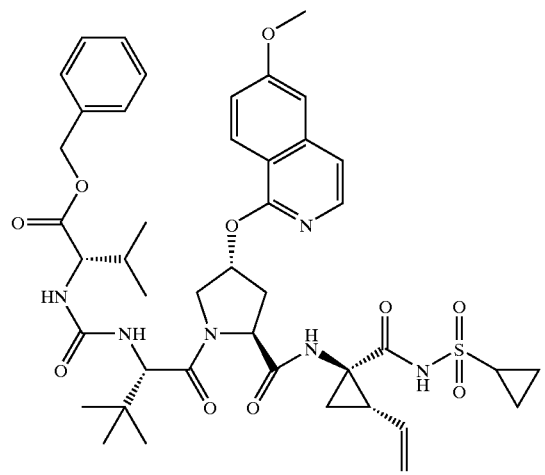

Compound 150 was prepared by following Scheme 1 of Example 141 except that the scale was increased and that L-valine benzyl ester hydrochloride was used in place of L-valine methyl ester hydrochloride in step 2.

Step 1:

Modifications: 100 mg (0.146 mmol) of the product of Example 55, Step 1; 62.2 mg (0.219 mmol) N,N'-disuccinimidyl carbonate, 47.0 mg (0.364 mmol) N,N-diisopropylethylamine used.

Step 2:

Modifications: 356 mg (1.46 mmol) L-valine benzyl ester hydrochloride, 188 mg (1.46 mmol) N,N-diisopropylethylamine used, 41.0 mg product obtained as a white powder (33.2% yield): MS m/z 848 (MH$^+$).

Example 151

Preparation of Compound 151

Compound 151

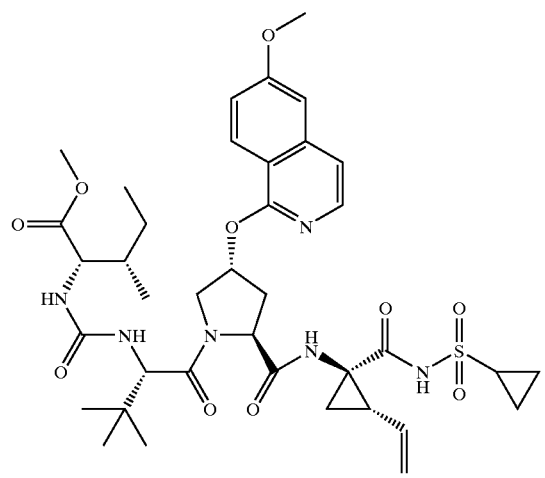

Compound 151 was prepared by following Scheme 1 of Example 141 except that the scale was increased and that L-isoleucine methyl ester hydrochloride was used in place of L-valine methyl ester hydrochloride in step 2.

Step 1:

Modifications: 100 mg (0.146 mmol) of the product of Example 55, Step 1; 62.2 mg (0.219 mmol) N,N'-disuccinimidyl carbonate, 47.0 mg (0.364 mmol) N,N-diisopropylethylamine used.

Step 2:

Modifications: 265 mg (1.46 mmol) L-isoleucine methyl ester hydrochloride, 188 mg (1.46 mmol) N,N-diisopropylethylamine used, 75.5 mg product obtained as a white powder (65.9% yield): $^1$H NMR (CD$_3$OD) δ 0.78–0.80 (m, 3 H), 0.83–0.84 (m, 3 H), 0.90–0.95 (m, 1 H), 1.01–1.03 (m, 2 H), 1.06 (d, J=3.05 Hz, 9 H), 1.17–1.21 (m, 2 H), 1.32–1.42 (m, 2 H), 1.68–1.72 (m, 1 H), 1.84–1.87 (m, 1 H), 2.14–2.20 (m, 1 H), 2.30–2.36 (m, 1 H), 2.57–2.62 (m, 1 H), 2.90–2.95 (m, 1 H), 3.66 (d, J=2.75 Hz, 3 H), 3.92 (d, J=2.75 Hz, 3 H), 4.05–4.12 (m, 2 H), 4.39–4.42 (m, 2 H), 4.50–4.53 (m, 1 H), 5.07–5.10 (m, 1 H), 5.23–5.28 (m, 1 H), 5.73–5.79 (m, 1 H), 5.81–5.83 (m, 1 H), 7.10–7.13 (m, 1 H), 7.17 (t, J=2.44 Hz, 1 H), 7.22–7.24 (m, 1 H), 7.85–7.87 (m, 1 H), 8.10 (dd, J=9.16, 2.75 Hz, 1 H); MS m/z 785 (MH$^+$).

Example 152

Preparation of Compound 152

Compound 152

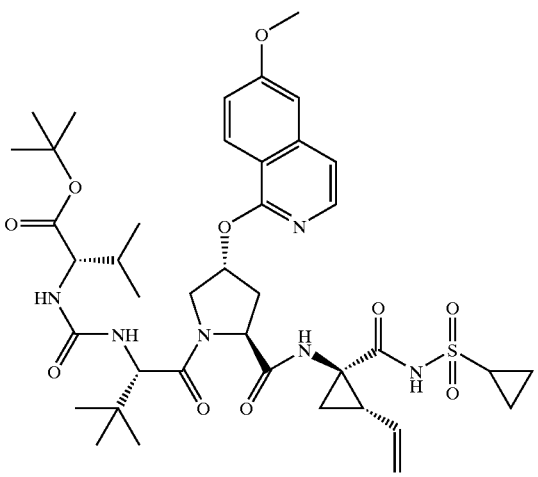

Compound 152 was prepared by following Scheme 1 of Example 141 except that the scale was increased and that L-valine tert-butyl ester hydrochloride was used in place of L-valine methyl ester hydrochloride in step 2.

Step 1:

Modifications: 100 mg (0.146 mmol) of the product of Example 55, Step 1; 62.2 mg (0.219 mmol) N,N'-disuccinimidyl carbonate, 47.0 mg (0.364 mmol) N,N-diisopropylethylamine used.

Step 2:

Modifications: 306 mg (1.46 mmol) L-valine tert-butyl ester hydrochloride, 188 mg (1.46 mmol) N,N-diisopropylethylamine used, 93.5 mg product obtained as a white powder (78.8% yield): MS m/z 814 (MH$^+$).

Example 153

Preparation of Compound 153

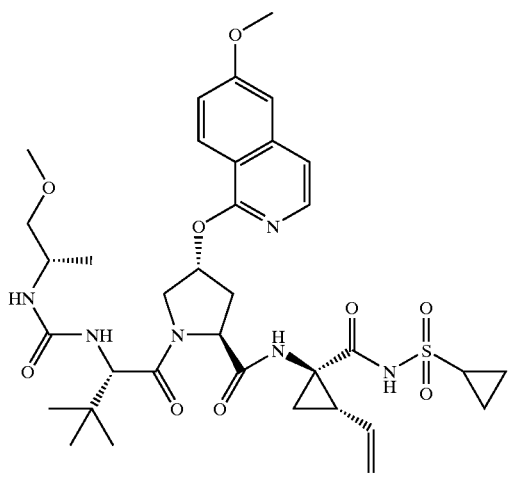

Compound 153

Compound 153 was prepared by following Scheme 1 of Example 141 except that the scale was increased and that (S)-(+)-1-methoxy-2-propylamine was used in place of L-valine methyl ester hydrochloride in step 2.

Step 1:

Modifications: 100 mg (0.446 mmol) of the product of Example 55, Step 1; 62.2 mg (0.219 mmol) N,N'-disuccinimidyl carbonate, 47.0 mg (0.364 mmol) N,N-diisopropylethylamine used.

Step 2:

Modifications: 130 mg (1.46 mmol) (S)-(+)-1-methoxy-2-propylamine, 188 mg (1.46 mmol) N,N-diisopropylethylamine used, 50.3 mg product obtained as a white powder (47.3% yield): $^1$H NMR (CD$_3$OD) δ 0.96 (d, J=7.02 Hz, 3 H), 0.99–1.01 (m, 2 H), 1.04 (s, 9 H), 1.15–1.18 (m, 2 H), 1.39 (dd, J=9.61, 5.34 Hz, 1H), 1.84 (dd, J=7.93, 5.19 Hz, 1 H), 1.93 (s, 3 H), 2.15 (q, J=9.05 Hz, 1H), 2.37 (ddd, J=13.96, 9.84, 4.58 Hz, 1 H), 2.61 (dd, J=14.04, 7.32 Hz, 1 H), 2.90 (ddd, J=12.89, 8.16, 4.88 Hz, 1 H), 3.19–3.28 (m, 2 H), 3.64–3.67 (m, 1 H), 3.92 (s, 3 H), 4.12 (dd, J=11.60, 3.97 Hz, 1 H), 4.40 (s, 1 H), 4.44 (d, J=11.90 Hz, 1 H), 4.53 (dd, J=9.77, 7.32 Hz, 1 H), 5.07 (dd, J=10.22, 1.68 Hz, 1 H), 5.24 (dd, J=17.24, 1.37 Hz, 1 H), 5.76–5.81 (m, 1 H), 5.83 (s, 1 H), 7.10 (dd, J=9.16, 2.44 Hz, 1 H), 7.17 (d, J=2.44 Hz, 1 H), 7.23 (d, J=5.80 Hz, 1 H), 7.87 (d, J=5.80 Hz, 1 H), 8.10 (d, J=9.16 Hz, 1 H); MS m/z 729 (MH$^+$).

Example 154

Preparation of Compound 154

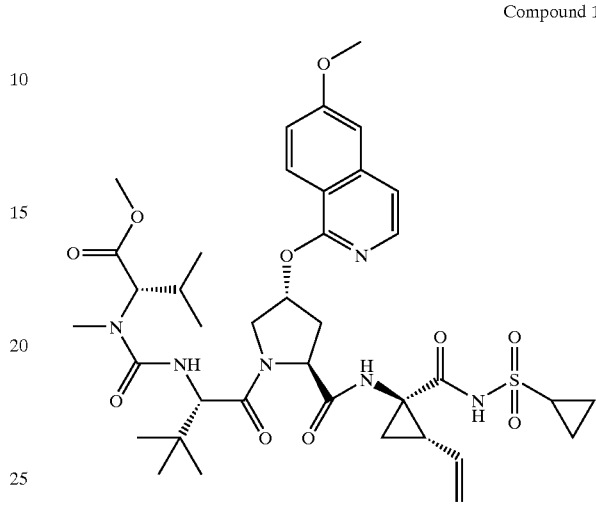

Compound 154

Compound 154 was prepared by following Scheme 1 of Example 141 except that the scale was increased and that N-methyl L-valine methyl ester hydrochloride was used in place of L-valine methyl ester hydrochloride in step 2.

Step 1:

Modifications: 100 mg (0.146 mmol) of the product of Example 55, Step 1; 62.2 mg (0.219 mmol) N,N'-disuccinimidyl carbonate, 47.0 mg (0.364 mmol) N,N-diisopropylethylamine used.

Step 2:

Modifications: 265 mg (1.46 mmol) N-methyl L-valine methyl ester hydrochloride, 188 mg (1.46 mmol) N,N-diisopropylethylamine used, 68.2 mg product obtained as a white powder (59.5% yield): $^1$H NMR (CD$_3$OD) δ 0.70 (dd, J=6.71, 2.14 Hz, 3 H), 0.89 (dd, J=6.41, 2.44 Hz, 3 H), 0.96–0.98 (m, 1 H), 1.02–1.04 (m, 2 H), 1.07 (d, J=2.14 Hz, 9 H), 1.18–1.22 (m, 2 H), 1.43–1.47 (m, 1 H), 1.84–1.87 (m, 1 H), 2.11–2.19 (m, 2 H), 2.31–2.37 (m, 1 H), 2.58–2.63 (m, 1 H), 2.87 (d, J=2.44 Hz, 3 H), 2.90–2.94 (m, 1 H), 3.65 (d, J=2.14 Hz, 3 H), 3.92 (d, J=2.14 Hz, 3 H), 4.10–4.14 (m, 1 H), 4.25 (dd, J=10.07, 1.22 Hz, 1 H), 4.48 (d, J=2.44 Hz, 1 H), 4.50–4.54 (m, 1 H), 5.08–5.10 (m, 1 H), 5.25–5.28 (dd, J=17.09, 1.53 Hz, 1 H), 5.78–5.85 (m, 2 H), 7.10–7.13 (m, 1 H), 7.18–7.19 (m, 1 H), 7.24 (dd, J=5.95, 2.59 Hz, 1 H), 7.87–7.89 (m, 1 H), 8.10 (dd, J=9.00, 2.59 Hz, 1 H); MS m/z 785 (MH$^+$).

Example 155

Preparation of Compound 155

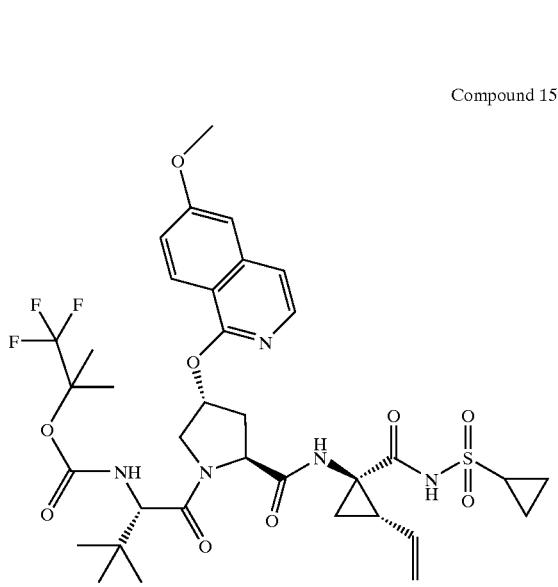

Compound 155

Scheme 1

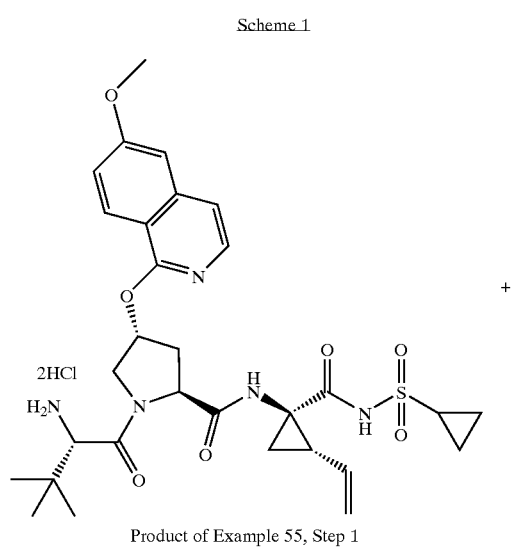

Product of Example 55, Step 1

+

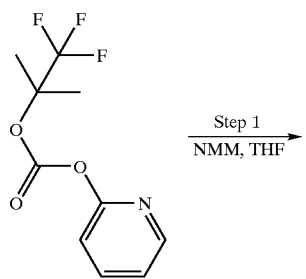

Step 1
NMM, THF
→

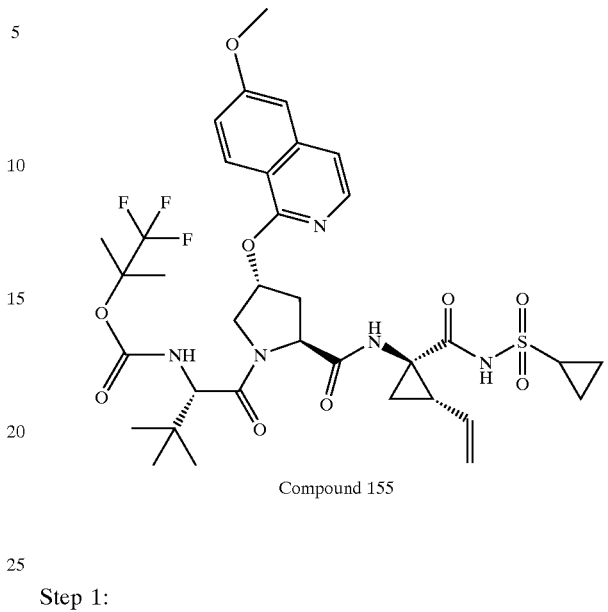

Compound 155

Step 1:

To a solution of the product of Example 55, Step 1 (100 mg, 0.146 mmol) in anhydrous THF (2 mL) was added carbonic acid pyridin-2-yl ester 2,2,2-trifluoro-1,1-dimethyl-ethyl ester (44.0 mg, 0.175 mmol) and N-methylmorpholine (59 mg, 0.58 mmol). The mixture was agitated at rt for 24 h. The reaction mixture was washed concentrated in vacuo and the residue was dissolved in DCM (2 mL). The solution was washed with pH=4 buffer solution (3×3 mL), and the washes were back-extracted with DCM (3 mL). The organic phases were combined and concentrated in vacuo. The crude product was then dissolved in MeOH and purified by reverse phase preparative HPLC to give Compound 155 as a white powder (38.5 mg, 34.3% yield): $^1$H NMR (CD$_3$OD) δ 1.04 (s, 11 H), 1.19–1.22 (m, 2 H), 1.23 (s, 3 H), 1.43 (dd, J=9.31, 5.34 Hz, 1 H), 1.46 (s, 3 H), 1.87 (dd, J=7.93, 5.49 Hz, 1 H), 2.19 (q, J=8.85 Hz, 1 H), 2.34 (m, 1 H), 2.62 (dd, J=13.73, 7.02 Hz, 1 H), 2.92 (ddd, J=12.67, 8.09, 4.88 Hz, 1 H), 3.92 (s, 3 H), 4.06 (dd, J=11.90, 3.36 Hz, 1 H), 4.23 (s, 1 H), 4.43 (d, J=11.60 Hz, 1 H), 4.56 (dd, J=10.38, 7.32 Hz, 1 H), 5.10 (d, J=10.38 Hz, 1 H), 5.27 (d, J=17.09 Hz, 1 H), 5.75–5.80 (m, 1 H), 5.82 (s, 1 H), 7.10 (dd, J=9.16, 2.44 Hz, 1 H), 7.18 (d, J=2.44 Hz, 1 H), 7.25 (d, J=6.10 Hz, 1H), 7.89 (d, J=5.80 Hz, 1 H), 8.07 (d, J=9.16 Hz, 1 H); MS m/z 768 (MH$^+$).

Section E:

LC-MS conditions for section E

"method A" is 3.0×50 mm Xterra @4 min gradient and 4 mL/min flow

"method B" is 3.0×50 mm Xterra @3 min gradient and 4 mL/min flow

"method C" is 4.6×50 mm Xterra @4 min gradient and 4 mL/min flow

"method D" is 4.6×50 mm Xterra @3 min gradient and 4 mL/min flow

Example 180
Preparation of Compound 180
General Synthetic Scheme
Compound 180 to 183 were prepared by the general synthetic scheme as depicted above. These individual reactions were described in detail elsewhere. With the exception of the first alkylation step for which potassium tert-butoxide
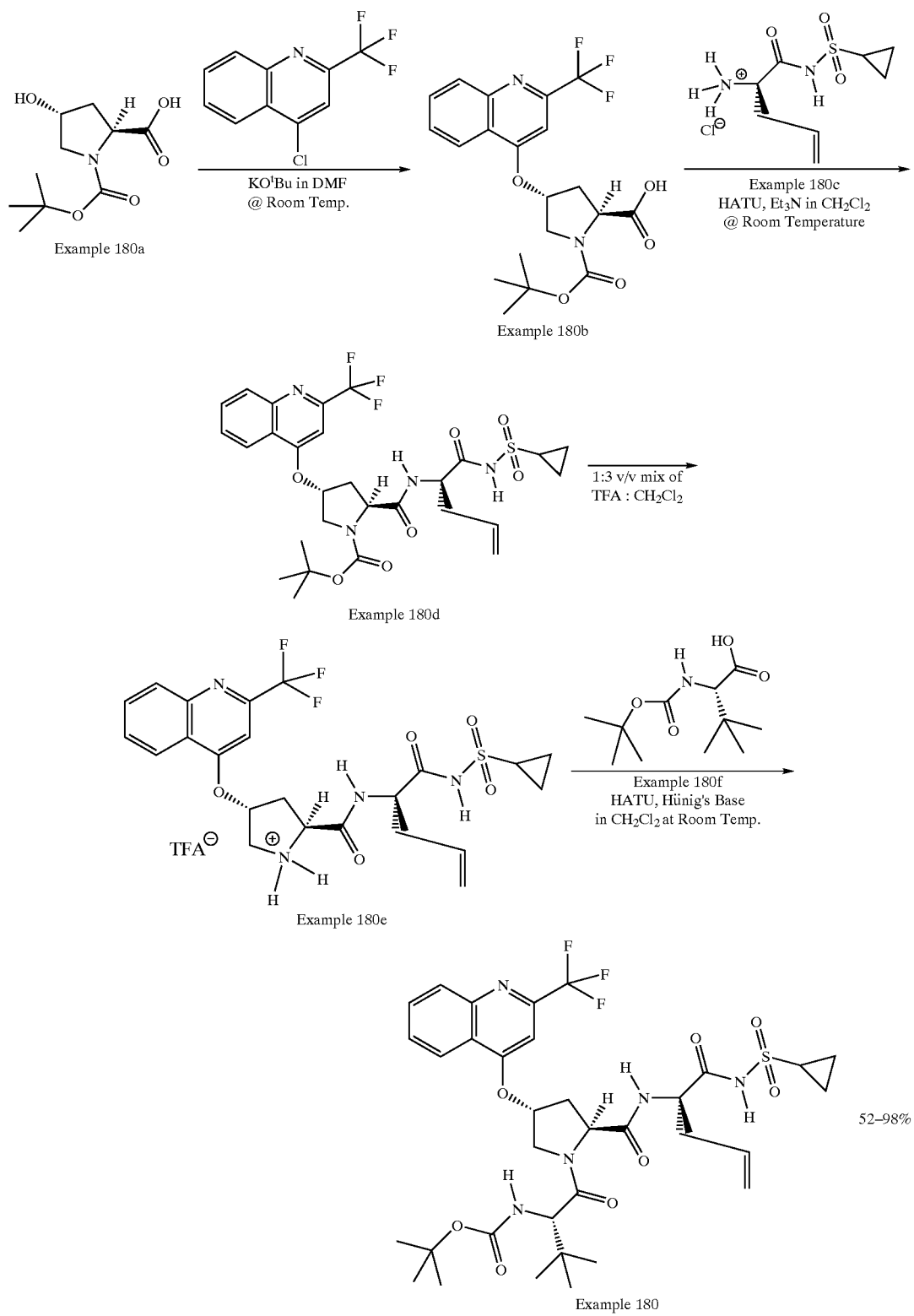

in THF (as supplied by Aldrich Chemicals) in DMF offered a more convenient work up procedure: most of the DMF solvent was washed away with water once the alkylation was complete.

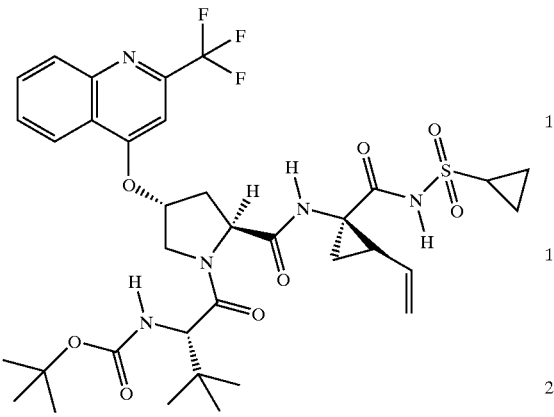

Thus Compound 180: BOCNH-P3(L-tert-BuGly)-P2[(4R)-(2-trifluoromethyl quinolin-4-oxo)-S-proline]-P1 (1R, 2S Vinyl Acca)-CONHSO$_2$-Cyclopropane: the material was obtained as a white foam in 61% yield. LC/MS R$_t$-min (MNa$^+$) [method A]: 3.35 (774). $^1$H NMR (400 MHz, CD$_3$OD) δ ppm 1.05 (m, 13 H) 1.21 (s, 9 H) 1.42 (dd, J=9.17, 5.26 Hz, 1 H) 1.86 (dd, J=8.07, 5.38 Hz, 1 H) 2.21 (m, 1H) 2.33 (m, 1 H) 2.64 (dd, J=13.94, 6.60 Hz, 1H) 2.93 (m, 1H) 4.09 (dd, J=11.49, 2.69 Hz, 1 H) 4.21 (s, 1 H) 4.52 (m, 1 H) 4.56 (d, J=12.23 Hz, 1 H) 5.10 (dd, J=10.39, 1.59 Hz, 1 H) 5.27 (d, J=16.87 Hz, 1 H) 5.58 (s, 1 H) 5.72 (m, 1 H) 7.36 (s, 1 H) 7.61 (t, J=7.70 Hz, 1 H) 7.83 (t, J=7.34 Hz, 1 H) 8.07 (d, J=8.56 Hz, 1 H) 8.26 (d, J=8.56 Hz, 1 H).

Example 181

Preparation of Compound 181

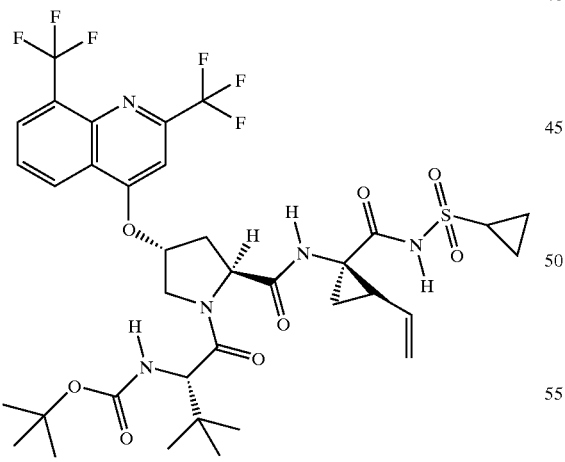

BOCNH-P3 (L-tert-BuGly)-P2[(4R)-(2,8-bistrifluoromethyl quinolin-4-oxo)-S-proline]-P1(1R,2S Vinyl Acca)-CONHSO$_2$-Cyclopropane: the material was obtained as a white foam in 52% yield. LC/MS R$_t$-min (MNa$^+$) [method A]: 3.60 (843). $^1$H NMR (400 MHz, CD$_3$OD) δ ppm 1.05 (m, 11 H) 1.16 (s, 9 H) 1.22 (m, 2 H) 1.42 (dd, J=9.29, 5.38 Hz, 1 H) 1.86 (dd, J=8.07, 5.38 Hz, 1 H) 2.21 (q, J=8.97 Hz, 1 H) 2.33 (m, 1 H) 2.65 (dd, J=13.94, 6.85 Hz, 1 H) 2.93 (m, 1 H) 4.07 (dd, J=11.98, 2.69 Hz, 1 H) 4.17 (s, 1 H) 4.52 (dd, J=10.52, 6.85 Hz, 1 H) 4.58 (d, J=11.98 Hz, 1 H) 5.10 (d, J=10.27 Hz, 1 H) 5.27 (d, J=17.12 Hz, 1 H) 5.60 (s, 1 H) 5.72 (m, 1 H) 7.46 (s, 1 H) 7.69 (t, J=7.83 Hz, 1 H) 8.18 (d, J=7.34 Hz, 1 H) 8.50 (d, J=8.31 Hz, 1 H).

Example 182

Preparation of Compound 182

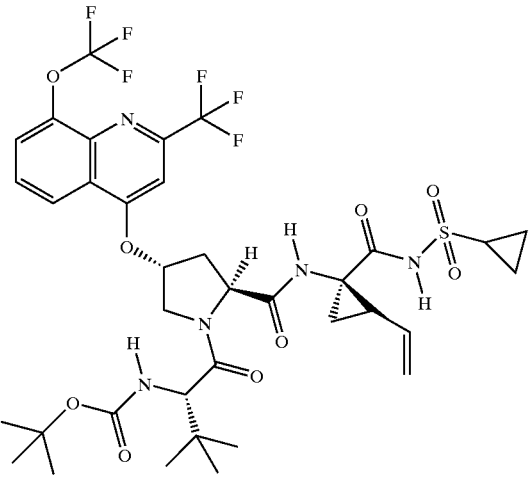

BOCNH-P3(L-tert-BuGly)-P2[(4R)-(2-trifluoromethyl, 8-trifluoromethoxy quinolin-4-oxo)-S-proline]-P1(1R,2S Vinyl Acca)-CONHSO$_2$-Cyclopropane: the material was obtained as a white foam in 99% yield. LC/MS R$_t$-min (MNa$^+$) [method A]: 3.62 (858). $^1$H NMR (400 MHz, CD$_3$OD) δ ppm 1.05 (m, 11 H) 1.21 (m, 11 H) 1.42 (dd, J=9.05, 5.14 Hz, 1 H) 1.86 (dd, J=8.07, 5.38 Hz, 1 H) 2.21 (q, J=8.64 Hz, 1 H) 2.33 (m, 1 H) 2.64 (dd, J=13.94, 6.60 Hz, 1 H) 2.93 (m, 1 H) 4.08 (dd, J=11.98, 2.69 Hz, 1 H) 4.18 (s, 1 H) 4.51 (dd, J=10.52, 6.85 Hz, 1 H) 4.57 (d, J=12.23 Hz, 1H) 5.10 (dd, J=10.52, 1.22 Hz, 1 H) 5.27 (d, J=17.12 Hz, 1 H) 5.59 (s, 1 H) 5.72 (m, 1 H) 7.44 (s, 1 H) 7.63 (t, J=8.07 Hz, 1 H) 7.78 (d, J=7.58 Hz, 1 H) 8.24 (d, J=8.56 Hz, 1 H).

Example 183

Preparation of Compound 183

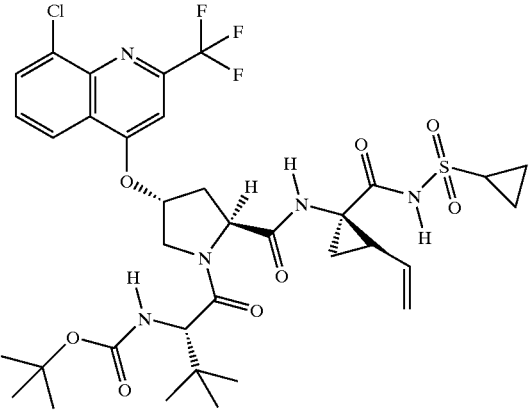

BOCNH-P3(L-tert-BuGly)-P2[(4R)-(2-trifluoromethyl, 8-chloro quinolin-4-oxo)-S-proline]-P1(1R,2S Vinyl Acca)-

CONHSO$_2$-Cyclopropane: the material was obtained as a white foam in 64% yield. LC/MS R$_t$-min (MNa$^+$) [method A]: 3.52 (808). $^1$H NMR (400 MHz, CD$_3$OD) δ ppm 1.04 (m, 11 H) 1.21 (m, 11 H) 1.41 (dd, J=9.41, 5.50 Hz, 1 H) 1.86 (dd, J=8.07, 5.62 Hz, 1 H) 2.20 (q, J=8.80 Hz, 1H) 2.32 (m, 1 H) 2.63 (dd, J=13.82, 6.72 Hz, 1 H) 2.92 (m, 1 H) 4.07 (dd, J=12.10, 2.81 Hz, 1 H) 4.19 (s, 1 H) 4.50 (dd, J=10.52, 6.85 Hz, 1 H) 4.56 (d, J=11.98 Hz, 1 H) 5.10 (dd, J=10.27, 1.47 Hz, 1 H) 5.26 (d, J=17.12 Hz, 1 H) 5.57 (s, 1 H) 5.72 (m, 1 H) 7.41 (s, 1 H) 7.52 (t, J=8.07 Hz, 1 H) 7.93 (d, J=7.58 Hz, 1 H) 8.19 (d, J=8.56 Hz, 1 H).

Example 184

General Procedure for Alkylation with the Tripeptide (Compound 184) and P2*

General Scheme—Preparation of Example 184 (Compound 184)

The preparation of the tripeptide component, Example 184 was achieved by a sequential amide coupling using HATU as the coupling agent. It is understood that many standard coupling agents could be employed for the following scheme.

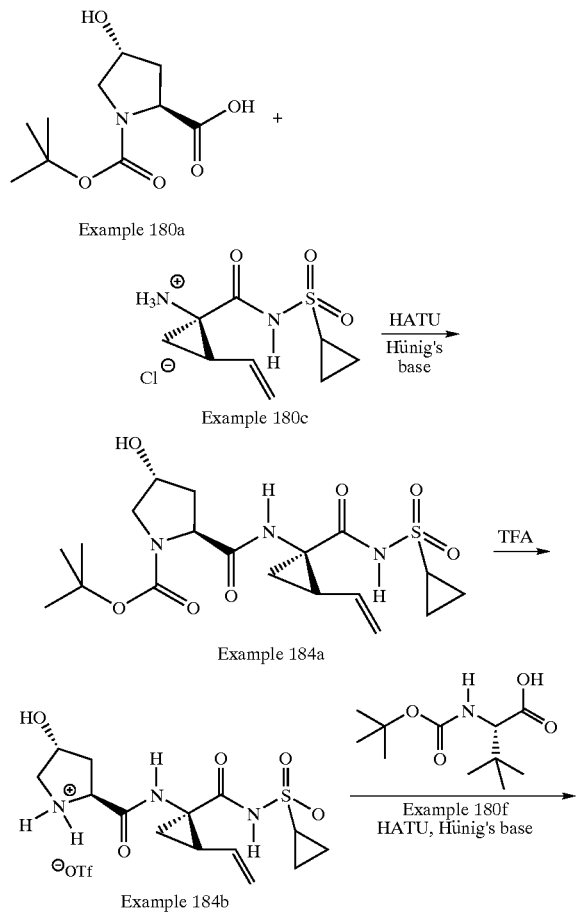

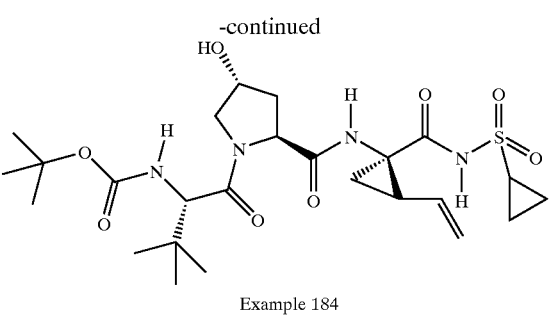

Example 184

Preparation of Intermediate Example 184a:
To a mixture of HATU (820 mg, 2.2 mmol), Example 180a (Boc-4R-hydroxyproline, 417 mg, 1.8 mmol) and Example 180c (cyclopropanesulfonic acid (1(R)-amino-2 (S)-vinyl-cyclopropanecarbonyl)-amide hydrochloride salt, 490 mg, 1.8 mmol) in a flame dried flask at room temperature was added dry CH$_2$Cl$_2$ (8 mL). The mixture was kept under dry N$_2$ before it was chilled to −78° C. Hunig's base (diisopropylethylamine, 625 μL, 3.6 mmol) was added slowly over a period 5 min and the mixture turned into a pale orange suspension. Stirring was continued for an hour while temperature was allow to raise to ambient. LC/MS showed complete conversion into the desired product 184a. The crude reaction was worked up as usual, washed with three portions (5 mL) of water, organic residues were extracted into ethyl acetate (3×5 mL). The crude product was obtained by removal of organic solvents in vacuo. The material was used in the next step without further purification.

Preparation of Intermediate Example 184b:
The dried solid from the previous step was taken into 9 mL of CH$_2$Cl$_2$ at room temperature. To this solution was added 3 mL of trifluoroacetic acid forming a pale yellowish solution. Stirring was continued for 2 hours at room temperature. LC/MS showed no starting material 184a while the desired product 184b was the major signal along with a signal correponding to a side product carried over from HATU in the step earlier. The solvents were evaporated and the solid residue was used in the next step immediately without further purification.

Preparation of the Tripeptide, Compound 184:

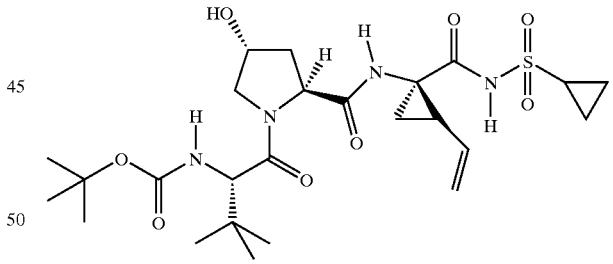

BOCNH-P3(L-tert-BuGly)-P2[(4R)-hydroxy-S-proline]-P1 (1R,2S Vinyl Acca)-CONHSO$_2$-Cyclopropane [Notebook 46877-128]

The crude product from the previous step (Example 184b, 1.8 mmol) was mixed with HATU (700 mg, 1.8 mmol) and BOC-L-tert-leucine (Example 180f, Fluka Chemicals, 420 mg, 1.8 mmol) in CH$_2$Cl$_2$ (10 mL) at room temperature. To this suspension was treated Huinig's base (1 mL, excess) forming a somewhat thinner, orange suspension. LC/MS showed some conversion into compound 184. Complete conversion into the desired product 184 was observed after stirring was continued for two days at room temperature. Crude reaction mixture was evaporated to dryness. The residue was taken into ethyl acetate. Most of HATU residue was removed by extractions with half saturated, freshly prepared sodium bicarbonate solution. The last traces of HATU residue (1-hydroxy 7-azabenzotriazole) was removed by washing with deionized water. Evaporation of solvents gave 990 mg (98%) of the desired product as white foam. This material is suitable for the subsequent alkylation with electrophiles such as quinolines and isoquinolines directly without further purification. LC/MS $R_t$-min (MNa$^+$) [method A]: 2.65 (579). $^1$H NMR (400 MHz, CD$_3$OD) δ ppm 0.95 (s, 2 H) 0.99 (s, 9 H) 1.05 (m, 2 H) 1.21 (m, 1 H) 1.39 (m, 9 H) 1.84 (dd, J=8.31, 5.38 Hz, 1 H) 1.96 (m, 1 H) 2.11 (m, 1 H) 2.20 (m, 1 H) 2.91 (m, 1 H) 3.80 (m, 2 H) 4.28 (d, J=9.78 Hz, 1 H) 4.35 (dd, J=9.90, 6.97 Hz, 1 H) 4.47 (s, 1 H) 5.11 (m, 1 H) 5.29 (d, J=17.12 Hz, 1 H) 5.75 (m, 1 H). Alkylation of the Tripeptide (Compound 184) with Electrophiles:

To a flame-dried 25 mL round bottom flask was charged with Compound 184, (0.5–1.0 mmol), substituted 4-chloroquinoline (1.0 equivalent) and lanthanum chloride (LaCl$_3$ anhydrous beads, used as supplied by Aldrich, M.W. 245 g/mol; 1.0 equivalent. Note: the inclusion of such additive was found to be helpful in some cases especially with those less reactive electrophiles. This reagent can, at times, be omitted if the electrophiles are sufficiently reactive towards anionic alkylation) in 2 mL dry DMF. The inorganic salt was only sparingly soluble in DMF at room temperature. The mixture was chilled to –78° C. (dry-ice/acetone bath) with stirring under nitrogen. To this chilled mixture was added a THF solution of potassium tert-butoxide (1.0 M, used as supplied by Aldrich, 5.5 equivalents) and the color of mixture changed from colorless to pale yellowish or greenish. It was stirred at –78° C. for a period dependent upon the 4-chloroquinoline reactivity (a few hrs. at –78° C. to overnight at room temperature). The inorganic salt was also found to change into a fine emulsion at the end. It was quenched with a half saturated NH$_4$Cl aqueous solution (2 mL). Organic materials were extracted into ethyl acetate (10 mL×3). Organic layers were combined, back washed with deionized water (10 mL×2). Evaporation of the organic fraction gave a crude mixture rich in the desired product as determined by LC/MS. The desired product was isolated by preparative HPLC using standard separation parameters (typically: 3.0×50 mm Xterra column @4 min gradient and 4 mL/min flow rate) to give the analytically pure desired product. The alkylation of 1-halo isoquinoline series was carried out in exactly the same way.

Example 185

Preparation of Compound 185

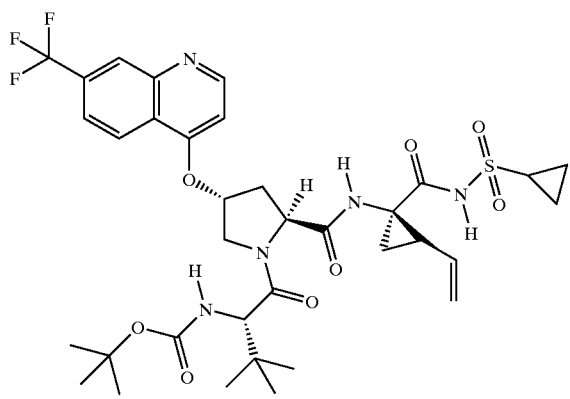

Following the general tripeptide alkylation procedure as described in Example 184, BOCNH-P3(L-tert-BuGly)-P2 [(4R)-(7-trifluoromethyl quinolin-4-oxo)-S-proline]-P1(1R, 2S Vinyl Acca)-CONHSO$_2$-Cyclopropane was obtained as a white foam in 50% yield. LC/MS $R_t$-min (MH$^+$) [method B]: 2.32 (752). $^1$H NMR (400 MHz, CD$_3$OD) δ ppm 1.02 (s, 9 H) 1.06 (m, 11 H) 1.22 (m, 2 H) 1.43 (dd, J=9.41, 5.26 Hz, 1 H) 1.88 (dd, 1=8.19, 5.50 Hz, 1 H) 2.23 (q, 1=8.80 Hz, 1 H) 2.42 (m, 1 H) 2.75 (dd, J=14.06, 6.48 Hz, 1 H) 2.93 (m, 1H) 4.10 (m, 2 H) 4.61 (m, 2H) 5.12 (dd, J=10.39, 1.59 Hz, 1 H) 5.29 (d, J=17.12 Hz, 1 H) 5.72 (m, 2 H) 7.61 (d, J=6.36 Hz, 1 H) 7.96 (d, J=8.80 Hz, 1 H) 8.38 (s, 1 H) 8.59 (d, J=8.56 Hz, 1 H) 9.14 (d, J=6.36 Hz, 1 H).

Example 186

Preparation of Compound 186

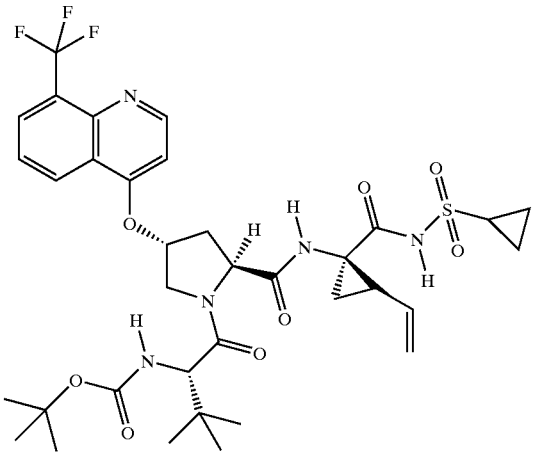

Following the general tripeptide alkylation procedure as described in Example 184, BOCNH-P3(L-tert-BuGly)-P2 [(4R)-(8-trifluoromethyl quinolin-4-oxo)-S-proline]-P1(1R, 2S Vinyl Acca)-CONHSO$_2$-Cyclopropane: the desired product was obtained as a white foam in 50% yield. LC/MS $R_t$-min (MH$^+$) [method B]: 2.48 (752). $^1$H NMR (400 MHz, CD$_3$OD) δ ppm 1.02 (s, 9 H) 1.05 (m, 2 H) 1.13 (s, 9 H) 1.23 (m, 2 H) 1.42 (dd, J=8.68, 5.50 Hz, 1 H) 1.87 (dd, J=8.07, 5.38 Hz, 1 H) 2.21 (q, J=8.80 Hz, 1 H) 2.36 (m, 1 H) 2.69 (dd, J=14.06, 6.97 Hz, 1 H) 2.93 (m, 1 H) 4.08 (dd, J=11.98, 2.93 Hz, 1 H) 4.15 (s, 1 H) 4.54 (dd, J=10.52, 7.09 Hz, 1 H) 4.60 (d, J=12.47 Hz, 1 H) 5.11 (dd, J=10.52, 1.71 Hz, 1 H) 5.28 (d, J=15.90 Hz, 1 H) 5.58 (s, 1 H) 5.72 (m, 1 H) 7.32 (d, J=5.87 Hz, 1 H) 7.69 (t, J=7.95 Hz, 1 H) 8.22 (d, J=7.09 Hz, 1 H) 8.55 (d, J=8.07 Hz, 1 H) 8.88 (d, J=5.62 Hz, 1 H).

Preparation of isoquinoline intermediates for 6-F, 6-Ethyl, 6-isopropyl and 6-tert-butyl isoquinoline P2* building blocks.

In general, the 6-fluoro and 6-alkyl isoquinolines used in the following experiments were prepared via a Pomeranz-Fritsch synthesis (Typical procedure: Preparation of optically active 8,8-disubstituted 1,1-biisoquinoline, K. Hirao, R. Tsuchiya, Y. Yano, H. Tsue, *Heterocycles* 42(1) 1996, 415–422) as outlined below. The products were converted into the 1-chloro derivatives via N-oxide intermediates as described elsewhere.

235

General Synthetic Scheme

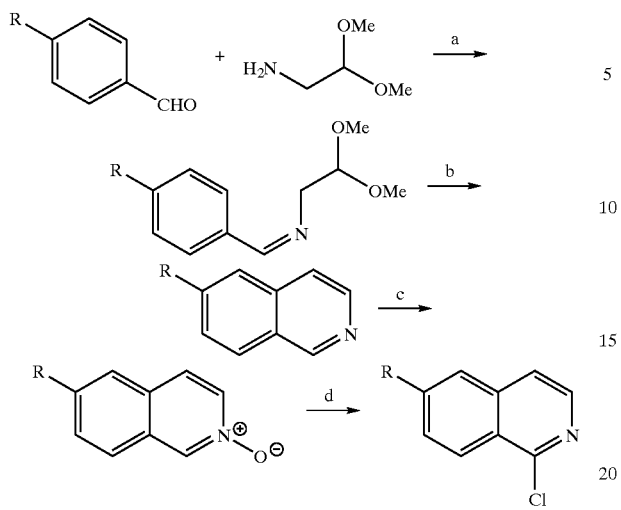

Reagents and reaction conditions: (a) reflux in benzene, azeotropic removal of water; (b) first step: ethyl chloroformate, trimethyl phosphite in THF, second step: titanium tetrachloride in chloroform; (c) MCPBA in CH₂Cl₂; (d) POCl₃ in benzene

| R | Isoquinoline, Yield | 1-Chloride, combined yield |
|---|---|---|
| F | 20 | 43 |
| Et | 76 | 65 |
| i-Pr | 14 | 18 |
| t-Bu | 47 | 55 |

Example 187

Preparation of Compound 187

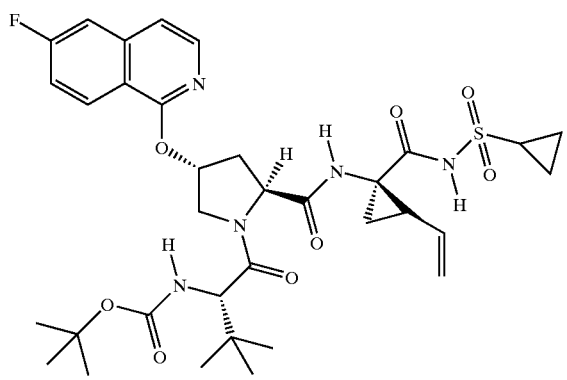

BOCNH-P3(L-tert-BuGly)-P2[(4R)-(6-fluoro isoquinolin-1-oxo)-S-proline]-P1(1R,2S Vinyl Acca)-CONHSO₂-Cyclopropane: the material was obtained as a white foam in 12% yield. LC/MS $R_t$-min (MNa⁺) [method C]: 3.81 (724). ¹H NMR (400 MHz, CD₃OD) δ ppm 1.05 (m, 13 H) 1.22 (s, 9 H) 1.42 (m, 1 H) 1.86 (m, 1 H) 2.21 (m, 2 H) 2.61 (dd, J=13.69, 6.60 Hz, 1 H) 2.93 (m, 1 H) 4.05 (d, J=13.69 Hz, 1 H) 4.21 (s, 1 H) 4.49 (m, 2 H) 5.11 (d, J=10.03 Hz, 1 H) 5.28 (d, J=17.61 Hz, 1 H) 5.72 (m, 1 H) 5.86 (d, J=4.40 Hz, 1 H) 7.31 (m, 2 H) 7.48 (d, J=8.31 Hz, 1 H) 7.97 (d, J=6.36 Hz, 1 H) 8.26 (d, J=6.11 Hz, 1 H).

236

Example 188

Preparation of Compound 188

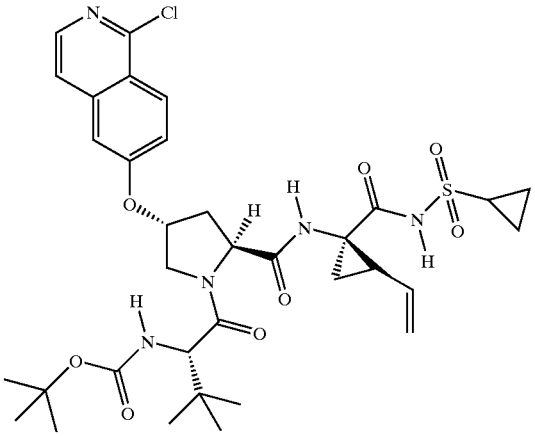

The alkylation described above gave the 1-chloroisoquinoline as the major product: BOCNH-P3 (L-tert-BuGly)-P2[(4R)-(1-chloro isoquinolin-6-oxo)-S-proline]-P1(1R,2S Vinyl Acca)-CONHSO₂-Cyclopropane: the material was obtained as a white foam in 40.2% yield. LC/MS $R_t$-min (MH⁺) [method C]: 3.81 (718). ¹H NMR (400 MHz, CD₃OD) δ ppm 1.00 (s, 9 H) 1.06 (m, 2 H) 1.25 (s, 11 H) 1.41 (m, 1 H) 1.86 (dd, J=8.07, 5.38 Hz, 1 H) 2.25 (m, 2 H) 2.54 (dd, J=12.96, 6.60 Hz, 1H) 2.92 (m, 1 H) 4.06 (dd, J=11.98, 2.69 Hz, 1 H) 4.20 (s, 1 H) 4.31 (d, J=11.74 Hz, 1 H) 4.45 (dd, J=9.78, 7.58 Hz, 1 H) 5.11 (dd, J=10.27, 1.71 Hz, 1 H) 5.28 (dd, J=17.36, 1.47 Hz, 1 H) 5.36 (s, 1 H) 5.74 (m, 1 H) 7.35 (d, J=9.29 Hz, 1H) 7.40 (s, 1 H) 7.70 (d, J=5.87 Hz, 1 H) 8.13 (d, J=5.87 Hz, 1 H) 8.25 (d, J=9.29 Hz, 1 H).

Example 189

Preparation of Compound 189

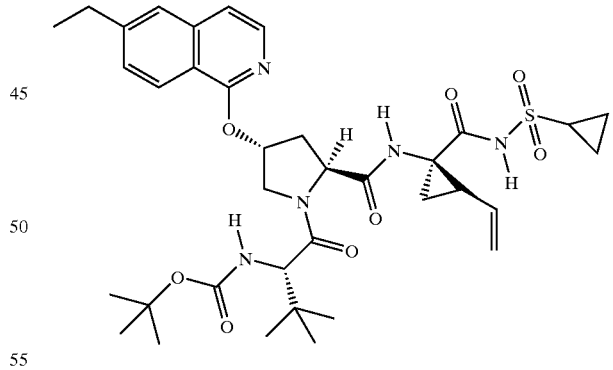

BOCNH-P3 (L-tert-BuGly)-P2[(4R)-(6-ethyl isoquinolin-1-oxo)-S-proline]-P1 (1R,2S Vinyl Acca)-CONHSO₂-Cyclopropane: the material was obtained as a white foam in 4.6 mg of yellow solid was obtained (4.2%). LC/MS rt-min (MH⁺) [method B]: 2.70 (712). ¹H NMR (400 MHz, CD3OD) δ ppm 1.01 (s, 9 H) 1.07 (m, 2 H) 1.22 (m, 11 H) 1.28 (t, J=7.91 Hz, 3 H) 1.41 (m, 1 H) 1.85 (m, 1 H) 2.25 (m, 2 H) 2.60 (dd, J=13.69, 6.85 Hz, 1 H) 2.80 (q, J=7.66 Hz, 2 H) 2.93 (m, 1 H) 4.02 (d, J=31.06 Hz, 1 H) 4.23 (s, 1 H) 4.42 (m, 1 H) 4.54 (m, 1 H) 5.10 (d, J=10.27 Hz, 1 H) 5.28 (d, J=17.12 Hz, 1 H) 5.74 (m, 1 H) 5.84 (s, 1 H) 7.25

(d, J=5.87 Hz, 1 H) 7.38 (d, J=8.56 Hz, 1 H) 7.59 (s, 1 H) 7.90 (d, J=6.24 Hz, 1 H) 8.09 (d, J=8.56 Hz, 1 H).

Example 190

Preparation of Compound 190

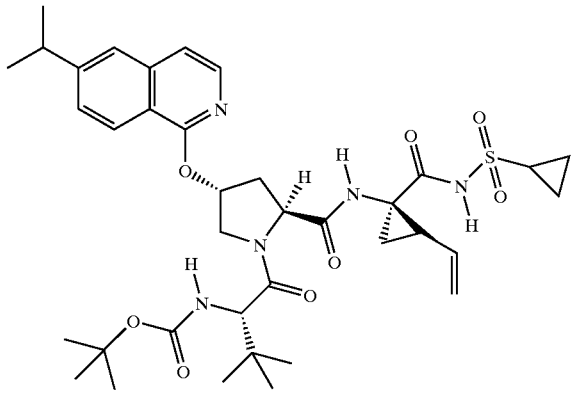

BOCNH-P3(L-tert-BuGly)-P2[(4R)-(6-isopropyl isoquinolin-1-oxo)-S-proline]-P1(1R,2S Vinyl Acca)-CONHSO$_2$-Cyclopropane: the material was obtained as a white foam in 69% yield. LC/MS R$_t$-min (MNa$^+$) [method B]: 2.76 (749). $^1$H NMR (400 MHz, CD$_3$OD) δ ppm 1.05 (m, 13 H) 1.20 (m, 9 H) 1.31 (d, J=6.85 Hz, 6 H) 1.42 (m, 1 H) 1.86 (dd, J=8.07, 5.62 Hz, 1 H) 2.26 (m, 2H) 2.62 (dd, J=13.69, 6.85 Hz, 1 H) 2.93 (m, 1 H) 3.07 (m, 1 H) 4.06 (m, 1 H) 4.21 (s, 1 H) 4.52 (m, 2H) 5.11 (d, J=10.27 Hz, 1 H) 5.28 (d, J=17.12 Hz, 1 H) 5.74 (m, 1 H) 5.84 (s, 1 H) 7.32 (d, J=6.11 Hz, 1 H) 7.46 (d, J=8.56 Hz, 1 H) 7.64 (s, 1 H) 7.90 (d, J=6.11 Hz, 1 H) 8.13 (d, J=8.56 Hz, 1 H).

Example 191

Preparation of Compound 191

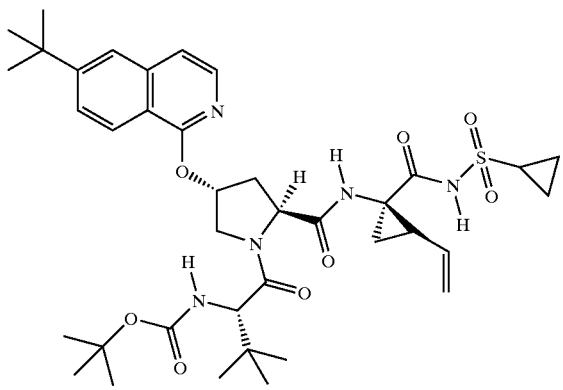

BOCNH-P3(L-tert-BuGly)-P2[(4R)-(6-tert-butyl isoquinolin-1-oxo)-S-proline]-P1(1R,2S Vinyl Acca)-CONHSO$_2$-Cyclopropane: the material was obtained as a white foam in 81% yield. LC/MS R$_t$-min (MH$^+$) [method B]: 2.84 (740). $^1$H NMR (400 MHz, CD$_3$OD) δ ppm 1.01 (s, 9 H) 1.06 (m, 2 H) 1.18 (s, 9 H) 1.22 (m, 2 H) 1.39 (s, 9 H) 1.43 (m, 1 H) 1.87 (dd, J=8.19, 5.50 Hz, 1 H) 2.27 (m, 2 H) 2.63 (dd, J=13.57, 6.97 Hz, 1 H) 2.93 (m, 1 H) 4.06 (m, 1 H) 4.20 (s, 1 H) 4.52 (m, 2 H) 5.10 (d, J=11.49 Hz, 1 H) 5.28 (d, J=17.12 Hz, 1 H) 5.73 (m, 1 H) 5.84 (s, 1 H) 7.36 (d, J=6.11 Hz, 1 H) 7.66 (dd, J=8.80, 1.22 Hz, 1 H) 7.78 (s, 1 H) 7.91 (d, J=5.87 Hz, 1 H) 8.15 (d, J=8.80 Hz, 1 H).

Preparation of 6-isopropoxyl and 6-tert-butoxyl Isoquinoline Intermediates:

Some 6-alkoxy-1-chloro isoquinolines were prepared by a direct, ipso displacement of the 6-fluoro-1-chloroisoquinoline with the corresponding alkoxide metal ions such as potassium tert-butoxide (53%) and sodium isopropoxide (54%).

General Synthetic Scheme

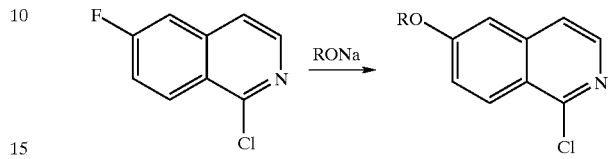

R=alkoxide anions such as tert-Bu, iso-Pr

The 6-fluoro-1-chloroisoquinoline was subjected to an aromatic nucleophilic displacement with sodium isopropoxide and potassium tert-butoxide in DMF to give the corresponding 6-isopropoxyl (54%): $^1$H NMR (400 MHz, CHLOROFORM-d) δ ppm 1.43 (d, J=6.11 Hz, 6 H) 4.76 (m, J=6.11 Hz, 1 H) 7.08 (d, J=2.45 Hz, 1 H) 7.29 (dd, J=9.29, 2.45 Hz, 1 H) 7.50 (d, J=5.62 Hz, 1 H) 8.18 (d, J=5.87 Hz, 1 H) 8.24 (d, J=9.29 Hz, 1 H) and 6-tert-butoxyl-1-chloro isoquinolines (55%): $^1$H NMR (400 MHz, CHLOROFORM-d) δ ppm 1.48 (s, 9 H) 7.31 (m, 2 H) 7.47 (d, J=5.62 Hz, 1 H) 8.18 (d, J=5.62 Hz, 1 H) 8.21 (d, J=9.78 Hz, 1 H) as the major product respectively. These 6-alkoxyl-1-chloro isoquinolines were alkylated with the tripeptide as described in Example 184 to give the desired products shown below.

Example 192

Preparation of Compound 192

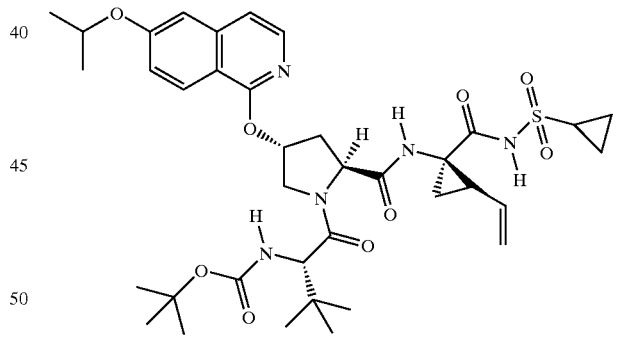

BOCNH-P3(L-tert-BuGly)-P2[(4R)-(6-isopropoxy isoquinolin-1-oxo)-S-proline]-P1(1R,2S Vinyl Acca)-CONHSO$_2$-Cyclopropane: the material was obtained as a white foam in 59% yield. LC/MS R$_t$-min (MH$^+$) [method C]: 3.87 (742). $^1$H NMR (400 MHz, CD$_3$OD) δ ppm 0.99 (s, 11 H) 1.06 (m, 2 H) 1.21 (s, 9 H) 1.37 (d, J=5.87 Hz, 6 H) 1.42 (m, 1 H) 1.86 (dd, J=8.07, 5.38 Hz, 1 H) 2.25 (m, 2 H) 2.61 (dd, J=13.69, 6.85 Hz, 1 H) 2.92 (m, 1 H) 4.04 (dd, J=11.86, 3.30 Hz, 1 H) 4.21 (br. s, 1 H) 4.49 (m, 2 H) 4.78 (h, J=5.87 Hz, 1 H) 5.10 (dd, J=10.39, 1.35 Hz, 1 H) 5.28 (d, J=16.87 Hz, 1 H) 5.73 (m, 1 H) 5.79 (d, J=11.25 Hz, 1 H) 7.07 (dd, J=9.05, 1.96 Hz, 1 H) 7.18 (d, J=2.20 Hz, 1 H) 7.26 (d, J=6.11 Hz, 1 H) 7.85 (d, J=6.11 Hz, 1 H) 8.10 (d, J=9.05 Hz, 1 H).

Example 193

Preparation of Compound 193

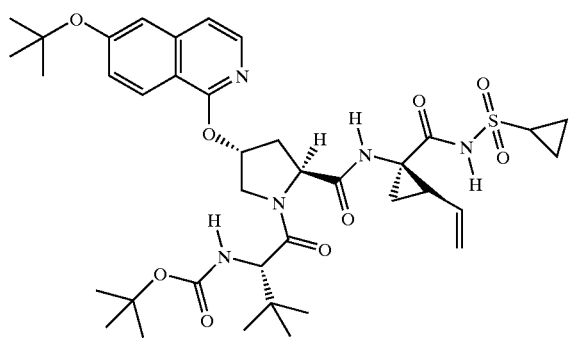

BOCNH-P3(L-tert-BuGly)-P2[(4R)-(6-tert-butoxy isoquinolin-1-oxo)-S-proline]-P1(1R,2S Vinyl Acca)-CONHSO$_2$-Cyclopropane: the material was obtained as a white foam in 39% yield. LC/MS R$_t$-min (MH$^+$) [method C]: 3.99 (756). $^1$H NMR (400 MHz, CD$_3$OD) δ ppm 1.03 (br s, 13 H) 1.19 (s, 9 H) 1.42 (m, 10 H) 1.86 (dd, J=7.83, 5.62 Hz, 1 H) 2.24 (m, 2 H) 2.60 (dd, J=13.69, 6.85 Hz, 1 H) 2.93 (m, 1H) 4.04 (dd, J=11.49, 2.93 Hz, 1 H) 4.23 (s, 1 H) 4.49 (m, 2 H) 5.10 (d, J=11.25 Hz, 1 H) 5.27 (d, J=16.87 Hz, 1 H) 5.73 (m, 1 H) 5.81 (s, 1 H) 7.13 (dd, J=8.80, 1.47 Hz, 1 H) 7.25 (d, J=5.87 Hz, 1 H) 7.33 (d, J=2.20 Hz, 1 H) 7.87 (d, J=6.11 Hz, 1 H) 8.10 (d, J=9.05 Hz, 1 H).

Preparation of Phthalazine P2* Derivatives:

In general, both 1-chlorophthalazine and 1,4-dichlorophthalazine undergo alkylation smoothly to give the desired products. However, the commercially available 1-chlorophthalazine and 1,4-dichlorophthalazine are often contaminated with some hydrolyzed materials. A pretreatment with POCl$_3$ followed by alkylation immediately afterward furnished more consistent results.

General Synthetic Scheme

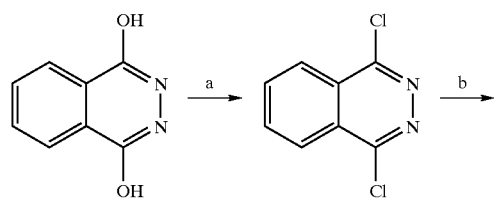

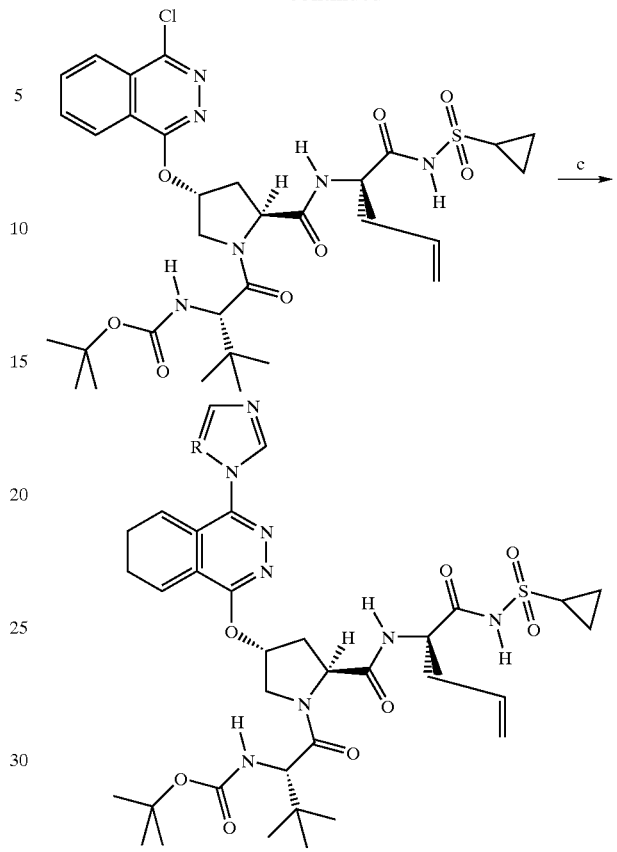

Reaction Conditions: (a) POCl$_3$ in DCE; (b) Alkylation with tripeptide; (c) sodio derivatives of imidazole (R=CH), triazole (R=N)

Example 194

Preparation Compound 194

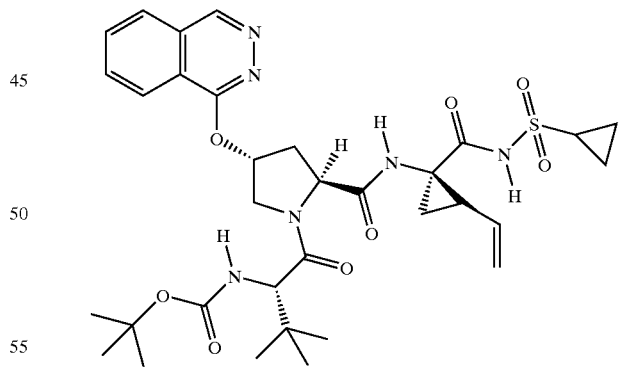

BOCNH-P3(L-tert-BuGly)-P2 [(4R)-(phthalazine-1-oxo)-S-proline]-P1(1R,2S Vinyl Acca)-CONHSO$_2$-Cyclopropane: the material was obtained as a white foam in 41% yield. LC/MS R$_t$-min (MNa$^+$) [method B]: 2.07 (707). $^1$H NMR (400 MHz, CD$_3$OD) δ ppm 1.03 (m, 9 H) 1.06 (m, 4 H) 1.14 (s, 9 H) 1.20 (m, 1 H) 1.43 (m, 1H) 1.87 (dd, J=8.07, 5.62 Hz, 1 H) 2.24 (q, J=8.80 Hz, 1 H) 2.38 (m, 1 H) 2.76 (dd, J=14.18, 7.09 Hz, 1 H) 2.92 (m, 1 H) 4.11 (m, 2 H) 4.62 (m, 1 H) 5.11 (dd, J=10.27, 1.71 Hz, 1 H) δ 5.29

(dd, J=17.12, 1.22 Hz, 1 H) 5.72 (m, 1 H) 5.96 (s, 1 H) 8.26 (m, 2 H) 8.46 (m, 2 H) 9.84 (s, 1 H).

Example 195

Preparation of Compound 195

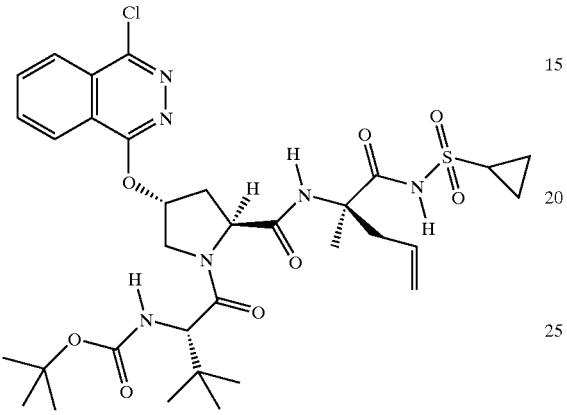

BOCNH-P3(L-tert-BuGly)-P2[(4R)-(4-chloro phthalazine-1-oxo)-S-proline]-P1(1R,2S Vinyl Acca)-CONHSO₂-Cyclopropane: the material was obtained as a white foam in 23% yield. LC/MS R_t-min (MNa⁺) [method C]: 3.52 (742). ¹H NMR (400 MHz, CD₃OD) δ ppm 1.01 (s, 11 H) 1.06 (m, 2 H) 1.14 (s, 9H) 1.22 (m, 1H) 1.43 (m, 1 H) 1.87 (m, 1 H) 2.21 (m, 1 H) 2.35 (m, J=10.27 Hz, 1 H) 2.70 (m, 1 H) 2.93 (m, 1 H) 4.05 (d, J=3.42 Hz, 1 H) 4.58 (m, 2 H) 5.11 (dd, J=10.39, 1.10 Hz, 1 H) 5.28 (d, J=17.36 Hz, 1 H) 5.73 (m, 1 H) 5.93 (s, 1 H) 7.99 (m, 1 H) 8.07 (t, J=7.70 Hz, 1 H) 8.26 (dd, J=8.19, 2.32 Hz, 2 H).

Preparation of 4-(imidazo-1-yl)phthalazine and 4-(1,2,4-triazo-1-yl)phthalazine P2* Derivatives:

The product, compound 195 from above, BOCNH-P3(L-tert-BuGly)-P2[(4R)-(4-chloro phthalazine-1-oxo)-S-proline]-P1(1R,2S Vinyl Acca)-CONHSO₂-Cyclopropane, was subjected to displacement by the anions of typical azoles such as imidazole and triazole to give 4-azole substituted phthalazine derivatives shown below:

Example 196

Preparation of Compound 196

This was made by displacing the 4-chloro phthalazine (Compound 195) with the sodium salt of imidazole in DMF at 55–65° C.

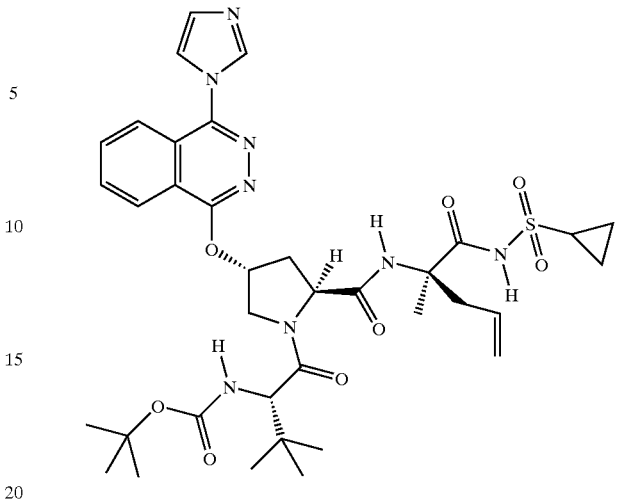

BOCNH-P3(L-tert-BuGly)-P2[(4R)-(4-(imidazo-1-yl) phthalazine-1-oxo)-S-proline]-P1(1R,2S Vinyl Acca)-CONHSO₂-Cyclopropane: the material was obtained as a white foam in 23% yield. LC/MS R_t-min (MNa⁺) [method B]: 1.94 (773). ¹H NMR (400 MHz, CD₃OD) δ ppm 1.03 (s, 9 H) 1.07 (m, 2 H) 1.20 (m, 9 H) 1.24 (m, 1H) 1.41 (m, 2 H) 1.88 (dd, J=8.19, 5.50 Hz, 1H) 2.23 (m, 1H) 2.41 (m, 1H) 2.75 (m, J=14.92 Hz, 1 H) 2.93 (m, 1 H) 4.14 (m, 2 H) 4.60 (dd, J=10.15, 6.97 Hz, 2 H) 5.12 (dd, J=10.27, 1.47 Hz, 1 H) 5.29 (dd, J=17.24, 1.35 Hz, 1 H) 5.74 (m, 1 H) 6.09 (s, 1 H) 7.85 (s, 1 H) 7.94 (m, 1 H) 8.10 (m, 2 H) 8.43 (m, 1 H) 9.17 (s, 1 H) 9.46 (s, 1 H).

During the displacement reaction, small amount of de-BOC by-product (Compound 197) was also isolated:

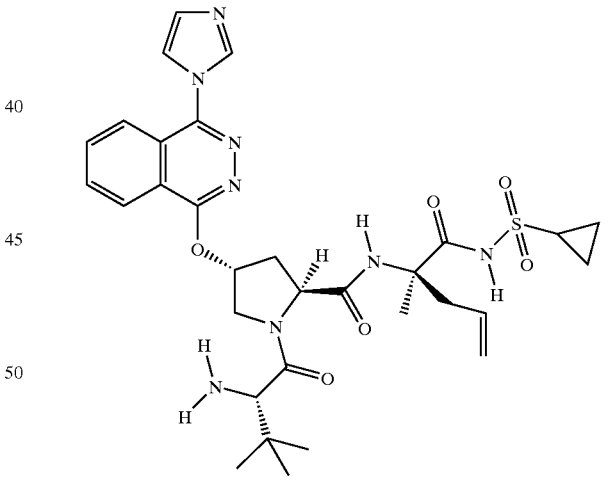

NH₂—P3(L-tert-BuGly)-P2[(4R)-(4-(imidazo-1-yl) phthalazine-1-oxo)-S-proline]-P1(1R,2S Vinyl Acca)-CONHSO₂-Cyclopropane: the material was obtained as a white foam in 17% yield. LC/MS R_t-min (MH⁺) [method B]: 1.22 (651). ¹H NMR (400 MHz, CD₃OD) δ ppm 1.16 (s, 9 H) 1.23 (m, 2 H) 1.42 (dd, J=9.41, 5.50 Hz, 1H) 1.89 (m, 1 H) 2.26 (q, J=8.97 Hz, 1 H) 2.43 (m, 1H) 2.78 (dd, J=14.06, 7.21 Hz, 1 H) 2.93 (m, 1 H) 3.74 (m, 1 H) 4.11 (s, 1 H) 4.22 (dd, J=12.23, 3.91 Hz, 1H) 4.47 (m, 2 H) 4.71 (dd, J=10.27, 7.09 Hz, 1 H) 5.12 (m, 1 H) 5.29 (d, J=17.36 Hz, 1 H) 5.71 (m, 1 H) 6.13 (t, J=3.67 Hz, 1 H) 7.87 (s, 1 H) 7.97 (m, 1 H) 8.14 (m, 3 H) 8.41 (m, 1 H) 9.47 (s, 1 H).

Example 198

Preparation Compound 198

This was made by displacing the 4-chloro phthalazine (Compound 195) with the sodium salt of 1,2,4-triazole in DMF at 55–65° C.

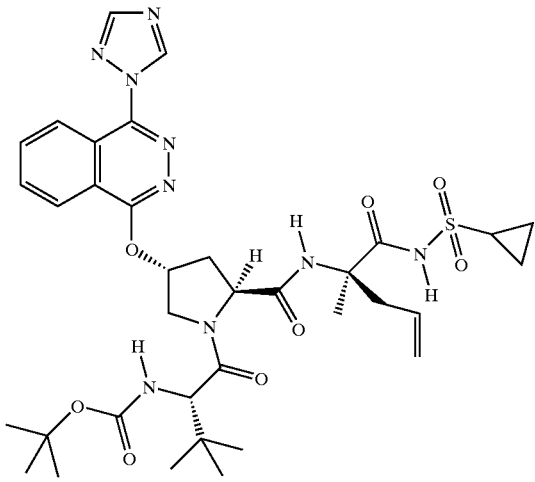

BOCNH-P3(L-tert-BuGly)-P2[(4R)-(4-(1,2,4-triazo-1-yl) phthalazine-1-oxo)-S-proline]-P1(1R,2S Vinyl Acca)-CONHSO$_2$-Cyclopropane: the material was obtained as a white foam in 62% yield. LC/MS R$_t$-min (MNa$^+$) [method C]: 3.35 (774). $^1$H NMR (500 MHz, CD$_3$OD) δ ppm 0.97 (s, 9 H), 1.01 (m, 2H) 1.10 (s, 9H) 1.16 (m, 1H) 1.37 (m, 2 H) 1.82 (m, 1 H) 2.18 (d, J=8.55 Hz, 1 H) 2.32 (m, 1 H) 2.69 (dd, J=13.58, 6.87 Hz, 1 H) 2.88 (br s, 1 H) 4.06 (d, J=11.60 Hz, 1 H) 4.13 (s, 1 H) 4.53 (m, J=9.16 Hz, 1 H) 4.61 (d, J=11.90 Hz, 1H) 5.06 (d, J=10.07 Hz, 1H) 5.23 (d, J=17.40 Hz, 1 H) 5.68 (m, 1 H) 5.98 (s, 1 H) 7.97 (m, 2 H) 8.30 (m, J=11.90 Hz, 2 H) 8.44 (d, J=7.63 Hz, 1 H) 9.14 (s, 1 H).

Preparation of 4-Hydroxy and 4-Alkoxy Phthalazine P2* Derivatives

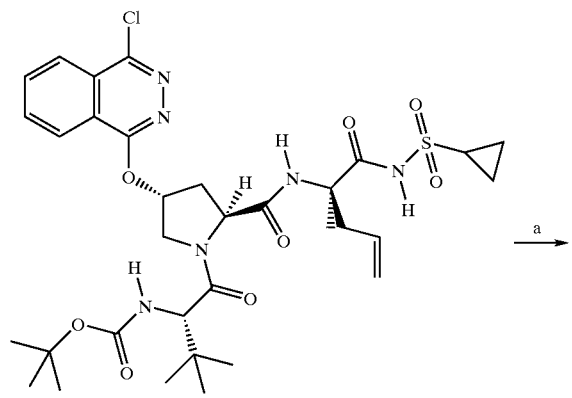

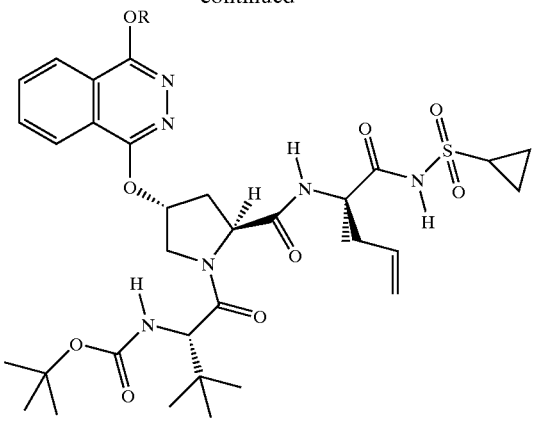

Reaction Conditions: (a) sodium alkoxides such as methoxide, ethoxide and isopropoxide

Example 199

Preparation of Compound 199

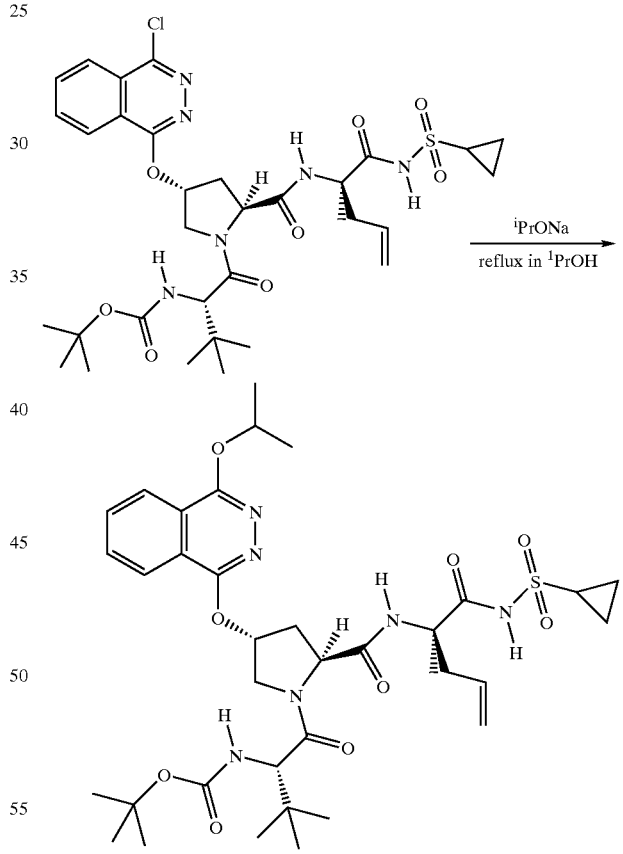

The 4-chloro phthalazine (Example 195) was dissoved in dry isopropyl alcohol at room temperature and 1.0 eq of sodium isoproxide was added, the resulted suspension was brought to reflux. The desired product, 4.5 mg of yellow solid was obtained (20.0%). LC/MS rt-min (MH$^+$): 2.68 (743) [method B]. $^1$H NMR (400 MHz, CD3OD) δ ppm 1.02 (m, 11 H) 1.20 (m, 11H) 1.42 (m, 1 H) 1.49 (d, J=6 Hz, 6 H) 1.87 (dd, J=7.95, 5.50 Hz, 1 H) 2.21 (m, 1 H) 2.23 (m, 1 H) 2.66 (m, 1 H) 2.93 (m, 1 H) 4.08 (q, J=7.09 Hz, 1 H)

4.19 (s, 1 H) 4.55 (m, 2 H) 5.11 (d, J=10.27 Hz, 1 H) 5.28 (d, J=17.61 Hz, 1 H) 5.48 (m, 1 H) 5.70 (d, J=10.03 Hz, 1 H) 5.81 (m, 1 H) 7.90 (m, 2 H) 8.16 (m, 2 H).

Example 200

Preparation of Compound 200

Likewise, the 4-ethoxy derivative was prepared: BOCNH-P3 (L-t-BuGly)-P2[(4R)-(4-ethoxyphthalazine-1-oxo)-S-proline]-P1(1R,2S VinylAcca)-CONHSO₂Cyclopropane.

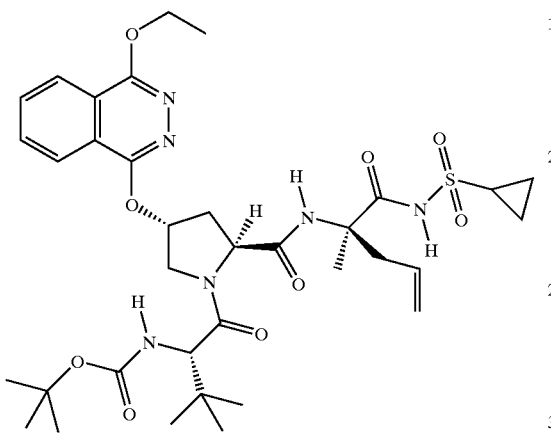

4.0 mg of yellow solid was obtained (16.0%). LC/MS rt-min (MH⁺): 2.52 (729) [method B]. ¹H NMR (400 MHz, CD3OD) δ ppm 1.01 (s, 9 H) 1.06 (m, 2 H) 1.16 (s, 9 H) 1.24 (m, 2 H) 1.43 (dd, J=9.78, 5.14 Hz, 1 H) 1.53 (t, J=6.97 Hz, 3H) 1.87 (dd, J=8.19, 5.50 Hz, 1 H) 2.22 (q, J=8.97 Hz, 1 H) 2.32 (m, 1 H) 2.67 (m, 1 H) 2.93 (m, 1 H) 4.06 (d, J=8.56 Hz, 1 H) 4.19 (s, 1 H) 4.56 (m, 4 H) 5.10 (m, 1 H) 5.30 (m, 1 H) 5.74 (m, 1 H) 5.82 (s, 1 H) 7.94 (m, 2 H) 8.16 (d, J=7.83 Hz, 1 H) 8.21 (m, 1 H).

Example 201

Preparation of Compound 201

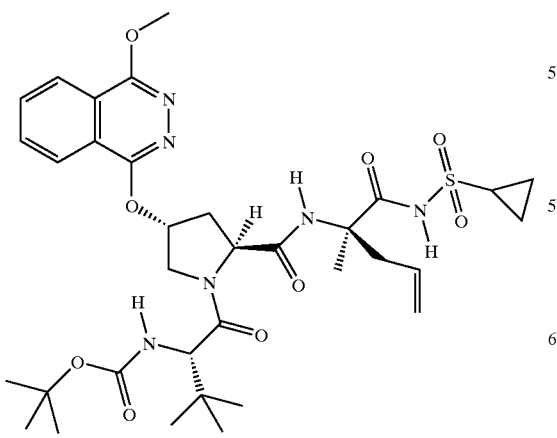

BOCNH-P3 (L-t-BuGly)-P2 [(4R)-(4-methoxyphthalazine-1-oxo)-S-proline]-P1 (1R,2S VinylAcca)-CONHSO₂Cyclopropane was prepared in 30.2% yield. LC/MS rt-min (MH⁺): 2.42 (715) [method B] ¹H NMR (400 MHz, CD₃OD) δ ppm 0.96 (s, 9 H) 1.07 (m, 2 H) 1.20 (m, 11 H) 1.43 (dd, J=9.29, 5.38 Hz, 1 H) 1.87 (dd, J=8.07, 5.62 Hz, 1H) 2.22 (q, J=8.80 Hz, 1H) 2.31 (m, 1H) 2.66 (d, J=8.07 Hz, 1 H) 2.93 (m,1 H) 4.06 (dd, J=11.98, 3.18 Hz, 1 H) 4.19 (d, J=3.42 Hz, 4 H) 4.54 (m, 2 H) 5.11 (m, 1 H) 5.28 (d, J=17.36 Hz, 1 H) 5.73 (m, 1 H) 5.83 (s, 1 H) 7.95 (m, 2 H) 8.19 (m, 2 H).

Example 202

Preparation of Compound 202

An attempt was made to displace BOCNH-P3(L-tert-BuGly)-P2[(4R)-(4-chloro phthalazine-1-oxo)-S-proline]-P1 (1R,2S Vinyl Acca)-CONHSO₂-Cyclopropane (Example 195), with the sodium salt of tetrazole gave mostly the 4-hydroxy, hydrolyzed material.

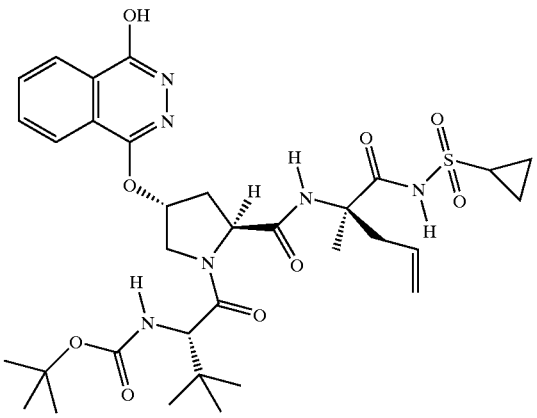

BOCNH-P3(L-t-BuGly)-P2[(4R)-(4-hydroxyphthalazine-1-oxo)-S-proline]P1(1R,2S VinylAcca)-CONHSO₂Cyclopropane was obtained (44.2%) as a pale creamy solid. LC/MS rt-min (MH⁺): 2.18 (701) [method B]. ¹H NMR (400 MHz, CD3OD) δ ppm 1.01 (s, 9 H) 1.05 (m, 2 H) 1.23 (m, 11 H) 1.42 (dd, J=9.29, 5.38 Hz, 1 H) 1.87 (dd, J=8.07, 5.38 Hz, 1 H) 2.21 (m, 2 H) 2.63 (m, 1 H) 2.93 (m, 1 H) 4.00 (s, 1 H) 4.20 (s, 1 H) 4.50 (m, 2 H) 5.11 (dd, J=10.27, 1.47 Hz, 1 H) 5.29 (d, J=16.87 Hz, 1 H) 5.59 (s, 1 H) 5.73 (m, 1 H) 7.86 (dd, J=5.75, 3.30 Hz, 2 H) 8.01 (dd, J=5.87, 3.42 Hz, 1 H) 8.29 (dd, J=5.87, 3.42 Hz, 1 H).

Preparation of 5,6-Disubstituted Isoquinoline P2* Derivatives Via an Alkylation Protocol.
General Synthetic Scheme

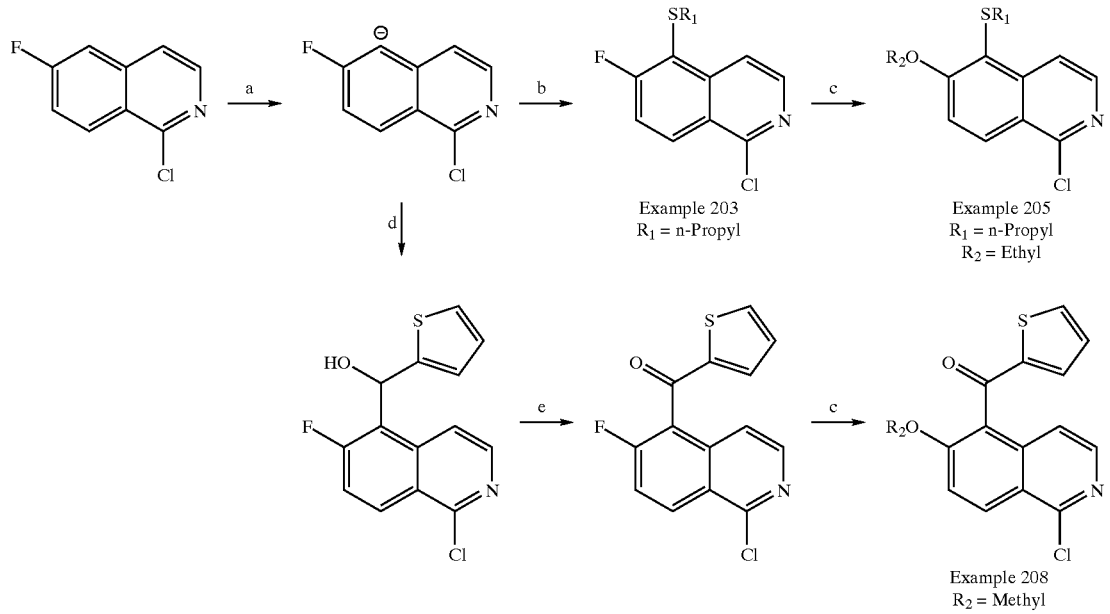

Example 203
R₁ = n-Propyl

Example 205
R₁ = n-Propyl
R₂ = Ethyl

Example 208
R₂ = Methyl

Reaction Conditions: (a) LDA in THF; (b) Alkyl disulfide such as (n-PrS)$_2$; (c) Sodium alkoxide such as MeONa; (d) Thiophene 2-carboxaldehyde; (e) MnO$_2$ in benzene Example 203

Preparation of 1-chloro-5-propylthio-6-fluoro Isoquinoline:

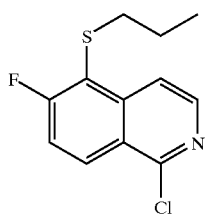

To a chilled (−78° C.) solution of 1-chloro-6-fluoro isoquinoline (59 mg, 0.32 mmol) in 2 mL of THF was added LDA solution in cyclohexane (1.5 Molar, 0.23 mL, 0.35 mmol). The orange solution was stirred for 2 hrs before it was treated with n-propyl disulfide (60 μL, neat material, excess). The reaction was allowed to warm to room temperature over 30 min. It was quenched with a solution of half saturated NH$_4$Cl, the organic residues were extracted into ethyl acetate. LC-MS analysis indicated about 50% conversion into the desired product along with mainly starting material. The desired product was purified by a short column (4 cm×2 cm, silica gel type-H) eluted with 5% ether in hexanes, 29 mg (36% yield) of the desired product was obtained. LC/MS R$_t$-min (MH$^+$) [method C]: 3.79 (256). $^1$H NMR (400 MHz, CHLOROFORM-D) δ ppm 0.96 (t, J=7.34 Hz, 3 H) 1.52 (m, 2 H) 2.86 (m, 2 H) 7.45 (dd, J=9.29, 8.56 Hz, 1 H) 8.34 (d, J=0.73 Hz, 2 H) 8.37 (m, 1 H). This compound was alkylated with the tripeptide by way of the procedure described in Example 184 to give the following compound:

Example 204

Preparation of Compound 204

BOCNH-P3(L-t-BuGly)-P2[(4R)-(1-Chloro-5-propylthio-isoquinolin-6-oxo)-S-proline]-P1(1R,2S VinylAcca)-CONHSO$_2$Cyclopropane, Shown below

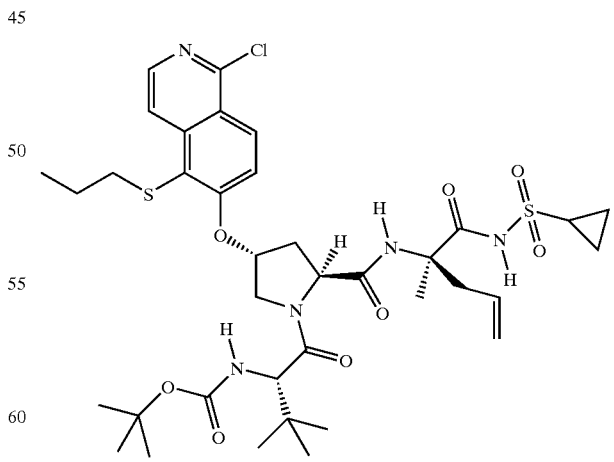

Following the general procedure, 4.6 mg of yellow solid was obtained (3.2%). LC/MS rt-min (MH$^+$): 2.73 (792) (method B). $^1$H NMR (400 MHz, CD$_3$OD) δ ppm 0.93 (t, J=7.34 Hz, 3 H) 0.97 (s, 9 H) 1.08 (m, 2 H) 1.24 (m, 11 H) 1.43 (m, 3 H) 1.86 (m, 1 H) 2.24 (m, 2 H) 2.56 (m, 1 H) 2.78 (q, J=7.09 Hz, 2 H) 2.92 (m, 1 H) 4.01 (d, J=9.29 Hz, 1 H) 4.22 (s, 1 H) 4.29 (s, 1 H) 4.59 (d, J=6.85 Hz, 1 H) 5.11 (d, J=10.76 Hz, 1 H) 5.28 (d, J=17.36 Hz, 1 H) 5.49 (s, 1 H) 5.74 (m, 1 H) 7.66 (d, J=9.29 Hz, 1 H) 8.18 (d, J=6.11 Hz, 1 H) 8.41 (m, 2 H).

Example 205

Preparation of 5-propylthio-6-ethoxy isoquinoline P2* Derivatives

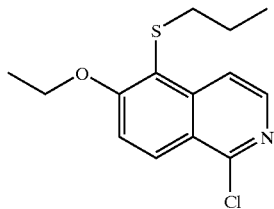

The following procedure is equally applicable to other 5-alkylthio-6-alkoxy isoquinolines by changing the reagents shown here. To a solution of 1-chloro-6-fluoro isoquinoline (88 mg, 0.48 mmol) in 2.0 mL THF under nitrogen at −78° C. was added LDA (1.5 Molar in cyclohexane, 0.42 mL, 0.63 mmol) forming a dark brownish solution. Neat n-propyl disulfide (85 μL, excess) was introduced after it was stirred at −78° C. for 30 min. The reaction was allowed to warm to room temperature over a period of 30 min. It was quenched with a solution of half saturated NH$_4$Cl, the organic residues were extracted into ethyl acetate. The organic layers were combined and dried under vacuum to 50 microns (Hg). The crude product was taken into 2 mL of TBF, cooled to −78° C., added with excess potassium ethoxide (60 mg). The isoquinoline intermediate was finally purified by a silica gel column (type-H, Merck) eluted with ether-hexanes mixture, 32.2 mg (24%) of the pure compound was obtained. LC-MS showed 1-chloro-5-propylthio-6-ethoxyl isoquinoline at rt-min (MH$^+$) [method C]: 3.77 (282). $^1$H NMR (400 MHz, CHLOROFORM-D) δ ppm 0.94 (t, J=7.34 Hz, 3 H) 1.46 (m, 2 H) 1.55 (t, J=6.97 Hz, 3 H) 2.83 (t, J=7.21 Hz, 2 H) 4.32 (q, J=6.85 Hz, 2 H) 7.36 (d, J=9.29 Hz, 1 H) 8.22 (d, J=6.11 Hz, 1 H) 8.32 (d, J=9.29 Hz, 1 H) 8.35 (d, J=6.11 Hz, 1 H).

Following the general tripeptide alkylation procedure (Example 184), this 1-chloro-5-propylthio-6-ethoxy isoquinoline was alkylated with the tripeptide (compound 184) to give 40.7 mg (44.8%) of the desired product shown below.

Example 206

Preparation of Compound 206

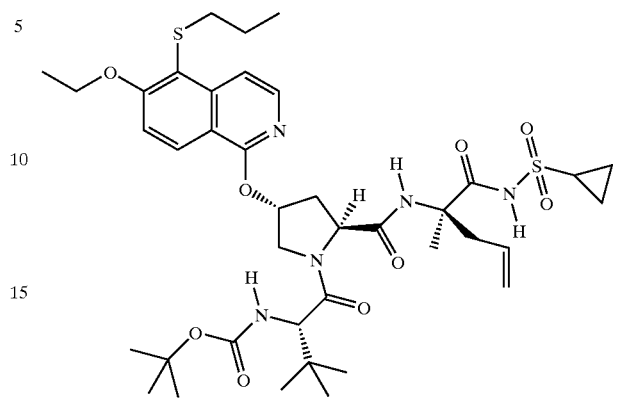

BOCNH-P3(L-t-BuGly)-P2[(4R)-(6-ethoxy-5-propylthio-isoquinoline-1-oxo)-S-proline]-P1(1R,2S VinylAcca)-CONHSO$_2$Cyclopropane. LC/MS rt-min (MH$^+$): 2.93 (803) [method B]. $^1$H NMR (400 MHz, CD$_3$OD) δ ppm 0.93 (t, J=7.34 Hz, 3H) 1.01 (s, 9 H) 1.07 (m, 2 H) 1.21 (m, 11 H) 1.41 (m, 3 H) 1.48 (t, J=6.85 Hz, 3 H) 1.86 (dd, J=8.07, 5.62 Hz, 1 H) 2.25 (m, 2 H) 2.60 (dd, J=13.69, 6.85 Hz, 1 H) 2.81 (q, J=6.97 Hz, 2 H) 2.93 (m, 1 H) 4.05 (m, 1 H) 4.21 (s, 1 H) 4.27 (q, J=7.09 Hz, 2 H) 4.43 (d, J=11.74 Hz, 1 H) 4.52 (m, 1 H) 5.10 (d, J=10.76 Hz, 1 H) 5.28 (d, J=17.12 Hz, 1 H) 5.74 (m, 1 H) 5.82 (s, 1 H) 7.30 (d, J=9.05 Hz, 1 H) 7.92 (d, J=6.36 Hz, 1 H) 7.97 (m, 1 H), 8.22 (d, J=9.05 Hz, 1 H).

Example 207

Preparation of Compound 207

Likewise the same procedure was applied to the preparation of BOCNH-P3(L-t-BuGly)-P2[(4R)-(6-methoxy-5-methylthio-isoquinolin-1-oxo)-S-proline]-P1 (1R,2S VinylAcca)-CONHSO$_2$Cyclopropane.

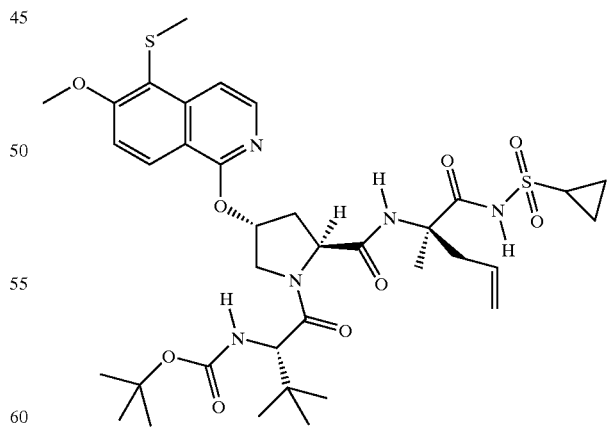

To the solution of 100 mg 1-Chloro-6-fluoro-isoquinoline (0.55 mmole) in 2 ml dry THF at −78° C. was added LDA in TBF (1.3 eq). Dark brown solution was formed, then disulfide was added and the color of solution changed to greenish, then light brown. The reaction was quenched with 2 mL of water and 2 mL of NH₄Cl, extracted with ethyl acetate, dried over sodium sulfate. The solvent was evaporated under vacuum and the resulted residue was used as crude. LC/MS rt-min (MH⁺): 2.23 (228) [method B]. The crude material was redissolved in 2 ml of dry THF at −78° C. and 1.3 eq. of KOMe was added then the reaction mixture was allowed to warmed up to RT, stirred overnight. The reaction mixture was diluted with ethyl acetate and washed with brine, dried over sodium sulfate. 104 mg was obtained (79%). LC/MS rt-min (MH⁺): 2.04 (240) [method B]. The intermediate, 1-chloro-5-methylthio-6-methoxy isoquinoline was subjected to the tripeptide alkylation protocol described previously. Following the general procedure, 70.0 mg of yellow solid was obtained (42.7%). LC/MS rt-min (MH⁺): 2.65 (760) [method B]. ¹H NMR (400 MHz, CHLOROFORM-D) δ ppm 0.94 (m, 11 H) 1.17 (s, 9 H) 1.26 (m, 2 H) 1.39 (m, 1 H) 1.83 (dd, J=8.07, 5.62 Hz, 1 H) 2.01 (m, 2 H) 2.23 (s, 3 H) 2.45 (m, 1 H) 2.79 (m, 1 H) 3.94 (s, 3 H) 3.97 (d, J=3.91 Hz, 1 H) 4.15 (s, 1 H) 4.25 (d, J=11.74 Hz, 1 H) 4.36 (dd, J=9.66, 7.21 Hz, 1 H) 4.99 (d, J=10.27 Hz, 1 H) 5.12 (d, J=16.87 Hz, 1 H) 5.69 (m, 1 H) 5.74 (s, 1 H) 7.08 (d, J=9.05 Hz, 1 H) 7.83 (m, 2 H) 8.06 (d, J=9.05 Hz, 1 H).

Example 208

Preparation of 1-chloro-6-methoxy-isoquinolin-5-yl-thiophen-2-yl-methanone

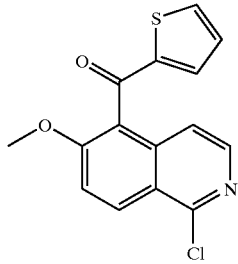

Following the same LDA deprotonation protocol (preparation of Example 203) of 1-chloro-6-fluoro isoquinoline described previously, the initial anion was quenched with 2-thiophenecarboxaldehyde instead, to give 1-chloro-6-fluoro isoquinolin-5-yl-thiophen-2-yl-methanol. The material was oxidized to the 1-chloro-6-fluoro-isoquinolin-5-yl-thiophen-2-yl-methanone using MnO₂ in benzene in 49.6% overall yield after chromatographic purification. LC/MS rt-min (MH⁺) [method C]: 2.98 (292). ¹H NMR (400 MHz, CHLOROFORM-D) δ ppm 7.12 (dd, J=4.89, 3.91 Hz, 1H) 7.40 (m, 1 H) 7.53 (m, 1 H) 7.56 (dd, J=5.87, 0.73 Hz, 1 H) 7.82 (dd, J=5.01, 1.10 Hz, 1 H) 8.27 (d, J=5.87 Hz, 1 H) 8.54 (ddd, J=9.29, 5.38, 0.73 Hz, 1 H). Ipso nucleophilic aromatic displacement of the fluorine atom was accomplished in a solution of excess of potassium methoxide to give, mainly 1-chloro-6-methoxy-isoquinolin-5-yl-thiophen-2-yl-methanone along with 25–33% of 1,6-dimethoxy-isoquinolin-5-yl-thiophen-2-yl-methanone. The crude material (77 mg) was used in the alkylation step with the tripeptide without further purification.

Example 209

Preparation of Compound 209

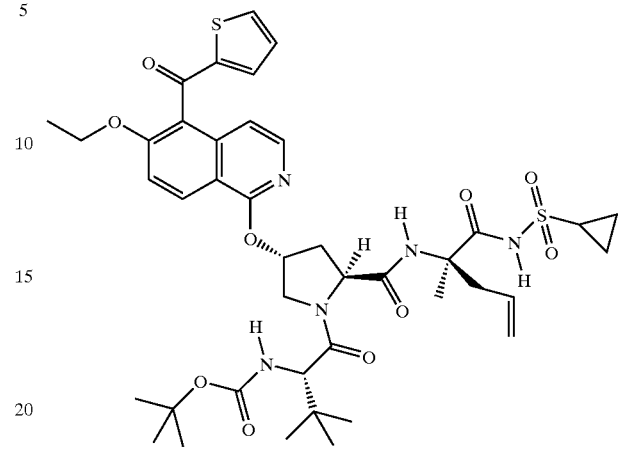

Following the general procedure of tripeptide alkylation (Example 184), 35.3 mg of BOCNH-P3(L-t-BuGly)-P2 [(4R)-6-methoxy-5-(thiophene-2-carbonyl)-isoquinoline-1-oxo)-S-proline]-P1(1R,2S VinylAcca)-CONHSO₂Cyclopropane was obtained as pale solid (26.5%). LC/MS rt-min (MH⁺): 2.54 (825) [method B]. ¹H NMR (400 MHz, CD₃OD) δ ppm 1.02 (s, 9 H) 1.06 (m, 2 H) 1.22 (m, 2 H) 1.26 (s, 9 H) 1.43 (m, 1 H) 1.87 (dd, J=7.95, 5.50 Hz, 1 H) 2.28 (m, 2 H) 2.62 (dd, J=13.82, 6.97 Hz, 1 H) 2.93 (m, 1 H) 3.90 (s, 3 H) 4.07 (dd, J=11.62, 3.06 Hz, 1 H) 4.23 (s, 1 H) 4.43 (m, 1 H) 4.55 (dd, J=9.78, 7.34 Hz, 1 H) 5.09 (m, 1 H) 5.29 (d, J=17.12 Hz, 1 H) 5.74 (m, 1 H) 5.86 (s, 1 H) 6.93 (d, J=6.11 Hz, 1 H) 7.11 (m, 1 H) 7.32 (dd, J=3.91, 0.98 Hz, 1 H) 7.46 (d, J=9.29 Hz, 1 H) 7.86 (t, J=6.72 Hz, 1 H) 7.91 (dd, J=4.89, 1.22 Hz, 1 H) 8.39 (d, J=9.29 Hz, 1 H).

Preparation of P2* by way of cinnamic acid derivatives. The general procedure depicted below has been described extensively elsewhere.

General Synthetic Scheme

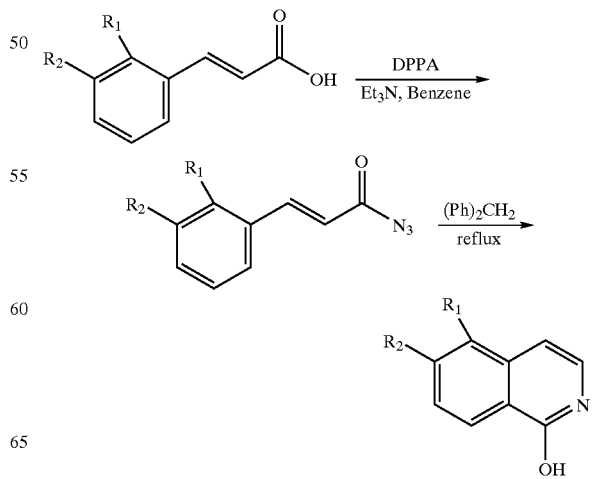

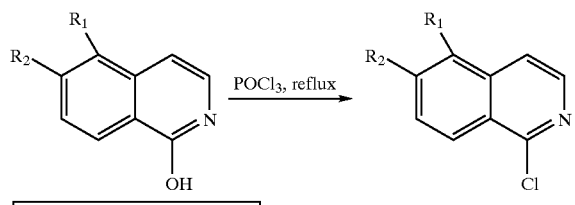

R$_1$, R$_2$ = H, Methyl for Example 210
R$_1$, R$_2$ = OCH$_2$O for Example 211

Example 210

Preparation of Compound 210

10.0 g of meta-tolyl-acrylic acid (61.7 mmole) was suspended in 50 ml of benzene, 12.6 mL of DPPA (0.95 eq) was added followed by 10.3 ml of triethylamine (1.2 eq). The resulted solution was stirred at room temperature for 1 hr. The volatile was removed under vacuum and the meta-tolyl-acryloyl azide was purified by flash chromatograph to yield 11.5 g of pure compound (quantitative). This material, in 100 mL of diphenylmethane, was introduced dropwise into 100 ml of diphenylmethane previously heated up to 200° C. over a period of an hr. The resulted solution was kept at this temperature for another 4 hour then cooled down to room temp. White precipitate was formed, it was filtered off. The solid was washed with hexanes three times and dried. The filtrate was diluted with 200 ml of hexanes, the solution was left standing overnight to allow for separation of the second crop. The materials were combined to give 4.2 g of 6-methyl-isoquinolin-1-ol (50%). LC/MS rt-min (MH$^+$): 1.31 (160) [method B]. $^1$H NMR (400 MHz, CD$_3$OD) δ ppm 2.49 (s, 3 H) 6.61 (d, J=7.32 Hz, 1 H) 7.13 (d, J=7.02 Hz, 1 H) 7.36 (d, J=8.24 Hz, 1 H) 7.45 (s, 1 H) 8.18 (d, J=8.24 Hz, 1 H). The material was suspended in 15 ml of POCl$_3$ and brought to reflux for 3 hours. After removal of the POCl$_3$ in vacuo, the residue was partitioned between EtOAc (1L), and cold aqueous NaOH (generated from 1.0N 200 mL NaOH and 20 mL 10.0 N NaOH) and stirred for 15 min. The organic layer was washed with water (2×200 mL), brine (200 mL), dried (MgSO$_4$), and concentrated in vacuo to supply 1-chloro-6-methyl-isoquinoline (67.4%). LC/MS rt-min (MH$^+$): 1.92 (178) [method B]. $^1$H NMR (400 MHz, CHLOROFORM-D) δ ppm 2.53 (s, 3 H) 7.47 (d, J=6.11 Hz, 2 H) 7.56 (s, 1 H) 8.18 (m, 2 H). The final alkylation of 1-chloro-6-methyl-isoquinoline with the tripeptide was carried out using the protocol described previously (Example 184).

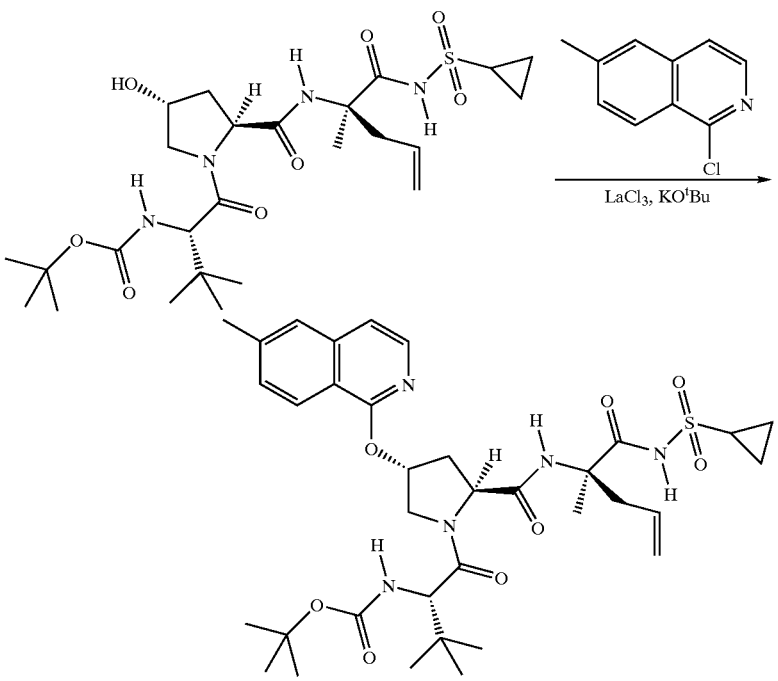

BOCNH-P3(L-tert-BuGly)-P2 [(4R)-(6-methyl isoquinolin-1-oxo)-S-proline]-P1(1R,2S Vinyl Acca)-CONHSO$_2$-Cyclopropane: the material was obtained as a white foam in 18% yield. LC/MS R$_t$-min (MNa$^+$) [method B]: 2.64 (720). $^1$H NMR (400 MHz, CD$_3$OD) δ ppm 1.05 (m, 13 H) 1.23 (m, 9 H) 1.42 (m, 1 H) 1.86 (dd, J=7.95, 5.50 Hz, 1 H) 2.25 (m, 2 H) 2.49 (s, 3 H) 2.61 (dd, J=13.82, 6.48 Hz, 1 H) 2.93 (m, 1 H) 4.05 (dd, J=11.86, 3.30 Hz, 1 H) 4.23 (s, 1 H) 4.43 (d, J=11.49 Hz, 1 H) 4.52 (m, 1 H) 5.10 (d, J=11.49 Hz, 1 H) 5.28 (d, J=17.12 Hz, 1 H) 5.74 (m, 1 H) 5.83 (s, 1 H) 7.24 (d, J=5.87 Hz, 1 H) 7.35 (d, J=8.07 Hz, 1 H) 7.58 (s, 1 H) 7.89 (d, J=5.87 Hz, 1 H) 8.07 (d, J=8.56 Hz, 1 H).

Example 211

Preparation of Compound 211

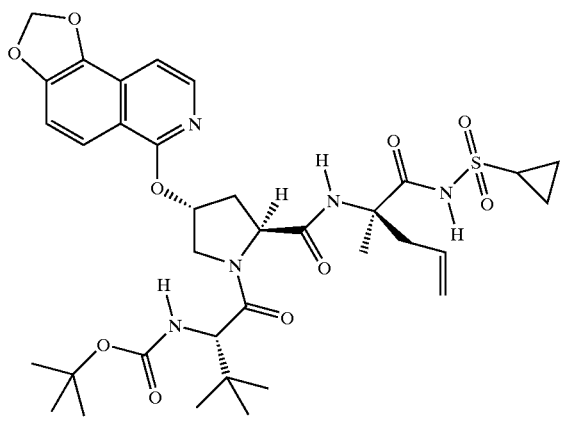

Following the general procedure described previously, BOCNH-P3(L-t-BuGly)-P2 [(4R)-(1,3-Dioxa-7-aza-cyclopenta[α]naphthalen-6-ol)-S-proline]-P1 (1R,2S VinylAcca)-CONHSO₂Cyclopropane, 51.0 mg was obtained as a pale solid (64.9%). LC/MS rt-min (MH⁺): 2.57 (728) [method B]. ¹H NMR (400 MHz, CD3OD) δ ppm 0.99 (s, 9 H) 1.07 (m, 2 H) 1.18 (m, 11 H) 1.42 (m, 1 H) 1.86 (dd, J=8.07, 5.62 Hz, 1 H) 2.23 (m, 2 H) 2.59 (dd, J=13.69, 6.85 Hz, 1 H) 2.93 (m, 1 H) 4.04 (dd, J=11.74, 2.20 Hz, 1 H) 4.22 (s, 1 H) 4.43 (d, J=11.74 Hz, 1 H) 4.51 (m, 1 H) 5.10 (d, J=10.27 Hz, 1 H) 5.28 (d, J=17.12 Hz, 1 H) 5.73 (m, 1 H) 5.82 (s, 1 H) 6.18 (s, 2 H) 7.13 (d, J=8.56 Hz, 1 H) 7.19 (d, J=6.11 Hz, 1 H) 7.81 (d, J=8.56 Hz, 1 H) 7.85 (d, J=6.11 Hz, 1 H).

Preparation of 5,6,7-trisubstituted Isoquinoline P2* Derivatives:

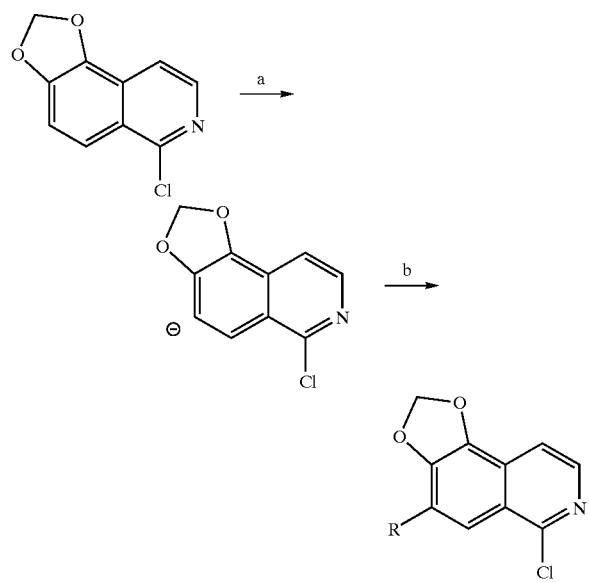

Reaction Conditions: (a) LDA in THF; (b) N-fluorobenzenesulfonimide (NFSI) for R=F, or dimethyl sulfide (MeS)₂, for R=SMe.

The 5,6-methylenedioxy-1-chloroisoquinoline prepared above was deprotonated directly in the presence of strong base such as LDA to provide the corresponding 7-anion without interferring with the 1-chloro functionality. The 7-anion was quenched with electrophiles such as NFSI (N-fluorobenzenesulfonimide) and dimethylsulfide to produce the corresponding 7-substituted isoquinoline ring system.

Example 212

Preparation of Compound 212

Step 1:

Preparation of 5,6-methylenedioxy-7-fluoro-1-chloro isoquinoline. To a solution of 5,6-methylenedioxy-1-chloro isoquinoline (126 mg, 0.61 mmol) in 4 mL of THF under nitrogen at −78° C. was added LDA solution in cyclohexane (1.5 Molar, 0.65 mL, 0.98 mmol). The light brownish solution was stirred for 15 min before it was treated with N-fluorobenzenesulfonimide (NFSI, 0.3 g, 1.5 equivalents). TLC analysis showed the formation of a new spot, in addition of the unchanged starting material. Aqueous work up followed by extractions with ethyl acetate, furnished an oily crude product which was purified by preparative HPLC to give 52 mg (38%). LC/MS rt-min (MH⁺) [method C]: 3.09 (226). ¹H NMR (400 MHz, CHLOROFORM-D) δ ppm 6.33 (s, 2 H) 7.52 (d, J=5.87 Hz, 1 H) 7.71 (d, J=10.51 Hz, 1 H) 8.16 (d, J=5.87 Hz, 1 H). Step 2: The alkylation of 5,6-methylenedioxy-7-fluoro-1-chloro isoquinoline with the tripeptide was carried out as described previously (Example 184) to provide the major product as a result of fluorine displacement.

BOCNH-P3(L-t-BuGly)-P2[(4R)-(6-Chloro-1,3-dioxa-7-aza-cyclopenta[α]naphthalen-4-oxo)-S-proline]-P1(1R,2S VinylAcca)-CONHSO₂Cyclopropane, Shown below

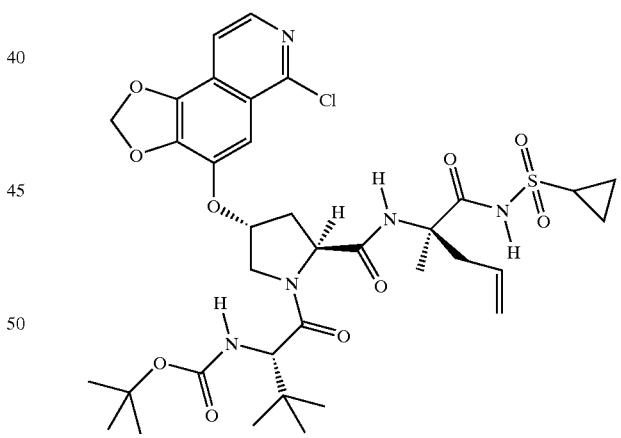

Following the general procedure, 24.3 mg of yellow solid was obtained (24.3%). LC/MS rt-min (MH⁺): 2.54 (763) [method B]. ¹H NMR (400 MHz, CD₃OD) δ ppm 1.00 (s, 9 H) 1.06 (m, 2 H) 1.20 (m, 2 H) 1.29 (s, 9 H) 1.42 (dd, J=9.41, 5.26 Hz, 1 H) 1.86 (dd, J=8.07, 5.38 Hz, 1 H) 2.24 (m, 2H) 2.54 (dd, J=13.57, 6.48 Hz, 1 H) 2.92 (m, 1 H) 4.04 (dd, J=12.10, 2.81 Hz, 1 H) 4.20 (d, J=7.34 Hz, 1 H) 4.33 (d, J=12.23 Hz, 1 H) 4.47 (dd, J=10.52, 6.85 Hz, 1 H) 5.10 (dd, J=10.39, 1.59 Hz, 1 H) 5.28 (dd, J=17.12, 1.22 Hz, 1 H) 5.46 (d, J=5.87 Hz, 1 H) 5.74 (m, 1 H) 6.29 (m, 2 H) 7.40 (s, 1 H) 7.56 (m, 1 H) 8.01 (d, J=5.62 Hz, 1 H).

Example 213

Preparation of Compound 213

To a solution of 5,6-methylenedioxy-1-chloro isoquinoline (84 mg, 0.41 mmol) in 4 mL of THF under nitrogen at −78° C. was added LDA solution in cyclohexane (1.5 Molar, 0.60 mL, 0.9 mmol). The light brownish solution was stirred for 15 min at −78° C. before it was treated with methyl disulfide (50 μL of neat reagent, 1.4 equivalents). TLC analysis showed the formation of a new spot, in addition of the unchanged starting material. Aqueous work up followed by extractions with ethyl acetate furnished an oily crude product which was purified by preparative HPLC to give 51 mg (49%). LC/MS rt-min (MH$^+$) [method C]: 3.39 (254). $^1$H NMR (400 MHz, CHLOROFORM-D) δ ppm 2.64 (s, 3 H) 6.29 (s, 2 H) 7.49 (d, J=4.89 Hz, 1 H) 7.71 (s, 1 H) 8.11 (d, J=5.87 Hz, 1 H). The alkylation of 5,6-methylenedioxy-7-methylthio-1-chloro isoquinoline with the tripeptide was carried out as described previously (Example 184) to provide the desired product shown below:

BOCNH-P3(L-t-BuGly)-P2[(4R)-(4-methylthio-1,3-dioxa-7-azacyclopenta[a]naphthalen-6-yloxy)-S-proline]-P1(1R, 2S VinylAcca)-CONHSO$_2$Cyclopropane

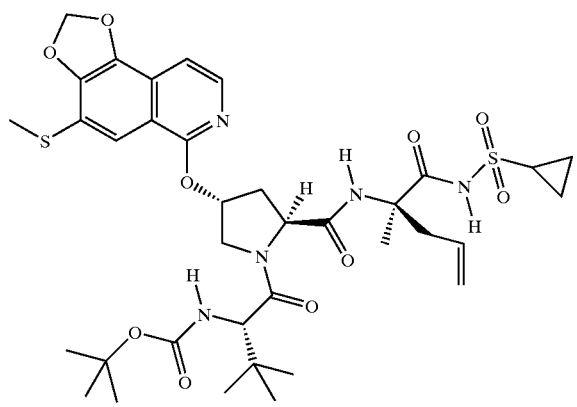

Following the general procedure, 59.6 mg of yellow solid was obtained (42.2%). LC/MS rt-min (MH$^+$): 2.70 (774) [method B]. $^1$H NMR (400 MHz, CHLOROFORM-D) δ ppm 1.02 (m, 11 H) 1.16 (s, 9 H) 1.32 (s, 2 H) 1.45 (m, 1 H) 1.94 (m, 1 H) 2.12 (d, J=8.56 Hz, 1 H) 2.56 (s, 3 H) 2.62 (m, 2 H) 2.90 (d, J=4.40 Hz, 1 H) 4.15 (d, J=7.83 Hz, 2 H) 4.48 (d, J=12.47 Hz, 1 H) 4.62 (t, J=7.83 Hz, 1 H) 5.13 (d, J=10.52 Hz, 1 H) 5.26 (d, J=17.12 Hz, 1 H) 5.74 (d, J=16.38 Hz, 1 H) 5.95 (s, 1 H) 6.28 (s, 2 H) 7.41 (s, 1 H) 7.59 (s, 1 H) 7.85 (d, J=6.11 Hz, 1 H).

Preparation of 3,4-Disubstituted Isoquinoline P2* Derivatives

Example 215

Preparation of Compound 215

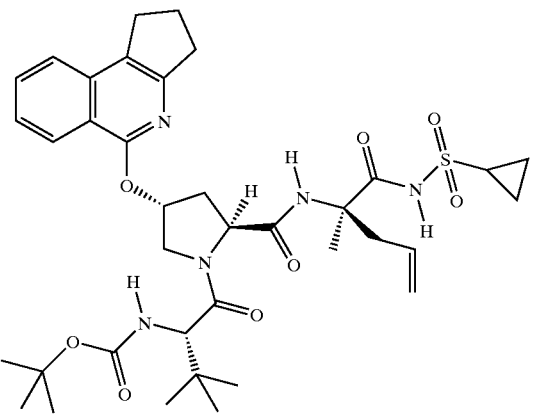

Example 215

BOCNH-P3(L-t-BuGly)-P2[(1R)-(2,3-dihydro-1H-4-azacyclopenta[α]naphthalen-5-yloxy)-S-proline]-P1(1R,2S VinylAcca)-CONHSO$_2$Cyclopropane, shown below was prepared as depicted in the following scheme:

General Synthetic Scheme of the Isoquinoline Component Compound 214

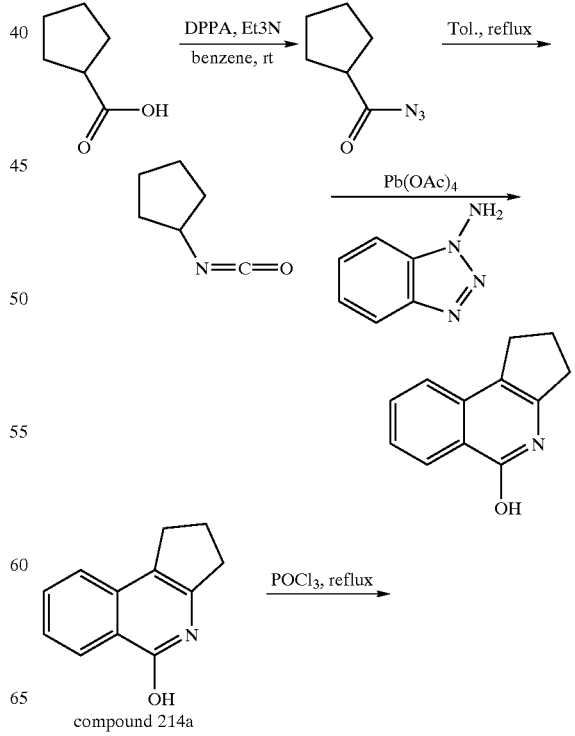

compound 214a

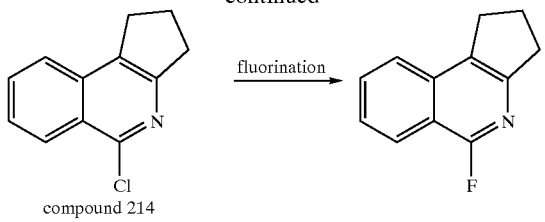

compound 214 → (fluorination) → F compound

Notes:

The synthesis of the novel 1-fluoro P2* was made successful by the technologies cited below:

(1) Rigby, James H.; Holsworth, Daniel D.; James, Kelly. Vinyl Isocyanates In Synthesis. [4+2] Cycloaddition Reactions With Benzyne Addends. *Journal Of Organic Chemistry* (1989), 54(17), 4019–20

(2) Uchibori, Y.; Umeno, M.; Yoshiokai, H.; *Heterocycles*, 1992, 34 (8), 1507–1510

Example 214

Preparation of Compounds 214, 5-chloro-2,3-dihydro-1H-4-aza-cyclopenta[α]naphthalene, and Compound 215 of Example 215

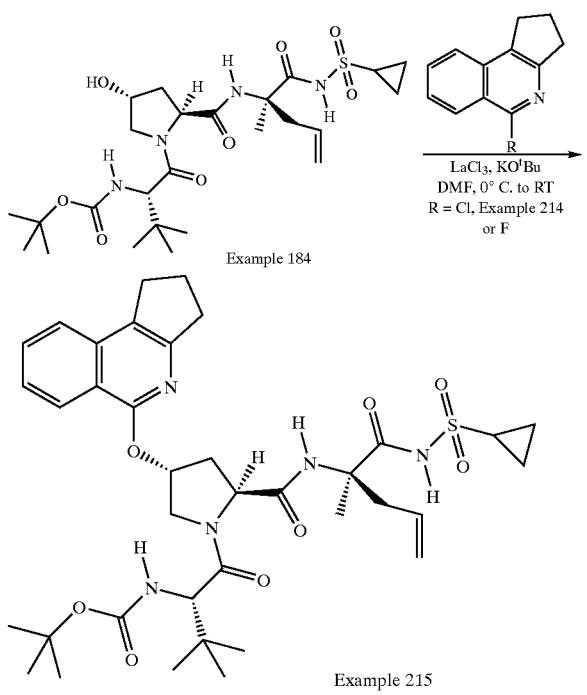

2,3-Dihydro-1H-4-aza-cyclopenta[α]naphthalen-5-ol was prepared in accordance to the method of Rigby described in (reference 1) cited above. Using POCl₃ as described elsewhere, Compound 214, was synthesized in 59.8% (430 mg). LC/MS rt-min (MH⁺): 2.29 (204) [method B]. ¹H NMR (400 MHz, CHLOROFORM-D) □ppm 2.28 (m, 2 H) 3.19 (q, J=7.74 Hz, 4 H) 7.58 (m, 1 H) 7.71 (m, 2 H) 8.32 (d, J=8.56 Hz, 1 H). The chloride is sufficiently reactive to be alkylated with the tripeptide according to the procedure of Example 184, to give the desired product Compound 215. However the overall yield could be doubled if the chloride was exchanged into the fluoride by the method of Uchibori described in (reference 2). Thus 17.0 mg of Compound 215, isolated as a pale yellow solid (23.6%). LC/MS nr-min (MH⁺): 2.80 (724) [method B]. ¹H NMR (500 MHz, CD₃OD) δ ppm 1.03 (s, 9 H) 1.09 (m, 2 H) 1.24 (m, 11 H) 1.44 (dd, J=8.24, 5.49 Hz, 1 H) 1.88 (dd, J=7.93, 5.49 Hz, 1 H) 2.25 (m, 4 H) 2.63 (dd, J=13.73, 7.0 Hz, 1 H) 2.94 (m, 1 H) 3.05 (m, 2 H) 3.10 (m, 2 H) 4.08 (dd, J=11.60, 2.75 Hz, 1 H) 4.24 (d, J=20.45 Hz, 1 H) 4.45 (d, J=11.90 Hz, 1 H) 4.54 (dd, J=9.46, 7.63 Hz, 1 H) 5.11 (m, 1 H) 5.30 (d, J=17.09 Hz, 1 H) 5.75 (m, 1 H) 5.87 (s, 1 H) 7.44 (t, J=7.02 Hz, 1 H) 7.69 (m, 2 H) 8.18 (d, J=8.24 Hz, 1 H).

Preparation of 3,4-Dihydrofuranyl and Furanyl Isoquinoline P2* Components, Examples 217 and 218, General Synthetic Scheme

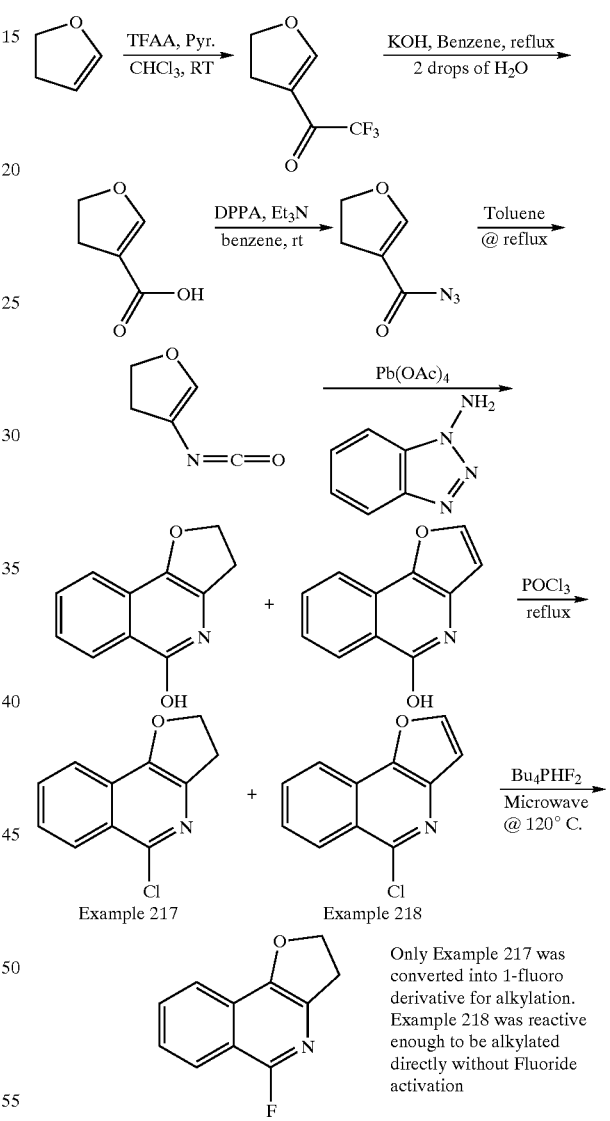

Only Example 217 was converted into 1-fluoro derivative for alkylation. Example 218 was reactive enough to be alkylated directly without Fluoride activation Example 217

Preparation of Compound 217, 5-chloro-2,3-dihydro-1-oxa-4-aza-cyclopenta[α]naphthalene and Compound 218, 5-chloro-1-oxa-4-aza-cyclopenta[α]naphthalene.

This synthesis made use of the technologies described, in part, in the following references:

(1) Hojo, Masaru; Masuda, Ryoichi; Sakaguchi, Syuhei; Takagawa, Makoto, *Synthesis* (1986), (12), 1016–17

(2) Rigby, James H.; Holsworth, Daniel D.; James, Kelly. Vinyl Isocyanates In Synthesis. [4+2] Cycloaddition Reactions With Benzyne Addends. *Journal Of Organic Chemistry* (1989), 54(17), 4019–20

(3) Uchibori, Y.; Umeno, M.; Yoshiokai, H.; *Heterocycles,* 1992, 34 (8), 1507–1510

Both 2,3-dihydro-1-oxa-4-aza-cyclopenta[a]naphthalen-5-ol and 1-oxa-4-aza cyclopenta[α]naphthalen-5-ol were produced together when the procedures (references 1 and 2) cited above were followed. Conversion of the pair into their chloro derivatives was accomplished by $POCl_3$ as usual: The crude hydroxy products (about 2 g, pale yellow oil) was treated with 15 mL of $POCl_3$ and the mixture was brought to reflux for 3 hours. After removal of the $POCl_3$ in vacuo, the residue was stirred with EtOAc (1L), and cold aqueous NaOH (220 mL, 1.0 N) for 15 min. The organic layer was separated, washed with water (2×200 mL), brine (200 mL), and dried over $MgSO_4$, and concentrated in vacuo to supply 300 mg of Example 217, 5-chloro-2,3-dihydro-1-oxa-4-aza-cyclopenta[α]naphthalene (13.2%) and 100 mg of Example 218, 5-chloro-1-oxa-4-aza cyclopenta[α]naphthalene (4.4%) as light brown solids after silica gel chromatographic separation. Compound 217: LC/MS rt-min ($MH^+$): 2.05 (206) [method B]. $^1H$ NMR (400 MHz, CHLOROFORM-D) δ ppm 3.46 (t, J=9.05 Hz, 2 H) 4.82 (t, J=9.17 Hz, 2 H) 7.58 (m, 1 H) 7.66 (m, 1 H) 7.85 (d, J=8.31 Hz, 1 H) 8.21 (d, J=8.56 Hz, 1 H). Compound 218: LC/MS rt-min ($MH^+$): 2.16 (204) [method B]. $^1H$ NMR (400 MHz, CHLOROFORM-D) ☐ ppm 7.15 (d, J=2.20 Hz, 1 H) 7.70 (m, 1 H) 7.89 (m, 2 H) 8.27 (d, J=8.31 Hz, 1 H) 8.44 (d, J=8.80 Hz, 1 H).

Preparation of 5-fluoro-2,3-dihydro-1-oxa-4-aza-cyclopenta[α]naphthalene, and Final P2* Coupling Products.

The chloride/fluoride exchange was achieved by the method (reference 3) cited above. Thus 90 mg of 5-chloro-2,3-dihydro-1-oxa-4-aza-cyclopenta[α]naphthalene (Example 217) was suspended in 1.5 mL of $Bu_4PHF_2$ and was irradaited under microwave (Smith Reactor) to about 120° C. for 2 hours. After aqueous work up and column purification, 22 mg of fluoride product was obtained (26.9%). LC/MS rt-min ($MH^+$): 1.91 (190) [method B]. The furan derivative (Example 218), 5-chloro-1-oxa-4-aza-cyclopenta[α]naphthalene was sufficiently reactive to be alkylated with the tripeptide directly without fluoride activation.

Example 219

Preparation of Compound 219

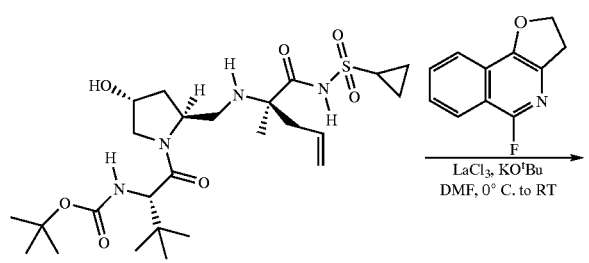

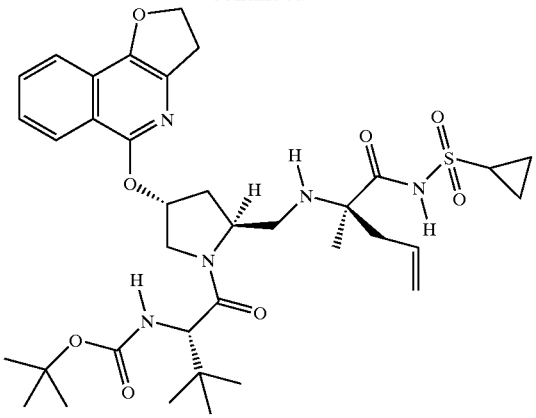

BOCNH-P3(L-t-BuGly)-P2 [(4R)-(2,3-dihydro-1-oxa-4-aza-cyclopenta[α]naphthalen-5-yloxy)-S-proline]-P1 (1R, 2S VinylAcca)-CONHSO$_2$Cyclopropane. Following the general alkylation procedure, 22.0 mg of yellow solid was obtained (26.3%). LC/MS rt-min ($MH^+$): 2.65 (726) [method B]. $^1H$ NMR (400 MHz, CD$_3$OD) δ ppm 0.99 (s, 9H) 1.07 (m, 2 H) 1.20 (m, 11 H) 1.40 (m, 1H) 1.86 (dd, J=8.07, 5.62 Hz, 1H) 2.21 (dd, J=17.48, 8.93 Hz, 2 H) 2.60 (dd, J=13.45, 6.85 Hz, 1 H) 2.93 (m, 1 H) 3.34 (m, 2 H) 4.04 (dd, J=11.74, 3.18 Hz, 1 H) 4.24 (s, 1 H) 4.41 (d, J=11.49 Hz, 1 H) 4.51 (m, 1 H) 4.74 (t, J=9.05 Hz, 2 H) 5.11 (d, J=10.27 Hz, 1 H) 5.28 (d, J=17.36 Hz, 1 H) 5.73 (m, 1 H) 5.78 (s, 1 H) 7.43 (m, 1 H) 7.65 (t, J=7.46 Hz, 1 H) 7.74 (d, J=8.31 Hz, 1 H) 8.12 (d, J=8.56 Hz, 1 H).

Example 220

Preparation of Compound 220

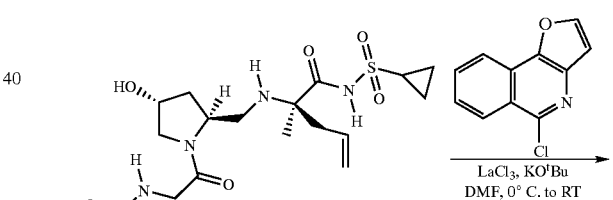

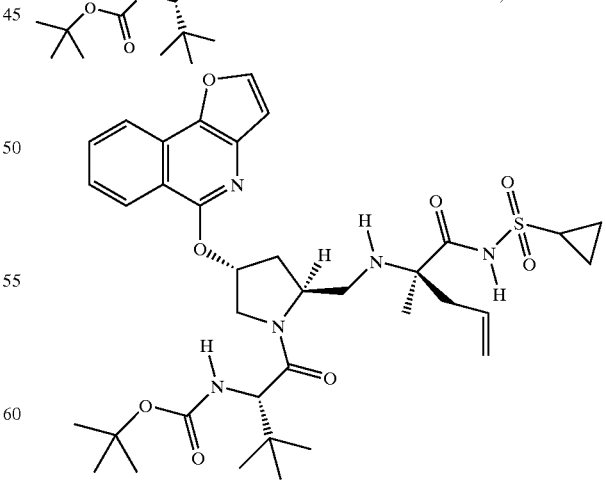

BOCNH-P3(L-t-BuGly)-P2[(4R)-(1-oxa-4-aza-cyclopenta[α]naphthalen-5-yloxy)-S-proline]-P1(1R,2S VinylAcca)-CONHSO$_2$Cyclopropane. Following the general alkylation procedure, 13.0 mg of yellow solid was obtained (20%). LC/MS rt-min (MH+): 2.70 (724) [method B]. ¹H NMR (500 MHz, CD₃OD) δ ppm 1.01 (S, 9 H) 1.09 (m, 2 H) 1.22 (s, 9 H) 1.27 (m, 2 H) 1.46 (m, 1 H) 1.89 (dd, J=7.78, 5.65 Hz, 1 H) 2.24 (d, J=8.55 Hz, 1 H) 2.33 (t, J=9.92 Hz, 1 H) 2.68 (dd, J=13.73, 7.02 Hz, 1 H) 2.95 (m, 1 H) 4.14 (m, 1 H) 4.26 (s, 1 H) 4.50 (d, J=11.90 Hz, 1 H) 4.57 (d, J=17.09 Hz, 1 H) 5.12 (d, J=10.07 Hz, 1 H) 5.30 (d, J=17.40 Hz, 1 H) 5.75 (m, 1 H) 5.93 (s, 1 H) 6.97 (d, J=2.14 Hz, 1 H) 7.51 (t, J=7.32 Hz, 1 H) 7.81 (t, J=7.48 Hz, 1 H) 7.92 (s, 1 H) 8.13 (d, J=7.94 Hz, 1 H) 8.28 (d, J=8.24 Hz, 1 H).

Preparation of 3-halo and 3-heteroaryl 4-alkoxy and 4-hydroxy isoquinoline P2 * Derivatives
General Synthetic Scheme

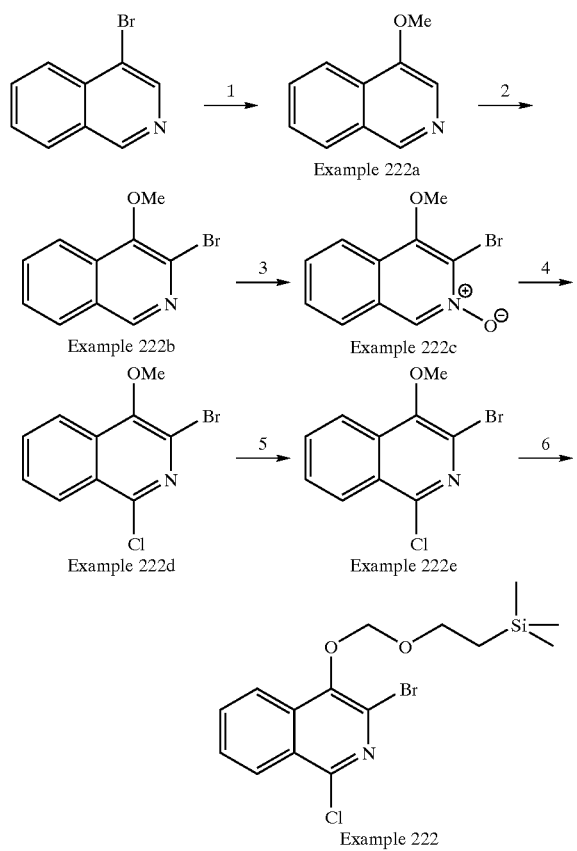

Reaction conditions: (1) MeOK in DMPU; (2) NBS in dichloroethane; (3) MCPBA in CH₂Cl₂; (4) POCl₃ in dichloroethane; (5) BBr₃ in CH₂Cl₂; (6) SEM-Chloride and Hunig's Base in CH₂Cl₂

4-Methoxy isoquinoline (Example 222a) was prepared from 4-bromo isoquinoline by a novel and convenient procedure using ordinary laboratory equipments and reagents. A regioselective NBS bromination gave 3-bromo-4-methoxy isoquinoline (Example 222b) in good yields. MCPBA oxidation proceeded uneventfully to furnish the corresponding N-oxide (Example 222c), which was isomerized into 1-chloro-3-bromo-4-methoxy isoquinoline (Example 222d) using the usual POCl₃ procedure. The 4-methoxy isoquinoline was alkylated with the tripeptide to give the corresponding 3-bromo-4-methoxy P2* derivative suitable for Stille and Suzuki coupling. Alternatively the 4-methoxy isoquinoline was de-methylated in BBr₃ to give the 4-hydroxy-3-bromo-1-chloro isoquinoline (Example 222e). The 4-hydroxy group was re-protected with SEM-chloride to give the 4-SEM protected intermediate Example 222. The 4-hydroxy compound was re-generated once the coupling was achieved by either an acid induced, or a fluoride induced deprotection protocol.

Example 222d

Preparation of 1-chloro-3-bromo-4-methoxy isoquinoline

Step 1:
A solution of 4-bromo isoquinoline (15 g, 73 mmol, commercial material) in 200 mL dimethyl-3,4,5,6-tetrahydro-2(1 H)-pyrimidinone (DMPU, Aldrich) was added solid potassium methoxide (5.6 gm, 80 mmol). The reaction vessel was immersed in an oil bath at 105° C. for 20 min. The color of mixture changed rapidly from its initial very pale to dark greenish brown immediately after warming. The reaction vessel was removed from the oil bath and was diluted with water, the organic residues were partitioned into ether by multiple extraction with portions of ether. TLC analysis showed two new, spots (1:1 v/v mixture of hexanes and ethyl acetate as eluent) of roughly equal size. These were separated on silica-gel (Merck, type-H) column eluted with straight hexanes, followed by gradual addition of ether into the mobil phase. The desired product, 4-methoxy isoquinoline (4.1 gm, 35.3%) was isolated after evaporation of solvents. The other product was also isolated as the reduction by-product isoquinoline. The identity of the by-product was confirmed by NMR comparison with authentic material. Example 222a: LC/MS R$_t$-min (MH+) [method C]: 1.16 (160). ¹H NMR (400 MHz, CHLOROFORM-D) δ 4.07 (s, 3 H) 7.61 (m, 1 H) 7.69 (m, 1 H) 7.93 (d, J=8.07 Hz, 1 H) 8.08 (s, 1 H) 8.19 (d, J=8.56 Hz, 1 H) 8.89 (s, 1 H). [Note: this compound was previously prepared in Zoltewicz, John A.; Oestreich, Terence M.; Sale, Alan A, Journal of the American Chemical Society (1975), 97(20), 5889–96 in a "Monel Bomb", and later by a "focused microwave" initiated procedure in Cherng, Yie-Jia, Tetrahedron (2002), 58(6), 1125–1129. The present procedure required neither special high pressure apparatus nor preparative scale microwave equipment].

Step 2:
The material (Example 222a) was subjected to NBS bromination, thus 4-methoxy isoquinoline (Example 222a, 2.1 gm, 13.2 mmol) in 1,2-dichloroethane (DCE, 150 mL) was treated with N-bromosuccinimide (NBS, 1.5 gm, 8.4 mmol, 0.6x) at 70° C. for an hr followed by addition of second portion of 1.5 gm NBS. The dark brownish mixture was stirred for another hr before the addition of third portion of 1.0 gm NBS. The bromination was monitored by LC-MS until there was no starting material left. The crude mixture was evaporated to dryness and the desired product was filtered over a short bed of silica-gel (Type-H, Merck, 3 cm diameter by 1.5 cm height) eluted with straight hexanes first followed by gradually increasing the amount of ether. The desired product, (Example 222b), was isolated as an oily material (1.7 gm, 54%). LC/MS R$_t$-min (MH+) [method C]: 2.65 (238). ¹H NMR (400 MHz, CHLOROFORM-D) δ ppm 4.04 (s, 3 H) 7.64 (t, J=7.58 Hz, 1 H) 7.76 (t, J=7.09 Hz, 1 H) 7.99 (d, J=8.31 Hz, 1 H) 8.11 (d, J=8.31 Hz, 1 H) 8.85 (s, 1 H). [3-Bromo-4-methoxy isoquinoline was previously prepared by a different procedure: Finkentey, Christel; Langhals, Elke; Langhals, Heinz. Chemische Berichte (1983), 116(6), 2394–7. NMR of the product was identical to that reported].

Step 3:
The product from NBS bromination was subjected to MCPBA oxidation in methylene chloride at room temperature. Thus MCPBA (1.80 gm, 77% pure, 8.0 mmol) was added into a solution of 3-bromo-4-methoxy isoquinoline (Example 222b, 1.65 gm, 6.9 mmol) in 35 mL of $CH_2Cl_2$. The solution was stirred for 4 hrs forming a white suspension. Sodium bicarbonate solution (5%, freshly prepared, 20 mL) was added into the mixture, organic residues were extracted into $CH_2Cl_2$ (10×25 mL). Multiple extraction in organic solvent was necessary to recover the somewhat water solution N-oxide product. The crude material obtained after evaporation of solvents was further purified by a filtration over silica-gel to give 1.36 gm (5.4 mmol, 78%) of the N-oxide (Example 222c) as a ceraceous solid.

LC/MS $R_t$-min ($MH^+$) [method C]: 1.79 (254). $^1H$ NMR (400 MHz, CHLOROFORM-D) δ ppm 4.07 (s, 3 H) 7.63 (m, 2 H) 7.72 (m, 1 H) 8.00 (m, 1 H) 8.86 (s, 1 H).

Step 4:

The final N-oxide rearrangement was done as usual in $POCl_3$ using procedure described elsewhere. Yield of Example 222d was essentially quantitative. LC/MS $R_t$-min ($MH^+$) [method D]: 2.69 (272). $^1H$ NMR as HCl salt, (400 MHz, CHLOROFORM-D) δ ppm 4.07 (s, 3 H) 7.81 (m, 1 H) 7.92 (m, 1 H) 8.17 (d, J=8.31 Hz, 1 H) 8.34 (d, J=8.31 Hz, 1 H). $^1H$ NMR as free base, (400 MHz, CHLOROFORM-D) δ ppm 4.03 (s, 3 H) 7.72 (m, 1 H) 7.81 (m, 1 H) 8.12 (d, J=8.56 Hz, 1 H) 8.28 (d, J=8.56 Hz, 1 H).

Example 223

Preparation of Compound 223

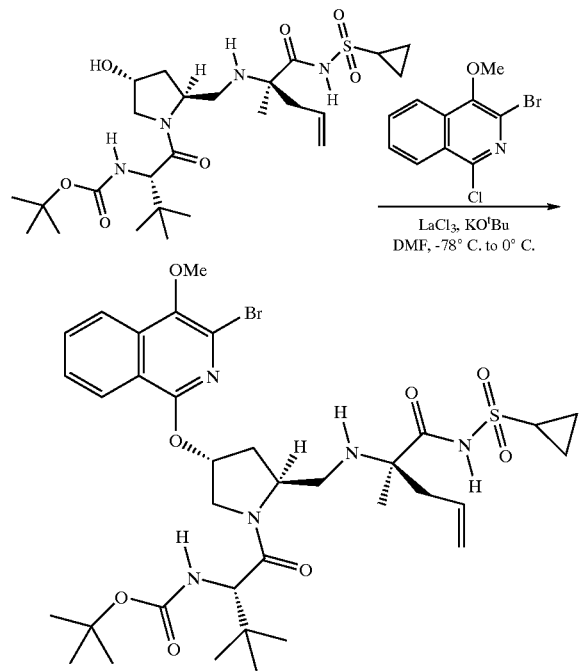

The free base (Example 222d) obtained in the previous step was alkylated with the tripeptide fragment using the alkylation protocol (Example 184) described elsewhere to give 79% of the desired product as a paper-white solid. LC/MS $R_t$-min ($MNa^+$) [method C]: 3.91 (814). $^1H$ NMR (400 MHz, $CD_3OD$) δ ppm 1.02 (s, 9 H) 1.06 (dd, J=8.07, 1.47 Hz, 2 H) 1.22 (m, 11 H) 1.42 (dd, J=9.78, 5.14 Hz, 1 H) 1.86 (dd, J=8.07, 5.38 Hz, 1 H) 2.22 (dd, J=18.10, 9.29 Hz, 1 H) 2.28 (m, 1 H) 2.61 (dd, J=13.57, 6.97 Hz, 1 H) 2.93 (m, 1 H) 3.92 (s, 3 H) 4.06 (dd, J=11.86, 2.81 Hz, 1H) 4.22 (s, 1 H) 4.43 (d, J=11.49 Hz, 1 H) 4.51 (m, 1 H) 5.10 (d, J=10.52 Hz, 1 H) 5.28 (d, J=17.12 Hz, 1 H) 5.74 (m, 1 H) 5.81 (s, 1 H) 7.56 (t, J=7.58 Hz, 1 H) 7.78 (t, J=7.58 Hz, 1 H) 8.00 (d, J=8.31 Hz, 1 H) 8.16 (d, J=8.56 Hz, 1 H).

Example 224 and 225

Preparation of Compounds 224 and Compound 225

The 4-methoxy group in 1-chloro-3-bromo-4-methoxy isoquinoline (Example 222d) described previously was converted into α-trimethylsilyl ethoxy methyl (SEM) moiety by the following procedure. 1-Chloro-3-bromo-4-methoxy iso-quinoline (Example 222d) was demethylated using $BBr_3$ (final adjusted reaction concentration was 0.2–0.3 Molar $BBr_3$) at room temperature for 12 hrs. The high $BBr_3$ concentration for such de-methylation was found to be necessary and efficient. The crude reaction mixture was diluted with 50 volumes of anhydrous methanol prior to evaporation to dryness. The demethylation was essentially quantitative. Example 222e: LC/MS $R_t$-min ($MH^+$) [method D]: 2.32 (258). $^1H$ NMR of free HCl salt (400 MHz, CHLOROFORM-D) δ ppm 5.83 (br. s, 1 H) 7.73 (t, J=7.70 Hz, 1 H) 7.79 (t, J=7.58 Hz, 1 H) 8.22 (m, 2 H). The 4-hydroxy-3-bromo-1-chloro isoquinoline (Example 222e) was re-protected with 2-(trimethylsilyl) ethoxy methyl chloride (SEM-Cl). The crude free base from the previous preparation was dried to 40 microns (Hg) at room temperature prior to re-protection with SEM-chloride. To a solution of the 4-hydroxy compound (Example 222e, 1.33 gm, 5.2 mmol) in methylene chloride (50 ml) at 0° C. was added sequentially diisopropylethyl amine (2 mL, 11.5 mmol) and SEM-chloride (1.8 mL, 10 mmol). The mixture was stirred for 10 min before it was washed with a freshly prepared $NaHCO_3$ solution (5%, 100 mL). The organic residues were extracted into several portions of methylene chloride, the combined organic layers were back-washed with 20 mL deionized water before it was concentrated in vacuo. The SEM protection was essentailly quantitative. Example 222 LC/MS $R_t$-min ($MH^+$) [method D]: 3.40 (410). $^1H$ NMR (400 MHz CHLOROFORM-D) δ ppm 0.03 (s, 9. H) 0.99 (m, 2 H) 3.98 (m, 2 H) 5.33 (s, 2 H) 7.72 (m, 1 H) 7.80 (m, 1 H) 8.17 (d, J=8.56 Hz, 1H) 8.27 (d, J=8.07 Hz, 1H). Alkylation of 4-SEM protected isoquinoline with tripeptide: Compound 224 and Compound 225 were generated from the same tripeptide alkylation reaction. The 4-hydroxy compound (Compound 224) was produced most probably as a result of the V TFA present during the preparative HPLC purification.

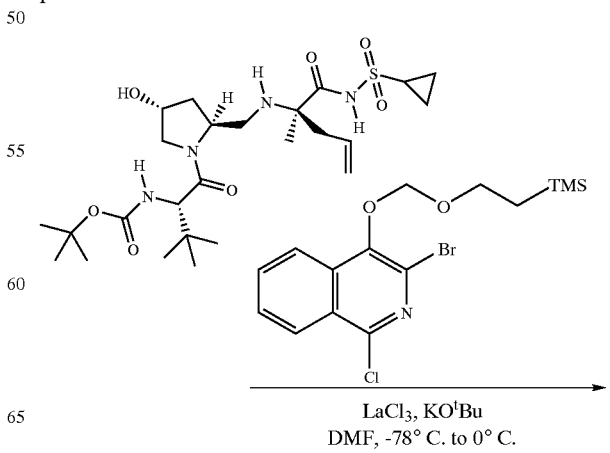

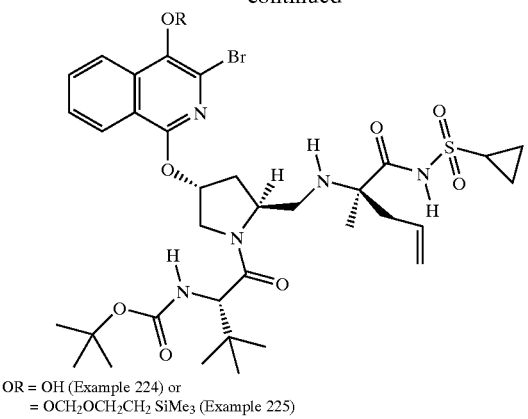

OR = OH (Example 224) or
= OCH₂OCH₂CH₂ SiMe₃ (Example 225)

Example 224 (15.4%): LC/MS $R_t$-min (MNa⁺) [method D]: 2.87 (800). ¹H NMR (400 MHz, CD₃OD) δ ppm 1.02 (s, 9 H) 1.06 (d, J=8.31 Hz, 2 H) 1.25 (s, 9 H) 1.42 (s, 2 H) 1.86 (m, 1 H) 2.23 (m, 2 H) 2.60 (dd, J=13.21, 7.34 Hz, 1 H) 2.93 (m, 1 H) 4.06 (d, J=11.00 Hz, 1 H) 4.24 (m, 2 H) 4.38 (d, J=11.98 Hz, 1 H) 4.49 (dd, J=9.78, 7.09 Hz, 1 H) 5.10 (d, J=10.03 Hz, 1 H) 5.28 (d, J=17.36 Hz, 1 H) 5.72 (m, 1 H) 5.76 (s, 1 H) 7.52 (t, J=7.46 Hz, 1 H) 7.71 (t, J=7.09 Hz, 1 H) 8.09 (d, J=4.40 Hz, 1 H) 8.11 (d, J=4.16 Hz, 1 H).

Example 225 (8.0%): LC/MS $R_t$-min ([M-BOC]+) [method D]: 3.46 (808). ¹H NMR (400 MHz, CD₃OD) δ ppm 0.01 (s, 9 H) 0.96 (m, 2 H) 1.02 (s, 11 H) 1.06 (d, J=6.60 Hz, 2 H) 1.24 (s, 9 H) 1.42 (m, 1 H) 1.86 (dd, J=7.83, 5.38 Hz, 1H) 2.25 (m, 2H) 2.62 (dd, J=13.69, 7.34 Hz, 1 H) 2.93 (m, 1H) 3.97 (m, 2H) 4.07 (dd, J=10.88, 3.55 Hz, 1 H) 4.23 (s, 1 H) 4.43 (d, J=11.25 Hz, 1 H) 4.50 (m, 1 H) 5.10 (d, J=10.76 Hz, 1 H) 5.25 (m, 3 H) 5.74 (m, 1 H) 5.82 (s, 1 H) 7.57 (m, 1 H) 7.77 (t, J=7.83 Hz, 1 H) 8.06 (d, J=8.56 Hz, 1 H) 8.16 (d, J=8.31 Hz, 1 H).

Preparation of 4H-[1,3]dioxino[5,4-c]isoquinolin P2* Derivatives

General Synthetic Scheme

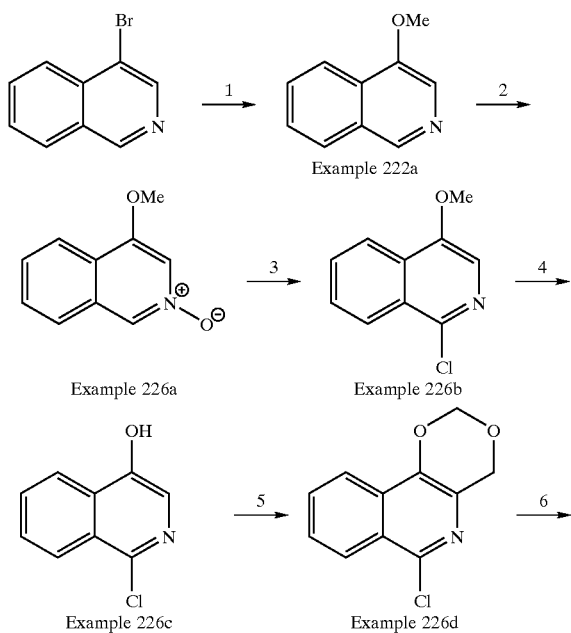

Reaction Conditions: (1) MeOK in DMPU; (2) MCPBA in CH₂Cl₂; (3) POCl₃ in DCE; (4) BBr₃ in CH₂Cl₂; (5) HCHO solution in 40% H₂SO₄ by procedure of Synthesis of 1,3-oxazino[5,6-c]isoquinolines and related compounds. Miyoko Toyama and Hirotaka Otomasu, *Chem. Pharm. Bull.* 33(12), 5543–5546, 1985; (6) Fluororination procedure by Uchibori, Y.; Umeno, M.; Yoshiokai, H.; *Heterocycles*, 1992, 34 (8), 1507–1510

Example 227

Preparation of Compound 227

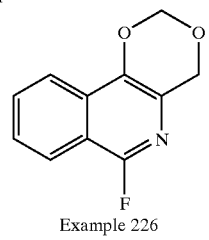

Example 226

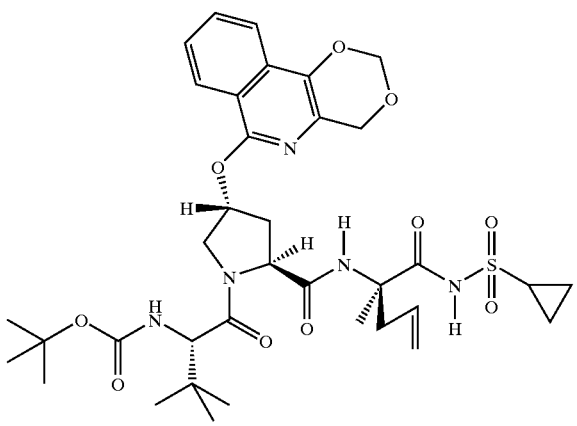

6-Chloro-1,3-Oxazino[5,6-c]isoquinoline was prepared by the procedure of Miyoko Toyama and Hirotaka Otomasu starting from 1-chloro-4-hydroxy isoquinoline. The starting material: 1-chloro-4-hydroxy isoquinoline (Example 226c) was prepared by the synthetic sequence shown above. MCPBA oxidation of 4-methoxy isoquinoline (Example 222a) was carried as usual to give 79.1% of the corresponding N-oxide (Example 226a). The material was converted into the 1-chloro derivative immediately afterward in POCl₃ to give the chloride (Example 226b) in essentially quantitative yield. The crude 1-chloro-4-methoxy isoquinoline was de-methylated in BBr₃ at room temperature to give the corresponding 1-chloro-4-hydroxy isoquinoline (Example 226c) after treating the crude BBr₃ mixture with anhydrous methanol at room temperature, followed by evaporation to get rid of excess of borate residues. The reaction of Miyoko Toyama and Hirotaka Otomasu gave 266 mg of 6-chloro-1,3-oxazino[5,6-c]isoquinoline (Example 226d, 62.3%) overall yield from 300 mg of 4-methoxy isoquinoline in 4 steps. LC/MS $R_t$-min ([M−HCHO]H⁺) [method D]: 2.45 (192). ¹H NMR (400 MHz, CHLOROFORM-D) δ ppm 5.02 (s, 2 H) 5.41 (s, 2 H) 7.68 (m, 1 H) 7.77 (ddd, J=8.25, 6.91, 1.22 Hz, 1 H) 8.10 (d, J=8.31 Hz, 1 H) 8.26 (d, J=8.56 Hz, 1 H).

The chloride was found to be unreactive under the alkylation protocol of Example 184. The corresponding 6-fluoro-1,3-oxazino[5,6-c]isoquinoline (Example 226) was prepared by the method of [Uchibori, Y.; Umeno, M.; Yoshiokai, H.; Heterocycles, 1992, 34 (8), 1507–1510] cited earlier. The reaction was not allowed to go to completion, and the crude reaction mixture was recovered as a mixture of ratio of 1:2.4 (Cl:F). Without further purification, the chloride/fluoride mixture was alkylated with the tripeptide using the procedure of Example 184 to give 66 mg (50.0%) of BOCNH-P3(L-t-BuGly)-P2[(4R)-(1,3-oxazino[5,6-c] isoquinoline-6-oxo)-S-proline]-P1(1R,2S VinylAcca)-CONHSO$_2$Cyclopropane after preparative HPLC purification. LC/MS R$_t$-min (MNa$^+$) [method D]: 3.03 (764). $^1$H NMR (400 MHz, CD$_3$OD) δ ppm 1.01 (s, 9 H) 1.06 (dd, J=8.07, 1.96 Hz, 2 H) 1.22 (s, 10 H) 1.34 (d, J=6.11 Hz, 1 H) 1.42 (m, 1 H) 1.86 (dd, J=8.07, 5.38 Hz, 1 H) 2.23 (m, 2 H) 2.59 (dd, J=13.82, 6.97 Hz, 1 H) 2.93 (m, 1 H) 4.03 (dd, J=11.86, 3.06 Hz, 1 H) 4.23 (s, 1 H) 4.41 (d, J=11.98 Hz, 1 H) 4.50 (dd, J=9.66, 6.97 Hz, 1 H) 4.87 (m, 2 H) 5.11 (d, J=10.52 Hz, 1 H) 5.28 (d, J=17.12 Hz, 1 H) 5.34 (s, 2 H) 5.74 (m, 2 H) 7.51 (t, J=7.46 Hz, 1 H) 7.70 (t, J=7.58 Hz, 1 H) 7.95 (d, J=8.31 Hz, 1 H) 8.12 (d, J=8.31 Hz, 1 H).

Preparation of 4-methoxy-3-heteroaryl and 3-azoyl isoquinoline P2* Derivatives Via Suzuki and Stille Coupling Reactions The coupling technologies shown below demonstrated the general ultility with the bromo derivative of Example 223. It is understood that a similar protocol is equally applicable to other combinations coupling reagents and catalysts other than boron and tin.

Example 229

Preparation of Compound 229

BOCNH-P3(L-t-BuGly)-P2[(4R)-(3-furan-3-yl-4-methoxy-isoquinolin-1-oxo)-S-proline]-P1(1R,2S VinylAcca)-CONHSO$_2$Cyclopropane via a Suzuki coupling shown below:

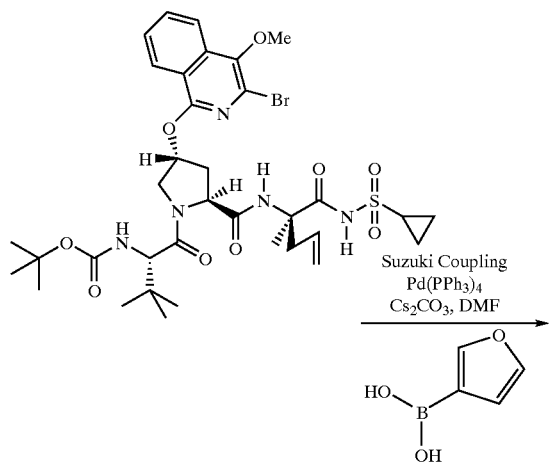

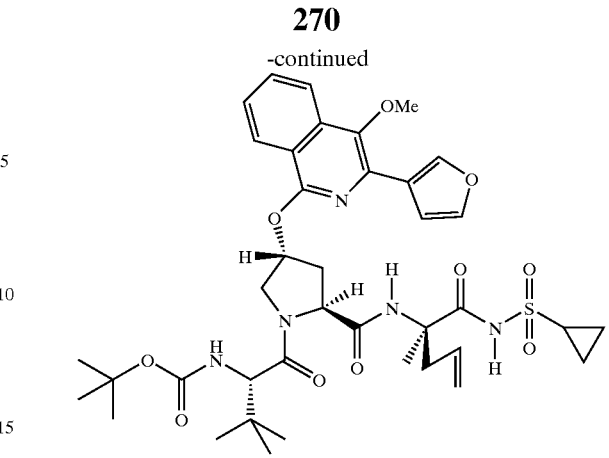

22 mg (0.028 mmole) of Example 223 was dissolve in 1 ml of DMF, 9.4 mg of the commercial boronic acid (3 eq), 3 mg of catalyst (10% mmole) and 18 mg of cesium carbonate were added. The mixture was degassed twice, and then heated up to 110° C. for 3 hours. The final product was purified by prep-HPLC, 13.6 mg of yellow solid was obtained (64.0%). LC/MS rt-min (MH$^+$): 2.85 (780) [method B]. $^1$H NMR (500 MHz, CD$_3$OD) δ ppm 1.09 (m, 11 H) 1.26 (m, 12 H) 1.68 (m, 1 H) 2.27 (s, 1 H) 2.64 (m, 2 H) 2.97 (m, 1 H) 3.86 (s, 3 H) 4.15 (d, J=10.38 Hz, 1 H) 4.28 (s, 1 H) 4.43 (d, J=10.99 Hz, 1 H) 4.56 (m, 1 H) 5.11 (m, 2 H) 5.63 (m, 1 H) 5.99 (s, 1 H) 7.20 (s, 1 H) 7.51 (m, 1 H) 7.61 (m, 1 H) 7.75 (t, J=7.17 Hz, 1 H) 8.03 (d, J=8.24 Hz, 1 H) 8.16 (d, J=8.24 Hz, 1 H) 8.27 (s, 1 H).

Example 230

Preparation of Compound 230

BOCNH-P3 (L-t-BuGly)-P2[(4R)-(3-furan-2-yl-4-methoxy-isoquinolin-1-oxo)-S-proline]-P1(1R,2S VinylAcca)-CONHSO$_2$Cyclopropane was synthesized via a Stille coupling reaction shown below:

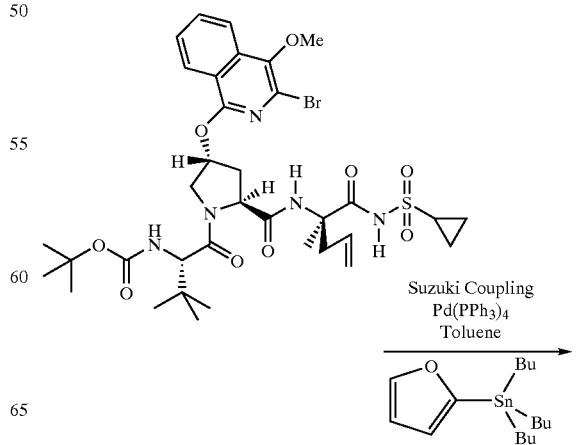

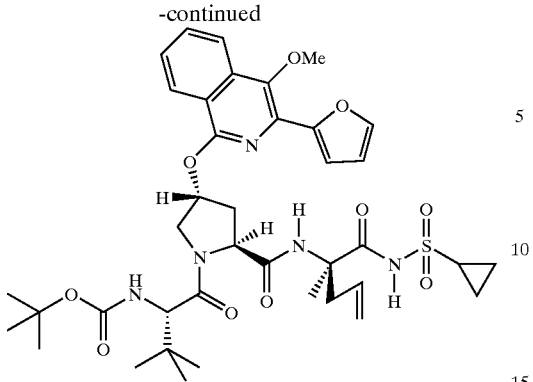

40 mg (0.05 mmole) of Example 223, 4 mg of catalyst (5% mmole) and 100 μl H (4 eq) of the commercial tin reagent was dissoled in 1 ml of toluene, the mixture was degassed twice and then heated up to 90° C. for overnight. After prep HPLC separation, 19.6 mg of greenish solid was obtained (50.0%). LC/MS rt-min (MH$^+$): 2.76 (780) [method B]. $^1$H NMR (400 MHz, CD$_3$OD) δ ppm 0.94 (m, 2 H) 0.98 (s, 9 H) 1.09 (m, 2 H) 1.25 (s, 9 H) 1.39 (m, 1 H) 1.60 (m, 1 H) 2.35 (m, 1 H) 2.48 (m, 1 H) 2.74 (m, 1 H) 2.95 (m, 1 H) 3.87 (s, 3 H) 4.14 (m, 1 H) 4.22 (d, J=4.16 Hz, 1 H) 4.41 (s, 1 H) 4.69 (m, 1 H) 5.26 (m, 1 H) 5.35 (m, 1 H) 5.93 (s, 1 H) 6.03 (m, 1 H) 6.61 (m, 1 H) 7.16 (d, J=3.18 Hz, 1 H) 7.50 (d, J=7.58 Hz, 1 H) 7.67 (s, 1 H) 7.73 (t, J=7.34 Hz, 1 H) 8.04 (m, 1 H) 8.17 (d, J=8.31 Hz, 1 H).

Example 231

Preparation of Compound 231

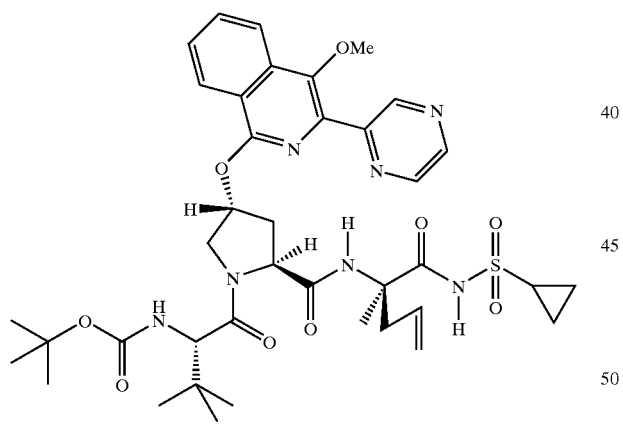

BOCNH-P3(L-t-BuGly)-P2[(4R)-(3-pyrazine-2-yl-4-methoxy-isoquinolin-1-oxo)-S-proline]-P1(1R,2S VinylAcca)-CONHSO$_2$Cyclopropane was similarly prepared by a Stille coupling reaction in 7.1% yield. LC/MS rt-min (MH$^+$): 2.51 (792) [method B].

$^1$H NMR (400 MHz, CD$_3$OD) δ ppm 0.98 (m, 9 H) 1.11 (m, 2 H) 1.19 (s, 9H) 1.27 (m, 2 H) 1.42 (m, 1 H) 2.37 (m, 1 H) 2.48 (m, 2 H) 2.81 (m, 1 H) 2.97 (m, 1 H) 3.83 (s, 3 H) 4.07 (s, 1 H) 4.20 (d, J=4.16 Hz, 1 H) 4.54 (d, J=11.49 Hz, 1 H) 4.72 (m, 1 H) 5.27 (m, 1 H) 5.39 (m, 1 H) 5.96 (s, 1 H) 6.04 (m, 1 H) 7.63 (s, 1 H) 7.83 (s, 1 H) 8.17 (s, 1 H) 8.26 (s, 1 H) 8.60 (d, J=2.20 Hz, 1 H) 8.76 (d, J=2.20 Hz, 1 H) 9.33 (s, 1 H).

Example 232

Preparation of Compound 232

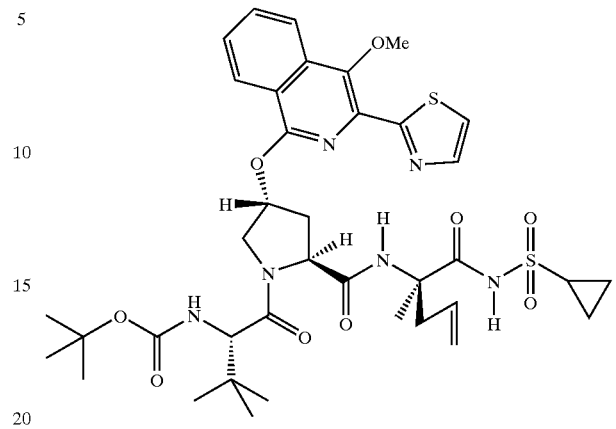

BOCNH-P3(L-t-BuGly)-P2[(4R)-(4-methoxy-3-thiazol-2-yl-isoquinolin-1-oxo)-S-proline]-P1(1R,2S VinylAcca)-CONHSO$_2$Cyclopropane was similarly prepared by a Stille coupling reaction in 32.2% yield. LC/MS rt-min (MH$^+$): 2.42 (797) [method B].

$^1$H NMR (400 MHz, CD$_3$OD) δ ppm 1.03 (S, 9 H) 1.07 (m, 2 H) 1.13 (S, 9H) 1.22 (m, 2 H) 1.43 (dd, J=9.78, 5.14 Hz, 1 H) 1.88 (dd, J=8.07, 5.38 Hz, 1 H) 2.23 (q, J=8.97 Hz, 1 H) 2.36 (m, 1 H) 2.67 (m, 1 H) 2.94 (m, 1 H) 4.10 (s, 3 H) 4.15 (m, 1 H) 4.18 (s, 1 H) 4.53 (d, J=25.92 Hz, 1H) 4.59 (dd, J=10.27, 7.09 Hz, 1H) 5.12 (m, 1 H) 5.29 (d, J=17.36 Hz, 1 H) 5.73 (m, 1 H) 6.09 (s, 1 H) 7.74 (t, J=7.58 Hz, 1 H) 7.91 (t, J=7.70 Hz, 1 H) 8.00 (d, J=3.42 Hz, 1 H) 8.18 (d, J=3.18 Hz, 1 H) 8.22 (d, J=8.31 Hz, 1 H) 8.29 (d, J=8.31 Hz, 1 H).

Example 233

Preparation of Compound 233

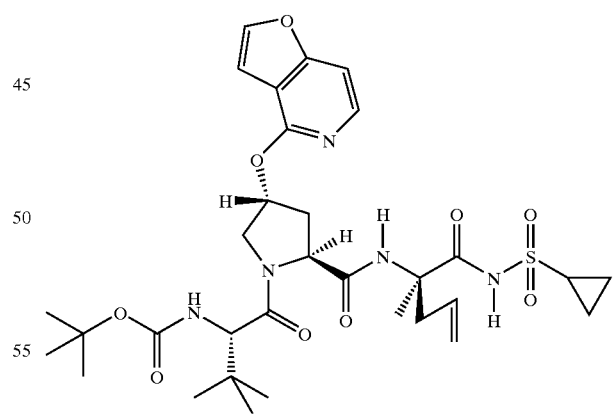

Following the general tripeptide alkylation procedure with the commercial 4-chlorofuro[3,2-c]pyridine, 5.7 mg of yellow solid was obtained (8.2%). LC/MS rt-min (MH$^+$): 2.32 (674) [method B]. $^1$H NMR (400 MHz, CD$_3$OD) δ ppm 1.00 (s, 9 H) 1.07 (m, 2 H) 1.21 (m, 11 H) 1.41 (m, 1 H) 1.86 (dd, J=8.07, 5.38 Hz, 1 H) 2.22 (dd, J=17.61, 9.05 Hz, 2 H) 2.54 (dd, J=13.69, 7.09 Hz, 1 H) 2.92 (m, 1 H) 4.06 (m, 1 H) 4.21 (m, 1 H) 4.32 (s, 1 H) 4.49 (m, 1 H) 5.11 (dd, J=10.27, 1.47 Hz, 1 H) 5.29 (dd, J=17.36, 1.22 Hz, 1 H) 5.74 (m, 1 H) 5.81 (s, 1 H) 6.83 (d, J=1.22 Hz, 1 H) 7.19 (d, J=5.87 Hz, 1 H) 7.76 (d, J=1.22 Hz, 1 H) 7.97 (d, J=5.87 Hz, 1 H).

Example 235

Preparation of Compound 235

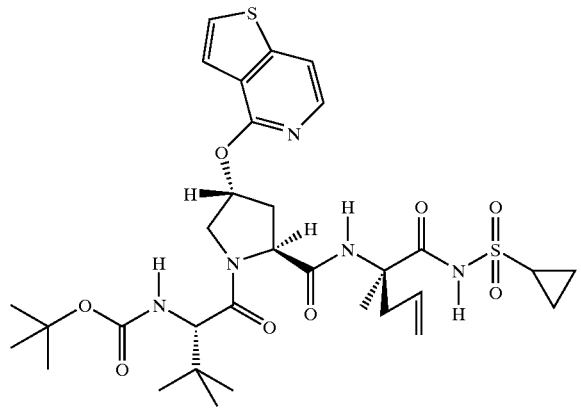

Following the general tripeptide alkylation procedure with the commercial 4-chlorothieno[3,2-c]pyridine, 20.0 mg of yellow solid was obtained (28.1%). LC/MS rt-min (MH+): 2.50 (690) [method B]. $^1$H NMR (400 MHz, CD$_3$OD) δ ppm 1.01 (s, 9 H) 1.06 (m, 2 H) 1.21 (m, 11 H) 1.42 (m, 1 H) 1.86 (dd, J=8.19, 5.50 Hz, 1 H) 2.24 (m, 2 H) 2.57 (dd, J=13.69, 6.85 Hz, 1 H) 2.93 (m, 1 H) 4.05 (dd, J=11.98, 3.18 Hz, 1 H) 4.22 (s, 1 H) 4.39 (d, J=11.74 Hz, 1 H) 4.50 (dd, J=9.90, 7.21 Hz, 1H) 5.10 (dd, J=10.39, 1.34 Hz, 1 H) 5.28 (d, J=17.12 Hz, 1 H) 5.73 (m, 1 H) 5.81 (s, 1H) 7.45 (d, J=5.62 Hz, 1 H) 7.53 (m, 2 H) 7.94 (d, J=5.87 Hz, 1 H).

Example 236

Preparation of Compound 236

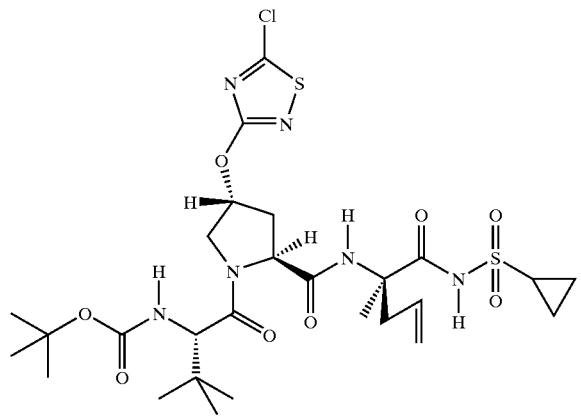

Following the general tripeptide alkylation procedure with the commercial 3,5-dichloro-1,2,4-thiadiazole, 8.0 mg of yellow solid was obtained (11.9%). LC/MS rt-min (MNa+): 2.37 (697) [method B]. $^1$H NMR (400 MHz, CD$_3$OD) δ ppm 1.00 (s, 9 H) 1.06 (m, 2 H) 1.22 (m, 2 H) 1.36 (s, 9 H) 1.42 (m, 1 H) 1.86 (dd, J=8.07, 5.38 Hz, 1 H) 2.25 (m, 2 H) 2.60 (dd, J=14.18, 6.85 Hz, 1 H) 2.92 (m, 1 H) 4.03 (dd, J=12.47, 3.18 Hz, 1 H) 4.17 (s, 1 H) 4.42 (m, 2 H) 5.11 (dd, J=10.27, 1.71 Hz, 1 H) 5.29 (dd, J=17.12, 1.47 Hz, 1 H) 5.68 (s, 1 H) 5.74 (m, 1 H).

Example 237

Preparation of Compound 237

BOCNH-P3(L-t-BuGly)-P2[(4R)-(quinoxaline-2-oxo)-S-proline]-P1 (1R,2S VinylAcca)-CONHSO$_2$Cyclopropane, Shown below

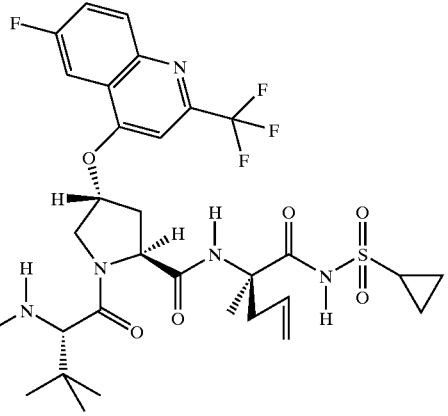

Following the general tripeptide alkylation procedure with commercial 2-chloroquinoxaline, 113.0 mg of yellow solid was obtained (19.2%). LC/MS rt-min (MNa+): 2.48 (707) [method B]. $^1$H NMR (400 MHz, CD$_3$OD) δ ppm 1.01 (s, 9 H) 1.06 (m, 2 H) 1.22 (m, 11 H) 1.42 (m, 1 H) 1.87 (dd, J=8.19, 5.50 Hz, 1 H) 2.24 (m, 1 H) 2.31 (m, 1 H) 2.57 (dd, J=13.57, 6.97 Hz, 1 H) 2.93 (m, 1 H) 4.09 (dd, J=11.98, 3.18 Hz, 1 H) 4.17 (s, 1 H) 4.38 (d, J=11.74 Hz, 1 H) 4.50 (dd, J=10.27, 7.09 Hz, 1 H) 5.11 (dd, J=10.27, 1.71 Hz, 1 H) 5.29 (dd, J=17.12, 1.47 Hz, 1 H) 5.74 (m, 1 H) 5.87 (s, 1 H) 7.62 (t, J=7.46 Hz, 1 H) 7.73 (t, J=7.70 Hz, 1 H) 7.87 (m, 1 H) 7.96 (d, J=8.31 Hz, 1 H) 8.42 (s, 1 H).

Example 238

Preparation of Compound 238

BOCNH-P3(L-t-BuGly)-P2[(4R)-(2-trifluoro-6-fluoroquinoline-4-oxo)-S-proline]-P1(1R,2S VinylAcca)-CONHSO$_2$Cyclopropane, Shown below Following the general tripeptide alkylation procedure with the commercial 2-trifluoromethyl-4-chloro-6-fluoro quinoline, 17.0 mg of yellow solid was obtained (23.2%). LC/MS rt-min (MNa+): 2.66 (792) [method B]. $^1$H NMR (400 MHz, CD₃OD) δ ppm 1.02 (s, 9 H) 1.06 (m, 2 H) 1.17 (s, 9 H) 1.23 (m, 2 H) 1.42 (m, 1 H) 1.86 (dd, J=8.07, 5.38 Hz, 1 H) 2.21 (q, J=8.64 Hz, 1 H) 2.32 (m, 1 H) 2.63 (dd, J=13.94, 6.85 Hz, 1 H) 2.93 (m, 1 H) 4.08 (m, 1 H) 4.18 (s, 1 H) 4.53 (m, 2 H) 5.10 (m, 1 H) 5.27 (d, J=17.12 Hz, 1 H) 5.58 (s, 1 H) 5.72 (m, 1 H) 7.39 (s, 1 H) 7.65 (m, 1 H) 7.83 (dd, J=9.29, 2.69 Hz, 1 H) 8.12 (dd, J=9.29, 5.14 Hz, 1 H).

Example 239

Preparation of Compound 239

BOCNH-P3(L-t-BuGly)-P2[(4R)-(6-fluoroquinoline-4-oxo)-S-proline]-P1 (1R,2S VinylAcca)-CONHSO₂Cyclopropane, Shown below

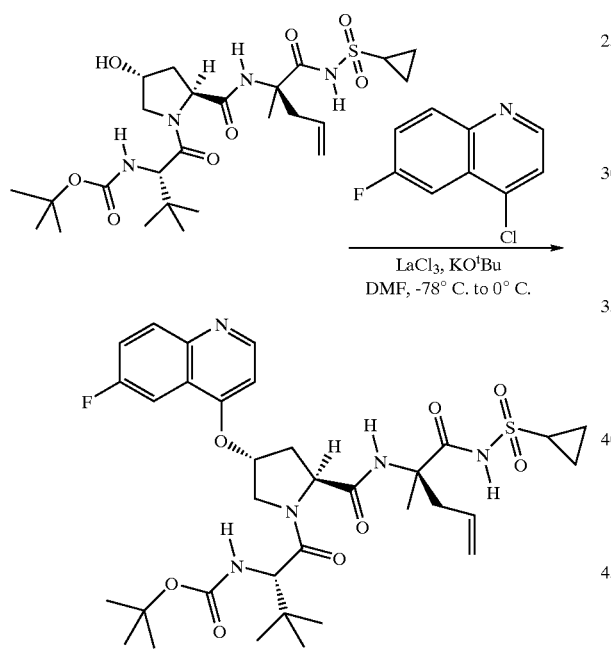

Following the general tripeptide alkylation procedure with the commercial 4-chloro-6-fluoro quinoline, 26.0 mg of yellow solid was obtained (39.0%). LC/MS rt-min (MH⁺): 1.98 (702) [method B]. ¹H NMR (400 MHz, CD₃OD) δ ppm 1.04 (m, 11 H) 1.14 (s, 9 H) 1.23 (m, 2 H) 1.42 (m, 1 H) 1.87 (dd, J=8.07, 5.38 Hz, 1 H) 2.23 (q, J=8.80 Hz, 1 H) 2.41 (m, 1 H) 2.75 (dd, J=14.43, 6.85 Hz, 1 H) 2.93 (m, 1 H) 4.09 (s, 1 H) 4.12 (d, J=2.69 Hz, 1 H) 4.61 (m, 2 H) 5.11 (dd, J=10.39, 1.59 Hz, 1 H) 5.28 (dd, J=17.24, 1.34 Hz, 1 H) 5.70 (m, 1 H) 5.75 (s, 1 H) 7.62 (d, J=6.60 Hz, 1 H) 7.93 (m, 1 H) 8.06 (dd, J=8.68, 2.57 Hz, 1 H) 8.20 (dd, J=9.29, 4.40 Hz, 1 H) 9.06 (d, J=6.60 Hz, 1 H). A small amount of the by-product due to F-displacement was also isolated from the same reaction and was separated by preparative HPLC.

Example 240

Isolation of Compound 240

BOCNH-P3(L-t-BuGly)-P2[(4R)-(4-chloroquinoline-6-oxo)-S-proline]-P1 (1R,2S VinylAcca)-CONHSO₂Cyclopropane, Shown below

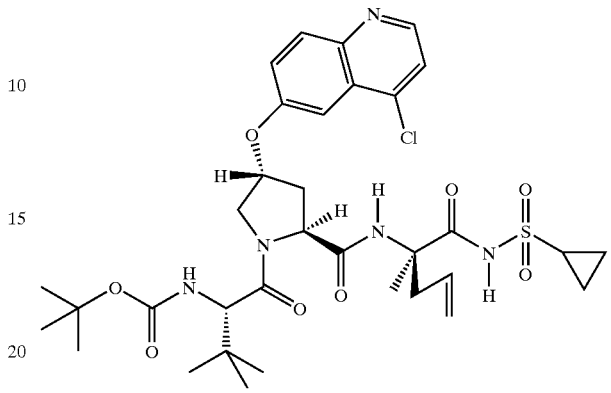

By-product, 8.0 mg of yellow solid was obtained (11.7%). LC/MS rt-min (MNa⁺): 2.240 (740) [method B]. ¹HNMR (400 MHz, CD₃OD) δ ppm 1.00 (s, 9 H) 1.06 (m, 2 H) 1.23 (m, 11 H) 1.42 (m, 1 H) 1.86 (dd, J=8.19, 5.50 Hz, 1 H) 2.22 (m, 1 H) 2.29 (m, 1 H) 2.55 (m, 1 H) 2.92 (m, 1 H) 4.09 (m, 1 H) 4.21 (s, 1 H) 4.30 (m, 1 H) 4.46 (dd, J=10.27, 6.85 Hz, 1 H) 5.11 (dd, J=10.27, 1.47 Hz, 1 H) 5.28 (dd, J=17.36, 1.47 Hz, 1 H) 5.43 (s, 1 H) 5.74 (m, 1 H) 7.60 (dd, J=9.29, 2.45 Hz, 1 H) 7.64 (d, J=2.45 Hz, 1 H) 7.81 (d, J=4.89 Hz, 1 H) 8.06 (d, J=9.29 Hz, 1 H) 8.72 (d, J=5.14 Hz, 1 H).

Example 241

Preparation of Compound 241

BOCNH-P3(L-t-BuGly)-P2[(4R)-(8-fluoroquinoline-4-oxo)-S-proline]-P1(1R,2S VinylAcca)-CONHSO₂Cyclopropane, Shown below

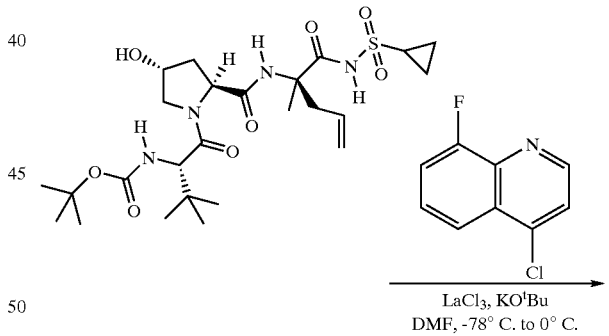

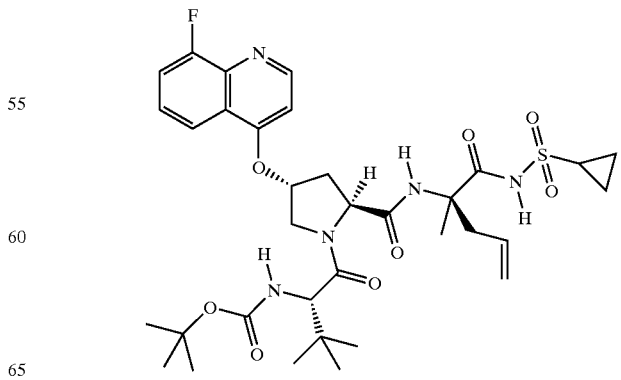

Following the general tripeptide alkylation procedure with the commercial 4-chloro-8-fluoro quinoline, 10.3 mg of yellow solid was obtained (14.7%). LC/MS rt-min (MH$^+$): 1.95 (702) [method B]. $^1$H NMR (400 MHz, CD$_3$OD) δ ppm 0.98 (s, 9 H) 1.06 (m, 2 H) 1.14 (s, 9 H) 1.22 (m, 2 H) 1.42 (m, 1 H) 1.87 (dd, J=8.07, 5.62 Hz, 1 H) 2.22 (q, J=8.72 Hz, 1 H) 2.41 (m, 1 H) 2.74 (dd, J=14.06, 6.97 Hz, 1 H) 2.93 (m, 1 H) 4.11 (m, 2 H) 4.57 (dd, J=10.39, 6.97 Hz, 1 H) 4.66 (d, J=12.23 Hz, 1 H) 5.11 (dd, J=10.27, 1.22 Hz, 1 H) 5.28 (d, J=17.12 Hz, 1 H) 5.71 (m, 2 H) 7.59 (d, J=6.36 Hz, 1 H) 7.75 (m, 1 H) 7.86 (m, 1 H) 8.23 (d, J=8.56 Hz, 1 H) 9.02 (d, J=6.36 Hz, 1 H). During the preparative HPLC purification, a by-product was also isolated. The 4-chloroquinoline-8-oxo-quinoline derivative was formed as a result of displacement of the fluorine atom instead of the chlorine leaving group.

Example 242

Isolation of Compound 242

BOCNH-P3(L-t-BuGly)-P2[(4R)-(4-chloroquinoline-8-oxo)-S-proline]-P1(1R,2S VinylAcca)-CONHSO$_2$Cyclopropane, Shown below

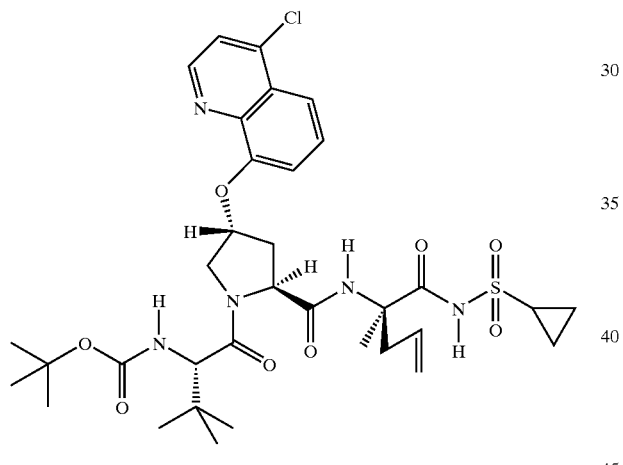

Thus the by-product, 9.0 mg of yellow solid was obtained (13.2%). LC/MS rt-min (MH$^+$): 2.37 (718) [method B]. $^1$H NMR (400 MHz, CD$_3$OD) δ ppm 1.00 (s, 9 H) 1.06 (m, 2 H) 1.12 (s, 9 H) 1.23 (m, 2 H) 1.43 (dd, J=9.41, 5.50 Hz, 1 H) 1.87 (dd, J=8.19, 5.50 Hz, 1 H) 2.25 (m, 1 H) 2.35 (m, 1 H) 2.67 (dd, J=13.94, 7.09 Hz, 1H) 2.93 (m, 1 H) 4.10 (m, 1 H) 4.13 (s, 1 H) 4.43 (d, J=11.98 Hz, 1 H) 4.65 (dd, J=10.03, 7.09 Hz, 1 H) 5.12 (dd, J=10.27, 1.47 Hz, 1 H) 5.30 (dd, J=17.12, 1.22 Hz, 1 H) 5.51 (s, 1 H) 5.75 (m, 1 H) 7.61 (d, J=7.83 Hz, 1 H) 7.88 (t, J=8.19 Hz, 1 H) 8.04 (m, 2 H) 8.91 (d, J=5.38 Hz, 1 H).

Example 243

Preparation of Compound 243

BOCNH-P3(L-t-BuGly)-P2[(4R)-(3-hydroxyquinoxaline-2-oxo)-S-proline]-P1 (1R,2S VinylAcca)-CONHSO$_2$Cyclopropane, Shown below

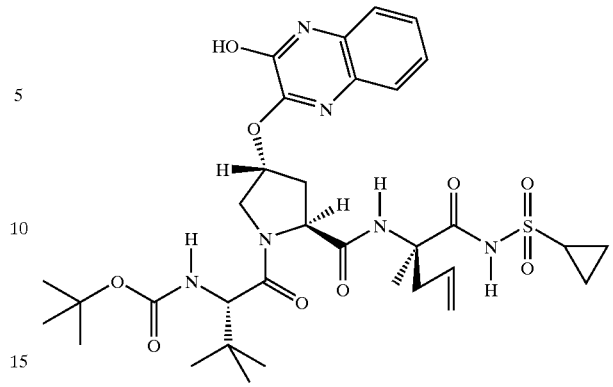

Following the general tripeptide alkylation procedure with commercial 2,3-dichloroquinoxaline, the mono alkylation product was spontaneously hydrolyzed to give 8.0 mg of pale yellow solid (11.4%). LC/MS rt-min (MNa$^+$): 2.42 (723) [method B]. $^1$H NMR (400 MHz, CD$_3$OD) δ ppm 0.99 (s, 9 H) 1.05 (m, 2 H) 1.24 (s, 9 H) 1.40 (m, 3 H) 1.86 (m, 1 H) 2.24 (m, 2 H) 2.53 (m, 1 H) 2.92 (m, 1 H) 4.06 (m, 1 H) 4.16 (s, 1 H) 4.40 (m, 1 H) 4.55 (dd, J=10.39, 6.97 Hz, 1 H) 5.11 (m, 1 H) 5.29 (m, 1 H) 5.73 (m, 1 H) 5.78 (s, 1 H) 7.15 (s, 1 H) 7.26 (m, 2 H) 7.36 (t, J=7.83 Hz, 1 H) 7.61 (d, J=8.07 Hz, 1 H).

Example 244

Preparation of Compound 244

Using a combination of Pd° coupling scheme and a step by step procedure starting from 6-bromo-1-chloro isoquinoline, BOCNH-P3(L-t-BuGly)-P2[(4R)-(6-carboxylic acid dimethylamideisoquinoline-1-oxo)-S-proline]-P1(1R,2S VinylAcca)-CONHSO$_2$Cyclopropane, was prepared.

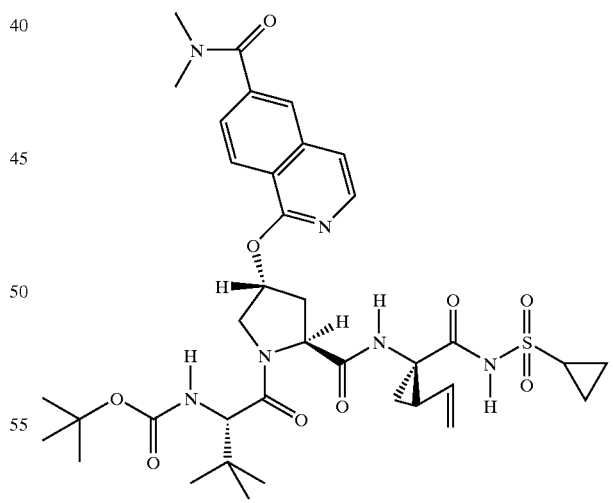

LC/MS rt-min (MNa$^+$): 2.34 (777) [method B]. $^1$H NMR (400 MHz, CD$_3$OD) δ ppm 0.98 (m, 11 H) 1.23 (m, 11 H) 1.35 (m, 11 H) 1.91 (m, 1 H) 2.29 (m, 2 H) 2.47 (m, 1 H) 2.58 (m, 1 H) 2.97 (s, 3 H) 3.11 (s, 3 H) 4.09 (m, 1 H) 4.24 (s, 1 H) 4.44 (m, 1 H) 4.61 (m, 1 H) 5.16 (m, 2 H) 5.57 (m, 1 H) 5.90 (s, 1 H) 7.38 (d, J=5.87 Hz, 1 H) 7.50 (d, J=8.07 Hz, 1 H) 7.86 (s, 1 H) 8.03 (d, J=5.87 Hz, 1 H) 8.27 (d, J=8.56 Hz, 1 H),

Example 245

Preparation of Compound 245

During one of the Pd⁰ catalyzed Stille coupling preparations (Example 230), a side product was isolated as a minor product which was subsequently identified as: BOCNH-P3 (L-t-BuGly)-P2[(4R)-(3-chloro-4-methoxyisoquinoline-1-oxo)-S-proline]-P1(1R,2S VinylAcca)-CONHSO₂Cyclopropane, shown below

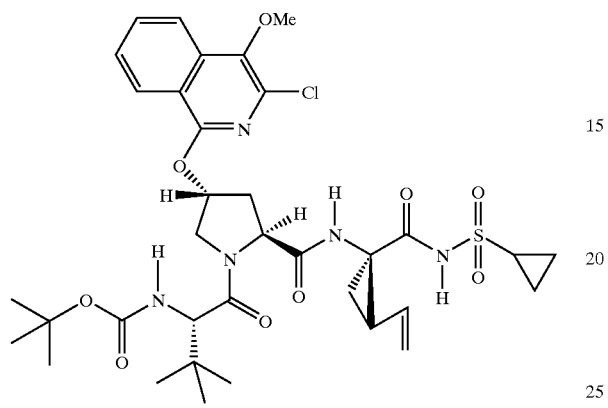

LC/MS rt-min (MNa⁺): 2.62 (770) [method B]. ¹H NMR (400 MHz, CD₃OD) δ ppm 1.01 (s, 9 H) 1.08 (m, 2 H) 1.18 (s, 9 H) 1.27 (m, 2 H) 1.37 (m, 1 H) 1.62 (m, 1 H) 2.36 (m, 2 H) 2.73 (m, 1 H) 2.97 (m, 1 H) 3.92 (s, 3 H) 4.02 (m, 1 H) 4.18 (s, 1 H) 4.48 (m, 1 H) 4.66 (m, 1 H) 5.30 (m, 2 H) 5.78 (s, 1 H) 6.04 (m, 1 H) 7.53 (t, J=7.70 Hz, 1 H) 7.77 (t, J=7.58 Hz, 1 H) 8.00 (d, J=8.56 Hz, 1 H) 8.19 (d, J=8.07 Hz, 1 H).

Section F:

Example 250

Preparation of Compound 250

Compound 250

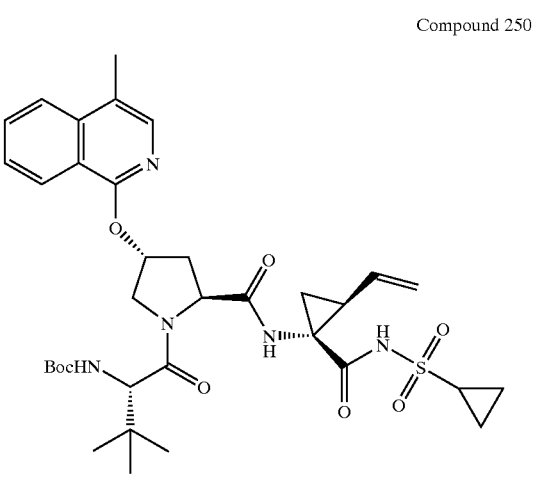

Scheme 1

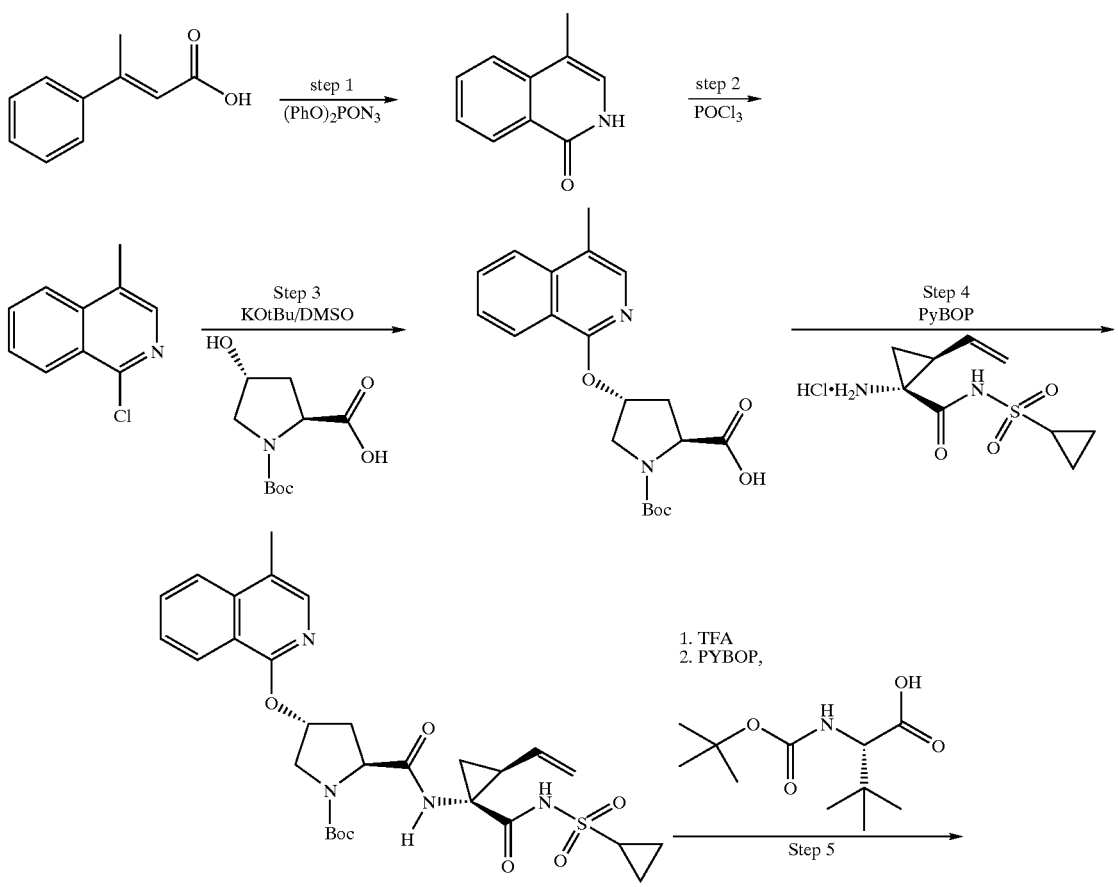

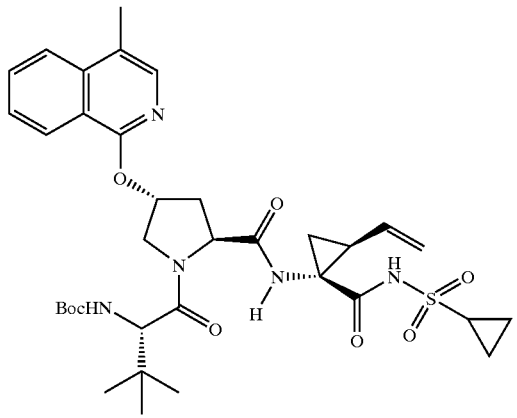

Compound 250

Step 1:

A solution of 3-phenyl-but-2-enoic acid (16.2 g), diphenylphosphoryl azide (27.5 g), and triethylamine (10.1 g) in benzene (100 mL) was stirred for 1 h. After filtration through a silica gel plug washing with benzene and concentration, the residue was dissolved in diphenylmethane (80 mL) and refluxed for 3 h. After cooling to rt, solids were collected through a plug washing with benzene and dried to give 10 g (63%) of the desired product as a solid. $^1$H NMR (400 MHz, CD$_3$OD) δ ppm 2.30 (s, 3 H), 7.00 (s, 1 H), 7.54 (m, 1 H), 7.77 (m, 2 H), 8.33 (d, J=7.34 Hz, 1 H).

Step 2

A solution of 4-methyl-2H-isoquinolin-1-one (4.8 g) in POCl$_3$ (50 mL) was refluxed for 3 h. After cooling and concentration, the residue was based with 5 N NaOH and extracted with CH$_2$Cl$_2$. The organic layer was washed with brine and dried over MgSO$_4$. After concentration, purification by flash chromatography of Biotage with 5% ethyl acetate in hexanes gave 4.8 g (90%) of the desired product as a solid. $^1$H NMR (400 MHz, CDCl$_3$) δ ppm 2.59 (s, 3 H), 7.68 (t, J=7.70 Hz, 1 H), 7.78 (m, 1 H), 7.94 (d, J=8.31 Hz, 1 H), 8.11 (s, 1 H), 8.35 (d, J=8.31 Hz, 1 H).

Step 3:

A solution of Boc-Hyp-OH (231 mg) and tert-BuOK (336 mg) in DMSO (10 mL) was stirred for 0.5 h. To the solution was added 1-chloro-4-methyl-isoquinoline (178 mg) and the resulting mixture was stirred for 1 day. The reaction was quenched with 5% citric acid and extracted with ethyl acetate. The organic layer was washed with brine and dried over MgSO$_4$. Concentration gave 350 mg (94%) of the desired product as a solid which was used in the next step without further purification. $^1$H NMR (400 MHz, CD$_3$OD) δ ppm 1.39, 1.43 (2s, 9 H, rotamers), 2.40 (dd, J=17.97, 4.52 Hz, 1 H), 2.48 (s, 3 H), 2.68 (m, 1 H), 3.84 (m, 2 H), 4.46 (m, 1 H), 5.71 (s, 1 H), 7.58 (t, J=7.70 Hz, 1 H), 7.75 (m, 2 H), 7.91 (d, J=8.31 Hz, 1 H), 8.19 (m, 1 H); MS: (M+Na)$^+$ 396.

Step 4:

A solution of 4-(4-methyl-isoquinolin-1-yloxy)-pyrrolidine-1,2-dicarboxylic acid 1-tert-butyl ester) (74 mg), cyclopropanesulfonic acid (1(R)-amino-2(S)-vinyl-cyclopropanecarbonyl)-amide hydrochloride (59 mg), PyBOP (114 mg) and i-Pr$_2$NEt (0.2 mL) in CH$_2$Cl$_2$ (2 mL) was stirred for 2 h. Purification by flash chromatograph of Biotage with 5% MeOH in ethyl acetate gave 105 mg (90%) of the desired product. $^1$H NMR (400 MHz, Methanol-D4) δ ppm 1.18 (m, 5 H), 1.39 (s, 9 H), 1.87 (dd, J=8.2, 5.3 Hz, 1 H), 2.28 (m, 2 H), 2.54 (m, 4 H), 2.95 (m, 1 H), 3.86 (m, 2 H), 4.40 (dd, J=9.8, 6.9 Hz, 1 H), 5.12 (d, J=10.5 Hz, 1 H), 5.31 (d, J=17.6 Hz, 1 H), 5.79 (m, 2 H), 7.60 (t, J=7.5 Hz, 1 H), 7.78 (m, 2 H), 7.93 (d, J=8.3 Hz, 1 H), 8.20 (d, J=8.1 Hz, 1 H); MS: (M+Na)$^+$ 607.

Step 5:

A solution of 2-(1-cyclopropanesulfonylaminocarbonyl-2-vinyl-cyclopropylcarbamoyl)-4-(4-methyl-isoquinolin-1-yloxy)-pyrrolidine-1-carboxylic acid tert-butyl ester (100 mg) and TFA (3 mL) in CH$_2$Cl$_2$ (3 mL) was stirred for 1 h. After concentration, the residue was dissolved in CH$_2$Cl$_2$ (2 mL), and Boc-L-tert-leucine (40 mg), PyBOP (104 mg) and i-Pr$_2$NEt (0.2 mL) was added. The mixture was stirred for 1 h. After work-up, purification Prep HPLC gave 60 mg (52%) of the desired product compound 250 as a solid. $^1$H NMR (400 MHz, CD$_3$OD) δ ppm 1.04 (m, 12 H), 1.26 (m, 10 H), 1.44 (dd, J=9.5, 5.1 Hz, 1 H), 1.88 (dd, J=8.1, 5.4 Hz, 1 H), 2.26 (m, 2 H), 2.49 (s, 3 H), 2.62 (dd, J=13.7, 7.1 Hz, 1 H), 2.94 (m, 1 H), 4.06 (dd, J=12.0, 3.4 Hz, 1 H), 4.25 (m, 1 H), 4.45 (d, J=11.3 Hz, 1 H), 4.53 (dd, J=10.3, 6.6 Hz, 1 H), 5.12 (d, J=10.0 Hz, 1 H), 5.29 (d, J=17.1 Hz, 1 H), 5.77 (m, 2 H), 6.63 (d, J=8.6 Hz, 1 H), 7.53 (t, J=7.8 Hz, 1 H), 7.76 (t, J=8.1 Hz, 1 H), 7.80 (s, 1 H), 7.91 (d, J=8.1 Hz, 1 H), 8.22 (d, J=8.3 Hz, 1 H); MS: (M+Na)$^+$ 720.

Example 251

Preparation of Compound 251

Compound 251

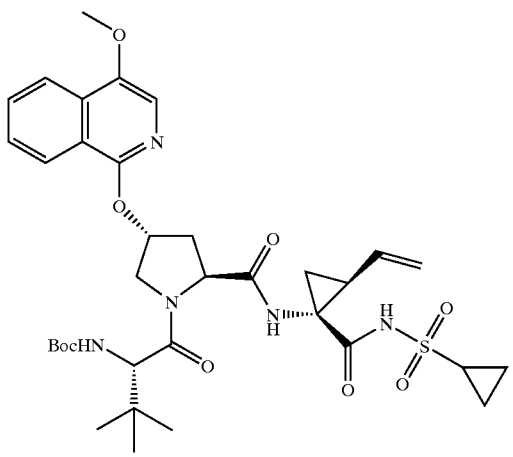

Compound 251 was prepared by following Scheme 1 of Example 250 except that 3-methoxy-3-phenyl-acrylic acid was used in place of 3-phenyl-but-2-enoic acid in step 1.

Step 1:

Modifications: 15 g 3-methoxy-3-phenyl-acrylic acid used, 250 mg product obtained (2% yield).

Product:

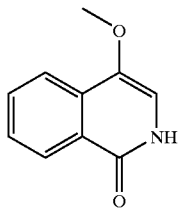

$^1$H NMR (400 MHz, CD$_3$COCD$_3$) δ ppm 3.85 (s, 3 H), 6.96 (s, 1 H), 7.54 (m, 1 H), 7.71 (m, 1 H), 7.86 (d, J=8.07 Hz, 1 H), 8.31 (d, J=8.07 Hz, 1 H).

Step 2:

Modifications: 200 mg 4-methoxy-2H-isoquinolin-1-one used, 150 mg product obtained (68% yield).

Product:

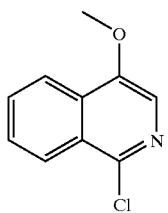

$^1$H NMR (400 MHz, CDCl$_3$) δ ppm 4.05 (s, 2 H), 7.71 (m, 1 H), 7.72 (m, 2 H), 7.80 (s, 1 H), 8.23 (dd, J=18.71, 7.70 Hz, 2 H).

Step 3:

Modifications: 122 mg 1-chloro-4-methoxy-isoquinoline used, 218 mg product obtained (89% yield).

Product:

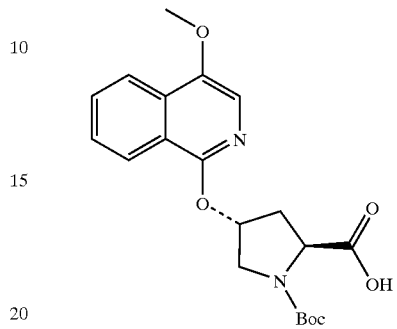

MS: (M+Na)$^+$ 411.

Step 4:

Modifications: 194 mg 4-(4-methoxy-isoquinolin-1-yloxy)-pyrrolidine-1,2-dicarboxylic acid 1-tert-butyl ester used, 298 mg product obtained (99% yield).

Product:

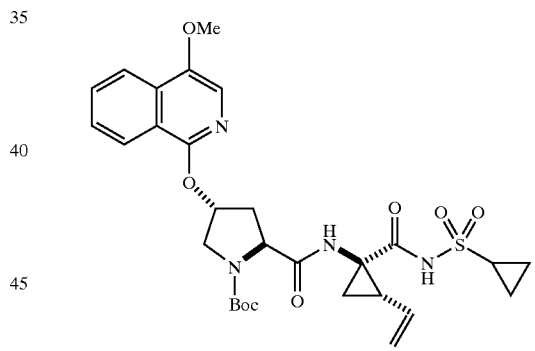

$^1$H NMR (400 MHz, CD$_3$OD) δ ppm 1.17 (m, 5 H), 1.42 (s, 9 H), 1.87 (dd, J=8.2, 5.5 Hz, 1 H), 2.27 (m, 2 H), 2.54 (dd, J=13.3, 6.2 Hz, 1 H), 2.95 (m, 1 H), 3.85 (m, 2 H), 4.00 (s, 3 H), 4.39 (dd, J=9.8, 6.9 Hz, 1 H), 5.12 (d, J=10.5 Hz, 1 H), 5.31 (d, J=17.1 Hz, 1 H), 5.76 (m, 2 H), 7.52 (s, 1 H), 7.62 (t, J=7.6 Hz, 1 H), 7.74 (t, J=7.2 Hz, 1 H), 8.12 (t, J=8.3 Hz, 2 H).

Step 5:

Modifications: 190 mg 2-(1-cyclopropanesulfonylaminocarbonyl-2-vinyl-cyclopropylcarbamoyl)-4-(4-methoxy-isoquinolin-1-yloxy)-pyrrolidine-1-carboxylic acid tert-butyl ester used, 270 mg product obtained (51% yield).

Product:

Compound 251

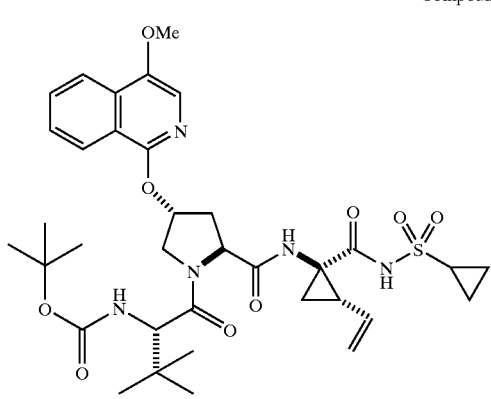

Data: ¹H NMR (500 MHz, CD₃OD) δ ppm 1.06 (m, 12 H), 1.26 (m, 10 H), 1.43 (dd, J=8.6, 4.6 Hz, 1 H), 1.88 (dd, J=7.9, 5.5 Hz, 1 H), 2.24 (m, 2 H), 2.61 (dd, J=13.6, 6.9 Hz, 1 H), 2.94 (m, 1 H), 4.00 (s, 3H), 4.06 (dd, J=11.3, 3.1 Hz, 1H), 4.25 (d, J=8.9 Hz, 1 H), 4.43 (d, J=11.3 Hz, 1 H), 4.52 (m, 1 H), 5.12 (d, J=10.1 Hz, 1 H), 5.29 (d, J=17.1 Hz, 1 H), 5.75 (m, 2 H), 6.60 (d, J=8.6 Hz, 1 H), 7.55 (m, 2 H), 7.71 (t, J=7.3 Hz, 1 H), 8.09 (d, J=8.2 Hz, 1 H), 8.14 (d, J=8.2 Hz, 1 H); MS: (M+Na)⁺ 736.

Example 252

Preparation of Compound 252

Compound 252

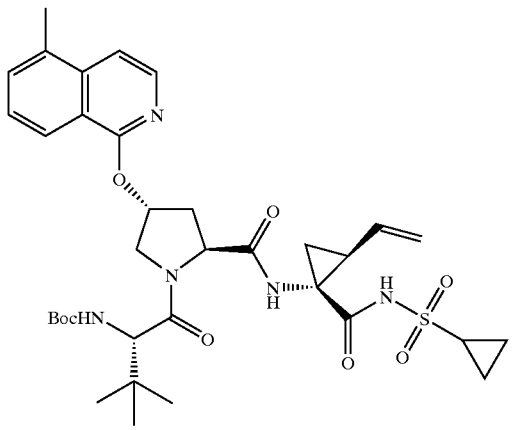

Compound 252 was prepared by following Scheme 1 of Example 250 except 2-methylcinnamic acid was used in place of 3-phenyl-but-2-enoic acid in step 1.

Step 1:

Modifications: 20 g 2-methylcinnamic acid used, 14.3 g product obtained (72% yield)

Product:

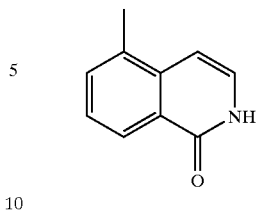

Data: ¹H NMR (400 MHz, CD₃OD) δ ppm 2.54 (s, 1 H), 6.69 (d, J=7.3 Hz, 1 H), 7.23 (d, J=7.3 Hz, 1 H), 7.39 (t, J=7.8 Hz, 1 H), 7.50 (d, J=7.1 Hz, 1 H), 8.30 (d, J=8.1 Hz, 1 H), 11.62 (s, 1 H); MS: (M+H)⁺ 160.

Step 2:

Modifications: 14.4 g 5-methyl-2H-isoquinolin-1-one used, 10.6 g product obtained (66% yield).

Product:

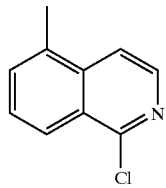

Data: ¹H NMR (400 MHz, CDCl₃) δ ppm 2.67 (s, 3 H), 7.55 (m, 2 H), 7.70 (dd, J=5.9, 1.0 Hz, 1 H), 8.19 (m, 1 H), 8.28 (d, J=5.9 Hz, 1 H); MS: (M+H)⁺ 178.

Step 3:

Modifications: 533 mg 1-chloro-5-methyl-isoquinoline used, 1116 mg product obtained (100% yield).

Product:

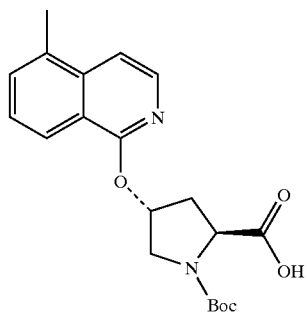

Data: MS: (M+H)⁺ 373.

Step 4:

Modifications: 372 mg 4-(5-methyl-isoquinolin-1-yloxy)-pyrrolidine-1,2-dicarboxylic acid 1-tert-butyl ester used, 551 mg product obtained (94% yield).

Product:

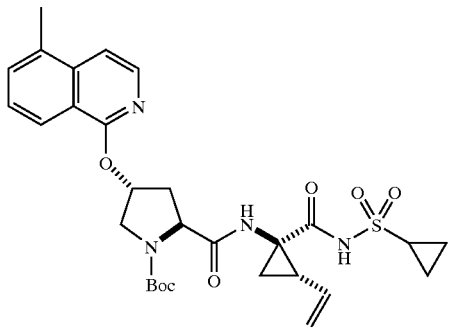

Data: MS: (M+Na)$^+$ 607.

Step 5:

Modifications: 551 mg 2-(1-cyclopropanesulfonylaminocarbonyl-2-vinyl-cyclopropylcarbamoyl)-4-(5-methyl-isoquinolin-1-yloxy)-pyrrolidine-1-carboxylic acid tert-butyl ester used, 274 mg product obtained (44% yield).

Product:

Compound 252

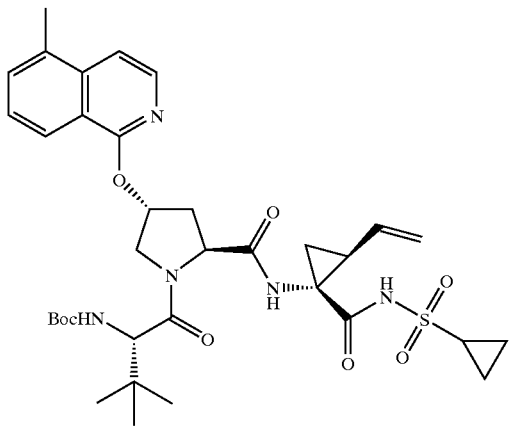

Data: $^1$H NMR (400 MHz, CD$_3$OD) δ ppm 1.00 (m, 12 H) 1.23 (m, 10 H), 1.44 (m, 1 H), 1.87 (dd, J=8.1, 5.4 Hz, 1 H), 2.26 (m, 2 H), 2.62 (m, 4 H), 2.94 (m, 1 H), 4.07 (dd, J=11.9, 3.3 Hz, 1 H), 4.25 (d, J=9.5 Hz, 1 H), 4.46 (d, J=11.5 Hz, 1 H), 4.53 (dd, J=10.3, 7.1 Hz, 1 H), 5.12 (d, J=10.5 Hz, 1 H), 5.29 (d, J=16.9 Hz, 1 H), 5.75 (m, 1 H), 5.86 (s, 1 H), 6.62 (d, J=9.3 Hz, 1 H), 7.39 (t, J=7.7 Hz, 1 H), 7.44 (d, J=5.9 Hz, 1 H), 7.53 (d, J=7.1 Hz, 1 H), 8.00 (d, J=6.1 Hz, 1 H), 8.06 (d, J=8.3 Hz, 1 H); MS: (M+H)$^+$ 698.

Example 253

Preparation of Compound 253

Compound 253

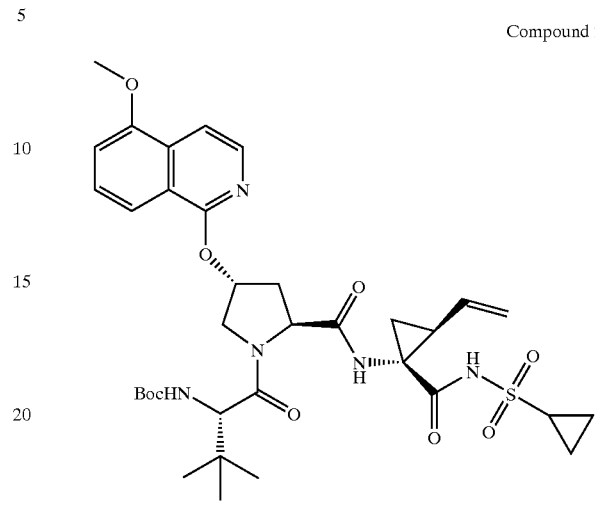

Compound 253 was prepared by following Scheme 1 of Example 250 except 2-methoxy cinnamic acid was used in place of 3-phenyl-but-2-enoic acid in step 1.

Step 1:

Modifications: 10 g 2-methoxy cinnamic acid used, 5.3 g product obtained (53% yield).

Product:

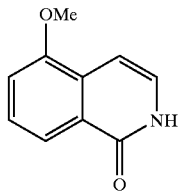

Data: $^1$H NMR (400 MHz, CD$_3$OD) δ ppm 3.95 (s, 3 H), 6.94 (d, J=7.3 Hz, 1 H), 7.08 (d, J=8.1 Hz, 1 H), 7.14 (d, J=7.3 Hz, 1 H), 7.43 (t, J=8.1 Hz, 1 H), 7.99 (d, J=8.1 Hz, 1 H), 10.92 (s, 1 H); MS: (M+H)$^+$ 176.

Step 2:

Modifications: 5.3 g 5-methoxy-2H-isoquinolin-1-one used, 5.38 g product obtained (92% yield).

Product:

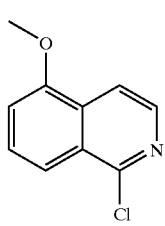

Data: $^1$H NMR (400 MHz, CDCl$_3$) δ ppm 4.01 (s, 3 H), 7.04 (d, J=7.8 Hz, 1 H), 7.57 (t, J=8.1 Hz, 1 H), 7.88 (d, J=8.6 Hz, 1 H), 7.97 (d, J=5.9 Hz, 1 H), 8.25 (d, J=5.9 Hz, 1 H); MS: (M+H)⁺ 194.

Step 3:

Modifications: 581 mg 1-chloro-5-methoxy-isoquinoline used, 1163 mg product obtained (100% yield).

Product:

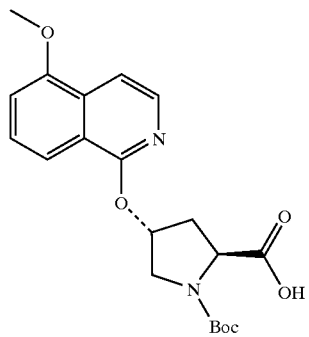

Data: MS: (M+H)⁺ 389.

Step 4:

Modifications: 117 mg 4-(5-methoxy-isoquinolin-1-yloxy)-pyrrolidine-1,2-dicarboxylic acid 1-tert-butyl ester used, 180 mg product obtained (100% yield).

Product:

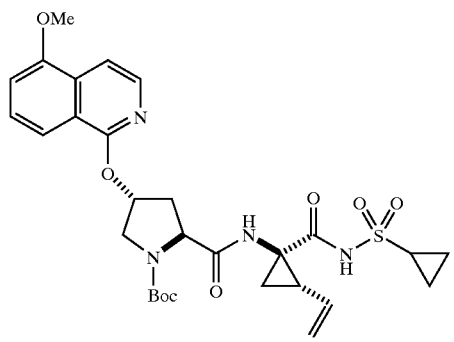

Data: MS: (M+H)⁺ 601.

Step 5:

Modifications: 177 mg 2-(1-cyclopropanesulfonylaminocarbonyl-2-vinyl-cyclopropylcarbamoyl)-4-(5-methoxy-isoquinolin-1-yloxy)-pyrrolidine-1-carboxylic acid tert-butyl ester used, 63 mg product obtained (44% yield).

Product:

Compound 253

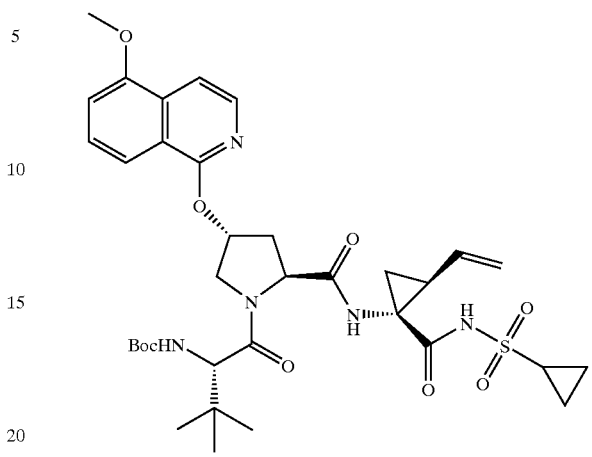

Data: ¹H NMR (400 MHz, CD₃OD) δ ppm 1.00 (m, 12 H), 1.21 (m, 10 H), 1.38 (m, 1 H), 1.82 (dd, J=8.1, 5.6 Hz, 1 H), 2.20 (m, 2 H), 2.56 (dd, J=13.6, 6.7 Hz, 1 H), 2.88 (m, 1 H), 3.08 (m, 2 H), 3.93 (s, 3 H), 4.01 (dd, J=11.9, 3.3 Hz, 1 H), 4.20 (d, J=9.1 Hz, 1 H), 4.39 (d, J=12.2 Hz, 1 H), 4.47 (dd, J=9.7, 7.0 Hz, 1 H), 5.06 (d, J=10.0 Hz, 1 H), 5.23 (d, J=16.9 Hz, 1 H), 5.70 (m, 1 H), 5.79 (s, 1 H), 6.55 (d, J=9.5 Hz, 1 H), 7.08 (d, J=7.6 Hz, 1 H), 7.37 (t, J=8.0 Hz, 1 H), 7.54 (d, J=5.9 Hz, 1 H), 7.68 (d, J=8.3 Hz, 1 H), 7.89 (d, J=5.9 Hz, 1 H); MS: (M+H)⁺ 714.

Example 254

Preparation of Compound 254

Compound 254

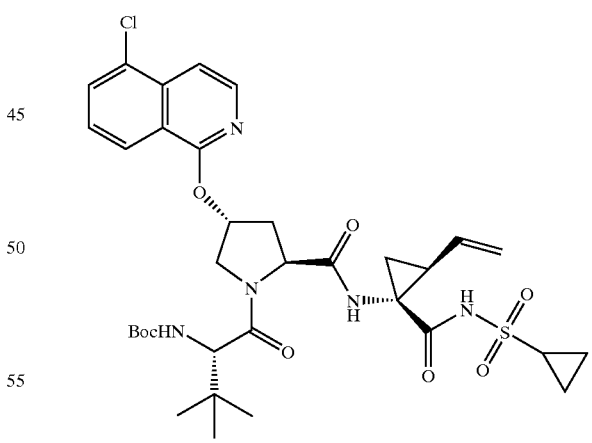

Compound 254 was prepared by following Scheme 1 of Example 250 except that 2-chlorocinnamic acid was used in place of 3-phenyl-but-2-enoic acid in step 1.

Step 1:

Modifications: 25 g 2-chlorocinnamic acid used, 14.6 g product obtained (59% yield).

Product:

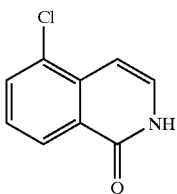

Data: ¹H NMR (400 MHz, CD₃OD) δ ppm 7.22 (d, J=7.3 Hz, 1 H), 7.42 (t, J=7.8 Hz, 1 H), 7.73 (d, J=7.8 Hz, 1 H), 8.34 (d, J=8.1 Hz, 1 H), 10.61 (s, 1 H); MS: (M+H)⁺ 180.

Step 2:

Modifications: 14.2 g 5-chloro-2H-isoquinolin-1-one used, 8.28 g product obtained (53% yield).

Product:

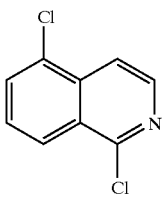

Data: ¹H NMR (400 MHz, CDCl₃) δ ppm 7.60 (dd, J=8.6, 7.6 Hz, 1 H), 7.83 (m, 1 H), 8.00 (d, J=5.9 Hz, 1 H), 8.29 (dt, J=8.9, 1.0 Hz, 1 H), 8.38 (d, J=5.9 Hz, 1 H); MS: (M+H)⁺ 198.

Step 3:

Modifications: 594 mg 1,5-dichloro-isoquinoline used, 1174 mg product obtained (100% yield).

Product:

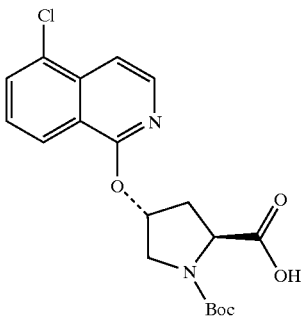

Data: MS: (M+H)⁺ 393.

Step 4:

Modifications: 118 mg 4-(5-chloro-isoquinolin-1-yloxy)-pyrrolidine-1,2-dicarboxylic acid 1-tert-butyl ester used, 154 mg product obtained (85% yield).

Product:

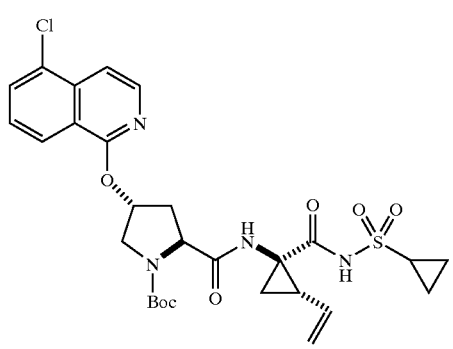

Data: MS: (M+H)⁺ 605.

Step 5:

Modifications: 150 mg 2-(1-cyclopropanesulfonylaminocarbonyl-2-vinyl-cyclopropylcarbamoyl)-4-(5-chloro-isoquinolin-1-yloxy)-pyrrolidine-1-carboxylic acid tert-butyl ester used, 91 mg product obtained (51% yield).

Product:

Compound 254

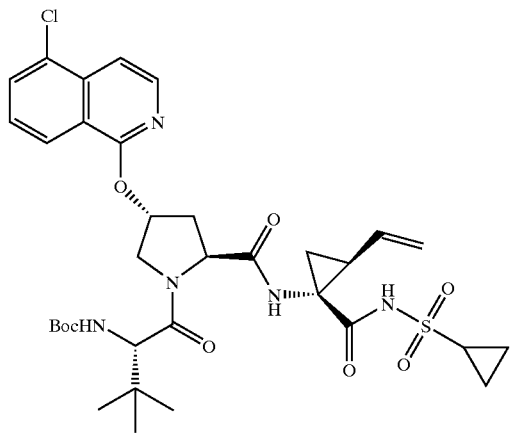

Data: ¹H NMR (400 MHz, CD₃OD) δ ppm 0.97 (m, 12 H), 1.17 (m, 10 H), 1.38 (dd, J=9.4, 5.3 Hz, 1 H), 1.82 (dd, J=8.0, 5.5 Hz, 1 H), 2.21 (m, 2 H), 2.58 (dd, J=13.8, 7.0 Hz, 1 H), 2.88 (m, 1 H), 4.01 (dd, J=11.9, 2.8 Hz, 1 H. 4.16 (d, J=9.3 Hz, 1 H), 4.47 (m, 2 H), 5.06 (d, J=10.3 Hz, 1 H), 5.24 (d, J=16.9 Hz, 1 H), 5.70 (m, 1 H), 5.82 (s, 1 H), 6.52 (d, J=9.3 Hz, 1 H), 7.42 (t, J=8.0 Hz, 1 H), 7.57 (d, J=6.1 Hz, 1 H), 7.76 (d, J=7.6 Hz, 1 H), 8.05 (d, J=6.1 Hz, 1 H), 8.13 (d, J=8.3 Hz, 1H); MS: (M+H)⁺ 718.

Example 255

Preparation of Compound 255

Compound 255

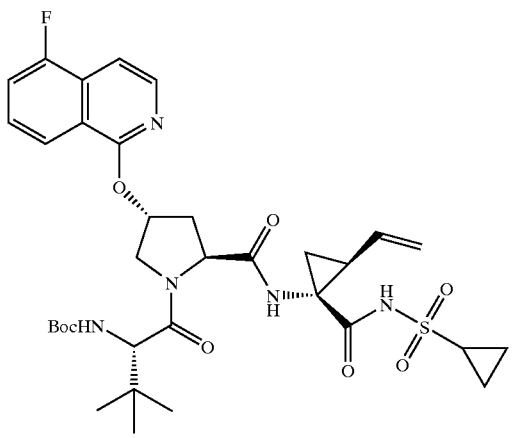

Compound 255 was prepared by following Scheme 1 of Example 250 except that 2-fluorocinnamic acid was used in place of 3-phenyl-but-2-enoic acid in step 1.

Step 1:

Modifications: 16.6 g 2-fluorocinnamic acid used, 8.55 g product obtained (51% yield).

Product:

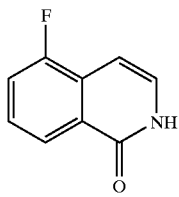

Data: $^1$H NMR (400 MHz, CD$_3$COCD$_3$) δ ppm 6.62 (d, J=7.3 Hz, 1 H), 7.32 (d, J=7.3 Hz, 1 H), 7.47 (m, 2 H), 8.09 (m, 1 H).

Step 2:

Modifications: 8.4 g 5-fluoro-2H-isoquinolin-1-one used, 7.5 g product obtained (80% yield).

Product:

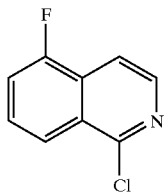

Data: $^1$H NMR (400 MHz, CDCl$_3$) δ ppm 7.43 (ddd, J=9.7, 7.8, 0.9 Hz, 1 H), 7.62 (td, J=8.2, 5.4 Hz, 1 H), 7.84 (d, J=5.6 Hz, 1 H), 8.14 (d, J=8.6 Hz, 1 H), 8.33 (d, J=5.9 Hz, 1 H); MS: (M+H)$^+$ 182.

Step 3:

Modifications: 203 mg 1-chloro-5-fluoro-isoquinoline used, 384 mg product obtained (90% yield).

Product:

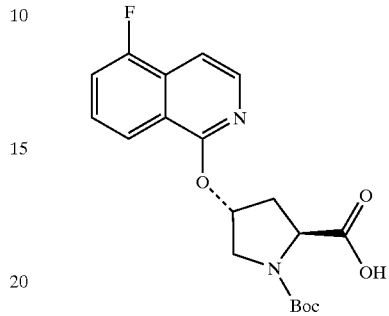

Data: $^1$H NMR (400 MHz, CD$_3$SOCD$_3$) δ ppm 1.34, 1.36 (2s, 9 H, rotamers), 2.35 (m, 1 H), 2.61 (m, 1 H), 3.65 (d, J=12.23 Hz, 1 H), 3.80 (m, 1 H), 4.35 (m, 1 H), 5.70 (s, 1 H), 7.48 (d, J=6.11 Hz, 1 H), 7.63 (m, 2 H), 7.99 (m, 1 H), 8.10 (d, J=5.87 Hz, 1 H); MS: (M+Na)$^+$ 399.

Step 4:

Modifications: 76 mg 4-(5-fluoro-isoquinolin-1-yloxy)-pyrrolidine-1,2-dicarboxylic acid 1-tert-butyl ester used, 116 mg product obtained (99% yield).

Product:

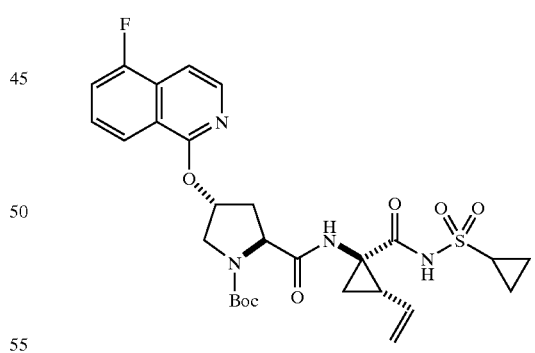

Step 5:

Modifications: 110 mg 2-(1-cyclopropanesulfonylaminocarbonyl-2-vinyl-cyclopropylcarbamoyl)-4-(5-fluoro-isoquinolin-1-yloxy)-pyrrolidine-1-carboxylic acid tert-butyl ester used, 39 mg product obtained (30% yield).

Product:

Compound 255

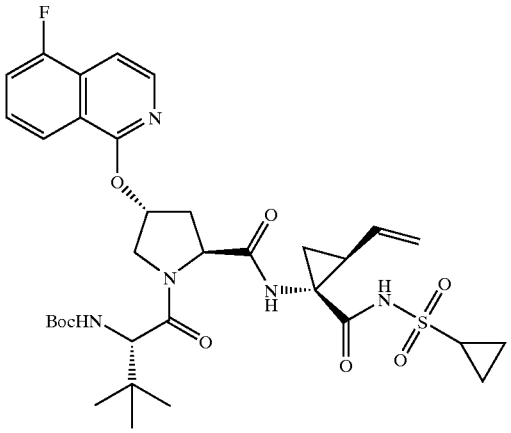

Data: ¹H NMR (400 MHz, CD₃OD) δ ppm 1.05 (m, 12 H), 1.25 (m, 10 H), 1.44 (dd, J=9.5, 5.4 Hz, 1 H), 1.88 (dd, J=8.1, 5.4 Hz, 1 H), 2.28 (m, 2 H), 2.63 (dd, J=13.8, 7.0 Hz, 1 H), 2.94 (m, 1 H), 4.07 (dd, J=11.9, 3.1 Hz, 1 H), 4.23 (d, J=9.3 Hz, 1 H), 4.52 (m, 2 H), 5.12 (dd, J=10.3, 1.5 Hz, 1 H), 5.29 (d, J=17.4 Hz, 1 H), 5.75 (m, 1 H), 5.89 (s, 1 H), 6.59 (d, J=9.1 Hz, 1 H), 7.47 (m, 3 H), 8.02 (d, J=8.1 Hz, 1 H), 8.06 (d, J=6.1 Hz, 1 H); MS: (M+Na)⁺ 724.

Example 256

Preparation of Compound 256

Compound 256

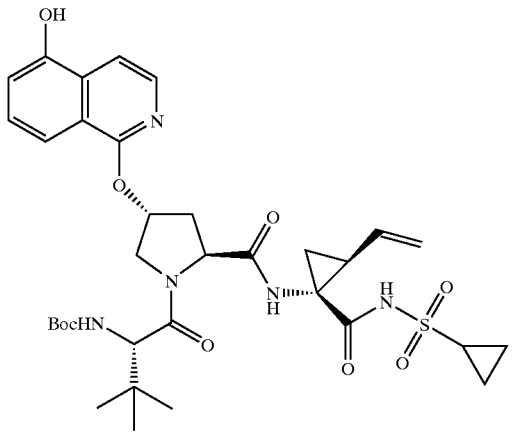

Compound 256 was prepared by following Scheme 1 of Example 250 except 2-difluormethoxycinnamic acid was used in place of 3-phenyl-but-2-enoic acid in step 1.

Step 1:

Modifications: 10.7 g 2-difluormethoxycinnamic acid used, 2 g product obtained (18% yield).

Product:

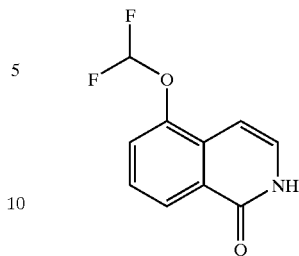

Data: ¹H NMR (400 MHz, CD₃SOCD₃) δ ppm 6.06 (m, 2 H), 6.42 (m, 2 H), 6.71 (s, 2 H), 7.35 (s, 1 H); MS: (M+H)⁺ 212.

Step 2:

Modifications: 300 mg 5-difluoromethoxy-2H-isoquinolin-1-one used, 300 mg product obtained (92% yield).

Product:

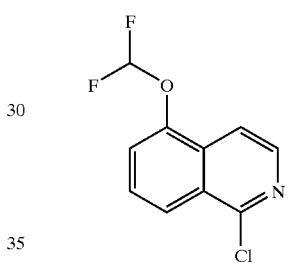

Data: ¹H NMR (400 MHz, CDCl₃) δ ppm 6.70 (t, J=72.87 Hz, 1 H), 7.48 (m, 1 H), 7.64 (m, 1 H), 7.92 (d, J=5.87 Hz, 1 H), 8.21 (d, J=8.56 Hz, 1 H), 8.35 (d, J=5.62 Hz, 1 H).

Step 3:

Modifications: 230 mg 1-chloro-5-difluoromethoxy-isoquinoline used, 360 mg product obtained (96% yield).

Product:

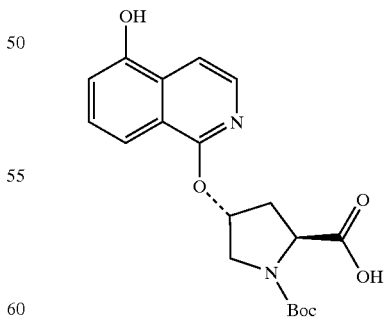

Step 4:

Modifications: 37 mg 4-(5-hydroxy-isoquinolin-1-yloxy)-pyrrolidine-1,2-dicarboxylic acid 1-tert-butyl ester used, 57 mg product obtained (99% yield).

Product:

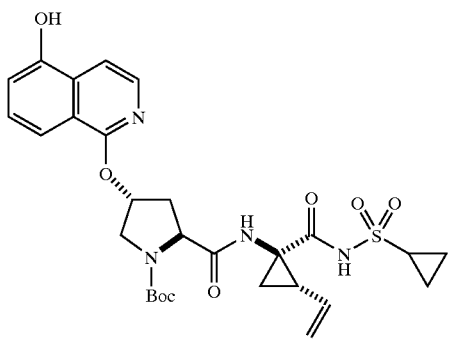

Step 5:

Modifications: 57 mg 2-(1-cyclopropane-sulfonylaminocarbonyl-2-vinyl-cyclopropylcarbamoyl)-4-(5-hydroxy-isoquinolin-1-yloxy)-pyrrolidine-1-carboxylic acid tert-butyl ester used, 10 mg product obtained (15% yield).

Product:

Compound 256

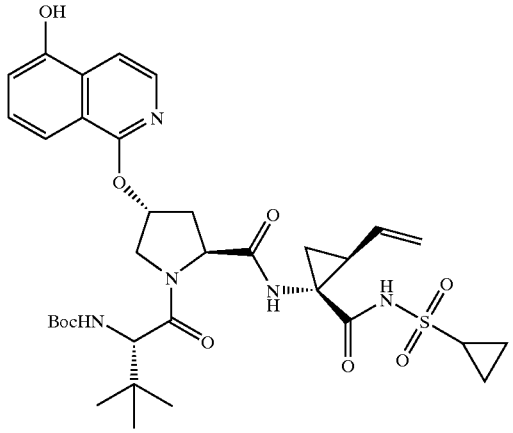

Data: $^1$H NMR (400 MHz, CD$_3$OD) δ ppm 0.93 (m, 4 H), 1.13 (s, 9 H), 1.31 (m, 1 H), 1.49 (s, 9 H), 1.89 (dd, J=7.8, 5.4 Hz, 1 H), 2.16 (q, J=8.8 Hz, 1 H), 2.40 (m, 1 H), δ 2.81 (m, 1 H), 2.90 (m, 1 H), 3.76 (m, 2 H), 4.30 (m, 1 H), 4.59 (dd, J=10.2, 7.7 Hz, 1 H), 5.07 (dd, J=10.3, 1.7 Hz, 1 H), 5.26 (dd, J=17.2, 1.3 Hz, 1 H), 5.77 (dt, J=17.2, 9.6 Hz, 1 H), 5.93 (s, 1 H), 7.24 (d, J=8.6 Hz, 1 H), 7.51 (m, 2 H), 7.63 (t, J=8.0 Hz, 1 H), 7.98 (d, J=6.1 Hz, 1 H), 8.24 (d, J=8.3 Hz, 1 H); MS: (M+H)$^+$ 700.

Example 257

Preparation of Compound 257

Compound 257

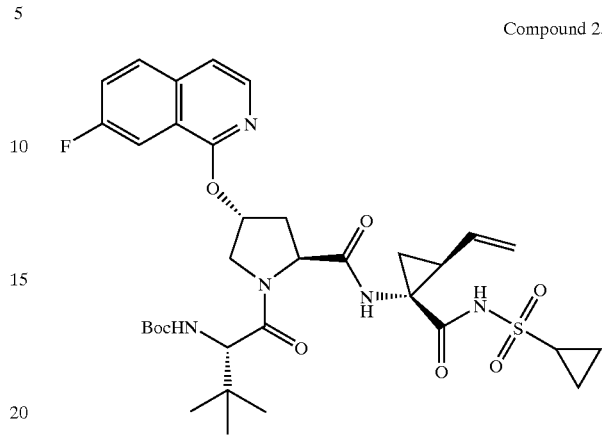

Compound 257 was prepared by following Scheme 1 of Example 250 except 4-fluorocinnamic acid was used in place of 3-phenyl-but-2-enoic acid in step 1.

Step 1:

Modifications: 16.6 g 4-fluorocinnamic acid used, 8.2 g product obtained (49% yield).

Product:

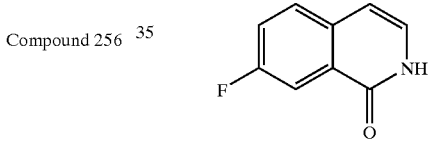

Data: $^1$H NMR (400 MHz, CD$_3$COCD$_3$) δ ppm 6.57 (d, J=7.09 Hz, 1 H), 7.21 (d, J=7.09 Hz, 1 H), 7.50 (m, 1 H), 7.72 (dd, J=8.68, 5.26 Hz, 1 H), 7.90 (dd, J=9.54, 2.93 Hz, 1 H).

Step 2:

Modifications: 8.15 g 7-fluoro-2H-isoquinolin-1-one used, 7.6 g product obtained (84% yield).

Product:

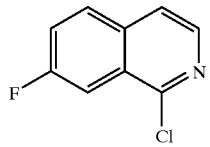

Data: $^1$H NMR (400 MHz, CDCl$_3$) δ ppm 7.52 (td, J=8.6, 2.6 Hz, 1 H), 7.59 (d, J=5.6 Hz, 1 H), 7.86 (dd, J=9.1, 5.4 Hz, 1 H), 7.95 (dd, J=9.5, 2.5 Hz, 1 H), 8.26 (d, J=5.6 Hz, 1 H); MS: (M+H)$^+$ 182.

Step 3:

Modifications: 191 mg 1-chloro-7-fluoro-isoquinoline used, 350 mg product obtained (93% yield).

Product:

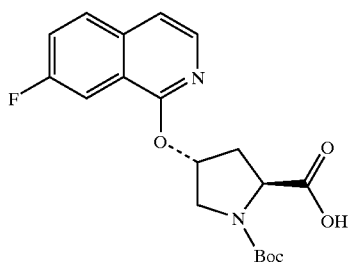

Data: MS: (M+Na)+ 399.

Step 4:

Modifications: 75 mg 4-(7-fluoro-isoquinolin-1-yloxy)-pyrrolidine-1,2-dicarboxylic acid 1-tert-butyl ester used, 100 mg product obtained (85% yield)

Product:

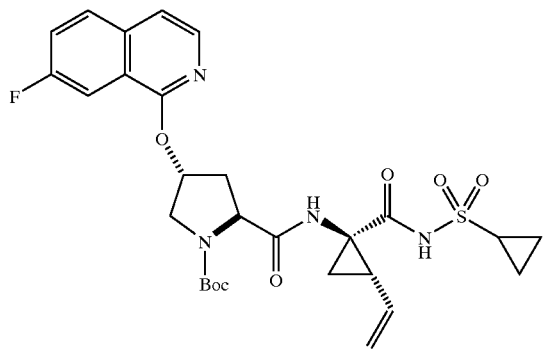

Data: $^1$H NMR (400 MHz, CD$_3$OD) δ ppm 1.16 (m, 4 H), 1.41 (m, 10 H), 1.88 (dd, J=8.1, 5.4 Hz, 1 H), 2.28 (m, 2 H), 2.56 (m, 1 H) 2.94 (m, 1 H), 3.87 (m, 2 H), 4.41 (dd, J=9.7, 7.0 Hz, 1 H), 5.12 (d, J=10.8 Hz, 1 H), 5.31 (d, J=17.1 Hz, 1 H), 5.78 (m, 2 H), 7.36 (d, J=5.9 Hz, 1 H), 7.54 (m, 1 H), 7.78 (dd, J=9.3, 2.5 Hz, 1 H), 7.90 (dd, J=9.1, 5.1 Hz, 1 H), 7.96 (d, J=5.9 Hz, 1 H); MS: (M+Na)+ 611.

Step 5:

Modifications: 95 mg 2-(1-cyclopropanesulfonylaminocarbonyl-2-vinyl-cyclopropylcarbamoyl)-4-(7-fluoro-isoquinolin-1-yloxy)-pyrrolidine-1-carboxylic acid tert-butyl ester used, 55 mg product obtained (44% yield).

Product:

Compound 257

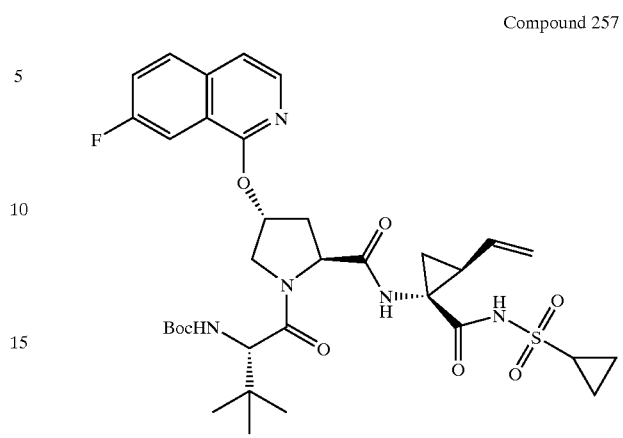

Data: $^1$H NMR (400 MHz, CD$_3$OD) δ ppm 1.05 (m, 12 H), 1.22 (m, 10 H), 1.44 (dd, J=9.3, 5.4 Hz, 1 H), 1.88 (dd, J=8.2, 5.5 Hz, 1 H), 2.27 (m, 2 H), 2.63 (dd, J=13.8, 7.0 Hz, 1 H), 2.94 (m, 1 H), 4.07 (dd, J=11.5, 3.2 Hz, 1 H), 4.22 (d, J=9.5 Hz, 1 H), 4.47 (d, J=11.7 Hz, 1 H), 4.55 (dd, J=10.6, 7.5 Hz, 1 H), 5.12 (d, J=10.3 Hz, 1 H), 5.29 (d, J=17.1 Hz, 1 H), 5.75 (m, 1 H), 5.87 (s, 1 H), 6.61 (d, J=9.5 Hz, 1 H), 7.36 (d, J=5.9 Hz, 1 H), 7.52 (td, J=8.9, 2.5 Hz, 1 H), 7.79 (dd, J=9.4, 2.6 Hz, 1 H), 7.88 (dd, J=8.7, 5.5 Hz, 1 H), 7.96 (d, J=5.9 Hz, 1 H); MS: (M+Na)+ 724.

Example 258

Preparation of Compound 258

Compound 258

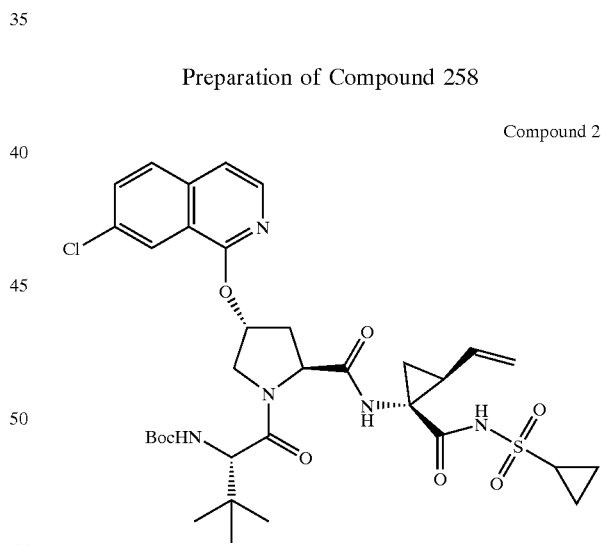

Compound 258 was prepared by following Scheme 1 of Example 250 except that 4-chlorocinnamic acid was used in place of 3-phenyl-but-2-enoic acid in step 1.

Step 1:

Modifications: 9.13 g 4-chlorocinnamic acid used, 4 g product obtained (44% yield).

Product:

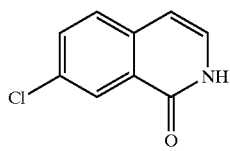

Data: ¹H NMR (400 MHz, CD₃SOCD₃) δ ppm 6.58 (d, J=7.1 Hz, 1 H), 7.20 (dd, J=7.1, 5.9 Hz, 1 H), 7.72 (m, 2 H), 8.10 (m, 1 H).

Step 2:

Modifications: 3.5 g 7-chloro-2H-isoquinolin-1-one used, 2.8 g product obtained (72% yield).

Product:

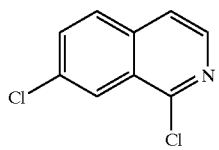

Data: ¹H NMR (500 MHz, CDCl₃) δ ppm 7.59 (d, J=5.5 Hz, 1 H), 7.69 (dd, J=8.9, 2.1 Hz, 1 H), 7.80 (d, J=8.6 Hz, 1 H), 8.29 (d, J=5.5 Hz, 1 H), 8.34 (s, 1 H); MS: (M+H)⁺ 198.

Step 3:

Modifications: 208 mg 1,7-dichloro-isoquinoline used, 350 mg product obtained (89% yield).

Product:

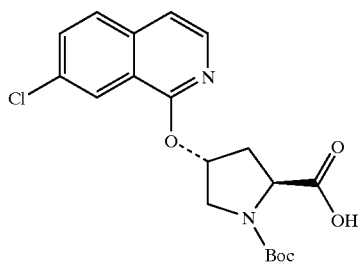

Data: MS: (M+Na)⁺ 415.

Step 4:

Modifications: 79 mg 4-(7-chloro-isoquinolin-1-yloxy)-pyrrolidine-1,2-dicarboxylic acid 1-tert-butyl ester used, 119 mg product obtained (99% yield).

Product:

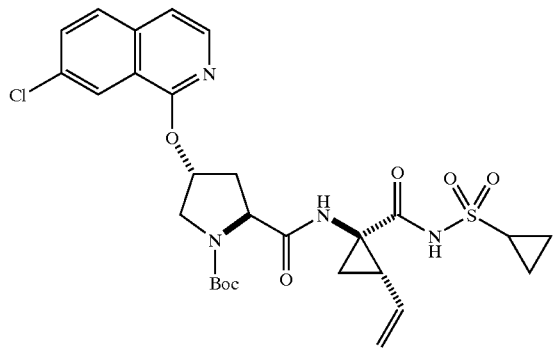

Data: ¹H NMR (400 MHz, CD₃OD) δ ppm 1.17 (m, 4 H), 1.43 (m, 10 H), 1.88 (dd, J=8.31 5.4 Hz, 1 H), 2.29 (m, 2 H), 2.57 (dd, J=13.7, 6.9 Hz, 1 H), 2.95 (m, 1H), 3.87 (m, 2 H), 4.42 (dd, J=9.9, 6.9 Hz, 1 H), 5.13 (d, J=10.3 Hz, 1 H), 5.31 (dd, J=17.1, 1.2 Hz, 1 H), 5.78 (m, 2 H), 7.35 (d, J=5.9 Hz, 1 H), 7.69 (dd, J=8.7, 2.1 Hz, 1 H), 7.84 (d, J=8.8 Hz, 1 H), 7.99 (d, J=5.9 Hz, 1 H), 8.12 (d, J=1.7 Hz, 1 H); MS: (M+Na)⁺ 627.

Step 5:

Modifications: 115 mg 2-(1-cyclopropanesulfonylarminocarbonyl-2-vinyl-cyclopropylcarbamoyl)-4-(7-chloro-isoquinolin-1-yloxy)-pyrrolidine-1-carboxylic acid tert-butyl ester used, 36 mg product obtained (25% yield)

Product:

Compound 258

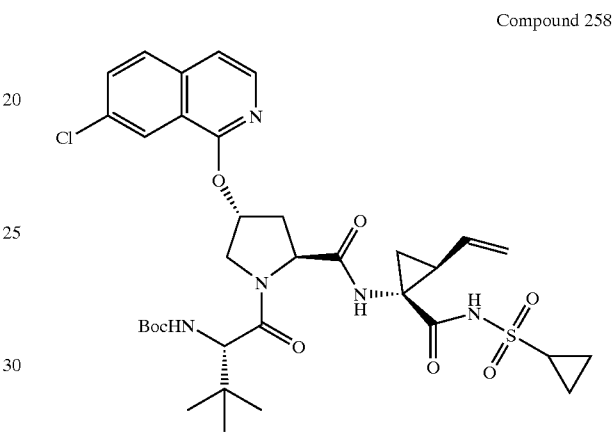

Data: MS: (M+Na)⁺ 740.

Example 259

Preparation of Compound 259

Compound 259

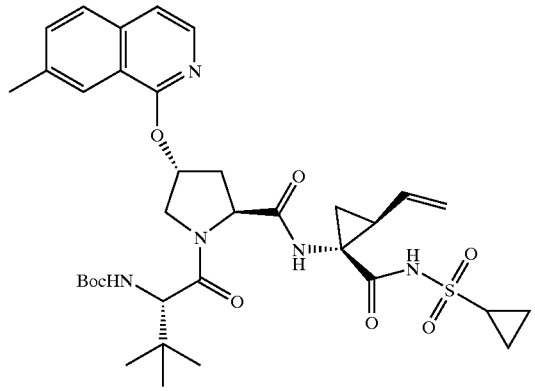

Compound 259 was prepared by following Scheme 1 of Example 250 except that 4-methylcinnamic acid was used in place of 3-phenyl-but-2-enoic acid in step 1.

Step 1:

Modifications: 25 g 4-methylcinnamic acid used, 15.3 g product obtained (62% yield).

Product:

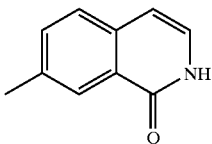

Data: ¹H NMR (400 MHz, CD₃OD) δ ppm 2.50 (s, 3 H), 6.54 (d, J=7.1 Hz, 1 H), 7.13 (d, J=7.1 Hz, 1 H), 7.49 (m, 2 H), 8.22 (s, 1 H), 11.49 (s, 1 H); MS: (M+H)⁺ 160.

Step 2:
Modifications: 15.3 g 7-methyl-2H-isoquinolin-1-one used, 5.15 g product obtained (30% yield).
Product:

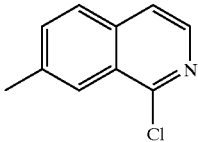

Data: ¹H NMR (400 MHz, CDCl₃) δ ppm 2.58 (s, 3 H), 7.56 (m, 2 H), 7.73 (d, J=8.3 Hz, 1 H), 8.09 (s, 1 H), 8.20 (d, J=5.6 Hz, 1 H); MS: (M+H)⁺ 178.

Step 3:
Modifications: 205 mg 1-chloro-7-methyl-isoquinoline used, 350 mg product obtained (89% yield).
Product:

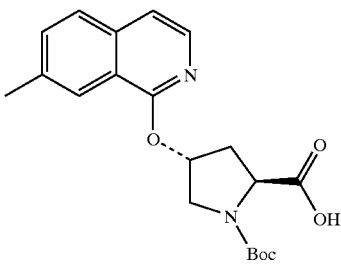

Data: MS: (M+H)⁺ 373.

Step 4:
Modifications: 75 mg 4-(7-methyl-isoquinolin-1-yloxy)-pyrrolidine-1,2-dicarboxylic acid 1-tert-butyl ester used, 107 mg product obtained (95% yield).
Product:

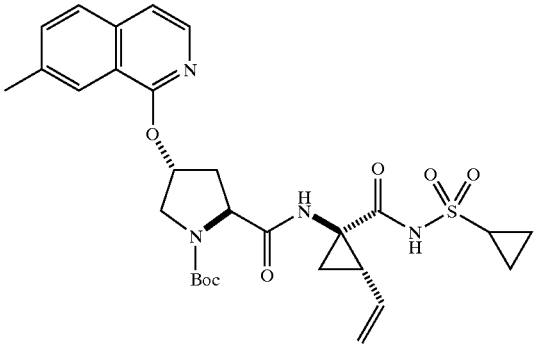

Data: MS: (M+Na)⁺ 607.

Step 5:
Modifications: 107 mg 2-(1-cyclopropanesulfonylaminocarbonyl-2-vinyl-cyclopropylcarbamoyl)-4-(7-methyl-isoquinolin-1-yloxy)-pyrrolidine-1-carboxylic acid tert-butyl ester used, 53 mg product obtained (41% yield).
Product:

Compound 259

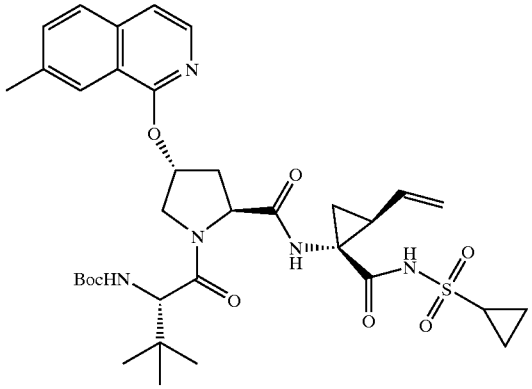

Data: ¹H NMR (400 MHz, CD₃OD) δ ppm 1.02 (m, 12 H), 1.18 (s, 9 H), 1.24 (m, 1 H), 1.45 (dd, J=9.4, 5.5 Hz, 1 H), 1.88 (dd, J=8.2, 5.5 Hz, 1 H), 2.28 (m, 2 H), 2.50 (s, 3 H), 2.61 (dd, J=13.8, 6.7 Hz, 1 H), 3.34 (s, 1 H), 4.09 (dd, J=11.7, 3.2 Hz, 1 H), 4.23 (s, 1 H), 4.42 (d, J=12.0 Hz, 1 H), 4.57 (dd, J=10.0, 7.1 Hz, 1 H), 12 (dd, J=10.3, 1.5 Hz, 1 H), 5.30 (d, J=17.1 Hz, 1 H), 5.76 (m, 1 H), 5.87 (s, 1 H), 7.28 (d, J=5.9 Hz, 1 H), 7.55 (d, J=8.3 Hz, 1 H), 7.71 (d, J=8.3 Hz, 1 H), 7.89 (d, J=5.9 Hz, 1 H), 7.93 (s, 1 H); MS: (M+H)⁺ 698.

Example 260

Preparation of Compound 260

Compound 260

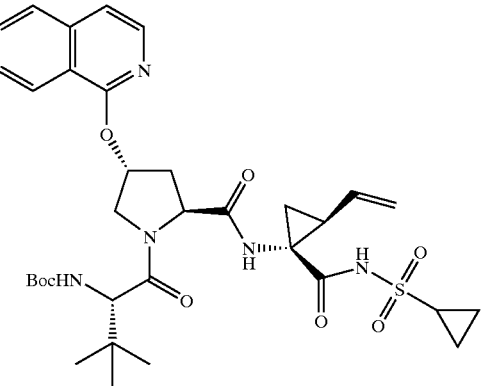

Compound 260 was prepared by following Scheme 1 of Example 250 except that 4-methoxycinnamic acid was used in place of 3-phenyl-but-2-enoic acid in step 1.

Step 1:
Modifications: 33 g using 4-methoxycinnamic acid used, 7 g product obtained (33% yield).

Product:

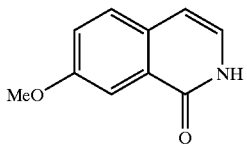

Data: ¹H NMR (500 MHz, CD₃COCD₃) δ ppm 3.90 (s, 3 H), 6.49 (d, J=7.0 Hz, 1 H), 7.10 (d, J=7.3 Hz, 1 H), 7.28 (dd, J=8.6, 2.8 Hz, 1 H), 7.57 (d, J=8.9 Hz, 1 H), 7.71 (d, J=2.8 Hz, 1 H).

Step 2:
Modifications: 4 g 7-methoxy-2H-isoquinolin-1-one used, 3 g product obtained (68% yield).
Product:

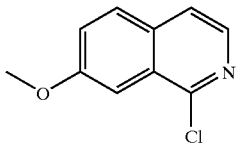

Data: ¹H NMR (400 MHz, CDCl₃) δ ppm 3.98 (s, 3 H), 7.38 (dd, J=8.9, 2.6 Hz, 1 H), 7.52 (m, 2 H), 7.73 (d, J=8.8 Hz, 1 H), 8.16 (d, J=5.4 Hz, 1 H).

Step 3:
Modifications: 533 mg 1-chloro-7-methoxy-isoquinoline used, 1115 mg product obtained (100% yield).
Product:

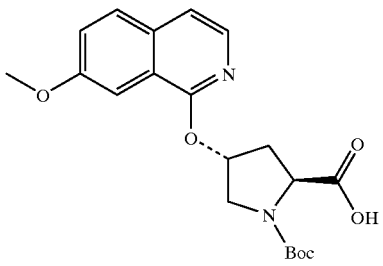

Step 4:
Modifications: 78 mg 4-(7-methoxy-isoquinolin-1-yloxy)-pyrrolidine-1,2-dicarboxylic acid 1-tert-butyl ester used, 108 mg product obtained (99% yield).
Product:

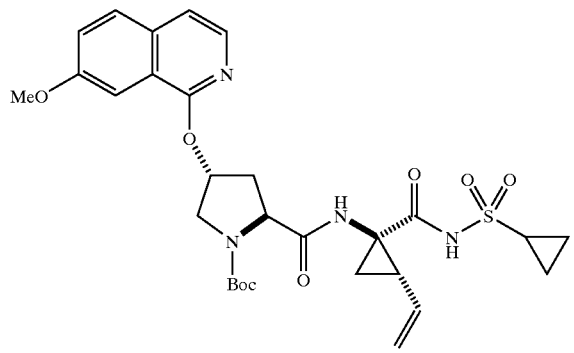

Data: ¹H NMR (400 MHz, CD₃OD) δ ppm 1.17 (m, 4 H), 1.40 (m, 1H), 1.43 (s, 9H), 1.85 (dd, J=8.1, 5.4 Hz, 1 H), 2.21 (m, 2 H), 2.51 (dd, J=13.7, 6.6 Hz, 1 H), 2.93 (s, 1 H), 3.80 (m, 2 H), 3.94 (s, 3 H), 4.41 (dd, J=10.0, 6.6 Hz, 1 H), 4.57 (s, 1 H), 5.11 (d, J=11.3 Hz, 1 H), 5.29 (d, J=17.1 Hz, 1 H), 5.77 (m, 2 H), 7.01 (d, J=7.8 Hz, 1 H), 7.22 (d, J=5.6 Hz, 1 H), 7.32 (d, J=8.1 Hz, 1 H), 7.58 (t, J=8.0 Hz, 1 H), 7.87 (d, J=5.9 Hz, 1 H); MS: (M+H)⁺ 601.

Step 5:
Modifications: 100 mg 2-(1-cyclopropanesulfonylaminocarbonyl-2-vinyl-cyclopropylcarbamoyl)-4-(7-methoxy-isoquinolin-1-yloxy)-pyrrolidine-1-carboxylic acid tert-butyl ester used, 30 mg product obtained (25% yield).
Product:

Compound 260

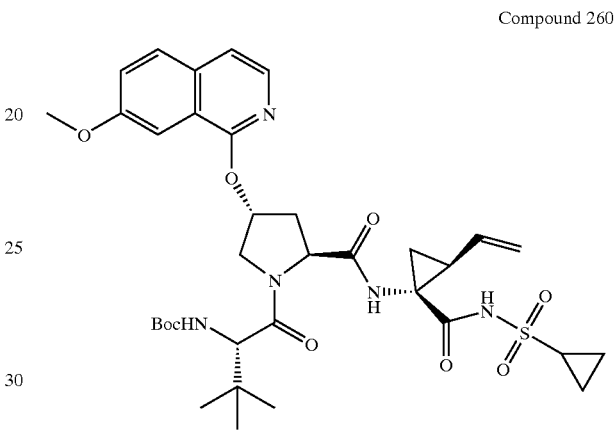

Data: ¹H NMR (400 MHz, CD₃SOCD₃) δ ppm 0.90 (m, 2 H), 0.95 (s, 9 H), 1.05 (m, 1 H), 1.12 (s, 9 H), 1.35 (m, 2 H), 1.70 (m, 1 H), 2.18 (m, 1 H), 2.92 (m, 1 H), 3.86 (s, 3 H), 4.00 (m, 2 H), 4.27 (d, J=12.0 Hz, 1 H), 4.45 (t, J=8.6 Hz, 1 H), 5.09 (d, J=10.8 Hz, 1 H), 5.23 (d, J=16.9 Hz, 1 H), 5.62 (m, 1 H), 5.79 (s, 1 H), 6.55 (d, J=8.1 Hz, 1 H), 7.35 (d, J=6.6 Hz, 1 H), 7.39 (d, J=2.5 Hz, 1 H), 7.43 (dd, J=8.8, 2.2 Hz, 1 H), 7.84 (d, J=8.8 Hz, 1 H), 7.88 (d, J=5.9 Hz, 1 H); MS: (M+H)⁺ 714.

Example 261 and 262

Preparation of Compounds 261 and 262

Compound 261

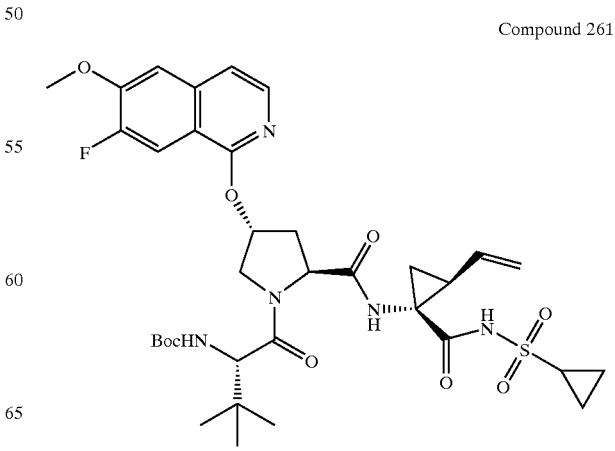

Compound 262

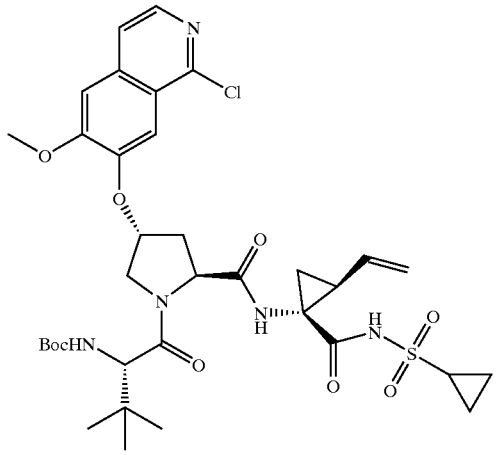

Compounds 261 and 262 were prepared by following Scheme 1 of Example 250 except that 4-fluoro-3-methoxycinnamic acid was used in place of 3-phenyl-but-2-enoic acid in step 1.

Step 1:

Modifications: 19.6 g 4-fluoro-3-methoxycinnamic acid used, 9.5 g product obtained (48% yield).

Product:

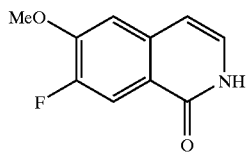

Data: $^1$H NMR (400 MHz, CD$_3$COCD$_3$) δ ppm 4.00 (s, 1 H), 6.49 (d, J=7.34 Hz, 1 H), 7.19 (d, J=7.09 Hz, 1 H), 7.29 (d, J=8.07 Hz, 1 H), 7.86 (d, J=11.74 Hz, 1 H).

Step 2:

Modifications: 9 g 7-fluoro-6-methoxy-2H-isoquinolin-1-one used, 7 g product obtained (70% yield).

Product:

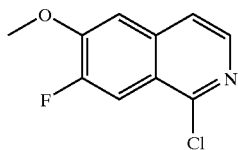

Data: $^1$H NMR (400 MHz, CDCl$_3$) δ ppm 4.04 (s, 3 H), 7.17 (d, J=8.07 Hz, 1 H), 7.48 (d, J=5.62 Hz, 1 H), 7.94 (d, J=11.49 Hz, 1 H), 8.20 (d, J=5.62 Hz, 1H).

Step 3:

Modifications: 222 mg 1-chloro-7-fluoro-6-methoxy-isoquinoline used, 406 mg products obtained.

Products:

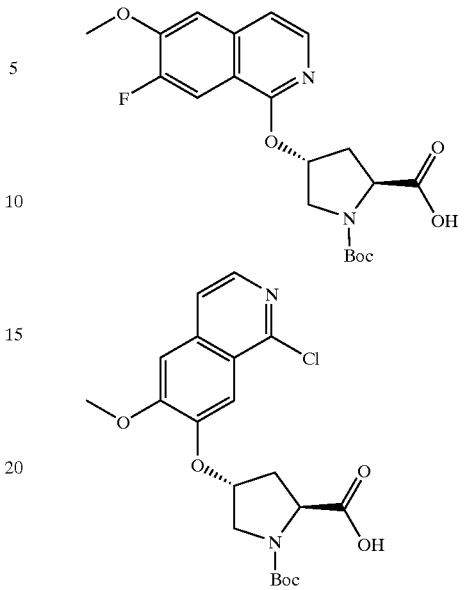

Step 4:

Modifications: 400 mg mixture of 4-(7-fluoro-6-methoxy-isoquinolin-1-yloxy)-pyrrolidine-1,2-dicarboxylic acid 1-tert-butyl ester and 4-(1-chloro-6-methoxy-isoquinolin-7-yloxy)-pyrrolidine-1,2-dicarboxylic acid 1-tert-butyl ester used, 700 mg products obtained.

Product:

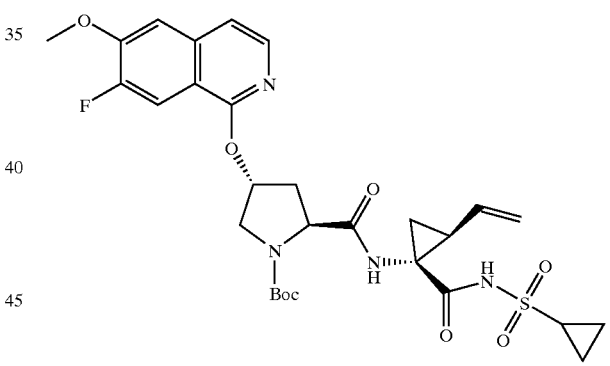

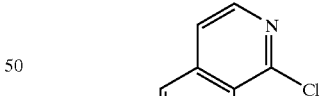

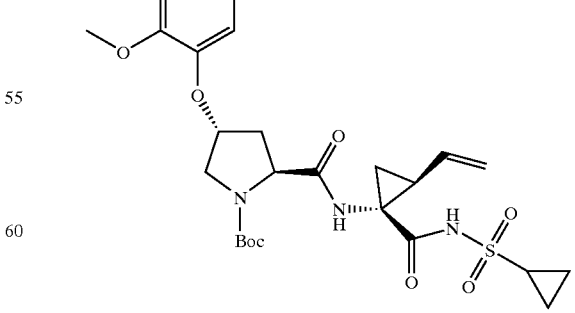

Step 5:

Modifications: 700 mg mixture of 2-(1-cyclopropanesulfonylaminocarbonyl-2-vinylcyclopropylcarbamoyl)-4-(7-fluoro-6-methoxy-isoquinolin-1-yloxy)-pyrrolidine-1-carboxylic acid tert-butyl ester and 4-(1-chloro-6-methoxy-isoquinolin-7-yloxy)-2-(1-cyclopropanesulfonylaminocarbonyl-2-vinyl-cyclopropyl carbamoyl)-pyrrolidine-1-carboxylic acid tert-butyl ester used, 79 mg of compound 261 and 80 mg compound 262 obtained.

Product:

Compound 261

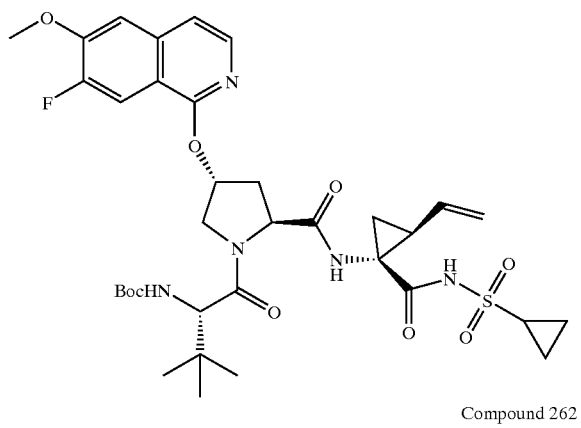

Compound 262

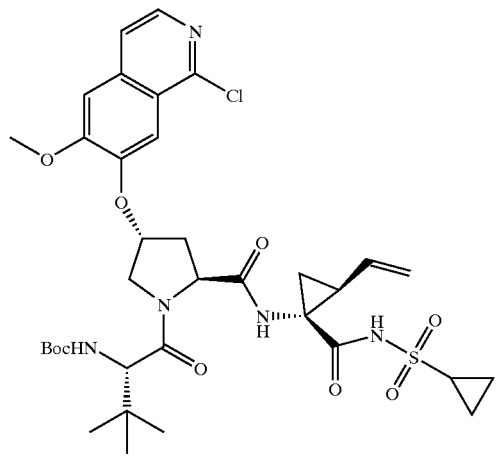

Data of compound 261: $^1$H NMR (400 MHz, CD$_3$OD) δ ppm 1.07 (m, 12 H), 1.25 (m, 10 H), 1.44 (m, 1 H), 1.88 (dd, J=8.1, 5.6 Hz, 1 H), 2.25 (m, 2 H), 2.60 (dd, J=13.7, 6.9 Hz, 1 H), 2.94 (m, 1 H), 4.02 (m, 4 H), 4.22 (s, 1 H), 4.43 (d, J=12.2 Hz, 1 H), 4.53 (dd, J=10.3, 6.6 Hz, 1 H), 5.12 (d, J=10.5 Hz, 1 H), 5.30 (d, J=16.6 Hz, 1 H), 5.75 (m, 1 H), 5.84 (s, 1 H), 7.28 (d, J=5.9 Hz, 1 H), 7.37 (d, J=8.1 Hz, 1 H), 7.75 (d, J=11.7 Hz, 1 H), 7.91 (d, J=5.9 Hz, 1 H); MS: (M+Na)$^+$ 754.

Data of compound 262: $^1$H NMR (400 MHz, CD$_3$OD) δ ppm 1.07 (m, 12 H), 1.25 (m, 10 H), 1.44 (m, J=9.41, 5.26 Hz, 1 H), 1.87 (dd, J=8.31, 5.38 Hz, 1 H), 2.24 (q, J=8.72 Hz, 2 H), 2.57 (dd, J=13.82, 7.21 Hz, 1 H), 2.94 (m, 1 H), 3.97 (d, J=5.14 Hz, 3 H), 4.09 (m, J=11.00 Hz, 1 H), 4.24 (s, 1 H), 4.32 (m, 1 H), 4.50 (m, J=16.87 Hz, 1 H), 5.12 (dd, J=10.52, 1.71 Hz, 1 H), 5.30 (dd, J=17.12, 1.47 Hz, 1 H), 5.38 (s, 1 H), 5.76 (m, 1 H), 7.39 (s, 1 H), 7.63 (s, 1 H), 7.66 (d, J=5.87 Hz, 1 H), 8.07 (d, J=5.62 Hz, 1 H); MS: (M+H)$^+$ 732.

Example 263

Preparation of Compound 263

Compound 263

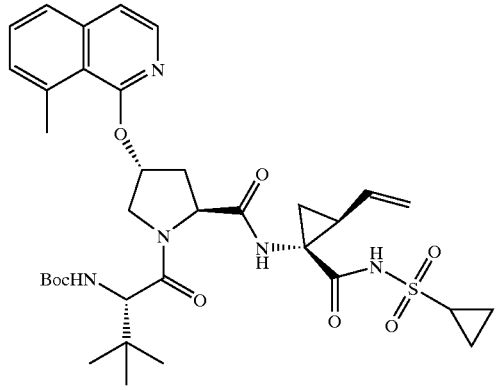

Compound 263 was prepared by following Scheme 1 of Example 250 except step 1 and step 2.

Step 3:
Modifications: 176 mg 1-chloro-8-methyl-isoquinoline used, 370 mg product obtained (100 mg % yield).
Product:

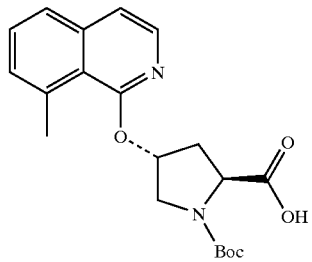

Step 4:
Modifications: 149 mg 8-methyl-isoquinolin-1-yloxy)-pyrrolidine-1,2-dicarboxylic acid 1-tert-butyl ester used, 230 mg product obtained (99% yield)
Product:

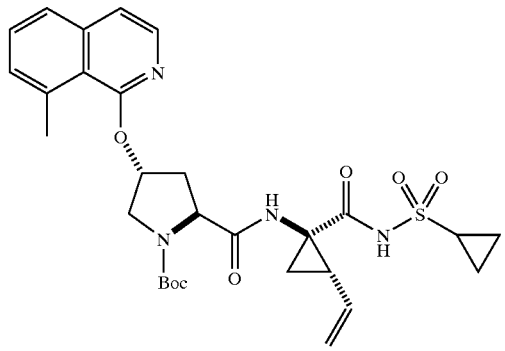

Data: $^1$H NMR (400 MHz, CD$_3$OD) δ ppm 1.13 (m, 4 H), 1.42 (m, 10 H), 1.87 (dd, J=8.2, 5.3 Hz, 1 H), 2.25 (m, 2 H), 2.58 (dd, J=13.9, 6.9 Hz, 1 H), 2.83 (s, 3 H), 2.96 (m, 1 H), 3.85 (m, 2 H), 4.38 (dd, J=10.2, 6.7 Hz, 1 H), 5.12 (dd, J=10.4, 1.6 Hz, 1 H), 5.30 (dd, J=17.1, 1.2 Hz, 1 H), 5.76 (m, 2 H), 7.28 (d, J=5.9 Hz, 1 H), 7.36 (d, J=6.9 Hz, 1 H), 7.53 (t, J=7.7 Hz, 1 H), 7.62 (m, 1 H), 7.88 (d, J=5.6 Hz, 1 H); MS: (M+Na)$^+$ 607.

Step 5:

Modifications: 220 mg 2-(1-cyclopropanesulfonylaminocarbonyl-2-vinyl-cyclopropylcarbamoyl)-4-(8-methyl-isoquinolin-1-yloxy)-pyrrolidine-1-carboxylic acid tert-butyl ester used, 90 mg product obtained (35% yield).

Product:

Compound 263

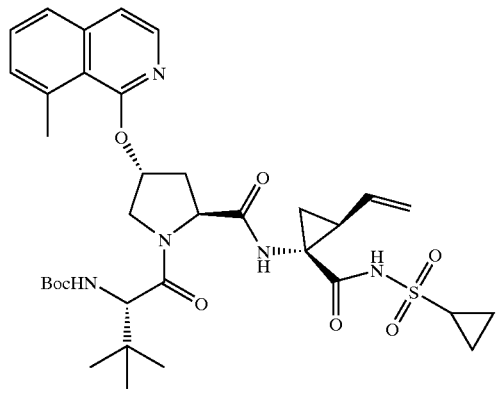

Data: $^1$H NMR (400 MHz, CD$_3$OD) δ ppm 1.05 (m, 12 H), 1.24 (m, 10 H), 1.44 (dd, J=9.3, 5.4 Hz, 1 H), 1.87 (dd, J=8.1, 5.4 Hz, 1 H), 2.25 (m, 2 H), 2.60 (dd, J=13.9, 7.3 Hz, 1 H), 2.77 (s, 3 H), 2.94 (m, 1 H), 4.04 (dd, J=11.9, 3.1 Hz, 1 H), 4.27 (d, J=9.5 Hz, 1 H), 4.42 (d, J=12.0 Hz, 1 H), 4.54 (dd, J=10.8, 7.1 Hz, 1 H), 5.12 (d, J=10.3 Hz, 1 H), 5.28 (d, J=17.1 Hz, 1 H), 5.75 (m, 1 H), 5.95 (s, 1 H), 6.63 (d, J=9.1 Hz, 1 H), 7.28 (m, 2 H), 7.50 (t, J=7.7 Hz, 1 H), 7.60 (d, J=7.8 Hz, 1 H), 7.89 (d, J=5.6 Hz, 1 H); MS: (M+Na)$^+$ 720.

Example 264

Preparation of Compound 264

Compound 264

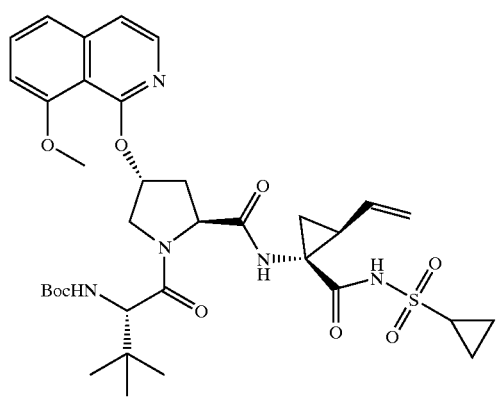

Compound 264 was prepared by following Scheme 1 of Example 250 except step 1 and step 2.

Step 3:

Modifications: 203 mg 1-chloro-8-methoxy-isoquinoline used, 340 mg product obtained (85% yield).

Product:

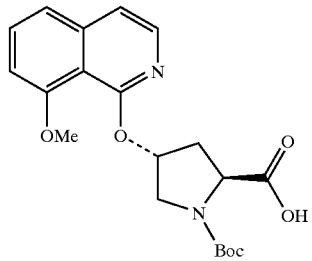

Data: $^1$H NMR (400 MHz, CD$_3$SOCD$_3$) δ ppm 1.34, 1.36 (2s, 9 H, rotamers), 2.26 (m, 1 H), 2.49 (m, 1 H), 3.67 (m, 2 H), 3.86 (s, 3 H), 4.31 (m, 1 H), 5.67 (br s, 1 H), 7.04 (d, J=7.8 Hz, 1 H), 7.30 (d, J=5.9 Hz, 1 H), 7.38 (d, J=8.1 Hz, 1 H), 7.62 (t, J=8.0 Hz, 1 H), 7.93 (d, J=5.6 Hz, 1 H), 12.64 (s, 1 H); MS: (M+Na)$^+$ 411.

Step 4:

Modifications: 78 mg 8-methoxy-isoquinolin-1-yloxy)-pyrrolidine-1,2-dicarboxylic acid 1-tert-butyl ester used, 115 mg product obtained (96% yield).

Product:

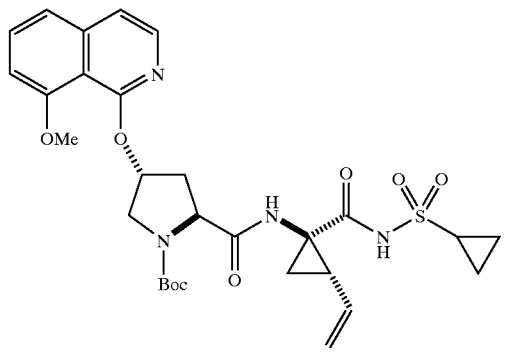

Step 5:

Modifications: 110 mg 2-(1-cyclopropanesulfonylaminocarbonyl-2-vinyl-cyclopropylcarbamoyl)-4-(8-methoxy-isoquinolin-1-yloxy)-pyrrolidine-1-carboxylic acid tert-butyl ester used, 45 mg product obtained (34% yield).

Product:

Compound 264

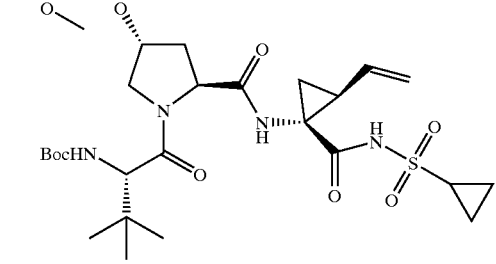

Data: MS: (M+H)$^+$ 714.

Example 265 and 266

Preparation of Compounds 265 and 266

Compound 265

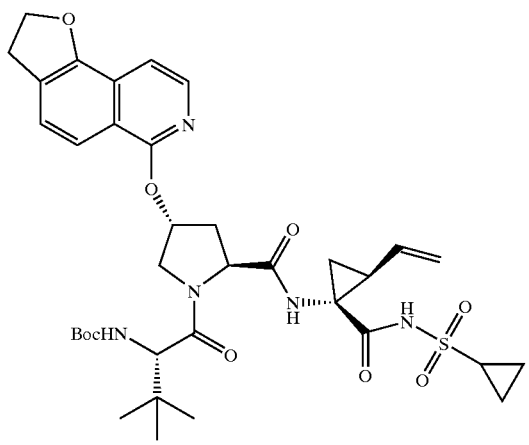

Compound 266

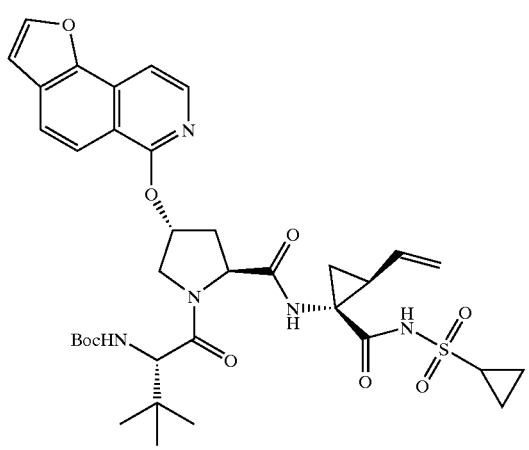

Compounds 265 and 266 were prepared by following Scheme 1 of Example 250 except that 3-(2,3-dihydro-benzofuran-7-yl)-acrylic acid was used in place of 3-phenyl-but-2-enoic acid in step 1.

Step 1:

Modifications: 3.8 g 3-(2,3-dihydro-benzofuran-7-yl)-acrylic acid used, 2 g product obtained (53% yield).

Product:

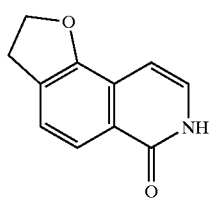

Data: $^1$H NMR (400 MHz, CD$_3$OD) δ ppm 3.37 (t, J=9.05 Hz, 1 H), 4.73 (t, J=9.05 Hz, 2 H), 6.67 (d, J=7.09 Hz, 1 H), 7.10 (d, J=7.09 Hz, 1 H), 7.37 (d, J=8.07 Hz, 1 H), 7.81 (d, J=8.07 Hz, 1 H); MS: (M+H)$^+$ 188.

Step 2:

Modifications: 1.87 g 2,3-dihydro-7H-furo[2,3-f]isoquinolin-6-one used, 1.84 g product obtained (90% yield).

Product:

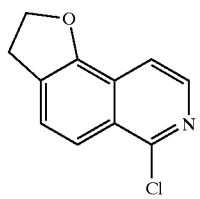

Data: $^1$H NMR (400 Hz, CDCl$_3$) δ ppm 3.43 (t, J=9.05 Hz, 2 H), 4.82 (t, J=9.05 Hz, 2 H), 7.52 (d, J=8.56 Hz, 1 H), 7.66 (d, J=5.62 Hz, 1 H), 7.84 (d, J=8.31 Hz, 1 H), 8.19 (d, J=5.62 Hz, 1 H); MS (M+H)$^+$ 206.

Step 3:

Modifications: 206 mg 6-chloro-2,3-dihydro-furo[2,3-f]isoquinoline used, 300 mg products mixture obtained.

Products:

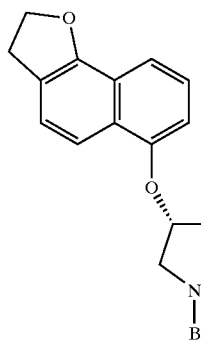

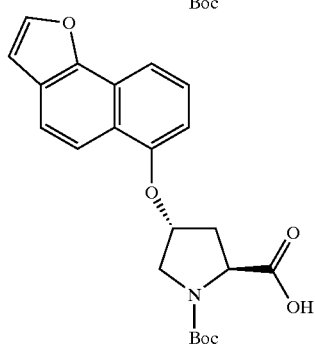

Step 4:

Modifications: 240 mg step 3 products mixture used, 350 mg products mixture obtained.

Products:

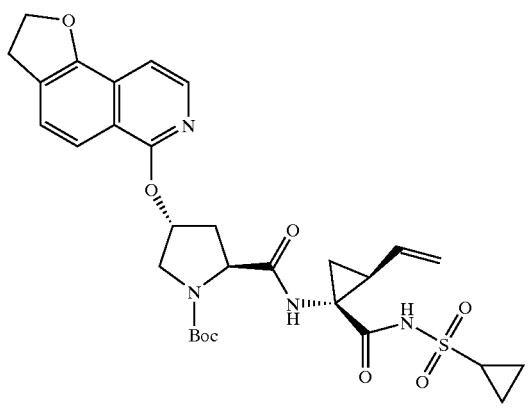

Step 5:

Modifications: 331 mg step 4 products mixture-used, 240 mg of compound 265 and 24 mg of compound 266 obtained.

Products:

Compound 265

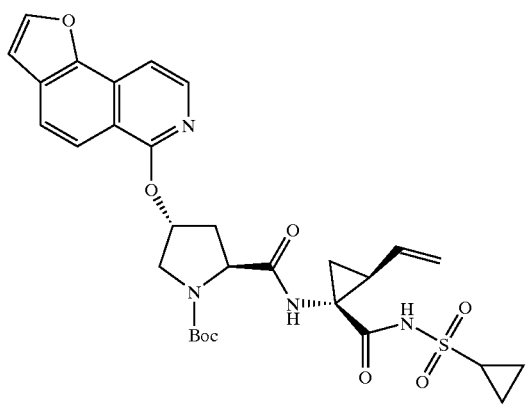

-continued

Compound 266

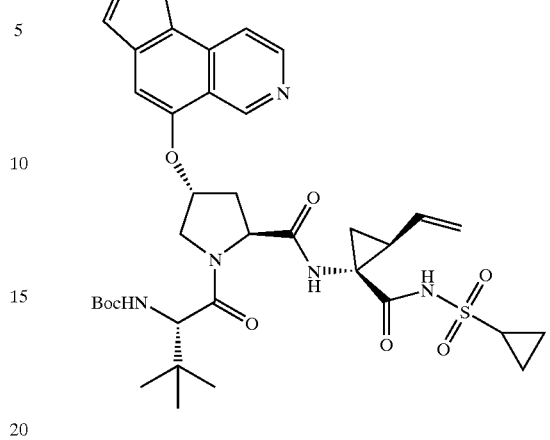

Data of compound 265: ¹H NMR (400 Hz, CD$_3$OD) δ ppm 0.99 (m, 12 H), 1.16 (m, 10 H), 1.36 (m, 1 H), 1.81 (dd, J=8.07, 5.62 Hz, 1 H), 2.18 (m, 2 H), 2.54 (dd, J=13.69, 6.85 Hz, 1 H), 2.87 (m, 1 H), 3.31 (t, J=9.05 Hz, 2 H), 4.01 (m, 1 H), 4.18 (s, 1 H), 4.36 (d, J=11.74 Hz, 1 H), 4.46 (dd, J=10.15, 7.21 Hz, 1 H), 4.70 (m, 2 H), 5.05 (d, J=10.27 Hz, 1 H), 5.23 (d, J=16.87 Hz, 1 H), 5.70 (m, 2 H), 7.23 (d, J=5.87 Hz, 1 H), 7.31 (d, J=8.31 Hz, 1 H), 7.63 (d, J=8.31 Hz, 1 H), 7.82 (d, J=5.87 Hz, 1 H); MS (M+H)⁺ 726.

Data of compound 266: ¹H NMR (400 MHz, CD$_3$OD) δ ppm 1.06 (m, 12 H), 1.24 (m, 10 H), 1.44 (dd, J=10.03, 5.14 Hz, 1 H), 1.88 (dd, J=7.83, 5.38 Hz, 11 H), 2.27 (m, 2 H), 2.65 (dd, J=12.96, 6.36 Hz, 1 H), 2.94 (m, 1 H), 4.08 (dd, J=12.35, 3.30 Hz, 1 H), 4.25 (s, 1 H), 4.54 (m, 2 H), 5.12 (d, J=10.27 Hz, 1 H), 5.29 (d, J=17.12 Hz, 1 H), 5.75 (m, 1 H), 5.91 (s, 1 H), 7.05 (d, J=1.96 Hz, 1 H), 7.72 (m, 2 H), 8.02 (m, 2 H), 8.11 (d, J=5.87 Hz, 1 H), 9.19 (s, 1 H); MS: (M+H)⁺ 724.

Example 267 and 268

Preparation of Compounds 267 and 268

Compound 267

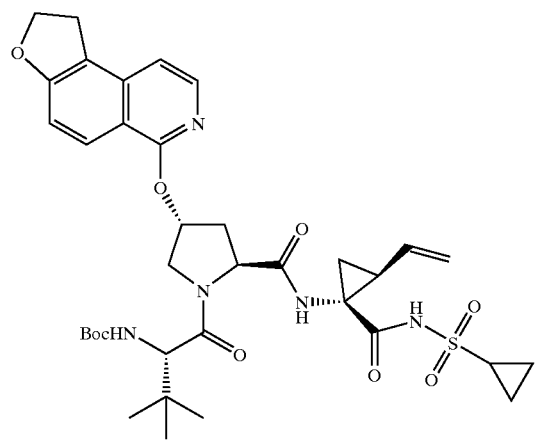

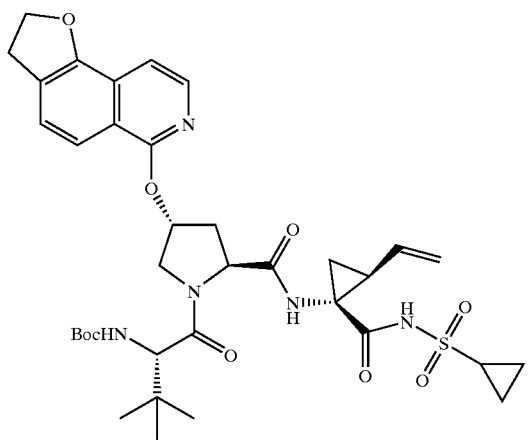

Compound 268

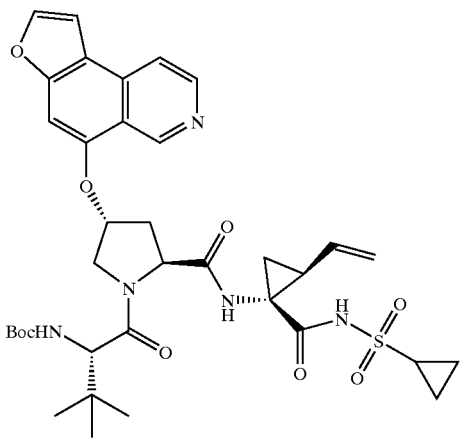

Compounds 267 and 268 were prepared by following Scheme 1 of Example 250 except that 3-(2,3-dihydro-benzofuran-4-yl)-acrylic acid was used in place of 3-phenyl-but-2-enoic acid in step 1.

Step 1:

Modifications: 1.14 g 3-(2,3-dihydro-benzofuran-4-yl)-acrylic acid used, 600 mg product obtained (52% yield).

Product:

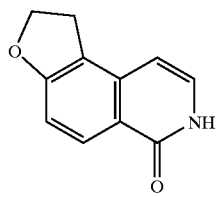

Data: $^1$H NMR (400 MHz, CD$_3$OD) δ ppm 3.35 (t, J=8.93 Hz, 2 H), 4.74 (t, J=8.93 Hz, 2 H), 6.49 (d, J=7.09 Hz, 1 H), 6.95 (d, J=8.56 Hz, 1 H), 7.25 (d, J=7.09 Hz, 1 H), 8.13 (d, J=8.80 Hz, 1 H); MS (M+H)$^+$ 188.

Step 2:

Modifications: 560 mg 1,7-dihydro-2H-furo[3,2-f]isoquinolin-6-one used, 380 mg product obtained (48% yield).

Product:

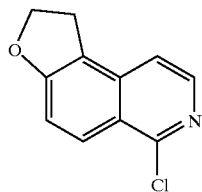

Data: $^1$H NMR (400 Hz, CDCl$_3$) δ ppm 3.47 (t, J=9.05 Hz, 2 H), 4.84 (t, J=9.05 Hz, 2 H), 7.24 (d, J=8.56 Hz, 1 H), 7.33 (d, J=5.87 Hz, 1 H), 8.20 (m, 2 H); MS (M+H)$^+$ 206.

Step 3:

Modifications: 105 mg 6-chloro-1,2-dihydro-furo[3,2-f]isoquinoline used, 390 mg products mixture obtained.

Products:

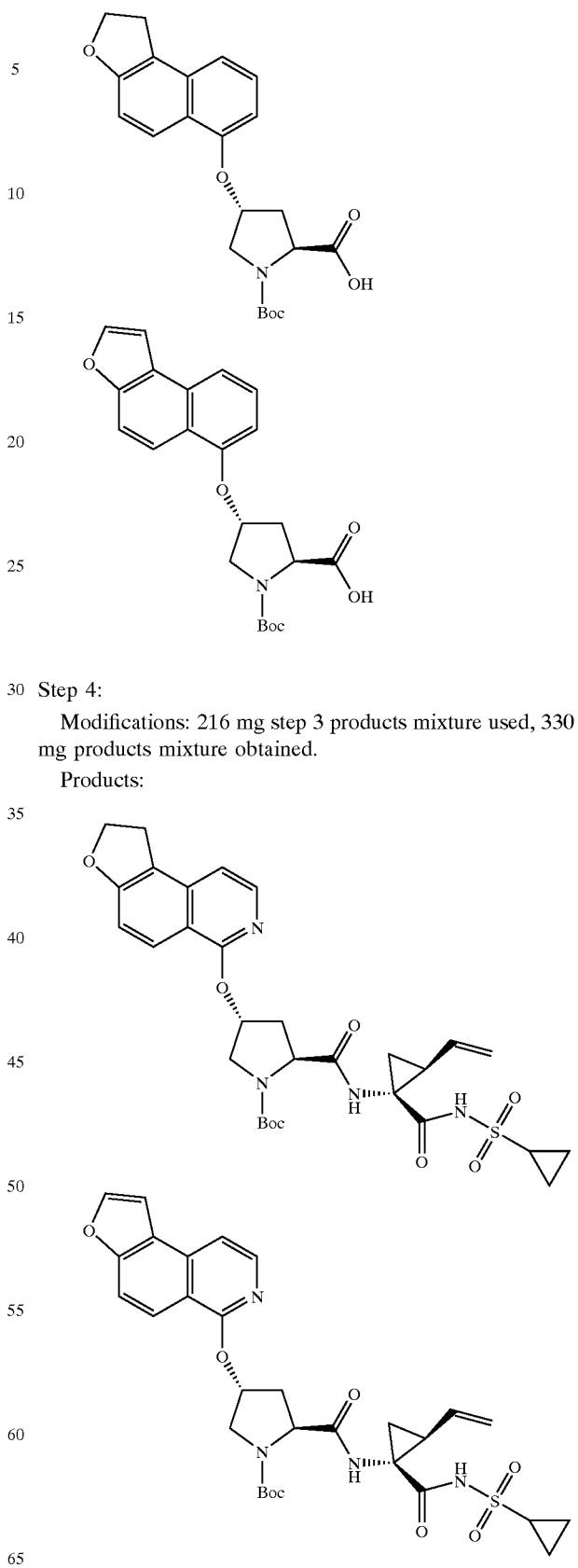

Step 4:

Modifications: 216 mg step 3 products mixture used, 330 mg products mixture obtained.

Products:

Step 5:
Modifications: 330 mg step 4 products mixture used, 140 mg of compound 267 and 25 mg of compound 268 obtained.
Products:

Compound 267

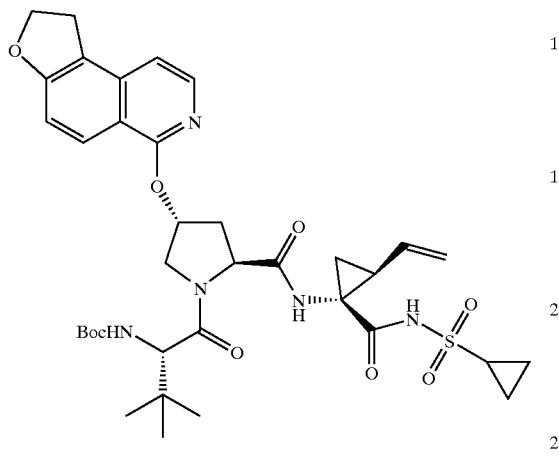

Compound 268

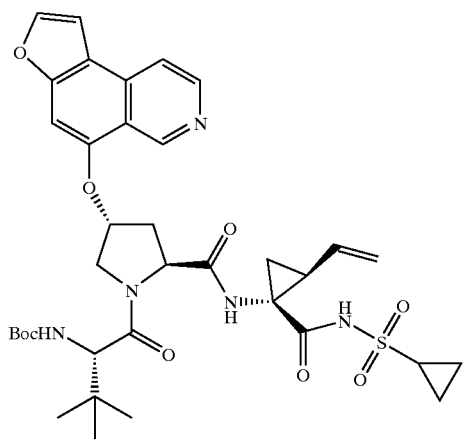

Data of compound 267: $^1$H NMR (400 Hz, CD$_3$OD) δ ppm 1.07 (m, 12 H), 1.24 (m, 10 H), 1.43 (m, 1 H), 1.88 (dd, J=8.07, 5.38 Hz, 1 H), 2.26 (m, 2 H), 2.61 (dd, J=13.69, 7.09 Hz, 1 H), 2.94 (m, 1 H), 3.42 (t, J=9.05 Hz, 2 H), 4.05 (dd, J=11.86, 3.55 Hz, 1 H), 4.24 (s, 1 H), 4.50 (m, 2 H), 4.77 (t, J=8.93 Hz, 2 H), 5.12 (m, 1 H), 5.29 (d, J=17.12 Hz, 1 H), 5.76 (m, 2 H), 7.03 (d, J=8.80 Hz, 1 H), 7.12 (d, J=6.11 Hz, 1 H), 7.91 (d, J=5.87 Hz, 1 H), 8.06 (d, J=8.80 Hz, 1 H); MS: (M+H)$^+$726.

Data of compound 268: $^1$H NMR (400 Hz, CD$_3$OD) δ ppm 1.06 (m, 12 H), 1.19 (s, 9 H) 1.26 (m, 1 H), 1.44 (m, 1 H), 1.88 (dd, J=8.07, 5.62 Hz, 1 H), 2.24 (d, J=8.56 Hz, 2 H), 2.64 (m, 1 H), 2.95 (m, 1 H), 4.07 (m, J=3.42 Hz, 1 H), 4.24 (s, 1 H), 4.54 (m, 2 H), 5.12 (d, J=10.52 Hz, 1 H), 5.30 (d, J=17.12 Hz, 1 H), 5.76 (m, 1 H), 5.91 (s, 1 H), 7.39 (d, J=1.47 Hz, 1 H), 7.68 (m, 2 H), 7.96 (d, J=1.96 Hz, 1 H), 8.12 (m, 2 H); MS: (M+H)$^+$ 724.

Example 269

Preparation of Compound 269

Compound 269

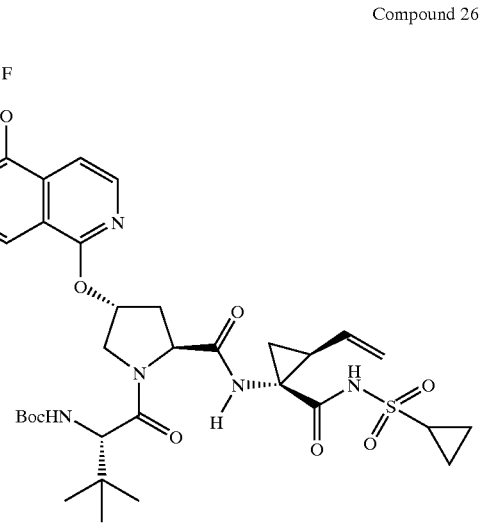

Scheme 2

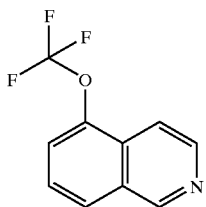
step 1
(PhO)$_2$PON$_3$

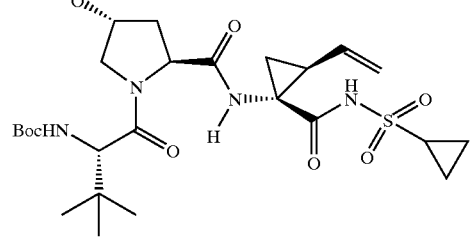
step 2
POCl$_3$

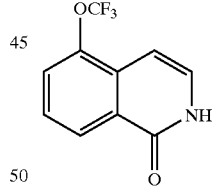
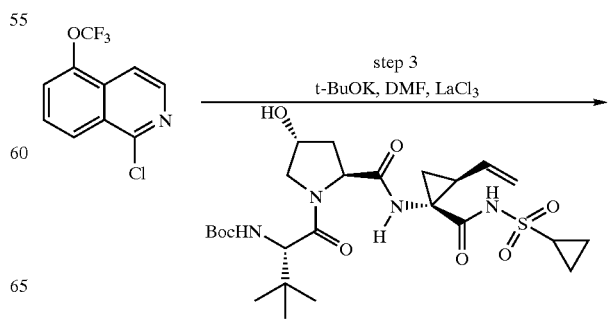
step 3
t-BuOK, DMF, LaCl$_3$

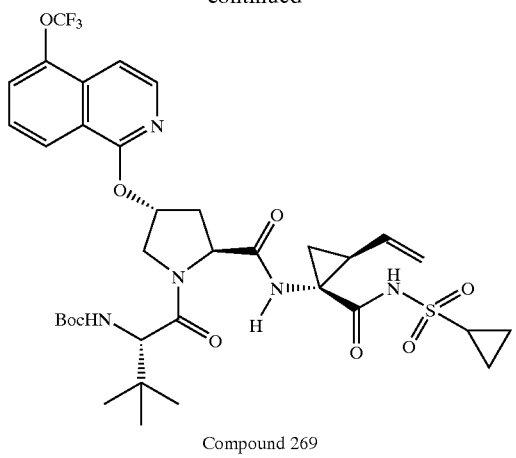

Compound 269

Step 1:

A solution of 2-trifluoromethoxycinnamic acid (11.6 g), diphenylphosphoryl azide (13.75 g), and triethylamine (7.07 g) in benzene (50 mL) was stirred for 1 h. After filtration through a silica gel plug washing with benzene and concentration, the residue was dissolved in diphenylmethane (80 mL) and refluxed for 3 h. After cooling to rt, solids were collected through a plug washing with benzene and dried to give 5.1 g (44%) of the desired product as a solid. $^1$H NMR (400 MHz, CD$_3$OD) δ ppm 6.79 (d, J=7.3 Hz, 1 H), 7.29 (d, J=7.3 Hz, 1 H), 7.57 (t, J=8.1 Hz, 1 H), 7.70 (d, J=7.8 Hz, 1 H), 8.30 (d, J=8.1 Hz; 1 H); MS: (M+H)$^+$ 230.

Step 2:

A solution of 5-trifluoromethoxy-2H-isoquinolin-1-one (4.58 g) in POCl$_3$ (50 mL) was refluxed for 3 h. After cooling and concentration, the residue was based with 5 N NaOH and extracted with CH$_2$Cl$_2$. The organic layer was washed with brine and dried over MgSO$_4$. After concentration, purification by flash chromatography of Biotage with 5% ethyl acetate in hexanes gave 4.347 g (88%) of the desired product as a solid. $^1$H NMR (400 MHz, CDCl$_3$) δ ppm 7.66 (m, 2 H), 7.87 (d, J=5.9 Hz, 1 H), 8.31 (m, 1 H), 8.37 (d, J=5.9 Hz, 1 H); MS: (M+H)$^+$ 248.

Step 3:

To a suspension of {1-[2-(1-cyclopropanesulfonylaminocarbonyl-2-vinyl-cyclopropylcarbamoyl)-4-hydroxy-pyrrolidine-1-carbonyl]-2,2-dimethyl-propyl}-carbamic acid tert-butyl ester (56 mg), 1-chloro-5-trifluoromethoxy-isoquinoline (25 mg), and LaCl$_3$ (25 mg) in DMF (1 mL) at −78° C. was added tert-BuOK (0.5 mL, 1 M in THF) and warmed to rt. After stirring for 30 min, the reaction was quenched with saturated NH$_4$Cl solution and extracted with ethyl acetate. After concentration, purification by prep HPLC. gave 35 mg (46%) of the desired compound 269 as a solid. $^1$H NMR (400 MHz, CD$_3$OD) δ ppm 1.03 (m, 12 H), 1.24 (m, 10 H), 1.44 (dd, J=9.7, 5.3 Hz, 1 H), 1.88 (dd, J=8.1, 5.6 Hz, 1 H) 2.28 (m, 2 H), 2.64 (dd, J=13.7, 7.1 Hz, 1 H), 2.94 (m, 1 H), 4.09 (m, H), 4.21 (d, J=9.3 Hz, 1 H), 4.53 (m, 2 H), 5.12 (d, J=11.5 Hz, 1 H), 5.30 (d, J=17.1 Hz, 1 H), 5.75 (m, 1 H), 5.92 (m, 1 H), 6.60 (d, J=9.5 Hz, 1 H), 7.49 (d, J=6.1 Hz, 1 H), 7.60 (m, 1 H), 7.69 (d, J=7.3 Hz, 1 H), 8.11 (d, J=6.1 Hz, 1 H), 8.22 (d, J=8.3 Hz, 1 H); MS: (M+Na)$^+$ 790.

Example 270

Preparation of Compound 270

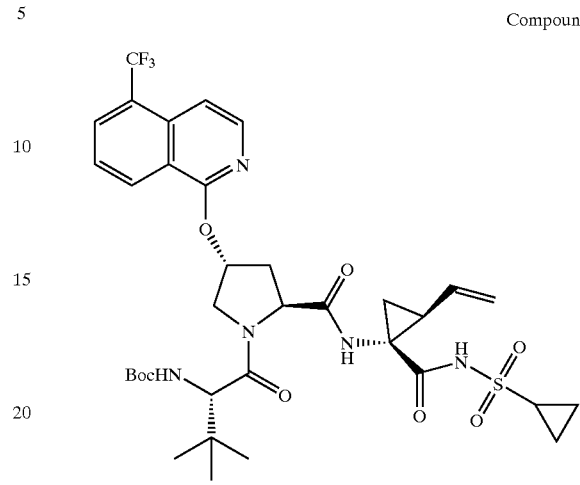

Compound 270

Compound 270 was prepared by following Scheme 2 of Example 269 except that 2-trifluromethylcinnamic acid was used in place of 2-trifluormethoxycinnamic acid in Step 1.

Step 1:

Modifications: 10 g 2-trifluoromethylcinnamic acid used, 5 g product obtained (50% yield).

Product:

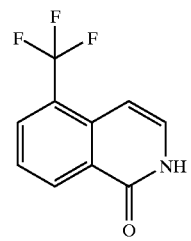

Data: $^1$H NMR (400 MHz, CD$_3$OD) δ ppm 6.83 (m, 1 H), 7.33 (d, J=7.58 Hz, 1 H), 7.63 (t, J=7.83 Hz, 1 H), 8.09 (d, J=7.58 Hz, 1 H), 8.57 (d, J=8.07 Hz, 1 H).

Step 2:

Modifications: 4.4 g 5-trifluoromethyl-2H-isoquinolin-1-one used, 3.5 g product obtained (73% yield).

Product:

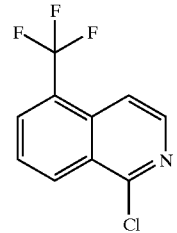

Data: $^1$H NMR (400 MHz, CDCl$_3$) δ ppm 7.75 (t, J=7.95 Hz, 1 H), 7.90 (m, 1 H), 8.12 (d, J=7.34 Hz, 1 H), 8.41 (d, J=6.11 Hz, 1 H), 8.60 (d, J=8.56 Hz, 1 H).

Step 3:

Modifications: 46 mg 1-chloro-5-trifluoromethyl-isoquinoline and 111 mg {1-[2-(1-Cyclopropanesulfonylaminocarbonyl-2-vinyl-cyclopropylcarbamoyl)-4-hydroxy-pyrrolidine-1-carbonyl]-2,2-dimethyl-propyl}-carbamic acid tert-butyl ester used, 70 mg product obtained (47% yield).

Product:

Compound 270

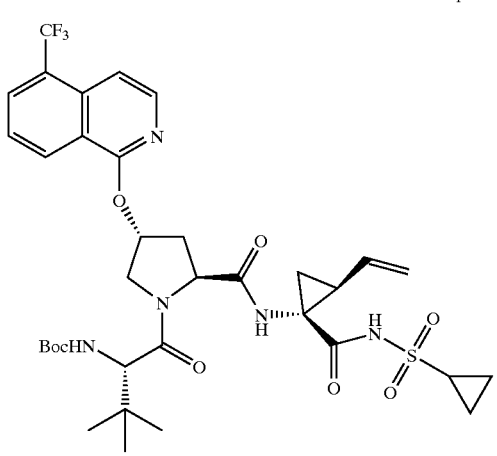

Data: $^1$H NMR (400 MHz, CD$_3$OD) δ ppm 1.06 (m, 12 H), 1.23 (m, 10 H), 1.44 (dd, J=9.54, 5.38 Hz, 1 H), 1.88 (dd, J=8.07, 5.38 Hz, 1 H), 2.28 (m, 2 H), 2.65 (dd, J=13.82, 6.97 Hz, 1 H), 2.94 (m, 1 H), 4.07 (m, 1 H), 4.20 (m, 1 H), 4.56 (m, 2 H), 5.12 (m, 1 H), 5.30 (d, J=17.12 Hz, 1 H), 5.75 (m, 1 H), 5.90 (s, 1 H), 6.59 (d, J=9.05 Hz, 1 H), 7.53 (d, J=4.40 Hz, 1 H), 7.65 (t, J=7.83 Hz, 1 H), 8.12 (d, J=7.09 Hz, 1 H), 8.15 (d, J=6.36 Hz, 1 H), 8.50 (d, J=8.31 Hz, 1 H); MS: (M+Na)$^+$ 774.

Example 271

Preparation of Compound 271

Compound 271

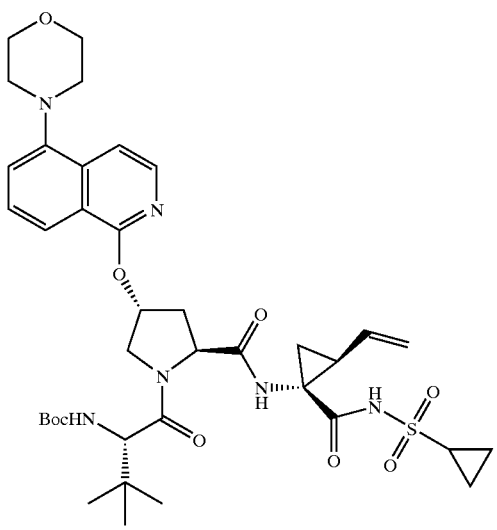

Compound 271 was prepared by following Scheme 2 of Example 269 except that 2-chlorocinnamic acid was used in place of 2-trifluormethoxycinnamic acid in step 1.

Step 1:

Modifications: 7 g 2-chlorocinnamic acid used, 5 g product obtained (71% yield).

Product:

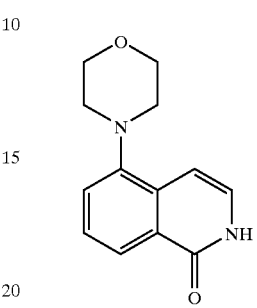

Data: $^1$H NMR (400 MHz, CD$_3$OD) δ ppm 3.02 (m, 4 H), 3.91 (m, 4 H), 6.97 (d, J=7.34 Hz, 1 H), 7.18 (d, J=7.34 Hz, 1 H), 7.44 (m, 2 H), 8.02 (d, J=7.83 Hz, 1 H); MS (M+H)$^+$ 231.

Step 2:

Modifications: 2.2 g 5-morpholin-4-yl-2H-isoquinolin-1-one used, 2.1 g product obtained (87% yield).

Product:

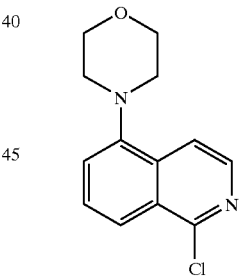

Data: $^1$H NMR (400 MHz, CCl$_3$D) δ ppm 3.09 (m, 4 H), 3.97 (m, 4 H), 7.32 (d, J=7.58 Hz, 1 H), 7.60 (m, 1 H), 7.91 (d, J=5.87 Hz, 1 H), 8.06 (d, J=8.56 Hz, 1 H), 8.26 (d, J=5.87 Hz, 1 H).

Step 3:

Modifications: 50 mg 1-chloro-5-morpholin-4-yl-isoquinoline and 111 mg {1-[2-(1-Cyclopropanesulfonylaminocarbonyl-2-vinyl-cyclopropylcarbamoyl)-4-hydroxy-pyrrolidine-1-carbonyl]-2,2-dimethyl-propyl}-carbamic acid tert-butyl ester used, 40 mg product obtained (26% yield).

Product:

Compound 271

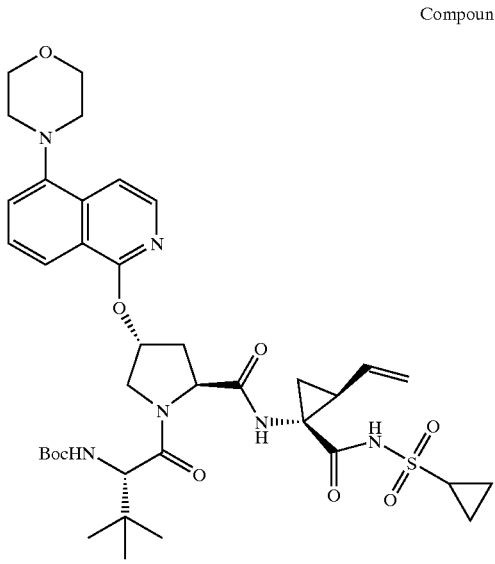

Data: ¹H NMR (500 MHz, CD₃OD) δ ppm 1.07 (m, 12 H), 1.26 (m, 10 H), 1.44 (d, J=7.93 Hz, 1 H), 1.88 (dd, J=7.93, 5.19 Hz, 1 H), 2.25 (m, 2 H), 2.62 (dd, J=13.73, 7.02 Hz, 1 H), 2.94 (m, 1 H), 3.06 (d, J=3.97 Hz, 4 H), 3.94 (m, 4 H), 4.07 (d, J=14.04 Hz, 1 H), 4.25 (s, 1 H), 4.45 (d, J=12.21 Hz, 1 H), 4.52 (m, 1 H), 5.12 (d, J=9.46 Hz, 1 H), 5.29 (d, J=16.79 Hz, 1 H), 5.75 (m, 1 H), 5.85 (s, 1 H), 7.34 (d, J=7.32 Hz, 1 H), 7.45 (t, J=7.78 Hz, 1 H), 7.59 (d, J=6.10 Hz, 1 H), 7.91 (d, J=7.63 Hz, 1 H), 7.97 (d, J=5.80 Hz, 1 H).

Example 272

Preparation of Compound 272

Compound 272

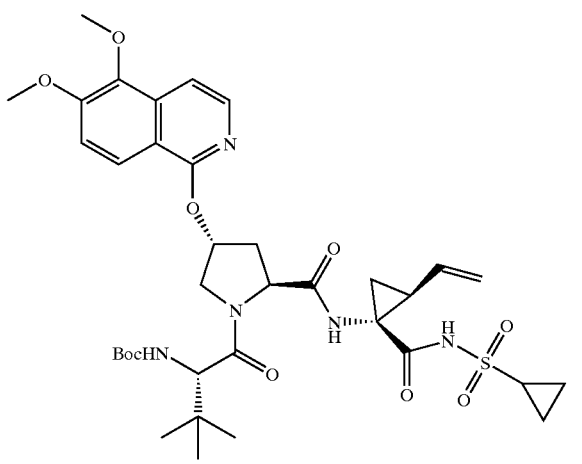

Compound 272 was prepared by following Scheme 2 of Example 269 except that 2,3-dimethoxycinnamic acid was used in place of 2-trifluormethoxycinnamic acid in step 1.

Step 1:
Modifications: 10.4 g 2,3-dimethoxycinnamic acid used, 4.1 g product obtained (40% yield).

Product:

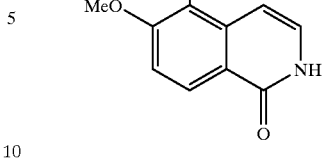

Data: ¹H NMR (400 MHz, CD₃OD) δ ppm 3.86 (s, 3 H), 3.96 (s, 3 H), 6.82 (d, J=7.2 Hz, 1 H), 7.10 (d, J=7.2 Hz, 1 H), 7.28 (d, J=8.8 Hz, 1 H), 8.07 (d, J=8.8 Hz, 1 H); MS: (M+H)⁺ 206.

Step 2:
Modifications: 4.1 g 5,6-dimethoxy-2H-isoquinolin-1-one used, 4.03 g product obtained (90% yield).

Product:

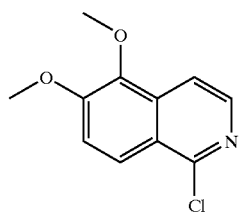

Data: ¹H NMR (400 MHz, CD₃OD) δ ppm 3.97 (s, 3 H), 4.05 (s, 3 H), 7.65 (d, J=9.29 Hz, 1 H), 7.90 (dd, J=5.87, 0.98 Hz, 1 H), 8.12 (m, 2 H).

Step 3:
Modifications: 22 mg 1-chloro-5,6-dimethoxy-isoquinoline and 56 mg {1-[2-(1-cyclopropanesulfonylaminocarbonyl-2-vinyl-cyclopropylcarbamoyl)-4-hydroxy-pyrrolidine-1-carbonyl]-2,2-dimethyl-propyl}-carbamic acid tert-butyl ester used, 31 mg product obtained (42% yield).

Product:

Compound 272

Data: ¹H NMR (500 MHz, CD₃OD) δ ppm 1.06 (m, 12 H), 1.26 (m, 10 H), 1.44 (s, 1 H), 1.88 (d, J=7.32 Hz, 1 H), 2.24 (s, 2 H), 2.60 (m, 1 H), 2.94 (m, 1 H), 3.92 (s, 3 H), 3.99 (s, 3 H), 4.06 (d, J=11.90 Hz, 1 H), 4.23 (s, 1 H), 4.43 (d, J=10.68 Hz, 1 H), 4.53 (m, 1 H), 5.12 (d, J=10.38 Hz, 1 H), 5.30 (d, J=17.40 Hz, 1 H), 5.77 (m, 2 H), 7.35 (d, J=9.16 Hz, 1 H), 7.46 (d, J=5.80 Hz, 1 H), 7.89 (d, J=5.80 Hz, 1 H), 7.97 (d, J=8.85 Hz, 1 H).

Example 273

Preparation of Compound 273

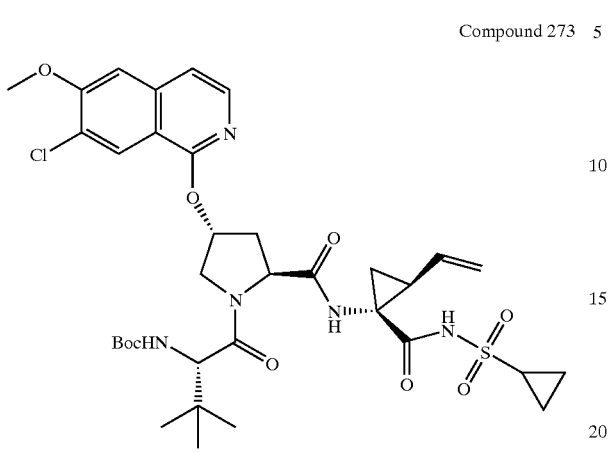

Compound 273

Compound 273 was prepared by following Scheme 2 of Example 269 except that 4-chloro-3-methoxycinnamic acid was used in place of 2-trifluormethoxycinnamic acid in step 1.

Step 1:
Modifications: 2.5 g 4-chloro-3-methoxycinnamic acid used, 1.2 g product obtained (48% yield).
Product:

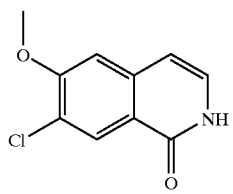

Data: $^1$HNMR (400 MHz, CD$_3$OD) δ 4.00 (s, 3 H), 6.64 (d, J=7.09 Hz, 1 H), 7.15 (d, J=7.34 Hz, 1 H), 7.21 (s, 1 H), 8.22 (s, 1 H).

Step 2:
Modifications: 1.05 g 7-Chloro-6-methoxy-2H-isoquinolin-1-one used, 0.8 g product obtained (70% yield).
Product:

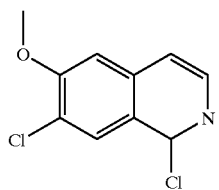

Data: $^1$H NMR (400 Hz, CDCl$_3$) δ ppm 4.05 (s, 3 H), 7.13 (s, 1 H), 7.48 (d, J=5.38 Hz, 1 H), 8.21 (d, J=5.62 Hz, 1 H), 8.34 (s, 1 H); MS: (M+H)$^+$ 229.

Step 3:
Modifications: 44 mg 1,7-dichloro-6-methoxy-isoquinoline and 113 mg {1-[2-(1-cyclopropanesulfonylaminocarbonyl-2-vinyl-cyclopropylcarbamoyl)-4-hydroxy-pyrrolidine-1-carbonyl]-2,2-dimethyl-propyl}-carbamic acid tert-butyl ester used, 25 mg product obtained (17% yield)

Product:

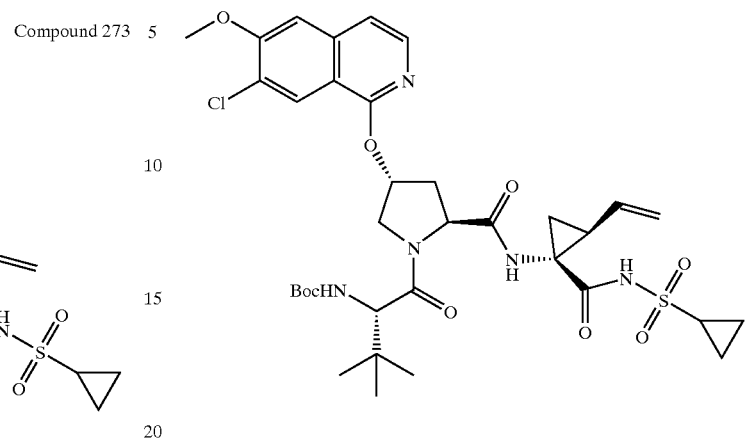

Compound 273

Data: $^1$H NMR (400 Hz, CD$_3$OD) δ ppm 1.07 (m, 12 H), 1.24 (m, 10 H), 1.44 (dd, J=9.54, 5.38 Hz, 1 H), 1.88 (dd, J=8.07, 5.38 Hz, 1 H), 2.26 (m, 1 H) 2.60 (m, J=13.69, 6.85 Hz, 1 H), 2.94 (m, 2 H), 3.98 (s, 3 H), 4.06 (m, 1 H), 4.20 (m, 1 H), 4.42 (d, J=12.23 Hz, 1 H), 4.57 (m, 1 H), 5.12 (d, J=11.74 Hz, 1 H), 5.30 (d, J=17.36 Hz, 1 H), 5.76 (m, 1 H), 5.86 (s, 1 H), 7.28 (d, J=5.62 Hz, 1 H), 7.33 (s, 1 H), 7.92 (d, J=5.87 Hz, 1 H), 8.09 (s, 1 H); MS: (M+H)$^+$ 749.

Example 274

Preparation of Compound 274

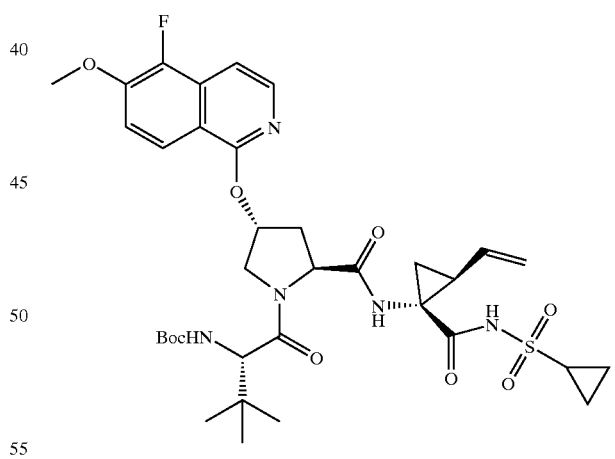

Compound 274

Compound 274 was prepared by following Scheme 2 of Example 269 except that 2-fluoro-3-cinnamic acid was used in place of 2-trifluormethoxycinnamic acid in step 1.

Step 1:

Modifications: 3.92 g 2-fluoro-3-cinnamic acid used, 2.4 g product obtained (61% yield).

Product:

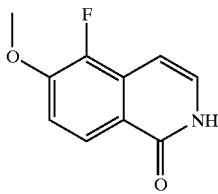

Data: ¹H NMR (400 MHz, CD₃OD) δ ppm 4.00 (s, 3 H), 6.72 (m, 1 H), 7.16 (d, J=7.34 Hz, 1 H), 7.35 (t, J=8.44 Hz, 1 H), 8.09 (d, J=8.80 Hz, 1 H).

Step 2:

Modifications: 1.93 g 5-fluoro-6-methoxy-2H-isoquinolin-1-one used, 1.688 g product obtained (80% yield).

Product:

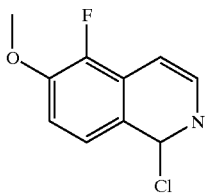

Data: ¹H NMR (CDCl₃) δ ppm 4.08 (s, 3 H), 7.44 (dd, J=9.29, 7.83 Hz, 1 H), 7.75 (d, J=5.87 Hz, 1 H), 8.12 (d, J=9.29 Hz, 1 H), 8.22 (d, J=5.87 Hz, 1 H); MS: (M+H)⁺ 212.

Step 3:

Modifications: 41 mg 1-chloro-5-fluoro-6-methoxy-isoquinoline and 133 mg {1-[2-(1-cyclopropanesulfonylaminocarbonyl-2-vinyl-cyclopropylcarbamoyl)-4-hydroxy-pyrrolidine-1-carbonyl]-2,2-dimethyl-propyl}-carbamic acid tert-butyl ester used, 70 mg product obtained (48% yield).

Product:

Compound 274

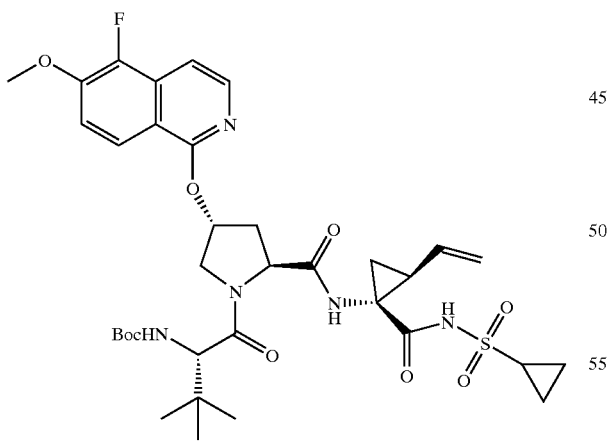

Data: ¹H NMR (CD₃OD) δ ppm 1.06 (m, 13 H), 1.21 (s, 9 H), 1.44 (dd, J=9.78, 5.38 Hz, 1 H), 1.88 (dd, J=8.19, 5.50 Hz, 1 H), 2.24 (d, J=9.29 Hz, 2 H), 2.62 (d, J=13.94 Hz, 1 H), 2.94 (m, 1 H), 4.05 (m, 4 H), 4.22 (d, J=9.29 Hz, 1 H), 4.45 (m, 1 H), 4.54 (dd, J=9.66, 7.21 Hz, 1 H), 5.12 (d, J=10.52 Hz, 1 H), 5.30 (d, J=16.87 Hz, 1 H), 5.76 (m, 1 H), 5.86 (s, 1 H), 7.39 (m, 2 H), 7.95 (d, J=6.11 Hz, 1 H), 8.00 (d, J=9.29 Hz, 1 H).

Example 275

Preparation of Compound 275

Compound 275

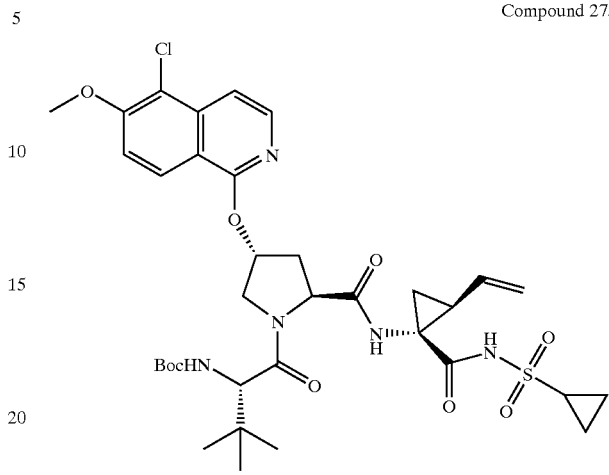

Compound 2 was prepared by following Scheme 2 of Example 269 except that 2-chloro-3-methoxycinnamic acid was used in place of 2-trifluormethoxycinnamic acid in step 1.

Step 1:

Modifications: 658 mg 2-chloro-3-methoxycinnamic acid used, 360 mg product obtained (54% yield).

Product:

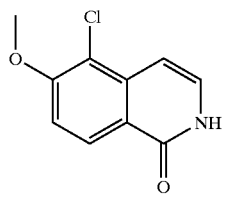

Data: ¹H NMR (400 MHz, CD₃OD) δ ppm 4.02 (s, 3 H), 6.91 (d, J=7.34 Hz, 1 H), 7.23 (d, J=7.58, Hz, 1 H), 7.35 (d, J=9.05 Hz, 1 H), 8.27 (d, J=9.05 Hz, 1 H).

Step 2:

Modifications: 350 mg 5-chloro-6-methoxy-2H-isoquinolin-1-one used, 300 mg product obtained (80% yield).

Product:

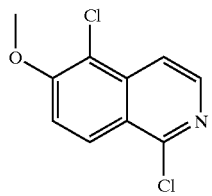

Data: ¹H NMR (400 Hz, CDCl₃) δ ppm 4.09 (s, 3 H), 7.43 (d, J=9.29 Hz, 1 H), 7.93 (d, J=6.11 Hz, 1 H), 8.30 (m, 2 H); MS (M+H)⁺ 229.

Step 3:

Modifications: 68 mg 1,5-dichloro-6-methoxy-isoquinoline and 167 mg {1-[2-(1-cyclopropanesulfonylaminocarbonyl-2-vinyl-cyclopropylcarbamoyl)-4-hydroxy-pyrrolidine-1-carbonyl]-

2,2-dimethyl-propyl}-carbamic acid tert-butyl ester used, 130 mg product obtained (60% yield).

Product:

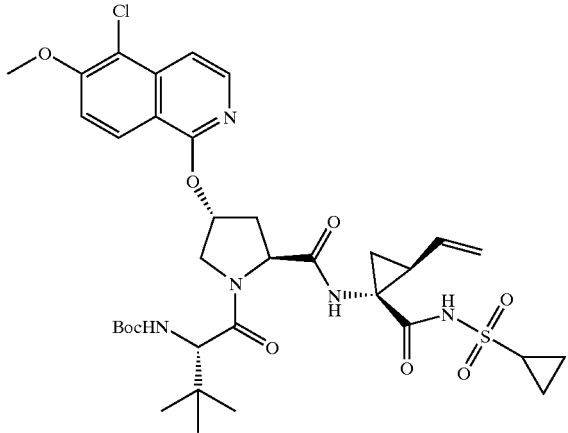

Compound 275

Data: ¹H NMR (400 MHz, CD₃OD) δ ppm 1.06 (m, 12 H), 1.25 (m, 10 H), 1.46 (d, J=5.62 Hz, 1 H), 1.88 (dd, J=8.07, 5.62 Hz, 1 H), 2.27 (m, 2 H), 2.62 (m, 1 H), 2.94 (m, 1 H), 4.05 (m, 4 H), 4.22 (d, J=9.05 Hz, 1 H), 4.46 (d, J=11.49 Hz, 1 H), 4.54 (dd, J=9.78, 6.36 Hz, 1 H), 5.13 (d, J=10.52 Hz, 1 H), 5.30 (d, J=15.89 Hz, 1 H), 5.76 (m, 1 H), 5.86 (s, 1 H), 7.40 (d, J=9.29 Hz, 1 H), 7.55 (d, J=6.36 Hz, 1 H), 8.01 (d, J=6.36 Hz, 1 H), 8.20 (d, J=9.29 Hz, 1 H); MS: (M+H)⁺ 749.

Example 276

Preparation of Compound 276

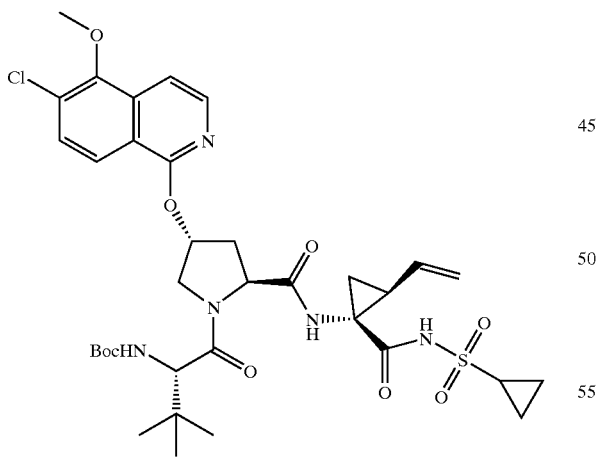

Compound 276

Compound 276 was prepared by following Scheme 2 of Example 269 except that 3-chloro-2-methoxycinnamic acid was used in place of 2-trifluormethoxycinnamic acid in step 1.

Step 1:

Modifications: 4.24 g 3-chloro-2-methoxycinnamic acid used, 2.4 g product obtained (57% yield).

Product:

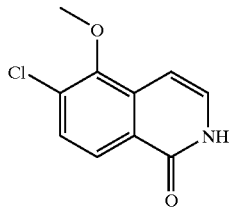

Data: ¹H NMR (400 MHz, CD₃OD) δ ppm 3.93 (s, 1 H), 6.85 (d, J=7.34 Hz, 1 H), 7.24 (d, J=7.34 Hz, 1 H), 7.52 (d, J=8.80 Hz, 1 H), 8.03 (d, J=8.80 Hz, 1 H); MS: (M+H)⁺ 210.

Step 2:

Modifications: 2.09 g 6-chloro-5-methoxy-2H-isoquinolin-1-one used, 1.9 g product obtained (83% yield).

Product:

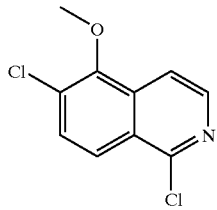

Data: ¹H NMR (400 Hz, CDCl₃) δ ppm 4.03 (s, 2 H), 7.63 (d, J=9.05 Hz, 1 H), 7.86 (d, J=5.14 Hz, 1 H), 8.06 (d, J=9.05 Hz, 1 H), 8.32 (d, J=5.62 Hz, 1 H); MS: (M+H)⁺ 229.

Step 3:

Modifications: 91 mg 1,6-dichloro-5-methoxy-isoquinoline and 226 mg {1-[2-(1-cyclopropanesulfonylaminocarbonyl-2-vinyl-cyclopropylcarbamoyl)-4-hydroxy-pyrrolidine-1-carbonyl]-2,2-dimethyl-propyl}-carbamic acid tert-butyl ester used, 114 mg product obtained (38% yield).

Product:

Compound 276

Data: ¹H NMR (400 Hz, CD₃OD) δ ppm 1.06 (m, 12 H), 1.23 (m, 10 H), 1.44 (t, J=6.72 Hz, 1 H), 1.88 (dd, J=7.95, 5.26 Hz, 1 H), 2.25 (m, 2 H), 2.62 (dd, J=13.33, 6.48 Hz, 1 H), 2.94 (m, 1 H), 3.98 (s, 3 H), 4.03 (m, 1 H), 4.20 (m, 1 H), 4.51 (m, 2 H), 5.12 (d, J=10.52 Hz, 1 H), 5.32 (s, 1 H), 5.75 (m, 1 H), 5.87 (s, 1 H), 7.50 (m, 2 H), 7.95 (d, J=8.80 Hz, 1 H), 8.06 (d, J=5.87 Hz, 1 H); MS (MH⁺) 749.

Example 277

Preparation of Compound 277

Compound 277

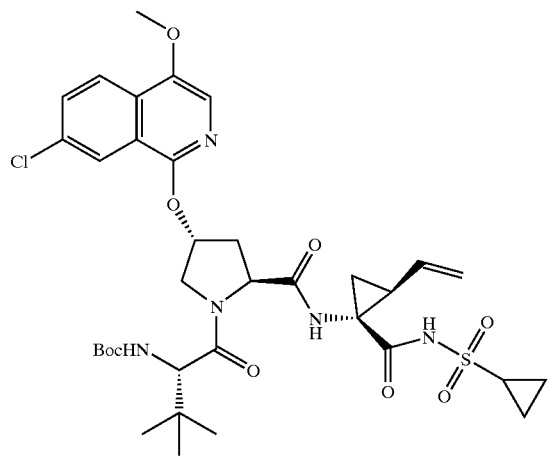

Compound 277 was prepared by following Scheme 2 of Example 269 except that 3-(4-chloro-phenyl)-3-methoxy-acrylic acid was used in place of 2-trifluornethoxycinnamic acid in step 1.

Step 1:
Modifications: 4.24 g 3-(4-chloro-phenyl)-3-methoxy-acrylic acid used, 130 mg product obtained (3% yield)
Product:

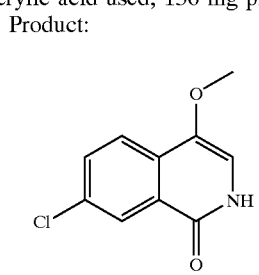

Data: $^1$H NMR (400 MHz, CD$_3$OD) δ ppm 3.96 (s, 3 H), 7.19 (dd, J=8.80, 2.45 Hz, 1 H), 7.28 (d, J=2.45 Hz, 1 H), 7.34 (s, 1 H), 8.25 (d, J=9.05 Hz, 1 H); MS: (M+H)$^+$ 210.

Step 2:
Modifications: 105 mg 7-chloro-4-methoxy-2H-isoquinolin-1-one used, 60 mg product obtained (71% yield).
Product:

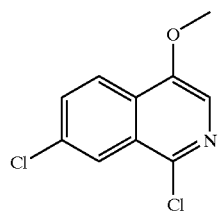

Data: $^1$H NMR (400 Hz, CDCl$_3$) δ ppm 4.05 (s, 3 H), 7.67 (dd, J=8.80, 1.96 Hz, 1 H), 7.80 (s, 1 H), 8.16 (d, J=9.05 Hz, 1 H), 8.24 (d, J=1.96 Hz, 1 H); MS: (M+H)$^+$ 229.

Step 3:
Modifications: 46 mg 1,7-dichloro-4-methoxy-isoquinoline and 113 mg {1-[2-(1-cyclopropanesulfonylaminocarbonyl-2-vinyl-cyclopropylcarbamoyl)-4-hydroxy-pyrrolidine-1-carbonyl]-2,2-dimethyl-propyl}-carbamic acid tert-butyl ester used, 50 mg product obtained (31% yield).
Product:

Compound 277

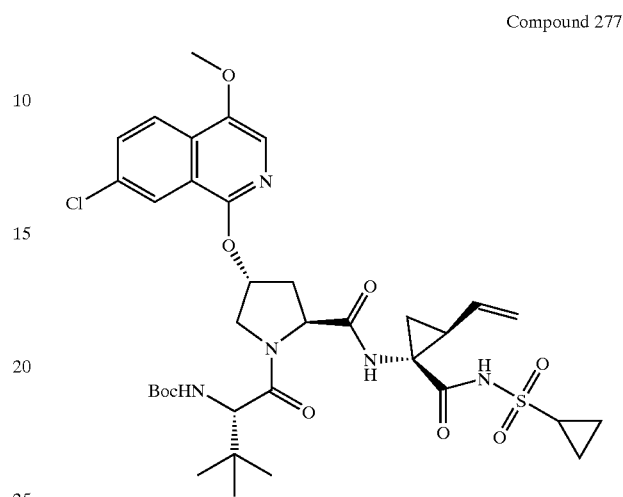

Data: $^1$H NMR (400 Hz, CD$_3$OD) δ ppm 1.06 (m, 11 H), 1.16 (s, 9 H), 1.24 (m, 2 H), 1.44 (dd, J=9.54, 5.38 Hz, 1 H), 1.88 (dd, J=8.07, 5.62 Hz, 1 H), 2.28 (m, 2 H), 2.59 (dd, J=13.69, 6.85 Hz, 1 H), 2.94 (m, 1 H), 4.00 (s, 3 H), 4.05 (d, J=11.74 Hz, 1 H), 4.19 (s, 1 H), 4.43 (d, J=11.49 Hz, 1 H), 4.56 (dd, J=10.03, 6.85 Hz, 1 H), 5.12 (d, J=11.49 Hz, 1 H), 5.30 (d, J=17.12 Hz, 1 H), 5.76 (m, 2 H), 7.57 (s, 1 H), 7.67 (d, J=8.56 Hz, 1 H), 8.04 (s, 1 H), 8.08 (d, J=8.80 Hz, 1 H); MS: (M+H)$^+$ 749.

Example 278

Preparation of Compound 278

Compound 278

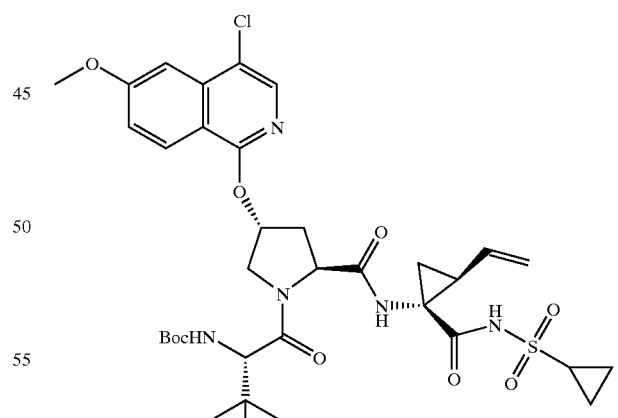

Compound 278 was prepared by following Scheme 2 of Example 269 except step 1.

Step 1:
Modifications: A mixture of 6-methoxy-2H-isoquinolin-1-one (700 mg) and NCS (532 mg) in MeCN (10 mL) was refluxed for 3 h. Filtration gave 600 mg (72%) of the desired product as a solid.

Product:

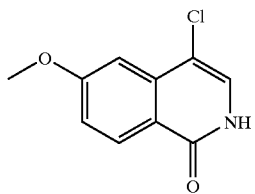

Data: ¹H NMR (400 MHz, CD₃OD) δ ppm 3.96 (s, 1 H), 7.19 (dd, J=8.80, 2.45 Hz, 1 H), 7.28 (d, J=2.45 Hz, 1 H), 7.34 (s, 1 H), 8.25 (d, J=9.05 Hz, 1 H); MS: (M+H)⁺ 210.

Step 2:
Modifications: 500 mg 4-chloro-6-methoxy-2H-isoquinolin-1-oneused, 400 mg product obtained.
Product:

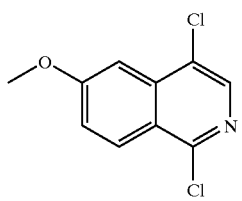

Data: ¹H NMR (400 Hz, CDCl₃) δ ppm 4.01 (s, 3 H), 7.35 (d, J=2.45 Hz, 1 H), 7.41 (d, J=2.45 Hz, 1 H), 8.24 (d, J=9.29 Hz, 1 H), 8.27 (s, 1 H); MS: (M+H)⁺ 229.

Step 3:
Modifications: 42 mg 1,4-dichloro6-methoxy-isoquinoline and 117 mg {1-[2-(1-cyclopropanesulfonylaminocarbonyl-2-vinyl-cyclopropylcarbamoyl)-4-hydroxy-pyrrolidine-1-carbonyl]-2,2-dimethyl-propyl}-carbamic acid tert-butyl ester used, 70 mg product obtained (47% yield).
Product:

Compound 278

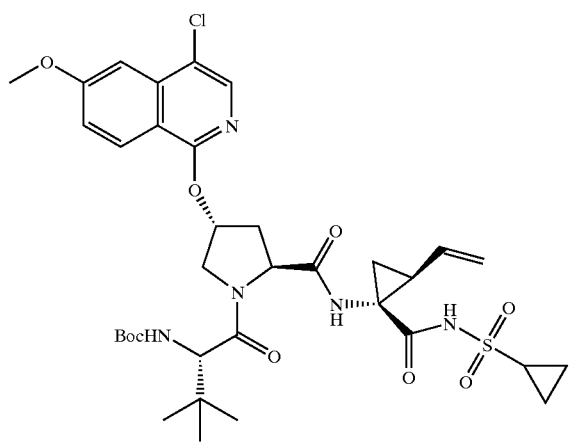

Data: ¹H NMR (400 Hz, CD₃OD) δ ppm 1.05 (m, 12 H), 1.25 (m, 10 H), 1.44 (m, 1 H), 1.88 (dd, J=8.07, 5.62 Hz, 1 H), 2.24 (m, 2 H), 2.61 (dd, J=13.82, 6.72 Hz, 1 H), 2.94 (m, 1 H), 3.97 (s, 3 H), 4.04 (dd, J=11.74, 2.69 Hz, 1 H), 4.21 (s, 1 H), 4.49 (m, 2 H), 5.12 (d, J=10.52 Hz, 1 H), 5.29 (d, J=17.12 Hz, 1 H), 5.75 (m, 2 H), 7.19 (d, J=8.80 Hz, 1 H), 7.37 (s, 1 H), 8.00 (s, 1 H), 8.13 (d, J=9.05 Hz, 1 H); MS: (M+H)⁺ 749.

Example 279

Preparation of Compound 279

Compound 279

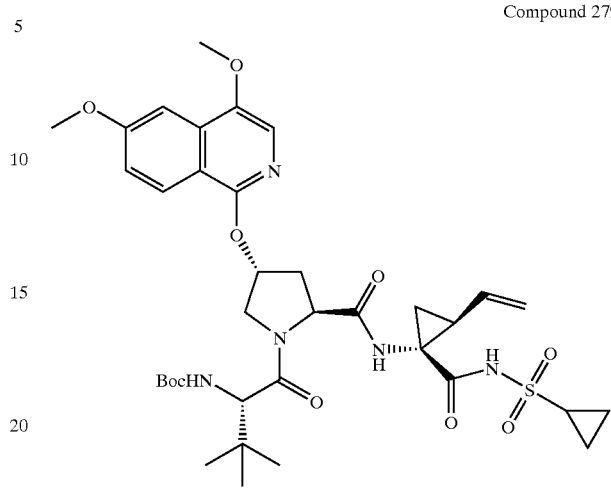

Compound 279 was prepared by following Scheme 2 of Example 269 except that 3-methoxy-3-(3-methoxy-phenyl)-acrylic acid was used in place of 2-trifluormethoxycinnamic acid in step 1.

Step 1:
Modifications: 4.24 g 3-methoxy-3-(3-methoxy-phenyl)-acrylic acid used, 400 mg product obtained (10% yield).
Product:

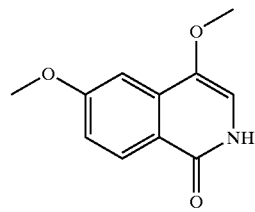

Step 2:
Modifications: 400 mg 4,6-dimethoxy-2H-isoquinolin-1-one used, 300 mg product obtained (69% yield).
Product:

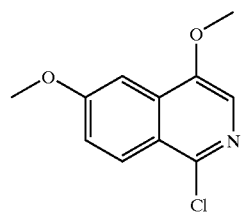

Data: ¹H NMR (400 Hz, CDCl₃) δ ppm 3.97 (s, 3 H), 4.05 (s, 3 H), 7.31 (dd, J=9.17, 2.57 Hz, 1 H), 7.45 (d, J=2.69 Hz, 1 H), 7.75 (s, 1 H), 8.16 (d, J=9.29 Hz, 1 H); MS: (M+H)⁺ 224.

Step 3:
Modifications: 89 mg 1-chloro-4,6-dimethoxy-isoquinoline and 223 mg {1-[2-(1-Cyclopropanesulfonylaminocarbonyl-2-vinyl-cyclopropylcarbamoyl)-4-hydroxy-pyrrolidine-1-carbonyl]-2,2-dimethyl-propyl}-carbamic acid tert-butyl ester used, 160 mg product obtained (54% yield).

Product:

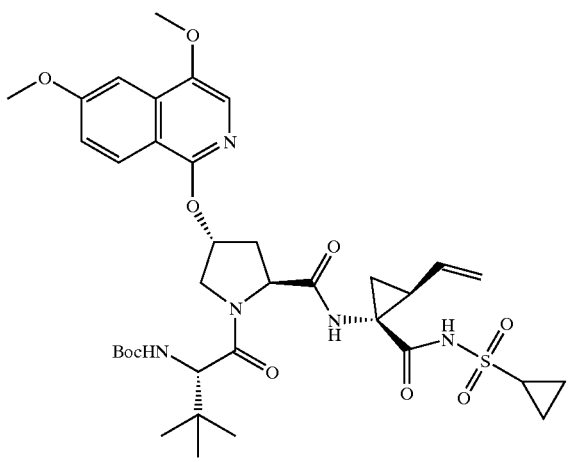

Compound 279

Data: $^1$H NMR (400 Hz, CD$_3$OD) δ ppm 1.07 (m, 12 H), 1.21 (m, 10 H), 1.43 (m, 1 H), 1.87 (dd, J=8.07, 5.62 Hz, 1 H), 2.24 (m, 2 H), 2.58 (dd, J=13.57, 6.97 Hz, 1 H), 2.94 (m, 1 H), 3.92 (s, 3 H), 3.99 (s, 3 H), 4.04 (dd, J=11.74, 2.93 Hz, 1 H), 4.24 (s, 1 H), 4.39 (d, J=11.98 Hz, 1 H), 4.50 (m, 1 H), 5.12 (d, J=10.52 Hz, 1 H), 5.29 (d, J=16.87 Hz, 1 H), 5.75 (m, 2 H), 7.12 (d, J=9.05 Hz, 1 H), 7.40 (d, J=2.20 Hz, 1 H), 7.48 (s, 1 H), 8.04 (d, J=9.05 Hz, 1 H); MS: (M+H)$^+$ 744.

Example 280

Preparation of Compound 280

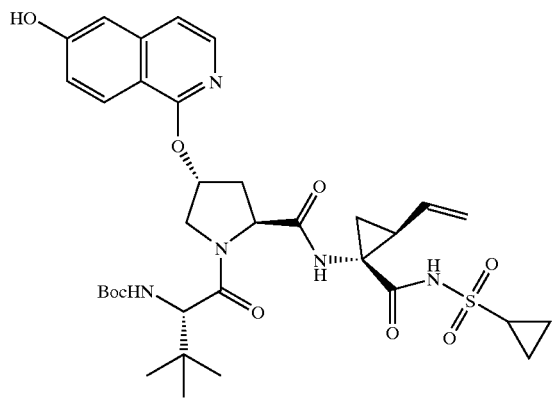

Compound 280

Compound 280 was prepared by following Scheme 2 of Example 269 except that 3-(3-difluoromethoxy-phenyl)-acrylic acid was used in place of 2-trifluormethoxycinnamic acid in step 1.

Step 1:

Modifications: 4.28 g 3-(3-difluoromethoxy-phenyl)-acrylic acid used, 3.1 g product obtained (72% yield).

Product:

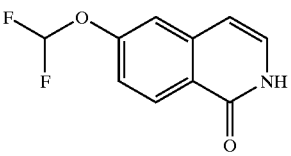

Data: MS: (M+H)$^+$ 212.

Step 2:

Modifications: 2 g 6-difluoromethoxy-2H-isoquinolin-1-one used, 1.5 g product obtained (61% yield).

Product:

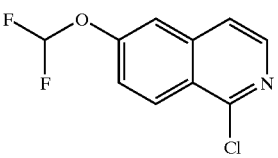

Data: $^1$H NMR (400 Hz, CDCl$_3$) δ ppm 6.69 (t, J=72.75 Hz, 1 H), 7.49 (m, 2 H), 8.28 (d, J=5.62 Hz, 1 H), 8.36 (d, J=9.05 Hz, 1 H); MS: (M+H)$^+$ 230.

Step 3:

Modifications: 46 mg 1-chloro-6-difluoromethoxy-isoquinoline and 113 mg {1-[2-(1-Cyclopropanesulfonylaminocarbonyl-2-vinyl-cyclopropylcarbamoyl)-4-hydroxy-pyrrolidine-1-carbonyl]-2,2-dimethyl-propyl}-carbamic acid tert-butyl ester used, 8 mg product obtained (5% yield).

Product:

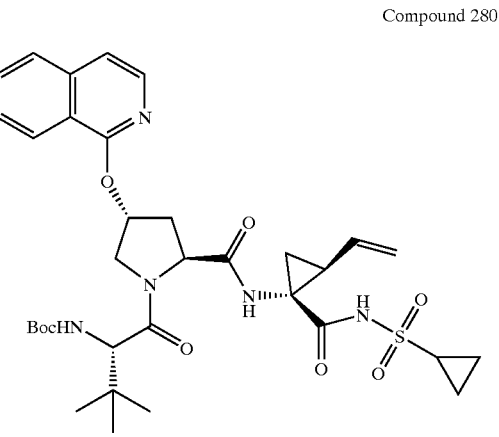

Compound 280

Data: $^1$H NMR (400 Hz, CD$_3$OD) δ ppm 1.05 (m, 12 H), 1.23 (m, 10 H), 1.44 (m, 2 H), 1.88 (dd, J=8.19, 5.50 Hz, 1 H), 2.30 (m, 2 H), 2.67 (d, J=13.94 Hz, 1 H), 2.93 (m, 1 H), 4.07 (d, J=10.27 Hz, 1 H), 4.21 (s, 1 H), 4.53 (d, J=6.85 Hz, 2 H), 5.13 (m, 1 H), 5.31 (s, 1 H), 5.76 (d, J=47.93 Hz, 2 H), 7.11 (m, 2 H), 7.26 (d, J=6.11 Hz, 1 H), 7.81 (d, J=6.11 Hz, 1 H), 8.16 (m, 1 H); MS: (M+H)$^+$ 700.

Example 281

Preparation of Compound 281

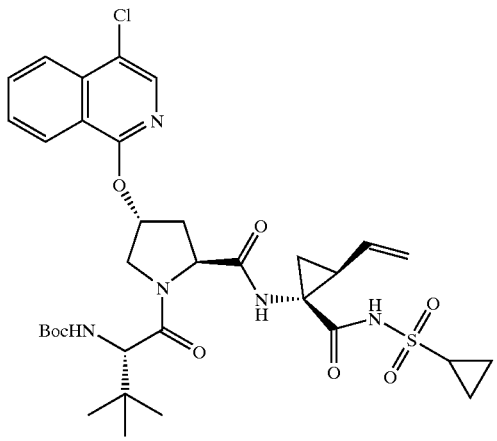

Compound 281

Compound 281 was prepared by following Scheme 2 of Example 269 except that 3-chloro-3-phenyl-acrylic acid was used in place of 2-trifluormethoxycinnamic acid in Step 1.

Step 1:
Modifications: 11 g 3-chloro-3-phenyl-acrylic acid used, 3.1 g product obtained (29% yield).
Product:

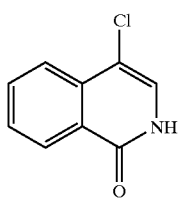

Data: $^1$H NMR (400 MHz, CD$_3$OD) δ ppm 7.34 (s, 1 H), 7.52 (t, J=7.58 Hz, 1 H), 7.77 (t, J=7.46 Hz, 1 H), 7.90 (d, J=8.07 Hz, 1 H), 8.39 (d, J=8.07 Hz, 1 H), 11.37 (s, 1 H); MS: MS: (M+H)$^+$ 180.

Step 2:
Modifications: 3.1 g 4-chloro-2H-isoquinolin-1-one used, 2.3 g product obtained (66% yield)
Product:

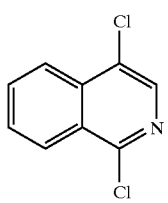

Data: $^1$H NMR (400 MHz, CDCl$_3$) δ ppm 7.77 (ddd, J=8.31, 7.09, 1.22 Hz, 1 H), 7.88 (ddd, J=8.31, 7.09, 1.22 Hz, 1 H), 8.23 (d, J=8.31 Hz, 1 H), 8.34 (s, 1 H), 8.36 (d, J=8.56 Hz, 1 H); MS: (M+H)$^+$ 198.

Step 3:
Modifications: 20 mg 1,4-dichloro-isoquinoline and 56 mg {1-[2-(1-cyclopropanesulfonylaminocarbonyl-2-vinyl-cyclopropylcarbamoyl)-4-hydroxy-pyrrolidine-1-carbonyl]-2,2-dimethyl-propyl}-carbamic acid tert-butyl ester used, 33 mg product obtained (30% yield).

Product:

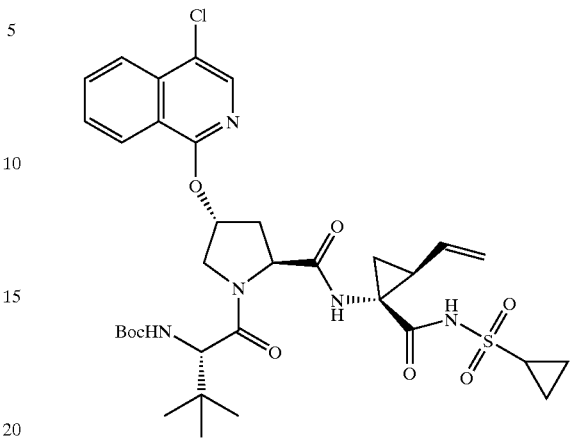

Compound 281

Data: $^1$H NMR (400 MHz, CD$_3$OD) δ ppm 1.06 (m, 12 H), 1.24 (m, 10 H), 1.44 (dd, J=9.41, 5.26 Hz, 1 H), 1.88 (dd, J=7.83, 5.62 Hz, 1 H), 2.27 (m, 2 H), 2.63 (dd, J=13.82, 6.97 Hz, 1 H), 2.94 (m, 1 H), 4.06 (dd, J=11.49, 2.45 Hz, 1 H), 4.22 (d, J=9.29 Hz, 1 H), 4.53 (m, 2 H), 5.12 (d, J=10.76 Hz, 1 H), 5.29 (d, J=17.12 Hz, 1 H), 5.75 (m, 1 H), 5.85 (s, 1 H), 6.60 (d, J=8.80 Hz, 1 H), 7.63 (t, J=7.58 Hz, 1 H), 7.86 (t, J=7.70 Hz, 1 H), 8.06 (s, 1 H), 8.11 (d, J=8.56 Hz, 1 H), 8.25 (d, J=8.31 Hz, 1 H); MS: (M+H)$^+$ 718.

Example 282

Preparation of Compound 282

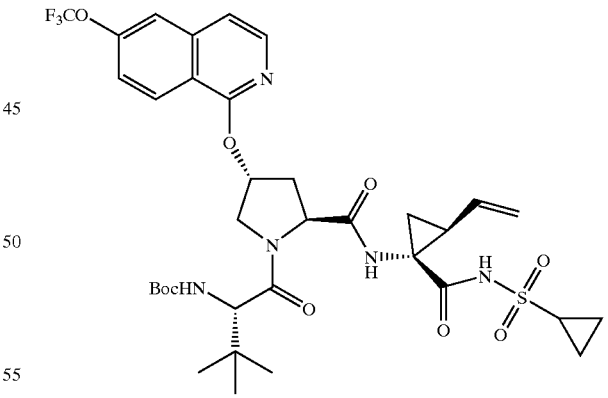

Compound 282

Compound 2 was prepared by following Scheme 2 of Example 269 except that 3-chloro-3-phenyl-acrylic acid was used in place of 2-trifluormethoxycinnamic acid in step 1.

Step 1:

Modifications: 20 g 3-chloro-3-phenyl-acrylic acid used, 2 g product obtained (8% yield).

Product:

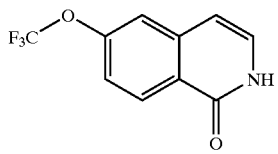

Data: MS: (M+H)⁺ 230.

Step 2:

Modifications: 2 g 6-trifluoromethoxy-2H-isoquinolin-1-one used, 0.7 product obtained (33% yield).

Product:

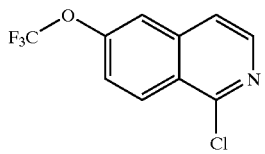

Data: ¹H NMR (400 MHz, CDCl₃) δ ppm 7.51 (d, J=9.29 Hz, 1 H), 7.59 (d, J=5.62 Hz, 1 H), 7.64 (s, 1 H), 8.31 (d, J=5.62 Hz, 1 H), 8.40 (d, J=9.05 Hz, 1 H); MS: (M+H)⁺ 248.

Step 3:

Modifications: 50 mg 1-chloro-6-trifluoromethoxy-isoquinoline and 113 mg {1-[2-(1-cyclopropanesulfonylaminocarbonyl-2-vinyl-cyclopropylcarbamoyl)-4-hydroxy-pyrrolidine-1-carbonyl]-2,2-dimethyl-propyl}-carbamic acid tert-butyl ester used, 42 mg product obtained (27% yield).

Product:

Compound 282

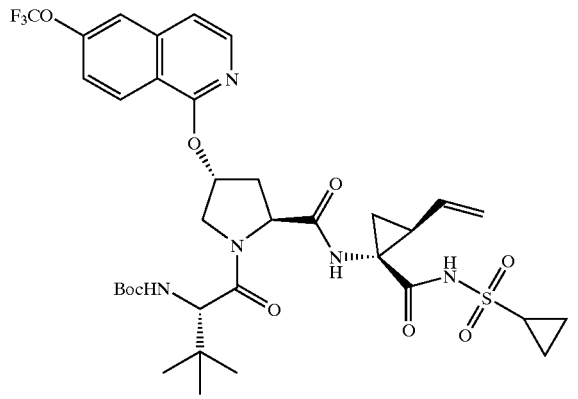

Data: ¹H NMR (400 MHz, CD₃OD) δ ppm 1.05 (m, 12 H), 1.24 (m, 10 H), 1.44 (dd, J=9.17, 5.50 Hz, 1 H), 1.88 (dd, J=8.07, 5.62 Hz, 1 H), 2.28 (m, 2 H), 2.63 (dd, J=13.45, 7.09 Hz, 1 H), 2.94 (m, 1 H), 4.06 (dd, J=11.25, 2.45 Hz, 1 H), 4.21 (s, 1 H), 4.53 (m, 2 H), 5.13 (d, J=10.52 Hz, 1 H), 5.30 (d, J=17.12 Hz, 1 H), 5.75 (m, 1 H), 5.89 (s, 1 H), 7.39 (m, 2 H), 7.72 (s, 1 H), 8.05 (d, J=5.87 Hz, 1 H), 8.31 (d, J=9.05 Hz, 1 H), 9.18 (s, 1 H); MS: (M+H)⁺ 768.

Example 283

Preparation of Compound 283

Compound 283

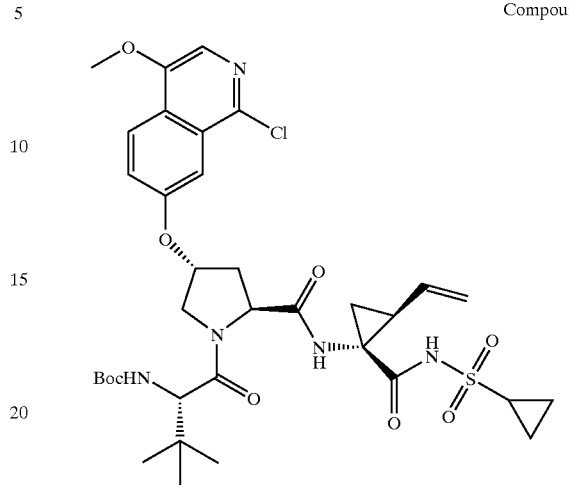

Compound 283 was prepared by following Scheme 2 of Example 269 except that 3-(4-fluoro-phenyl)-3-methoxy-acrylic acid was used in place of 2-trifluormethoxycinnamic acid in step 1.

Step 1:

Modifications: 3.82 g 3-(4-Fluoro-phenyl)-3-methoxy-acrylic acid used, 198 mg product obtained (5% yield).

Product:

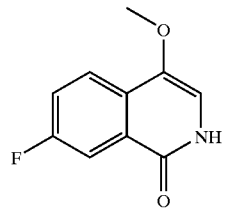

Data: MS: (M+H)⁺ 194.

Step 2:

Modifications: 193 mg 7-fluoro-4-methoxy-2H-isoquinolin-1-one used, 199 mg product obtained (94% yield).

Product:

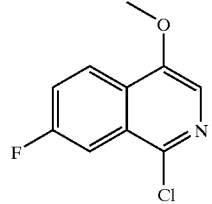

Data: ¹H NMR (400 MHz, CDCl₃) δ ppm 4.05 (s, 3 H), 7.49 (m, 1 H), 7.78 (s, 1 H), 7.86 (dd, J=9.66, 2.57 Hz, 1 H), 8.23 (dd, J=9.29, 5.38 Hz, 1 H); MS: (M+H)⁺ 212.

Step 3:

Modifications: 42 mg 1-chloro-7-fluoro-4-methoxy-isoquinoline and 112 mg {1-[2-(1-cyclopropanesulfonylaminocarbonyl-2-vinyl-cyclopropylcarbamoyl)-4-hydroxy-pyrrolidine-1-carbonyl]-

2,2-dimethyl-propyl}-carbamic acid tert-butyl ester used, 40 mg product obtained (14% yield).

Product:

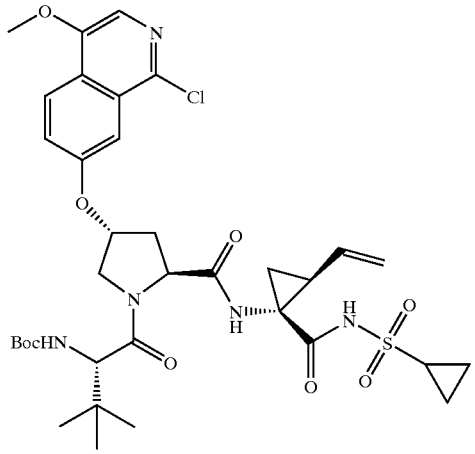

Compound 283

Data: $^1$H NMR (400 MHz, CD$_3$OD) δ ppm 1.06 (m, 12 H), 1.24 (m, 10 H), 1.42 (m, 1 H), 1.87 (dd, J=7.95, 5.50 Hz, 1 H), 2.23 (m, 2 H), 2.55 (dd, J=13.08, 6.48 Hz, 1 H), 2.93 (m, 1 H), 4.06 (s, 3 H), 4.09 (m, 1 H), 4.23 (s, 1 H), 4.30 (d, J=11.49 Hz, 1 H), 4.46 (m, 1 H), 5.12 (d, J=10.27 Hz, 1 H), 5.29 (d, J=17.36 Hz, 1 H), 5.40 (s, 1 H), 5.76 (m, 1 H), 7.46 (d, J=9.05 Hz, 1 H), 7.56 (d, J=2.20 Hz, 1 H), 7.75 (s, 1 H), 8.18 (d, J=9.05 Hz, 1 H); MS: (M+H)$^+$ 749.

Example 284

Preparation of Compound 284

Compound 284

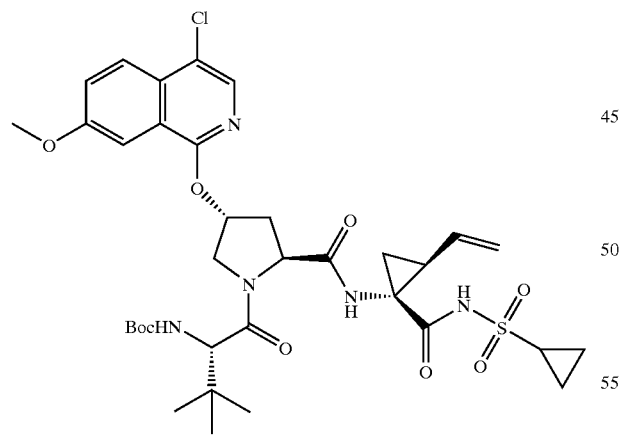

Compound 284 was prepared by following Scheme 2 of Example 269 except step 1.

Step 1:

Modifications: A mixture of 7-methoxy-2H-isoquinolin-1-one (876 mg) and NCS (665 mg) in MeCN (10 mL) was refluxed for 3 h. Filtration gave 500 mg (47%) of the desired product as a solid.

Product:

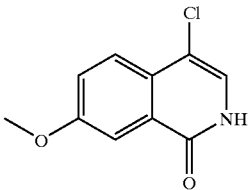

Data: $^1$H NMR (400 MHz, CD$_3$OD) δ ppm 4.00 (s, 3 H), 7.58 (m, 2 H), 8.14 (d, J=10.03 Hz, 1 H), 8.17 (s, 1 H).

Step 2:

Modifications: 418 mg 4-chloro-7-methoxy-2H-isoquinolin-1-oneused, 410 mg product obtained (90% yield).

Product:

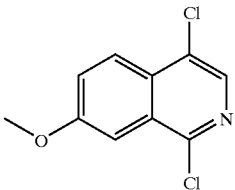

Data: $^1$H NMR (400 Hz, CDCl$_3$) δ ppm 4.00 (s, 3 H), 7.49 (dd, J=9.16, 2.44 Hz, 1 H), 7.55 (d, J=2.44 Hz, 1 H), 8.12 (d, J=9.16 Hz, 1 H), 8.21 (s, 1 H); MS: (M+H)$^+$ 229.

Step 3:

Modifications: 42 mg 1,4-dichloro-7-methoxy-isoquinoline and 117 mg {1-[2-(1-cyclopropanesulfonylaminocarbonyl-2-vinyl-cyclopropylcarbamoyl)-4-hydroxy-pyrrolidine-1-carbonyl]-2,2-dimethyl-propyl}-carbamic acid tert-butyl ester used, 50 mg product obtained (33% yield).

Product:

Compound 284

Data: $^1$H NMR (400 Hz, CD$_3$OD) δ ppm 1.05 (m, 20 H), 1.24 (m, 2 H), 1.44 (m, 1 H), 1.89 (dd, J=8.19, 5.50 Hz, 1 H), 2.28 (m, 2 H), 2.62 (dd, J=13.69, 6.85 Hz, 1 H), δ 2.94 (m, 1 H), 3.92 (s, 3 H), 4.07 (dd, J=11.98, 3.42 Hz, 1 H), 4.19 (m, 1 H), 4.44 (d, J=11.74 Hz, 1 H), 4.58 (dd, J=10.27, 7.09 Hz, 1 H), 5.12 (m, 1 H), 5.31 (d, J=17.12 Hz, 1 H), 5.78 (m, 2 H), 7.49 (m, 2 H), 7.91 (s, 1 H), 8.02 (m, 1 H); MS: (M+H)$^+$ 749.

Example 285

Preparation of Compound 285

Compound 285

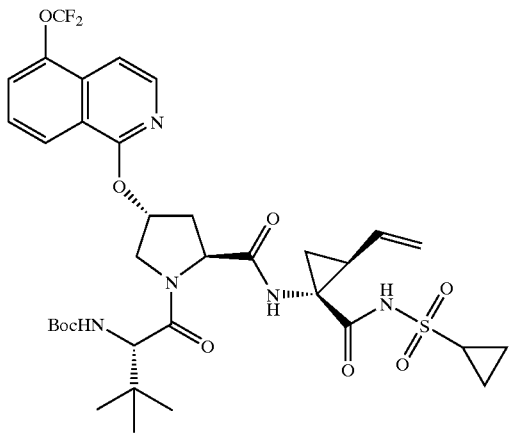

Compound 285 was prepared by following Scheme 2 of Example 269 except that was used in place of 2-difluormethoxycinnamic acid in step 1.

Step 1 and step 2:
See compound 256

Step 3:
Modifications: 46 mg 1-chloro-5-difluoromethoxy-isoquinoline and 111 mg {1-[2-(1-yclopropanesulfonylaminocarbonyl-2-vinyl-cyclopropylcarbamoyl)-4-hydroxy-pyrrolidine-1-carbonyl]-2,2-dimethyl-propyl}-carbamic acid tert-butyl ester used, 40 mg product obtained (27% yield).

Product:

Compound 285

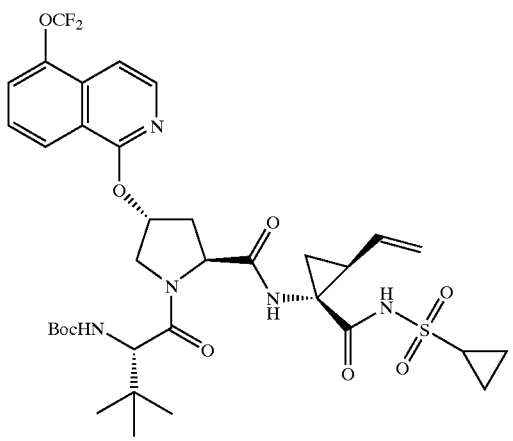

Data: $^1$H NMR (400 MHz, CD$_3$OD) δ ppm 1.06 (m, 12 H), 1.25 (m, 10 H), 1.44 (m, 1 H, 1.89 (m, 1 H), 2.22 (m, 2 H), 2.62 (m, 1 H), 2.94 (m, 1 H), 4.08 (m, 1 H), 4.23 (d, J=9.54 Hz, 1 H), 4.52 (m, 2 H), 5.12 (d, J=10.76 Hz, 1 H), 5.29 (d, J=17.61 Hz, 1 H), 5.75 (m, J=10.03 Hz, 1 H), 5.88 (s, 1 H), 6.60 (s, 1 H), 7.02 (t, J=73.48 Hz, 1 H), 7.52 (m, 3 H), 8.07 (m, J=5.75, 5.75 Hz, 2 H); MS: (M+Na)$^+$ 772.

Example 286

Preparation of Compound 286

Compound 286

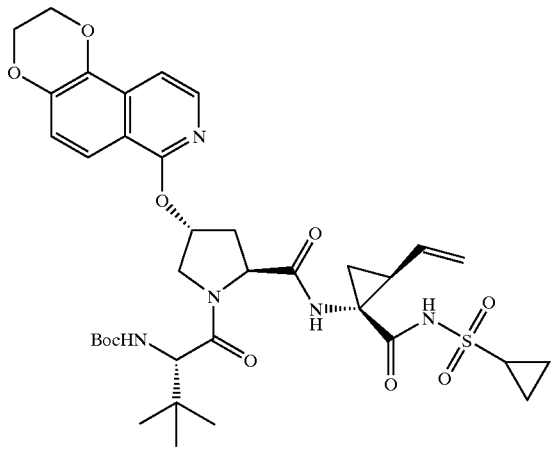

Compound 286 was prepared by following Scheme 2 of Example 269 except that 3-(2,3-dihydro-benzo[1,4]dioxin-5-yl)-acrylic acid was used in place of 2-trifluormethoxycinnamic acid in step 1.

Step 1:
Modifications: 4.12 g 3-(2,3-dihydro-benzo[1,4]dioxin-5-yl)-acrylic acid used, 2.2 g product obtained (53% yield).

Product:

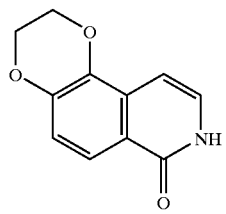

Data: $^1$H NMR (400 MHz, CD$_3$OD) δ ppm 4.37 (m, 4 H), 6.83 (d, J=7.09 Hz, 1 H), 7.02 (d, J=8.80 Hz, 1 H), 7.12 (d, J=7.34 Hz, 1 H), 7.79 (d, J=8.80 Hz, 1 H); MS: (M+H)$^+$ 204.

Step 2:
Modifications: 2.05 g 2,3-dihydro-7H-1,4-dioxa-7-aza-phenanthren-8-one used, 1.5 g product obtained (68% yield).

Product:

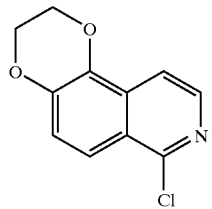

Data: $^1$H NMR (400 Hz, CDCl$_3$) δ ppm 4.42 (m, 4 H), 7.24 (d, J=9.05 Hz, 1 H), 7.77 (d, J=5.87 Hz, 1 H), 7.84 (d, J=9.05 Hz, 1 H), 8.18 (d, J=5.87 Hz, 1 H); MS: (M+H)$^+$ 222.

Step 3:
Modifications: 88 mg 8-Chloro-2,3-dihydro-1,4-dioxa-7-aza-phenanthrene and 223 mg {1-[2-(1-Cyclopropanesulfonylaminocarbonyl-2-vinylcyclopropylcarbamoyl)-4-hydroxy-pyrrolidine-1-carbonyl]-2,2-dimethyl-propyl}-carbamic acid tert-butyl ester used, 140 mg product obtained (47% yield).

Product:

Compound 286

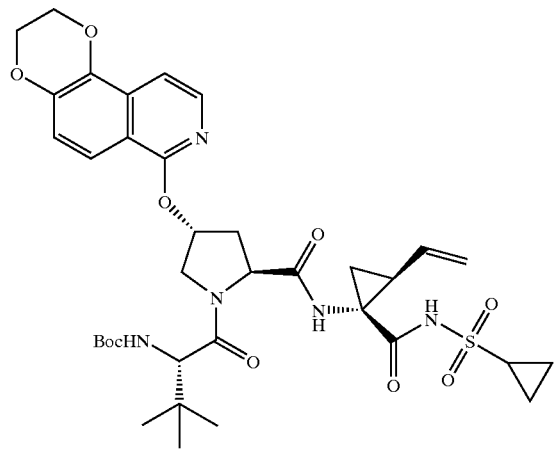

Data: ¹H NMR (400 Hz, CD₃OD) δ ppm 1.06 (m, 12 H), 1.24 (m, 10 H), 1.43 (dd, J=9.05, 5.14 Hz, 1 H), 1.87 (m, 1 H), 2.22 (d, J=9.29 Hz, 2 H), 2.60 (dd, J=13.45, 7.09 Hz, 1 H), 2.94 (m, 1 H), 4.05 (dd, J=11.62, 2.81 Hz, 1 H), 4.24 (s, 1 H), 4.44 (m, 6 H), 5.13 (d, J=17.36 Hz, 1 H), 5.29 (d, J=17.36 Hz, 1 H), 5.75 (m, 2 H), 7.04 (d, J=9.29 Hz, 1 H), 7.44 (d, J=5.87 Hz, 1 H), 7.69 (d, J=9.05 Hz, 1 H), 7.88 (d, J=6.11 Hz, 1 H); MS: (M+H)⁺ 742.

Example 287

Preparation of Compound 287

Compound 287

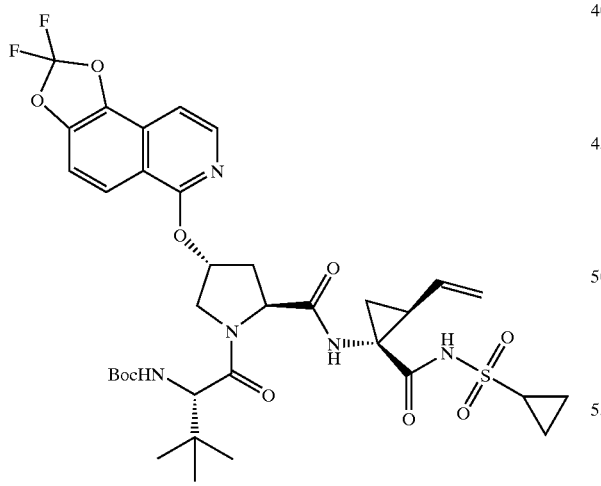

Compound 287 was prepared by following Scheme 2 of Example 269 except that 3-(2,2-difluoro-benzo[1,3]dioxol-4-yl)-acrylic acid was used in place of 2-trifluormethoxycinnamic acid in step 1.

Step 1:

Modifications: 4.56 g 3-(2,2-difluoro-benzo[1,3]dioxol-4-yl)-acrylic acid used, 2.2 g product obtained (55% yield).

Product:

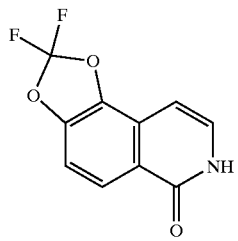

Data: ¹H NMR (400 MHz, CD₃DOD) δ ppm 6.63 (d, J=7.09 Hz, 1 H), 7.29 (d, J=7.34 Hz, 1 H), 7.40 (d, J=8.80 Hz, 1 H), 8.19 (d, J=8.80 Hz, 1 H); MS: (M+H)⁺ 226.

Step 2:

Modifications: 2.2 g 2,2-difluoro-7H-1,3-dioxa-7-aza-cyclopenta[a]naphthalen-6-one used, 2.1 g product obtained (87% yield).

Product:

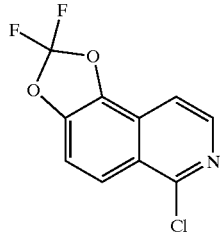

Data: ¹H NMR (500 Hz, CDCl₃) ppm 7.51 (d, J=9.29 Hz, 1 H), 7.65 (d, J=5.87 Hz, 1 H), 8.22 (d, J=9.05 Hz, 1 H), 8.32 (d, J=5.87 Hz, 1 H); MS: (M+H)⁺ 244.

Step 3:

Modifications: 48 mg 6-chloro-2,2-difluoro-1,3-dioxa-7-aza-cyclopenta[a]naphthalene and 113 mg {1-[2-(1-cyclopropanesulfonylaminocarbonyl-2-vinyl-cyclopropylcarbamoyl)-4-hydroxy-pyrrolidine-1-carbonyl]-2,2-dimethyl-propyl}-carbamic acid tert-butyl ester used, 40 mg product obtained (27% yield).

Product:

Compound 287

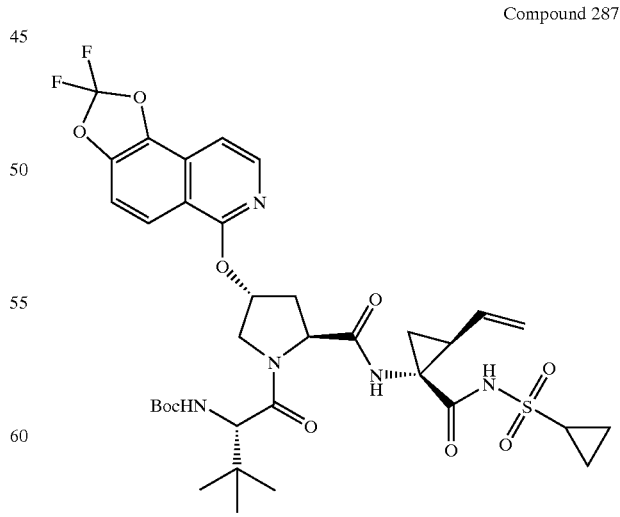

Data: ¹H NMR (400 Hz, CD₃OD) δ ppm 1.02 (s, 12 H), 1.24 (m, 10 H), 1.43 (m, 1 H), 1.88 (dd, J=8.07, 5.38 Hz, 1 H), 2.32 (d, J=3.67 Hz, 2 H), 2.64 (d, J=13.45 Hz, 1 H), 2.95

(m, 1 H), 4.05 (d, J=11.49 Hz, 1 H), 4.19 (d, J=9.29 Hz, 1 H), 4.53 (m, 2 H), 5.12 (d, J=9.78 Hz, 1 H), 5.32 (s, 1 H), 5.77 (m, 2 H), 7.34 (d, J=5.87 Hz, 1 H), 7.46 (d, J=9.05 Hz, 1 H), 8.11 (m, 2 H); MS: (M+H)$^+$ 764.

Example 288

Preparation of Compound 288

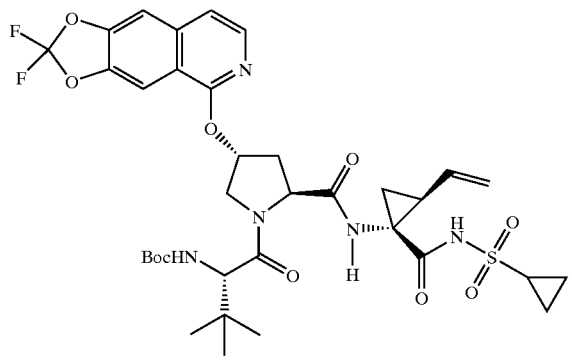

Compound 288

Compound 288 was prepared by following Scheme 2 of Example 269 except that 3-(2,2-difluoro-benzo[1,3]dioxol-5-yl)-acrylic acid was used in place of 2-trifluormethoxycinnamic acid in step 1.

Step 1:
Modifications: 1 g 3-(2,2-difluoro-benzo[1,3]dioxol-5-yl)-acrylic acid used, 0.55 g product obtained.
Product:

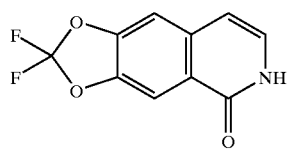

Data: $^1$H NMR (400 MHz, CD$_3$DOD) δ ppm 6.69 (d, J=7.09 Hz, 1 H), 7.19 (d, J=7.09 Hz, 1 H), 7.47 (s, 1 H) 7.98 (s, 1 H); MS: (M+H)$^+$ 226.

Step 2:
Modifications: 0.5 g 2,2-difluoro-6H-[1,3]dioxolo[4,5-g]isoquinolin-5-one used, 0.4 g product obtained.
Product:

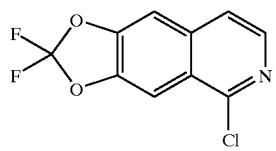

Data: $^1$H NMR (400 Hz, CDCl$_3$) δ 7.41 (s, 1 H), 7.57 (d, J=5.49 Hz, 1 H), 7.94 (s, 1 H), 8.27 (d, J=5.80 Hz, 1 H); MS (M+H)$^+$ 244.

Step 3:

Modifications: 48 mg 5-chloro-2,2-difluoro-[1,3]dioxolo[4,5-g]isoquinoline and 112 mg {1-[2-(1-Cyclopropanesulfonylaminocarbonyl-2-vinyl-cyclopropylcarbamoyl)-4-hydroxy-pyrrolidine-1-carbonyl]-2,2-dimethyl-propyl}-carbamic acid tert-butyl ester used, 30 mg product obtained.

Product:

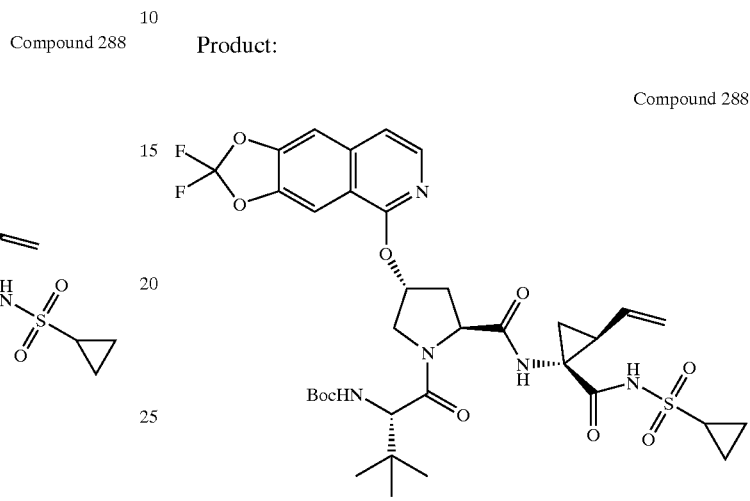

Compound 288

Data: $^1$H NMR (400 Hz, CD$_3$OD) δ ppm 1.06 (m, 12 H), 1.25 (m, 10 H), 1.42 (m, 1 H), 1.87 (dd, J=8.07, 5.62 Hz, 1 H), 2.26 (m, 2 H), 2.61 (dd, J=13.57, 6.97 Hz, 1 H), 2.93 (m, 1 H), 4.07 (dd, J=11.86, 2.81 Hz, 1 H), 4.22 (m, 1 H), 4.40 (d, J=11.98 Hz, 1 H), 4.52 (m, 1 H), 5.11 (d, J=10.52 Hz, 1 H), 5.29 (d, J=17.12 Hz, 1 H), 5.37 (s, 1 H), 5.74 (m, 1 H), 7.39 (s, 1 H), 7.56 (s, 1 H), 7.63 (d, J=5.62 Hz, 1 H), 7.99 (d, J=5.62 Hz, 1 H).

Example 289

Preparation of Compound 289

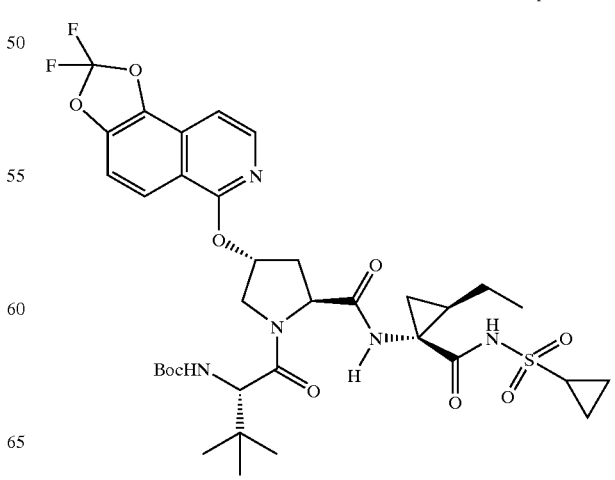

Compound 289

-continued
Scheme 3

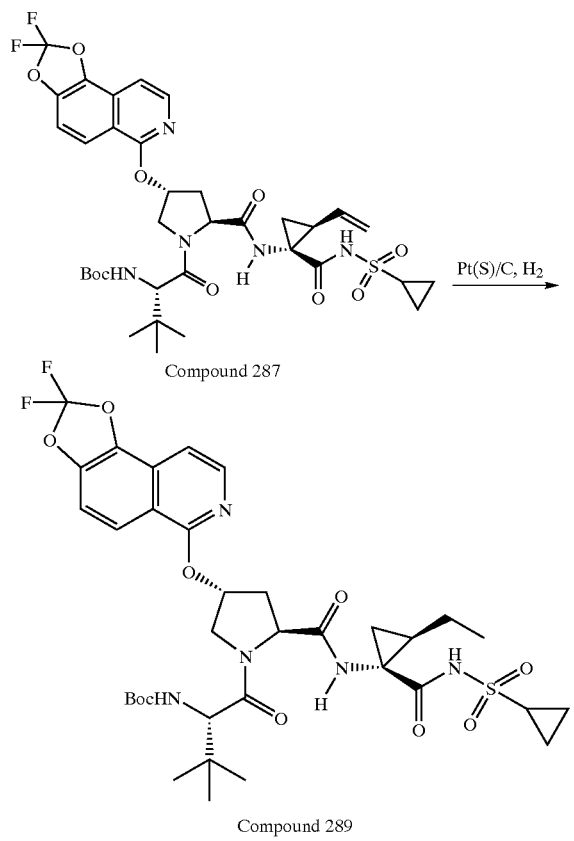

Compound 287

Compound 289

A suspension of compound 287 (15 mg) and Pt(S)/C (5%, 5 mg) in ethyl acetate (5 mL) was hydrogenated at 10.psi for 30 min. After filtration, concentration quantitatively gave 15 mg of compound 289 as a solid. $^1$H NMR (400 MHz, CD$_3$OD) δ ppm 1.09 (m, 26 H), 1.57 (m, 4 H), 2.30 (m, 1 H), 2.61 (m, J=13.82, 7.21 Hz, 1 H), 2.96 (m, 1 H), 4.05 (m, J=13.94 Hz, 1 H), 4.19 (d, J=9.54 Hz, 1 H), 4.53 (m, 2 H), 5.89 (s, 1 H), 7.34 (d, J=5.87 Hz, 1 H), 7.46 (d, J=9.05 Hz, 1 H), 8.09 (d, J=5.87 Hz, 1 H), 8.12 (d, J=8.80 Hz, 1 H); MS: (M+H)$^+$ 766.

Example 290

Preparation of Compound 290

Compound 290

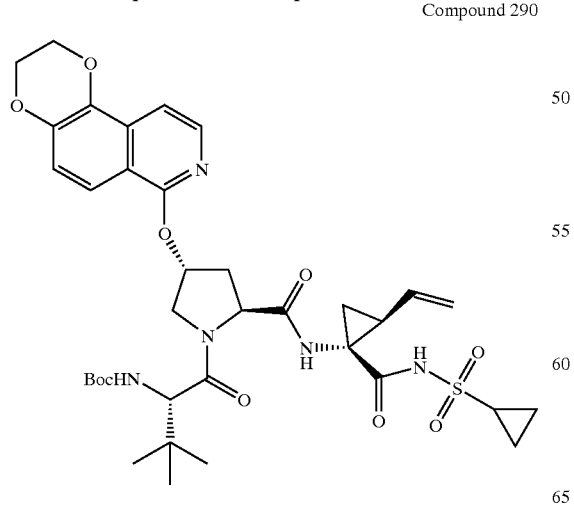

Compound 290 (15 mg, 100%) was prepared by following Scheme 3 of Example 289 by using 15 mg of compound 286. Data: $^1$H NMR (400 Hz, CD$_3$OD) δ ppm 1.02 (m, 14 H), 1.23 (m, 12 H), 1.58 (m, 4 H), 2.25 (m, 1 H), 2.58 (dd, J=13.82, 7.21 Hz, 1 H), 2.96 (m, 1 H), 4.05 (m, J=11.25, 2.93 Hz, 1 H), 4.25 (d, J=9.54 Hz, 1 H), 4.39 (m, 5 H), 4.52 (m, J=10.03, 7.34 Hz, 1 H), 5.81 (s, 1 H), 7.03 (d, J=9.05 Hz, 1 H), 7.43 (d, J=6.11 Hz, 1 H), 7.69 (d, J=9.05 Hz, 1 H), 7.88 (d, J=6.11 Hz, 1 H); MS: (M+H)$^+$ 744.

Example 291

Preparation of Compound 291

Compound 291

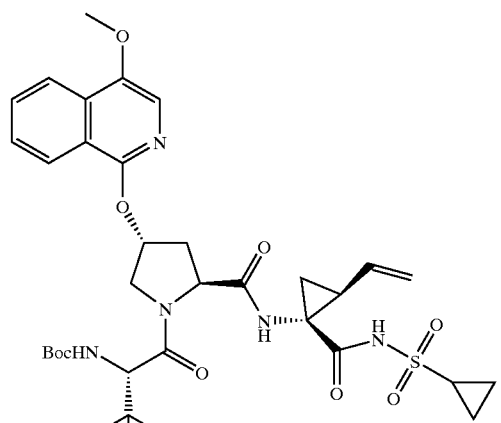

Compound 291 (28 mg, 100%) was prepared by following Scheme 3 of Example 289 by using 28 mg of compound 251. Data: $^1$H NMR (400 MHz, CD$_3$OD) δ ppm 1.01 (m, 15 H), 1.26 (m, 11 H), 1.37 (m, 1 H), 1.58 (m, 3 H), 2.25 (m, 1 H), 2.58 (dd, J=13.6, 7.0 Hz, 1 H), 2.96 (m, 1 H), 3.99 (s, 3 H), 4.06 (m, 1 H), 4.25 (m, 1 H), 4.44 (m, 1 H), 4.53 (dd, J=10.3, 7.6 Hz, 1 H), 5.78 (s, 1 H), 6.64 (d, J=9.8 Hz, 1 H), 7.55 (m, 2 H), 7.71 (t, J=7.3 Hz, 1 H), 8.09 (d, J=8.6 Hz, 1 H), 8.14 (d, J=8.1 Hz, 1 H); MS: (M+Na)$^+$ 738.

Example 292

Preparation of Compound 292

Compound 292

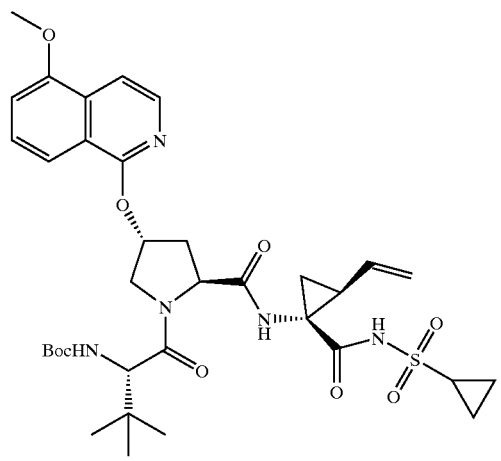

Compound 292 (16 mg, 84%) was prepared by following Scheme 3 of Example 289 by using 19 mg of compound 253.

¹H NMR (400 MHz, CD₃OD) δ ppm 0.90 (m, 15 H), 1.15 (m, 12 H), 1.48 (m, 3 H), 2.18 (m, 1 H), 2.51 (dd, J=13.7, 6.9 Hz, 1 H), 2.88 (m, 1 H), 3.90 (s, 3 H), 3.98 (dd, J=11.6, 3.1 Hz, 1 H), 4.18 (d, J=9.5 Hz, 1 H), 4.36 (d, J=11.0 Hz, 1 H), 4.45 (dd, J=10.2, 7.2 Hz, 1 H), 5.76 (s, 1 H), 6.56 (d, J=9.3 Hz, 1 H), 7.05 (d, J=7.6 Hz, 1 H), 7.34 (t, J=8.1 Hz, 1 H), 7.51 (d, J=5.9 Hz, 1 H), 7.65 (d, J=8.3 Hz, 1 H), 7.86 (d, J=6.1 Hz, 1 H); MS: (M+Na)⁺ 738.

Example 293

Preparation of Compound 293

Compound 293

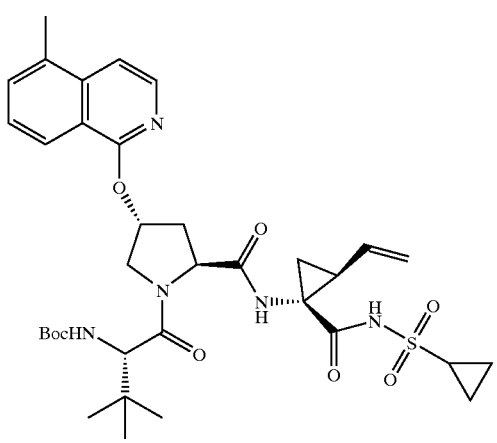

Compound 293 (7 mg, 35%) was prepared by following Scheme 3 of Example 289 by using 20 mg of compound 252. ¹H NMR (400 MHz, CD₃OD) δ ppm 1.04 (m, 15 H), 1.27 (m, 12 H), 1.58 (m, 3 H), 2.27 (m, 1 H), 2.60 (m, 4 H), 2.96 (m, 1 H), 4.07 (dd, J=11.7, 2.9 Hz, 1 H), 4.25 (s, 1 H), 4.46 (d, J=12.0 Hz, 1 H), 4.54 (dd, J=10.0, 7.6 Hz, 1 H), 5.85 (s, 1 H), 7.39 (t, J=7.7 Hz, 1 H), 7.44 (d, J=5.9 Hz, 1 H), 7.53 (d, J=6.9 Hz, 1 H), 8.00 (d, J=6.1 Hz, 1 H), 8.06 (d, J=8.6 Hz, 1 H); MS: (M+H)⁺ 700.

Example 294

Preparation of Compound 294

Compound 294

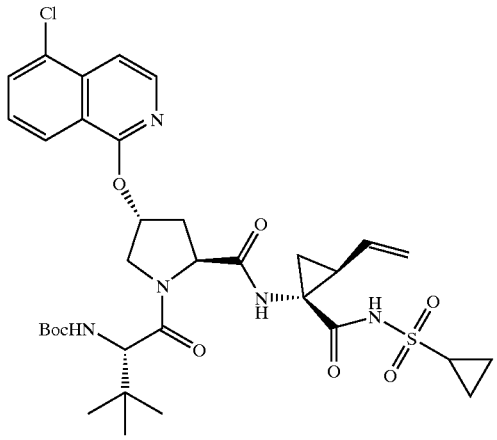

Compound 294 (14 mg, 78%) was prepared by following Scheme 3 of Example 289 by using 18 mg of compound 254. ¹H NMR (400 MHz, CD₃OD) δ ppm 0.94 (m, 15 H), 1.13 (m, 10 H), 1.20 (m, 2 H), 1.50 (m, 3 H), 2.21 (m, 1 H), 2.53 (dd, J=13.8, 7.0 Hz, 1 H), 2.88 (m, 1 H), 3.99 (dd, J=11.4, 2.6 Hz, 1 H), 4.14 (d, J=9.3 Hz, 1 H), 4.45 (m, 2 H), 5.79 (s, 1 H), 6.53 (d, J=9.1 Hz, 1 H), 7.40 (t, J=8.0 Hz, 1 H), 7.54 (d, J=5.9 Hz, 1 H), 7.73 (d, J=7.3 Hz, 1 H), 8.02 (d, J=6.1 Hz, 1 H), 8.10 (d, J=8.6 Hz, 1 H); MS: (M+Na)⁺ 742.

Example 295

Preparation of Compound 295

Compound 294

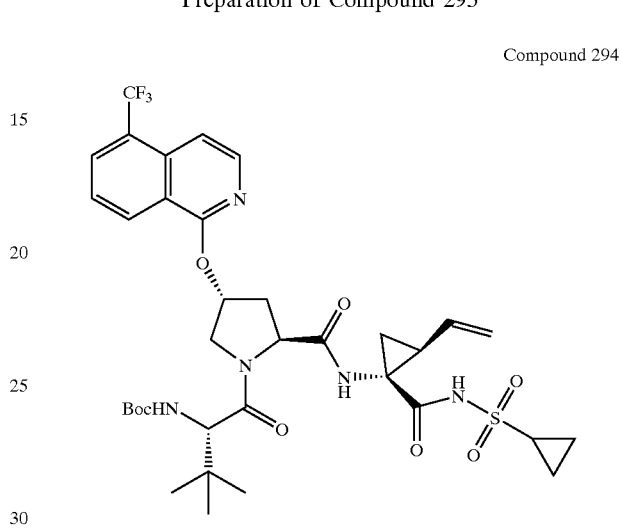

Compound 295 (30 mg, 100%) was prepared by following Scheme 3 of Example 289 by using 30 mg of compound 270. MS: (M+Na)⁺ 776.

Example 296

Preparation of Compound 296

Compound 296

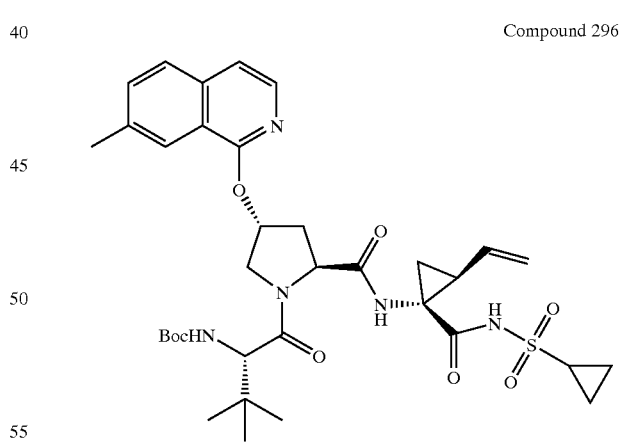

Compound 296 (6.3 mg, 33%) was prepared by following Scheme 3 of Example 289 by using 20 mg of compound 259. ¹H NMR (400 MHz, CD₃OD) δ ppm 1.04 (m, 15 H), 1.24 (m, 12 H), 1.59 (m, 3 H), 2.29 (m, 1 H), 2.50 (s, 3 H), 2.60 (dd, J=13.69, 6.85 Hz, 1 H), 2.97 (m, 1 H), 4.09 (dd, J=11.74, 2.93 Hz, 1 H) 4.22 (s, 1 H) 4.43 (d, J=11.74 Hz, 1 H), 4.59 (dd, J=10.27, 6.85 Hz, 1 H), 5.87 (s, 1 H), 7.30 (d, J=5.87 Hz, 1 H), 7.57 (dd, J=8.31, 1.47 Hz, 1 H), 7.72 (d, J=8.31 Hz, 1 H), 7.89 (d, J=5.87 Hz, 1 H), 7.94 (s, 1 H); MS: (M+H)⁺ 700.

Example 297

Preparation of Compound 297

Compound 297

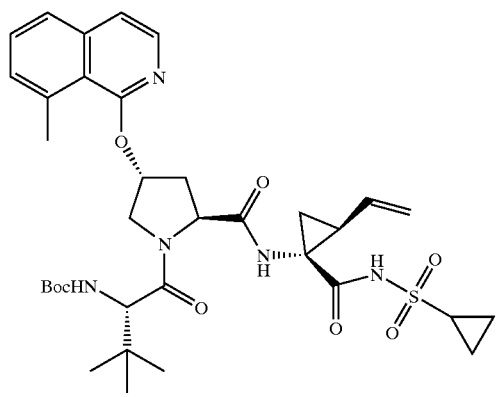

Compound 297 (40 mg, 100%) was prepared by following Scheme 3 of Example 289 by using 40 mg of compound 263. $^1$H NMR (400 MHz, CD$_3$OD) δ ppm 0.98 (m, 13 H) 1.07 (m, 2 H) 1.27 (m, 12 H) 1.57 (m, 3 H) 2.27 (m, 1 H) 2.58 (dd, J=14.7, 7.1 Hz, 1 H) 2.77 (s, 3 H) 2.96 (m, 1 H) 4.04 (m, 1 H) 4.27 (m, 1 H) 4.42 (d, J=11.5 Hz, 1 H) 4.55 (dd, J=10.6, 7.0 Hz, 1 H) 5.94 (s, 1 H) 6.65 (d, J=9.5 Hz, 1 H) 7.28 (m, 2 H) 7.50 (t, J=7.6 Hz, 1 H) 7.60 (d, J=7.6 Hz, 1 H) 7.89 (d, J=5.6 Hz, 1 H); MS: (M+Na)$^+$ 722.

Example 298

Preparation of Compound 298

Compound 298

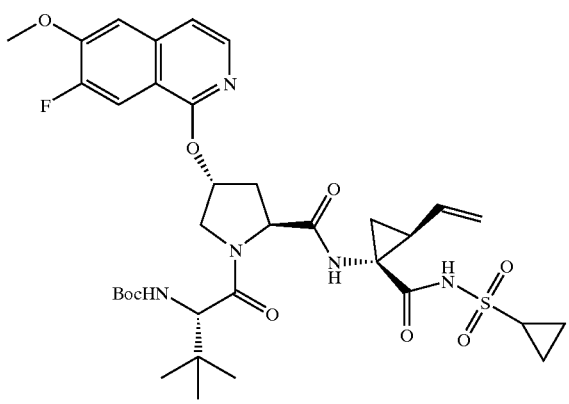

Compound 298 (29 mg, 100%) was prepared by following Scheme 3 of Example 289 by using 29 mg of compound 261. $^1$H NMR (400 MHz, CD$_3$OD) δ ppm 0.99 (m, 15 H), 1.25 (m, 12 H), 1.60 (m, 3 H), 2.28 (m, 1 H), 2.58 (m, 1 H), 2.96 (m, 1 H), 4.02 (m, 4 H), 4.22 (dd, J=8.8, 4.4 Hz, 1 H), 4.48 (m, 2 H), 5.83 (s, 1 H), 7.27 (d, J=5.6 Hz, 1 H), 7.36 (d, J=8.8 Hz, 1 H), 7.75 (d, J=11.3 Hz, 1 H), 7.90 (d, J=5.9 Hz, 1 H); MS: (M+Na)$^+$ 756.

Example 299

Preparation of Compound 299

Compound 299

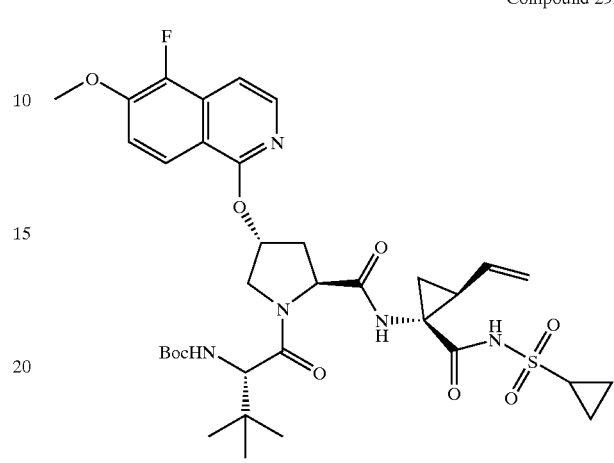

Compound 299 (34 mg, 97%) was prepared by following Scheme 3 of Example 289 by using 35 mg of compound 274. $^1$H NMR (400 MHz, CD$_3$OD) δ ppm 1.01 (m, 16 H), 1.28 (m, 12 H), 1.58 (m, 2 H), 2.27 (s, 1 H), 2.59 (dd, J=13.82, 6.97 Hz, 1 H), 2.96 (m, 1 H), 4.02 (s, 3 H), 4.07 (m, 1 H), 4.21 (m, 1 H), 4.44 (m, J=11.98 Hz, 1 H), 4.55 (d, J=10.27 Hz, 1 H), 5.85 (s, 1 H), 7.39 (m, 2 H), 7.95 (d, J=6.11 Hz, 1 H), 8.00 (d, J=9.29 Hz, 1 H); MS: (M+Na)$^+$ 756.

Example 300

Preparation of Compound 300

Compound 300

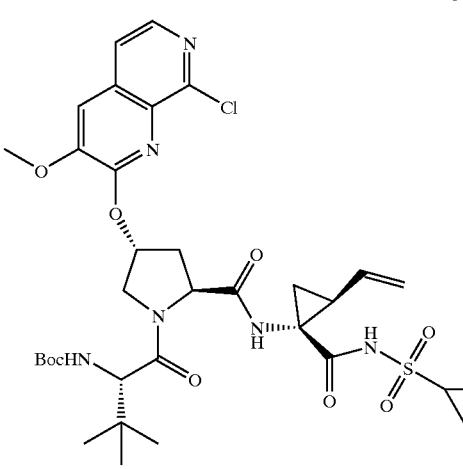

Compound 300 (30 mg, 100%) was prepared by following Scheme 3 of Example 289 by using 30 mg of compound 262. $^1$H NMR (400 MHz, CD$_3$OD) δ ppm 1.27 (m, 30 H), 2.25 (s, 1 H), 2.54 (s, 1 H), 2.96 (m, 1 H), 3.97 (s, 3 H), 4.20 (m, 3 H), 4.51 (m, J=10.52, 6.85 Hz, 1 H), 5.37 (s, 1 H), 7.38 (s, 1 H), 7.62 (s, 1 H), 7.65 (d, J=5.38 Hz, 1 H) 8.06 (d, J=5.62 Hz, 1 H); MS: (M+Na)$^+$ 773.
Section G:
The LC/MS method used in section G is the following:
4.6×50 mm Xterra @3 min gradient and 4 mL/min flow
Scheme 1: (General Scheme)
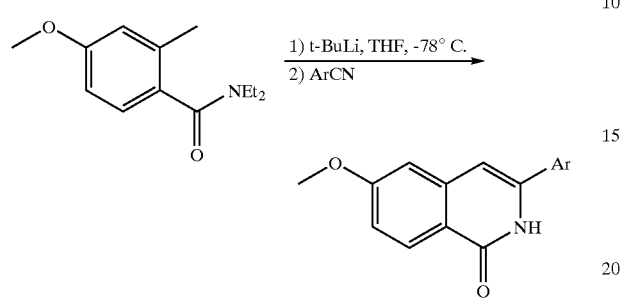
Scheme 2: (General Scheme)
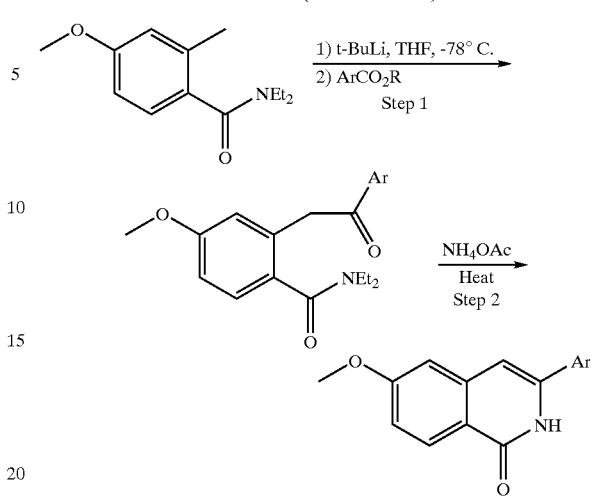
Scheme 3: (General Scheme)
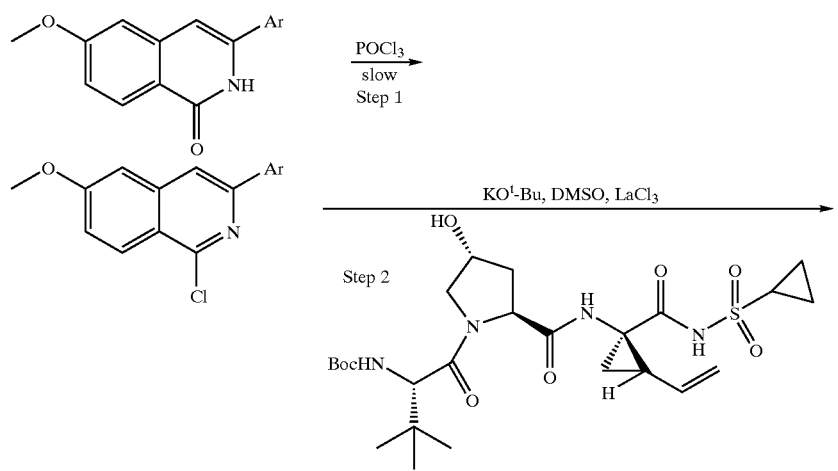
For prep. see section D, Example 184
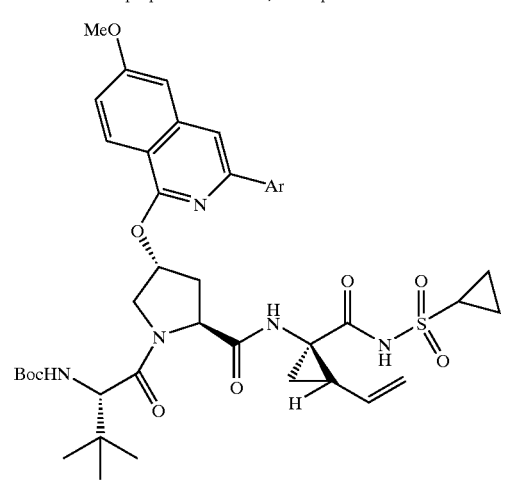

Scheme 4: (General Scheme)

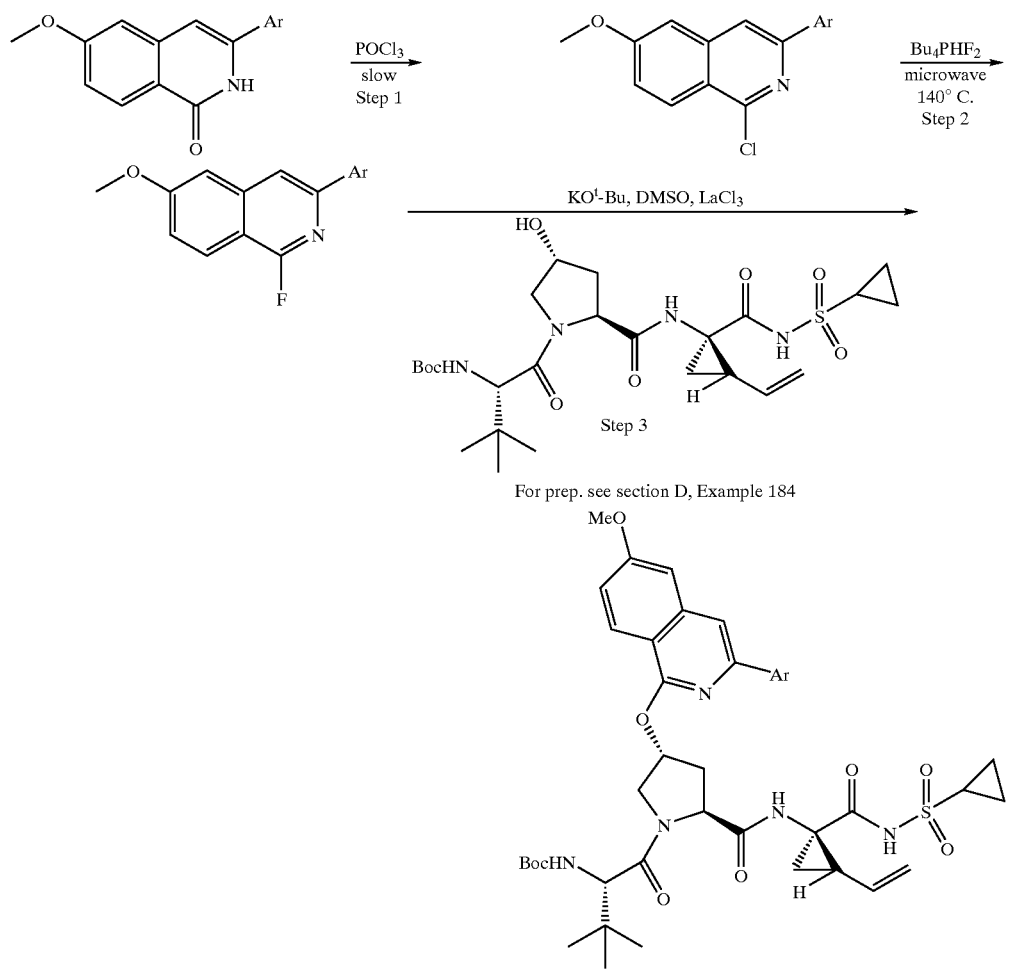

For prep. see section D, Example 184

Example 320

Preparation of Compound 320

Compound 320

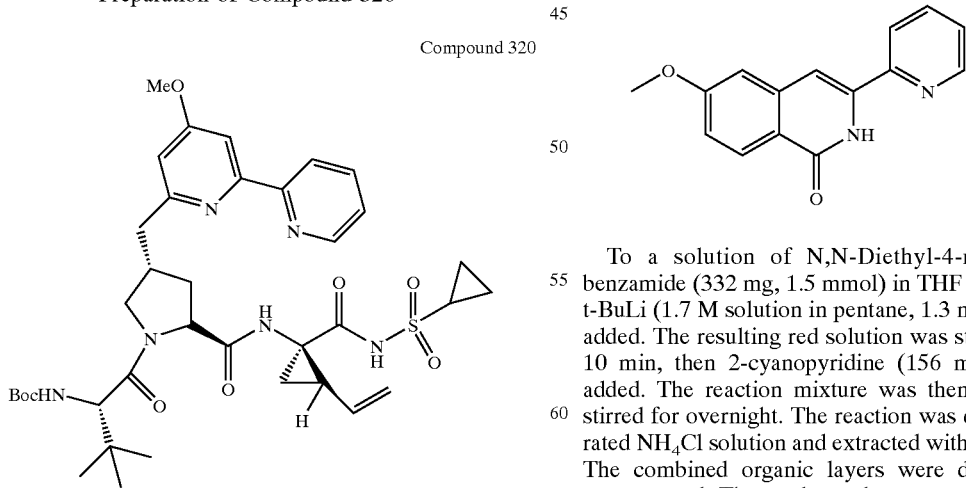

Compound 320 was prepared by following Scheme 1 and Scheme 3 of above.

Step 1 (Scheme 1):

To a solution of N,N-Diethyl-4-methoxy-2-methyl-benzamide (332 mg, 1.5 mmol) in THF (15 mL) at −78° C., t-BuLi (1.7 M solution in pentane, 1.3 mL, 2.25 mmol) was added. The resulting red solution was stirred at −78° C. for 10 min, then 2-cyanopyridine (156 mg, 1.5 mmol) was added. The reaction mixture was then warmed to rt and stirred for overnight. The reaction was quenched with saturated $NH_4Cl$ solution and extracted with ethyl acetate twice. The combined organic layers were dried ($MgSO_4$) and concentrated. The crude product was purified by Prep. HPLC to give yellowish solid as TFA salt. (85 mg, 15% yield)

$^1$H NMR (400 MHz, $CD_3OD$) δ 3.91 (m, 3 H), 7.09 (dd, J=9.05, 2.45 Hz, 1 H), 7.17 (d, J=2.45 Hz, 1 H), 7.37 (s, 1

H), 7.42 (m, 1 H), 7.92 (m, 1 H), 8.08 (d, J=8.07 Hz, 1 H), 8.18 (d, J=9.05 Hz, 1 H), 8.65 (d, J=4.89 Hz, 1 H).
LC-MS (retention time: 2.14 min.), MS m/z 253 (MH⁺).

Step 2 (Scheme 3, Step 1):

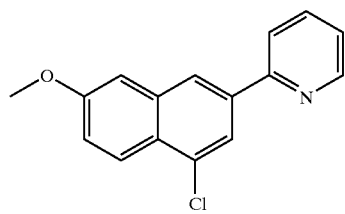

6-Methoxy-3-pyridin-2-yl-2H-isoquinolin-1-one TFA salt (85 mg, 0.232 mmol) was heated under reflux with POCl₃ (3.0 mL) for 2 days. Then POCl₃ was distilled off and the residue was quenched with ice. It was then neutralized with 10 N NaOH solution and the brown solid was collected as pure product. (62 mg, 99% yield)
LC-MS (retention time: 2.063 min.), MS m/z 271 (MH⁺).

Step 3 (Scheme 3, Step 2):

Compound 320

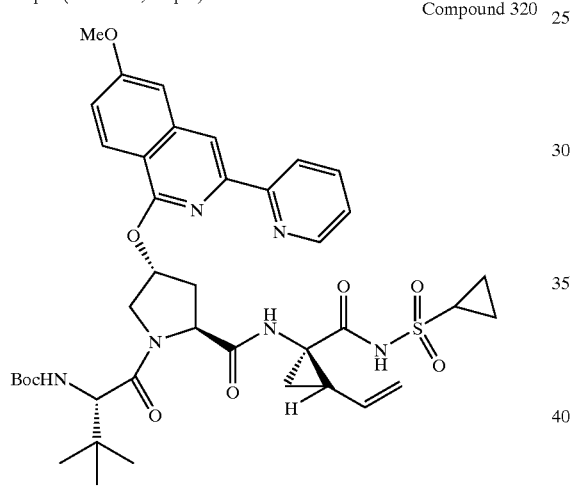

To a solution of {1-[2-(1-Cyclopropanesulfonylaminocarbonyl-2-vinyl-cyclopropylcarbamoyl)-4-hydroxy-pyrrolidine-1-carbonyl]-2,2-dimethyl-propyl}-carbamic acid tert-butyl ester (82 mg, 0.148 mmol) and LaCl₃ (36 mg, 0.148 mmol) in DMF (1.5 mL), potassium t-butoxide (1.0 M solution in TBF, 0.74 mL, 0.74 mmol) was added at −78° C. The reaction mixture was stirred for 1 hr, then 1-chloro-6-methoxy-3-pyridin-2-yl-isoquinoline (40 mg, 0.148 mmol) was added. It was warmed to rt and stirred for overnight. Then it was quenched with water and filtered. The filtrated was concentrated and the residue was purified by Prep. HPLC to give an off-white solid as product (Compound 320). (23 mg, 20% yield)
¹H NMR (400 MHz, CD₃OD) δ 0.87–1.08 (m, 11 H), 1.20–1.30 (m, 11 H), 1.43 (m, 1 H), 1.87 (m, 1 H), 2.22 (m, 1 H), 2.35 (m, 1 H), 2.69 (m, 1 H), 2.93 (m, 1 H), 3.94 (s, 3 H), 4.16 (m, 1 H), 4.27 (m, 1 H), 4.45 (m, 1 H), 4.56 (m, 1 H), 5.10 (d, J=11.3 Hz, 1 H), 5.27 (d, J=15.9 Hz, 1 H), 5.74 (m, 1 H), 6.07 (s, 1 H), 7.12 (d, J=7.33 Hz, 1 H), 7.31 (d, J=1.96 Hz, 1 H), 7.40 (m, 1 H), 7.94 (dd, J=7.8 Hz, 1.5 Hz, 1 H), 8.11 (d, J=9.29 Hz, 1 H), 8.22 (s, 1 H), 8.45 (d, J=8.07 Hz, 1 H), 8.62 (m, 1 H).
LC-MS (retention time: 2.393 min.), MS m/z 791 (MH⁺).

Example 321

Preparation of Compound 321

Scheme 5:

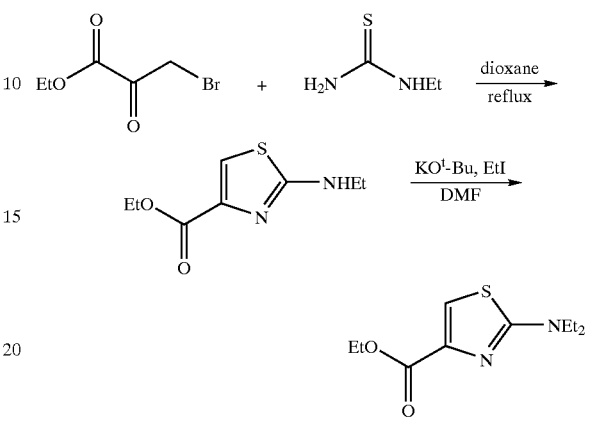

Condensation of ethyl bromopyruvate with ethyl thiourea in refluxing dioxane afforded the monoalkylamino thiazole as HBr salt in quantitative yield. Alkylation of 2-ethylamino-thiazole-4-carboxylic acid ethyl ester with EtI in DMF provided 2-diethylamino-thiazole-4-carboxylic acid ethyl ester.

LC/MS m/z 229 (MH)⁺

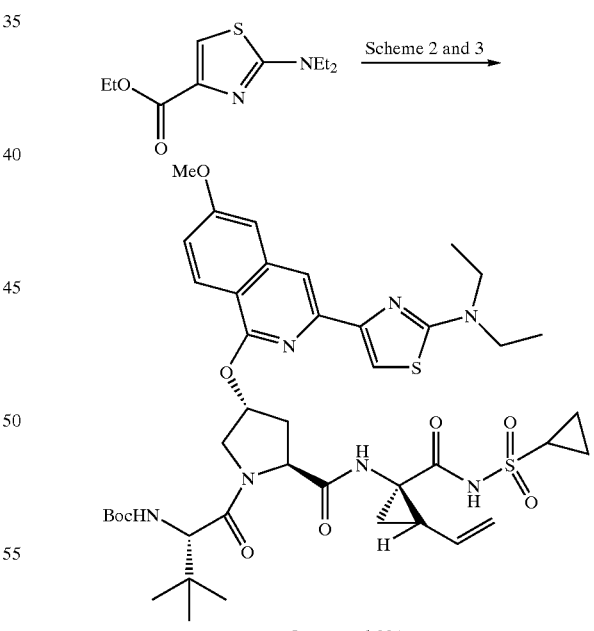

Compound 321

Compound 321 was prepared by following Scheme 2 and Scheme 3 above with that 2-diethylamino-thiazole-4-carboxylic acid ethyl ester was used in the step 1 of Scheme 2.

LC/MS (Retention time 2.76 min): m/z 868 (MH⁺).

Example 322

Preparation of Compound 322


Compound 322

Compound 322 was prepared by following Example 321, except that 2-dimethylamino-thiazole-4-carboxylic acid ethyl ester (Prepared according to Scheme 5, except that methyl thiourea and methyl iodide were used in the place of ethyl thiourea and ethyl iodide) was used in the place of 2-dimethylamino-thiazole-4-carboxylic acid ethyl ester in step 1 of Scheme 2.

LC/MS (Retention time 2.56 min): m/z 840 (MH$^+$)

Example 323

Preparation of Compound 323

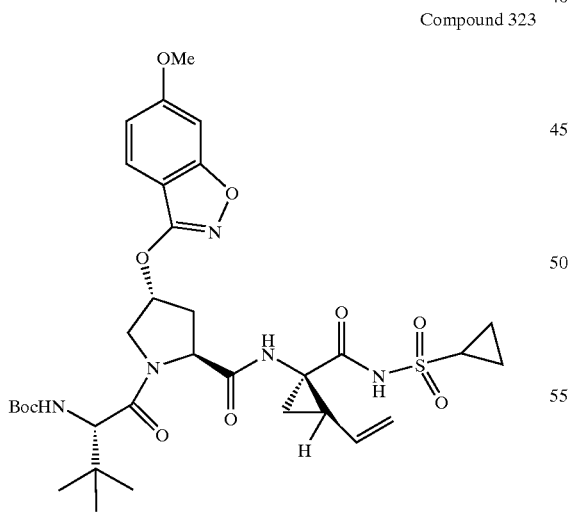

Compound 323

Compound 323 was prepared by following Step 3 of Example 324, except that 3-chloro-6-methoxy-benzo[d]isoxazole was used in the place of 1-chloro-6-methoxy-3-pyridin-2-yl-isoquinoline.

MS m/z 702 (M–H)$^-$

Example 324

Preparation of Compound 324

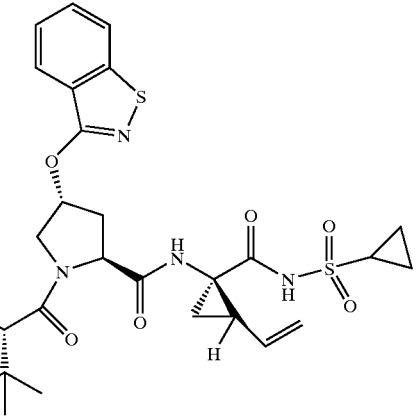

Compound 324

Compound 324 was prepared by following Step 3 of Example 324, except that 3-chloro-benzo[d]isothiazole was used in the place of 1-chloro-6-methoxy-3-pyridin-2-yl-isoquinoline.

LC/MS (Retention time 1.83 min): m/z 688 (M–H)$^-$

Example 325

Preparation of Compound 325

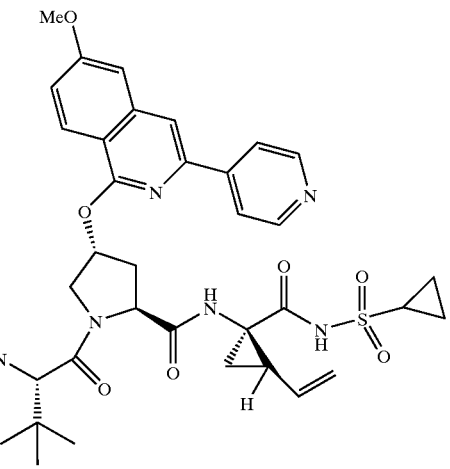

Compound 325

Compound 325 was prepared by following Scheme 1 and Scheme 3 of above.
Step 1(scheme1):

Step 1 (Scheme 1):

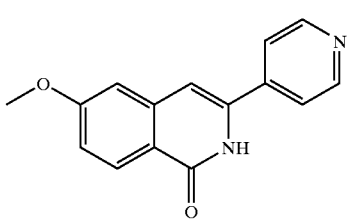

To a solution of N,N-Diethyl-4-methoxy-2-methyl-benzamide (332 mg, 1.5 mmol) in THF (15 mL) at –78° C., t-BuLi (1.7 M solution in pentane, 1.3 mL, 2.25 mmol) was added. The resulting red solution was stirred at −78° C. for 10 min, then 4-cyanopyridine (164 mg, 1.575 mmol) was added. The reaction mixture was then warmed to rt and stirred for overnight. The reaction was quenched with saturated NH$_4$Cl solution and the yellow precipitate was collected as pure product. (145 mg, 38% yield)

$^1$H NMR(CD$_3$OD, 400 MHz) δ 3.91 (s, 3 H), 7.18 (dd, J=8.8 Hz, 2.8 Hz, 1 H), 7.26 (m, 2 H), 8.06 (d, J=6.0 Hz, 2 H), 8.16 (d, J=8.8 Hz, 1 H), 8.84 (d, J=6.0 Hz, 2 H).

LC-MS (retention time: 1.300 min.), MS m/z 253 (MH$^+$).

Step 2 (Scheme 3, step 1):

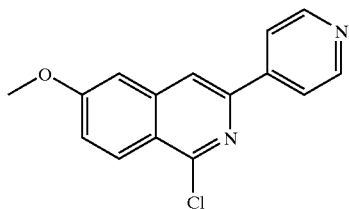

6-Methoxy-3-pyridin-4-yl-2H-isoquinolin-1-one (134 mg, 0.531 mmol) was heated under reflux with POCl$_3$ (6.0 mL) for 5 days. Then POCl$_3$ was distilled off and the residue was quenched with ice. It was then neutralized with saturated NaHCO$_3$ solution and the brown solid was collected as pure product. (125 mg, 87% yield)

$^1$H NMR (DMSO-d$^6$, 400 MHz) δ 3.99 (s, 3 H), 7.53 (dd, J=9.04 Hz, 2.44 Hz, 1 H), 7.59 (d, J=2.69 Hz, 1 H), 8.26 (d, J=9.05 Hz, 1 H), 8.30 (d, J=5.38 Hz, 2 H), 8.73 (s, 1 H), 8.85 (d, J=6.36 Hz, 2 H).

LC-MS (retention time: 2.027 min.), MS m/z 271 (MH$^+$).

Step 3 (Scheme 3, Step 2):

Compound 325

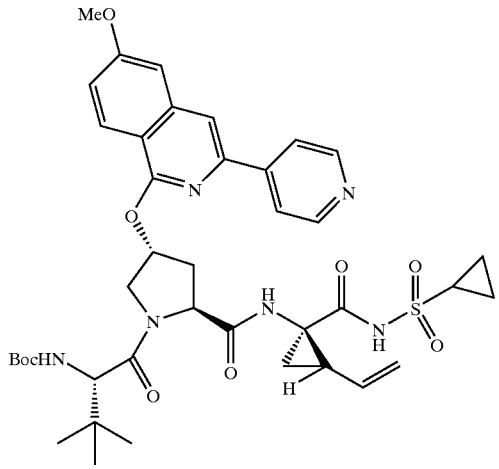

To a solution of {1-[2-(1-Cyclopropanesulfonylaminocarbonyl-2-vinyl-cyclopropylcarbamoyl)-4-hydroxy-pyrrolidine-1-carbonyl]-2,2-dimethyl-propyl}-carbamic acid tert-butyl ester (83.5 mg, 0.15 mmol) and LaCl$_3$ (36.8 mg, 0.15 mmol) in DME (1.5 mL), potassium t-butoxide (1.0 M solution in THF, 0.75 mL, 0.75 mmol) was added at −78° C. The reaction mixture was stirred for 1 hr, then 1-chloro-6-methoxy-3-pyridin-4-yl-isoquinoline (40.6 mg, 0.15 mmol) was added. It was warmed to rt and stirred for overnight. Then it was quenched with water and filtered. The filtrated was concentrated and the residue was purified by Prep. HPLC to give an off-white solid as product (Compound 325). (1.6 mg, 1.3% yield)

$^1$H NMR (400 MHz, CD$_3$OD) δ 0.90 (m, 2 H), 1.02 (s, 9 H), 1.17–1.31 (m, 11 H), 1.42 (m, 1 H), 1.87 (m, 1 H), 2.23 (m, 1 H), 2.35 (m, 1 H), 2.68 (m, 1 H), 2.93 (m, 1 H), 3.95 (s, 3 H), 4.15 (m, 1 H), 4.25 (m, 1 H), 4.45 (m, 1 H), 4.56 (m, 1 H), 5.10 (d, J=10.76 Hz, 1 H), 5.27 (d, J=17.61 Hz, 1 H), 5.74 (m, 1 H), 6.06 (s, 1 H), 7.14 (d, J=8.07 Hz, 1 H), 7.34 (s, 1 H), 8.01 (s, 1 H), 8.12 (d, J=8.81 Hz, 1 H), 8.19 (d, J=6.12 Hz, 2 H), 8.61 (d, J=5.63 Hz, 2 H).

LC-MS (retention time: 2.523 min.), MS m/z 791 (MH$^+$).

Example 326

Preparation of Compound 326

Compound 326

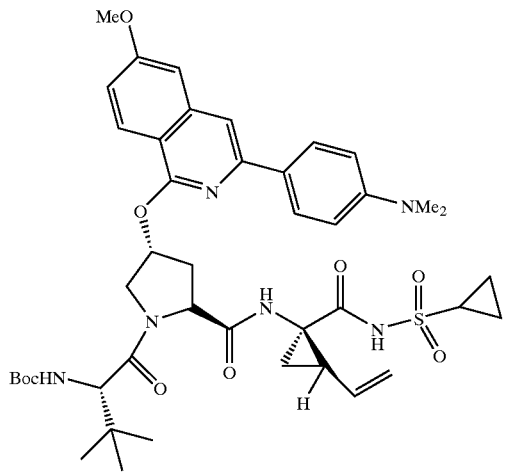

Compound 326 was prepared by following Scheme 1 and Scheme 4 of above.

Step 1 (Scheme 1):

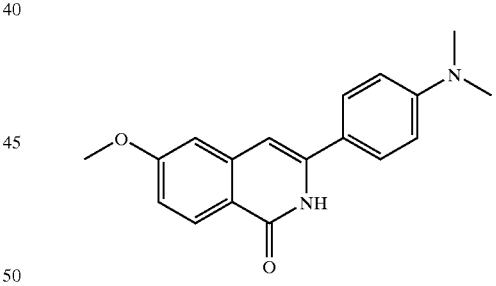

To a solution of N,N-Diethyl-4-methoxy-2-methyl-benzamide (332 mg, 1.5 mmol) in THF (15 mL) at −78° C., t-BuLi (1.7 M solution in pentane, 1.3 mL, 2.25 mmol) was added. The resulting red solution was stirred at −78° C. for 10 min, then 4-dimethylamino benzonitrile (219 mg, 1.5 mmol) was added. The reaction mixture was then warmed to rt and stirred for overnight. The reaction was quenched with saturated NH$_4$Cl solution and the yellow precipitate was collected and triturated with ether to give an off-white solid as pure product. (247 mg, 56% yield)

$^1$H NMR (DMSO-d$^6$, 400 MHz) δ 2.97 (s, 6 H), 3.87 (s, 3 H), 6.72 (s, 1 H), 6.78 (d, J=8.80 Hz, 2 H), 6.97 (dd, J=8.80, 2.45 Hz, 1 H), 7.10 (d, J=2.45 Hz, 1 H), 7.65 (d, J=8.80 Hz, 2 H), 8.05 (d, J=8.80 Hz, 1 H), 11.11 (s, 1 H).

LC-MS (retention time: 2.023 min.), MS m/z 295 (MH$^+$).

Step 2 (Scheme 4, Step 1):

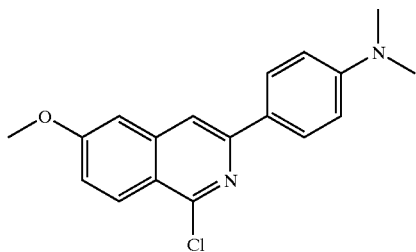

3-(4-Dimethylamino-phenyl)-6-methoxy-2H-isoquinolin-1-one (245 mg, 0.83 mmol) was heated under reflux with POCl$_3$ (10.0 mL) for 2 days. Then POCl$_3$ was distilled off and the residue was quenched with ice. It was then neutralized with 10 N NaOH solution and extracted with ethyl acetate twice. The organic layers were combined and dried (MgSO4). Evaporation of solvent gave an orange solid as product (215 mg, 83% yield)

$^1$H NMR (400 MHz, CD$_3$OD) δ 3.01 (s, 6 H), 3.96 (s, 3 H), 6.88 (d, J=9.05 Hz, 2 H), 7.20 (dd, J=9.17, 2.57 Hz, 1 H), 7.28 (d, J=2.45 Hz, 1 H), 7.94 (s, 1 H), 7.96 (d, J=9.05 Hz, 2 H), 8.13 (d, J=9.29 Hz, 1 H).

LC-MS (retention time: 2.543 min.), MS m/z 313 (MH$^+$).

Step 3 (Scheme 4, Step 2):

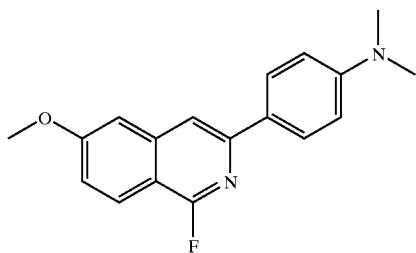

A mixture of [4-(1-Chloro-6-methoxy-isoquinolin-3-yl)-phenyl]-dimethyl-amine (110 mg, 0.35 mmol) and tetrabutyl phosphonium hydrogen difluoride (0.5 g) was heated at 140° C. in Smith microwave reactor for 20 min. Then it was added water and extracted with ethyl acetate. The organic layer was separated, washed with water and dried (MgSO$_4$). Evaporation of solvent gave a brownish solid as product. (85 mg, 82% yield)

LC-MS (retention time: 2.320 min.), MS m/z 297 (MH$^+$).

Step 4 (Scheme 4, Step 3):

Compound 326

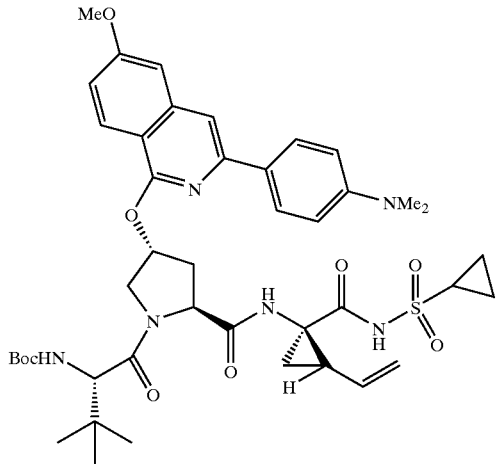

To a solution of {1-[2-(1-Cyclopropanesulfonylaminocarbonyl-2-vinyl-cyclopropyl-carbamoyl)-4-hydroxy-pyrrolidine-1-carbonyl]-2,2-dimethyl-propyl}-carbamic acid tert-butyl ester (111 mg, 0.2 mmol) and LaCl$_3$ (49 mg, 0.2 mmol) in DMF (2.0 mL), potassium t-butoxide (1.0 M solution in THF, 1.0 mL, 1.0 mmol) was added at −78° C. The reaction mixture was stirred for 1 hr, then [4-(1-fluoro-6-methoxy-isoquinolin-3-yl)-phenyl]-dimethylamine (59 mg, 0.2 mmol) was added. It was warmed to rt and stirred for overnight. Then it was quenched with water and filtered. The filtrated was concentrated and the residue was purified by Prep. HPLC to give yellowish solid as product (Compound 326). (17.5 mg, 11% yield)

$^1$H NMR (400 MHz, CD$_3$OD) δ 0.97–1.08 (m, 11 H), 1.23 (m, 2 H), 1.31 (s, 9 H), 1.44 (m, 1 H), 1.87 (m, 1 H), 2.22 (m, 1 H), 2.34 (m, 1 H), 2.68 (m, 1 H), 2.93 (m, 1 H), 2.99 (m, 6 H), 3.91 (s, 3 H), 4.17 (m, 1 H), 4.29 (m, 1 H), 4.39 (m, 1 H), 4.52 (m, 1 H), 5.10 (d, J=10.76 Hz, 1 H), 5.27 (d, J=17.11 Hz, 1 H), 5.74 (m, 1 H), 6.03 (s, 1 H), 6.83 (m, 2 H), 6.95 (m, 1 H), 7.16 (s, 1 H), 7.59 (s, 1 H), 8.01 (m, 3 H).

LC-MS (retention time: 2.850 min.), MS m/z 834 (MH$^+$).

Example 327

Preparation of Compound 327

Compound 327

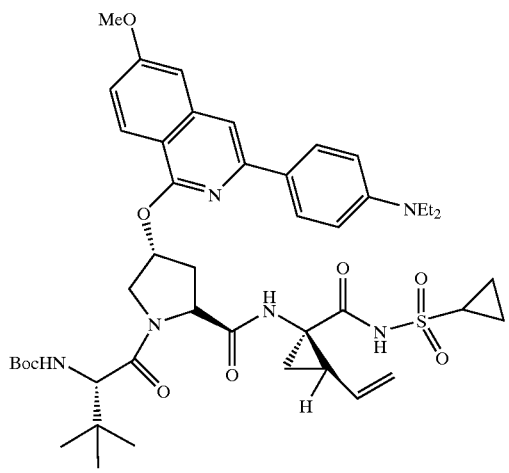

Compound 327 was prepared by following Scheme 1 and Scheme 4 of above.

Step 1 (Scheme 1):

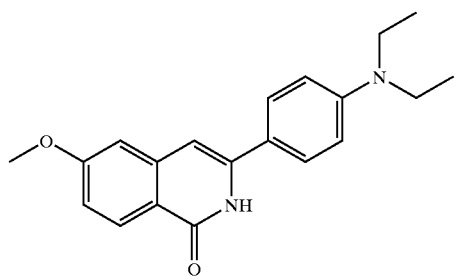

To a solution of N,N-Diethyl-4-methoxy-2-methyl-benzamide (332 mg, 1.5 mmol) in THF (15 mL) at −78° C., t-BuLi (1.7 M solution in pentane, 1.3 mL, 2.25 mmol) was added. The resulting red solution was stirred at −78° C. for 10 min, then 4-diethylamino benzonitrile (261 mg, 1.5 mmol) was added. The reaction mixture was then warmed to rt and stirred for overnight. The reaction was quenched with saturated NH$_4$Cl solution and the yellow precipitate was collected as pure product. (215 mg, 44% yield)

$^1$H NMR (400 MHz, DMSO-d$^6$) δ 1.12 (m, 6 H), 3.39 (m, 4 H), 3.87 (s, 3 H), 6.69 (s, 1 H), 6.72 (d, J=9.05 Hz, 2 H), 6.96 (dd, J=8.80, 2.45 Hz, 1 H), 7.09 (d, J=2.45 Hz, 1 H), 7.61 (d, J=9.05 Hz, 2 H), 8.04 (d, J=8.80 Hz, 1 H), 11.06 (s, 1 H).

LC-MS (retention time: 1.883 min.), MS m/z 323 (MH$^+$).

Step 2 (Scheme 4, Step 1):

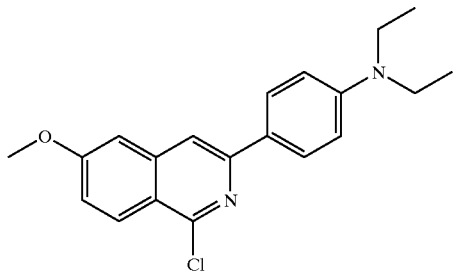

3-(4-Diethylamino-phenyl)-6-methoxy-2H-isoquinolin-1-one (207 mg, 0.642 mmol) was heated under reflux with POCl$_3$ (8.0 mL) for one day. Then POCl$_3$ was distilled off and the residue was quenched with ice. It was then neutralized with saturated NaHCO$_3$ solution and extracted with ethyl acetate twice. The organic layers were combined and dried (MgSO$_4$). Evaporation of solvent gave a brownish solid as product. (180 mg, 82% yield)

LC-MS (retention time: 2.397 min.), MS m/z 341 (MH$^+$).

Step 3 (Scheme 4, Step 2):

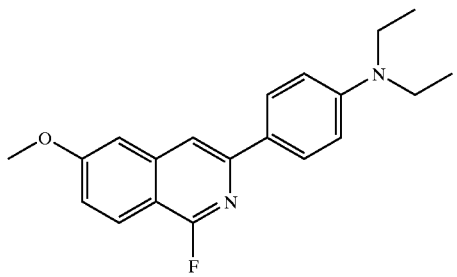

A mixture of [4-(1-Chloro-6-methoxy-isoquinolin-3-yl)-phenyl]-diethylamine (90 mg, 0.264 mmol) and tetrabutyl phosphonium hydrogen difluoride (0.5 g) was heated at 140° C. in Smith microwave reactor for 20 min. Then it was added water and extracted with ethyl acetate. The organic layer was separated, washed with water and dried (MgSO$_4$). Evaporation of solvent gave a yellowish oil as product. (70 mg, 82% yield)

LC-MS (retention time: 2.253 min.), MS m/z 325 (MH$^+$).

Step 4 (Scheme 4, Step 3):

Compound 327

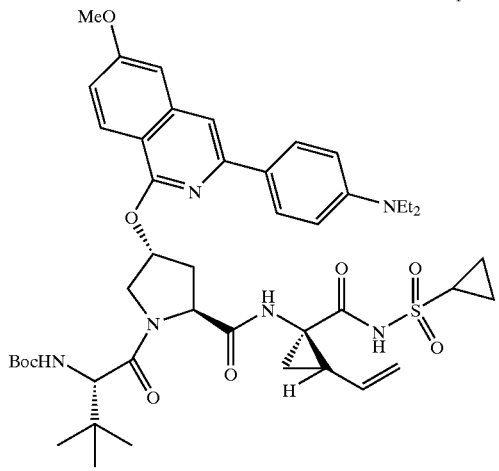

To a solution of {1-[2-(1-Cyclopropanesulfonylaminocarbonyl-2-vinyl-cyclopropyl-carbamoyl)-4-hydroxy-pyrrolidine-1-carbonyl]-2,2-dimethyl-propyl}-carbamic acid tert-butyl ester (100 mg, 0.18 mmol) and LaCl$_3$ (66 mg, 0.27 mmol) in DMF (2.0 mL), potassium t-butoxide (1.0 M solution in TBF, 0.9 mL, 0.9 mmol) was added at −78° C. The reaction mixture was stirred for 1 hr, then [4-(1-Fluoro-6-methoxy-isoquinolin-3-yl)-phenyl]-diethylamine (70 mg, 0.216 mmol) was added. It was warmed to rt and stirred for overnight. Then it was quenched with water and filtered. The filtrated was concentrated and the residue was purified by Prep. HPLC to give white solid as product (Compound 327). (18 mg, 12% yield)

$^1$H NMR (400 MHz, CD$_3$OD) δ 0.95–1.07 (m, 11 H), 1.18 (m, 6 H), 1.25–1.38 (m, 11 H), 1.58 (m, 1 H), 1.85 (m, 1 H), 2.19 (m, 1 H), 2.34 (m, 1 H), 2.68 (m, 1 H), 2.92 (m, 1 H), 3.42 (m, 4 H), 3.90 (s, 3 H), 4.16 (m, 1 H), 4.28 (m, 1 H), 4.37 (m, 1 H), 4.53 (m, 1 H), 5.07 (d, J=11.0 Hz, 1 H), 5.25 (d, J=17.36 Hz, 1 H), 5.74 (m, 1 H), 5.99 (s, 1 H), 6.77 (d, J=8.8 Hz, 2 H), 6.94 (d, J=9.05 Hz, 1 H), 7.14 (s, 1 H), 7.56 (s, 1 H), 7.95–8.02 (m, 3 H).

LC-MS (retention time: 2.690 min.), MS m/z 862(MH$^+$).

Example 328

Preparation of Compound 328

Compound 328

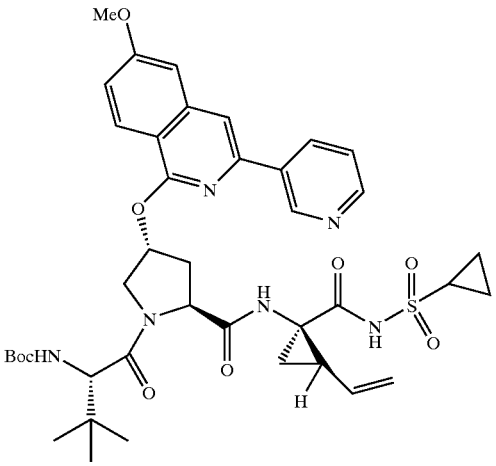

Compound 328 was prepared by following Scheme 2 and Scheme 3 of above.

Step 1 (Scheme 2, Step 1):

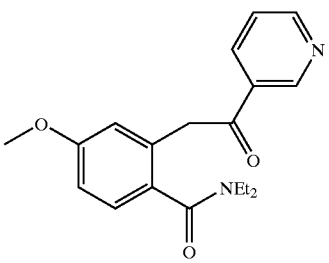

To a solution of N,N-Diethyl-4-methoxy-2-methyl-benzamide (332 mg, 1.5 mmol) in THF (15 mL) at −78° C., t-BuLi (1.7 M solution in pentane, 2.12 mL, 3.6 mmol) was added. The resulting red solution was stirred at −78° C. for 10 min, then methyl nicotinate (206 mg, 1.5 mmol) was added. The reaction mixture was stirred at −78° C. for 2 h. Then the reaction was quenched with saturated NH$_4$Cl solution and extracted with ethyl acetate twice. The combined organic layers were dried (MgSO$_4$) and concentrated. The crude product was purified by Prep. HPLC to give yellowish thick oil as TFA salt. (124 mg, 19% yield)

LC-MS (retention time: 1.740 min.), MS m/z 349 (M+Na⁺).

Step 2 (Scheme 2, Step 2):

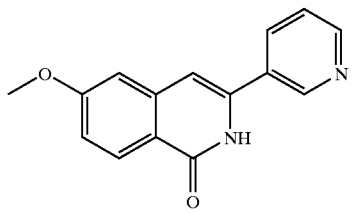

N,N-Diethyl-4-methoxy-2-(2-oxo-2-pyridin-3-yl-ethyl)-benzamide (120 mg, 0.272 mmol) was heated with ammonium acetate (1 g) for 3 hr. Then it was cooled down and added water. Extracted with ethyl acetate and the organic layer was separated. It was then dried (MgSO$_4$) and concentrated to give a brownish solid as product. (65 mg, 95% yield)

¹H NMR (400 MHz, DMSO-d⁶) δ 3.89 (s, 3 H), 6.93 (s, 1 H), 7.10 (dd, J=8.80, 2.45 Hz, 1 H), 7.19 (d, J=2.45 Hz, 1 H), 7.52 (dd, J=7.46, 4.77 Hz, 1 H), 8.15 (m, 2 H), 8.64 (dd, J=4.89, 1.47 Hz, 1 H), 8.96 (d, J=1.71 Hz, 1 H), 11.51 (s, 1 H).

LC-MS (retention time: 1.377 min.), MS m/z 253 (MH⁺).

Step 3 (Scheme 3, Step 1):

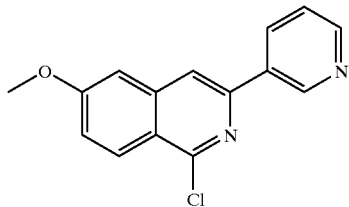

6-Methoxy-3-pyridin-3-yl-2H-isoquinolin-1-one (65 mg, 0.258 mmol) was heated under reflux with POCl$_3$ (2.5 mL) for 7 days. Then POCl$_3$ was distilled off and the residue was quenched with ice. It was then neutralized with 10 N NaOH solution and extracted with ethyl acetate twice. The combined organic layers were dried (MgSO$_4$) and concentrated to give yellow solid as product. (27 mg, 39% yield)

LC-MS (retention time: 2.090 min.), MS m/z 271 (MH⁺).

Step 4 (Scheme 3, Step 2):

Compound 328

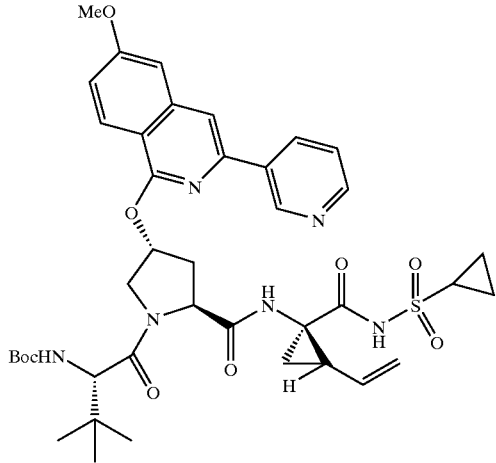

To a solution of {1-[2-(1-Cyclopropanesulfonylaminocarbonyl-2-vinyl-cyclopropylcarbamoyl)-4-hydroxy-pyrrolidine-1-carbonyl]-2,2-dimethyl-propyl}-carbamic acid tert-butyl ester (56 mg, 0.10 mmol) and LaCl$_3$ (25 mg, 0.10 mmol) in DMF (1.5 mL), potassium t-butoxide (1.0 M solution in THF, 0.5 mL, 0.5 mmol) was added at –78° C. The reaction mixture was stirred for 1 hr, then 1-chloro-6-methoxy-3-pyridin-3-yl-isoquinoline (27 mg, 0.10 mmol) was added. It was warmed to rt and stirred for overnight. Then it was quenched with water and filtered. The filtrated was concentrated and the residue was purified by Prep. HPLC to give white solid as product (Compound 328). (17 mg, 21% yield)

¹H NMR (400 MHz, CD$_3$OD) δ 0.95 (m, 2 H), 1.02 (s, 9 H), 1.20–1.30 (m, 11 H), 1.41 (m, 1 H), 1.86 (m, 1 H), 2.21 (m, 1 H), 2.35 (m, 1 H), 2.67 (m, 1 H), 2.93 (m, 1 H), 3.93 (s, 3 H), 4.14 (m, 1 H), 4.26 (m, 1 H), 4.47 (d, J=11.99 Hz, 1 H), 4.55 (m, 1 H), 5.09 (d, J=10.02 Hz, 1 H), 5.26 (d, J=17.85 Hz, 1 H), 5.74 (m, 1 H), 6.07 (s, 1 H), 7.09 (m, 1 H), 7.29 (d, J=1.96 Hz, 1 H), 7.53 (m, 1 H), 7.86 (s, 1 H), 8.09 (d, J=9.05 Hz, 1 H), 8.50–8.58 (m, 2 H), 9.28 (s, 1 H).

LC-MS (retention time: 2.453 min.), MS m/z 791 (MH⁺).

Example 329

Preparation of Compound 329

Compound 329

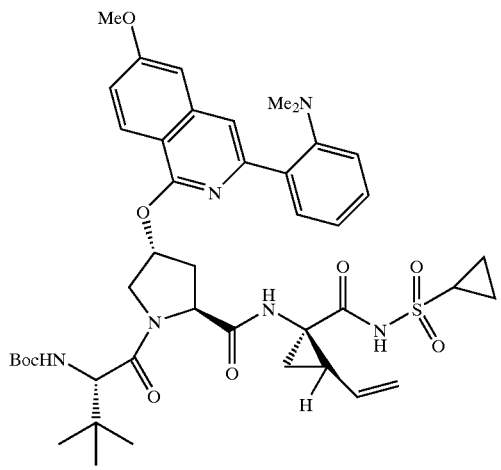

Compound 329 was prepared by following Scheme 2 and Scheme 4 of above.

Step 1 (Scheme 2, Step 1):

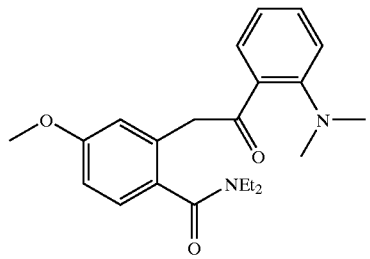

To a solution of N,N-Diethyl-4-methoxy-2-methyl-benzamide (332 mg, 1.5 mmol) in THF (15 mL) at –78° C., t-BuLi (1.7 M solution in pentane, 2.2 mL, 3.75 mmol) was added. The resulting red solution was stirred at –78° C. for 10 min, then N,N-dimethylanthranilic acid methyl ester (269 mg, 1.5 mmol) was added. The reaction mixture was stirred at –78° C. for 2 h. Then the reaction was quenched with saturated NH$_4$Cl solution and extracted with ethyl acetate twice. The combined organic layers were dried (MgSO$_4$)

and concentrated. The crude product was purified by Prep. HPLC to give yellowish thick oil as product. (256 mg, 46% yield)

$^1$H NMR (400 MHz, CD$_3$OD) δ 0.99–1.13 (m, 6 H), 3.23–3.31 (m, 8 H), 3.39 (m, 2 H), 3.82 (s, 3 H), 4.35 (s, 2 H), 6.91 (dd, J=8.44, 2.57 Hz, 1 H), 6.99 (d, J=2.45 Hz, 1 H), 7.22 (d, J=8.56 Hz, 1 H), 7.69 (t, J=7.70 Hz, 1 H), 7.84 (m, 1 H), 7.96 (d, J=8.31 Hz, 1 H), 8.18 (d, J=7.83 Hz, 1 H).

LC-MS (retention time: 1.557 min.), MS m/z 369(MH$^+$).

Step 2 (Scheme 2, Step 2):

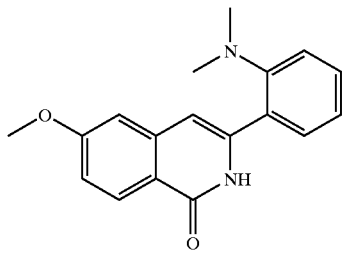

2-[2-(2-Dimethylamino-phenyl)-2-oxo-ethyl]-N,N-diethyl-4-methoxy-benzamide (250 mg, 0.678 mmol) was heated with ammonium acetate (1.5 g) for 2 hr. Then it was cooled down and added water. Extracted with ethyl acetate and the organic layer was separated. It was then dried (MgSO$_4$) and concentrated to give a yellowish solid as product. (125 mg, 63% yield)

$^1$H NMR (400 MHz, CD$_3$OD) δ 2.95 (s, 6 H), 3.92 (s, 3 H), 6.92 (s, 1 H), 7.12 (dd, J=8.80, 2.45 Hz, 1 H); 7.16 (d, J=2.45 Hz, 1 H), 7.35 (m, 1 H), 7.55 (m, 2 H), 7.63 (d, J=7.83 Hz, 1 H), 8.20 (d, J=9.05 Hz, 1 H).

LC-MS (retention time: 2.097 min.), MS m/z 295 (MH$^+$).

Step 3 (Scheme 4, Step 1):

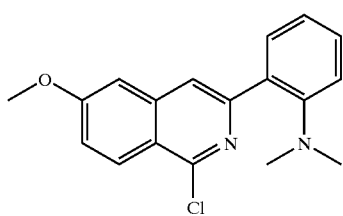

3-(2-Dimethylamino-phenyl)-6-methoxy-2H-isoquinolin-1-one (125 mg, 0.425 mmol) was heated under reflux with POCl$_3$ (4.0 mL) for one day. Then POCl$_3$ was distilled off and the residue was quenched with ice. It was then neutralized with 10 N NaOH solution and extracted with ethyl acetate twice. The organic layers were combined and dried (MgSO$_4$). Evaporation of solvent gave a brownish solid as product (82 mg, 62% yield)

LC-MS (retention time: 2.040 min.), MS m/z 313 (MH$^+$).

Step 4 (Scheme 4, Step 2):

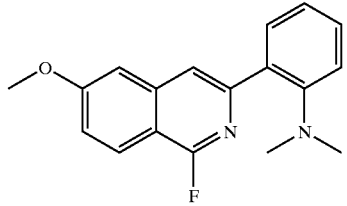

A mixture of [2-(1-Chloro-6-methoxy-isoquinolin-3-yl)-phenyl]-dimethyl-amine (82 mg, 0.262 mmol) and tetrabutyl phosphonium hydrogen difluoride (1.0 g) was heated at 140° C. in Smith microwave reactor for 20 min. Then it was added water and extracted with ethyl acetate. The organic layer was separated, washed with water and dried (MgSO$_4$). Evaporation of solvent gave the crude product which was purified by Prep. HPLC to afford a yellowish oil as product. (85 mg)

$^1$H NMR (400 MHz, CD$_3$OD) δ 3.41 (s, 6 H), 4.00 (s, 3 H), 7.42 (dd, J=9.05, 2.45 Hz, 1 H), 7.53 (s, 1 H), 7.71 (m, 2 H), 7.99 (m, 1 H), 8.16 (m, 2 H), 8.31 (s, 1 H).

LC-MS (retention time: 1.873 min.), MS m/z 297 (MH$^+$).

Step 5 (Scheme 4, Step 3):

Compound 329

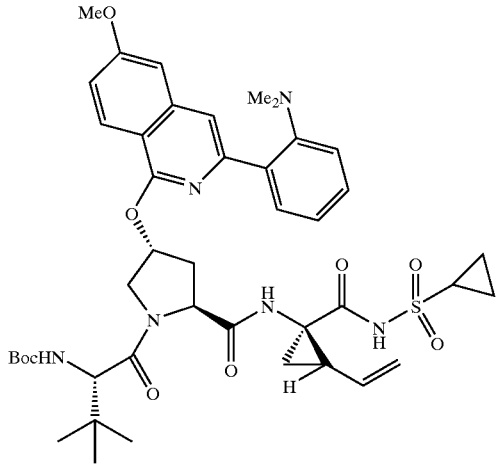

To a solution of {1-[2-(1-Cyclopropanesulfonylaminocarbonyl-2-vinyl-cyclopropyl-carbamoyl)-4-hydroxy-pyrrolidine-1-carbonyl]-2,2-dimethyl-propyl}-carbamic acid tert-butyl ester (56 mg, 0.1 mmol) and LaCl$_3$ (25 mg, 0.1 mmol) in DMF (1.0 mL), potassium t-butoxide (1.0 M solution in THF, 0.5 mL, 0.5 mmol) was added at −78° C. The reaction mixture was stirred for 1 hr, then [2-(1-Fluoro-6-methoxy-isoquinolin-3-yl)-phenyl]-dimethyl-amine (30 mg, 0.1 mmol) was added. It was warmed to rt and stirred for overnight. Then it was quenched with water and filtered. The filtrated was concentrated and the residue was purified by Prep. HPLC to give white solid as product (Compound 329). (4.0 mg, 5% yield)

$^1$H NMR (400 MHz, CD$_3$OD) δ 0.98–1.08 (m, 11 H), 1.16–1.32 (m, 11 H), 1.40 (m, 1 H), 1.85 (m, 1 H), 2.16–2.32 (m, 2 H), 2.60–2.71 (m, 7 H), 2.92 (m, 1 H), 3.91 (s, 3 H), 4.08 (m, 1 H), 4.26 (m, 1 H), 4.45 (m, 1 H), 4.55 (m, 1 H), 5.10 (d, J=10.27 Hz, 1 H), 5.28 (d, J=18.09 Hz, 1 H), 5.74 (m, 1 H), 5.89 (s, 1 H), 7.05 (d, J=6.85 Hz, 1 H), 7.10–7.20 (m, 2 H), 7.29 (m, 1 H), 7.63 (d, J=7.58 Hz, 1 H), 7.78 (s, 1 H), 8.07 (d, J=8.56 Hz, 1 H).

LC-MS (retention time: 2.550 min.), MS m/z 834 (MH$^+$).

Example 330

Preparation of Compound 330

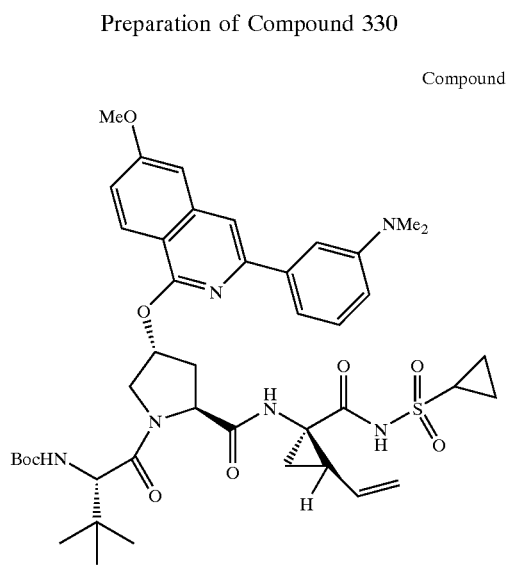

Compound 330

Compound 330 was prepared by following Scheme 2 and Scheme 4 of above.

Step 1 (Scheme 2, Step 1):

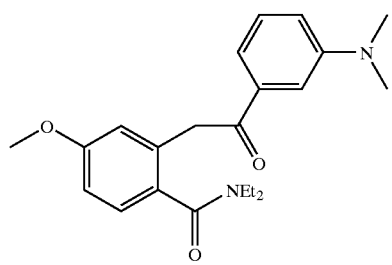

To a solution of N,N-Diethyl-4-methoxy-2-methyl-benzamide (332 mg, 1.5 mmol) in THF (15 mL) at −78° C., t-BuLi (1.7 M solution in pentane, 2.2 mL, 3.75 mmol) was added. The resulting red solution was stirred at −78° C. for 10 min, then (3-dimethylamino)benzoic acid methyl ester (269 mg, 1.5 mmol) was added. The reaction mixture was stirred at −78° C. for 2 h. Then the reaction was quenched with saturated NH$_4$Cl solution and extracted with ethyl acetate twice. The combined organic layers were dried (MgSO$_4$) and concentrated. The crude product was purified by Prep. HPLC to give yellowish thick oil as TFA salt. (245 mg, 33% yield)

$^1$H NMR (400 MHz, CD$_3$OD) δ 1.01 (t, J=6.85 Hz, 3 H), 1.09 (m, 3 H), 3.11 (s, 6 H), 3.21 (m, 2 H), 3.40 (m, 2 H), 3.79 (s, 3 H), 4.39 (s, 2 H), 6.84–6.91 (m, 2 H), 7.19 (d, J=8.32 Hz, 1 H), 7.35 (m, 1 H), 7.49 (t, J=8.07 Hz, 1 H), 7.66–7.71 (m, 2 H).

LC-MS (retention time: 1.930 min.), MS m/z 369 (MH$^+$).

Step 2 (Scheme 2, Step 2):

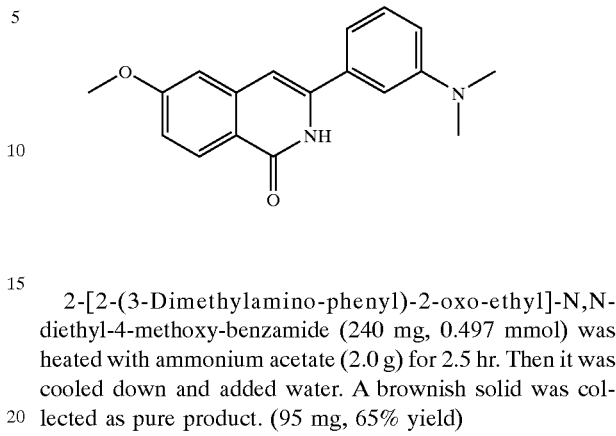

2-[2-(3-Dimethylamino-phenyl)-2-oxo-ethyl]-N,N-diethyl-4-methoxy-benzamide (240 mg, 0.497 mmol) was heated with ammonium acetate (2.0 g) for 2.5 hr. Then it was cooled down and added water. A brownish solid was collected as pure product. (95 mg, 65% yield)

1H NMR (400 MHz, CD$_3$OD) δ 2.98 (s, 6 H), 3.88 (s, 3 H), 6.74–6.87 (m, 2 H), 7.01–7.07 (m, 3 H), 7.18 (d, J=2.44 Hz, 1 H), 7.28 (t, J=7.82 Hz, 1 H), 8.10 (d, J=8.80 Hz, 1 H).

LC-MS (retention time: 1.773 min.), MS m/z 295 (MH$^+$).

Step 3 (Scheme 4, Step 1):

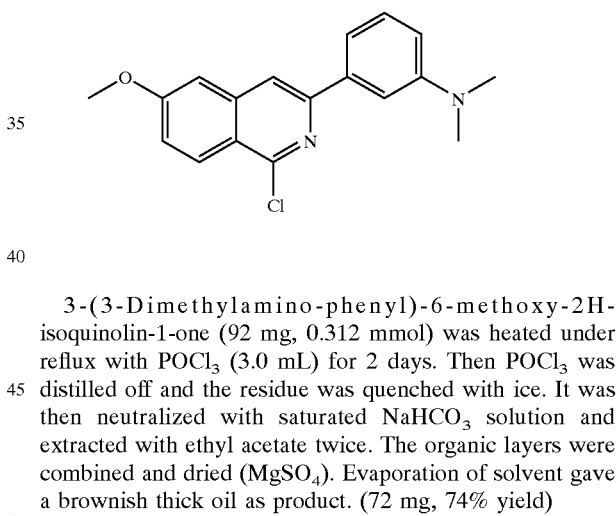

3-(3-Dimethylamino-phenyl)-6-methoxy-2H-isoquinolin-1-one (92 mg, 0.312 mmol) was heated under reflux with POCl$_3$ (3.0 mL) for 2 days. Then POCl$_3$ was distilled off and the residue was quenched with ice. It was then neutralized with saturated NaHCO$_3$ solution and extracted with ethyl acetate twice. The organic layers were combined and dried (MgSO$_4$). Evaporation of solvent gave a brownish thick oil as product. (72 mg, 74% yield)

LC-MS (retention time: 2.297 min.), MS m/z 313 (MH$^+$).

Step 4 (Scheme 4, Step 2):

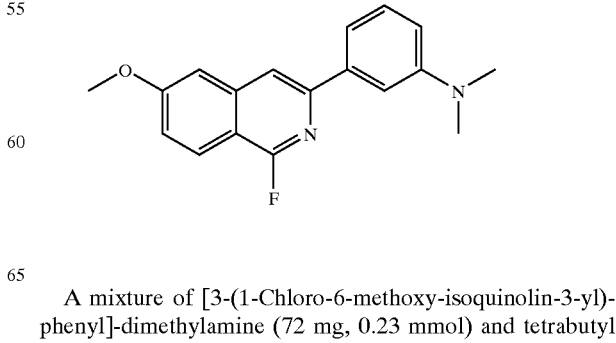

A mixture of [3-(1-Chloro-6-methoxy-isoquinolin-3-yl)-phenyl]-dimethylamine (72 mg, 0.23 mmol) and tetrabutyl phosphonium hydrogen difluoride (0.5 g) was heated at 140° C. in Smith microwave reactor for 20 min. Then it was added water and extracted with ethyl acetate. The organic layer was separated, washed with water and dried (MgSO₄). Evaporation of solvent gave a brownish oil as product. (58 mg, 85% yield)

LC-MS (retention time: 2.193 min.), MS m/z 297 (MH⁺).

Step 5 (Scheme 4, Step 3):

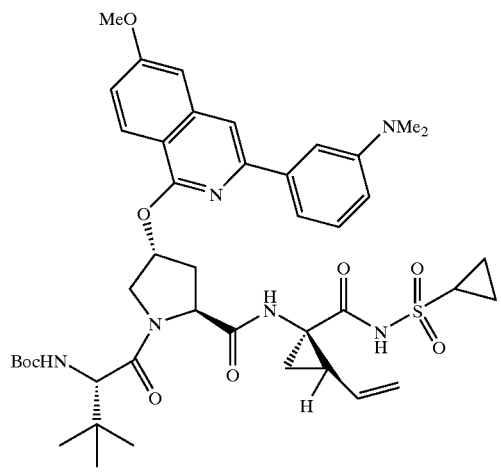

Compound 330

To a solution of {1-[2-(1-Cyclopropane-sulfonylaminocarbonyl-2 vinyl-cyclopropyl-carbamoyl)-4-hydroxy-pyrrolidine-1-carbonyl]-2,2-dimethyl-propyl}-carbamic acid tert-butyl ester (86 mg, 0.155 mmol) and LaCl₃ (57 mg, 0.233 mmol) in DMF (1.5 mL), potassium t-butoxide (1.0 M solution in THF, 0.5 mL, 0.5 mmol) was added at −78° C. The reaction mixture was stirred for 1 hr, then [3-(1-Fluoro-6-methoxy-isoquinolin-3-yl)-phenyl]-dimethylamine (55 mg, 0.185 mmol) was added. It was warmed to rt and stirred for overnight. Then it was quenched with water and filtered. The filtrated was concentrated and the residue was purified by Prep. HPLC to give an off-white solid as product (Compound 330). (8.0 mg, 6% yield)

¹H NMR (400 MHz, CD₃OD) δ 0.99–1.09 (m, 11 H), 1.23 (m, 2 H), 1.29 (s, 9 H), 1.42 (m, 1 H), 1.86 (m, 1 H), 2.21 (m, 1 H), 2.33 (m, 1 H), 2.70 (m, 1 H), 2.93 (m, 1 H), 3.00 (s, 6 H), 3.92 (s, 3 H), 4.14 (m, 1 H), 4.29 (m, 1 H), 4.44–4.57 (m, 2 H), 5.10 (d, J=11.00 Hz, 1 H), 5.27 (d, J=16.87 Hz, 1 H), 5.74 (m, 1 H), 6.01 (s, 1 H), 6.63 (d, J=8.80 Hz, 1 H), 7.03 (d, J=6.85 Hz, 1 H), 7.24 (s, 1 H), 7.28 (t, J=8.07 Hz, 1 H), 7.45 (d, J=7.82 Hz, 1 H), 7.59 (s, 1 H), 7.72 (s, 1 H), 8.05 (d, J=8.80 Hz, 1 H).

LC-MS (retention time: 2.707 min.), MS m/z 834 (MH⁺).

Example 331

Preparation of Compound 331

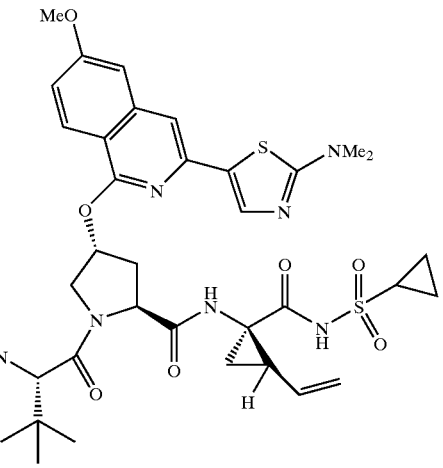

Compound 331

Compound 331 was prepared by the methods described herein.

Example 334

Preparation of Compound 334

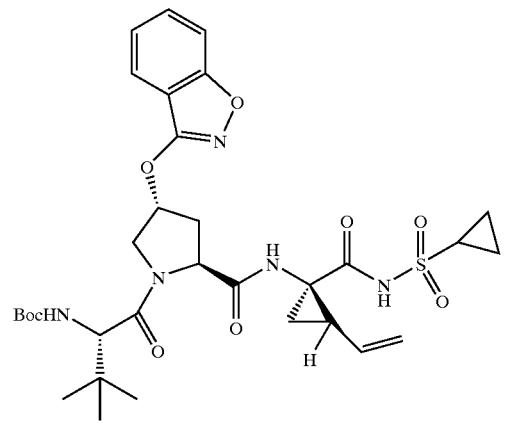

Compound 334

Compound 334 was prepared in the following manner:
Step 1:

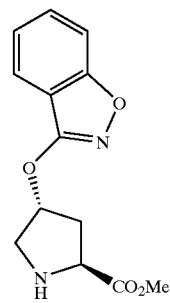

To a solution of Boc-cis-HYP-OMe (122.6 mg, 0.5 mmol) in THF (15 mL) at 0° C., triphenylphosphine (196.7 mg, 0.75 mmol) and benzo[d]isoxazol-3-ol (81 mg, 0.6 mmol) were added. Then DEAD (0.118 mL, 0.75 mmol) was added. The reaction mixture was warmed to rt. and stirred for 3 hr. Then solvent was evaporated and the residue was purified by Prep. HPLC to give a colorless thick oil. (117 mg, 54% yield)

1H NMR (400 MHz, CD$_3$OD) δ 1.41 (m, 9 H), 2.38 (m, 1 H), 2.75 (m, 1 H), 3.75 (m, 3 H), 3.81 (m, 1 H), 3.90 (m, 1 H), 4.47 (m, 1 H), 5.44 (m, 1 H), 7.31 (t, J=7.46 Hz, 1 H), 7.47 (d, J=8.56 Hz, 1 H), 7.59 (t, J=7.83 Hz, 1 H), 7.66 (d, J=8.07 Hz, 1 H).

LC-MS (retention time: 2.65 min.), MS m/z 363(MH$^+$).

Some of the coupling product (85 mg, 0.235 mmol) was then dissolved in 4N HCl in dioxane (1.5 mL) and stirred for 3 hr. Evaporation of solvent gave a yellowing oil as HCl salt. (85 mg, >100% yield)

LC-MS (retention time: 1.327 min.), MS m/z 263(MH$^+$).

Step 2:

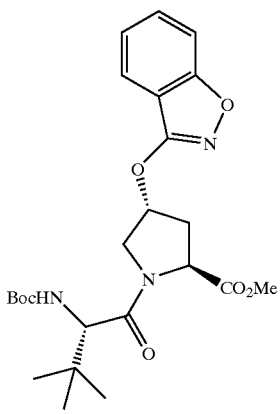

To a solution of 4-(Benzo[d]isoxazol-3-yloxy)-pyrrolidine-2-carboxylic acid methyl ester hydrochloride salt (85 mg, 0.285 mmol) in CH$_3$CN (10 mL) was added N-boc-L-t-leucine (99 mg, 0.427 mmol), DIEA (0.25 mL, 1.425 mmol) and the coupling reagent HOBt (65 mg, 0.427 mmol) and HBTU (162 mg, 0.427 mmol). The solution was stirred at rt. overnight. Then it was concentrated, washed with water and extracted with ethyl acetate twice. The combined organic layers were washed with brine, dried over MgSO$_4$ and concentrated. It was then purified by Prep. HPLC column to give a colorless thick oil as product. (63 mg, 46% yield)

1H NMR (400 MHz, CD$_3$OD) δ 1.01 (s, 9 H), 1.17 (s, 9 H), 2.34 (m, 1 H), 2.78 (dd, J=14.13, 7.83 Hz, 1 H), 3.72 (s, 3 H), 4.00 (dd, J=12.22, 3.42 Hz, 1 H), 4.19 (s, 1 H), 4.57 (d, J=12.23 Hz, 1 H), 4.68 (m, 1 H), 5.51 (m, 1 H), 7.27 (m, 1 H), 7.47 (d, J=8.56 Hz, 1 H), 7.57 (m, 1 H), 7.63 (d, J=8.07 Hz, 1 H).

LC-MS (retention time: 2.737 min.), MS m/z 498 (M+Na$^+$).

Step 3:

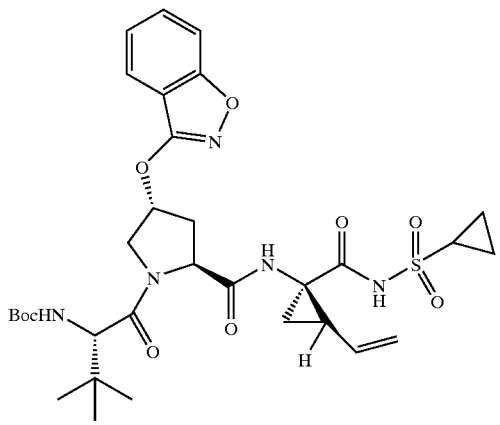

Compound 334

To a solution of 4-(Benzo[d]isoxazol-3-yloxy)-1-(2-tert-butoxycarbonylamino-3,3-dimethyl-butyryl)-pyrrolidine-2-carboxylic acid methyl ester (63 mg, 0.132 mmol) in THF (3.5 mL), methanol (2.0 mL) and water (0.5 mL) mixture, lithium hydroxide monohydrate (83 mg, 1.89 mmol) was added. The reaction mixture was stirred at rt. for overnight. Then it was acidified with 1N HCl solution to pH=3 to 5 and concentrated. Extracted with ethyl acetate (2×30 mL) and the organic layers were combined and dried (MgSO$_4$). Evaporation of solvent gave a yellowish oil to carry on. (61 mg, 100% yield)

To a solution of above compound (61 mg, 0.132 mmol) in CH$_3$CN (8 mL) was added (1R,2S) (1-cyclopropanesulfonyl-aminocarbonyl-2-vinyl-cyclopropyl)-carbamic acid hydrochloride (42 mg, 0.158 mmol), DIEA (0.115 mL, 0.66 mmol) and the coupling reagent HOBt (30 mg, 0.198 mmol) and HBTU (75 mg, 0.198 mmol). The solution was stirred at rt. overnight. Then it was concentrated, washed with water and extracted with ethyl acetate twice. The combined organic layers were washed with brine, dried over MgSO$_4$ and concentrated. It was then purified by Prep. HPLC column to give a yellow film as final product (Compound 334). (24 mg, 27% yield)

1H NMR (400 MHz, CD$_3$OD) δ 1.01 (s, 9 H), 1.05 (m, 2 H), 1.12–1.26 (m, 11 H), 1.43 (m, 1 H), 1.86 (dd, J=8.07, 5.38 Hz, 1 H), 2.17–2.33 (m, 2 H), 2.67 (dd, J=12.96, 5.87 Hz, 1 H), 2.93 (m, 1 H), 4.05 (m, 1 H), 4.22 (m, 1 H), 4.49 (m, 2 H), 5.11 (d, J=10.21 Hz, 1 H), 5.29 (d, J=17.12 Hz, 1 H), 5.55 (s, 1 H), 5.74 (m, 1 H), 7.29 (m, 1 H), 7.48 (d, J=8.32 Hz, 1 H), 7.54–7.64 (m, 2 H).

LC-MS (retention time: 2.767 min.), MS m/z 696 (M+Na$^+$).

Example 335

Preparation of Compound 335

Scheme 1:

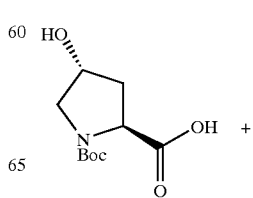

381
-continued
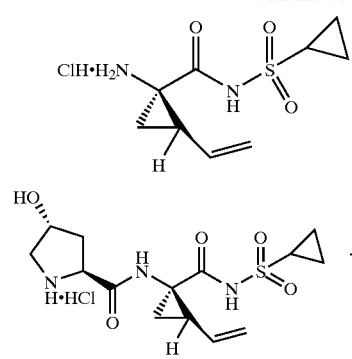
382
-continued
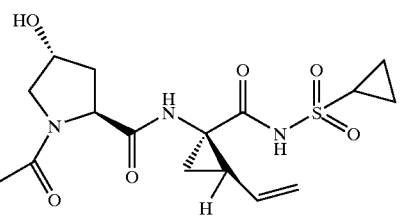
intermediate 2
Scheme 2:
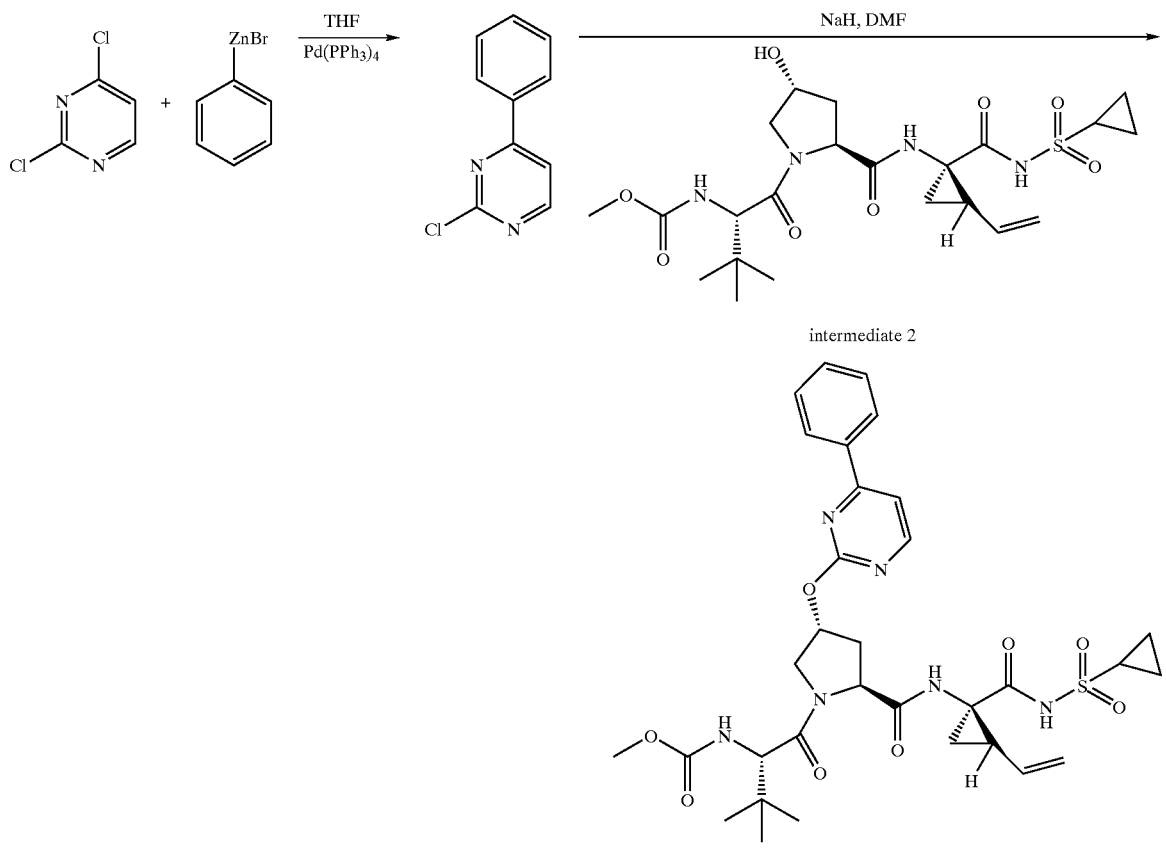
intermediate 2
Compound 335

383

Step 1: (Scheme 1, Step 1)

To a solution of (2S,4R) 4-hydroxy-pyrrolidine-1,2-dicarboxylic acid 1-tert-butyl ester (0.25 g, 1.08 mmol) in CH$_3$CN (10 mL) was added (1R, 2S) (1-cyclopropanesulfonyl-aminocarbonyl-2-vinyl-cyclopropyl)-carbamic acid hydrochloride (0.346 g, 1.30 mmol), DIEA (0.94 mL, 5.41 mmol) and the coupling reagent HOBt (0.248 g, 1.62 mmol) and HBTU (0.615 mg, 1.62 mmol). The solution was stirred at rt. overnight. Then it was concentrated, washed with water and extracted with ethyl acetate twice. The combined organic layers were washed with brine, dried over MgSO$_4$ and concentrated to give yellow oil. It was purified by Prep. HPLC column to give a colorless thick oil which was then dissolved in 4N HCl in dioxane (5 mL). The reaction mixture was stirred at rt. for overnight. Evaporation of solvent gave white solid as product to carry on. (200 mg, 49% yield)

LC-MS (retention time: 0.647 min.), MS m/z 344 (MH$^+$).

Step 2: (Scheme 1, Step 2)

To a solution of above compound (200 mg, 0.527 mmol) in CH$_3$CN (10 mL) was added 2-methoxycarbonylamino-3,3-dimethyl-butyric acid (0.15 g, 0.79 mmol), DIEA (0.46 mL, 2.63 mmol) and the coupling reagent HOBt (0.121 g, 0.79 mmol) and HBTU (0.30 g, 0.79 mmol). The solution was stirred at rt. overnight. Then it was concentrated, washed with water and extracted with ethyl acetate twice. The combined organic layers were washed with brine, dried over MgSO$_4$ and concentrated to give yellowish oil. It was purified by Prep. HPLC column to give white solid as final product (intermediate 2). (145 mg, 54% yield)

$^1$H NMR(CD$_3$OD, 500 MHz) δ 0.99–1.10 (m, 11 H), 1.24 (m, 2 H), 1.41 (dd, J=9.5, 5.5 Hz, 1 H), 1.87 (dd, J=7.9, 5.5 Hz, 1 H), 1.97 (m, 1 H), 2.13 (m, 1 H), 2.24 (m, 1 H), 2.93 (m, 1 H), 3.65 (s, 3 H), 3.77–3.88 (m, 2 H), 4.33–4.39 (m, 2 H), 4.49 (m, br, 1 H), 5.13 (d, J=10.4 Hz, 1 H), 5.31 (d, J=17.1 Hz, 1 H), 5.76 (m, 1 H).

LC-MS (retention time: 1.590 min.), MS m/z 515 (MH$^+$).

Step 3: (Scheme 2)

To a solution of 2,4-dichloropyrimidine (149 mg, 1 mmol) in THF (5 mL), tetrakis(triphenylphosphine)palladium (23 mg, 2 mol %) and 0.5M solution of phenylzinc bromide (2.1 mL, 1.05 mmol) in THF were added. The reaction mixture was stirred at 50° C. for overnight. Then it was added saturated ammonium chloride solution and extracted with EtOAc twice. The organic layers were combined, washed with water and dried (MgSO$_4$). Evaporation of solvent gave a yellow residue which was purified by Prep. HPLC to afford a yellowish oil as 2-chloro-4-phenyl-pyrimidine to carry on.

To a solution of intermediate 2 (20 mg, 0.039 mmol) in DMF (3 mL), NaH (3.9 mg: of 60% dispersion in mineral oil, 0.0975 mmol) was added at 0° C. The reaction mixture was then warmed to rt. and stirred for 1 hr. Then 2-chloro-4-phenyl-pyrimidine prepared above (18 mg as crude) was added. The reaction mixture was stirred at rt. for overnight. It was then quenched with water and extracted with EtOAc. The organic layer was separated, washed with brine and dried (MgSO$_4$). Evaporation of solvent gave yellowish oil which was then purified by Prep. HPLC to give a thick colorless oil as final product (Compound 335) as TFA salt.(5.5 mg, 18% yield)

$^1$H NMR(CD$_3$OD, 300 MHz) δ 0.92–1.12 (m, 11 H). 1.25 (m, 2 H), 1.44 (dd, J=9.2, 5.5 Hz, 1 H), 1.89 (dd, J=8.1, 5.5 Hz, 1 H), 2.17–2.37 (m, 2 H), 2.57 (m, 1 H), 2.95 (m, 1 H), 3.52 (s, 3 H), 4.14 (m, 1 H), 4.24–4.38 (m, 2 H), 4.51 (m, 1 H), 5.13 (d, J=10.2 Hz, 1 H), 5.31 (d, J=17.2 Hz, 1 H), 5.77 (m, 1 H), 5.86 (s, 1 H), 7.48–7.60 (m, 3 H), 7.66 (d, J=5.3 Hz, 1 H), 8.18 (m, 2 H), 8.60 (d, J=5.1 Hz, 1 H).

LC-MS (retention time: 1.947 min.), MS m/z 669 (MH$^+$).

384

Example 336

Preparation of Compound 336

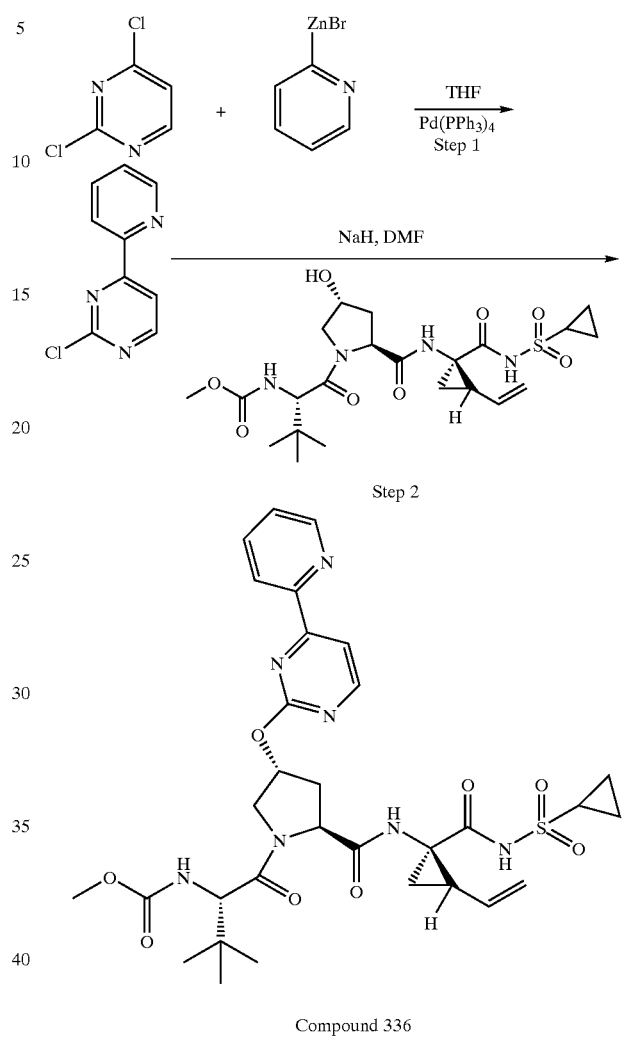

Compound 336

Step 1:

To a solution of 2,4-dichloropyrimidine (149 mg, 1 mmol) in THF (5 mL), tetrakis(triphenylphosphine)palladium (58 mg, 5 mol %) and 0.5M solution of 2-pyridinylzinc bromide (2.4 mL, 1.2 mmol) in THF were added. The reaction mixture was stirred at 50° C. for overnight. Then it was added saturated ammonium chloride solution and extracted with EtOAc twice. The organic layers were combined, washed with water and dried (MgSO$_4$). Evaporation of solvent gave a yellow residue which was purified by Prep. HPLC to afford a yellowish oil as product. (11 mg, 3.6% yield)

$^1$H NMR (500 MHz, CD$_3$OD) δ 7.61 (m, 1 H), 8.07 (m, 1 H), 8.36 (d, J=5.19 Hz, 1 H), 8.50 (d, J=7.94 Hz, 1 H), 8.75 (d, J=3.97 Hz, 1 H), 8.82 (d, J=5.19 Hz, 1 H).

LC-MS (retention time: 1.440 min.), MS m/z 192 (MH$^+$).

Step 2:

To a solution of intermediate 2 from Example 335 (15 mg, 0.029 mmol) in DMF (3 mL), NaH (1.75 mg of 60% dispersion in mineral oil, 0.0728 mmol) was added at 0° C. The reaction mixture was then warmed to rt. and stirred for 1 hr. Then 2-Chloro-4-pyridin-2-yl-pyrimidine (9.5 mg, 0.0311 mmol) was added. The reaction mixture was stirred at rt. for overnight. It was then quenched with water and extracted with EtOAc. The organic layer was separated, washed with brine and dried (MgSO₄). Evaporation of solvent gave yellowish oil which was then purified by Prep. HPLC to give a yellowish film as final product (Compound 336) as TFA salt. (3.5 mg, 15% yield)

¹H NMR(CD₃OD, 500 MHz) δ 1.03 (s, 9 H), 1.08 (m, 2 H), 1.24 (m, 2 H), 1.43 (dd, J=9.77, 5.50 Hz, 1 H), 1.89 (m, 1 H), 2.24 (m, 1 H), 2.31 (m, 1 H), 2.57 (m, 1 H), 2.95 (m, 1 H), 3.50 (s, 3 H), 4.13 (m, 1 H), 4.29 (s, 1 H), 4.36 (d, J=11.91 Hz, 1 H), 4.52 (m, 1 H), 5.13 (d, J=10.08 Hz, 1 H), 5.31 (d, J=16.79 Hz, 1 H), 5.76 (m, 1 H), 5.88 (m, 1 H), 7.64 (m, 1 H), 8.06–8.13 (m, 2 H), 8.54 (d, J=7.93 Hz, 1 H), 8.73–8.76 (m, 2 H).

LC-MS (retention time: 1.787 min.), MS m/z 670 (MH⁺).

Example 337

Preparation of Compound 337

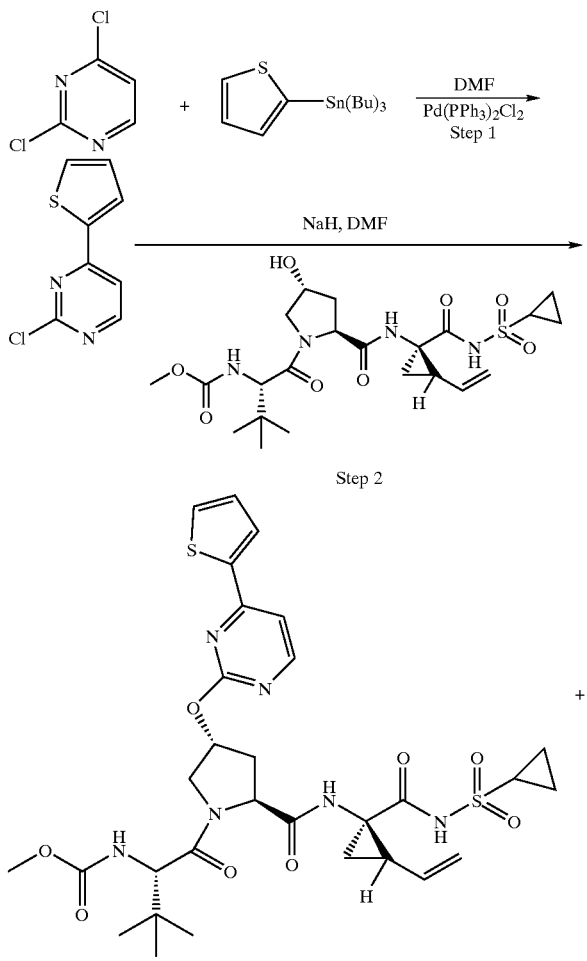

Compound 337

-continued

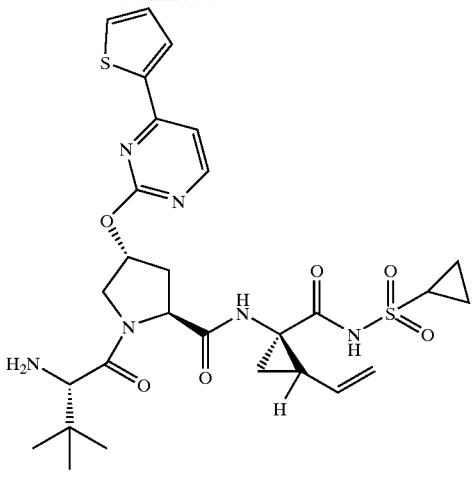

intermediate 3

To a solution of 2,4-dichloropyrimidine (149 mg, 1 mmol) in DMF (5 mL), dichloro bis(triphenylphosphine)palladium (II) (35 mg, 5 mol %) and 2-(tributylstannyl)thiophene (0.38 mL, 1.2 mmol) were added. The reaction mixture was heated at 70° C. for 3 hr. Then it was added saturated KF solution in methanol (20 mL) and stirred at rt for 4 hr. The reaction mixture was concentrated with a small amount of silica gel and the residue was filtered through filter paper and washed with EtOAc. The filtrate was then concentrated and the residue was purified by Prep. HPLC to afford an off-white solid as product. (110 mg, 35% yield)

¹H NMR (400 MHz, CD₃OD) δ 7.20 (dd, J=5.01, 3.79 Hz, 1 H), 7.74 (dd, J=5.01, 1.10 Hz, 1 H), 7.77 (d, J=5.38 Hz, 1 H), 7.98 (dd, J=3.79, 1.10 Hz, 1 H), 8.55 (d, J=5.38 Hz, 1 H).

LC-MS (retention time: 1.453 min.), MS m/z 197 (MH⁺).

Step 2:

To a solution of intermediate 2 from Example 335 (20 mg, 0.039 mmol) in DMF (3 mL), NaH (7.8 mg of 60% dispersion in mineral oil, 0.195 mmol) was added at 0° C. The reaction mixture was then warmed to rt. and stirred for 1 hr. Then 2-Chloro-4-thiophen-2-yl-pyrimidine (16.9 mg, 0.0544 mmol) was added. The reaction mixture was stirred at rt. for overnight. It was then quenched with water and extracted with EtOAc. The organic layer was separated, washed with brine and dried (MgSO₄). Evaporation of solvent gave yellowish oil which was then purified by Prep. HPLC to give two products (Compound 337 and intermediate 3).

Compoun 337: (yellowish film, 3.0 mg, 11% yield))

¹H NMR(CD₃OD, 500 MHz) 60.98–1.07 (m, 11 H), 1.22 (m, 2 H), 1.41 (dd, J=9.54, 5.62 Hz, 1 H), 1.86 (dd, J=8.32, 5.63 Hz, 1 H), 2.19–2.31 (m, 2 H), 2.52 (m, 1 H), 2.92 (m, 1 H), 3.50 (s, 3 H), 4.09 (m, 1 H), 4.25–4.32 (m, 2 H), 4.47 (dd, J=10.03, 7.34 Hz, 1 H), 5.11 (dd, J=10.27, 1.71 Hz, 1 H), 5.28 (dd, J=17.11, 1.46 Hz, 1 H), 5.69–5.79 (m, 2 H), 7.20 (dd, J=4.89, 3.66 Hz, 1 H), 7.51 (d, J=5.38 Hz, 1 H), 7.70 (d, J=4.89 Hz, 1 H), 7.95 (d, J=3.67 Hz, 1 H), 8.54 (d, J=5.14 Hz, 1 H).

LC-MS (retention time: 1.787 min.), MS m/z 696 (M+Na⁺).

Intermediate 3: (10 mg, 35% yield)

LC-MS (retention time: 1.477 min.), MS m/z 617(MH⁺).

Example 338

Preparation of Compound 338

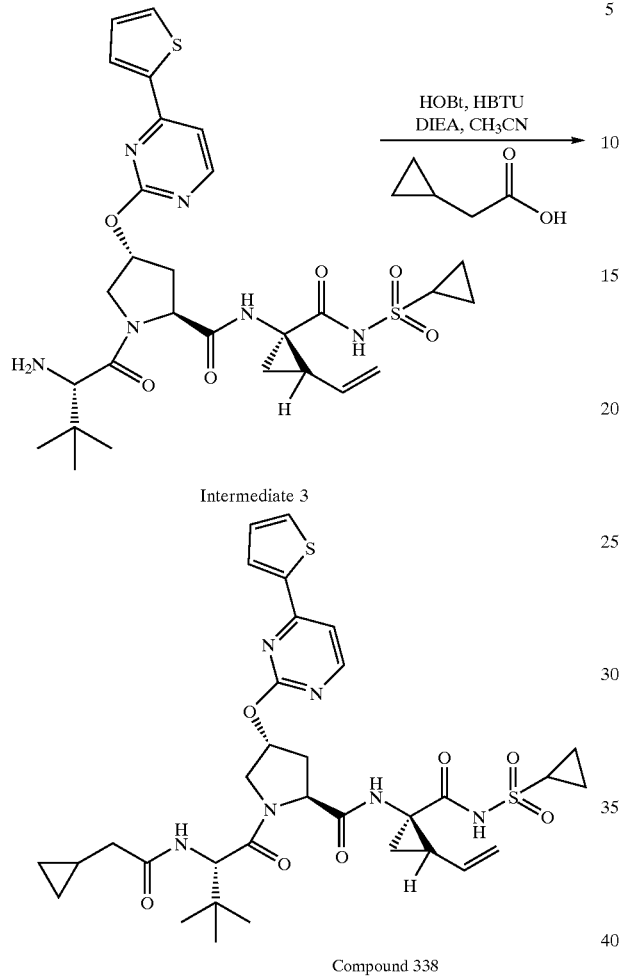

To a solution of 1-(2-Amino-3,3-dimethyl-butyryl)-4-(4-thiophen-2-yl-pyrimidin-2-yloxy)-pyrrolidine-2-carboxylic acid (1-cyclopropanesulfonylaminocarbonyl-2-vinyl-cyclopropyl)-amide (10 mg, 0.0137 mmol) in CH$_3$CN (5 mL) was added cyclopropylacetic acid (2.1 mg, 0.0205 mmol), DIEA (0.012 mL, 0.742 mmol) and the coupling reagent HOBt (3.1 g, 0.0205 mmol) and HBTU (7.8 mg, 0.0205 mmol). The solution was stirred at rt. overnight. Then it was concentrated, washed with water and extracted with ethyl acetate twice. The combined organic layers were washed with brine, dried over MgSO$_4$ and concentrated to give yellow oil. It was purified by Prep. HPLC column to give a yellowish film as TFA salt (Compound 338). (4.6 mg, 41% yield)

$^1$H NMR(CD$_3$OD, 400 MHz) δ 0.12 (m, 2 H), 0.48 (m, 2 H), 0.90 (m, 1 H), 1.01–1.09 (m, 11 H), 1.23 (m, 2 H), 1.43 (dd, J=9.29, 5.38 Hz, 1 H), 1.87 (dd, J=8.31, 5.62 Hz, 1 H), 2.06 (m, 2 H), 2.19–2.31 (m, 2 H), 2.52 (dd, J=13.45, 6.85 Hz, 1 H), 2.93 (m, 1 H), 4.12 (dd, J=11.98, 3.91 Hz, 1 H), 4.27 (d, J=11.74 Hz, 1 H), 4.47 (dd, J=10.27, 6.85 Hz, 1 H), 4.63 (s, 1 H), 5.11 (dd, J=10.27, 1.47 Hz, 1 H), 5.28 (dd, J=17.12, 1.47 Hz, 1 H), 5.71–5.80 (m, 2 H), 7.20 (dd, J=4.89, 3.67 Hz, 1 H), 7.51 (d, J=5.38 Hz, 1 H), 7.70 (d, J=5.20 Hz, 1 H), 7.95 (d, J=3.67 Hz, 1 H), 8.48 (d, J=5.13 Hz, 1 H).

LC-MS (retention time: 1.833 min.), MS m/z 699 (MH$^+$).

Example 339

Preparation of Compound 339

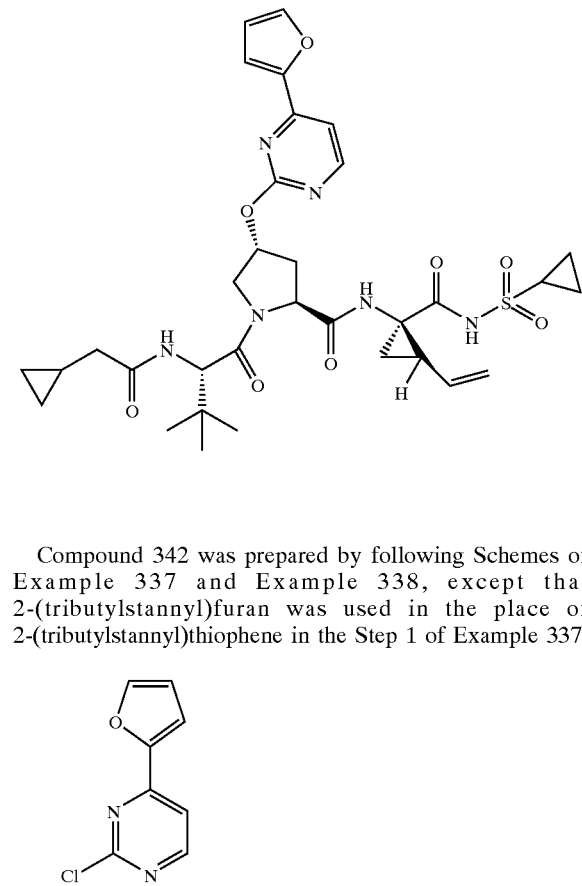

Compound 342 was prepared by following Schemes of Example 337 and Example 338, except that 2-(tributylstannyl)furan was used in the place of 2-(tributylstannyl)thiophene in the Step 1 of Example 337.

To a solution of 2,4-dichloropyrimidine (149 mg, 1 mmol) in DMF (5 mL), dichloro bis(triphenylphosphine)palladium (II) (35 mg, 5 mol %) and 2-(tributylstannyl)furan (0.35 mL, 1.1 mmol) were added. The reaction mixture was heated at 70° C. for 3 hr. Then it was added saturated KF solution in methanol (20 mL) and stirred at rt for 4 hr. The reaction mixture was concentrated with a small amount of silica gel and the residue was filtered through filter paper and washed with EtOAc. The filtrate was then concentrated and the residue was purified by Prep. HPLC to afford a brownish solid as product. (80 mg, 27% yield)

$^1$H NMR (400 MHz, CD$_3$OD) δ 6.68 (dd, J=3.67, 1.71 Hz, 1 H), 7.42 (d, J=3.67 Hz, 1 H), 7.67 (d, J=5.13 Hz, 1 H), 7.30 (d, J=1.71 Hz, 1 H), 8.62 (d, J=5.14 Hz, 1 H).

LC-MS (retention time: 1.233 min.), MS m/z 181 (MH$^+$).

Step 2:

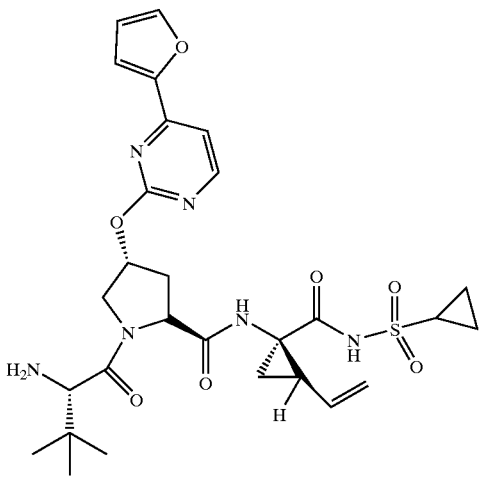

To a solution of {1-[2-(1-cyclopropanesulfonylaminocarbonyl-2-vinyl-cyclopropyl-carbamoyl)-4-hydroxy-pyrrolidine-1-carbonyl]-2,2-dimethyl-propyl}-carbamic acid methyl ester (20 mg, 0.039 mmol) in DMF (3 mL), NaH (7.8 mg of 60% dispersion in mineral oil, 0.195 mmol) was added at 0° C. The reaction mixture was then warmed to rt. and stirred for 1 hr. Then 2-Chloro-4-thiophen-2-yl-pyrimidine (16.0 mg, 0.0544 mmol) was added. The reaction mixture was stirred at rt. for overnight. It was then quenched with water and extracted with EtOAc. The organic layer was separated, washed with brine and dried (MgSO$_4$). Evaporation of solvent gave yellowish oil which was then purified by Prep. HPLC to give deboced coupling product. (3 mg, 11% yield)

LC-MS (retention time: 1.420 min.), MS m/z 601 (MH$^+$).

Step 3:

Compound 339

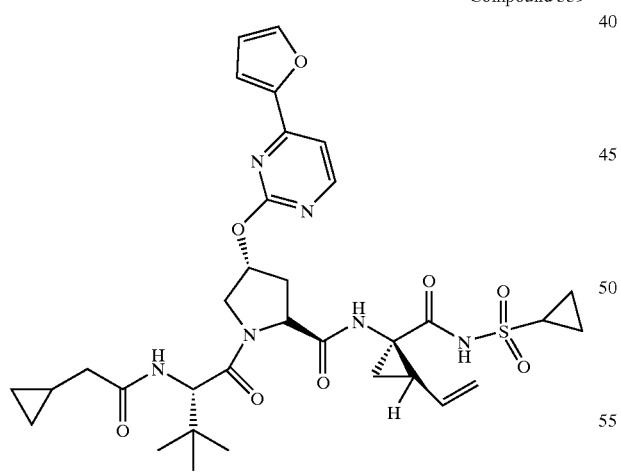

To a solution of 1-(2-Amino-3,3-dimethyl-butyryl)-4-(4-furan-2-yl-pyrimidin-2-yloxy)-pyrrolidine-2-carboxylic acid (1-cyclopropanesulfonylaminocarbonyl-2-vinyl-cyclopropyl)-amide (3 mg, 0.0042 mmol) in CH$_3$CN (5 mL) was added cyclopropylacetic acid (0.6 mg, 0.0063 mmol), DIEA (0.004 mL, 0.021 mmol) and the coupling reagent HOBt (1.0 g, 0.0063 mmol) and HBTU (2.4 mg, 0.0063 mmol). The solution was stirred at rt. overnight. Then it was concentrated, washed with water and extracted with ethyl acetate twice. The combined organic layers were washed with brine, dried over MgSO$_4$ and concentrated to give yellow oil. It was purified by Prep. HPLC column to give a yellowish film as TFA salt (Compound 339). (1.0 mg, 30% yield)

$^1$H NMR(CD$_3$OD, 400 MHz) δ 0.12 (m, 2 H), 0.48 (m, 2 H), 0.90 (m, 1 H), 0.99–1.09 (m, 11 H), 1.23 (m, 2 H), 1.43 (dd, J=9.05, 5.31 Hz, 1 H), 1.87 (m, 1 H), 2.05 (m, 2 H), 2.19–2.29 (m, 2 H), 2.50 (m, 1 H), 2.93 (m, 1 H), 4.10 (dd, J=12.23, 3.91 Hz, 1 H), 4.25 (d, J=11.99 Hz, 1 H), 4.47 (dd, J=10.52, 7.09 Hz, 1 H), 4.63 (s, 1 H), 5.11 (dd, J=10.52, 1.71 Hz, 1 H), 5.29 (dd, J=17.12, 1.47 Hz, 1 H), 5.71–5.79 (m, 2 H), 6.65 (dd, J=3.67, 1.96 Hz, 1 H), 7.38 (d, J=3.67 Hz, 1 H), 7.40 (d, J=5.38 Hz, 1 H), 7.76 (m, 1 H), 8.54 (d, J=5.38 Hz, 1 H).

LC-MS (retention time: 1.790 min.), MS m/z 683 (MH$^+$).

Example 340

Preparation of Compound 340

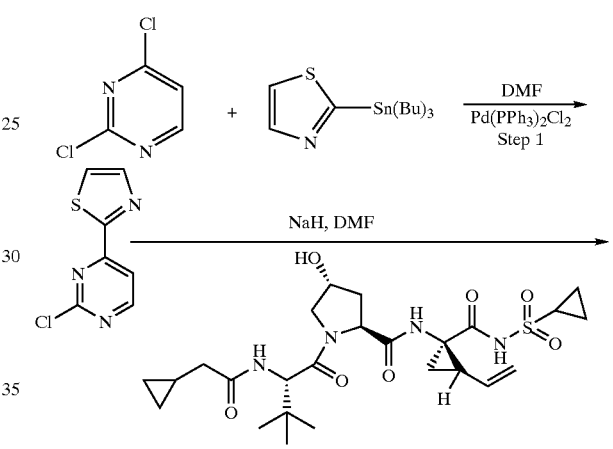

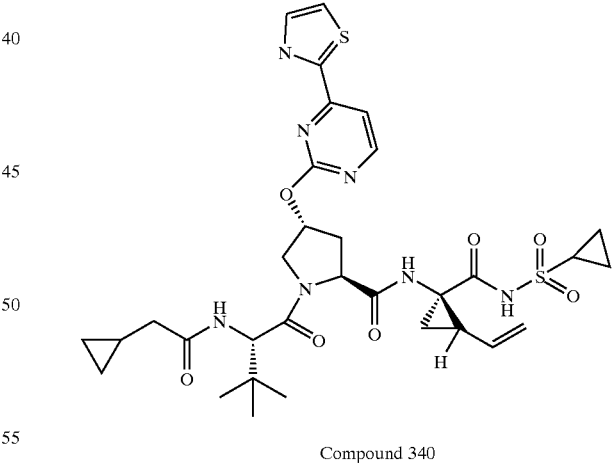

Compound 340

Step 1:

To a solution of 2,4-dichloropyrimidine (149 mg, 1 mmol) in DMF (5 mL), dichloro bis(triphenylphosphine)palladium (II) (35 mg, 5 mol %) and 2-(tributylstannyl)thiazole (412 mg, 1.1 mmol) were added. The reaction mixture was heated at 80° C. for 3 hr. Then it was added saturated KF solution in methanol (20 mL) and stirred at rt for 4 hr. The reaction mixture was concentrated with a small amount of silica gel and the residue was filtered through filter paper and washed with EtOAc. The filtrate was then concentrated and the residue was purified by Prep. HPLC to afford a brownish solid as product. (9 mg, 3% yield)

LC-MS (retention time: 1.320 min.), MS m/z 198 (MH⁺).

Step 2:

To a solution of 1-[2-(2-Cyclopropyl-acetylamino)-3,3-dimethyl-butyryl]-4-hydroxy-pyrrolidine-2-carboxylic acid (1-cyclopropanesulfonylaminocarbonyl-2-vinyl-cyclopropyl)-amide (12.5 mg, 0.0232 mmol) in DMF (3 mL), NaH (3.7 mg of 60% dispersion in mineral oil, 0.0.0928 mmol) was added at 0° C. The reaction mixture was then warmed to rt. and stirred for 1 hr. Then 2-Chloro-4-thiazole-2-yl-pyrimidine (9.0 mg, 0.0289 mmol) was added. The reaction mixture was stirred at rt. for overnight. It was then quenched with water and extracted with EtOAc. The organic layer was separated, washed with brine and dried (MgSO₄). Evaporation of solvent gave crude product which was then purified by Prep. HPLC to give white solid as final product (Compound 340). (2.8 mg, 17% yield)

$^1$H NMR(CD$_3$OD, 400 MHz) δ 0.12 (m, 2 H), 0.47 (m, 2 H), 0.89 (m, 1 H), 1.00–1.09 (m, 11 H), 1.22 (m, 2 H), 1.44 (dd, J=9.54, 5.38 Hz, 1 H), 1.87 (dd, J=8.07, 5.38 Hz, 1 H), 2.06 (m, 2 H), 2.20–2.32 (m, 2 H), 2.52 (dd, J=13.70, 6.85 Hz, 1 H), 2.93 (m, 1 H), 4.13 (dd, J=11.98, 3.91 Hz, 1 H), 4.30 (d, J=11.98 Hz, 1 H), 4.48 (dd, J=10.51, 7.09 Hz, 1 H), 4.63 (d, J=9.54 Hz, 1 H), 5.11 (d, J=10.51 Hz, 1 H), 5.29 (d, J=17.12 Hz, 1 H), 5.73–5.80 (m, 2 H), 7.81 (d, J=5.14 Hz, 1 H), 7.84 (d, J=3.18 Hz, 1 H), 8.03 (d, J=2.93 Hz, 1 H), 8.68 (d, J=5.13 Hz, 1 H).

LC-MS (retention time: 1.710 min.), MS m/z 700 (MH⁺).

Example 341

Preparation of Compound 341

Scheme 1:

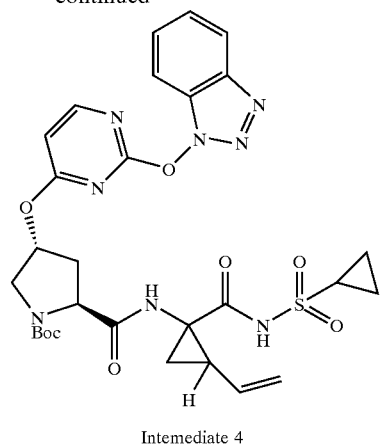

Intermediate 4

Scheme 2:

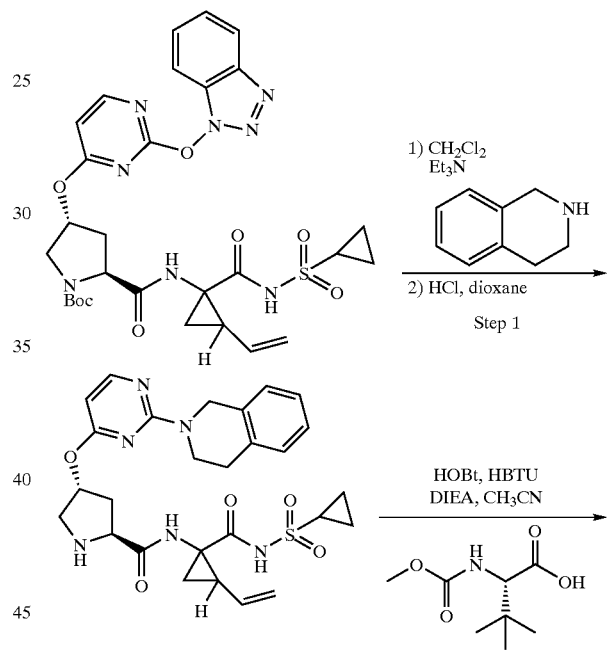

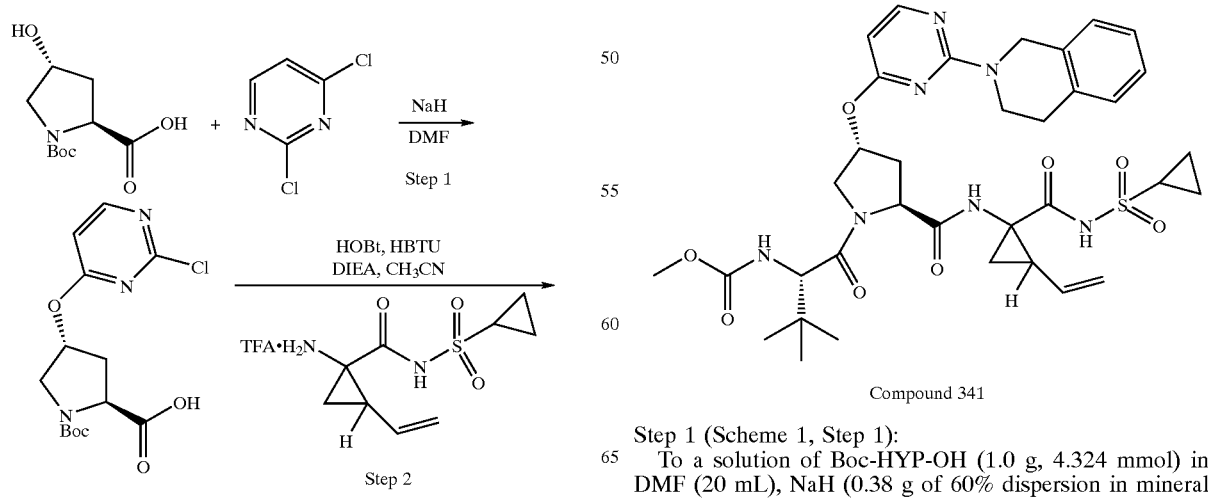

Compound 341

Step 1 (Scheme 1, Step 1):
To a solution of Boc-HYP-OH (1.0 g, 4.324 mmol) in DMF (20 mL), NaH (0.38 g of 60% dispersion in mineral oil, 9.513 mmol) was added at 0° C. The reaction mixture was stirred for 1 hr. Then 2,4-dichloropyrimidine (0.709 g, 0.0289 mmol) was added. The reaction mixture was warmed to rt and stirred for overnight. It was then quenched with 1N HCl solution and extracted with EtOAc. The organic layer was separated, washed with brine and dried (MgSO$_4$). Evaporation of solvent gave crude product which was then purified by Prep. HPLC to give colorless oil as product. (0.4 g, 27% yield)

$^1$H NMR(CD$_3$OD, 300 MHz) δ 1.13 (m, 9 H), 2.37 (m, 1 H), 2.62 (m, 1 H), 3.70–3.84 (m, 2 H), 4.38 (m, 1 H), 5.65 (m, 1 H), 6.88 (d, J=5.86 Hz, 1 H), 8.37 (d, J=5.86 Hz, 1 H).

LC-MS (retention time: 1.370 min.), MS m/z 344(MH$^+$).

Step 2: (Scheme 1, Step 2)

To a solution of (2S, 4R) 4-(2-Chloro-pyrimidin-4-yloxy)-pyrrolidine-1,2-dicarboxylic acid 1-tert-butyl ester (0.34 g, 0.99 mmol) in CH$_3$CN (20 mL) was added (1R, 2S)/(1S, 2R) (1-cyclopropanesulfonyl-aminocarbonyl-2-vinyl-cyclopropyl)-carbamic acid (0.511 g, 1.48 mmol), DIEA (0.86 mL, 4.95 mmol) and the coupling reagent HOBt (0.226 g, 1.48 mmol) and HBTU (0.561 g, 1.48 mmol). The solution was stirred at rt. overnight. Then it was concentrated, washed with water and extracted with ethyl acetate twice. The combined organic layers were washed with brine, dried over MgSO$_4$ and concentrated. It was then purified by Prep. HPLC column to give a yellow solid (intermediate 4). (0.33 g, 41% yield)

$^1$H NMR(CD$_3$OD, 300 MHz) 6 diasteoromer mixture.

LC-MS (retention time: 2.907 min.), MS m/z 655 (MH$^+$).

Step 3: (Scheme 2, Step 1)

To a solution of intermediate 4 (50 mg, 0.061 mmol) in CH$_2$Cl$_2$ (2.5 mL), 1,2,3,4-tetrahydroisoquinoline (0.011 mL, 0.0915 mmol) and Et$_3$N (0.021 mL, 0.153 mmol) were added. The reaction mixture was stirred at rt for overnight and at 40° C. for 1 day. The solvent was stripped and the residue was purified by Prep. HPLC to give a colorless oil. It was then dissolved in 4N HCl in dioxane (1 mL) and stirred for overnight. Evaporation of solvent gave a colorless oil as hydrochloride salt. (20 mg, 52% yield)

LC-MS (retention time: 1.160 min.), MS m/z 553 (MH$^+$).

Step 4: (Scheme 2, Step 2)

To a solution of 4-[2-(3,4-Dihydro-1H-isoquinolin-2-yl)-pyrimidin-4-yloxy]-pyrrolidine-2-carboxylic acid (1-cyclopropanesulfonylaminocarbonyl-2-vinyl-cyclopropyl)-amide hydrochloride (20 mg, 0.032 mmol) in CH$_3$CN (5 mL) was added 2-methoxycarbonylamino-3,3-dimethyl-butyric acid (9.1 mg, 0.048 mmol), DIEA (0.028 mL, 0.16 mmol) and the coupling reagent HOBt (7.3 mg, 0.048 mmol) and HBTU (18.2 mg, 0.048 mmol). The solution was stirred at rt. overnight. Then it was concentrated, washed with water and extracted with ethyl acetate twice. The combined organic layers were washed with brine, dried over MgSO$_4$ and concentrated to give yellowish oil. It was purified by Prep. HPLC column to give a colorless oil as TFA salt (Compound 341). (16 mg, 60% yield)

$^1$H NMR(CD$_3$OD, 500 MHz) & 0.98–1.06 (m, 13 H), 1.13 (m, 1 H), 1.22–1.32 (m, 1 H), 1.35–1.44 (m, 1 H), 1.82 (dd, J=8.24, 5.19 Hz, 0.5 H), 1.90 (dd, J=8.24, 5.49 Hz, 0.5 H), 2.26 (m, 1 H), 2.32–2.43 (m, 1 H), 2.56 (m, 1 H), 2.96 (m, 1 H), 3.11 (m, br, 2 H), 3.56 (s, 3 H), 4.14 (m, 1 H), 4.21 (m, 1 H), 4.38 (m, 1 H), 4.47 (m, 1 H), 5.15 (m, 1 H), 5.31 (m, 1 H), 5.75 (m, 1 H), 5.94 (s, 1 H), 6.47 (d, J=7.02 Hz, 1 H), 7.29 (s, 4 H), 7.49 (m, 1 H), 7.56 (m, 1 H), 7.74 (d, J=8.24 Hz, 1 H), 7.88 (d, J=8.24 Hz, 1 H), 8.11 (d, J=7.02 Hz, 1 H).

LC-MS (retention time: 1.517 min.), MS m/z 724 (MH$^+$).

Example 342

Preparation of Compound 342

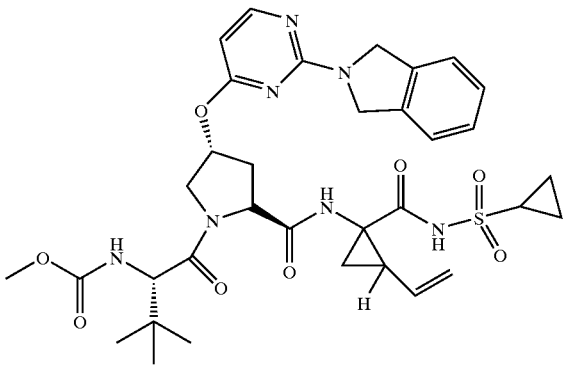

Compound 342

Compound 342 was prepared by following Scheme 2 of Example 341, except that isoindoline was used in the place of 1,2,3,4-tetrahydroisoquinoline in step 1 of scheme 2.

Step 1:

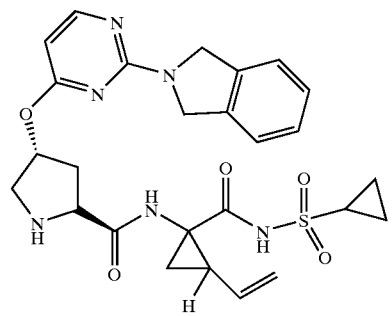

To a solution of intermediate 4 from Example 341 (50 mg, 0.061 mmol) in CH$_2$Cl$_2$ (2.5 mL), isoindoline (0.013 mL, 0.115 mmol) and Et$_3$N (0.026 mL, 0.19 mmol) were added. The reaction mixture was stirred at rt for 2 days. The solvent was stripped and the residue was purified by Prep. HPLC to give a colorless oil. It was then dissolved in 4N HCl in dioxane (1 mL) and stirred for overnight. Evaporation of solvent gave crude product which was purified by Prep.HPLC again to afford yellowish solid as TFA salt. (8.5 mg, 14% yield)

LC-MS (retention time: 1.860 min.), MS m/z 539 (MH$^+$)

Step 2:

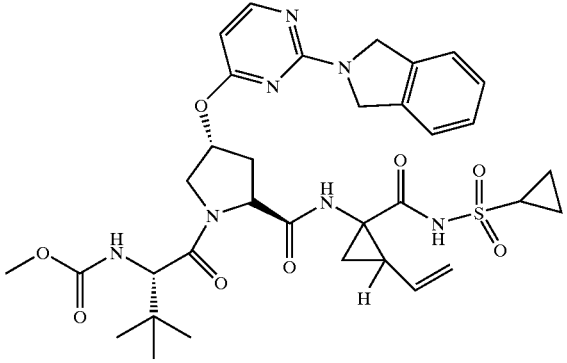

Compound 342

To a solution of 4-[2-(1,3-Dihydro-isoindol-2-yl)-pyrimidin-4-yloxy]-pyrrolidine-2-carboxylic acid (1-cyclopropanesulfonylaminocarbonyl-2-vinyl-cyclopropyl)-amide hydrochloride (8.5 mg, 0.0104 mmol) in CH₃CN (5 mL) was added 2-methoxycarbonylamino-3,3-dimethyl-butyric acid (3.0 mg, 0.0156 mmol), DIEA (0.009 mL, 0.052 mmol) and the coupling reagent HOBt (2.4 mg, 0.0156 mmol) and HBTU (5.9 mg, 0.0156 mmol). The solution was stirred at rt. overnight. Then it was concentrated, washed with water and extracted with ethyl acetate twice. The combined organic layers were washed with brine, dried over MgSO₄ and concentrated to give yellowish oil. It was purified by Prep. HPLC column to give a colorless oil as TFA salt (Compound 342). (3 mg, 35% yield)

¹H NMR(CD₃OD, 300 MHz) 6 diasteoromer mixture.

LC-MS (retention time: 2.547 min.), MS m/z 710 (MH⁺).

Example 343

Preparation of Compound 343

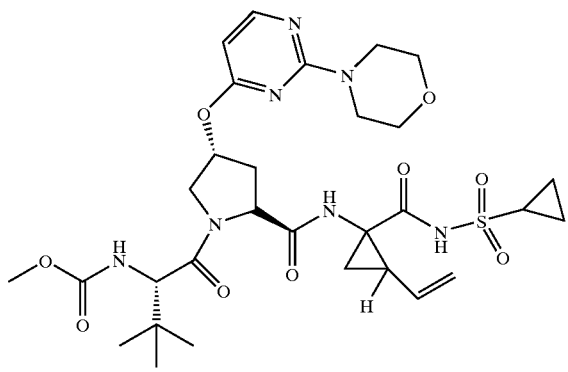

Compound 343

Compound 342 was prepared by following Scheme 2 of Example 341, except that morpholine was used in the place of 1,2,3,4-tetrahydroisoquinoline in step 1 of scheme 2.

Step 1:

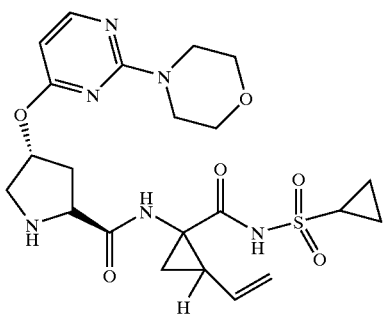

To a solution of intermediate 4 from Example 341 (50 mg, 0.061 mmol) in CH₂Cl₂ (2.5 mL), morpholine (0.008 mL, 0.0915 mmol) and Et₃N (0.021 mL, 0.153 mmol) were added. The reaction mixture was stirred at rt for overnight and at 40° C. for 1 day. The solvent was stripped and the residue was purified by Prep. HPLC to give a colorless oil. It was then dissolved in 4N HCl in dioxane (1 mL) and stirred for overnight. Evaporation of solvent gave a colorless oil as hydrochloride salt. (12.6 mg, 36% yield)

LC-MS (retention time: 0.810 min.), MS m/z 507 (MH⁺).

Step 2:

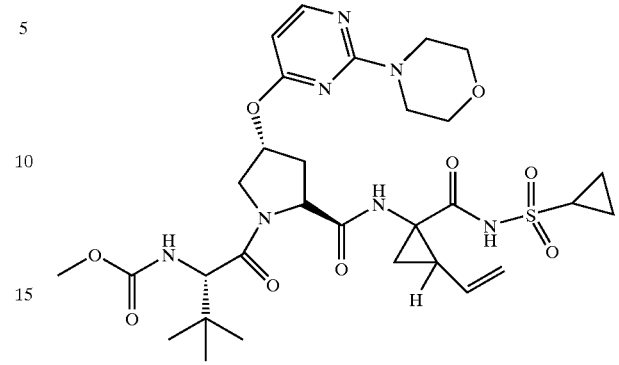

Compound 343

To a solution of 4-(2-Morpholin-4-yl-pyrimidin-4-yloxy)-pyrrolidine-2-carboxylic acid (1-cyclopropanesulfonylaminocarbonyl-2-vinyl-cyclopropyl)-amide hydrochloride (12.6 mg, 0.0217 mmol) in CH₃CN (5 mL) was added 2-methoxycarbonylamino-3,3-dimethyl-butyric acid (6.2 mg, 0.0326 mmol), DIEA (0.019 mL, 0.1085 mmol) and the coupling reagent HOBt (5.0 mg, 0.0326 mmol) and HBTU (12.4 mg, 0.0326 mmol). The solution was stirred at rt. overnight. Then it was concentrated, washed with water and extracted with ethyl acetate twice. The combined organic layers were washed with brine, dried over MgSO₄ and concentrated to give yellowish oil. It was purified by Prep. HPLC column to give a colorless oil as TFA salt (Compound 343). (7 mg, 41% yield)

¹H NMR(CD₃OD, 500 MHz) δ diasteoromer mixture.

LC-MS (retention time: 1.280 min.), MS m/z 678 (MH⁺).

Example 344

Preparation of Compound 344

Scheme 1:

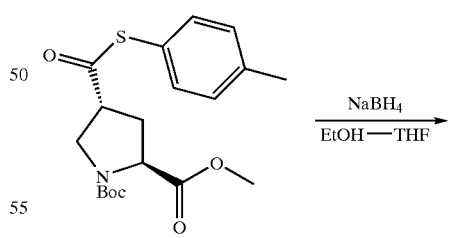

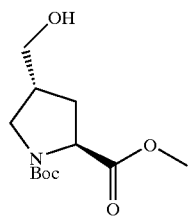

intermediate 5

Scheme 2:

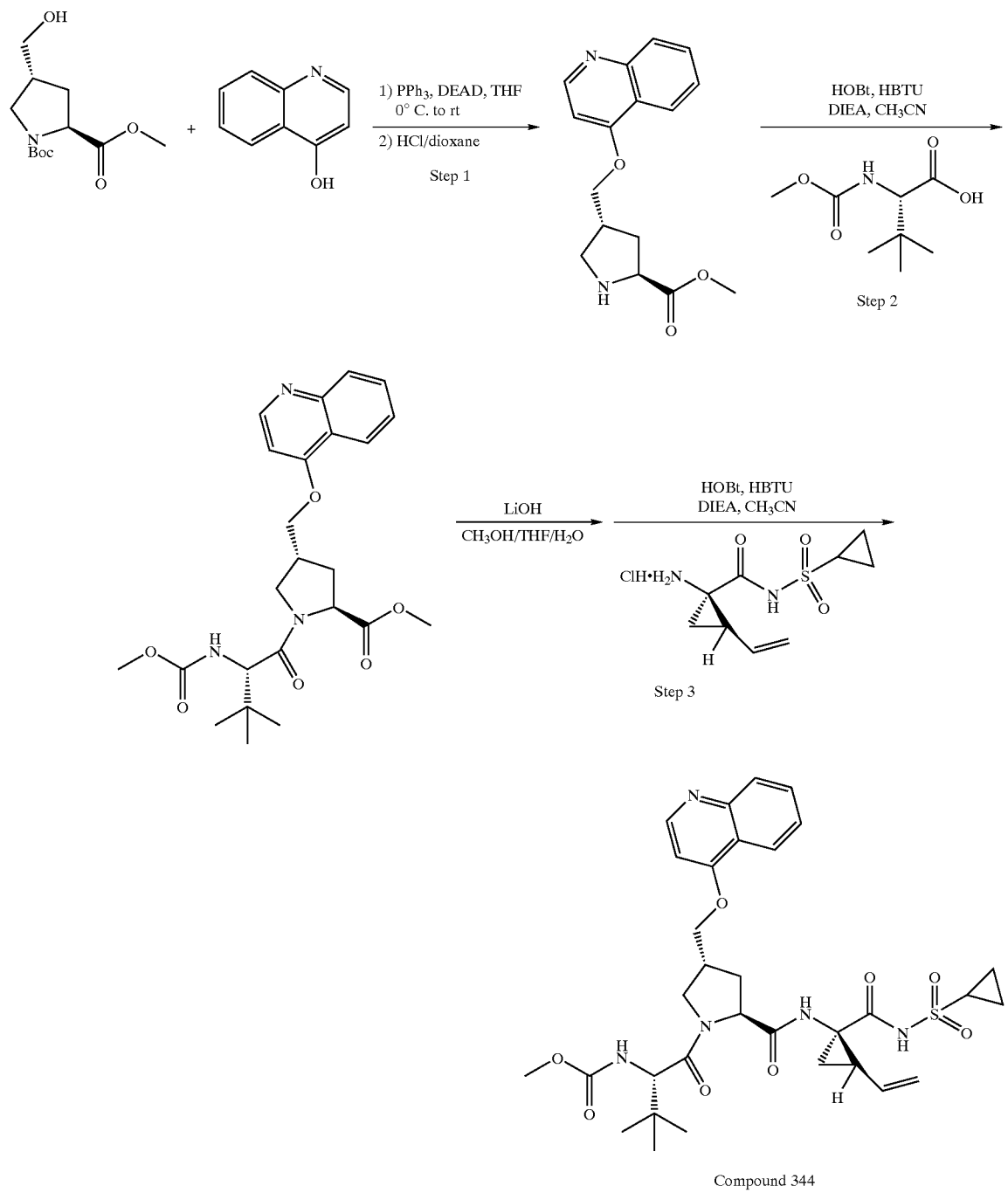

Compound 344

To a solution of 4-p-tolylsulfanylcarbonyl-pyrrolidine-1,2-dicarboxylic acid 1-tert-butyl ester 2-methyl ester (3.0 g, 7.91 mmol) in ethanol (15 mL) and THF (30 mL) mixture, sodium borohydride (0.6 g, 15.8 mmol) was added. The reaction mixture was stirred at rt. for overnight. Then it was concentrated, washed with 1 N HCl solution and extracted with EtOAc three times. The organic layers were combined, washed with saturated $NaHCO_3$ solution and dried ($MgSO_4$). Evaporation of solvent gave yellowish oil which was purified by flash column chromatography (silica gel, 3:1 EtOAc: Hexanes) to afford colorless oil as product (intermediate 5). (1.77 g, 86% yield)

$^1$H NMR ($CD_3OD$, 500 MHz) δ 1.43 (m, 9 H), 2.00–2.13 (m, 2 H), 2.46 (m, 1 H), 3.19 (m, 1 H), 3.47–3.53 (m, 2 H), 3.61 (m, 1 H), 3.73 (m, 3 H), 4.31 (m, 1 H).

LC-MS (retention time: 1.240 min.), MS m/z 282 (M+Na⁺).

Step 2: (Scheme 2, Step 1)

To a solution of intermediate 5 (80 mg, 0.309 mmol) in THF (10 mL) at 0° C., triphenylphosphine (121.4 mg, 0.463 mmol) and 4-hydroxyquinoline (67.2 mg, 0.463 mmol) were added. Then DEAD (80.6 mg, 0.463 mmol) was added. The reaction mixture was warmed to rt. and stirred for 2 days. Then solvent was evaporated and the residue was purified by Prep. HPLC to give colorless oil. It was then dissolved in 4N HCl in dioxane (3 mL) and stirred for 2 hr. Evaporation of solvent gave thick colorless oil as bis HCl salt. (110 mg, 99% yield)

¹H NMR (500 MHz, CD₃OD) δ 2.52 (m, 1 H). 2.60 (m, 1 H), 3.19 (m, 1 H), 3.45 (m, 1 H), 3.66 (s, 3 H), 3.86 (m, 1 H), 4.61–4.75 (m, 3 H), 7.56 (d, J=6.7 Hz, 1 H), 7.94 (t, J=7.3 Hz, 1 H), 8.10–8.20 (m, 2 H), 8.55 (d, J=8.2 Hz, 1 H), 9.07 (d, J=6.7 Hz, 1 H).

LC-MS (retention time: 0.570 min.), MS m/z 287 (MH⁺).

Step 3: (Scheme 2, Step 2)

To a solution of 4-(quinolin-4-yloxymethyl)-pyrrolidine-2-carboxylic acid methyl ester bis hydrochloride salt (110 mg, 0.306 mmol) in CH₃CN (10 mL) was added 2-methoxycarbonylamino-3,3-dimethyl-butyric acid (87 mg, 0.46 mmol), DIEA (0.27 mL, 1.53 mmol) and the coupling reagent HOBt (70 mg, 0.46 mmol) and HBTU (174 mg, 0.46 mmol). The solution was stirred at rt. overnight. Then it was concentrated, washed with water and extracted with ethyl acetate twice. The combined organic layers were washed with brine, dried over MgSO₄ and concentrated to give yellowish oil. It was purified by Prep. HPLC column to give colorless oil as TFA salt. (105 mg, 60% yield)

¹H NMR (CD₃OD, 500 MHz) δ 1.07 (s, 9 H). 2.34 (m, 1 H), 2.45 (m, 1 H), 3.14 (m, 1 H), 3.27 (s, 3 H), 3.75 (s, 3 H), 4.05 (m, 1 H), 4.20 (m, 1 H), 4.31 (s, 1 H), 4.57–4.63 (m, 2 H), 4.73 (m, 1 H), 7.53 (d, J=6.7 Hz, 1 H), 7.91 (t, J=7.6 Hz, 1 H), 8.06–8.16 (m, 2 H), 8.43 (d, J=8.6 Hz, 1 H), 9.02 (d, J=6.4 Hz, 1 H).

LC-MS (retention time: 1.250 min.), MS m/z 458 (MH⁺).

Step 4:(Scheme 2, Step 3)

To a solution of 1-(2-Methoxycarbonylamino-3,3-dimethyl-butyryl)-4-(quinolin-4-yloxymethyl)-pyrrolidine-2-carboxylic acid methyl ester (100 mg, 0.175 mmol) in THF (6 mL), methanol (3.25 mL) and water (1.0 mL) mixture, lithium hydroxide monohydrate (110 mg, 2.62 mmol) was added. The reaction mixture was stirred at rt. for overnight. Then it was acidified with 1N HCl solution to pH=3 to 5 and concentrated. Extracted with ethyl acetate (3×40 mL) and the organic layers were combined and dried (MgSO₄). Evaporation of solvent gave thick colorless oil to carry on (25 mg, 32% yield).

To a solution of above compound (25 mg, 0.056 mmol) in CH₃CN (5 mL) was added (1R,2S) (1-cyclopropanesulfonyl-aminocarbonyl-2-vinyl-cyclopropyl)-carbamic acid hydrochloride (22.5 mg, 0.085 mmol), DIEA (0.05 mL, 0.28 mmol) and the coupling reagent HOBt (12.9 mg, 0.085 mmol) and HBTU (32 mg, 0.085 mmol). The solution was stirred at rt. overnight. Then it was concentrated, washed with water and extracted with ethyl acetate twice. The combined organic layers were washed with brine, dried over MgSO₄ and concentrated to give yellow oil. It was purified by Prep. HPLC column to give colorless thick oil as TFA salt (Compound 344). (20 mg, 46% yield)

¹H NMR(CD₃OD, 500 MHz) δ 1.02–1.10 (m, 11 H), 1.24 (m, 2 H), 1.40 (dd, J=9.2, 5.5 Hz, 1 H), 1.90 (dd, J=7.9, 5.5 Hz, 1 H), 2.19–2.38 (m, 3 H), 2.95 (m, 1 H), 3.19 (m, 1 H), 3.28 (s, 3 H), 4.10 (m, 1 H), 4.15 (m, 1 H), 4.34 (s, 1 H), 4.55 (m, 1 H), 4.62 (d, J=4.6 Hz, 2 H), 5.15 (d, J=10.7 Hz, 1 H), 5.30 (d, J=17.1 Hz, 1 H), 5.72 (m, 1 H), 7.54 (d, J=6.7 Hz, 1 H), 7.93 (m, 1 H), 8.07–8.18 (m, 2 H), 8.41 (d, J=8.6 Hz, 1 H), 9.03 (d, J=6.7 Hz, 1 H), 9.09 (s, 1 H).

LC-MS (retention time: 1.617 min.), MS m/z 656 (MH⁺).

Example 345

Preparation of Compound 345

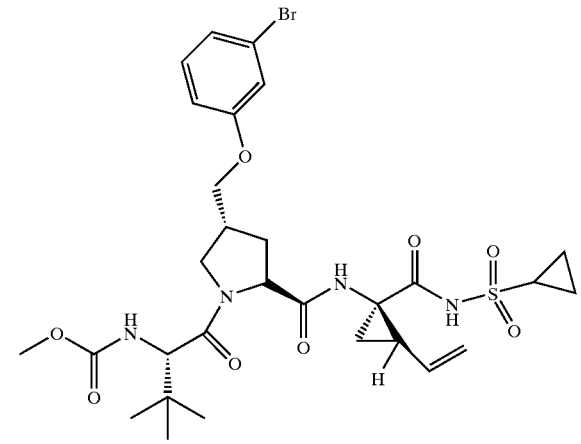

Compound 345

Compound 345 was prepared by following Scheme 2 of Example 344, except that 3-bromophenol was used in the place of 4-hydroxyquinoline in step 1 of scheme 2.

Step 1:

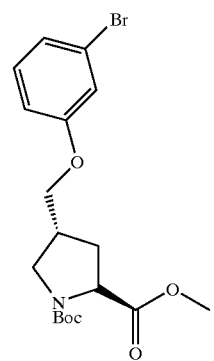

To a solution of Intermediate 5 from Example 344 (150 mg, 0.578 mmol) in THF (15 mL) at 0° C., triphenylphosphine (228 mg, 0.868 mmol) and 3-bromophenol (150 mg, 0.868 mmol) were added. Then DEAD (0.14 mL, 0.868 mmol) was added. The reaction mixture was warmed to rt. and stirred for 2 days. Then solvent was evaporated and the residue was purified by Prep. HPLC to give colorless oil as product. (105 mg, 44% yield)

LC-MS (retention time: 2.023 min.), MS m/z 436 (M+Na⁺).

Step 2:

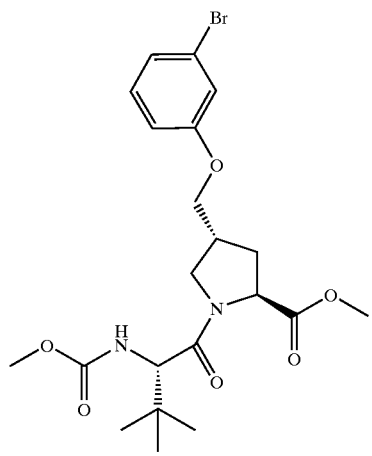

4-(3-Bromo-phenoxymethyl)-pyrrolidine-1,2-dicarboxylic acid 1-tert-butyl ester 2-methyl ester (35 mg, 0.085 mmol) was dissolved in 4N HCl in dioxane (1.5 mL) and stirred for 2 hr. Evaporation of solvent gave thick colorless oil. To a solution of this oil in CH$_3$CN (10 mL) was added 2-methoxycarbonylamino-3,3-dimethyl-butyric acid (21.9 mg, 0.1155 mmol), DIEA (0.067 mL, 0.385 mmol) and the coupling reagent HOBt (17.7 mg, 0.1155 mmol) and HBTU (43.8 mg, 0.1155 mmol). The solution was stirred at rt. overnight. Then it was concentrated, washed with water and extracted with ethyl acetate twice. The combined organic layers were washed with brine, dried over MgSO$_4$ and concentrated. It was then purified by Prep. HPLC column to give colorless oil as product. (20 mg, 49% yield)

$^1$H NMR (CD$_3$OD, 400 MHz) δ 1.03 (s, 9 H), 2.15 (m, 1 H), 2.24 (m, 1 H), 2.83 (m, 1 H), 3.54 (s, 3 H), 3.70 (s, 3 H), 3.87 (m, 1 H), 3.91–3.98 (m, 3 H), 4.31 (s, 1 H), 4.59 (dd, J=8.80, 5.38 Hz, 1 H), 6.89 (d, J=8.32 Hz, 1 H), 7.03–7.10 (m, 2 H), 7.15 (t, J=8.07 Hz, 1 H).

LC-MS (retention time: 1.943 min.), MS r/z 485 (MH$^+$).

Step 3:

Compound 345

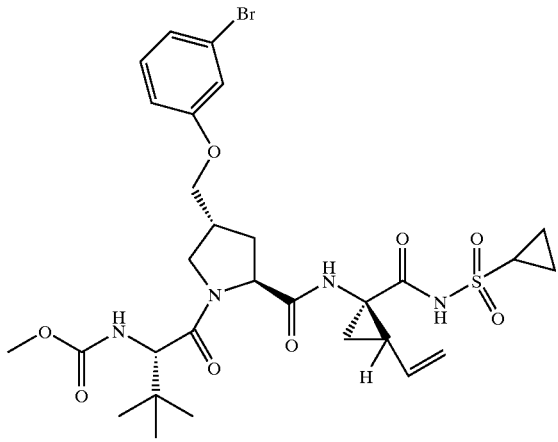

To a solution of 4-(3-Bromo-phenoxymethyl)-1-(2-methoxycarbonylamino-3,3-dimethyl-butyryl)-pyrrolidine-2-carboxylic acid methyl ester (17 mg, 0.035 mmol) in THF (1.5 mL), methanol (0.8 mL) and water (0.25 mL) mixture, lithium hydroxide monohydrate (22 mg, 0.525 mmol) was added. The reaction mixture was stirred at rt. for 3 days.

Then it was acidified with 1N HCl solution to pH=3 to 5 and concentrated. Extracted with ethyl acetate (2×20 mL) and the organic layers were combined and dried (MgSO$_4$). Evaporation of solvent gave thick colorless oil to carry on (15 mg, 91% yield).

To a solution of above acid (15 mg, 0.0318 mmol) in CH$_3$CN (5 mL) was added (1R,2S)(1-cyclopropanesulfonyl-aminocarbonyl-2-vinyl-cyclopropyl)-carbamic acid hydrochloride (12.7 mg, 0.0477 mmol), DIEA (0.028 mL, 0.159 mmol) and the coupling reagent HOBt (7.3 mg, 0.0477 mmol) and HBTU (18.1 mg, 0.0477 mmol). The solution was stirred at rt. overnight. Then it was concentrated, washed with water and extracted with ethyl acetate twice. The combined organic layers were washed with brine, dried over MgSO$_4$ and concentrated. It was then purified by Prep. HPLC column to give colorless thick oil as final product (Compound 345). (14 mg, 64% yield)

$^1$H NMR(CD$_3$OD, 400 MHz) δ 1.00–1.06 (m, 11 H), 1.21 (m, 2 H), 1.37 (dd, J=9.53 Hz, 5.62 Hz, 1 H), 1.86 (dd, J=8.07 Hz, 5.62 Hz, 1 H), 2.06 (m, 1 H), 2.14–2.24 (m, 2 H), 2.81–2.94 (m, 2 H), 3.53 (s, 3 H), 3.91–3.97 (m, 4 H), 4.33 (s, 1 H), 4.38 (m, 1 H), 5.11 (dd, J=10.27, 1.47 Hz, 1 H), 5.28 (dd, J=17.12, 1.22 Hz, 1 H), 5.70 (m, 1 H), 6.89 (m, 1 H), 7.05–7.11 (m, 2 H), 7.16 (t, J=8.07 Hz, 1 H).

LC-MS (retention time: 3.500 min.), MS m/z 683 (MH$^+$).

Example 346

Preparation of Compound 346

Scheme 1:

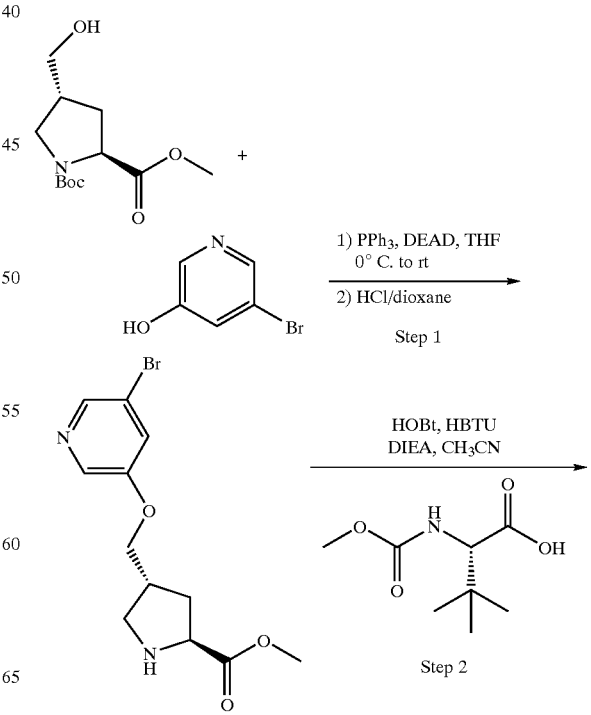

-continued

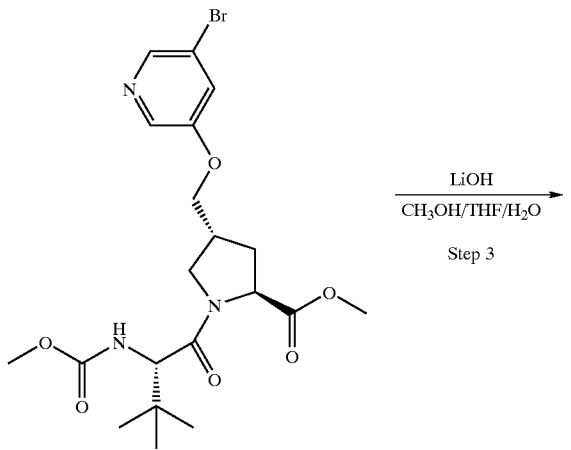

Scheme 2:

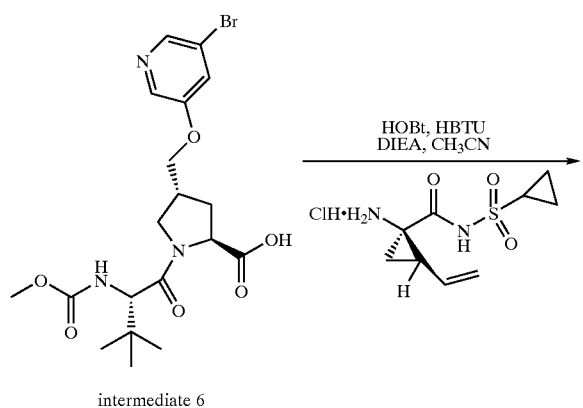

intermediate 6

-continued

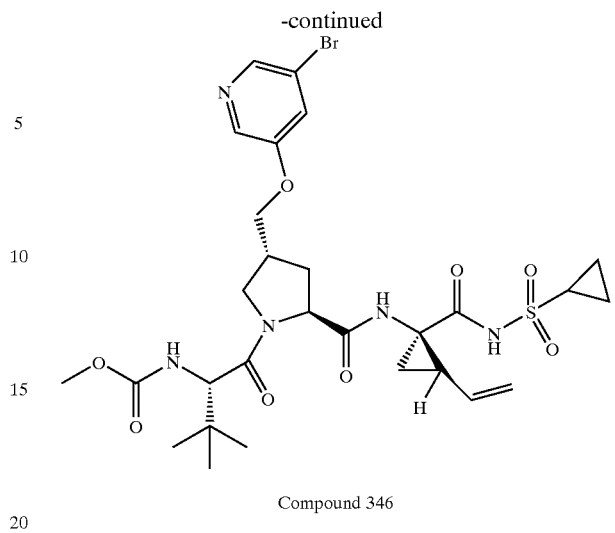

Compound 346

Step 1: (Scheme 1, Step 1)
To a solution of 4-hydroxymethyl-pyrrolidine-1,2-dicarboxylic acid 1-tert-butyl ester 2-methyl ester (300 mg, 1.157 mmol) in THF (15 mL) at 0° C., triphenylphosphine (455 mg, 1.735 mmol) and 5-bromo-pyridin-3-ol (prepared according to F. E. Ziegler et al., J. Am. Chem. Soc., (1973), 95, 7458) (302 mg, 1.735 mmol) were added. Then DEAD (0.273 mL, 1.735 mmol) was added. The reaction mixture was warmed tort. and stirred for 2 days. Then solvent was evaporated and the residue was purified by Prep. HPLC to give a yellowish oil. Then it was dissolved in 4N HCl solution in dioxane (3.0 mL) and stirred for 4 hr. Evaporation of solvent gave crude product which was further purified by Prep. HPLC to afford a yellowish oil as TFA salt. (70 mg, 11% yield)

LC-MS (retention time: 0.890 min.), MS m/z 315 (MH$^+$).
Step 2: (Scheme 1, Step 2)
To a solution of 4-(5-Bromo-pyridin-3-yloxymethyl)-pyrrolidine-2-carboxylic acid methyl ester (70 mg, 0.129 mmol) in CH$_3$CN (10 mL) was added 2-methoxycarbonylamino-3,3-dimethyl-butyric acid (36.5 mg, 0.193 mmol), DIEA (0.135 mL, 0.744 mmol) and the coupling reagent HOBt (30 mg, 0.193 mmol) and HBTU (73 mg, 0.193 mmol). The solution was stirred at rt. overnight. Then it was concentrated, washed with water and extracted with ethyl acetate twice. The combined organic layers were washed with brine, dried over MgSO$_4$ and concentrated. It was then purified by Prep. HPLC column to give colorless oil as product. (80 mg, 100% yield)

$^1$H NMR (CD$_3$OD, 400 MHz) δ 1.04 (s, 9 H), 2.17 (m, 1 H), 2.26 (m, 1 H), 2.87 (m, 1 H), 3.50 (s, 3 H), 3.70 (s, 3 H), 3.88–3.98 (m, 2 H), 4.04–4.12 (m, 2 H), 4.28 (s, 1 H), 4.60 (dd, J=9.05, 5.87 Hz, 1 H), 7.86 (m, 1 H) 8.31–8.35 (m, 2 H).

LC-MS (retention time: 1.697 min.), MS m/z 486 (MH$^+$).
Step 3: (Scheme 1, Step 3)
To a solution of 4-(5-Bromo-pyridin-3-yloxymethyl)-1-(2-methoxycarbonylamino-3,3-dimethyl-butyryl)-pyrrolidine-2-carboxylic acid methyl ester (80 mg, 0.133 mmol) in THF (5.6 mL), methanol (3 mL) and water (1 mL) mixture, lithium hydroxide monohydrate (84 mg, 2.0 mmol) was added. The reaction mixture was stirred at rt. for 3 days. Then it was acidified with 1N HCl solution to pH=3 to 5. Extracted with ethyl acetate (2×20 mL) and the organic layers were combined and dried (MgSO$_4$). Evaporation of solvent gave thick colorless oil as product (intermediate 6) (50 mg, 80% yield).

<sup>1</sup>H NMR (CD<sub>3</sub>OD, 400 MHz) δ 1.04 (s, 9 H), 2.16–2.30 (m, 2 H), 2.88 (m, 1 H), 3.51 (s, 3 H), 3.92 (m, 2 H), 4.07 (m, 2 H), 4.29 (s, 1 H), 4.57 (dd, J=8.56, 5.87 Hz, 1 H), 7.79 (m, 1 H) 8.29 (m, 2 H).

LC-MS (retention time: 1.590 min.), MS m/z 472 (MH$^+$).

Step 4: (Scheme 2)

To a solution of 4-(5-Bromo-pyridin-3-yloxymethyl)-1-(2-methoxycarbonylamino-3,3-dimethyl-butyryl)-pyrrolidine-2-carboxylic acid (5 mg, 0.0106 mmol) in CH<sub>3</sub>CN (5 mL) was added (1R, 2S)(1-cyclopropanesulfonyl-aminocarbonyl-2-vinyl-cyclopropyl)-carbamic acid hydrochloride (4.2 mg, 0.0159 mmol), DIEA (0.009 mL, 0.053 mmol) and the coupling reagent HOBt (2.4 mg, 0.0159 mmol) and HBTU (6.0 mg, 0.0159 mmol). The solution was stirred at rt. overnight. Then it was concentrated, washed with water and extracted with ethyl acetate twice. The combined organic layers were washed with brine, dried over MgSO<sub>4</sub> and concentrated. It was then purified by Prep. HPLC column to give colorless thick oil as final product (Compound 346). (2 mg, 24% yield)

<sup>1</sup>H NMR(CD<sub>3</sub>OD, 400 MHz) δ 1.00–1.07 (m, 11 H), 1.20 (m, 2 H), 1.37 (dd, J=9.29 Hz, 5.14 Hz, 1 H), 1.86 (dd, J=8.07 Hz, 5.38 Hz, 1 H), 2.08 (m, 1 H), 2.15–2.25 (m, 2 H), 2.87–2.94 (m, 2 H), 3.51 (s, 3 H), 3.92–3.97 (m, 2 H), 4.02–4.07 (m, 2 H), 4.31 (s, 1 H), 4.39 (m, 1 H), 5.10 (dd, J=10.27, 1.47 Hz, 1 H), 5.28 (dd, J=17.12, 1.46 Hz, 1 H), 5.70 (m, 1 H), 7.68 (m, 1 H), 8.24 (m, 2 H).

LC-MS (retention time: 1.727 min.), MS m/z 684 (MH$^+$).

Example 347

Preparation of Compound 347

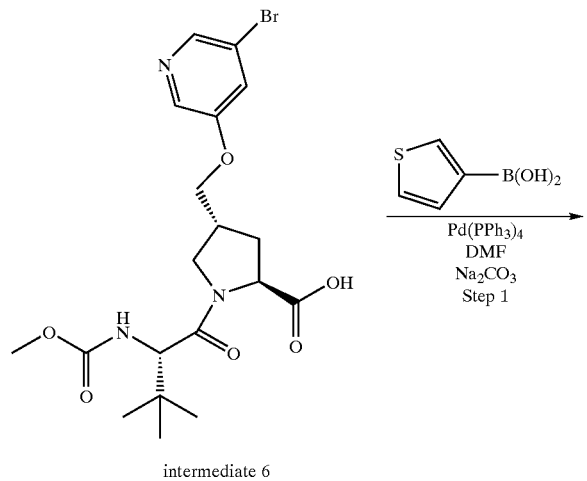

intermediate 6

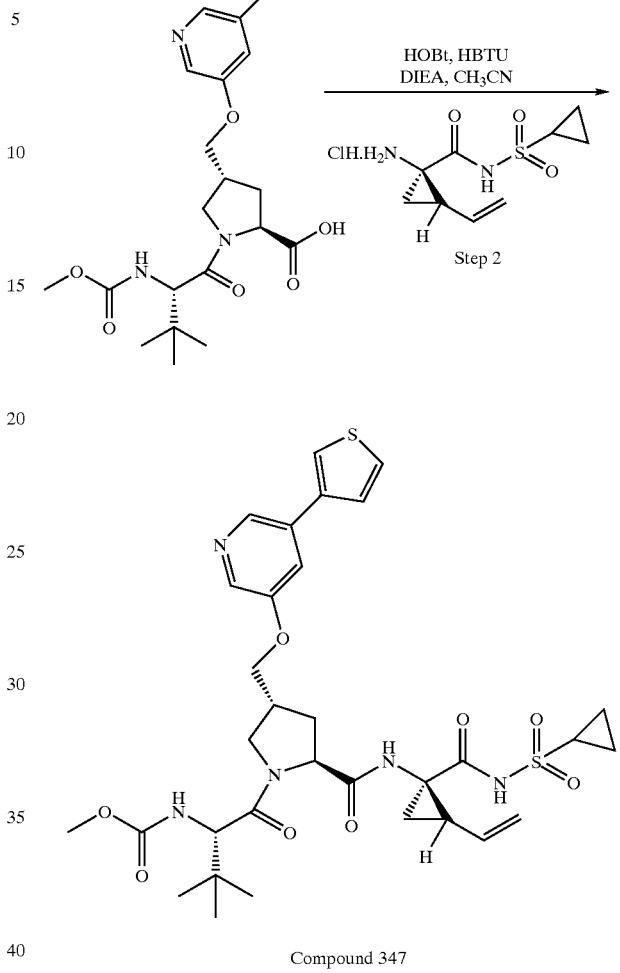

Compound 347

Step 1:

To a solution of intermediate 6 from Example 346 (16 mg, 0.0339 mmol) in DMF (1 mL), 3-thiopheneboronic acid (5.6 mg, 0.044 mmol), tetrakis(triphenylphosphine)palladium (2.0 mg, 0.0017 mmol) and 2M Na<sub>2</sub>CO<sub>3</sub> solution (0.051 mL, 0.1017 mmol) were added. The reaction mixture was heated at 110° C. for 4 hr. Then it was filtered and washed with methanol. The filtrate was concentrated and purified by Prep.HPLC to give brownish oil as product. (6 mg, 37% yield)

<sup>1</sup>H NMR (CD<sub>3</sub>OD, 400 MHz) δ 1.05 (s, 9 H), 2.21–2.30 (m, 2 H), 2.95 (m, 1 H), 3.42 (s, 3 H), 3.93 (m, 1 H), 4.01 (m, 1 H), 4.20–4.30 (m, 3 H), 4.60 (dd, J=8.56, 5.87 Hz, 1 H), 7.64 (m, 2 H), 8.12 (m, 1 H) 8.37 (m, 1 H), 8.45 (m, 1 H), 8.75 (s, 1 H).

LC-MS (retention time: 1.353 min.), MS m/z 476 (MH$^+$).

Step 2:

To a solution of 1-(2-Methoxycarbonylamino-3,3-dimethyl-butyryl)-4-(5-thiophen-3-yl-pyridin-3-yloxymethyl)-pyrrolidine-2-carboxylic acid (6 mg, 0.0126 mmol) in CH<sub>3</sub>CN (5 mL) was added (1R, 2S)(1-cyclopropanesulfonyl-aminocarbonyl-2-vinyl-cyclopropyl)-carbamic acid hydrochloride (5.0 mg, 0.0189 mmol), DIEA (0.011 mL, 0.063 mmol) and the coupling reagent HOBt (2.9 mg, 0.0189 mmol) and HBTU (7.2 mg, 0.0189 mmol). The solution was stirred at rt. overnight.

Then it was concentrated, washed with water and extracted with ethyl acetate twice. The combined organic layers were washed with brine, dried over MgSO$_4$ and concentrated. It was then purified by Prep. HPLC column to give yellowish film as TFA salt (Compound 347). (2.2 mg, 22% yield)

$^1$H NMR(CD$_3$OD, 400 MHz) δ 1.01–1.07 (m, 11 H), 1.19 (m, 2 H), 1.36 (m, 1 H), 1.88 (dd, J=8.07 Hz, 5.62 Hz, 1 H), 2.09–2.24 (m, 3 H), 2.91 (m, 1 H), 3.00 (m, 1 H), 3.45 (s, 3 H), 3.98 (d, J=5.86 Hz, 2 H), 4.20–4.31 (m, 3 H), 4.43 (m, 1 H), 5.12 (dd, J=10.27, 1.71 Hz, 1 H), 5.29 (dd, J=17.12, 1.22 Hz, 1 H), 5.69 (m, 1 H), 7.64 (m, 2 H), 8.11 (m, 1 H), 8.31 (m, 1 H), 8.43 (m, 1 H), 8.75 (s, 1 H).

LC-MS (retention time: 1.540 min.), MS m/z 688 (MH$^+$).

Example 348

Preparation of Compound 348

Scheme 1:

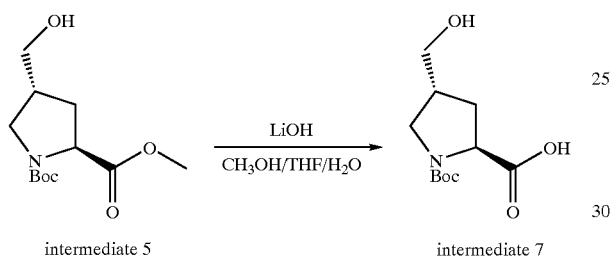

intermediate 5 → intermediate 7

Scheme 2:

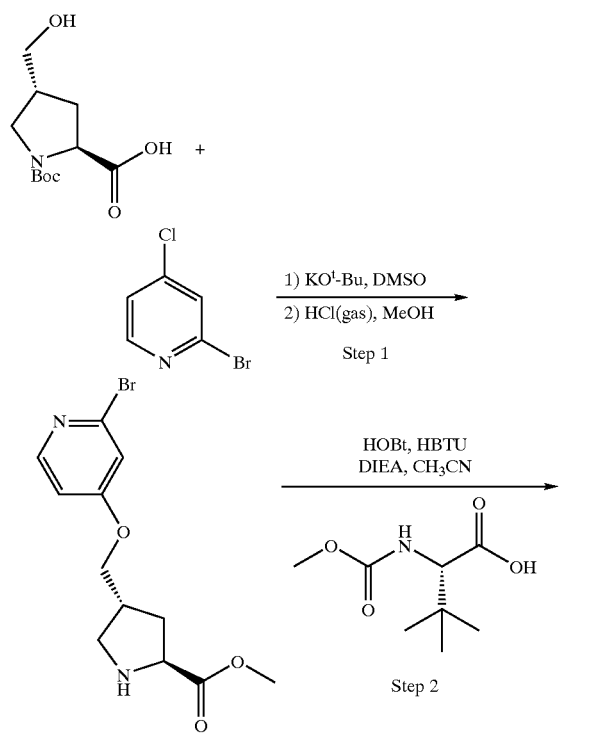

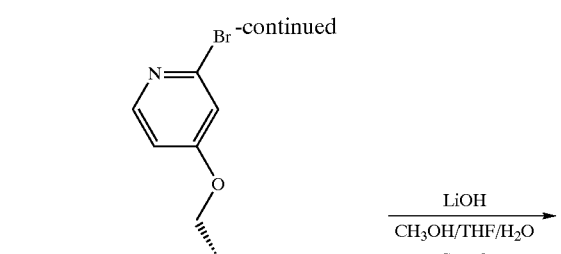

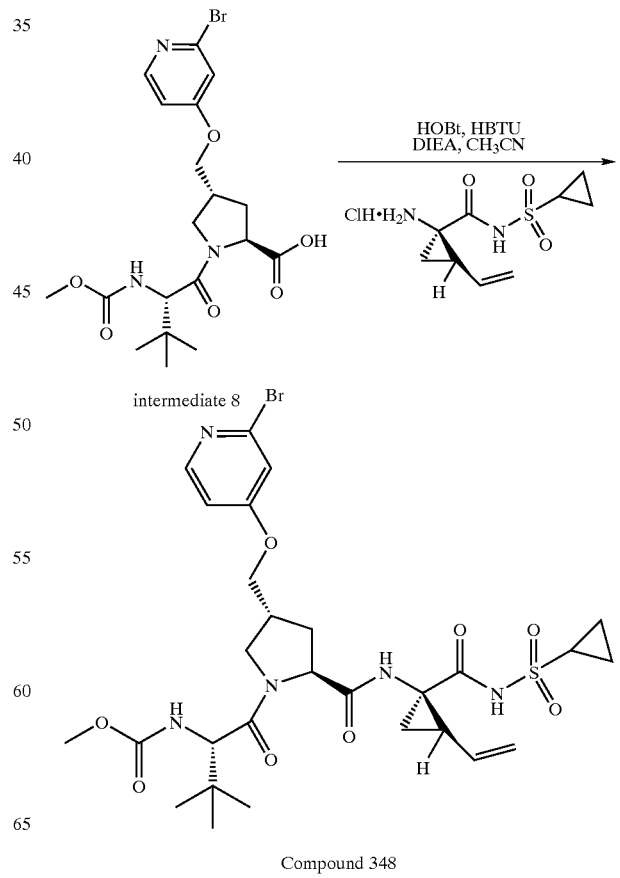

Scheme 3:

intermediate 8

Compound 348

Step 1: (Scheme 1)

To a solution of intermediate 5 from Example 344 (700 mg, 2.7 mmol) in THF (90 mL), methanol (50 mL) and water (12 mL) mixture, lithium hydroxide monohydrate (1700 mg, 2.0 mmol) was added. The reaction mixture was stirred at rt. for overnight. Then it was acidified with 1N HCl solution to pH=3 to 5. Extracted with ethyl acetate (2×20 mL) and the organic layers were combined and dried (MgSO$_4$). Evaporation of solvent gave thick colorless oil as product (intermediate 7) (0.58, 88% yield).

$^1$H NMR (CD$_3$OD, 400 MHz) δ 1.42 (m, 9 H), 2.00–2.09 (m, 2 H), 2.45 (m, 1 H), 3.17 (m, 1 H), 3.49 (m, 2 H), 3.59 (m, 1 H), 4.24 (m, 1 H).

LC-MS (retention time: 1.08 min.), MS m/z 268 (M+Na$^+$).

Step 2: (Scheme 2, Step 1)

To a solution of intermediate 7 (270 mg, 1.11 mmol) in DMSO (10 mL), potassium t-butoxide (309 mg, 2.75 mmol) was added. The reaction mixture was stirred at rt for 1 hr. Then 2-Bromo-4-chloro-pyridine (254 mg, 1.32 mmol) was added. The reaction mixture was stirred at rt for overnight. Then it was quenched with water and washed with ethyl acetate. The aqueous layer was separated and acidified with 1N HCl solution to pH=3. Extracted with ethyl acetate twice and the organic layers were combined and dried (MgSO$_4$). Evaporation of solvent gave an orange oil. It was then dissolved in methanol and HCl (gas) was bubbled through for 2 min at −78° C. Then the reaction mixture was warmed to rt and stirred for overnight. Evaporation of solvent gave an orange oil as crude to carry on.

LC-MS (retention time: 0.65 min.), MS m/z 315 (MH$^+$).

Step 3: (Scheme 2, Step 2)

To a solution of crude 4-(2-Bromo-pyridin-4-yloxymethyl)-pyrrolidine-2-carboxylic acid methyl ester in CH$_3$CN (20 mL) was added 2-methoxycarbonylamino-3,3-dimethyl-butyric acid (312 mg, 1.65 mmol), DIEA (1.15 mL, 6.6 mmol) and the coupling reagent HOBt (252 mg, 1.65 mmol) and HBTU (626 mg, 1.65 mmol). The solution was stirred at rt. overnight. Then it was concentrated, washed with water and extracted with ethyl acetate twice. The combined organic layers were washed with brine, dried over MgSO$_4$ and concentrated. It was then purified by Prep. HPLC column to give colorless oil as product. (270 mg, 41% yield two steps)

$^1$H NMR (CD$_3$OD, 400 MHz) δ 1.03 (s, 9 H), 2.13–2.19 (m, 2 H), 2.87 (m, 1 H), 3.51 (s, 3 H), 3.70 (s, 3 H), 3.93 (d, J=6.36 Hz, 2 H), 4.11 (m, 2 H), 4.27 (s, 1 H), 4.60 (dd, J=8.80, 5.87 Hz, 1 H), 7.06 (d, J=5.87 Hz, 2.20 Hz, 1 H) 7.32 (d, J=2.20 Hz, 1 H), 8.18 (d, J=6.11 Hz, 1 H).

LC-MS (retention time: 1.657 min.), MS m/z 486 (MH$^+$).

Step 4: (Scheme 2, Step 3)

To a solution of 4-(2-Bromo-pyridin-4-yloxymethyl)-1-(2-methoxycarbonylamino-3,3-dimethyl-butyryl)-pyrrolidine-2-carboxylic acid methyl ester (270 mg, 0.45 mmol) in THF (18 mL), methanol (10 mL) and water (3.3 mL) mixture, lithium hydroxide monohydrate (283 mg, 6.75 mmol) was added. The reaction mixture was stirred at rt. for overnight. Then it was concentrated and acidified with 1N HCl solution to pH=3 to 5. The off-white solid was collected as product (intermediate 8) (180 mg, 85% yield).

$^1$H NMR (CD$_3$OD, 500 MHz) δ 1.06 (s, 9 H), 2.20–2.29 (m, 2 H), 2.89 (m, 1 H), 3.54 (s, 3 H), 3.92 (d, J=6.4 Hz, 2 H), 4.06–4.13 (m, 2 H), 4.31 (d, J=8.85 Hz, 1 H), 4.59 (dd, J=8.85, 5.50 Hz, 1 H), 7.00 (dd, J=6.10, 2.24 Hz, 1 H), 7.22 (d, J=1.83 Hz, 1 H), 8.12 (d, J=5.80 Hz, 1 H).

LC-MS (retention time: 2.113 min.), MS m/z 472 (MH$^+$).

Step 5: (Scheme 3)

To a solution of intermediate 8 (10 mg, 0.0212 mmol) in CH$_3$CN (5 mL) was added (1R, 2S)(1-cyclopropanesulfonyl-aminocarbonyl-2-vinyl-cyclopropyl)-carbamic acid hydrochloride (8.5 mg, 0.00318 mmol), DIEA (0.018 mL, 0.106 mmol) and the coupling reagent HOBt (4.9 mg, 0.0318 mmol) and HBTU (12.1 mg, 0.0318 mmol). The solution was stirred at rt. overnight. Then it was concentrated, washed with water and extracted with ethyl acetate twice. The combined organic layers were washed with brine, dried over MgSO$_4$ and concentrated. It was then purified by Prep. HPLC column to give colorless thick oil as final product (Compound 348). (9 mg, 53% yield)

$^1$H NMR(CD$_3$OD, 400 MHz) δ 1.00–1.06 (m, 11 H), 1.20 (m, 2 H), 1.36 (dd, J=9.54 Hz, 5.38 Hz, 1 H), 1.87 (dd, J=8.07 Hz, 5.38 Hz, 1 H), 2.04–2.24 (m, 3 H), 2.88–2.94 (m, 2 H), 3.52 (s, 3 H), 3.93 (d, J=5.87 Hz, 2 H), 4.09 (m, 2 H), 4.30 (s, 1 H), 4.38 (t, J=7.58 Hz, 1 H), 5.11 (dd, J=10.27, 1.47 Hz, 1 H), 5.28 (dd, J=17.12, 1.47 Hz, 1 H), 5.70 (m, 1 H), 7.00 (dd, J=5.87, 2.20 Hz, 1 H), 7.24 (d, J=2.20 Hz, 1 H), 8.14 (d, J=5.87 Hz, 1 H).

LC-MS (retention time: 1.670 min.), MS m/z 684 (MH$^+$).

Example 349

Preparation of Compound 349

Compound 349

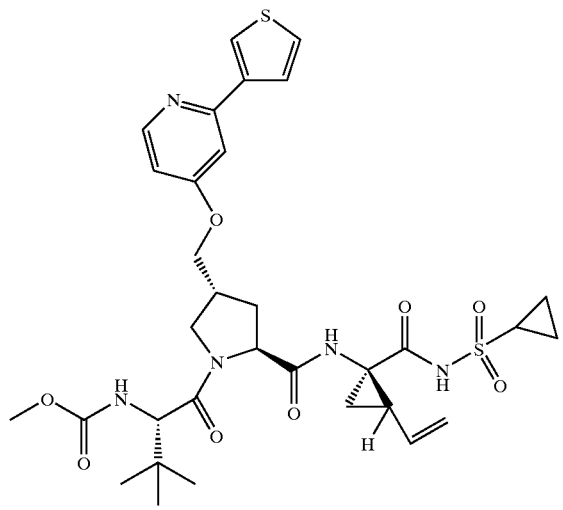

Compound 349 was prepared by following scheme of Example 347, except that intermediate 8 from Example 348 was used in the place of intermediate 6 from Example 346 in step 1.

Step 1:

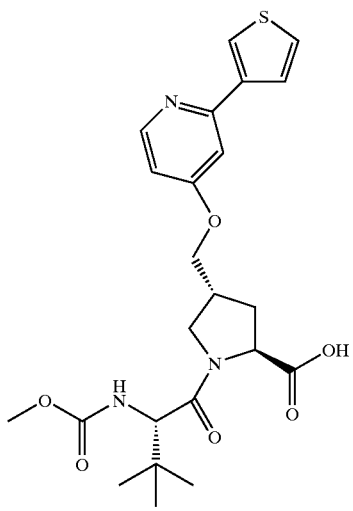

To a solution of intermediate 8 (20 mg, 0.0423 mmol) in DMF (1 mL), 3-thiopheneboronic acid (7.0 mg, 0.055 mmol), tetrakis (triphenylphosphine)palladium (2.4 mg, 0.00212 mmol) and 2M $Na_2CO_3$ solution (0.063 mL, 0.127 mmol) were added. The reaction mixture was heated at 110° C. for 30 hr. Then it was filtered and washed with methanol. The filtrate was concentrated and purified by Prep.HPLC to give brownish oil as product. (10.5 mg, 42% yield) (50177-165)

LC-MS (retention time: 1.690 min.), MS m/z 476 (MH$^+$).

Step 2:

Compound 349

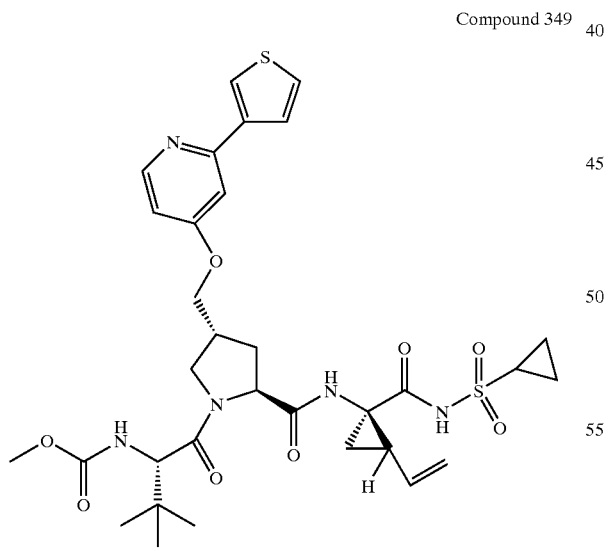

To a solution of 1-(2-Methoxycarbonylamino-3,3-dimethyl-butyryl)-4-(2-thiophen-3-yl-pyridin-4-yloxymethyl)-pyrrolidine-2-carboxylic acid (10 mg, 0.017 mmol) in $CH_3CN$ (5 mL) was added (1R, 2S)(1-cyclopropanesulfonyl-aminocarbonyl-2-vinyl-cyclopropyl)-carbamic acid hydrochloride (6.8 mg, 0.0254 mmol), DIEA (0.015 mL, 0.085 mmol) and the coupling reagent HOBt (3.9 mg, 0.0254 mmol) and HBTU (9.6 mg, 0.0254 mmol). The solution was stirred at rt. overnight. Then it was concentrated, washed with water and extracted with ethyl acetate twice. The combined organic layers were washed with brine, dried over $MgSO_4$ and concentrated. It was then purified by Prep. HPLC column to give brownish film as TFA salt (Compound 349). (2.2 mg, 16% yield). (50177-172)

$^1$H NMR($CD_3OD$, 400 MHz) δ 1.00–1.07 (m, 11 H), 1.20 (m, 2 H), 1.37 (dd, J=9.04, 5.38 Hz, 1 H), 1.88 (dd, J=8.07 Hz, 5.38 Hz, 1 H), 2.10–2.25 (m, 3 H), 2.90 (m, 1 H), 3.04 (m, 1 H), 3.47 (s, 3 H), 3.93–4.02 (m, 2 H), 4.29 (s, 1 H), 4.35–4.45 (m, 3 H), 5.12 (d, J=10.51 Hz, 1 H), 5.28 (d, J=17.61 Hz, 1 H), 5.69 (m, 1 H), 7.40 (dd, J=6.84, 2.44 Hz, 1 H), 7.71–7.80 (m, 3 H), 8.38 (m, 1 H), 8.51 (d, J=7.09 Hz, 1 H).

LC-MS (retention time: 1.443 min.), MS m/z 688 (MH$^+$).

Example 350

Preparation of Compound 350

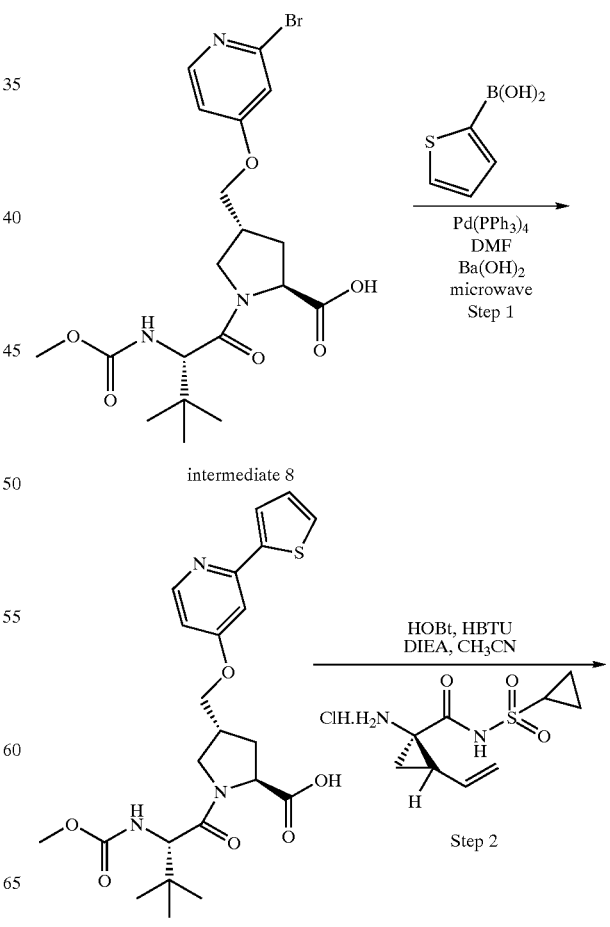

413

-continued

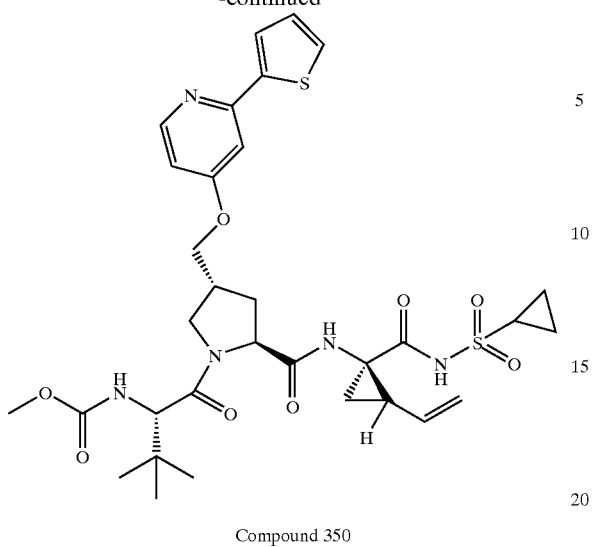

Compound 350

Step 1:

To a solution of intermediate 8 from Example 348 (20 mg, 0.0423 mmol) in DMF (2 mL), 2-thiopheneboronic acid (7.0 mg, 0.055 mmol), tetrakis(triphenylphosphine)palladium (2.4 mg, 0.00212 mmol) and barium hydroxide (40 mg, 0.127 mmol) were added. The reaction mixture was heated at 150° C. in Smith microwave reactor for 110 min. Then it was filtered and washed with methanol. The filtrate was concentrated and purified by Prep.HPLC to give yellowish oil as product. (5.0 mg, 20% yield)

LC-MS (retention time: 2.137 min.), MS m/z 476 (MH$^+$).

Step 2:

To a solution of above carboxylic acid (5.0 mg, 0.0085 mmol) in CH$_3$CN (5 mL) was added (1R, 2S) (1-cyclopropanesulfonyl-aminocarbonyl-2-vinyl-cyclopropyl)-carbamic acid hydrochloride (3.4 mg, 0.0127 mmol), DIEA (0.007 mL, 0.0424 mmol) and the coupling reagent HOBt (1.9 mg, 0.0127 mmol) and HBTU (4.8 mg, 0.0127 mmol). The solution was stirred at rt. overnight. Then it was concentrated, washed with water and extracted with ethyl acetate twice. The combined organic layers were washed with brine, dried over MgSO$_4$ and concentrated. It was then purified by Prep. HPLC column to give yellowish oil as TFA salt (Compound 350). (2.6 mg, 38% yield)

$^1$H NMR(CD$_3$OD, 400 MHz) δ 0.99–1.07 (m, 11 H), 1.19 (m, 2 H), 1.37 (dd, J=9.54, 5.63 Hz, 1 H), 1.87 (dd, J=8.07 Hz, 5.38 Hz, 1 H), 2.10–2.25 (m, 3 H), 2.91 (m, 1 H), 3.03 (m, 1 H), 3.48 (s, 3 H), 3.92–4.02 (m, 2 H), 4.30 (s, 1 H), 4.32–4.45 (m, 3 H), 5.11 (dd, J=10.27, 1.22 Hz, 1 H), 5.28 (d, J=17.11 Hz, 1 H), 5.69 (m, 1 H), 7.30–7.38 (m, 2 H), 7.66 (d, J=2.45 Hz, 1 H), 7.92 (m, 1 H), 7.95 (m, 1 H), 8.48 (d, J=6.85 Hz, 1 H).

LC-MS (retention time: 2.067 min.), MS m/z 688 (MH$^+$).

414

Example 351

Preparation of Compound 351

Compound 351

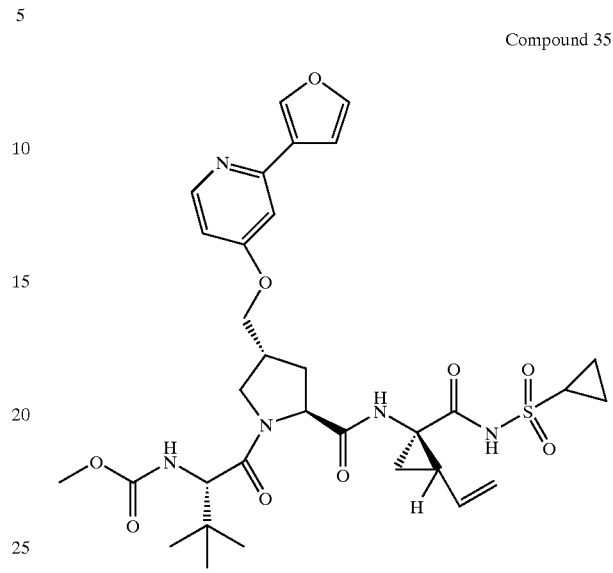

Compound 351 was prepared by following scheme of Example 350, except that 3-furanboronic acid was used in the place of 2-thiopheneboronic acid in step 1.

Step 1:

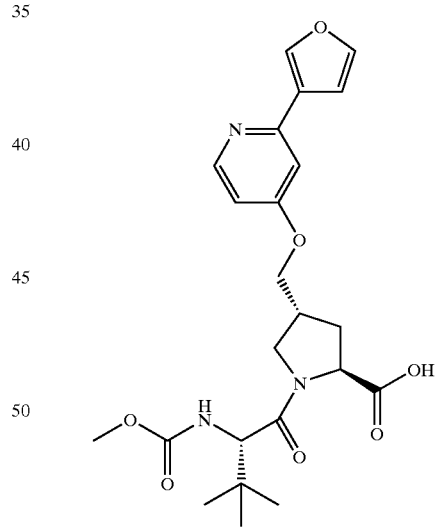

To a solution of intermediate 8 from Example 348 (20 mg, 0.0423 mmol) in DMF (2 mL), 3-furanboronic acid (6.2 mg, 0.055 mmol), tetrakis(triphenylphosphine)palladium (2.4 mg, 0.00212 mmol) and barium hydroxide (40 mg, 0.127 mmol) were added. The reaction mixture was heated at 150° C. in Smith microwave reactor for 30 min. Then it was filtered and washed with methanol. The filtrate was concentrated and purified by Prep.HPLC to give yellowish oil as product. (12 mg, 49% yield)

LC-MS (retention time: 1.937 min.), MS m/z 460 (MH$^+$).

Step 2:

Compound 351

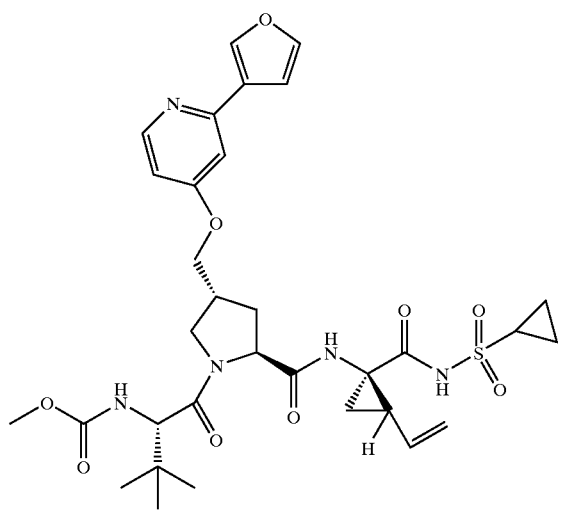

To a solution of above carboxylic acid (5.0 mg, 0.0209 mmol) in CH₃CN (5 mL) was added (1R, 2S) (1-cyclopropanesulfonyl-aminocarbonyl-2-vinyl-cyclopropyl)-carbamic acid hydrochloride (8.4 mg, 0.0314 mmol), DIEA (0.018 mL, 0.1046 mmol) and the coupling reagent HOBt (4.8 mg, 0.0314 mmol) and HBTU (11.9 mg, 0.0314 mmol). The solution was stirred at rt. overnight. Then it was concentrated, washed with water and extracted with ethyl acetate twice. The combined organic layers were washed with brine, dried over MgSO₄ and concentrated. It was then purified by Prep. HPLC column to give yellowish oil as TFA salt (Compound 351). (4.0 mg, 24% yield).

$^1$H NMR(CD₃OD, 400 MHz) δ 1.00–1.08 (m, 11 H), 1.21 (m, 2 H), 1.37 (dd, J=8.80, 5.62 Hz, 1 H), 1.87 (dd, J=8.32 Hz, 5.38 Hz, 1 H), 2.11–2.24 (m, 3 H), 2.91 (m, 1 H), 3.03 (m, 1 H), 3.49 (s, 3 H), 3.91–4.03 (m, 2 H), 4.29 (s, 1 H), 4.35–4.46 (m, 3 H), 5.12 (dd, J=10.27, 1.47 Hz, 1 H), 5.28 (d, J=17.12 Hz, 1 H), 5.69 (m, 1 H), 7.11 (m, 1 H), 7.38 (dd, J=7.10, 2.69 Hz, 1 H), 7.71 (d, J=2.69 Hz, 1 H), 7.81 (m, 1 H), 8.48 (s, 1 H), 8.50 (d, J=7.09 Hz, 1 H).

LC-MS (retention time: 1.410 min.), MS m/z 672 (MH⁺).

Example 352

Preparation of Compound 352

Compound 352

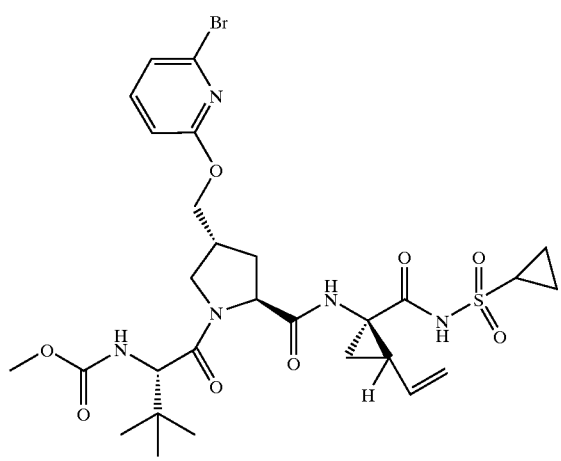

Compound 352 was prepared by following scheme 2 and scheme 3 of Example 348, except that 2,6-dibromopyridine was used in the place of 2-bromo-4-chloro-pyridine in step 1 of scheme 2.

Step 1: (Scheme 2, step 1)

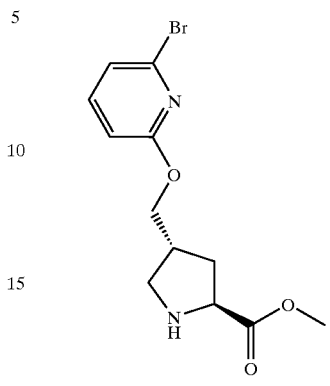

To a solution of intermediate 7 from Example 348 (270 mg, 1.1 mmol) in DMSO (10 mL), potassium t-butoxide (309 mg, 2.75 mmol) was added. The reaction mixture was stirred at rt for 1 hr. Then 2,6-dibromopyridine (313 mg, 1.32 mmol) was added. The reaction mixture was stirred at rt for overnight. Then it was quenched with water and washed with ethyl acetate. The aqueous layer was separated and acidified with 1N HCl solution to pH=3. Extracted with ethyl acetate twice and the organic layers were combined and dried (MgSO₄). Evaporation of solvent gave an orange oil. It was then dissolved in methanol and HCl (gas) was bubbled through for 2 min at −78° C. Then the reaction mixture was warmed to rt and stirred for overnight. Evaporation of solvent gave an orange oil as crude to carry on.

LC-MS (retention time: 1.480 min.), MS m/z 315 (MH⁺).

Step 2: (Scheme 2, step 2)

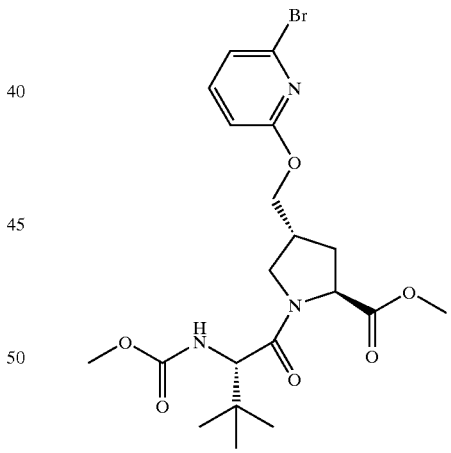

To a solution of crude 4-(6-Bromo-pyridin-2-yloxymethyl)-pyrrolidine-2-carboxylic acid methyl ester in CH₃CN (20 mL) was added 2-methoxycarbonylamino-3,3-dimethyl-butyric acid (312 mg, 1.65 mmol), DIEA (1.15 mL, 6.6 mmol) and the coupling reagent HOBt (252 mg, 1.65 mmol) and HBTU (626 mg, 1.65 mmol). The solution was stirred at rt. overnight. Then it was concentrated, washed with water and extracted with ethyl acetate twice. The combined organic layers were washed with brine, dried over MgSO₄ and concentrated. It was then purified by flash column chromatography (silica gel, 1:1 hexanes:ethyl acetate) to give a colorless oil as product. (340 mg, 63% yield two steps)

¹H NMR (CD₃OD, 400 MHz) δ 1.03 (s, 9 H), 2.10–2.24 (m, 2 H), 2.84 (m, 1 H), 3.55 (s, 3 H), 3.70 (s, 3 H), 3.83 (m, 1 H), 3.94 (m, 1 H), 4.20–4.29 (m, 2 H), 4.31 (s, 1 H), 4.59 (dd, J=8.80, 5.13 Hz, 1 H), 6.76 (d, J=8.07 Hz, 1 H) 7.11 (d, J=7.58 Hz, 1 H), 7.53 (t, J=7.83 Hz, 1 H).

LC-MS (retention time: 1.820 min.), MS m/z 486 (MH⁺).

Step 3: (Scheme 2, step 3)

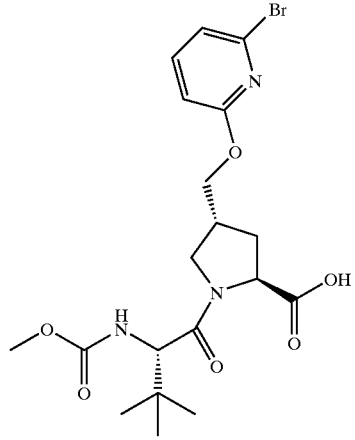

intermediate 9

To a solution of 4-(6-Bromo-pyridin-2-yloxymethyl)-1-(2-methoxycarbonylamino-3,3-dimethyl-butyryl)-pyrrolidine-2-carboxylic acid methyl ester (330 mg, 0.679 mmol) in THF (28 mL), methanol (15 mL) and water (5 mL) mixture, lithium hydroxide monohydrate (427 mg, 10.18 mmol) was added. The reaction mixture was stirred at rt. for 2 days. Then it was concentrated and acidified with 1N HCl solution to pH=3 to 5. The white solid was collected as product (intermediate 9) (310 mg, 97% yield).

¹H NMR (CD₃OD, 500 MHz) δ 1.06 (s, 9 H), 2.18–2.25 (m, 2 H), 2.88 (m, 1 H), 3.57 (s, 3 H), 3.84 (m, 1 H), 3.96 (m, 1 H), 4.25 (m, 1 H), 4.28–4.35 (m, 2 H), 4.58 (m, 1 H), 6.79 (d, J=7.94 Hz, 1 H), 7.13 (d, J=7.32 Hz, 1 H), 7.55 (m, 1 H).

LC-MS (retention time: 3.030 min.), MS m/z 472 (MH⁺).

Step 4: (Scheme 3)

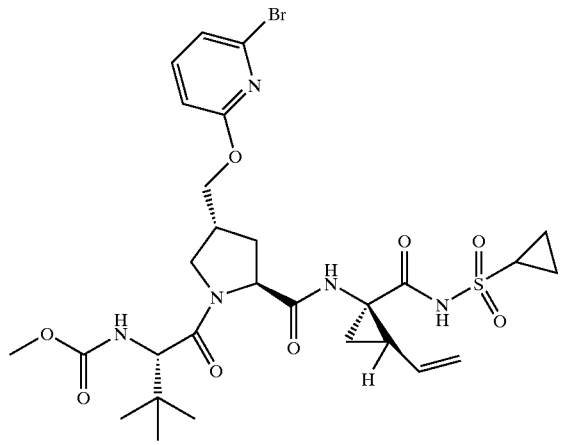

Compound 352

To a solution of intermediate 9 (10 mg, 0.0212 mmol) in CH₃CN (5 mL) was added (1R, 2S) (1-cyclopropanesulfonyl-aminocarbonyl-2-vinyl-cyclopropyl)-carbamic acid hydrochloride (8.5 mg, 0.00318 mmol), DIEA (0.018 mL, 0.106 mmol) and the coupling reagent HOBt (4.9 mg, 0.0318 mmol) and HBTU (12.1 mg, 0.0318 mmol). The solution was stirred at rt. overnight. Then it was concentrated, washed with water and extracted with ethyl acetate twice. The combined organic layers were washed with brine, dried over MgSO₄ and concentrated. It was then purified by Prep. HPLC column to give yellowish film as TFA salt (Compound 352). (10.2 mg, 60% yield).

¹H NMR(CD₃OD, 400 MHz) δ 1.00–1.06 (m, 11 H), 1.20 (m, 2 H), 1.37 (dd, J=9.54 Hz, 5.63 Hz, 1 H), 1.86 (dd, J=8.07 Hz, 5.38 Hz, 1 H), 2.05 (m, 1 H), 2.12–2.25 (m, 2 H), 2.86–2.94 (m, 2 H), 3.54 (s, 3 H), 3.87 (m, 1 H), 3.94 (m, 1 H), 4.18–4.27 (m, 2 H), 4.33 (s, 1 H), 4.37 (m, 1 H), 5.11 (dd, J=10.27, 1.72 Hz, 1 H), 5.28 (dd, J=17.12, 1.47 Hz, 1 H), 5.70 (m, 1 H), 6.76 (d, J=8.32 Hz, 1 H), 7.11 (d, J=7.33 Hz, 1 H), 7.53 (t, J=7.82 Hz, 1 H).

LC-MS (retention time: 1.837 min.), MS m/z 684 (MH⁺).

Example 353

Preparation of Compound 353

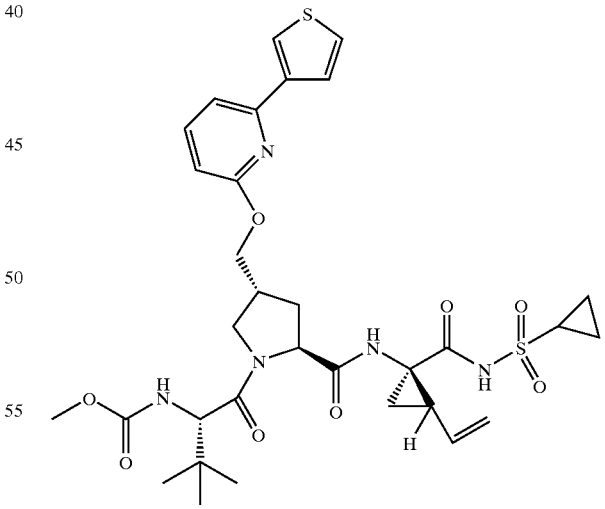

Compound 353

Compound 353 was prepared by following scheme of Example 347, except that intermediate 9 from Example 352 was used in the place of intermediate 6 from Example 346 in step 1.

Step 1:

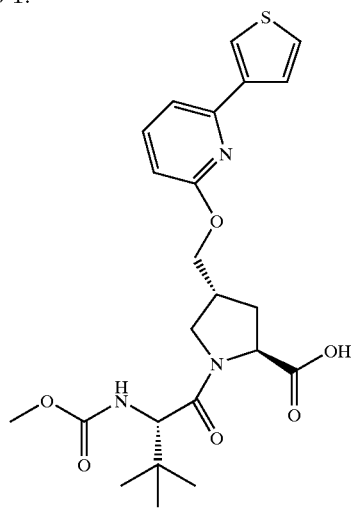

To a solution of intermediate 9 (25 mg, 0.053 mmol) in DMF (1 mL), 3-thiopheneboronic acid (8.8 mg, 0.0688 mmol), tetrakis(triphenylphosphine)palladium (3.1 mg, 0.00265 mmol) and 2M Na$_2$CO$_3$ solution (0.080 mL, 0.159 mmol) were added. The reaction mixture was heated at 110° C. for overnight. Then it was filtered and washed with methanol. The filtrate was concentrated and purified by Prep.HPLC to give brownish oil as product. (15 mg, 48% yield)

$^1$H NMR (CD$_3$OD, 500 MHz) δ 1.06 (s, 9 H), 2.20–2.31 (m, 2 H), 2.94 (m, 1 H), 3.55 (s, 3 H), 3.91 (m, 1 H), 3.98 (m, 1 H), 4.34 (s, 1 H), 4.37–4.46 (m, 2 H), 4.61 (dd, J=8.85, 5.19 Hz, 1 H), 6.7–7 (d, J=8.24 Hz, 1 H), 7.39 (d, J=7.32 Hz, 1 H), 7.48 (dd, J=5.19, 3.05 Hz, 1 H), 7.68 (dd, J=4.88, 1.22 Hz, 1 H), 7.77 (t, J=7.93 Hz, 1 H), 8.04 (m, 1 H).

LC-MS (retention time: 1.857 min.), MS m/z 476 (MH$^+$).

Step 2:

Compound 353

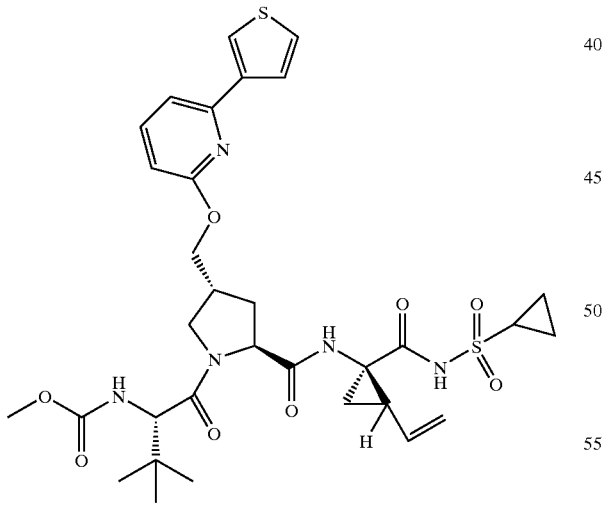

To a solution of 1-(2-Methoxycarbonylamino-3,3-dimethyl-butyryl)-4-(6-thiophen-3-yl-pyridin-2-yloxymethyl)-pyrrolidine-2-carboxylic acid (15 mg, 0.0254 mmol) in CH$_3$CN (5 mL) was added (1R, 2S)(1-cyclopropanesulfonyl-aminocarbonyl-2-vinyl-cyclopropyl)-carbamic acid hydrochloride (10.2 mg, 0.0382 mmol), DIEA (0.022 mL, 0.127 mmol) and the coupling reagent HOBt (5.8 mg, 0.0382 mmol) and HBTU (14.5 mg, 0.0382 mmol). The solution was stirred at rt. overnight. Then it was concentrated, washed with water and extracted with ethyl acetate twice. The combined organic layers were washed with brine, dried over MgSO$_4$ and concentrated. It was then purified by Prep. HPLC column to give yellowish film as TFA salt (Compound 353). (6 mg, 29% yield)

$^1$H NMR(CD$_3$OD, 400 MHz) δ 1.00–1.06 (m, 11 H), 1.20 (m, 2 H), 1.36 (dd, J=9.29, 5.38 Hz, 1 H), 1.86 (dd, J=8.07 Hz, 5.38 Hz, 1 H), 2.07 (m, 1 H), 2.16–2.25 (m, 2 H), 2.87–2.99 (m, 2 H), 3.54 (s, 3 H), 3.87–3.99 (m, 2 H), 4.31–4.44 (m, 4 H), 5.11 (dd, J=10.27, 1.46 Hz, 1 H), 5.28 (d, J=17.12 Hz, 1 H), 5.70 (m, 1 H), 6.67 (d, J=8.31 Hz, 1 H), 7.33 (d, J=7.34 Hz, 1 H), 7.44 (dd, J=4.89, 2.93 Hz, 1 H), 7.63–7.70 (m, 2 H), 7.99 (m, 1 H).

LC-MS (retention time: 2.770 min.), MS m/z 688 (MH$^+$).

Example 354

Preparation of Compound 354

Compound 354

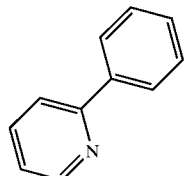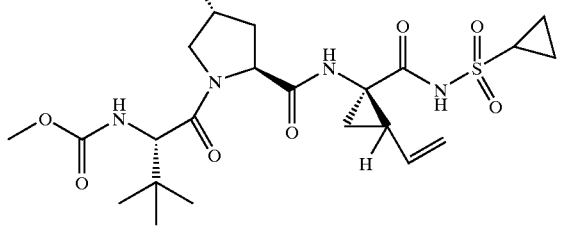

Compound 354 was prepared by following scheme of Example 347, except that intermediate 9 from Example 352 was used in the place of intermediate 6 from Example 346 and phenyl boronic acid was used in the place of 3-thiopheneboronic acid in step 1.

Step 1:

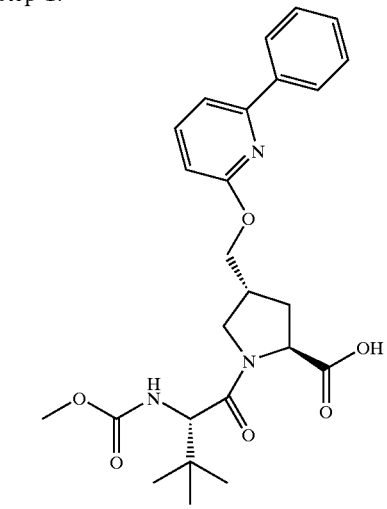

To a solution of intermediate 9 (20 mg, 0.0423 mmol) in DMF (1 mL), phenyl boronic acid (6.7 mg, 0.0688 mmol), tetrakis(triphenylphosphine)palladium (2.4 mg, 0.00212 mmol) and Cs₂CO₃ (41 mg, 0.127 mmol) were added. The reaction mixture was heated at 110° C. for overnight. Then it was filtered and washed with methanol. The filtrate was concentrated and purified by Prep.HPLC to give yellowish oil as product. (12 mg, 49% yield)

LC-MS (retention time: 2.733 min.), MS m/z 470 (MH⁺).

Step 2:

Compound 354

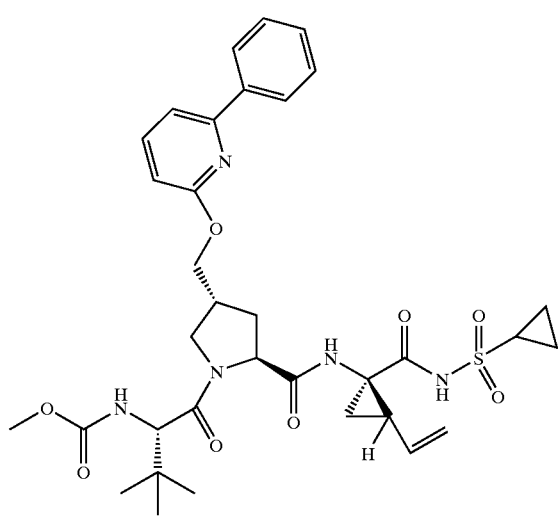

To a solution of 1-(2-Methoxycarbonylamino-3,3-dimethyl-butyryl)-4-(6-phenyl-pyridin-2-yloxymethyl)-pyrrolidine-2-carboxylic acid (12 mg, 0.0206 mmol) in CH₃CN (5 mL) was added (1R, 2S)(1-cyclopropanesulfonyl-aminocarbonyl-2-vinyl-cyclopropyl)-carbamic acid hydrochloride (8.2 mg, 0.0308 mmol), DIEA (0.018 mL, 0.1028 mmol) and the coupling reagent HOBt (4.7 mg, 0.0308 mmol) and HBTU (11.7 mg, 0.0308 mmol). The solution was stirred at rt. overnight. Then it was concentrated, washed with water and extracted with ethyl acetate twice. The combined organic layers were washed with brine, dried over MgSO₄ and concentrated. It was then purified by Prep. HPLC column to give a white solid as TFA salt (Compound 354). (1.5 mg, 9% yield)

¹H NMR(CD₃OD, 400 MHz) δ 1.00–1.07 (m, 11 H), 1.20 (m, 2 H), 1.36 (m, 1 H), 1.85 (m, 1 H), 2.09 (m, 1 H), 2.17–2.25 (m, 2 H), 2.87–3.00 (m, 2 H), 3.52 (s, 3 H), 3.84–4.00 (m, 2 H), 4.33–4.44 (m, 4 H), 5.11 (dd, J=10.27, 1.71 Hz, 1 H), 5.28 (d, J=17.12, 1.22 Hz, 1 H), 5.70 (m, 1 H), 6.71 (d, J=8.31 Hz, 1 H), 6.78 (m, 1 H), 7.34–7.44 (m, 3 H), 7.74 (m, 1 H), 7.95 (m, 1 H), 8.01 (d, J=8.31 Hz, 1 H).

LC-MS (retention time: 3.553 min.), MS m/z 682 (MH⁺).

Example 355

Preparation of Compound 355

Compound 355

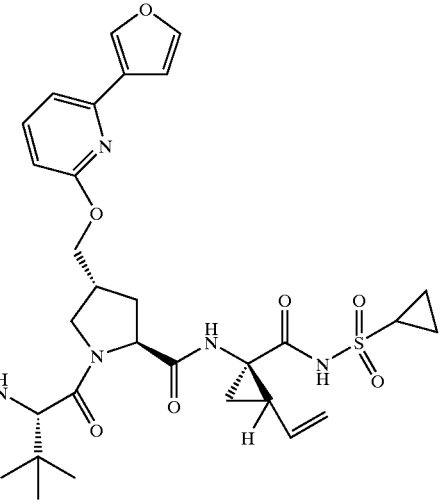

Compound 354 was prepared by following scheme of Example 347, except that intermediate 9 from Example 352 was used in the place of intermediate 6 from Example 346 and 3-furan boronic acid was used in the place of 3-thiopheneboronic acid in step 1.

Step 1:

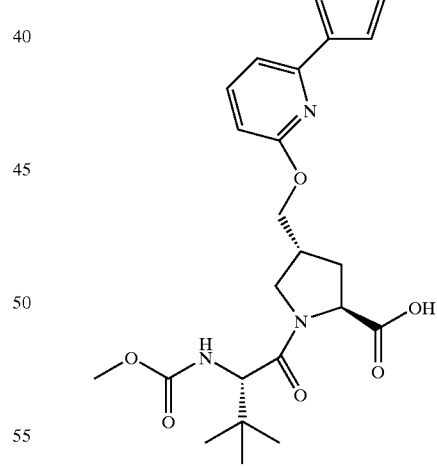

To a solution of intermediate 9 (20 mg, 0.0423 mmol) in DMF (1 mL), 3-furan boronic acid (6.2 mg, 0.055 mmol), tetrakis(triphenylphosphine)palladium (2.4 mg, 0.002115 mmol) and 2M Na₂CO₃ solution (0.064 mL, 0.127 mmol) were added. The reaction mixture was heated at 110° C. for 2 days. Then it was filtered and washed with methanol. The filtrate was concentrated and purified by Prep.HPLC to give yellowish oil as product. (7.0 mg, 29% yield)

Step 2:

Compound 355

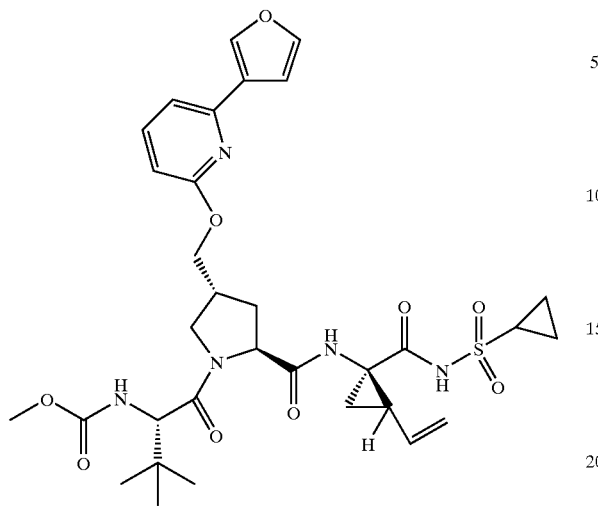

To a solution of above carboxylic acid (6.0 mg, 0.0109 mmol) in CH$_3$CN (5 mL) was added (1R,2S)(1-cyclopropanesulfonyl-aminocarbonyl-2-vinyl-cyclopropyl)-carbamic acid hydrochloride (4.4 mg, 0.0163 mmol), DIEA (0.0095 mL, 0.0544 mmol) and the coupling reagent HOBt (2.5 mg, 0.0163 mmol) and HBTU (6.2 mg, 0.0163 mmol). The solution was stirred at rt. overnight. Then it was concentrated, washed with water and extracted with ethyl acetate twice. The combined organic layers were washed with brine, dried over MgSO$_4$ and concentrated. It was then purified by Prep. HPLC column to give yellowish film as TFA salt (Compound 355). (1.5 mg, 18% yield)

$^1$H NMR(CD$_3$OD, 400 MHz) δ 0.98–1.07 (m, 11 H), 1.20 (m, 2 H), 1.35 (dd, J=9.54, 5.87 Hz, 1 H), 1.86 (dd, J=8.07 Hz, 5.62 Hz, 1 H), 2.06 (m, 1 H), 2.15–2.25 (m, 2 H), 2.85–2.98 (m, 2 H), 3.55 (s, 3 H), 3.89 (m, 1 H), 3.95 (m, 1 H), 4.28–4.42 (m, 4 H), 5.11 (dd, J=10.27, 1.71 Hz, 1 H), 5.28 (dd, J=17.12, 1.22 Hz, 1 H), 5.69 (m, 1 H), 6.63 (d, J=8.07 Hz, 1 H), 6.90 (m, 1 H), 7.16 (d, J=7.33 Hz, 1 H), 7.53 (m, 1 H), 7.63 (m, 1 H), 8.08 (s, 1 H).

LC-MS (retention time: 3.340 min.), MS m/z 672 (MW$^+$).

Example 356

Preparation of Compound 356

Compound 356

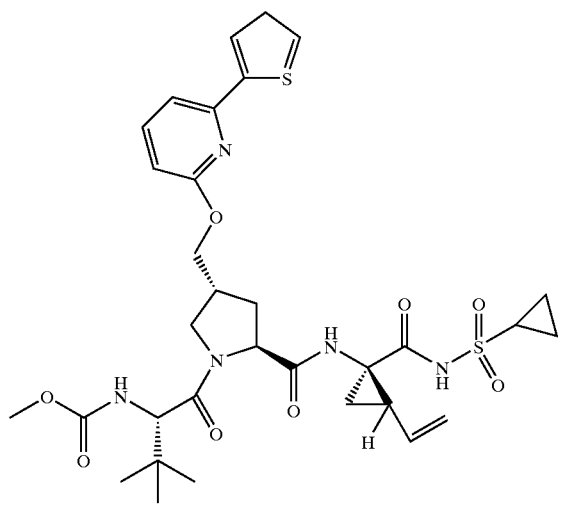

Compound 356 was prepared by following scheme of Example 350, except intermediate 9 from Example 352 was used in the place of intermediate 8 from Example 348 in step 1.

Step 1:

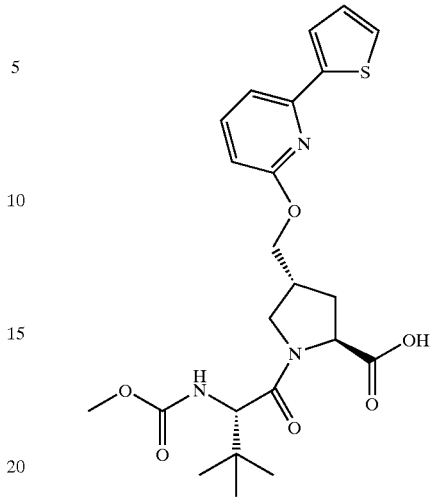

To a solution of intermediate 9 (20 mg, 0.0423 mmol) in DMF (2 mL), 2-thiopheneboronic acid (7.0 mg, 0.055 mmol), tetrakis(triphenylphosphine)palladium (2.4 mg, 0.00212 mmol) and barium hydroxide (40 mg, 0.127 mmol) were added. The reaction mixture was heated at 150° C. in Smith microwave reactor for 30 min. Then it was filtered and washed with methanol. The filtrate was concentrated and purified by Prep.HPLC to give brownish oil as product. (13.0 mg, 52% yield)

$^1$H NMR (CD$_3$OD, 400 MHz) δ 1.03 (s, 9 H), 2.18–2.25 (m, 2 H), 2.93 (m, 1 H), 3.55 (s, 3 H), 3.83 (m, 1 H), 3.98 (m, 1 H), 4.34 (s, 1 H), 4.38 (m, 2 H), 4.58 (dd, J=8.05, 5.14 Hz, 1 H), 6.63 (d, J=8.07 Hz, 1 H), 7.07 (dd, J=4.89, 3.67 Hz, 1 H), 7.33 (d, J=7.34 Hz, 1 H), 7.42 (d, J=5.14 Hz, 1 H), 7.60–7.66 (m, 2 H).

LC-MS (retention time: 3.393 min.), MS m/z 476 (MH$^+$)

Step 2:

Compound 356

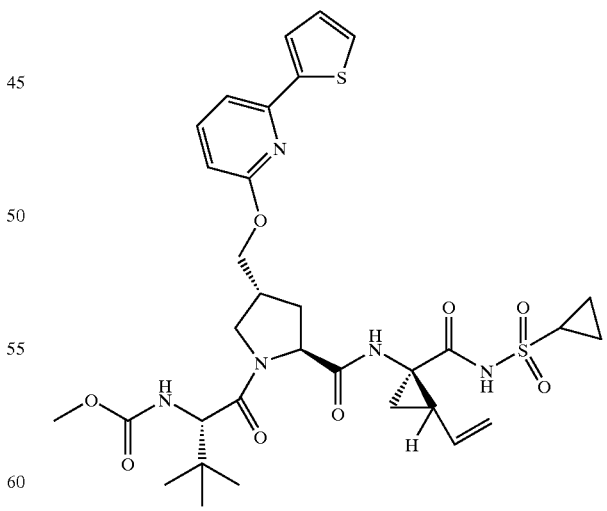

To a solution of 1-(2-Methoxycarbonylamino-3,3-dimethyl-butyryl)-4-(6-thiophen-2-yl-pyridin-2-yloxymethyl)-pyrrolidine-2-carboxylic acid (11.5 mg, 0.0195 mmol) in CH$_3$CN (5 mL) was added (1R, 2S)(1-cyclopropanesulfonyl-aminocarbonyl-2-vinyl-cyclopropyl)-carbamic acid hydrochloride (7.8 mg, 0.0293 mmol), DIEA (0.017 mL, 0.0975 mmol) and the coupling reagent HOBt (4.5 mg, 0.0293 mmol) and HBTU (11.1 mg, 0.0293 mmol). The solution was stirred at rt. overnight. Then it was concentrated, washed with water and extracted with ethyl acetate twice. The combined organic layers were washed with brine, dried over MgSO₄ and concentrated. It was then purified by Prep. HPLC column to give an off-white solid as TFA salt (Compound 356). (8.5 mg, 54% yield)

¹H NMR(CD₃OD, 400 MHz) δ 0.99–1.06 (m, 11 H), 1.21 (m, 2 H), 1.36 (dd, J=9.54, 5.38 Hz, 1 H), 1.86 (dd, J=8.07 Hz, 5.62 Hz, 1 H), 2.06 (m, 1 H), 2.15–2.25 (m, 2 H), 2.87–2.99 (m, 2 H), 3.54 (s, 3 H), 3.89 (m, 1 H), 3.96 (m, 1 H), 4.30–4.44 (m, 4 H), 5.11 (dd, J=10.51, 1.71 Hz, 1 H), 5.28 (dd, J=17.11, 1.22 Hz, 1 H), 5.70 (m, 1 H), 6.62 (d, J=8.07 Hz, 1 H), 7.07 (dd, J=4.89, 3.66 Hz, 1 H), 7.33 (d, J=7.59 Hz, 1 H), 7.42 (d, J=4.89 Hz, 1H), 7.60–7.66 (m, 2 H).

LC-MS (retention time: 1.967 min.), MS m/z 688 (MH⁺).

Example 357

Preparation of Compound 357

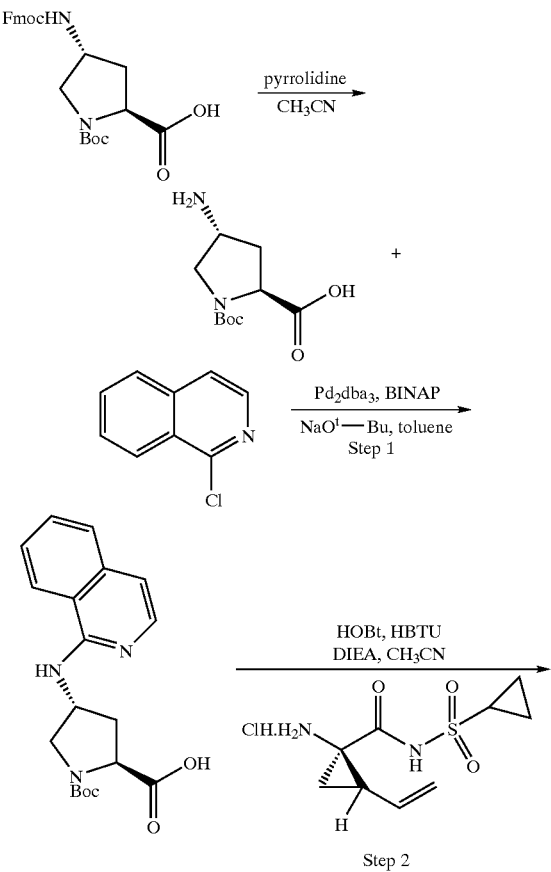

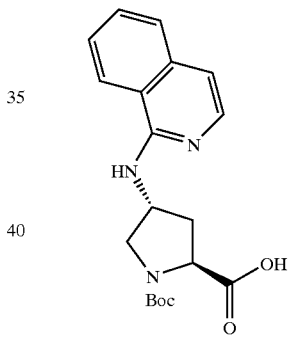

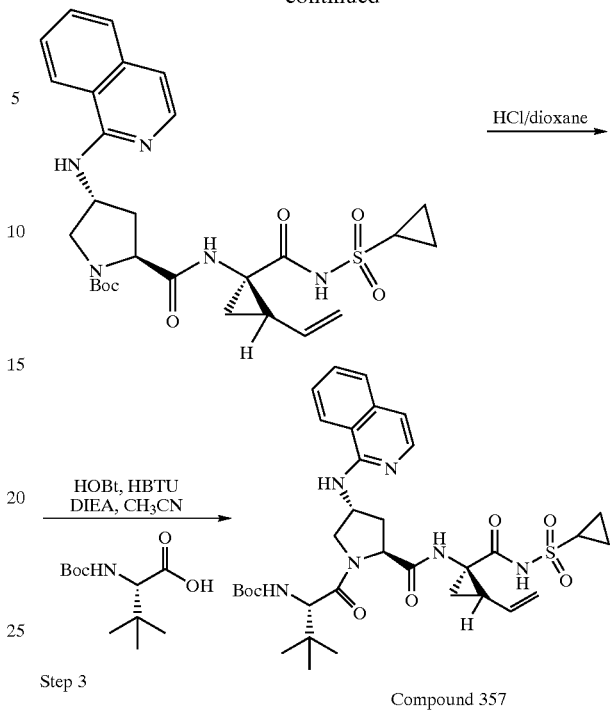

Step 1:

To a solution of (2S,4R) Fmoc-4-amino-1-boc-pyrrolidine-2-carboxylic acid (400 mg, 0.884 mmol) in acetonitrile (15 mL), five drops of pyrrolidine was added. The reaction mixture was stirred at rt for 3 hr. Then it was concentrated and put on high vacuum to give crude 4-amino-1-boc-pyrrolidine-2-carboxylic acid. In another round-bottomed flask, a solution of Pd₂ dba₃ (40 mg, 5% mol) and racemic-BINAP (56 mg, 10% mol) was stirred under nitrogen in degassed toluene (8 mL) at rt for 1 h. Then 1-chloroisoquinoline (216 mg, 1.326 mmol) and sodium t-butoxide (340 mg, 3.536 mmol) were added and the reaction mixture was stirred for 30 min. Then 4-amino-1-boc-pyrrolidine-2-carboxylic acid was added and the reaction mixture was heated under reflux for 1 h. Water was added to quench the reaction and the aqueous layer was separated and filtered through filter paper. It was then concentrated and purified by Prep. HPLC to give coupled product as TFA salt. (165 mg, 40% yield)

¹H NMR (CD₃OD, 400 MHz) δ 1.44 (m, 9H), 2.51–2.74 (m, 2H), 3.64 (m, 1H), 4.01 (m, 1H), 4.49 (m, 1H), 4.64 (m, 1H), 7.30 (d, J=6.85 Hz, 1H), 7.58 (d, J=6.85 Hz, 1H), 7.79 (m, 1H), 7.91–7.99 (m, 2H), 8.56 (d, J=8.56 Hz, 1H).

LC-MS (retention time: 1.707 min.), MS m/z 358 (MH⁺).
Step 2:

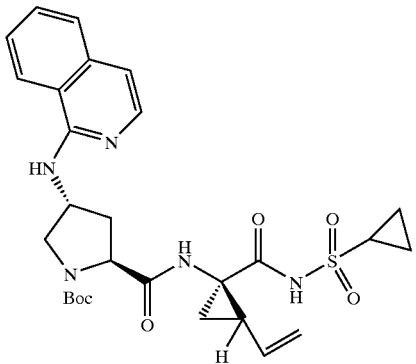

To a solution of 4-(Isoquinolin-1-ylamino)-pyrrolidine-1,2-dicarboxylic acid 1-tert-butyl ester (115 mg, 0.244 mmol) in CH₃CN (10 mL) was added (1R,2S)(1-cyclopropanesulfonyl-aminocarbonyl-2-vinyl-cyclopropyl)-carbamic acid hydrochloride (97 mg, 0.366 mmol), DIEA (0.255 mL, 1.464 mmol) and the coupling reagent HOBt (56 mg, 0.366 mmol) and HBTU (139 mg, 0.366 mmol). The solution was stirred at rt. overnight. Then it was concentrated, washed with water and extracted with ethyl acetate twice. The combined organic layers were washed with brine, dried over MgSO₄ and concentrated to give yellow oil. It was purified by Prep. HPLC column to a yellowish solid as TFA salt (112 mg, 67% yield).

¹H NMR (CD₃OD, 400 MHz) δ 1.05 (m, 2H), 1.20 (m, 2H), 1.40–1.48 (m, 10H), 1.87 (dd, J=8.19, 5.50 Hz, 1H), 2.23 (m, 1H), 2.39 (m, 1H), 2.50 (m, 1H), 2.93 (m, 1H), 3.65 (m, 1H), 4.08 (m, 1H), 4.33 (t, J=7.09 Hz, 1H), 4.69 (m, 1H), 5.12 (d, J=10.27 Hz, 1H), 5.29 (d, J=17.12 Hz, 1H), 5.74 (m, 1H), 7.31 (d, J=6.85 Hz, 1H), 7.60 (d, J=7.09 Hz, 1H), 7.80 (m, 1H), 7.93–8.00 (m, 2H), 8.56 (d, J=8.19 Hz, 1H).

LC-MS (retention time: 2.023 min.), MS m/z 570 (MH⁺).
Step 3::

Compound 357

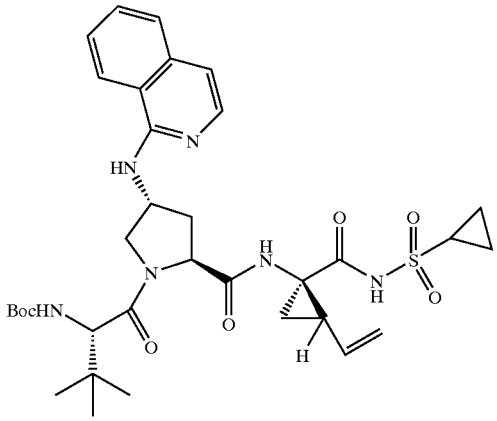

2-(1-Cyclopropanesulfonylaminocarbonyl-2-vinylcyclopropyl-carbamoyl)-4-(isoquinolin-1-ylamino)-pyrrolidine-1-carboxylic acid tert-butyl ester (31 mg, 0.0453 mmol) was dissolved in 4N HCl in dioxane (1.5 mL) and stirred at rt. for 2 hr. Evaporation of solvent gave yellowish oil as bis hydrochloride salt. To a solution of bis hydrochloride salt in CH₃CN (5 mL) was added N-boc-L-t-leucine (11.5 mg, 0.0498 mmol), DIEA (0.047 mL, 0.272 mmol) and the coupling reagent HOBt (10.4 mg, 0.068 mmol) and HBTU (25.8 mg, 0.068 mmol). The solution was stirred at rt. overnight. Then it was concentrated, washed with water and extracted with ethyl acetate twice. The combined organic layers were washed with brine, dried over MgSO₄ and concentrated to give yellowish oil. It was purified by Prep. HPLC column to give an off-white solid as final product (Compound 357).(9 mg, 29% yield)

¹H NMR (CD₃OD, 400 MHz) δ 0.98 (m, 2H), 1.05 (s, 9H), 1.20 (m, 2H), 1.36–1.43 (m, 10H), 1.84 (m, 1H), 2.10–2.30 (m, 2H), 2.52 (m, 1H), 2.90 (m, 1H), 4.07 (m, 1H), 4.17–4.27 (m, 2H), 4.47 (m, 1H), 4.79 (m, 1H), 5.07 (d, J=9.29 Hz, 1H), 5.24 (d, J=16.87 Hz, 1H), 5.72 (m, 1H), 6.62 (m, 1H), 6.98 (d, J=6.11 Hz, 1H), 7.47 (m, 1H), 7.62 (m, 1H), 7.69 (d, J=8.07 Hz, 1H), 7.84 (d, J=5.87 Hz, 1H), 8.20 (d, J=8.56 Hz, 1H).

LC-MS (retention time: 2.043 min.), MS m/z 683 (MH⁺).
Section H:
LC-MS Condition for Section H

| | |
|---|---|
| Columns: | (Method A) - YMC ODS S7 C18 3.0 × 50 mm |
| | (Method B) - YMC ODS-A S7 C18 3.0 × 50 mm |
| | (Method C) - YMC S7 C18 3.0 × 50 mm |
| | (Method D) - YMC Xterra ODS S7 3.0 × 50 mm |
| | (Method E) - YMC Xterra ODS S7 3.0 × 50 mm |
| | (Method F) - YMC ODS-A S7 C18 3.0 × 50 mm |
| | (Method H) - Xterra S7 3.0 × 50 mm |
| | (Method I) - Xterra S7 C18 3.0 × 50 mm |
| | (Method G) - YMC C18 S5 4.6 × 50 mm |
| | (Method J) - Xterra ODS S7 3.0 × 50 mm |
| | (Method K) - YMC ODS-A S7 C18 3.0 × 50 mm |
| Gradient: | 100% Solvent A/0% Solvent B to 0% Solvent A/100% Solvent B |
| Gradient time: | 2 min. (A, B, D, F, G, H, I); 8 min. (C, E); 4 min (J); 3 min (K) |
| Hold time: | 1 min. (A, B, D, F, G, H, I, J, K); 2 min. (C, E) |
| Flow rate: | 5 mL/min (A, B, C, D, E, F, G) |
| Flow rate: | 4 mL/min (J, K) |
| Detector Wavelength: | 220 nm |
| Solvent A: | 10% MeOH/90% H₂O/0.1% TFA |
| Solvent B: | 10% H₂O/90% MeOH/0.1% TFA. |

Example 370

Preparation of Compound 370

Compound 370

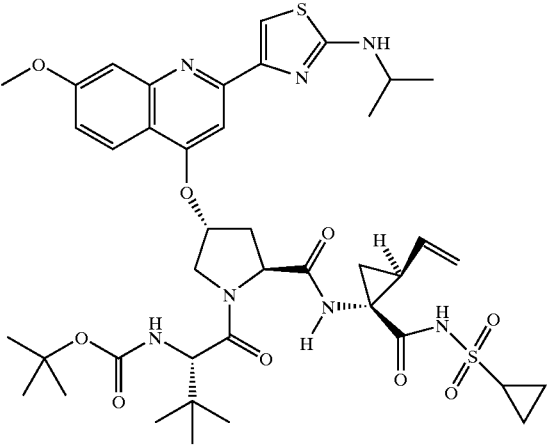

429

-continued

Scheme 1

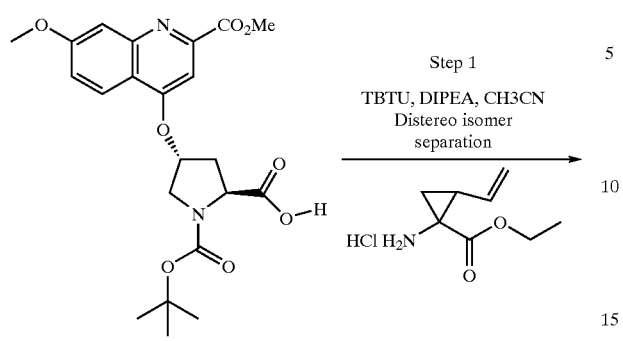

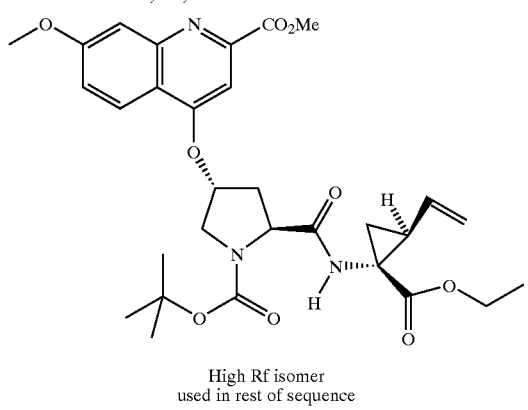

High Rf isomer
used in rest of sequence

430

-continued

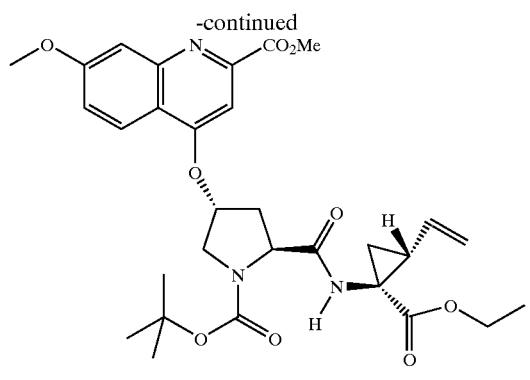

Low Rf isomer

Step 1:

A solution of (1R,2S)/(1S,2R)-1-amino-2-vinylcyclopropane carboxylic acid ethyl ester hydrochloride (2.54 g, 12 mmol) in CH$_3$CN (70 mL) was treated with a solution of diisopropylethylamine (9.5 mL, 67 mmol), [(4R)-(2-methoxycarbonyl-7-methoxylquinoline-4-oxo)-S-proline] (5.9 g, 13.2 mmol), and TBTU (3.89 g, 12.21 mmol) in CH$_3$CN (50 mL). The reaction mixture was stirred for 14 h and concentrated. The residue dissolved in EtOAc was repeatedly washed with NaHCO$_3$ (aq.), brine, dried (MgSO$_4$), and concentrated. The residue was purified over Biotage 65M column (EtOAc/hexane: 45–100%) to provide the high Rf stereo isomer (Boc-P2[(4R)-(2-methoxycarbonyl-7-methoxylquinoline-4-oxo)-S-proline]-P1 (1R,2S Vinyl Acca) Acid ethyl ester 2.0 g (52%) as a white solid: $^1$H NMR (methanol-d$_4$) δ ppm 1.24 (t, J=7.02 Hz, 3H), 1.38 (m, 11H), 1.76 (m, 1H), 2.21 (m, 1H), 2.45 (m, 1H), 2.71 (m, 1H), 3.92 (m, 2H), 3.96 (s, 3H), 4.03 (s, 3H), 4.16 (q, J=7.22 Hz, 2H), 4.42 (m, 1H), 5.10 (m, 1H), 5.30 (m, 1H), 5.44 (s, 1H), 5.77 (m, 1H), 7.27 (d, J=9.16 Hz, 1H), 7.48 (s, 1H), 7.52 (s, 1H), 8.05 (s, 1H).

Scheme 2

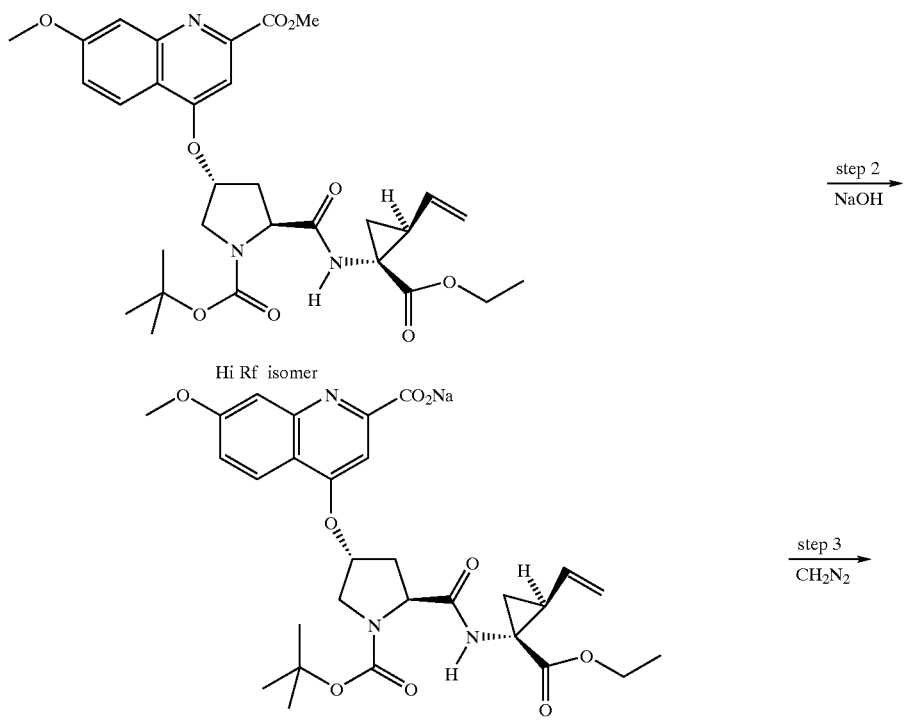

-continued
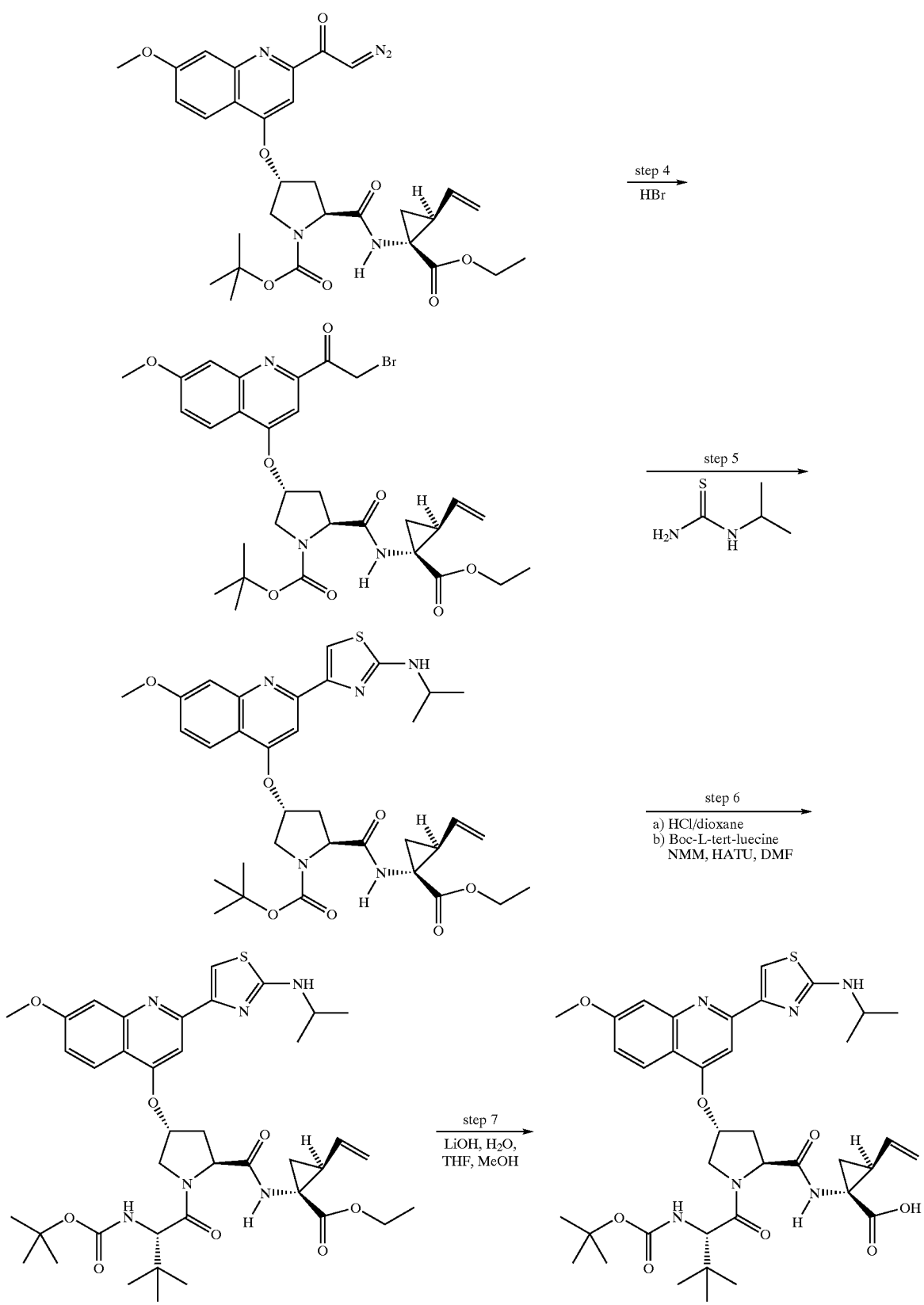

Step 2:

A solution of the high Rf product (3.16 g, 5.40 mmol) of Step 1 of Example 370 {Boc-P2[(4R)-(2-methoxycarbonyl-7-methoxylquinoline-4-oxo)-S-proline]-P1(1R,2S Vinyl Acca) COOEt} at 0° C. dissolved in MeOH/THF (1/1, 13.2 mL) was treated with aqueous 1.0 N NaOH (5.5 mL, 5.5 mmol), stirred for 1 h, neutralized by the addition of AcOH. The solvent was removed in vacuo. The residue was redissolved in THF/CH$_2$Cl$_2$ (1/1, 150 mL), dried (MgSO$_4$) and concentrated in vacuo to provide the product which was directly used in next step: LC-MS (retention time: 1.53 Method D), MS m/z 570 (M$^+$+1).

Step 3:

To a solution of the product (assumed at 5.4 mmol) of step 2 example 370 at 0° C. dissolved in THF (35 mL) was added a solution of fresh made CH$_2$N$_2$ (30 mmol) in Et$_2$O (80 mL). The reaction mixture was stirred at the temperature for 0.5 h, and stirred at rt for 18.5 h. After bubbling nitrogen for 1 h to the reaction mixture, the solution was removed in vacuo. The residue redissolved in EtOAc (1 L) was washed with saturated NaHCO$_3$ (aq.), (2×200 mL), brine (100 mL), and dried (MgSO$_4$). The solvent was removed in vacuo to afford the product 3.10 g (97% two steps): LC-MS (retention time: 3.06, Method J), MS m/z 594 (M$^+$+1).

Step 4:

To a solution of the product (3.03 g, 5.10 mmol) of step 3 of example 370 {Boc-P2[(4R)-(2-diazoacetyl-7-methoxylquinoline-4-oxo)-S-proline]-P1 (1R,2S Vinyl Acca) COOEt} at 0° C. dissolved in THF (110 mL) was added 2 mL of 48% HBr. The mixture was stirred for 1 h, partitioned between EtOAc (500 mL) and saturated NaHCO$_3$ (aq.) (100 mL). The EtOAC layer was separated, dried (MgSO$_4$). The solvent was removed to afford the product (3.12 g, 95%): LC-MS (retention time: 1.56 Method D). MS m/z 648 (M$^+$+1), MS m/z 646 (M—1).

Step 5:

The product (1.0 g, 1.54 mmol) of step 4 of example 370 {Boc-P2[(4R)-(2-bromoacetyl-7-methoxylquinoline-4-oxo)-S-proline]-P1 (1R,2S Vinyl Acca) COOEt} was treated with isopropylthiourea (0.365 g, 3.09 mmol) in isopropyl alcohol (57 mL) for 2 h, and then the solvent was removed. The residue dissolved in aqueous 1.0 N HCl (30 mL) and EtOAC (200 mL) was adjusted pH to 7 by addition of 1.0 N NaOH (aq.). The aqueous layer was extracted with EtOAc (2×100 mL) and the combined extract was dried (MgSO$_4$), concentrated. The residue was purified by over Biotage 40+M column (EtOAc-hexanes: 30–100%) to afford the product 870 mg (84%) and ready for the next step.

Step 6:

The product (0.250 g, 0.375 mmol) of step 5 of example 370 {Boc-P2{(4R)-[2-(2-isopropylaminothiazol-4-yl)-7-methoxylquinoline-4-oxo]-S-proline}-P1 (1R,2S Vinyl Acca) COOEt} was treated with 4N HCl/dioxane (2.5 mL, 10 mmol) for 2.5 h and concentrated in vacuo. To the residue was added N-methylmorpholine (0.206 mL, 1.875 mmol) in DMF (3 mL), N-Boc-L-tert-leucine (0.117 g, 0.506 mmol), and HATU (0.192 g, 0.506 mmol). The mixture was stirred ovenite and partitioned between EtOAc and pH 4.0 buffer. The EtOAc layer was washed with water, NaHCO$_3$ (aq.), dried (MgSO$_4$), concentrated. The residue was purified over a Biotage 40M column (MeOH—CH$_2$Cl$_2$: 0–8%) to afford the product 0.289 g (99%):

LC-MS (retention time: 2.53, Method K), MS m/z 779 (M$^+$+1).

Step 7:

To a suspension of the product of Step 6 (274 mg, 0.352 mmol) of Example 370 {BOCNH-P3(L-t-BuGly)-{[2-(2-isopropylaminothiazol-4-yl)-7-methoxylquinoline-4-oxo]-S-proline}-P1(1R,2S Vinyl Acca)-COOEt} in THF(10.6 mL), CH$_3$OH (2.6 mL), and H$_2$O (5.3 mL) was added LiOH (0.068 g, 2.86 mmol). The reaction mixture was stirred for 24, adjusted to pH 6, removed the organic solvents in vacuo. The aqueous residue was acidified to pH 4, and extracted with CH$_2$Cl$_2$ repeatedly. Combined organic solvent was dried (MgSO$_4$), and concentrated in vacuo to afford the desired product 255 mg (95%): LC-MS (retention time: 2.58, Method K), MS m/z 751 (M$^+$+1).

Scheme 3

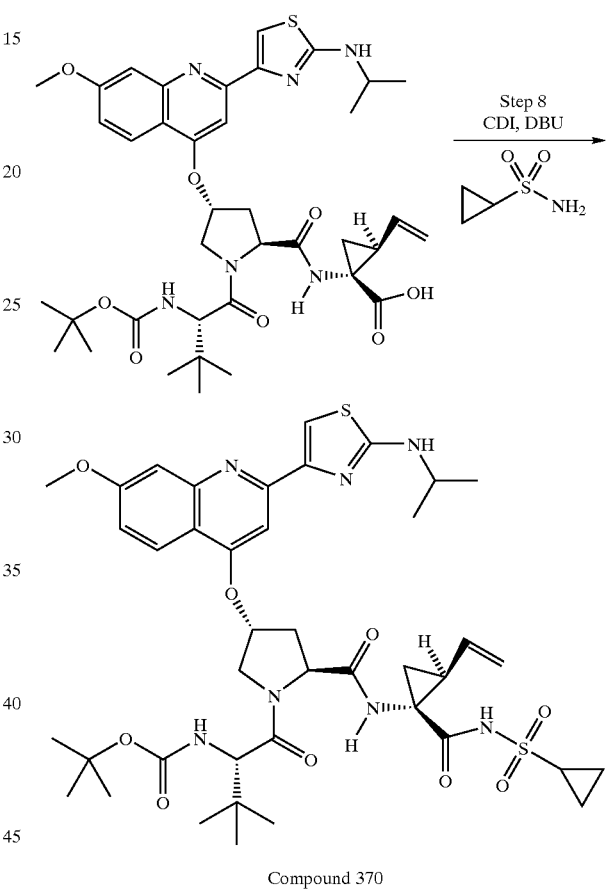

Compound 370

Step 8:

A solution of CDI (0.024 g, 0.15 mmol) and the product of Step 7 of Example 370 (0.0683 g, 0.09 mmol) {BOCNH-P3(L-t-BuGly)-{[2-(2-isopropylaminothiazol-4-yl)-7-methoxylquinoline-4-oxo]-S-proline}-1(1R,2S Vinyl Acca)-COOH} in THF (2 mL) was refluxed for 60 min and allowed to cool down to rt. Cyclopropanesulfonamide (0.022 g. 0.18 mmol) was added followed by the addition of neat DBU (0.027 mL, 0.18 mmol). The reaction was stirred for overnite, worked up by diluting with EtOAc and washed with pH 4.0 buffer, dried (MgSO$_4$), and concentrated. The residue was purified repeatedly by preparative HPLC (0–100% solvent B) and over 1000 μM preparative TLC plate from Analtech (20×40 cM) to afford 0.0032 g (4%) the desired product (Compound 370) as a pale yellow foam:

LC-MS (Retention time: 1.71, method I) MS m/z 854 (M$^+$+1).

Example 371

Preparation of Compound 371

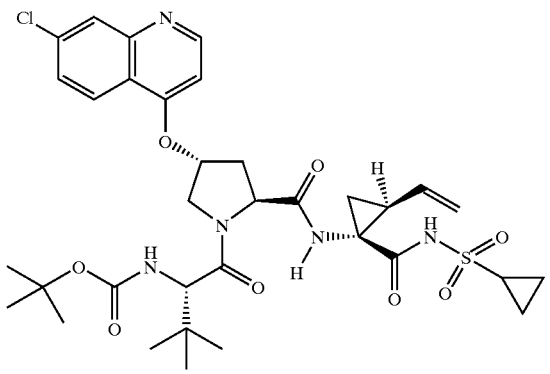
Compound 371

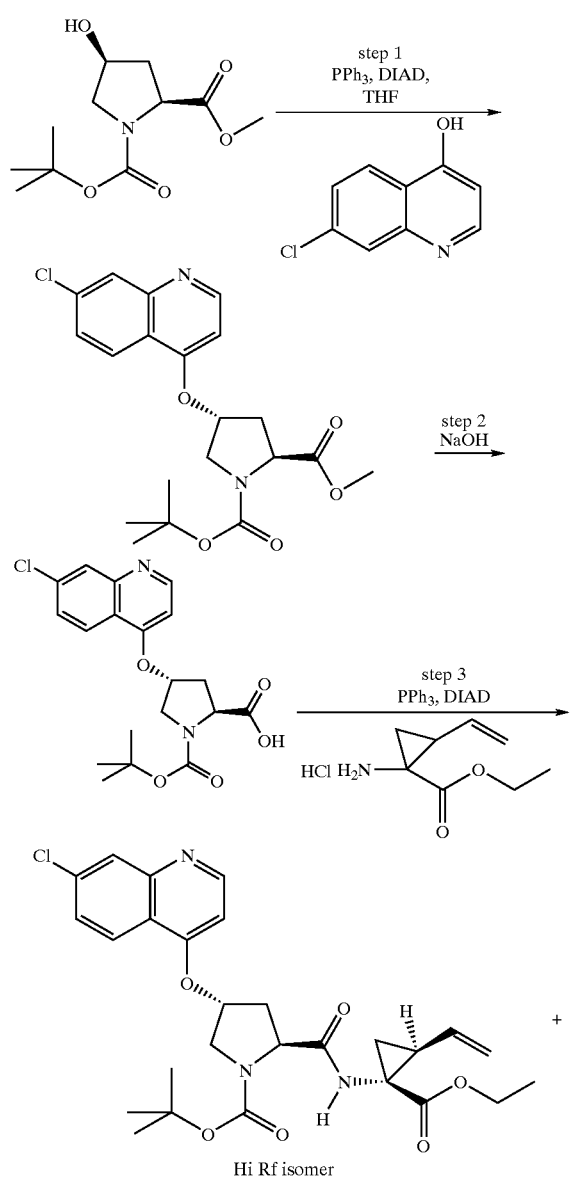

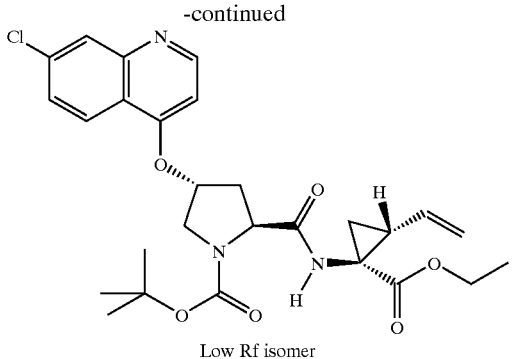
Low Rf isomer

Step 1:
To a suspension of N-Boc-cis-L-4-Hydroxyproline methyl ester (10 g, 40.7 mmol) and 7-chloroquinolin-4-ol (8.73 g, 49.0 mmol) in THF (200 mL) cooled to 0° C. was added $PPh_3$ (12.82 g, 48.9 mmol) and DIAD. (8.80 g, 42.13 mmol). The mixture was slowly allowed to warm to rt overnite, stirred at total of 30 h. The mixture was dissolved in EtOAc (800 mL), washed with 1N aqueous HCl, 5% aqueous $K_2CO_3$ (3×100 mL), brine (2×100 mL) and dried ($MgSO_4$), and concentrated. The residue was purified several times over a Biotage 65M (MeOH—$CH_2Cl_2$: 0–10%) to afford cumulatively 10.57 g (68%) of the desired product as a glass: $^1$H NMR ($CDCl_3$) δ 1.40 (s, 9H), 2.33–2.42 (m, 1H), 2.61–2.72 (m, 1H), 3.75 (s, 3H), 3.91 (m, 2H), 4.45–4.59 (m, 1H), 5.13 (m, 1H), 6.61–6.64 (m, 1H), 7.41 (dd, J=9, 2 Hz, 1H), 7.98 (d, J=2 Hz, 1H), 8.03 (d, J=9 Hz, 1H), 8.67–8.71 (m, 1H). LC-MS (retention time: 1.39, method D), MS m/e 407 ($M^+$+1).

Step 2:
To a solution of the product (10.57 g, 26.0 mmol) of Step 1 of Example 371 {BOC-N-P2[(4R)-(7-chloroquinoline-4-oxo) proline methyl ester} dissolved in MeOH (800 mL) cooled to 0° C. was added an aqueous 1N NaOH solution (44.5 mL, 44.5 mmol). The mixture was warmed to rt after 6 h, stirred overnite, and the pH adjusted to pH 7 using 1.0 N aqueous HCl. The solution was concentrated until only the water layer remained, the pH adjusted to 4 using 6N aqueous HCl and the mixture was partitioned repeatedly with EtOAc (3×500 mL). The combined organic layers were dried ($MgSO_4$) and concentrated to afford 10.16 g (100%) of the as a white solid. $^1$H NMR (DMSO-$d_6$) δ 1.32, 1.34 (two s (rotamers) 9H), 2.31–2.40 (m, 1H), 2.58–2.69 (m, 1H), 3.65–3.81 (m, 2H), 4.33–4.40 (m, 1H), 5.34 (m, 1H) 7.10–7.11 (m, 1H), 7.57 (d, J=9 Hz, 1H), 7.98 (s, 1H), 8.09–8.14 (m, 1H), 8.75 (d, J=5 Hz, 1H), 12.88 (brs, 1H). $^{13}$C NMR (DMSO-$d_6$) δ 27.82, 35.84, 51.52, 57.75, 76.03, 79.33, 102.95, 119.54, 123.86, 126.34, 127.24, 134.49, 149.32, 152.88, 153.25, 159.08, 173.74. LC-MS (retention time: 1.48, method D), MS m/e 393 ($M^+$+1)

Step 3:
To a solution of the product (5.11 g, 13 mmol) of Step 2 of Example 371 {Boc-4(R)-(7-chloroquinoline-4-oxo) proline}, the HCl salt (3.48 g, 18.2 mmol) of vinyl Acca (existing as a 1:1 mixture of diastereoisomers (1R,2S/1S,2R where cyclopropyl carboxyethyl group is syn to vinyl moiety) and NMM (7.1 mL 65 mmol) in DMF (30 mL) was added HATU (6.92 g, 18.2 mmol). The mixture was stirred for 3 days. The reaction mixture was diluted with EtOAc (180 mL) and was partitioned with pH 4.0 buffer (3×100 mL). The organic layer was washed with saturated aqueous $NaHCO_3$ (2×50 mL), water (2×50 mL), and brine (2×50 mL). The organic solution was dried ($MgSO_4$) and concentrated. The residue was purified over a Biotage 40M column (EtOAc-Hexanes: 50% to 100%) to afford 2.88 g of the product existing as a diastereomeric mixture. This mixture was partially separated using a Biotage 65M column (MeOH-EtOAc: 0% to 9%) to afford BOC-NH-P2[(4R)-(7-chloroquinoline-4-oxo)-S-proline]-P1(1R,2S vinyl acca P1 moiety)-COOEt as the initial eluted high Rf isomer (1.20 g, 17.4%). $^1$H NMR (CDCl$_3$/Methanol-d$_4$) δ 1.16 (t, J=7 Hz, 3H), 1.35 (s, 9H), 1.37–1.43 (m, 1H), 1.76–1.84 (m, 1H), 2.06–2.11 (m, 1H), 2.35–2.45 (m, 1H), 2.63 (m, 1H), 3.72–3.93 (m, 2H), 4.02–4.15 (m, 1H), 4.33–4.40 (m, 1H), 5.06 (d, J=9 Hz, 1H), 5.16 (m, 1H), 5.24 (d, J=17 Hz, 1H), 5.63–5.70 (m, 1H), 6.74 (m, 1H), 7.39 (dd, J=9, 2 Hz, 1H), 7.74–7.78 (m, 1H), 7.89 (d, J=2 Hz, 1H), 7.97 (d, J=9 Hz, 1H), 8.60 (d, J=5 Hz, 1H). $^1$H NMR (methanol-d$_4$, 60/40 Rotomers) δ 1.24 (t, J=7 Hz, 3H), 1.39, 1.43 (2s, 9H, ratio 4:6), 1.71–1.74 (m, 0.4H), 178–1.81 (m, 0.6H), 2.18–2.23 (m, 1H), 2.65–2.69 (m, 0.4H), 2.71–2.76 (m, 0.6H), 3.88–3.96 (m, 2H), 4.11–4.18 (m, 2H), 4.39–4.45 (m, 1H), 5.09–5.13 (m, 1H), 5.28–5.33 (m, 1H), 5.37 (m, 1H), 5.73–5.81 (m, 1H), 7.05 (d, J=5 Hz, 1H), 7.53 (d, J=8.9 Hz, 1H), 7.92 (s, 1H), 8.12 (d, J=8.9 Hz, 1H), 8.70 (d, J=5 Hz, 1H). LC-MS (retention time: 1.54, method A) MS m/z 530 (M$^+$+1). The rest of the material (~1.66 g, 24%) was mixed fractions greatly enriched in the lower Rf isomer.

Scheme 2

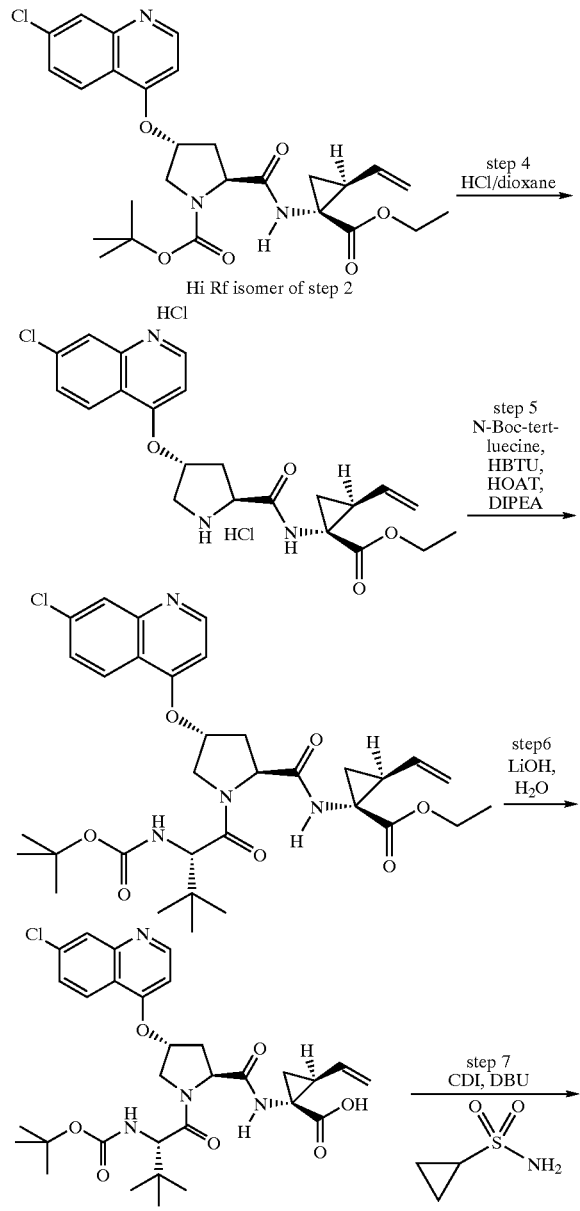

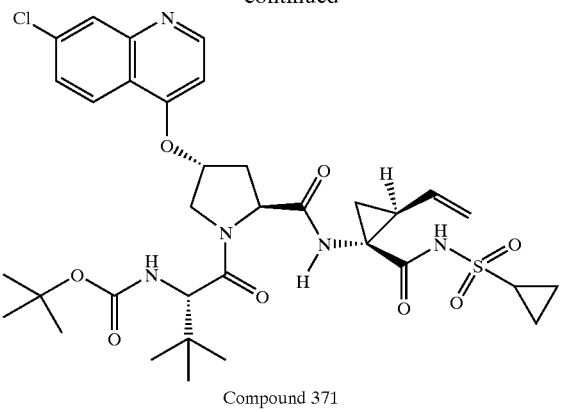

Compound 371

Step 4:

The product (0.65 g, 1.22 mmol) of step 3 of Example 371 {BOC-P2 [(4R)-(7-chloroquinoline-4-oxo)-S-proline]-P1 (1R,2S Vinyl Acca-CO$_2$Et} was dissolved in 4N HCl/dioxane (4.5 ml, 18 mmol) and stirred for 1 h at rt. The reaction mixture was concentrated and the crude product was directly used in next step: LC-MS (retention time: 0.94, method A) LC-MS m/z 430 (M$^+$+1).

Step 5:

To suspension of the product 1(0.22 mmol) of step 4 Example 371 {Bis HCl Salt of NH$_2$-P2[(4R)-(7-chloroquinoline-4-oxo)-S-proline]-1(1R,2S-Vinyl Acca)-COOEt), N-BOC-L-tert-leucine (BOC L-tBuGly) (0.34 g, 1.47 mmol), DIPEA (1.0 ml, 5.74 mmol), HOBT.H$_2$O (0.22 g, 1.47 mmol) in CH$_2$Cl$_2$ (15 mL) was added HBTU (0.56 g, 1.47 mmol) at rt. The reaction mixture was stirred overnite, diluted with CH$_2$Cl$_2$ (50 mL), washed with pH 4.0 buffer (2×20 mL), saturated aqueous NaHCO$_3$ (50 mL), brine (50 mL), dried (MgSO$_4$), and concentrated. The residue was purified over a Biotage 40 M column (EtOAc-Hexanes: 15% to 60%) to afford 607 mg (77%) of the product as a foam. $^1$H NMR (CDCl$_3$-methanol-d$_4$) δ 1.00 (s, 9H), 1.19 (t, J=7 Hz, 1H), 1.30 (s, 9H), 1.38 (m, 1H), 1.78–1.83 (m, 1H), 2.01–2.46 (m, 2H), 2.73–2.82 (m 1H), 3.96–4.03 (m, 1H), 4.04 (d, J=10 Hz, 1H), 4.11 (q, J=7 Hz, 2H), 4.42 (d, J=12 Hz, 1H), 4.68–4.73 (m, 1H), 5.09–5.13 (m, 1H), 5.23–5.31 (m, 2H), 5.67–5.79 (m, 1H), 6.78 (d, J=9 Hz, 1H), 7.38 (d, J=9 Hz, 1H), 7.70 (s, 1H), 7.96 (s, 1H), 8.08 (d, J=9 Hz, 1H), 8.68 (d, J=5 Hz, 1H). LC-MS (retention time: 1.64, method A), MS m/z 643 (M$^+$+1).

Step 6:

To a suspension of the product (207 mg, 0.32 mmol) of Step 5 of Example 371 {BOCNH-P3(L-t-BuGly)-P2[(4R)-7-chloroquinoline-4-oxo)-S-proline]-1(1R,2S Vinyl Acca)-CO$_2$Et} in THF(14 mL), CH$_3$OH (2 mL), and H$_2$O (8 mL) was added LiOH (62 mg, 2.60 mmol). The reaction mixture was stirred for one day, adjusted to neutral pH, and concentrated in vacuo until only the aqueous layer remained. The resulting aqueous residue was acidified to pH 4.0 by addition of 1.0 N aqueous HCl and then saturated with solid NaCl. This aqueous mixture was extracted repeatedly with EtOAc (3×60 mL), the combined organic solvent was dried (Mg$_2$SO$_4$) and concentrated in vacuo to afford 107 mg (54%) of the product {BOCNH-P3(L-t-BuGly)-P2[(4R)-(7-chloroquinoline-4-oxo)-S-proline]-1(1R,2S Vinyl Acca)-CO$_2$H} as a white solid. $^1$H NMR (CDCl$_3$) δ 1.06 (s, 9H), 1.23 (2s, 9H), 1.31–1.43 (m 1H), 1.63–1.70 (m, 1H), 1.85–1.89 (m, 1H), 2.19 (m, 1H), 2.65–2.78 (m, 1H), 4.03–4.10 (m, 1H), 4.18–4.21 (m, 1H), 4.55–4.62 (m, 1H), 5.03–5.12 (m, 1H), 5.23–5.31 (m, 1H), 5.51 (m, 1H), 5.88–5.95 (m, 1H), 7.12 (m, 1H), 7.47–7.50 (m, 1H), 7.96 (m, 1H), 8.26 (d, J=9 Hz, 1H), 8.75 (d, J=5 Hz, 1H). LC-MS (retention time: 1.46, method A), MS m/z 615 (M$^+$+1).

Step 7:

To a solution of the tripeptide acid (0.0453 g, 0.074 mmol) of Step 6 Example 371 {BOCNH-P3(L-t-BuGly)-P2[(4R)-(7-chloroquinoline-4-oxo)-S-proline]-1(1R,2S Vinyl Acca)-CO$_2$H} in THF(4 mL) was added CDI (17 mg, 0.10 mmol), and the resulting solution refluxed for 45 min and allowed to cool down to rt. Cyclopropylsulfonamide (0.013 g, 0.10 mmol) was added in one portion before the addition of neat DBU (0.015 mL, 0.10 mmol). The reaction was stirred for 18 h, diluted with EtOAc (200 mL) and washed pH 4.0 buffer (3×30 mL), water (2×30 mL), brine (30 mL), dried (MgSO$_4$) and purified using one 20×40 cM 1000□ Analtech PTLC plate (MeOH—CH$_2$Cl$_2$: 0 to 2%) to afford the desired product (Compound 371) as a foam (0.040 g, 76%): $^1$H NMR δ 0.95–1.23 (m, 4H), 1.03 (s, 9H), 1.19 (s, 9H), 1.40–1.43 (m, 1H), 1.85 (dd, J=8, 5 Hz, 1H), 2.12–2.20 (m, 1H), 2.43 (m, 1H), 2.82 (m, 1H), 4.07–4.19 (m, 2H), 4.51–4.57 (m, 2H), 5.07 (d, J=10 Hz, 1H), 5.25 (d, J=17 Hz, 1H), 5.85 (m, 1H), 5.48 (s, 1H), 7.09 (d, J=5 Hz, 1H), 7.45 (d, J=9 Hz, 1H), 7.92 (m, 1H), 8.20 (d, J=9 Hz, 1H), 8.72 (d, J=5 Hz, 1H); LC-MS (retention time: 1.52, method B), MS m/z 718 (M$^+$+1). HRMS m/z (M+H)$^+$ calcd for C$_{41}$H$_{51}$N$_5$SO$_9$: 718.2677 found 718.2674.

Example 372

Preparation of Compound 372

Compound 372

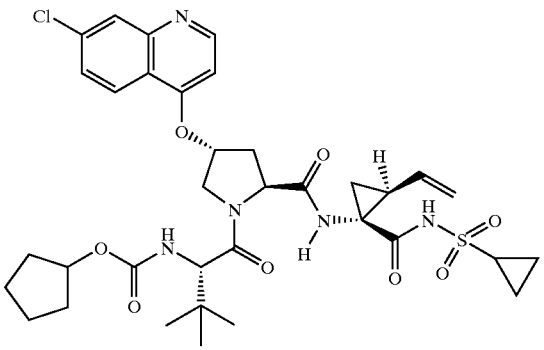

Scheme 1

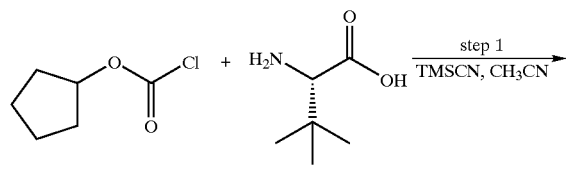

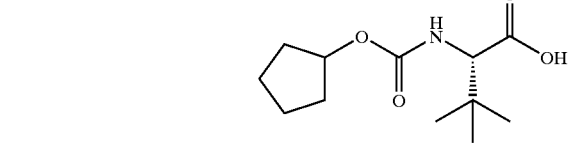

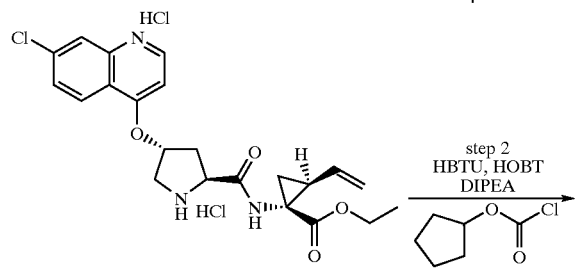

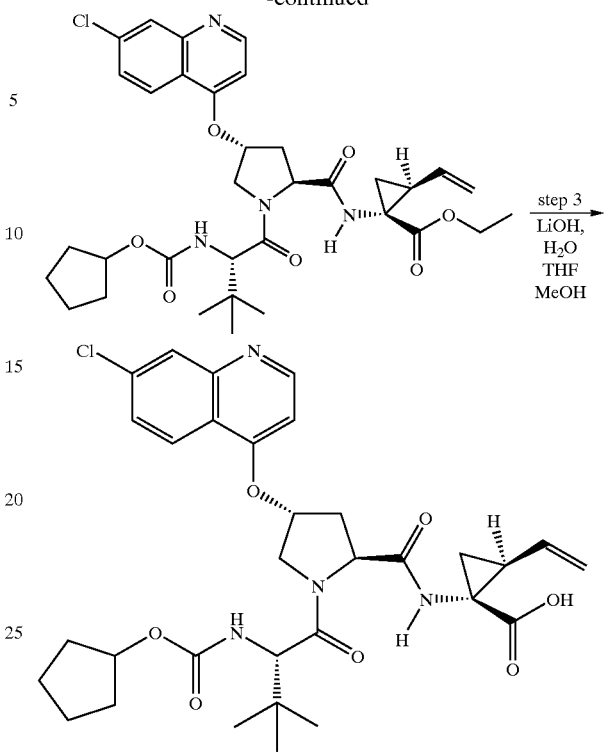

Step 1:

To a solution of L-tert-leucine (2 g, 15.25 mmol) dissolved in CH$_3$CN (50 mL) was added TMSCN (7.06 mL, 56.41 mmol) and stirred for 15 min. The reaction mixture was heated to 75° C. for 30 min. Cyclopentyl chloroformate (2.83 g, 19.06 mmol) was added to the reaction mixture and the reaction mixture was heated at 80° C. overnite, concentrated in vacuo. The residue was treated with MeOH (40 mL), stirred for 10 min, and concentrated in vacuo. The residue was adjusted pH to 8.5, and extracted with Et$_2$O (2×200 mL). The aqueous layer was acidified to pH 3 and extracted with CH$_2$Cl$_2$ (2×200 mL). The combined extract was dried (MgSO$_4$), and concentrated in vacuo. The residue was recrystallized from minimal amount of Et$_2$O/hexanes to afford the product 3.48 g (94%): $^1$H NMR (500 MHz, methanol-d$_4$) δ ppm 1.00 (s, 9H), 1.59 (m, 2H), 1.73 (m, 4H), 1.84 (dd, J=5.95, 3.20 Hz, 2H), 3.98 (s, 1H), 5.02 (m, 1H).

Step 2:

To a solution of the product (530.1 mg, 1.04 mmol) of Step 4 of Example 371 {HCl salt of P2[(4R)-7-chloroquinoline-4-oxo)-S-proline]-P1(1R,2S Vinyl Acca) COOEt, the product (328 mg, 1.35 mmol) of Step 1 of Example 372 {(L)-2-cyclopentyloxycarbonylamino-3,3-dimethyl-butyric acid}, HOBT (146 mg, 1.08 mmol), and diisopropylethylamine (0.755 mL, 4.32 mmol) in CH$_2$Cl$_2$ (7 mL) was added HBTU (512 mg, 1.35 mmol). The reaction mixture was stirred for overnite and partitioned between CH$_2$Cl$_2$ and pH 4.0 buffer. The CH$_2$Cl$_2$ layer was washed with water, saturated NaHCO$_3$ (aq.), dried (MgSO$_4$), concentrated. The residue was purified over a Biotage 40M column (EtOAc-Hexanes: 35–100%) to afford the product 640 mg (92%): $^1$H NMR (methanol-d$_4$) δ ppm 1.02 (s, 9 H), 1.26 (m, 4 H), 1.56 (m, 10 H), 2.19 (q, J=8.75 Hz, 1 H), 2.41 (m, 1 H), 2.70 (dd, J=14.19, 8.09 Hz, 1 H), 4.01 (dd, J=11.90, 3.05 Hz, 1 H), 4.13 (m, 2 H), 4.20 (s, 1 H), 4.53 (m, 1 H), 4.62 (m, 1 H), 5.09 (d, J=10.38 Hz, 1 H), 5.26 (d, J=17.09 Hz, 1 H), 5.47 (m, 1 H), 5.77 (m, 1 H), 7.07 (d, J=5.49 Hz, 1 H), 7.47 (m, 1 H), 7.94 (m, 1 H), 8.20 (d, J=8.85. Hz, 1 H), 8.72 (d, J=5.49 Hz, 1 H). LC-MS (retention time: 1.71, Method B), MS m/z 655 (M⁺+1).

Step 3:

Tripeptide acid was prepared by following Step 7 of Scheme 2 of Example 370, except that cyclopentoxycarbonyl-NH-P3(L-tert-BuGly)-P2[(4R)-(7-chloroquinoline-4-oxo)-S-proline]-P1(1R,2S Vinyl Acca)-COOEt used in place of the product of Step 6 of Example 370.

Modification: 0.636 g (0.97 mmol) of the product of Step 2 of Example 372 used, 0.424 g obtained (69% yield).

Product:

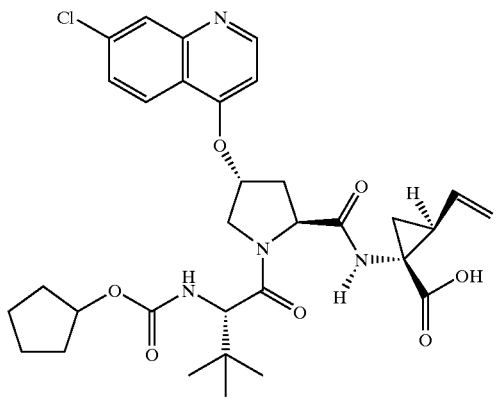

Data: ¹H NMR (methanol-d₄) δ ppm 1.02 (s, 9 H), 1.57 (m, 11 H), 2.14 (q, J=9.03 Hz, 1 H), 2.46 (m, 1 H), 2.68 (m, 1 H), 4.02 (dd, J=11.89, 3.11 Hz, 1 H), 4.19 (m, 1 H), 4.50 (d, J=26.35 Hz, 1 H), 4.64 (t, J=8.42 Hz, 1 H), 5.04 (m, 1 H), 5.24 (d, J=17.20 Hz, 1 H), 5.44 (s, 1 H), 5.87 (m, 1 H), 7.05 (d, J=5.12 Hz, 1 H), 7.48 (m, 1 H), 7.92 (m, 1 H), 8.18 (d, J=8.78 Hz, 1 H), 8.71 (d, J=5.49 Hz, 1 H). LC-MS (retention time: 2.32, Method A), MS m/z 627 (M⁺+1).

Step 4:

A solution of CDI (0.021 g, 0.13 mmol) and the product of Step 3 of Example 372 (0.058 g, 0.09 mmol) {BOCNH-P3(L-t-BuGly)-P2[(4R)-7-chloroquinoline-4-oxo)-S-proline]-P1(1R,2S Vinyl Acca)-CO₂H} in THF(2 mL) was refluxed for 40 min and allowed to cool down to rt. A total of 0.016 g (0.13 mmol) of cyclopropanesulfonamide, followed by the addition of a solution of neat DBU (0.019 mL, 0.13 mmol). The reaction was stirred for overnite, then diluted with EtOAc (100 mL) and washed pH 4.0 buffer (2×), dried (MgSO₄), concentrated and purified over three 1000 µM preparative TLC plate from Analtech (20×40 cM, eluted sequentially with 50% to 0% to 2% MeOH in CH₂Cl₂) to provide product (Compound 372) 27.3 mg (40%): ¹H NMR (methanol-d₄) δ ppm 0.94 (m, 2 H), 1.02 (s, 9 H), 1.14 (m, 1 H), 1.49 (m, 11 H), 1.86 (m, 1 H), 2.14 (m, 1 H), 2.49 (m, 1 H), 2.68 (dd, J=13.89, 7.48 Hz, 1 H), 2.78 (m, 1 H), 4.08 (m, 1 H), 4.22 (s, 1 H), 4.55 (m, 2 H), 5.05 (d, J=10.07 Hz, 1 H), 5.22 (d, J=17.09 Hz, 1 H), 5.46 (m, 1 H), 5.86 (m, 1 H), 7.07 (d, J=5.19 Hz, 1 H), 7.46 (d, J=8.55 Hz, 1 H), 7.91 (s, 1 H), 8.18 (d, J=8.85 Hz, 1 H), 8.72 (d, J=5.19 Hz, 1 H). LC-MS (retention time: 1.52 Method I), MS m/z 730 (M⁺+1).

Example 373

Preparation of Compound 373

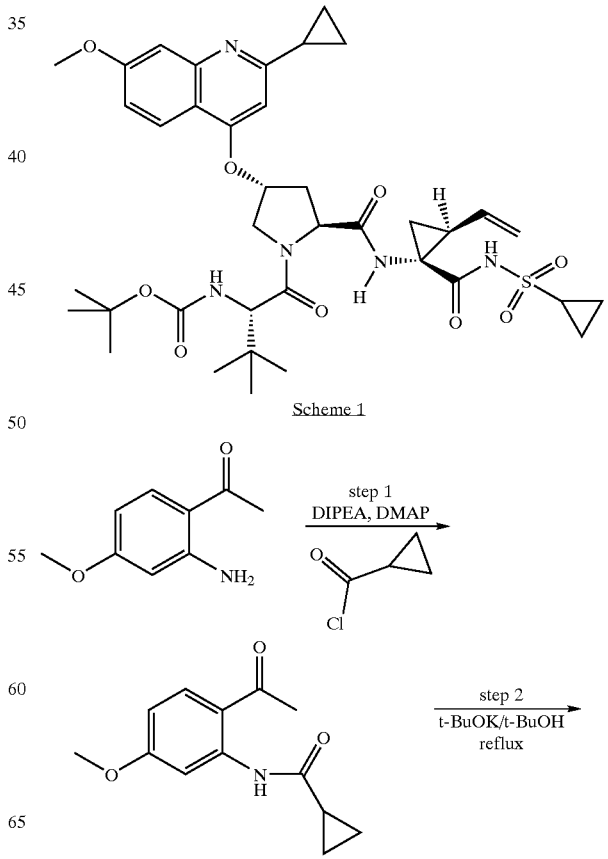

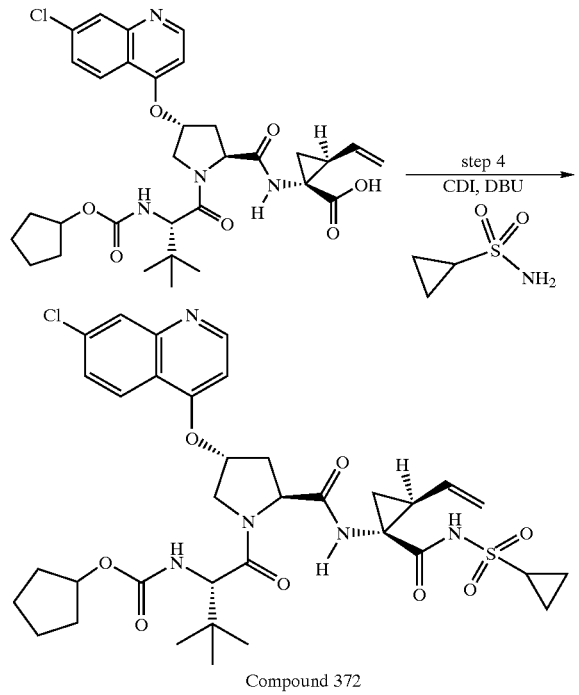

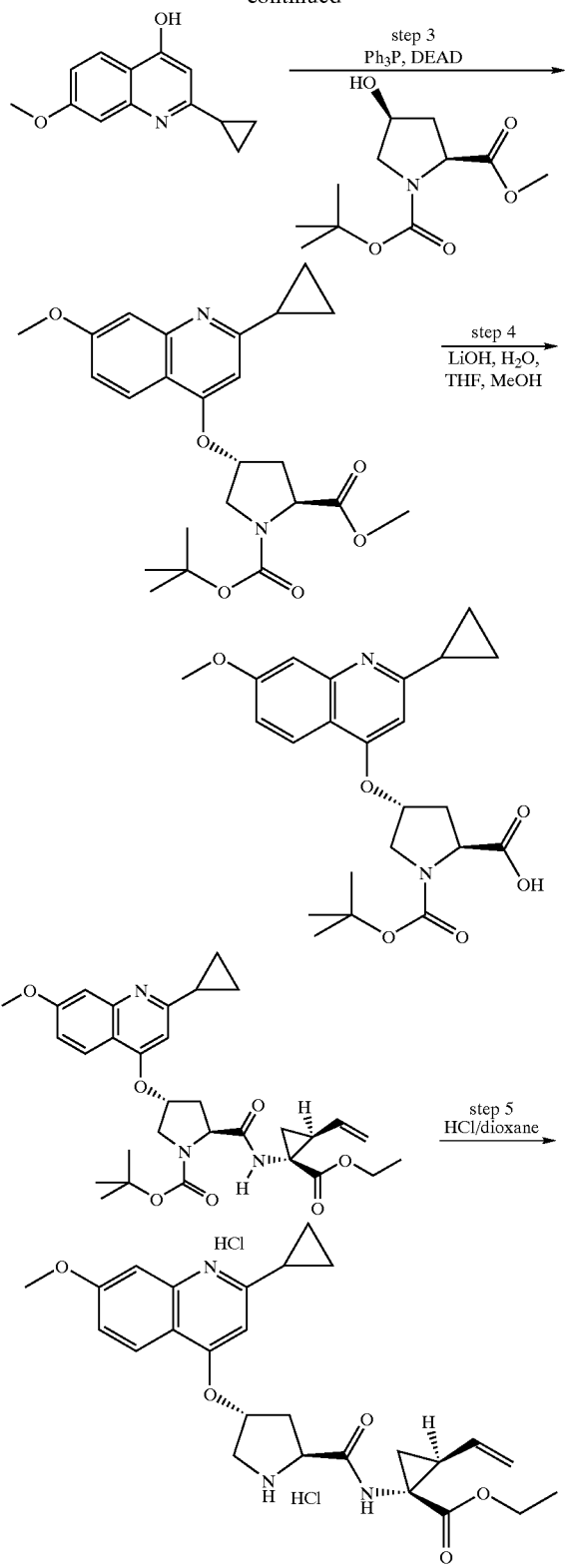

Step 1:

A solution of 2-amino-4-methoxyacetophenone (4.45 g, 26.94 mmol) at 0° C. dissolved in CH₂Cl₂ (100 mL) was treated with cyclopropanecarbonyl chloride (3.1 mL, 33.68 mmol) diisopropylethylamine (19 mL, 107.8 mmol), DMAP (0.780 g, 6.4 mmol). The reaction mixture was stirred at rt overnite and concentrated in vacuo. The residue dissolved in CH₂Cl₂ (500 mL) was washed with aqueous 1 N HCl, water, NaHCO₃ (aq.), and dried (MgSO₄). The solvent was removed in vacuo and the solid residue was treated with EtOAc/hexanes (1/1) to provide the product (5.35 g, 85%):

¹H NMR (methanol-d₄) δ ppm 0.94 (m, 4 H), 1.69 (m, J=3.97 Hz, 1 H), 2.60 (s, 3 H), 3.84 (s, 3 H), 6.69 (d, J=7.93 Hz, 1 H), 7.98 (d, J=8.85 Hz, 1 H), 8.23 (s, 1 H).

Step 2:

A solution of product (5.35 g, 22.72 mmol) of Step 1 example 373 {cyclopropanecarboxylic acid (2-acetyl-5-methoxy-phenyl)-amide} and tert-BuOK (5.45 g, 48.6 mmol) in tert-butanol (130 g) was refluxed for 6 h. The reaction mixture was cooled, poured into ice cold buffer and adjusted to pH 7, filtered. The solid collection was recrystallized from MeOH/Et₂O to provide the product (1 g, 20%): ¹H NMR (methanol-d₄) δ ppm 0.96 (m, 2 H), 1.15 (m, 2 H) 1.94 Hz, 1 H), 3.87 (s, 3 H), 5.86 (m, 1 H), 6.93 (m, 2 H), 8.04 (d, J=8.85 Hz, 1 H).

Step 3:

To a solution of N-Boc-L-3-hydroxyproline (1.06 g, 4.32 mmol) and triphenylphosphine (2.27 g, 8.64 mmol) at 0° C. dissolved THF(25 mL) was added a solution of the product (0.93 g, 4.32 mmol) of Step 2 Example 373 {2-Cyclopropyl-7-methoxy-quinolin-4-ol} and DEAD (1.50 g, 8.64 mmol) in THF(25 mL) over 30 min. The reaction mixture was stirred overnite and concentrated. The residue was purified twice by a Biotage 40+M column (EtOAc-Hexanes: 20–65%) to afford the product 1.74 g (90%): LC-MS (retention time: 2.56, Method J), MS m/z 443 (M⁺+1).

Step 4:

To a suspension of (1.70 g, 3.86 mmol) of the product of Step 3 of Example 373 (Boc-(4R)-(2-cyclopropyl-7-methoxy-quinoline-4-oxo)-S-proline methyl ester} in THF (91 mL), CH₃OH (18.2 mL), and H₂O (27 mL) was added LiOH (0.73 g, 30 mmol). The reaction mixture was stirred for 16 h, adjusted to pH 6, the organic solvent was removed in vacuo. The residue was acidified to pH 4, and extracted with EtOAc (4×100 mL). The combined organic extract was dried (MgSO₄), and concentrated in vacuo to supply the product 1.64 g (100%): ¹H NMR (methanol-d₄) δ ppm 1.32 (m, 13 H), 2.37 (m, 2 H), 2.71 (m, 1 H), 3.86 (m, 1 H), 3.95 (s, 3 H), 4.14 (m, 1 H), 4.43 (m, 1 H), 5.41 (s, 1 H), 6.65 (s, 1 H), 7.19 (m, 1 H), 7.30 (m, 1 H), 8.02 (dd, J=12.63, 9.33 Hz, 1 H).

Step 5:

The product (1.61 g, 2.79 mmol) of Step 4 of Example 373 {Boc-P2{(4R)-[2-cyclopropyl-7-methoxylquinoline-4-oxo]-S-proline}-1(1R,2S Vinyl Acca) COOEt} was dissolved in HCl/dioxane (15 mL; 60 mmol) and stirred for 3 h at rt. The reaction mixture was concentrated and azeotroped with dry THF to afford the product (1.58 g, 100%): LC-MS (retention time: 2.12, Method K), MS m/z 566 (M⁺+1).

Scheme 2

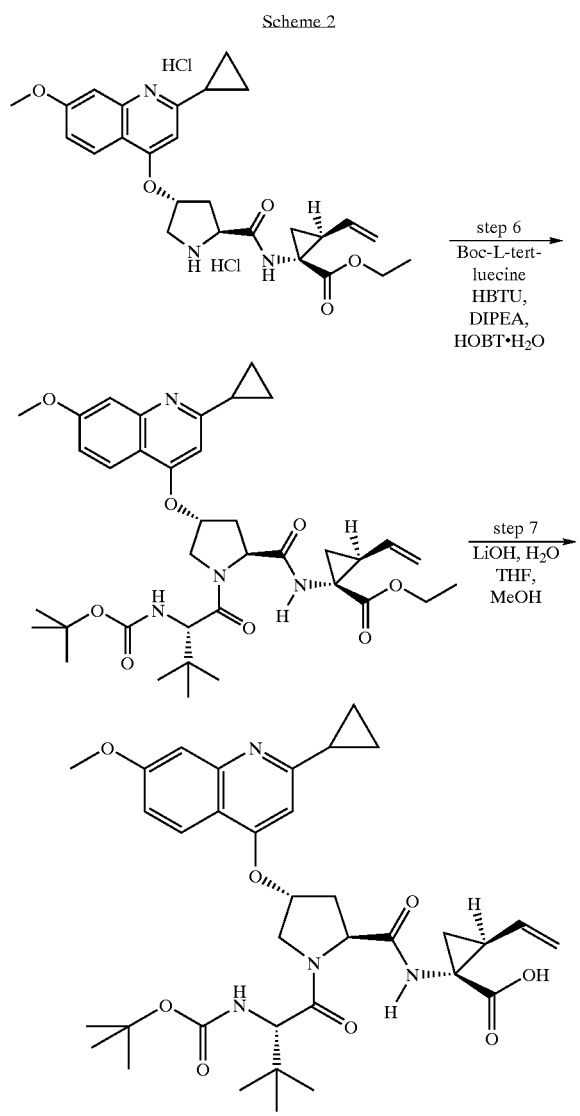

Step 6:
To a suspension of the product (1.58 g, 2.79 mmol) of Step 5 of Example 373 {Bis HCl salt of P2 {(4R)-[2-cyclopropyl-7-methoxylquinoline-4-oxo]-S-proline}-P1 (1R,2S Vinyl Acca) COOEt}, diisopropylethylamine (1.65 mL, 9.25 mmol), N-Boc-L-tert-leucine (0.775 g, 3.35 mmol), HOBT.H$_2$O (0.515 g, 3.36 mmol) in CH$_2$Cl$_2$ (13 mL) was added HBTU (1.28 g, 3.36 mmol). The mixture was stirred for 14 h and partitioned between EtOAc and pH 4.0 buffer. The EtOAc layer was dried (MgSO$_4$), concentrated. The resisdue was purified over a Biotage 40+M column (EtOAc-hexanes: 20–100%, followed MeOH) and further purified by 20×40 cM 1000□ Analtech PTLC plate (MeOH—CH$_2$Cl$_2$ 2%) to afford the product 1.4 g (63%):

$^1$H NMR (methanol-d$_4$) δ ppm 1.04 (s, 9 H), 1.20 (m, 5 H), 1.28 (s, 9 H), 1.39 (m, 2 H), 1.69 (m, 1 H), 2.19 (m, 2 H), 2.36 (m, 1 H), 2.63 (dd, J=13.54, 7.68 Hz, 1 H), 3.90 (s, 3 H), 4.08 (m, 4 H), 4.19 (d, J=11.34 Hz, 1 H), 4.47 (d, J=11.71 Hz, 1 H), 4.56 (t, J=8.60 Hz, 1 H), 5.08 (m, 1 H), 5.24 (m, 1 H), 5.39 (s, 1 H), 5.78 (m, 1 H), 6.56 (s, 1 H), 6.96 (dd, J=9.15, 2.20 Hz, 1 H), 7.21 (d, J=2.56 Hz, 1 H), 7.97 (d, J=9.15 Hz, 1 H). LC-MS (retention time: 2.34, Method K), MS m/z 679 (M$^+$+1).

Step 7:
To a suspension of the product of Step 6 of Example 373 (1.28 g, 1.89 mmol), Boc-NH-P3(L-tert-BuGly)-P2[(4R)-(2-cyclopropyl-7-methoxylquinoline-4-oxo)-S-proline]-P1 (1R,2S Vinyl Acca)-COOEt, in THF(93 mL), CH$_3$OH (23 mL), and H$_2$O (45 mL) was added LiOH (0.491 g, 20.4 mmol). The reaction mixture was stirred for 18.5 h, adjusted to pH 4, removed the organic solvent in vacuo. The residue was extracted with EtOAc (5×100 mL). Combined organic solvent was dried (MgSO$_4$), and concentrated in vacuo to afford the desired product 1.17 g (97%): $^1$H NMR (methanol-d$_4$) δ ppm 1.04 (s, 9 H), 1.24 (s, 9 H), 1.27 (m, 3 H), 1.42 (m, 2 H), 1.68 (dd, J=8.05, 5.12 Hz, 1 H), 2.17 (m, 1 H), 2.33 (m, 1 H), 2.47 (m, 1 H), 2.66 (m, 1 H), 3.95 (s, 3 H), 4.09 (m, 2 H), 4.51 (d, J=11.71 Hz, 1 H), 4.59 (t, J=8.60 Hz, 1 H), 5.07 (m, 1 H), 5.26 (m, 1 H), 5.52 (s, 1 H), 5.85 (m, 1 H), 6.69 (s, 1 H), 7.10 (dd, J=9.15, 2.20 Hz, 1 H), 7.27 (d, J=2.20 Hz, 1 H), 8.10 (d, J=9.15 Hz, 1 H). LC-MS (retention time: 2.21, Method K), MS m/z 651 (M$^+$+1).

Scheme 3

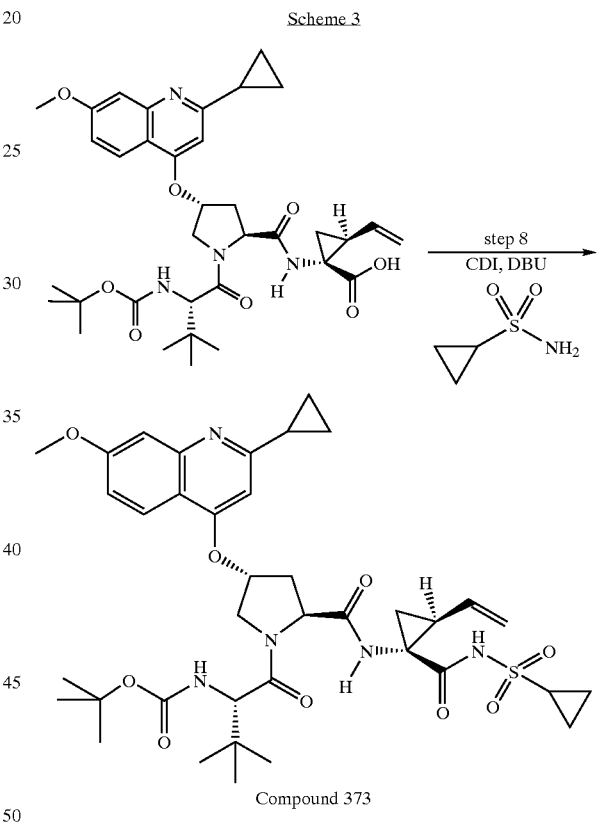

Compound 373

Step 8:
A solution of CDI (0.058 g, 0.344 mmol) and the product of Step 7 of Example 373 (0.160 g, 0.246 mmol) {Boc-NH-P3(L-tert-BuGly)-P2[(4R)-(2-cyclopropyl-7-methoxylquinoline-4-oxo)-S-proline]-P1(1R,2S Vinyl Acca)-COOH} in THF(2 mL) was refluxed for 60 min and allowed to cool down to rt. Cyclopropanesulfonamide (0.041 g, 0.344 mmol) followed by the addition of neat DBU (0.051 mL, 0.344 mmol). The reaction was stirred for 24 h and worked up by partition the reaction mixture between pH 4.0 buffer and EtOAc. The organic layer was dried (MgSO$_4$), concentrated and purified by preparative HPLC (0–100% solvent B) to supply the product (Compound 373) 0.086 g (46%): $^1$H NMR (TRIFLUOROACETIC ACID-D) δ ppm 1.04 (s, 9 H), 1.21 (m, 16 H), 1.41 (m, 1 H), 1.87 (dd, J=8.05, 5.49 Hz, 1 H), 2.26 (m, 3 H), 2.61 (dd, J=12.99, 6.77 Hz, 1 H), 2.93 (m, 1 H), 3.92 (s, 3 H), 4.09 (m, 1 H), 4.21 (m, 1 H), 4.49 (m, 2 H), 5.11 (d, J=11.71 Hz, 1 H), 5.27 (d, J=17.20 Hz, 1 H), 5.46 (s, 1 H), 5.76 (m, 1 H), 6.62 (m, 2 H), 7.01 (dd, J=8.97, 2.01 Hz, 1 H), 7.23 (d, J=2.56 Hz, 1 H), 8.00 (d, J=8.78 Hz, 1 H).

Example 374

Preparation of Compound 374

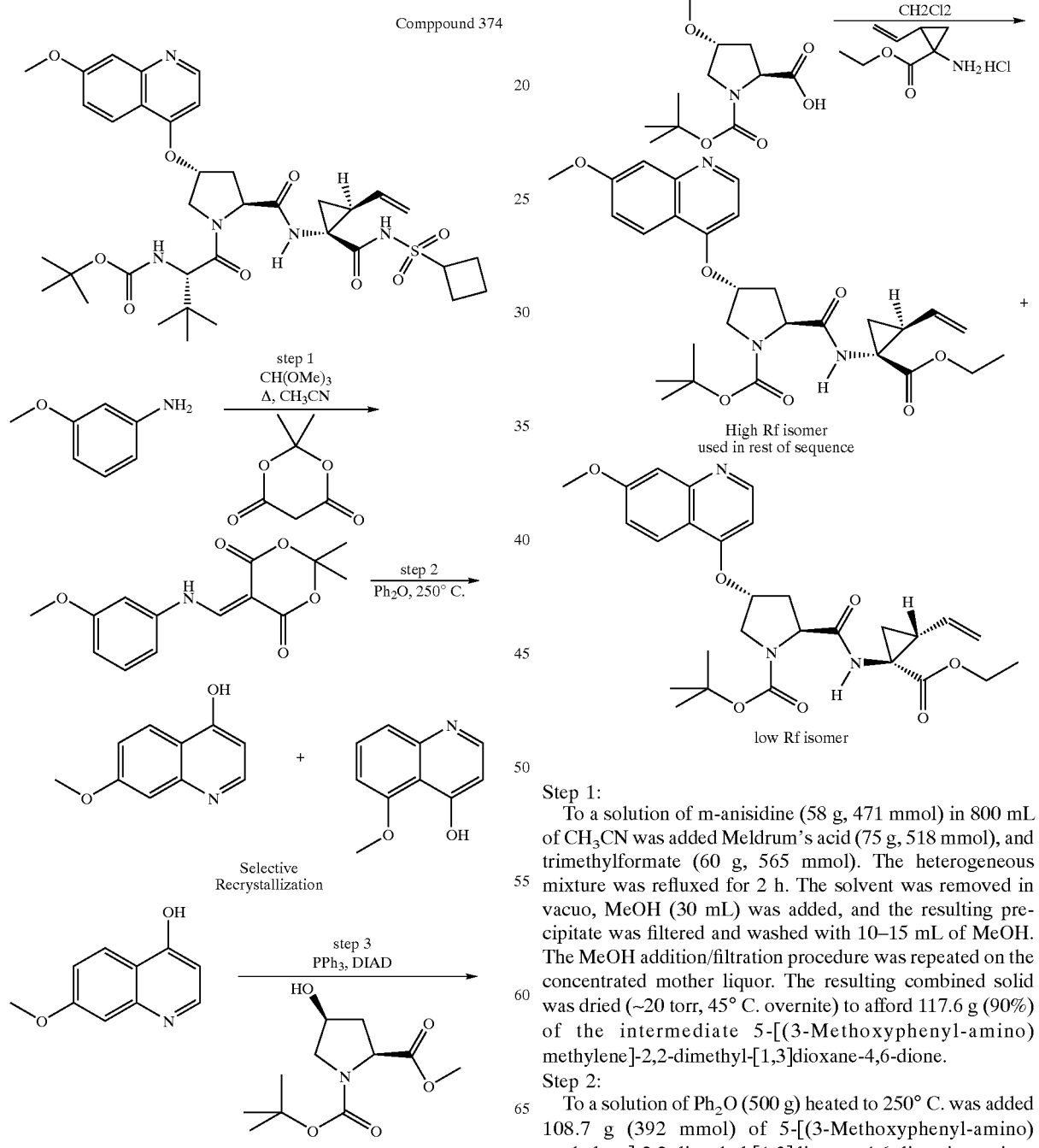

Step 1:

To a solution of m-anisidine (58 g, 471 mmol) in 800 mL of $CH_3CN$ was added Meldrum's acid (75 g, 518 mmol), and trimethylformate (60 g, 565 mmol). The heterogeneous mixture was refluxed for 2 h. The solvent was removed in vacuo, MeOH (30 mL) was added, and the resulting precipitate was filtered and washed with 10–15 mL of MeOH. The MeOH addition/filtration procedure was repeated on the concentrated mother liquor. The resulting combined solid was dried (~20 torr, 45° C. overnite) to afford 117.6 g (90%) of the intermediate 5-[(3-Methoxyphenyl-amino) methylene]-2,2-dimethyl-[1,3]dioxane-4,6-dione.

Step 2:

To a solution of $Ph_2O$ (500 g) heated to 250° C. was added 108.7 g (392 mmol) of 5-[(3-Methoxyphenyl-amino) methylene]-2,2-dimethyl-[1,3]dioxane-4,6-dione in portions over a 30 min period. The mixture was heated an additional 15 min, cooled to rt, diluted with hexanes (800 mL) and the resulting slurry stirred overnite. The hexanes was decanted off, the solid residue dissolved in 600 mL of MeOH at reflux, cooled to rt and the resulting solid filtered and washed with minimal CH$_2$Cl$_2$. The analogous recrystallization procedure was followed to afford a total of 20.73 g (30%) of 7-methoxyquinolin-4-ol as a light brown solid. $^1$H NMR (methanol-d$_4$) δ 3.87 (s, 3H), 6.23 d, J=7.3 Hz, 1H), 6.68 (d, J=2.4 Hz, 1H), 6.96 (dd, J=9.0, 2.4 Hz, 1H), 8.11 (d, J=9 Hz, 1H); LC-MS (retention time: 0.77, method D), MS m/z 176 (M$^+$+1).

Step 3:

To a solution of) of N-Boc-cis-L-4-Hydroxyproline methyl ester (12.24 g, 49.8 mmol) and PPh$_3$ (26.14 g, 99.7 mmol) in THF(200 mL) cooled to 0° C. was added a solution of DEAD (17.36 g, 99.7 mmol) and 7-methoxyquinolin-4-ol (8.73 g, 49.8 mmol) in (THF 700 mL) over a 45 min period. The mixture was slowly allowed to warm to rt overnite, concentrated in vacuo. The residue was purified over a Biotage 65M column (MeOH-EtOAc: 0–10%) to afford 12.78 g (64%) of the product as a colorless glass: $^1$H NMR (CDCl$_3$) δ 1.36 (s, 9H), 2.26–2.35 (m, 1H), 2.57–2.68 (m, 1H), 3.71 (s, 3H), 3.75–3.92 (m, 2H), 3.86, 3.87 (two s (rotamers) 3H), 4.41–4.53 (m, 1H), 5.09 (m, 1H), 6.52 (d, J=5.5 Hz, 1H), 7.06–7.09 (m, 1H), 7.24–7.26 (m, 1H), 7.94 (d, J=9.1 Hz, 1H), 8.50–8.56 (m, 1H); LC-MS (retention time: 1.34, method D), MS m/e 403 (M$^+$+1).

Step 4:

To a solution of the product (8.54 g, 21.2 mmol) of step 3 of Eaxmple 374 {BOC-N—P2[(4R)-(7-methoxyquinoline-4-oxo) proline methyl ester} in 600 mL of 5:1 TBF/MeOH was added a solution of LiOH (4.0 g, 167 mmol) in 150 mL of water. The mixture was stirred overnite, the pH was adjusted to pH 7 using 6N aqueous HCl, and the solution concentrated until only the water layer remained. The residue was adjusted to pH 4 using 1N aqueous HCl, NaCl added to saturate the mixture and was partitioned repeatedly with first EtOAc and then THF as the product was aqueous soluble. The combined organic layers were dried (MgSO$_4$) and concentrated to afford the product 8.18 g (99%) as a white solid. $^1$H NMR (CDCl$_3$-Methanol-d$_4$) δ 1.42 (s, 9H), 2.40–2.49 (m, 1H), 2.68–2.77 (m, 1H), 3.88 (m, 2H), 3.94 (s, 3H), 4.41–4.53 (m, 1H), 5.32 (m, 1H), 6.86–6.92 (m, 1H), 7.21 (dd, J=9, 2 Hz, 1H), 7.30 (d, J=2 Hz, 1H), 8.05–8.10 (m, 1H), 8.62 (d, J=6 Hz, 1H); LC-MS (retention time 1.20, method A), MS m/z 389 (M$^+$+1).

Step 5:

To a solution of the product (4.50 g, 11.60 mmol) of Step 4 of Example 374 {Boc-4(R)-(7-methoxyquinoline-4-oxo) proline}, 2.66 g (13.9 mmol) of the HCl salt of vinyl Acca (existing as a 1:1 mixture of diastereoisomers (1R,2S/1S,2R where cyclopropyl carboxyethyl group is syn to vinyl moiety), 10 mL (57.4 mmol) of DIPEA, and 2.13 g (13.9 mmol) of HOBT.H$_2$O in 150 mL of CH$_2$Cl$_2$ was added 5.27 g (13.9 mmol) of HBTU, and the mixture stirred overnite. The solution was diluted with 200 mL of CH$_2$Cl$_2$ and was partitioned with pH 4.0 buffer (2×50 mL). The organic layer was washed with saturated aqueous NaHCO$_3$ (2×50 mL), water (2×50 mL), and brine (2×50 mL). The organic solution was dried (MgSO$_4$), concentrated and purified using a Biotage 65M column (eluted with 0–9% MeOH/EtOAc) to provide of BOC-NH-P2[(4R)-(7-methoxyquinoline-4-oxo)-S-proline]-P1(1R,2S vinyl acca P1 moiety)-COOEt as the initial eluted isomer (2.21 g, 36% overall), followed by 1.13 g (19%) of pure lower Rf isomer BOC-NH-P2[(4R)-(7-methoxyquinoline-4-oxo)-S-proline]-P1(1S,2R Vinyl Acca P1 moiety)-CO$_2$Et. Mixed fractions were also obtained. Data for BOCN-P2[(4R)-(7-methoxyquinoline-4-oxo)-S-proline]-P1(1R,2S)-(VinylAcca)-COOEt: $^1$H NMR (CDCl$_3$) δ 1.16 (t, J=7 Hz, 3H), 1.35 (s, 9H), 1.37–1.47 (m, 1H), 1.74–1.88 (m, 1H), 2.04–2.13 (m, 1H), 2.32–2.46 (m, 1H), 2.58–2.69 (m, 1H), 3.76 (m, 1H), 3.87 (s, 3H), 4.02–4.13 (m, 2H), 4.30–4.44 (m, 1H), 5.05–5.19 (m, 2H), 5.24 (d, J=17 Hz, 1H), 5.63–5.71 (m, 1H), 6.61 (m, 1H), 7.07 (dd, J=9, 2 Hz, 1H), 7.22 (d, J=2 Hz, 1H), 7.76–7.83 (m, 1H), 7.92 (d, J=9 Hz, 1H), 8.50 (d, J=5 Hz, 1H). LC-MS (retention time: 1.38, method A), MS m/z 526 (M$^+$+1).

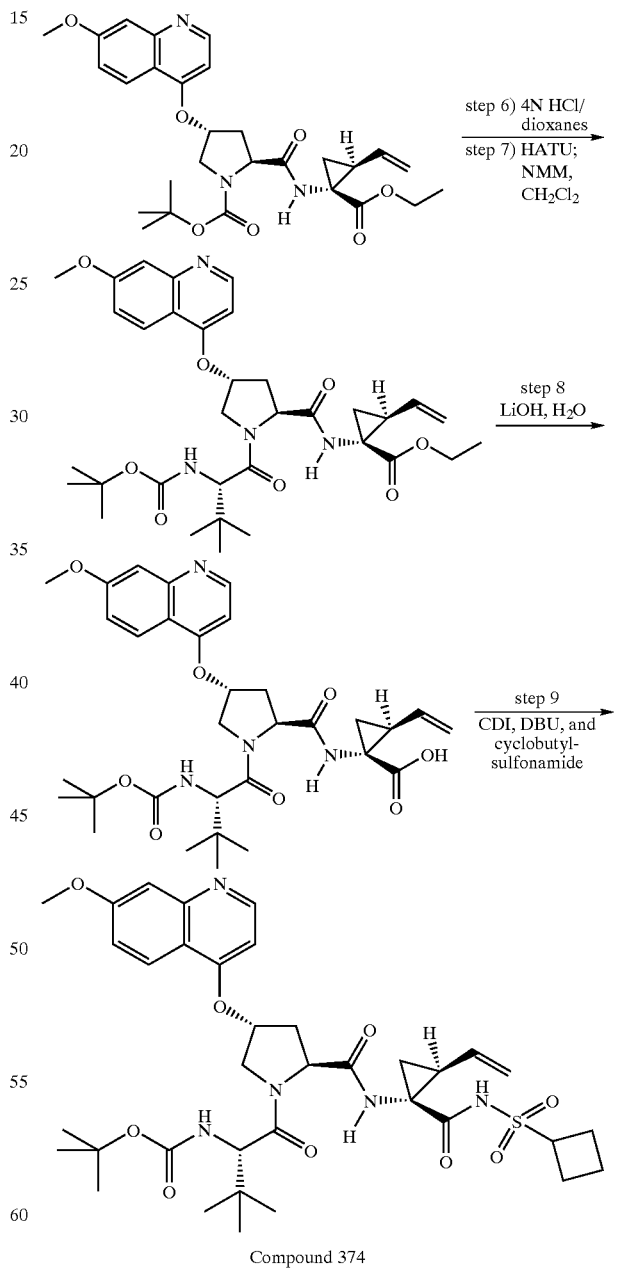

Scheme 2

Compound 374

Step 6:

A total of product (1.35 g, 2.90 mmol) of Step 5 of Example 374 {BOC-P2 [(4R)-(7-methoxyquinoline-4-oxo)-S-proline]-1(1R,2S Vinyl Acca)-COOEt}-was dissolved in 4N HCl/dioxane (15 ml, 60 mmol) and was stirred for 2.5 h at rt. The reaction mixture was concentrated in vacuo to supply 1.3 g (100%) of the product as a tan solid which was directly used in next step. ¹H NMR (methanol-d₄) δ 1.25 (t, J=7 Hz, 1H), 1.47–1.52 (m, 1H), 1.78 (dd, J=8, 5 Hz, 1H), 2.21–2.32 (m, 1H), 2.55–2.64 (m, 1H), 2.99 (dd, J=15, 7 Hz, 1H), 3.96 (s, 2H), 4.06 (s, 3H), 4.14 (q, J=7 Hz, 2H), 4.69–4.75 (m, 1H), 5.13 (d, J=10 Hz, 1H), 5.33 (d, J=17 Hz, 1H), 5.71–5.83 (m, 1H), 5.89 (m, 1H), 7.44 (m, 1H), 7.49–7.52 (m, 1H), 8.51–8.55 (m, 1H), 8.94–8.96 (m, 1H); ¹³C NMR (methanol-d₄) δ 14.62, 23.08, 30.89, 34.73, 36.97, 41.03, 52.42, 57.11, 60.17, 62.70, 81.13, 100.06, 103.07, 117.02, 118.53, 122.70, 126.86, 134.74, 143.15, 146.75, 166.62, 167.71, 169.37, 171.18. LC-MS (retention time: 0.94, method D), MS m/z 426 (M⁺+1)

Step 7:

To suspension of product (1.3 g, 2.61 mmol) of Step 6 of Example 374 {NH₂—P2[(4R)-(7-methoxyquinoline-4-oxo)-S-proline]-1(1R,2S-Vinyl Acca)-COOEt, Bis HCl Salt}, N-BOC-L-tert-leucine (BOC L-tBuGly) (0.94 g, 4.25 mmol), NMM (1.7 ml, 15.5 mmol) in DMF (20 mL) was added HATU (1.55 g, 3.40 mmol) at rt. The reaction mixture was stirred overnite, diluted with 75% EtOAc-THF(300 mL), washed with pH 4.0 buffer (2×50 mL), saturated aqueous NaHCO₃ (50 mL), brine (50 mL), dried (MgSO₄), purified by a Biotage 40 M column (eluted with 15% to 100% EtOAc in Hexanes) to supply the product 0.702 g (42%) {BOCNH-P3(L-t-BuGly)-P2[(4R)-(7-methoxyquinoline-4-oxo)-S-proline]-P1-CO₂Et as a foam. ¹H NMR (Methanol-d₄) δ 1.06 (s, 9H), 1.22–1.32 (m, 3H), 1.28 (s, 9H), 1.42–1.46 (m, 1H), 1.73 (dd, J=8, 5 Hz, 1H), 2.19–2.25 (m, 1H), 2.67–2.72 (m, 1H), 3.95 (s, 3H), 4.03–4.07 (m, 1H), 4.10–4.18 (m, 2H), 4.20–4.24 (m, 1H), 4.54 (d, J=12 Hz, 1H), 4.60–4.63 (m, 1H), 5.11 (dd, J=10, 2 Hz, 1H), 5.28–5.30 (m, 1H), 5.43 (m, 1H), 5.76–5.83 (m, 1H), 6.50 (d, J=9 Hz, NH), 6.93 (d, J=5 Hz, 1H), 7.10 (dd, J=9, 2 Hz, 1H), 7.28 (m, 1H), 7.99 (m, 1H), 8.11 (d, J=9 Hz, 1H), 8.62 (d, J=5H); LC-MS m/z 639 (retention time: 1.53 method D).

Step 8:

To a suspension of product (702 mg, 1.11 mmol) of Step 7 of Example 374 {BOCNH-P3(L-t-BuGly)-P2[(4R)-7-methoxyquinoline-4-oxo)-S-proline]-P1 (1R,2S Vinyl Acca)-COOEt} in THF(50 mL), CH₃OH (7 mL), and H₂O (22 mL) was added LiOH (211 mg, 8.80 mmol). The reaction mixture was stirred for one day, acidified to neutral pH, and concentrated in vacuo until only the aqueous layer remained. The resulting aqueous residue was acidified to pH 4.0 by addition of 1.0 N aqueous HCl and then saturated with solid NaCl. This aqueous mixture was extracted repeatedly with EtOAc and THF, the combined organic solvent washed with brine (50 mL), dried (MgSO₄), filtered, and concentrated in vacuo to supply the product 631 mg (92%), BOCNH-P3(L-t-BuGly)-P2[(4R)-(7-methoxyquinoline-4-oxo)-S-proline]-P1(1R,2S Vinyl Acca)-CO₂H, as a solid. ¹H NMR (Methanol-d₄) δ 1.04 (s, 9H), 1.22 (s, 9H), 1.34–1.39 (m, 1H), 1.67 (dd, J=8, 5 Hz, 1H), 2.03–2.13 (m, 1H), 2.43–2.49 (m, 1H), 2.67–2.73 (m, 1H), 3.96 (s, 3H), 4.00–4.05 (m, 1H), 4.15–4.21 (m, 1H), 4.56–4.62 (m, 2H), 5.02 (d, J=10 Hz, 1H), 5.20 (d, J=17 Hz, 1H), 5.52 (m, 1H), 5.87–5.99 (m, 11H), 6.47 (d, J=8 Hz, 11H), 6.91 (s, 11H), 7.12 (d, J=5 Hz, 11H), 7.19 (dd, J=9, 2 Hz, 1H), 7.31 (d, J=2 Hz, 1H), 8.22 (d, J=9 Hz, 1H), 8.72 (d, J=5 Hz, 1H). LC-MS (retention time: 1.44, method D), MS m/z 611 (M⁺+1).

Step 9:

To a solution of the tripeptide acid (0.120 g, 0.195 mmol) of Step 8 of Example 374 in THF(2 mL) was added CDI (44.3 mg, 0.27 mmol) and the resulting solution was refluxed for 60 min and allowed to cool down to rt. Cyclobutylsulfonamide (0.037 g, 0.273 mmol) was added in one portion before the addition of neat DBU (0.041 mL, 0.273 mmol). The reaction was stirred for 24 h, another one equivalent of CDI and cyclobutylsulfonamide added and the mixture stirred 48 h more. The mixture was diluted with 50% THF/EtOAc (200 mL) and washed brine saturated pH 4.0 buffer (30 mL), dried (MgSO₄) and concentrated in vacuo. The residue was dissolved in 2 mL of 50% THF-CH₂Cl₂, 75 mg (0.39 mmol) of EDAC, 48 mg (0.39 mmol) of 4-DMAP, 58 □L (0.39 mmol) of DBU and 53 mg (0.39 mmol) of cyclobutylsulfonamide added, and the mixture stirred 4 days. The mixture was purified by one 1000□ Analtech PTLC plate (20×40 cM, eluted with 2% MeOH in CH₂Cl₂) to supply the desired product Compound 374, BOCNH-P3(L-t-BuGly)-P2[(4R)-(7-methoxyquinoline-4-oxo)-S-proline]-1(1R,2S Vinyl Acca)-CONHSO₂-Cyclobutane, as a foam 2 mg (2%): ¹H NMR (methanol-d₄) δ 1.07, 1.08 (two s (rotamers) 9H), 1.20, 1.21 (two s (rotamers) 9H), 1.41–1.48 (m, 1H), 1.64–1.70 (m, 1H), 1.72–1.91 (m, 2H), 1.95–2.11 (m, 2H), 2.23–2.37 (m, 2H), 2.40–2.58 (m, 2H), 2.72–2.75 (m, 1H), 4.06 (s, 3H), 4.12–4.17 (m, 2H), 4.35–4.38 (m, 1H), 4.58–4.62 (m, 1H), 4.65–4.70 (m, 1H), 5.16–5.18 (m, 1H), 5.24–5.37 (m, 1H), 5.69–5.76 (m, 2H), 7.40–7.46 (m, 3H), 8.35–8.40 (m, 1H), 8.92 (d, J=7 Hz, 1H). LC-MS (retention time: 1.58 method B), MS m/z 728 (M⁺+1).

Example 375

Preparation of Compound 375

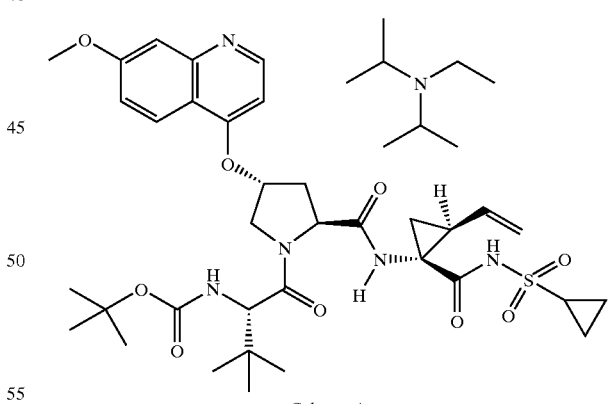

Compound 375

Scheme 1

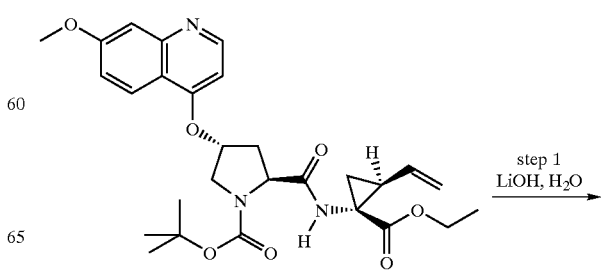

step 1
LiOH, H₂O

453

-continued

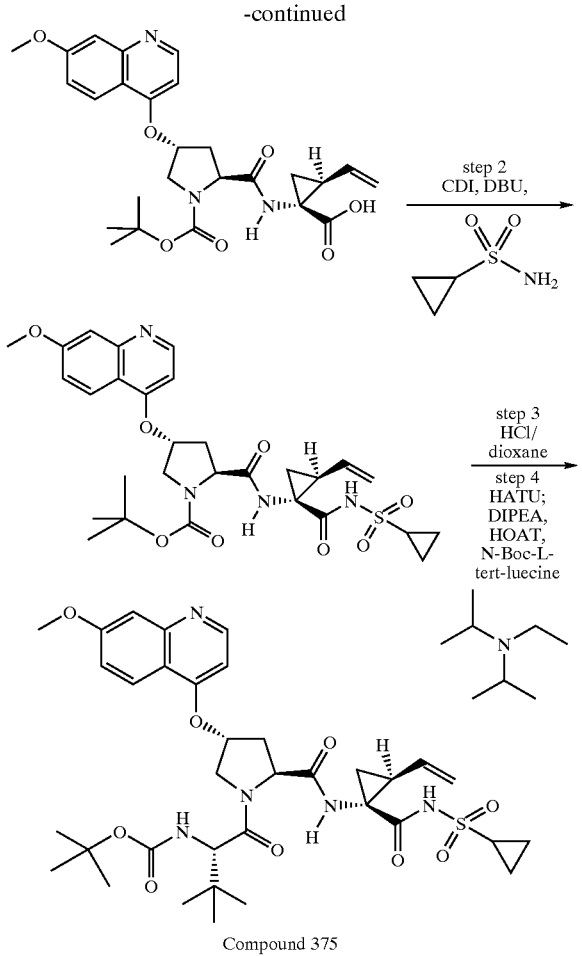

Compound 375

Step 1:

To a solution of product (794 mg, 1.51mmol) of Step 5 of Example 374 {N-BOC-P2[(4R)-(7-methoxyquinoline-4-oxo)-S-proline]-1(1R,2S VinylAcca)-CO₂Et} in 68 mL of 12% MeOH/THF was added a solution of 218 mg (9.08 mmol) of lithium hydroxide in 30 mL of water and the mixture was stirred 16 h. The pH was adjusted to neutral by addition of 6N aqueous HCl, concentrated until only the water remained, the solution adjusted to pH 4 using aqueous 1N HCl and was then extracted with 50% THF-EtOAc (5×200-mL portions). The combined organic layers were dried (MgSO₄) and concentrated to provide the product 752 mg (100%) {N-BOC-P2[(4R)-(7-methoxyquinoline-4-oxo)-S-proline]-1(1R,2S VinylAcca)-CO₂H}:

$^1$H NMR (Methanol-d₄) δ 1.37–1.43 (m, 1H), 1.39 (s, 9H), 1.69–1.78 (m, 1 of), 2.16–2.24 (m, 1H), 2.44–2.54 (m, 1H), 2.64–2.74 (m, 1H), 3.89–3.94 (m, 2H), 3.96 (s, 3H), 4.40–4.43 (m, 1H), 5.11 (d, J=10 Hz, 1H), 5.31 (d, J=17 Hz, 1H), 5.40 (m, 1H), 5.79–5.87 (m, 1H), 6.91 (s, 1H), 7.04 (d, J=6 Hz, 1H), 7.25 (dd, J=9.1, 2 Hz, 1H), 7.29 (m, 1H), 8.09 (d, J=9.1 Hz, 1H), 8.66 (d, J=6 Hz, 1H). LC-MS (retention time: 1.05, method H). MS m/z 498 (M⁺+1).

Step 2:

To a solution of product (399.5 mg, 0.668 mmol of Step 1 of Example 375 {N-BOC-2 [(4R)-(7-methoxyquinoline-4-oxo)-S-proline]-1(1R,2S VinylAcca)-CO₂H} in THF(4 mL) and CDI (434 mg, 2.68 mmol) was refluxed for 60 ml and allowed to cool down to rt. Cyclopropylsulfonamide (406 mg, 3.35 mmol) was added in one portion before the addition of neat DBU (0.50 mL, 3.35 mmol). The reaction was stirred for 16 h, diluted with 50% THF-EtOAc (200 mL)

454 and washed with brine saturated pH 4.0 buffer (2×40 mL). Organic layer was dried (MgSO₄), concentrated, and purified over a Biotage 25M column (MeOH in CH₂Cl₂, 0% to 15%) to supply 217 mg (54%) of the desired product {N-BOC-P2[(4R)-(7-methoxyquinoline-4-oxo)-S-proline]-1(1R,2S VinylAcca)-CONHSO₂Cyclopropane}: $^1$H NMR (Methanol-d₄) δ 1.01–1.10 (m, 2H), 1.11–1.18 (m, 1H), 1.20–1.27 (m, 1H), 1.39–1.48 (m, 1H), 1.44 (s, 9H), 1.87 (dd, J=8, 5 Hz, 1H), 2.01–2.38 (m, 2H), 2.57 (dd, J=14, 7 Hz, 1H), 2.91–2.96 (m, 1H), 3.83–3.92 (m, 2H), 3.94 (s, 3H), 4.36–4.39 (m, 1H), 5.11 (d, J=10 Hz, 1H), 5.29 (d, J=17 Hz, 1H), 5.38 (m, 1H), 5.74–5.81 (m, 1H), 6.91 (d, J=5.5 Hz, 1H), 7.20 (dd, J=9.2, 2.4 Hz, 1H), 7.29 (m, 1H), 8.07 (d, J=9.2 Hz, 1H), 8.60 (d, J=5.5 Hz, 1H). LC-MS (retention time: 1.28, method I). MS m/z 601 (M⁺+1)

Steps 3:

A total of product (198 mg, 0.33 mmol) of Step 2 of Example 375 {BOC-P2 [(4R)-(7-methoxyquinoline-4-oxo)-S-proline]-P1(1R,2S Vinyl Acca)-CONHSO₂Cyclopropane} was dissolved in 4N HCl/dioxane (4 ml, 16 mmol) and stirred for 2 h at rt. The reaction mixture was concentrated to supply the crude product as a tan solid which was used immediately in the next reaction.

Step 4:

The crude product of Step 3 of Example 375 {HN-P2 [(4R)-(7-methoxyquinoline-4-oxo)-S-proline]-P1(1R,2S Vinyl Acca)-CONHSO₂Cyclopropane, Bis HCl Salt} was suspended in 10 mL of dichloromethane. To this mixture was added N-BOC-L-tert-leucine (BOC L-tBuGly) [120 mg, 0.52 mmol], HOAT (30 mg, 0.20 mmol), DIPEA (0.29 ml, 1.65 mmol), and HATU (160 mg, 0.43 mmol) at rt. The reaction mixture was stirred for 16 h, diluted with 50% EtOAc-THF(300 mL), washed with brine saturated pH 4.0 buffer (3×50 mL), dried (MgSO₄), concentrated. The residue was purified by a Isco 35 g column (eluted with 0% to 15% MeOH in CH₂Cl₂) to supply the product (130.1 mg, 47%) as a Hunning's base salt (Compound 375): $^1$H NMR (methanol-d₄) δ ppm 1.00–1.48 (m, 29 H), 1.47 (s, 9 H), 1.89 (m, 1 H), 2.26 (m, 1 H), 2.36 (m, 1 H), 2.69 (m, 1 H), 2.97 (m, 1 H), 3.25 (q, J=7.43 Hz, 2 H), 3.74 (m, 2 H), 3.97 (s, 3 H), 4.10 (m, 1 H), 4.23 (dd, J=19.68, 9.92 Hz, 1 H), 4.57 (m, 2 H), 5.15 (m, 1 H), 5.31 (m, 1 H), 5.50 (s, 1 H), 5.77 (m, 1 H), 7.01 (t, J=5.34 Hz, 1 H), 7.16 (d, J=9.16 Hz, 1 H), 7.31 (d, J=1.83 Hz, 1 H), 8.14 (m, 1 H), 8.67 (d, J=5.49 Hz, 1 H).

LC-MS (retention time: 1.49 Method d), MS m/z 714 (M⁺+1).

Example 376

Preparation of Compound 376

Compound 376

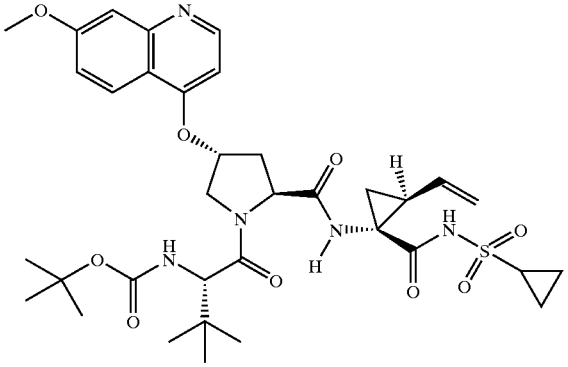

455

-continued
Scheme 1

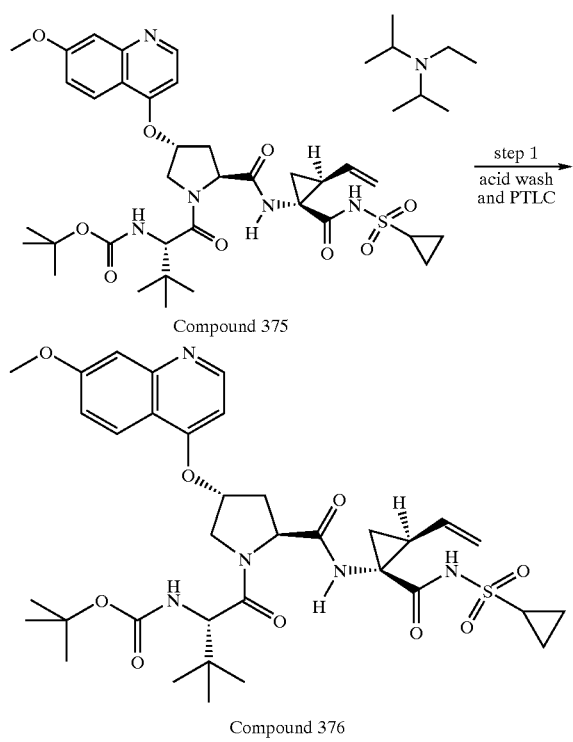

Compound 375

Compound 376

Step 1:

Of Compound 375 (130 mg) was dissolved in EtOAc, washed one more time with pH 4 buffer, brine and then dried (MgSO$_4$). The crude mixture was purified over two 1000□ PTLC plate from Analtech (20×40 cm, eluted with 3% MeOH in CH$_2$Cl$_2$) to afford the product (Compound 376) 54 mg (23% yield from the tripeptide acid): $^1$H NMR (Methanol-d$_4$) δ 0.88–1.00 (m, 2H), 1.01–1.14 (m, 2H), 1.03 (s, 9H), 1.25 (s, 9H), 1.34 (dd, J=9, 5 Hz, 1H), 1.81–1.89 (m, 1H), 2.06–2.13 (m, 1H), 2.45–2.50 (m, 1H), 2.65–2.75 (m, 1H), 3:91 (s, 3H), 3.98–4.11 (m, 1H), 4.21–4.22 (m, 1H), 4.46–4.50 (m, 1H), 4.54–4.57 (m, 1H), 4.97–5.02 (m, 1H), 5.14–5.22 (m, 1H), 5.33–5.41 (m, 1H), 5.81–5.99 (m, 1H), 6.87–6.95 (m, 1H), 7.06–7.09 (m, 1H), 7.25 (m, 1H), 8.07–8.10 (m, 1H), 8.59 (d, J=5.2 Hz, 1H). HRMS m/z (M−H)— calcd. for C$_{35}$H$_{46}$N$_5$O$_9$S: 712.3016, found: 712.3024; LC-MS m/e 714 (retention time: 1.42, method I).

Example 377

Preparation of Compound 377

Compound 377

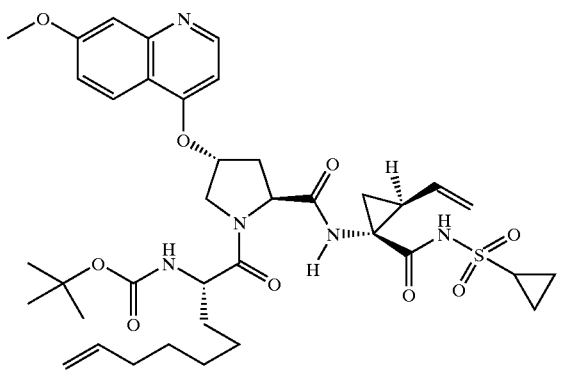

456

-continued
Scheme 1

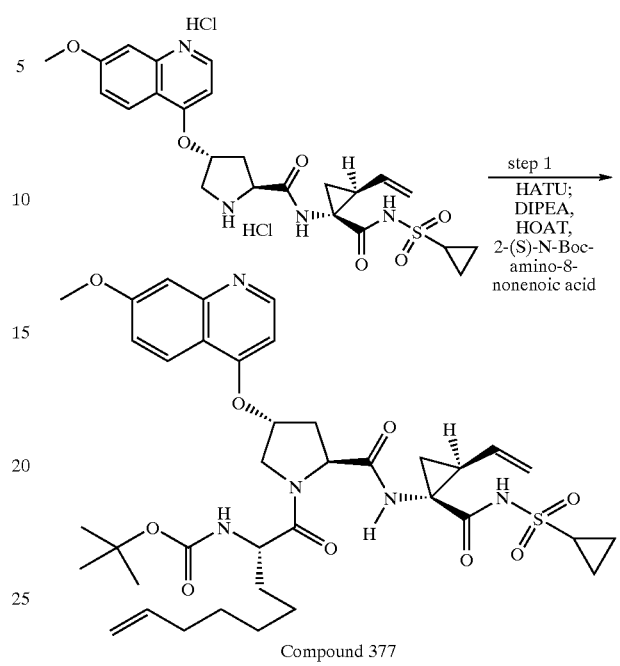

Compound 377

Step 1:

A total of 1.0 mmol the product of Step 2 of Example 375 {The Bis HCl Salt of HN-P2[(4R)-(7-methoxyquinoline-4-oxo)-S-proline]-P1(1R,2S Vinyl Acca)-CONHSO$_2$Cyclopropane} suspended in 20 mL of dichloromethane was added 352 mg (1.30 mmol) of 2-(S)-tert-butoxycarbonylamino-8-nonenoic acid purchased from RSP Amino Acids, HOAT (82 mg, 0.60 mmol), DIPEA (0.74 ml, 5.0 mmol), and HATU (494 mg, 1.30 mmol) at rt. The reaction mixture was stirred 16 h, and the majority of the CH$_2$Cl$_2$ removed in vacuo. The mixture was diluted with saturated pH 4.0 buffer (150 mL), and extracted into EtOAc (4×200 mL). The combined organic layers were dried (MgSO$_4$), concentrated. The residue was purified over a Biotage 40M column (eluted with 0% to 15% MeOH in CH$_2$Cl$_2$) to afford the product (Compoud 377) 574 mg (76%): LC-MS m/z 754 (retention time: 1.64, method I).

Example 378

Preparation of Compound 378

Compound 378

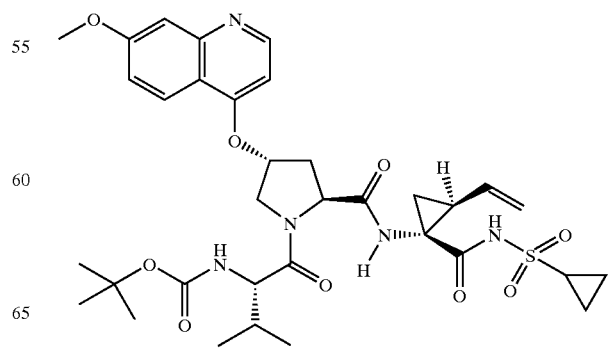

-continued
Scheme 1

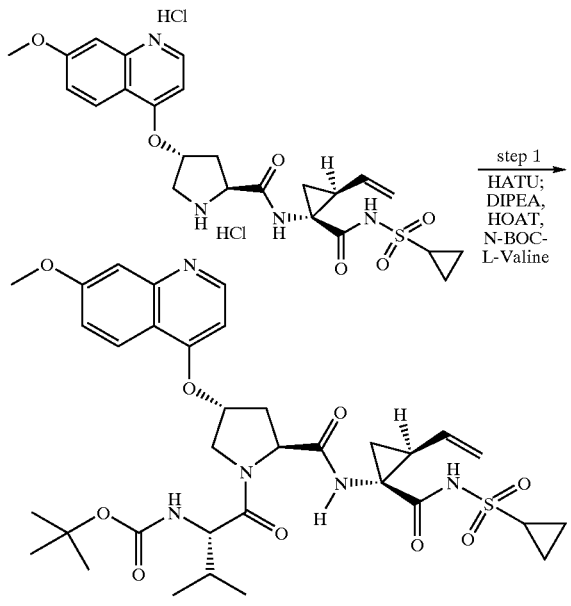

Compound 378

Step 1:

A total of 0.34 mmol of the product of Step 2 of Example 375 {The Bis HCl Salt of HN—P2 [(4R)-(7-methoxyquinoline-4-oxo)-S-proline]-P1(1R,2S Vinyl Acca)-CONHSO$_2$Cyclopropane} was suspended in 3 mL of dichloromethane. To this mixture was added N-BOC-L-Valine (L-Val) (120 mg, 0.55 mmol), HOAT (30 mg, 0.20 mmol), DIPEA (0.29 ml, 1.65 mmol), and HATU (160 mg, 0.43 mmol) at rt. The reaction mixture was stirred 16 h, diluted with saturated pH 4.0 buffer (150 mL), and extracted into EtOAc (3×200 mL). The combined organic layers were washed with brine, dried (MgSO$_4$), and concentrated. The residue was purified over an Isco 35 g column (MeOH in CH$_2$Cl$_2$: 0% to 15%). This material was further purified over two 6 PTLC plate from Analtech (20×40 cm, eluted with 3% MeOH in CH$_2$Cl$_2$) to afford the product 104.1 mg (44%), Compound, 378: HRMS m/z (M−H)$^-$ calcd. for C$_{34}$H$_{44}$N$_5$O$_9$S: 698.2860, found: 698.2865. LC-MS m/e 700 (retention time: 1.60, method D).

Example 379

Preparation of Compound 379

Compound 379

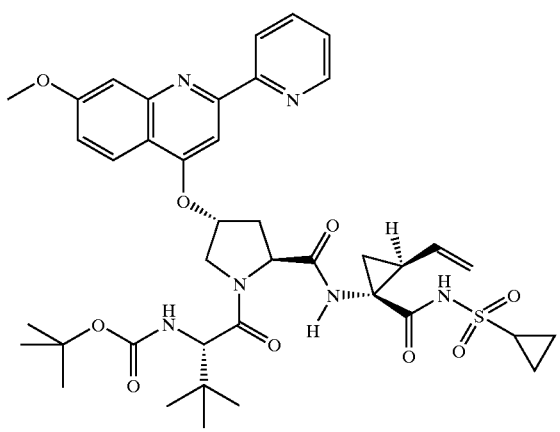

-continued
Scheme 1

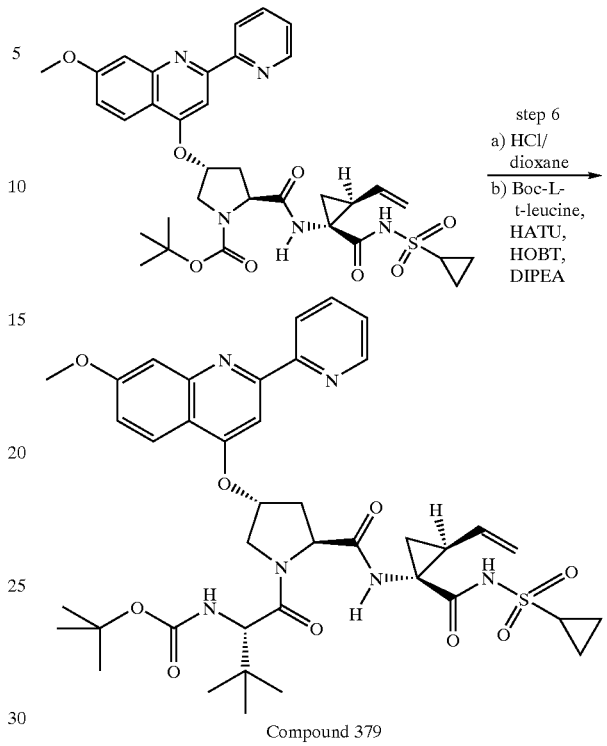

Compound 379

Step 1:

To a suspension of 2-picolic acid (3.73 g, 30.3 mmol) and 2-amino-4-methoxybenzophenone (5.0 g, 30.3 mmol) at −30° C. dissolved in pyridine (150 mL) was added POCl$_3$ (3.7 mL, 45.4 mmol) in 5 min. the reaction mixture was stirred for 3 hr at the temperature, and stirred at rt overnite. The reaction mixture was poured into cold water and extracted with EtOAc (3x). The combined extract was dried to provide the product (7.67 g, 93%): $^1$H NMR (methanol-d$_4$) δ ppm 2.65 (s, 3 H), 3.92 (s, 3 H), 6.78 (m, 1 H), 7.60 (m, 1 H), 8.00 (m, 1 H), 8.06 (m, 1 H), 8.21 (d, J=7.63 Hz, 1 H), 8.59 (t, J=2.29 Hz, 1 H), 8.76 (d, J=3.97 Hz, 1 H). LC-MS (retention time: 1.56, Method D), MS m/z 271 (M$^+$+1).

Step 2:

To a suspension suspension of Pyridine-2-carboxylic acid (2-acetyl-5-methoxy-phenyl)-amide (2.90 g, 10.7 mmol) in THF(50 mL) was added t-BuOK/THF(1M, 24 mL, 24 mmol). The reaction mixture was heated at 70° C. for 3 h and stirred overnite. The solvent was removed the in vacuo. Cold water was added to the residue and adjusted pH to 4.6 with aqueous 1.0 N HCl, filtered. The solid residue was purified over a Biotage 65M column (MeOH/CH$_2$Cl$_2$: 0–15%) to provide the product (2.26 g, 84%): LC-MS (retention time: 1.19, Method D), MS m/z 253 (M$^+$+1).

Step 3:

A mixture of 7-Methoxy-2-pyridin-2-yl-quinolin-4-ol (2.2 g, 8.71 mmol) in POCl$_3$ (92 mL) was refluxed for 3 h and then removed the solvent in vacuo. Ice water was added to the residue, adjusted the pH>10 with 1.0 N NaOH, and extrated with EtOAc (2×). The combined extract was washed with water, brine, dried (MgSO$_4$), removed solvent to supply the product as a yellow solid (89%, 2.1 g): DMSO-D6) δ ppm 3.97 (s, 3 H), 7.40 (dd, J=9.16, 2.44 Hz, 1 H), 7.53 (m, 1 H), 8.01 (m, 1 H), 8.09 (d, J=9.16 Hz, 1 H), 8.46 (s, 1 H), 8.56 (d, J=7.93 Hz, 1 H), 8.74 (d, J=3.97 Hz, 1 H).

LC-MS (retention time: 1.50, Method D), MS m/z 271 (M$^+$+1).

Step 4:

To a solution of N-Boc-4-hydroxyproline (1.6 g, 6.7 mmol) in DMSO (20 mL) was added t-BuOK (1.9 g, 16.8 mmol). The generated mixture was stirred for 1.5 h and 4-Chloro-7-methoxy-2-pyridin-2-yl-quinoline (2.0 g, 7.4 mmol) and DMSO (10 mL) were added. The reaction mixture was stirred for 38 h, diluted with cold water and extracted with EtOAc/ether (1/4, 2×). the aqueous layer was acidified to pH 4 and extracted with EtOAc/THF(5×), the combined extract was dried (Na$_2$SO$_4$/MgSO$_4$), removed the solvent in vacuo and the residue was purified by preparative HPLC (0–80% solvent B) to provide the product (1.6 g, 50%): LC-MS (retention time: 1.23, Method I), MS m/z 466 (M$^+$+1).

Step 5:

A solution of product (0.21 g, 0.65 mmol) of Step 4 of Example 379 {N-boc-(1R,2S)-1-amino-2-vinylcyclopropane carboxylic acid ethyl ester} in HCl/dioxane (4M, 5 mL, 20 mmol) was stirred for 3 h, and the solvent was removed in vacuo. To the residue was added CH$_2$Cl$_2$ (10 mL), diisopropylethylamine (0.4 mL, 3.23 mmol), HOBT (0.20 g, 1.35 mmol), Boc-(4R)-(2-cyclopropyl-7-methoxy-quinoline-4-oxo)-S-proline (0.20 g, 0.5 mmol) and HATU (0.415 g, 1.07 mmol). The reaction mixture was stirred overnite and diluted with pH 4.0 buffer, extracted with EtOAc. The extract was dried (MgSO$_4$) and purified by Biotage 40 M column using MeOH/CH$_2$Cl$_2$ (0 to 15%) as eluent to provide the product (204.7 mg, 70%): $^1$H NMR (methanol-d$_4$) δ ppm 0.64 (m, 1 H), 0.96 (m, 2 H), 1.33 (m, 8 H), 1.39 (m, 9 H), 1.90 (m, 2 H), 2.18 (m, 1 H), 2.54 (m, 1 H), 2.81 (m, 1 H), 4.01 (m, 5 H), 4.44 (d, J=28.99 Hz, 1 H), 5.08 (m, 1 H), 5.31 (m, 1 H), 5.57 (s, 1 H), 6.03 (m, 1 H), 6.94 (s, 1 H), 7.27 (d, J=8.24 Hz, 1 H), 7.64 (m, 1 H), 7.92 (m, 1 H), 8.14 (m, 2 H), 8.66 (s, 1 H), 8.74 (s, 1 H).

Step 6:

A slurry of P2 Boc-(4R)-(7-methoxy-2-Pyridin-2-yl-quinoline-4-oxo)-S-proline]-P1(1R,2S Vinyl Acca)-CONHSO$_2$(1-cyclopropylmethylcyclopropan-1-yl) (Step 5, Example 379) (203 mg, 0.3 mmol) in 4M HCl/dioxane (3.5 mL, 14 mmol) was stirred for 2 h, removed the solvent in vacuo. To the residue was added CH$_2$Cl$_2$ (2 mL), diisopropylethylamine (0.63 mL, 3.6 mmol), Boc-L-tert-leucine (83 mg, 0.36 mmol), HOAt (41 mg, 0.3 mmol), and HATU (148 mg, 0.39 mmol). The reaction mixture was stirred at rt for 7 h and removed the solvent in vacuo. The residue was purified by preparative HPLC (35–85% solvent B) to provide the desired product (Compound 379) 25.1 mg (11%): $^1$H NMR (methanol-d$_4$) δ ppm-0.05 (m, 1 H), 0.30 (m, 1 H), 0.66 (m, 1 H), 0.91 (m, 2 H), 1.05 (s, 9 H), 1.28 (s, 9 H), 1.67 (m, 8 H), 2.15 (m, 1 H), 2.58 (m, 1 H), 2.77 (m, 1 H), 3.96 (s, 3 H), 4.19 (d, J=40.25 Hz, 2 H), 4.51 (d, J=16.47 Hz, 2 H), 4.95 (m, 1 H), 5.15 (m, 1 H), 5.53 (s, 1 H), 5.89 (dd, J=16.65, 9.33 Hz, 1 H), 7.09 (d, J=8.42 Hz, 1 H), 7.43 (d, J=1.83 Hz, 1 H), 7.50 (m, 1 H), 7.82 (s, 1 H), 7.99 (m, 1 H), 8.10 (d, J=9.15 Hz, 1 H), 8.48 (d, J=7.68 Hz, 1 H), 8.72 (s, 1 H). LC-MS (retention time: 1.59, Method I), MS m/z 791 (M$^+$+1).

Example 380

Preparation of Compound 380

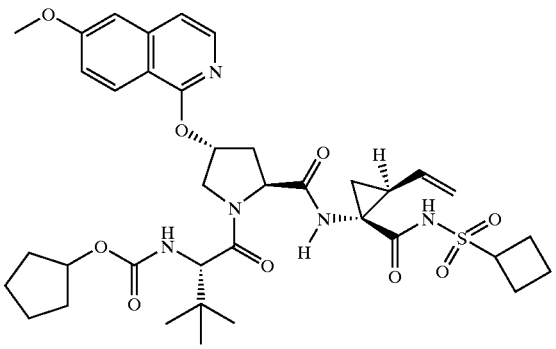

Compound 380

Scheme 1

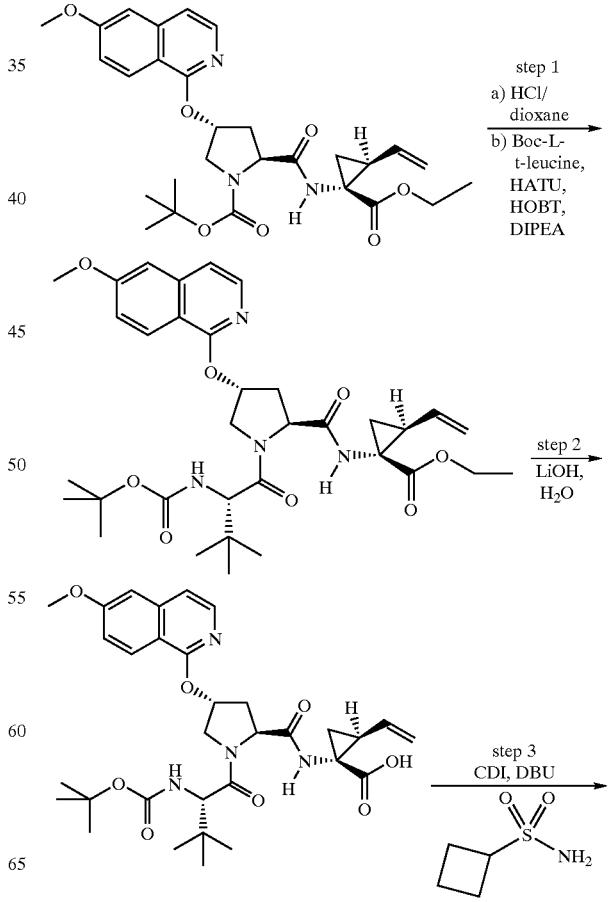

461
-continued

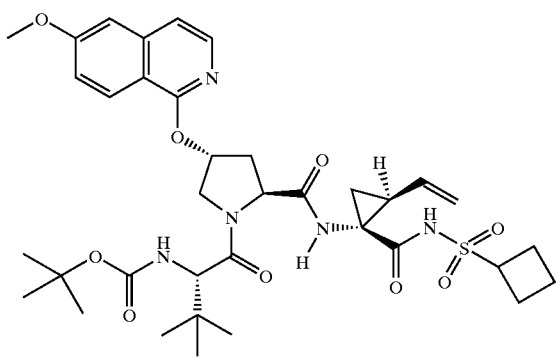

Step 1:

The starting material in Scheme 1 of the present example was prepared by coupling of the product of step 3 in Example 11 of section B with the amino terminus of P1(1R,2S Vinyl Acca)-COOEt. A slurry of said coupling product, P2 Boc-(4R)-(6-methoxy-isoquinoline-1-oxo)-S-proline]-P1(1R,2S Vinyl Acca)-COOEt (7.88 g, 14.99 mmol) in 4M HCl/dioxane (120 mL, 480 mmol) was stirred for 2 h, removed the solvent in vacuo and azeotroped with dry dioxane. To the residue was added DMF (75 mL), N-mehtylmorpholine (6.27 mL, 57.07 mmol), Boc-L-tert-leucine (5.20 g, 22.49 mmol), and HATU (8.53 g, 22.49 mmol). The reaction mixture was stirred at rt overnite and worked up by pouring the reaction mixture into ice water and adjusted to pH 5 with aqueous 1.0 N HCl and extracted with EtOAc. The extract was washed with $NaHCO_3$ (aq.), brine, dried ($MgSO_4$) and concentrated. The residue was purified over Biotage 65M column (EtOAc-hexanes: 5–100%) to provide the product (8.07 g, 84%): Retention time: 1.88 method I) MS m/z 639 (M$^+$+1).

Step 2:

To a suspension of the product (4.0 g, 6.26 mmol) of Step 1 of Example 384 {Boc-NH-P3(L-tert-BuGly)-P2[(4R)-(6-methoxyl-isoquinoline-1-oxo)-S-proline]-P1(1R,2S Vinyl Acca)-COOEt} in THF(250 mL), $CH_3OH$ (31 mL), and $H_2O$ (125 mL) was added LiOH (2.4 g, 100.2 mmol). The reaction mixture was stirred for overnite and then adjusted to pH 7 with aqueous 1.0 N HCl. The organic solvents were removed in vacuo. The aqueous residue was acidified to pH 4 and extracted with EtOAc (2×).

The combined organic solvent was dried ($Na_2SO_4$/ $MgSO_4$), and concentrated in vacuo to supply the product (3.79 g, 99%): $^1$H NMR (methanol-$d_4$) □ ppm 1.05 (s, 9 H), 1.25 (m, 1 H), 1.29 (s, 9 H), 1.46 (m, 1 H), 1.72 (dd, J=8.24, 5.19 Hz, 1 H), 2.23 (q, J=8.55 Hz, 1 H), 2.68 (dd, J=13.89, 7.78 Hz, 1 H), 3.94 (s, 3 H), 4.05 (dd, J=11.60, 3.05 Hz, 1 H), 4.23 (d, J=8.85 Hz, 1 H), 4.46 (d, J=11.60 Hz, 1 H), 4.63 (t, J=8.39 Hz, 1 H), 5.10 (d, J=10.38 Hz, 1 H), 5.29 (d, J=17.40 Hz, 1 H), 5.85 (m, 2 H), 7.10 (d, J=9.16 Hz, 1 H), 7.19 (s, 1 H), 7.26 (d, J=5.49 Hz, 1 H), 7.91 (d, J=5.80 Hz, 1 H), 8.12 (d, J=9.16 Hz, 1 H). Retention time: 1.81 method I) MS m/z 611 (M$^+$+1).

Step 3:

A solution of CDI (0.052 g, 0.32 mmol) and the product (0.130 g, 0.21 mmol) of Step 2 of Example 384 {BOCNH-P3(L-t-BuGly)-P2[(4R)-6-methoxy-sioquinoline-1-oxo)-S-proline]-P1(1R,2S Vinyl Acca)-$CO_2H$} in THF(2 mL) was refluxed for 60 min and allowed to cool down to rt. Cyclobutanesulfonamide (0.043 g, 0.32 mmol) was added followed by the addition of a solution of neat DBU (0.048 mL, 0.32 mmol). The reaction was stirred for overnite, then filtered through syringe filter and purified by preparative HPLC (30% to 100% solvent B) to provide the desired product 0.1422 mg (92%): $^1$H NMR (methanol-$d_4$) δ ppm 1.04 (s, 9 H), 1.26 (d, J=13.43 Hz, 9 H), 1.39 (m, 1 H), 1.85 (dd, J=7.63, 5.19 Hz, 1 H), 1.98 (m, 2 H), 2.26 (m, 41 H), 2.50 (m, 2 H), 2.61 (m, 1 H), 3.92 (s, 3 H), 4.05 (m, 1 H), 4.24 (m, 1 H), 4.33 (m, 1 H), 4.43 (d, J=11.60 Hz, 1 H), 4.52 (m, 1 H), 5.13 (m, 1 H), 5.30 (m, 1 H), 5.71 (m, 1 H), 5.82 (s, 1 H), 7.08 (d, J=8.85 Hz, 1 H), 7.18 (s, 1 H), 7.24 (d, J=5.80 Hz, 1 H), 7.88 (m, 1 H), 8.08 (d, J=9.16 Hz, 1 H). Retention time: 1.89 method I) MS m/z 728 (M$^+$+1).

Scheme 2

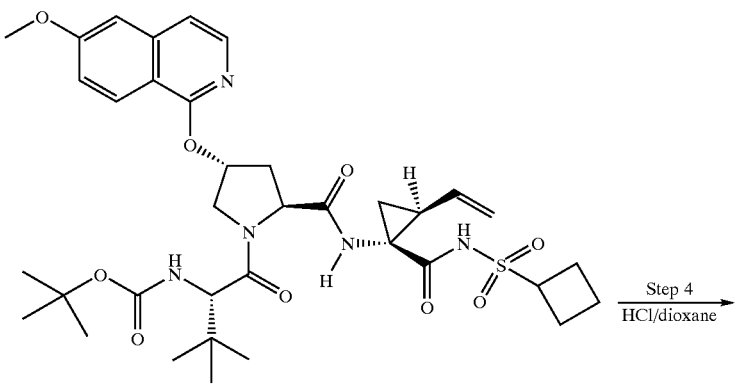

-continued

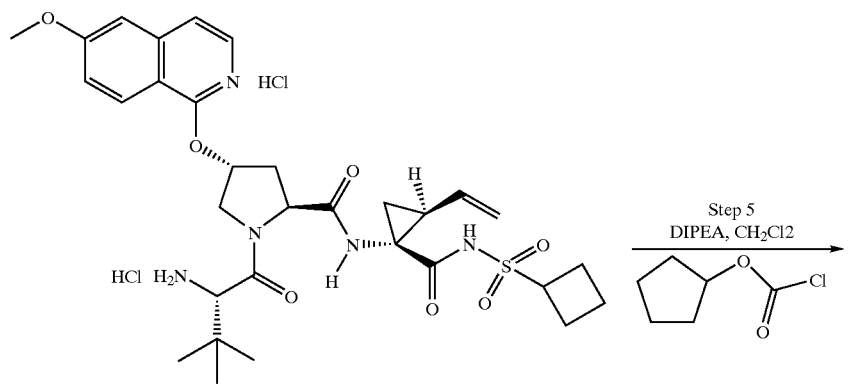

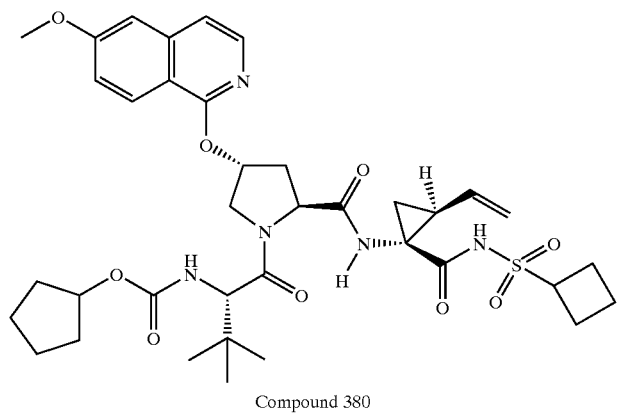

Compound 380

Step 4:

Example 380, Step 3 (0.196 mg, 0.27 mmol) {(BOCNH-P3(L-t-BuGly)-P2-(4R)-(6-methoxy-isoquinoline-1-oxo)-S-proline]-P1(1R,2S Vinyl Acca)-CONHSO₂ Cyclobutyl} was dissolved in HCl/dioxane (5 mL; 20 mmol) and was stirred for 2 h at rt. Removed the solvent in vacuo to supply the titled product 100% (0.1887 g) which was ready to next step.

Step 5:

To a mixture of the product (0.037 g, 0.053 mmol) of Step 4 of Example 380{HCl salt of NH₂—P3(L-t-BuGly)-P2-(4R)-(6-methoxy-isoquinoline-1-oxo)-S-proline]-1(1R,2S Vinyl Acca)-CONHSO₂ Cyclobutyl} and diisopropylethylamine (0.046 mL), 0.26 mmol) in CH₂Cl₂ (2 mL) was added cyclopentyl chloroformate (0.7 M, 0.151 mL, 0.069 mmol). The reaction mixture was stirred overnite and purified by preparative HPLC (30% to 100% solvent B) to provide the desired product (Comound 380) (0.0303 g, 77%): $^1$H NMR (methanol-d₄) δ ppm 1.03 (s, 9 H), 1.48 (m, 9 H), 1.86 (dd, J=8.24, 5.49 Hz, 1 H), 1.99 (m, 2 H), 2.27 (m, 4 H), 2.51 (m, 2 H), 2.60 (dd, J=13.89, 6.87 Hz, 1 H), 3.92 (s, 3 H), 4.05 (dd, J=12.21, 3.97 Hz, 1 H), 4.32 (m, 2 H), 4.41 (d, J=11.90 Hz, 1 H), 4.53 (m, 1 H), 4.69 (m, 1 H), 5.12 (d, J=10.38 Hz, 1 H), 5.29 (d, J=17.09 Hz, 1 H), 5.71 (m, 1 H), 5.83 (s, 1 H), 7.11 (d, J=9.46 Hz, 1 H), 7.19 (s, 1 H), 7.25 (d, J=5.80 Hz, 1 H), 7.88 (d, J=5.80 Hz, 1 H), 8.08 (d, J=9.16 Hz, 1 H). retention time: 1.85 method H), MS m/z 740 (M⁺+1)

Example 381

Preparation of Compound 381

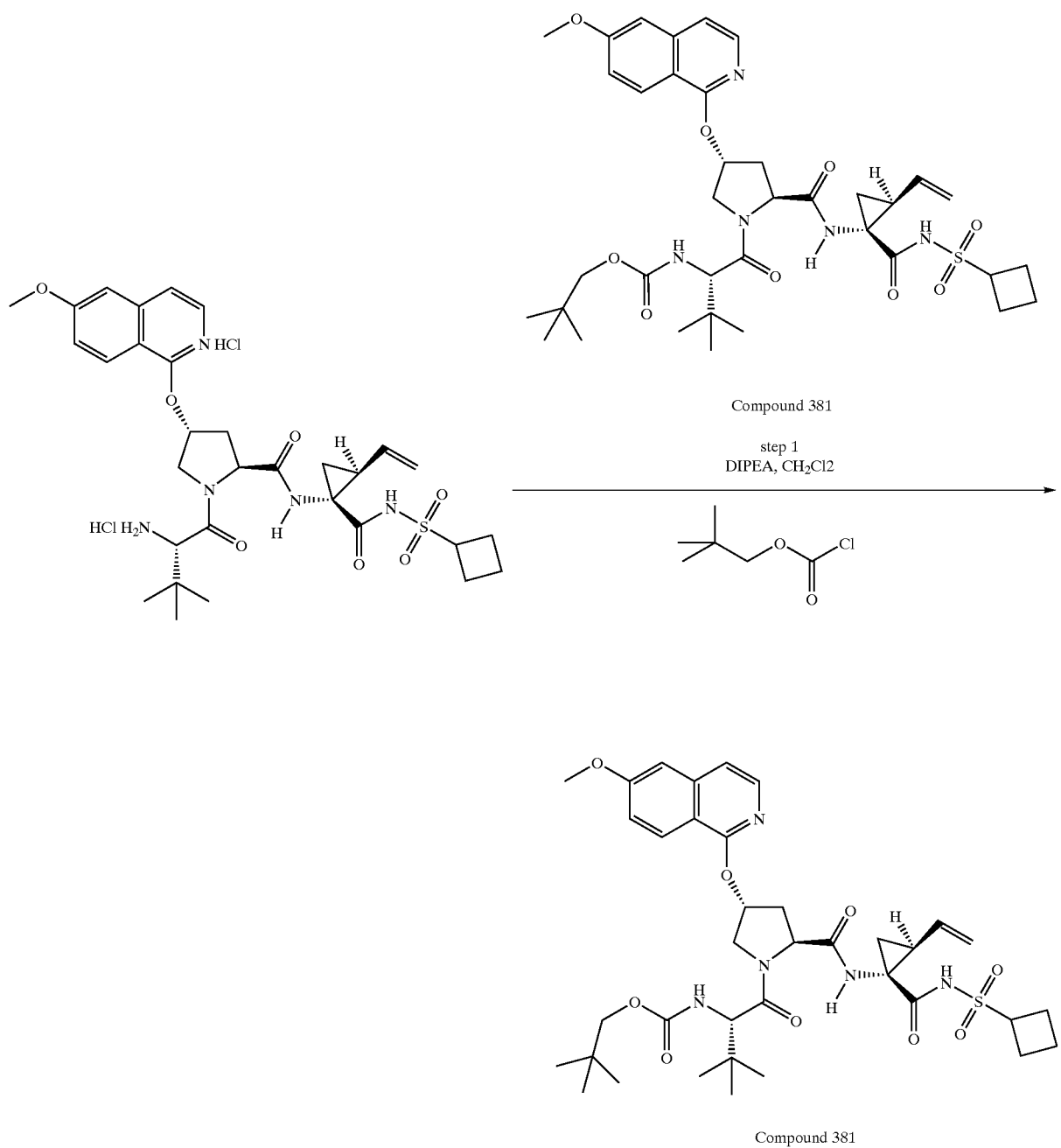

Step 1:
To a mixture of the product (0.037 g, 0.053 mmol) of Step 4 of Example 380 {HCl salt of NH$_2$—P3(L-t-BuGly)-P2-(4R)-(6-methoxy-isoquinoline-1-oxo)-S-proline]-P1(1R,2S Vinyl Acca)-CONHSO$_2$ Cyclobutyl} and iisopropylethylamine (0.046 mL), 0.26 mmol) in CH$_2$Cl$_2$ (2 mL) was added new-pentyl chloroformate (0.012 mL, 0.069 mmol). The reaction mixture was stirred overnite and direcity purified by preparative HPLC (30% to 100% solvent B) to provide the desired product (Comound 381) (0.0252 g, 64%): 1H NMR (methanol-d$_4$) δ ppm 0.84 (s, 9 H), 1.05 (s, 9 H), 1.40 (m, 1 H), 1.86 (m, 1 H), 2.00 (m, 2 H), 2.28 (m, 4 H), 2.51 (m, 2 H), 2.57 (m, 1 H), 3.39 (d, J=10.07 Hz, 1 H), 3.55 (d, J=10.38 Hz, 1 H), 3.92 (s, 3 H), 4.05 (m, 1 H), 4.33 (m, 2 H), 4.41 (d, J=111.29 Hz, 1 H), 4.53 (m, 1 H), 5.12 (d, J=10.07 Hz, 1 H), 5.29 (d, J=17.09 Hz, 1 H), 5.71 (m, 1 H), 5.82 (s, 1 H), 7.10 (d, J=9.16 Hz, 1 H), 7.19 (s, 1 H), 7.25 (d, J=5.80 Hz, 1 H), 7.88 (d, J=5.80 Hz, 1 H), 7.97 (s, 1 H), 8.07 (d, J=8.85 Hz, 1 H). retention time: 1.89 method H), MS m/z 742 (M$^+$+1).
Example 382
Preparation of Compound 382
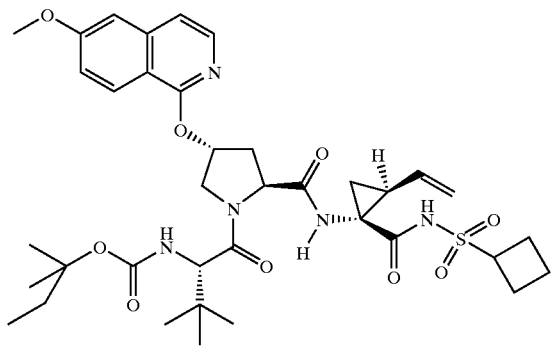
Compound 382
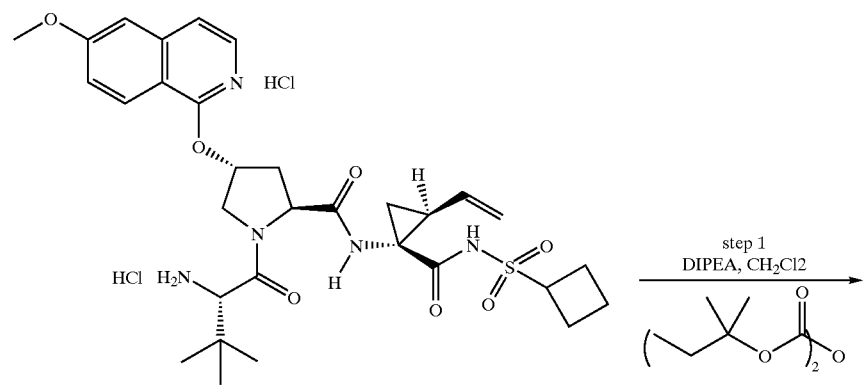
Scheme 1
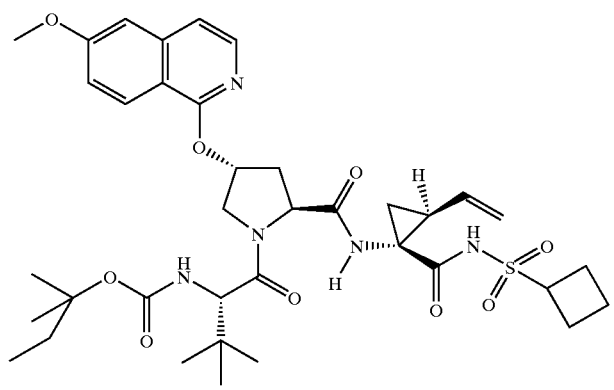
Copmund 382

469

Step 1:
To a mixture of the product (0.037 g, 0.053 mmol) of Step 4 of Example 380 {HCl salt of NH₂-P3(L-t-BuGly)-P2-(4R)-(6-methoxy-isoquinoline-1-ox o)-S-proline]-P1(1R,2S Vinyl Acca)-CONHSO₂Cyclobutyl} and diisopropylethy-

470

Example 383

Preparation of Compound 383

Compound 383

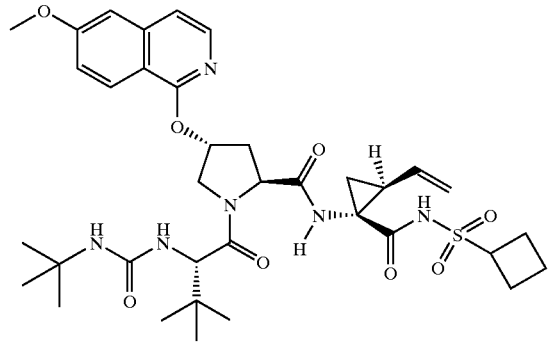

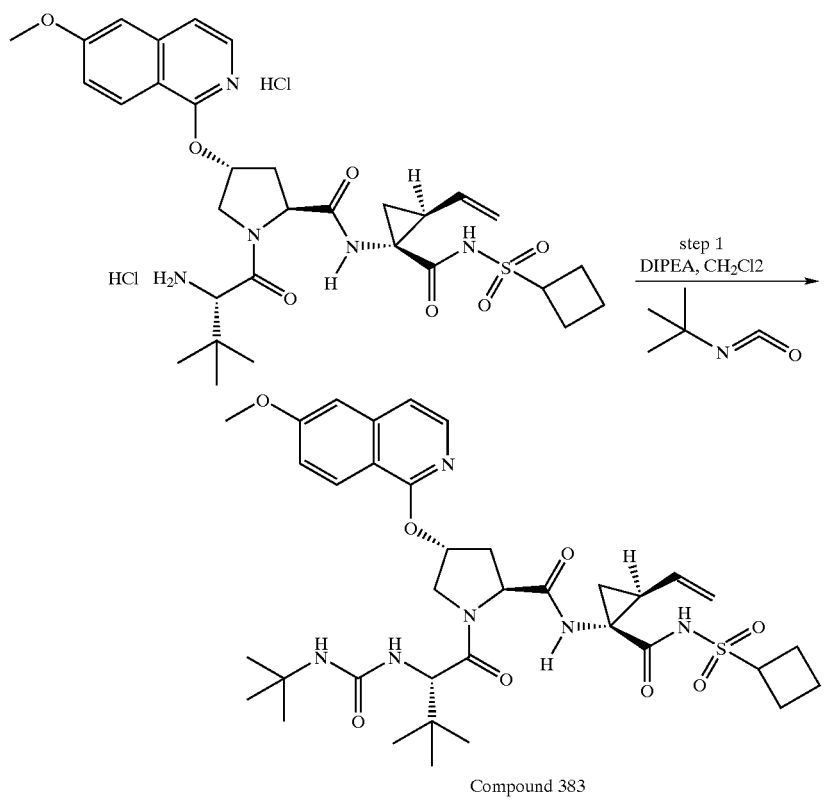

lamine (0.046 mL), 0.26 mmol) in CH₂Cl₂ (2 mL) was added di-t-amyl dicarbonate (0.0169 g, 0.069 mmol). The reaction mixture was stirred overnite and directly purified by HPLC (30% to 100% solvent B) to provide the desired product (Comound 382) (0.0175 g, 44%): $^1$H NMR (methanol-d₄) δ ppm 0.79 (t, J=6.87 Hz, 3 H), 1.04 (s, 8 H), 1.21 (s, 3 H), 1.23 (s, 3 H), 1.41 (m, 2 H), 1.64 (m, 2 H), 1.83 (m, 1 H), 2.00 (m, 2 H), 2.26 (m, 4 H), 2.51 (m, 2 H), 2.60 (m, 1 H), 3.92 (s, 3 H), 4.07 (m, 1 H), 4.24 (m, 1 H), 4.33 (m, 1 H), 4.43 (d, J=11.60 Hz, 1 H), 4.52 (m, 1 H), 5.13 (m, 1 H), 5.29 (m, 1 H), 5.71 (m, 1 H), 5.82 (s, 1 H), 7.09 (d, J=8.85 Hz, 1 H), 7.18 (s, 1 H), 7.25 (d, J=5.49 Hz, 1 H), 7.88 (d, J=5.80 Hz, 1 H), 8.08 (d, J=8.85 Hz, 1 H). retention time: 1.90, method H), MS 4 m/z 742 (M⁺+1).

Step 1:
To a mixture of the product (0.037 g, 0.053 mmol) of Step 4 of Example 380 {HCl salt of NH₂-P3(L-t-BuGly)-P2-(4R)-(6-methoxy-isoquinoline-1-oxo)-S-proline]-P1(1R,2S Vinyl Acca)-CONHSO₂ Cyclobutyl} and iisopropylethylamine (0.046 mL), 0.26 mmol) in CH₂Cl₂ (2 mL) was added t-butyl-isocianate (0.008 mL, 0.069 mmol). The reaction mixture was stirred overnite and directly purified by preparative HPLC (30% to 100% solvent B) to provide the desired product (Comound 383) (0.024 g, 62%): $^1$H NMR (methanol-d₄) δ ppm 1.05 (s, 9 H), 1.19 (s, 9 H), 1.37 (m, 1 H), 1.85 (dd, J=8.09, 5.34 Hz, 1 H), 2.00 (m, 2 H), 2.26 (m, 4 H), 2.50 (m, 2 H), 2.58 (m, 1 H), 3.92 (s, 3 H), 4.06 (m, 1 H), 4.32 (m, 2 H), 4.49 (m, 2 H), 5.11 (d, J=10.38 Hz, 1 H), 5.27 (d, J=17.40 Hz, 1 H), 5.69 (m, 1 H), 5.83 (s, 1 H), 7.08 (dd, J=9.16, 2.44 Hz, 1 H), 7.17 (d, J=2.44 Hz, 1 H), 7.24 (d, J=5.80 Hz, 1 H), 7.87 (d, J=6.10 Hz, 1 H), 8.12 (d, J=8.85 Hz, 1 H). retention time: 1.77, method H), MS m/z 727 (M$^+$+1).

Example 384

Preparation of Compound 384 at 80° C. for 15 min. KH (0.046 g, 1.14 mmol) and 1-methylcyclopentanol (0.079 mL, 0.714 mmol) was added. The reaction mixture was stirred for 20 min and worked up by diluting with cold water, adjusted pH to 4, extracted with EtOAc. The extract was dried (MgSO$_4$) and the residue was purified by preparative HPLC (30% to 100% solvent B) to provide the desired product (Comound 384) (0.018 g, 33%): (methanol-d$_4$) δ ppm 1.04 (s, 9 H), 1.29–1.79 (m, 10 H), 1.84 (m, 2 H), 1.99 (m, 3 H), 2.26 (m, 4 H), 2.49 (m, 2 H),

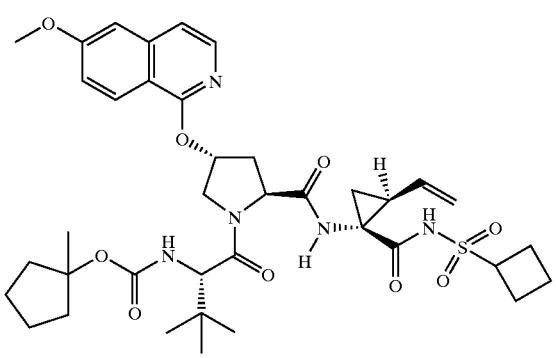

Compound 384

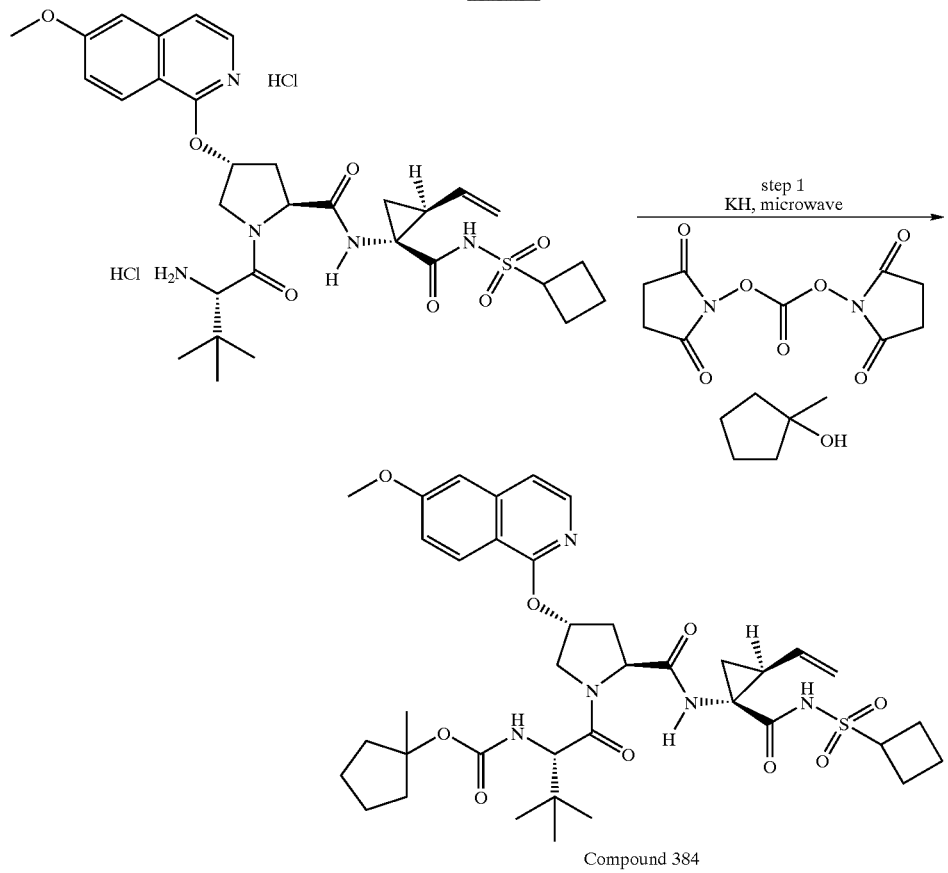

Compound 384

Step 1:

A suspension of diisopropylethylamine (0.031 mL, 0.018 mmol), N,N'-disuccinimidyl carbonate (0.0274 g, 0.107 mmol) and the product (0.050 g, 0.0714 mmol) of Step 4 of Example 380{HCl salt of NH$_2$-P3(L-t-BuGly)-P2-(4R)-(6-methoxy-isoquinoline-1-oxo)-S-proline]-Pt (1R,2S Vinyl Acca)-CONHSO$_2$ Cyclobutyl} in THF(2 mL) was sonicated 2.60 (dd, J=13.73, 7.02 Hz, 1 H), 3.92 (s, 3 H), 4.05 (dd, J=11.29, 2.44 Hz, 1 H), 4.26 (s, 1 H), 4.32 (m, 1 H), 4.44 (d, J=11.90 Hz, 1 H), 4.52 (m, 1 H), 5.12 (d, J=10.07 Hz, 1 H), 5.28 (d, J=16.79 Hz, 1 H), 5.71 (m, 1 H), 5.82 (s, 1 H), 7.10 (d, J=8.85 Hz, 1 H), 7.19 (s, 1 H), 7.26 (d, J=5.80 Hz, 1 H), 7.88 (d, J=5.80 Hz, 1 H), 8.08 (d, J=9.16 Hz, 1 H).

LC-MS retention time: 1.91 method H), MS m/z 754 (M$^+$+1).

Example 385
Preparation of Compound 385
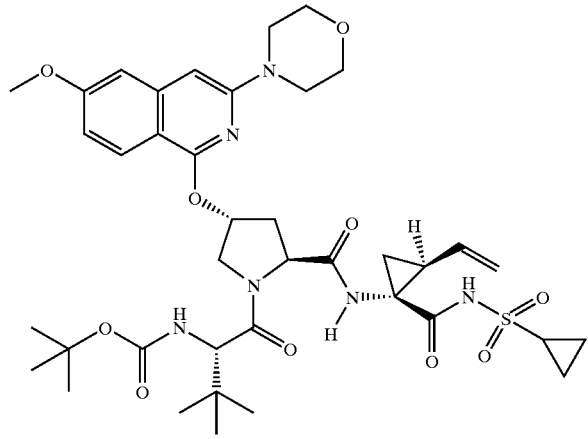
Compound 385
Scheme 1
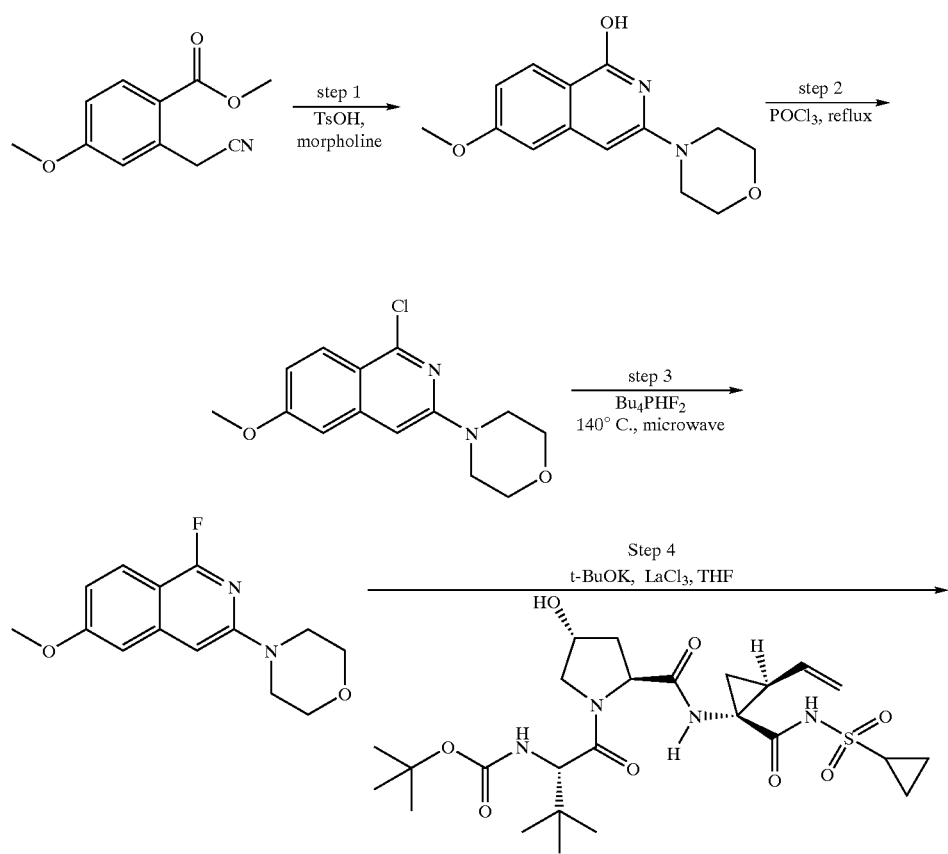

-continued

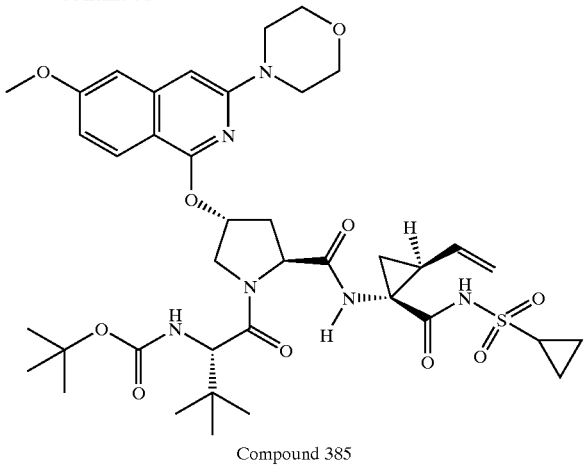

Compound 385

Step 1:

A suspension of 2-cyanomethyl-4-methoxy-benzoic acid methyl ester (1.9 g and TsOH. $H_2O$ (0.15 g, mmol) in morpholine 5 mL) was refluxed for 4 h and removed the solvent in vavuo. The residue was recrystalyzed from EtOAc/hexanes with drops of MeOH to provide the product (0.43 g, 17%): LC-MS retention time: 1.07 method H), MS m/z 266 ($M^+$+1).

Step 2:

A mixture of 6-methoxy-3-morpholin-4-yl-isoquinolin-1-ol (0.298 g, 1.15 mmol) in $POCl_3$ (20 mL) was refluxed for 2 h, removed the solvent in vacuo and cold water was added. The pH was adjustde to >11 by addition of 1.0 N NaOH. The aqueous layer was extracted with EtOAc. The extract was dried ($MgSO_4$), removed the solvent in vacuo to provide the produt (0.299 g, 94%): LC-MS retention time: 1.68 method H), MS m/z 279 ($M^+$+1).

Step 3:

A mixture of 1-Chloro-6-methoxy-3-morpholin-4-yl-isoquinoline (0.050 g, 0.18 mmol) and tetrabutyl phosphorium hydrgen difloride (0.8 g, 2.8 mmol) [Synlett 1992, (4), 345–6] was heated at 140° C. in microwave for 10 min. the reaction mixture was diluted with EtOAc and filtered through an ISCO 25 g precolumn with a layer of silicon gel on the top, removed the solvent to provide the product (0.037 mg, 77%): $^1$H NMR (CHLOROFORM-D) δ ppm 3.48 (m, 4 H), 3.84 (m, 4 H), 3.89 (s, 3 H), 6.46 (d, J=1.22 Hz, 1 H), 6.85 (s, 1 H), 6.90 (dd, J=9.16, 2.44 Hz, 1 H), 7.82 (d, J=8.85 Hz, 1 H). LC-MS retention time: 1.56 method H), MS m/z 263 ($M^+$+1).

Step 4:

A mixture of 1-floro-6-methoxy-3-morpholin-4-yl-isoquinoline (0.037 g, 0.14 mmol), $LaCl_3$ (0.020 g, 0.8 mmol), t-BuOK (1M/THF, 0.32 mL, 0.32 mmol), and Boc-NH-P3(L-tert-BuGly)-P2 [(4R)-4-hydroxyl-S-proline]-1 (1R,2S VinylAcca)-$CONHSO_2$Cyclopropane (0.045 g, 0.08 mmol) in THF(3 mL) was stirred for 3 days. The reaction mixture was diluted with methanol filtered through syringe filter and purified by preparative HPLC to provide the product as a pale yellow foam (0.0158 g, 24%): $^1$H NMR (methanol-$d_4$) δ ppm 1.03 (s, 9 H), 1.24 (m, 4 H), 1.31 (s, 9 H), 1.43 (m, 2 H), 1.88 (m, 1 H), 2.24 (m, 2 H), 2.59 (dd, J=13.43, 6.71 Hz, 1 H), 2.94 (m, 1 H), 3.47 (m, 4 H), 3.83 (m, 4 H), 3.86 (s, 3 H), 4.08 (m, 1 H), 4.28 (s, 1 H), 4.48 (m, 1 H), 5.12 (d, J=10.38 Hz, 1 H), 5.29 (d, J=16.48 Hz, 1 H), 5.76 (m, 2 H), 6.74 (d, J=9.16 Hz, 1 H), 6.94 (s, 1 H), 7.85 (d, J=8.85 Hz, 1 H), 9.19 (s, 1 H). retention time: 1.86 method H), MS m/z 799 ($M^+$+1).

Example 386

Preparation of Compound 386

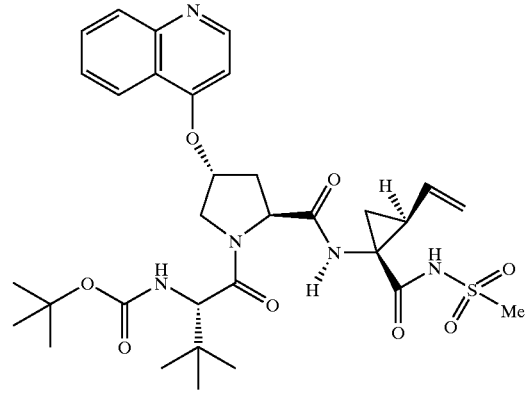

Compound 386

Compounds 386 was prepared using the methods described herein.

Section I:

All compounds in section I were analyzed by the LC/MS methodology, which has the following conditions.

Method A: Xterra C18 S7 3.0×50 mm

Gradient: 100% solvent A/0% solvent B to 0% solvent A/100% solvent B

Gradient time: 3 min.

Hold time: 1 min.

Flow rate: 4 mL/min.

Detector Wavelength: 220 nm

Solvent A: 10% MeOH/90% $H_2O$/0.1% TFA

Solvent B: 10% $H_2O$/90% MeOH/0.1% TFA

Example 410

Preparation of Compound 410

Compound 410

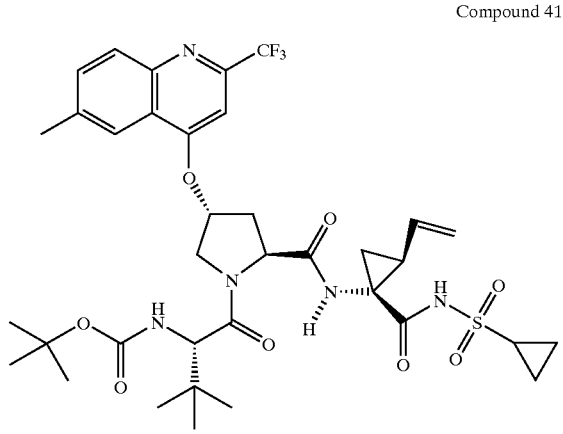

Scheme 1

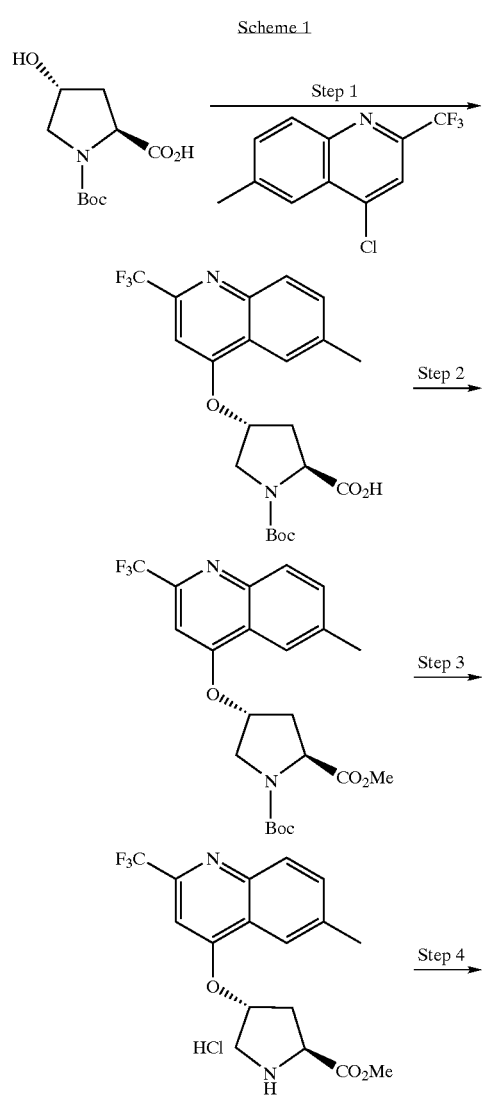

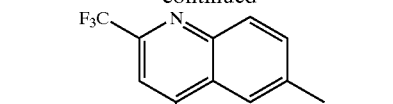

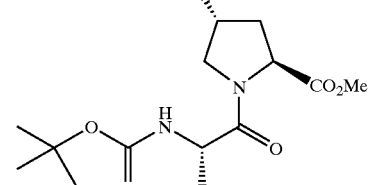

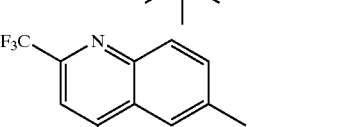

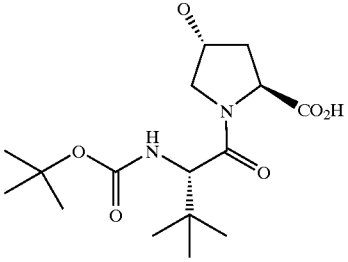

Step 1:

To a solution of Boc-L-hydroxyproline (0.723 g, 3.13 mmol) in DMSO, KO$^t$Bu (0.808 g, 7.2 mmol) was added under a nitrogen atmosphere. The suspension was stirred at room temperature for 1.5 hours, and 4-chloro-6-methyl-2-(trifluoromethyl)quinoline (0.916 g, 3.75 mmol) was added in two portions. The mixture was stirred at room temperature for three hours, and 1.3 equivalents of HCl (1N) was used to neutralize the reaction. Buffer solution of pH 4.0 was added and the pH was adjusted to pH 4–5. The aqueous layer was extracted with ethyl acetate, (3×25 mL) and the combined organic layers were washed with brine (20 mL) and dried over MgSO$_4$ to yield the titled compound as a white solid (crude yield not calculated). The crude product was taken into the next step.

LC/MS rt-min (MH$^+$): 2.48 (441.5) (method A).

Step 2:

A solution of the crude product from Step 1,4-(6-methyl-2-trifluoromethyl-quinolin-4-yloxy)-pyrrolidine-1,2-dicarboxylic acid 1-tert-butyl ester (assumed 3.13 mmol), in THF(10 mL) and methanol (10 mL) was cooled to 0° C. TMSCN$_2$ 2M in hexanes (~1.3 eq) was slowly added to the stirring solution under a nitrogen atmosphere until gas was no longer emitted from the solution. The fully reacted solution was then concentrated in vacuo, and purification by a Biotage 40M column (eluted 10%–30% ethyl acetate in hexanes) afforded the pure titled compound as a white foam (976 mg, 69% over Step 1&2)

LC/MS rt-min (MH$^+$): 2.60 (477) (method A).

Step 3:

A solution of the product from Step 2 (0.976 g, 2.15 mmol) in DCM (7 mL) and TFA (6.62 mL) was stirred at room temperature for one hour. The solvent was removed in vacuo and the residue was suspended in 1N HCl in diethyl ether (8 mL), gently stirred, and concentrated in vacuo. This procedure was repeated and the resulting product was placed on an oil pump overnight to yield a white solid in quantitative yield.

$^1$H NMR: (DMSO-d$_6$) δ 2.50 (s, 3H), 2.57–2.6 (m, 1H), 2.66–2.71 (m, 1H), 3.62–3.65 (br d, J=15 Hz, 1H), 3.80–3.81 (m, 4H), 4.8 (br s, 1H), 5.7 (s, 1H), 7.46 (s, 1H), 7.72–7.75 (d, J=7.5 Hz, 1H), 7.98–7.8 (d, J=8.5 Hz, 1H), 8.24 (s, 1H), 9.54 (br s, 1H); LC/MS rt-min (MH$^+$): 1.61 (355) (method A).

Step 4:

The product from Step 3 (assumed quantitative yield, 2.746 mmol) was added to a solution of BOC-t-Butyl-L-glycine (0.635 g, 2.746 mmol) in DCM (20 mL) under a nitrogen atmosphere. This step was followed by the addition of HOBt (0.408 g, 3.02 mmol), DIPEA (3.35 mL, 19.2 mmol), and HBTU (1.56 g, 4.12 mmol). A peach colored solution immediately resulted and the reaction was left to stir at room temperature overnight. 10 mL DCM was added to the completed reaction in order to increase the volume, and the reaction was quenched with pH 4.00 buffer solution (25 mL). The mixture was acidified to a pH of 4.5 using 1N HCl, and the aqueous phase was extracted with DCM (3×20 mL). The organic phase was washed twice with pH 4.00 buffer solution (20 mL), saturated NaOH (25 mL), and brine (20 mL), and then dried with MgSO$_4$. The resulting solution was concentrated in vacuo and purified by a Biotage 40M column (eluted 10%–40% ethyl acetate in 15: hexanes). This purification afforded the pure titled compound as a white solid (1.11 g, 89%).

$^1$H NMR: (DMSO-d$_6$) δ 0.96–1.02 (rotamers, 3:2, s, 18H), 2.27–2.33 (m, 1H), 2.50 (s, 3H), 2.68–2.72 (m, 1H), 3.67 (s, 3H), 4.02–4.04 (m, 1H), 4.43–4.45 (br d, J=15 Hz, 2H), 4.58–4.61 (t, 1H), 5.60 (br s, 1H), 6.72–6.74 (br d, J=15 Hz, 1H), 7.38 (s, 1H), 7.68–7.73 (m, 1H), 7.95–7.97 (m, 2H);

LC/MS rt-min (MH$^+$): 2.61 (590) (method A).

Step 5:

LiOH (0.138 g, 5.78 mmol) was dissolved in water (10 mL) by heating and sonication. The LiOH solution and MeOH (10 mL) were added to a solution of the pure material from Step 4 (1.09 g, 1.93 mmol) in THF(10 mL). The mixture immediately turned a vivid blue color. The reaction was left to stir at room temperature for 3 hours and was then acidified with 1N HCl (5.78 mL, 5.78 mmol). The reaction was quenched with pH 4.00 buffer solution and the pH was adjusted to pH 4.5 using 1N aqueous NaOH. The aqueous layer was extracted with EtOAc (3×25 mL), washed with brine (20 mL), and dried over MgSO$_4$. The filtered solution was concentrated in vacuo and left on a vacuum line overnight. The crude product (957 mg, 90% yield) was taken into the next step.

LC/MS rt-min (MH$^+$): 2.51 (577) (method A).

Step 6:

The crude product from Step 5 (60 mg, 0.11 mmol) was dissolved in DCM (5 mL) and cyclopropanesulfonic acid (1 (R)-amino-2 (S)-vinyl-cyclopropanecarbonyl)-amide hydrochloride salt (Example 1, Step 8) (0.029 g, 0.11 mmol) was added. DIPEA (0.094 mL, 0.541 mmol), and then HATU (0.0575, 0.151 mmol) were added under a nitrogen atmosphere. The reaction was left to stir at room temperature for about 8 hours. 10 mL DCM was added to the solution in order to increase the volume, and the reaction was quenched with pH 4.00 buffer solution (10 mL). The mixture was acidified using 1N HCl to a pH of 4–5, and the aqueous phase was extracted with DCM (3×20 mL). The organic phase was washed twice with pH 4.00 buffer solution (10 mL) and brine (10 mL), and then dried over MgSO$_4$. The resulting solution was concentrated in vacuo and purified by a Biotage 12M column (eluted 10%–40% acetone in hexanes). This purification afforded Compound 410 as a white powder (29 mg, 35%).

$^1$H NMR: (DMSO-d$_6$) δ 0.976–1.12 (m, 24H), 1.36–1.39 (m, 1H), 1.70–1.72 (m, 1H), 2.15–2.25 (m, 2H), 2.50–2.52 (m, 4H), 2.91–2.96 (m, 1H), 3.97–4.01 (m, 2H); 4.40–4.47 (m, 2H), 5.09–5.11 (d, J=10 Hz, 1H), 5.21–5.24 (d, J=15 Hz, 1H), 5.59–5.66 (m, 2H), 6.65–6.67 (d, NH), 7.43 (s, 1H), 7.72–7.74 (d, J=10 Hz, 1H), 7.90 (s, 1H), 7.98–8.0 (d, J=10 Hz, 1H), 8.87 (s, NH), 10.35 (s, NH);

LC/MS rt-min (MH$^+$): 2.65 (789.61) (method A).

Example 411

Preparation of Compound 411

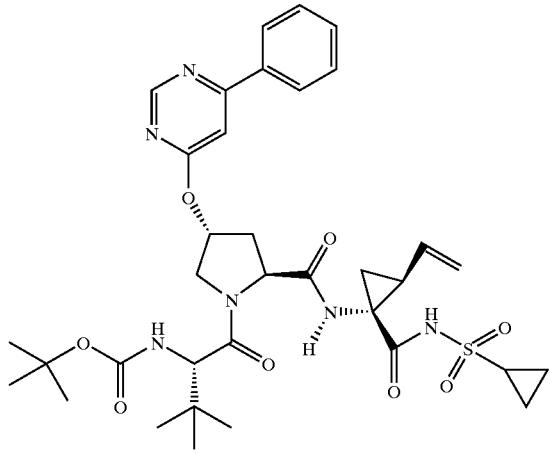

Compound 411

Step 1:

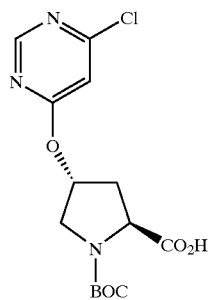

To a solution of Boc-L-hydroxyproline (2.00 g, 8.65 mmol) in THF(25 mL), NaH (0.795 g, 19.87 mmol) was added under a nitrogen atmosphere. The suspension was stirred at room temperature for 15 minutes, and 4,6-dichloropyrimidine (2.58 g, 17.30 mmol) was added in two portions. The mixture was stirred at room temperature for one hour and 1.3 equivalents of HCl (1N) were used to neutralize the reaction. pH 4.0 buffer solution was added and the pH was adjusted to pH 5. Ethyl acetate was used to extract the aqueous phase (3×25 mL) and the organic layers were washed with brine (20 mL) and dried over MgSO$_4$ to yield the titled compound as a white solid (crude yield not calculated). The crude product was taken into the next step.

LC/MS rt-min (MH$^+$): 1.91 (366.2) (method A).

Step 2:

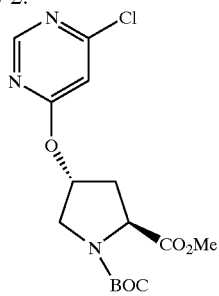

A solution of the crude product from Step 1, (assumed 8.65 mmol), in THF(40 mL) and methonal (40 mL) was cooled to 0° C. TMSCN₂ 2M in hexanes (~1.3 eq) was slowly added to the stirring solution under a nitrogen atmosphere until gas was no longer emitted from the solution. The fully reacted solution was then concentrated in vacuo, and purification by a Biotage 40M column (eluted 20%–40% ethyl acetate in hexanes) to afford the pure titled compound as a white foam (497 mg, 16% over steps 2a–2b).

¹H NMR: (DMSO-d₆) δ 1.34–1.38 (rotamers, 2:1, 9H), 2.25–2.29 (m, 1H), 2.53–2.56 (m, 1H), 3.58–3.75 (m, 2H), 3.69 (s, 3H), 4.28–4.33 (m, 1H), 5.59 (s, 1H), 7.24 (s, 1H), 8.69 (s, 1H);

LC/MS rt-min (MH⁺): 2.08 (380.14) (method A).

Step 3:

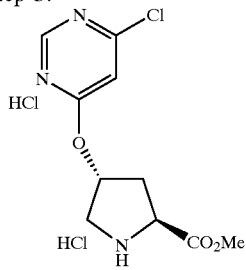

A solution of the pure product from Step 2 (472 mg, 1.83 mmol) in DCM (3 mL) and TFA (5.65 mL) was stirred at room temperature for one hour. The solvent was removed in vacuo, the residue was suspended in 1N HCl in diethyl ether (7.33 mL), gently stirred and concentrated in vacuo. This procedure was repeated, and the resulting product was placed on an oil pump overnight to yield a white solid in quantitative yield.

LC/MS rt-min (MH⁺): 0.55 (258.35) (method A).

Step 4:

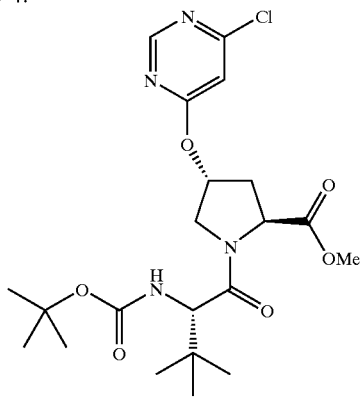

The product from Step 3 (assumed quantitative yield, 1.83 mmol) was added to a solution of BOC-t-Butyl-L-glycine (0.424 g, 1.83 mmol) in DCM (11 mL) under a nitrogen atmosphere. This step was followed by the addition of HOBt (0.272 g, 2.02 mmol), DIPEA (2.23 mL, 12.82 mmol), and HBTU (1.04 g, 2.75 mmol). The reaction was left to stir at room temperature for 15 hours. 15 mL DCM was added to the solution in order to increase the volume, and the reaction was quenched with pH 4.00 buffer solution (15 mL). The mixture was acidified to a pH of 4.5 using 1N HCl, and the aqueous phase was extracted with DCM (3×20 mL). The organic phase was washed twice with pH 4.00 buffer solution (20 mL), saturated NaOH (25 mL), brine (20 mL), and dried over MgSO₄. The resulting solution was concentrated in vacuo and purified by a Biotage 40S column (eluted 20%–50% ethyl acetate in hexanes). This purification afforded the pure titled compound as a white solid (454 mg, 53%).

¹H NMR: (DMSO-d₆) δ 0.94 (s, 9H), 1.25 (s, 9H), 2.21–2.27 (m, 1H), 2.48–2.55 (m, 1H), 3.64 (s, 3H), 3.86–4.02 (m, 2H), 4.29–4.31 (d, J=10 Hz, 1H), 4.46–4.49 (t, 1H), 5.75 (br s, 1H), 6.72–6.74 (d, NH), 7.12 (s, 1H), 8.71 (s, 1H);

LC/MS rt-min (MH⁺): 2.27 (493.5) (method A).

Step 5:

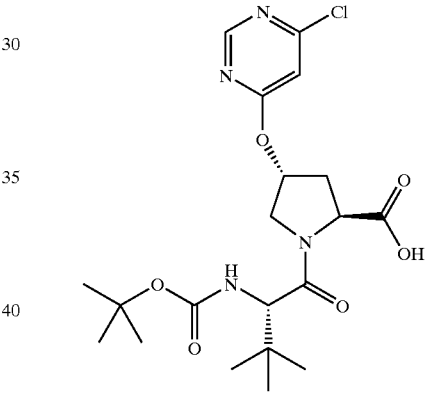

LiOH (0.0141 g, 0.589 mmol) was dissolved in water (7.5 mL) by heating and sonication. The LiOH solution was added to a solution of the pure material from Step 4 (252 mg, 0.535 mmol) in THF(7.5 mL), and left to stir at room temperature. The reaction was complete after 3 hours. It was quenched with pH 4.0 buffer and acidified to a pH of approximately 4.5 with 1N HCl. The aqueous phase was extracted with EtOAc (3×25 mL), and the organic phase was washed with brine (20 mL) and dried over MgSO₄. The filtered solution was concentrated in vacuo and left on a vacuum line overnight. The crude product (231 mg, 95% yield) was taken into the next step.

¹H NMR: (DMSO-d₆) δ 0.94 (s, 9H), 1.25 (s, 9H), 2.14–2.22 (m, 1H), 2.50–2.54 (m, 1H), 3.84–3.876 (d, J=150 Hz, 1H), 3.97–3.99 (d, J=10 Hz, 1H), 4.27–4.30 (d, J=15 Hz, 1H), 4.37–4.40 (t, 1H), 5.63 (br s, 1H), 6.69–6.71 (d, NH), 7.12 (s, 1H), 8.71 (s, 1H), 12.56 (br s, OH);

LC/MS rt-min (MH⁺): 2.24 (479.5) (method A).

Step 6:

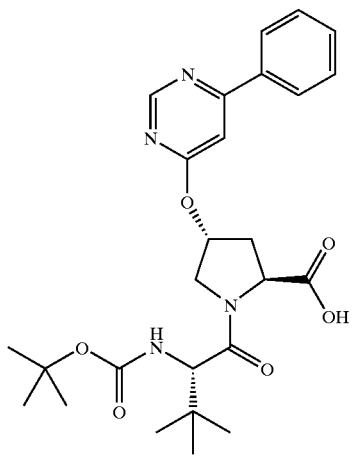

The pure material from Step 5 (80 mg, 0.146 mmol), and phenylboronic acid (0.0178 g, 0.146 mmol) were solvated in DMF (2 mL). The solution was placed under a nitrogen atmosphere and 2M aqueous $Na_2CO_3$ (0.146 mL, 0.292 mmol) was added. Five mole percent of Tetrakis(triphenyl) phosphine)-palladium (0) was added (8.44 mg, 0.0073 mmol) and the mixture was heated by microwave using the Personal Chemistry Emrys Optimizer for 50 minutes at 140° C. Palladium black precipitated out of the reaction upon completion. The mixture was acidified with one equivalent of 1N HCl, and filtered through a syringe, using MeOH to extract the product. The product was purified by prep HPLC (column—4 Xterra S5 30×75 mm, solvent—70% A/30% B—30% A/70% B (where solvent A is 10% MeOH, 90% $H_2O$, 0.1% TFA and solvent B is 90% MeOH, 10% $H_2O$, 0.1% TFA), gradient time—15 min., hold time—1 min., flow rate—40 mL/min, retention time of pure product—10.45–11.37). Fractions containing the desired product were neutralized with 1N NaOH and placed in the speed vacuum for approximately 4 hours. The fractions were combined and pH 4.0 buffer (15 mL) was added. The pH was adjusted to pH 4–5 using 1N HCl, and the aqueous layer was extracted with ethyl acetate (3×20 mL). The organic layer was washed with brine (15 mL), dried over $MgSO_4$ and concentrated in vacuo. The product was placed on an oil pump to dry overnight, and an viscous oil was obtained (37 mg, 50%).

LC/MS rt-min (MH+): 2.37(499.3) (method A).

Step 7:

The product from Example 411, Step 6 (36.7 mg, 0.061 mmol) was dissolved in DCM (4 mL) and cyclopropanesulfonic acid (1 (R)-amino-2 (S)-vinyl-cyclopropanecarbonyl)-amide hydrochloride salt (Example 1, Step 8) (0.0164 g, 0.161 mmol) was added. DIPEA (0.0534 mL, 0.307 mmol), and then HATU (0.0326, 0.0858 mmol) were added under a nitrogen atmosphere. The reaction was left to stir at room temperature for 3 hours. 10 mL DCM was added to the solution in order to increase the volume, and the reaction was quenched with pH 4.00 buffer solution (10 mL). The mixture was acidified to a pH of 4–5 using 1N HCl, and the aqueous phase was extracted with DCM (3×15 mL). The organic phase was washed twice with pH 4.00 buffer solution (10 mL) and brine (10 mL), and then dried over $MgSO_4$. The resulting solution was concentrated in vacuo and purified by a Biotage 12M column (eluted 20%–40% acetone in hexanes). This purification afforded the pure Compound 411 as a white powder (7 mg, 15%).

$^1$H NMR: δ 1.07–1.46 (m, 24H), 1.87–1.90 (m, 1H), 2.22–2.32 (m, 2H), 2.51–2.55 (m, 1H), 2.92–2.97 (m, 1H), 4.04–4.07 (d, J=15 Hz, 1H), 4.20–4.22 (d, J=10 Hz, 1H), 4.36–4.38 (d, J=10 Hz, 1H), 4.47–4.50 (t, 1H), 5.12–5.14 (d, J=10 Hz, 1H), 5.29–5.33 (d, J=20 Hz, 1H), 5.73–5.82 (m, 2H), 6.59–6.60 (d, NH), 7.29 (s, 1H), 7.50–7.51 (m, 3H), 8.03–8.05 (m, 2H), 8.81 (s, 1H); LC/MS rt-min (MH+): 2.50 (711.4) (method A).

Example 412

Preparation of Compound 412

Compound 412

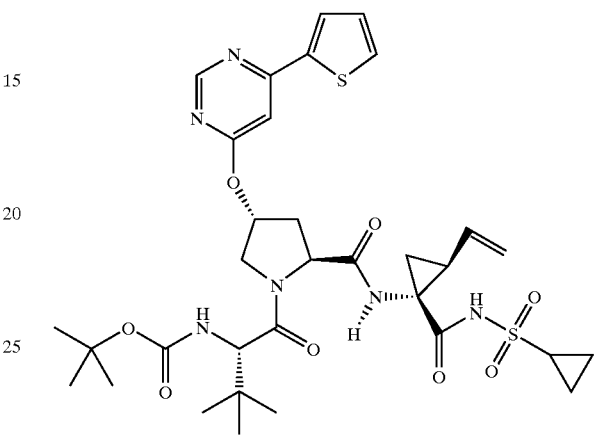

Step 1:

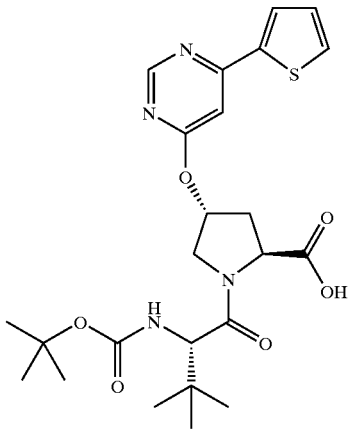

The product from Example 411, Step 5 (80 mg, 0.146 mmol) was solvated in DMF (2 mL), and 2-thiopheneboronic acid (0.028 g, 0.219 mmol) was added to the solution. The reaction was placed under a nitrogen atmosphere and 2M aqueous $Na_2CO_3$ (0.146 mL, 0.292 mmol), and 5 mole percent of Tetrakis(triphenyl) phosphine)-palladium (0) were added (8.44 mg, 0.0073 mmol). The reaction was heated by microwave using the Personal Chemistry Emrys Optimizer for 30 minutes at 150° C. Palladium black precipitated out of the reaction upon completion. The mixture was acidified with one equivalent of 1N HCl, and filtered through a syringe, using MeOH to extract the product. The product was purified by prep HPLC (column—4 Xterra S5 30×75 mm, solvent—70% A/30% B—30% A/70% B (where solvent A is 10% MeOH, 90% $H_2O$, 0.1% TFA and solvent B is 90% MeOH, 10% $H_2O$, 0.1% TFA), gradient time—15 min., hold time—1 min., flow rate—40 mL/min, retention time of pure product—

10.45–11.37). The fractions containing the desired product were neutralized with 1N NaOH and placed in the speed vacuum for approximately 4 hours. The fractions were then combined, and pH 4.0 buffer (15 mL) was added. The pH was adjusted to pH 4–5 using 1N HCl and the aqueous layer was extracted with ethyl acetate (3×20 mL). The organic layer was washed with brine (15 mL), dried over MgSO$_4$ and concentrated in vacuo. The product was placed on an oil pump to dry overnight, and an oily liquid was obtained (37 mg, 50%).

LC/MS rt-min (MH$^+$): 2.37 (499.3) (method A).

Step 2:

The product from Example 412, Step 1 (39 mg, 0.0773 mmol) was dissolved in DCM (4 mL) and cyclopropanesulfonic acid (1 (R)-amino-2 (S)-vinyl-cyclopropanecarbonyl)-amide hydrochloride salt (Example 1, Step 8) (0.0206 g, 0.0773 mmol) was added. DIPEA (0.015 mL, 0.387 mmol), and then HATU (0.0411 g, 0.108 mmol) were added under a nitrogen atmosphere. The reaction was left to stir at room temperature for 15 hours. 10 mL DCM was added to the solution in order to increase the volume, and the reaction was quenched with pH 4.00 buffer solution (10 mL). The mixture was acidified to a pH of 4–5 using 1N HCl and the aqueous phase was extracted with DCM (3×15 mL). The organic phase was washed twice with pH 4.00 buffer solution (10 mL) and brine (10 mL), and then dried over MgSO$_4$. The resulting solution was concentrated in vacuo and purified by a Biotage 12M column (eluted 20%–50% acetone in hexanes). This purification afforded the pure Compound 412 as a white powder (4 mg, 7%).

$^1$HNMR: δ 1.04–1.29 (m, 24H), 1.45–1.47 (m, 1H), 1.89–1.91 (m, 1H), 2.26–2.31 (m, 2H), 2.51–2.53 (m, 1H), 2.92–2.95 (m, 1H), 4.05–4.07 (d, J=10 Hz, 1H), 4.22–4.24 (d, J=10 Hz, 1H), 4.38–4.40 (d, J=10 Hz, 1H), 4.48–4.52 (m, 1H), 5.15–5.17 (d, J=10 Hz, 1H), 5.32–5.36 (d, J=20 Hz, 1H), 5.76–5.83 (m, 2H), 6.65–6.67 (d, NH), 7.19–7.21 (m, 2H), 7.66–7.67 (d, J=5 Hz, 1H), 7.86–7.87 (d, J=5 Hz, 1H), 8.69 (s, 1H);

LC/MS rt-min (MH$^+$): 2.45 (739.4) (method A).

Example 413

Preparation of Compound 413

Compound 413

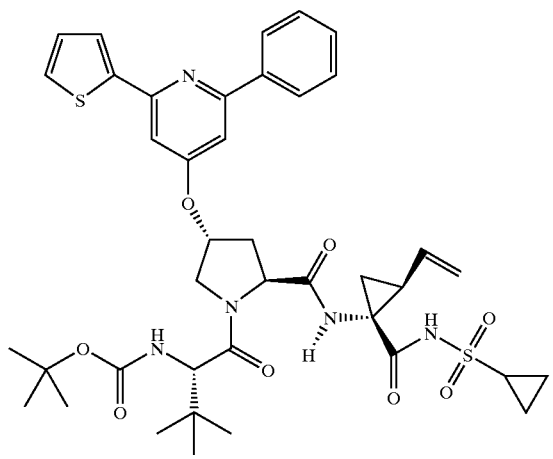

Step 1:

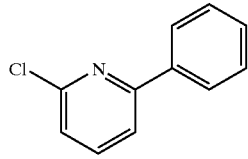

2-Bromo-6-chloropyridine (3.0 g, 15.55 mmol) and phenylboronic acid (1.896 g, 15.55 mmol) were solvated in a mixture of EtOH, toluene and water (2:1:1; 120 mL). Aqueous 1M Na$_2$CO$_3$ (15.55 mL, 31.10 mmol) and 5 mole percent of Tetrakis(triphenyl)phosphine)-palladium (0) (0.896 g, 0.775 mmol) were added under a nitrogen atmosphere. The reaction was refluxed at 90° C. for one hour. Water (20 mL) was added to quench the reaction, and the aqueous layer was extracted with diethyl ether (4×25 mL). The organic layer was then washed with brine, dried over MgSO$_4$, and concentrated in vacuo. The crude mixture was purified by a Biotage 40S column (eluted 2%–10% ethyl acetate in hexanes), to afford the pure titled compound (1.45 g, 74%).

$^1$H NMR: δ 7.24–7.26 (m, 1H), 7.42–7.48 (m, 3H), 7.63–7.70 (m, 2H), 7.98–8.00 (m, 2H);

LC/MS rt-min (MH$^+$): 2.04 (190.18) (method A)

Step 2:

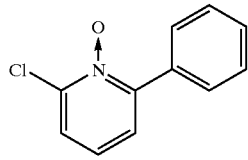

TFA (20 mL) was added to the pure solid obtained in Step 1 (3.27 g, 17.24 mmol). A 30% solution of H$_2$O$_2$ (5.55 mL, 48.9 mmol) was slowly added dropwise to the stirring solution under a nitrogen atmosphere. The reaction was heated to reflux at 100° C. for 3 hours, and 0.5 additional equivalents of H$_2$O$_2$ (2.27 mL, 25 mmol) were added to the solution. The reaction continued to stir at 100° C. for 2 hours. The flask was allowed to cool to room temperature before the solution was concentrated in vacuo to approximately half of the original volume. Water (40 mL) was added to quench the reaction and the aqueous layer was extracted with ethyl acetate (5×30 mL). The organic layer was washed once with brine (20 mL), dried over MgSO$_4$, and concentrated in vacuo. The crude product was purified by Biotate 40M column (eluted 10%–75% ethyl acetate in hexanes) to yield a pale yellow liquid (0.81 g, 23%). Pure starting material was also recovered for future use (1.895 g, 58%).

$^1$H NMR: δ 7.40–7.42 (t, 1H), 7.49–7.50 (m, 3H), 7.59–7.61 (d, J=10 Hz, 1H), 7.77–7.82 (m, 3H);

LC/MS rt-min (MH$^+$): 1.12 (206.37) (method A).

Step 3:

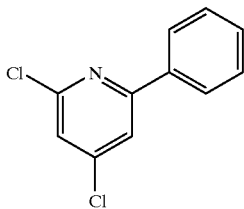

The purified product from Step 2 (0.81 g, 3.94 mmol) was added to a solution of $SOCl_2$ (25 mL) and stirred at 60° C. for 2 hours. The temperature was then increased to 80° C. in order to force the reaction to completion, and it was heated for an additional 30 min. The solution was concentrated in vacuo and quenched carefully with ice. The pH was adjusted to a pH of 4–5 using 10N NaOH, keeping the flask in an ice bath. The aqueous phase was extracted with ether (4×25 mL), and the organic layer was washed with brine (20 mL), dried over $MgSO_4$, and concentrated in vacuo. The crude, yellow liquid was purified by Biotage 40S column (eluted 2%–10% ethyl acetate in hexanes). A slightly yellow, viscous liquid was obtained (538 mg, 61%).

$^1$H NMR: δ 7.52–7.55 (m, 3H), 7.73 (s, 1H), 8.10–8.11 (m, 2H), 8.17 (s, 1H);

LC/MS rt-min (MH$^+$): 2.62 (225.33) (method A).

Step 4:

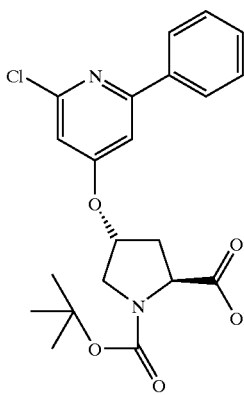

To a solution of Boc-L-hydroxyproline (555 mg, 2.40 mmol) in DMSO (4 mL), KO$^t$Bu (0.619 g, 5.52 mmol) was added under a nitrogen atmosphere. The suspension was stirred at room temperature for 45 min., and 2,4-dichloro-6-phenyl-pyridine (purified in Step 3.) (538 mg, 2.40 mmol) was added in two portions. The mixture was stirred at room temperature for two hours and 1.3 equivalents of HCl (1N) were used to neutralize the reaction. Buffer solution of pH 4.0 was added, and the pH was adjusted to pH 4–5. Ethyl acetate was used to extract the aqueous phase, (3×25 mL) and the organic phase was washed with brine (20 mL) and dried over $MgSO_4$ to yield the titled compound as a white solid (crude yield=962 mg). The crude product was taken into the next step.

LC/MS rt-min (MH$^+$): 2.55 (419.27) (method A).

Step 5:

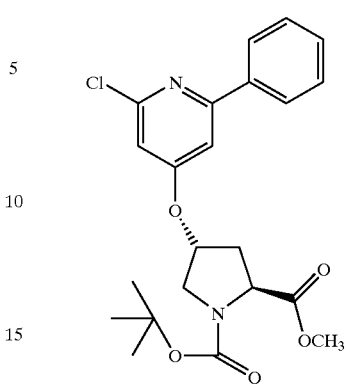

A solution of the crude product from Step 4 (assumed 2.4 mmol) in THF(10 mL) and methnal (10 mL) was cooled to 0° C. $TMSCN_2$ 2M in hexanes (~1.3 eq) was slowly added to the stirring solution under a nitrogen atmosphere until gas was no longer emitted from the solution. The fully reacted solution was then concentrated in vacuo, and purification by a Biotage 25S column (eluted 10%–50% ethyl acetate in hexanes) afforded the pure titled compound as a white foam (503 mg, 48% over steps 4d–4e).

$^1$H NMR: (DMSO-d$_6$) δ 1.35–1.38 (rotamers, 3:2, 9H), 2.21–2.26 (m, 1H), 2.50–2.58 (m, 1H), 3.67–3.70 (m, 5H), 4.26–4.34 (m, 1H), 5.35 (br s, 1H), 7.14–7.15 (m, 1H), 7.47–7.55 (m, 4H), 8.05–8.09 (m, 2H);

LC/MS rt-min (MH$^+$): 2.69 (455.52) (method A).

Step 6:

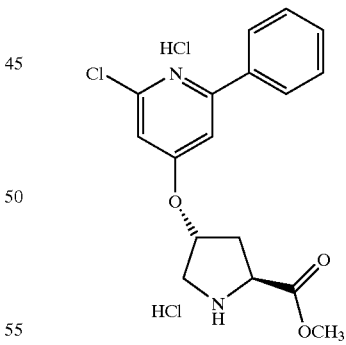

A solution of the pure product from Step 5 (503 mg, 1.16 mmol) in DCM (2.5 mL) and TFA (3.58 mL) was stirred at room temperature for one hour. The solvent was removed in vacuo, and the residue was suspended in 1N HCl in diethyl ether (6 mL), gently stirred, and concentrated in vacuo. This procedure was repeated and the resulting product was placed on an oil pump to yield a white solid in quantitative yield. The crude product was carried into the next step.

Step 7:

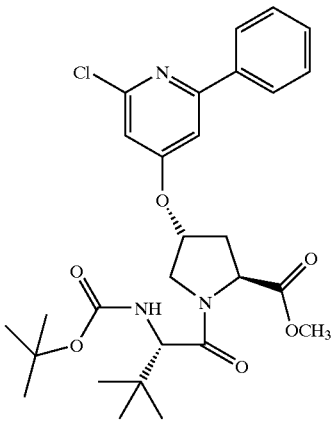

The product from Step 6 (assumed quantitative yield, 1.83 mmol) was added to a solution of BOC-t-Butyl-L-glycine (0.424 g, 1.83 mmol) in DCM (11 mL) under a nitrogen atmosphere. This step was followed by the addition of HOBt (0.272 g, 2.02 mmol), DIPEA (2.23 mL, 12.82 mmol), and HBTU (1.04 g, 2.75 mmol). The reaction was left to stir at room temperature for 15 hours. 15 mL DCM was added to the solution in order to increase the volume, and the reaction was quenched with pH 4.00 buffer solution (15 mL). The mixture was acidified to a pH of 4.5 using 1N HCl, and the aqueous phase was extracted with DCM (3×20 mL). The organic phase was washed twice with pH 4.00 buffer solution (20 mL), saturated NaOH (25 mL), brine (20 mL), and dried over $MgSO_4$. The resulting solution was concentrated in vacuo and purified by a Biotage 40S column (eluted 20%–50% ethyl acetate in hexanes). This purification afforded the pure titled compound as a white solid (454 mg, 53%).

$^1$H NMR: (DMSO-$d_6$) δ 0.96 (s, 9H), 1.19 (s, 9H), 2.17–2.29 (m, 1H), 2.48–2.58 (m, 1H), 3.65 (s, 3H), 3.81–3.89 (m, 1H), 4.05–4.08 (m, 1H), 4.21–4.26 (m, 1H), 4.44–4.50 (t, 1H), 5.45 (br s, 1H), 6.72–6.75 (d, J=15 Hz, 1H), 7.09 (s, 1H), 7.46–7.51 (m, 4H), 8.02–8.06 (m, 2H);

LC/MS rt-min (MH$^+$): 2.27 (493.5) (method A).

Step 8:

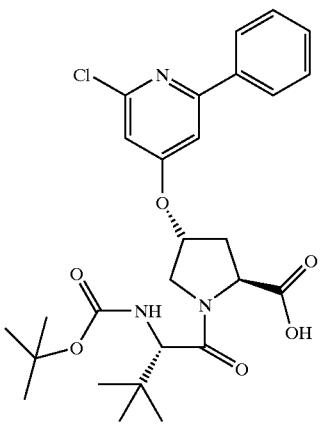

LiOH (0.0233 g, 0.973 mmol) was dissolved in water (10 mL) by heating and sonication. The LiOH solution was added to a solution of the pure material from Step 7 (483 mg, 0.885 mmol) in THF(10 mL), and the mixture immediately turned a pale peach color. The reaction was left to stir at room temperature for 1 hour and was acidified with 1N HCl (0.973 mL, 0.974 mmol). The reaction was quenched with pH 4.00 buffer solution and the pH was adjusted to a pH between 4 and 5. The aqueous layer was extracted with EtOAc (3×20 mL), washed with brine (15 mL) and dried over $MgSO_4$. The filtered solution was concentrated in vacuo and left on a vacuum line overnight. The crude product (480 mg, >95% yield) was taken into the next step.

$^1$H NMR: (DMSO-$d_6$) δ 0.94 (s, 9H), 1.20 (s, 9H), 1.32–1.34 (m, 1H), 2.12–2.4 (m, 1H), 2.51–2.55 (m, 1H), 3.81–3.83 (d, J=10 Hz, 1H), 4.21–4.23 (d, J=10 Hz, 1H), 4.32–4.35 (t, 1H), 5.4 (br s, 1H), 6.63–6.65 (d, NH), 7.09 (s, 1H), 7.47–7.49 (m, 4H), 8.03–8.06 (m, $^2$H), 12.56 (s, 1H).

Step 9:

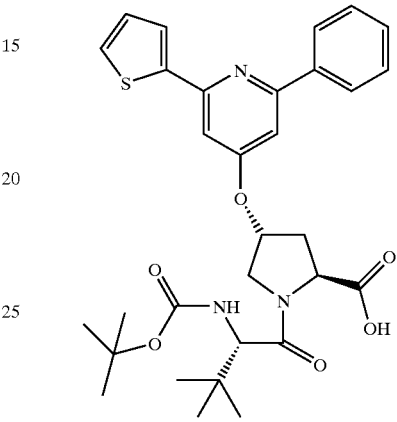

The dipeptide from Step 8 (100 mg, 0.188 mmol) and 2-thiopheneboronic acid (0.0481 g, 0.376 mmol) were solvated in DMF (2 mL). The solution was placed under a nitrogen atmosphere and 2M aqueous KF (0.282 mL, 0.376 mmol) was added. Five mole percent of Tetrakis(triphenyl) phosphine)-palladium (0) was added (0.011 mg, 0.0094 mmol) and the mixture was heated by microwave using the Personal Chemistry Emrys Optimizer for 30 minutes at 150° C. Palladium black precipitated out of the reaction upon completion. The mixture was acidified with one equivalent of 1N HCl and filtered through a syringe, using MeOH to extract the product. The product was purified by prep HPLC (column—4 Xterra S5 5 um 30×75 mm, solvent—85% A/15% B—10% A/90% B (where solvent A is 10% MeOH, 90% $H_2O$, 0.1% TFA and solvent B is 90% MeOH, 10% $H_2O$, 0.1% TFA), gradient time—15 min., hold time—1 min., flow rate—40 mL/min, retention time of pure product—16.23). Fractions containing the desired product were neutralized with 1N NaOH and placed in the speed vac for approximately 2 hours. The fractions were combined, and pH 4.0 buffer (15 mL) was added. The pH was adjusted to pH 4–5 using 1N HCl, and the aqueous layer was extracted with ethyl acetate (3×20 mL). The organic layer was washed with brine (15 mL), dried over $MgSO_4$, and concentrated in vacuo. The product was placed on an oil pump to dry overnight, and a pale yellow oil was obtained (44 mg, 40%).

LC/MS rt-min (MH$^+$): 2.7 (580.54) (method A).

Step 10:

The product from Example 413, Step 9 (43 mg, 0.0742 mmol) was dissolved in DCM (2 mL) and cyclopropanesulfonic acid (1 (R)-amino-2 (S)-vinylcyclopropanecarbonyl)-amide hydrochloride salt (Example 1, Step 8) (0.0198 g, 0.0742 mmol) was added. DIPEA (0.0646 mL, 0.371 mmol), and then HATU (0.039 g, 0.0104 mmol) were added under a nitrogen atmosphere. The reaction was left to stir at room temperature for 4.5 hours. 10 mL of DCM was added to the solution in order to increase the volume, and the reaction was quenched with pH 4.00 buffer solution (10 mL). The mixture was acidified to a pH of 4–5 using 1N HCl, and the aqueous phase was extracted with DCM (3×15 mL). The organic phase was washed twice with pH 4.00 buffer solution (10 mL) and brine (10 mL), and then dried over MgSO$_4$. The resulting solution was concentrated in vacuo and purified by a Biotage 12S column (eluted 10%–50% acetone in hexanes). The compound was isolated and re-purified by prep-HPLC (column—YMC ODS-A 20×50 mm s5, solvent—60% A/40% B—10% A/90% B (where solvent A is 10% MeOH, 90% H$_2$O, 0.1% TFA and solvent B is 90% MeOH, 10% H$_2$O, 0.1% TFA), gradient time—8 min., hold time—2 min., flow rate—25 mL/min, retention time of pure product—8.702). This purification afforded the pure Compound 413 as a pale orange oil (22.3 mg, 38%).

$^1$H NMR: δ 1.02–1.29 (m, 24H), 1.42–1.45 (m, 1H), 1.87–1.89 (m, 1H), 2.24–2.30 (m, 2H), 2.53–2.57 (m, 1H), 2.92–2.97 (m, 1H), 4.06–4.08 (d, J=10 Hz, 1H), 4.25 (s, 1H), 4.31–4.33 (d, J=10 Hz, 1H), 4.45–4.49 (t, 1H), 5.12–5.14 (d, J=10 Hz, 1H), 5.29–5.32 (d, J=15 Hz, 1H), 5.46 (br s, 1H), 5.73–5.80 (m, 1H), 7.13–7.15 (m, 1H), 7.29–7.30 (d, J=5 Hz, 2H), 7.42–7.53 (m, 4H), 7.75–7.56 (d, J=5 Hz, 1H), 8.07–8.09 (d, J=10 Hz, 2H).

LC/MS rt-min (MH$^+$): 2.79 (792.72) (method A).

Example 414

Preparation of Compound 414

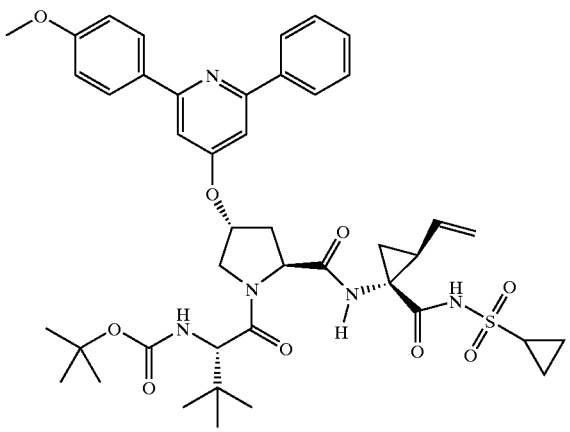

Compound 414

Step 1:

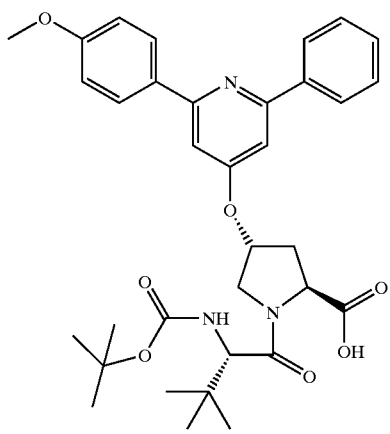

The pure material from Example 413, Step 8 (100 mg, 0.188 mmol), and 4-methoxyphenylboronic acid (0.0429 g, 0.282 mmol) were solvated in DMF (2.5 mL). The solution was placed under a nitrogen atmosphere and 2M aqueous Na$_2$CO$_3$ (0.188 mL, 0.376 mmol) was added. Five mole percent of Tetrakis(triphenyl)phosphine)-palladium (0) was added (0.011 mg, 0.0094 mmol), and the mixture was heated by microwave using the Personal Chemistry Emrys Optimizer for 30 minutes at 150° C. Palladium black precipitated out of the reaction upon completion. The mixture was acidified with one equivalent of 1N HCl and filtered through a syringe, using MeOH to extract product. The product was purified by prep HPLC (column—Xterra MS C18 Sum 30×50 mm, solvent—90% A/10% B—10% A/90% B (where solvent A is 10% MeOH, 90% H$_2$O, 0.1% TFA and solvent B is 90% MeOH, 10% H$_2$O, 0.1% TFA), gradient time—15 min., hold time—1 min., flow rate—45 mL/min, retention time of pure product—13.72). Fractions containing the desired product were neutralized with 1N NaOH and placed in the speed vac for approximately 2 hours. The fractions were combined, and pH 4.0 buffer (15 mL) was added. The pH was adjusted to pH 4–5 using 1N HCl, and the aqueous layer was extracted with ethyl acetate (3×20 mL). The organic layer was washed with brine (15 mL), dried over MgSO$_4$, and concentrated in vacuo. The product was placed on an oil pump to dry overnight, and a viscous oil was obtained (44 mg, 50%).

LC/MS rt-min (MH$^+$): 2.23 (604.61) (method A).

Step 2:

The product from Example 414, Step 1 (43 mg, 0.0712 mmol) was dissolved in DCM (2 mL) and cyclopropanesulfonic acid (1 (R)-amino-2 (S)-vinyl-cyclopropanecarbonyl)-amide hydrochloride salt (Example 1, Step 8) (0.01899 g, 0.0712 mmol) was added. DIPEA (0.062 mL, 0.356 mmol), and then HATU (0.038 g, 0.0997 mmol) were added under a nitrogen atmosphere. The reaction was left to stir at room temperature for 4.5 hours. 10 mL DCM was added to the solution in order to increase the volume, and the reaction was quenched with pH 4.00 buffer solution (10 mL). The mixture was acidified to a pH of 4–5 using 1N HCl, and the aqueous phase was extracted with DCM (3×15 mL). The organic phase was washed twice with pH 4.00 buffer solution (10 mL) and brine (10 mL), and then dried over MgSO$_4$. The resulting solution was concentrated in vacuo and purified by a Biotage 12S column (eluted 20%–50% acetone in hexanes). The compound was isolated and re-purified by prep-HPLC (column—YMC ODS-A 20×50 mm s5, solvent—60% A/40% B—10% A/90% B (where solvent A is 10% MeOH, 90% H$_2$O, 0.1% TFA and solvent B is 90% MeOH, 10% H$_2$O, 0.1% TFA), gradient time—10 min., hold time—2 min., flow rate—25 mL/min, retention time of pure product—7.43–8.24). This purification afforded the pure Compound 414 as a pale orange oil (19.4 mg, 34%).

$^1$H NMR: δ 1.02–1.23 (m, 24H), 1.29–1.44 (m, 1H), 1.89–1.95 (m, 1H), 2.24–2.30 (q, 1H), 2.32–2.40 (m, 1H), 2.59–2.62 (m, 1H), 3.90 (s, 3H), 4.10–4.12 (d, J=10 Hz, 1H), 4.21 (s, 1H), 4.42–4.56 (m, 2H), 5.12–5.14 (d, J=10 Hz, 1H), 5.28–5.31 (d, J=15 Hz, 1H), 5.61 (br s, 1H), 5.72–5.80 (m, 1H), 7.14–7.16 (d, J=10 Hz, 2H), 7.52–7.54 (d, J=10 Hz, 2H), 7.61–7.62 (m, 2H), 7.95–7.98 (m, 4H);

LC/MS rt-min (MH$^+$): 2.35 (816.76) (method A).

Example 415

Preparation of Compound 415

Compound 415

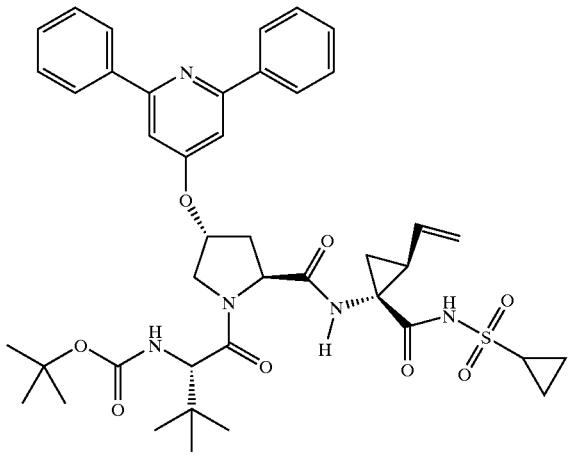

Step 1:

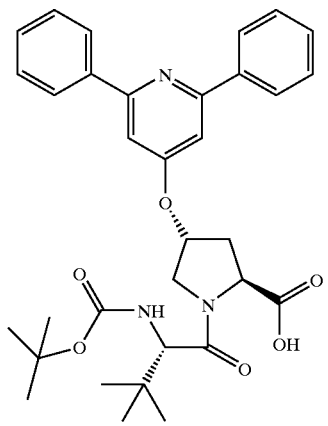

The dipeptide from Example 413, Step 8 (174 mg, 0.327 mmol) and phenylboronic acid (0.06 g, 0.491 mmol) were solvated in DMF (4 mL). The solution was placed under a nitrogen atmosphere and 2M aqueous $NaCO_3$ (0.33 mL, 0.654 mmol) was added. Five mole percent of Tetrakis (triphenyl)phosphine)-palladium (0) was added (0.019 mg, 0.0164 mmol) and the mixture was heated by microwave using the Personal Chemistry Emrys Optimizer for 30 minutes at 150° C. Palladium black precipitated out of the reaction upon completion. The mixture was acidified with one equivalent of 1N HCl and filtered through a syringe, using MeOH to extract the product. The product was purified by prep HPLC (column—5 Xterra c-18 5 um 30×100 mm, solvent—80% A/20% B—0% A/100% B (where solvent A is 10% MeOH, 90% $H_2O$, 0.1% TFA and solvent B is 90% MeOH, 10% $H_2O$, 0.1% TFA), gradient time—20 min., hold time—1 min., flow rate—40 mL/min, retention time of pure product—11.28–11.72). Fractions containing the desired product were neutralized with 1N NaOH and placed in the speed vac for approximately 2 hours. The fractions were combined, and pH 4.0 buffer (15 mL) was added. The pH was adjusted to pH 4–5 using 1N HCl, and the aqueous layer was extracted with ethyl acetate (4×15 mL).

The organic layer was washed with brine (15 mL), dried over $MgSO_4$, and concentrated in vacuo. The product was placed on an oil pump to dry overnight. (31.5 mg, 17%).

LC/MS rt-min ($MH^+$): 2.54 (574.37) (method A).

Step 2:

The product from Example 415, Step 1 (31.5 mg, 0.055 mmol) was dissolved in DCM (3 mL) and cyclopropanesulfonic acid (1 (R)-amino-2 (S)-vinyl-cyclopropanecarbonyl)-amide hydrochloride salt (Example 1, Step 8) (0.0147 g, 0.055 mmol) was added. DIPEA (0.048 mL, 0.275 mmol), and then HATU (0.029 g, 0.077 mmol) were added under a nitrogen atmosphere. The reaction was left to stir at room temperature for 3.5 hours and an additional 0.3 equivalents of cyclopropanesulfonic acid (1 (R)-amino-2 (S)-vinyl-cyclopropanecarbonyl)-amide hydrochloride salt were added. The reaction was left to stir for 8 more hours. 10 mL of DCM was added to the solution in order to increase the volume, and the reaction was quenched with pH 4.00 buffer solution (10 mL). The mixture was acidified to a pH of 4–5 using 1N HCl, and the aqueous phase was extracted with DCM (4×10 mL). The organic phase was washed twice with pH 4.00 buffer solution (10 mL) and brine (10 mL), and then dried over $MgSO_4$. The resulting solution was concentrated in vacuo and purified by prep HPLC (column —YMC ODS-A 30×50 mm, solvent— 80% A/20% B—10% A/90% B (where solvent A is 10% MeOH, 90% $H_2O$, 0.1% TFA and solvent B is 90% MeOH, 10% $H_2O$, 0.1% TFA), gradient time—20 min., hold time—3 min., flow rate—30 mL/min, retention time of pure product—19.6). This purification did not afford a pure compound so it was re-purified by a Biotage12 S column (eluted 10%–50% acetone in hexanes). This purification afforded the pure titled compound as a pale orange oil (22.3 mg, 38%).

$^1$H NMR: δ 1.02–1.45 (m, 24H), 1.85–1.86 (m, 1H), 2.03–2.11 (m, 2H), 2.42–2.46 (m, 1H), 2.77–2.85 (m, 1H), 4.10–4.12 (m, 1H), 4.25 (s, 1H), 4.31–4.33 (d, J=10 Hz, 1H), 4.49–4.54 (m, 1H), 5.03–5.05 (d, J=10 Hz, 1H), 5.20–5.24 (d, J=20 Hz, 1H), 5.44 (br s, 1H), 5.82–5.94 (m, 1H), 7.33 (s, 2H), 7.43–7.50 (m, 6H), 8.09–8.10 (d, J=5 Hz, 4H);

LC/MS rt-min ($MH^+$): 2.37 (786.37) (method A).

Section J:

In section J the LC/MS method utilized was the following:

| | |
|---|---|
| Columns: | Method A: YMC ODS-A C18 S7 (4.6 × 33 mm) |
| | Method B: YMC Xterra ODS S7 (3.0 × 50 mm) |
| | Method C: Xterra ms C18 (4.6 × 33 mm) |
| | Method D: YMC ODS-A C18 S3 (4.6 × 33 mm) |
| Gradient: | 100% solvent A/0% solvent B to 0% solvent A/100% solvent B |
| Gradient time: | 3 min. |
| Hold Time: | 1 min. |
| Flow Rate: | 5 mL/min. |
| Detector Wavelength: | 220 nm. |
| Solvents: | Solvent A: 10% MeOH/90% water/0.1% TFA. |
| | Solvent B: 90% MeOH/10% water/0.1% TFA. |

Example 420

Preparation of Compound 420

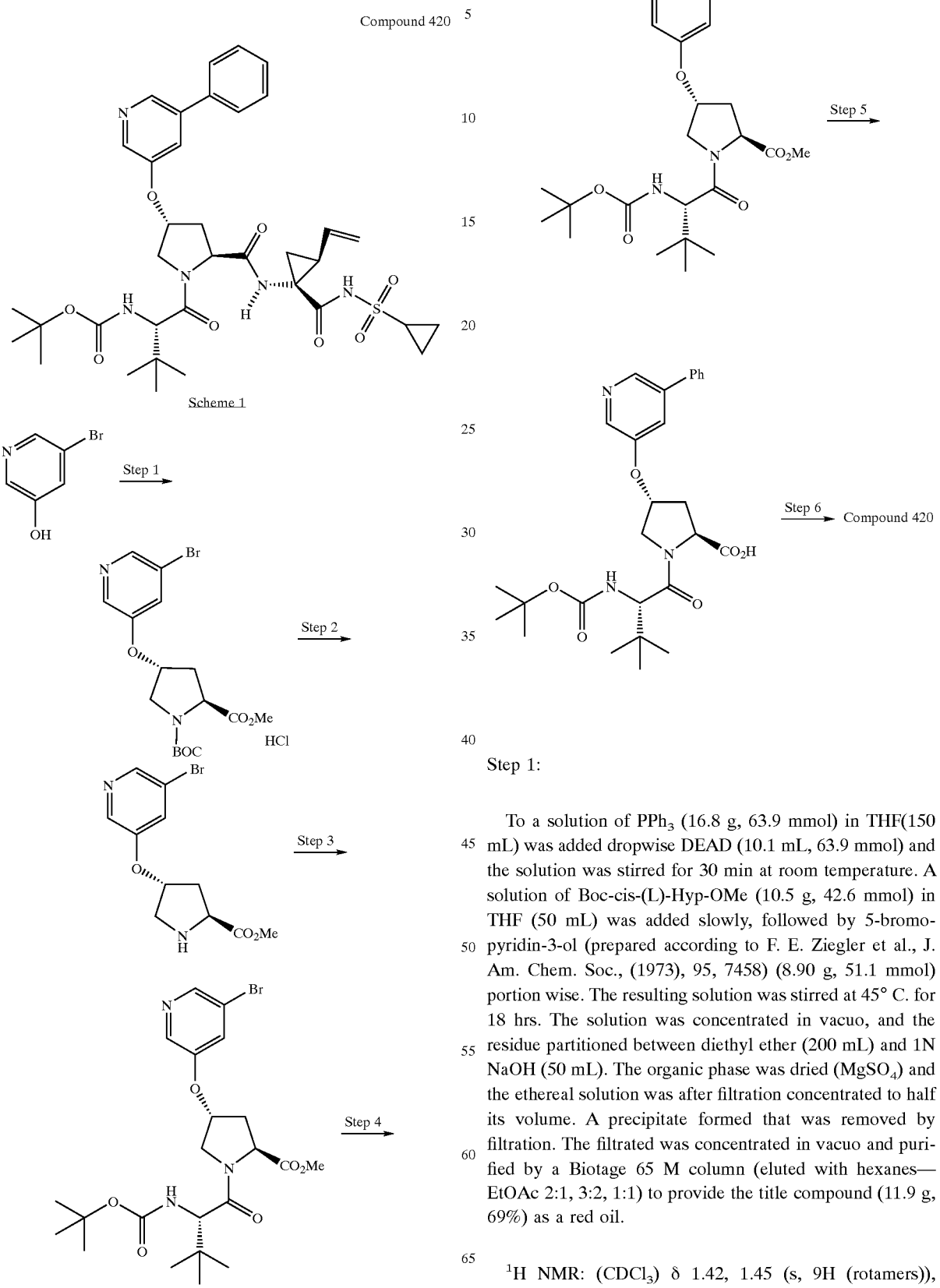

Step 1:

To a solution of PPh₃ (16.8 g, 63.9 mmol) in THF(150 mL) was added dropwise DEAD (10.1 mL, 63.9 mmol) and the solution was stirred for 30 min at room temperature. A solution of Boc-cis-(L)-Hyp-OMe (10.5 g, 42.6 mmol) in THF (50 mL) was added slowly, followed by 5-bromo-pyridin-3-ol (prepared according to F. E. Ziegler et al., J. Am. Chem. Soc., (1973), 95, 7458) (8.90 g, 51.1 mmol) portion wise. The resulting solution was stirred at 45° C. for 18 hrs. The solution was concentrated in vacuo, and the residue partitioned between diethyl ether (200 mL) and 1N NaOH (50 mL). The organic phase was dried (MgSO₄) and the ethereal solution was after filtration concentrated to half its volume. A precipitate formed that was removed by filtration. The filtrated was concentrated in vacuo and purified by a Biotage 65 M column (eluted with hexanes—EtOAc 2:1, 3:2, 1:1) to provide the title compound (11.9 g, 69%) as a red oil.

¹H NMR: (CDCl₃) δ 1.42, 1.45 (s, 9H (rotamers)), 2.25–2.30 (m, 1H), 2.49–2.58 (m, 1H), 3.75, 3.81 (s, 3H (rotamers)), 3.66–3.81 (m, 2H (hidden)), 4.42, 4.50 (t, J=8 Hz, 1H (rotamers)), 4.92 (m, 1H), 7.36 (s, 1H), 8.20 (s, 1H), 8.32 (s, 1H).

LC/MS rt-min (MH$^+$): 2.26 (401, 403) (method B).

Step 2:

The product of Step 1 (2.34 g, 5.83 mmol) was dissolved in DCM (20 mL) and TFA (18 mL, 0.23 mole) and stirred at room temperature for 2 hrs. The volatiles were removed in vacuo and the residue partitioned between EtOAc and water. The organic phase was extracted with 1N HCl (25 mL) and the combined aqueous extracts were neutralized with satd. NaHCO$_3$ (40 mL). The aqueous phase was extracted with EtOAc (twice) and the combined organic extracts washed with brine and dried (MgSO$_4$) to give the title compound (1.02 g, 58%, free base) as a colorless oil.

$^1$H NMR: (DMSO-d$_6$) δ 2.12–2.20 (m, 2H), 2.94 (d, J=12 Hz, 1H), 3.19 (dd, J=4.5, 12 Hz, 1H), 3.64 (s, 3H), 3.90 (t, J=8 Hz, 1H), 5.07 (m, 1H), 7.69 (s, 1H), 8.26 (s, 1H), 8.29 (s, 1H).

LC/MS rt-min (MH$^+$): 0.78 (301, 302) (method B).

Step 3:

To a suspension of the product of Step 2 (1.02 g, 3.39 mmol), N-BOC-L-tert-leucine (862 mg, 3.73 mmol), and HOBt (458 mg, 3.39 mmol) in DCM (15 mL) were added DIPEA (2.36 mL, 13.6 mmol) followed by HBTU (1.61 g, 4.24 mmol). The resulting solution was stirred at room temperature for 15 hrs and quenched with DCM and buffer pH 4 and some 1N HCl to adjust the pH to 4–5. The organic phase was washed with buffer pH 4, satd. NaHCO$_3$ (twice), brine, and dried (MgSO$_4$). Purification using a Biotage 40 M column (eluted hexane—EtOAc 3:2, 1:1) afforded the title compound (1.48 g, 85%) as a white solid.

$^1$H NMR: (DMSO-d$_6$) δ 0.94 (s, 9H), 1.17 (s, 9H), 2.16–2.21 (m, 1H), 2.50 (m, (hidden), 1H), 3.64 (s, 3H), 3.82 (d, J=12 Hz, 1H), 4.06 (d, J=9.5 Hz, 1H), 4.16 (d, J=12 Hz, 1H), 4.45 (dd, J=8, 9.5 Hz, 1H), 5.26 (m, 1H), 6.71 (d, J=9 Hz, NH), 7.75 (s, 1H), 8.28 (s, 1H), 8.32 (s, 1H).

LC/MS rt-min (MH$^+$): 2.35 (514, 516) (method B).

Step 4:

To a mixture of the product of Step 3 (98 mg, 0.19 mmol), Pd(PPh$_3$)$_4$ (6.6 mg, 0.00573 mmol), 2M aqueous Na$_2$CO$_3$ (0.191 mL, 0.381 mmol) in toluene (2 mL) was added a solution of phenyl boronic acid (29 mg, 0.24 mmol) in methanol (0.1 mL). The solution was heated at 85° C. for 6 h under nitrogen. After cooling to room temperature the mixture was quenched with buffer pH 4 and extracted with EtOAc (2×10 mL), and dried (Na$_2$SO$_4$). Purification using a Biotage 12 M column (eluted hexane—EtOAc 2:3) afforded the title compound (72 mg, 74%) as a colorless oil.

$^1$HNMR: (methanol-d$_4$) δ 1.05 (s, 9H), 1.31 (s, 9H), 2.29–2.35 (m, 1H), 2.68–2.72 (m, 1H), 3.77 (s, 3H), 4.00 (d, J=12 Hz, 1H), 4.24 (d, J=9.5 Hz, 1H), 4.41 (d, J=12 Hz, 1H), 4.67 (dd, J=7.5, 10 Hz, 1H), 5.36 (m, 1H), 6.51 (d, J=9.5 Hz, NH), 7.79–7.85 (m, 3H), 8.39 (s, 1H), 8.59 (s, 1H), 8.67–8.68 (m, 2H).

LC/MS rt-min (MH$^+$): 2.16 (512) (method B).

Step 5:

To a solution of the product of Step 4 (150 mg, 0.293 mmol) in THF(2 mL) and methanol (2 mL) was added LiOH (14 mg, 0.59 mmol) in water (2 mL). The mixture was stirred for 2 h at room temperature and quenched with 1N HCl until neutral pH. The organic volatiles were removed in vacuo and to the residue was added buffer pH 4. The product was extracted into EtOAc (3×10 mL), washed with brine/buffer pH 4 and dried (MgSO$_4$) to yield the title compound in quantitative yield as a white solid after trituration from pentane.

$^1$H NMR: (methanol-d$_4$) δ 1.05 (s, 9H), 1.32 (s, 9H), 2.32–2.38 (m, 1H), 2.69–2.74 (m, 1H), 3.99 (dd, J=3, 12 Hz, 1H), 4.25 (s, 1H), 4.40 (d, J=12 Hz, 1H), 4.64 (dd, J=7.5, 9.5 Hz, 1H), 5.36 (m, 1H), 7.85–7.87 (m, 3H), 8.40 (s, 1H), 8.60 (s, 1H), 8.69–8.70 (m, 2H).

LC/MS rt-min (MH$^+$): 2.03 (499) (method B).

Step 6:

To a suspension of the product of Step 5 (93 mg, 0.19 mmol), and the product from Example 1, Step 8 (50 mg, 0.19 mmol) in DCM (2 mL) was added DIPEA (0.163 mL, 0.935 mmol), followed by HATU (92 mg, 0.243 mmol). The resulting mixture was stirred at room temperature for 18 hrs and quenched with DCM and buffer pH 4 and some 1N HCl to adjust the pH to 4–5. The layers were separated and the aqueous phase extracted with DCM (10 mL) and dried (Na$_2$SO$_4$). Purification using a Biotage 12 M column (eluted gradient hexane-acetone 20–60%) afforded the title compound (65 mg, 49%) as a white powder.

$^1$H NMR: (DMSO-d$_6$) δ 0.95 (s, 9H), 1.03–1.05 (m, 2H), 1.08–1.10 (m, 2H), 1.26 (s, 9H), 1.36–1.39 (m, 1H), 1.69–1.72 (m, 1H), 2.09–2.21 (m, 2H), 2.41–2.45 (m, 1H), 2.92–2.94 (m, 1H), 3.91 (d, J=11.5 Hz, 1H), 4.08 (d, J=7.5 Hz, 1H), 4.16 (d, J=11.5 Hz, 1H), 4.36 (t, J=8.5 Hz, 1H), 5.10 (d, J=10 Hz, 1H), 5.23 (d, J=17.5 Hz, 11H), 5.38 (m, 1H), 5.59–5.67 (n, 1H), 6.54 (s, NH), 7.41–7.46 (m, 1H), 7.50–7.53 (m, 2H), 7.65 (s, 1H), 7.74–7.75 (m, 2H), 8.28 (s, 1H), 8.52 (s, 1H): 8.92 (s, NH).

LC/MS rt-min (MH$^+$): 2.08 (710) (method B).

Example 421

Preparation of Compound 421

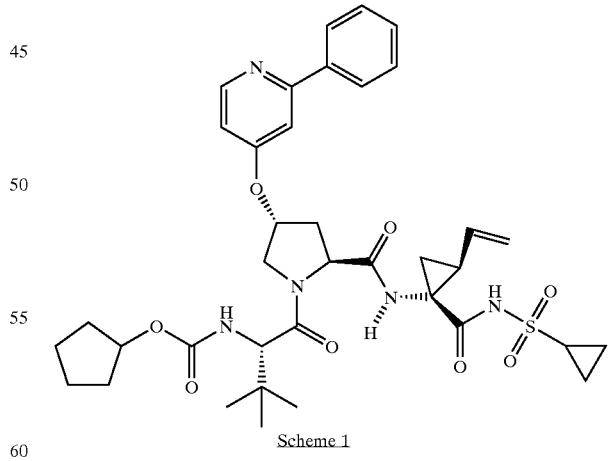

Compound 421

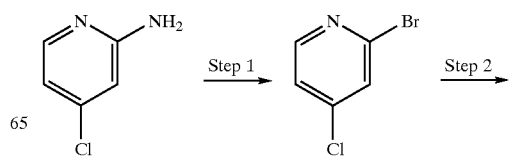

Scheme 1

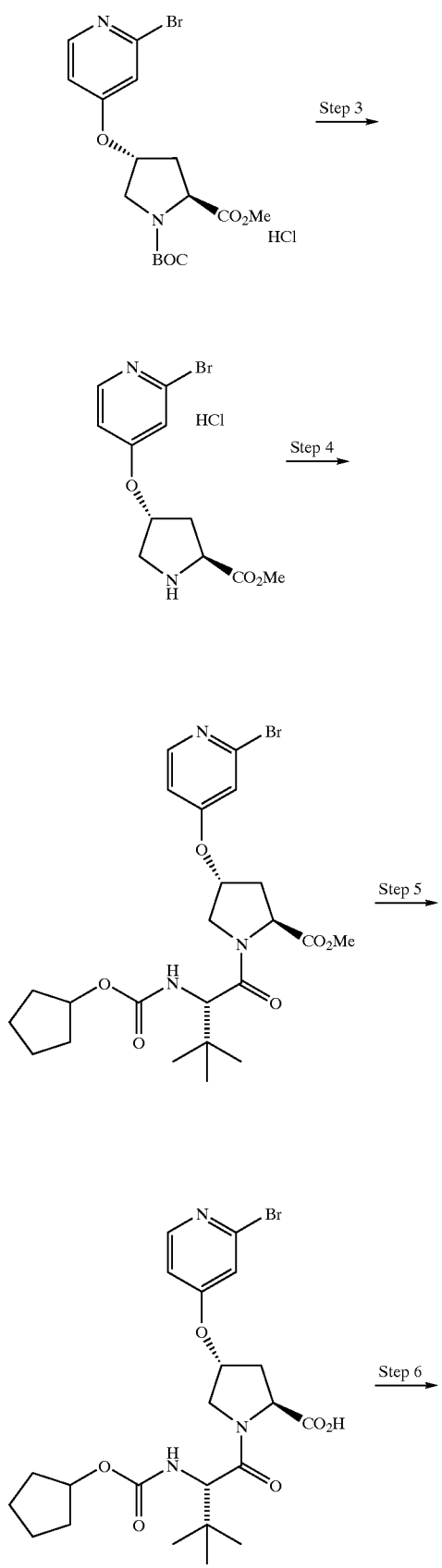

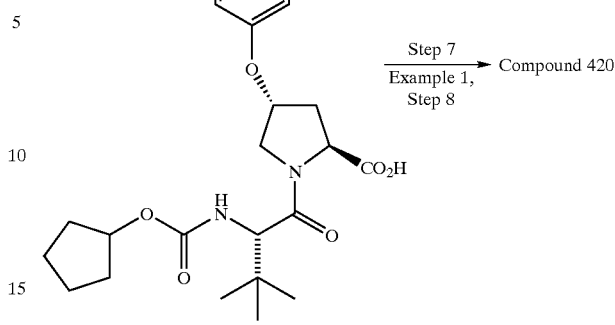

Step 1:

To a cold (−5° C.) 48% aqueous HBr solution (35 mL) was added 4-chloro-pyridin-2-ylamine (4.18 g, 32.5 mmol; prepared according to K. S. Gudmundsson et al; Synth. Commun. (1997), 27, 861), followed by the slow addition of bromine (6.7 mL, 0.13 mole). After 20 min sodium nitrite (8.63 g, 0.125 mole) in water (40 mL) was added at the same temperature and stirring was continued for 30 min. The reaction was quenched under ice cooling with 10 N NaOH (ca 40 mL) to alkaline pH. The product was extracted into EtOAc (2×100 mL) and dried ($Na_2SO_4$). The crude material was purified using a Biotage 40 M column (eluted with 10% EtOAc in hexanes) to afford the title compound (2.50 g, 40%) as a colorless oil that solidified upon standing.

$^1$H NMR: (DMSO-$d_6$) δ 7.64 (dd, J=1.5, 5.5 Hz, 1H), 7.94 (d, J=1.5 Hz, 1H), 8.40 (d, J=5.5 Hz, 1H); LC/MS rt-min (MH$^+$): 1.65 (192, 194, 196) (method B).

Step 2:

To a solution of N-BOC-trans-L-Hyp-OH (3.22 g, 13.9 mmol) in DMSO (30 mL) was added potassium tert.butoxide (3.90 g, 34.8 mmol) in portions at room temperature under a nitrogen atmosphere. After 1.5 h the product of Step 1 was added in DMSO (5 mL). The mixture was stirred overnight and quenched with water (150 mL). The solution was washed with EtOAc (100 mL). The aqueous phase was acidified to pH 4 with 1N HCl. The crude carboxylic acid was extracted into EtOAc (thrice) and dried ($MgSO_4$). The residue, as a brown solid, was suspended in THF(20 mL) and MeOH (20 mL) and cooled to 0° C. A solution of trimethylsilyl diazomethane (2 M in hexane, 12 mL) was dropwise added, and the solution concentrated in vacuo after 15 min. Purification using a Biotage 40 M column (eluted with hexanes-EtOAc 2:1, 1:1) gave the title compound (3.47 g, 62%) as an off-white powder.

$^1$H NMR: (DMSO-$d_6$) δ 1.34, 1.38 (s, 9H (rotamers)), 2.24–2.29 (m, 1H), 2.43–2.50 (m, 1H), 3.57 (d, J=12.5 Hz, 1H), 3.64–3.68 (m, 1H), 3.66, 3.69 (s, 3H (rotamers)), 4.27–4.34 (m, 1H), 5.21 (m, 1H), 7.06 (d, J=6 Hz, 1H), 7.28 (s, 1H), 8.20 (d, J=6 Hz, 1H);

LC/MS rt-min (MH$^+$): 2.59 (401, 403) (method B).

Step 3:

The product of Step 2 (2.00 g, 4.98 mmol) was suspended in 4N HCl in dioxane (10 mL) and 1N HCl in diethyl ether (40 mL) and stirred overnight at room temperature. The resulting suspension was concentrated in vacuo and the residue triturated from pentane to give the title compound in quantitative yield as a white powder.

LC/MS rt-min (MH$^+$): 0.24 (301, 303) (method B).

Step 4:

To a suspension of the product of Step 3 (assumed 4.98 mmol), N-cyclopentyloxycarbonyl-L-tert-leucine (1.24 g, 5.10 mmol), and HOBt (673 mg, 4.98 mmol) in DCM (25 mL) was added DIPEA (4.34 mL, 24.9 mmol) followed by HBTU (2.36 g, 6.23 mmol). The resulting solution was stirred at room temperature for 15 hrs and quenched with DCM and buffer pH 4 and 10 mL 1N HCl to adjust the pH to 4. The aqueous phase was extracted with DCM (twice). The combined organic extracts were washed with satd. NaHCO$_3$ (twice), brine, and dried (MgSO$_4$). Purification using a Biotage 40 M column (eluted hexane-EtOAc 3:2, 1:1) afforded the title compound (2.09 g, 80%) as a white foam.

$^1$H NMR: (DMSO-d$_6$) δ 0.94 (s, 9H), 1.43–1.74 (m, 8H), 2.18–2.23 (m, 1H), 2.46–2.49 (m, 1H), 3.64 (s, 3H), 3.87 (d, J=12 Hz, 1H), 4.08–4.13 (m, 1H), 4.42 (dd, J=7.5, 9.5 Hz, 1H), 4.78 (m, 1H), 5.30 (m, 1H), 7.03–7.05 (m, 1H), 7.24 (s, 1H), 8.120 (d, J=6 Hz, 1H).

LC/MS rt-min (MH$^+$): 2.34 (526, 528) (method C).

Step 5:

To a solution of the product of Step 4 (206 mg, 0.391 mmol) in THF(2 mL) and methanol (2 mL) was added LiOH (28 mg, 1.2 mmol) in water (2 mL). The mixture was stirred for 2 h at room temperature and quenched with 1N HCl until neutral pH. The organic volatiles were removed in vacuo and to the residue was added buffer pH 4. The product was extracted into EtOAc (2×20 mL) and dried (MgSO$_4$) to yield the title compound (196 mg, 100%) as a white solid.

$^1$H NMR: (methanol-d$_4$) δ 1.05 (s, 9H), 1.60–1.85 (m, 8H), 2.30–2.36 (m, 1H), 2.62–2.67 (m, 11H), 3.97 (d, J=12 Hz, 11H), 4.26 (s, 11H), 4.32 (d, J=12 Hz, 1H), 4.58 (dd, J=7.5, 9.5 Hz, 1H), 4.89 (m (hidden), 1H), 5.29 (m, 1H), 7.03–7.05 (m, 1H), 7.26 (s, 1H), 8.19 (d, J=6 Hz, 11H);

LC/MS rt-min (MH$^+$): 2.17 (512, 514) (method B).

Step 6:

This product was prepared according to Example 420, Step 4 (reaction time 20 h) in 20% yield starting from the product of Example 421, Step 5.

$^1$H NMR: (methanol-d$_4$) δ 1.03 (s, 9H), 1.45–1.74 (m, 8H), 2.31–2.37 (m, 1H), 2.65–2.69 (m, 11H), 3.99 (dd, J=12, 3.0 Hz, 11H), 4.26 (d, J=9.5 Hz, 11H), 4.33 (d, J=11.5 Hz, 1H), 4.60 (dd, J=8.0, 9.5 Hz, 1H), 4.80 (m, 1H), 5.35 (m, 1H), 6.72 (d, J=9.0 Hz, NH), 7.02 (dd, J=2.5, 6.0 Hz, 1H), 7.39 (s, 1H), 7.50 (m, 3H (hidden)), 7.91 (d, J=6.5 Hz, 1H), 8.46 (d, J=6.0 Hz, 1H).

LC/MS rt-min (MH$^+$): 2.03 (510) (method A).

Step 7:

Compound 421 was prepared according to Example 420, Step 6 in 68% yield, starting from the product of Example 421, Step 6.

$^1$H NM: (methanol-d$_4$) δ 1.03 (s, 9H), 1.06–1.09 (m, 2H), 1.23–1.26 (m, 2H), 1.43 (dd, J=5.5, 9.5 Hz, 1H), 1.47–1.77 (m, 8H), 1.88 (dd, J=5.5, 8.5 Hz, 1H), 2.21–2.29 (m, 2H), 2.50–2.54 (m, 1H), 2.91–2.96 (m, 1H), 4.06 (dd, J=3.0, 11.5 Hz, 1H), 4.28–4.30 (m, 2H), 4.44 (dd, J=7.0, 10.5 Hz, 1H), 4.82 (m, 1H (hidden)), 5.12 (d, J=10 Hz, 1H), 5.30 (d, J=17 Hz, 1H), 5.37 (m, 1H), 5.73–5.80 (m, 1H), 6.92 (d, J=9.5 Hz, NH), 6.98 (dd, J=5.5, 2.0 Hz, 1H), 7.37 (s, 1H), 7.43–7.50 (m, 3H), 7.90 (d, J=7.0 Hz, 1H), 8.45 (d, J=5.5 Hz, 1H).

LC/MS rt-min (MH$^+$): 2.37 (723) (method A).

Example 422

Preparation of Compound 422

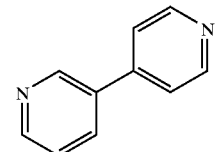

Compound 422

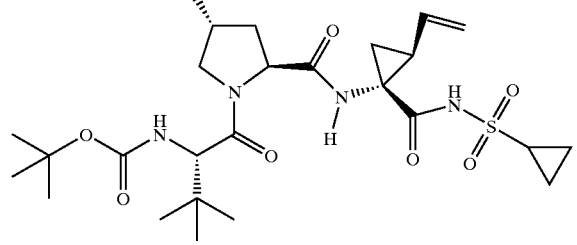

Step 1:

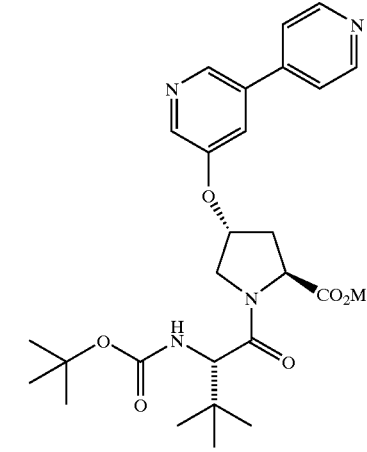

To a mixture of the product of Example 420, Step 3 (102 mg, 0.198 mmol) and Pd(PPh$_3$)$_4$ (23 mg, 0.0198 mmol) in toluene (2 mL) was added 4-tributylstannanyl-pyridine (87 mg, 0.24 mmol). The solution was heated at 105° C. for 20 h under nitrogen. After cooling to room temperature the mixture was quenched with satd. NaHCO$_3$ and extracted with EtOAc (2×10 mL), and dried (Na$_2$SO$_4$). Purification using a Biotage 12 M column (eluted gradient hexane-acetone 20–60%) afforded the title compound (49 mg, 49%) as a white solid.

$^1$H NMR: (methanol-d$_4$) δ 1.05 (s, 9H), 1.31 (s, 9H), 2.29–2.35 (m, 1H), 2.68–2.72 (m, 1H), 3.77 (s, 3H), 4.00 (d, J=12 Hz, 1H), 4.24 (d, J=9.5 Hz, 1H), 4.41 (d, J=12 Hz, 1H), 4.67 (dd, J=7.5, 10 Hz, 1H), 5.36 (m, 1H), 6.51 (d, J=9.5 Hz, NH), 7.79–7.85 (m, 3H), 8.39 (s, 1H), 8.59 (s, 1H), 8.67–8.68 (m, 2H).

LC/MS rt-min (MH$^+$): 1.77 (514) (method C).

Step 2:

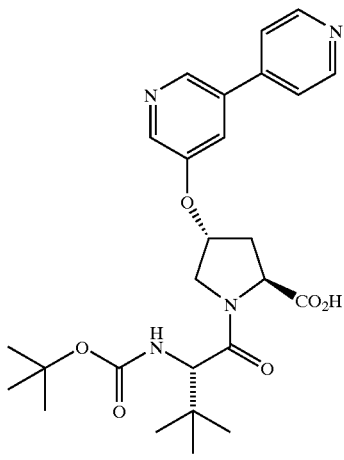

This product was prepared by the same procedure as described in Example 420, Step 5 in quantitative yield, except using the product from Example 422, Step 1 instead.

¹H NMR: (methanol-d₄) δ 1.05 (s, 9H), 1.32 (s, 9H), 2.32–2.38 (m, 1H), 2.69–2.74 (m, 1H), 3.99 (dd, J=3, 12 Hz, 1H), 4.25 (s, 1H), 4.40 (d, J=12 Hz, 1H), 4.64 (dd, J=7.5, 9.5 Hz, 1H), 5.36 (m, 1H), 7.85–7.87 (m, 3H), 8.40 (s, 1H), 8.60 (s, 1H), 8.69–8.70 (m, 2H).

LC/MS rt-min (MH⁺): 1.57 (500) (method B).

Step 3:

Compound 422 was prepared by the same procedure as described in Example 420, Step 6 in 51% yield as a white solid, except using the product from Example 422, Step 2 instead.

¹H NMR: (DMSO-d₆) δ 0.95 (s, 9H), 1.03 (m, 1H), 1.08 (m, 1H), 1.23 (s, 9H), 1.34–1.37 (m, 1H), 1.68–1.70 (m, 1H), 2.12–2.18 (m, 2H), 2.41–2.45 (m, 1H), 2.93 (m, 1H), 3.90 (d, J=11 Hz, 1H), 4.06 (d, J=9 Hz, 1H), 4.17 (d, J=11 Hz, 1H), 4.36 (dd, J=7, 10 Hz, 1H), 5.10 (d, J=12 Hz, 1H), 5.23 (d, J=16.5 Hz, 1H), 5.40 (m, 1H), 5.59–5.66 (m, 1H), 6.60 (d, J=9 Hz, NH), 7.81–7.82 (m, 3H), 8.38 (s, 1H), 8.65 (s, 1H), 8.68–8.70 (m, 2H), 8.93 (s, NH), 10.4 (s, NH).

LC/MS rt-min (MH⁺): 2.14 (711) (method D).

Example 423

Preparation of Compound 423

Compound 423

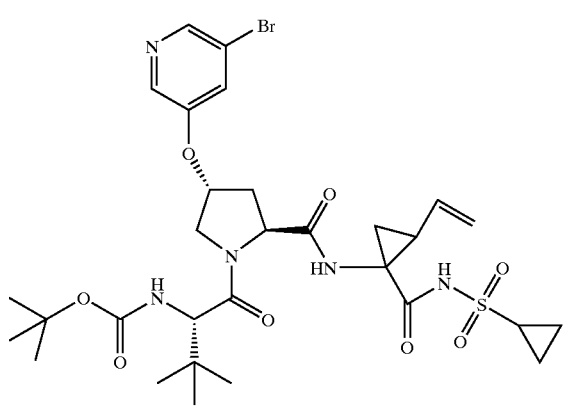

Step 1:

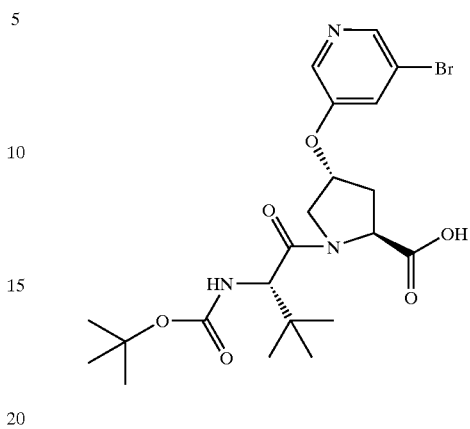

To a solution of the product of Example 420, Step 3 (1.00 g, 1.94 mmol) in THF(5 mL) and methanol (5 mL) was added LiOH (140 mg, 5.83 mmol) in water (5 mL). The mixture was stirred for 2 h at room temperature and quenched with 1N HCl until neutral pH. The organic volatiles were removed in vacuo, buffer pH 4 was added and the product was extracted into EtOAc (3×25 mL) and dried (MgSO₄) to yield the title compound (1.0 g, 100%) as a white solid.

¹H NMR: (DMSO-d₆) δ 0.95 (s, 9H), 1.27 (s, 9H), 2.14–2.19 (m, 1H), 2.47–2.50 (m, 1H), 3.80 (d, J=11.5 Hz, 1H), 3.99–4.07 (m, 2H), 4.15 (d, J=11.5 Hz, 1H), 4.36 (dd, J=8, 10 Hz, 1H), 5.25 (m, 1H), 6.66 (d, J=9 Hz, NH), 7.75 (s, 1H), 8.28 (s, 1H), 8.31 (s, 1H), 12.5 (s, 1H).

LC/MS rt-min (MH⁺): 2.47 (500, 502) (method A).

Step 2:

Compound 423 was accomplished according to Example 420, Step 6 in 52% yield, starting from the products of Example 423, Step 1 and Example 8, Step 3 (racemic P₁, (1R, 2S) and (1S, 2R)).

¹H NMR: (DMSO-d₆) δ 0.93, 0.95 (s, 9H), 1.00–1.09 (m, 4H), 1.28, 1.29 (s, 9H), 1.37–1.39 (m, 1H), 1.69–1.72 (m, 1H), 2.09–2.22 (m, 2H), 2.36–2.46 (m, 1H), 2.88–2.94 (m, 1H), 3.82–3.87 (m, 1H), 4.02–4.04 (m, 1H), 4.10–4.15 (m, 1H), 4.31–4.34 (m, 1H), 5.10 (d, J=10.5 Hz, 1H), 5.22–5.28 (m, 1H), 5.54–5.66 (m, 1H), 6.56, 6.60 (d, J=9.5 Hz, NH), 7.74, 7.76 (s, 1H), 8.28–8.29 (m, 1H), 8.32 (s, 1H), 8.79, 8.89 (s, 1H).

LC/MS rt-min (MH⁺): 2.42 (712, 714) (method B).

Example 424

Preparation of Compound 424

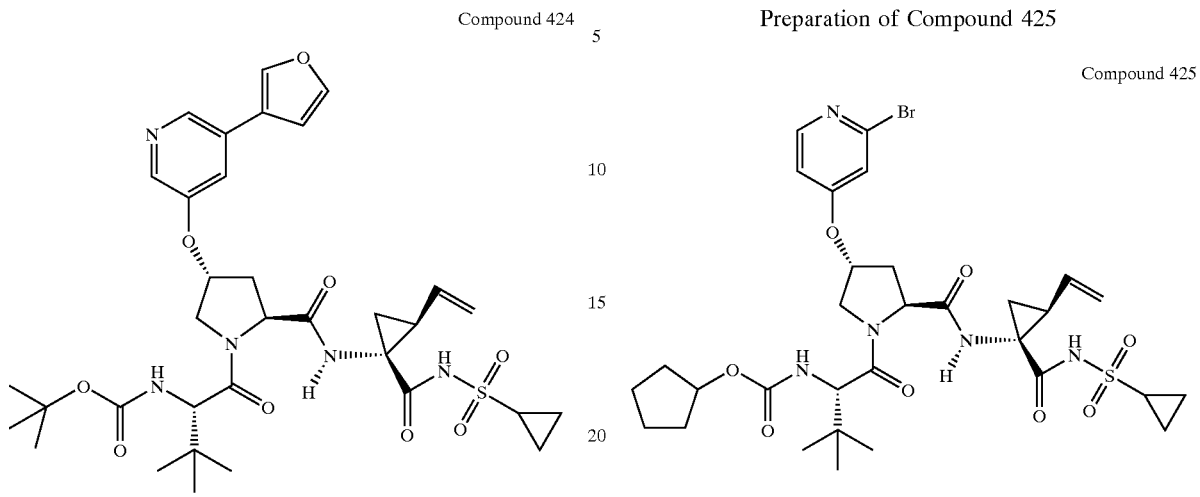

Compound 424

Step 1:

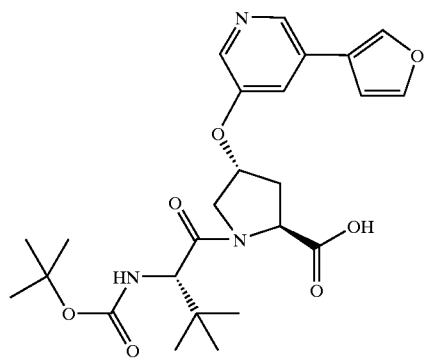

To a solution of the product of Example 423, Step 1 (91 mg, 0.18 mmol), Pd(PPh₃)₄ (10.5 mg, 0.0091 mmol), and 3-furyl boronic acid (25.4 mg, 0.227 mmol) in DMF (2 mL) was added 2M aqueous Na₂CO₃ (0.273 mL, 0.546 mmol). The mixture was heated at 110 C for 2.5 h under nitrogen. After cooling to room temperature the solid was removed by filtration, and the filtrate concentrated in vacuo. The residue was purified by preparative HPLC (gradient 30–80% B) to afford the title compound (64 mg, 72%) as a white solid.

¹HNMR: (DMSO-d₆) δ 0.95 (s, 9H), 1.25 (s, 9H), 2.17–2.21 (m, 1H), 2.50 (m (hidden), 1H), 3.84–3.86 (m, 1H), 4.09–4.15 (m, 0.2H), 4.37 (t, J=9 Hz, 1H), 5.28 (m, 1H), 6.67 (d, J=9 Hz, NH), 7.08 (s, 1H), 7.62 (s, 1H), 7.79 (s, 1H), 8.17 (s, 1H), 8.33 (s, 1H), 8.51 (s, 1H), 12.6 (s, 1H).

LC/MS rt-min (MH⁺): 1.60 (488) (method B).

Step 2:

Compound 424 was prepared according to Example 420, Step 6 in 55% yield, starting from the product of Example 424, Step 1.

¹H NMR: (methanol-d₄) δ 1.02 (s, 9H), 1.05–1.09 (m, 2H), 1.22–1.25 (m, 2H), 1.34 (s, 9H), 1.42–1.45 (m, 1H), 1.86–1.89 (m, 1H), 2.21–2.26 (m, 1H), 2.48–2.52 (m, 1H), 2.91–2.96 (m, 1H), 4.02 (d, J=12 Hz, 1H), 4.24–4.29 (m, 2H), 4.43–4.47 (dd, J=7.5, 10.5 Hz, 1H), 5.12 (d, J=10.5 Hz, 1H), 5.28–5.32 (m, 1H), 5.73–5.81 (m, 1H), 6.63 (d, J=9 Hz, NH), 6.90 (s, 1H), 7.60–7.62 (m, 2H), 8.07 (s, 1H), 8.12 (s, 1H), 8.39 (s, NH).

LC/MS rt-min (MH⁺): 2.30 (700) (method E).

Example 425

Preparation of Compound 425

Compound 425

Compound 425 was accomplished according to Example 421, Step 7 in 45% yield, starting from the product of Example 421, Step 5.

¹H NMR: (DMSO-d₆) δ 0.95 (s, 9H), 1.03–1.04 (m, 1H), 1.08–1.09 (m, 1H), 1.33–1.36 (m, 1H), 1.46–1.75 (m, 9H), 2.08–2.12 (m, 1H), 2.17 (q, J=9 Hz, 1H), 2.35–2.38 (m, 1H), 2.88–2.93 (m, 1H), 3.91 (d, J=9.5 Hz, 1H), 4.05–4.10 (m, 2H), 4.27 (dd, J=10, 7 Hz, 1H), 4.80 (m, 1H), 5.10 (d, J=12 Hz, 1H), 5.23 (d, J=16.5 Hz, 1H), 5.32 (m, 1H), 5.58–5.66 (m, 1H), 6.94 (d, J=9 Hz, NH), 7.03–7.05 (m, 1H), 7.26 (s, 1H), 8.21 (d, J=6 Hz, 1H), 8.86 (s, NH), 10.4 (s, NH).

LC/MS rt-min (MH⁺): 2.56 (724, 726) (method D).

Example 426

Preparation of Compound 426

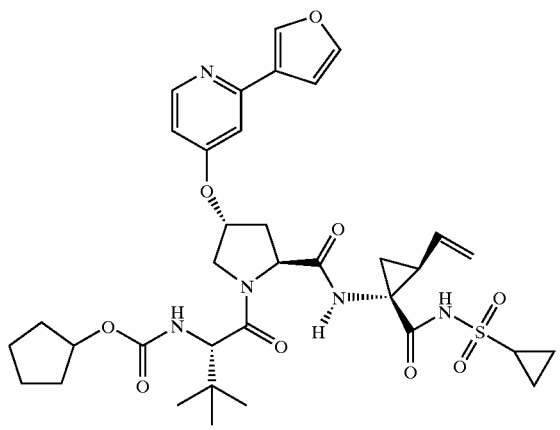

Compound 426

Step 1:

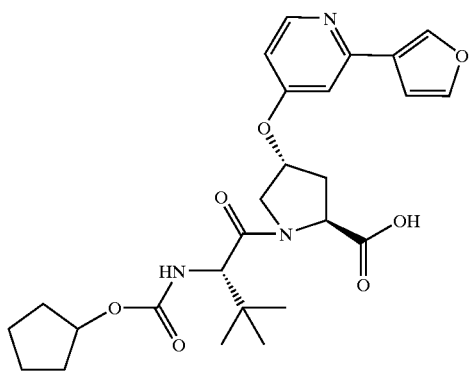

This product was prepared according to Example 421, Step 6 in 65% yield, except using 3-furanoboronic acid.

$^1$H NMR: (methanol-d$_4$) δ 1.03 (s, 9H), 1.49–1.76 (m, 8H), 2.30–2.35 (m, 1H), 2.63–2.67 (m, 1H), 3.98 (d, J=12 Hz, 1H), 4.26 (t, J=9 Hz, 1H), 4.31 (d, J=12 Hz, 1H), 4.58 (t, J=8.0 Hz, 1H), 5.32 (m, 1H), 6.71 (d, J=9.5 Hz, NH), 6.92 (dd, J=2.5, 6.0 Hz, 1H), 6.98 (s, 1H), 7.25 (d, J=2.5 Hz, 1H), 7.60 (s, 1H), 8.15 (s, 1H), 8.35 (d, J=5.5 Hz, 1H).

LC/MS rt-min (MH$^+$): 1.94 (500) (method D).

Step 2:

Compound 426 was prepared according to Example 421, Step 7 in 57% yield, starting from the product of Example 426, Step 1.

$^1$H NMR: (DMSO-d$_6$) δ 0.95 (s, 9H), 1.03–1.04 (m, 2H), 1.08–1.09 (m, 2H), 1.34–1.71 (m, 8H), 2.09–2.20 (m, 2H), 2.37–2.41 (m, 1H), 2.93 (m, 1H), 3.96 (d, J=9.5 Hz, 1H), 4.07–4.11 (m, 2H), 4.29 (m, 1H), 4.78 (m, 1H), 5.10 (d, J=10.5 Hz, 1H), 5.23 (d, J=17 Hz, 1H), 5.34 (m, 1H), 5.59–5.66 (m, 1H), 6.87–6.91 (m, 2H), 7.08 (s, 1H), 7.27 (s, 1H), 7.75 (s, 1H), 8.33 (s, 1H), 8.39 (d, J=6 Hz, 1H), 8.90 (s, NH), 10.4 (s, 1H).

LC/MS rt-min (MH$^+$): 2.38 (712) (method D).

Example 427

Preparation of Compound 427

Compound 427

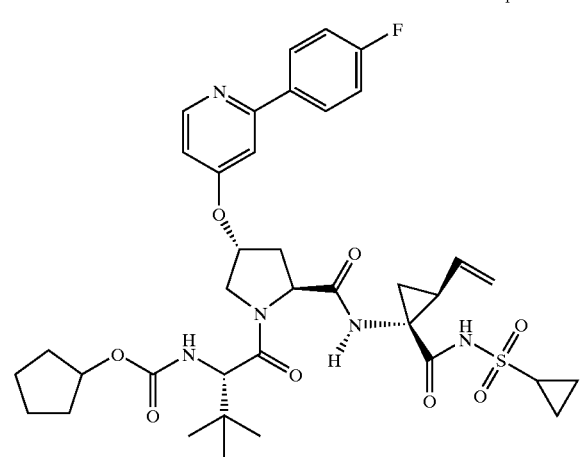

Step 1:

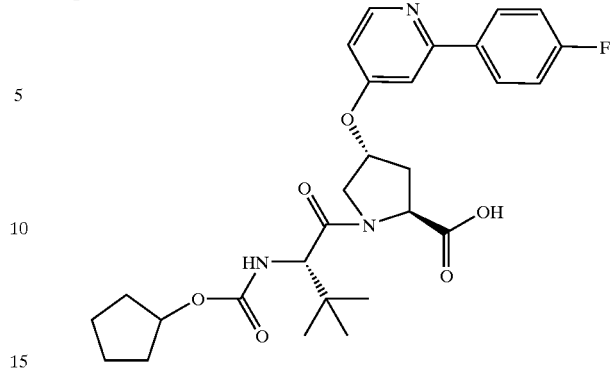

This product was prepared according to Example 421, Step 6 in 86% yield, except using 4-fluorophenylboronic acid.

$^1$H NMR: (methanol-d$_4$) δ 1.03 (s, 9H), 1.44–1.75 (m, 8H), 2.30–2.36 (m, 1H), 2.64–2.69 (m, 1H), 3.99 (dd, J=12, 3.5 Hz, 1H), 4.26 (d, J=9.5 Hz, 1H), 4.32 (d, J=12 Hz, 1H), 4.59 (dd, J=8.0, 9.5 Hz, 1H), 4.81 (m, 1H), 5.34 (m, 1H), 6.73 (d, J=9.5 Hz, NH), 6.99 (dd, J=2.5, 6.0 Hz, 1H), 7.20 (t, 2H (hidden)), 7.36 (s, 1H (hidden)), 7.94–7.97 (m, 2H), 8.44 (d, J=6.0 Hz, 1H).

LC/MS rt-min (MH$^+$): 2.22 (528) (method A).

Step 2:

Compound 427 was prepared according to Example 421, Step 7 in 53% yield, starting from the product of Example 427, Step 1.

$^1$H NMR: (methanol-d$_4$) δ 1.03 (s, 9H), 1.06–1.09 (m, 2H), 1.23–1.26 (m, 2H), 1.43 (dd, J=5.0, 9.5 Hz, 1H), 1.47–1.78 (m, 8H), 1.88 (dd, J=5.5, 8.0 Hz, 1H), 2.21–2.29 (m, 2H), 2.49–2.53 (m, 1H), 2.91–2.96 (m, 1H), 4.05 (dd, J=3.0, 11.5 Hz, 1H), 4.27 –4.25 (m, 2H), 4.44 (dd, J=7.0, 10.5 Hz, 1H), 4.83 (m, 1H (hidden)), 5.12 (d, J=10 Hz, 1H), 5.29 (d, J=17 Hz, 1H), 5.37 (m, 1H), 5.73–5.80 (m, 1H), 6.93 (d, J=9.5 Hz, NH), 6.98 (m, 1H), 7.21 (t, J=9.0 Hz, 2H), 7.36 (s, 1H), 7.94–7.97 (m, 2H), 8.44 (d, J=6.0 Hz, 1H).

LC/MS rt-min (MH$^+$): 2.42 (741) (method A).

Example 428

Preparation of Compound 428

Compound 428

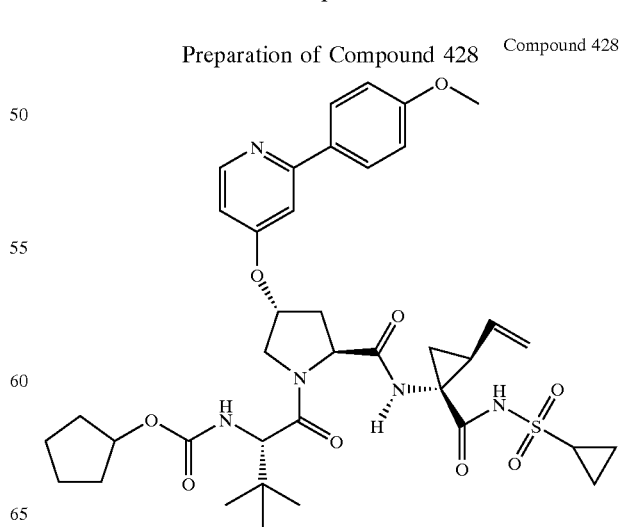

Step 1:

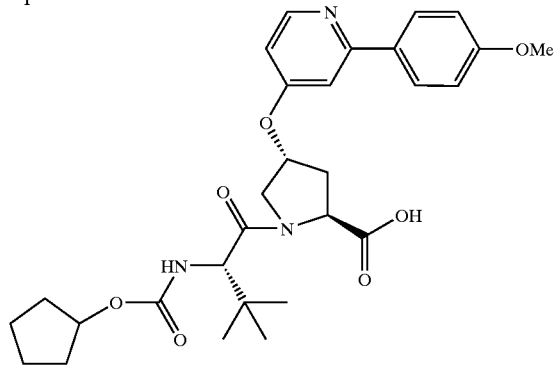

This product was prepared according to Example 421, Step 6 in 37% yield, except using 4-methoxyphenylboronic acid.

$^1$H NMR: (methanol-d$_4$) δ 1.03 (s, 9H), 1.45–1.74 (m, 8H), 2.31–2.36 (m, 1H), 2.64–2.68 (m, 1H), 3.85 (s, 3H), 3.98 (dd, J=12, 3.5 Hz, 1H), 4.25 (d, J=9.0 Hz, 1H), 4.33 (d, J=11.5 Hz, 1H), 4.59 (dd, J=8.0, 10 Hz, 1H), 4.77 (m, 1H), 5.36 (m, 1H), 6.72 (d, J=9.0 Hz, NH), 7.01 (m, 1H), 7.04 (d, J=9.0 Hz, 2H), 7.37 (d, J=2.0 Hz), 7.86 (d, J=9.0 Hz, 2H), 8.42 (d, J=6.0 Hz, 1H).

LC/MS rt-min (MH$^+$): 2.09 (540) (method A).

Step 2:

Compound 428 was prepared according to Example 420, Step 6 in 72% yield, starting from the product of Example 428, Step 1.

$^1$H NMR: (methanol-d$_4$) δ 1.03 (s, 9H), 1.06–1.09 (m, 2H), 1.23–1.25 (m, 2H), 1.43 (dd, J=5.5, 9.5 Hz, 1H), 1.48–1.77 (m, 8H), 1.88 (dd, J=5.0, 8.0 Hz, 1H), 2.21–2.28 (m, 2H), 2.50–2.54 (m, 1H), 2.91–2.96 (m, 1H), 3.85 (s, 3H), 4.05 (d, J=12 Hz, 1H), 4.27–4.29 (m, 2H), 4.44 (dd, J=7.0, 10.5 Hz, 1H), 4.84 (m, 1H (hidden)), 5.12 (d, J=10 Hz, 1H), 5.30 (d, J=17 Hz, 1H), 5.37 (m, 1H), 5.72–5.80 (m, 1H), 6.89 (d, J=9.5 Hz, NH), 6.95 (dd, J=2.5, 6.0 Hz, 1H), 7.03 (d, J=9.0 Hz, 1H), 7.33 (d, J=2.5 Hz, 1H), 7.86 (d, J=9.0 Hz, 2H), 8.41 (d, J=6.0 Hz, 1H).

LC/MS rt-min (MH$^+$): 2.40 (753) (method A).

Example 429

Preparation of Compound 429

Compound 429

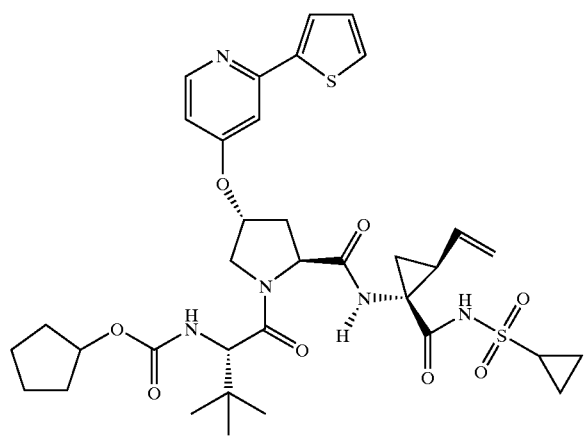

Step 1:

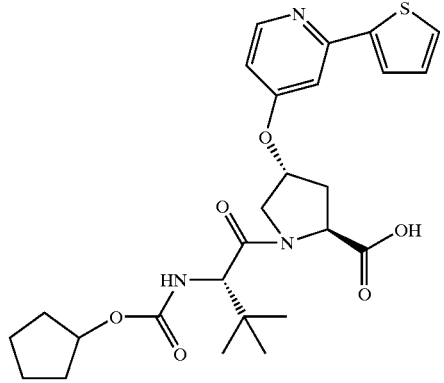

This product was prepared according to Example 421, Step 6 in 22% yield, except using 2-thiopheneboronic acid.

$^1$H NMR: (methanol-d$_4$) δ 1.03 (s, 9H), 1.46–1.74 (m, 8H), 2.29–2.35 (m, 1H), 2.63–2.67 (m, 1H), 3.97 (d, J=12 Hz, 1H), 4.26 (d, J=8.5 Hz, 1H), 4.31 (d, J=12 Hz, 1H), 4.60 (t, J=8.5 Hz, 1H), 4.81 (m, 1H (hidden)), 5.31 (m, 1H), 6.87–6.89 (m, 2H), 7.13 (d, J=5.0 Hz, 1H), 7.52 (s, 1H (hidden)), 7.70 (d, J=2.5 Hz, 1H), 8.32 (d, J=6.0 Hz, 1H).

LC/MS rt-min (MH$^+$): 1.96 (516) (method A).

Step 2:

Compound 429 was prepared according to Example 420, Step 6 in 57% yield, starting from the product of Example 429, Step 1.

$^1$H NMR: (methanol-d$_4$) δ 1.02 (s, 9H), 1.07 (m, 2H), 1.24 (m, 2H), 1.43 (dd, J=5.5, 9.5 Hz, 1H), 1.53–1.78 (m, 8H), 1.88 (dd, J=5.5, 8.0 Hz, 1H), 2.21–2.28 (m, 2H), 2.49–2.53 (m, 1H), 2.92–2.96 (m, 1H), 4.04 (d, J=10 Hz, 1H), 4.26–4.29 (m, 2H), 4.43 (t, J=9.0 Hz, 1H), 4.82 (m, 1H (hidden)), 5.12 (d, J=10.5 Hz, 1H), 5.29 (d, J=17.5 Hz, 1H), 5.35 (m, 1H), 5.73–5.80 (m, 1H), 6.89 (d, J=4.5 Hz, 1H), 6.92 (d, J=4.5 Hz, NH), 7.13 (s, 1H), 7.35 (s, 1H), 7.51 (d, J=4.5 Hz, 1H), 7.70 (s, 1H), 8.32 (d, J=5.5 Hz, 1H).

LC/MS rt-min (MH$^+$): 2.37 (728) (method A).

Example 430

Preparation of Compound 430

Compound 430

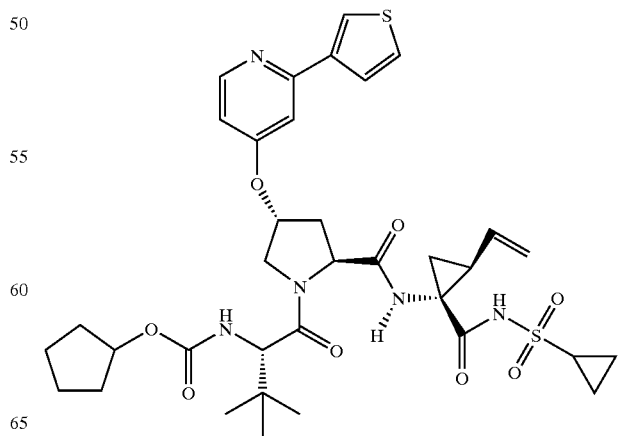

Step 1:

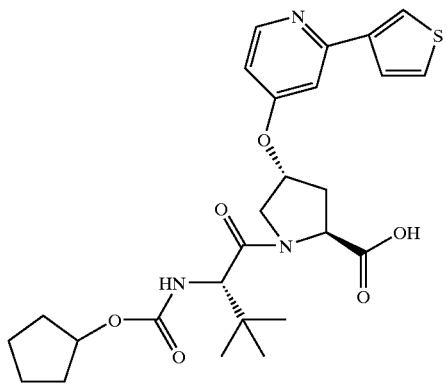

This product was prepared according to Example 421, Step 6 in 17% yield, except using 3-thiopheneboronic acid.

$^1$H NMR: (methanol-$d_4$) δ 1.03 (s, 9H), 1.43–1.74 (m, 8H), 2.30–2.36 (m, 1H), 2.64–2.68 (m, 1H), 3.98 (dd, J=11.5, 3.0 Hz, 1H), 4.25 (d, J=9.0 Hz, 1H), 4.32 (d, J=11.5 Hz, 1H), 4.60 (dd, J=8.0, 9.5 Hz, 1H), 4.80 (m, 1H (hidden)), 5.33 (m, 1H), 6.96 (dd, J=2.5, 6.0 Hz, 1H), 7.36 (s, 1H (hidden)), 7.51 (s, 1H (hidden)), 7.67 (d, J=5.0 Hz, 1H), 8.03 (s, 1H), 8.39 (d, J=6.0 Hz, 1H).

LC/MS rt-min (MH$^+$): 1.94 (516) (method A).

Step 2:

Compound 430 was prepared according to Example 420, Step 6 in 45% yield, starting from the product of Example 430, Step 1.

$^1$H NMR: (methanol-$d_4$) δ 1.02 (s, 9H), 1.06 (m, 2H), 1.29 (m, 2H), 1.43 (dd, J=5.5, 9.5 Hz, 1H), 1.43–1.75 (m, 8H), 1.87 (dd, J=6.0, 7.5 Hz, 1H), 2.20–2.27 (m, 2H), 2.49–2.53 (m, 1H), 2.93–2.95 (m, 1H), 4.05 (d, J=9.0 Hz, 1H), 4.27–4.29 (m, 2H), 4.42–4.45 (m, 1H), 4.85 (m, 1H (hidden)), 5.12 (d, J=10.0 Hz, 1H), 5.29 (d, J=17.5 Hz, 1H), 5.36 (m, 1H), 5.73–5.80 (m, 1H), 6.92–6.94 (m, 2H), 7.35 (s, 1H), 7.51 (s, 1H), 7.66 (d, J=4.5 Hz, 1H), 8.00 (s, 1H), 8.38 (d, J=5.5 Hz, 1H).

LC/MS rt-min (MH$^+$): 2.36 (728) (method A).

Example 431

Preparation of Compound 431

Compound 431

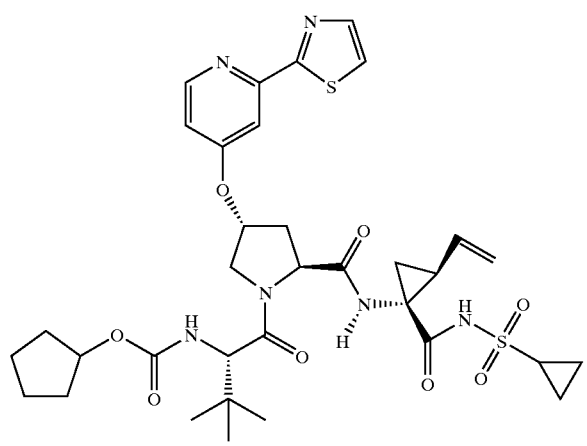

Step 1:

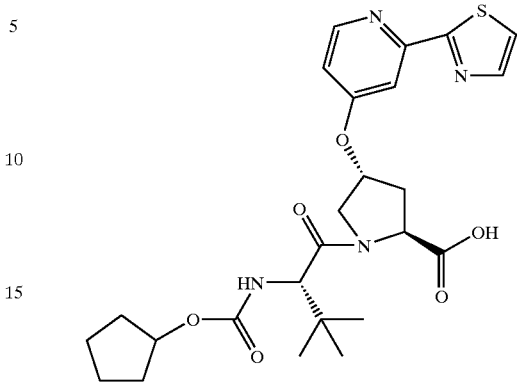

To a mixture of the product of Example 421, Step 5 (100 mg, 0.195 mmol) and Pd(PPh$_3$)$_4$ (23 mg, 0.0195 mmol) in dioxane (3 mL) was added 2-tributylstannnylthiazole (95 mg, 0.254 mmol) and triethylamine (82 μL, 0.585 mmol). The solution was heated at 95° C. for 5 h under nitrogen, then at 105° C. for 15 h. After cooling to room temperature the mixture was filtered and concentrated. The residue was purified by preparative HPLC (gradient 30–80% B). The combined fractions were partitioned between buffer pH 4 and dichloromethane. The aqueous phase was extracted with dichloromethane and the combined organic extracts washed with brine and dried (MgSO$_4$). The title compound (31 mg) was obtained as a colorless oil, significantly contaminated with tributylstannyl residue.

$^1$H NMR: (methanol-$d_4$) δ 1.03 (s, 9H), 1.4 (m, 8H (hidden)), 2.32–2.36 (m, 1H), 2.64–2.68 (m, 1H), 4.00 (d, J=11.5 Hz, 1H), 4.25 (s, 1H), 4.33 (d, J=11.5 Hz, 1H), 4.60 (t, J=8.5 Hz, 1H), 4.80 (m, 1H (hidden)), 5.33 (m, 1H), 7.03 (br s, 1H), 7.70 (s, 1H), 7.73 (s, 1H), 7.93 (s, 1H), 8.41 (d, J=5.5 Hz, 1H).

LC/MS rt-min (MH$^+$): 2.25 (517) (method A).

Step 2:

Compound 431 was prepared according to Example 420, Step 6 in 41% yield, starting from the product of Example 431, Step 1.

$^1$H NMR: (methanol-$d_4$) δ 1.02 (s, 9H), 1.06–1.70 (m, 13H), 1.86–1.89 (m, 1H), 2.22–2.31 (m, 2H), 2.51–2.55 (m, 1H), 2.92–2.94 (m, 1H), 4.06 (d, J=11.5 Hz, 1H), 4.23–4.32 (m, 2H), 4.44–4.47 (m, 1H), 4.82 (m, 1H (hidden)), 5.12 (d, J=11 Hz, 1H), 5.30 (d, J=17 Hz, 1H), 5.36 (m, 1H), 5.73–5.81 (m, 1H), 6.90 (d, J=9.0 Hz, NH), 7.04 (m, 1H), 7.71 (m, 2H), 7.93 (s, 1H), 8.42 (d, J=5.5 Hz, 1H).

LC/MS rt-min (MH$^+$): 2.46 (729) (method A).

Example 432

Preparation of Compound 432

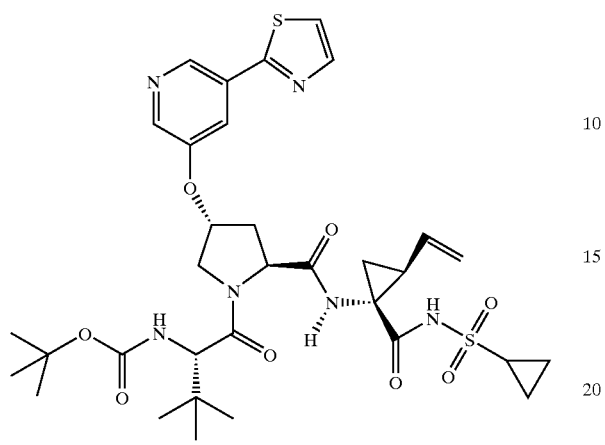

Compound 432

Step 1:

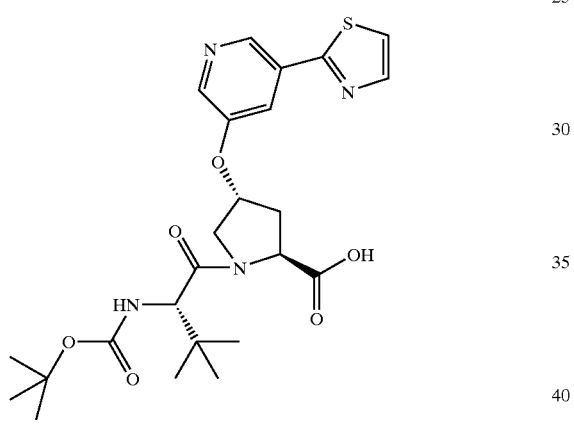

To a mixture of the product of Example 423, Step 1 (102 mg, 0.204 mmol) and Pd(PPh$_3$)$_4$ (24 mg, 0.0204 mmol) in dioxane (3 mL) was added 2-tributylstannnylthiazole (99 mg, 0.265 mmol) and triethylamine (85 µL, 0.612 mmol). The solution was heated at 95° C. for 5 h under nitrogen, then at 105° C. for 15 h. After cooling to room temperature the mixture was filtered and concentrated. The residue was purified by preparative HPLC (gradient 30–80% B). The combined fractions were neutralized with conc. ammonia and concentrated. The residue was partitioned between buffer pH 4 and dichloromethane. The aqueous phase was extracted with dichloromethane and the combined organic extracts washed with brine and dried (MgSO$_4$). The title compound (33 mg) was obtained as a colorless oil, significantly contaminated with tributylstannyl containing residue.

$^1$H NMR: (methanol-d$_4$) δ 1.03 (s, 9H), 1.30 (s, 9H), 2.28–2.32 (m, 1H), 2.62–2.67 (m, 1H), 3.98 (d, J=11.5 Hz, 1H), 4.21 (s, 1H), 4.34 (d, J=11.5 Hz, 1H), 4.58 (t, J=9.0 Hz, 1H), 5.31 (m, 1H), 7.71 (d, J=2.5 Hz, 1H), 7.94–7.96 (m, 2H), 8.33 (s, 1H), 8.73 (s, 1H).

LC/MS rt-min (MH$^+$-Boc): 2.21 (405) (method A).

Step 2:

Compound 432 was prepared according to Example 420, Step 6 in 42% yield, starting from the product of Example 432, Step 1.

$^1$H NMR: (methanol-d$_4$) δ 1.02 (s, 9H), 1.07–1.08 (m, 2H), 1.24 (m, 2H), 1.32 (s, 9H), 1.44 (m, 1H (hidden)), 1.86–1.89 (m, 1H), 2.21–2.29 (m, 2H), 2.51–2.55 (m, 1H), 2.93–2.95 (m, 1H), 4.04 (d, J=12 Hz, 1H), 4.23 (d, J=9.5 Hz, 1H), 4.33 (d, J=12 Hz, 1H), 4.47 (t, J=9.5 Hz, 1H), 5.12 (d, J=10.0 Hz, 1H), 5.30 (d, J=18 Hz, 11H), 5.36 (m, 1H), 5.72–5.81 (m, 1H), 6.62 (d, J=8.5 Hz, NH), 7.73 (s, 1H), 7.96 (m, 1H), 8.34 (s, 1H), 8.74 (s, 1H).

LC/MS rt-min (MH$^+$): 2.42 (717) (method A).

Example 433

Preparation of Compound 433

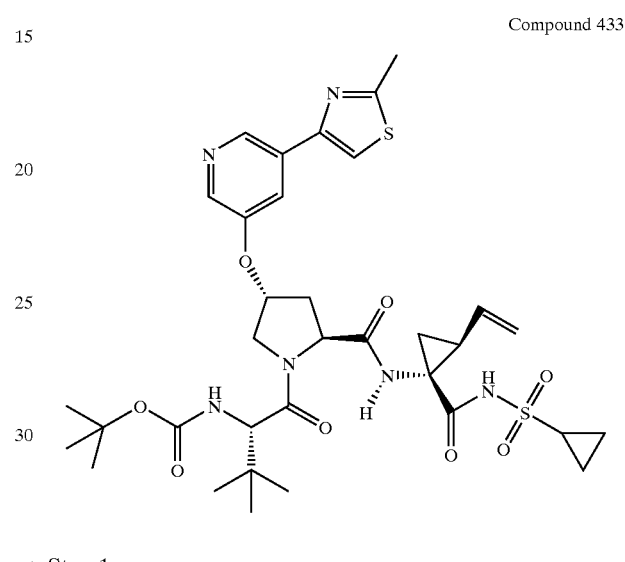

Compound 433

Step 1:

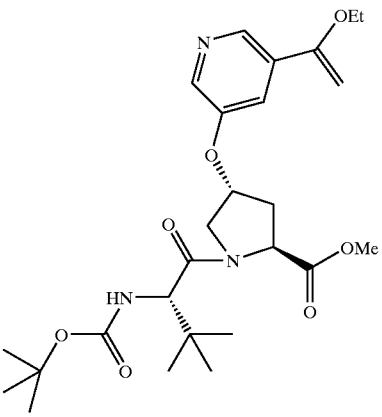

To a mixture of the product of Example 420, Step 3 (1.00 g, 1.94 mmol) and Pd(PPh$_3$)$_4$ (112 mg, 0.097 mmol) in dioxane (15 mL) was added tributyl(1-ethoxyvinyl)tin (876 mg, 2.43 mmol. The solution was heated at 105° C. for 6 h under nitrogen. After cooling to room temperature the mixture was filtered and concentrated. The residue was partitioned between satd NaHCO$_3$ and ethyl acetate. The aqueous phase was extracted with ethyl acetate and the combined organic extracts washed with 5% aq. KF and brine and dried (MgSO$_4$). Purification using a Biotage 40 M column (eluted gradient hexane—EtOAc 40–70%) afforded the title compound (624 mg, 64%) as a yellow oil.

$^1$H NMR: (DMSO-d$_6$) δ 0.95 (s, 9H), 1.27 (s, 9H), 1.35 (t, J=7.0 Hz, 3H), 2.16–2.21 (m, 1H), 2.50 (m, 1H (hidden)), 3.64 (s, 3H), 3.85 (d, J=11 Hz, 1H), 3.90 (q, J=7.0 Hz, 2H), 4.09 (d, J=9.0 Hz, 1H), 4.13 (d, J=11 Hz, 1H), 4.40 (d, J=2.5 Hz, 1H), 4.45 (t, J=8.0 Hz, 1H), 4.91 (d, J=2.5 Hz, 1H), 5.27 (m, 1H), 6.69 (d, J=9.0 Hz, NH), 7.48 (s, 1H), 8.25 (s, 1H), 8.46 (s, 1H).

LC/MS rt-min (MH+): 2.14 (507) (method B).

Step 2:

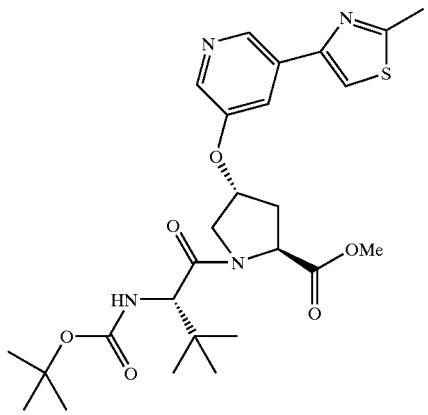

To a solution of the product of Example 433, Step 1 (125 mg, 0.247) in THF(3 mL) and water (111 µL, 6.18 mmol) was added NBS (44 mg, 0.247 mmol). After stirring at room temperature for 20 min. the mixture was concentrated and partitioned between ethyl acetate and brine. The organic phase was dried (MgSO$_4$) to give the intermediate bromomethyl ketone. This intermediate was dissolved in DMF and treated with thioacetamide (24 mg, 0.321 mmol) and NaHCO$_3$ (31 mg, 0.371 mmol). The mixture was stirred for 2 h at room temperature, concentrated and suspended in satd. NaHCO$_3$. The product was extracted with ethyl acetate (2×), washed with brine, and dried (MgSO$_4$). Purification using a Biotage 12 M column (eluted gradient hexane—EtOAc 50–70%) afforded the title compound (50 mg, 38%) as a pale oil. $^1$H NMR: (methanol-d$_4$) δ 1.02 (s, 9H), 1.31 (s, 9H), 2.27–2.31 (m, 1H), 2.63–2.67 (m, 11), 2.77 (s, 3H), 3.74 (s, 3H), 3.98 (d, J=10.0 Hz, 1H), 4.22 (d, J=9.5 Hz, 1H), 4.34 (d, J=10.5 Hz, 1H), 4.64 (t, J=9.0 Hz, 1H), 5.29 (m, 1H), 6.38 (s, NH), 7.87 (s, 1H), 7.91 (s, 1H), 8.20 (s, 1H), 8.71 (s, 1H).

LC/MS rt-min (MH+): 1.96 (533) (method B).

Step 3:

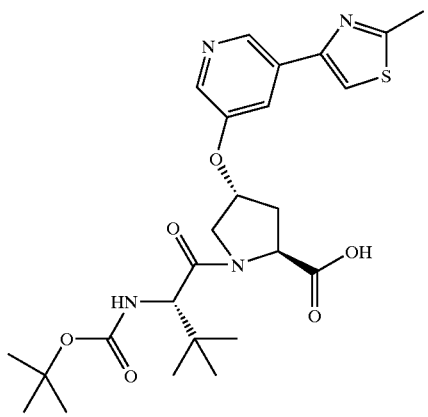

This product was prepared according to Example 420, Step 5, except using the product of Example 433, Step 2 instead.

$^1$H NMR: (DMSO-d$_6$) δ 0.96 (s, 9H), 1.25 (s, 9H), 2.18–2.23 (m, 1H), 2.50 (m, 1H (hidden)), 2.73 (s, 3H), 3.86 (d, J=11.5 Hz, 1H), 4.10 (d, J=9.0 Hz, 1H), 4.14 (d, J=11.5 Hz, 1H), 4.39 (t, J=8.5 Hz, 1H), 5.30 (m, 1H), 6.60 (br s, NH), 7.84 (s, 1H), 8.14 (s, 11H), 8.24 (s, 11H), 8.78 (s, 1H).

LC/MS rt-min (MH+): 1.84 (519) (method B).

Step 4:

Compound 433 was prepared according to Example 420, Step 6 in 46% yield, starting from the product of Example 433, Step 3.

$^1$H NMR: (methanol-d$_4$) δ 1.05. (s, 9H), 1.09–1.11 (m, 2H), 1.26–1.29 (m, 2H), 1.36 (s, 9H), 1.45–1.48 (m, 1H), 1.89–1.92 (m, 1H), 2.25–2.30 (m, 2H), 2.53–2.57 (m, 1H), 2.80 (s, 3H), 2.94–3.00 (m, 1H), 4.06 (d, J=10.5 Hz, 1H), 4.27 (s, 1H), 4.32 (d, J=12 Hz, 1H), 4.48 (dd, J=10.5, 7.0 Hz, 1H), 5.15 (d, J=10.5 Hz, 1H), 5.33 (d, J=17 Hz, 1H), 5.35 (m, 1H), 5.76–5.83 (m, 1H), 7.93 (s, 1H), 7.95 (m, 1H), 8.22 (s, 1H), 8.74 (s, 1H).

LC/MS rt-min (MH+): 2.21 (732) (method B).

Example 434

Preparation of Compound 434

Compound 434

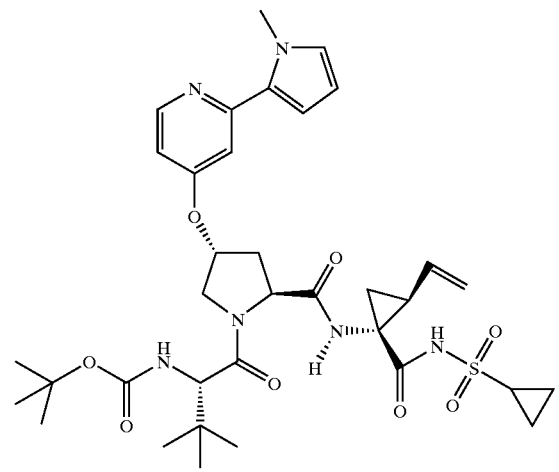

Step 1:

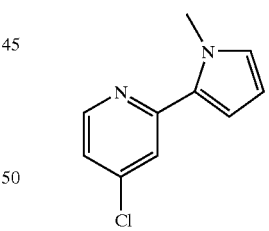

To a solution of the product of Example 421, Step 1 (300 mg, 1.56 mmol) and Pd(PPh$_3$)$_4$ (90 mg, 0.078 mmol) in DMF (6 mL) was added 1-methyl-2-(tributylstannyl)-1H-pyrrole (750 mg, 2.03 mmol) and triethylamine (0.435 mL, 3.12 mmol). The solution was heated at 150° C. for 30 min under nitrogen in a microwave oven (Emrys, Personal Chemistry). After cooling to room temperature the mixture was diluted with diethyl ether and 5% aq. KF and filtered. The aqueous phase was extracted with diethyl ether (2×). The combined organic extracts were washed with 5% aq. KF, water and brine and dried (MgSO$_4$). Purification using a Biotage 25 S column (eluted gradient hexane—diethyl ether 0–5%) afforded the title compound (169 mg, 56%) as a colorless oil.

¹H NMR: (DMSO-d₆) δ 3.94 (s, 3H), 6.10 (s, 1H), 6.77 (d, J=2.0 Hz, 1H), 6.93 (s, 1H), 7.27 (d, J=4.0 Hz, 1H), 7.77 (s, 1H), 8.49 (d, J=5.0 Hz, 1H),

LC/MS rt-min (MH⁺): 1.15 (193, 195) (method B).

Step 2:

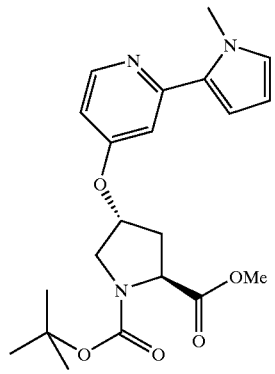

This product was prepared according to Example 421, Step 2 in 39% yield, starting from the product of Example 434, Step 1.

¹H NMR: (methanol-d₄) δ 1.42, 1.43 (s, 9H (rotamers)), 2.27–2.34 (m, 1H), 2.55–2.62 (m, 1H), 3.75 (m, 2H), 3.76, 3.74 (s, 3H (rotamers)), 3.84 (s, 3H), 4.39–4.45 (m, 1H), 5.19 (m, 1H), 6.10 (m, 1H), 6.49 (m, 1H), 6.78 (s, 1H), 6.80–6.82 (m, 1H), 7.07 (s, 1H), 8.35 (d, J=6.0 Hz, 1H).

LC/MS rt-min (MH⁺, carboxylic acid): 1.49 (389) (method B).

Step 3:

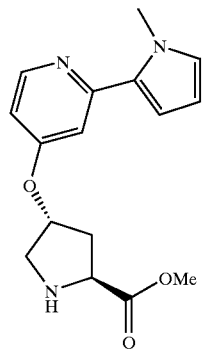

The product of Example 434, Step 2 (90 mg, 0.22 mmol) was dissolved in dichloromethane (1.5 mL) and TFA (1.0 mL, 9.0 mmol). The solution was stirred at room temperature for 45 min., and concentrated. The residue was treated with 1N HCl in diethyl ether (5 mL) and concentrated. The title compound was obtained in quantitative yield as a pale oil.

LC/MS rt-min (MH⁺): 0.32 (302) (method B).

Step 4:

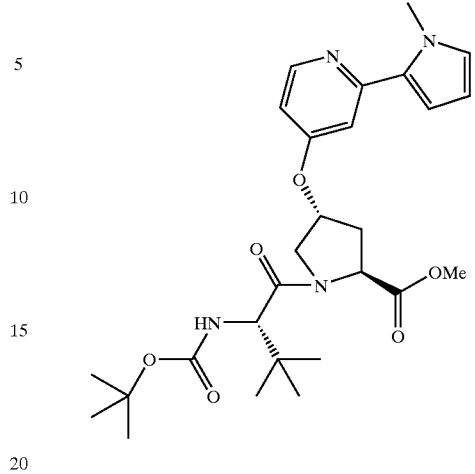

This product was prepared according to Example 420, Step 3 in 80% yield, starting from the product of Example 434, Step 3.

¹H NMR: (methanol-d₄) δ 1.02 (s, 9H), 1.31 (s, 9H), 2.25–2.31 (m, 1H), 2.61–2.64 (m, 1H), 3.73 (s, 3H), 3.84 (s, 3H), 3.97–3.99 (m, 1H), 4.22 (d, J=9.5 Hz, 1H), 4.32 (d, J=11.5 Hz, 1H), 4.61 (t, J=7.5 Hz, 1H), 5.27 (m, 1H), 6.10 (m, 1H), 6.42 (br d, J=9.0 Hz, NH), 6.49 (m, 1H), 6.78 (m, 1H), 6.81 (m, 1H), 7.07 (s, 1H), 8.34 (d, J=5.5 Hz, 1H).

LC/MS rt-min (MH⁺): 1.81 (516) (method B).

Step 5:

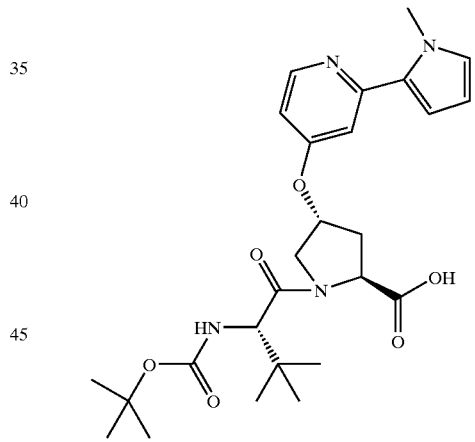

To a solution of the product of Example 434, Step 4 (92 mg, 0.179 mmol) in THF(1 mL) and methanol (1 mL) was added LiOH (13 mg, 0.536 mmol) in water (1 mL). The mixture was stirred for 1.5 h at room temperature and quenched with 1N HCl until neutral pH. The organic volatiles were removed in vacuo, and the residue purified by preparative HPLC (gradient 10–80% B). The combined fractions were neutralized with conc. ammonia and concentrated. The residue was partitioned between buffer pH 4 and ethyl acetate. The aqueous phase was extracted with ethyl acetate and the combined organic extracts washed with brine and dried (MgSO₄). The title compound (56 mg, 62%) was obtained as a white solid.

¹H NMR: (methanol-d₄) δ 1.03 (s, 9H), 1.32 (s, 9H), 2.31–2.35 (m, 1H), 2.62–2.67 (m, 1H), 3.85 (s, 3H), 3.98 (d, J=11.5 Hz, 1H), 4.21–4.23 (m, 1H), 4.33 (d, J=11.5 Hz, 1H), 4.58 (t, J=8.0 Hz, 1H), 5.31 (m, 1H), 6.12 (m, 1H), 6.40 (br d, J=8.0 Hz, NH), 6.52 (m, 1H), 6.82 (m, 1H), 6.87 (m, 1H), 7.12 (s, 1H), 8.36 (d, J=5.5 Hz, 1H).

LC/MS rt-min (MH⁺): 1.73 (502) (method B).

Step 6:

Compound 434 was prepared according to Example 420, Step 6 in 68% yield, starting from the products of Example 434, Step 5.

¹H NMR: (methanol-d₄) δ 1.02 (s, 9H), 1.06–1.09 (m, 2H), 1.23–1.26 (m, 2H), 1.33 (s, 9H), 1.42–1.45 (m, 1H), 1.86–1.89 (m, 1H), 2.21–2.27 (m, 2H), 2.47–2.51 (m, 1H), 2.91–2.96 (m, 1H), 3.85 (s, 3H), 4.04 (d, J=12 Hz, 1H), 4.24 (d, J=10.0 Hz, 1H), 4.28 (d, J=12 Hz, 1H), 4.43 (dd, J=10.0, 7.0 Hz, 1H), 5.12 (d, J=10.0 Hz, 1H), 5.30 (d, J=17 Hz, 1H), 5.32 (m, 1H), 5.73–5.80 (m, 1H), 6.10 (m, 1H), 6.49 (m, 1H), 6.64 (br d, J=9.0 Hz, NH), 6.79 (m, 1H), 6.82 (m, 1H), 7.08 (s, 1H), 8.35 (d, J=5.5 Hz, 1H).

LC/MS rt-min (MH⁺): 2.08 (714) (method B).

Example 435

Preparation of Compound 435

Compound 435

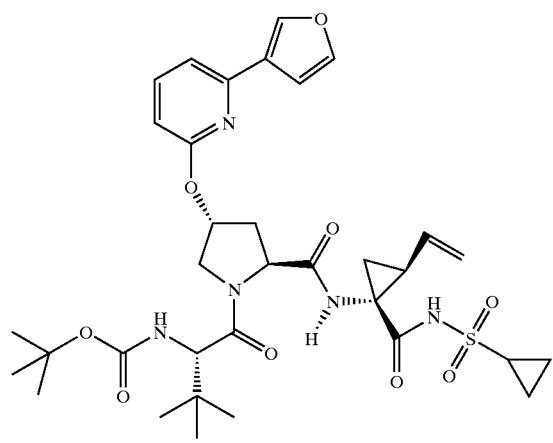

Step 1:

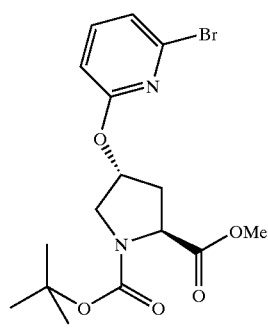

This product was prepared according to Example 421, Step 2 in 74% yield, starting from 2,6-dibromopyridine ¹H NMR: (DMSO-d₆) δ 1.34, 1.38 (s, 9H (rotamers)), 2.23–2.31 (m, 1H), 2.43–2.47 (m, 1H (hidden)), 3.53 (d, J=12 Hz, 1H), 3.66, 3.69 (s, 3H (rotamers)), 3.72–3.75 (m, 1H), 4.29–4.34 (m, 1H), 5.42 (m, 1H), 6.89 (d, J=7.5 Hz, 1H), 7.26 (d, J=7.5 Hz, {H), 7.68 (t, J=7.5 Hz, 1H).

LC/MS rt-min (MH⁺): 2.62 (523, 425) (method A).

Step 2:

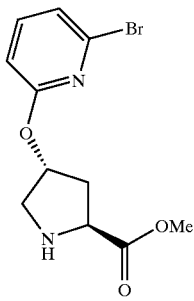

This product was prepared according to Example 420, Step 2 in quantitative yield, starting from the product of Example 435, Step 1.

LC/MS rt-min (MH⁺): 1.42 (301, 303) (method B).

Step 3:

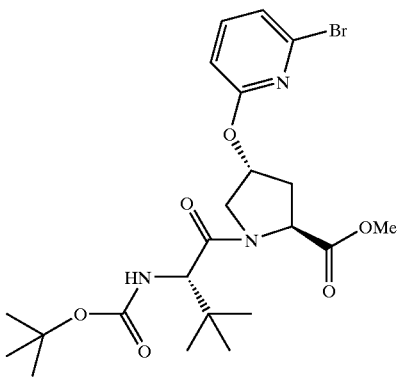

This product was prepared according to Example 420, Step 3 in 96% yield, starting from the product of Example 435, Step 2.

¹H NMR: (DMSO-d₆) δ 0.95 (s, 9H), 1.28 (s, 9H), 2.20–2.26 (m, 1H), 2.45–2.48 (m, 1H), 3.64 (s, 3H), 3.94 (d, J=9.5 Hz, 1H), 4.01–4.08 (m, 2H), 4.45 (t, J=8.5 Hz, 1H), 5.53 (m, 1H), 6.66 (d, J=7.0 Hz, 1H), 6.82 (d, J=7.0 Hz, 1H), 7.25 (d, J=7.0 Hz, 1H), 7.64–7.69 (m, 1H).

LC/MS rt-min (MH⁺): 2.73 (514, 516) (method A).

Step 3:

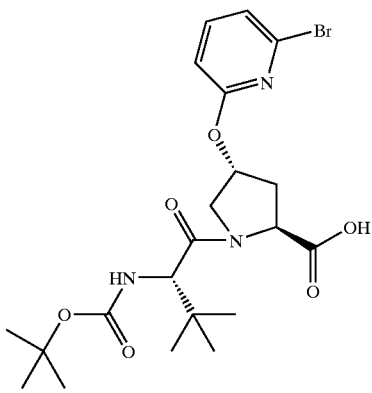

This product was prepared according to Example 420, Step 5 in quantitative yield, starting from the product of Example 435, Step 2.

¹H NMR: (DMSO-d₆) δ 0.95 (s, 9H), 1.28 (s, 9H), 2.19–2.25 (m, 1H), 2.43–2.47 (m, 1H), 3.94 (m, 1H), 4.01–4.08 (m, 2H), 4.36 (t, J=8.5 Hz, 1H), 5.52 (m, 1H), 6.65 (d, J=8.0 Hz, 1H), 6.82 (d, J=7.5 Hz, 1H), 7.25 (d, J=7.5 Hz, 1H), 7.67 (t, J=7.5 Hz, 1H), 12.6 (s, 1H).

LC/MS rt-min (MNa+): 2.51 (522, 524) (method B).

Step 4:

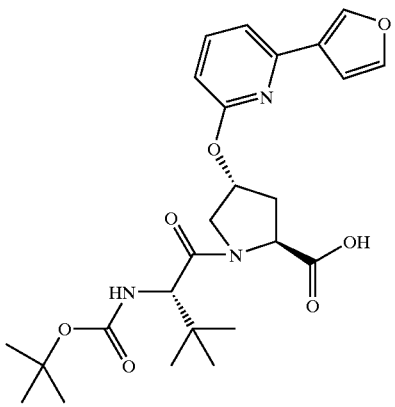

To a solution of the product of Example 435, Step 3 (125 mg, 0.250 mmol), Pd(PPh₃)₄ (14.4 mg, 0.0125 mmol), and 3-furyl boronic acid (35 mg, 0.313 mmol) in DMF (2 mL) and water (0.025 mL) was added Cs₂CO₃ (244 mg, 0.750 mmol). The mixture was heated at 105° C. for 3 h under nitrogen. After cooling to room temperature the solid was removed by filtration, and the filtrate concentrated in vacuo. The residue was purified by preparative HPLC (gradient 30–100% B). The combined fractions were neutralized with conc. ammonia and concentrated. The residue was partitioned between buffer pH 4 and dichloromethane. The aqueous phase was extracted with dichloromethane and the combined organic extracts washed with brine and dried (MgSO₄). The title compound (90 mg, 76%) was obtained as a white foam.

¹H NMR: (methanol-d₄) δ 1.06 (s, 9H), 1.39 (s, 9H), 2.36–2.42 (m, 1H), 2.61–2.65 (m, 1H), 4.12 (dd, J=4.0.11 Hz, 1H), 4.19 (d, J=11 Hz, 1H), 4.28 (s, 1H), 4.62 (t, J=8.5 Hz, 1H), 5.79 (m, 1H), 6.64 (d, J=8.0 Hz, 1H), 6.96 (s, 1H), 7.22 (d, J=8.0 Hz, 1H), 7.58 (m, 1H), 7.66 (t, J=8.0 Hz, 1H), 8.13 (s, 1H).

LC/MS rt-min (MNa+): 2.53 (511) (method B).

Step 5:

Compound 435 was prepared according to Example 420, Step 6 in 57% yield, starting from the product of Example 435, Step 4.

¹HNMR: (DMSO-d₆) δ 0.96 (s, 9H), 1.02–1.05 (m, 2H), 1.09–1.11 (m, 2H), 1.19 (s, 9H), 1.35–1.38 (m, 1H), 1.71 (dd, J=5.5, 8.0 Hz, 1H), 2.15–2.22 (m, 2H), 2.37–2.41 (m, 1H), 2.93 (br m, 1H), 4.03–4.08 (m, 3H), 4.35 (br t, 1H), 5.10 (d, J=10.5 Hz, 1H), 5.24 (d, J=17 Hz, 1H), 5.60–5.67 (m, 1H), 5.73 (m, 1H), 6.47 (br s, 1H), 6.64 (d, J=7.5 Hz, 1H), 7.04 (s, 1H), 7.31 (d, J=7.5 Hz, 1H), 7.72 (t, J=7.5 Hz, 1H), 7.77 (s, 1H), 8.32 (s, 1H), 8.92 (s, NH), 10.4 (s, NH).

LC/MS rt-min (MNa+): 2.64 (723) (method B).

Example 436

Preparation of Compound 436

Compound 436

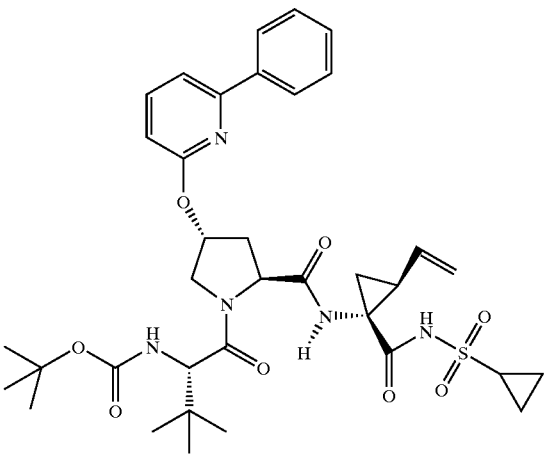

Step 1:

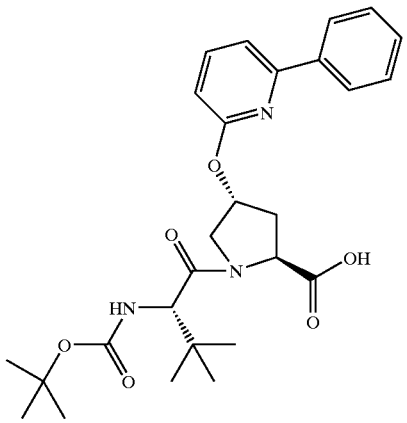

This product was prepared according to Example 435, Step 4 in 73% yield, except using phenylboronic acid instead.

¹H NMR: (methanol-d₄) δ 1.06 (s, 9H), 1.39 (s, 9H), 2.39–2.45 (m, 1H), 2.65–2.77 (m, 1H), 4.18–4.30 (m, 3H), 4.64 (t, J=8.0 Hz, 1H), 5.72 (m, 1H), 6.74 (d, J=8.0 Hz, 1H), 7.44–7.55 (m, 4H), 7.75 (t, J=8.0 Hz, 1H), 8.07 (d, J=7.5 Hz, 2H).

LC/MS rt-min (MNa+): 2.72 (521) (method B).

Step 2:

Compound 436 was prepared according to Example 420, Step 6 in 66% yield, starting from the product of Example 436, Step 1.

¹H NMR: (DMSO-d₆) δ 0.96 (s, 9H), 1.04–1.05 (m, 2H), 1.09 (m, 2H), 1.30 (s, 9H), 1.36–1.39 (m, 1H), 1.71 (t, J=7.5 Hz, 1H), 2.16–2.24 (m, 2H), 2.41–2.45 (m, 1H), 2.93 (m, 1H), 4.06–4.09 (m, 3H), 4.38 (br t, 1H), 5.10 (d, J=10.5 Hz, 1H), 5.30 (d, J=17 Hz, 1H), 5.60–5.67 (m, 1H), 5.80 (m, 1H), 6.49 (br s, 1H), 6.75 (d, J=7.5 Hz, 1H), 7.43–7.51 (m, 3H), 7.59 (d, J=7.5 Hz, 1H), 7.81 (t, J=7.5 Hz, 1H), 8.09 (d, J=7.0 Hz, 2H), 8.91 (s, NH), 10.4 (s, NH).

LC/MS rt-min (MH+): 2.77 (711) (method B).

Example 437

Preparation of Compound 437

Compound 437

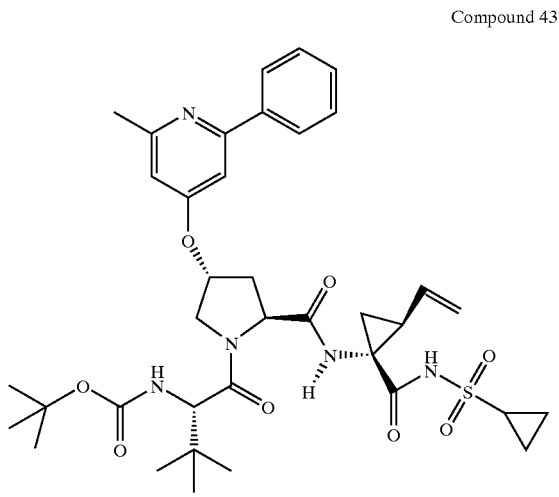

Step 1:

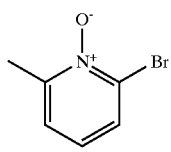

To a solution of 2-bromo-6-methyl-pyridine (7.65 g, 44.4 mmol) in dichloromethane (50 mL) was added a solution of mCPBA (77%, 12.9 g, 57.7 mmol) in dichloromethane (100 mL). The solution was stirred for 18 h at ambient temperature. The mixture was neutralized with solid $Na_2CO_3$ and water was added. The aqueous phase was extracted with dichloromethane (2×). The combined organic fractions were washed with 5% $Na_2S_2O_3$, 5% $Na_2CO_3$, brine and dried ($MgSO_4$). Purification using a Biotage 40 M column (eluted gradient hexane—ethyl acetate 40–70%) afforded the title compound (5.0 g, 60%) as a colorless oil that solidified upon standing.

$^1$H NMR: (DMSO-$d_6$) δ 2.43 (s, 3H), 7.15 (t, J=8.0 Hz, 1H), 7.50 (s, 1H), 7.78 (s, 1H).
LC/MS rt-min (MH$^+$): 0.32 (188, 190) (method B).

Step 2:

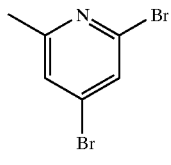

To a solution of the product of Example 437, Step 1 (4.5 g, 24 mmol) in DMF (20 mL) was added POBr$_3$ (8.2 g, 29 mmol) in portions. A strong exothermic reaction occurred and a precipitate formed. The mixture was left for 2 h at ambient temperature. The mixture was quenched with water and satd. NaHCO$_3$ until neutral pH. The aqueous phase was extracted with diethyl ether (2×). The combined organic fractions were washed with brine and dried (MgSO$_4$). Purification using a Biotage 40 M column (eluted gradient hexane-diethyl ether 0–10%) afforded the title compound (1.78 g, 30%) as a colorless oil.

$^1$H NMR: (DMSO-$d_6$) δ 2.45 (s, 3H), 7.64 (s, 1H), 7.80 (s, 1H).
LC/MS rt-min (MH$^+$): 1.85 (250, 252, 254) (method B).

Step 3:

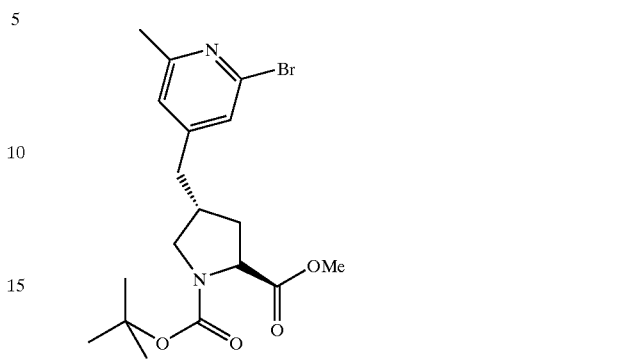

This product was prepared according to Example 421, Step 2 in 46% yield, starting from the product of Example 437, Step 1.

$^1$H NMR: (DMSO-$d_6$) δ 1.34, 1.38 (s, 9H (rotamers)), 2.20–2.27 (m, 1H), 2.38 (s, 3H), 2.43–2.50 (m, 1H), 3.55 (d, J=12.5 Hz, 1H), 3.64–3.67 (m, 1H), 3.66, 3.69 (s, 3H (rotamers)), 4.26–4.32 (m, 1H), 5.17 (m, 1H), 6.93 (s, 1H), 7.08 (s, 1H).
LC/MS rt-min (MH$^+$): 2.17 (415, 417) (method B).

Step 4:

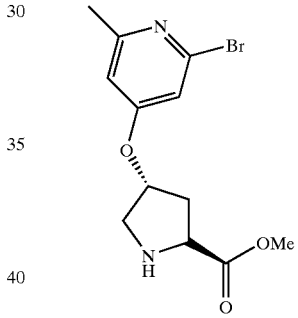

This product was prepared according to Example 420, Step 3 in quantitative yield, starting from the product of Example 437, Step 3.

Step 4:

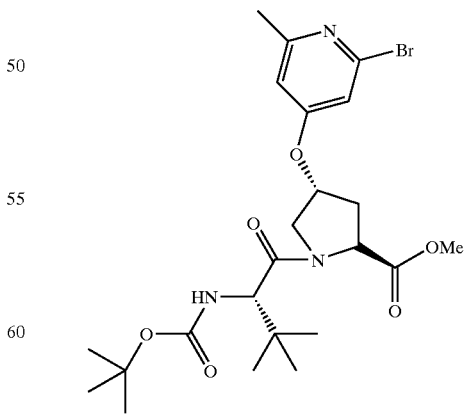

This product was prepared according to Example 420, Step 3 in 75% yield, starting from the product of Example 437, Step 3.

¹H NMR: (DMSO-d₆) δ 0.94 (s, 9H), 1.27 (s, 9H), 2.16–2.21 (m, 1H), 2.36 (s, 3H), 2.48 (m, 1H (hidden)), 3.64 (s, 3H), 3.83 (d, J=10.5 Hz, 1H), 4.06 (d, J=8.5 Hz, 1H), 4.14 (d, J=10.5 Hz, 1H), 4.42 (t, J=9.0 Hz, 1H), 5.27 (m, 1H), 6.68 (br s, NH), 6.88 (s, 1H), 7.03 (s, 1H).

LC/MS rt-min (MH⁺): 2.19 (528, 530) (method B).

Step 5:

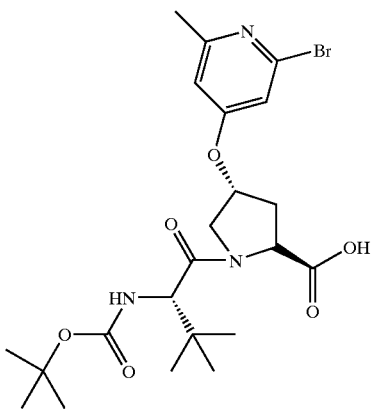

This product was prepared according to Example 420, Step 5 in quantitative yield, starting from the product of Example 437, Step 4.

¹H NMR: (DMSO-d₆) δ 0.95 (s, 9H), 1.27 (s, 9H), 2.15–2.19 (m, 1H), 2.36 (s, 3H), 2.44–2.48 (m, 1H), 3.81 (d, J=10.5 Hz, 1H), 4.04–4.06 (m, 1H), 4.13 (d, J=10.5 Hz, 1H), 4.33 (t, J=8.5 Hz, 1H), 5.26 (m, 1H), 6.66 (br d, J=9.0 Hz, NH), 6.88 (s, 1H), 7.03 (s, 1H).

LC/MS rt-min (MNa⁺): 2.14 (536, 538) (method B).

Step 6:

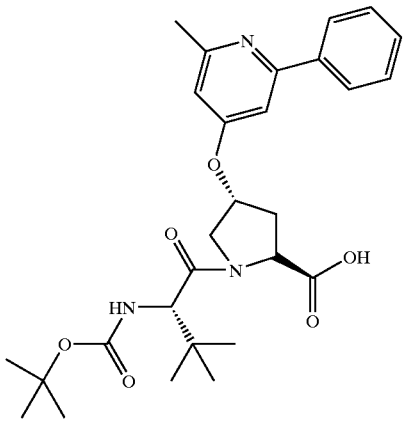

To a solution of the product of Example 437, Step 5 (101 mg, 0.196 mmol), Pd(PPh₃)₄ (11.3 mg, 0.0098 mmol), and phenyl boronic acid (34 mg, 0.275 mmol) in DMF (2 mL) was added 2M aqueous Na₂CO₃ (0.294 mL, 0.588 mmol). The tube was sealed and heated in a microwave oven (Emrys, Personal Chemistry) at 150° C. for 15 min. under nitrogen. After cooling to room temperature the mixture was acidified with 1N HCl (0.5 mL). The solid was removed by filtration, and the filtrate concentrated in vacuo. The residue was purified by preparative HPLC (gradient 20–80% B). The combined fractions were neutralized with conc. ammonia and concentrated. The residue was partitioned between buffer pH 4 and ethyl acetate. The aqueous phase was extracted with ethyl acetate (2×) and the combined organic extracts washed with brine and dried (MgSO₄). The title compound (115 mg, >100%) was obtained as a white solid.

¹H NM: (methanol-d₄) δ 1.06 (s, 9H), 1.30 (s, 9H), 2.36–2.41 (m, 1H), 2.69 (s, 3H), 2.65–2.76 (m, 1H), 4.01 (dd, J=3.0, 12 Hz, 1H), 4.21 (s, 1H), 4.44 (d, J=12 Hz, 1H), 4.64 (dd, J=8.0, 10 Hz, 1H), 5.46 (m, 1H), 6.91 (s, 1H), 7.29 (s, 1H), 7.39 (m, 3H), 7.57 (d, J=7.5 Hz, 2H).

LC/MS rt-min (MH⁺): 1.84 (513) (method B).

Step 7:

Compound 437 was prepared according to Example 420, Step 6 in 31% yield, starting from the product of Example 437, Step 6.

¹H NMR: (DMSO-d₆) δ 0.93 (s, 9H), 0.99–1.04 (m, 4H), 1.25 (s, 9H), 1.34–1.37 (m, 1H), 1.69–1.71 (m, 1H), 2.11–2.20 (m, 2H), 2.39–2.43 (m, 1H), 2.48 (s, 3H), 2.93 (m, 1H), 3.92 (d, J=8.5 Hz, 1H), 4.07 (d, J=9.0 Hz, 1H), 4.11 (d, J=12 Hz, 1H), 4.32 (t, J=7.0 Hz, 1H), 5.10 (d, J=10.5 Hz, 1H), 5.23 (d, J=17.5 Hz, 1H), 5.39 (m, 1H), 5.60–5.67 (m, 1H), 6.58 (d, J=8.5 Hz, 1H), 6.83 (s, 1H), 7.27 (s, 1H), 7.40–7.48 (m, 3H), 8.04–8.06 (m, 2H), 8.92 (s, NH), 10.4 (s, NH).

LC/MS rt-min (MH⁺): 2.10 (725) (method B).

Example 438

Preparation of Compound 438

Compound 438

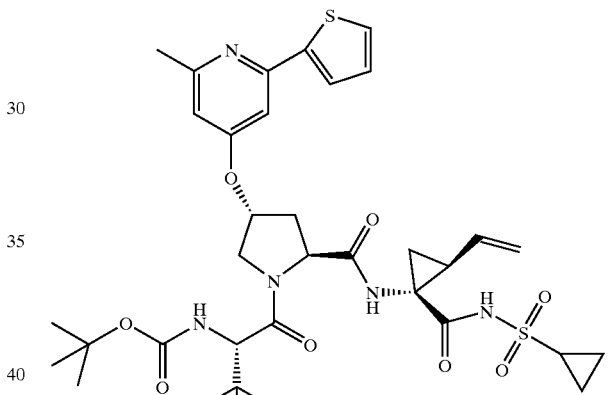

Step 1:

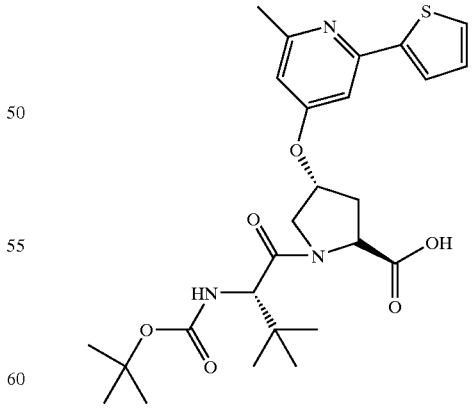

This product was prepared according to Example 437, Step 6 in quantitative yield, starting from 2-thiopheneboronic acid.

¹H NMR: (methanol-d₄) δ 1.05 (s, 9H), 1.32 (s, 9H), 2.32–2.38 (m, 1H), 2.56 (s, 3H), 2.66–2.70 (m, 1H), 3.99

(dd, J=3.0, 12 Hz, 1H), 4.23 (s, 1H), 4.36 (d, J=12 Hz, 1H), 4.61 (t, J=8.5 Hz, 1H), 5.35 (m, 1H), 5.86 (s, 1H), 7.16–7.18 (m, 1H), 7.21 (s, 1H), 7.56 (m, 1H), 7.72 (d, J=3.0 Hz, 1H).

LC/MS rt-min (MH+): 1.80 (519) (method B).

Step 2:

Compound 438 was prepared according to Example 420, Step 6 in 41% yield, starting from the product of Example 438, Step 1.

$^1$H NMR: (DMSO-d$_6$) δ 0.91 (s, 9H), 0.99–1.04 (m, 4H), 1.20 (s, 9H), 1.35–1.37 (m, 1H), 1.69–1.71 (m, 1H), 2.09–2.20 (m, 2H), 2.33 (m, 1H), 2.42 (s, 3H), 2.93 (m, 1H), 3.92 (d, J=8.5 Hz, 1H), 4.07–4.11 (m, 2H), 4.29–4.32 (m, 1H), 5.10 (d, J=10.5 Hz, 1H), 5.23 (d, J=17.0 Hz, 1H), 5.36 (m, 1H), 5.60–5.67 (m, 1H), 6.58 (d, J=8.5 Hz, 1H), 6.75 (s, 1H), 7.14 (t, J=4.5 Hz, 1H), 7.28 (s, 1H), 7.59 (d, J=5.5 Hz, 1H), 7.80 (d, J=3.5 Hz, 1H), 8.92 (s, NH), 10.4 (s, NH).

LC/MS rt-min (MH+): 2.06 (731) (method B).

Section K:

Example 450

Preparation of Compound 450

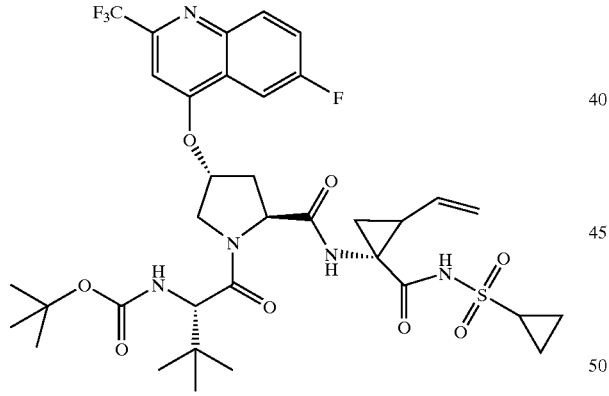

Compound 450

Compound 450 was prepared according to Example 8, Step 5, except using 4-chloro-6-fluoro-2-trifluoromethylquinoline instead.

$^1$H NMR (CD$_3$OD) δ 0.97–1.04 (m, 12H), 1.17–1.24 (m, 10H), 1.39–1.46 (m, 1H), 1.82–1.87 (m, 1H), 2.20–2.23 (m, 1H), 2.35–2.39 9m, 1H), 2.55–2.65 (m, 1H), 2.91–2.96 (m, 1H), 4.09–4.11 (m, 1H), 4.18–4.21 (m, 1H), 4.56 (b, 2H), 5.10–5.14 (m, 1H), 5.28–5.31 (m, 1H), 5.60 (b, 1H), 5.70–5.80 (m, 1H), 7.41 (s, 1H), 7.65–7.68 (m, 1H), 7.86 (s, 1H), 8.13–8.15 (m, 1H).

Example 451

Preparation of Compound 451

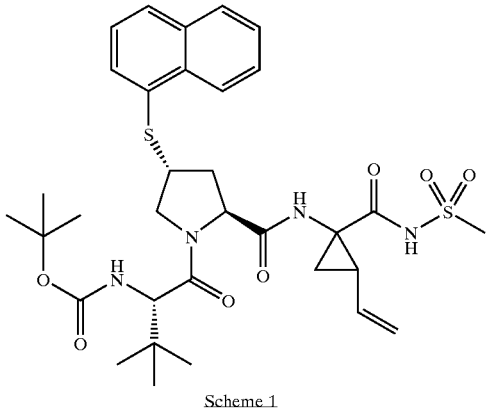

Compound 451

Scheme 1

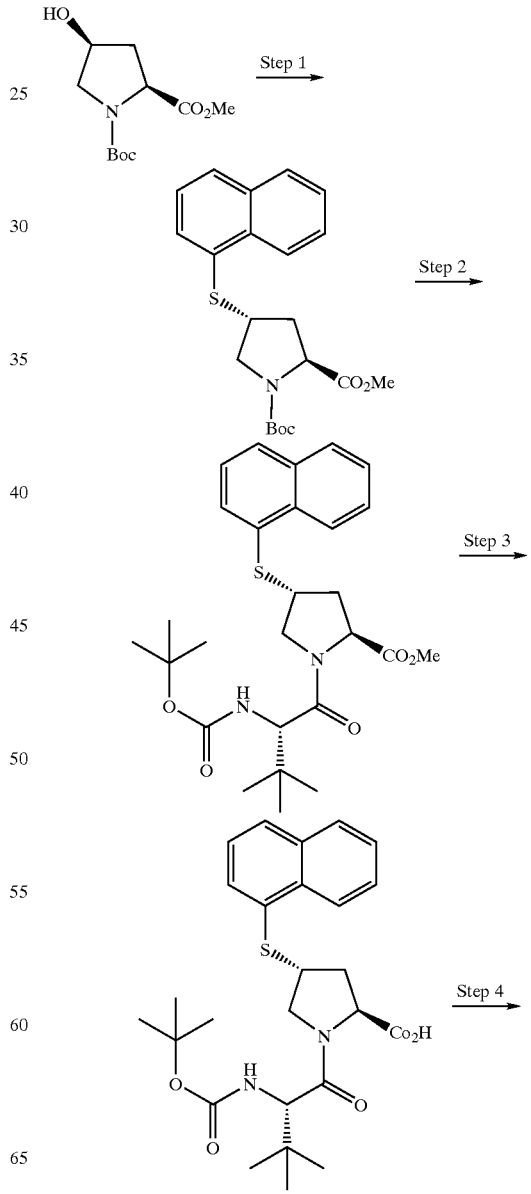

529

-continued

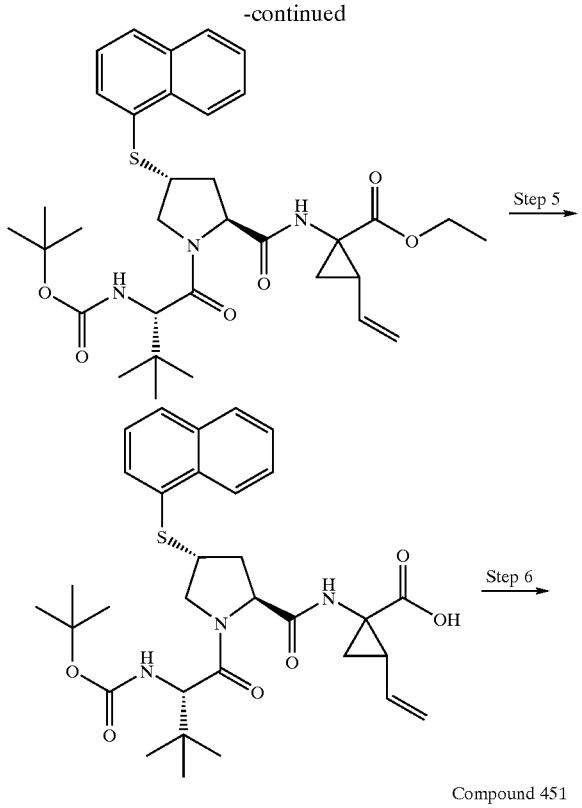

Compound 451

Step 1:

The tosylate was prepared as described in the literature (Patchett, A. A.; Witkof, B. J. Am. Chem. Soc. 1957, 185–192) and was used without further purification.

To a slurry of NaH (76 mg, 1.90 mmol) in DMF (20 ml) was added 1-thionaphthol (0.29 mg, 1.80 mmol) and the mixture stirred for 30 minutes. A solution of the tosylate (0.61 g, 1.80 mmol) was added and the mixture stirred for 12 h at 23° C. The mixture was concentrated and the residue partitioned between EtOAc/H$_2$O. The organic extracts are dried (MgSO4) and concentrated. The residue was purified by column chromatography (elution with 5% EtOAc/hexanes to 30% EtOAc/hexanes to give 261 mg (38%) of the product as a yellow oil.

$^1$H NMR (CDCl$_3$, 3:2 mixture of rotamers) δ 1.41 (s, 9H), 1.44 (s, 9H), 2.25–2.29 (m, 2H), 3.69 (s, 3H), 3.35–3.42 (m, 1H), 3.51–3.53 (m, 1H), 3.80–3.86 (m, 2H), 4.38–4.39 (m, 1H), 4.46–4.48 (m, 1H), 7.41–7.46 (m, 1H), 7.42–7–54 (m, 1H), 7.57–7.59 (m, 1H), 7.58 (d, J=4 Hz, 1H), 7.82–7.88 (m, 2H), 8.46 (d, J=5 Hz, 1H); LC-MS (retention time: 1.93), MS m/z 388 (M$^+$+1).

Step 2:

A mixture of 4-(naphthalen-1-ylsulfanyl)-pyrrolidine-1,2-dicarboxylic acid 1-tert-butyl ester 2-methyl ester (0.38 g, 0.98 mmol) and 4N HCl (1.0 ml) was stirred at 23° C. for 2 h. The solvent was removed and the residue dissolved in CH$_3$CN (20 ml) and treated with acid (0.37 g, 2.16 mmol), TBTU (0.23 g, 0.98 mmol) and DIPEA (0.37 g, 2.16 mmol) and stirred for 12 h. The mixture is concentrated and the residue dissolved in EtOAc and washed with 1 N HCl, saturated NaHCO$_3$ then dried over MgSO$_4$ and concentrated. The residue was used without further purification.

$^1$H NMR (CDCl$_3$, 1:1 mixture of rotamers) δ 0.99 (s, 9H), 1.02 (s, 9H), 1.44 (s, 9H), 1.46 (s, 9H) 2.2–2.25 (m, 2H), 3.70 (s, 3H), 3.82–3.86 (m, 1H), 3.89–3.92 (m, 2H) 4.26 (s, 1H), 4.28 (s, 11H), 4.70–4.75 (m, 1H), 7.40–7.48 (m, 1H), 7.54–7.55 (m, 11H), 7.59–7.62 (m, 1H), 7.72–7.74 (m, 1H), 7.86–7.89 (m, 2H), 8.48–8.50 (m, 1H);

LC-MS (retention time: 1.59), MS m/z 523 (M+Na).

Step 3:

To a mixture of 1-(2-tert-butoxycarbonylamino-3,3-dimethyl-butyryl)-4-(naphthalen-1-ylsulfanyl)-pyrrolidine-2-carboxylic acid methyl ester (Example 451, Step 2) (0.49 g, 0.98 mmol), in THF/H$_2$O (2:1) was added LiOH hydrate (0.20 g, 4.9 mmol) and the mixture stirred for 12 h. The solution was concentrated and washed with EtOAc. The aqueous layer is acidified with 1N HCl and extracted with EtOAc. The product was observed in the first EtOAc extract. The first organic extract was dried over MgSO$_4$ and concentrated to 328 mg (71%) of a tan solid.

$^1$H NMR (DMSO-d$_6$, 2:1 mixture of rotamers) δ 0.88 (s, 9H), 0.92 (s, 9H), 1.34 (s, 9H), 1.38 (s, 9H), 2.18–2.25 (m, 2H), 3.66–3.75 (m, 1H), 3.89–4.00 (m, 2H), 4.10–4.13 (m, 1H), 4.25–4.32 (m, 1H), 7.45–7.7.51 (m, 1H), 7.56–7.61 (m, 2H), 7.65–7.69 (m, 1H), 7.88–7.91 (m, 1H), 7.97 (d, J=4.8 Hz, 1H), 8.27–8.35 (m, 1H);

LC-MS (retention time: 1.52), MS m/z 486 (M+1).

Step 4:

To a solution of the acid (Example 451, Step 3) (0.32 g, 0.87 mmol) in CH$_3$CN (10 mL) and DMF (2 mL) was added the diastereomeric mixture of 1(R)-2(S) and 1-(S)-2(R) 1-amino-2-vinyl-cyclopropanecarboxylic acid ethyl ester hydrochloride (240 mg, 0.87 mmol) and TBTU (201 mg, 0.87 mmol) and DIPEA (0.32 mL, 0.742 mmol) and the mixture stirred at 23° C. for 12 h. The mixture was concentrated and the residue partitioned between EtOAc and water. The organic layer was separated, dried over MgSO$_4$ and concentrated. The residue was chromatographed with 30% EtOAc/hexanes as eluant to give 240 mg (38%) of a light yellow solid.

$^1$H NMR (DMSO-d$_6$, mixture of rotamers and diastereomers) δ 0.87 (s, 9H), 0.88 (s, 9H), 0.97–1.04 (m, 3H), 1.33 (s, 9H), 1.38 (s, 9H), 2.11–2.20 (m, 2H), 3.74–3.85 (m, 1H), 3.89–3.96 (m, 2H), 3.98–4.03 (m, 4H), 4.00–4.09 (m, 1H), 4.40–4.42 (m, 1H), 5.04–5.09 (m, 1H), 5.17–5.29 (m, 2H), 5.50–5.70 (m, 1H), 6.60–6.62 (m, 1H), 6.72–6.75 (m, 1H), 7.50–7.56 (m, 1H), 7.56–7.72 (m, 2H), 7.70–7.80 (m, 1H), 7.92–8.00 (m, 1H), 8.00–8.06 (m, 1H), 8.29–8.40 (m, 1H), 8.65 (s, 1H), 8.79 (s, 1H);

LC-MS (retention time: 1.59), MS m/z 623 (M+1).

Step 5:

The acid was prepared as previously described using LiOH in THF/MeOH/H$_2$O (4/2/1) in Example 451, Step 3, except using the product of Example 451, Step 4 instead.

$^1$H NMR (DMSO-d$_6$, mixture of rotamers and diastereomers) δ 0.90 (s, 9H), 1.17–1.23 (m, 2H), 1.32–1.37 (m, 9H), 2.10–2.12 (m, 1H), 2.20–2.31 (m, 2H), 3.97–4.05 (m, 2H), 4.10–4.12 (m, 1H), 4.32–4.40 (m, 1H), 4.55–4.61 (m, 1H), 4.80–4.98 (m, 2H), 5.03–5.08 (m, 1H), 5.10–5.20 (m, 1H), 5.75–5.90 (m, 1H), 6.55–6.70 (m, 1H), 7.42–7.57 (m, 1H), 7.60–7.64 (m, 2H), 7.70–7.72 (m, 1H), 7.80–7.97 (m, 1H), 7.96–7.99 (m, 1H), 8.20–8.50 (m, 2H);

LC-MS (retention time: 1.52), MS m/z 595 (M+1).

Step 6:

A mixture of the acid (Example 451, Step 5) (172 mg, 0.29 mmol), methanesulfonamide (110 mg, 1.16 mmol), EDAC (110 mg, 0.58 mmol) and DMAP (71 mg, 0.58 mmol) was dissolved in THF(10 ml) and stirred for 12 h. DBU (0.087 mL, 0.58 mmol) was added and the mixture stirred for 48 h. The solvent was removed and the residue dissolved in EtOAc and washed with water and 1N HCl, dried over MgSO4 and concentrated. The residue was purified by preparative thin layer chromatography to give 15 mg (8%) of Compound 451 as a tan solid.

$^1$H NMR (DMSO-$d_6$, mixture of rotamers and diastereomers) δ 0.98 (s, 9H), 1.27–1.42 (m, 2H), 1.46 (s, 9H), 1.76–1.79 (m, 1H), 1.83–1.86 (m, 1H), 1.92–2.10 (m, 1H), 2.16–2.25 (m, 2H), 3.01–3.10 (m, 1H), 3.80–3.83 (m, 1H), 3.86–3.89 (m, 1H), 3.98–3.99 (m, 1H), 3.99–4.05 (m, 1H), 4.24–4–29 (m, 1H), 4.44–4.53 (m, 1H), 4.86 (s, 3H), 5.08–5.15 (m, 1H), 5.25–5.29 (m, 1H), 5.65–5.85 (m, 1H), 6.5–6.8 (m, 1H), 7.48 (t, J=7.7 Hz, 11H), 7.54 (t, J=7.1 Hz, 1H), 7.59 (t, J=7.1 Hz, 1H), 7.75–7.77 (m, 1H), 7.88–7.91 (m, 2H), 8.46 (d, J=8.25 Hz, 1H);

LC-MS (retention time: 1.52), MS m/z 672 (M+1 minor), m/z 693 (M+Na Major).

Example 452

Preparation of Compound 452

Compound 452

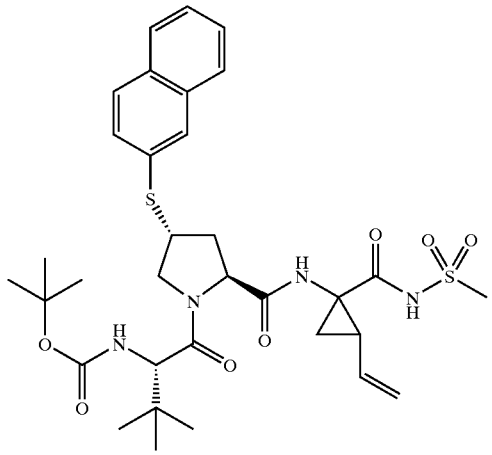

Step 1:

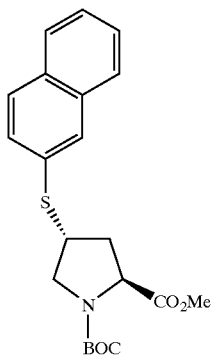

To a slurry of NaH (76 mg, 1.90 mmol) in DMF (20 mL) is added 2-thionaphthol (0.29 g, 1.80 mmol) and the mixture is stirred for 30 minutes. A solution of the tosylate (Example 451, Step 1) (0.61 g, 1.79 mmol) in DMF (2 ml) is added and the mixture stirred for 12 h ar 23° C. The mixture is concentrated then partitioned between EtOAc/H$_2$O. The organic layer was washed with saturated NaHCO3, dried (MgSO$_4$) and concentrated. The residue was chromatographed with 5% EtOAc/hexanes followed by 30% EtOAc/hexanes to give 261 mg (38%) of the product as a clear oil.

$^1$H NMR (DMSO-$d_6$) δ 1.32 (s, 9H), 2.29–2.35 (m, 2H), 3.33–3.47 (m, 2H), 3.66 (s, 3H), 3.71–3.81 (m, 1H), 4.29–4.32 (s, 1H), 7.49–7.55 (m, 3H), 7.70–7.80 (m, 1H), 7.81–7.97 (m, 3H);

LC-MS (retention time: 1.54), MS m/z 387 (M+1).

Step 2:

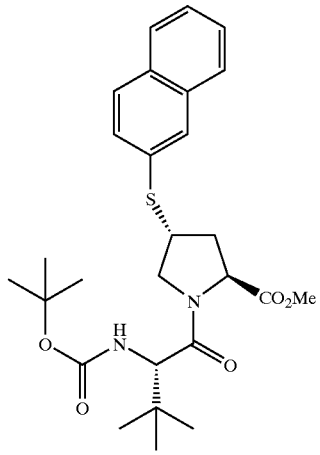

A mixture of 4-(naphthalen-2-ylsulfanyl)-pyrrolidine-1,2-dicarboxylic acid 1-tert-butyl ester 2-methyl ester (310 mg, 0.80 mmol) and 4N HCl in dioxane (1.49 ml, 2.69 mmol) was stirred for 2 h at 23° C. then concentrated. The residue is dissolved in CH$_3$CN (10 mL) and N-Boc-t-butylglycine (196 mg, 0.85 mmol), TBTU (0.27 g, 0.85 mmol) and DIPEA (0.32 mL, 1.85 mmol) were added and the mixture stirred overnight. The mixture was concentrated and the residue dissolved in EtOAc, washed with 1 N HCl, saturated NaHCO$_3$, dried and concentrated to give 300 mg (90%) of the product as a yellow oil.

$^1$H NMR (Methanol-$d_4$) δ 0.99 (s, 9H), 1.44 (s, 9H), 2.20–2.35 (m, 2H), 3.75 (s, 3H), 3.92–4.08 (m, 2H), 4.26 (d, J=9.4 Hz, 1H), 4.57 (t, J=9.5 Hz, 1H) 6.46 (d, J=9.5 Hz, 1H), 7.48–7.60 (m, 3H), 7.83–7.90 (m, 3H), 8.02 (s, 1H)

LC-MS (retention time: 1.98), MS m/z 523 (M+Na).

Step 3:

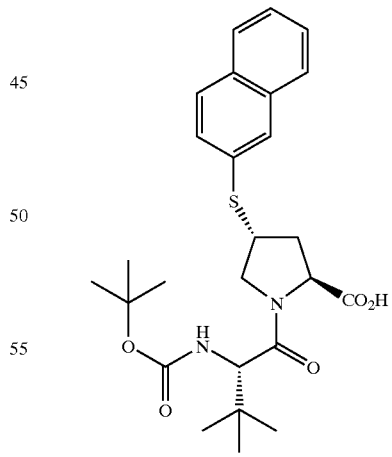

A solution of 4-(naphthalen-2-ylsulfanyl)-pyrrolidine-1,2-dicarboxylic acid 1-tert-butyl ester 2-methyl ester (0.48 g, 0.96 mmol) is dissolved in MeOH (20 mL) and stirred with LiOH (0.2 g, 4.8 mmol) for 12 h. the solution is concentrated and acidified and extracted with EtOAc. The organic extract was dried over MgSO$_4$ and concentrated to give 418 mg (91%) of a yellow solid.

¹H NMR (DMSO-d₆, 1:2 mixture of rotamers) δ 0.86, 0.93 (s, 9H) (1:2 mixture of rotamers), 1.35, 1.38 (s, 9H) (1:2 mixture of rotamers), 2.01–2.18, 2.25–2.35 (m, 2H), 3.25–3.40 (m, 2H), 3.70–3.80 (m, 1H), 4.00–4.20 (m, J=9.4 Hz, 2H), 4.30–4.40 (s, 1H), 5.61–5.70, 6.42–6.50 (m, 1H) (1:2 mixture of rotamers), 7.50–7.54 (m, 3H), 7.87–7.89 (m, 3H), 7.98 (s, 1H);

LC-MS (retention time: 1.93), MS m/z 487 (M+i).

Step 4:

Scheme 1

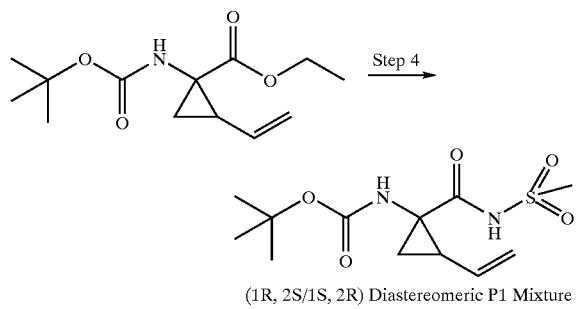

(1R, 2S/1S, 2R) Diastereomeric P1 Mixture

A solution of 1-tert-butoxycarbonylamino-2-vinyl-cyclopropanecarboxylic acid ethyl ester (4.3 g, 17.8 mmol) in MeOH (50 mL) was treated with LiOH (0.84 g, 20.0 mmol) and water (5 mL) and the mixture stirred for 12 h. The solvent was removed and the residue acidified and extracted with EtOAc. The organic layers are dried over MgSO₄, filtered and concentrated to give the acid 2.1 g (52%) as a yellow oil. The acid (2.1 g, 9.25 mmol) was dissolved in THF and treated with CDI (7.25 g, 13.8 mmol) and heated to reflux for 3 h then cooled to 23° C. Methane-sulfonamide (1.76 g, 18.5 mmol) was added followed by DBU (2.77 ml, 18.5 mmol) and stirred for 72 h at 23° C. The mixture was concentrated and the residue acidified to pH 4 (1 N HCl) and extracted with EtOAc. The organic extracts were dried over MgSO₄ and concentrated to give 1.99 g (71%) of a yellow oil that solidified on standing.

¹H NMR (DMSO-d₆) δ 1.16–1.23 (m, 1H), 1.43 (s, 9H), 1.65–1.75 (m, 1H), 2.15–2.25 (m, 2H), 3.16 (s, 3H), 5.08 (d, J=9.9 Hz, 1H), 5.22 (d, J=17.1 Hz, 1H), 5.40–5.52 (m, 1H);

LC-MS (retention time: 1.14), MS m/z 304 (M+1).

Step 5:

A solution of the product of Example 452, Step 4 in dioxane/4N HCl (2 ml) was stirred for 2 h then concentrated. The residue was dissolved in CH₃CN (5 mL) and added to a mixture of the acid (Example 452, Step 3) (120 mg, 0.25 mmol), TBTU (58 mg, 0.25 mmol) and DIPEA (0.06 ml, 0.35 mmol) was added and the mixture stirred for 12 h. The solvent was removed and the residue dissolved in EtOAc and washed with 1N HCl, saturated NaHCO3 dried over MgSO₄ and concentrated. The residue is purified with preparative TLC (Analtech 20×40 cM, 1000☐ SiO2) to give 128 mg (70%) of Compound 452 as a tan solid.

¹H NMR (DMSO-d₆, mixture of diasteromers) δ 0.97, 0.99 (s, 9H), 1.23–1.43 (m, 2H), 1.45 (s, 9H), 1.82–1.83 (m, 1H), 2.00–2.51 (m, 2H), 2.90–2.99 (m, 1H), 3.33 (s, 3H), 3.90–3.99 (m, 1H), 4.01–4.20 (m, 2H), 4.25–4.30 (m, 1H), 4.45–4.55 (m, 1H), 4.95–5.10 (m, 1H), 5.12–5.25 (m, 1H), 5.71–5.85 (m, 1H), 6.4–6.8 (br m, 1H), 7.46–7.53 (m, 3H), 7.80–7.86 (m, 3H), 7.98–7.99 (m, 1H);

LC-MS (retention time: 1.95), MS m/z 672 (M+1).

Example 453

Preparation of Compound 453

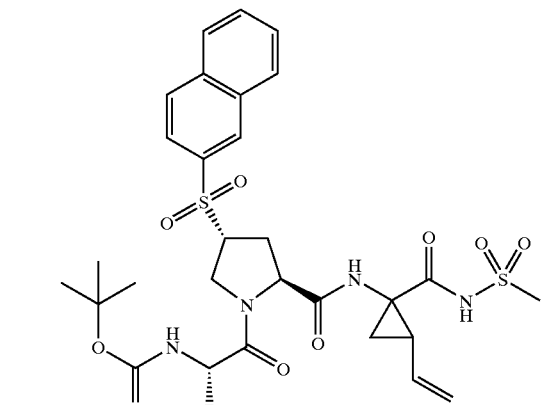

Step 1:

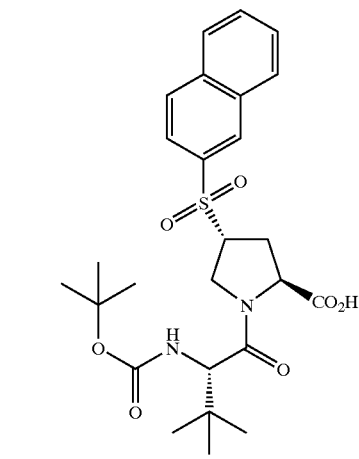

A mixture of Example 452, Step 3 (110 mg, 0.23 mmol) in DCM (20 ml), 3-chloroperbenzoic acid (121.6 mg, 0.57 mmol, 85% peracid), KHPO₄ (0.13 g, 0.94 mmol) and K₂HPO₄ (0.18 g, 1.05 mmol) are stirred at 23° C. for 12 h. The solution is diluted with DCM, washed with water, saturated NaHCO3, dried over MgSO₄ and concetrated to give the product 110 mg, (92%) as a clear oil.

¹H NMR (DMSO-d₆) δ 0.91 (s, 9H), 1.48 (s, 9H), 2.23–2.28 (m, 1H), 2.65–2.80 (m, 1H), 3.88–3.90 (m, 1H), 4.12 (t, J=8.0 Hz, 1H), 4.20 (d, J=9.5 Hz, 1H), 4.27 (d, J=9.9 Hz, 1H), 6.76 (d, J=9.3 Hz, 1H), 7.70–7.80 (m, 2H), 7.88–7.95 (m, 1H), 8.11 (d, J=8.1 Hz, 1H), 8.17 (d, J=8.6 Hz, 1H), 8.26 (d, J=8.1 Hz, 1H), 8.71 (s, 1H);

LC-MS (retention time: 1.72), MS m/z 519 (M+1).

Step 2:

A mixture of the product of Example 453, Step 1 (110 mg, 0.212 mmol), amine (Example 452, Step 5a) (0.65 mg, 0.212 mmol), TBTU (48.5 mg, 0.21 mmol) followed by DIPEA (60.8 ml, 0.35 mmol) and stirred for 12 h at 23° C. The solvent is removed and the residue dissolved in EtOAc and washed with 1N HCl, aturated NaHCO₃, dried over MgSO₄ and concentrated. The residue was purified by preparative TLC (eluted with 10% MeOH/CH₂Cl₂) to give 25 mg (17%) of Compound 453 as a white solid.

¹H NMR (DMSO-d₆, mixture of diastereomers) δ 0.93, 0.96 (s,9H), 1.38–1.45 (m, 2H), 1.53, 1.55 (m, 9H), 1.76–1.85 (m, 1H), 2.21–2.40 (m, 2H), 3.13–3.15 (m, 2H), 3.34 (s, 3H), 3.91–3.99 (m, 1H), 4.15 (m, 1H), 4.25 (m, 1H), 4.30 (m, 1H), 5.09–5.12 (m, 1H), 5.26–5.31 (m, 1H), 5.72–5.76 (m, 1H), 6.65–6.68 (m, 1H), 6.71–6.76 (m, 1H), 7.67–7.76 (m, 2H), 7.91–7.95 (m, 1H), 8.03 (d, J=7.8 Hz, 1H), 8.13 (d, J=8.5 Hz, 1H), 8.20 (d, J=7.6 Hz, 1H), 8.7 (s, 1H);

LC-MS (retention time: 1.76), MS m/z 705 (M+1).

Example 454

Preparation of Compound 454

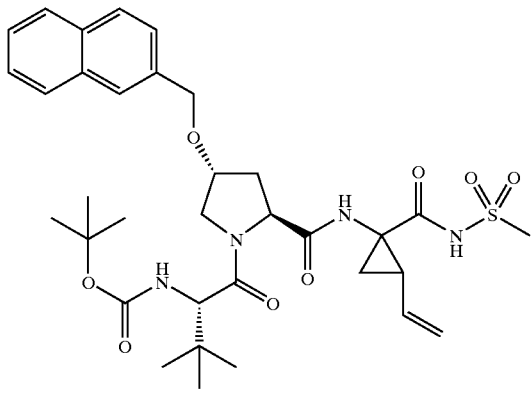

Step 1:

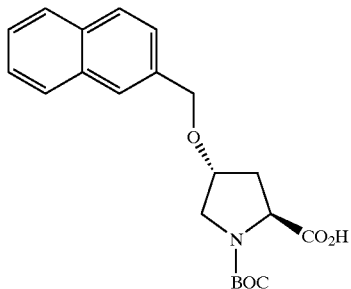

To slurry of the sodium hydride (0.91 g, 22.7 mmol) in THF(50 mL) was added N-BOC-trans-4(R)-hydroxy-L-proline (2.5 g, 10.8 mmol) and the mixture stirred at 23° C. for 1 h. 2-Chloromethylnapthalene (1.9 g, 10.8 mmol) was added and the mixture stirred for 12 h at room temperature. The solvent was removed and the residue poured into water and washed with hexanes. The aqueous layer was acidified (1 N HCl) and extracted with EtOAc. The EtOAc layer is separated, dried (MgSO$_4$), and concentrated to give a light yellow residue. The oil was purified by flash chromatography with 1:1 EtOAc/hexanes with 1% acetic acid added to give 1.56 g (39%) of the desired product as a thick oil.

$^1$H NMR (DMSO-d$_6$, 3:1 mixture of rotamers) δ 1.35, 1.37 (s, 9H, major and minor respectively), 1.92–2.02, 2.15–2.20 (m, 2H, major and minor respectively), 2.35–2.50 (m, 2H), 3.41–3.49 (m, 2H), 4.12–4.16, 4.20–4.21 (m, 2H), 4.65–4.68 (m, 2H), 7.46–7.52 (m, 3H), 7.74–7.91 (m, 4H), (Acid OH not observed); LC-MS (retention time: 1.44, YMC ODS-A C18 S7 3.0×50 mm, gradient 10% MeOH/H20 0.1% TFA to 90% MeOH/H20 0.1% TFA), MS m/z 394 (M$^+$+1+Na).

Step 2:

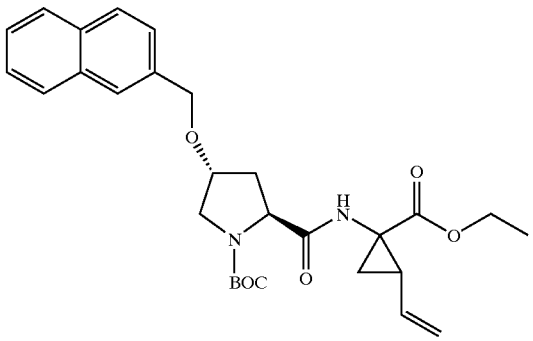

To a solution of the HCl salt of a 1:1 mixture of diastereoisomers (1R,2S/1S,2R where carboxy group is syn to vinyl moiety) of 2-(1-ethoxycarbonyl-2-vinyl—cyclopropylcarbamoyl)-4-(naphthalen-2ylmethoxy)-pyrrolidine-1-carboxylic acid tert-butyl ester (0.54 g, 1.3 mmole)[prepared by stirring the N-Boc amine with HCl (4N) in dioxane for 1 hr then removal of the solvent in vacuo] in CH$_3$CN (50 mL) is added Boc-4(R)-(2-methylnapthyl)proline (0.5 g, 1.3 mmol), TBTU (0.45 g, 1.4 mmol) followed by DIPEA (0.78 mL, 4.5 mmol). The mixture is stirred for 12 h and concentrated. The residue was dissolved in EtOAc/H$_2$O and washed with saturated NaHCO$_3$, saturated NaCl, dried (MgSO$_4$) and concentrated to give a thick yellow oil (0.6 g, 91%) of the product as a mixture of diastereomers.

$^1$H NMR (DMSO-d$_6$) δ: 1.08–1.22 (m, 7H), 1.23–1.39 (m, 9H), 2.02–2.18 (m, 1H), 2.25–2.35 (m, 1H), 3.33–3.53 (m, 2H), 3.90–4.14 (m, 4H), 4.45–4.70 (m, 2H), 5.07–5.11 (m, 1H), 5.24–5.30 (m, 1H), 5.58–5.63 (m, 1H), 7.43–7.51 (m, 4H), 7.84–7.96 (m, 3H); MS m/z 531 (M$^+$+1+Na).

Step 3:

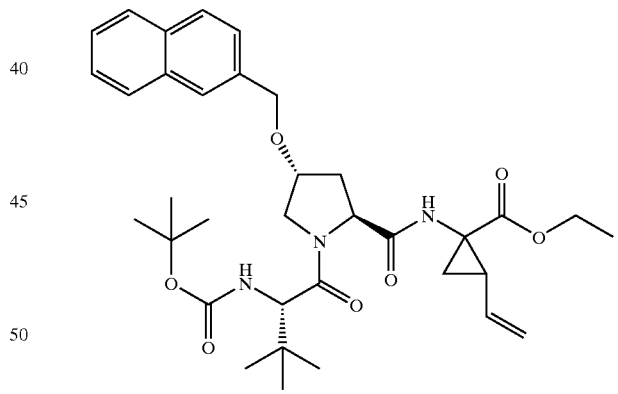

A solution of product of Example 454, Step 2 (600 mg, 1.18 mmol) was stirred with HCl (4N, 3 mL, 11.8 mmol) in dioxane for 1 hr then the solvent removed in vacuo. The residue is dissolved in CH$_3$CN (10 mL) treated with Boc-L-t-Bu-Gly (0.42 g, 1.38 mmol), TBTU (0.27 g, 1.18 mmol) followed by DIPEA (0.71 mL, 4.1 mmol). The mixture is stirred for 12 h and concentrated. The residue was dissolved in EtOAc/H$_2$O and washed with 1N HCl, saturated NaHCO3, saturated NaCl, dried (MgSO$_4$) and concentrated to give a thick yellow oil. The product was purified by flash chromatography using gradient elution 5% EtoAc/Hexanes 10% EtOAc/Hexanes, 30% EtOAc/Hexanes and finally as eluant to give the product as a thick oil (0.243 g, 33%) of the product as a mixture of diastereomers and rotamers.

¹H NMR (DMSO-d₆) o: 0.83–1.00 (m, 10H), 1.34 (s, 9H), 1.58–1.59, 1.65–1.67 (m, 2H), 1.95–1.99, 2.04–2.06, 2.10–2.19, 2.24–2.56 (m, 2H), 3.97–4.04 (m, 3H), 4.08–4.17 (m, 3H), 4.29–4.31 (m, 2H), 4.59–4.72 (m, 3H), 5.06–5.10 (m, 1H), 5.18–5.30 (m, 1H), 5.60–5.63 (m, 1H), 6.59–6.65, 6.70–6.74 (m, 1H), 7.43–7.51 (m, 4H), 7.84–7.96 (m, 3H), 8.66, 8.76 (s, 1H);

MS m/z 531 (M⁺+1+Na).

Step 4:

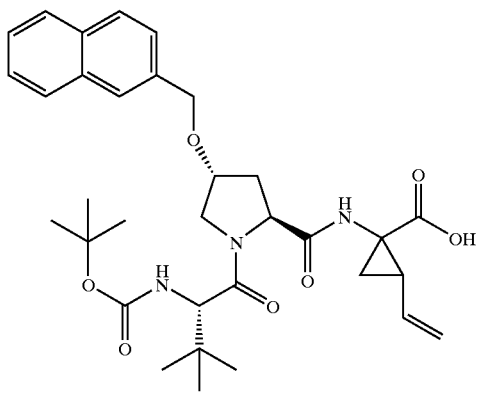

To a suspension of product of Example 454, Step 3 (240 mg, 0.39 mmol) in THF(15 mL), and H₂O (2 mL) was added LiOH (82 mg, 1.95 mmol). The reaction mixture was stirred for 12 h then concentrated in vacuo until only the aqueous layer remained. The resulting aqueous residue was acidified to pH 3.0 by addition of 1.0 N aqueous HCl, and extracted with EtOAc (2×80 mL). Combined organic extracts was dried (MgSO₄), filtered, and concentrated in vacuo to give the product as a tan solid (200 mg, 0.33 mmol, 85%):

¹H NMR (DMSO-d₆) δ: 0.86, 0.94 (s, 9H minor and major respectively), 1.23–1.42 (m, 2H), 1.34 (s, 9H), 1.8–2.1 (m, 2H), 2.18–2.30 (m, 1H), 3.59–3.73 (m, 3H), 4.0–4.09 (m, 1H), 4.18–4.34 (m, 3H), 4.56–4.62 (m, 1H), 4.66–4.67 (m, 1H), 4.82–4.92 (m, 1H), 5.0–5.20 (m, 1H), 5.91–6.08 (m, 1H), 6.5–6.7 (m, 1H), 7.45–7.59 (m, 3H), 7.82–7.97 (m, 4H), 8.2–8.3, 8.3–8.4 (s, 1H); LC-MS (retention time: 1.50), MS m/z 593 (M⁺+1).

Step 5:

To a solution of product of Example 454, Step 4 (190 mg, 0.32 mmol) and EDAC (122 mg, 0.64 mmol) and 4-DMAP (78 mg, 0.64 mmol) in THF(20 mL) was added commercially available methanesulfonamide (122 mg, 1.28 mmol). The resulting solution was stirred for 2 days, then DBU was added (95 μL, 0.64 mmol). The reaction was stirred for 24 h then concentrated. The residue was partitioned between EtOAc (80 mL) and water and washed with 1 N HCl, aqueous NaHCO₃ (2×30 mL), dried (MgSO₄) and purified by preparative HPLC (65–90% MeOH/Water/0.1% TFA) which gave 56 mg of a mixture of product and material in which the BOC group was removed. The material was further purified by preparative TLC (eluted with 10% MeOH/CH₂Cl₂ using 20×40cM plates from Analtech) to give Compound 454 as a tan solid (12 mg, 6%).

¹H NMR (MeOD-d₄ 50/50 mixture of P1 diastereomers) δ 0.88–0.99 (m, 2H), 1.01, 1.02 (s, 9H minor and major diastereomers respectively), 1.23–1.42 (m, 2H), 1.38 (s, 9H), 1.72–1.79 (m, 1H), 1.86–1.88 (m, 1H), 2.00–2.10 (m, 2H), 2.10–2.23 (m, 1H), 2.3–2.5 (m, 1H), 3.12, 3.17 (s, 3H), 3.72–3.79 (m, 1H), 4.26–4.41 (m, 3H), 4.72 (d, J=8.2 Hz, 1H), 4.76 (d, J=8.2 Hz, 1H), 5.09–5.12 (t, J=9.3 Hz, 1H), 5.28 (dd, J=3.5, 17.6 Hz, 1H) 5.7–5.8 (m, 1H), 6.55–6.80 (m, 1H), 7.45–7.47 (m, 3H), 7.79–7.83 (m, 4H);

LC-MS (retention time: 1.48), MS m/z 670 (M++1).

Example 470

Preparation of Compound 470

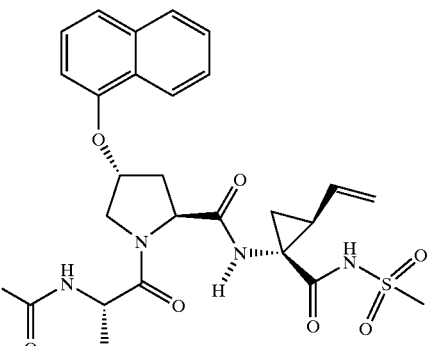

Scheme 1

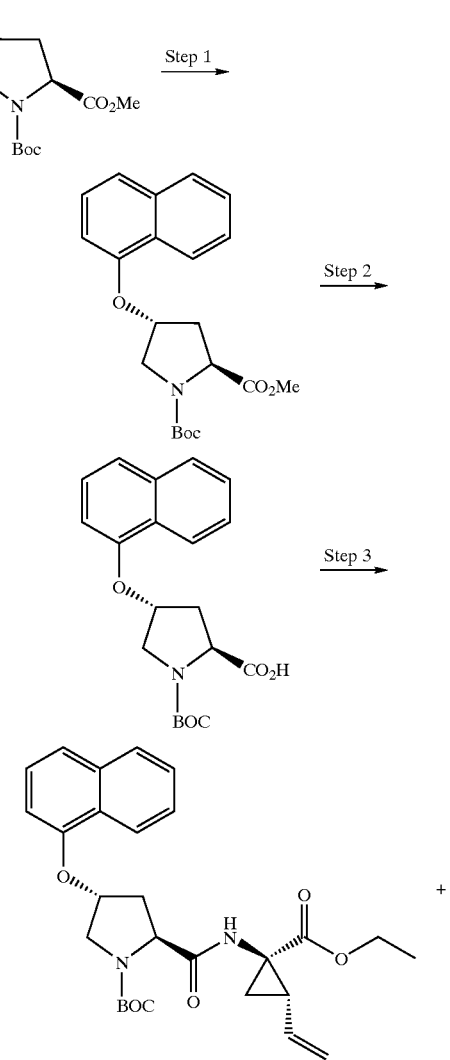

A, higher Rf, 1(R)-2(S)

-continued

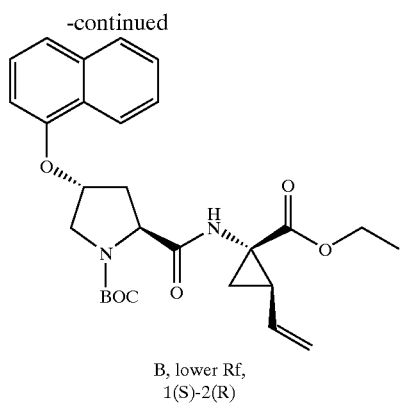

B, lower Rf,
1(S)-2(R)

Step 1:
To a solution of commercially available N-Boc-(4S)-(cis)-Hydroxyproline-OMe (200 mgs, 0.82 mmole), triphenylphosphine (320 mgs, 1.22 mmole) and 1-naphthol (176 mgs, 1.22 mmole) in 2.5 mL tetrahydrofuran was added dropwise a solution of diethyldiazodicarboxylate (190 μL, 1.22 mmole) in 1.0 mL THF over 10 minutes. After stirring for 5.5 days, the reaction was concentrated in vacuo. The crude yellow oil was chromatographed on a 20×40cM preparative TLC plate (Analtech SiO2) eluting with 6–1 hexanes-ethyl acetate to yield the desired product as a pale yellow oil (150 mgs, 33%).

$^1$H NMR (CDCl$_3$, 500 MHz) δ 1.44 (s, 9H) 2.33 (1H, m), 2.72 (1H, m), 3.77 and 3.38 (2s, 3H, rotamers), 3.88 (dd, 1H, J=4.3, 12.4 Hz), 3.97 (bd, 1H), 4.53 and 4.62 (2t, 1H, J=7.8 Hz, rotamers), 5.10 (bd, 1H), 6.76 (t, 1H, J=9.5 Hz), 7.37 (m, 1H), 7.46 (m, 3H), 7.80 (d, 1H, J=7.7 Hz), 8.18 (m, 1H);
LC-MS A (retention time: 1.86; MS m/z 394 (M+Na)$^+$ Step 2:
To a stirred solution of Boc-(4R)-naphthal-1-oxo)-Pro-OEt (150 mgs, 0.40 mmole) in 1.5 mL THF and 0.5 mL water was added lithium hydroxide (10 mgs). The solution was stirred for 21 hours at room temperature and then diluted with 0.5N NaHCO$_3$. The basic solution was extracted with ethyl acetate and then the aqueous layer was acidified to pH 2 with the dropwise addition of conc. HCl. This acidified layer was then extracted again with ethyl acetate. This second ethyl acetate layer was dried with magnesium sulfate, filtered and then concentrated in vacuo to yield Boc-(4R)-naphthal-1-oxo)-Pro-OH as pale-pink crystals (147 mgs, 100%).

$^1$H NMR (CDCl$_3$, 500 MHz) δ 1.47 and 1.48 (2s, 9H, rotamers), 2.40 and 2.52 (2m, 1H), 2.68 and 2.78 (2m, 1H), 3.78–4.07 (m, 2H), 4.57 and 4.69 (2t, 1H, J=7.6 and 8.0 Hz, rotamers), 5.12 (bd, 1H), 6.77 (dd, 1H, J=7.6, 21.2 Hz), 7.37 (m, 1H), 7.46 (m, 3H), 7.81 (t, 1H, J=5.8 Hz), 8.19 (m, 1H);
LC-MS A (retention time: 1.79; MS m/z 358 (M+H)$^+$ Step 3:
To a solution of Boc-((4R)-naphthal-1-oxo)-Pro-OH (147 mgs, 0.41 mmole) and racemic (1R/2S)/(1S/2R)-1-amino-2-vinylcyclopropane carboxylic acid ethyl ester hydrochloride salt (79 mgs, 0.41 mmole) in 2.8 mL methylene chloride was added DIPEA (250 μL, 1.44 mmole) and TBTU (158 mgs, 0.49 mmole). The resulting solution was stirred under nitrogen for 20 hours and then diluted with 40 mL methylene chloride. The organic layer was washed with water, 1N NaHCO$_3$, 1N HCl, water and brine. The solution was then dried with sodium sulfate and concentrated in vacuo. Purification by preparative TLC yielded two separate diastereomers, higher Rf diastereomer A (P2[Boc(4R)-(naphthal-1-oxo)proline]-P1(1R, 2S Vinyl Acca)-OEt, 78 mgs, 38%) and lower Rf diastereomer B (P2[Boc(4R)-(naphthal-1-oxo)proline]-P1(1S,2R Vinyl Acca)-OEt, 91 mgs, 45%) as off white solids:

Diastereomer A: P2[Boc(4R)-(naphthal-1-oxo)proline]-P1(1R, 2S Vinyl Acca)-OEt:
$^1$H NMR (CDCl$_3$, 500 MHz) δ 1.24 (t, 3H), 1.43 (s, 9H), 1.52 (m, 1H), 1.84 (m, 1H), 2.02 (m, 1H), 2.14 (m, 1H), 2.81 (m, 1H), 3.88 (m, 2H), 4.11 (q, 1H, J=7.15), 4.19 (m, 1H), 4.54 (m, 1H), 5.15 (m, 1H), 5.31 (dd, 1H, J=17, 0.8 Hz), 5.77 (m, 1H), 6.83 (m, 1H), 7.36 (t, 1H, J=7.8 Hz), 7.46 (m, 3H), 7.78 (d, 1H, J=7.6 Hz), 8.14 (d, 1H, J=8.15 Hz);
LC-MS B (retention time: 1.85; MS m/z 495 (M+H)$^+$ Diastereomer B, Example 10B: P2[Boc(4R)-(naphthal-1-oxo)proline]-P1(1S, 2R Vinyl Acca)-OEt: $^1$H NMR (dl-CHCl$_3$, 500 MHz) δ 1.24 (t, 3H), 1.42 (s, 9H), 1.85 (m, 1H), 2.15 (q, 1H, J=8.9 Hz), 2.40 (m, 1H), 2.78 (m, 1H), 3.78 (m, 1H), 4.12 (m, 2H), 4.52 (m, 1H), 5.15 (m, 1H), 5.31 (m, 1H), 5.79 (m, 1H), 6.80 (m, 1H), 7.35 (t, 1H, J=7.6 Hz), 7.46 (m, 3H), 7.78 (d, 1H, J=7.6 Hz), 8.14 (d, 1H, J=8.10 Hz).
LC-MS B (retention time: 1.85; MS m/z 495 (M+H)$^+$ Scheme 2

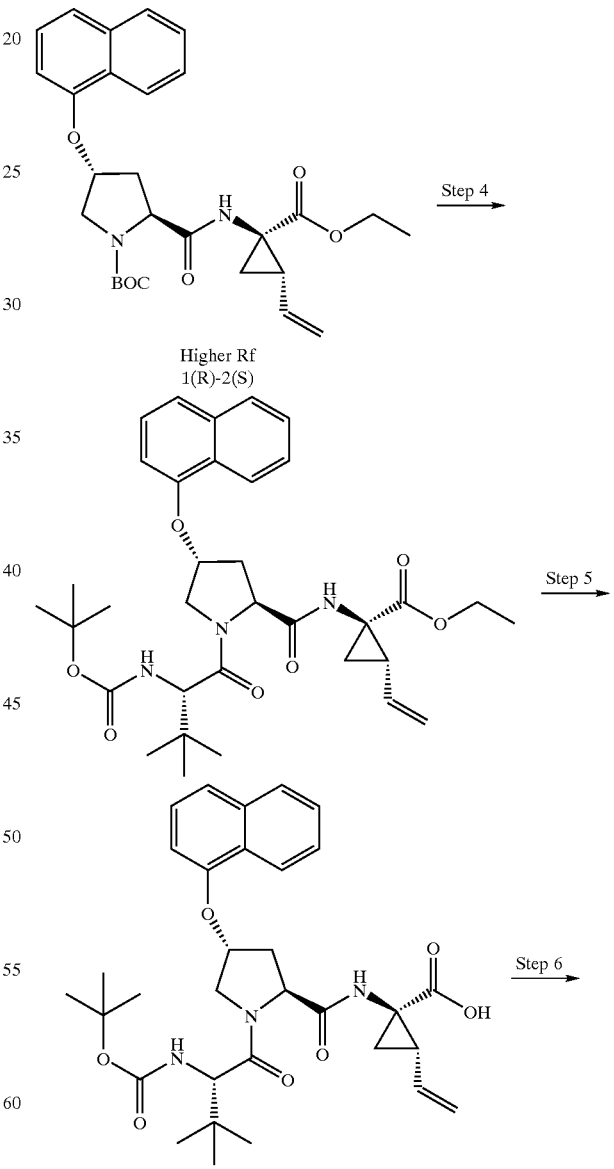

Higher Rf
1(R)-2(S)

Compound 470

Step 4:
To P2[Boc(4R)-(naphthal-1-oxo)proline]-P1(1R, 2S Vinyl Acca)-OEt (A, higher Rf) (78 mg, 0.16 mmol) was added 4N HCl in dioxane (2.0 mL) and the solution was allowed to stir for 30 minutes. Concentration in vacuo yielded the HCl salt of P2[(4R)-(naphthal-4-oxo) proline)]-P1(1R,2S Vinyl Acca)-OEt as a yellow oil which was taken on to the next step directly without further purification. To a solution of BOC L-tBuGly (73 mgs, 0.32 mmole) and the HCl salt of P2[(4R)-(naphthal-4-oxo) proline)]-P1(1R,2S Vinyl Acca)-OEt (0.16 mmole) in 11 mL acetonitrile was added DIPEA (140 μL, 0.79 mmole) and HATU (132 mgs, 0.35 mmole). The resulting solution was stirred under nitrogen for 17 hours and then diluted with 100 mL ethyl acetate. The organic layer was washed with water, 1N NaHCO$_3$, 1N HCl, water and brine. The solution was then dried with sodium sulfate and concentrated in vacuo to yield the title compound as a pale-yellow oily film (92 mgs, 96%).

$^1$H NMR (CDCl$_3$, 500 MHz) δ 1.06 (s, 9H), 1.22 (t, 3H, J=7.1), 1.38 (s, 9H), 1.41 (m, 1H), 1.82 (m, 1H), 2.13 (m, 1H), 2.42 (m, 1H), 2.79 (m, 1H), 3.92–4.2 (m, 1H), 4.12 (q, 2H, J=6.6 Hz), 4.38 (bt, 1H), 5.12 (d, 1H, J=10.3 Hz) 5.2–5.39 (m, 3H), 5.75 (m, 1H), 6.82 (d, 1H, J=7.5 Hz), 7.34–7.46 (m, 4H), 7.59 (bs, 1H, NH), 7.76 (d, 1H, J=7.9 Hz), 8.13 (d, 1H, J=8.3 Hz);

LC-MS C (retention time: 2.82; MS m/z 608 (M+H)$^+$

Step 5:

To a solution of product of Example 470, Step 4 (92 mgs, 0.15 mmole) in 750 mL tetrahydrofuran and 250 mL water was added lithium hydroxide (4 mgs). The resulting solution was stirred for 28.5 hours worked up as usual and then resubjected to the same conditions except adding twice as much lithium hydroxide (8 mgs). After 24 hours the reaction was diluted with ethyl acetate and washed with water. The organic layer was dried with sodium sulfate and concentrated in vacuo. The resulting semisolid was purified by flash chromatography eluting with 3–1 hexanes-ethyl acetate to yield BocNH-P3(t-BuGly)-P2[(Boc (4R)-(naphthal-1-oxo) proline)]-P1(1R,2S Vinyl Acca)-OH as a clear semisolid (30 mgs, 34%).

$^1$H NMR (d$_4$-MeOH, 500 MHz), 1.04 (s, 9H), 1.24 (t, 1H, J=3.9 Hz), 1.32 (s, 9H), 1.66 (m, 1H), 2.07 (m, 1H), 2.40 (m, 1H), 2.71 (m, 1H), 4.04–4.07 (m, 1H), 4.28 (m, 1H), 4.42 (m, 1H), 4.55 (m, 1H), 5.02 (m, 1H), 5.18–5.29 (m, 2H), 5.90 (m, 1H), 6.54 (m, 1H), 6.92 (m, 1H), 4.26 (m, 4H), 7.77 (m, 1H), 8.15 (m, 1H);

LC-MS C (retention time: 2.65; MS m/z 580 (M+H)$^+$

Step 6:

To a solution of BocNH-P3(t-BuGly)-P2[(Boc (4R)-(naphthal-1-oxo) proline)]-P1(1R,2S Vinyl Acca)-OH (Example 470, Step 5) (65 mgs, 0.11 mmole) in 3.7 mL tetrahydrofuran was added 1,1'-carbonyl diimidazole (22 mgs, 0.135 mmole). The resulting mixture was refluxed for 30 minutes and then cooled to room temperature. At this point, methanesulfonamide (27 mgs, 0.28 mmole) and DBU (34□L, 0.224 mmole) were added. The reaction was stirred for 2 days and then more DBU (10□L) and methanesulfonamide (9 mgs) were added. After 24 hours, the reaction was diluted with 50 mL ethyl acetate and washed with 50 mL 0.25N HCl and 50 mL brine. The solution was dried with sodium sulfate and concentrated in vacuo. The crude material was purified by preparative TLC (3–2 ethyl acetate-hexanes) to give Compound 470 (21 mgs, 28%) as a white filmy solid.

$^1$H NMR (d$_4$-MeOH, 500 MHz) δ 1.04 (s, 9H), 1.36 (s, 9H), 1.88 (t, 1H), 2.18 (m, 1H), 2.31 (m, 1H), 2.63 (m, 1H), 3.11 (bs, 3H), 4.076 (m, 1H), 4.30 (bd, 1H), 4.41 (bd, 1H), 4.52 (apparent t, 1H), 5.07 (m, 1H), 5.24–5.30 (m, 2H), 5.80 (m, 1H), 6.92 (d, 1H, J=7.45 Hz), 7.35–7.46 (m, 4H), 7.76 (d, 1H, J=8.1 Hz), 8.13 (d, 1H, J=8.3 Hz);

LC-MS C (retention time: 2.57; MS m/z 657 (M+H)$^+$

Example 471

Preparation of Compound 471

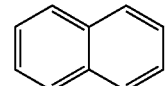

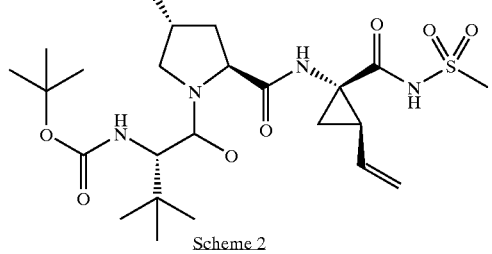

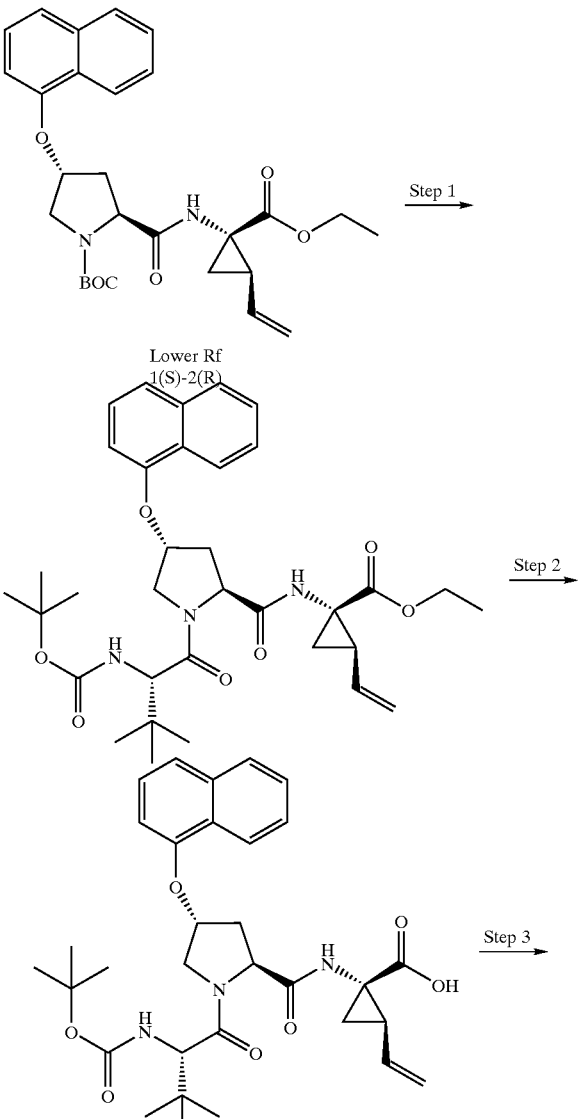

Step 1:

To P2[Boc(4R)-(naphthal-1-oxo)proline]-P1(1S, 2R Vinyl Acca)-OEt (Example 470, Step 3, lower Rf) (91 mgs, 0.18 mmole) was added 4N HCl in dioxane (2.0 mL) and the solution was allowed to stir for 30 minutes. Concentration in vacuo yielded the HCl salt of P2[(4R)-(naphthal-1-oxo) proline)]-P1(1S,2R Vinyl Acca)-OEt as a yellow oil which was taken on to the next step directly without further purification.

To a solution of N-Boc-L-tert-leucine-OH or BOC L-tBuGly (85 mgs, 0.37 mmole) and the HCl salt of P2[(4R)-(naphthal-1-oxo) proline)]-P1(1S,2R Vinyl Acca)-OEt (product obtained from reaction mentioned above) (0.18 mmole) in 13 mL acetonitrile was added DIPEA (160 μL, 0.92 mmole) and HATU (154 mgs, 0.41 mmole). The resulting solution was stirred under nitrogen for 17 hours and then diluted with 100 mL ethyl acetate. The organic layer was washed with water, 1N NaHCO3, 1N HCl, water and brine. The solution was then dried with sodium sulfate and concentrated in vacuo to yield the title compound as a clear film (53 mgs, 47%).

$^1$H NMR (dl-CHCl$_3$, 500 MHz) δ 1.02 (s, 9H), 1.22 (t, 3H, J=7.0 Hz), 1.39 (s, 9H), 1.47 (m, 1H), 1.88 (dd, 1H, J=8.0, 5.5 Hz), 2.07 (m, 1H), 2.42 (m, 1H), 2.80 (dt, J=13.8, 6.0 Hz, 1H), 3.96 (m, 1H), 4.14 (m, 2H), 4.34 (m, 2H), 4.77 (t, )1H, J=7.2 Hz), 5.09–5.33 (m, 3H), 5.72 (m, 1H), 6.82 (d, 1H, J=7.6 Hz), 7.34–7.50 (m, 4H), 7.77 (d, 1H, J=8.0 Hz), 8.15 (d, 1H, J=8.25 Hz);

LC-MS C (retention time: 2.81; MS m/z 608 (M+H)$^+$

Step 2:

This product was prepared according procedure described in Example 470, Step 5 (5 mg, 10%), except using the product of Example 471, Step 1 instead.

$^1$H NMR (d$_4$-MeOH, 500 MHz) δ 0.99 (s, 9H), 1.28 (m, 1H), 1.37 (s, 9H), 1.60 (m, 1H), 2.06 (m, 1H), 2.28 (m, 1H), 2.66 (m, 1H), 3.91 (m, 1H), 4.33 (m, 2H), 4.61 (bt, 1H), 4.97 (d, 1H, J=11.0 Hz), 5.19 (m 2H), 6.09 (m, 1H), 6.88 (d, 1H, J=7.1 Hz), 7.35–7.46 (m, 4H), 7.78 (d, 1H, J=8.2 Hz), 8.12 (d, 1H, J=8.3 Hz);

LC-MS C (retention time: 2.60; MS m/z 580 (M+H)$^+$

Step 3:

To a solution of BocN-P3(L-tBuGly)-P2[(Boc (4R)-(naphthal-1-oxo) proline)]-P1(1S,2R Vinyl Acca)-COOH (38 mgs, 0.066 mmole) (Example 471, Step 2) in 2.2 mL tetrahydrofuran was added 1,1'-carbonyl diimidazole (13 mgs, 0.079 mmole). The resulting mixture was refluxed for 30 minutes and then cooled to room temperature. At this point, methanesulfonamide (16 mgs, 0.16 mmole) and DBU (20 μL, 0.13 mmole) were added. The reaction was stirred for 2 days and then more DBU (10 μL) and methanesulfonamide (9 mgs) were added. After 24 hours, the reaction was diluted with 50 mL ethyl acetate and washed with 50 mL 0.25N HCl and 50 mL brine. The solution was dried with sodium sulfate and concentrated in vacuo. The crude product was purified using one 20×40cM preparative TLC plate from Analtech (eluent3–2 ethyl acetate-hexanes) to give Compound 471 (25 mgs, 58%) as a white filmy solid.

$^1$H NMR (d$_4$-MeOH, 500 MHz) δ 1.03 (s, 9H), 1.34 (s, 9H), 1.80 (m, 1H), 2.18 (m, 1H), 2.31 (m, 1H), 2.68 (m, 1H), 3.09 (bs, 3H), 4.04 (m, 1H), 4.20–4.44 (m, 2H), 4.51 (apparent t, 1H), 5.08 (m, 1H), 5.25–5.31 (m, 2H), 5.77 (m, 1H), 6.93 (d, 1H, J=7.6 Hz), 7.36–7.45 (m, 4H), 7.77 (d, 1H, J=8.0 Hz), 8.15 m, 1H);

LC-MS C (retention time: 2.57; MS m/z 657 (M+H)$^+$

Section L:

Example 472

Biological Studies

Recombinant HCV NS3/4A Protease Complex FRET Peptide Assay

The purpose of this in vitro assay was to measure the inhibition of HCV NS3 protease complexes, derived from the BMS, H$_{77}$C or J416S strains, as described below, by compounds of the present invention. This assay provides an indication of how effective compounds of the present invention would be in inhibiting HCV proteolytic activity.

Serum from an HCV-infected patient was obtained from Dr. T. Wright, San Francisco Hospital. An engineered full-length cDNA (compliment deoxyribonucleic acid) template of the HCV genome (BMS strain) was constructed from DNA fragments obtained by reverse transcription-PCR (RT-PCR) of serum RNA (ribonucleic acid) and using primers selected on the basis of homology between other genotype 1a strains. From the determination of the entire genome sequence, a genotype 1a was assigned to the HCV isolate according to the classification of Simmonds et al. (See P Simmonds, K A Rose, S Graham, S W Chan, F McOmish, B C Dow, E A Follett, P L Yap and H Marsden, J. Clin. Microbiol., 31(6), 1493–1503 (1993)). The amino acid sequence of the nonstructural region, NS2–5B, was shown to be>97% identical to HCV genotype 1a (H$_{77}$C) and 87% identical to genotype 1b (J4L6S). The infectious clones, H$_{77}$C (1a genotype) and J4L6S (1b genotype) were obtained from R. Purcell (NIH) and the sequences are published in Genbank (AAB67036, see Yanagi, M., Purcell, R. H., Emerson, S. U. and Bukh, J. Proc. Natl. Acad. Sci. U.S.A. 94 (16), 8738–8743 (1997); AF054247, see Yanagi, M., St Claire, M., Shapiro, M., Emerson, S. U., Purcell, R. H. and Bukh, J, Virology 244 (1), 161–172. (1998)).

The BMS, H77C and J4L6S strains were used for production of recombinant NS3/4A protease complexes. DNA encoding the recombinant HCV NS3/4A protease complex (amino acids 1027 to 1711) for these strains were manipulated as described by P. Gallinari et al. (see Gallinari P, Paolini C, Brennan D, Nardi C, Steinkuhler C, De Francesco R. Biochemistry. 38(17):5620–32, (1999)). Briefly, a three-lysine solubilizing tail was added at the 3'-end of the NS4A coding region. The cysteine in the P1 position of the NS4A-NS4B cleavage site (amino acid 1711) was changed to a glycine to avoid the proteolytic cleavage of the lysine tag. Furthermore, a cysteine to serine mutation was introduced by PCR at amino acid position 1454 to prevent the autolytic cleavage in the NS3 helicase domain. The variant DNA fragment was cloned in the pET21b bacterial expression vector (Novagen) and the NS3/4A complex was expressed in *Escherichia. coli* strain BL21 (DE3) (Invitrogen) following the protocol described by P. Gallinari et al. (see Gallinari P, Brennan D, Nardi C, Brunetti M, Tomei L, Steinkuhler C, De Francesco R., J. Virol. 72(8) :6758–69 (1998)) with modifications. Briefly, NS3/4A expression was induced with 0.5 mM Isopropyl β-D-1-thiogalactopyranoside (IPTG) for 22 hr at 20° C. A typical fermentation (10L) yielded approximately 80 g of wet cell paste. The cells were resuspended in lysis buffer (10 mL/g) consisting of 25 mM N-(2-Hydroxyethyl)Piperazine-N'-(2-Ethane Sulfonic acid) (HEPES), pH 7.5, 20% glycerol, 500 mM Sodium Chloride (NaCl), 0.5% Triton-X100, 1ug/ml lysozyme, 5 mM Magnesium Chloride (MgCl$_2$), 1 ug/ml DnaseI, 5 mM β-Mercaptoethanol (βME), Protease inhibitor-Ethylenediamine Tetraacetic acid (EDTA) free (Roche), homogenized and incubated for 20 mins at 4° C. The homogenate was sonicated and clarified by ultracentrifugation at 235000 g for 1 hr at 4° C. Imidazole was added to the supernatant to a final concentration of 15 mM and the pH adjusted to 8.0. The crude protein extract was loaded on a Nickel-Nitrilotriacetic acid (Ni—NTA) column pre-equilibrated with buffer B (25 mM HEPES, pH 8.0, 20% glycerol, 500 mM NaCl, 0.5% Triton-X100, 15 mM imidazole, 5 mM βME). The sample was loaded at a flow rate of 1 mL/min. The column was washed with 15 column volumes of buffer C (same as buffer B except with 0.2% Triton-X100). The protein was eluted with 5 column volumes of buffer D (same as buffer C except with 200 mM Imidazole).

NS3/4A protease complex-containing fractions were pooled and loaded on a desalting column Superdex-S200 pre-equilibrated with buffer D (25 mM HEPES, pH 7.5, 20% glycerol, 300 mM NaCl, 0.2% Triton-X100, 10 mM βME). Sample was loaded at a flow rate of 1 mL/min. NS3/4A protease complex-containing fractions were pooled and concentrated to approximately 0.5 mg/ml. The purity of the NS3/4A protease complexes, derived from the BMS, H77C and J4L6S strains, were judged to be greater than 90% by SDS-PAGE and mass spectrometry analyses.

The enzyme was stored at −80° C., thawed on ice and diluted prior to use in assay buffer. The substrate used for the NS3/4A protease assay was RET S1 (Resonance Energy Transfer Depsipeptide Substrate; AnaSpec, Inc. cat # 22991) (FRET peptide), described by Taliani et al. in Anal. Biochem. 240(2):60–67 (1996). The sequence of this peptide is loosely based on the NS4A/NS4B natural cleavage site except there is an ester linkage rather than an amide bond at the cleavage site. The peptide substrate was incubated with one of the three recombinant NS3/4A complexes, in the absence or presence of a compound of the present invention, and the formation of fluorescent reaction product was followed in real time using a Cytofluor Series 4000.

The reagents were as follow: HEPES and Glycerol (Ultrapure) were obtained from GIBCO-BRL. Dimethyl Sulfoxide (DMSO) was obtained from Sigma. β-Mercaptoethanol was obtained from Bio Rad.

Assay buffer: 50 mM HEPES, pH 7.5; 0.15M NaCl; 0.1% Triton; 15% Glycerol; 10 mM βME. Substrate: 2 µM final concentration (from a 2 mM stock solution in DMSO stored at −20° C.). HCV NS3/4A type 1a (1b), 2–3 nM final concentration (from a 5 µM stock solution in 25 mM HEPES, pH 7.5, 20% glycerol, 300 mM NaCl, 0.2% Triton-X100, 10 mM βME).

The assay was performed in a 96-well polystyrene black plate from Falcon. Each well contained 25 µl NS3/4A protease complex in assay buffer, 50 µl of a compound of the present invention in 10% DMSO/assay buffer and 25 µl substrate in assay buffer. A control (no compound) was also prepared on the same assay plate. The enzyme complex was mixed with compound or control solution for 1 min before initiating the enzymatic reaction by the addition of substrate. The assay plate was read immediately using the Cytofluor Series 4000 (Perspective Biosystems). The instrument was set to read an emission of 340 nm and excitation of 490 nm at 25° C. Reactions were generally followed for approximately 15 minutes.

The percent inhibition was calculated with the following equation:

$$100-[(\delta F_{inh}/\delta F_{con}) \times 100]$$

where δF is the change in fluorescence over the linear range of the curve. A non-linear curve fit was applied to the inhibition-concentration data, and the 50% effective concentration ($IC_{50}$) was calculated by the use of Excel Xl-fit software using the equation, $y=A+((B-A)/(1+((C/x)^{\wedge}D)))$.

All of the compounds tested were found to have IC50s of 10 µM or less. Further, compounds of the present invention, which were tested against more than one type of NS3/4A complex, were found to have similar inhibitory properties though the compounds uniformly demonstrated greater potency against the 1b strains as compared to the 1a strains.

Specificity Assays

The specificity assays were performed to demonstrate the selectivity of the compounds of the present invention in inhibiting HCV NS3/4A protease as compared to other serine or cysteine proteases.

The specificities of compounds of the present invention were determined against a variety of serine proteases: human leukocyte elastase (HLE), porcine pancreatic elastase (PPE) and human pancreatic chymotrypsin and one cysteine protease: human liver cathepsin B. In all cases a 96-well plate format protocol using colorimetric p-nitroaniline (pNA) substrate specific for each enzyme was used as described previously (Patent WO 00/09543) with some modifications to the serine protease assays. All enzymes were purchased from Sigma while the substrates were from Bachem.

Each assay included a 2 hr enzyme-inhibitor pre-incubation at RT followed by addition of substrate and hydrolysis to ~30% conversion as measured on a Spectramax Pro microplate reader. Compound concentrations varied from 100 to 0.4 µM depending on their potency.

The final conditions for each assay were as follows:

50 mM Tris(hydroxymethyl)aminomethane hydrochloride (Tris-HCl) pH 8, 0.5M Sodium Sulfate ($Na_2SO_4$), 50 mM NaCl, 0.1 mM EDTA, 3% DMSO, 0.01% Tween-20 with:

133 µM succ-AAA-pNA and 20 nM HNE or 8 nM PPE; 133 FM succ-AAV-pNA and 15 nM SE; 100 µM succ-AAPF-pNA and 250 pM Chymotrypsin.

100 mM $NaHPO_4$ (Sodium Hydrogen Phosphate) pH 6, 0.1 mM EDTA, 3% DMSO, 1 mM TCEP (Tris(2-carboxyethyl)phosphine hydrochloride), 0.01% Tween-20, 30 µM Z-FR-pNA and 5 nM Cathepsin B (enzyme stock activated in buffer containing 20 mM TCEP before use).

The percentage of inhibition was calculated using the formula:

$$[1-((UV_{inh}-UV_{blank})/(UV_{ctl}-UV_{blank}))] \times 100$$

A non-linear curve fit was applied to the inhibition-concentration data, and the 50% effective concentration ($IC_{50}$) was calculated by the use of Excel Xl-fit software.

HCV Replicon Cell-based Assay

An HCV replicon whole cell system was established as described by Lohmann V, Korner F, Koch J, Herian U, Theilmann L, Bartenschlager R., Science 285(5424): 110–3 (1999). This system enabled us to evaluate the effects of our HCV Protease compounds on HCV RNA replication. Briefly, using the HCV strain 1B sequence described in the Lohmann paper (Assession number:AJ238799), an HCV cDNA was generated encoding the 5' internal ribosome entry site (IRES), the neomycin resistance gene, the EMCV (encephalomyocarditis viurs)—IRES and the HCV non-structural proteins, NS3-NS5B, and 3' non-translated region (NTR). In vitro transcripts of the cDNA were transfected into the human hepatoma cell line, Huh7. Selection for cells constitutively expressing the HCV replicon was achieved in the presence of the selectable marker, neomycin (G418). Resulting cell lines were characterized for positive and negative strand RNA production and protein production over time.

Huh7 cells, constitutively expressing the HCV replicon, were grown in Dulbecco's Modified Eagle Media (DMEM) containing 10% Fetal calf serum (FCS) and 1 mg/ml G418 (Gibco-BRL). Cells were seeded the night before (1.5×10 cells/well) in 96-well tissue-culture sterile plates. Compound and no compound controls were prepared in DMEM containing 4% FCS, 1:100 Penicillin/Streptomysin, 1:100 L-glutamine and 5% DMSO in the dilution plate (0.5% DMSO final concentration in the assay). Compound/DMSO mixes were added to the cells and incubated for 4 days at 37° C. After 4 days, plates were rinsed thoroughly with Phosphate-Buffered Saline (PBS) (3 times 150 μl). The cells were lysed with 25 μl of a lysis assay reagent containing the FRET peptide (RET S1, as described for the in vitro enzyme assay). The lysis assay reagent was made from 5× cell Luciferase cell culture lysis reagent (Promega #E153A) diluted to 1× with distilled water, NaCl added to 150 mM final, the FRET peptide diluted to 10 μM final from a 2 mM stock in 100% DMSO. The plate was then placed into the Cytofluor 4000 instrument which had been set to 340 nm excitation/490 emission, automatic mode for 21 cycles and the plate read in a kinetic mode. $EC_{50}$ determinations were carried out as described for the $IC_{50}$ determinations.

As a secondary assay, $EC_{50}$ determinations from the replicon FRET assay were confirmed in a quantitative RNA assay. Cells were lyzed using the Rneasy kit (Qiagen). Purified total RNA was normalized using RiboGreen (Jones L J, Yue S T, Cheung C Y, Singer V L, Anal. Chem., 265(2):368–74 (1998)) and relative quantitation of HCV RNA expression assessed using the Taqman procedure (Kolykhalov A A, Mihalik K, Feinstone S M, Rice C M, Journal of Virology 74, 2046–2051 (2000)) and the Platinum Quantitative RT-PCR Thermoscript One-Step kit (Invitrogen cat # 11731-015). Briefly, RNA made to a volume of 5 μl (≦1 ng) was added to a 20 μl Ready-Mix containing the following: 1.25× Thermoscript reaction mix (containing Magnesium Sulfate and 2-deoxynucleoside 5'-triphosphates (dNTPs)), 3 mM dNTPs, 200 nM forward primer (sequence: 5'-gggagagccatagtggtctgc-3'), 600 nM reverse primer (5'-cccaaatctccaggcattga-3'), 100 nM probe (5'-6-FAM-cggaattgccaggacgaccgg-BHQ-1–3') (FAM: Fluorescein-aminohexyl amidite; BHQ: Black Hole Quencher), 1 μM Rox reference dye (Invitrogen cat # 12223-012) and Thermoscript Plus Platinum Taq polymerase mixture. All primers were designed with ABI Prism 7700 software and obtained from Biosearch Technologies, Novato, Calif. Samples containing known concentrations of HCV RNA transcript were run as standards. Using the following cycling protocol (50° C., 30 min; 95° C., 5 min; 40 cycles of 95° C., 15 sec, 60° C., 1 min), HCV RNA expression was quantitated as described in the Perkin Elmer manual using the ABI Prism 7700 Sequence Detector.

Biological Examples

Representative compounds of the invention were assessed in the HCV replicon cell assay and/or in several of the outlined specificity assays. For example, Compound 34 was found to have an $IC_{50}$ of 23 nanomolar (nM) against the NS3/4A BMS strain in the enzyme assay. Similar potency values were obtained with the published H77C ($IC_{50}$ of 3 nM) and J4L6S ($IC_{50}$ of 2.9 nM) strains. The $EC_{50}$ value in the replicon assay was 166 nM.

In the specificity assays, the same compound was found to have the following activity: HLE>100 μM; PPE>200 μM; Chymotrypsin>200 μM; Cathepsin B>200 μM. These results indicate this family of compounds are highly specific for the NS3 protease and many of these members inhibit HCV replicon replication.

The compounds of the current invention were tested and found to have activities in the ranges as follow:

IC50 Activity Ranges (NS3/4A BMS Strain): A is 10–100 micromolar (RM); B is 1–10 μM; C is 0.1–1 μM; D is <0.1 μM EC50 Activity Range (for compounds tested): A is 10–100 μM; B is 1–10 μM; C is 0.1–1 μM; D is <0.1 μM Note that by using the Patent example number and the Patent compound number shown in the table the structures of compounds can be found herein.

In accordance with the present invention, preferably the compounds have a biological activity ($EC_{50}$) of 10 μM or less, more preferably 1 μM or less and most preferably 100 nM or less.

TABLE 1

Biological Activity

| IC50 range | EC50 range | Patent Example Number | Patent Cmpd Number |
|---|---|---|---|
| D | D | 1 | 1 |
| D | C | 2 | 2 |
| D | D | 3 | 3 |
| D | D | 4 | 4 |
| D | D | 5 | 5 |
| C | C | 6 | 6 |
| D | C | 7 | 7 |
| C | B | 8 | 8 |
| D | C | 9 | 9 |
| D | D | 10 | 10 |
| D | D | 11 | 11 |
| D | D | 12 | 12 |
| D | D | 13 | 13 |
| D | D | 14 | 14 |
| C | B | 15 | 15 |
| D | C | 16 | 16 |
| D | D | 17 | 17 |
| D | D | 18 | 18 |
| D | D | 19 | 19 |
| D | C | 20 | 20 |
| D | D | 21 | 21 |
| D | C | 22 | 22 |
| D | D | 23 | 23 |
| D | D | 24 | 24 |
| D | D | 25 | 25 |
| D | D | 26 | 26 |
| D | D | 27 | 27 |
| D | D | 28 | 28 |
| D | D | 29 | 29 |
| D | D | 30 | 30 |
| D | D | 31 | 31 |
| D | D | 32 | 32 |
| D | D | 33 | 33 |
| D | C | 34 | 34 |
| D | D | 35 | 35 |
| D | D | 36 | 36 |
| D | D | 37 | 37 |
| D | D | 38 | 38 |
| D | D | 39 | 39 |
| D | C | 40 | 40 |
| D | D | 41 | 41 |
| D | D | 42 | 42 |
| C | B | 45 | 45 |
| C | B | 46 | 46 |
| D | C | 47 | 47 |
| B | | 48 | 48 |
| B | | 49 | 49 |
| C | B | 50 | 50 |
| B | | 52 | 52 |
| C | B | 53 | 53 |
| D | C | 55 | 55 |
| D | D | 56 | 56 |
| D | C | 57 | 57 |
| D | D | 58 | 58 |
| D | C | 59 | 59 |

TABLE 1-continued

Biological Activity

| IC50 range | EC50 range | Patent Example Number | Patent Cmpd Number |
|---|---|---|---|
| D | B | 60 | 60 |
| C | B | 61 | 61 |
| D | D | 62 | 62 |
| D | B | 63 | 63 |
| D | D | 64 | 64 |
| D | C | 65 | 65 |
| D | C | 66 | 66 |
| D | D | 67 | 67 |
| D | D | 68 | 68 |
| D | D | 69 | 69 |
| D | D | 70 | 70 |
| D | D | 71 | 71 |
| D | C | 72 | 72 |
| D | C | 73 | 73 |
| D | D | 74 | 74 |
| D | D | 75 | 75 |
| D | D | 76 | 76 |
| D | C | 77 | 77 |
| D | B | 78 | 78 |
| D | C | 79 | 79 |
| D | B | 80 | 80 |
| D | C | 81 | 81 |
| D | C | 82 | 82 |
| D | C | 83 | 83 |
| D | C | 84 | 84 |
| C | B | 85 | 85 |
| B | A | 86 | 86 |
| B | A | 87 | 87 |
| B | A | 88 | 88 |
| D | D | 89 | 89 |
| D | C | 91 | 91 |
| D | D | 92 | 92 |
| C | C | 93 | 93 |
| D | D | 94 | 94 |
| D | C | 95 | 95 |
| D | D | 96 | 96 |
| D | D | 97 | 97 |
| B |   | 99 | 99 |
| C | B | 100 | 100 |
| D | D | 101 | 101 |
| D | D | 102 | 102 |
| D | D | 103 | 103 |
| D | D | 104 | 104 |
| D | D | 105 | 105 |
| D | D | 106 | 106 |
| D | C | 107 | 107 |
| D | D | 108 | 108 |
| D | D | 109 | 109 |
| D | C | 110 | 110 |
| D | C | 120 | 120 |
| D | C | 121 | 121 |
| D | C | 122 | 122 |
| D | C | 123 | 123 |
| C | B | 124 | 124 |
| D | D | 125 | 125 |
| D | C | 126 | 126 |
| D | C | 127 | 127 |
| D | C | 128 | 128 |
| C | C | 129 | 129 |
| D | C | 130 | 130 |
| C | B | 131 | 131 |
| D | B | 132 | 132 |
| C | B | 133 | 133 |
| D | C | 134 | 134 |
| D | C | 135 | 135 |
| D | D | 137 | 137 |
| D | D | 138 | 138 |
| D | C | 139 | 139 |
| D | B | 140 | 140 |
| D | D | 141 | 141 |
| D | D | 142 | 142 |
| D | D | 143 | 143 |
| D | C | 144 | 144 |
| D | C | 145 | 145 |
| D | D | 146 | 146 |
| D | B | 147 | 147 |
| D | D | 148 | 148 |
| D | D | 149 | 149 |
| D | D | 150 | 150 |
| D | D | 151 | 151 |
| D | D | 152 | 152 |
| D | D | 153 | 153 |
| D | C | 154 | 154 |
| D | D | 155 | 155 |
| D | C | 180 | 180 |
| D | C | 181 | 181 |
| D | C | 182 | 182 |
| D | D | 183 | 183 |
| D | D | 185 | 185 |
| D | D | 186 | 186 |
| D | D | 187 | 187 |
| D | C | 188 | 188 |
| D | C | 189 | 189 |
| D | C | 190 | 190 |
| D | C | 191 | 191 |
| D | D | 192 | 192 |
| D | C | 193 | 193 |
| D | C | 194 | 194 |
| D | D | 195 | 195 |
| D | B | 196 | 196 |
| C | A | 197 | 197 |
| D | C | 198 | 198 |
| D | C | 199 | 199 |
| D | D | 200 | 200 |
| D | D | 201 | 201 |
| D | B | 202 | 202 |
| D | C | 204 | 204 |
| D | D | 206 | 206 |
| D | D | 207 | 207 |
| D | C | 209 | 209 |
| D | D | 210 | 210 |
| D | D | 211 | 211 |
| D | D | 212 | 212 |
| D | D | 213 | 213 |
| D | D | 215 | 215 |
| D | D | 219 | 219 |
| D | D | 220 | 220 |
| D | D | 223 | 223 |
| D | C | 224 | 224 |
| D | C | 225 | 225 |
| D | D | 227 | 227 |
| D | D | 229 | 229 |
| C | C | 230 | 230 |
| B |   | 231 | 231 |
| D | D | 232 | 232 |
| C | C | 233 | 233 |
| D | C | 235 | 235 |
| D | C | 237 | 237 |
| D | C | 238 | 238 |
| D | D | 239 | 239 |
| D | D | 240 | 240 |
| D | D | 241 | 241 |
| D | B | 242 | 242 |
| C | A | 243 | 243 |
| D | A | 244 | 244 |
| C |   | 245 | 245 |
| D | D | 250 | 250 |
| D | D | 251 | 251 |
| D | D | 252 | 252 |
| D | D | 253 | 253 |
| D | D | 254 | 254 |
| D | C | 255 | 255 |
| A |   | 256 | 256 |
| D | D | 257 | 257 |
| D | D | 258 | 258 |
| D | D | 259 | 259 |

TABLE 1-continued

Biological Activity

| IC50 range | EC50 range | Patent Example Number | Patent Cmpd Number |
|---|---|---|---|
| D | C | 260 | 260 |
| D | D | 261 | 261 |
| D | D | 262 | 262 |
| C | C | 263 | 263 |
| C | B | 264 | 264 |
| D | D | 265 | 265 |
| D | D | 266 | 266 |
| D | D | 267 | 267 |
| D | D | 268 | 268 |
| D | C | 269 | 269 |
| D | C | 270 | 270 |
| D | C | 271 | 271 |
| D | D | 272 | 272 |
| D | D | 273 | 273 |
| D | C | 274 | 274 |
| D | D | 275 | 275 |
| D | D | 276 | 276 |
| D | D | 277 | 277 |
| D | D | 278 | 278 |
| D | D | 279 | 279 |
| D | D | 280 | 280 |
| D | D | 281 | 281 |
| D | C | 282 | 282 |
| D | C | 283 | 283 |
| C | A | 284 | 284 |
| D | D | 285 | 285 |
| D | D | 286 | 286 |
| D | C | 287 | 287 |
| D | B | 288 | 288 |
| D | C | 289 | 289 |
| D | D | 290 | 290 |
| D | D | 291 | 291 |
| D | C | 292 | 292 |
| D | C | 293 | 293 |
| D | C | 294 | 294 |
| C | B | 295 | 295 |
| D | C | 296 | 296 |
| C | B | 297 | 297 |
| D | D | 298 | 298 |
| D | C | 299 | 299 |
| D | C | 300 | 300 |
| D | D | 320 | 320 |
| D | C | 321 | 321 |
| D | D | 322 | 322 |
| D | C | 323 | 323 |
| D | C | 324 | 324 |
| D | D | 325 | 325 |
| D | D | 326 | 326 |
| D | D | 327 | 327 |
| D | D | 328 | 328 |
| D | D | 329 | 329 |
| D | D | 330 | 330 |
| D |   | 331 | 331 |
| C | C | 334 | 334 |
| D | B | 335 | 335 |
| C | B | 336 | 336 |
| C | B | 337 | 337 |
| D | B | 338 | 338 |
| D | B | 339 | 339 |
| D | A | 340 | 340 |
| B |   | 341 | 341 |
| B |   | 342 | 342 |
| B |   | 343 | 343 |
| C |   | 344 | 344 |
| B | A | 345 | 345 |
| B |   | 346 | 346 |
| C | A | 347 | 347 |
| A |   | 348 | 348 |
| B |   | 349 | 349 |
| C | A | 350 | 350 |
| B |   | 351 | 351 |
| A |   | 352 | 352 |
| A |   | 353 | 353 |
| B |   | 354 | 354 |
| C | A | 355 | 355 |
| C | B | 356 | 356 |
| D | C | 357 | 357 |
| C | B | 370 | 370 |
| D | D | 371 | 371 |
| D | D | 372 | 372 |
| D | D | 373 | 373 |
| D | C | 374 | 374 |
| D | D | 375 | 375 |
| D | D | 376 | 376 |
| D | C | 377 | 377 |
| D | D | 378 | 378 |
| D | D | 379 | 379 |
| D | C | 380 | 380 |
| D | C | 381 | 381 |
| D | C | 382 | 382 |
| D | D | 383 | 383 |
| D | D | 384 | 384 |
| D | D | 385 | 385 |
| C | B | 386 | 386 |
| D | D | 410 | 410 |
| D | C | 411 | 411 |
| D | D | 412 | 412 |
| D | D | 413 | 413 |
| D | D | 414 | 414 |
| D | D | 415 | 415 |
| D | C | 420 | 420 |
| D | C | 421 | 421 |
| D | B | 422 | 422 |
| C |   | 423 | 423 |
| D | C | 424 | 424 |
| C | B | 425 | 425 |
| D | C | 426 | 426 |
| D | C | 427 | 427 |
| D | C | 428 | 428 |
| D | D | 429 | 429 |
| D | C | 430 | 430 |
| D | C | 431 | 431 |
| D | C | 432 | 432 |
| C | B | 433 | 433 |
| D | C | 434 | 434 |
| D | C | 435 | 435 |
| D | C | 436 | 436 |
| D | C | 437 | 437 |
| D | C | 438 | 438 |
| D | C | 450 | 450 |
| B |   | 451 | 451 |
| B |   | 452 | 452 |
|   |   | 453 | 453 |
| C | B | 454 | 454 |
| C |   | 470 | 470 |
| B |   | 471 | 471 |

Section M:

Table 2

The following compounds that can be made using the methods described herein and specifically in sections A through K of the exemplification section and more specifically in sections B, E, F and G. Moreover it should be made clear that each of the groups B, $R_3$, $R_2$ and $R_1$ shown below can be replaced by any of the groups exemplified in sections A through K and elsewhere herein or designated in Formula I. For example the $R_3$ group in Table 2 is shown as a t-butyl group but one skilled in the art would recognize that for each of the entries cited below this group could be replaced with an isopropyl group or a $C_{1-6}$ alkyl substituted with an alkoxy. Or the B group shown below could be replaced with a tert-butyl urea moiety for each of the entries cited below.

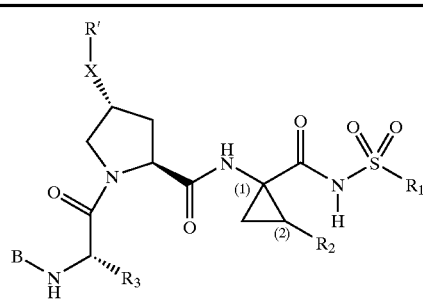

| Entry | B | R₃ | X | R' | R₂ | C(1,2)-Cyclopropane stereochemsitry | R₁ |
|---|---|---|---|---|---|---|---|
| A | *t*-BuO-C(O)- | *t*-Bu | O | 6-MeO-isoquinolin-3-yl(3-cyanophenyl) | vinyl | (1R, 2S) | cyclopropyl |
| B | *t*-BuO-C(O)- | *t*-Bu | O | 6-MeO-isoquinolin-3-yl(4-MeO-oxazol-2-yl) | vinyl | (1R, 2S) | cyclopropyl |
| C | *t*-BuO-C(O)- | *t*-Bu | O | 6-MeO-isoquinolin-3-yl(6-MeO-pyridin-3-yl) | vinyl | (1R, 2S) | cyclopropyl |
| D | *t*-BuO-C(O)- | *t*-Bu | O | 6-MeO-isoquinolin-3-yl(6-Me-pyridin-3-yl) | vinyl | (1R, 2S) | cyclopropyl |
| E | *t*-BuO-C(O)- | *t*-Bu | O | 6-MeO-isoquinolin-3-yl(pyrazol-1-yl) | vinyl | (1R, 2S) | cyclopropyl |

-continued

| Entry | B | R₃ | X | R' | R₂ | C(1,2)-Cyclopropane stereochemsitry | R₁ |
|---|---|---|---|---|---|---|---|
| F | *t*-BuO-C(O)-CH- | *t*-Bu | O | 6-MeO-3-(pyrrolidin-1-yl)isoquinolin-1-yl | vinyl | (1R, 2S) | cyclopropyl |
| G | *t*-BuO-C(O)-CH- | *t*-Bu | O | 6-MeO-3-(isoxazolidin-2-yl)isoquinolin-1-yl | vinyl | (1R, 2S) | cyclopropyl |
| H | *t*-BuO-C(O)-CH- | *t*-Bu | O | 6-MeO-3-(dimethylamino)isoquinolin-1-yl | vinyl | (1R, 2S) | cyclopropyl |
| I | *t*-BuO-C(O)-CH- | *t*-Bu | O | 6-MeO-3-(N-methyl-N-methoxyamino)isoquinolin-1-yl | vinyl | (1R, 2S) | cyclopropyl |
| J | *t*-BuO-C(O)-CH- | *t*-Bu | O | 6-MeO-3-(2-methoxythiazol-4-yl)isoquinolin-1-yl | vinyl | (1R, 2S) | cyclopropyl |

-continued

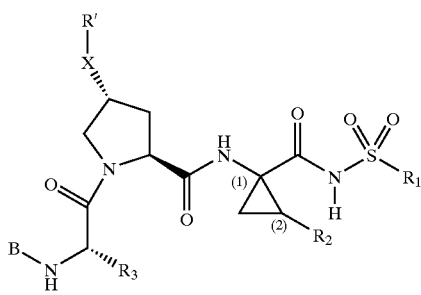

| Entry | B | R₃ | X | R' | R₂ | C(1,2)-Cyclopropane stereochemsitry | R₁ |
|---|---|---|---|---|---|---|---|
| K | tBuO-C(O)-CH< | tBu | O | 6-MeO-isoquinoline-3-yl with 1-methylimidazol-2-yl at C-3, attached at C-1 | vinyl | (1R, 2S) | cyclopropyl |
| L | tBuO-C(O)-CH< | tBu | O | 6-MeO-isoquinoline with 5-methyl-1,2,4-oxadiazol-3-yl | vinyl | (1R, 2S) | cyclopropyl |
| M | tBuO-C(O)-CH< | tBu | O | 6-MeO-isoquinoline with 3-methylpyrazol-1-yl | vinyl | (1R, 2S) | cyclopropyl |
| N | tBuO-C(O)-CH< | tBu | O | 6-MeO-isoquinoline with 4-methoxythiazol-2-yl | vinyl | (1R, 2S) | cyclopropyl |

-continued

| Entry | B | R₃ | X | R' | R₂ | C(1,2)-Cyclopropane stereochemistry | R₁ |
|---|---|---|---|---|---|---|---|
| O | t-BuO-C(O)- | t-Bu | O | 6-MeO-isoquinolin-3-yl substituted with 5-methoxypyridin-2-yl | vinyl | (1R, 2S) | cyclopropyl |
| P | t-BuO-C(O)- | t-Bu | O | 6-MeO-isoquinolin-3-yl substituted with 5-methyl-1,2,4-oxadiazol-3-yl | vinyl | (1R, 2S) | cyclopropyl |
| Q | t-BuO-C(O)- | t-Bu | O | 4-OH-isoquinolin-3-yl substituted with thiazol-2-yl | vinyl | (1R, 2S) | cyclopropyl |
| R | t-BuO-C(O)- | t-Bu | O | 6-MeO-4-OH-isoquinolin-3-yl substituted with thiazol-2-yl | vinyl | (1R, 2S) | cyclopropyl |
| S | t-BuO-C(O)- | t-Bu | O | 4-OH-isoquinolin-3-yl substituted with oxazol-2-yl | vinyl | (1R, 2S) | cyclopropyl |

-continued

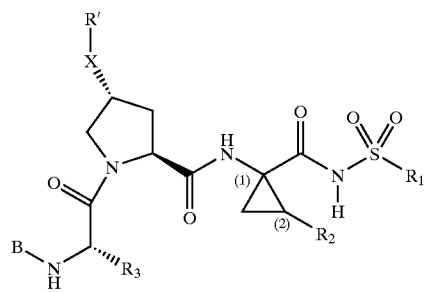

| Entry | B | R₃ | X | R' | R₂ | C(1,2)-Cyclopropane stereochemsitry | R₁ |
|---|---|---|---|---|---|---|---|
| T | *t*-BuO-C(O)- | *t*-Bu | O | 6-MeO-4-OH-3-(1-methylthiazol-2-yl)isoquinolin-1-yl | vinyl | (1R, 2S) | cyclopropyl |
| U | *t*-BuO-C(O)- | *t*-Bu | O | 6-MeO-3-(2H-1,2,3-triazol-2-yl)isoquinolin-1-yl | vinyl | (1R, 2S) | cyclopropyl |
| V | *t*-BuO-C(O)- | *t*-Bu | O | 6-MeO-3-(2H-tetrazol-2-yl)isoquinolin-1-yl | vinyl | (1R, 2S) | cyclopropyl |
| W | *t*-BuO-C(O)- | *t*-Bu | O | 6-MeO-3-(1H-1,2,4-triazol-1-yl)isoquinolin-1-yl | vinyl | (1R, 2S) | cyclopropyl |
| X | *t*-BuO-C(O)- | *t*-Bu | O | 6-MeO-3-(4-methylimidazol-1-yl)isoquinolin-1-yl | vinyl | (1R, 2S) | cyclopropyl |

-continued

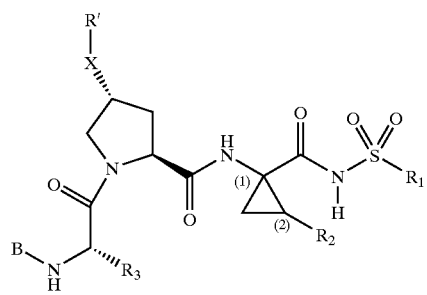

| Entry | B | R₃ | X | R' | R₂ | C(1,2)-Cyclopropane stereochemistry | R₁ |
|---|---|---|---|---|---|---|---|
| Y | tBuO-C(O)- | tBu | O | 7-MeO-3-(4-CF₃-pyrazol-1-yl)isoquinolin-1-yl | vinyl | (1R, 2S) | cyclopropyl |
| Z | tBuO-C(O)- | tBu | O | 8-(pyrazol-1-yl)-2,3-dihydrofuro[3,2-h]isoquinolin-6-yl | vinyl | (1R, 2S) | cyclopropyl |
| Aa | tBuO-C(O)- | tBu | O | 8-(isoxazol-3-yl)-2,3-dihydrofuro[3,2-h]isoquinolin-6-yl | vinyl | (1R, 2S) | cyclopropyl |
| Bb | tBuO-C(O)- | tBu | O | 8-MeO-2,3-dihydrofuro[3,2-h]isoquinolin-6-yl | vinyl | (1R, 2S) | cyclopropyl |
| Cc | tBuO-C(O)- | tBu | O | 9-MeO-2,3-dihydrofuro[3,2-h]isoquinolin-6-yl | vinyl | (1R, 2S) | cyclopropyl |

-continued

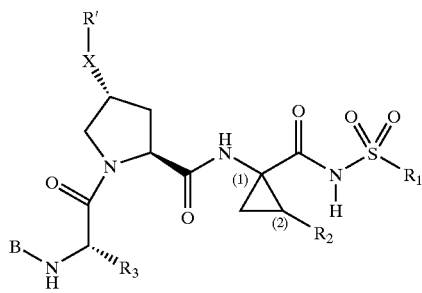

| Entry | B | R₃ | X | R' | R₂ | C(1,2)-Cyclopropane stereochemsitry | R₁ |
|---|---|---|---|---|---|---|---|
| Dd | tBuO-C(O)- | tBu- | O | 2,3-dihydrofuro-isoquinoline-oxazole | vinyl | (1R, 2S) | cyclopropyl |
| Ee | tBuO-C(O)- | tBu- | O | 9-chloro-2,3-dihydrofuro-isoquinoline | vinyl | (1R, 2S) | cyclopropyl |
| Ff | tBuO-C(O)- | tBu- | O | 3-Me-isoxazolo-pyridine | vinyl | (1R, 2S) | cyclopropyl |
| Gg | tBuO-C(O)- | tBu- | O | 3-Me-5-phenyl-isoxazolo-pyridine | vinyl | (1R, 2S) | cyclopropyl |
| Hh | tBuO-C(O)- | tBu- | O | 3-Me-5-(4-cyanophenyl)-isoxazolo-pyridine | vinyl | (1R, 2S) | cyclopropyl |

-continued

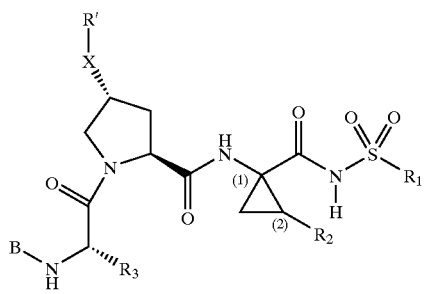

| Entry | B | R₃ | X | R' | R₂ | C(1,2)-Cyclopropane stereochemsitry | R₁ |
|---|---|---|---|---|---|---|---|
| Ii | tBuO-C(O)- | tBu | O | isoquinolin-4-yl | vinyl | (1R, 2S) | cyclopropyl |
| Jj | tBuO-C(O)- | tBu | O | 1,7-dimethoxyisoquinolin-4-yl | vinyl | (1R, 2S) | cyclopropyl |
| Kk | tBuO-C(O)- | tBu | O | 7-methoxyisoquinolin-4-yl | vinyl | (1R, 2S) | cyclopropyl |
| Ll | tBuO-C(O)- | tBu | O | 6-(4-cyanophenyl)-2-methyloxazolo[4,5-c]pyridin-? | vinyl | (1R, 2S) | cyclopropyl |
| Mm | tBuO-C(O)- | tBu | O | 5-(4-cyanophenyl)-2-methyloxazolo[?]pyridin-? | vinyl | (1R, 2S) | cyclopropyl |

What is claimed is:

1. A compound having the formula

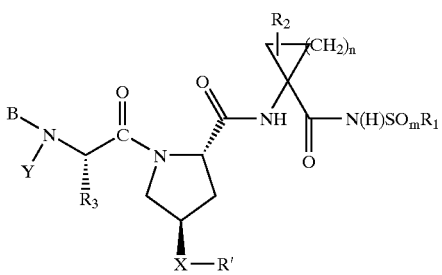

(I)

wherein:
- (a) $R_1$ is $C_{1-8}$ alkyl, $C_{3-7}$ cycloalkyl, or $C_{4-10}$ alkylcycloalkyl;
- (b) m is 1 or 2;
- (c) n is 1 or 2;
- (d) $R_2$ is H, $C_{1-6}$ alkyl, $C_{2-6}$ alkenyl or $C_{3-7}$ cycloalkyl, each optionally substituted with halogen;
- (e) $R_3$ is $C_{1-8}$ alkyl optionally substituted with halo, cyano, amino, $C_{1-6}$ dialkylamino, $C_{6-10}$ aryl, $C_{7-14}$ alkylaryl, $C_{1-6}$ alkoxy, carboxy, hydroxy, aryloxy, $C_{7-14}$ alkylaryloxy, $C_{2-6}$ alkylester, $C_{8-15}$ alkylarylester; $C_{3-12}$ alkenyl, $C_{3-7}$ cycloalkyl, or $C_{4-10}$ alkylcycloalkyl, wherein the cycloalkyl or alkylcycloalkyl are optionally substituted with hydroxy, $C_{1-6}$ alkyl, $C_{2-6}$ alkenyl or $C_{1-6}$ alkoxy; or $R_3$ together with the carbon atom to which it is attached forms a $C_{3-7}$ cycloalkyl group optionally substituted with $C_{2-6}$ alkenyl;
- (f) Y is H, phenyl substituted with nitro, pyridyl substituted with nitro, or $C_{1-6}$ alkyl optionally substituted with cyano, OH or $C_{3-7}$ cycloalkyl; provided that if $R_4$ or $R_5$ is H then Y is H;
- (g) B is H, $C_{1-6}$ alkyl, $R_4$—(C=O)—, $R_4O(C=O)$—, $R_4$—N($R_5$)—C(=O)—, $R_4$—N($R_5$)—C(=S)—, $R_4SO_2$—, or $R_4$—N($R_5$)—$SO_2$—;
- (h) $R_4$ is (i) $C_{1-10}$ alkyl optionally substituted with phenyl, carboxyl, $C_{1-6}$ alkanoyl, 1–3 halogen, hydroxy, —OC(O)$C_{1-6}$ alkyl, $C_{1-6}$ alkoxy, amino optionally substituted with $C_{1-6}$ alkyl, amido, or (lower alkyl) amido; (ii) $C_{3-7}$ cycloalkyl, $C_{3-7}$ cycloalkoxy, or $C_{4-10}$ alkylcycloalklyl, each optionally substituted with hydroxy, carboxyl, ($C_{1-6}$ alkoxy)carbonyl, amino optionally substituted with $C_{1-6}$ alkyl, amido, or (lower alkyl) amido; (iii) $C_{6-10}$ aryl or $C_{7-16}$ arylalkyl, each optionally substituted with $C_{1-6}$ alkyl, halogen, nitro, hydroxy, amido, (lower alkyl) amido, or amino optionally substituted with $C_{1-6}$ alkyl; (iv) Het; (v) bicyclo (1.1.1)pentane; or (vi) —C(O)OC$_{1-6}$ alkyl, $C_{2-6}$alkenyl or $C_{2-6}$ alkynyl;
- (i) $R_5$ is H; $C_{1-6}$alkyl optionally substituted with 1–3 halogens; or $C_{1-6}$ alkoxy provided $R_4$ is $C_{1-10}$ alkyl;
- (j) X is O, S, SO, $SO_2$, $OCH_2$, $CH_2O$ or NH;
- (k) R' is Het; or $C_{6-10}$ aryl or $C_{7-14}$ alkylaryl, optionally substituted with $R^a$; and
- (l) $R^a$ is $C_{1-6}$ alkyl, $C_{3-7}$ cycloalkyl, $C_{1-6}$ alkoxy, $C_{3-7}$ cycloalkoxy, halo-$C_{1-6}$ alkyl, $CF_3$, mono-or di-halo-$C_{1-6}$ alkoxy, cyano, halo, thioalkyl, hydroxy, alkanoyl, $NO_2$, SH, ) amino, $C_{1-6}$alkylamino, di($C_{1-6}$) alkylamino, di($C_{1-6}$)alkylamide carboxyl, ($C_{1-6}$) carboxyester, $C_{1-6}$ alkylsulfone, $C_{1-6}$ alkylsulfonamide, di($C_{1-6}$) alkyl(alkoxy)amine, $C_{5-10}$ aryl, $C_{7-14}$ alkylaryl, or a 5–7 membered monocyclic heterocycle;

with the proviso that X—R' is not

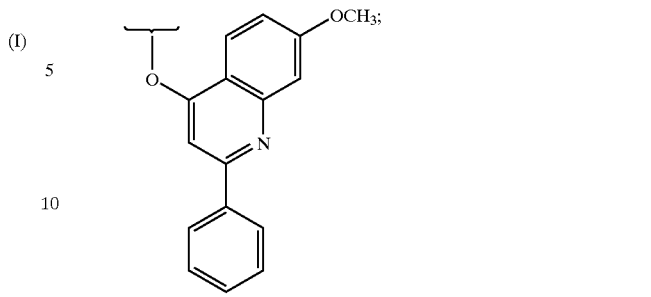

or a pharmaceutically acceptable salt, solvate or prodrug thereof.

2. The compound of claim 1 wherein $R_1$ is $C_{3-7}$ cycloalkyl.

3. The compound of claim 1 wherein $R_2$ is $C_{1-6}$ alkyl, $C_{2-6}$ alkenyl or $C_{3-7}$ cycloalkyl.

4. The compound of claim 3 wherein $R_2$ is $C_{2-6}$ alkenyl.

5. The compound of claim 1 wherein $R_3$ is $C_{1-8}$ alkyl optionally substituted with $C_6$aryl, $C_{1-6}$ alkoxy, carboxy, hydroxy, aryloxy, $C_{7-14}$ alkylaryloxy, $C_{2-6}$ alkylester, $C_{8-15}$ alkylarylester; $C_{3-12}$ alkenyl, $C_{3-7}$ cycloalkyl, or $C_{4-10}$ alkylcycloalkyl.

6. The compound of claim 5 wherein $R_3$ is $C_{1-8}$ alkyl optionally substituted with $C_{1-6}$ alkoxy; or $C_{3-7}$ cycloalkyl.

7. The compound of claim 1 wherein Y is H.

8. The compound of claim 1 wherein B is H, $C_{1-6}$ alkyl, $R_4$—(C=O)—, $R_4O(C=O)$—, $R_4$—N($R_5$)—C(=O)—, $R_4$—N($R_5$)—C(=S)—, $R_4SO_2$—, or $R_4$—N($R_5$)—$SO_2$—.

9. The compound of claim 8 wherein B is $R_4$—(C=O)—, $R_4O(C=O)$—, or $R_4$—N($R_5$)—C(=O)—.

10. The compound of claim 9 wherein B is $R_4O(C=O)$— and $R_4$ is $C_{1-6}$ alkyl.

11. The compound of claim 1 wherein $R_4$ is (i) $C_{1-10}$ alkyl optionally substituted with phenyl, carboxyl, $C_{1-6}$ alkanoyl, 1–3 halogen, hydroxy, $C_{1-6}$ alkoxy; (ii) $C_{3-7}$ cycloalkyl, $C_{3-7}$ cycloalkoxy, or $C_{4-10}$ alkylcycloalklyl; or (iii) $C_{6-10}$ aryl or $C_{7-16}$ arylalkyl, each optionally substituted with $C_{1-6}$ alkyl or halogen.

12. The compound of claim 11 wherein $R_4$ is (i) $C_{1-10}$ alkyl optionally substituted with 1–3 halogen or $C_{1-6}$ alkoxy; or (ii) $C_{3-7}$ cycloalkyl or $C_{4-10}$ alkylcycloalkyl.

13. The compound of claim 1 wherein $R_5$ is H or $C_{1-6}$ alkyl optionally substituted with 1–3 halogens.

14. The compound of claim 13 wherein $R_5$ is H.

15. The compound of claim 1 wherein X is O or NH.

16. The compound of claim 1 wherein R' is Het; or $C_{6-10}$ aryl optionally substituted with $R^a$.

17. The compound of claim 16 wherein R' is Het.

18. The compound of claim 1 wherein the heterocycle contains 1 or 2 nitrogen atoms and optionally a sulfur atom or an oxygen atom in the ring.

19. The compound of claim 18 wherein the heterocycle is substituted with at least one of $C_{1-6}$ alkyl, $C_{1-6}$ alkoxy, halo, $C_{6-10}$ aryl, $C_{7-14}$ alkylaryl, or a 5–7 membered monocyclic heterocycle.

20. The compound of claim 1 wherein $R^a$ is $C_{1-6}$ alkyl, $C_{3-7}$ cycloalkyl, $C_{1-6}$ alkoxy, halo-$C_{1-6}$ alkyl, halo, amino, $C_6$ aryl, or a 5–7 membered monocyclic heterocycle.

21. A compound having the formula

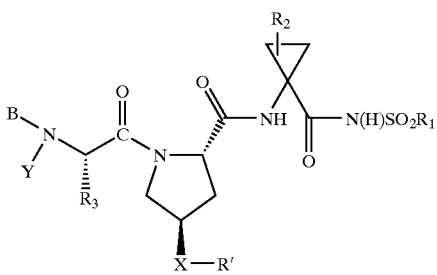

(II)

wherein:

(a) $R_1$ is $C_{3-7}$ cycloalkyl;
(b) $R_2$ is $C_{1-6}$ alkyl, $C_{2-6}$ alkenyl or $C_{3-7}$ cycloalkyl;
(c) $R_3$ is $C_{1-8}$ alkyl optionally substituted with $C_6$aryl, $C_{1-6}$ alkoxy, carboxy, hydroxy, aryloxy, $C_{7-14}$ alkylaryloxy, $C_{2-6}$ alkylester, $C_{8-15}$ alkylarylester; $C_{3-12}$ alkenyl, $C_{3-7}$ cycloalkyl, or $C_{4-10}$ alkylcycloalkyl;
(d) Y is H;
(e) B is H, $C_{1-6}$ alkyl, $R_4$—(C=O)—, $R_4O(C=O)$—, $R_4$—N($R_5$)—C(=O)—, $R_4$—N($R_5$)—C(=S)—, $R_4SO_2$—, or $R_{41}$—N($R_5$)—$SO_2$—;
(f) $R_4$ is (i) $C_{1-10}$ alkyl optionally substituted with phenyl, carboxyl, $C_{1-6}$ alkanoyl, 1-3 halogen, hydroxy, $C_{1-6}$ alkoxy; (ii) $C_{3-7}$ cycloalkyl, $C_{3-7}$ cycloalkoxy, or $C_{4-10}$ alkylcycloalklyl; or (iii) $C_{6-10}$ aryl or $C_{7-16}$ arylalkyl, each optionally substituted with $C_{1-6}$ alkyl or halogen;
(g) $R_5$ is H or $C_{1-6}$ alkyl optionally substituted with 1-3 halogens;
(h) X is O or NH;
(i) R' is Het; or $C_{6-10}$ aryl optionally substituted with $R^a$; and
(j) $R^a$ is $C_{1-6}$ alkyl, $C_{3-7}$ cycloalkyl, $C_{1-6}$ alkoxy, halo-$C_{1-6}$ alkyl, halo, amino, $C_6$ aryl, or a 5–7 membered monocyclic heterocycle; with the proviso that $X_a$—R' is not

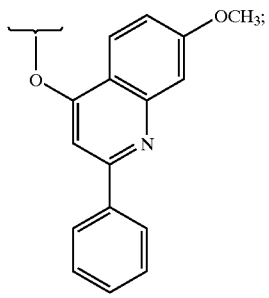

or a pharmaceutically acceptable salt, solvate or prodrug thereof.

22. The compound of claim 21 wherein R' is a bicyclic heterocycle.
23. The compound of claim 22 wherein the heterocycle contains 1 or 2 nitrogen atoms and optionally a sulfur atom or an oxygen atom in the ring.
24. The compound of claim 22 wherein the heterocycle is substituted with at least one of $C_{1-6}$ alkyl, $C_{1-6}$ alkoxy, halo, $C_6$ aryl, and a 5–7 membered monocyclic heterocycle.
25. The compound of claim 21 wherein R' is a bicyclic heterocycle containing 1 nitrogen atom and substituted with methoxy and at least one of a $C_6$ aryl and a 5–7 membered monocyclic heterocycle.

26. The compound of claim 21 wherein R' is a monocyclic heterocycle.
27. The compound of claim 26 wherein the heterocycle contains 1 or 2 nitrogen atoms and optionally a sulfur atom or an oxygen atom in the ring.
28. The compound of claim 26 wherein the heterocycle is substituted with at least one of $C_{1-6}$ alkyl, $C_{1-6}$ alkoxy, halo, $C_{6-10}$ aryl, $C_{7-14}$ alkylaryl, or a 5–7 membered monocyclic heterocycle.
29. The compound of claim 21 wherein R' is a monoyclic heterocycle containing 1 or 2 nitrogen atoms and substituted with methoxy and at least one of a $C_6$ aryl and a 5–7 membered monocyclic heterocycle.
30. A compound having the formula

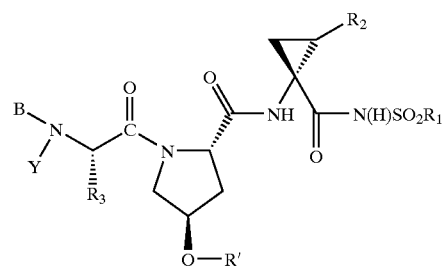

(III)

wherein:

(a) $R_1$ is $C_{3-7}$ cycloalkyl;
(b) $R_2$ is $C_{2-6}$ alkenyl;
(c) $R_3$ is $C_{1-8}$ alkyl;
(d) Y is H;
(e) B is $R_4O(C=O)$—, or $R_4$—N($R_5$)—C(=O)—;
(f) $R_4$ is $C_{1-10}$ alkyl;
(g) $R_5$ is H;
(h) R' is a bicyclic heterocycle optionally substituted with $R^a$; and
(i) $R^a$ is $C_{1-6}$ alkyl, $C_{1-6}$ alkoxy, halo, $C_6$ aryl, or a 5–7 membered monocyclic heterocycle; with the proviso that O—R' is not

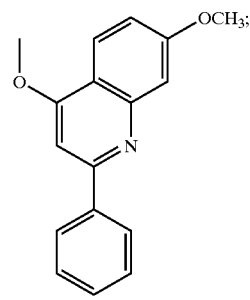

or a pharmaceutically acceptable salt, solvate or prodrug thereof.

31. The compound of claim 30 wherein $R_1$ is cyclopropyl or cyclobutyl.
32. The compound of claim 30 wherein $R_2$ is vinyl.
33. The compound of claim 30 wherein $R_3$ is t-butyl.
34. The compound of claim 30 wherein $R_4$ is t-butyl.
35. The compound of claim 30 wherein R' is quinoline or isoquinoline optionally substituted with $R^a$.
36. The compound of claim 30 wherein $R_1$ is cyclopropyl, $R_2$ is vinyl, $R_3$ is t-butyl, $R_4$ is t-butyl, and R' is isoquinoline substituted with $R^a$.
37. The compound of claim 36 wherein $R^3$ is $C_{1-6}$ alkoxy.

38. The compound of claim 37 wherein $R^a$ further includes at least one of $C_6$ aryl or a 5–7 membered monocyclic heterocycle.

39. A method of treating an HCV infection in a patient, comprising administering to the patient a therapeutically effective amount of the compound of claim 1 or a pharmaceutically acceptable salt, solvate or prodrug thereof.

40. A method of inhibiting HCV NS3 protease comprising administering to a patient in need thereof a therapeutically effective amount of the compound of claim 1 or a pharmaceutically acceptable salt, solvate or prodrug thereof.

41. A composition comprising the compound of claim 1 or a pharmaceutically acceptable salt, solvate or prodrug thereof and a pharmaceutically acceptable carrier.

42. The composition of claim 41 further comprising an additional immunomodulatory agent.

43. The composition of claim 42 wherein the additional immunomodulatory agent is selected from the group consisting of α-, β-, and δ-interferons.

44. The composition of claim 41 further comprising an antiviral agent.

45. The composition of claim 44 wherein the antiviral agent is selected from the group consisting of ribavirin and amantadine.

46. The composition of claim 41 further comprising an inhibitor of HCV protease other than the compound of claim 1.

47. The composition of claim 46 further comprising an inhibitor of a target in the HCV life cycle other than HCV NS3 protease.

48. The composition of claim 47 wherein the other target is selected from the group consisting of helicase, polymerase, metalloprotease and mixtures thereof.

* * * * *

UNITED STATES PATENT AND TRADEMARK OFFICE
CERTIFICATE OF CORRECTION

PATENT NO. : 6,995,174 B2
APPLICATION NO. : 10/441657
DATED : February 7, 2006
INVENTOR(S) : Xiangdong Alan Wang et al.

It is certified that error appears in the above-identified patent and that said Letters Patent is hereby corrected as shown below:

Column 2, line 42; column 10, line 56, the text "$R_2$ is H $C_{1-6}$ alkyl," should read --$R_2$ is H, $C_{1-6}$ alkyl,--.

Column 2, line 67; column 11, line 13; claim 1, line 46; claim 11, line 43; claim 21, line 30, "alkylcycloaklyl" should be --alkylcycloalkyl--.

Column 3, line 18; column 11, line 31; claim 1, line 63, the text "SH,) amino," should read --SH, amino,--.

Column 11, line 11; column 11, line 33; "C-6" should be --$C_{1-6}$--.

Column 11, line 58, "cycloalklyl" should be --cycloalkyl--.

Column 75, lines 40-45, the structure should appear as follows:

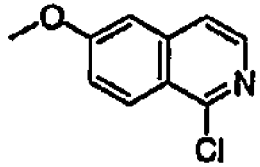

Column 79, lines 27-33, the text beginning with "$^1$H NMR" and ending with "(d, J=15 Hz, 1H)." should read --$^1$H NMR (500 MHz, DMSO-$d_6$) δ 0.52 - 0.65 (m, 2H), 0.66 - 0.82 (m, 2H), 0.96 (s, 9H), 1.21 - 1.24 (m, 10H), 1.44 - 1.63 (m, 1H), 1.72 - 1.92 (m, 1H), 2.30 - 2.42 (m, 1H), 2.46 (d, $J$=7.93 Hz, 1H), 2.60 - 2.85 (m, 1H), 3.89 (s, 3H), 3.93 - 4.05 (m, 1H), 4.07 - 4.24 (m, 1H), 4.41 (t, $J$=8.39 Hz, 1H), 4.79 - 4.95 (m, 1H), 4.97 - 5.17 (m, 1H), 5.71 (b, 1H), 5.80 - 6.10 (m, 1H), 6.64 (d, $J$=8.54 Hz, 1H), 7.10 (d, $J$=8.85 Hz, 1H), 7.24 - 7.37 (m, 2H), 7.90 - 7.96 (m, 1H), 7.99 - 8.04 ( b, 1H), 8.06 (d, $J$=9.15 Hz, 1H).--.

Column 334, line 35, the text "$(M+H)^+$ 749" should be --$(M+H)^+$ 748--.

Claim 1, line 66, "$C_{5-10}$ aryl" should be --$C_{6-10}$ aryl--.

Claim 9, line 37, "$R_{40}(C=O)$-," should be --$R_4O(C=O)$-,--.

Claim 18, line 57, "claim 1" should be --claim 17--.

Claim 21, line 26, "$R_{41}$-N($R_5$)-SO$_2$„-;" should be --$R_{41}$-N($R_5$)-SO$_2$-;--.

Claim 21, line 40, "$X_a$-R' is not" should be --X-R' is not--.

UNITED STATES PATENT AND TRADEMARK OFFICE
CERTIFICATE OF CORRECTION

| | |
|---|---|
| PATENT NO. | : 6,995,174 B2 |
| APPLICATION NO. | : 10/441657 |
| DATED | : February 7, 2006 |
| INVENTOR(S) | : Xiangdong Alan Wang et al. |

It is certified that error appears in the above-identified patent and that said Letters Patent is hereby corrected as shown below:

Claim 29, line 10, "monoyclic" should be --monocyclic--.

Signed and Sealed this

Thirteenth Day of February, 2007

JON W. DUDAS
*Director of the United States Patent and Trademark Office*